US010272074B2

(12) United States Patent
Pinkerton et al.

(10) Patent No.: US 10,272,074 B2
(45) Date of Patent: Apr. 30, 2019

(54) INHIBITORS OF GLUCOCORTICOID RECEPTOR TRANSLOCATION

(71) Applicant: Sanford Burnham Prebys Medical Discovery Institute, La Jolla, CA (US)

(72) Inventors: Anthony B. Pinkerton, La Jolla, CA (US); Christian A. Hassig, La Jolla, CA (US); Michael R. Jackson, La Jolla, CA (US); Robert John Ardecky, La Jolla, CA (US); Ian Pass, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 15/546,165

(22) PCT Filed: Jan. 28, 2016

(86) PCT No.: PCT/US2016/015451
§ 371 (c)(1),
(2) Date: Jul. 25, 2017

(87) PCT Pub. No.: WO2016/123392
PCT Pub. Date: Aug. 4, 2016

(65) Prior Publication Data
US 2018/0207140 A1    Jul. 26, 2018

Related U.S. Application Data

(60) Provisional application No. 62/109,598, filed on Jan. 29, 2015.

(51) Int. Cl.
*C07D 401/14* (2006.01)
*A61K 31/437* (2006.01)
*C07D 471/04* (2006.01)
*A61K 45/06* (2006.01)
*A61P 35/00* (2006.01)

(52) U.S. Cl.
CPC ............ *A61K 31/437* (2013.01); *A61K 45/06* (2013.01); *A61P 35/00* (2018.01); *C07D 471/04* (2013.01)

(58) Field of Classification Search
CPC .......................... C07D 401/14; A61K 31/437
USPC .......................................... 546/119; 514/303
See application file for complete search history.

(56) References Cited

U.S. PATENT DOCUMENTS

| 4,012,373 | A  | * | 3/1977  | Denzel ................. C07D 231/38 540/493 |
| 6,949,648 | B2 | * | 9/2005  | Uchikawa ............. A61K 31/00 544/126 |
| 7,465,743 | B2 | * | 12/2008 | Coe ...................... C07D 471/04 514/303 |
| 2006/0035921 | A1 |  | 2/2006  | Castelhano et al. |

FOREIGN PATENT DOCUMENTS

| WO | WO-0172749 A1    | 10/2001 |
| WO | WO-2005090353 A1 | 9/2005  |
| WO | WO-2016123392 A2 | 8/2016  |

OTHER PUBLICATIONS

Chakravorti et al., Indian Journal of Chemistry, Section B: Organic Chemistry Including Medicinal Chemistry (1978), 16B(2), 161-3.*
PCT/US2016/015451 International Search Report and Written Opinion dated Sep. 2, 2016.
Rimland et al. The identification a novel, selective, non-steroidal, functional glucocorticoid receptor antagonist. Bioorg Med Chem Lett 20(7):2340-2343 (2010).
RN 1026816-80-7 (Entered STN: Jun. 9, 2008) (1 pg.).
RN 1027509-22-3 (Entered STN: Jun. 12, 2008) (1 pg.).
RN 1027596-51-5 (Entered STN: Jun. 12, 2008) (1 pg.).
RN 1327563-30-3 (Entered STN: Sep. 4, 2011) (1 pg.).
RN 1328596-90-2 (Entered STN: Sep. 5, 2011) (1 pg.).
RN 1329637-40-2 (Entered STN: Sep. 7, 2011) (1 pg.).
RN 1329892-41-2 (Entered STN: Sep. 8, 2011) (1 pg.).
RN 1329892-48-9 (Entered STN: Sep. 8, 2011) (1 pg.).
RN 1329945-05-2 (Entered STN: Sep. 8, 2011) (1 pg.).
RN 1330398-93-0 (Entered STN: Sep. 9, 2011) (1 pg.).
RN 649664-85-7 (Entered STN: Feb. 12, 2004) (1 pg.).
RN 649664-91-5 (Entered STN: Feb. 12, 2004) (1 pg.).
RN 899746-10-2 (Entered STN: Aug. 8, 2006) (1 pg.).
RN 899746-35-1 (Entered STN: Aug. 8, 2006) (1 pg.).
RN 899746-38-4 (Entered STN: Aug. 8, 2006) (1 pg.).
RN 899746-44-2 (Entered STN: Aug. 8, 2006) (1 pg.).
RN 899746-47-5 (Entered STN: Aug. 8, 2006) (1 pg.).
RN 899746-50-0 (Entered STN: Aug. 8, 2006) (1 pg.).
RN 899952-71-7 (Entered STN: Aug. 9, 2006) (1 pg.).
RN 899952-75-1 (Entered STN: Aug. 9, 2006) (1 pg.).
RN 899952-89-7 (Entered STN: Aug. 9, 2006) (1 pg.).
RN 899952-95-5 (Entered STN: Aug. 9, 2006) (1 pg.).
RN 899985-42-3 (Entered STN: Aug. 9, 2006) (1 pg.).
RN 899985-51-4 (Entered STN: Aug. 9, 2006) (1 pg.).

(Continued)

*Primary Examiner* — Niloofar Rahmani
(74) *Attorney, Agent, or Firm* — Wilson Sonsini Goodrich & Rosati

(57) ABSTRACT

Provided herein are compounds and pharmaceutical compositions comprising said compounds. The subject compounds and compositions are useful as modulators of Glucocorticoid Receptor (GR) translocation. Furthermore, the subject compounds and compositions are useful for the treatment of diseases involved in the hypothalamic-pituitary-adrenal (HPA) axis.

16 Claims, No Drawings

(56) References Cited

OTHER PUBLICATIONS

RN 899985-53-6 (Entered STN: Aug. 9, 2006) (1 pg.).
RN 899985-55-8 (Entered STN: Aug. 9, 2006) (1 pg.).
RN 899985-57-0 (Entered STN: Aug. 9, 2006) (1 pg.).
RN 899985-70-7 (Entered STN: Aug. 9, 2006) (1 pg.).

* cited by examiner

INHIBITORS OF GLUCOCORTICOID RECEPTOR TRANSLOCATION

CROSS REFERENCE

This application is filed pursuant to 35 U.S.C. § 371 as a United States National Phase Application of International Application No. PCT/US2016/015451, filed Jan. 28, 2016; which claims benefit of U.S. Provisional Application No. 62/109,598, filed Jan. 29, 2015, all of which are herein incorporated by reference in their entirety.

BACKGROUND

The glucocorticoid receptor (GR) is a member of the steroid thyroid nuclear hormone receptor superfamily, which includes, but is not limited to, mineral corticoid, androgen, progesterone and estrogen receptors. The glucocorticoid receptor is activated in vivo by binding of natural agonists such as cortisol and corticosterone. The glucocorticoid receptor may also be activated by binding of synthetic agonists such as dexamethasone, prednisone and prednisilone. Mifepristone is known to induce mixed GR passive antagonism, GR active antagonism, and GR agonism. Passive antagonism is the mechanism by which the formation of a ligand competent GR complex and the receptor nuclear translocation are blocked.

Currently available drugs that bind to the glucocorticoid receptor are typically cortisol analogues, which produce undesired side effects that are caused by: (1) unselective binding to other steroid receptors; and (2) failure to disassociate the different response elements when binding to the glucocorticoid receptor. Thus, there exists a need for compounds that selectively inhibit all glucocorticoid receptor-mediated nuclear functions.

BRIEF SUMMARY OF THE INVENTION

This disclosure provides, for example, compounds and compositions which are modulators or inhibitors of glucocorticoid receptor (GR) translocation, and their use as medicinal agents, processes for their preparation, and pharmaceutical compositions that include disclosed compounds as at least one active ingredient. The disclosure also provides for the use of disclosed compounds for the treatment of conditions that are mediated by glucocorticoid receptor in a subject in need thereof. The disclosure also provides for the use of disclosed compounds in combination with a glucocorticoid receptor (GR) agonist.

One aspect provides a compound of Formula (II), or a pharmaceutically acceptable salt, solvate, tautomer, or N-oxide thereof:

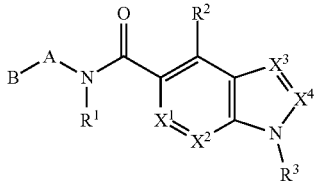

Formula (II)

wherein:
$X^1$-$X^4$ are independently selected from the group consisting of N and $CR^4$.

A is selected from the group consisting of bond and —$CH_2CH_2$—;
B is selected from the group consisting of heterocycloalkyl, phenyl, and 5- or 6-membered heteroaryl;
  wherein the heterocycloalkyl, phenyl, and heteroaryl are optionally substituted with one or more groups independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —(C=O)$OR^c$, —CN, —(C=O)$R^d$, alkynyl, and —O($C_1$-$C_4$ alkylene)$NR^aR^b$;
$R^1$ is selected from the group consisting of hydrogen, alkyl, and cycloalkyl;
  wherein the alkyl and cycloalkyl are optionally substituted with one or more groups independently selected from the group consisting of halogen, alkoxy, and —$NR^aR^b$;
$R^2$ is selected from the group consisting of halogen, hydroxyl, alkoxy, alkyl, and cycloalkyl;
  wherein the alkyl and cycloalkyl are optionally substituted with one or more halogen;
$R^3$ is selected from the group consisting of alkyl, cycloalkyl, heterocycloalkyl, phenyl, and 5- or 6-membered heteroaryl;
  wherein the alkyl, cycloalkyl, heterocycloalkyl, phenyl, and heteroaryl are optionally substituted with one or more groups independently selected from the group consisting of halogen, hydroxyl, alkyl, haloalkyl, alkoxy, haloalkoxy, hydroxyalkyl, —$NR^aR^b$, —Oaralkyl, —C(=O)Otbutyl, —S(=O)$_{0-2}R^e$, acetyl, aryl, heteroaryl, aralkyl, cycloalkyl, and heterocycloalkyl;
  wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}R^e$, acetyl, azidyl, —$CH_2$azidyl, aryl, and aralkyl;
    wherein the aryl and aralkyl are optionally substituted with one or more groups independently selected from the group consisting of alkyl and alkoxy;
each $R^4$ are independently selected from the group consisting of hydrogen, halogen, alkyl, and cycloalkyl;
  wherein the alkyl and cycloalkyl are optionally substituted with one or more groups independently selected from the group consisting of halogen and hydroxy;
each $R^a$ and $R^b$ are independently selected from the group consisting of hydrogen and alkyl; or $R^a$ and $R^b$ taken together with the nitrogen to which they are attached form a heterocycloalkyl optionally substituted with alkyl;
$R^c$ is selected from the group consisting of hydrogen and alkyl;
$R^d$ is selected from the group consisting of aryl or heteroaryl; wherein the aryl and heteroaryl are optionally substituted with one or more groups independently selected from halogen, alkyl, and alkoxy; and
$R^e$ is selected from the group consisting of alkyl and —$NR^aR^b$.

In some embodiments of a compound of Formula (II), or a pharmaceutically acceptable salt, solvate, tautomer, or N-oxide thereof, $X^1$ is CH; $X^3$ is $CR^4$; and $X^2$ and $X^4$ are N.

In some embodiments of a compound of Formula (II), or a pharmaceutically acceptable salt, solvate, tautomer, or N-oxide thereof, $X^1$ and $X^4$ are CH; and $X^2$ and $X^3$ are N.

In some embodiments of a compound of Formula (II), or a pharmaceutically acceptable salt, solvate, tautomer, or N-oxide thereof, $X^3$ is $CR^4$; $X^2$ is CH; and $X^1$ and $X^4$ are N.

In some embodiments of a compound of Formula (II), or a pharmaceutically acceptable salt, solvate, tautomer, or N-oxide thereof, $X^2$ and $X^4$ are CH; and $X^1$ and $X^3$ are N.

In some embodiments of a compound of Formula (II), or a pharmaceutically acceptable salt, solvate, tautomer, or N-oxide thereof, $X^1$ and $X^4$ are CH; $X^2$ is N; and $X^3$ is $CR^4$.

In some embodiments of a compound of Formula (II), or a pharmaceutically acceptable salt, solvate, tautomer, or N-oxide thereof, the compound of Formula (II) is of Formula (IIa):

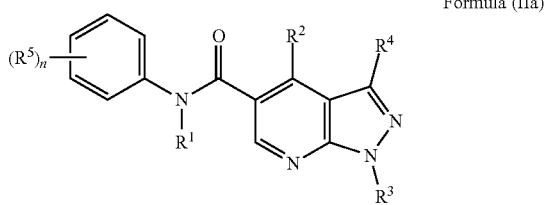

Formula (IIa)

wherein:
$R^1$ is selected from the group consisting of hydrogen, alkyl, and cycloalkyl;
   wherein the alkyl and cycloalkyl are optionally substituted with one or more groups independently selected from the group consisting of halogen, alkoxy, and —$NR^aR^b$;
$R^2$ is selected from the group consisting of halogen, hydroxyl, alkoxy, alkyl, and cycloalkyl;
   wherein the alkyl and cycloalkyl are optionally substituted with one or more halogen;
$R^3$ is selected from the group consisting of alkyl, cycloalkyl, heterocycloalkyl, phenyl, and 5- or 6-membered heteroaryl;
   wherein the alkyl, cycloalkyl, heterocycloalkyl, phenyl, and heteroaryl are optionally substituted with one or more groups independently selected from the group consisting of halogen, hydroxyl, alkyl, haloalkyl, alkoxy, haloalkoxy, hydroxyalkyl, —$NR^aR^b$, —Oaralkyl, —C(=O)Otbutyl, —$S(=O)_{0-2}R^e$, acetyl, aryl, heteroaryl, aralkyl, cycloalkyl, and heterocycloalkyl;
      wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —$S(=O)_{0-2}R^e$, acetyl, azidyl, —$CH_2$azidyl, aryl, and aralkyl;
         wherein the aryl and aralkyl are optionally substituted with one or more groups independently selected from the group consisting of alkyl and alkoxy;
$R^4$ is selected from the group consisting of hydrogen, halogen, alkyl, and cycloalkyl;
   wherein the alkyl and cycloalkyl are optionally substituted with one or more groups independently selected from the group consisting of halogen and hydroxy;

each $R^5$ are independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —C(=O)$OR^c$, —CN, —C(=O)$R^d$, alkynyl, and —O($C_1$-$C_4$ alkylene)$NR^aR^b$;

each $R^a$ and $R^b$ are independently selected from the group consisting of hydrogen and alkyl; or $R^a$ and $R^b$ taken together with the nitrogen to which they are attached form a heterocycloalkyl optionally substituted with alkyl;

$R^c$ is selected from the group consisting of hydrogen and alkyl;

$R^d$ is selected from the group consisting of aryl or heteroaryl; wherein the aryl and heteroaryl are optionally substituted with one or more groups independently selected from halogen, alkyl, and alkoxy;

$R^e$ is selected from the group consisting of alkyl and —$NR^aR^b$; and n is 1, 2, 3, 4, or 5.

In some embodiments of a compound of Formula (IIa), or a pharmaceutically acceptable salt, solvate, tautomer, or N-oxide thereof, $R^3$ is alkyl optionally substituted with one or more groups independently selected from the group consisting of halogen, hydroxyl, haloalkyl, alkoxy, haloalkoxy, hydroxyalkyl, —$NR^aR^b$, —Oaralkyl, acetyl, aryl, heteroaryl, cycloalkyl, and heterocycloalkyl; wherein the aryl, heteroaryl, cycloalkyl, and heterocycloalkyl are optionally substituted with one or more groups independently selected from the group consisting of halogen, alkyl, haloalkyl, alkoxy, haloalkoxy, heteroalkyl, —$S(=O)_{0-2}Re$, acetyl, and aralkyl; wherein the aralkyl is optionally substituted with one or more groups independently selected from the group consisting of alkyl and alkoxy.

In some embodiments of a compound of Formula (IIa), or a pharmaceutically acceptable salt, solvate, tautomer, or N-oxide thereof, $R^3$ is alkyl optionally substituted with one or more groups independently selected from the group consisting of aryl, heteroaryl, and heterocycloalkyl; wherein the aryl, heteroaryl, and heterocycloalkyl are optionally substituted with one or more groups independently selected from the group consisting of halogen, alkyl, haloalkyl, alkoxy, haloalkoxy, and heteroalkyl.

In some embodiments of a compound of Formula (IIa), or a pharmaceutically acceptable salt, solvate, tautomer, or N-oxide thereof, $R^3$ is phenyl optionally substituted with one or more groups independently selected from the group consisting of halogen, hydroxyl, alkyl, haloalkyl, alkoxy, haloalkoxy, hydroxyalkyl, and —$NR^aR^b$.

In some embodiments of a compound of Formula (IIa), or a pharmaceutically acceptable salt, solvate, tautomer, or N-oxide thereof, $R^3$ is heterocycloalkyl optionally substituted with one or more groups independently selected from the group consisting of alkyl, haloalkyl, alkoxy, haloalkoxy, hydroxyalkyl, —C(=O)Otbutyl, —$S(=O)_{0-2}R^e$, acetyl, aryl, and aralkyl; wherein the aralkyl is optionally substituted with one or more groups independently selected from the group consisting of alkylnyl, alkoxy, azidyl, and —$CH_2$azidyl.

In some embodiments of a compound of Formula (IIa), or a pharmaceutically acceptable salt, solvate, tautomer, or N-oxide thereof, $R^3$ is heterocycloalkyl and the heterocycloalkyl is selected from the group consisting of tetrahydro-2H-pyranyl, piperidinyl, 1,1-dioxidotetrahydro-2H-thiopyranyl, and tetrahydro-2H-thiopyranyl.

In some embodiments of a compound of Formula (IIa), or a pharmaceutically acceptable salt, solvate, tautomer, or N-oxide thereof, n is 1.

In some embodiments of a compound of Formula (IIa), or a pharmaceutically acceptable salt, solvate, tautomer, or N-oxide thereof, the compound of Formula (IIa) is of Formula (IIa-1):

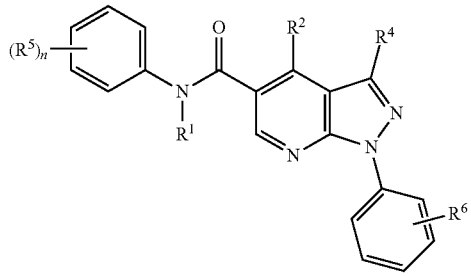

Formula (IIa-1)

wherein:
R$^1$ is selected from the group consisting of hydrogen, alkyl, and cycloalkyl;
  wherein the alkyl and cycloalkyl are optionally substituted with one or more groups independently selected from the group consisting of halogen, alkoxy, and —NR$^a$R$^b$;
R$^2$ is selected from the group consisting of halogen, hydroxyl, alkoxy, alkyl, and cycloalkyl;
  wherein the alkyl and cycloalkyl are optionally substituted with one or more halogen;
R$^4$ is selected from the group consisting of hydrogen, halogen, alkyl, and cycloalkyl;
  wherein the alkyl and cycloalkyl are optionally substituted with one or more groups independently selected from the group consisting of halogen and hydroxyl;
R$^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NR$^a$R$^b$, tetrazoyl, —(C=O)OR$^c$, —CN, —(C=O)R$^d$, alkynyl, and —O(C$_1$-C$_4$ alkylene)NR$^a$R$^b$;
R$^6$ is selected from the group consisting of hydrogen, halogen, hydroxyl, alkyl, haloalkyl, alkoxy, haloalkoxy, hydroxyalkyl, and —NR$^a$R$^b$;
each R$^a$ and R$^b$ are independently selected from the group consisting of hydrogen and alkyl; or R$^a$ and R$^b$ taken together with the nitrogen to which they are attached form a heterocycloalkyl optionally substituted with alkyl;
R$^c$ is selected from the group consisting of hydrogen and alkyl; and
R$^d$ is selected from the group consisting of aryl or heteroaryl; wherein the aryl and heteroaryl are optionally substituted with one or more groups independently selected from halogen, alkyl, and alkoxy.

In some embodiments of a compound of Formula (IIa), or a pharmaceutically acceptable salt, solvate, tautomer, or N-oxide thereof, the compound of Formula (IIa) is of Formula (IIa-2):

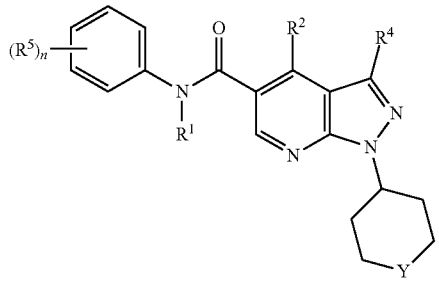

Formula (IIa-2)

wherein:
Y is selected from the group consisting of —O—, —S—, —S(=O)—, —S(=O)$_2$—, —NR$^7$—, and —CH$_2$—;
R$^1$ is selected from the group consisting of hydrogen, alkyl, and cycloalkyl;
  wherein the alkyl and cycloalkyl are optionally substituted with one or more groups independently selected from the group consisting of halogen, alkoxy, and —NR$^a$R$^b$;
R$^2$ is selected from the group consisting of halogen, hydroxyl, alkoxy, alkyl, and cycloalkyl;
  wherein the alkyl and cycloalkyl are optionally substituted with one or more halogen;
R$^4$ is selected from the group consisting of hydrogen, halogen, alkyl, and cycloalkyl;
  wherein the alkyl and cycloalkyl are optionally substituted with one or more groups independently selected from the group consisting of halogen and hydroxyl;
R$^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NR$^a$R$^b$, tetrazoyl, —(C=O)OR$^c$, —CN, —(C=O)R$^d$, alkynyl, and —O(C$_1$-C$_4$ alkylene)NR$^a$R$^b$;
R$^7$ is selected from the group consisting of hydrogen, alkyl, haloalkyl, hydroxyalkyl, —C(=O)Otbutyl, —S(=O)$_{0-2}$R$^e$, acetyl, aryl, heteroaryl, aralkyl, cycloalkyl, and heterocycloalkyl;
  wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}$R$^e$, acetyl, azidyl, —CH$_2$azidyl, aryl, and aralkyl;
    wherein the aryl and aralkyl are optionally substituted with one or more groups independently selected from the group consisting of alkyl and alkoxy;
each R$^a$ and R$^b$ are independently selected from the group consisting of hydrogen and alkyl; or R$^a$ and R$^b$ taken together with the nitrogen to which they are attached form a heterocycloalkyl optionally substituted with alkyl;
R$^c$ is selected from the group consisting of hydrogen and alkyl;
R$^d$ is selected from the group consisting of aryl or heteroaryl; wherein the aryl and heteroaryl are optionally substituted with one or more groups independently selected from halogen, alkyl, and alkoxy; and
R$^e$ is selected from the group consisting of alkyl and —NR$^a$R$^b$.

In some embodiments of a compound of Formula (IIa-2), or a pharmaceutically acceptable salt, solvate, tautomer, or N-oxide thereof, the compound of Formula (IIa-2) is of Formula (IIa-2a):

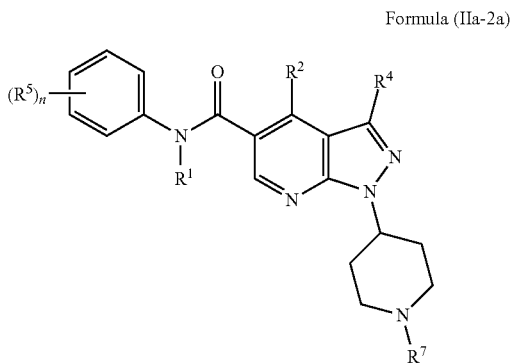

Formula (IIa-2a)

wherein:
R$^1$ is selected from the group consisting of hydrogen, alkyl, and cycloalkyl;
  wherein the alkyl and cycloalkyl are optionally substituted with one or more groups independently selected from the group consisting of halogen, alkoxy, and —NR$^a$R$^b$;
R$^2$ is selected from the group consisting of halogen, hydroxyl, alkoxy, alkyl, and cycloalkyl;
  wherein the alkyl and cycloalkyl are optionally substituted with one or more halogen;
R$^4$ is selected from the group consisting of hydrogen, halogen, alkyl, and cycloalkyl;
  wherein the alkyl and cycloalkyl are optionally substituted with one or more groups independently selected from the group consisting of halogen and hydroxyl;
R$^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NR$^a$R$^b$, tetrazoyl, —(C═O)OR$^c$, —CN, —(C═O)R$^d$, alkynyl, and —O(C$_1$-C$_4$ alkylene)NR$^a$R$^b$;
each R$^a$ and R$^b$ are independently selected from the group consisting of hydrogen and alkyl; or R$^a$ and R$^b$ taken together with the nitrogen to which they are attached form a heterocycloalkyl optionally substituted with alkyl;
R$^7$ is selected from the group consisting of hydrogen, alkyl, haloalkyl, hydroxyalkyl, —C(═O)Otbutyl, —S(═O)$_{0-2}$R$^e$, acetyl, aryl, heteroaryl, aralkyl, cycloalkyl, and heterocycloalkyl;
  wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(═O)$_{0-2}$R$^e$, acetyl, azidyl, —CH$_2$azidyl, aryl, and aralkyl;
    wherein the aryl and aralkyl are optionally substituted with one or more groups independently selected from the group consisting of alkyl and alkoxy;
R$^c$ is selected from the group consisting of hydrogen and alkyl;
R$^d$ is selected from the group consisting of aryl or heteroaryl; wherein the aryl and heteroaryl are optionally substituted with one or more groups independently selected from halogen, alkyl, and alkoxy; and
R$^e$ is selected from the group consisting of alkyl and —NR$^a$R$^b$.

In some embodiments of a compound of Formula (IIa-2a), or a pharmaceutically acceptable salt, solvate, tautomer, or N-oxide thereof, R$^7$ is selected from the group consisting of hydrogen, alkyl, hydroxyalkyl, —C(═O)Otbutyl, —S(═O)$_{0-2}$R$^e$, acetyl, and aralkyl; wherein the aralkyl is optionally substituted with one or more groups independently selected from the group consisting of alkylnyl, azidyl, and —CH$_2$azidyl.

In some embodiments of a compound of Formula (IIa-2a), or a pharmaceutically acceptable salt, solvate, tautomer, or N-oxide thereof, R$^7$ is selected from the group consisting of hydrogen and alkyl.

In some embodiments of a compound of Formula (IIa), or a pharmaceutically acceptable salt, solvate, tautomer, or N-oxide thereof, the compound of Formula (IIa) is of Formula (IIa-3):

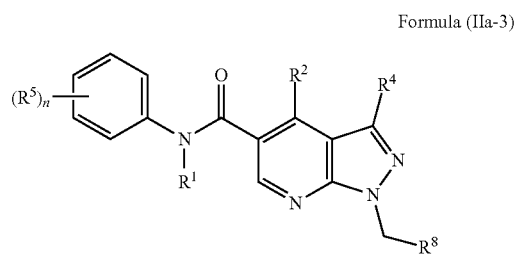

Formula (IIa-3)

wherein:
R$^1$ is selected from the group consisting of hydrogen, alkyl, and cycloalkyl;
  wherein the alkyl and cycloalkyl are optionally substituted with one or more groups independently selected from the group consisting of halogen, alkoxy, and —NR$^a$R$^b$;
R$^2$ is selected from the group consisting of halogen, hydroxyl, alkoxy, alkyl, and cycloalkyl;
  wherein the alkyl and cycloalkyl are optionally substituted with one or more halogen;
R$^4$ is selected from the group consisting of hydrogen, halogen, alkyl, and cycloalkyl;
  wherein the alkyl and cycloalkyl are optionally substituted with one or more groups independently selected from the group consisting of halogen and hydroxyl;
R$^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NR$^a$R$^b$, tetrazoyl, —(C═O)OR$^c$, —CN, —(C═O)R$^d$, alkynyl, and —O(C$_1$-C$_4$ alkylene)NR$^a$R$^b$;
R$^8$ is selected from the group consisting of aryl, heteroaryl, and heterocycloalkyl;
  wherein the aryl, heteroaryl, and heterocycloalkyl are optionally substituted with one or more groups independently selected from the group consisting of halogen, alkyl, haloalkyl, alkoxy, haloalkoxy, heteroalkyl, —S(═O)$_{0-2}$R$^e$, acetyl, and aralkyl;
    wherein the aralkyl is optionally substituted with one or more groups independently selected from the group consisting of alkyl and alkoxy;

each $R^a$ and $R^b$ are independently selected from the group consisting of hydrogen and alkyl; or $R^a$ and $R^b$ taken together with the nitrogen to which they are attached form a heterocycloalkyl optionally substituted with alkyl;

$R^c$ is selected from the group consisting of hydrogen and alkyl;

$R^d$ is selected from the group consisting of aryl or heteroaryl; wherein the aryl and heteroaryl are optionally substituted with one or more groups independently selected from halogen, alkyl, and alkoxy;

$R^e$ is selected from the group consisting of alkyl and —$NR^aR^b$.

In some embodiments of a compound of Formula (IIa-3), or a pharmaceutically acceptable salt, solvate, tautomer, or N-oxide thereof, $R^8$ is heteroaryl optionally substituted with one or more groups independently selected from the group consisting of halogen, alkyl, haloalkyl, alkoxy, haloalkoxy, heteroalkyl, and aralkyl; wherein the aralkyl is optionally substituted with one or more groups independently selected from the group consisting of alkyl and alkoxy.

In some embodiments of a compound of Formula (IIa-3), or a pharmaceutically acceptable salt, solvate, tautomer, or N-oxide thereof, $R^8$ is heteroaryl selected from the group consisting of pyridinyl, pyrimidinyl, pyrazinyl, furanyl, thiophenyl, pyrrolyl, thiazolyl, imidazolyl, triazolyl, tetrazolyl, pyrazolyl, and 4,5,6,7-tetrahydropyrazolo[1,5-a]pyridinyl In some embodiments of a compound of Formula (IIa-1), (IIa-2), (IIa-2a) or (IIa-3), or a pharmaceutically acceptable salt, solvate, tautomer, or N-oxide thereof

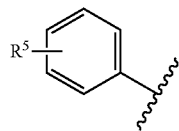

is

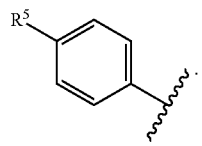

In some embodiments of a compound of Formula (IIa-1), (IIa-2), (IIa-2a) or (IIa-3), or a pharmaceutically acceptable salt, solvate, tautomer, or N-oxide thereof, $R^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, —CN, and alkynyl.

In some embodiments of a compound of Formula (IIa-1), (IIa-2), (IIa-2a) or (IIa-3), or a pharmaceutically acceptable salt, solvate, tautomer, or N-oxide thereof, $R^5$ is selected from the group consisting of halogen, alkyl, haloalkyl, alkoxy, haloalkoxy, and alkynyl.

In some embodiments of a compound of Formula (IIa-1), (IIa-2), (IIa-2a) or (IIa-3), or a pharmaceutically acceptable salt, solvate, tautomer, or N-oxide thereof, $R^5$ is selected from the group consisting of chloro, methyl, isopropyl, methoxy, and ethynyl.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^1$ is selected from the group consisting of hydrogen, methyl, ethyl, —$CH_2CH_2OCH_3$, and —$CH_2CH_2N(CH_3)_2$.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^1$ is hydrogen.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^2$ is selected from the group consisting of chloro, fluoro, hydroxyl, —$CF_3$, methoxy, ethoxy, and methyl.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^2$ is chloro.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^4$ is selected from the group consisting of hydrogen, methyl, ethyl, isopropyl, cyclopropyl, fluoro, chloro, and bromo.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^4$ is selected from the group consisting of hydrogen and methyl.

In another aspect, provided herein is a compound of Formula III, or a pharmaceutically acceptable salt, solvate, tautomer, or N-oxide thereof:

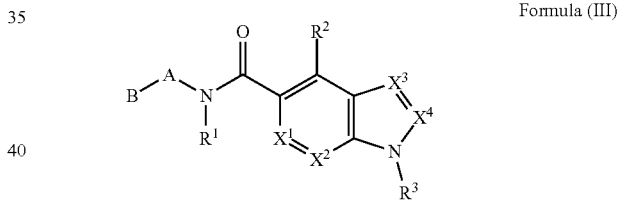

Formula (III)

wherein:
$X^1$-$X^4$ are independently selected from the group consisting of N and $CR^4$.

A is selected from the group consisting of bond, —$CH_2CH_2$—, and —$CH_2CH_2CH_2$—;

B is selected from the group consisting of heterocycloalkyl, phenyl, and 5- or 6-membered heteroaryl;
  wherein the heterocycloalkyl, phenyl, and heteroaryl are optionally substituted with one or more groups independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —(C═O)$OR^c$, —CN, —(C═O)$R^d$, alkynyl, and —O($C_1$-$C_4$ alkylene)$NR^aR^b$;

$R^1$ is selected from the group consisting of hydrogen, alkyl, and cycloalkyl;
  wherein the alkyl and cycloalkyl are optionally substituted with one or more groups independently selected from the group consisting of halogen, alkoxy, and —$NR^aR^b$;

$R^2$ is selected from the group consisting of hydrogen, —CN, —$NR^aR^b$, halogen, hydroxyl, alkoxy, alkyl, and cycloalkyl;

wherein the alkyl and cycloalkyl are optionally substituted with one or more halogen;

$R^3$ is selected from the group consisting of alkyl, cycloalkyl, heterocycloalkyl, phenyl, and 5- or 6-membered heteroaryl;
  wherein the alkyl, cycloalkyl, heterocycloalkyl, phenyl, and heteroaryl are optionally substituted with one or more groups independently selected from the group consisting of halogen, hydroxyl, alkyl, haloalkyl, alkoxy, haloalkoxy, hydroxyalkyl, —$NR^aR^b$, —Oaralkyl, —C(=O)Otbutyl, —$S(=O)_{0-2}R^e$, acetyl, aryl, heteroaryl, aralkyl, cycloalkyl, and heterocycloalkyl;
    wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —$S(=O)_{0-2}R^e$, acetyl, azidyl, —$CH_2$azidyl, aryl, and aralkyl;
      wherein the aryl and aralkyl are optionally substituted with one or more groups independently selected from the group consisting of alkyl and alkoxy;

each $R^4$ are independently selected from the group consisting of hydrogen, halogen, alkyl, and cycloalkyl;
  wherein the alkyl and cycloalkyl are optionally substituted with one or more groups independently selected from the group consisting of halogen and hydroxyl;

each $R^a$ and $R^b$ are independently selected from the group consisting of hydrogen and alkyl; or $R^a$ and $R^b$ taken together with the nitrogen to which they are attached form a heterocycloalkyl optionally substituted with alkyl;

$R^c$ is selected from the group consisting of hydrogen and alkyl;

$R^d$ is selected from the group consisting of aryl or heteroaryl; wherein the aryl and heteroaryl are optionally substituted with one or more groups independently selected from halogen, alkyl, and alkoxy;

$R^e$ is selected from the group consisting of alkyl and —$NR^aR^b$.

In some embodiments of a compound of Formula (III), or a pharmaceutically acceptable salt, solvate, tautomer, or N-oxide thereof, $X^1$ is CH; $X^3$ is $CR^4$; and $X^2$ and $X^4$ are N.

In some embodiments of a compound of Formula (III), or a pharmaceutically acceptable salt, solvate, tautomer, or N-oxide thereof, $X^1$ and $X^4$ are CH; and $X^2$ and $X^3$ are N.

In some embodiments of a compound of Formula (III), or a pharmaceutically acceptable salt, solvate, tautomer, or N-oxide thereof, $X^3$ is $CR^4$; $X^2$ is CH; and $X^1$ and $X^4$ are N.

In some embodiments of a compound of Formula (III), or a pharmaceutically acceptable salt, solvate, tautomer, or N-oxide thereof, $X^2$ and $X^4$ are CH; and $X^1$ and $X^3$ are N.

In some embodiments of a compound of Formula (III), or a pharmaceutically acceptable salt, solvate, tautomer, or N-oxide thereof, $X^1$ and $X^4$ are CH; $X^2$ is N; and $X^3$ is $CR^4$.

In some embodiments of a compound of Formula (III), or a pharmaceutically acceptable salt, solvate, tautomer, or N-oxide thereof, the compound of Formula (III) is of Formula (IIIa):

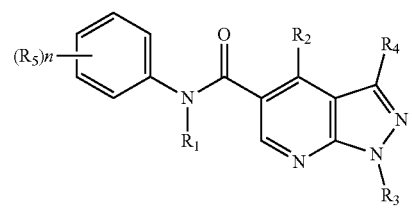

Formula (IIIa)

wherein:
$R^1$ is selected from the group consisting of hydrogen, alkyl, and cycloalkyl;
  wherein the alkyl and cycloalkyl are optionally substituted with one or more groups independently selected from the group consisting of halogen, alkoxy, and —$NR^aR^b$;

$R^2$ is selected from the group consisting of hydrogen, —CN, —$NR^aR^b$, halogen, hydroxyl, alkoxy, alkyl, and cycloalkyl;
  wherein the alkyl and cycloalkyl are optionally substituted with one or more halogen;

$R^3$ is selected from the group consisting of alkyl, cycloalkyl, heterocycloalkyl, phenyl, and 5- or 6-membered heteroaryl;
  wherein the alkyl, cycloalkyl, heterocycloalkyl, phenyl, and heteroaryl are optionally substituted with one or more groups independently selected from the group consisting of halogen, hydroxyl, alkyl, haloalkyl, alkoxy, haloalkoxy, hydroxyalkyl, —$NR^aR^b$, —Oaralkyl, —C(=O)Otbutyl, —$S(=O)_{0-2}R^e$, acetyl, aryl, heteroaryl, aralkyl, cycloalkyl, and heterocycloalkyl;
    wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —$S(=O)_{0-2}R^e$, acetyl, azidyl, —$CH_2$azidyl, aryl, and aralkyl;
      wherein the aryl and aralkyl are optionally substituted with one or more groups independently selected from the group consisting of alkyl and alkoxy;

$R^4$ is selected from the group consisting of hydrogen, halogen, alkyl, and cycloalkyl;
  wherein the alkyl and cycloalkyl are optionally substituted with one or more groups independently selected from the group consisting of halogen and hydroxyl;

each $R^5$ are independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —C(=O)$OR^c$, —CN, —C(=O)$R^d$, alkynyl, and —O($C_1$-$C_4$ alkylene)$NR^aR^b$;

each $R^a$ and $R^b$ are independently selected from the group consisting of hydrogen and alkyl; or $R^a$ and $R^b$ taken together with the nitrogen to which they are attached form a heterocycloalkyl optionally substituted with alkyl;

$R^c$ is selected from the group consisting of hydrogen and alkyl;

$R^d$ is selected from the group consisting of aryl or heteroaryl; wherein the aryl and heteroaryl are optionally substituted with one or more groups independently selected from halogen, alkyl, and alkoxy;

$R^e$ is selected from the group consisting of alkyl and —$NR^aR^b$; and n is 1, 2, 3, 4, or 5.

In some embodiments of a compound of Formula (IIIa), or a pharmaceutically acceptable salt, solvate, tautomer, or N-oxide thereof, $R^3$ is alkyl optionally substituted with one or more groups independently selected from the group consisting of halogen, hydroxyl, haloalkyl, alkoxy, haloalkoxy, hydroxyalkyl, —$NR^aR^b$, —Oaralkyl, acetyl, aryl, heteroaryl, cycloalkyl, and heterocycloalkyl; wherein the aryl, heteroaryl, cycloalkyl, and heterocycloalkyl are optionally substituted with one or more groups independently selected from the group consisting of halogen, alkyl, haloalkyl, alkoxy, haloalkoxy, heteroalkyl, —$S(=O)_{0-2}R^e$, acetyl, and aralkyl; wherein the aralkyl is optionally substituted with one or more groups independently selected from the group consisting of alkyl and alkoxy.

In some embodiments of a compound of Formula (IIIa), or a pharmaceutically acceptable salt, solvate, tautomer, or N-oxide thereof, $R^3$ is alkyl optionally substituted with one or more groups independently selected from the group consisting of aryl, heteroaryl, and heterocycloalkyl; wherein the aryl, heteroaryl, and heterocycloalkyl are optionally substituted with one or more groups independently selected from the group consisting of halogen, alkyl, haloalkyl, alkoxy, haloalkoxy, and heteroalkyl.

In some embodiments of a compound of Formula (IIIa), or a pharmaceutically acceptable salt, solvate, tautomer, or N-oxide thereof, $R^3$ is phenyl optionally substituted with one or more groups independently selected from the group consisting of halogen, alkyl, hydroxyl, haloalkyl, alkoxy, haloalkoxy, hydroxyalkyl, and —$NR^aR^b$.

In some embodiments of a compound of Formula (IIIa), or a pharmaceutically acceptable salt, solvate, tautomer, or N-oxide thereof, $R^3$ is heterocycloalkyl optionally substituted with one or more groups independently selected from the group consisting of alkyl, haloalkyl, alkoxy, haloalkoxy, hydroxyalkyl, —C(=O)Otbutyl, —$S(=O)_{0-2}R^e$, acetyl, aryl, and aralkyl; wherein the aralkyl is optionally substituted with one or more groups independently selected from the group consisting of alkylnyl, alkoxy, azidyl, and —$CH_2$azidyl.

In some embodiments of a compound of Formula (IIIa), or a pharmaceutically acceptable salt, solvate, tautomer, or N-oxide thereof, $R^3$ is heterocycloalkyl and the heterocycloalkyl is selected from the group consisting of tetrahydro-2H-pyranyl, piperidinyl, 1,1-dioxidotetrahydro-2H-thiopyranyl, and tetrahydro-2H-thiopyranyl.

In some embodiments of a compound of Formula (IIIa), or a pharmaceutically acceptable salt, solvate, tautomer, or N-oxide thereof, n is 1.

In some embodiments of a compound of Formula (IIIa), or a pharmaceutically acceptable salt, solvate, tautomer, or N-oxide thereof, is

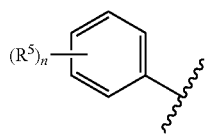

is

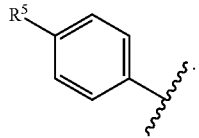

In some embodiments of a compound of Formula (IIIa), or a pharmaceutically acceptable salt, solvate, tautomer, or N-oxide thereof, $R^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, —CN, and alkynyl.

In some embodiments of a compound of Formula (IIIa), or a pharmaceutically acceptable salt, solvate, tautomer, or N-oxide thereof, $R^5$ is selected from the group consisting of halogen, alkyl, haloalkyl, alkoxy, haloalkoxy, and alkynyl.

In some embodiments of a compound of Formula (IIIa), or a pharmaceutically acceptable salt, solvate, tautomer, or N-oxide thereof, $R^5$ is selected from the group consisting of chloro, methyl, isopropyl, methoxy, and ethynyl.

In some embodiments of a compound of Formula (IIIa), or a pharmaceutically acceptable salt, solvate, tautomer, or N-oxide thereof, $R^1$ is selected from the group consisting of hydrogen, methyl, ethyl, —$CH_2CH_2OCH_3$, and —$CH_2CH_2N(CH_3)_2$.

In some embodiments of a compound of Formula (IIIa), or a pharmaceutically acceptable salt, solvate, tautomer, or N-oxide thereof, $R^1$ is hydrogen.

In some embodiments of a compound of Formula (IIIa), or a pharmaceutically acceptable salt, solvate, tautomer, or N-oxide thereof, $R^2$ is selected from the group consisting of hydrogen, —CN, and —$NR^aR^b$.

In some embodiments of a compound of Formula (IIIa), or a pharmaceutically acceptable salt, solvate, tautomer, or N-oxide thereof, $R^4$ is selected from the group consisting of hydrogen, methyl, ethyl, isopropyl, cyclopropyl, fluoro, chloro, and bromo.

In some embodiments of a compound of Formula (IIIa), or a pharmaceutically acceptable salt, solvate, tautomer, or N-oxide thereof, $R^4$ is selected from the group consisting of hydrogen and methyl.

Another aspect provides a pharmaceutical composition comprising a compound disclosed herein, or a pharmaceutically acceptable salt, solvate, tautomer, or N-oxide thereof, and a pharmaceutically acceptable excipient.

Another aspect provides a method of treating a disease in a subject mediated by glucocorticoid receptor, wherein the method comprises administering to the subject a compound disclosed herein, or a pharmaceutically acceptable salt, solvate, tautomer, or N-oxide thereof.

Another aspect provides a method of treating a disease in a subject mediated by glucocorticoid receptor, wherein the method comprises administering to the subject a pharmaceutical composition disclosed herein.

In some embodiments of a method of treating a disease in a subject, the disease involves dysfunction of the hypothalamic-pituitary-adrenal (HPA) axis.

In some embodiments of a method of treating a disease involving dysfunction of the hypothalamic-pituitary-adrenal (HPA) axis in a subject, the disease involving dysfunction of the hypothalamic-pituitary-adrenal (HPA) axis is selected from metabolic diseases (Cushing's syndrome, obesity, type 2 diabetes, AAPD induced weight gain), neuropsychiatric diseases (bipolar disorder, post-traumatic stress disorder, major depression, dysthemia, seasonal affective disorder, sleep disorders, or other stress disorders), cardiovascular disease and osteoporosis.

In some embodiments of a method of treating a disease in a subject with a compound disclosed herein, or a pharmaceutically acceptable salt, solvate, tautomer, or N-oxide thereof, or a pharmaceutical composition disclosed herein, the disease is cancer.

In some embodiments of a method of treating cancer in a subject with a compound disclosed herein, or a pharmaceutically acceptable salt, solvate, tautomer, or N-oxide thereof, or a pharmaceutical composition disclosed herein, the cancer is prostate cancer. In some embodiments of a method of treating prostate cancer in a subject with a compound disclosed herein, or a pharmaceutically acceptable salt, solvate, tautomer, or N-oxide thereof, or a pharmaceutical composition disclosed herein, the prostate cancer is a drug resistant prostate cancer.

In some embodiments of a method of treating cancer in a subject with a compound disclosed herein, or a pharmaceutically acceptable salt, solvate, tautomer, or N-oxide thereof, or a pharmaceutical composition disclosed herein, the cancer is breast cancer. In some embodiments of a method of treating breast cancer in a subject with a compound disclosed herein, or a pharmaceutically acceptable salt, solvate, tautomer, or N-oxide thereof, or a pharmaceutical composition disclosed herein, the breast cancer is a drug resistant breast cancer.

In some embodiments of a method of treating cancer in a subject with a compound disclosed herein, or a pharmaceutically acceptable salt, solvate, tautomer, or N-oxide thereof, or a pharmaceutical composition disclosed herein, the cancer is ovarian cancer. In some embodiments of a method of treating ovarian cancer in a subject with a compound disclosed herein, or a pharmaceutically acceptable salt, solvate, tautomer, or N-oxide thereof, or a pharmaceutical composition disclosed herein, the ovarian cancer is a drug resistant ovarian cancer.

In some embodiments of a method of treating a disease in a subject, the compound disclosed herein, or a pharmaceutically acceptable salt, solvate, tautomer, or N-oxide thereof, or the pharmaceutical composition disclosed herein is used in combination with a glucocorticoid agonist to treat inflammatory and autoimmune diseases.

In some embodiments of a method of treating a disease in a subject, with a compound disclosed herein, or a pharmaceutically acceptable salt, solvate, tautomer, or N-oxide thereof, or a pharmaceutical composition disclosed herein used in combination with a glucocorticoid agonist to treat inflammatory and autoimmune diseases selected from rheumatoid arthritis, asthma, Crohn's disease, ulcerative colitis, inflammatory bowel disease, and multiple sclerosis.

DETAILED DESCRIPTION OF THE INVENTION

The glucocorticoid receptor (GR) is a member of the nuclear receptor (NR) superfamily of ligand activated transcription factors. Activation of GR leads to either positive regulation of gene expression (via the trans-activation pathway) or negative regulation (via the trans-repression pathway). GR agonists have found great utility as therapeutic agents, primarily as anti-inflammatory agents (e.g., dexamethasone). In contrast, the therapeutic potential of antagonism of the GR receptor remains largely unexploited despite a strong therapeutic rationale in a wide range of disease states, including for example, metabolic diseases, neuropsychiatric disorders, cancer, and inflammation.

This disclosure is directed to glucocorticoid receptor modulators. In some embodiments the compounds described herein are glucocorticoid receptor translocation inhibitors. For example, provided herein are compounds that are glucocorticoid receptor antagonists. In some embodiments, the glucocorticoid receptor antagonism is passive antagonism. In some embodiments, the glucocorticoid receptor antagonism is active antagonism.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising " (and related terms such as "comprise" or "comprises" or "having" or "including ") is not intended to exclude that which in other certain embodiments, for example, an embodiment of any composition of matter, composition, method, or process, or the like, described herein, "consist of "or "consist essentially of "the described features.

Definitions

As used in the specification and appended claims, unless specified to the contrary, the following terms have the meaning indicated below.

"Amino" refers to the —NH$_2$ radical.
"Cyano" or "nitrile" refers to the —CN radical.
"Hydroxy" or "hydroxyl" refers to the —OH radical.
"Nitro" refers to the —NO$_2$ radical.
"Oxo" refers to the =O substituent.
"Oxime" refers to the =N—OH substituent.
"Thioxo" refers to the =S substituent.
"Alkyl" refers to a linear or branched hydrocarbon chain radical, which is fully saturated, has from one to thirty carbon atoms, and is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl, $C_4$-$C_8$ alkyl, and $C_5$-$C_{12}$ alkyl. Representative alkyl groups include, but are not limited to, methyl, ethyl, n-propyl, 1-methylethyl (isopropyl), n-butyl, i-butyl, s-butyl, n-pentyl, 1,1-dimethylethyl (t-butyl), 2-ethylpropyl, and the like. Representative linear alkyl groups include, but are not limited to, methyl, ethyl, n-propyl, n-butyl, n-pentyl and the like. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each R$^f$ is independently alkyl, fluoroalkyl, cycloalkyl, cycloalkylalkyl, aryl, aralkyl, heterocycloalkyl, heterocycloalkylalkyl, heteroaryl or heteroarylalkyl.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In certain embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each R$^f$ is independently alkyl, fluoroalkyl, cycloalkyl, cycloalkylalkyl, aryl, aralkyl, heterocycloalkyl, heterocycloalkylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In certain embodiments, an alkynyl comprises two to six carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each R$^f$ is independently alkyl, fluoroalkyl, cycloalkyl, cycloalkylalkyl, aryl, aralkyl, heterocycloalkyl, heterocycloalkylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each R$^f$ is independently alkyl, fluoroalkyl, cycloalkyl, cycloalkylalkyl, aryl, aralkyl, heterocycloalkyl, heterocycloalkylalkyl, heteroaryl or heteroarylalkyl.

"Aminoalkyl" refers to a radical of the formula —R$^c$—N(R$^a$)$_2$ or —R$^c$—N(R$^a$)—R$^c$, where each R$^c$ is independently an alkylene chain as defined above, for example, methylene, ethylene, and the like; and each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Alkoxy" refers to a radical of the formula —OR$^a$ where R$^a$ is an alkyl radical as defined. Unless stated otherwise specifically in the specification, an alkoxy group may be optionally substituted as described above for alkyl.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted by one or more of the following substituents: alkyl, alkenyl, alkynyl, halo, fluoroalkyl, cyano, nitro, aryl, aralkyl, aralkenyl, aralkynyl, cycloalkyl, cycloalkylalkyl, heterocycloalkyl, heterocycloalkylalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2), and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocycloalkyl (optionally substituted with one or more alkyl groups), heterocycloalkylalkyl, heteroaryl or heteroarylalkyl, or two $R^a$ attached to the same nitrogen atom are combined to form a heterocycloalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain "Cycloalkyl" or "carbocycle" refers to a stable, non-aromatic, monocyclic or polycyclic carbocyclic ring, which may include fused (when fused with an aryl or a heteroaryl ring, the cycloalkyl is bonded through a non-aromatic ring atom) or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, the cycloalkyl is optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^e$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Cycloalkylalkyl" refers to a radical of the formula —$R^e$-cycloalkyl where $R^e$ is an alkylene chain as defined above. The alkylene chain and the cycloalkyl radical are optionally substituted as defined above.

"Fused" refers to any ring structure described herein which is fused to an existing ring structure. When the fused ring is a heretocycloalkyl ring or a heteroaryl ring, any carbon atom on the existing ring structure which becomes part of the fused heretocycloalkyl ring or the fused heteroaryl ring may be replaced with a nitrogen atom.

"Heteroalkyl" refers to a straight or branched hydrocarbon chain alkyl radical containing no unsaturation, having from one to fifteen carbon atoms (e.g., $C_1$-$C_{15}$ alkyl) consisting of carbon and hydrogen atoms and one or two heteroatoms selected from O, N, and S, wherein the nitrogen or sulfur atoms may be optionally oxidized and the nitrogen atom may be quaternized. The heteroatom(s) may be placed at any position of the heteroalkyl group including between the rest of the heteroalkyl group and the fragment to which it is attached. The heteroalkyl is attached to the rest of the molecule by a single bond. Unless stated otherwise specifically in the specification, a heteroalkyl group is optionally substituted by one or more of the following substituents: halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)$OR^a$, —C(O)N($R^a$)$_2$, —N($R^a$)C(O)$OR^f$, —OC(O)—NR$^a$R$^f$, —N($R^a$)C(O)$R^f$, —N($R^a$)S(O)$_t$$R^f$ (where t is 1 or 2), —S(O)$_t$$OR^a$ (where t is 1 or 2), —S(O)$_t$$R^f$ (where t is 1 or 2) and —S(O)$_t$N($R^a$)$_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl.

"Halo" or "halogen" refers to bromo, chloro, fluoro or iodo. In some embodiments, halogen refers to chloro or fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —ORa where Ra is a haloalkyl radical as defined. Unless stated otherwise specifically in the specification, a haloalkoxy group may be optionally substituted as described below.

"Heterocycloalkyl" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized; and the heterocycloalkyl radical may be partially or fully saturated. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, 2-oxo-1,3-dioxol-4-yl, 1,1-dioxidotetrahydro-2H-thiopyranyl, tetrahydro-2H-thiopyranyl, and tetrahydro-2H-pyranyl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group is optionally substituted by one or more of the following substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and is a straight or branched alkylene or alkenylene chain, and where each of the above substituents is unsubstituted unless otherwise indicated.

"Heterocycloalkyllalkyl" refers to a radical of the formula $-R^c$-heterocycloalkyl where $R^c$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylslkyl radical is optionally substituted as defined above for an alkylene chain. The heterocycloalkyl part of the heterocycloalkylalkyl radical is optionally substituted as defined above for a heterocycloalkyl group.

"heterocycloalkylalkoxy" refers to a radical bonded through an oxygen atom of the formula $-O-R^c$-heterocycloalkyl where $R^c$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkoxy radical is optionally substituted as defined above for an alkylene chain The heterocycloalkyl part of the heterocycloalkylalkoxy radical is optionally substituted as defined above for a heterocycloalkyl group.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. In some embodiments, the heteroaryl is a 5-membered heteroaryl. In some embodiments, the heteroaryl is a 6-membered heteroaryl. For purposes of this invention, the heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted by one or more of the following substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para- isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

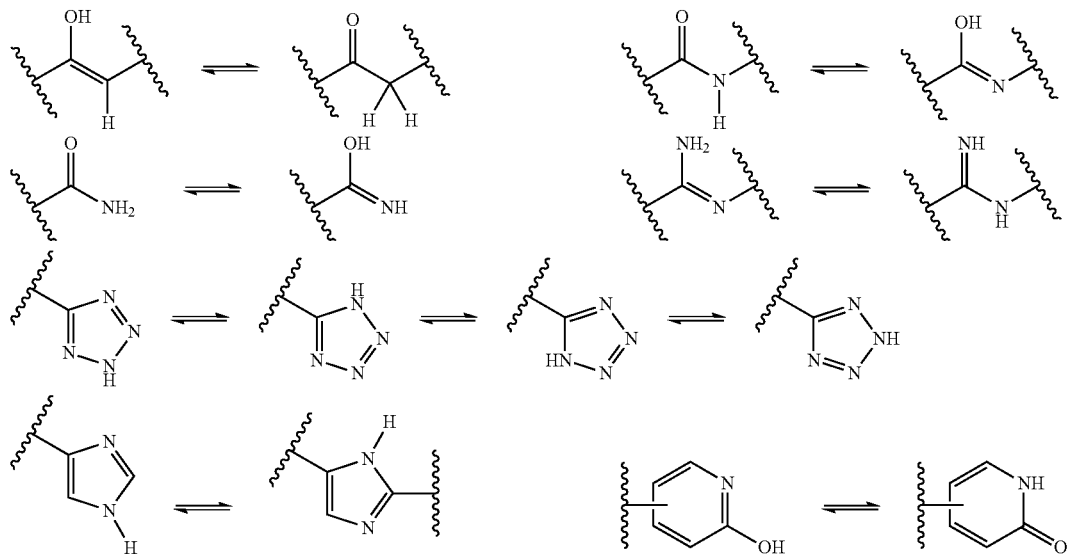

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution. "Optionally substituted" and "substituted or unsubstituted" and "unsubstituted or substituted" are used interchangeably herein.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating " or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has been made.

As used herein, "modulating a glucocorticoid receptor" refers to methods for adjusting the response of a glucocorticoid receptor towards glucocorticoids, glucocorticoid antagonists, agonists, and partial agonists. The methods include directly or indirectly contacting a glucocorticoid receptor with an effective amount of either an antagonist, an agonist, or a partial agonist and detecting a change in GR activity.

As used herein, "Glucocorticoid receptor" ("GR") refers to a family of intracellular receptors which specifically bind to cortisol and/or cortisol analogs (e.g. dexamethasone). The glucocorticoid receptor is also referred to as the cortisol receptor. The term includes isoforms of GR, recombinant GR and mutated GR.

As used herein, "Glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," we intend the drug to preferentially bind to the GR rather than other nuclear receptors, such as mineralocorticoid receptor (MR) or progesterone receptor (PR).

As used herein, "GR modulator" refers to compounds that agonize and/or antagonize the glucocorticoid receptor.

Compounds

Compounds described herein which are modulators of glucocorticoid receptor (GR) translocation. These compounds, and compositions comprising these compounds, are useful for the treatment of metabolic disease, neuropsychiatric disorders, cancer, and inflammation.

One aspect provides a compound of Formula I, or a pharmaceutically acceptable salt, polymorph, solvate, tautomer, or N-oxide thereof:

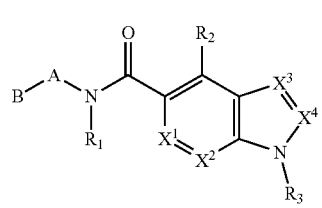

Formula (I)

wherein:
$X^1$-$X^4$ are independently selected from the group consisting of N and $CR^4$.

A is selected from the group consisting of bond, —$CH_2$—, and —$CH_2CH_2$—;

B is selected from the group consisting of optionally substituted alkyl, optionally substituted cycloalkyl, optionally substituted heterocycloalkyl, optionally substituted phenyl, and optionally substituted 5- or 6-membered heteroaryl;

$R^1$ is independently selected from the group consisting of hydrogen, optionally substituted alkyl, and optionally substituted cycloalkyl;

$R^2$ is independently selected from the group consisting of halogen, hydroxyl, alkoxy, alkyl, optionally substituted alkyl, and optionally substituted cycloalkyl;

R³ is independently selected from the group consisting of optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl; and R⁴ is independently selected from the group consisting of hydrogen, halogen, optionally substituted alkyl, and optionally substituted cycloalkyl.

Another aspect provides a compound of Formula (II), or a pharmaceutically acceptable salt, solvate, tautomer, or N-oxide thereof:

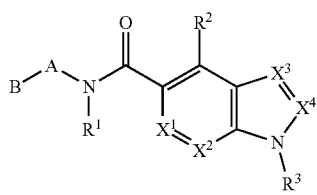

Formula (II)

wherein:
- X¹-X⁴ are independently selected from the group consisting of N and CR⁴.
- A is selected from the group consisting of bond and —CH₂CH₂—;
- B is selected from the group consisting of heterocycloalkyl, phenyl, and 5- or 6-membered heteroaryl;
  - wherein the heterocycloalkyl, phenyl, and heteroaryl are optionally substituted with one or more groups independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NRᵃRᵇ, tetrazoyl, —(C═O)ORᶜ, —CN, —(C═O)Rᵈ, alkynyl, and —O(C₁-C₄ alkylene)NRᵃRᵇ;
- R¹ is selected from the group consisting of hydrogen, alkyl, and cycloalkyl;
  - wherein the alkyl and cycloalkyl are optionally substituted with one or more groups independently selected from the group consisting of halogen, alkoxy, and —NRᵃRᵇ;
- R² is selected from the group consisting of halogen, hydroxyl, alkoxy, alkyl, and cycloalkyl;
  - wherein the alkyl and cycloalkyl are optionally substituted with one or more halogen;
- R³ is selected from the group consisting of alkyl, cycloalkyl, heterocycloalkyl, phenyl, and 5- or 6-membered heteroaryl;
  - wherein the alkyl, cycloalkyl, heterocycloalkyl, phenyl, and heteroaryl are optionally substituted with one or more groups independently selected from the group consisting of halogen, hydroxyl, alkyl, haloalkyl, alkoxy, haloalkoxy, hydroxyalkyl, —NRᵃRᵇ, —Oaralkyl, —C(═O)Otbutyl, —S(═O)₀₋₂Rᵉ, acetyl, aryl, heteroaryl, aralkyl, cycloalkyl, and heterocycloalkyl;
    - wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(═O)₀₋₂Rᵉ, acetyl, azidyl, —CH₂azidyl, aryl, and aralkyl;
      - wherein the aryl and aralkyl are optionally substituted with one or more groups independently selected from the group consisting of alkyl and alkoxy;
- each R⁴ are independently selected from the group consisting of hydrogen, halogen, alkyl, and cycloalkyl;
  - wherein the alkyl and cycloalkyl are optionally substituted with one or more groups independently selected from the group consisting of halogen and hydroxy;
- each Rᵃ and Rᵇ are independently selected from the group consisting of hydrogen and alkyl; or Rᵃ and Rᵇ taken together with the nitrogen to which they are attached form a heterocycloalkyl optionally substituted with alkyl;
- Rᶜ is selected from the group consisting of hydrogen and alkyl;
- Rᵈ is selected from the group consisting of aryl or heteroaryl; wherein the aryl and heteroaryl are optionally substituted with one or more groups independently selected from halogen, alkyl, and alkoxy;
- Rᵉ is selected from the group consisting of alkyl and —NRᵃRᵇ.

In some embodiments of a compound of Formula (II), or a pharmaceutically acceptable salt, solvate, tautomer, or N-oxide thereof, A is a bond.

In some embodiments of a compound of Formula (II), or a pharmaceutically acceptable salt, solvate, tautomer, or N-oxide thereof, B is phenyl optionally substituted with one or more groups independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NRᵃRᵇ, tetrazoyl, —(C═O)ORᶜ, —CN, —(C═O)Rᵈ, alkynyl, and —O(C₁-C₄ alkylene)NRᵃRᵇ.

In some embodiments of a compound of Formula (II), or a pharmaceutically acceptable salt, solvate, tautomer, or N-oxide thereof, B is phenyl substituted with one or more groups independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NRᵃRᵇ, tetrazoyl, —(C═O)ORᶜ, —CN, —(C═O)Rᵈ, alkynyl, and —O(C₁-C₄ alkylene)NRᵃRᵇ.

In some embodiments of a compound of Formula (II), or a pharmaceutically acceptable salt, solvate, tautomer, or N-oxide thereof, X¹ is CH; X³ is CR⁴; and X² and X⁴ are N.

In some embodiments of a compound of Formula (II), or a pharmaceutically acceptable salt, solvate, tautomer, or N-oxide thereof, X¹ and X⁴ are CH; and X² and X³ are N.

In some embodiments of a compound of Formula (II), or a pharmaceutically acceptable salt, solvate, tautomer, or N-oxide thereof, X³ is CR⁴; X² is CH; and X¹ and X⁴ are N.

In some embodiments of a compound of Formula (II), or a pharmaceutically acceptable salt, solvate, tautomer, or N-oxide thereof, X² and X⁴ are CH; and X¹ and X³ are N.

In some embodiments of a compound of Formula (II), or a pharmaceutically acceptable salt, solvate, tautomer, or N-oxide thereof, X¹ and X⁴ are CH; X² is N; and X³ is CR⁴.

In some embodiments of a compound of Formula (II), or a pharmaceutically acceptable salt, solvate, tautomer, or N-oxide thereof, the compound of Formula (II) is of Formula (IIa):

Formula (IIa)

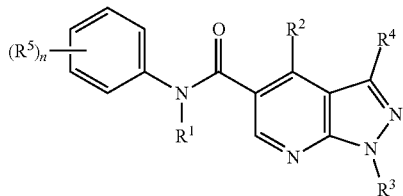

wherein:
R¹ is selected from the group consisting of hydrogen, alkyl, and cycloalkyl;
  wherein the alkyl and cycloalkyl are optionally substituted with one or more groups independently selected from the group consisting of halogen, alkoxy, and —NR$^a$R$^b$;
R² is selected from the group consisting of halogen, hydroxyl, alkoxy, alkyl, and cycloalkyl;
  wherein the alkyl and cycloalkyl are optionally substituted with one or more halogen;
R³ is selected from the group consisting of alkyl, cycloalkyl, heterocycloalkyl, phenyl, and 5- or 6-membered heteroaryl;
  wherein the alkyl, cycloalkyl, heterocycloalkyl, phenyl, and heteroaryl are optionally substituted with one or more groups independently selected from the group consisting of halogen, hydroxyl, alkyl, haloalkyl, alkoxy, haloalkoxy, hydroxyalkyl, —NR$^a$R$^b$, —Oaralkyl, —C(=O)Otbutyl, —S(=O)$_{0-2}$R$^e$, acetyl, aryl, heteroaryl, aralkyl, cycloalkyl, and heterocycloalkyl;
    wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}$R$^e$, acetyl, azidyl, —CH$_2$azidyl, aryl, and aralkyl;
      wherein the aryl and aralkyl are optionally substituted with one or more groups independently selected from the group consisting of alkyl and alkoxy;
R⁴ is selected from the group consisting of hydrogen, halogen, alkyl, and cycloalkyl;
  wherein the alkyl and cycloalkyl are optionally substituted with one or more groups independently selected from the group consisting of halogen and hydroxy;
each R⁵ are independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NR$^a$R$^b$, tetrazoyl, —(C=O)OR$^c$, —CN, —(C=O)R$^d$, alkynyl, and —O(C$_1$-C$_4$ alkylene)NR$^a$R$^b$;
each R$^a$ and R$^b$ are independently selected from the group consisting of hydrogen and alkyl; or R$^a$ and R$^b$ taken together with the nitrogen to which they are attached form a heterocycloalkyl optionally substituted with alkyl;
R$^c$ is selected from the group consisting of hydrogen and alkyl;
R$^d$ is selected from the group consisting of aryl or heteroaryl; wherein the aryl and heteroaryl are optionally substituted with one or more groups independently selected from halogen, alkyl, and alkoxy;
R$^e$ is selected from the group consisting of alkyl and —NR$^a$R$^b$; and
n is 1, 2, 3, 4, or 5.

In some embodiments of a compound of Formula (IIa), or a pharmaceutically acceptable salt, solvate, tautomer, or N-oxide thereof, R³ is alkyl optionally substituted with one or more groups independently selected from the group consisting of halogen, hydroxyl, haloalkyl, alkoxy, haloalkoxy, hydroxyalkyl, —NR$^a$R$^b$, —Oaralkyl, acetyl, aryl, heteroaryl, cycloalkyl, and heterocycloalkyl; wherein the aryl, heteroaryl, cycloalkyl, and heterocycloalkyl are optionally substituted with one or more groups independently selected from the group consisting of halogen, alkyl, haloalkyl, alkoxy, haloalkoxy, heteroalkyl, —S(=O)$_{0-2}$R$^e$, acetyl, and aralkyl; wherein the aralkyl is optionally substituted with one or more groups independently selected from the group consisting of alkyl and alkoxy.

In some embodiments of a compound of Formula (IIa), or a pharmaceutically acceptable salt, solvate, tautomer, or N-oxide thereof, R³ is alkyl substituted with one or more groups independently selected from the group consisting of halogen, hydroxyl, haloalkyl, alkoxy, haloalkoxy, hydroxyalkyl, and —NR$^a$R$^b$. In some embodiments of a compound of Formula (IIa), or a pharmaceutically acceptable salt, solvate, tautomer, or N-oxide thereof, R³ is alkyl substituted with one or more groups independently selected from the group consisting of hydroxyl, alkoxy, and —NR$^a$R$^b$.

In some embodiments of a compound of Formula (IIa), or a pharmaceutically acceptable salt, solvate, tautomer, or N-oxide thereof, R³ is alkyl substituted with one or more groups independently selected from the group consisting of aryl, heteroaryl, and heterocycloalkyl; wherein the aryl, heteroaryl, and heterocycloalkyl are optionally substituted with one or more groups independently selected from the group consisting of halogen, alkyl, haloalkyl, alkoxy, haloalkoxy, and heteroalkyl.

In some embodiments of a compound of Formula (IIa), or a pharmaceutically acceptable salt, solvate, tautomer, or N-oxide thereof, R³ is alkyl substituted with heteroaryl; wherein the heteroaryl is optionally substituted with one or more groups independently selected from the group consisting of halogen, alkyl, haloalkyl, alkoxy, haloalkoxy, and heteroalkyl. In some embodiments of a compound of Formula (IIa), or a pharmaceutically acceptable salt, solvate, tautomer, or N-oxide thereof, R³ is alkyl substituted with heteroaryl; wherein the heteroaryl is selected from the group consisting of pyridinyl, pyrimidinyl, pyrazinyl, furanyl, thiophenyl, pyrrolyl, thiazolyl, imidazolyl, triazolyl, tetrazolyl, pyrazolyl, and 4,5,6,7-tetrahydropyrazolo[1,5-a]pyridinyl. In some embodiments of a compound of Formula (IIa), or a pharmaceutically acceptable salt, solvate, tautomer, or N-oxide thereof, R³ is —CH$_2$(heteroaryl). In some embodiments of a compound of Formula (IIa), or a pharmaceutically acceptable salt, solvate, tautomer, or N-oxide thereof, R³ is —CH$_2$CH$_2$(heteroaryl).

In some embodiments of a compound of Formula (IIa), or a pharmaceutically acceptable salt, solvate, tautomer, or N-oxide thereof, R³ is alkyl substituted with aryl; wherein the aryl is optionally substituted with one or more groups independently selected from the group consisting of halogen, alkyl, haloalkyl, alkoxy, haloalkoxy, and heteroalkyl. In some embodiments of a compound of Formula (IIa), or a pharmaceutically acceptable salt, solvate, tautomer, or N-oxide thereof, R³ is alkyl substituted with aryl; wherein the aryl is phenyl. In some embodiments of a compound of Formula (IIa), or a pharmaceutically acceptable salt, tautomer, or N-oxide thereof, $R^3$ is —CH$_2$(aryl). In some embodiments of a compound of Formula (IIa), or a pharmaceutically acceptable salt, solvate, tautomer, or N-oxide thereof, $R^3$ is —CH$_2$CH$_2$(aryl).

In some embodiments of a compound of Formula (IIa), or a pharmaceutically acceptable salt, solvate, tautomer, or N-oxide thereof, $R^3$ is alkyl substituted with heterocycloalkyl; wherein the heterocycloalkyl is optionally substituted with one or more groups independently selected from the group consisting of halogen, alkyl, haloalkyl, alkoxy, haloalkoxy, heteroalkyl, —S(=O)$_{0-2}$R$^c$, acetyl, and aralkyl; wherein the aralkyl is optionally substituted with one or more groups independently selected from the group consisting of alkyl and alkoxy. In some embodiments of a compound of Formula (IIa), or a pharmaceutically acceptable salt, solvate, tautomer, or N-oxide thereof, $R^3$ is alkyl substituted with heterocycloalkyl; wherein the heterocycloalkyl is piperazinyl, morpholinyl, piperidinyl, or pyrrolidinyl. In some embodiments of a compound of Formula (IIa), or a pharmaceutically acceptable salt, solvate, tautomer, or N-oxide thereof, $R^3$ is —CH$_2$(heterocycloalkyl). In some embodiments of a compound of Formula (IIa), or a pharmaceutically acceptable salt, solvate, tautomer, or N-oxide thereof, $R^3$ is —CH$_2$CH$_2$(heterocycloalkyl).

In some embodiments of a compound of Formula (IIa), or a pharmaceutically acceptable salt, solvate, tautomer, or N-oxide thereof, $R^3$ is alkyl substituted with cycloalkyl; wherein the cycloalkyl is optionally substituted with one or more groups independently selected from the group consisting of halogen, alkyl, haloalkyl, alkoxy, haloalkoxy, and heteroalkyl. In some embodiments of a compound of Formula (IIa), or a pharmaceutically acceptable salt, solvate, tautomer, or N-oxide thereof, $R^3$ is alkyl substituted with cycloalkyl; wherein the cycloalkyl is cyclopropyl, cyclobutyl, cyclopentyl, or cyclobutyl. In some embodiments of a compound of Formula (IIa), or a pharmaceutically acceptable salt, solvate, tautomer, or N-oxide thereof, $R^3$ is —CH$_2$(cycloalkyl). In some embodiments of a compound of Formula (IIa), or a pharmaceutically acceptable salt, solvate, tautomer, or N-oxide thereof, $R^3$ is —CH$_2$CH$_2$(cycloalkyl).

In some embodiments of a compound of Formula (IIa), or a pharmaceutically acceptable salt, solvate, tautomer, or N-oxide thereof, $R^3$ is unsubstituted alkyl.

In some embodiments of a compound of Formula (IIa), or a pharmaceutically acceptable salt, solvate, tautomer, or N-oxide thereof, $R^3$ is phenyl optionally substituted with one or more groups independently selected from the group consisting of halogen, hydroxyl, alkyl, haloalkyl, alkoxy, haloalkoxy, hydroxyalkyl, and —NR$^a$R$^b$. In some embodiments of a compound of Formula (IIa), or a pharmaceutically acceptable salt, solvate, tautomer, or N-oxide thereof, $R^3$ is phenyl substituted with one or more groups independently selected from the group consisting of halogen, hydroxyl, alkyl, haloalkyl, alkoxy, haloalkoxy, hydroxyalkyl, and —NR$^a$R$^b$. In some embodiments of a compound of Formula (IIa), or a pharmaceutically acceptable salt, solvate, tautomer, or N-oxide thereof, $R^3$ is phenyl substituted with one or more groups independently selected from the group consisting of halogen, hydroxyl, alkyl, haloalkyl, alkoxy, haloalkoxy, hydroxyalkyl, and —NR$^a$R$^b$. In some embodiments of a compound of Formula (IIa), or a pharmaceutically acceptable salt, solvate, tautomer, or N-oxide thereof, $R^3$ is unsubstituted phenyl.

In some embodiments of a compound of Formula (IIa), or a pharmaceutically acceptable salt, solvate, tautomer, or N-oxide thereof, $R^3$ is heterocycloalkyl optionally substituted with one or more groups independently selected from the group consisting of alkyl, haloalkyl, alkoxy, haloalkoxy, hydroxyalkyl, —C(=O)Otbutyl, —S(=O)$_{0-2}$R$^e$, acetyl, aryl, and aralkyl; wherein the aralkyl is optionally substituted with one or more groups independently selected from the group consisting of alkylnyl, alkoxy, azidyl, and —CH$_2$azidyl.

In some embodiments of a compound of Formula (IIa), or a pharmaceutically acceptable salt, solvate, tautomer, or N-oxide thereof, $R^3$ is heterocycloalkyl substituted with one or more groups independently selected from the group consisting of alkyl, haloalkyl, alkoxy, haloalkoxy, hydroxyalkyl, —C(=O)Otbutyl, —S(=O)$_{0-2}$R$^e$, acetyl, aryl, and aralkyl; wherein the aralkyl is optionally substituted with one or more groups independently selected from the group consisting of alkylnyl, alkoxy, azidyl, and —CH$_2$azidyl. In some embodiments of a compound of Formula (IIa), or a pharmaceutically acceptable salt, solvate, tautomer, or N-oxide thereof, $R^3$ is heterocycloalkyl substituted with one or more alkyl. In some embodiments of a compound of Formula (IIa), or a pharmaceutically acceptable salt, solvate, tautomer, or N-oxide thereof, $R^3$ is heterocycloalkyl substituted with methyl, ethyl, propyl, or isopropyl. In some embodiments of a compound of Formula (IIa), or a pharmaceutically acceptable salt, solvate, tautomer, or N-oxide thereof, $R^3$ is unsubstituted heterocycloalkyl. In some embodiments of a compound of Formula (IIa), or a pharmaceutically acceptable salt, solvate, tautomer, or N-oxide thereof, $R^3$ is heterocycloalkyl selected from the group consisting of tetrahydro-2H-pyranyl, piperidinyl, 1,1-dioxidotetrahydro-2H-thiopyranyl, and tetrahydro-2H-thiopyranyl. In some embodiments of a compound of Formula (IIa), or a pharmaceutically acceptable salt, solvate, tautomer, or N-oxide thereof, $R^3$ is piperidinyl. In some embodiments of a compound of Formula (IIa), or a pharmaceutically acceptable salt, solvate, tautomer, or N-oxide thereof, $R^3$ is piperidin-4-yl.

In some embodiments of a compound of Formula (IIa), or a pharmaceutically acceptable salt, solvate, tautomer, or N-oxide thereof, $R^3$ is cycloalkyl optionally substituted with one or more groups independently selected from the group consisting of alkyl, haloalkyl, alkoxy, haloalkoxy, and hydroxyalkyl. In some embodiments of a compound of Formula (IIa), or a pharmaceutically acceptable salt, solvate, tautomer, or N-oxide thereof, $R^3$ is unsubstituted cycloalkyl. In some embodiments of a compound of Formula (IIa), or a pharmaceutically acceptable salt, solvate, tautomer, or N-oxide thereof, $R^3$ is cycloprpyl, cyclobutyl, cyclopentyl, or cyclohexyl.

In some embodiments of a compound of Formula (IIa), or a pharmaceutically acceptable salt, solvate, tautomer, or N-oxide thereof, n is 1. In some embodiments of a compound of Formula (IIa), or a pharmaceutically acceptable salt, solvate, tautomer, or N-oxide thereof, n is 2. In some embodiments of a compound of Formula (IIa), or a pharmaceutically acceptable salt, solvate, tautomer, or N-oxide thereof, n is 3. In some embodiments of a compound of Formula (IIa), or a pharmaceutically acceptable salt, solvate, tautomer, or N-oxide thereof, n is 4. In some embodiments of a compound of Formula (IIa), or a pharmaceutically acceptable salt, solvate, tautomer, or N-oxide thereof, n is 5.

In some embodiments of a compound of Formula (IIa), or a pharmaceutically acceptable salt, solvate, tautomer, or N-oxide thereof, the compound of Formula (IIa) is of Formula (IIa-1):

Formula (IIa-1)

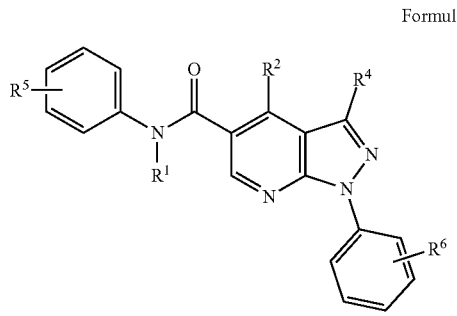

Formula (IIa-2)

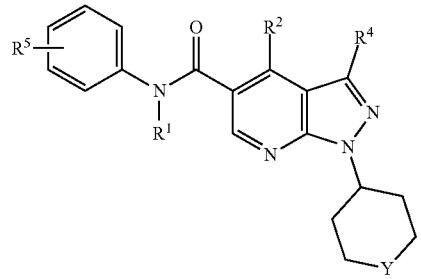

wherein:
- R¹ is selected from the group consisting of hydrogen, alkyl, and cycloalkyl;
  - wherein the alkyl and cycloalkyl are optionally substituted with one or more groups independently selected from the group consisting of halogen, alkoxy, and —NR$^a$R$^b$;
- R² is selected from the group consisting of halogen, hydroxyl, alkoxy, alkyl, and cycloalkyl;
  - wherein the alkyl and cycloalkyl are optionally substituted with one or more halogen;
- R⁴ is selected from the group consisting of hydrogen, halogen, alkyl, and cycloalkyl;
  - wherein the alkyl and cycloalkyl are optionally substituted with one or more groups independently selected from the group consisting of halogen and hydroxyl;
- R⁵ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NR$^a$R$^b$, tetrazoyl, —(C=O)OR$^c$, —CN, —(C=O)R$^d$, alkynyl, and —O(C₁-C₄ alkylene)NR$^a$R$^b$;
- R⁶ is selected from the group consisting of hydrogen, halogen, hydroxyl, alkyl, haloalkyl, alkoxy, haloalkoxy, hydroxyalkyl, and —NR$^a$R$^b$;
- each R$^a$ and R$^b$ are independently selected from the group consisting of hydrogen and alkyl; or R$^a$ and R$^b$ taken together with the nitrogen to which they are attached form a heterocycloalkyl optionally substituted with alkyl;
- R$^c$ is selected from the group consisting of hydrogen and alkyl; and
- R$^d$ is selected from the group consisting of aryl or heteroaryl; wherein the aryl and heteroaryl are optionally substituted with one or more groups independently selected from halogen, alkyl, and alkoxy.

In some embodiments of a compound of Formula (IIa), or a pharmaceutically acceptable salt, solvate, tautomer, or N-oxide thereof, the compound of Formula (IIa) is of Formula (IIa-2):

wherein:
- Y is selected from the group consisting of —O—, —S—, —S(=O)—, —S(=O)₂—, —NR⁷—, and —CH₂—;
- R¹ is selected from the group consisting of hydrogen, alkyl, and cycloalkyl;
  - wherein the alkyl and cycloalkyl are optionally substituted with one or more groups independently selected from the group consisting of halogen, alkoxy, and —NR$^a$R$^b$;
- R² is selected from the group consisting of halogen, hydroxyl, alkoxy, alkyl, and cycloalkyl;
  - wherein the alkyl and cycloalkyl are optionally substituted with one or more halogen;
- R⁴ is selected from the group consisting of hydrogen, halogen, alkyl, and cycloalkyl;
  - wherein the alkyl and cycloalkyl are optionally substituted with one or more groups independently selected from the group consisting of halogen and hydroxyl;
- R⁵ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NR$^a$R$^b$, tetrazoyl, —(C=O)OR$^c$, —CN, —(C=O)R$^d$, alkynyl, and —O(C₁-C₄ alkylene)NR$^a$R$^b$;
- R⁷ is selected from the group consisting of hydrogen, alkyl, haloalkyl, hydroxyalkyl, —C(=O)Otbutyl, —S(=O)₀₋₂R$^e$, acetyl, aryl, heteroaryl, aralkyl, cycloalkyl, and heterocycloalkyl;
  - wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)₀₋₂R$^e$, acetyl, azidyl, —CH₂azidyl, aryl, and aralkyl;
    - wherein the aryl and aralkyl are optionally substituted with one or more groups independently selected from the group consisting of alkyl and alkoxy;
- each R$^a$ and R$^b$ are independently selected from the group consisting of hydrogen and alkyl; or R$^a$ and R$^b$ taken together with the nitrogen to which they are attached form a heterocycloalkyl optionally substituted with alkyl;
- R$^c$ is selected from the group consisting of hydrogen and alkyl;
- R$^d$ is selected from the group consisting of aryl or heteroaryl; wherein the aryl and heteroaryl are optionally substituted with one or more groups independently selected from halogen, alkyl, and alkoxy; and
- R$^e$ is selected from the group consisting of alkyl and —NR$^a$R$^b$.

In some embodiments of a compound of Formula (IIa-2), or a pharmaceutically acceptable salt, solvate, tautomer, or N-oxide thereof, the compound of Formula (IIa-2) is of Formula (IIa-2a):

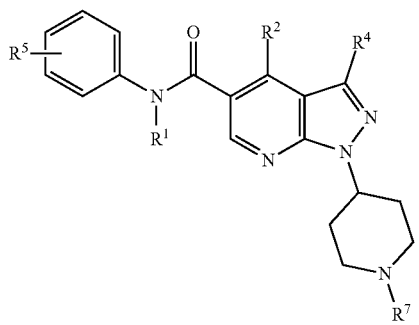

Formula (IIa-2a)

wherein:
$R^1$ is selected from the group consisting of hydrogen, alkyl, and cycloalkyl;
  wherein the alkyl and cycloalkyl are optionally substituted with one or more groups independently selected from the group consisting of halogen, alkoxy, and —$NR^aR^b$;
$R^2$ is selected from the group consisting of halogen, hydroxyl, alkoxy, alkyl, and cycloalkyl;
  wherein the alkyl and cycloalkyl are optionally substituted with one or more halogen;
$R^4$ is selected from the group consisting of hydrogen, halogen, alkyl, and cycloalkyl;
  wherein the alkyl and cycloalkyl are optionally substituted with one or more groups independently selected from the group consisting of halogen and hydroxyl;
$R^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —(C=O)$OR^c$, —CN, —(C=O)$R^d$, alkynyl, and —O($C_1$-$C_4$ alkylene)$NR^aR^b$;
$R^7$ is selected from the group consisting of hydrogen, alkyl, haloalkyl, hydroxyalkyl, —C(=O)Otbutyl, —S(=O)$_{0-2}R^e$, acetyl, aryl, heteroaryl, aralkyl, cycloalkyl, and heterocycloalkyl;
  wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}R^e$, acetyl, azidyl, —$CH_2$azidyl, aryl, and aralkyl;
    wherein the aryl and aralkyl are optionally substituted with one or more groups independently selected from the group consisting of alkyl and alkoxy;
each $R^a$ and $R^b$ are independently selected from the group consisting of hydrogen and alkyl; or $R^a$ and $R^b$ taken together with the nitrogen to which they are attached form a heterocycloalkyl optionally substituted with alkyl;
$R^c$ is selected from the group consisting of hydrogen and alkyl;
$R^d$ is selected from the group consisting of aryl or heteroaryl; wherein the aryl and heteroaryl are optionally substituted with one or more groups independently selected from halogen, alkyl, and alkoxy; and
$R^e$ is selected from the group consisting of alkyl and —$NR^aR^b$.

In some embodiments of a compound of Formula (IIa-2a), or a pharmaceutically acceptable salt, solvate, tautomer, or N-oxide thereof, $R^7$ is selected from the group consisting of hydrogen, alkyl, hydroxyalkyl, —C(=O)Otbutyl, —S(=O)$_{0-2}R^e$, acetyl, and aralkyl; wherein the aralkyl is optionally substituted with one or more groups independently selected from the group consisting of alkylnyl, azidyl, and —$CH_2$azidyl.

In some embodiments of a compound of Formula (IIa-2a), or a pharmaceutically acceptable salt, solvate, tautomer, or N-oxide thereof, $R^7$ is selected from the group consisting of hydrogen and alkyl.

In some embodiments of a compound of Formula (IIa), or a pharmaceutically acceptable salt, solvate, tautomer, or N-oxide thereof, the compound of Formula (IIa) is of Formula (IIa-3):

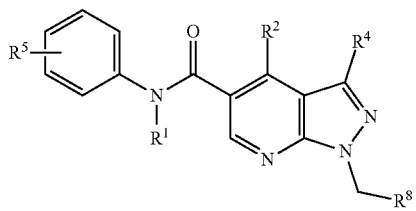

Formula (IIa-3)

wherein:
$R^1$ is selected from the group consisting of hydrogen, alkyl, and cycloalkyl;
  wherein the alkyl and cycloalkyl are optionally substituted with one or more groups independently selected from the group consisting of halogen, alkoxy, and —$NR^aR^b$;
$R^2$ is selected from the group consisting of halogen, hydroxyl, alkoxy, alkyl, and cycloalkyl;
  wherein the alkyl and cycloalkyl are optionally substituted with one or more halogen;
$R^4$ is selected from the group consisting of hydrogen, halogen, alkyl, and cycloalkyl;
  wherein the alkyl and cycloalkyl are optionally substituted with one or more groups independently selected from the group consisting of halogen and hydroxyl;
$R^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —(C=O)$OR^c$, —CN, —(C=O)$R^d$, alkynyl, and —O($C_1$-$C_4$ alkylene)$NR^aR^b$;
$R^8$ is selected from the group consisting of aryl, heteroaryl, and heterocycloalkyl;
  wherein the aryl, heteroaryl, and heterocycloalkyl are optionally substituted with one or more groups independently selected from the group consisting of halogen, alkyl, haloalkyl, alkoxy, haloalkoxy, heteroalkyl, —S(=O)$_{0-2}R^e$, acetyl, and aralkyl;
    wherein the aralkyl is optionally substituted with one or more groups independently selected from the group consisting of alkyl and alkoxy;

each $R^a$ and $R^b$ are independently selected from the group consisting of hydrogen and alkyl; or $R^a$ and $R^b$ taken together with the nitrogen to which they are attached form a heterocycloalkyl optionally substituted with alkyl;

$R^c$ is selected from the group consisting of hydrogen and alkyl;

$R^d$ is selected from the group consisting of aryl or heteroaryl; wherein the aryl and heteroaryl are optionally substituted with one or more groups independently selected from halogen, alkyl, and alkoxy;

$R^e$ is selected from the group consisting of alkyl and —$NR^aR^b$.

In some embodiments of a compound of Formula (IIa-3), or a pharmaceutically acceptable salt, solvate, tautomer, or N-oxide thereof, $R^8$ is heteroaryl optionally substituted with one or more groups independently selected from the group consisting of halogen, alkyl, haloalkyl, alkoxy, haloalkoxy, heteroalkyl, and aralkyl; wherein the aralkyl is optionally substituted with one or more groups independently selected from the group consisting of alkyl and alkoxy.

In some embodiments of a compound of Formula (IIa-3), or a pharmaceutically acceptable salt, solvate, tautomer, or N-oxide thereof, $R^8$ is selected from the group consisting of pyridinyl, pyrimidinyl, pyrazinyl, furanyl, thiophenyl, pyrrolyl, thiazolyl, imidazolyl, triazolyl, tetrazolyl, pyrazolyl, and 4,5,6,7-tetrahydropyrazolo[1,5-a]pyridinyl.

In some embodiments of a compound of Formula (IIa-1), (IIa-2), (IIa-2a) or (IIa-3), or a pharmaceutically acceptable salt, solvate, tautomer, or N-oxide thereof

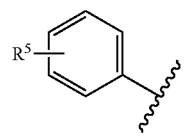

is

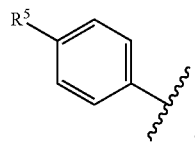

.

In some embodiments of a compound of Formula (IIa-1), (IIa-2), (IIa-2a) or (IIa-3), or a pharmaceutically acceptable salt, solvate, tautomer, or N-oxide thereof, $R^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, —CN, and alkynyl.

In some embodiments of a compound of Formula (IIa-1), (IIa-2), (IIa-2a) or (IIa-3), or a pharmaceutically acceptable salt, solvate, tautomer, or N-oxide thereof, $R^5$ is selected from the group consisting of halogen, alkyl, haloalkyl, alkoxy, haloalkoxy, and alkynyl.

In some embodiments of a compound of Formula (IIa-1), (IIa-2), (IIa-2a) or (IIa-3), or a pharmaceutically acceptable salt, solvate, tautomer, or N-oxide thereof, $R^5$ is selected from the group consisting of chloro, methyl, isopropyl, methoxy, and ethynyl.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^1$ is selected from the group consisting of hydrogen, methyl, ethyl, —$CH_2CH_2OCH_3$, and —$CH_2CH_2N(CH_3)_2$.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^1$ is hydrogen.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^2$ is selected from the group consisting of chloro, fluoro, hydroxyl, —$CF_3$, methoxy, ethoxy, and methyl.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^2$ is chloro.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^4$ is selected from the group consisting of hydrogen, methyl, ethyl, isopropyl, cyclopropyl, fluoro, chloro, and bromo.

In some embodiments of a compound of Formula (II), (IIa), (IIa-1), (IIa-2), (IIa-2a) or (IIa-3), or a pharmaceutically acceptable salt, solvate, tautomer, or N-oxide thereof, $R^4$ is selected from the group consisting of hydrogen and methyl.

In some embodiments of a compound of Formula (II), or a pharmaceutically acceptable salt, solvate, tautomer, or N-oxide thereof, the compound of Formula (II) is of Formula (IIb):

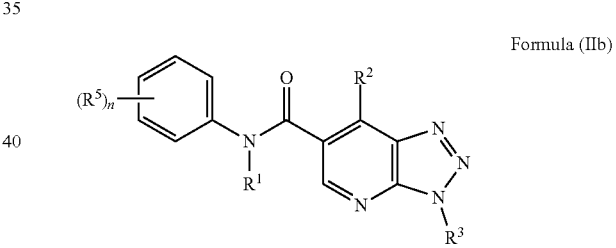

Formula (IIb)

wherein:
  $R^1$ is selected from the group consisting of hydrogen, alkyl, and cycloalkyl;
    wherein the alkyl and cycloalkyl are optionally substituted with one or more groups independently selected from the group consisting of halogen, alkoxy, and —$NR^aR^b$;
  $R^2$ is selected from the group consisting of halogen, hydroxyl, alkoxy, alkyl, and cycloalkyl;
    wherein the alkyl and cycloalkyl are optionally substituted with one or more halogen;
  $R^3$ is selected from the group consisting of alkyl, cycloalkyl, heterocycloalkyl, phenyl, and 5- or 6-membered heteroaryl;
    wherein the alkyl, cycloalkyl, heterocycloalkyl, phenyl, and heteroaryl are optionally substituted with one or more groups independently selected from the group consisting of halogen, hydroxyl, alkyl, haloalkyl, alkoxy, haloalkoxy, hydroxyalkyl, —$NR^aR^b$, —Oaralkyl, —C(=O)Otbutyl, —S(=O)$_{0-2}R^e$, acetyl, aryl, heteroaryl, aralkyl, cycloalkyl, and heterocycloalkyl;

wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}$R$^e$, acetyl, azidyl, —CH$_2$azidyl, aryl, and aralkyl;
  wherein the aryl and aralkyl are optionally substituted with one or more groups independently selected from the group consisting of alkyl and alkoxy;
each R$^5$ are independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NR$^a$R$^b$, tetrazoyl, —(C=O)OR$^c$, —CN, —(C=O)R$^d$, alkynyl, and —O(C$_1$-C$_4$ alkylene)NR$^a$R$^b$;
each R$^a$ and R$^b$ are independently selected from the group consisting of hydrogen and alkyl; or R$^a$ and R$^b$ taken together with the nitrogen to which they are attached form a heterocycloalkyl optionally substituted with alkyl;
R$^c$ is selected from the group consisting of hydrogen and alkyl;
R$^d$ is selected from the group consisting of aryl or heteroaryl; wherein the aryl and heteroaryl are optionally substituted with one or more groups independently selected from halogen, alkyl, and alkoxy;
R$^e$ is selected from the group consisting of alkyl and —NR$^a$R$^b$; and
n is 1, 2, 3, 4, or 5.

In some embodiments of a compound of Formula (II), or a pharmaceutically acceptable salt, solvate, tautomer, or N-oxide thereof, the compound of Formula (II) is of Formula (IIc):

Formula (IIc)

wherein:
R$^1$ is selected from the group consisting of hydrogen, alkyl, and cycloalkyl;
  wherein the alkyl and cycloalkyl are optionally substituted with one or more groups independently selected from the group consisting of halogen, alkoxy, and —NR$^a$R$^b$;
R$^2$ is selected from the group consisting of halogen, hydroxyl, alkoxy, alkyl, and cycloalkyl;
  wherein the alkyl and cycloalkyl are optionally substituted with one or more halogen;
R$^3$ is selected from the group consisting of alkyl, cycloalkyl, heterocycloalkyl, phenyl, and 5- or 6-membered heteroaryl;
  wherein the alkyl, cycloalkyl, heterocycloalkyl, phenyl, and heteroaryl are optionally substituted with one or more groups independently selected from the group consisting of halogen, hydroxyl, alkyl, haloalkyl, alkoxy, haloalkoxy, hydroxyalkyl, —NR$^a$R$^b$, —Oaralkyl, —C(=O)Otbutyl, —S(=O)$_{0-2}$R$^e$, acetyl, aryl, heteroaryl, aralkyl, cycloalkyl, and heterocycloalkyl;
  wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}$R$^e$, acetyl, azidyl, —CH$_2$azidyl, aryl, and aralkyl;
    wherein the aryl and aralkyl are optionally substituted with one or more groups independently selected from the group consisting of alkyl and alkoxy;
R$^4$ is selected from the group consisting of hydrogen, halogen, alkyl, and cycloalkyl;
  wherein the alkyl and cycloalkyl are optionally substituted with one or more groups independently selected from the group consisting of halogen and hydroxy;
each R$^5$ are independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NR$^a$R$^b$, tetrazoyl, —(C=O)OR$^c$, —CN, —(C=O)R$^d$, alkynyl, and —O(C$_1$-C$_4$ alkylene)NR$^a$R$^b$;
each R$^a$ and R$^b$ are independently selected from the group consisting of hydrogen and alkyl; or R$^a$ and R$^b$ taken together with the nitrogen to which they are attached form a heterocycloalkyl optionally substituted with alkyl;
R$^e$ is selected from the group consisting of hydrogen and alkyl;
R$^d$ is selected from the group consisting of aryl or heteroaryl; wherein the aryl and heteroaryl are optionally substituted with one or more groups independently selected from halogen, alkyl, and alkoxy;
R$^e$ is selected from the group consisting of alkyl and —NR$^a$R$^b$; and
n is 1, 2, 3, 4, or 5.

In some embodiments of a compound of Formula (II), or a pharmaceutically acceptable salt, solvate, tautomer, or N-oxide thereof, the compound of Formula (II) is of Formula (IId):

Formula (IId)

wherein:
R$^1$ is selected from the group consisting of hydrogen, alkyl, and cycloalkyl;
  wherein the alkyl and cycloalkyl are optionally substituted with one or more groups independently selected from the group consisting of halogen, alkoxy, and —NR$^a$R$^b$;
R$^2$ is selected from the group consisting of halogen, hydroxyl, alkoxy, alkyl, and cycloalkyl;
  wherein the alkyl and cycloalkyl are optionally substituted with one or more halogen;

$R^3$ is selected from the group consisting of alkyl, cycloalkyl, heterocycloalkyl, phenyl, and 5- or 6-membered heteroaryl;
  wherein the alkyl, cycloalkyl, heterocycloalkyl, phenyl, and heteroaryl are optionally substituted with one or more groups independently selected from the group consisting of halogen, hydroxyl, alkyl, haloalkyl, alkoxy, haloalkoxy, hydroxyalkyl, —$NR^aR^b$, —Oaralkyl, —C(=O)Otbutyl, —S(=O)$_{0-2}R^e$, acetyl, aryl, heteroaryl, aralkyl, cycloalkyl, and heterocycloalkyl;
    wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}R^e$, acetyl, azidyl, —CH$_2$azidyl, aryl, and aralkyl;
      wherein the aryl and aralkyl are optionally substituted with one or more groups independently selected from the group consisting of alkyl and alkoxy;
$R^4$ is selected from the group consisting of hydrogen, halogen, alkyl, and cycloalkyl;
  wherein the alkyl and cycloalkyl are optionally substituted with one or more groups independently selected from the group consisting of halogen and hydroxy;
each $R^5$ are independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —(C=O)$OR^c$, —CN, —(C=O)$R^d$, alkynyl, and —O(C$_1$-C$_4$ alkylene)$NR^aR^b$;
each $R^a$ and $R^b$ are independently selected from the group consisting of hydrogen and alkyl; or $R^a$ and $R^b$ taken together with the nitrogen to which they are attached form a heterocycloalkyl optionally substituted with alkyl;
$R^c$ is selected from the group consisting of hydrogen and alkyl;
$R^d$ is selected from the group consisting of aryl or heteroaryl; wherein the aryl and heteroaryl are optionally substituted with one or more groups independently selected from halogen, alkyl, and alkoxy;
$R^e$ is selected from the group consisting of alkyl and —$NR^aR^b$; and
n is 1, 2, 3, 4, or 5.

In some embodiments of a compound of Formula (IIb), (IIc), or (IId), or a pharmaceutically acceptable salt, solvate, tautomer, or N-oxide thereof, $R^3$ is alkyl optionally substituted with one or more groups independently selected from the group consisting of halogen, hydroxyl, haloalkyl, alkoxy, haloalkoxy, hydroxyalkyl, —$NR^aR^b$, —Oaralkyl, acetyl, aryl, heteroaryl, cycloalkyl, and heterocycloalkyl; wherein the aryl, heteroaryl, cycloalkyl, and heterocycloalkyl are optionally substituted with one or more groups independently selected from the group consisting of halogen, alkyl, haloalkyl, alkoxy, haloalkoxy, heteroalkyl, —S(=O)$_{0-2}R^e$, acetyl, and aralkyl; wherein the aralkyl is optionally substituted with one or more groups independently selected from the group consisting of alkyl and alkoxy.

In some embodiments of a compound of Formula (IIb), (IIc), or (IId), or a pharmaceutically acceptable salt, solvate, tautomer, or N-oxide thereof, $R^3$ is alkyl substituted with one or more groups independently selected from the group consisting of halogen, hydroxyl, haloalkyl, alkoxy, haloalkoxy, hydroxyalkyl, and —$NR^aR^b$. In some embodiments of a compound of Formula (IIb), (IIc), or (IId), or a pharmaceutically acceptable salt, solvate, tautomer, or N-oxide thereof, $R^3$ is alkyl substituted with one or more groups independently selected from the group consisting of hydroxyl, alkoxy, and —$NR^aR^b$.

In some embodiments of a compound of Formula (IIb), (IIc), or (IId), or a pharmaceutically acceptable salt, solvate, tautomer, or N-oxide thereof, $R^3$ is alkyl substituted with one or more groups independently selected from the group consisting of aryl, heteroaryl, and heterocycloalkyl; wherein the aryl, heteroaryl, and heterocycloalkyl are optionally substituted with one or more groups independently selected from the group consisting of halogen, alkyl, haloalkyl, alkoxy, haloalkoxy, and heteroalkyl.

In some embodiments of a compound of Formula (IIb), (IIc), or (IId), or a pharmaceutically acceptable salt, solvate, tautomer, or N-oxide thereof, $R^3$ is alkyl substituted with heteroaryl; wherein the heteroaryl is optionally substituted with one or more groups independently selected from the group consisting of halogen, alkyl, haloalkyl, alkoxy, haloalkoxy, and heteroalkyl. In some embodiments of a compound of Formula (IIb), (IIc), or (IId), or a pharmaceutically acceptable salt, solvate, tautomer, or N-oxide thereof, $R^3$ is alkyl substituted with heteroaryl; wherein the heteroaryl is selected from the group consisting of pyridinyl, pyrimidinyl, pyrazinyl, furanyl, thiophenyl, pyrrolyl, thiazolyl, imidazolyl, triazolyl, tetrazolyl, pyrazolyl, and 4,5,6,7-tetrahydropyrazolo[1,5-a]pyridinyl. In some embodiments of a compound of Formula (IIb), (IIc), or (IId), or a pharmaceutically acceptable salt, solvate, tautomer, or N-oxide thereof, $R^3$ is —CH$_2$(heteroaryl). In some embodiments of a compound of Formula (IIb), (IIc), or (IId), or a pharmaceutically acceptable salt, solvate, tautomer, or N-oxide thereof, $R^3$ is —CH$_2$CH$_2$(heteroaryl).

In some embodiments of a compound of Formula (IIb), (IIc), or (IId), or a pharmaceutically acceptable salt, solvate, tautomer, or N-oxide thereof, $R^3$ is alkyl substituted with aryl; wherein the aryl is optionally substituted with one or more groups independently selected from the group consisting of halogen, alkyl, haloalkyl, alkoxy, haloalkoxy, and heteroalkyl. In some embodiments of a compound of Formula (IIb), (IIc), or (IId), or a pharmaceutically acceptable salt, solvate, tautomer, or N-oxide thereof, $R^3$ is alkyl substituted with aryl; wherein the aryl is phenyl. In some embodiments of a compound of Formula (IIb), (IIc), or (IId), or a pharmaceutically acceptable salt, solvate, tautomer, or N-oxide thereof, $R^3$ is —CH$_2$(aryl). In some embodiments of a compound of Formula (IIb), (IIc), or (IId), or a pharmaceutically acceptable salt, solvate, tautomer, or N-oxide thereof, $R^3$ is —CH$_2$CH$_2$(aryl).

In some embodiments of a compound of Formula (IIb), (IIc), or (IId), or a pharmaceutically acceptable salt, solvate, tautomer, or N-oxide thereof, $R^3$ is alkyl substituted with heterocycloalkyl; wherein the heterocycloalkyl is optionally substituted with one or more groups independently selected from the group consisting of halogen, alkyl, haloalkyl, alkoxy, haloalkoxy, heteroalkyl, —S(=O)$_{0-2}R^e$, acetyl, and aralkyl; wherein the aralkyl is optionally substituted with one or more groups independently selected from the group consisting of alkyl and alkoxy. In some embodiments of a compound of Formula (IIb), (IIc), or (IId), or a pharmaceutically acceptable salt, solvate, tautomer, or N-oxide thereof, $R^3$ is alkyl substituted with heterocycloalkyl; wherein the heterocycloalkyl is piperazinyl, morpholinyl, piperidinyl, or pyrrolidinyl. In some embodiments of a compound of Formula (IIb), (IIc), or (IId), or a pharmaceutically acceptable salt, solvate, tautomer, or N-oxide thereof, $R^3$ is —CH$_2$(heterocycloalkyl). In some embodiments of a compound of Formula (IIb), (IIc), or (IId), or a pharmaceutically acceptable salt, solvate, tautomer, or N-oxide thereof, $R^3$ is —CH$_2$CH$_2$(heterocycloalkyl).

In some embodiments of a compound of Formula (IIb), (IIc), or (IId), or a pharmaceutically acceptable salt, solvate, tautomer, or N-oxide thereof, $R^3$ is alkyl substituted with cycloalkyl; wherein the cycloalkyl is optionally substituted with one or more groups independently selected from the group consisting of halogen, alkyl, haloalkyl, alkoxy, haloalkoxy, and heteroalkyl. In some embodiments of a compound of Formula (IIb), (IIc), or (IId), or a pharmaceutically acceptable salt, solvate, tautomer, or N-oxide thereof, $R^3$ is alkyl substituted with cycloalkyl; wherein the cycloalkyl is cyclopropyl, cyclobutyl, cyclopentyl, or cyclobutyl. In some embodiments of a compound of Formula (IIb), (IIc), or (IId), or a pharmaceutically acceptable salt, solvate, tautomer, or N-oxide thereof, $R^3$ is —CH$_2$(cycloalkyl). In some embodiments of a compound of Formula (IIb), (IIc), or (IId), or a pharmaceutically acceptable salt, solvate, tautomer, or N-oxide thereof, $R^3$ is —CH$_2$CH$_2$(cycloalkyl).

In some embodiments of a compound of Formula (IIb), (IIc), or (IId), or a pharmaceutically acceptable salt, solvate, tautomer, or N-oxide thereof, $R^3$ is unsubstituted alkyl.

In some embodiments of a compound of Formula (IIb), (IIc), or (IId), or a pharmaceutically acceptable salt, solvate, tautomer, or N-oxide thereof, $R^3$ is phenyl optionally substituted with one or more groups independently selected from the group consisting of halogen, hydroxyl, alkyl, haloalkyl, alkoxy, haloalkoxy, hydroxyalkyl, and —NR$^a$R$^b$. In some embodiments of a compound of Formula (IIb), (IIc), or (IId), or a pharmaceutically acceptable salt, solvate, tautomer, or N-oxide thereof, $R^3$ is phenyl substituted with one or more groups independently selected from the group consisting of halogen, hydroxyl, alkyl, haloalkyl, alkoxy, haloalkoxy, hydroxyalkyl, and —NR$^a$R$^b$. In some embodiments of a compound of Formula (IIb), (IIc), or (IId), or a pharmaceutically acceptable salt, solvate, tautomer, or N-oxide thereof, $R^3$ is phenyl substituted with one or more groups independently selected from the group consisting of halogen, hydroxyl, alkyl, haloalkyl, alkoxy, haloalkoxy, hydroxyalkyl, and —NR$^a$R$^b$. In some embodiments of a compound of Formula (IIb), (IIc), or (IId), or a pharmaceutically acceptable salt, solvate, tautomer, or N-oxide thereof, $R^3$ is unsubstituted phenyl.

In some embodiments of a compound of Formula (IIb), (IIc), or (IId), or a pharmaceutically acceptable salt, solvate, tautomer, or N-oxide thereof, $R^3$ is heterocycloalkyl optionally substituted with one or more groups independently selected from the group consisting of alkyl, haloalkyl, alkoxy, haloalkoxy, hydroxyalkyl, —C(=O)Otbutyl, —S(=O)$_{0-2}$R$^e$, acetyl, aryl, and aralkyl; wherein the aralkyl is optionally substituted with one or more groups independently selected from the group consisting of alkylnyl, alkoxy, azidyl, and —CH$_2$azidyl.

In some embodiments of a compound of Formula (IIb), (IIc), or (IId), or a pharmaceutically acceptable salt, solvate, tautomer, or N-oxide thereof, $R^3$ is heterocycloalkyl substituted with one or more groups independently selected from the group consisting of alkyl, haloalkyl, alkoxy, haloalkoxy, hydroxyalkyl, —C(=O)Otbutyl, —S(=O)$_{0-2}$R$^e$, acetyl, aryl, and aralkyl; wherein the aralkyl is optionally substituted with one or more groups independently selected from the group consisting of alkylnyl, alkoxy, azidyl, and —CH$_2$azidyl. In some embodiments of a compound of Formula (IIb), (IIc), or (IId), or a pharmaceutically acceptable salt, solvate, tautomer, or N-oxide thereof, $R^3$ is heterocycloalkyl substituted with one or more alkyl. In some embodiments of a compound of Formula (IIb), (IIc), or (IId), or a pharmaceutically acceptable salt, solvate, tautomer, or N-oxide thereof, $R^3$ is heterocycloalkyl substituted with methyl, ethyl, propyl, or isopropyl. In some embodiments of a compound of Formula (IIb), (IIc), or (IId), or a pharmaceutically acceptable salt, solvate, tautomer, or N-oxide thereof, $R^3$ is unsubstituted heterocycloalkyl. In some embodiments of a compound of Formula (IIb), (IIc), or (IId), or a pharmaceutically acceptable salt, solvate, tautomer, or N-oxide thereof, $R^3$ is heterocycloalkyl selected from the group consisting of tetrahydro-2H-pyranyl, piperidinyl, 1,1-dioxidotetrahydro-2H-thiopyranyl, and tetrahydro-2H-thiopyranyl. In some embodiments of a compound of Formula (IIb), (IIc), or (IId), or a pharmaceutically acceptable salt, solvate, tautomer, or N-oxide thereof, $R^3$ is piperidinyl. In some embodiments of a compound of Formula (IIb), (IIc), or (IId), or a pharmaceutically acceptable salt, solvate, tautomer, or N-oxide thereof, $R^3$ is piperidin-4-yl.

In some embodiments of a compound of Formula (IIb), (IIc), or (IId), or a pharmaceutically acceptable salt, solvate, tautomer, or N-oxide thereof, $R^3$ is cycloalkyl optionally substituted with one or more groups independently selected from the group consisting of alkyl, haloalkyl, alkoxy, haloalkoxy, and hydroxyalkyl. In some embodiments of a compound of Formula (IIb), (IIc), or (IId), or a pharmaceutically acceptable salt, solvate, tautomer, or N-oxide thereof, $R^3$ is unsubstituted cycloalkyl. In some embodiments of a compound of Formula (IIb), (IIc), or (IId), or a pharmaceutically acceptable salt, solvate, tautomer, or N-oxide thereof, $R^3$ is cycloprpyl, cyclobutyl, cyclopentyl, or cyclohexyl.

In some embodiments of a compound of Formula (IIb), (IIc), or (IId), or a pharmaceutically acceptable salt, solvate, tautomer, or N-oxide thereof, n is 1. In some embodiments of a compound of Formula (IIb), (IIc), or (IId), or a pharmaceutically acceptable salt, solvate, tautomer, or N-oxide thereof, n is 2. In some embodiments of a compound of Formula (IIb), (IIc), or (IId), or a pharmaceutically acceptable salt, solvate, tautomer, or N-oxide thereof, n is 3. In some embodiments of a compound of Formula (IIb), (IIc), or (IId), or a pharmaceutically acceptable salt, solvate, tautomer, or N-oxide thereof, n is 4. In some embodiments of a compound of Formula (IIb), (IIc), or (IId), or a pharmaceutically acceptable salt, solvate, tautomer, or N-oxide thereof, n is 5.

In some embodiments of a compound of Formula (IIb), (IIc), or (IId), or a pharmaceutically acceptable salt, solvate, tautomer, or N-oxide thereof

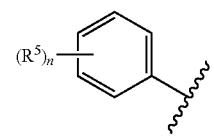

is

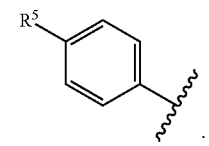

.

In some embodiments of a compound of Formula (IIb), (IIc), or (IId), or a pharmaceutically acceptable salt, solvate, tautomer, or N-oxide thereof, $R^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, —CN, and alkynyl.

In some embodiments of a compound of Formula (IIb), (IIc), or (IId), or a pharmaceutically acceptable salt, solvate, tautomer, or N-oxide thereof, $R^5$ is selected from the group consisting of halogen, alkyl, haloalkyl, alkoxy, haloalkoxy, and alkynyl.

In some embodiments of a compound of Formula (IIb), (IIc), or (IId), or a pharmaceutically acceptable salt, solvate, tautomer, or N-oxide thereof, $R^5$ is selected from the group consisting of chloro, methyl, isopropyl, methoxy, and ethynyl.

In some embodiments of a compound of Formula (IIb), (IIc), or (IId), or a pharmaceutically acceptable salt, solvate, tautomer, or N-oxide thereof, $R^1$ is selected from the group consisting of hydrogen, methyl, ethyl, —$CH_2CH_2OCH_3$, and —$CH_2CH_2N(CH_3)_2$.

In some embodiments of a compound of Formula (IIb), (IIc), or (IId), or a pharmaceutically acceptable salt, solvate, tautomer, or N-oxide thereof, $R^1$ is hydrogen.

In some embodiments of a compound of Formula (IIb), (IIc), or (IId), or a pharmaceutically acceptable salt, solvate, tautomer, or N-oxide thereof, $R^2$ is selected from the group consisting of chloro, fluoro, hydroxyl, —$CF_3$, methoxy, ethoxy, and methyl.

In some embodiments of a compound of Formula (IIb), (IIc), or (IId), or a pharmaceutically acceptable salt, solvate, tautomer, or N-oxide thereof, $R^2$ is chloro.

In some embodiments of a compound of Formula (IIc) or (IId), or a pharmaceutically acceptable salt, solvate, tautomer, or N-oxide thereof, $R^4$ is selected from the group consisting of hydrogen, methyl, ethyl, isopropyl, cyclopropyl, fluoro, chloro, and bromo.

In some embodiments of a compound of Formula (IIc) or (IId), or a pharmaceutically acceptable salt, solvate, tautomer, or N-oxide thereof, $R^4$ is selected from the group consisting of hydrogen and methyl.

In some embodiments of a compound of Formula (II), or a pharmaceutically acceptable salt, solvate, tautomer, or N-oxide thereof, the compound of Formula (II) is selected from:

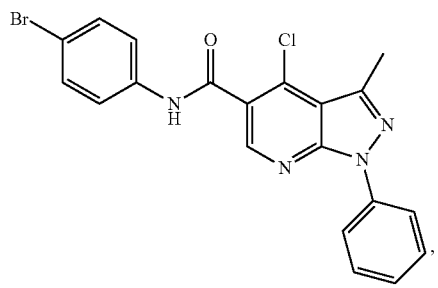

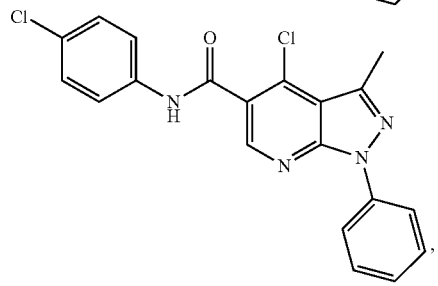

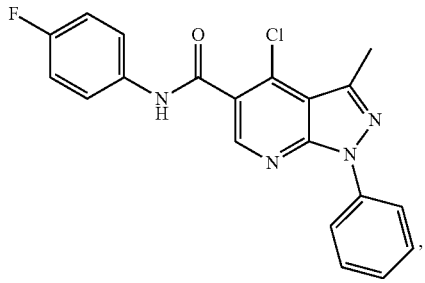

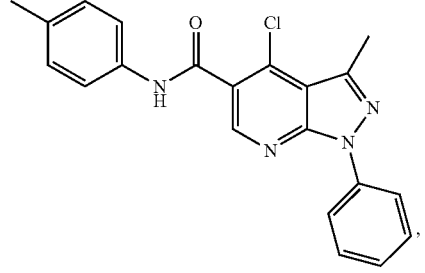

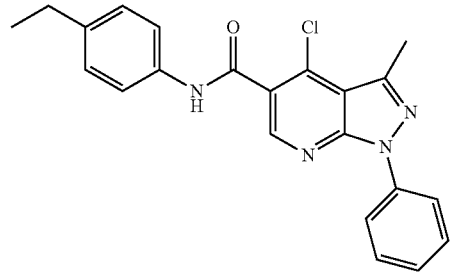

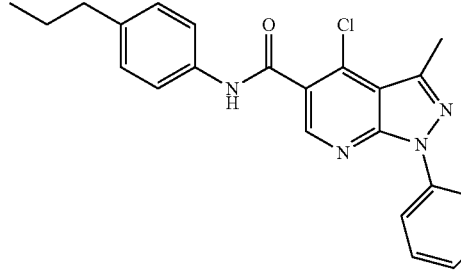

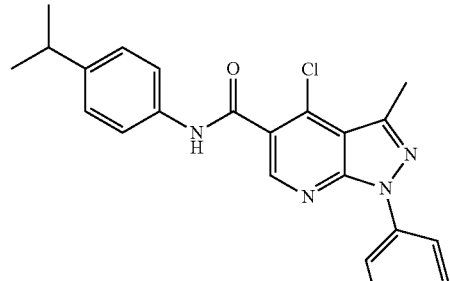

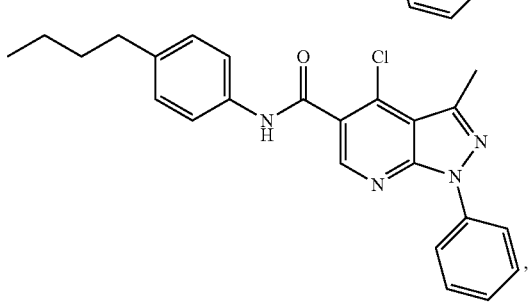

-continued
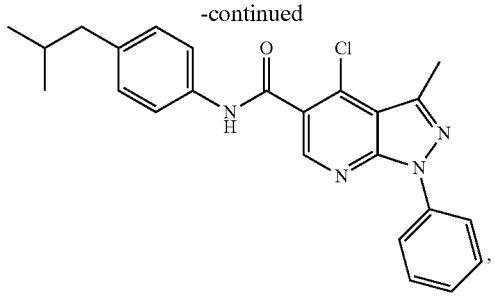
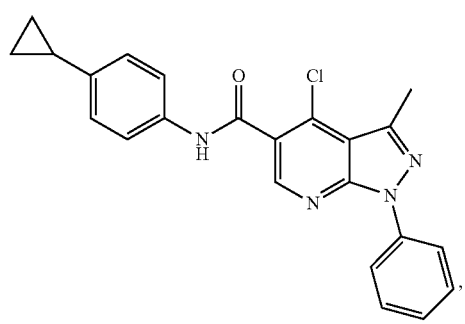
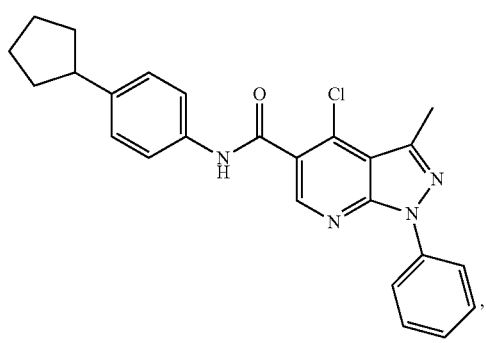
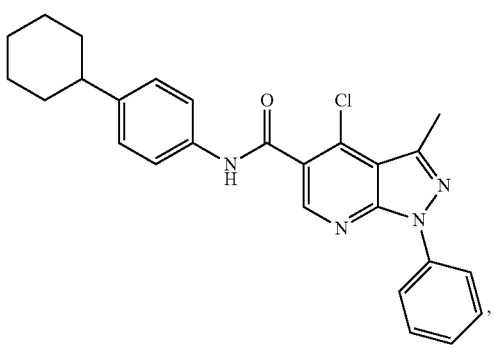
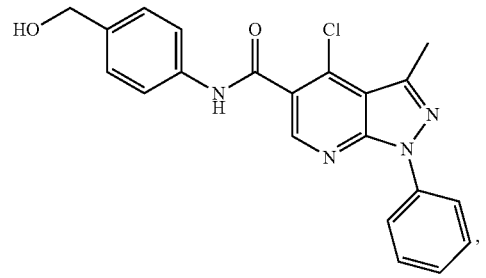
-continued
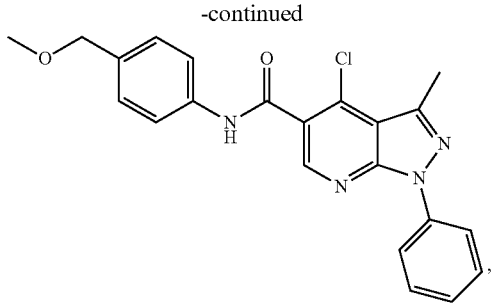
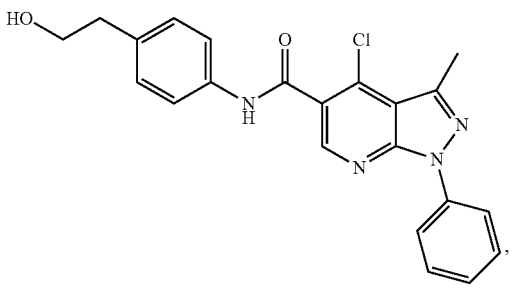
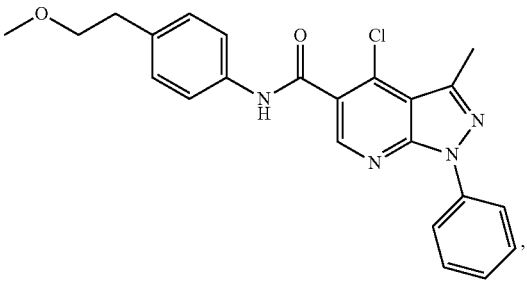
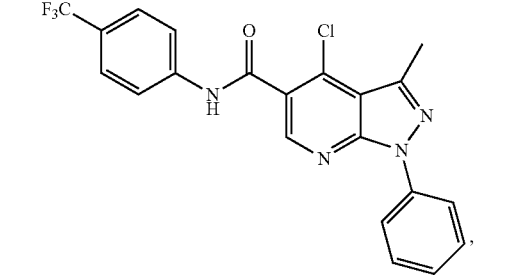
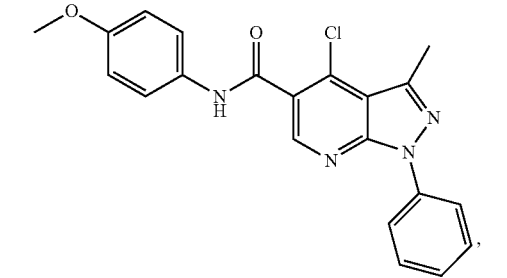
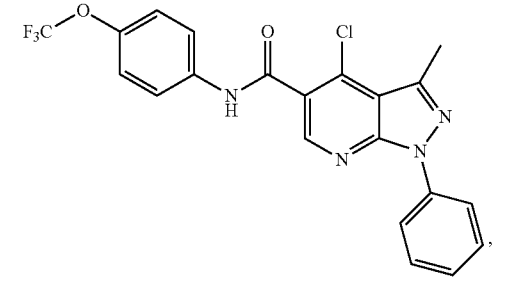

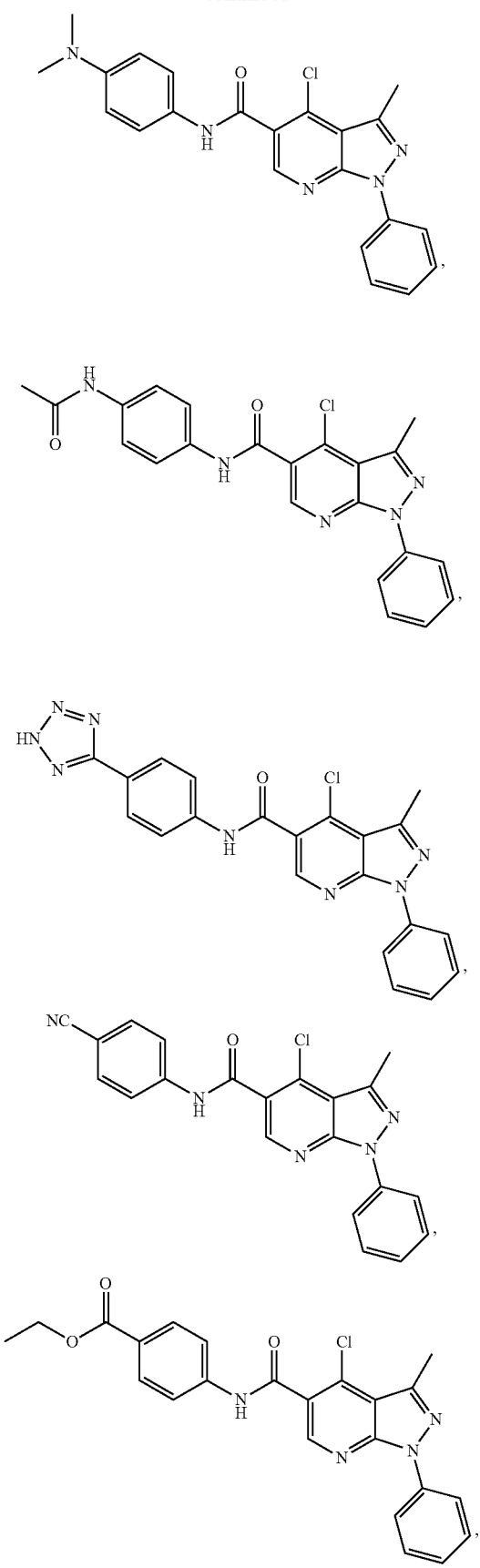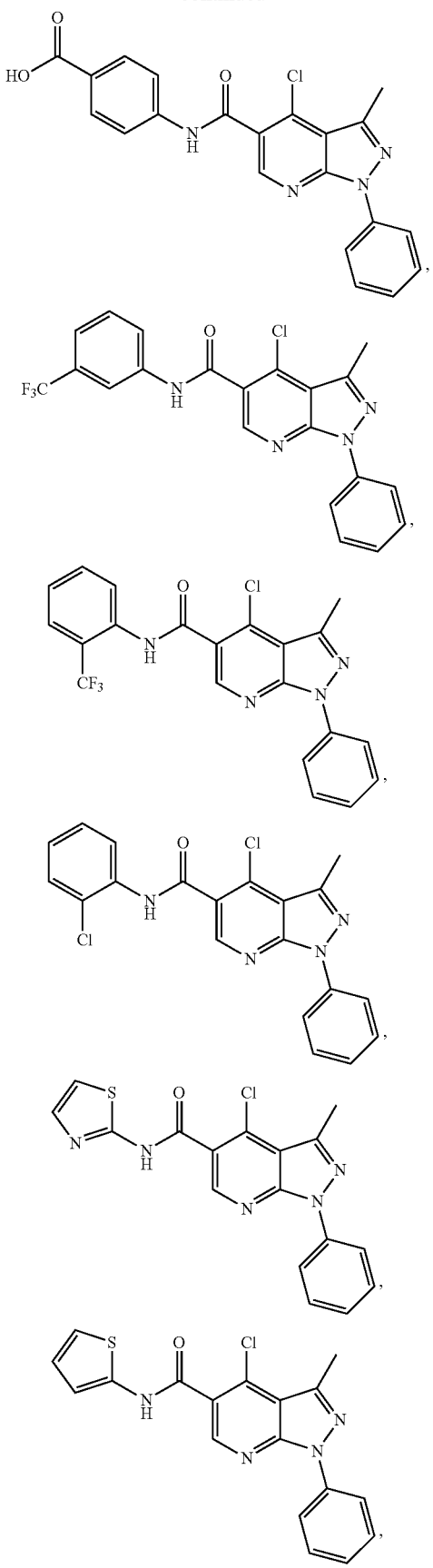

51
-continued
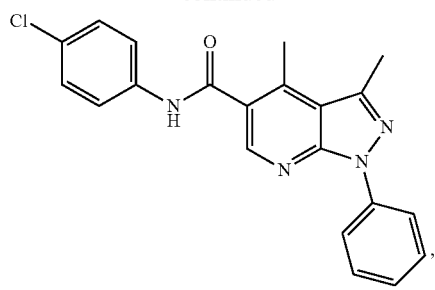
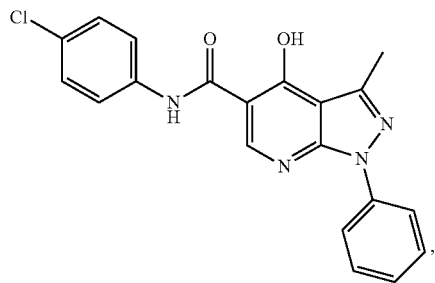
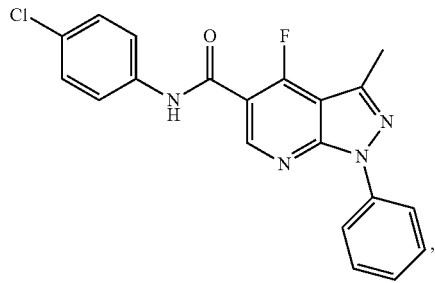
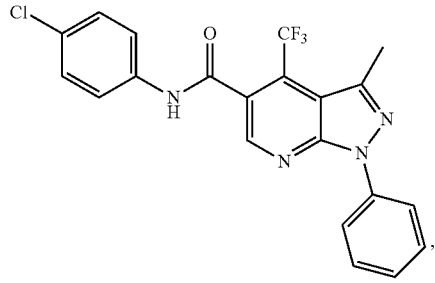
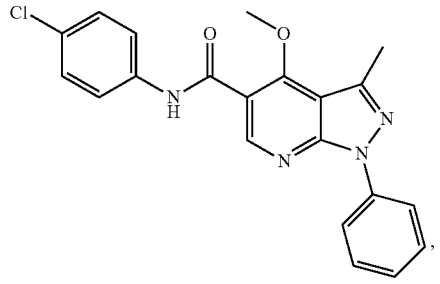
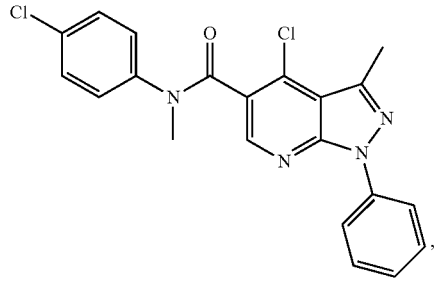
52
-continued
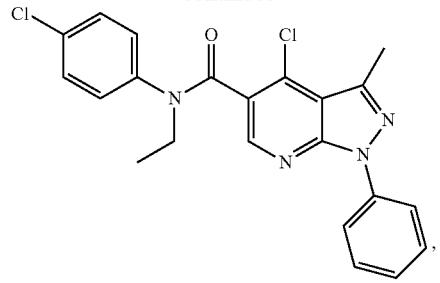
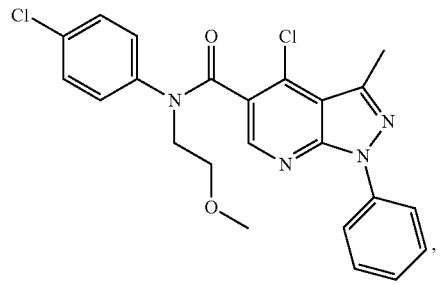
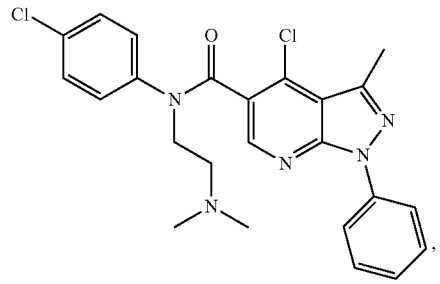
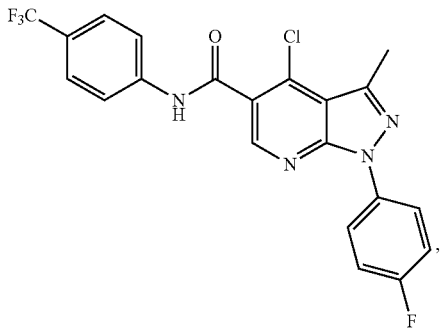
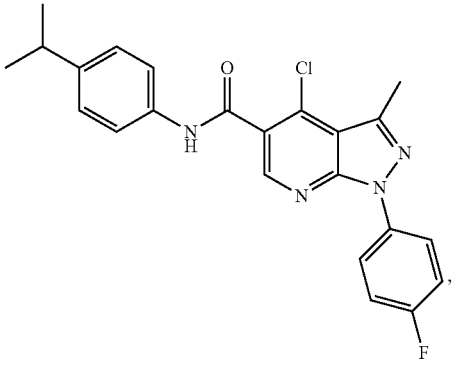

53
-continued
54
-continued
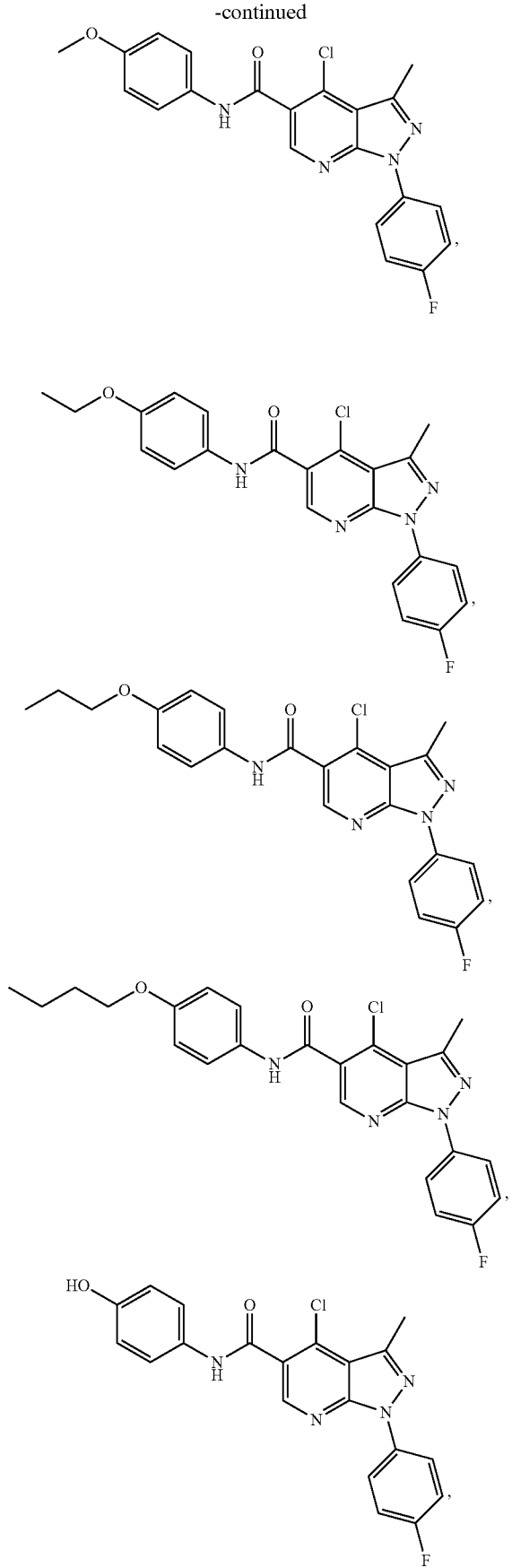
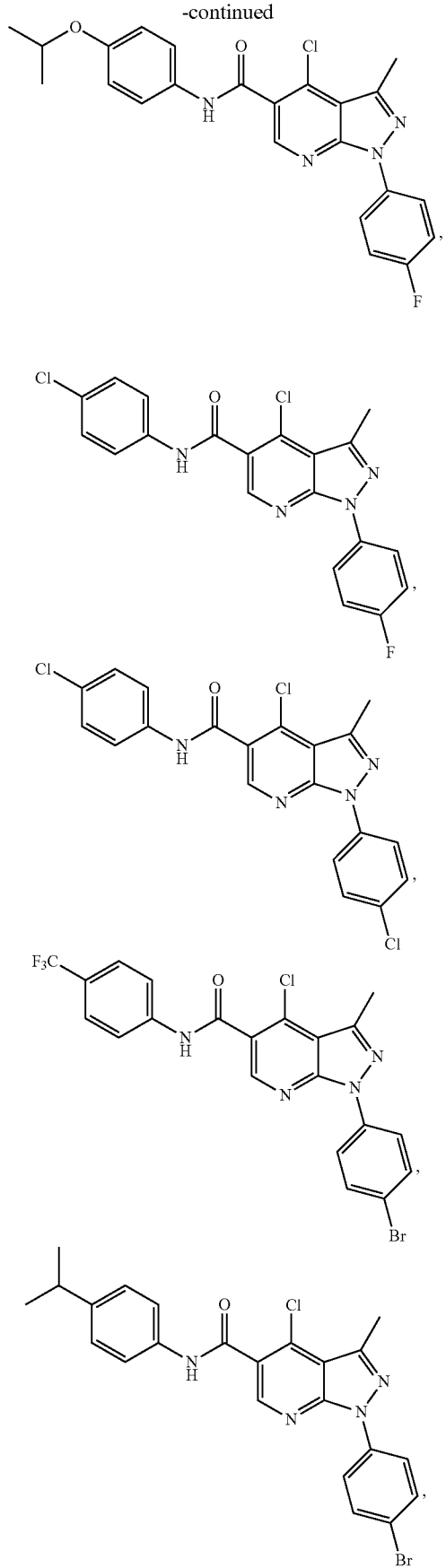

55
-continued
56
-continued
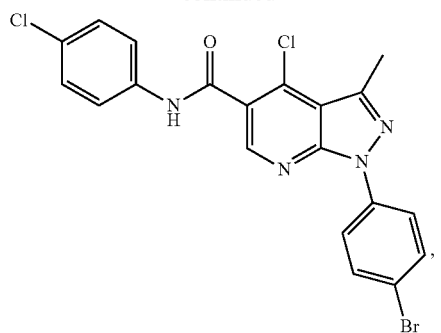
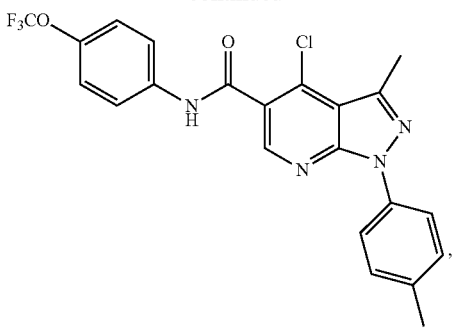

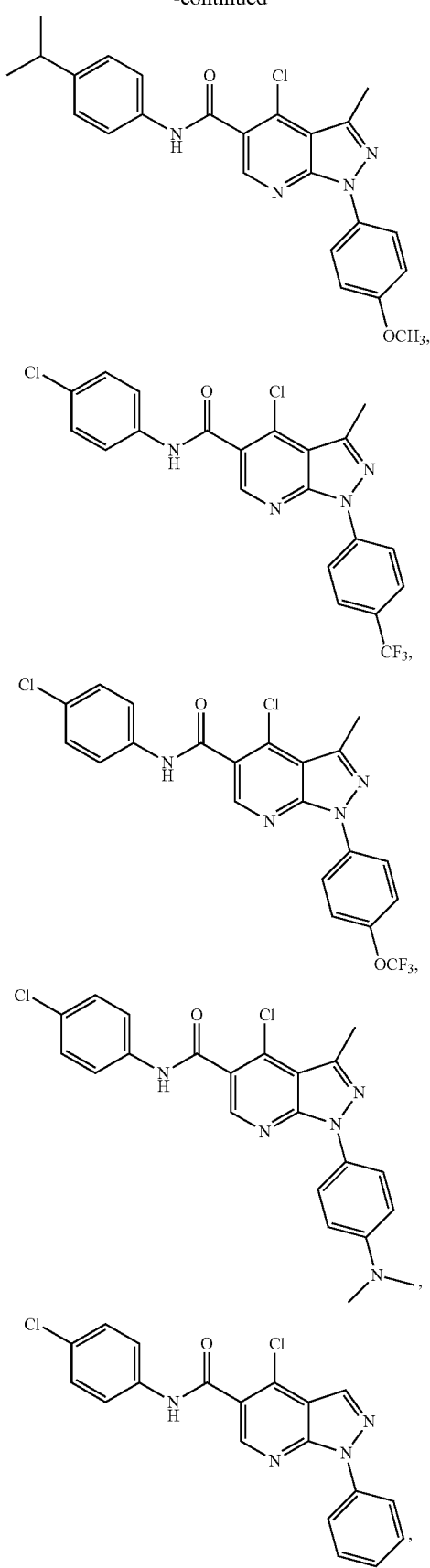
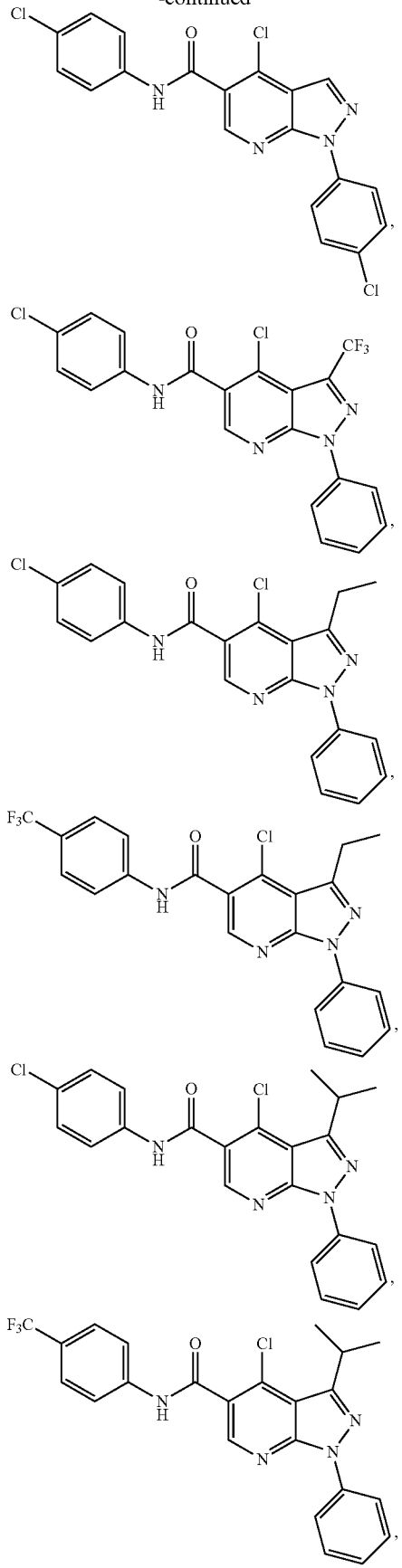

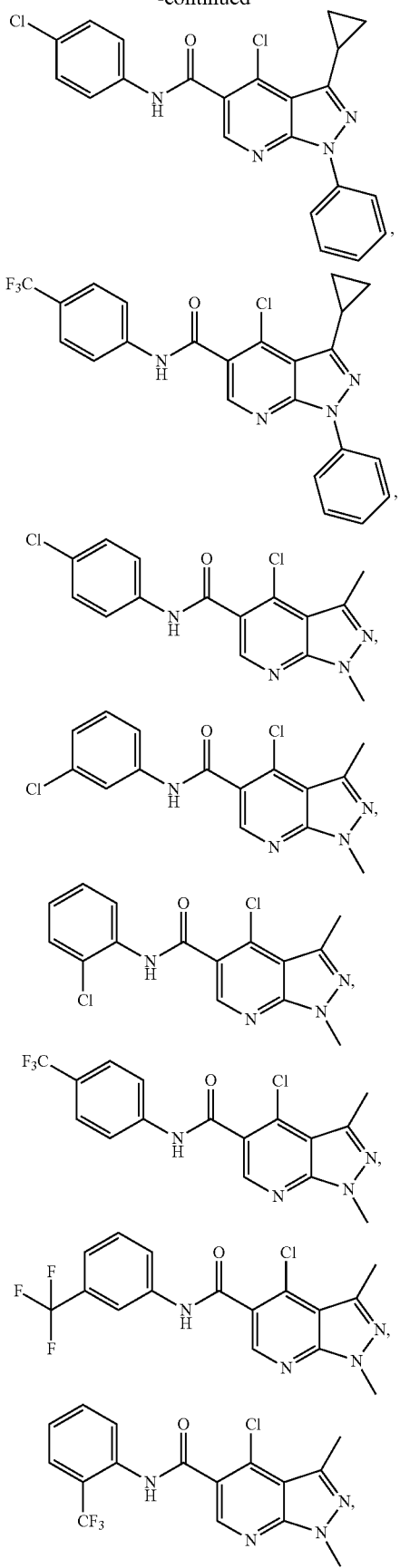
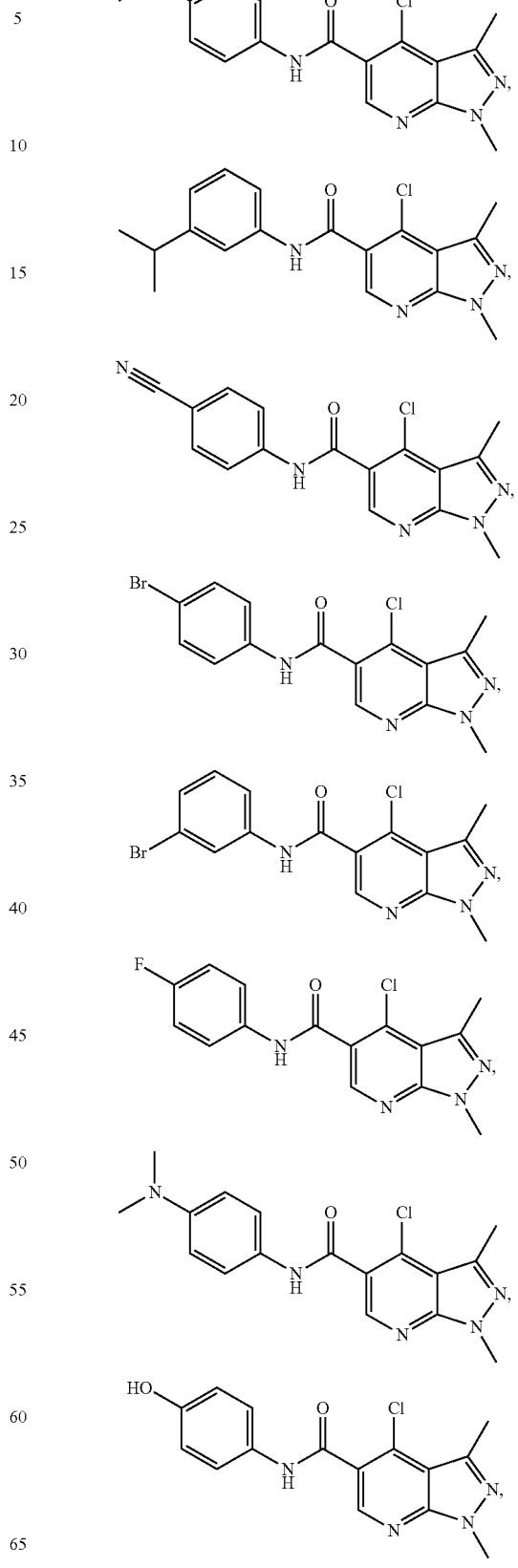

61
-continued
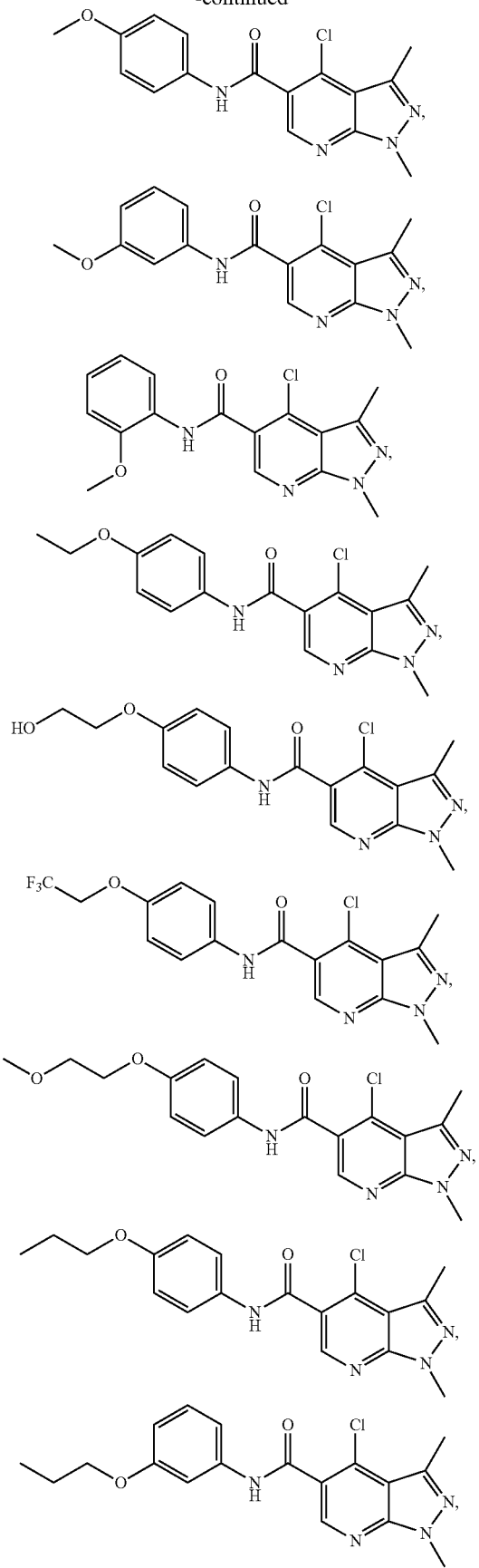
62
-continued
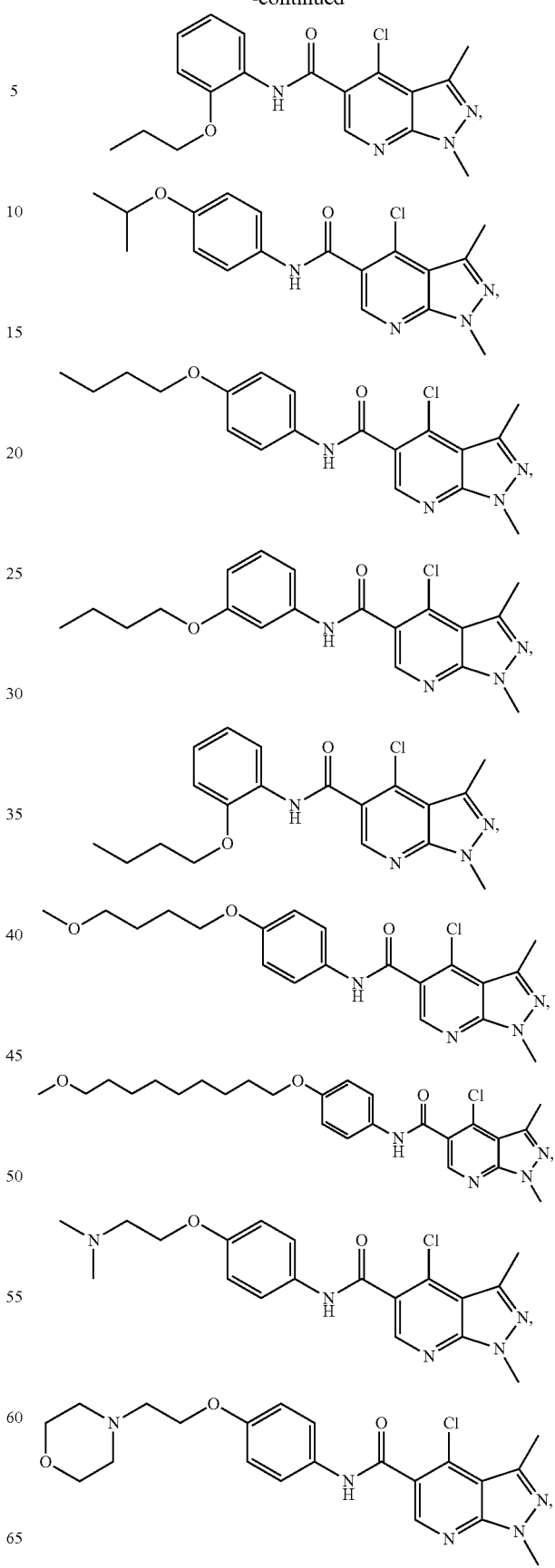

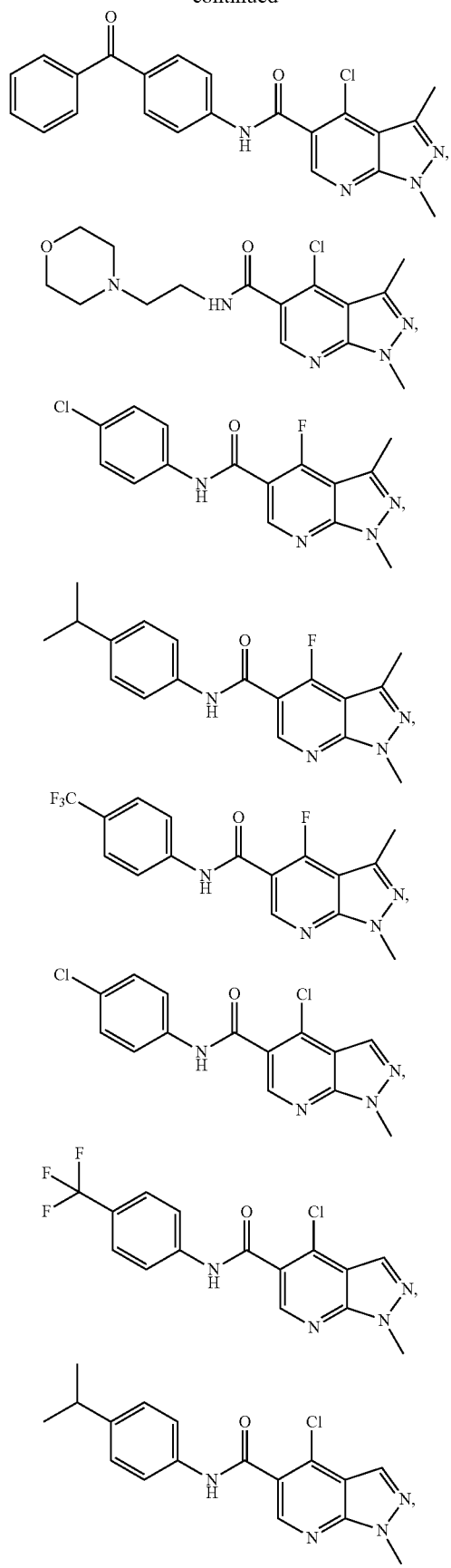
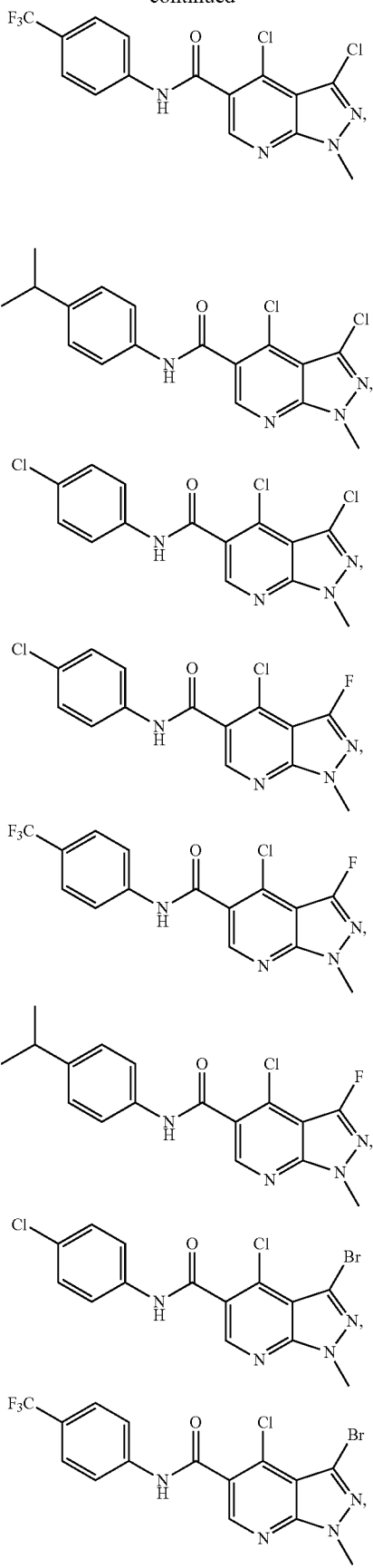

-continued
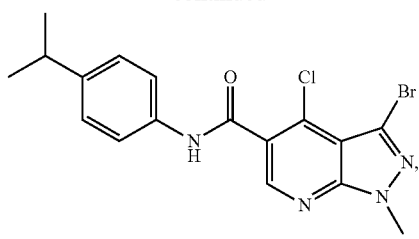
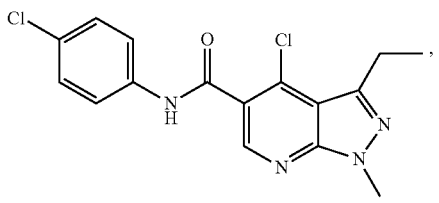
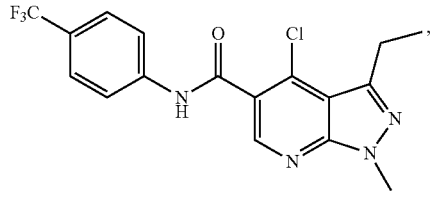
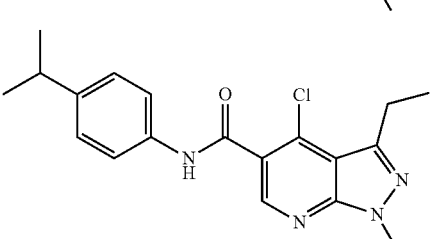
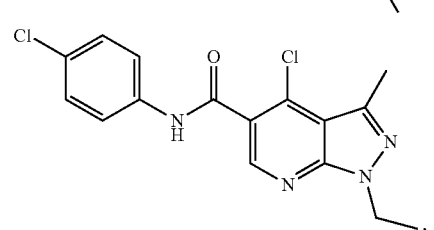
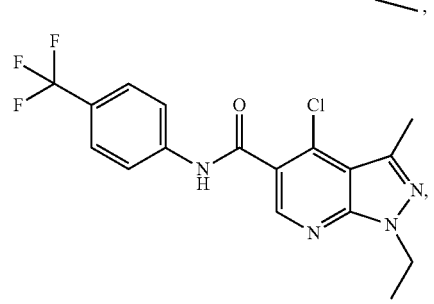
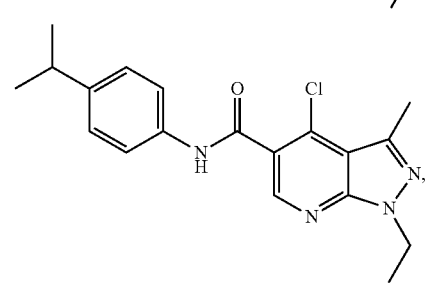
-continued
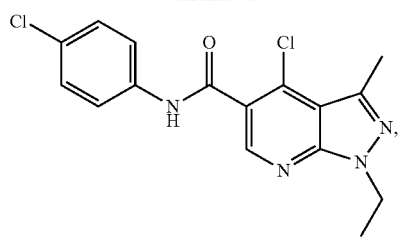
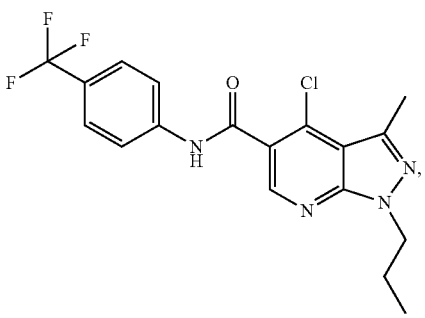
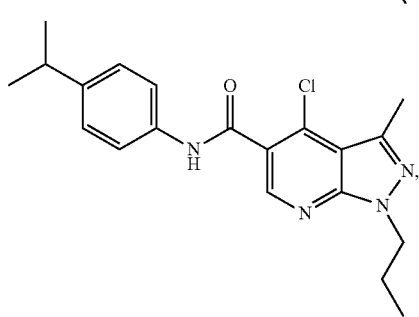
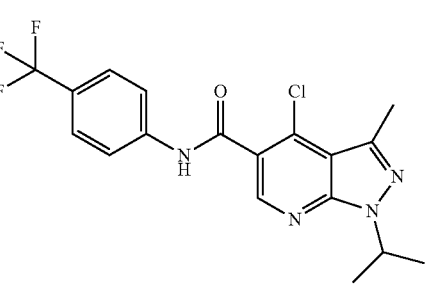
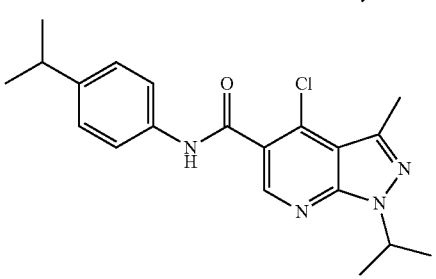
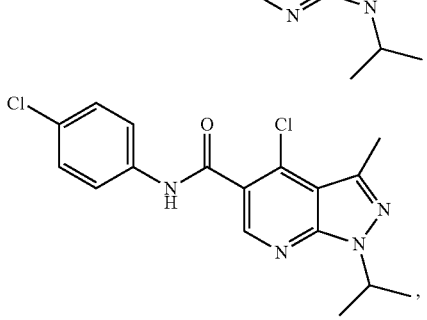

67
-continued
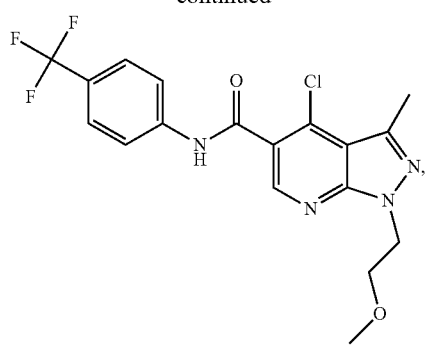
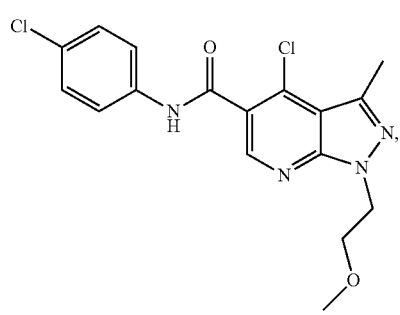
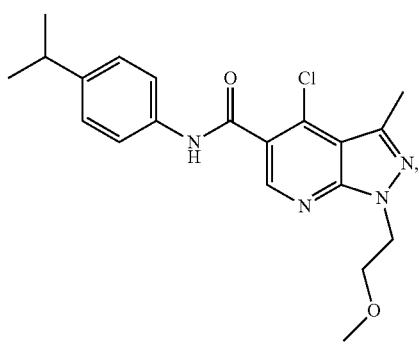
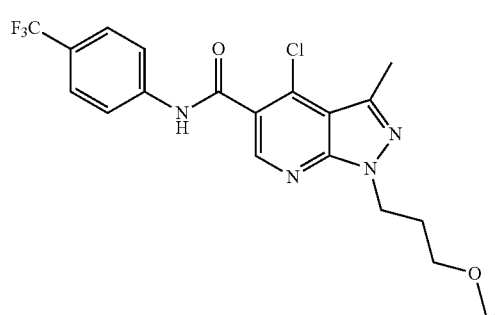
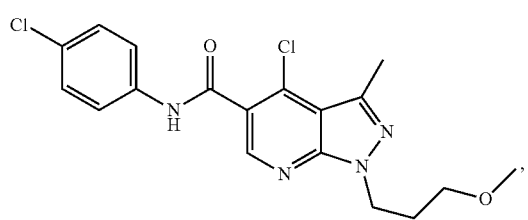
68
-continued
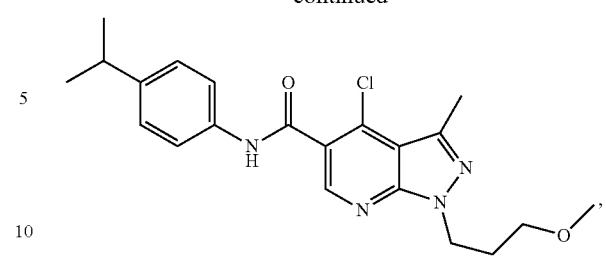
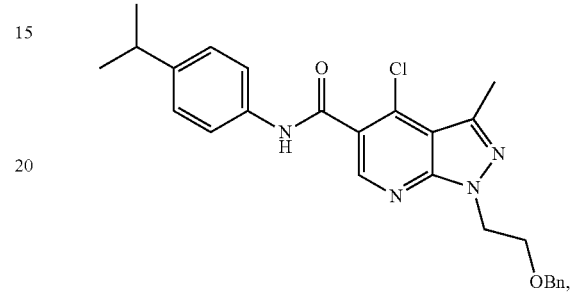
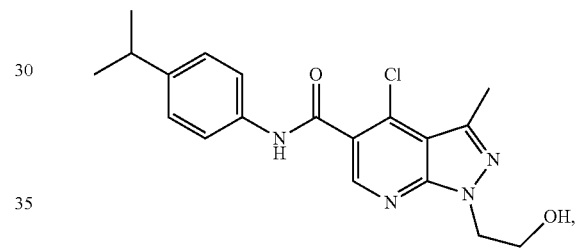
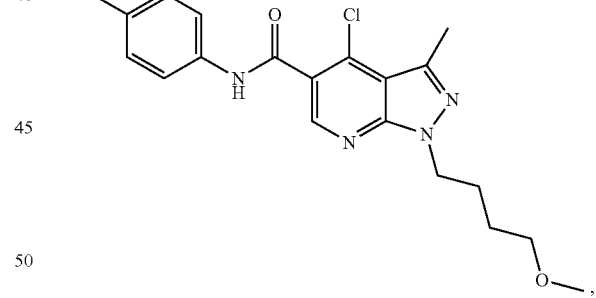
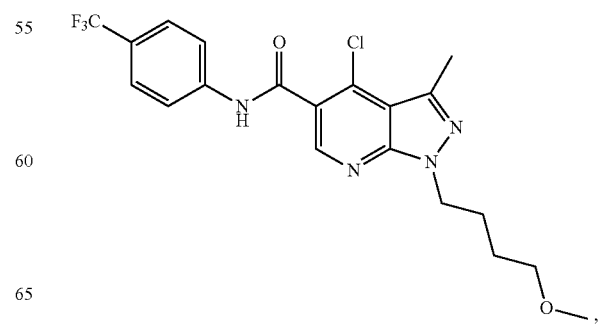

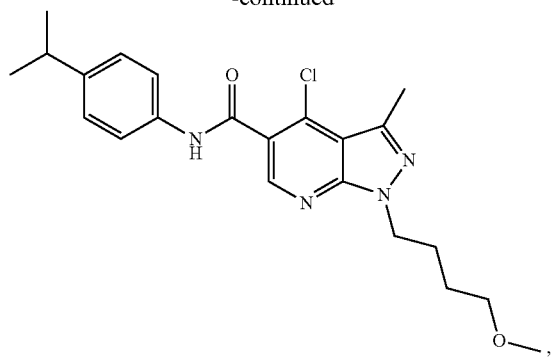
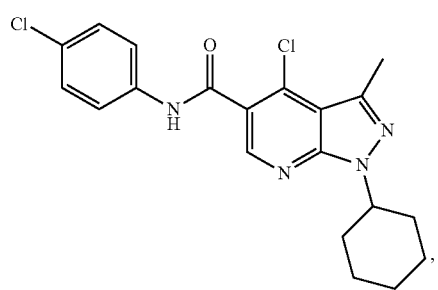
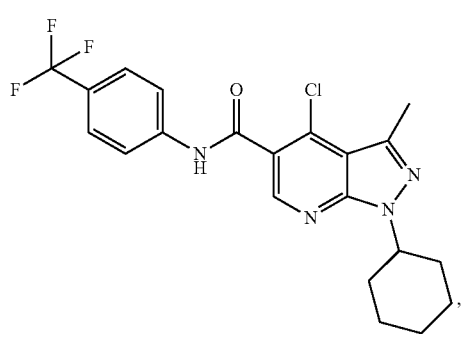
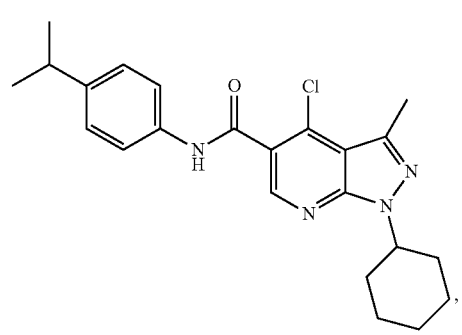
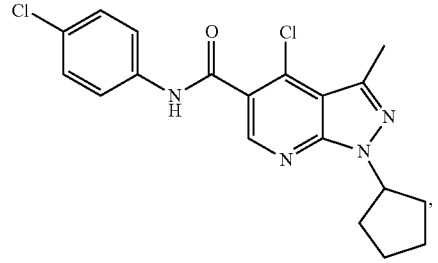
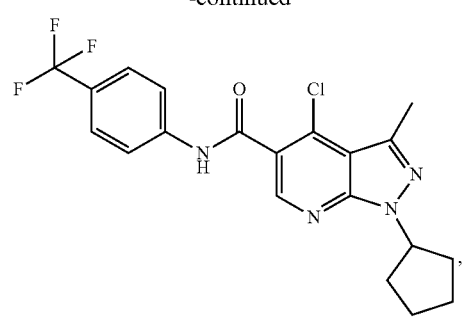
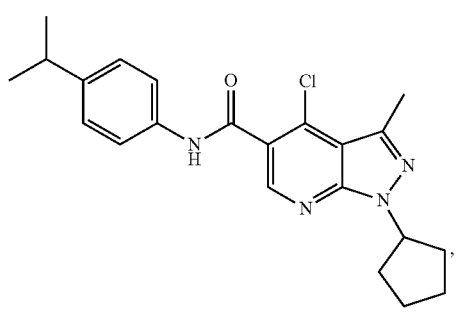
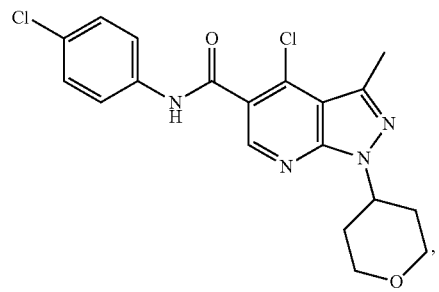
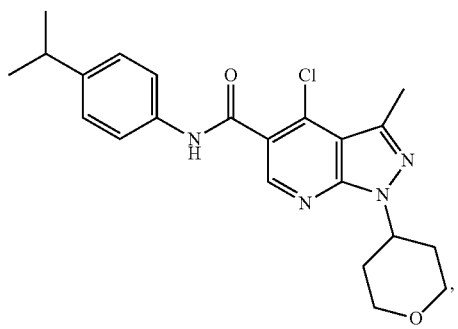
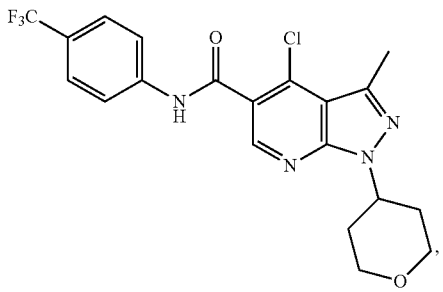

71
-continued
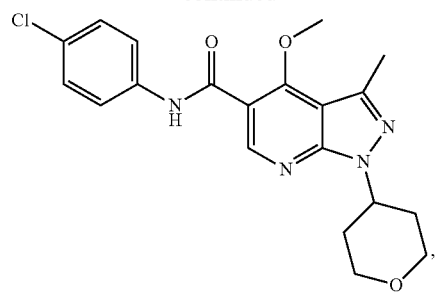
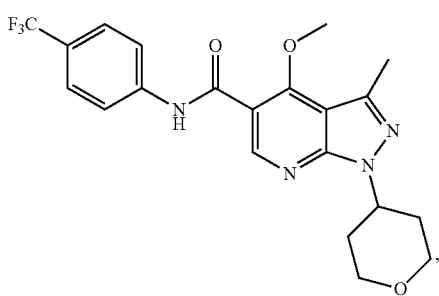
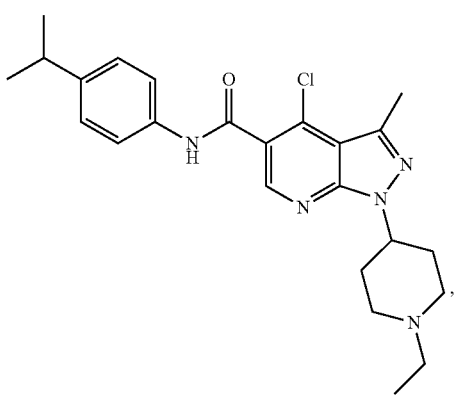
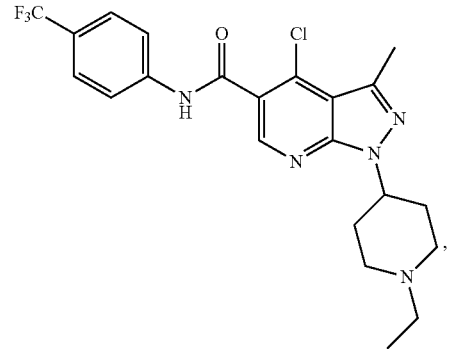
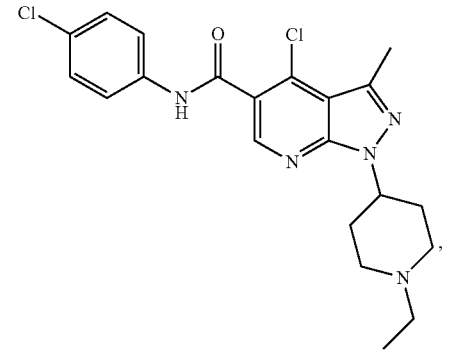
72
-continued
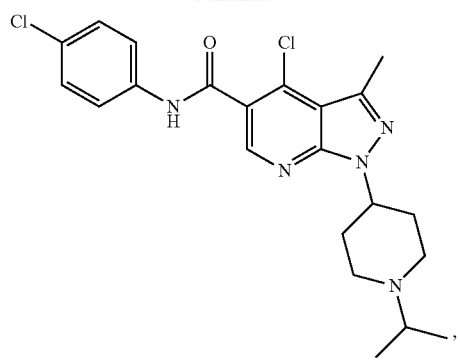
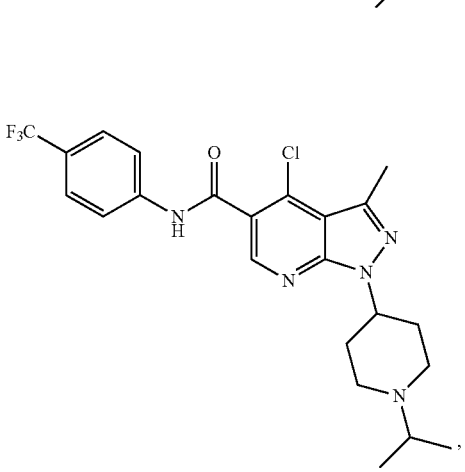
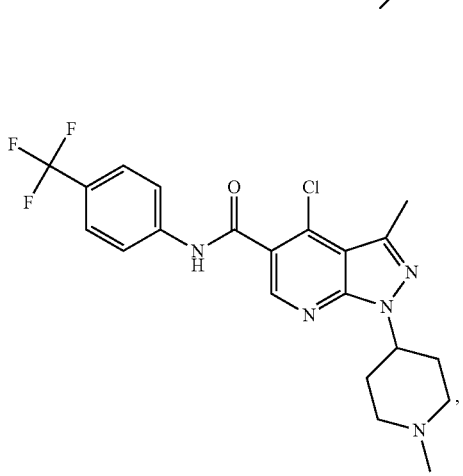
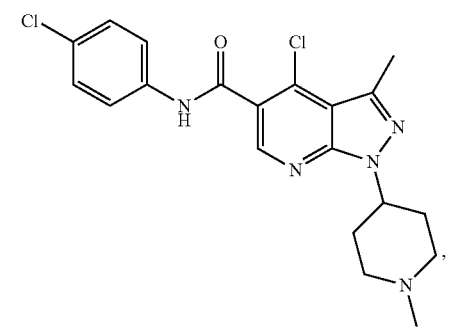

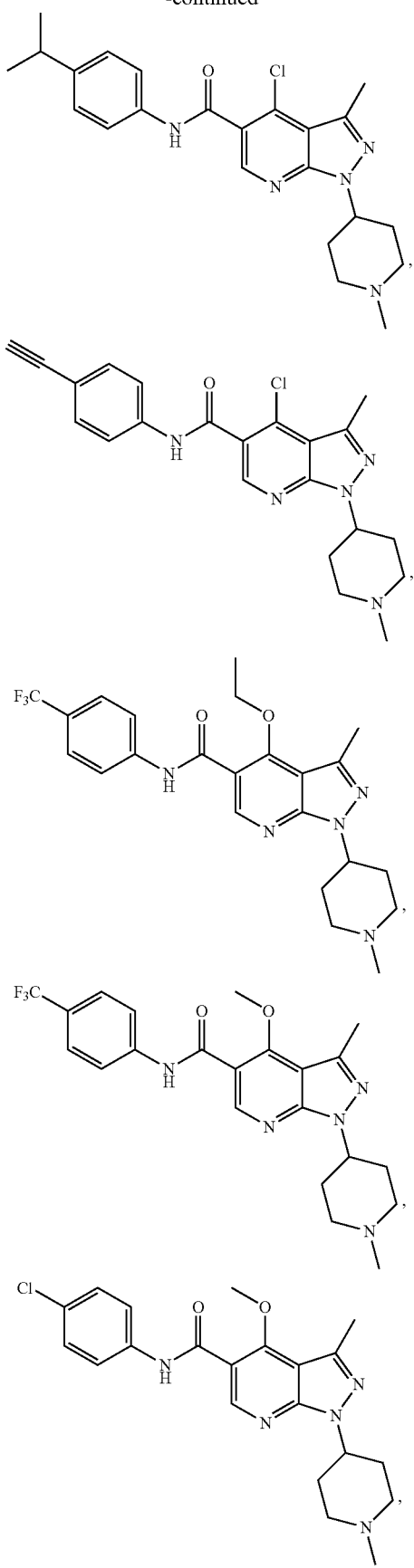
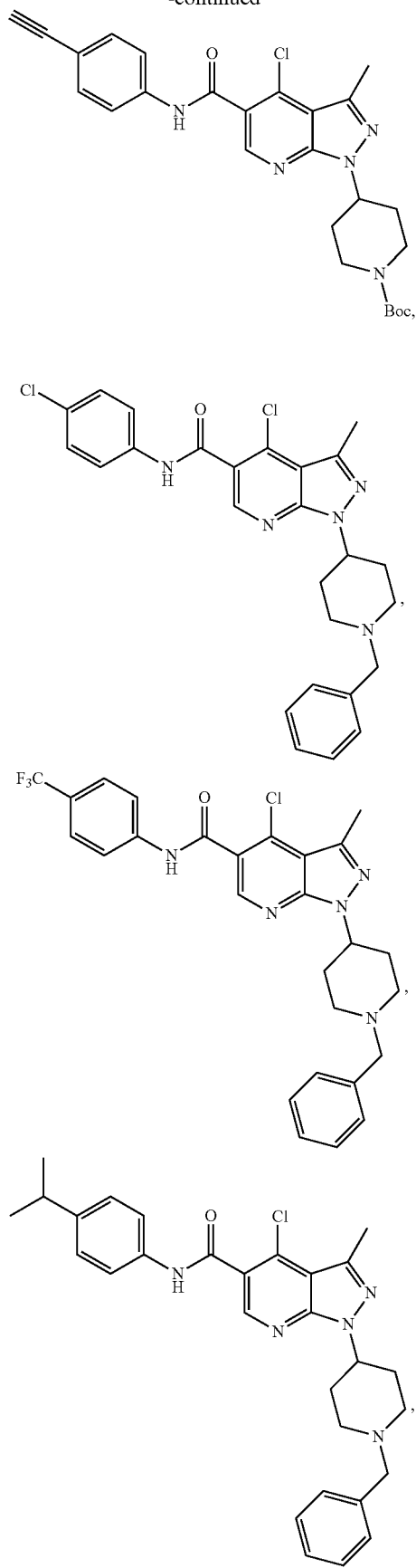

75
-continued
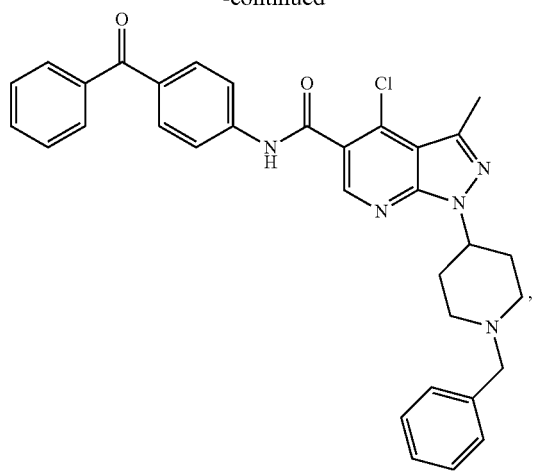
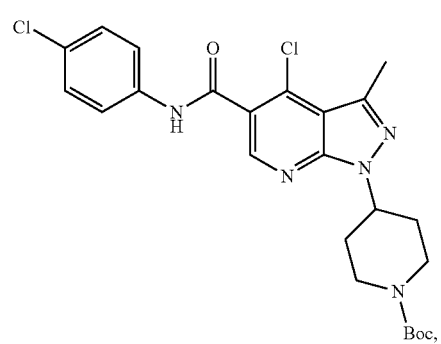
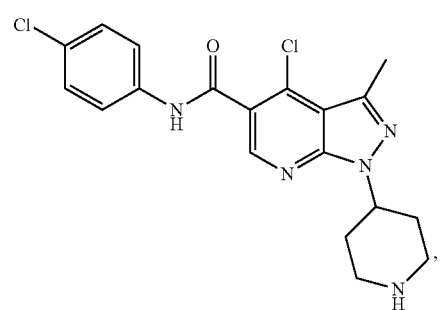
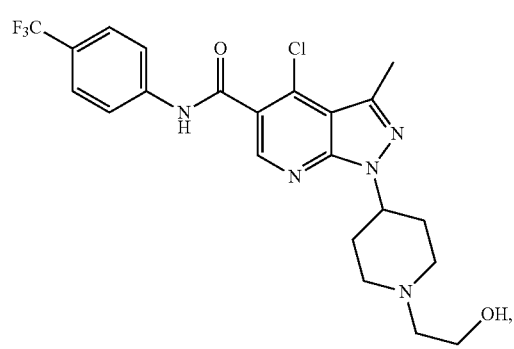
76
-continued
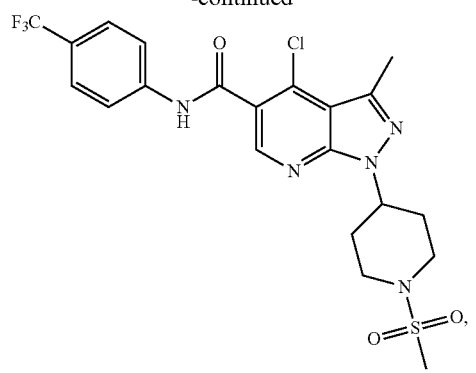
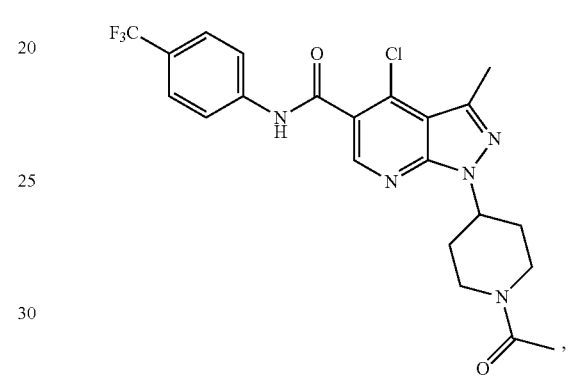
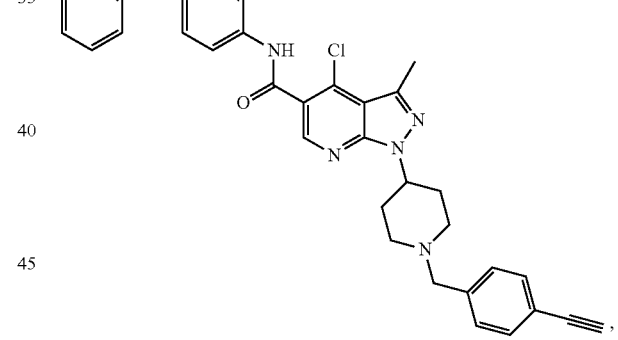
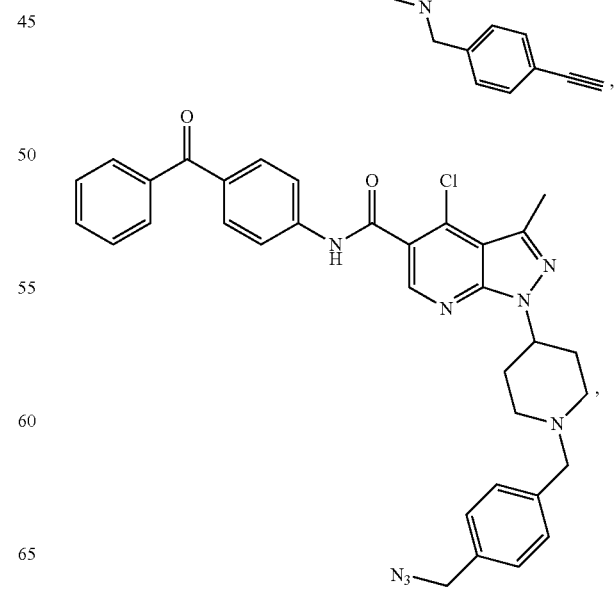

77
-continued
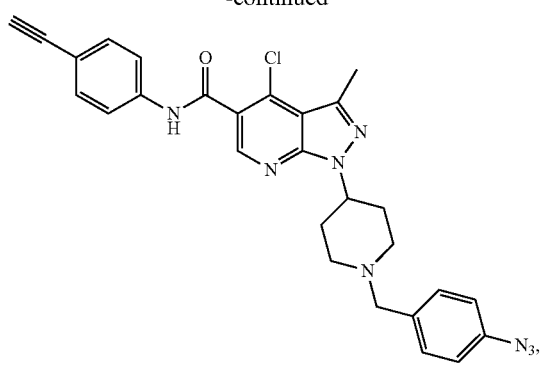
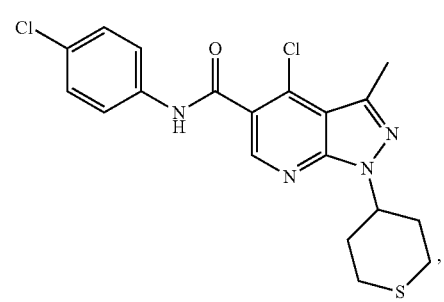
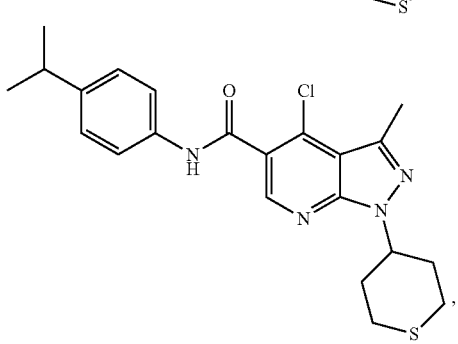
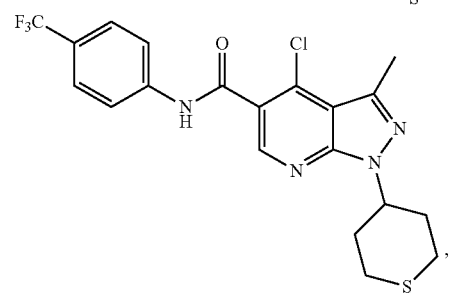
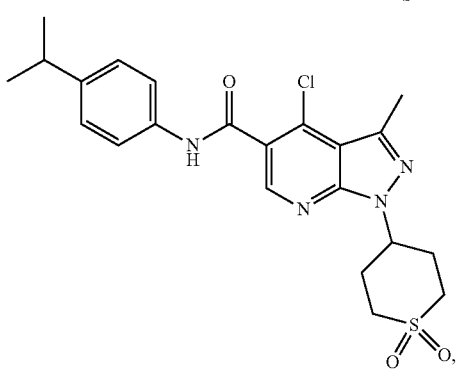
78
-continued
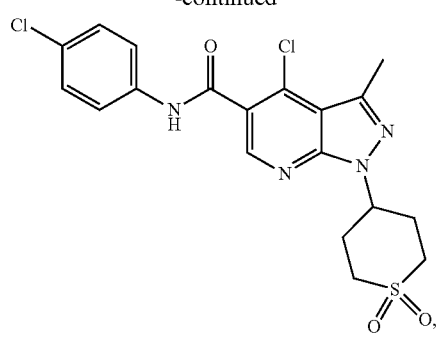
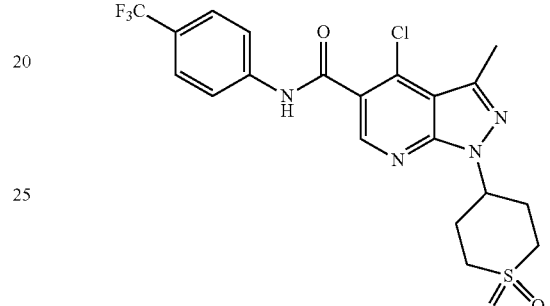
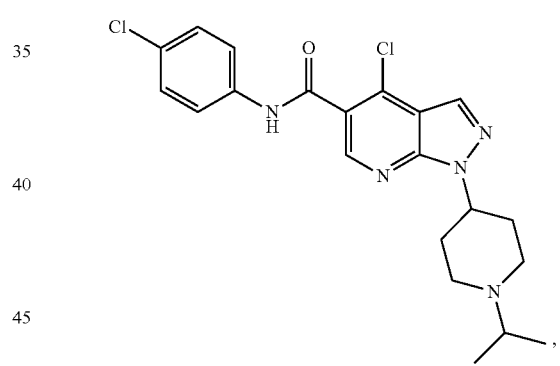
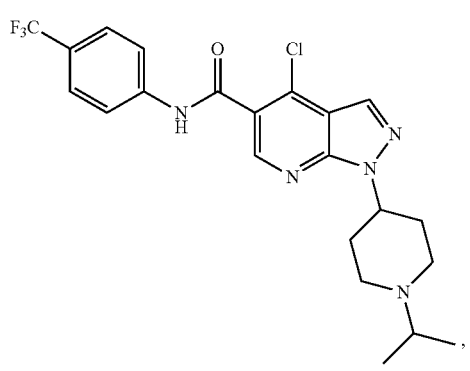

79
-continued
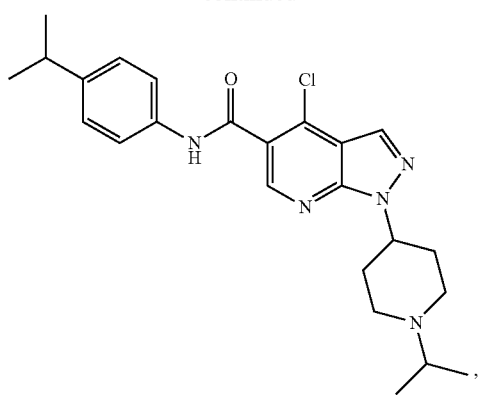
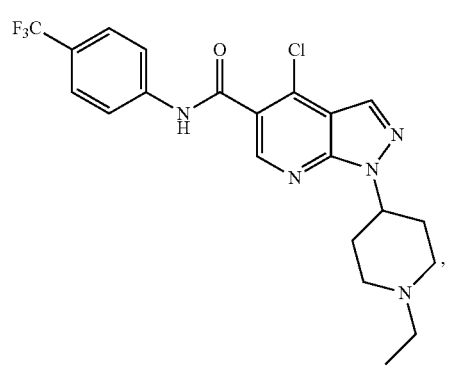
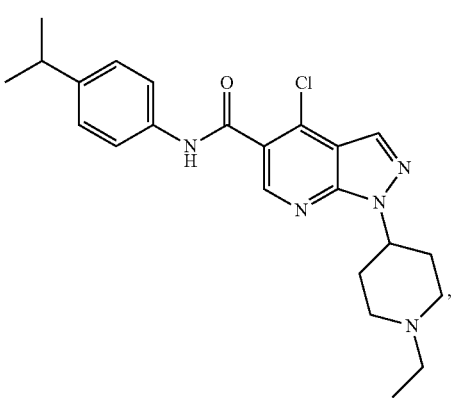
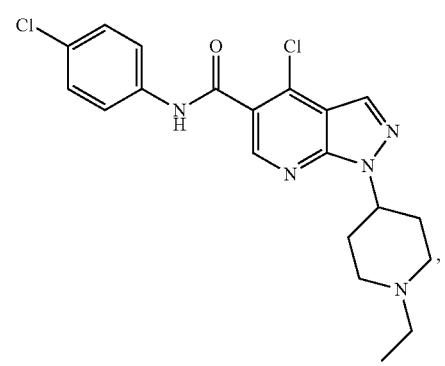
80
-continued
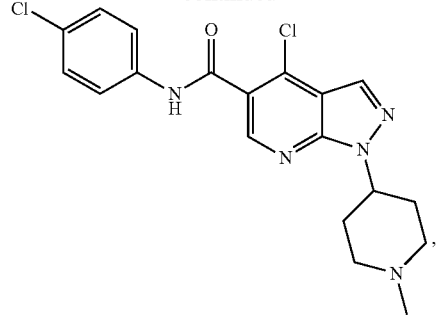
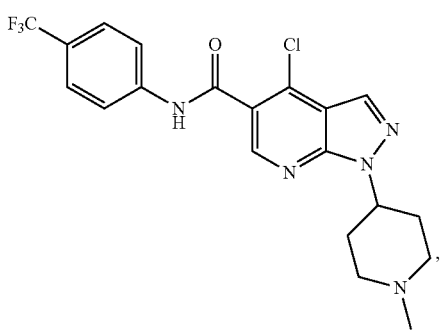
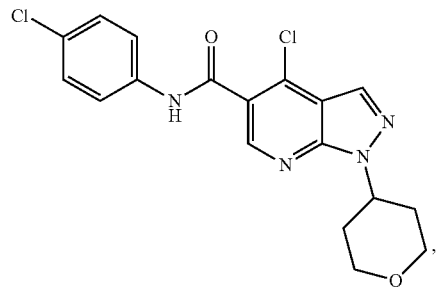
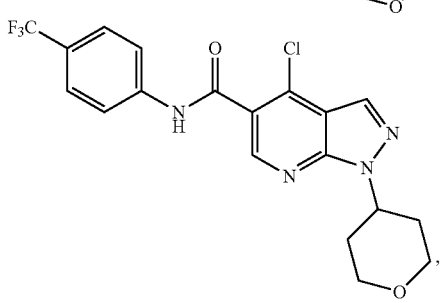
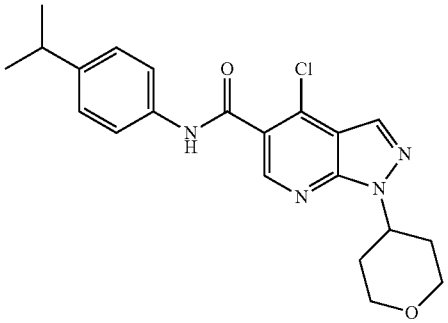

-continued
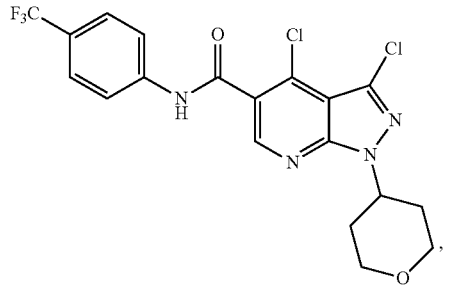
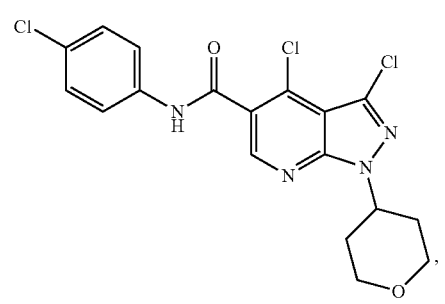
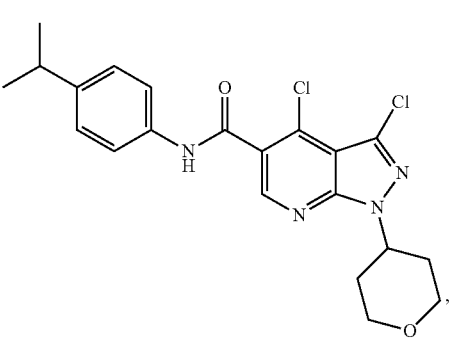
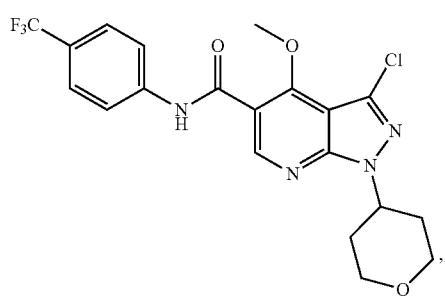
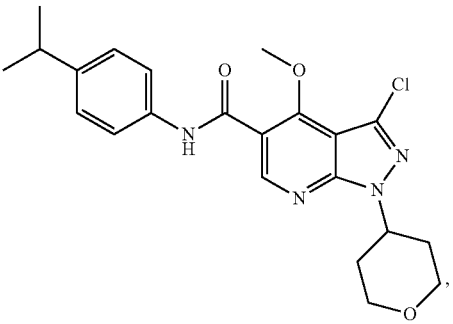
-continued
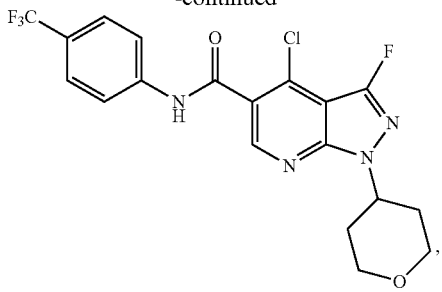
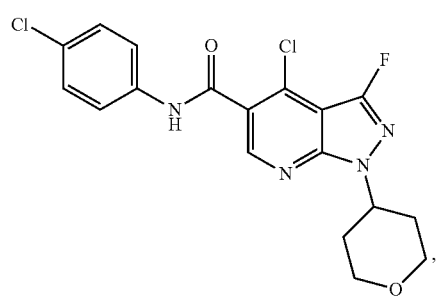
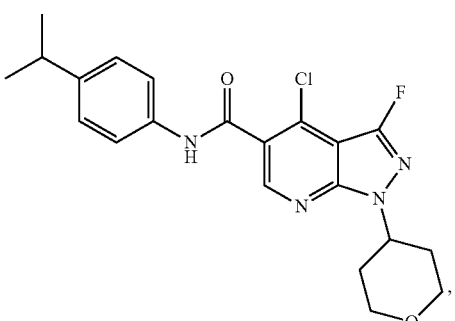
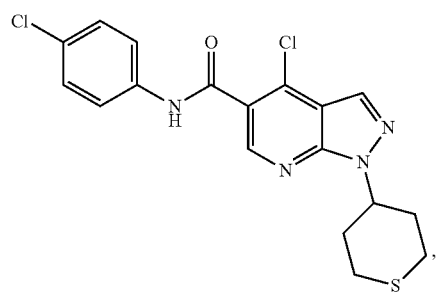
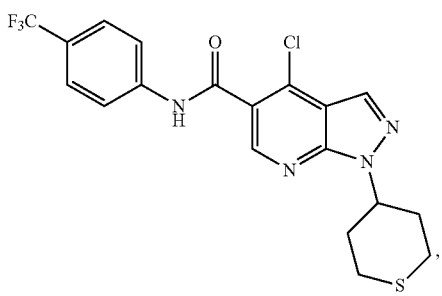

83
-continued
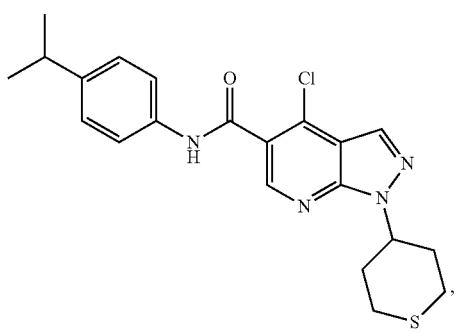
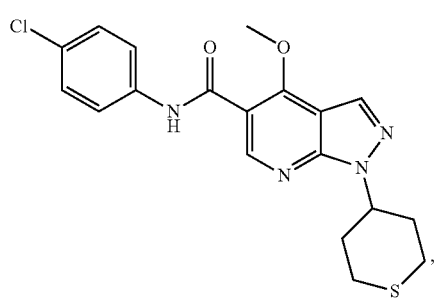
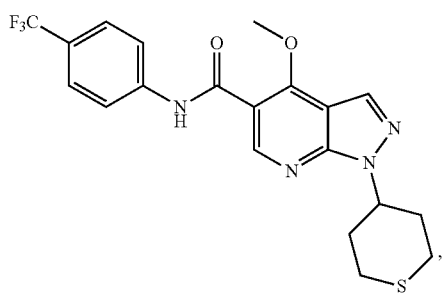
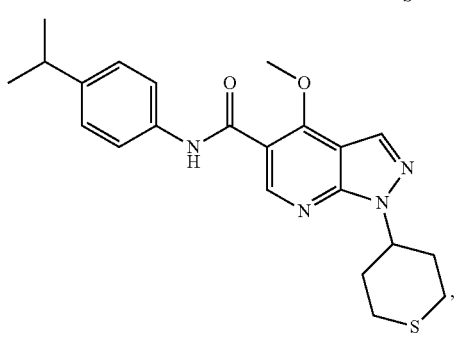
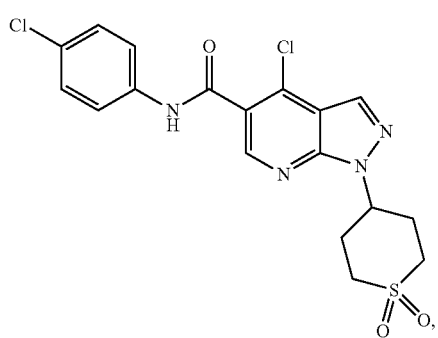
84
-continued
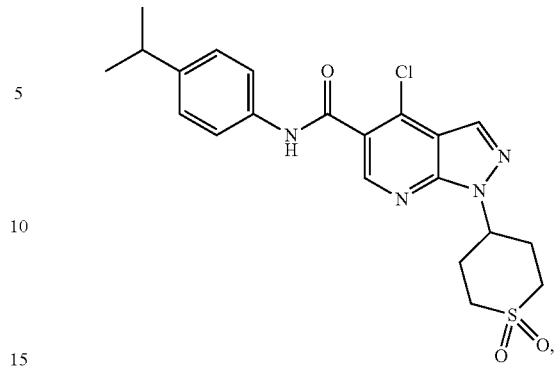
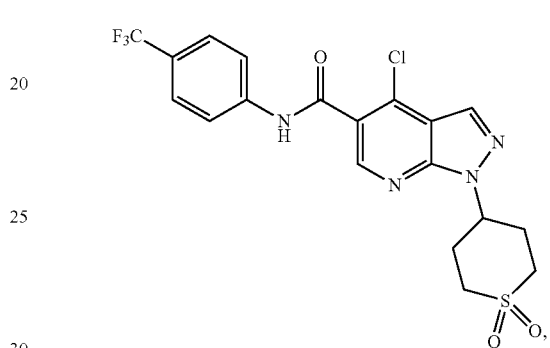
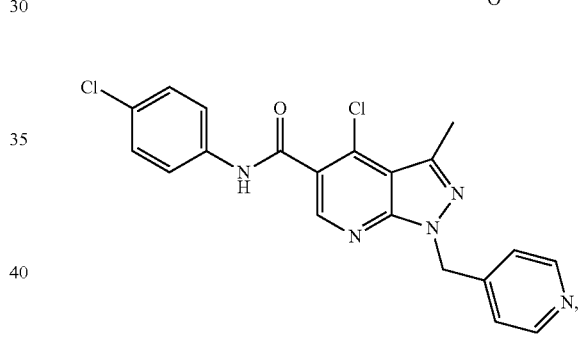
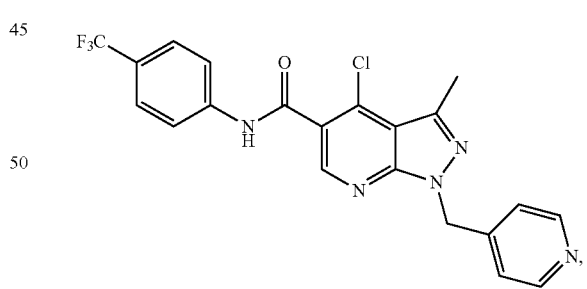
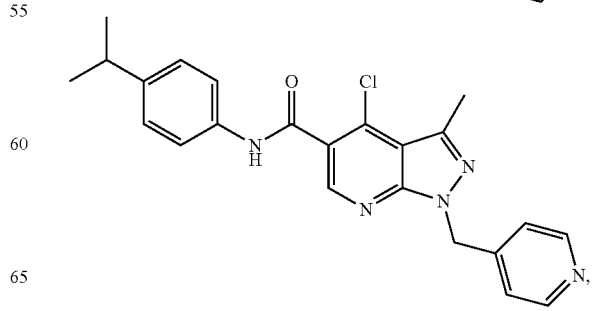

85
-continued
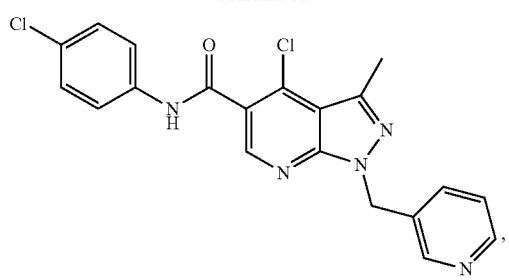
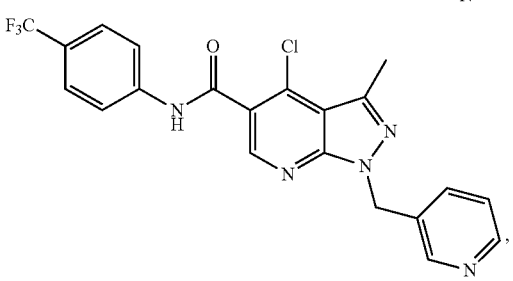
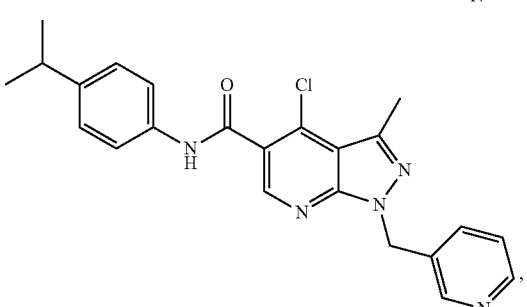
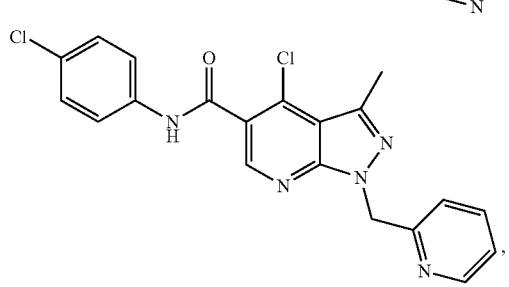
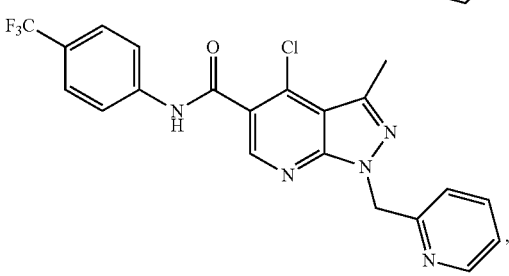
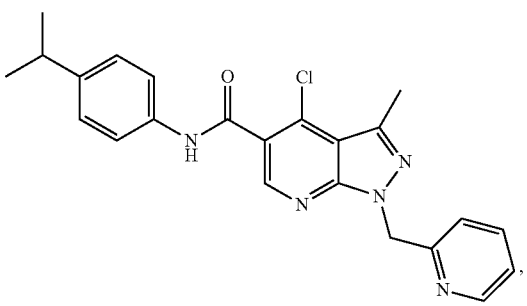
86
-continued
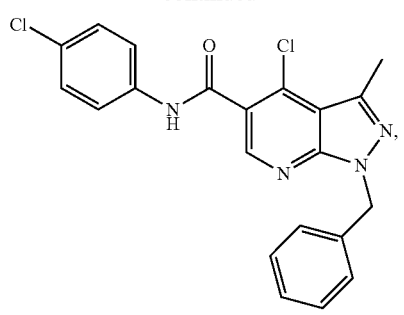
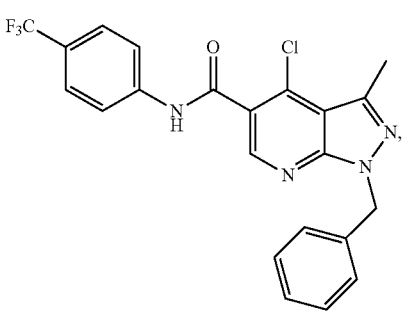
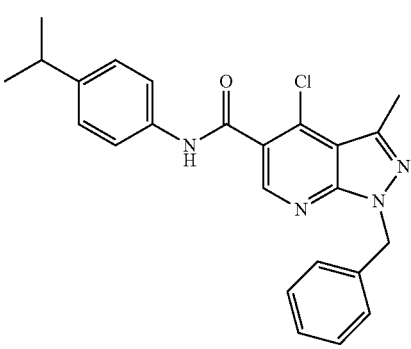
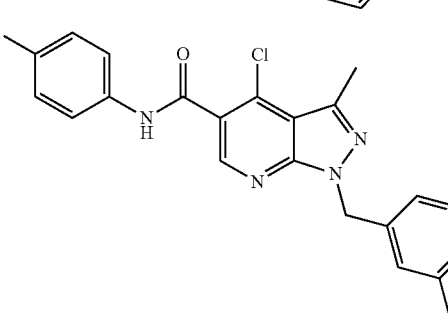
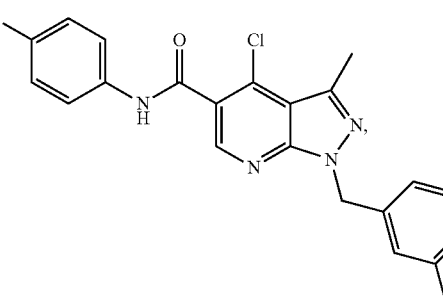

87
-continued
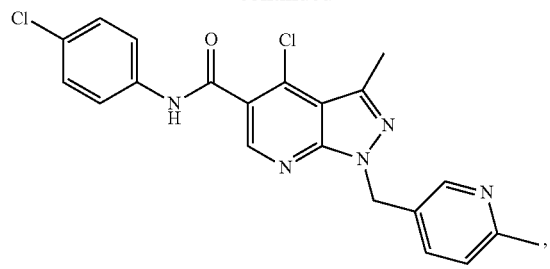
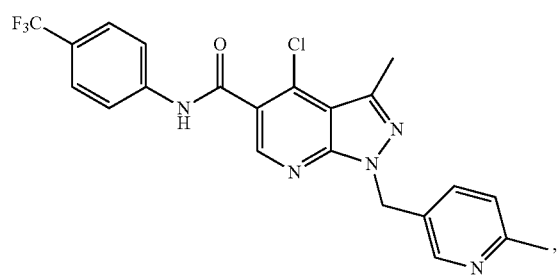
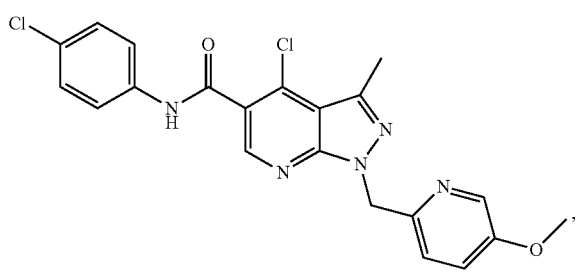
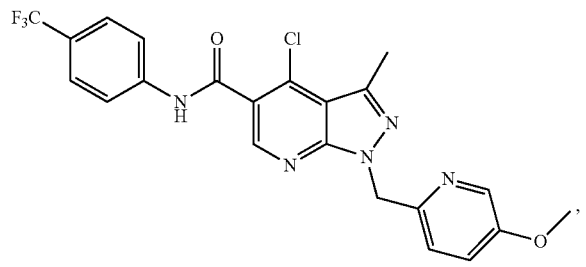
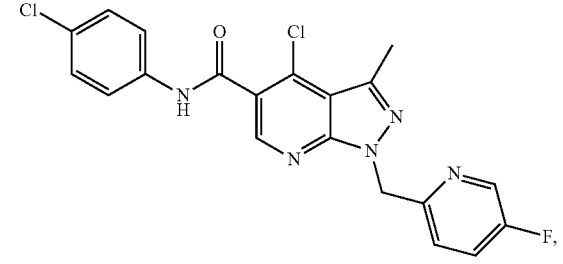
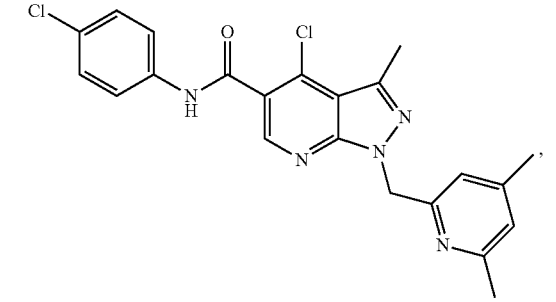
88
-continued
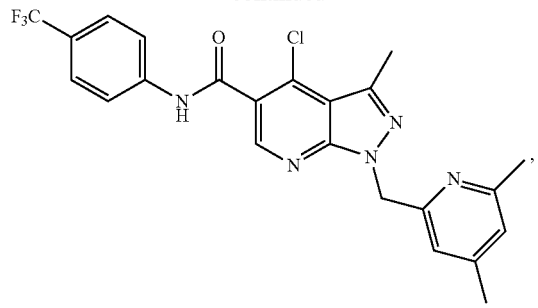
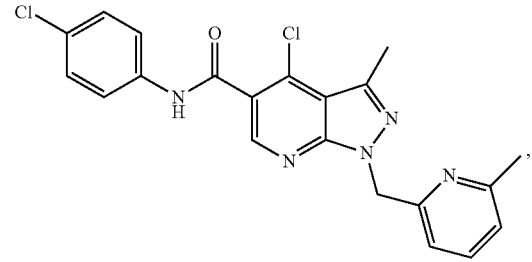
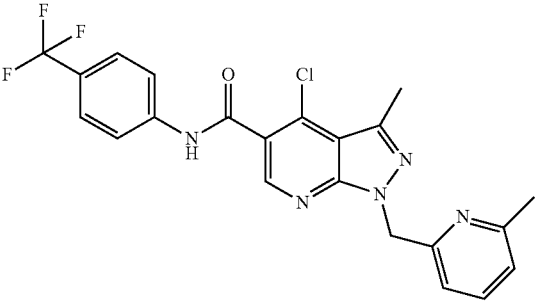
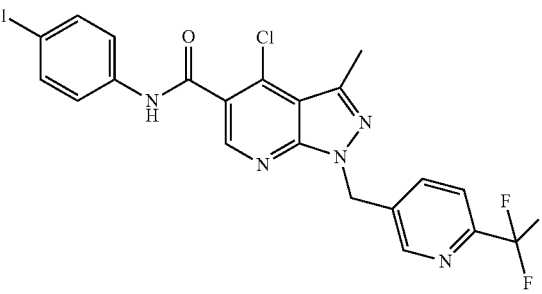
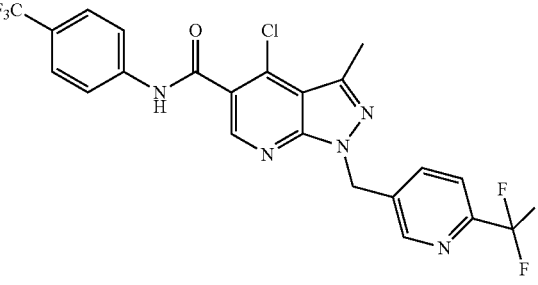
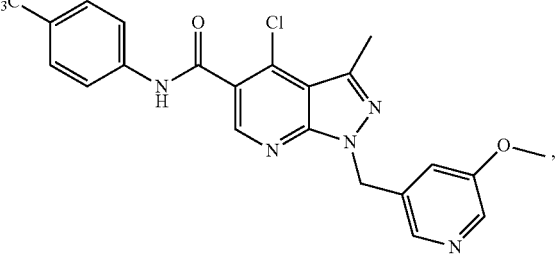

89
-continued
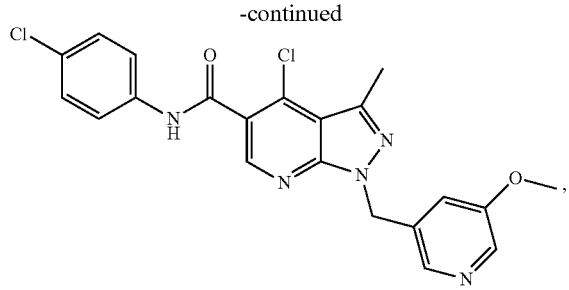
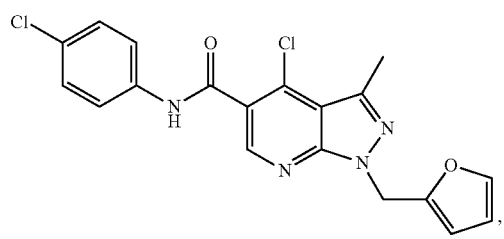
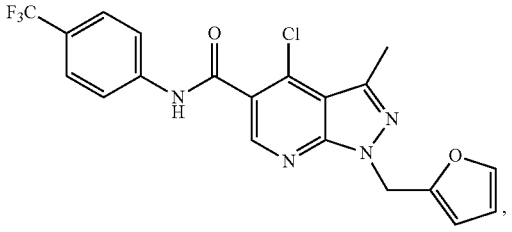
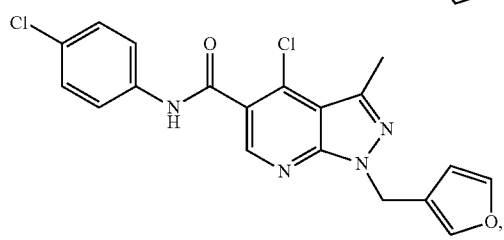
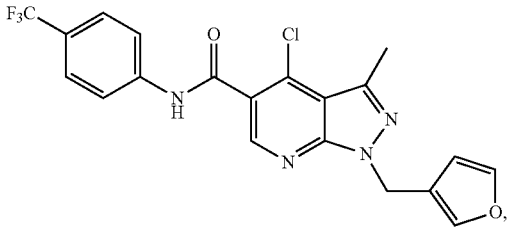
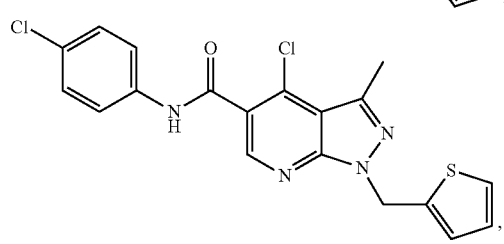
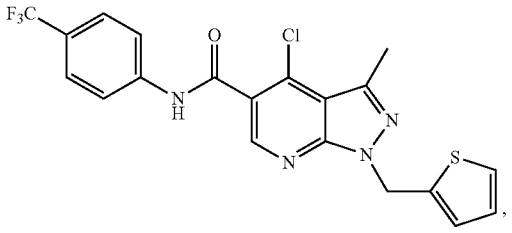
90
-continued
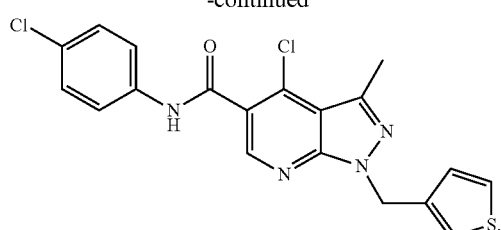
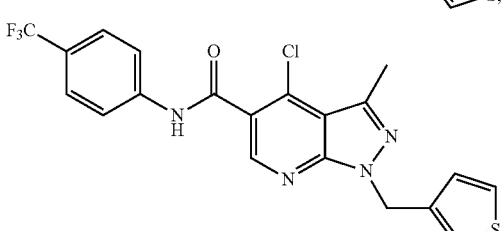
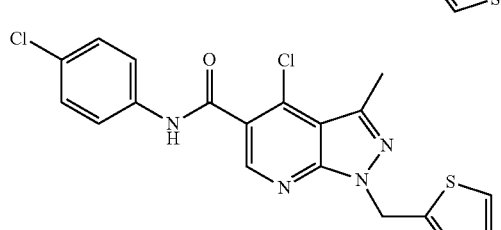
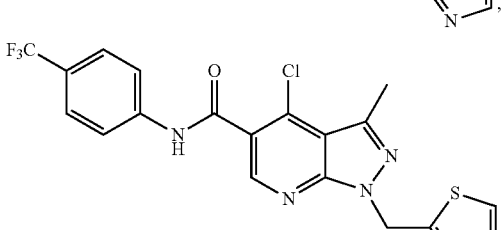
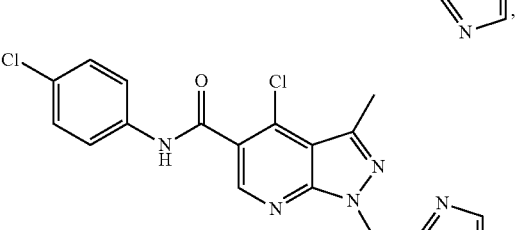
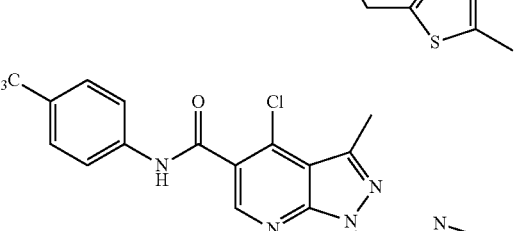
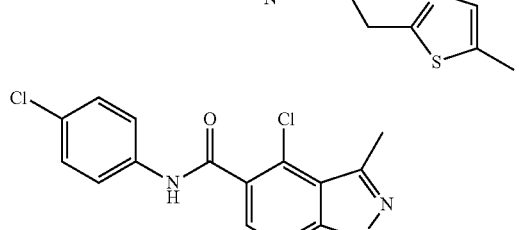

91
-continued
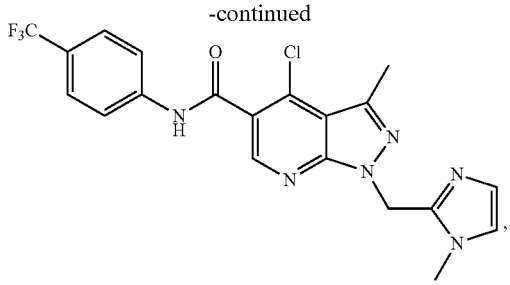
92
-continued
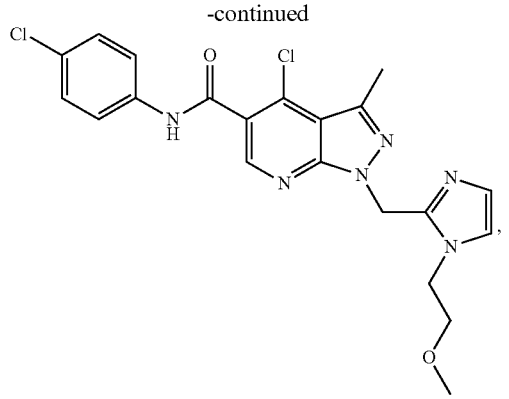
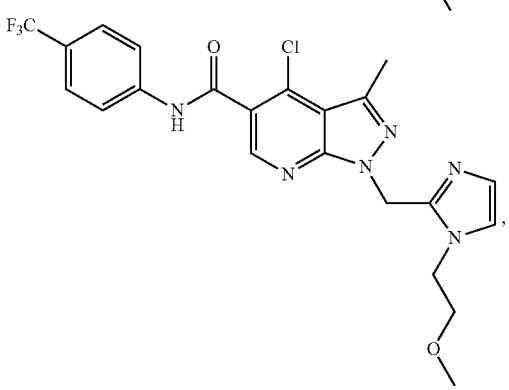
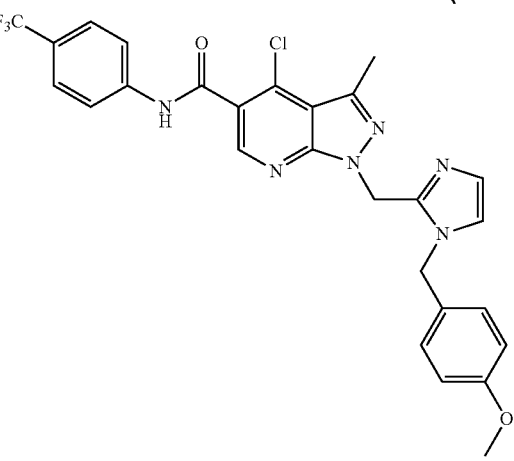
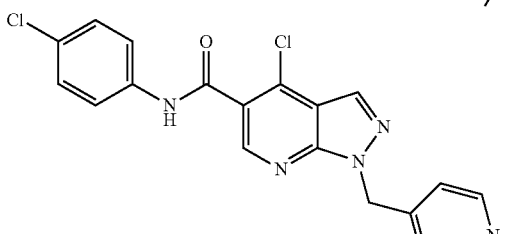
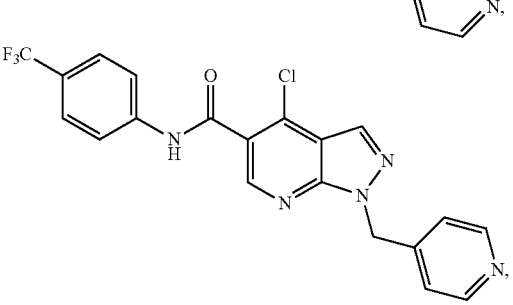

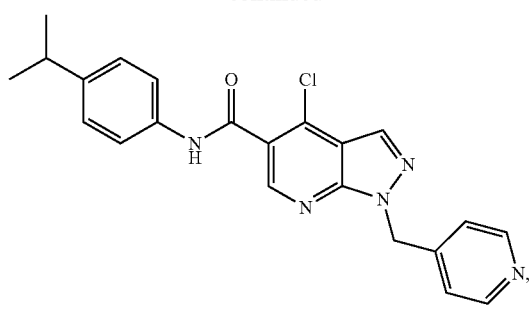
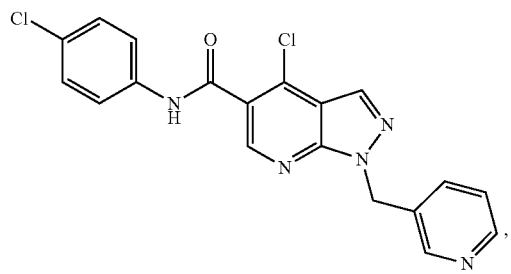
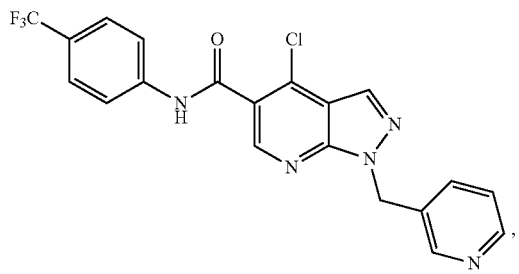
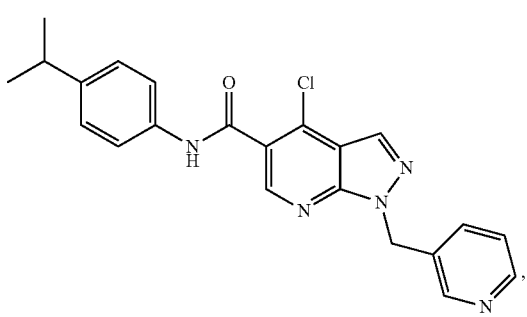
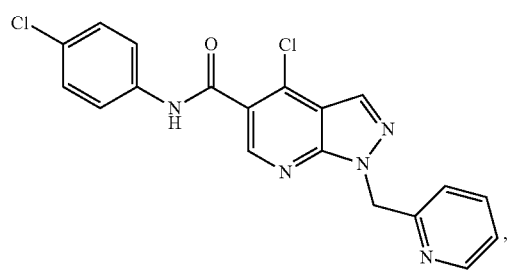
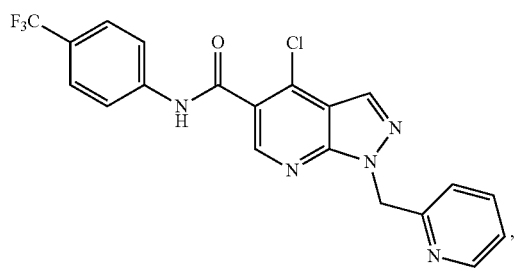
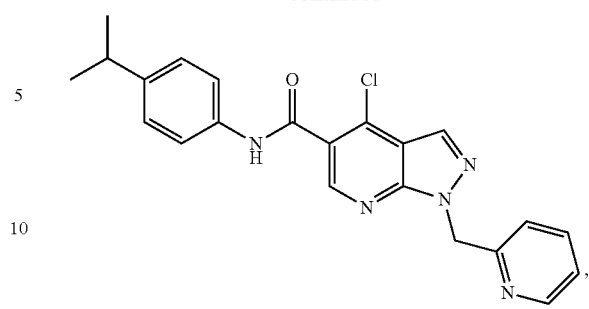
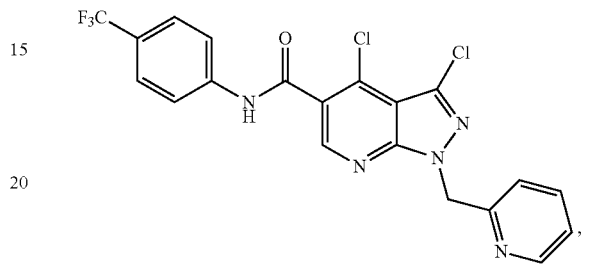
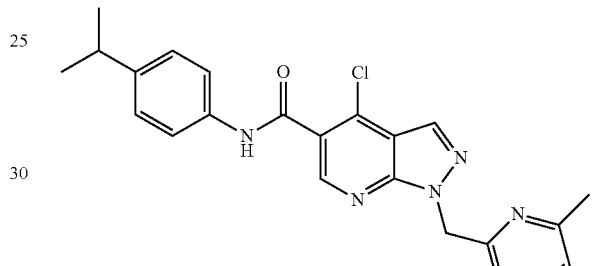
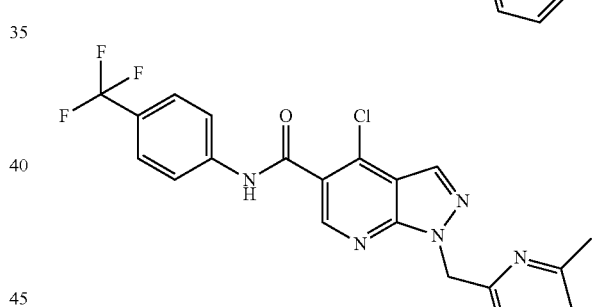
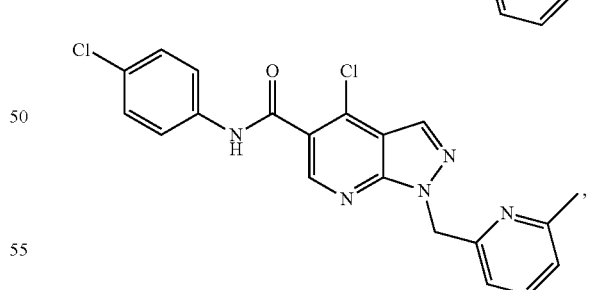
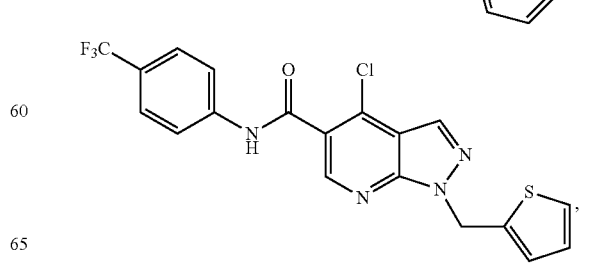

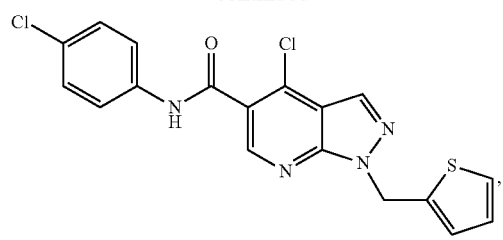
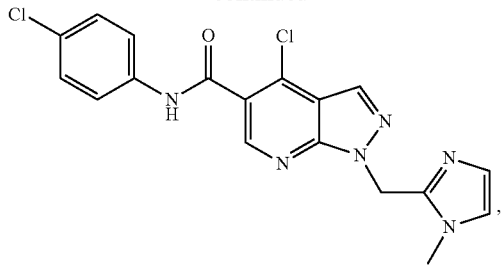
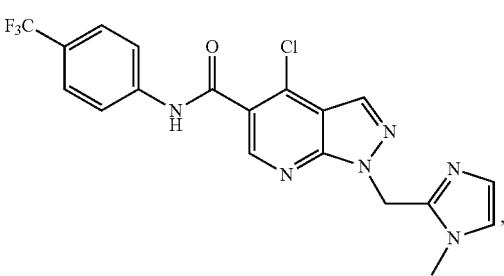
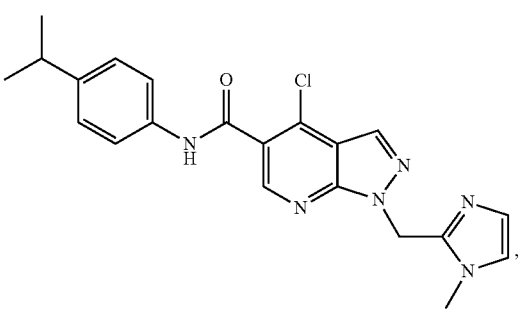
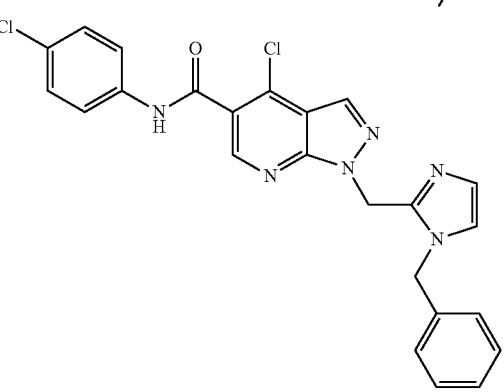
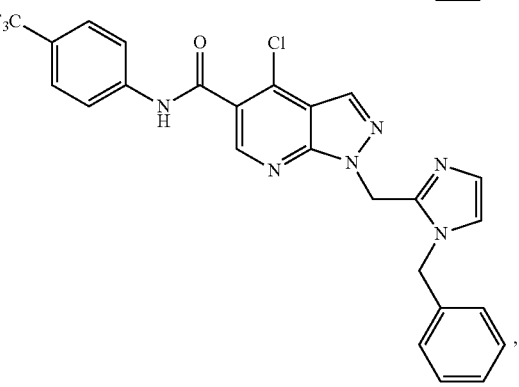

97
-continued
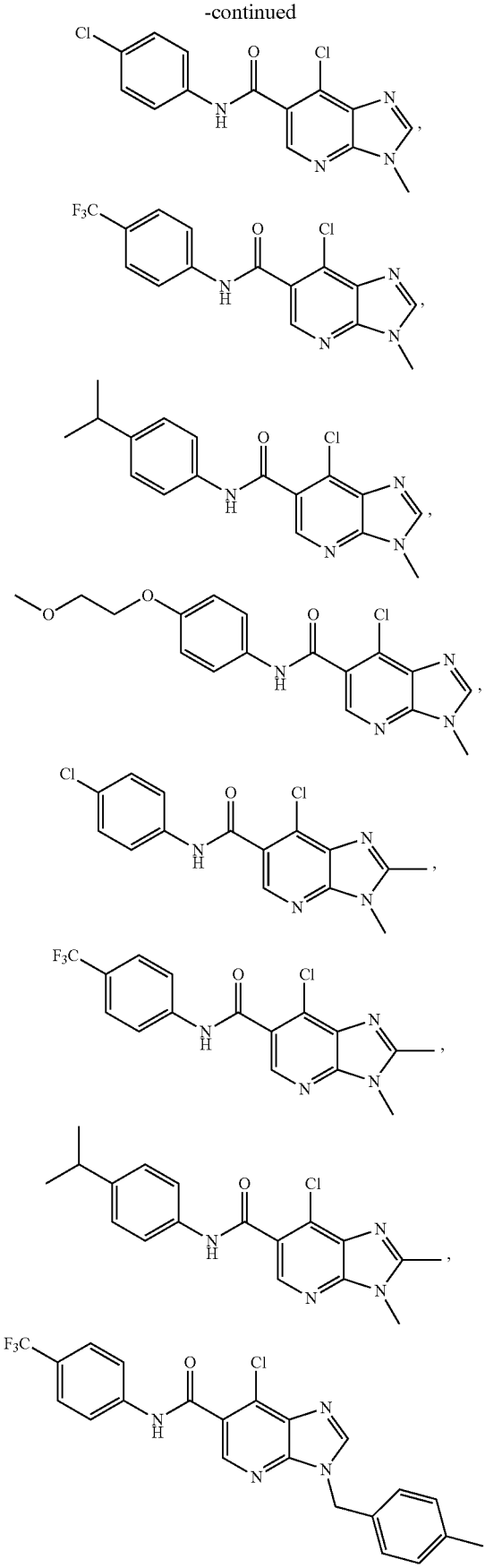
98
-continued
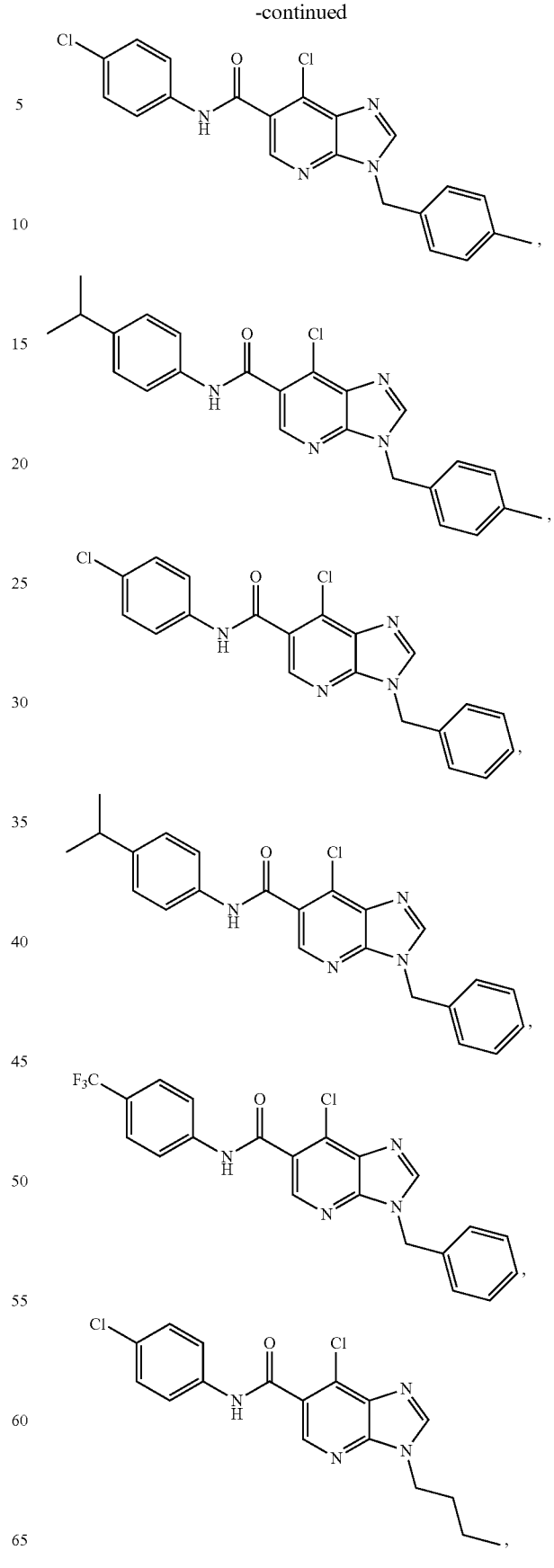

99
-continued
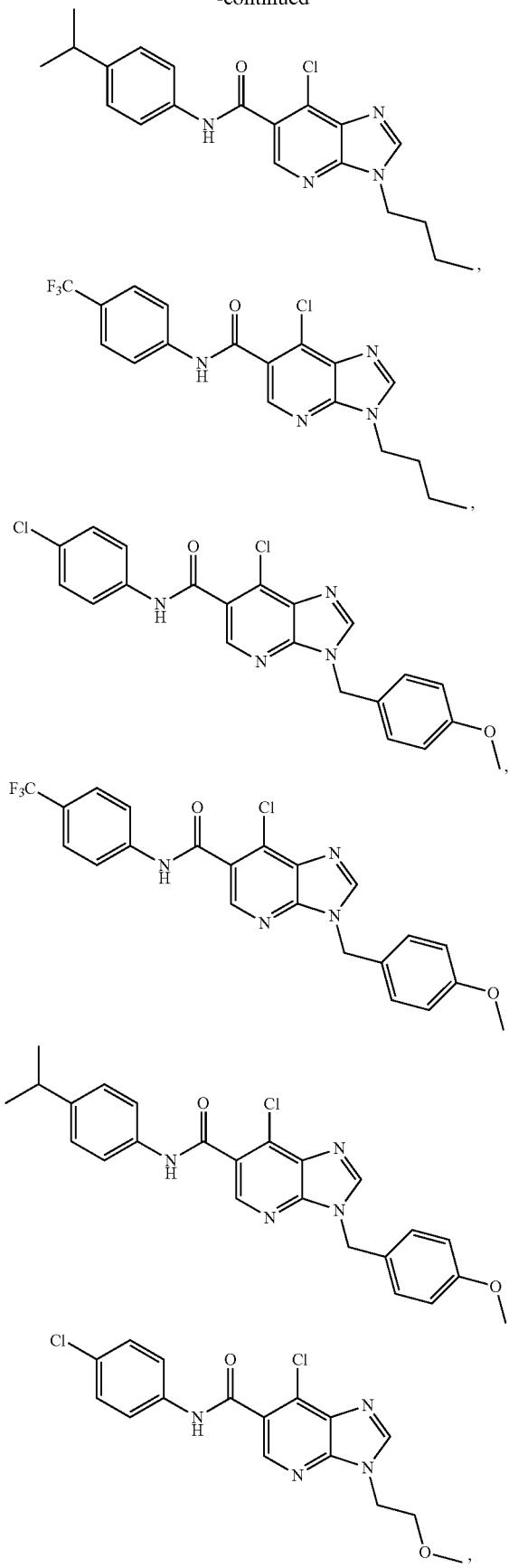
100
-continued
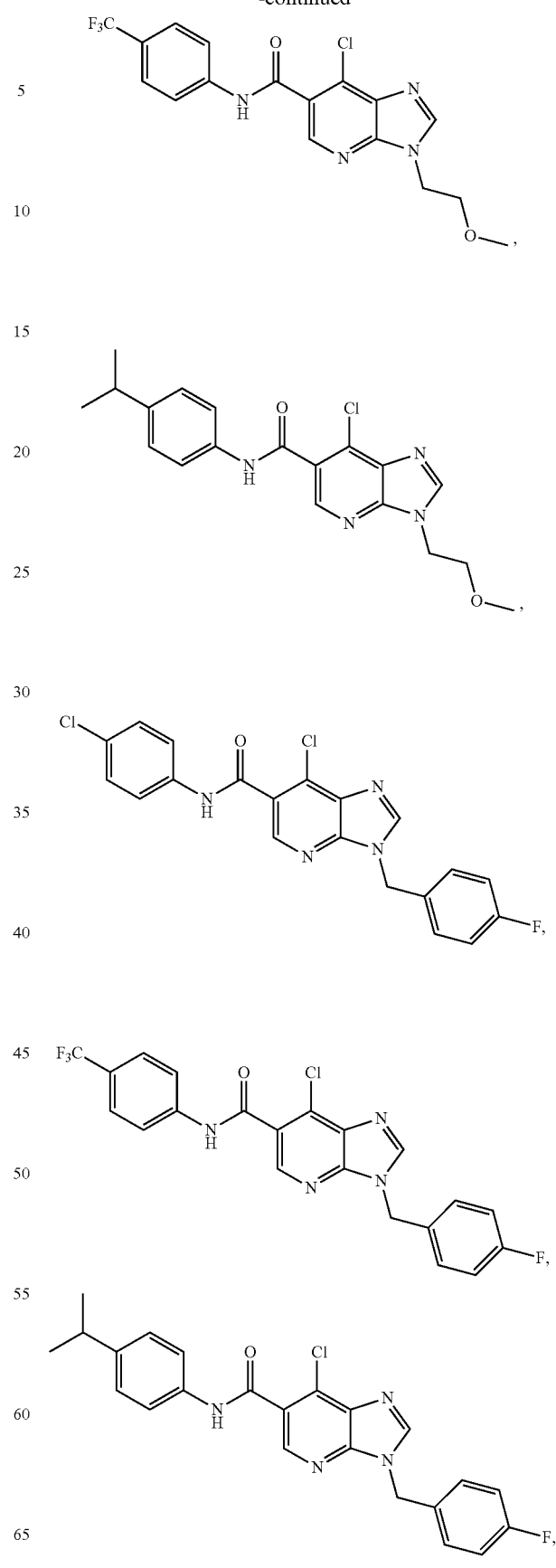

101
-continued
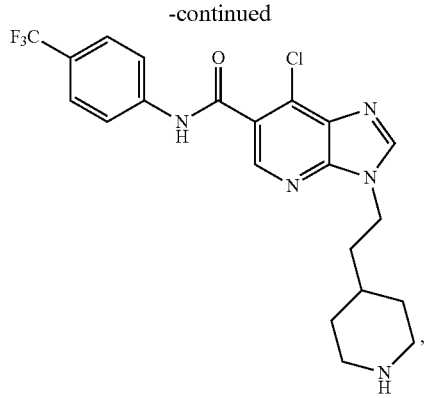
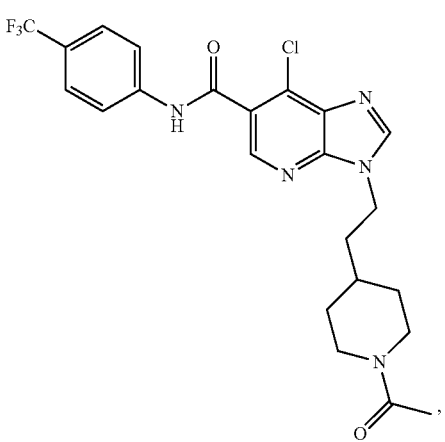
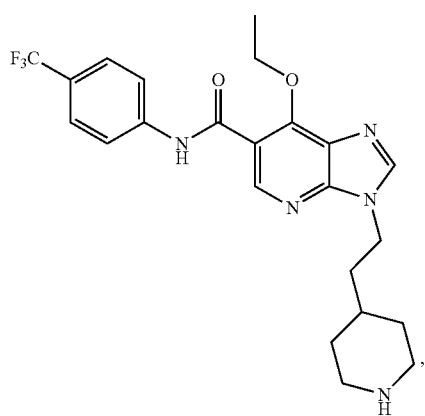
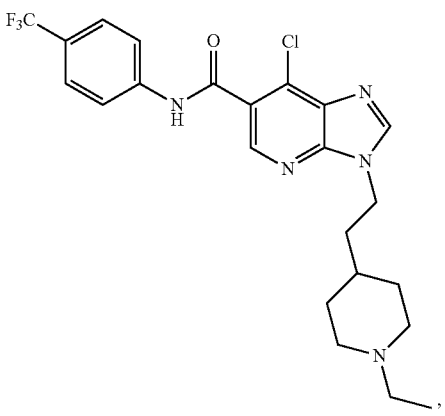
102
-continued
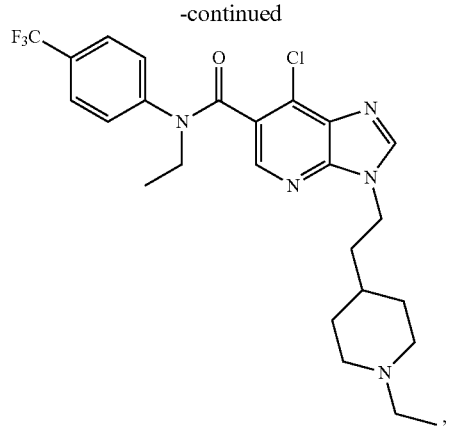
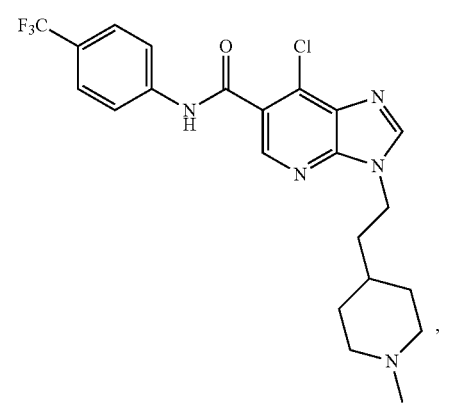
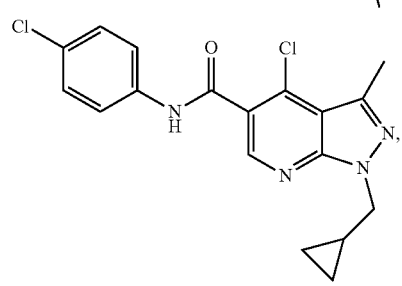
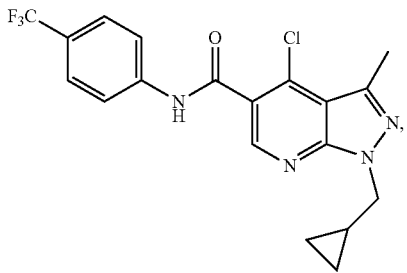
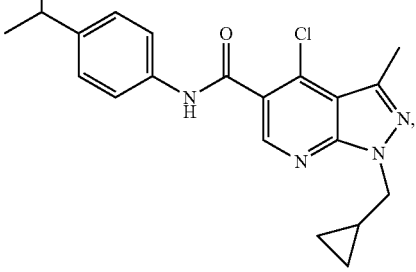

103
-continued
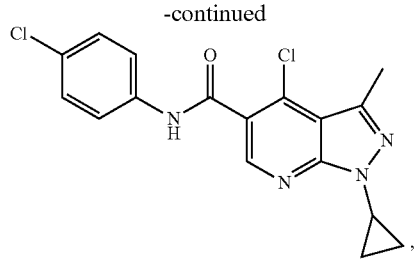
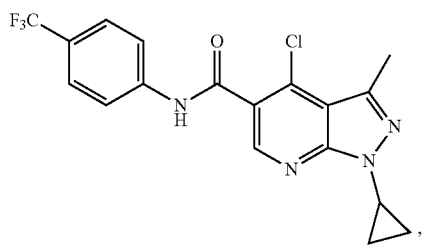
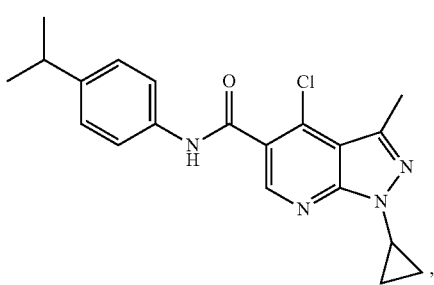
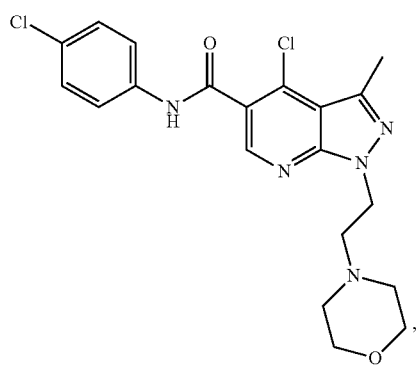
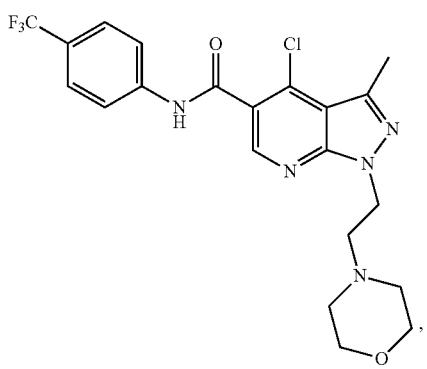
104
-continued
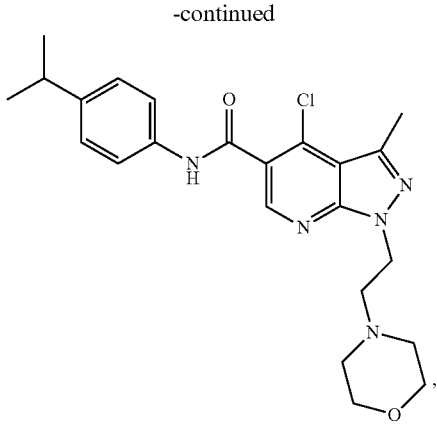
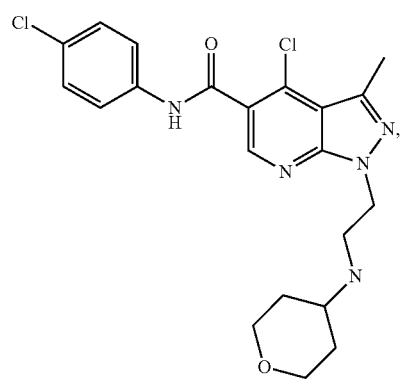
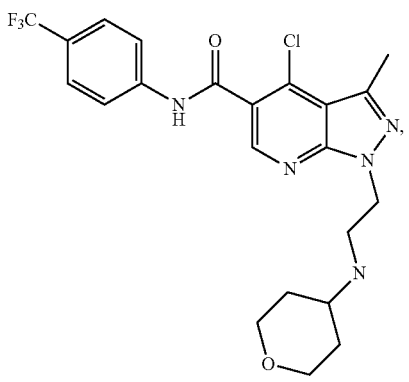
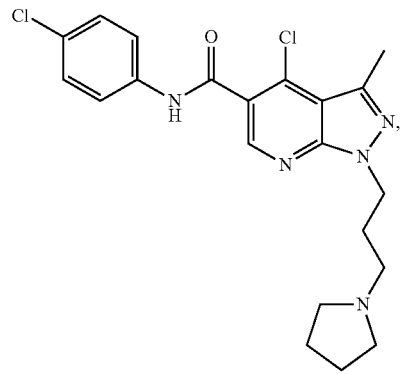

105
-continued
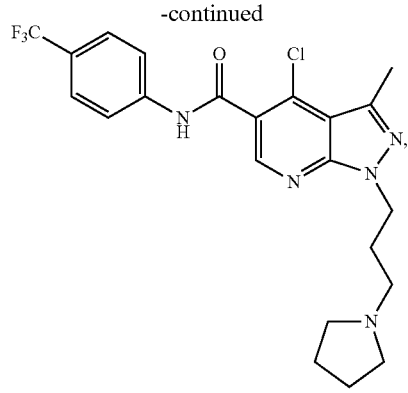
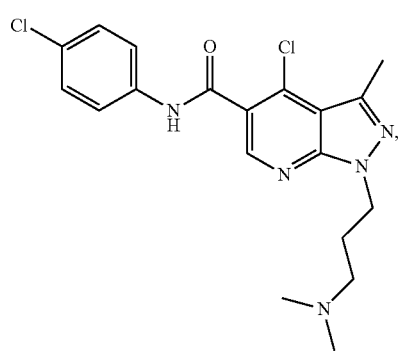
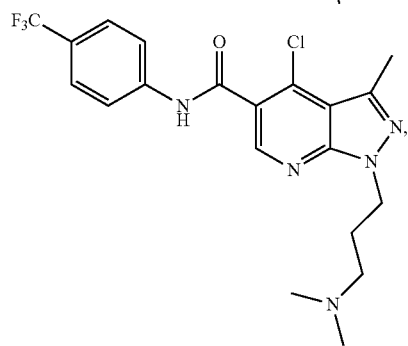
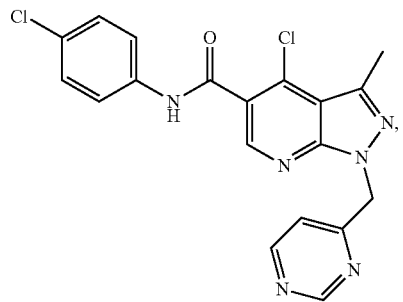
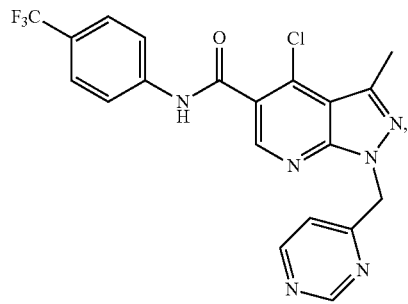
106
-continued
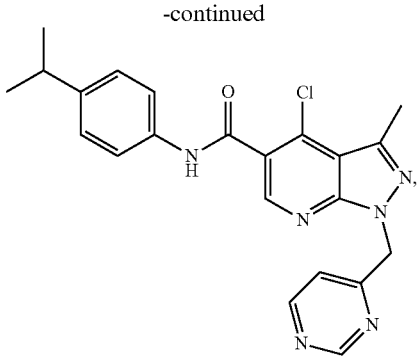
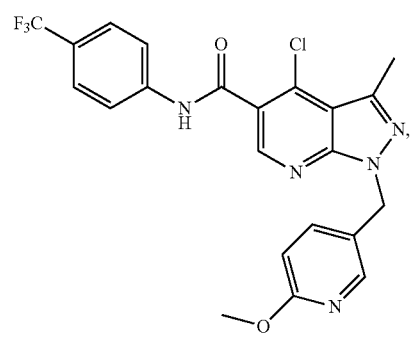
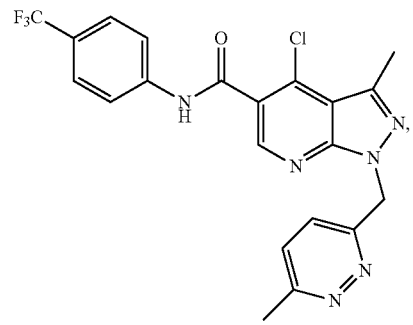
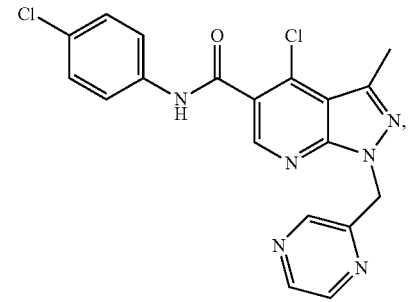
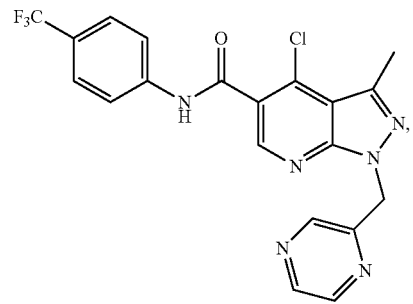

107
-continued
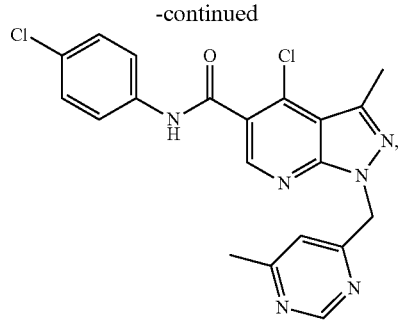
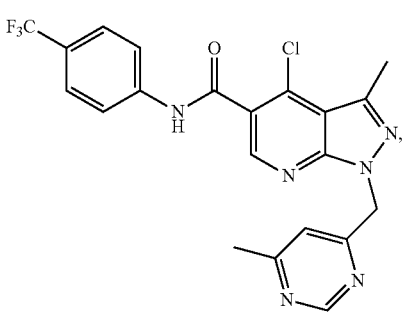
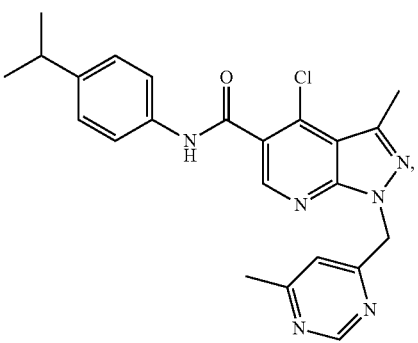
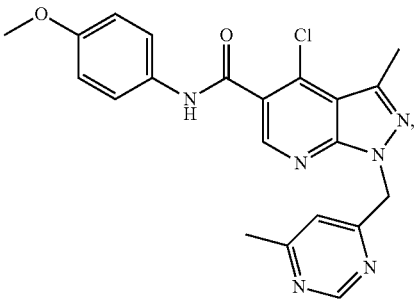
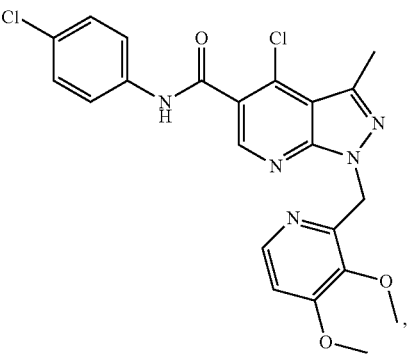
108
-continued
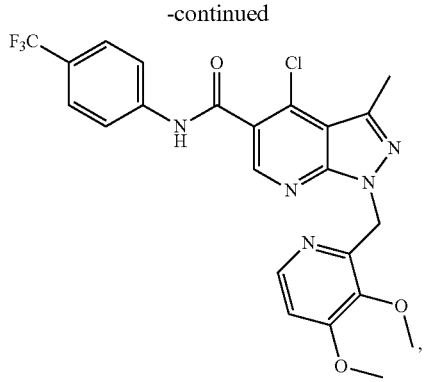
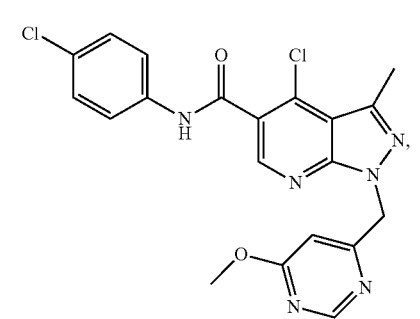
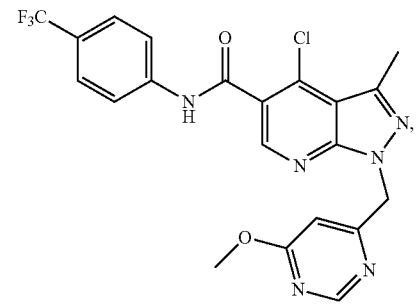
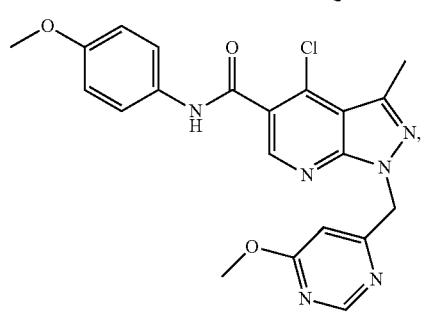
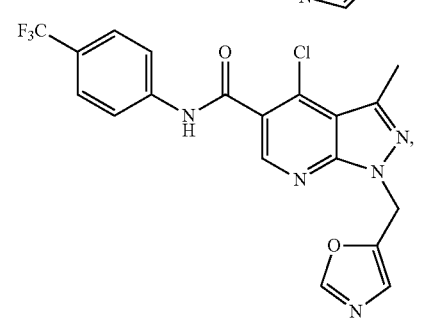

109
-continued
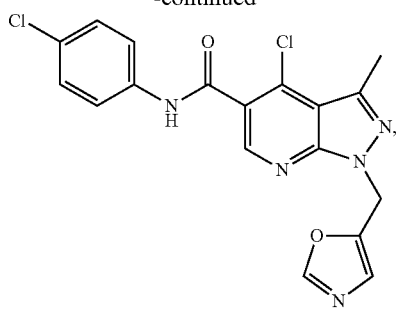
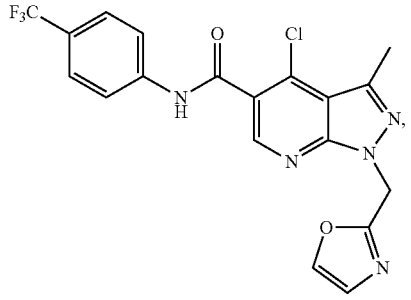
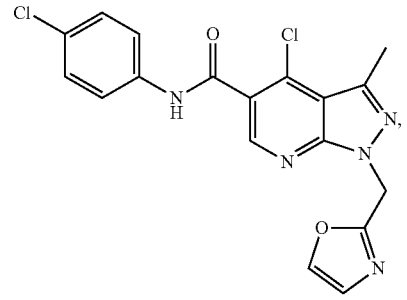
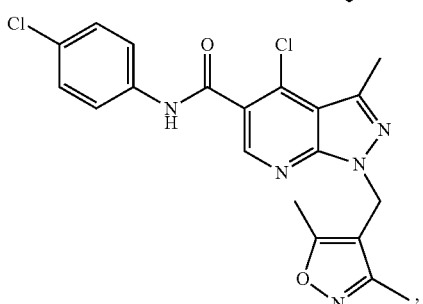
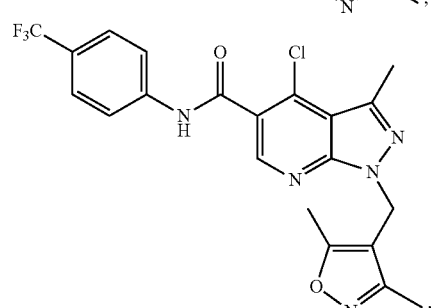
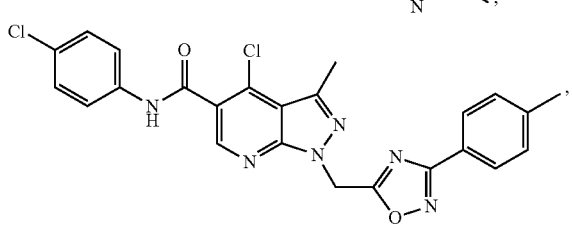
110
-continued
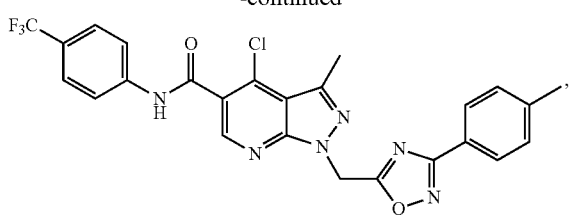
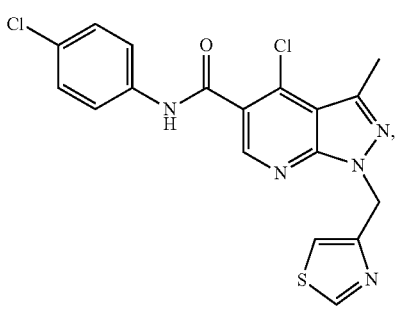
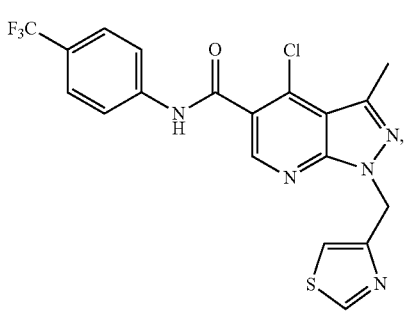
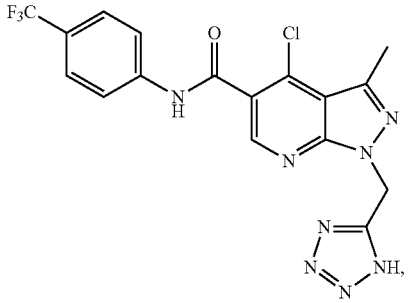
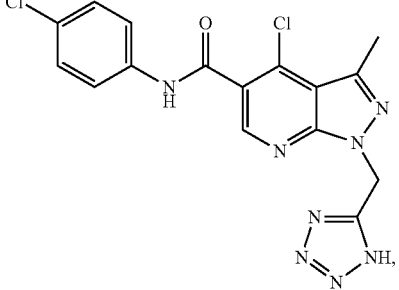

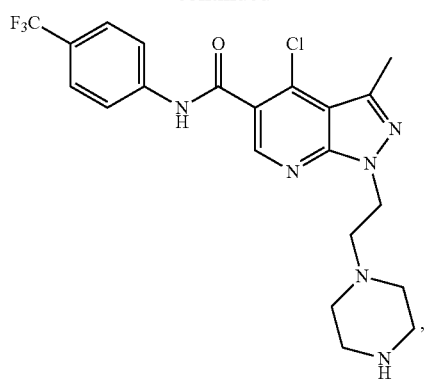
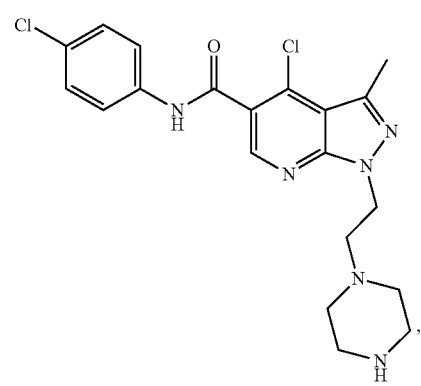
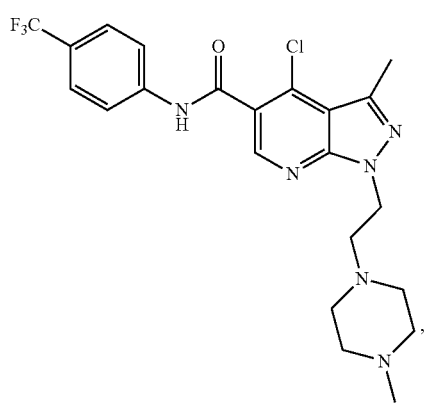
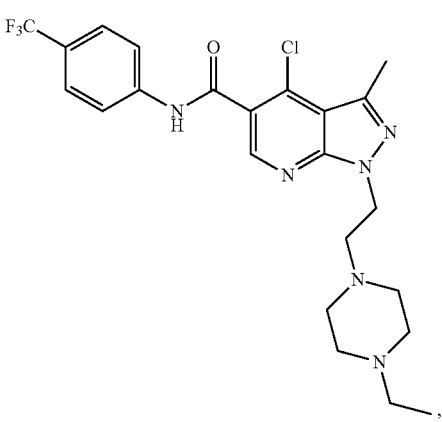
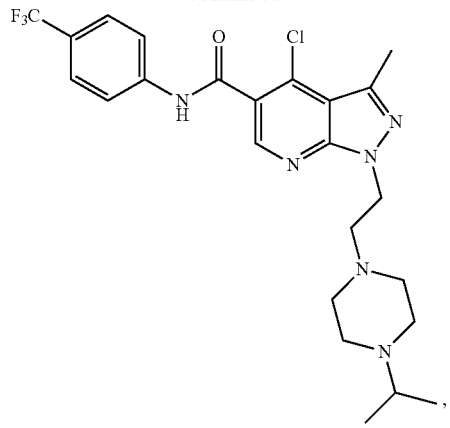
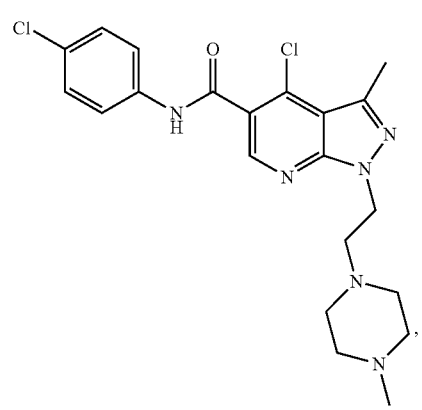
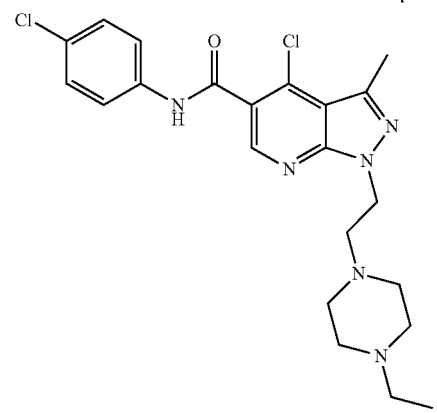
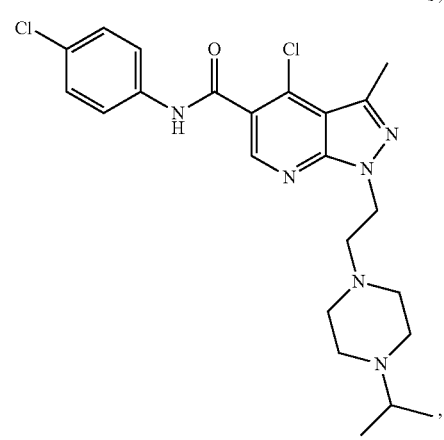

113
-continued
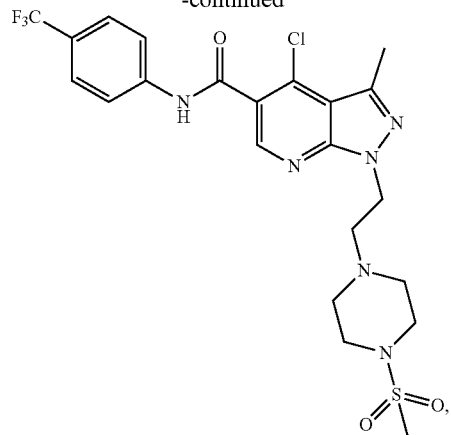
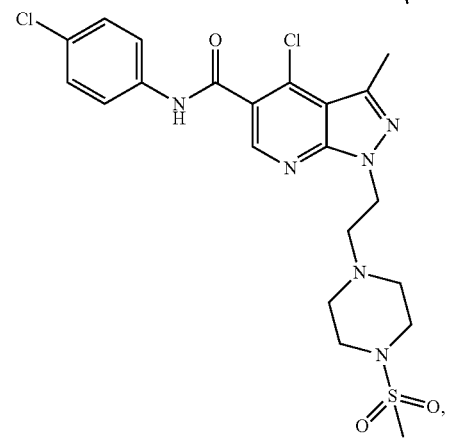
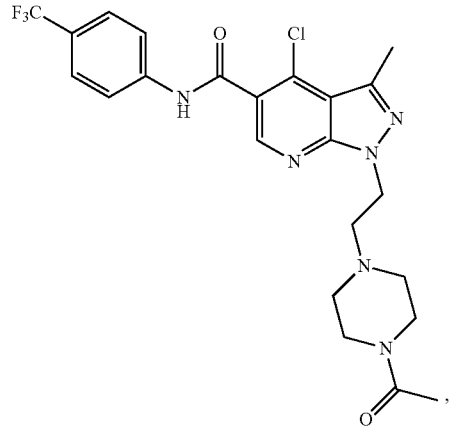
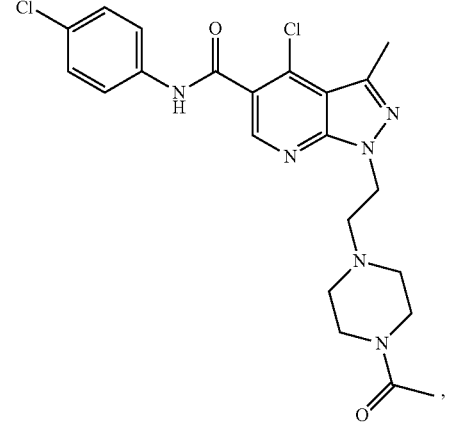
114
-continued
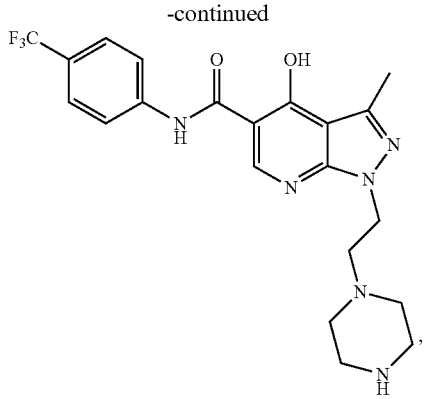
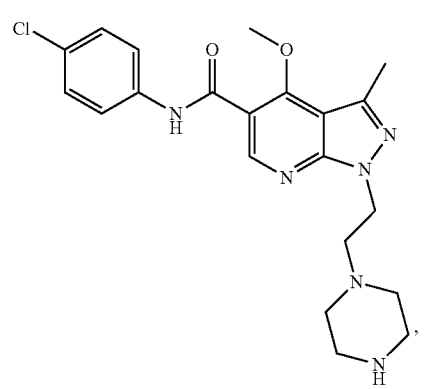
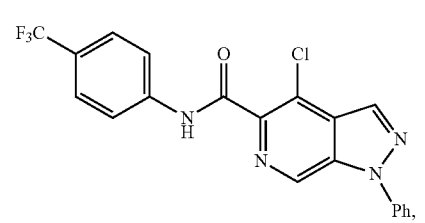
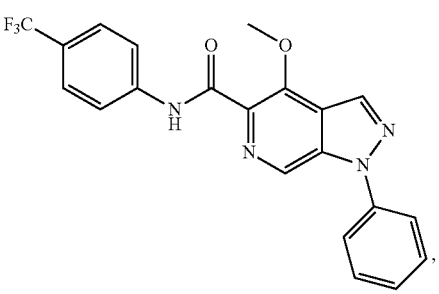
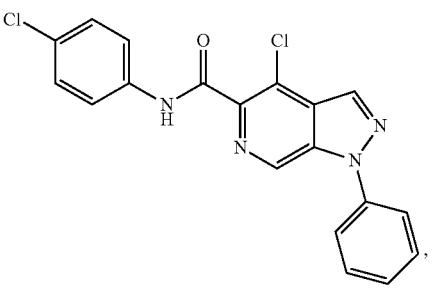

115
-continued
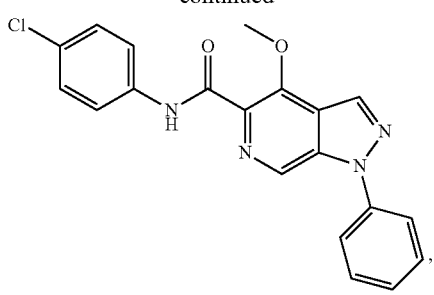
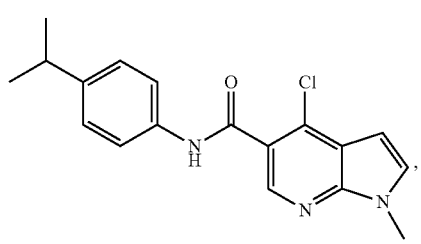
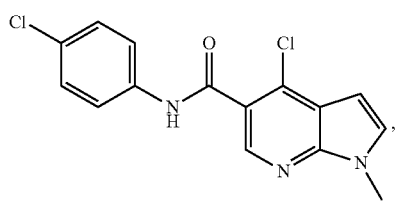
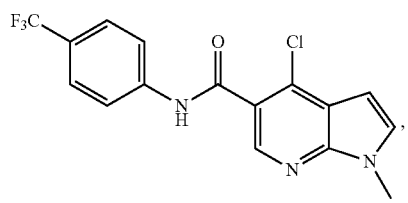
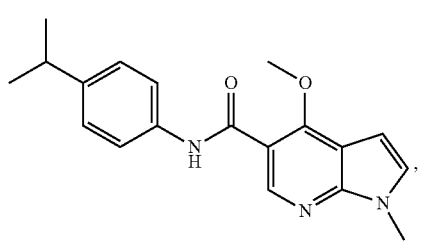
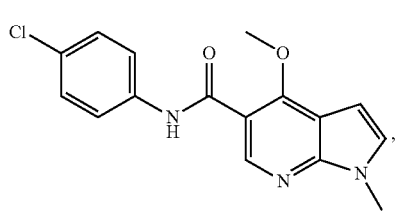
116
-continued
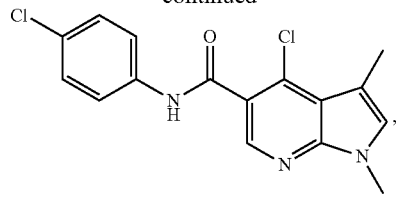
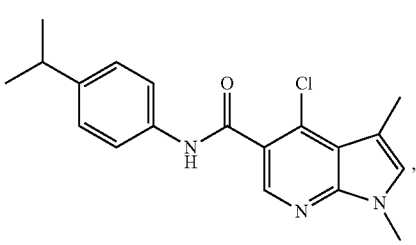
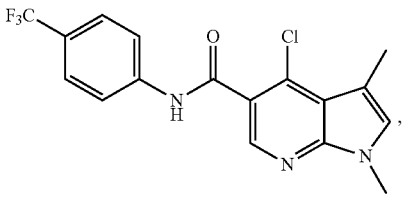
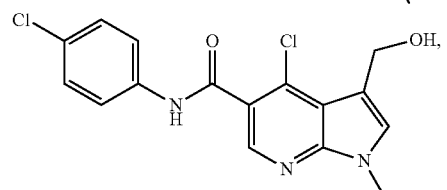
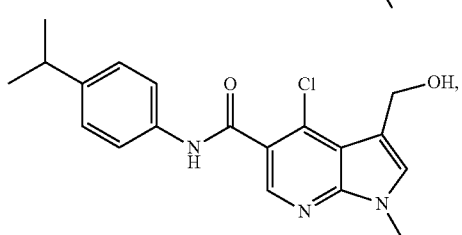
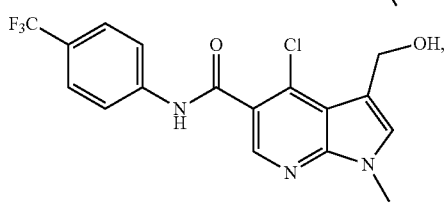
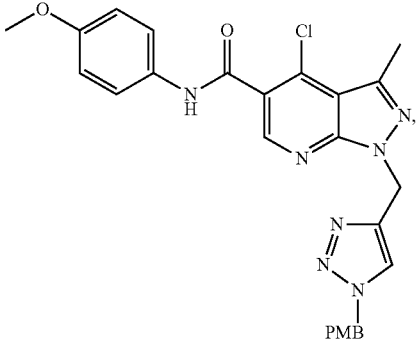

117
-continued
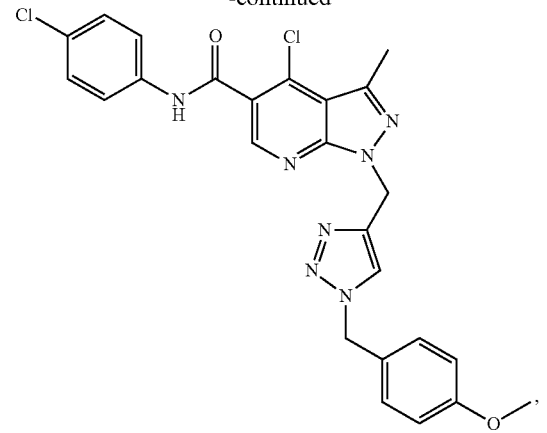
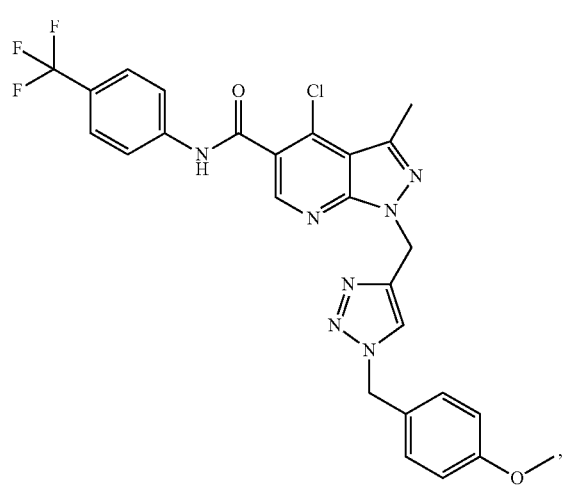
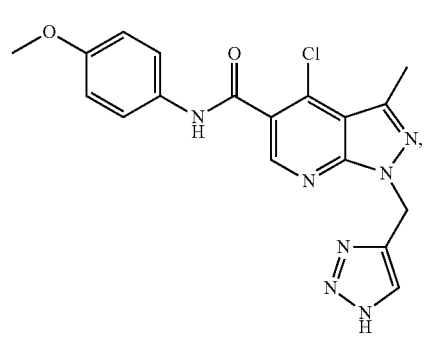
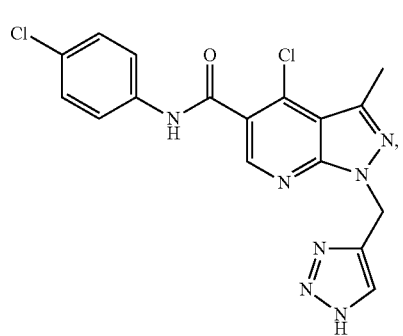
118
-continued
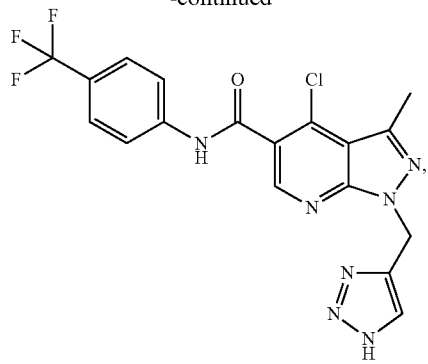
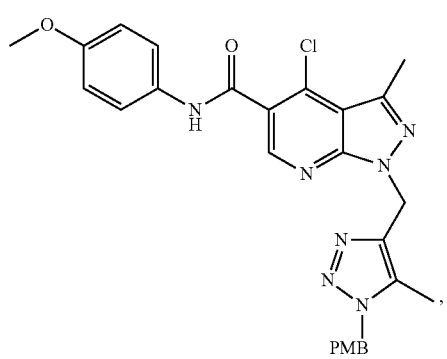
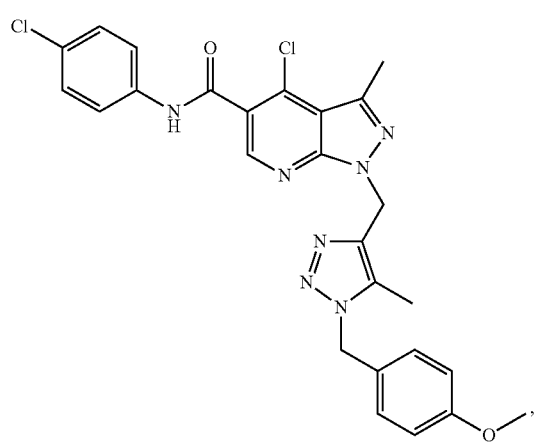
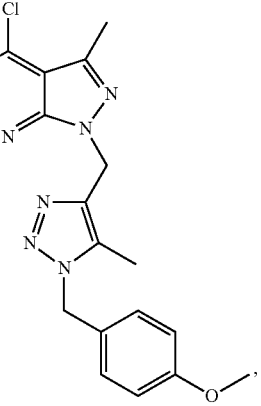

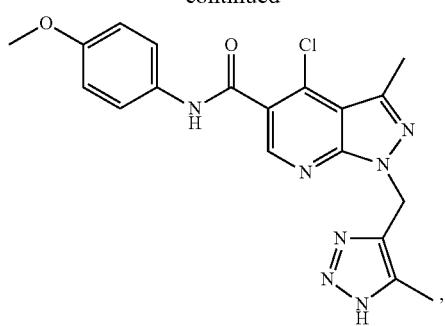
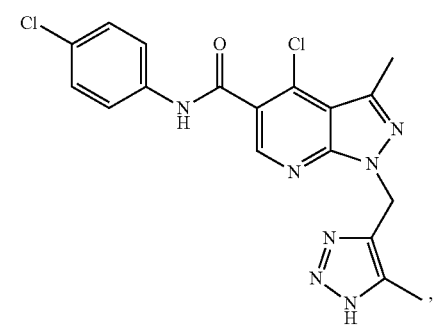
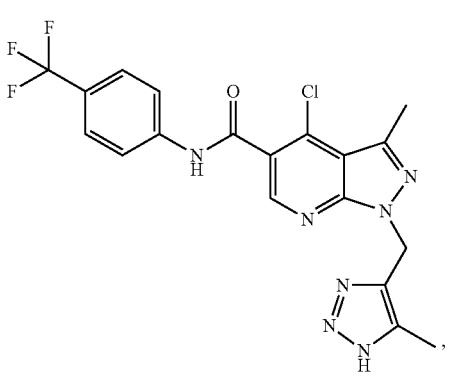
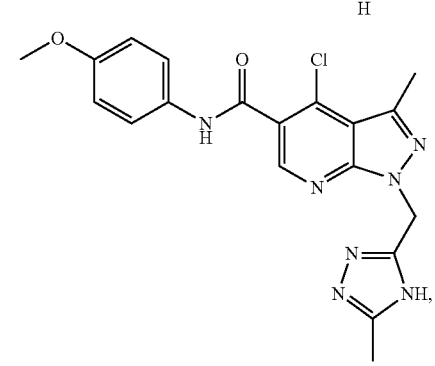
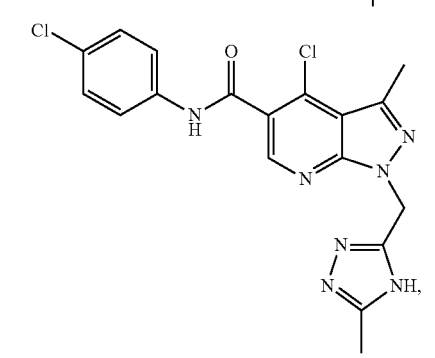
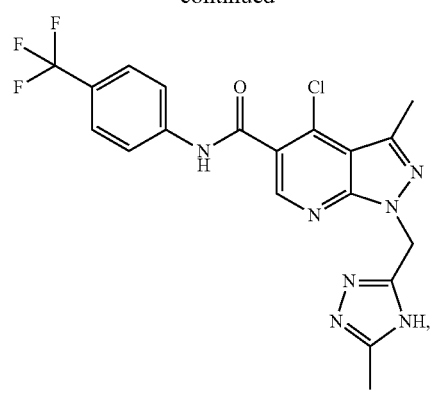
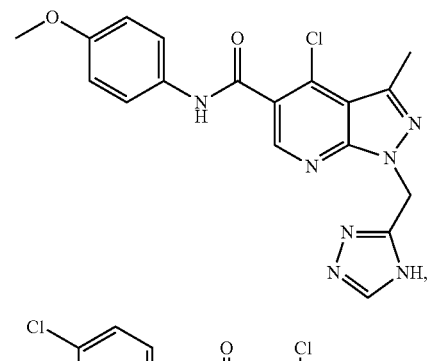
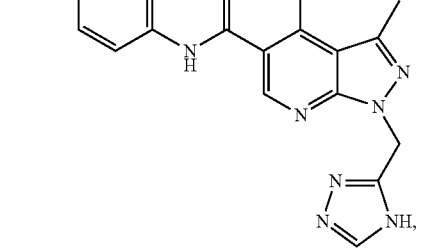
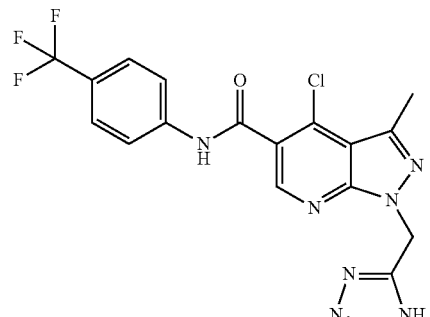
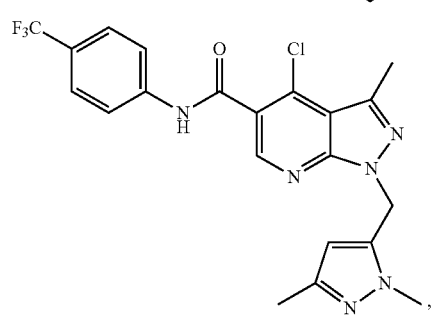

121
-continued
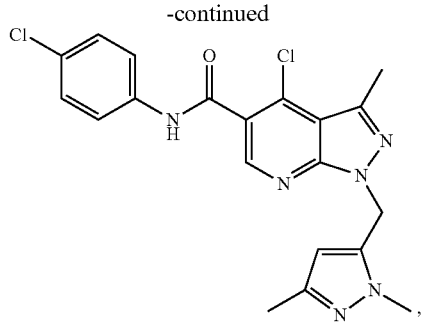
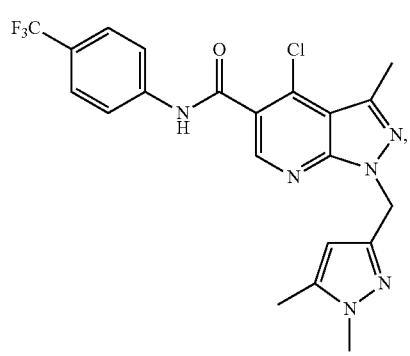
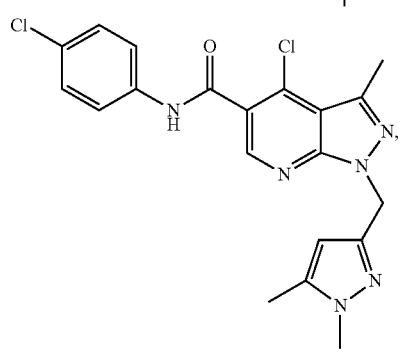
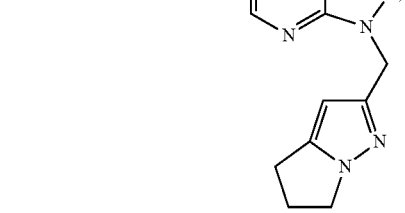
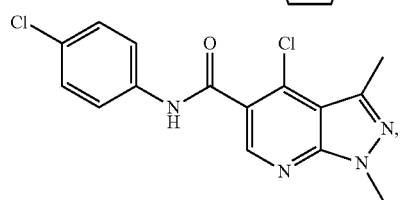
122
-continued
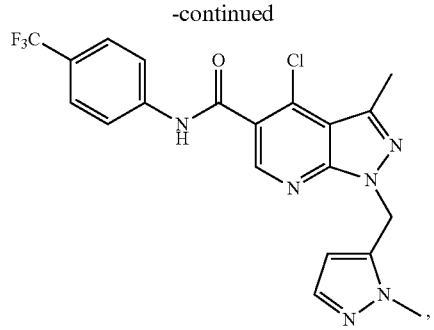
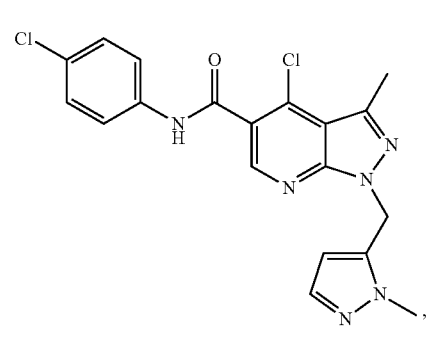
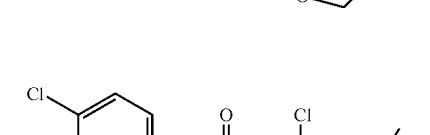
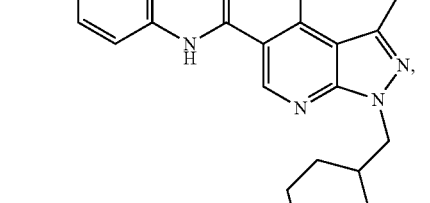
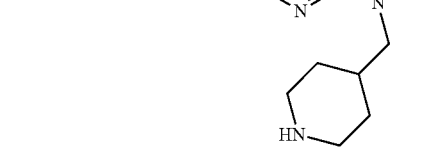

123
-continued
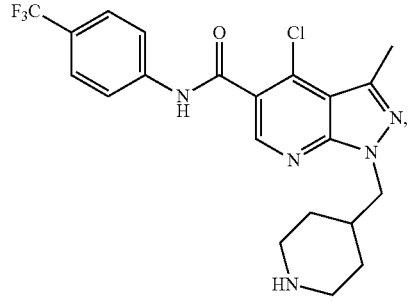
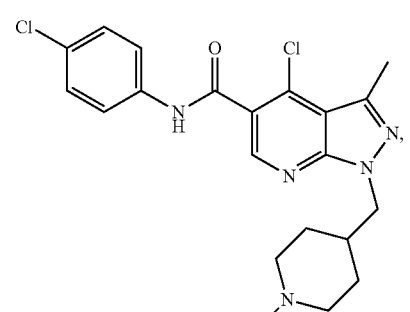
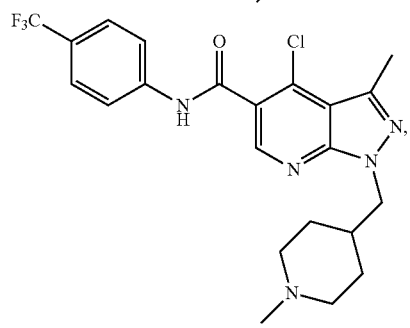
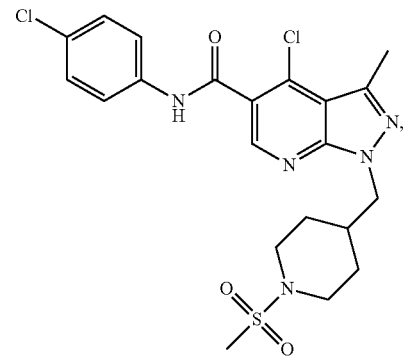
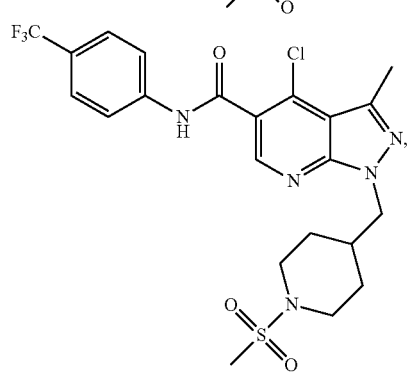
124
-continued
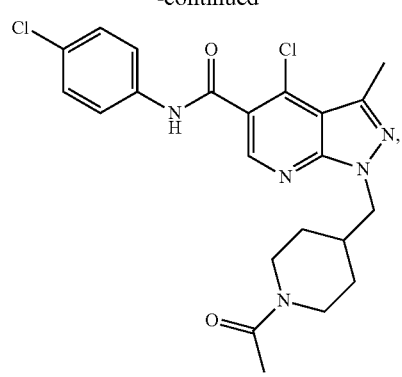
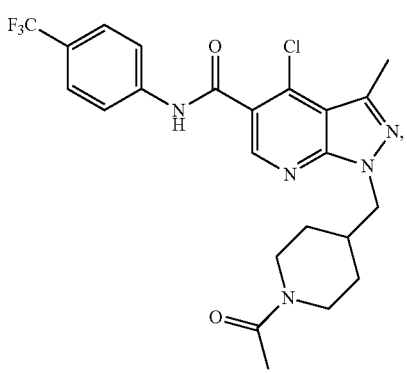
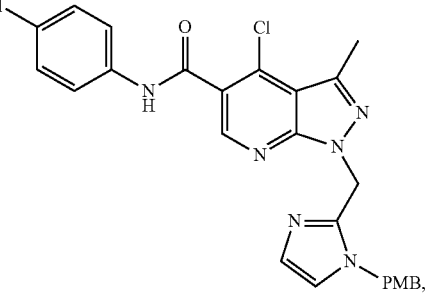
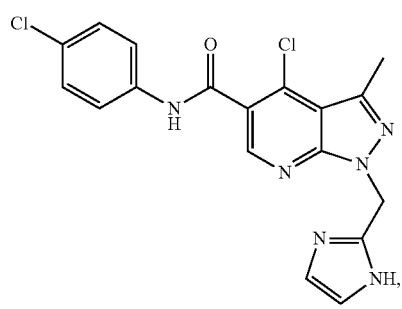
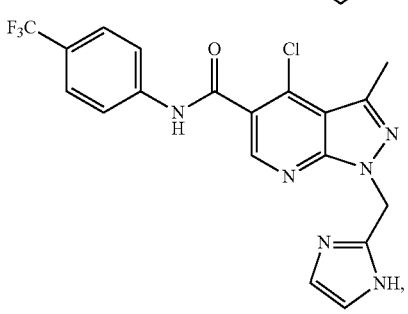

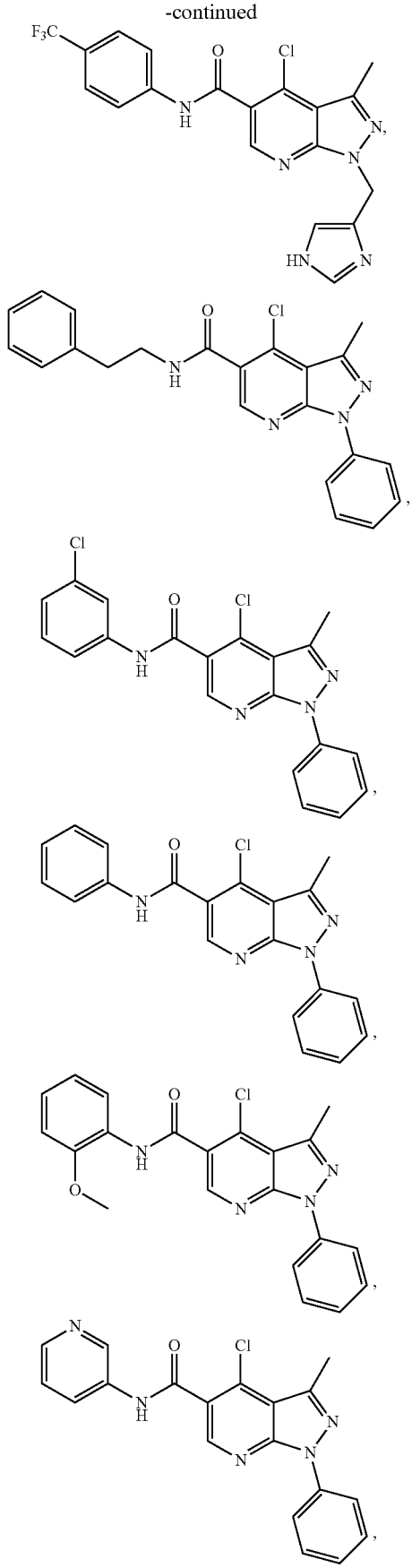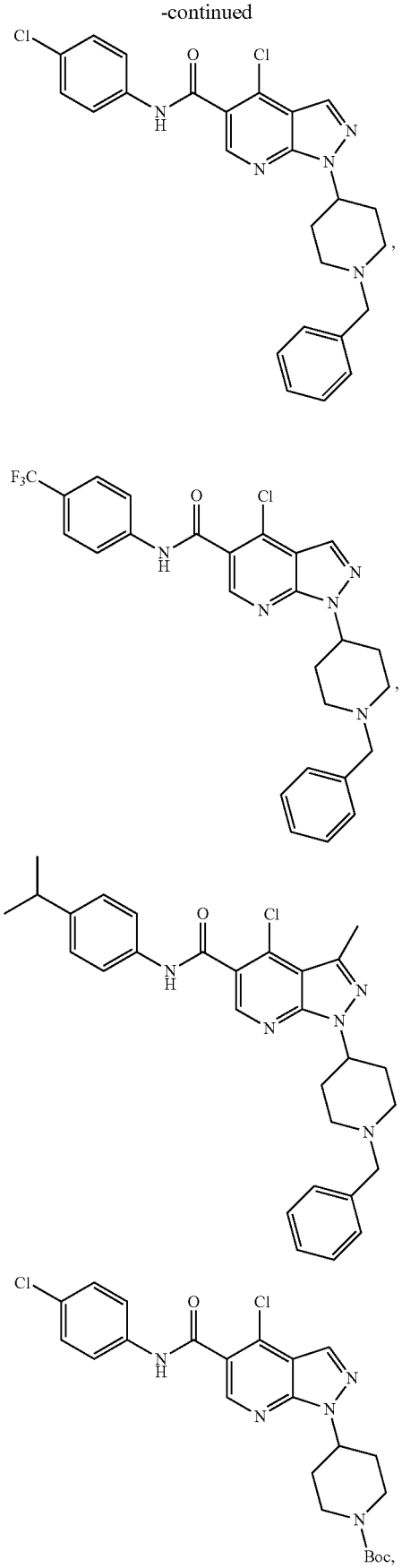

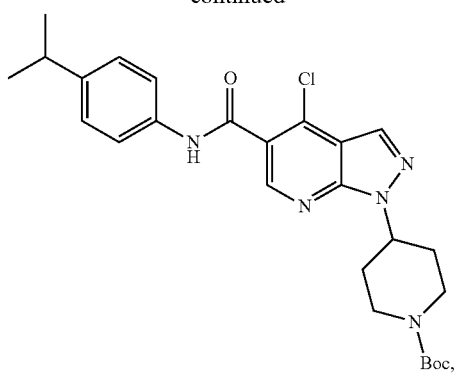
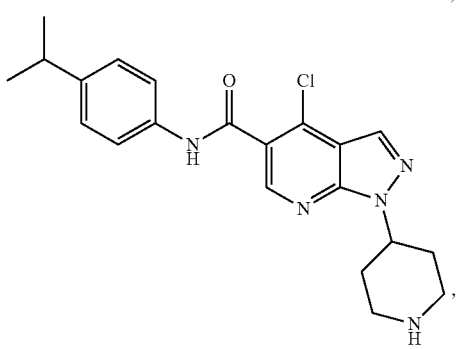
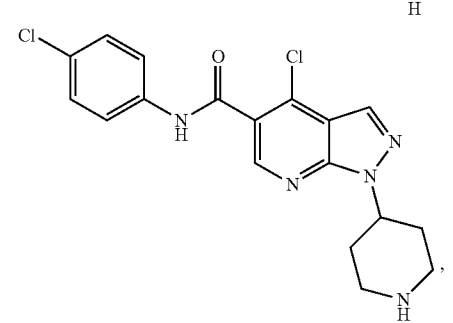
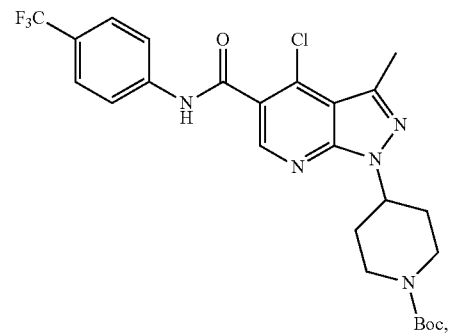
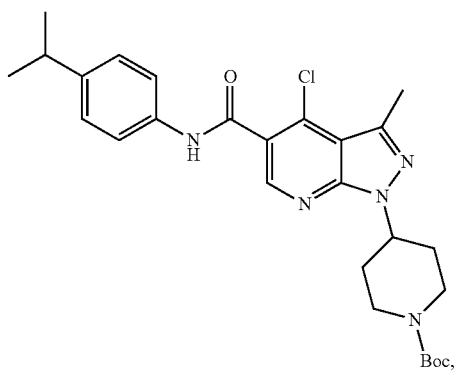
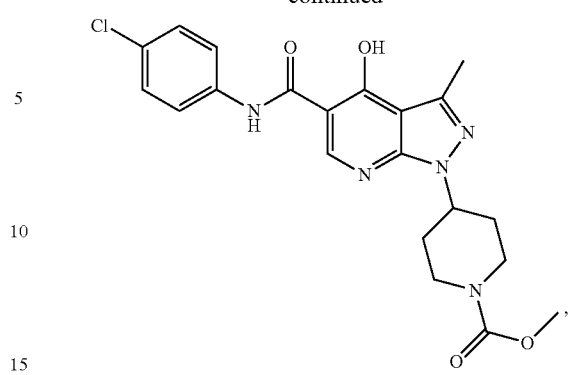
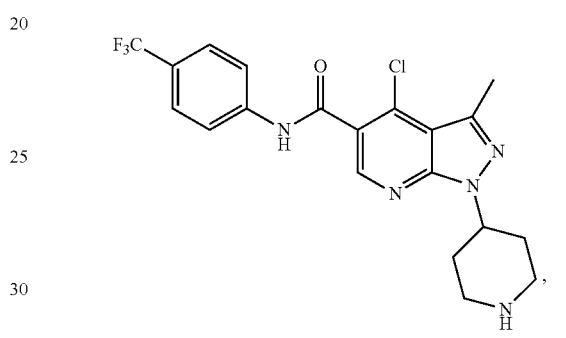
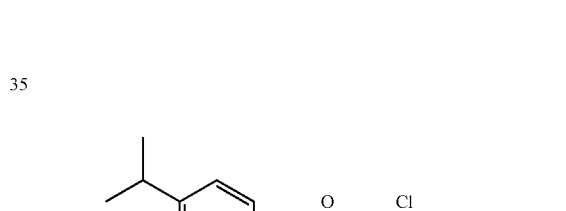
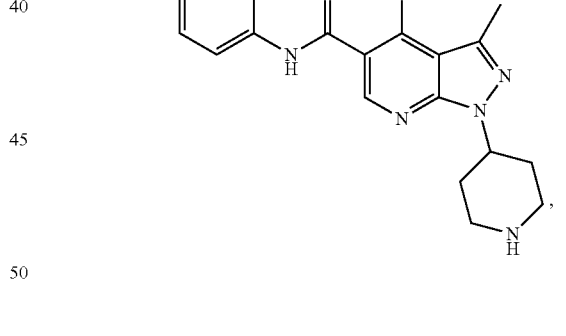
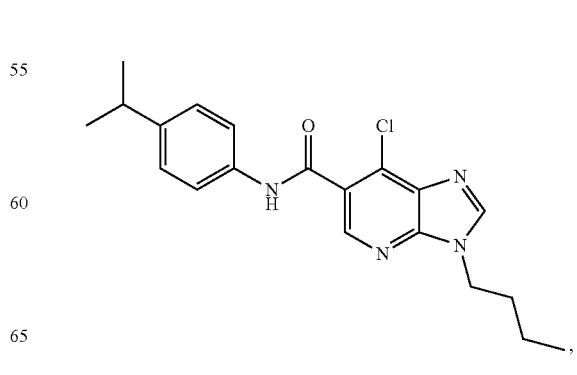

-continued

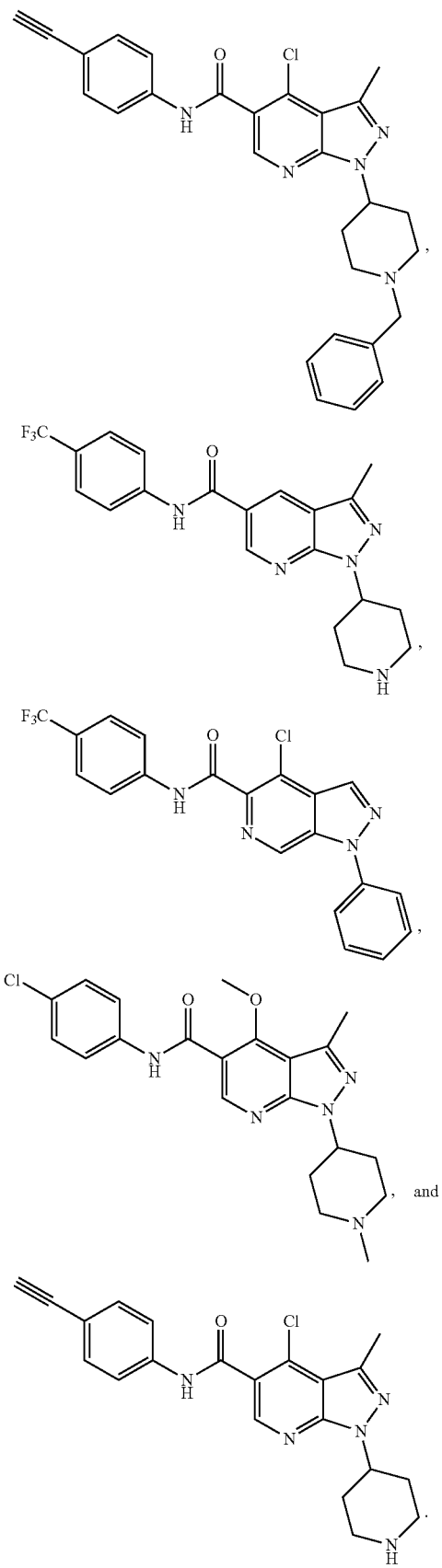 [SMILES: C#Cc1ccc(NC(=O)c2cnc3c(c(C)nn3C3CCN(Cc4ccccc4)CC3)c2Cl)cc1 ; Cc1nn(C2CCNCC2)c2ncc(C(=O)Nc3ccc(C(F)(F)F)cc3)cc12 ; O=C(Nc1ccc(C(F)(F)F)cc1)c1ncc2c(cnn2-c2ccccc2)c1Cl ; COc1c(C(=O)Nc2ccc(Cl)cc2)cnc2c1c(C)nn2C1CCN(C)CC1 ; C#Cc1ccc(NC(=O)c2cnc3c(c(C)nn3C3CCNCC3)c2Cl)cc1]

In another aspect, provided herein is a compound of Formula III, or a pharmaceutically acceptable salt, solvate, tautomer, or N-oxide thereof:

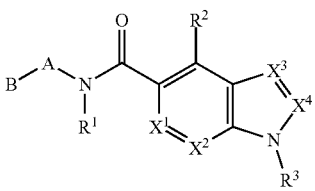

Formula (III)

wherein:
$X^1$-$X^4$ are independently selected from the group consisting of N and $CR^4$.
A is selected from the group consisting of bond, —$CH_2CH_2$—, and —$CH_2CH_2CH_2$—;
B is selected from the group consisting of heterocycloalkyl, phenyl, and 5- or 6-membered heteroaryl;
wherein the heterocycloalkyl, phenyl, and heteroaryl are optionally substituted with one or more groups independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —(C=O)$OR^c$, —CN, —(C=O)$R^d$, alkynyl, and —O($C_1$-$C_4$ alkylene)$NR^aR^b$;
$R^1$ is selected from the group consisting of hydrogen, alkyl, and cycloalkyl;
wherein the alkyl and cycloalkyl are optionally substituted with one or more groups independently selected from the group consisting of halogen, alkoxy, and —$NR^aR^b$;
$R^2$ is selected from the group consisting of hydrogen, —CN, —$NR^aR^b$, halogen, hydroxyl, alkoxy, alkyl, and cycloalkyl;
wherein the alkyl and cycloalkyl are optionally substituted with one or more halogen;
$R^3$ is selected from the group consisting of alkyl, cycloalkyl, heterocycloalkyl, phenyl, and 5- or 6-membered heteroaryl;
wherein the alkyl, cycloalkyl, heterocycloalkyl, phenyl, and heteroaryl are optionally substituted with one or more groups independently selected from the group consisting of halogen, hydroxyl, alkyl, haloalkyl, alkoxy, haloalkoxy, hydroxyalkyl, —$NR^aR^b$, —Oaralkyl, —C(=O)Otbutyl, —S(=O)$_{0-2}R^e$, acetyl, aryl, heteroaryl, aralkyl, cycloalkyl, and heterocycloalkyl;
wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}R^e$, acetyl, azidyl, —$CH_2$azidyl, aryl, and aralkyl;
wherein the aryl and aralkyl are optionally substituted with one or more groups independently selected from the group consisting of alkyl and alkoxy;
each $R^4$ are independently selected from the group consisting of hydrogen, halogen, alkyl, and cycloalkyl;
wherein the alkyl and cycloalkyl are optionally substituted with one or more groups independently selected from the group consisting of halogen and hydroxyl;

each $R^a$ and $R^b$ are independently selected from the group consisting of hydrogen and alkyl; or $R^a$ and $R^b$ taken together with the nitrogen to which they are attached form a heterocycloalkyl optionally substituted with alkyl;

$R^c$ is selected from the group consisting of hydrogen and alkyl;

$R^d$ is selected from the group consisting of aryl or heteroaryl; wherein the aryl and heteroaryl are optionally substituted with one or more groups independently selected from halogen, alkyl, and alkoxy;

$R^e$ is selected from the group consisting of alkyl and —$NR^aR^b$.

In some embodiments of a compound of Formula (III), or a pharmaceutically acceptable salt, solvate, tautomer, or N-oxide thereof, A is a bond.

In some embodiments of a compound of Formula (III), or a pharmaceutically acceptable salt, solvate, tautomer, or N-oxide thereof, B is phenyl optionally substituted with one or more groups independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —$(C=O)OR^c$, —CN, —$(C=O)R^d$, alkynyl, and —$O(C_1\text{-}C_4\text{ alkylene})NR^aR^b$.

In some embodiments of a compound of Formula (III), or a pharmaceutically acceptable salt, solvate, tautomer, or N-oxide thereof, B is phenyl substituted with one or more groups independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —$(C=O)OR^c$, —CN, —$(C=O)R^d$, alkynyl, and —$O(C_1\text{-}C_4\text{ alkylene})NR^aR^b$.

In some embodiments of a compound of Formula (III), or a pharmaceutically acceptable salt, solvate, tautomer, or N-oxide thereof, $X^1$ is CH; $X^3$ is $CR^4$; and $X^2$ and $X^4$ are N.

In some embodiments of a compound of Formula (III), or a pharmaceutically acceptable salt, solvate, tautomer, or N-oxide thereof, $X^1$ and $X^4$ are CH; and $X^2$ and $X^3$ are N.

In some embodiments of a compound of Formula (III), or a pharmaceutically acceptable salt, solvate, tautomer, or N-oxide thereof, $X^3$ is $CR^4$; $X^2$ is CH; and $X^1$ and $X^4$ are N.

In some embodiments of a compound of Formula (III), or a pharmaceutically acceptable salt, solvate, tautomer, or N-oxide thereof, $X^2$ and $X^4$ are CH; and $X^1$ and $X^3$ are N.

In some embodiments of a compound of Formula (III), or a pharmaceutically acceptable salt, solvate, tautomer, or N-oxide thereof, $X^1$ and $X^4$ are CH; $X^2$ is N; and $X^3$ is $CR^4$.

In some embodiments of a compound of Formula (III), or a pharmaceutically acceptable salt, solvate, tautomer, or N-oxide thereof, the compound of Formula (III) is of Formula (IIIa):

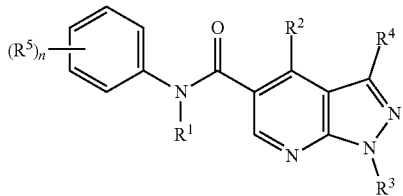

Formula (IIIa)

wherein:
$R^1$ is selected from the group consisting of hydrogen, alkyl, and cycloalkyl;

wherein the alkyl and cycloalkyl are optionally substituted with one or more groups independently selected from the group consisting of halogen, alkoxy, and —$NR^aR^b$;

$R^2$ is selected from the group consisting of hydrogen, —CN, —$NR^aR^b$, halogen, hydroxyl, alkoxy, alkyl, and cycloalkyl;

wherein the alkyl and cycloalkyl are optionally substituted with one or more halogen;

$R^3$ is selected from the group consisting of alkyl, cycloalkyl, heterocycloalkyl, phenyl, and 5- or 6-membered heteroaryl;

wherein the alkyl, cycloalkyl, heterocycloalkyl, phenyl, and heteroaryl are optionally substituted with one or more groups independently selected from the group consisting of halogen, hydroxyl, alkyl, haloalkyl, alkoxy, haloalkoxy, hydroxyalkyl, —$NR^aR^b$, —Oaralkyl, —$C(=O)$Otbutyl, —$S(=O)_{0\text{-}2}R^e$, acetyl, aryl, heteroaryl, aralkyl, cycloalkyl, and heterocycloalkyl;

wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —$S(=O)_{0\text{-}2}R^e$, acetyl, azidyl, —$CH_2$azidyl, aryl, and aralkyl;

wherein the aryl and aralkyl are optionally substituted with one or more groups independently selected from the group consisting of alkyl and alkoxy;

$R^4$ is selected from the group consisting of hydrogen, halogen, alkyl, and cycloalkyl;

wherein the alkyl and cycloalkyl are optionally substituted with one or more groups independently selected from the group consisting of halogen and hydroxyl;

each $R^5$ are independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —$(C=O)OR^c$, —CN, —$(C=O)R^d$, alkynyl, and —$O(C_1\text{-}C_4\text{ alkylene})NR^aR^b$;

each $R^a$ and $R^b$ are independently selected from the group consisting of hydrogen and alkyl; or $R^a$ and $R^b$ taken together with the nitrogen to which they are attached form a heterocycloalkyl optionally substituted with alkyl;

$R^c$ is selected from the group consisting of hydrogen and alkyl;

$R^d$ is selected from the group consisting of aryl or heteroaryl; wherein the aryl and heteroaryl are optionally substituted with one or more groups independently selected from halogen, alkyl, and alkoxy;

$R^e$ is selected from the group consisting of alkyl and —$NR^aR^b$; and n is 1, 2, 3, 4, or 5.

In some embodiments of a compound of Formula (IIIa), or a pharmaceutically acceptable salt, solvate, tautomer, or N-oxide thereof, $R^3$ is alkyl optionally substituted with one or more groups independently selected from the group consisting of halogen, hydroxyl, haloalkyl, alkoxy, haloalkoxy, hydroxyalkyl, —$NR^aR^b$, —Oaralkyl, acetyl, aryl, heteroaryl, cycloalkyl, and heterocycloalkyl; wherein the aryl, heteroaryl, cycloalkyl, and heterocycloalkyl are optionally substituted with one or more groups independently selected from the group consisting of halogen, alkyl, haloalkyl, alkoxy, haloalkoxy, heteroalkyl, —S(=O)$_{0-2}$R$^e$, acetyl, and aralkyl; wherein the aralkyl is optionally substituted with one or more groups independently selected from the group consisting of alkyl and alkoxy.

In some embodiments of a compound of Formula (IIIa), or a pharmaceutically acceptable salt, solvate, tautomer, or N-oxide thereof, R$^3$ is alkyl substituted with one or more groups independently selected from the group consisting of halogen, hydroxyl, haloalkyl, alkoxy, haloalkoxy, hydroxyalkyl, and —NR$^a$R$^b$. In some embodiments of a compound of Formula (IIIa), or a pharmaceutically acceptable salt, solvate, tautomer, or N-oxide thereof, R$^3$ is alkyl substituted with one or more groups independently selected from the group consisting of hydroxyl, alkoxy, and —NR$^a$R$^b$.

In some embodiments of a compound of Formula (IIIa), or a pharmaceutically acceptable salt, solvate, tautomer, or N-oxide thereof, R$^3$ is alkyl substituted with one or more groups independently selected from the group consisting of aryl, heteroaryl, and heterocycloalkyl; wherein the aryl, heteroaryl, and heterocycloalkyl are optionally substituted with one or more groups independently selected from the group consisting of halogen, alkyl, haloalkyl, alkoxy, haloalkoxy, and heteroalkyl.

In some embodiments of a compound of Formula (IIIa), or a pharmaceutically acceptable salt, solvate, tautomer, or N-oxide thereof, R$^3$ is alkyl substituted with heteroaryl; wherein the heteroaryl is optionally substituted with one or more groups independently selected from the group consisting of halogen, alkyl, haloalkyl, alkoxy, haloalkoxy, and heteroalkyl. In some embodiments of a compound of Formula (IIIa), or a pharmaceutically acceptable salt, solvate, tautomer, or N-oxide thereof, R$^3$ is alkyl substituted with heteroaryl; wherein the heteroaryl is selected from the group consisting of pyridinyl, pyrimidinyl, pyrazinyl, furanyl, thiophenyl, pyrrolyl, thiazolyl, imidazolyl, triazolyl, tetrazolyl, pyrazolyl, and 4,5,6,7-tetrahydropyrazolo[1,5-a]pyridinyl. In some embodiments of a compound of Formula (IIIa), or a pharmaceutically acceptable salt, solvate, tautomer, or N-oxide thereof, R$^3$ is —CH$_2$(heteroaryl). In some embodiments of a compound of Formula (IIIa), or a pharmaceutically acceptable salt, solvate, tautomer, or N-oxide thereof, R$^3$ is —CH$_2$CH$_2$(heteroaryl).

In some embodiments of a compound of Formula (IIIa), or a pharmaceutically acceptable salt, solvate, tautomer, or N-oxide thereof, R$^3$ is alkyl substituted with aryl; wherein the aryl is optionally substituted with one or more groups independently selected from the group consisting of halogen, alkyl, haloalkyl, alkoxy, haloalkoxy, and heteroalkyl. In some embodiments of a compound of Formula (IIIa), or a pharmaceutically acceptable salt, solvate, tautomer, or N-oxide thereof, R$^3$ is alkyl substituted with aryl; wherein the aryl is phenyl. In some embodiments of a compound of Formula (IIIa), or a pharmaceutically acceptable salt, solvate, tautomer, or N-oxide thereof, R$^3$ is —CH$_2$(aryl). In some embodiments of a compound of Formula (IIIa), or a pharmaceutically acceptable salt, solvate, tautomer, or N-oxide thereof, R$^3$ is —CH$_2$CH$_2$(aryl).

In some embodiments of a compound of Formula (IIIa), or a pharmaceutically acceptable salt, solvate, tautomer, or N-oxide thereof, R$^3$ is alkyl substituted with heterocycloalkyl; wherein the heterocycloalkyl is optionally substituted with one or more groups independently selected from the group consisting of halogen, alkyl, haloalkyl, alkoxy, haloalkoxy, heteroalkyl, —S(=O)$_{0-2}$R$^e$, acetyl, and aralkyl; wherein the aralkyl is optionally substituted with one or more groups independently selected from the group consisting of alkyl and alkoxy. In some embodiments of a compound of Formula (IIIa), or a pharmaceutically acceptable salt, solvate, tautomer, or N-oxide thereof, R$^3$ is alkyl substituted with heterocycloalkyl; wherein the heterocycloalkyl is piperazinyl, morpholinyl, piperidinyl, or pyrrolidinyl. In some embodiments of a compound of Formula (IIIa), or a pharmaceutically acceptable salt, solvate, tautomer, or N-oxide thereof, R$^3$ is —CH$_2$(heterocycloalkyl). In some embodiments of a compound of Formula (IIIa), or a pharmaceutically acceptable salt, solvate, tautomer, or N-oxide thereof, R$^3$ is —CH$_2$CH$_2$(heterocycloalkyl).

In some embodiments of a compound of Formula (IIa), or a pharmaceutically acceptable salt, solvate, tautomer, or N-oxide thereof, R$^3$ is alkyl substituted with cycloalkyl; wherein the cycloalkyl is optionally substituted with one or more groups independently selected from the group consisting of halogen, alkyl, haloalkyl, alkoxy, haloalkoxy, and heteroalkyl. In some embodiments of a compound of Formula (IIIa), or a pharmaceutically acceptable salt, solvate, tautomer, or N-oxide thereof, R$^3$ is alkyl substituted with cycloalkyl; wherein the cycloalkyl is cyclopropyl, cyclobutyl, cyclopentyl, or cyclobutyl. In some embodiments of a compound of Formula (IIIa), or a pharmaceutically acceptable salt, solvate, tautomer, or N-oxide thereof, R$^3$ is —CH$_2$(cycloalkyl). In some embodiments of a compound of Formula (IIa), or a pharmaceutically acceptable salt, solvate, tautomer, or N-oxide thereof, R$^3$ is —CH$_2$CH$_2$(cycloalkyl).

In some embodiments of a compound of Formula (IIIa), or a pharmaceutically acceptable salt, solvate, tautomer, or N-oxide thereof, R$^3$ is unsubstituted alkyl.

In some embodiments of a compound of Formula (IIIa), or a pharmaceutically acceptable salt, solvate, tautomer, or N-oxide thereof, R$^3$ is phenyl optionally substituted with one or more groups independently selected from the group consisting of halogen, hydroxyl, alkyl, haloalkyl, alkoxy, haloalkoxy, hydroxyalkyl, and —NR$^a$R$^b$. In some embodiments of a compound of Formula (IIIa), or a pharmaceutically acceptable salt, solvate, tautomer, or N-oxide thereof, R$^3$ is phenyl substituted with one or more groups independently selected from the group consisting of halogen, hydroxyl, alkyl, haloalkyl, alkoxy, haloalkoxy, hydroxyalkyl, and —NR$^a$R$^b$. In some embodiments of a compound of Formula (IIIa), or a pharmaceutically acceptable salt, solvate, tautomer, or N-oxide thereof, R$^3$ is phenyl substituted with one or more groups independently selected from the group consisting of halogen, hydroxyl, alkyl, haloalkyl, alkoxy, haloalkoxy, hydroxyalkyl, and —NR$^a$R$^b$. In some embodiments of a compound of Formula (IIIa), or a pharmaceutically acceptable salt, solvate, tautomer, or N-oxide thereof, R$^3$ is unsubstituted phenyl.

In some embodiments of a compound of Formula (IIIa), or a pharmaceutically acceptable salt, solvate, tautomer, or N-oxide thereof, R$^3$ is heterocycloalkyl optionally substituted with one or more groups independently selected from the group consisting of alkyl, haloalkyl, alkoxy, haloalkoxy, hydroxyalkyl, —C(=O)Otbutyl, —S(=O)$_{0-2}$R$^e$, acetyl, aryl, and aralkyl; wherein the aralkyl is optionally substituted with one or more groups independently selected from the group consisting of alkylnyl, alkoxy, azidyl, and —CH$_2$azidyl.

In some embodiments of a compound of Formula (IIIa), or a pharmaceutically acceptable salt, solvate, tautomer, or N-oxide thereof, R$^3$ is heterocycloalkyl substituted with one or more groups independently selected from the group consisting of alkyl, haloalkyl, alkoxy, haloalkoxy, hydroxyalkyl, —C(=O)Otbutyl, —S(=O)$_{0-2}$R$^e$, acetyl, aryl, and aralkyl; wherein the aralkyl is optionally substituted with one or more groups independently selected from the group consisting of alkylnyl, alkoxy, azidyl, and —CH₂azidyl. In some embodiments of a compound of Formula (IIIa), or a pharmaceutically acceptable salt, solvate, tautomer, or N-oxide thereof, R³ is heterocycloalkyl substituted with one or more alkyl. In some embodiments of a compound of Formula (IIIa), or a pharmaceutically acceptable salt, solvate, tautomer, or N-oxide thereof, R³ is heterocycloalkyl substituted with methyl, ethyl, propyl, or isopropyl. In some embodiments of a compound of Formula (IIIa), or a pharmaceutically acceptable salt, solvate, tautomer, or N-oxide thereof, R³ is unsubstituted heterocycloalkyl. In some embodiments of a compound of Formula (IIIa), or a pharmaceutically acceptable salt, solvate, tautomer, or N-oxide thereof, R³ is heterocycloalkyl selected from the group consisting of tetrahydro-2H-pyranyl, piperidinyl, 1,1-dioxidotetrahydro-2H-thiopyranyl, and tetrahydro-2H-thiopyranyl. In some embodiments of a compound of Formula (IIIa), or a pharmaceutically acceptable salt, solvate, tautomer, or N-oxide thereof, R³ is piperidinyl. In some embodiments of a compound of Formula (IIIa), or a pharmaceutically acceptable salt, solvate, tautomer, or N-oxide thereof, R³ is piperidin-4-yl.

In some embodiments of a compound of Formula (IIIa), or a pharmaceutically acceptable salt, solvate, tautomer, or N-oxide thereof, R³ is cycloalkyl optionally substituted with one or more groups independently selected from the group consisting of alkyl, haloalkyl, alkoxy, haloalkoxy, and hydroxyalkyl. In some embodiments of a compound of Formula (IIIa), or a pharmaceutically acceptable salt, solvate, tautomer, or N-oxide thereof, R³ is unsubstituted cycloalkyl. In some embodiments of a compound of Formula (IIIa), or a pharmaceutically acceptable salt, solvate, tautomer, or N-oxide thereof, R³ is cycloprpyl, cyclobutyl, cyclopentyl, or cyclohexyl.

In some embodiments of a compound of Formula (IIIa), or a pharmaceutically acceptable salt, solvate, tautomer, or N-oxide thereof, n is 1. In some embodiments of a compound of Formula (IIIa), or a pharmaceutically acceptable salt, solvate, tautomer, or N-oxide thereof, n is 2. In some embodiments of a compound of Formula (IIIa), or a pharmaceutically acceptable salt, solvate, tautomer, or N-oxide thereof, n is 3. In some embodiments of a compound of Formula (IIIa), or a pharmaceutically acceptable salt, solvate, tautomer, or N-oxide thereof, n is 4. In some embodiments of a compound of Formula (IIIa), or a pharmaceutically acceptable salt, solvate, tautomer, or N-oxide thereof, n is 5.

In some embodiments of a compound of Formula (IIIa), or a pharmaceutically acceptable salt, solvate, tautomer, or N-oxide thereof is

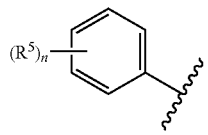

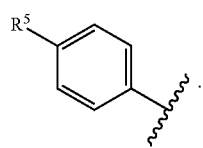

In some embodiments of a compound of Formula (IIIa), or a pharmaceutically acceptable salt, solvate, tautomer, or N-oxide thereof, R⁵ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —NRᵃRᵇ, —CN, and alkynyl.

In some embodiments of a compound of Formula (IIIa), or a pharmaceutically acceptable salt, solvate, tautomer, or N-oxide thereof, R⁵ is selected from the group consisting of halogen, alkyl, haloalkyl, alkoxy, haloalkoxy, and alkynyl.

In some embodiments of a compound of Formula (IIIa), or a pharmaceutically acceptable salt, solvate, tautomer, or N-oxide thereof, R⁵ is selected from the group consisting of chloro, methyl, isopropyl, methoxy, and ethynyl.

In some embodiments of a compound of Formula (III) or (IIIa), or a pharmaceutically acceptable salt, solvate, tautomer, or N-oxide thereof, R¹ is selected from the group consisting of hydrogen, methyl, ethyl, —CH₂CH₂OCH₃, and —CH₂CH₂N(CH₃)₂.

In some embodiments of a compound of Formula (III) or (IIIa), or a pharmaceutically acceptable salt, solvate, tautomer, or N-oxide thereof, R¹ is hydrogen.

In some embodiments of a compound of Formula (III) or (IIIa), or a pharmaceutically acceptable salt, solvate, tautomer, or N-oxide thereof, R² is selected from the group consisting of hydrogen, —CN, and —NRᵃRᵇ

In some embodiments of a compound of Formula (III) or (IIIa), or a pharmaceutically acceptable salt, solvate, tautomer, or N-oxide thereof, R⁴ is selected from the group consisting of hydrogen, methyl, ethyl, isopropyl, cyclopropyl, fluoro, chloro, and bromo.

In some embodiments of a compound of Formula (III) or (IIIa), or a pharmaceutically acceptable salt, solvate, tautomer, or N-oxide thereof, R⁴ is selected from the group consisting of hydrogen and methyl.

In some embodiments of a compound of Formula (III) or (IIIa), or a pharmaceutically acceptable salt, solvate, tautomer, or N-oxide thereof, the compound of Formula (IIII) is selected from:

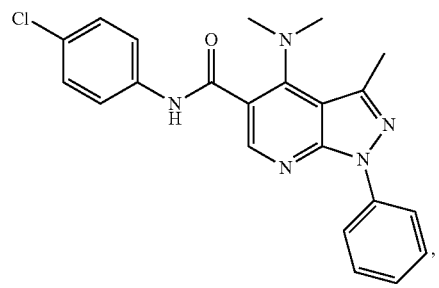

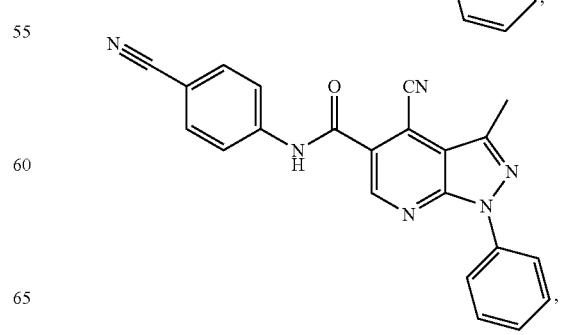

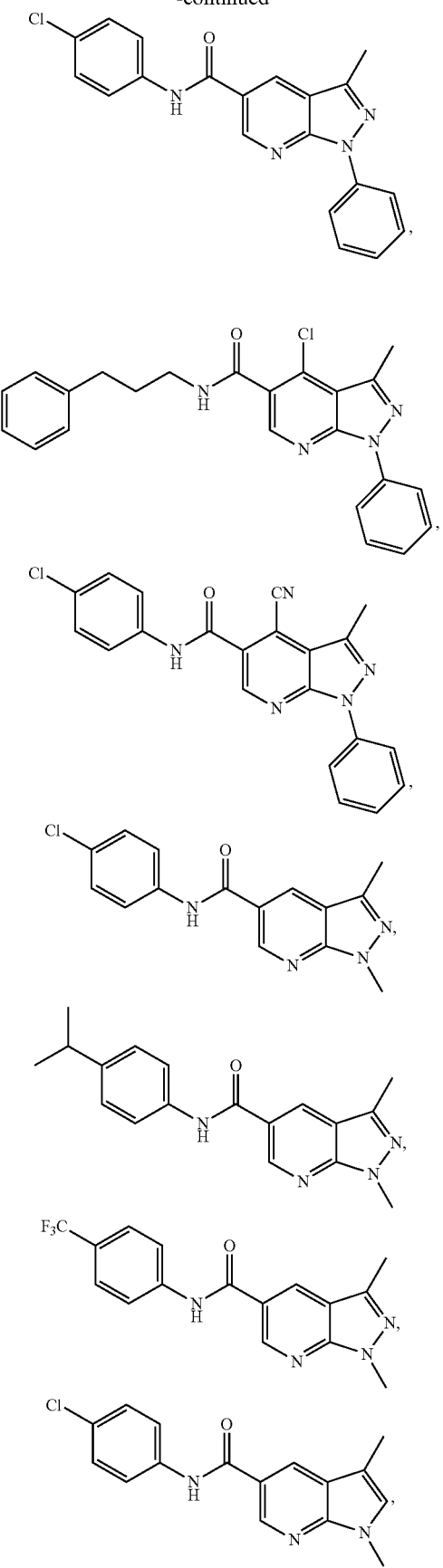
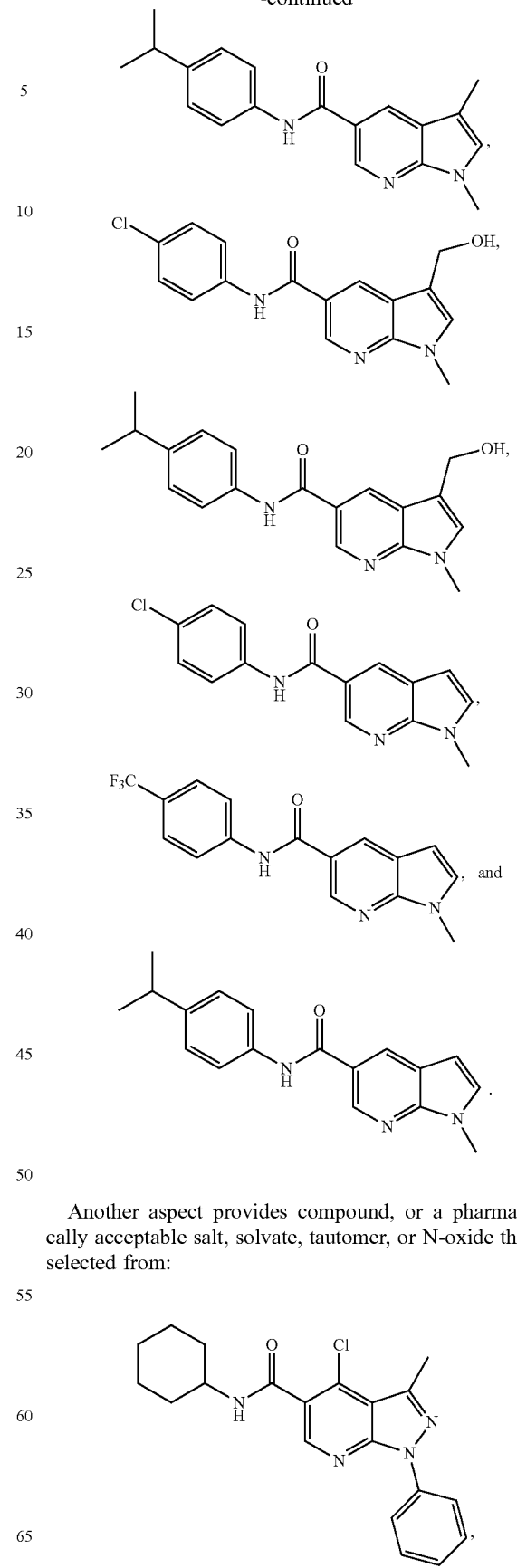
Another aspect provides compound, or a pharmaceutically acceptable salt, solvate, tautomer, or N-oxide thereof, selected from:
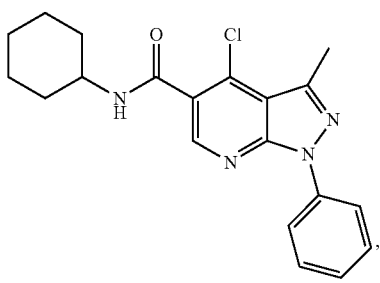

139
-continued
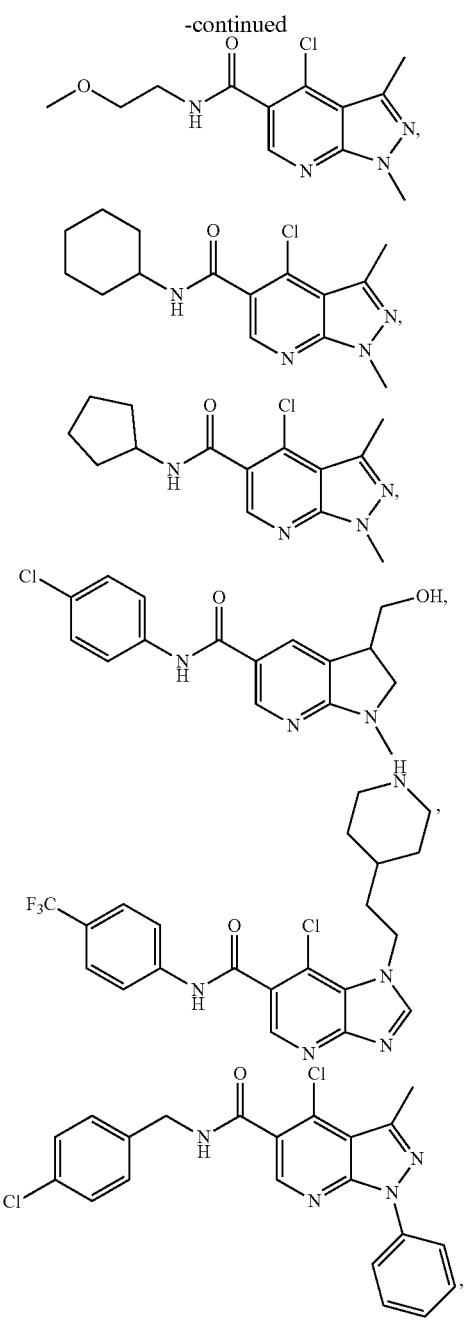
140
-continued
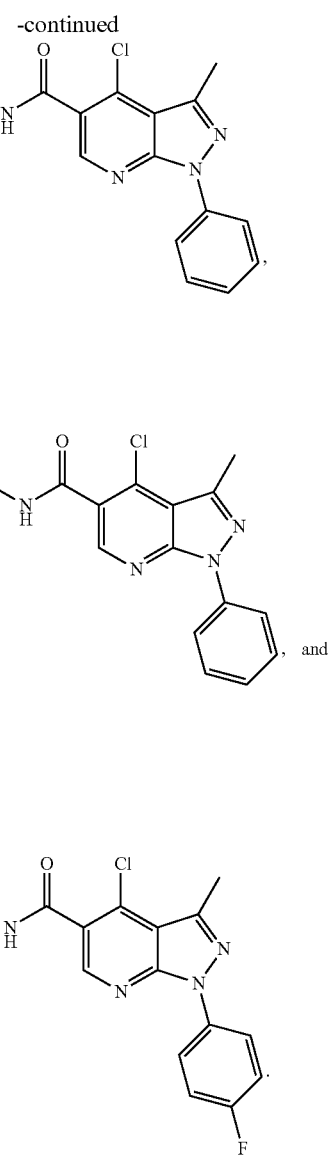
Further embodiments provided herein include combinations of one or more of the particular embodiments set forth above.
In some embodiments, the compound disclosed herein has the structure provided in Table 1.
TABLE 1
| Ex. | Names | Structures |
|---|---|---|
| 1 | 4-Chloro-3-methyl-1-phenyl-1H-pyrazolol[3,4-b]pyridine-5-carboxylic acid (4-bromo-phenyl)-amide | 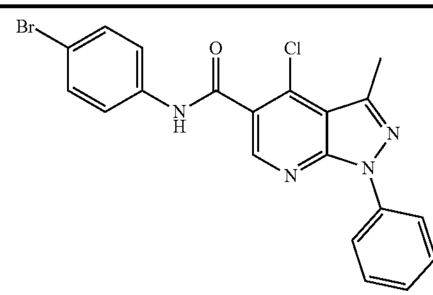 |

TABLE 1-continued

| Ex. | Names | Structures |
|---|---|---|
| 2 | 4-Chloro-3-methyl-1-phenyl-1H-pyrazolo[3,4-b]pyridine-5-carboxylic acid (4-chloro-phenyl)-amide | 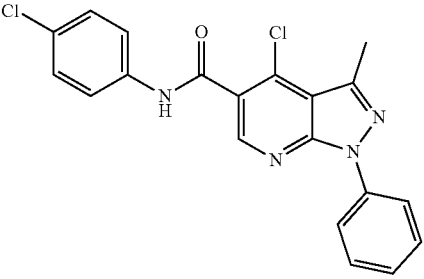 |
| 3 | 4-Chloro-3-methyl-1-phenyl-1H-pyrazolo[3,4-b]pyridine-5-carboxylic acid (4-fluoro-phenyl)-amide | 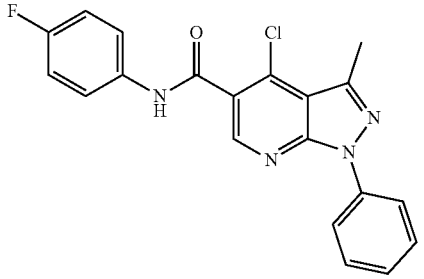 [SMILES: Cc1nn(-c2ccccc2)c2ncc(C(=O)Nc3ccc(F)cc3)c(Cl)c12] |
| 4 | 4-Chloro-3-methyl-1-phenyl-1H-pyrazolo[3,4-b]pyridine-5-carboxylic acid p-tolylamide | 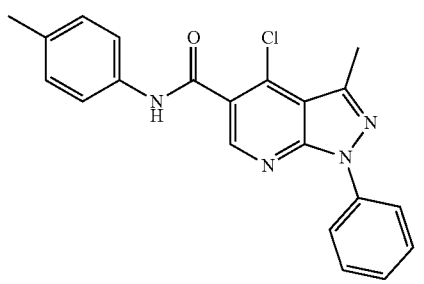 [SMILES: Cc1ccc(NC(=O)c2cnc3c(c(C)nn3-c3ccccc3)c2Cl)cc1] |
| 5 | 4-Chloro-3-methyl-1-phenyl-1H-pyrazolo[3,4-b]pyridine-5-carboxylic acid (4-ethyl-phenyl)-amide | 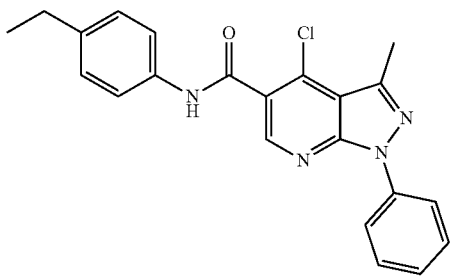 [SMILES: CCc1ccc(NC(=O)c2cnc3c(c(C)nn3-c3ccccc3)c2Cl)cc1] |
| 6 | 4-Chloro-3-methyl-1-phenyl-1H-pyrazolo[3,4-b]pyridine-5-carboxylic acid (4-propyl-phenyl)-amide | 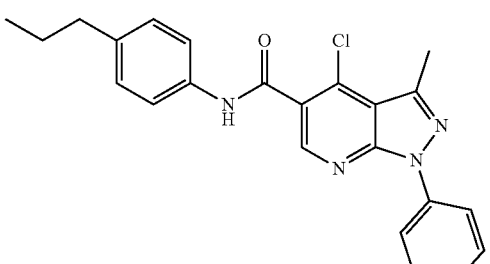 |

TABLE 1-continued

| Ex. | Names | Structures |
|---|---|---|
| 7 | 4-Chloro-3-methyl-1-phenyl-1H-pyrazolo[3,4-b]pyridine-5-carboxylic acid (4-isopropyl-phenyl)-amide | 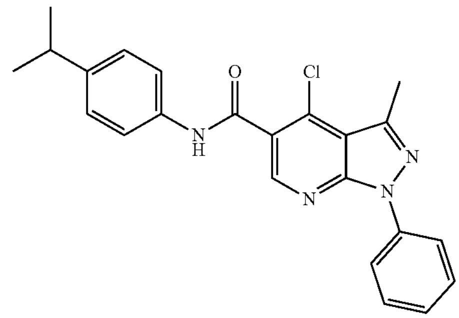 [SMILES: Cc1nn(-c2ccccc2)c2ncc(C(=O)Nc3ccc(C(C)C)cc3)c(Cl)c12] |
| 8 | 4-Chloro-3-methyl-1-phenyl-1H-pyrazolo[3,4-b]pyridine-5-carboxylic acid (4-butyl-phenyl)-amide | 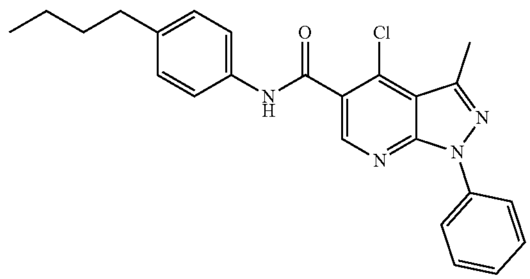 [SMILES: CCCCc1ccc(NC(=O)c2cnc3c(c(C)nn3-c3ccccc3)c2Cl)cc1] |
| 9 | 4-Chloro-3-methyl-1-phenyl-1H-pyrazolo[3,4-b]pyridine-5-carboxylic acid (4-isobutyl-phenyl)-amide | 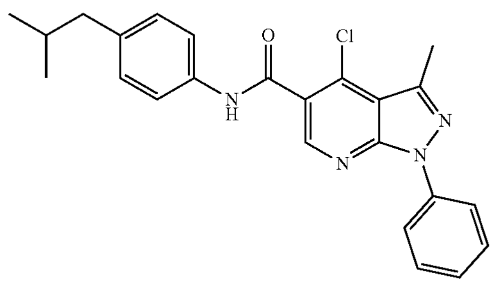 [SMILES: Cc1nn(-c2ccccc2)c2ncc(C(=O)Nc3ccc(CC(C)C)cc3)c(Cl)c12] |
| 10 | 4-Chloro-3-methyl-1-phenyl-1H-pyrazolo[3,4-b]pyridine-5-carboxylic acid (4-cyclopropyl-phenyl)-amide | 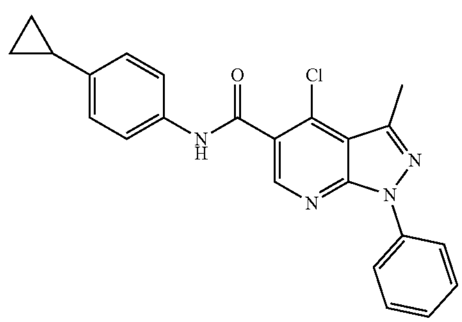 [SMILES: Cc1nn(-c2ccccc2)c2ncc(C(=O)Nc3ccc(C4CC4)cc3)c(Cl)c12] |
| 11 | 4-Chloro-3-methyl-1-phenyl-1H-pyrazolo[3,4-b]pyridine-5-carboxylic acid (4-cyclopentyl-phenyl)-amide | 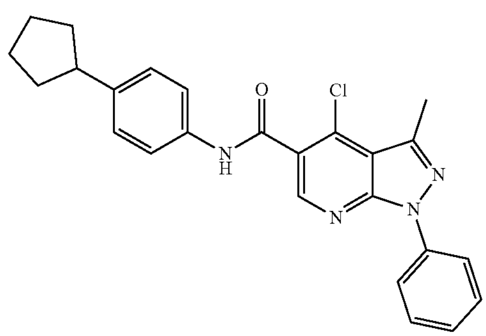 [SMILES: Cc1nn(-c2ccccc2)c2ncc(C(=O)Nc3ccc(C4CCCC4)cc3)c(Cl)c12] |

TABLE 1-continued

| Ex. | Names | Structures |
|---|---|---|
| 12 | 4-Chloro-3-methyl-1-phenyl-1H-pyrazolo[3,4-b]pyridine-5-carboxylic acid (4-cyclohexyl-phenyl)-amide | 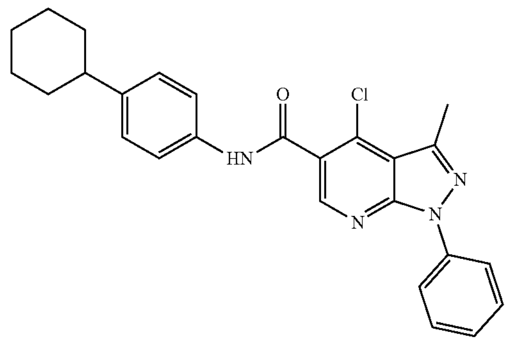 [SMILES: Cc1nn(-c2ccccc2)c2ncc(C(=O)Nc3ccc(C4CCCCC4)cc3)c(Cl)c12] |
| 13 | 4-Chloro-3-methyl-1-phenyl-1H-pyrazolo[3,4-b]pyridine-5-carboxylic acid (4-hydroxymethyl-phenyl)-amide | 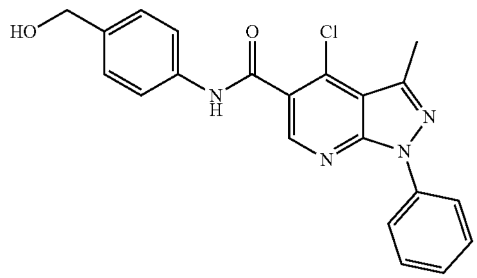 [SMILES: Cc1nn(-c2ccccc2)c2ncc(C(=O)Nc3ccc(CO)cc3)c(Cl)c12] |
| 14 | 4-Chloro-3-methyl-1-phenyl-1H-pyrazolo[3,4-b]pyridine-5-carboxylic acid (4-methoxymethyl-phenyl)-amide | 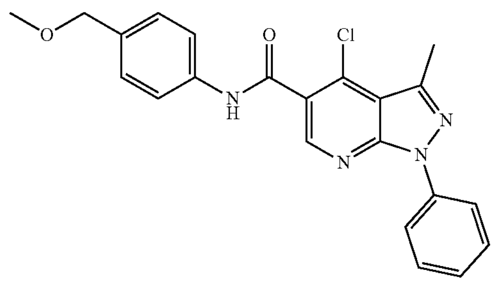 [SMILES: COCc1ccc(NC(=O)c2cnc3c(c(C)nn3-c3ccccc3)c2Cl)cc1] |
| 15 | 4-Chloro-3-methyl-1-phenyl-1H-pyrazolo[3,4-b]pyridine-5-carboxylic acid [4-(2-hydroxy-ethyl)-phenyl]-amide | 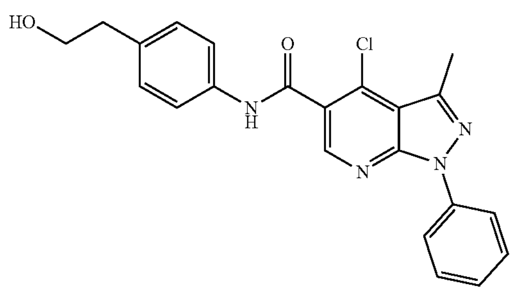 [SMILES: Cc1nn(-c2ccccc2)c2ncc(C(=O)Nc3ccc(CCO)cc3)c(Cl)c12] |
| 16 | 4-Chloro-3-methyl-1-phenyl-1H-pyrazolo[3,4-b]pyridine-5-carboxylic acid [4-(2-methoxy-ethyl)-phenyl]-amide | 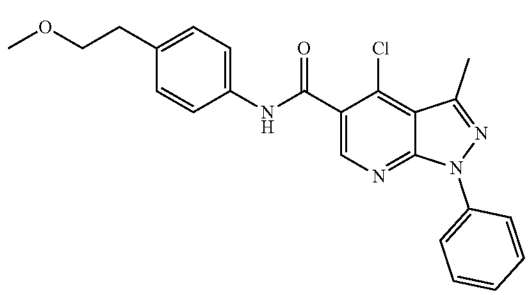 [SMILES: COCCc1ccc(NC(=O)c2cnc3c(c(C)nn3-c3ccccc3)c2Cl)cc1] |

TABLE 1-continued

| Ex. | Names | Structures |
|---|---|---|
| 17 | 4-Chloro-3-methyl-1-phenyl-1H-pyrazolo[3,4-b]pyridine-5-carboxylic acid (4-trifluoromethyl-phenyl)-amide | 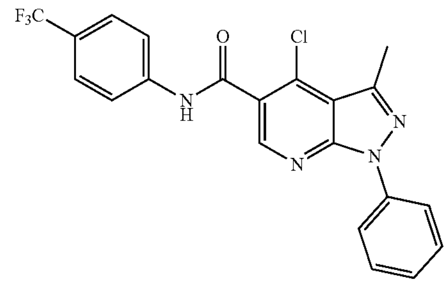 [SMILES: Cc1nn(-c2ccccc2)c2ncc(C(=O)Nc3ccc(C(F)(F)F)cc3)c(Cl)c12] |
| 18 | 4-Chloro-3-methyl-1-phenyl-1H-pyrazolo[3,4-b]pyridine-5-carboxylic acid (4-methoxy-phenyl)-amide | 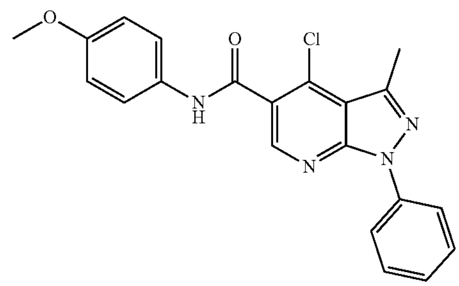 [SMILES: COc1ccc(NC(=O)c2cnc3c(c(C)nn3-c3ccccc3)c2Cl)cc1] |
| 19 | 4-Chloro-3-methyl-1-phenyl-1H-pyrazolo[3,4-b]pyridine-5-carboxylic acid (4-trifluoromethoxy-phenyl)-amide | 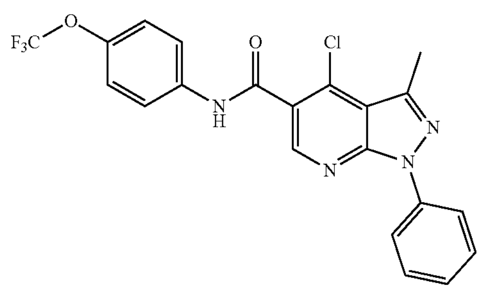 [SMILES: Cc1nn(-c2ccccc2)c2ncc(C(=O)Nc3ccc(OC(F)(F)F)cc3)c(Cl)c12] |
| 20 | 4-Chloro-3-methyl-1-phenyl-1H-pyrazolo[3,4-b]pyridine-5-carboxylic acid (4-dimethylamino-phenyl)-amide | 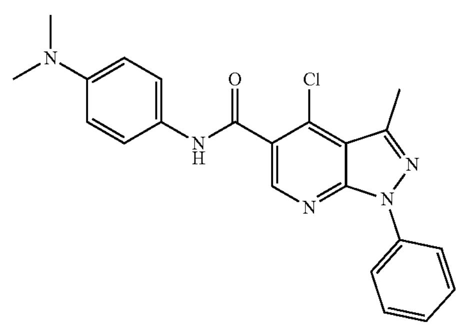 [SMILES: Cc1nn(-c2ccccc2)c2ncc(C(=O)Nc3ccc(N(C)C)cc3)c(Cl)c12] |
| 21 | 4-Chloro-3-methyl-1-phenyl-1H-pyrazolo[3,4-b]pyridine-5-carboxylic acid (4-acetylamino-phenyl)-amide | 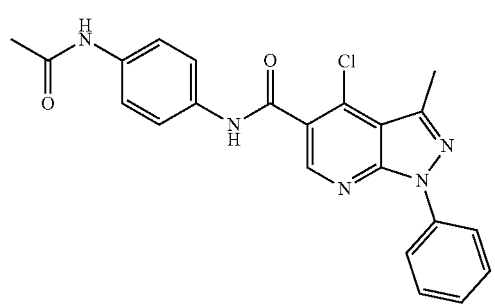 [SMILES: CC(=O)Nc1ccc(NC(=O)c2cnc3c(c(C)nn3-c3ccccc3)c2Cl)cc1] |

TABLE 1-continued

| Ex. | Names |
|---|---|
| 22 | 4-Chloro-3-methyl-1-phenyl-1H-pyrazolo[3,4-b]pyridine-5-carboxylic acid [4-(2H-tetrazol-5-yl)-phenyl]-amide |
| 23 | 4-Chloro-3-methyl-1-phenyl-1H-pyrazolo[3,4-b]pyridine-5-carboxylic acid (4-cyano-phenyl)-amide |
| 24 | 4-[(4-Chloro-3-methyl-1-phenyl-1H-pyrazolo[3,4-b]pyridine-5-carbonyl)-amino]-benzoic acid ethyl ester |
| 25 | 4-[(4-Chloro-3-methyl-1-phenyl-1H-pyrazolo[3,4-b]pyridine-5-carbonyl)-amino]-benzoic acid |
| 26 | 4-Chloro-3-methyl-1-phenyl-1H-pyrazolo[3,4-b]pyridine-5-carboxylic acid (3-trifluoromethyl-phenyl)-amide |

TABLE 1-continued

| Ex. | Names | Structures |
|---|---|---|
| 27 | 4-Chloro-3-methyl-1-phenyl-1H-pyrazolo[3,4-b]pyridine-5-carboxylic acid (2-trifluoromethyl-phenyl)-amide | 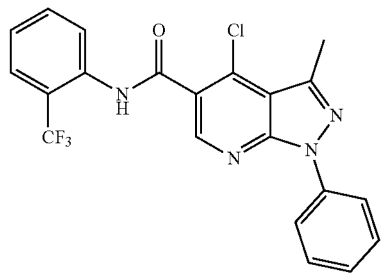 |
| 28 | 4-Chloro-3-methyl-1-phenyl-1H-pyrazolo[3,4-b]pyridine-5-carboxylic acid (2-chloro-phenyl)-amide | 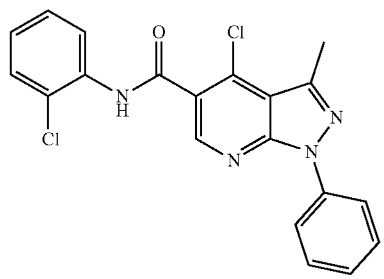 [SMILES: Cc1nn(-c2ccccc2)c2ncc(C(=O)Nc3ccccc3Cl)c(Cl)c12] |
| 29 | 4-Chloro-3-methyl-1-phenyl-1H-pyrazolo[3,4-b]pyridine-5-carboxylic acid (3-phenyl-propyl)-amide | 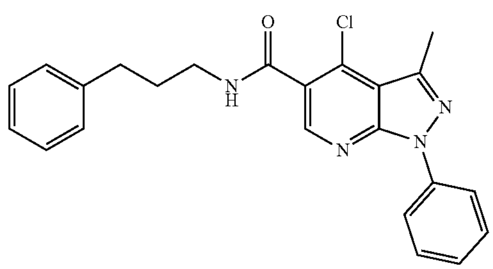 [SMILES: Cc1nn(-c2ccccc2)c2ncc(C(=O)NCCCc3ccccc3)c(Cl)c12] |
| 30 | 4-Chloro-3-methyl-1-phenyl-1H-pyrazolo[3,4-b]pyridine-5-carboxylic acid 4-(3,5-dimethyl-isoxazol-4-yl)-benzylamide | 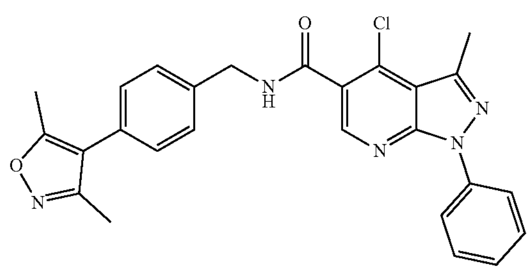 [SMILES: Cc1noc(C)c1-c1ccc(CNC(=O)c2cnc3c(c(C)nn3-c3ccccc3)c2Cl)cc1] |
| 31 | 4-Chloro-3-methyl-1-phenyl-1H-pyrazolo[3,4-b]pyridine-5-carboxylic acid thiazol-2-ylamide | 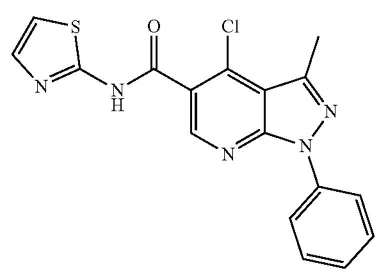 [SMILES: Cc1nn(-c2ccccc2)c2ncc(C(=O)Nc3nccs3)c(Cl)c12] |

TABLE 1-continued

| Ex. | Names | Structures |
|---|---|---|
| 32 | 4-Chloro-3-methyl-1-phenyl-1H-pyrazolo[3,4-b]pyridine-5-carboxylic acid thiophen-2-ylamide | 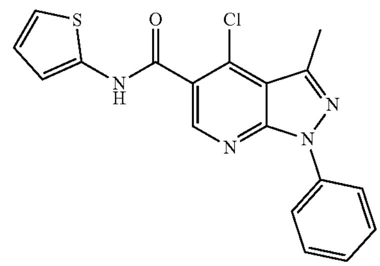 [SMILES: Cc1nn(-c2ccccc2)c2ncc(C(=O)Nc3cccs3)c(Cl)c12] |
| 33 | 4-Chloro-3-methyl-1-phenyl-1H-pyrazolo[3,4-b]pyridine-5-carboxylic acid cyclohexylamide | 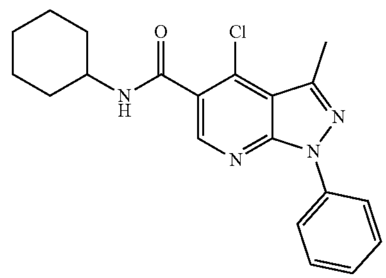 [SMILES: Cc1nn(-c2ccccc2)c2ncc(C(=O)NC3CCCCC3)c(Cl)c12] |
| 34 | 3-Methyl-1-phenyl-1H-pyrazolo[3,4-b]pyridine-5-carboxylic acid (4-chloro-phenyl)-amide | 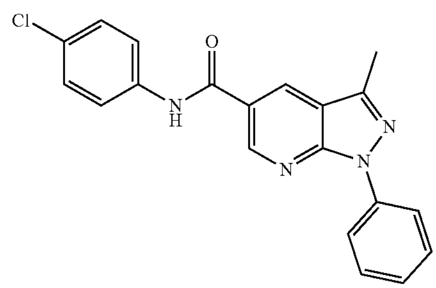 [SMILES: Cc1nn(-c2ccccc2)c2ncc(C(=O)Nc3ccc(Cl)cc3)cc12] |
| 35 | 3,4-Dimethyl-1-phenyl-1H-pyrazolo[3,4-b]pyridine-5-carboxylic acid (4-chloro-phenyl)-amide | 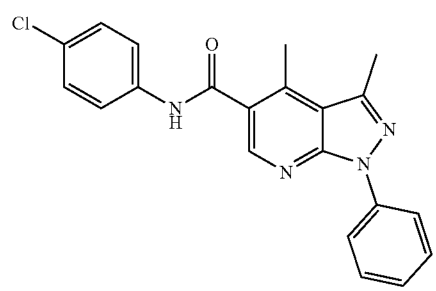 [SMILES: Cc1nn(-c2ccccc2)c2ncc(C(=O)Nc3ccc(Cl)cc3)c(C)c12] |
| 36 | 4-Hydroxy-3-methyl-1-phenyl-1H-pyrazolo[3,4-b]pyridine-5-carboxylic acid (4-chloro-phenyl)-amide | 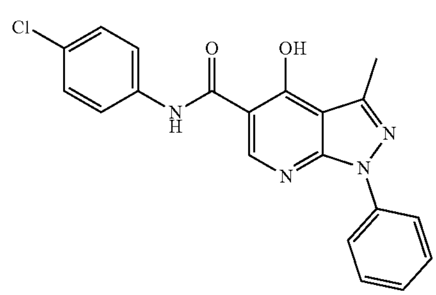 |

TABLE 1-continued

| Ex. | Names | Structures |
|---|---|---|
| 37 | 4-Cyano-3-methyl-1-phenyl-1H-pyrazolo[3,4-b]pyridine-5-carboxylic acid (4-chloro-phenyl)-amide | 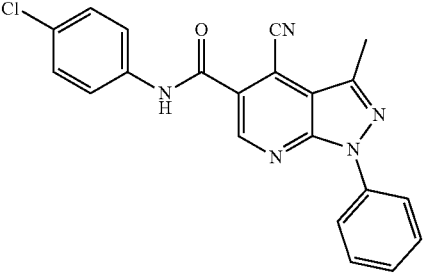 |
| 38 | 4-Cyano-3-methyl-1-phenyl-1H-pyrazolo[3,4-b]pyridine-5-carboxylic acid (4-cyano-phenyl)-amide | 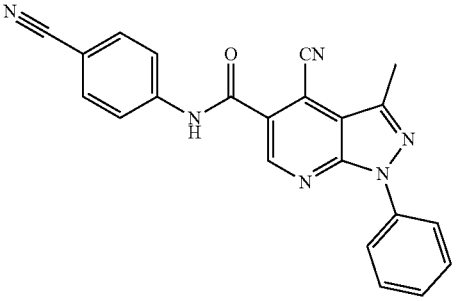 [SMILES: Cc1nn(-c2ccccc2)c2ncc(C(=O)Nc3ccc(C#N)cc3)c(C#N)c12] |
| 39 | 4-Fluoro-3-methyl-1-phenyl-1H-pyrazolo[3,4-b]pyridine-5-carboxylic acid (4-chloro-phenyl)-amide | 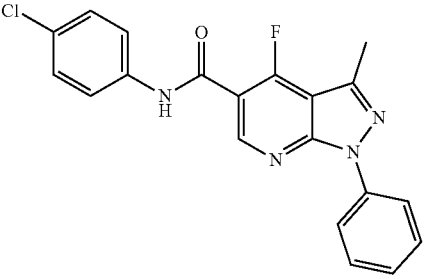 [SMILES: Cc1nn(-c2ccccc2)c2ncc(C(=O)Nc3ccc(Cl)cc3)c(F)c12] |
| 40 | 3-Methyl-1-phenyl-4-trifluoromethyl-1H-pyrazolo[3,4-b]pyridine-5-carboxylic acid (4-chloro-phenyl)-amide | 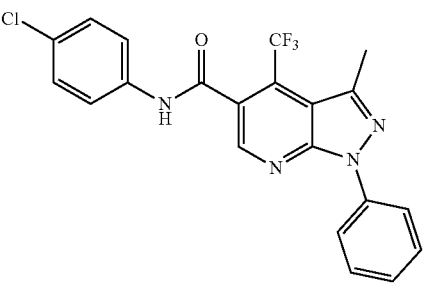 [SMILES: Cc1nn(-c2ccccc2)c2ncc(C(=O)Nc3ccc(Cl)cc3)c(C(F)(F)F)c12] |
| 41 | 4-Methoxy-3-methyl-1-phenyl-1H-pyrazolo[3,4-b]pyridine-5-carboxylic acid (4-chloro-phenyl)-amide | 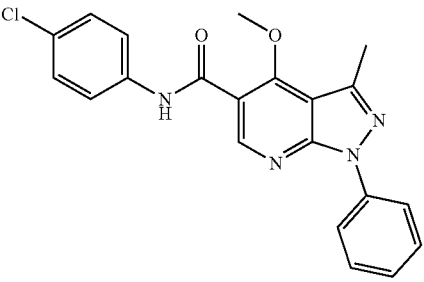 [SMILES: COc1c(C(=O)Nc2ccc(Cl)cc2)cnc2c1c(C)nn2-c1ccccc1] |

TABLE 1-continued

| Ex. | Names | Structures |
|---|---|---|
| 42 | N-(4-chlorophenyl)-4-(dimethylamino)-3-methyl-1-phenyl-1H-pyrazolo[3,4-b]pyridine-5-carboxamide | 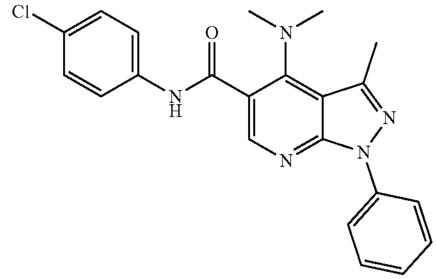 [SMILES: Cc1nn(-c2ccccc2)c2ncc(C(=O)Nc3ccc(Cl)cc3)c(N(C)C)c12] |
| 43 | 4-Chloro-3-methyl-1-phenyl-1H-pyrazolo[3,4-b]pyridine-5-carboxylic acid (4-chloro-phenyl)-methyl-amide | 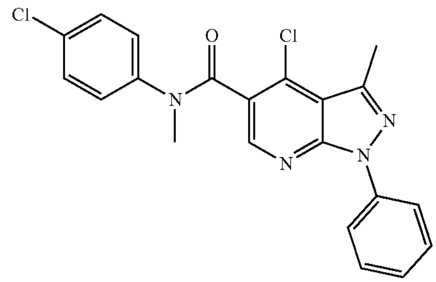 [SMILES: Cc1nn(-c2ccccc2)c2ncc(C(=O)N(C)c3ccc(Cl)cc3)c(Cl)c12] |
| 44 | 4-Chloro-3-methyl-1-phenyl-1H-pyrazolo[3,4-b]pyridine-5-carboxylic acid (4-chloro-phenyl)-ethyl-amide | 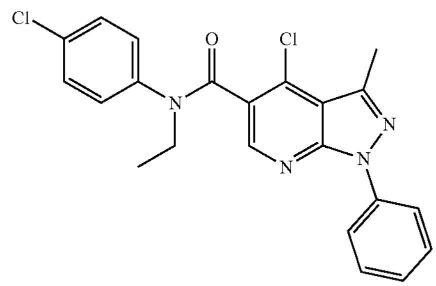 [SMILES: CCN(C(=O)c1cnc2c(c(C)nn2-c2ccccc2)c1Cl)c1ccc(Cl)cc1] |
| 45 | 4-Chloro-3-methyl-1-phenyl-1H-pyrazolo[3,4-b]pyridine-5-carboxylic acid (4-chloro-phenyl)-(2-methoxy-ethyl)-amide | 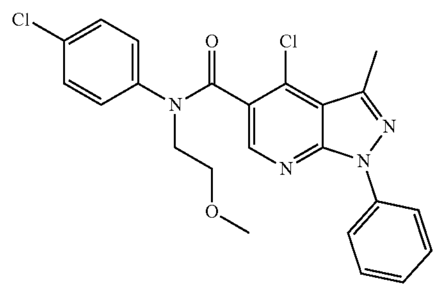 [SMILES: COCCN(C(=O)c1cnc2c(c(C)nn2-c2ccccc2)c1Cl)c1ccc(Cl)cc1] |
| 46 | 4-Chloro-3-methyl-1-phenyl-1H-pyrazolo[3,4-b]pyridine-5-carboxylic acid (4-chloro-phenyl)-(2-dimethylamino-ethyl)-amide | 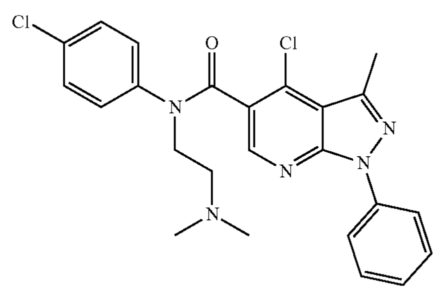 [SMILES: Cc1nn(-c2ccccc2)c2ncc(C(=O)N(CCN(C)C)c3ccc(Cl)cc3)c(Cl)c12] |

TABLE 1-continued

| Ex. | Names | Structures |
|---|---|---|
| 47 | 4-Chloro-1-(4-fluoro-phenyl)-3-methyl-1H-pyrazolo[3,4-b]pyridine-5-carboxylic acid (4-trifluoromethyl-phenyl)-amide | 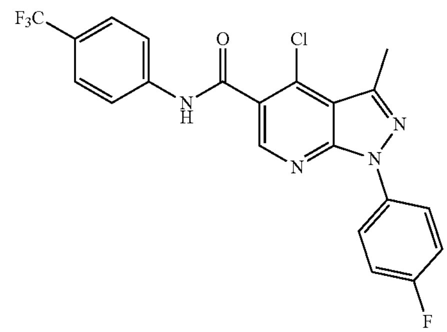 |
| 48 | 4-Chloro-1-(4-fluoro-phenyl)-3-methyl-1H-pyrazolo[3,4-b]pyridine-5-carboxylic acid (4-isopropyl-phenyl)-amide | 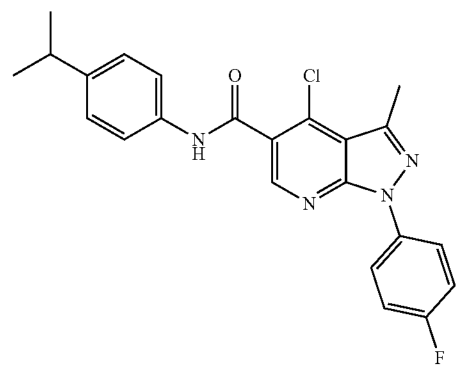 [SMILES: Cc1nn(-c2ccc(F)cc2)c2ncc(C(=O)Nc3ccc(C(C)C)cc3)c(Cl)c12] |
| 49 | 4-Chloro-1-(4-fluoro-phenyl)-3-methyl-1H-pyrazolo[3,4-b]pyridine-5-carboxylic acid (4-methoxy-phenyl)-amide | 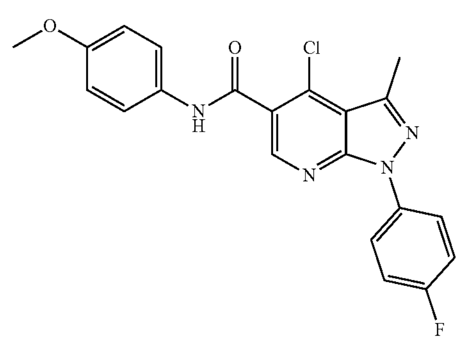 [SMILES: COc1ccc(NC(=O)c2cnc3c(c(C)nn3-c3ccc(F)cc3)c2Cl)cc1] |
| 50 | 4-Chloro-1-(4-fluoro-phenyl)-3-methyl-1H-pyrazolo[3,4-b]pyridine-5-carboxylic acid (4-ethoxy-phenyl)-amide | 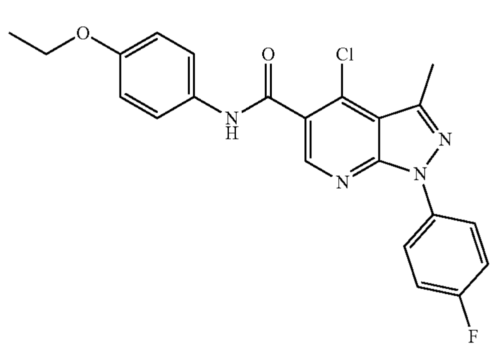 [SMILES: CCOc1ccc(NC(=O)c2cnc3c(c(C)nn3-c3ccc(F)cc3)c2Cl)cc1] |

TABLE 1-continued

| Ex. | Names | Structures |
|---|---|---|
| 51 | 4-Chloro-1-(4-fluoro-phenyl)-3-methyl-1H-pyrazolo[3,4-b]pyridine-5-carboxylic acid (4-propoxy-phenyl)-amide | 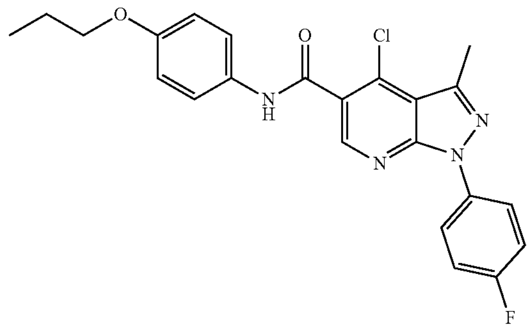 [SMILES: CCCOc1ccc(NC(=O)c2cnc3c(c(C)nn3-c3ccc(F)cc3)c2Cl)cc1] |
| 52 | 4-Chloro-1-(4-fluoro-phenyl)-3-methyl-1H-pyrazolo[3,4-b]pyridine-5-carboxylic acid (4-butoxy-phenyl)-amide | 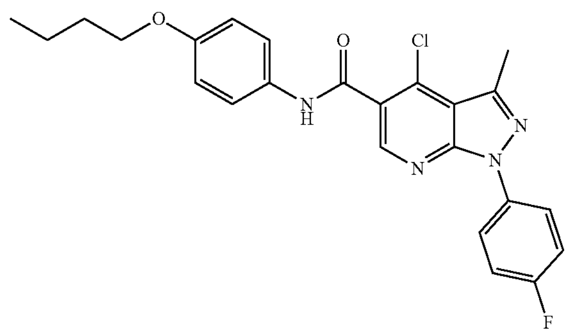 [SMILES: CCCCOc1ccc(NC(=O)c2cnc3c(c(C)nn3-c3ccc(F)cc3)c2Cl)cc1] |
| 53 | 4-Chloro-1-(4-fluoro-phenyl)-3-methyl-1H-pyrazolo[3,4-b]pyridine-5-carboxylic acid (4-hydroxy-phenyl)-amide | 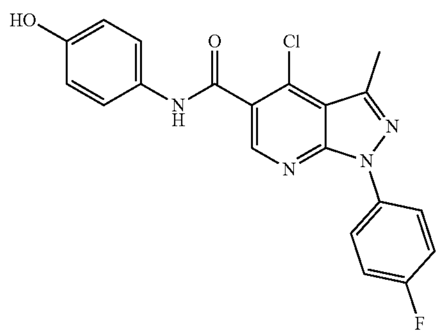 [SMILES: Cc1nn(-c2ccc(F)cc2)c2ncc(C(=O)Nc3ccc(O)cc3)c(Cl)c12] |
| 54 | 4-Chloro-1-(4-fluoro-phenyl)-3-methyl-1H-pyrazolo[3,4-b]pyridine-5-carboxylic acid (4-isopropoxy-phenyl)-amide | 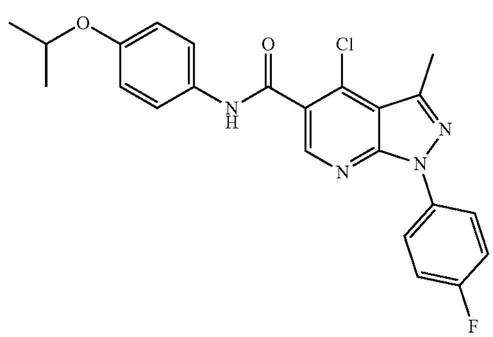 [SMILES: Cc1nn(-c2ccc(F)cc2)c2ncc(C(=O)Nc3ccc(OC(C)C)cc3)c(Cl)c12] |

TABLE 1-continued

| Ex. | Names | Structures |
|-----|-------|------------|
| 55 | 4-Chloro-1-(4-fluoro-phenyl)-3-methyl-1H-pyrazolo[3,4-b]pyridine-5-carboxylic acid (4-chloro-phenyl)-amide | 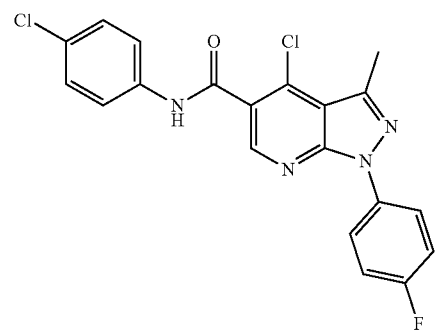 [SMILES: Cc1nn(-c2ccc(F)cc2)c2ncc(C(=O)Nc3ccc(Cl)cc3)c(Cl)c12] |
| 56 | 4-Chloro-1-(4-chloro-phenyl)-3-methyl-1H-pyrazolo[3,4-b]pyridine-5-carboxylic acid (4-chloro-phenyl)-amide | 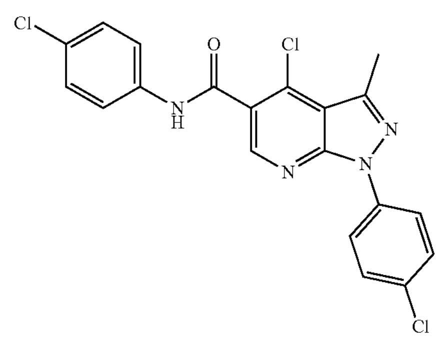 [SMILES: Cc1nn(-c2ccc(Cl)cc2)c2ncc(C(=O)Nc3ccc(Cl)cc3)c(Cl)c12] |
| 57 | 1-(4-Bromo-phenyl)-4-chloro-3-methyl-1H-pyrazolo[3,4-b]pyridine-5-carboxylic acid (4-trifluoromethyl-phenyl)-amide | 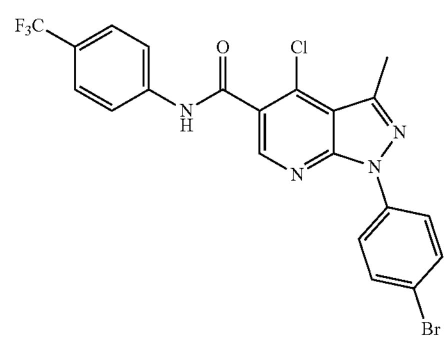 [SMILES: Cc1nn(-c2ccc(Br)cc2)c2ncc(C(=O)Nc3ccc(C(F)(F)F)cc3)c(Cl)c12] |
| 58 | 1-(4-Bromo-phenyl)-4-chloro-3-methyl-1H-pyrazolo[3,4-b]pyridine-5-carboxylic acid (4-isopropyl-phenyl)-amide | 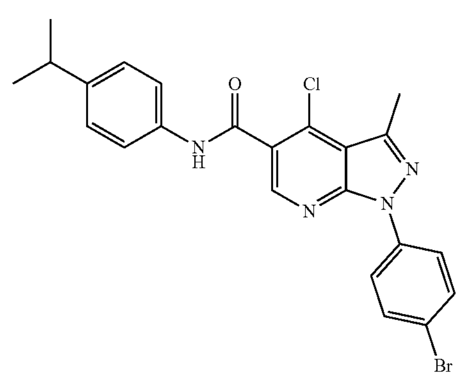 |

TABLE 1-continued

| Ex. | Names | Structures |
|---|---|---|
| 59 | 1-(4-Bromo-phenyl)-4-chloro-3-methyl-1H-pyrazolo[3,4-b]pyridine-5-carboxylic acid (4-chloro-phenyl)-amide | 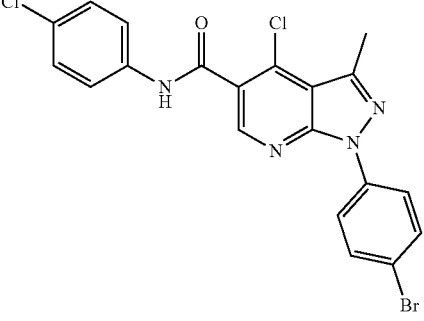 |
| 60 | 4-Chloro-1-(4-iodo-phenyl)-3-methyl-1H-pyrazolo[3,4-b]pyridine-5-carboxylic acid (4-trifluoromethyl-phenyl)-amide | 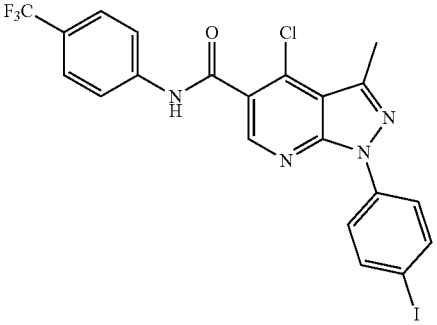 [SMILES: Cc1nn(-c2ccc(I)cc2)c2ncc(C(=O)Nc3ccc(C(F)(F)F)cc3)c(Cl)c12] |
| 61 | 4-Chloro-1-(4-iodo-phenyl)-3-methyl-1H-pyrazolo[3,4-b]pyridine-5-carboxylic acid (4-isopropyl-phenyl)-amide | 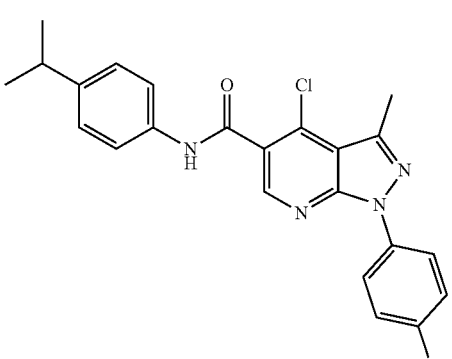 |
| 62 | 4-Chloro-1-(4-iodo-phenyl)-3-methyl-1H-pyrazolo[3,4-b]pyridine-5-carboxylic acid (4-chloro-phenyl)-amide | 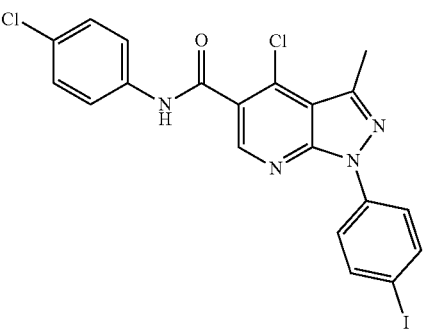 [SMILES: Cc1nn(-c2ccc(I)cc2)c2ncc(C(=O)Nc3ccc(Cl)cc3)c(Cl)c12] |

TABLE 1-continued

| Ex. | Names | Structures |
|---|---|---|
| 63 | 4-Chloro-3-methyl-1-p-tolyl-1H-pyrazolo[3,4-b]pyridine-5-carboxylic acid (4-chloro-phenyl)-amide | 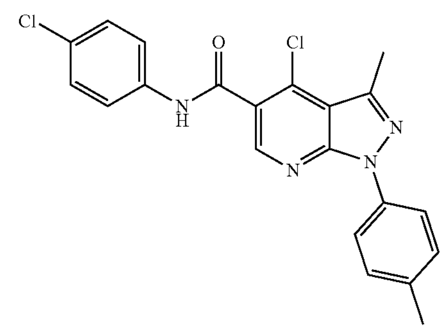 [SMILES: Cc1ccc(-n2nc(C)c3c(Cl)c(C(=O)Nc4ccc(Cl)cc4)cnc32)cc1] |
| 64 | 4-Chloro-3-methyl-1-p-tolyl-1H-pyrazolo[3,4-b]pyridine-5-carboxylic acid (4-trifluoromethoxy-phenyl)-amide | 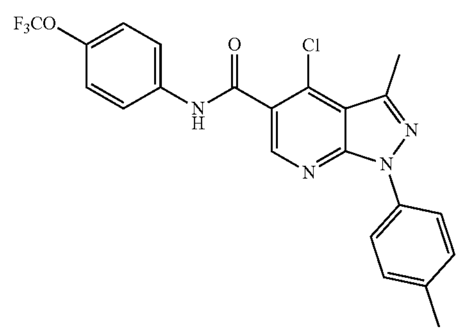 [SMILES: Cc1ccc(-n2nc(C)c3c(Cl)c(C(=O)Nc4ccc(OC(F)(F)F)cc4)cnc32)cc1] |
| 65 | 4-Chloro-3-methyl-1-p-tolyl-1H-pyrazolo[3,4-b]pyridine-5-carboxylic acid (4-isopropyl-phenyl)-amide | 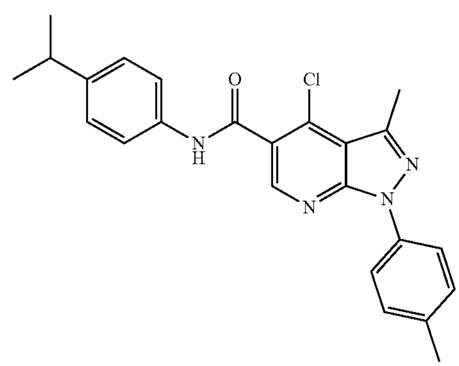 [SMILES: Cc1ccc(-n2nc(C)c3c(Cl)c(C(=O)Nc4ccc(C(C)C)cc4)cnc32)cc1] |
| 66 | 4-Chloro-3-methyl-1-p-tolyl-1H-pyrazolo[3,4-b]pyridine-5-carboxylic acid (4-trifluoromethyl-phenyl)-amide | 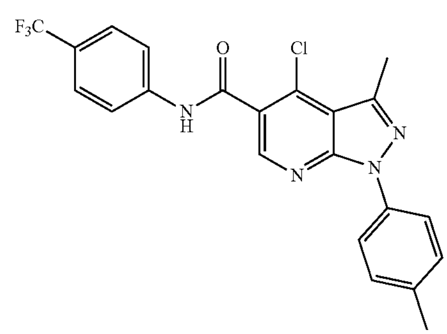 [SMILES: Cc1ccc(-n2nc(C)c3c(Cl)c(C(=O)Nc4ccc(C(F)(F)F)cc4)cnc32)cc1] |

TABLE 1-continued

| Ex. | Names | Structures |
|---|---|---|
| 67 | 4-Chloro-1-(4-methoxy-phenyl)-3-methyl-1H-pyrazolo[3,4-b]pyridine-5-carboxylic acid (4-chloro-phenyl)-amide | 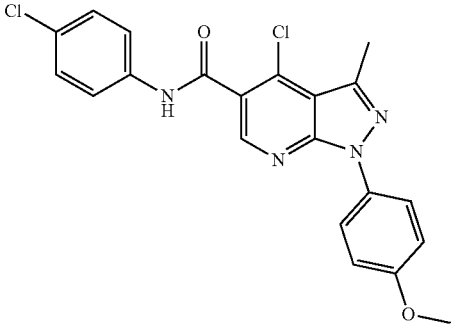 [SMILES: COc1ccc(-n2nc(C)c3c(Cl)c(C(=O)Nc4ccc(Cl)cc4)cnc32)cc1] |
| 68 | 4-Chloro-1-(4-methoxy-phenyl)-3-methyl-1H-pyrazolo[3,4-b]pyridine-5-carboxylic acid (4-trifluoromethyl-phenyl)-amide | 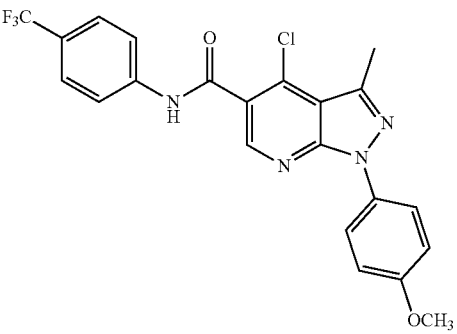 [SMILES: COc1ccc(-n2nc(C)c3c(Cl)c(C(=O)Nc4ccc(C(F)(F)F)cc4)cnc32)cc1] |
| 69 | 4-Chloro-1-(4-methoxy-phenyl)-3-methyl-1H-pyrazolo[3,4-b]pyridine-5-carboxylic acid (4-isopropyl-phenyl)-amide | 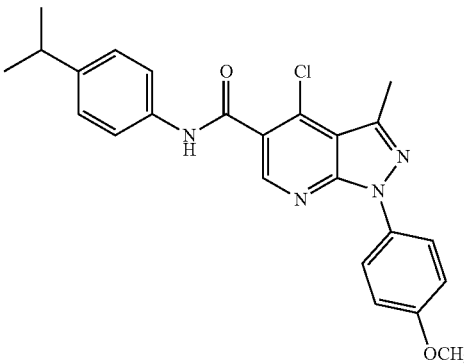 |
| 70 | 4-Chloro-3-methyl-1-(4-trifluoromethyl-phenyl)-1H-pyrazolo[3,4-b]pyridine-5-carboxylic acid (4-chloro-phenyl)-amide | 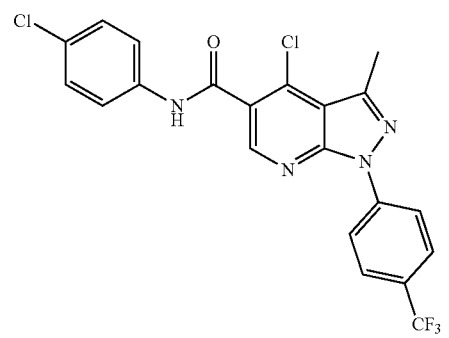 [SMILES: Cc1nn(-c2ccc(C(F)(F)F)cc2)c2ncc(C(=O)Nc3ccc(Cl)cc3)c(Cl)c12] |

TABLE 1-continued

| Ex. | Names | Structures |
|---|---|---|
| 71 | 4-Chloro-3-methyl-1-(4-trifluoromethoxy-phenyl)-1H-pyrazolo[3,4-b]pyridine-5-carboxylic acid (4-chloro-phenyl)-amide | 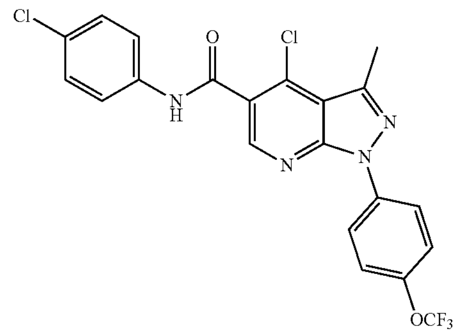 [SMILES: Cc1nn(-c2ccc(OC(F)(F)F)cc2)c2ncc(C(=O)Nc3ccc(Cl)cc3)c(Cl)c12] |
| 72 | 4-Chloro-1-(4-dimethylamino-phenyl)-3-methyl-1H-pyrazolo[3,4-b]pyridine-5-carboxylic acid (4-chloro-phenyl)-amide | 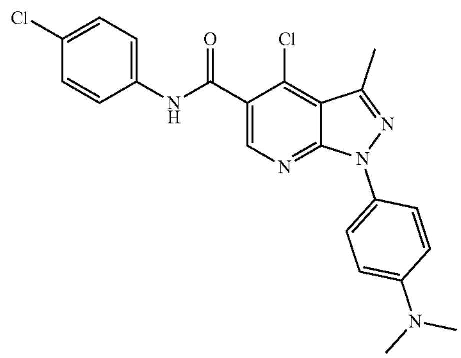 [SMILES: Cc1nn(-c2ccc(N(C)C)cc2)c2ncc(C(=O)Nc3ccc(Cl)cc3)c(Cl)c12] |
| 73 | 4-Chloro-1-phenyl-1H-pyrazolo[3,4-b]pyridine-5-carboxylic acid (4-chloro-phenyl)-amide | 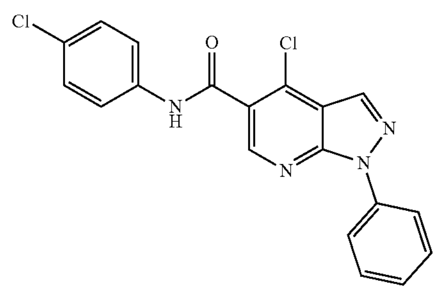 [SMILES: O=C(Nc1ccc(Cl)cc1)c1cnc2c(cnn2-c2ccccc2)c1Cl] |
| 74 | 4-Chloro-1-(4-chloro-phenyl)-1H-pyrazolo[3,4-b]pyridine-5-carboxylic acid (4-chloro-phenyl)-amide | 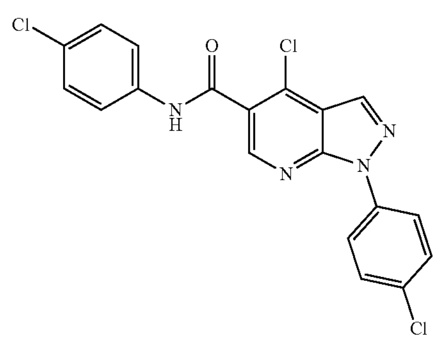 [SMILES: O=C(Nc1ccc(Cl)cc1)c1cnc2c(cnn2-c2ccc(Cl)cc2)c1Cl] |
| 75 | 4-Chloro-1-phenyl-3-trifluoromethyl-1H-pyrazolo[3,4-b]pyridine-5-carboxylic acid (4-chloro-phenyl)-amide | 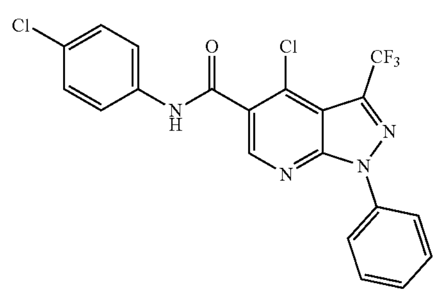 [SMILES: O=C(Nc1ccc(Cl)cc1)c1cnc2c(c(C(F)(F)F)nn2-c2ccccc2)c1Cl] |

TABLE 1-continued

| Ex. | Names | Structures |
|---|---|---|
| 76 | 4-Chloro-3-ethyl-1-phenyl-1H-pyrazolo[3,4-b]pyridine-5-carboxylic acid (4-chloro-phenyl)-amide | 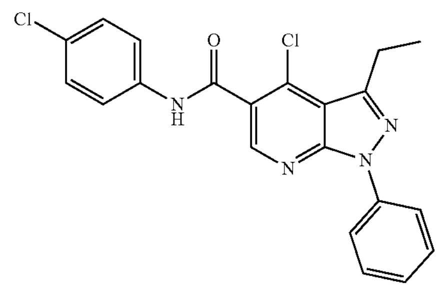 [SMILES: CCc1nn(-c2ccccc2)c2ncc(C(=O)Nc3ccc(Cl)cc3)c(Cl)c12] |
| 77 | 4-Chloro-3-ethyl-1-phenyl-1H-pyrazolo[3,4-b]pyridine-5-carboxylic acid (4-trifluoromethyl-phenyl)-amide | 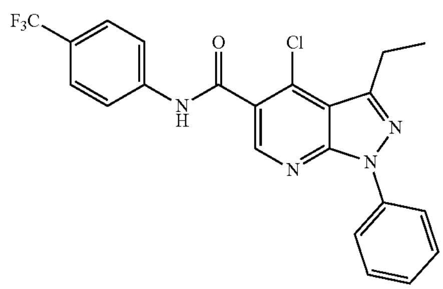 [SMILES: CCc1nn(-c2ccccc2)c2ncc(C(=O)Nc3ccc(C(F)(F)F)cc3)c(Cl)c12] |
| 78 | 4-Chloro-3-isopropyl-1-phenyl-1H-pyrazolo[3,4-b]pyridine-5-carboxylic acid (4-chloro-phenyl)-amide | 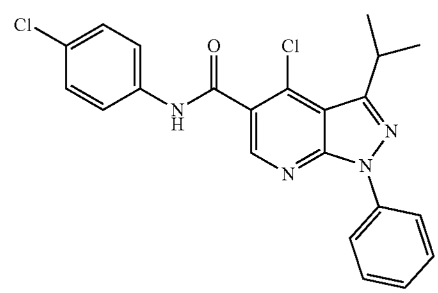 [SMILES: CC(C)c1nn(-c2ccccc2)c2ncc(C(=O)Nc3ccc(Cl)cc3)c(Cl)c12] |
| 79 | 4-Chloro-3-isopropyl-1-phenyl-1H-pyrazolo[3,4-b]pyridine-5-carboxylic acid (4-trifluoromethyl-phenyl)-amide | 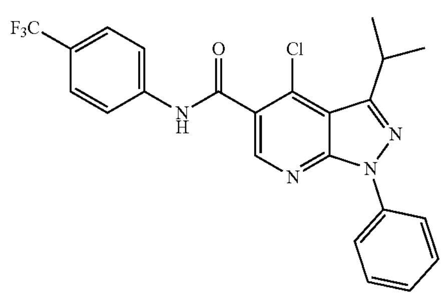 [SMILES: CC(C)c1nn(-c2ccccc2)c2ncc(C(=O)Nc3ccc(C(F)(F)F)cc3)c(Cl)c12] |
| 80 | 4-Chloro-3-cyclopropyl-1-phenyl-1H-pyrazolo[3,4-b]pyridine-5-carboxylic acid (4-chloro-phenyl)-amide | 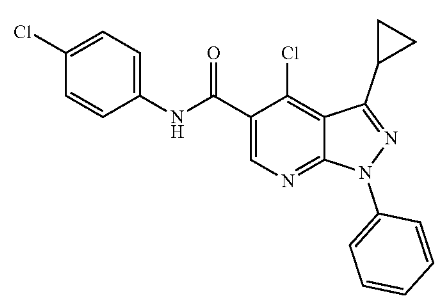 [SMILES: O=C(Nc1ccc(Cl)cc1)c1cnc2c(c(C3CC3)nn2-c2ccccc2)c1Cl] |

TABLE 1-continued

| Ex. | Names | Structures |
|---|---|---|
| 81 | 4-Chloro-3-cyclopropyl-1-phenyl-1H-pyrazolo[3,4-b]pyridine-5-carboxylic acid (4-trifluoromethyl-phenyl)-amide | 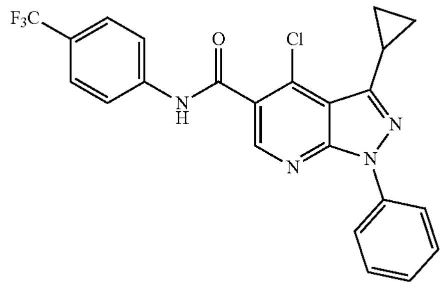 [SMILES: O=C(Nc1ccc(C(F)(F)F)cc1)c1cnc2c(c(C3CC3)nn2-c2ccccc2)c1Cl] |
| 82 | 4-Chloro-1,3-dimethyl-1H-pyrazolo[3,4-b]pyridine-5-carboxylic acid (4-chloro-phenyl)-amide | 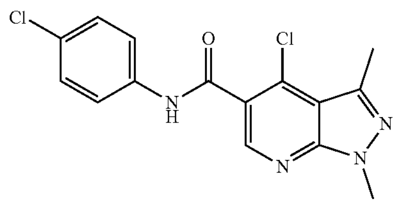 [SMILES: Cc1nn(C)c2ncc(C(=O)Nc3ccc(Cl)cc3)c(Cl)c12] |
| 83 | 4-Chloro-1,3-dimethyl-1H-pyrazolo[3,4-b]pyridine-5-carboxylic acid (3-chloro-phenyl)-amide | 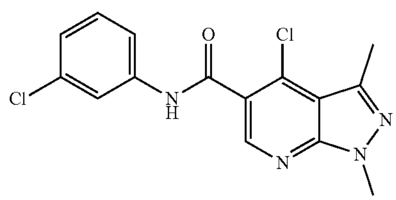 [SMILES: Cc1nn(C)c2ncc(C(=O)Nc3cccc(Cl)c3)c(Cl)c12] |
| 84 | 4-Chloro-1,3-dimethyl-1H-pyrazolo[3,4-b]pyridine-5-carboxylic acid (2-chloro-phenyl)-amide | 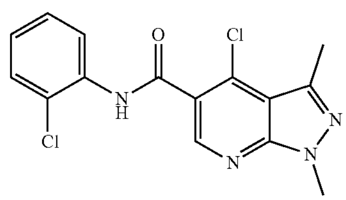 [SMILES: Cc1nn(C)c2ncc(C(=O)Nc3ccccc3Cl)c(Cl)c12] |
| 85 | 4-Chloro-1,3-dimethyl-1H-pyrazolo[3,4-b]pyridine-5-carboxylic acid (4-trifluoromethyl-phenyl)-amide | 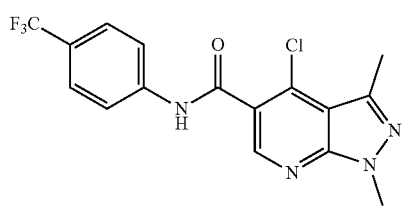 [SMILES: Cc1nn(C)c2ncc(C(=O)Nc3ccc(C(F)(F)F)cc3)c(Cl)c12] |
| 86 | 4-Chloro-1,3-dimethyl-1H-pyrazolo[3,4-b]pyridine-5-carboxylic acid (3-trifluoromethyl-phenyl)-amide | 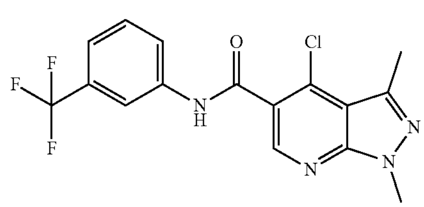 [SMILES: Cc1nn(C)c2ncc(C(=O)Nc3cccc(C(F)(F)F)c3)c(Cl)c12] |
| 87 | 4-Chloro-1,3-dimethyl-1H-pyrazolo[3,4-b]pyridine-5-carboxylic acid (2-trifluoromethyl-phenyl)-amide | 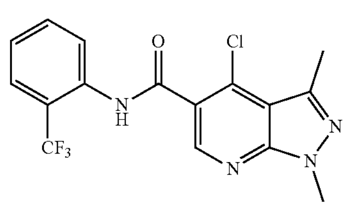 |

TABLE 1-continued

| Ex. | Names | Structures |
|---|---|---|
| 88 | 4-Chloro-1,3-dimethyl-1H-pyrazolo[3,4-b]pyridine-5-carboxylic acid (4-isopropyl-phenyl)-amide | 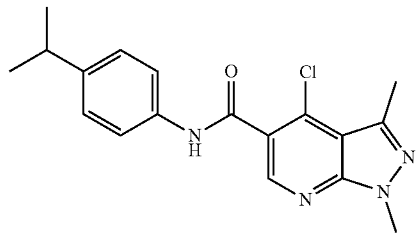 |
| 89 | 4-Chloro-1,3-dimethyl-1H-pyrazolo[3,4-b]pyridine-5-carboxylic acid (3-isopropyl-phenyl)-amide | 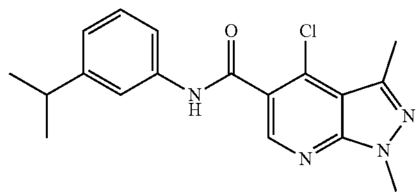 [SMILES: Cc1nn(C)c2ncc(C(=O)Nc3cccc(C(C)C)c3)c(Cl)c12] |
| 90 | 4-Chloro-1,3-dimethyl-1H-pyrazolo[3,4-b]pyridine-5-carboxylic acid (5-cyano-pyridin-2-yl)-amide | 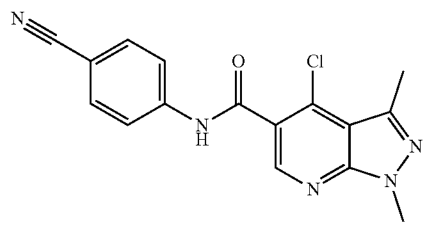 [SMILES: Cc1nn(C)c2ncc(C(=O)Nc3ccc(C#N)cc3)c(Cl)c12] |
| 91 | 4-Chloro-1,3-dimethyl-1H-pyrazolo[3,4-b]pyridine-5-carboxylic acid (4-bromo-phenyl)-amide | 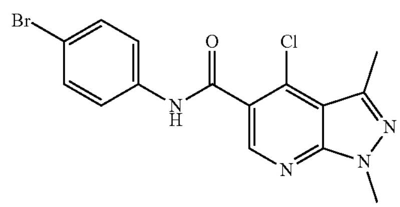 |
| 92 | 4-Chloro-1,3-dimethyl-1H-pyrazolo[3,4-b]pyridine-5-carboxylic acid (3-bromo-phenyl)-amide | 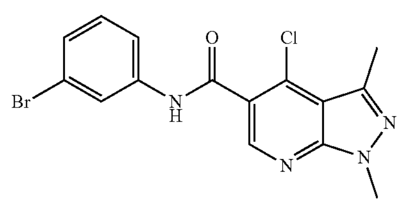 |
| 93 | 4-Chloro-1,3-dimethyl-1H-pyrazolo[3,4-b]pyridine-5-carboxylic acid (4-fluoro-phenyl)-amide | 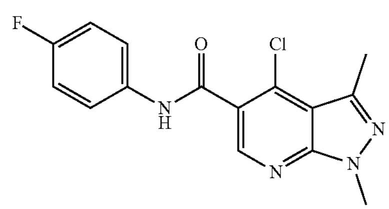 [SMILES: Cc1nn(C)c2ncc(C(=O)Nc3ccc(F)cc3)c(Cl)c12] |
| 94 | 4-Chloro-1,3-dimethyl-1H-pyrazolo[3,4-b]pyridine-5-carboxylic acid (4-dimethylamino-phenyl)-amide | 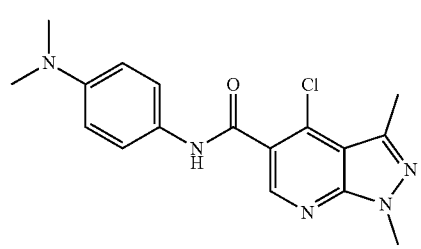 [SMILES: Cc1nn(C)c2ncc(C(=O)Nc3ccc(N(C)C)cc3)c(Cl)c12] |

TABLE 1-continued

| Ex. | Names | Structures |
|---|---|---|
| 95 | 4-Chloro-1,3-dimethyl-1H-pyrazolo[3,4-b]pyridine-5 carboxylic acid (4-hydroxy-phenyl)-amide | 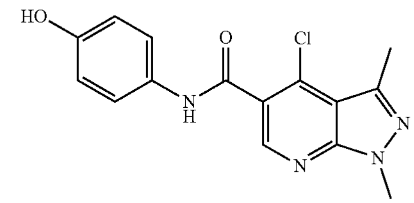 [SMILES: Cc1nn(C)c2ncc(C(=O)Nc3ccc(O)cc3)c(Cl)c12] |
| 96 | 4-Chloro-1,3-dimethyl-1H-pyrazolo[3,4-b]pyridine-5-carboxylic acid (5-methoxy-pyridin-2-yl)-amide | 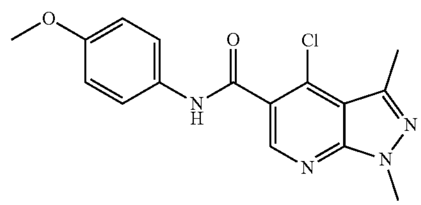 [SMILES: COc1ccc(NC(=O)c2cnc3c(c(C)nn3C)c2Cl)cc1] |
| 97 | 4-Chloro-1,3-dimethyl-1H-pyrazolo[3,4-b]pyridine-5-carboxylic acid (3-methoxy-phenyl)-amide | 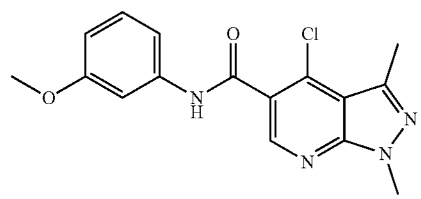 [SMILES: COc1cccc(NC(=O)c2cnc3c(c(C)nn3C)c2Cl)c1] |
| 98 | 4-Chloro-1,3-dimethyl-1H-pyrazolo[3,4-b]pyridine-5-carboxylic acid (2-trifluoromethyl-phenyl)-amide | 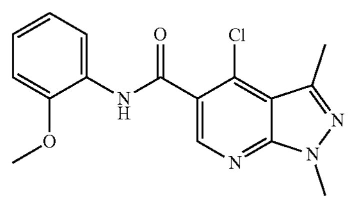 [SMILES: COc1ccccc1NC(=O)c1cnc2c(c(C)nn2C)c1Cl] |
| 99 | 4-Chloro-1,3-dimethyl-1H-pyrazolo[3,4-b]pyridine-5-carboxylic acid (4-ethoxy-phenyl)-amide | 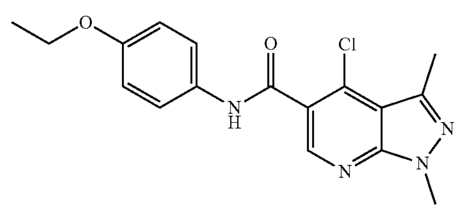 [SMILES: CCOc1ccc(NC(=O)c2cnc3c(c(C)nn3C)c2Cl)cc1] |
| 100 | 4-Chloro-1,3-dimethyl-1H-pyrazolo[3,4-b]pyridine-5-carboxylic acid [4-(2-hydroxy-ethoxy)-phenyl]-amide | 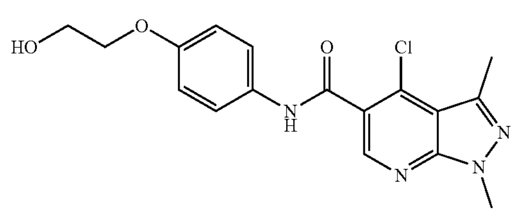 [SMILES: Cc1nn(C)c2ncc(C(=O)Nc3ccc(OCCO)cc3)c(Cl)c12] |
| 101 | 4-Chloro-1,3-dimethyl-1H-pyrazolo[3,4-b]pyridine-5-carboxylic acid [4-(2,2,2-trifluoro-ethoxy)-phenyl]-amide | 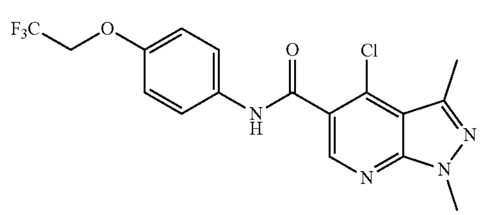 [SMILES: Cc1nn(C)c2ncc(C(=O)Nc3ccc(OCC(F)(F)F)cc3)c(Cl)c12] |

TABLE 1-continued

| Ex. | Names | Structures |
|---|---|---|
| 102 | 4-chloro-N-(4-(2-methoxyethoxy)phenyl)-1,3-dimethyl-1H-pyrazolo[3,4-b]pyridine-5-carboxamide | 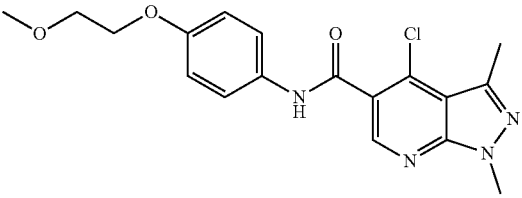 [SMILES: COCCOc1ccc(NC(=O)c2cnc3c(c(C)nn3C)c2Cl)cc1] |
| 103 | 4-Chloro-1,3-dimethyl-1H-pyrazolo[3,4-b]pyridine-5-carboxylic acid (4-propoxy-phenyl)-amide | 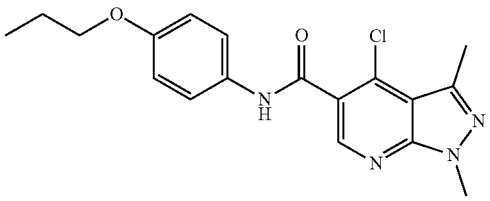 [SMILES: CCCOc1ccc(NC(=O)c2cnc3c(c(C)nn3C)c2Cl)cc1] |
| 104 | 4-chloro-1,3-dimethyl-N-(3-propoxyphenyl)-1H-pyrazolo[3,4-b]pyridine-5-carboxamide | 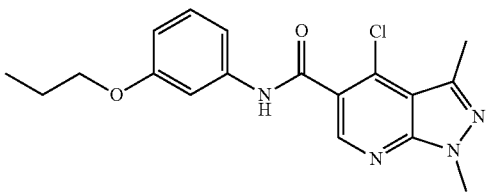 [SMILES: CCCOc1cccc(NC(=O)c2cnc3c(c(C)nn3C)c2Cl)c1] |
| 105 | 4-chloro-1,3-dimethyl-N-(2-propoxyphenyl)-1H-pyrazolo[3,4-b]pyridine-5-carboxamide | 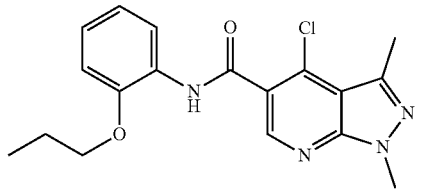 [SMILES: CCCOc1ccccc1NC(=O)c1cnc2c(c(C)nn2C)c1Cl] |
| 106 | 4-Chloro-1,3-dimethyl-1H-pyrazolo[3,4-b]pyridine-5-carboxylic acid (5-isopropoxy-pyridin-2-yl)-amide | 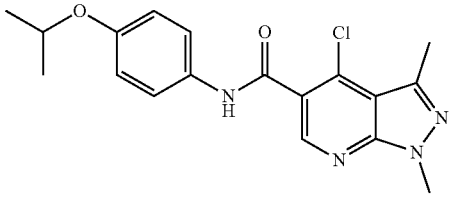 [SMILES: Cc1nn(C)c2ncc(C(=O)Nc3ccc(OC(C)C)cc3)c(Cl)c12] |
| 107 | 4-Chloro-1,3-dimethyl-1H-pyrazolo[3,4-b]pyridine-5-carboxylic acid (4-butoxy-phenyl)-amide | 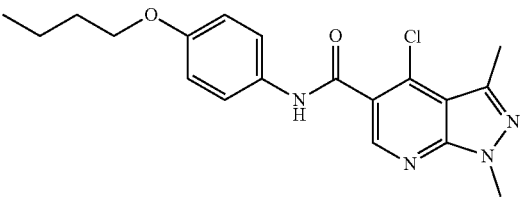 [SMILES: CCCCOc1ccc(NC(=O)c2cnc3c(c(C)nn3C)c2Cl)cc1] |
| 108 | 4-Chloro-1,3-dimethyl-1H-pyrazolo[3,4-b]pyridine-5-carboxylic acid (3-butoxy-phenyl)-amide | 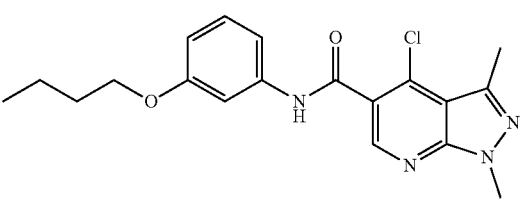 [SMILES: CCCCOc1cccc(NC(=O)c2cnc3c(c(C)nn3C)c2Cl)c1] |

TABLE 1-continued

| Ex. | Names |
|---|---|
| 109 | 4-Chloro-1,3-dimethyl-1H-pyrazolo[3,4-b]pyridine-5-carboxylic acid (2-butoxy-phenyl)-amide |
| 110 | 4-Chloro-1,3-dimethyl-1H-pyrazolo[3,4-b]pyridine-5-carboxylic acid [4-(4-methoxy-butoxy)-phenyl]-amide |
| 111 | 4-Chloro-1,3-dimethyl-1H-pyrazolo[3,4-b]pyridine-5-carboxylic acid [4-(9-methoxy-nonyloxy)-phenyl]-amide |
| 112 | 4-Chloro-1,3-dimethyl-1H-pyrazolo[3,4-b]pyridine-5-carboxylic acid [4-(2-dimethylamino-ethoxy)-phenyl]-amide |
| 113 | 4-Chloro-1,3-dimethyl-1H-pyrazolo[3,4-b]pyridine-5-carboxylic acid [4-(2-morpholin-4-yl-ethoxy)-phenyl]-amide |
| 114 | 4-Chloro-1,3-dimethyl-1H-pyrazolo[3,4-b]pyridine-5-carboxylic acid (4-benzoyl-phenyl)-amide |
| 115 | 4-Chloro-1,3-dimethyl-1H-pyrazolo[3,4-b]pyridine-5-carboxylic acid 4-(3,5-dimethyl-isoxazol-4-yl)-benzylamide |

TABLE 1-continued

| Ex. | Names | Structures |
|---|---|---|
| 116 | 4-Chloro-1,3-dimethyl-1H-pyrazolo[3,4-b]pyridine-5-carboxylic acid cyclohexylamide | 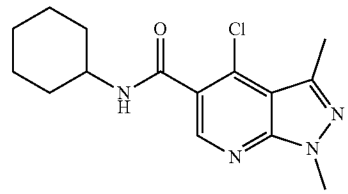 [SMILES: Cc1nn(C)c2ncc(C(=O)NC3CCCCC3)c(Cl)c12] |
| 117 | 4-Chloro-1,3-dimethyl-1H-pyrazolo[3,4-b]pyridine-5-carboxylic acid cyclopentylamide | 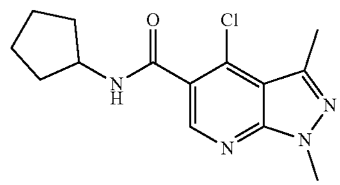 [SMILES: Cc1nn(C)c2ncc(C(=O)NC3CCCC3)c(Cl)c12] |
| 118 | 4-Chloro-1,3-dimethyl-1H-pyrazolo[3,4-b]pyridine-5-carboxylic acid (2-methoxy-ethyl)-amide | 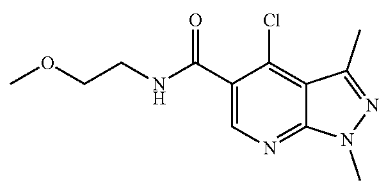 [SMILES: COCCNC(=O)c1cnc2c(c(C)nn2C)c1Cl] |
| 119 | 4-Chloro-1,3-dimethyl-1H-pyrazolo[3,4-b]pyridine-5-carboxylic acid (2-morpholin-4-yl-ethyl)-amide | 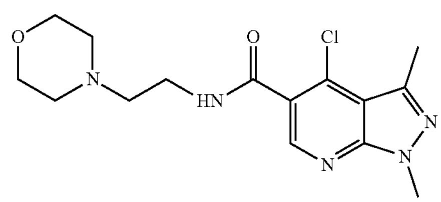 [SMILES: Cc1nn(C)c2ncc(C(=O)NCCN3CCOCC3)c(Cl)c12] |
| 120 | 1,3-Dimethyl-1H-pyrazolo[3,4-b]pyridine-5-carboxylic acid (4-chloro-phenyl)-amide | 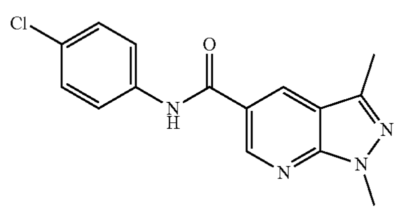 [SMILES: Cc1nn(C)c2ncc(C(=O)Nc3ccc(Cl)cc3)cc12] |
| 121 | 1,3-Dimethyl-1H-pyrazolo[3,4-b]pyridine-5-carboxylic acid (4-isopropyl-phenyl)-amide | 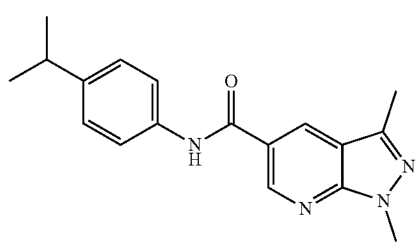 [SMILES: Cc1nn(C)c2ncc(C(=O)Nc3ccc(C(C)C)cc3)cc12] |
| 122 | 1,3-Dimethyl-1H-pyrazolo[3,4-b]pyridine-5-carboxylic acid (4-trifluoromethyl-phenyl)-amide | 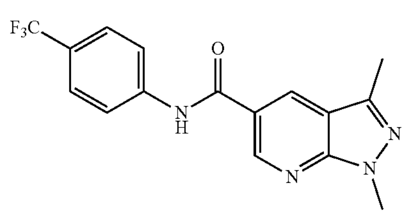 [SMILES: Cc1nn(C)c2ncc(C(=O)Nc3ccc(C(F)(F)F)cc3)cc12] |

TABLE 1-continued

| Ex. | Names | Structures |
|---|---|---|
| 123 | 4-Fluoro-1,3-dimethyl-1H-pyrazolo[3,4-b]pyridine-5-carboxylic acid (4-chloro-phenyl)-amide | 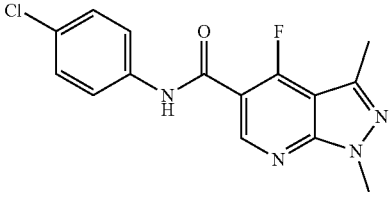 [SMILES: Cc1nn(C)c2ncc(C(=O)Nc3ccc(Cl)cc3)c(F)c12] |
| 124 | 4-Fluoro-1,3-dimethyl-1H-pyrazolo[3,4-b]pyridine-5-carboxylic acid (4-isopropyl-phenyl)-amide | 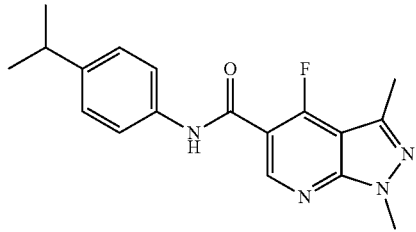 |
| 125 | 4-Fluoro-1,3-dimethyl-1H-pyrazolo[3,4-b]pyridine-5-carboxylic acid (4-trifluoromethyl-phenyl)-amide | 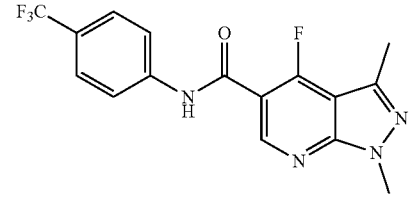 [SMILES: Cc1nn(C)c2ncc(C(=O)Nc3ccc(C(F)(F)F)cc3)c(F)c12] |
| 126 | 4-Chloro-1-methyl-1H-pyrazolo[3,4-b]pyridine-5-carboxylic acid (4-chloro-phenyl)-amide | 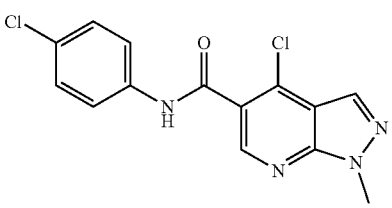 [SMILES: Cn1ncc2c(Cl)c(C(=O)Nc3ccc(Cl)cc3)cnc21] |
| 127 | 4-Chloro-1-methyl-1H-pyrazolo[3,4-b]pyridine-5-carboxylic acid (4-trifluoromethyl-phenyl)-amide | 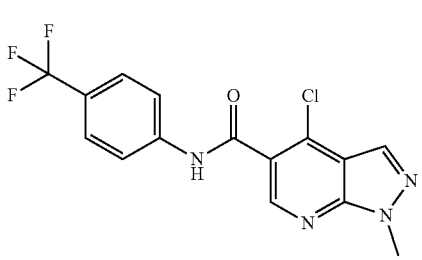 [SMILES: Cn1ncc2c(Cl)c(C(=O)Nc3ccc(C(F)(F)F)cc3)cnc21] |
| 128 | 4-Chloro-1-methyl-1H-pyrazolo[3,4-b]pyridine-5-carboxylic acid (4-isopropyl-phenyl)-amide | 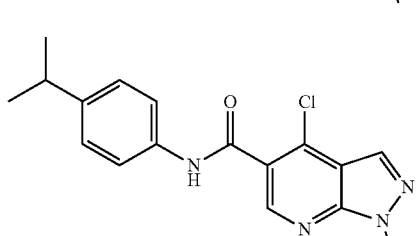 |
| 129 | 3,4-Dichloro-1-methyl-1H-pyrazolo[3,4-b]pyridine-5-carboxylic acid (4-trifluoromethyl-phenyl)-amide | 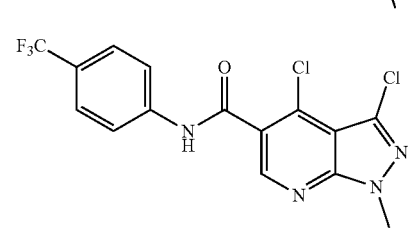 |

TABLE 1-continued

| Ex. | Names | Structures |
|---|---|---|
| 130 | 3,4-Dichloro-1-methyl-1H-pyrazolo[3,4-b]pyridine-5-carboxylic acid (4-isopropyl-phenyl)-amide | 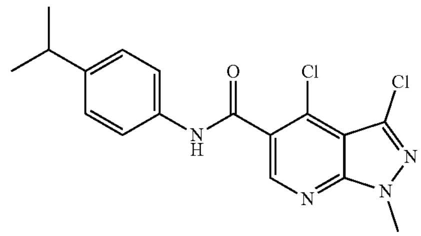 |
| 131 | 3,4-Dichloro-1-methyl-1H-pyrazolo[3,4-b]pyridine-5-carboxylic acid (4-chloro-phenyl)-amide | 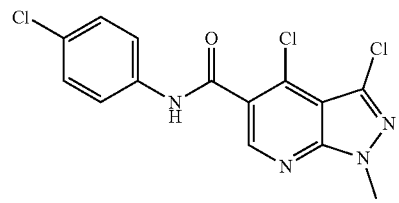 [SMILES: Cn1nc(Cl)c2c(Cl)c(C(=O)Nc3ccc(Cl)cc3)cnc21] |
| 132 | 4-Chloro-3-fluoro-1-methyl-1H-pyrazolo[3,4-b]pyridine-5-carboxylic acid (4-chloro-phenyl)-amide | 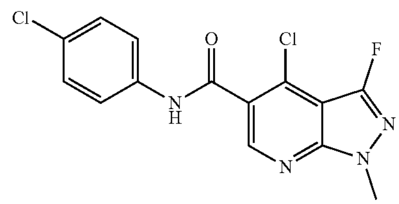 [SMILES: Cn1nc(F)c2c(Cl)c(C(=O)Nc3ccc(Cl)cc3)cnc21] |
| 133 | 4-Chloro-3-fluoro-1-methyl-1H-pyrazolo[3,4-b]pyridine-5-carboxylic acid (4-trifluoromethyl-phenyl)-amide | 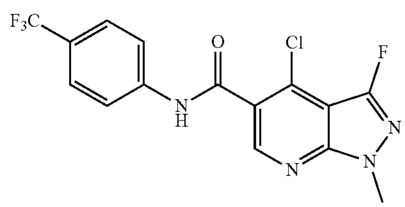 [SMILES: Cn1nc(F)c2c(Cl)c(C(=O)Nc3ccc(C(F)(F)F)cc3)cnc21] |
| 134 | 4-Chloro-3-fluoro-1-methyl-1H-pyrazolo[3,4-b]pyridine-5-carboxylic acid (4-isopropyl-phenyl)-amide | 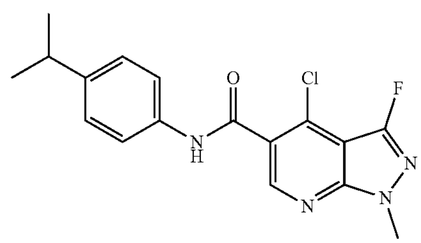 |
| 135 | 3-Bromo-4-chloro-1-methyl-1H-pyrazolo[3,4-b]pyridine-5-carboxylic acid (4-chloro-phenyl)-amide | 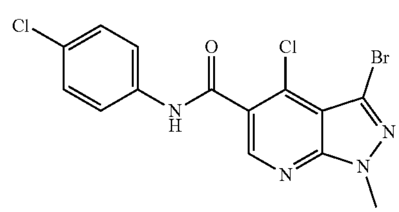 [SMILES: Cn1nc(Br)c2c(Cl)c(C(=O)Nc3ccc(Cl)cc3)cnc21] |
| 136 | 3-Bromo-4-chloro-1-methyl-1H-pyrazolo[3,4-b]pyridine-5-carboxylic acid (4-trifluoromethyl-phenyl)-amide | 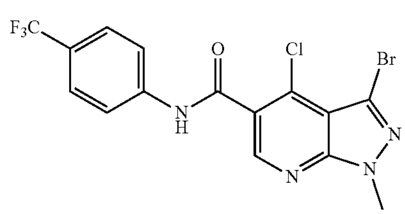 [SMILES: Cn1nc(Br)c2c(Cl)c(C(=O)Nc3ccc(C(F)(F)F)cc3)cnc21] |

TABLE 1-continued

| Ex. | Names | Structures |
|---|---|---|
| 137 | 3-Bromo-4-chloro-1-methyl-1H-pyrazolo[3,4-b]pyridine-5-carboxylic acid (4-isopropyl-phenyl)-amide | 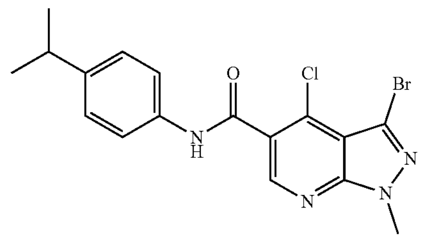 |
| 138 | 4-Chloro-3-ethyl-1-methyl-1H-pyrazolo[3,4-b]pyridine-5-carboxylic acid (4-chloro-phenyl)-amide | 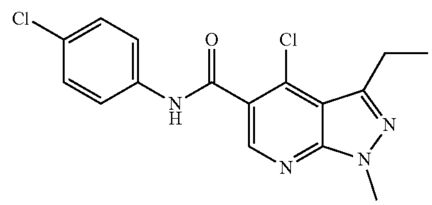 [SMILES: CCc1nn(C)c2ncc(C(=O)Nc3ccc(Cl)cc3)c(Cl)c12] |
| 139 | 4-Chloro-3-ethyl-1-methyl-1H-pyrazolo[3,4-b]pyridine-5-carboxylic acid (4-trifluoromethyl-phenyl)-amide | 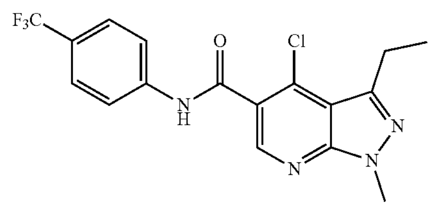 [SMILES: CCc1nn(C)c2ncc(C(=O)Nc3ccc(C(F)(F)F)cc3)c(Cl)c12] |
| 140 | 4-Chloro-3-ethyl-1-methyl-1H-pyrazolo[3,4-b]pyridine-5-carboxylic acid (4-isopropyl-phenyl)-amide | 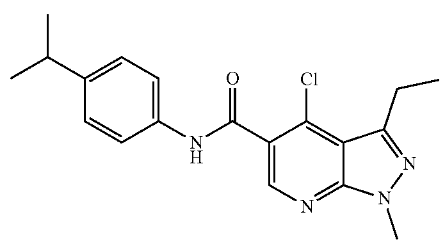 [SMILES: CCc1nn(C)c2ncc(C(=O)Nc3ccc(C(C)C)cc3)c(Cl)c12] |
| 141 | 4-Chloro-1-ethyl-3-methyl-1H-pyrazolo[3,4-b]pyridine-5-carboxylic acid (4-chloro-phenyl)-amide | 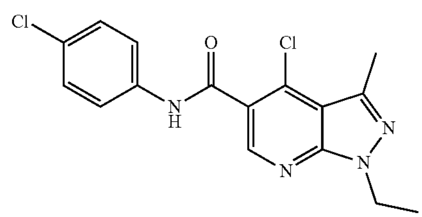 [SMILES: CCn1nc(C)c2c(Cl)c(C(=O)Nc3ccc(Cl)cc3)cnc21] |
| 142 | 4-Chloro-1-ethyl-3-methyl-1H-pyrazolo[3,4-b]pyridine-5-carboxylic acid (4-trifluoromethyl-phenyl)-amide | 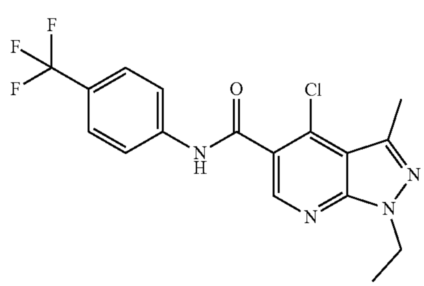 [SMILES: CCn1nc(C)c2c(Cl)c(C(=O)Nc3ccc(C(F)(F)F)cc3)cnc21] |

TABLE 1-continued

| Ex. | Names |
|---|---|
| 143 | 4-Chloro-1-ethyl-3-methyl-1H-pyrazolo[3,4-b]pyridine-5-carboxylic acid (4-isopropyl-phenyl)-amide |
| 144 | 4-chloro-N-(4-chlorophenyl)-3-methyl-1-propyl-1H-pyrazolo[3,4-b]pyridine-5-carboxamide |
| 145 | 4-chloro-3-methyl-1-propyl-N-(4-(trifluoromethyl)phenyl)-1H-pyrazolo[3,4-b]pyridine-5-carboxamide |
| 146 | 4-chloro-N-(4-isopropylphenyl)-3-methyl-1-propyl-1H-pyrazolo[3,4-b]pyridine-5-carboxamide |
| 147 | 4-chloro-1-isopropyl-3-methyl-N-(4-(trifluoromethyl)phenyl)-1H-pyrazolo[3,4-b]pyridine-5-carboxamide |

TABLE 1-continued

| Ex. | Names |
|---|---|
| 148 | 4-chloro-1-isopropyl-N-(4-isopropylphenyl)-3-methyl-1H-pyrazolo[3,4-b]pyridine-5-carboxamide |
| 149 | 4-chloro-N-(4-chlorophenyl)-1-isopropyl-3-methyl-1H-pyrazolo[3,4-b]pyridine-5-carboxamide |
| 150 | 4-chloro-1-(2-methoxyethyl)-3-methyl-N-(4-(trifluoromethyl)phenyl)-1H-pyrazolo[3,4-b]pyridine-5-carboxamide |
| 151 | 4-chloro-N-(4-chlorophenyl)-1-(2-methoxyethyl)-3-methyl-1H-pyrazolo[3,4-b]pyridine-5-carboxamide |
| 152 | 4-chloro-N-(4-isopropylphenyl)-1-(2-methoxyethyl)-3-methyl-1H-pyrazolo[3,4-b]pyridine-5-carboxamide |

TABLE 1-continued

| Ex. | Names | Structures |
|-----|-------|------------|
| 153 | 4-Chloro-1-(3-methoxy-propyl)-3-methyl-1H-pyrazolo[3,4-b]pyridine-5-carboxylic acid (4-trifluoromethyl-phenyl)-amide | 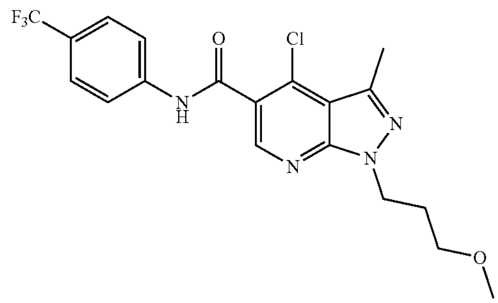 [SMILES: COCCCn1nc(C)c2c(Cl)c(C(=O)Nc3ccc(C(F)(F)F)cc3)cnc21] |
| 154 | 4-chloro-1-(3-methoxy-propyl)-3-methyl-1H-pyrazolo[3,4-b]pyridine-5-carboxylic acid (4-chloro-phenyl)-amide) | 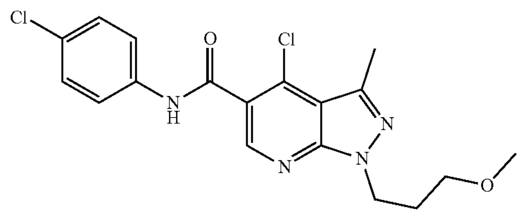 [SMILES: COCCCn1nc(C)c2c(Cl)c(C(=O)Nc3ccc(Cl)cc3)cnc21] |
| 155 | 4-chloro-1-(3-methoxy-propyl)-3-methyl-1H-pyrazolo[3,4-b]pyridine-5-carboxylic acid (4-isopropyl-phenyl)-amide | 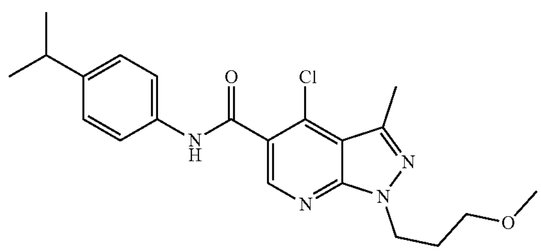 [SMILES: COCCCn1nc(C)c2c(Cl)c(C(=O)Nc3ccc(C(C)C)cc3)cnc21] |
| 156 | 1-(2-benzyloxy-ethyl)-4-chloro-3-methyl-1H-pyrazolo[3,4-b]pyridine-5-carboxylic acid (4-isopropyl-phenyl)-amide | 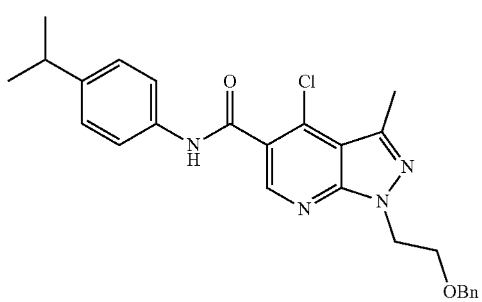 [SMILES: Cc1nn(CCOCc2ccccc2)c2ncc(C(=O)Nc3ccc(C(C)C)cc3)c(Cl)c12] |
| 157 | 4-chloro-1-(2-hydroxy-ethyl)-3-methyl-1H-pyrazolo[3,4-b]pyridine-5-carboxylic acid (4-isopropyl-phenyl)-amide | 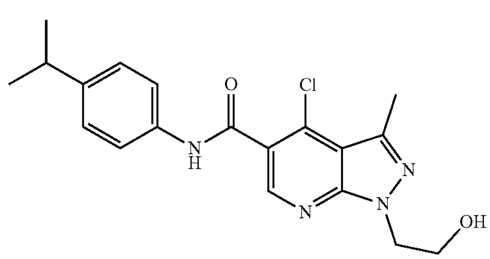 [SMILES: Cc1nn(CCO)c2ncc(C(=O)Nc3ccc(C(C)C)cc3)c(Cl)c12] |

TABLE 1-continued

| Ex. | Names | Structures |
|---|---|---|
| 158 | 4-chloro-1-(4-methoxy-butyl)-3-methyl-1H-pyrazolo[3,4-b]pyridine-5-carboxylic acid (4-chloro-phenyl)-amide | 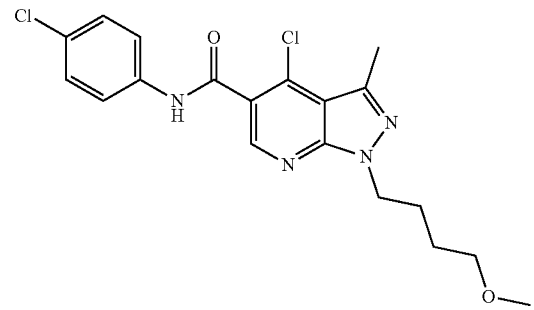 [SMILES: COCCCCn1nc(C)c2c(Cl)c(C(=O)Nc3ccc(Cl)cc3)cnc21] |
| 159 | 4-Chloro-1-(4-methoxy-butyl)-3-methyl-1H-pyrazolo[3,4-b]pyridine-5-carboxylic acid (4-trifluoromethyl-phenyl)-amide | 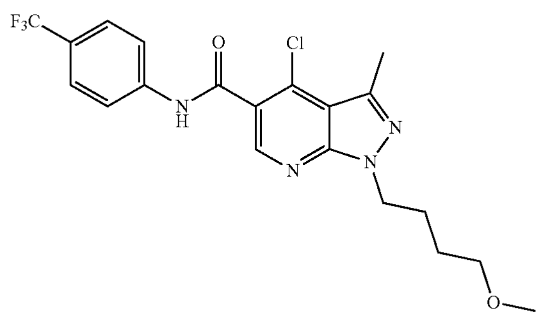 [SMILES: COCCCCn1nc(C)c2c(Cl)c(C(=O)Nc3ccc(C(F)(F)F)cc3)cnc21] |
| 160 | 4-chloro-1-(4-methoxy-butyl)-3-methyl-1H-pyrazolo[3,4-b]pyridine-5-carboxylic acid (4-isopropyl-phenyl)-amide | 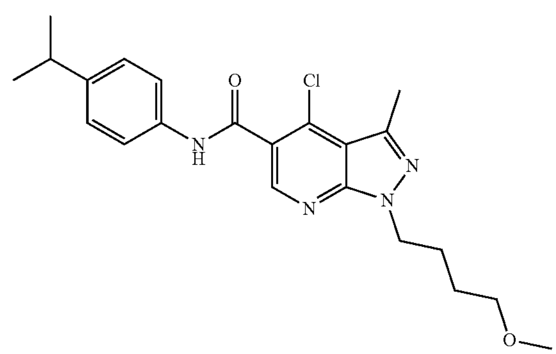 [SMILES: COCCCCn1nc(C)c2c(Cl)c(C(=O)Nc3ccc(C(C)C)cc3)cnc21] |
| 161 | 4-chloro-N-(4-chlorophenyl)-1-cyclohexyl-3-methyl-1H-pyrazolo[3,4-b]pyridine-5-carboxamide | 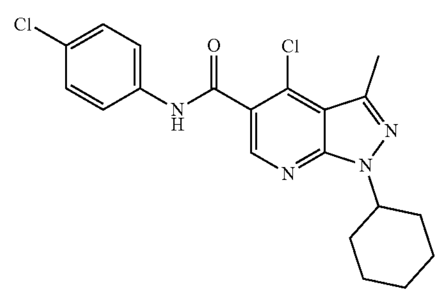 [SMILES: Cc1nn(C2CCCCC2)c2ncc(C(=O)Nc3ccc(Cl)cc3)c(Cl)c12] |
| 162 | 4-chloro-1-cyclohexyl-3-methyl-N-(4-(trifluoromethyl)phenyl)-1H-pyrazolo[3,4-b]pyridine-5-carboxamide | 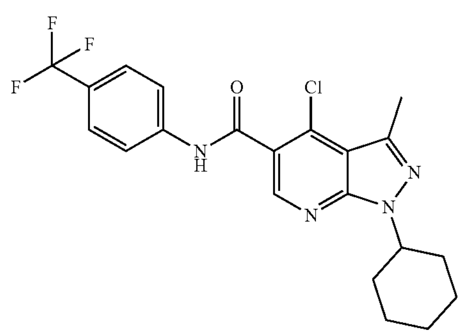 [SMILES: Cc1nn(C2CCCCC2)c2ncc(C(=O)Nc3ccc(C(F)(F)F)cc3)c(Cl)c12] |

| Ex. | Names | Structures |
|---|---|---|
| 163 | 4-chloro-1-cyclohexyl-N-(4-isopropylphenyl)-3-methyl-1H-pyrazolo[3,4-b]pyridine-5-carboxamide | 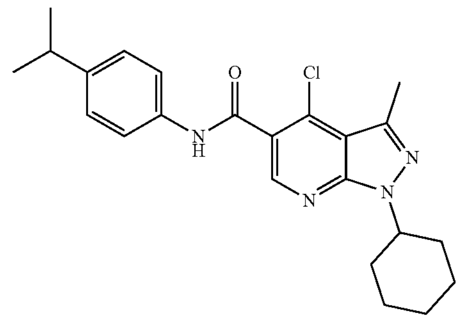 [SMILES: Cc1nn(C2CCCCC2)c2ncc(C(=O)Nc3ccc(C(C)C)cc3)c(Cl)c12] |
| 164 | 4-Chloro-1-cyclopentyl-3-methyl-1H-pyrazolo[3,4-b]pyridine-5-carboxylic acid (4-chloro-phenyl)-amide | 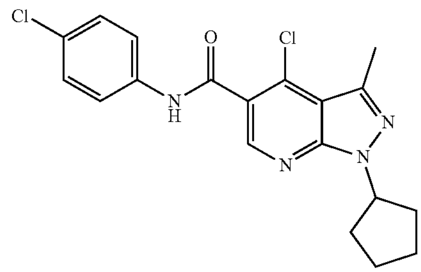 [SMILES: Cc1nn(C2CCCC2)c2ncc(C(=O)Nc3ccc(Cl)cc3)c(Cl)c12] |
| 165 | 4-Chloro-1-cyclopentyl-3-methyl-1H-pyrazolo[3,4-b]pyridine-5-carboxylic acid (4-trifluoromethyl-phenyl)-amide | 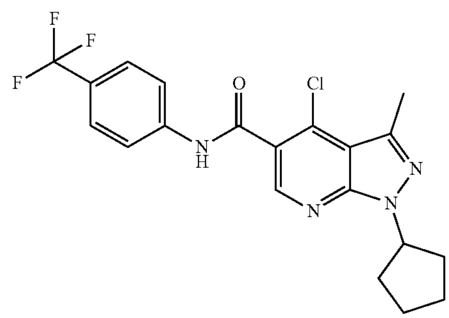 [SMILES: Cc1nn(C2CCCC2)c2ncc(C(=O)Nc3ccc(C(F)(F)F)cc3)c(Cl)c12] |
| 166 | 4-Chloro-1-cyclopentyl-3-methyl-1H-pyrazolo[3,4-b]pyridine-5-carboxylic acid (4-isopropyl-phenyl)-amide | 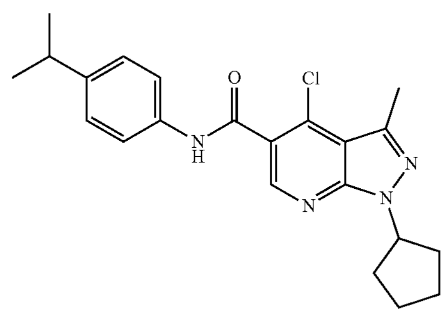 [SMILES: Cc1nn(C2CCCC2)c2ncc(C(=O)Nc3ccc(C(C)C)cc3)c(Cl)c12] |
| 167 | 4-Chloro-3-methyl-1-(tetrahydro-pyran-4-yl)-1H-pyrazolo[3,4-b]pyridine-5-carboxylic acid (4-chloro-phenyl)-amide | 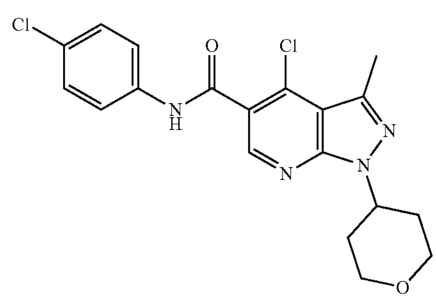 [SMILES: Cc1nn(C2CCOCC2)c2ncc(C(=O)Nc3ccc(Cl)cc3)c(Cl)c12] |

TABLE 1-continued

| Ex. | Names | Structures |
|---|---|---|
| 168 | 4-Chloro-3-methyl-1-(tetrahydro-pyran-4-yl)-1H-pyrazolo[3,4-b]pyridine-5-carboxylic acid (4-isopropyl-phenyl)-amide | 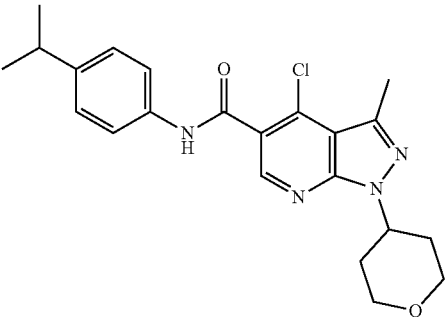 [SMILES: Cc1nn(C2CCOCC2)c2ncc(C(=O)Nc3ccc(C(C)C)cc3)c(Cl)c12] |
| 169 | 4-Chloro-3-methyl-1-(tetrahydro-pyran-4-yl)-1H-pyrazolo[3,4-b]pyridine-5-carboxylic acid (4-trifluoromethyl-phenyl)-amide | 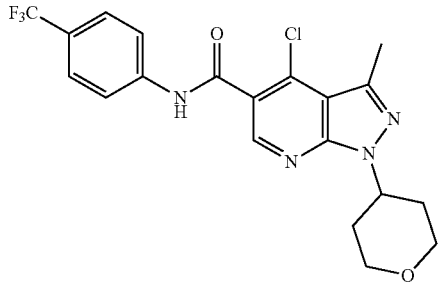 [SMILES: Cc1nn(C2CCOCC2)c2ncc(C(=O)Nc3ccc(C(F)(F)F)cc3)c(Cl)c12] |
| 170 | 4-Methoxy-3-methyl-1-(tetrahydro-pyran-4-yl)-1H-pyrazolo[3,4-b]pyridine-5-carboxylic acid (4-chloro-phenyl)-amide | 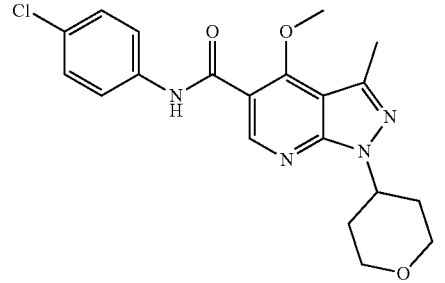 [SMILES: COc1c(C(=O)Nc2ccc(Cl)cc2)cnc2c1c(C)nn2C1CCOCC1] |
| 171 | N-(4-chlorophenyl)-4-methoxy-3-methyl-1-(tetrahydro-2H-pyran-4-yl)-1H-pyrazolo[3,4-b]pyridine-5-carboxamide | 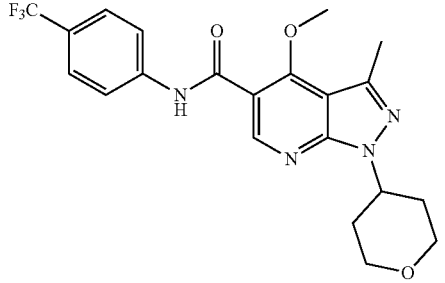 [SMILES: COc1c(C(=O)Nc2ccc(C(F)(F)F)cc2)cnc2c1c(C)nn2C1CCOCC1] |
| 172 | 4-chloro-1-(1-ethyl-piperidin-4-yl)-3-methyl-1H-pyrazolo[3,4-b]pyridine-5-carboxylic acid (4-isopropyl-phenyl)-amide | 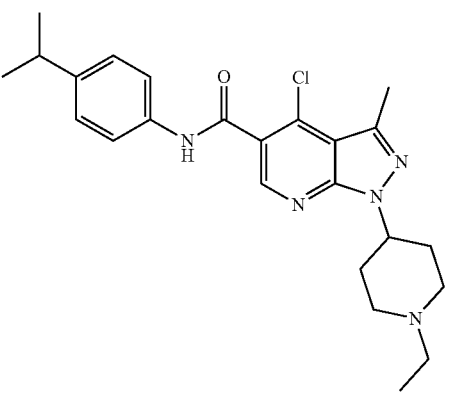 [SMILES: CCN1CCC(n2nc(C)c3c(Cl)c(C(=O)Nc4ccc(C(C)C)cc4)cnc32)CC1] |

TABLE 1-continued

| Ex. | Names | Structures |
|---|---|---|
| 173 | 4-chloro-1-(1-ethyl-piperidin-4-yl)-3-methyl-1H-pyrazolo[3,4-b]pyridine-5-carboxylic acid (4-trifluoromethyl-phenyl)-amide | 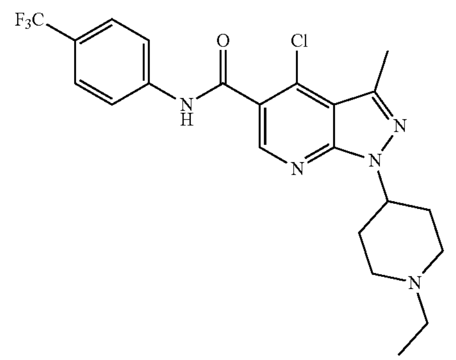 [SMILES: CCN1CCC(n2nc(C)c3c(Cl)c(C(=O)Nc4ccc(C(F)(F)F)cc4)cnc32)CC1] |
| 174 | 4-chloro-1-(1-ethyl-piperidin-4-yl)-3-methyl-1H-pyrazolo[3,4-b]pyridine-5-carboxylic acid (4-chloro-phenyl)-amide | 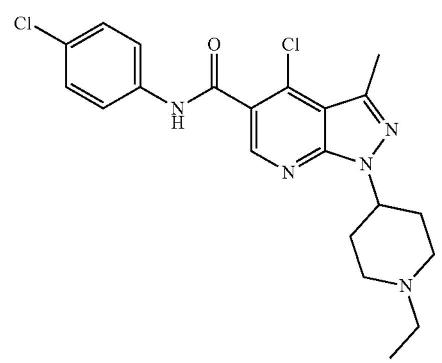 [SMILES: CCN1CCC(n2nc(C)c3c(Cl)c(C(=O)Nc4ccc(Cl)cc4)cnc32)CC1] |
| 175 | 4-Chloro-1-(1-isopropyl-piperidin-4-yl)-3-methyl-1H-pyrazolo[3,4-b]pyridine-5-carboxylic acid (4-chloro-phenyl)-amide | 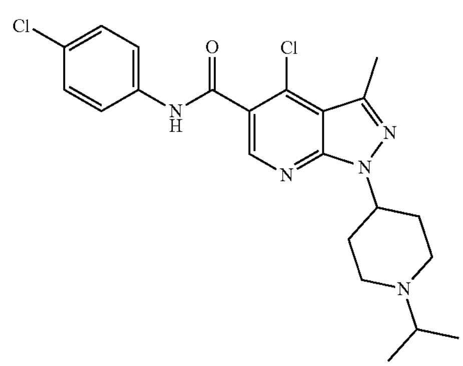 [SMILES: Cc1nn(C2CCN(C(C)C)CC2)c2ncc(C(=O)Nc3ccc(Cl)cc3)c(Cl)c12] |
| 176 | 4-Chloro-1-(1-isopropyl-piperidin-4-yl)-3-methyl-1H-pyrazolo[3,4-b]pyridine-5-carboxylic acid (4-trifluoromethyl-phenyl)-amide | 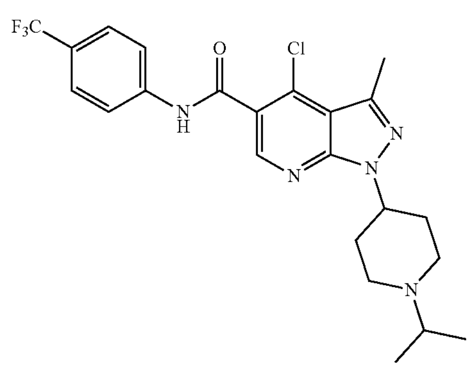 [SMILES: Cc1nn(C2CCN(C(C)C)CC2)c2ncc(C(=O)Nc3ccc(C(F)(F)F)cc3)c(Cl)c12] |

TABLE 1-continued

| Ex. | Names | Structures |
|---|---|---|
| 177 | 4-chloro-3-methyl-1-(1-methylpiperidin-4-yl)-N-(4-(trifluoromethyl)phenyl)-1H-pyrazolo[3,4-b]pyridine-5-carboxamide | 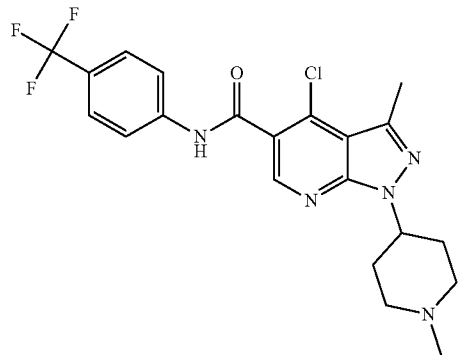 [SMILES: Cc1nn(C2CCN(C)CC2)c2ncc(C(=O)Nc3ccc(C(F)(F)F)cc3)c(Cl)c12] |
| 178 | 4-chloro-N-(4-chlorophenyl)-3-methyl-1-(1-methylpiperidin-4-yl)-1H-pyrazolo[3,4-b]pyridine-5-carboxamide | 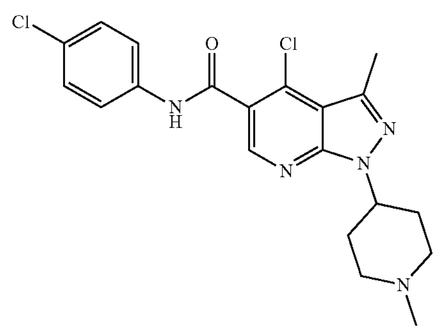 [SMILES: Cc1nn(C2CCN(C)CC2)c2ncc(C(=O)Nc3ccc(Cl)cc3)c(Cl)c12] |
| 179 | 4-chloro-N-(4-isopropylphenyl)-3-methyl-1-(1-methylpiperidin-4-yl)-1H-pyrazolo[3,4-b]pyridine-5-carboxamide | 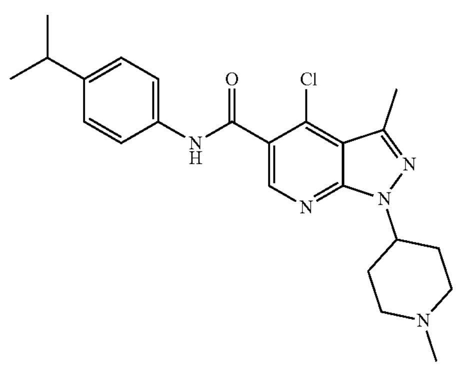 [SMILES: Cc1nn(C2CCN(C)CC2)c2ncc(C(=O)Nc3ccc(C(C)C)cc3)c(Cl)c12] |
| 180 | 4-Chloro-3-methyl-1-(1-methyl-piperidin-4-yl)-1H-pyrazolo[3,4-b]pyridine-5-carboxylic acid (4-ethynyl-phenyl)-amide | 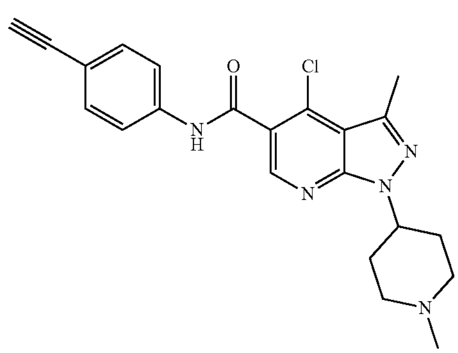 [SMILES: C#Cc1ccc(NC(=O)c2cnc3c(c(C)nn3C3CCN(C)CC3)c2Cl)cc1] |

TABLE 1-continued

| Ex. | Names | Structures |
|---|---|---|
| 181 | 4-ethoxy-3-methyl-1-(1-methylpiperidin-4-yl)-N-(4-(trifluoromethyl)phenyl)-1H-pyrazolo[3,4-b]pyridine-5-carboxamide | 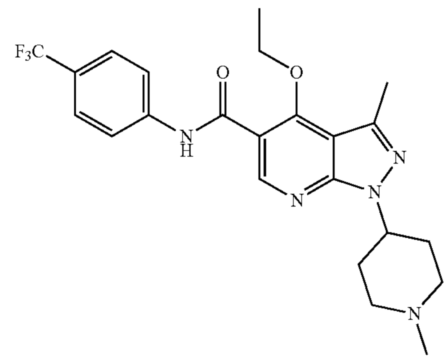 [SMILES: CCOc1c(C(=O)Nc2ccc(C(F)(F)F)cc2)cnc2c1c(C)nn2C1CCN(C)CC1] |
| 182 | 4-methoxy-3-methyl-1-(1-methylpiperidin-4-yl)-N-(4-(trifluoromethyl)phenyl)-1H-pyrazolo[3,4-b]pyridine-5-carboxamide | 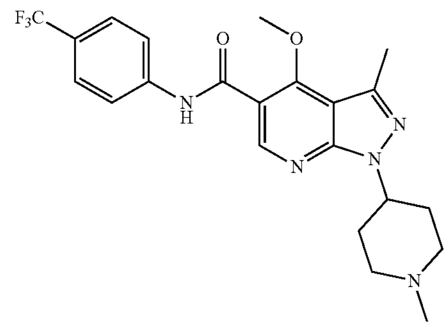 [SMILES: COc1c(C(=O)Nc2ccc(C(F)(F)F)cc2)cnc2c1c(C)nn2C1CCN(C)CC1] |
| 183 | N-(4-chlorophenyl)-4-methoxy-3-methyl-1-(1-methylpiperidin-4-yl)-1H-pyrazolo[3,4-b]pyridine-5-carboxamide | 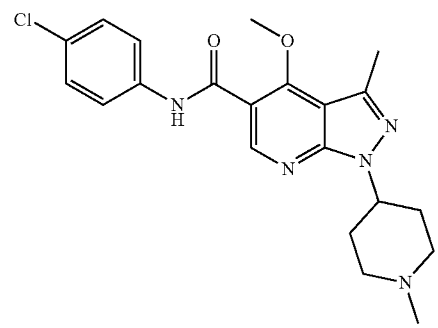 [SMILES: COc1c(C(=O)Nc2ccc(Cl)cc2)cnc2c1c(C)nn2C1CCN(C)CC1] |
| 184 | 4-chloro-N-(4-ethynylphenyl)-3-methyl-1-(piperidin-4-yl)-1H-pyrazolo[3,4-b]pyridine-5-carboxamide | 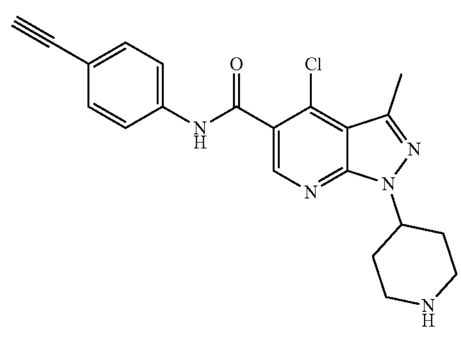 [SMILES: C#Cc1ccc(NC(=O)c2cnc3c(c(C)nn3C3CCNCC3)c2Cl)cc1] |

TABLE 1-continued

| Ex. | Names | Structures |
|---|---|---|
| 185 | 1-(1-benzylpiperidin-4-yl)-4-chloro-N-(4-chlorophenyl)-3-methyl-1H-pyrazolo[3,4-b]pyridine-5-carboxamide | 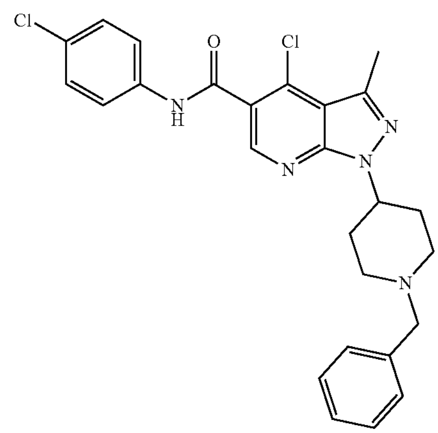 [SMILES: Cc1nn(C2CCN(Cc3ccccc3)CC2)c2ncc(C(=O)Nc3ccc(Cl)cc3)c(Cl)c12] |
| 186 | 1-(1-benzylpiperidin-4-yl)-4-chloro-3-methyl-N-(4-(trifluoromethyl)phenyl)-1H-pyrazolo[3,4-b]pyridine-5-carboxamide | 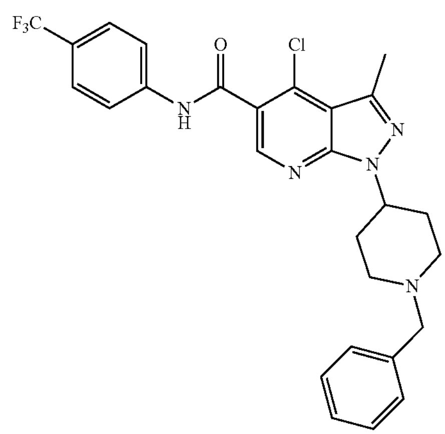 [SMILES: Cc1nn(C2CCN(Cc3ccccc3)CC2)c2ncc(C(=O)Nc3ccc(C(F)(F)F)cc3)c(Cl)c12] |
| 187 | 1-(1-benzylpiperidin-4-yl)-4-chloro-N-(4-isopropylphenyl)-3-methyl-1H-pyrazolo[3,4-b]pyridine-5-carboxamide | 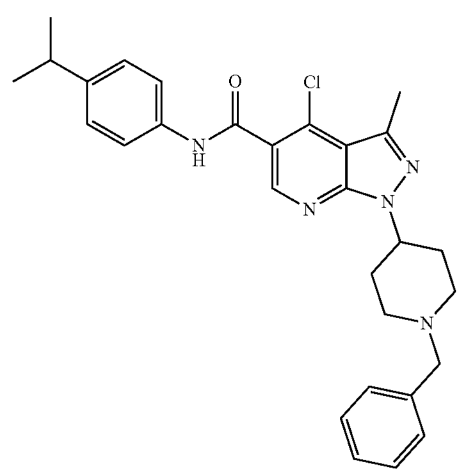 [SMILES: Cc1nn(C2CCN(Cc3ccccc3)CC2)c2ncc(C(=O)Nc3ccc(C(C)C)cc3)c(Cl)c12] |

TABLE 1-continued

| Ex. | Names | Structures |
|---|---|---|
| 188 | N-(4-benzoylphenyl)-1-(1-benzylpiperidin-4-yl)-4-chloro-3-methyl-1H-pyrazolo[3,4-b]pyridine-5-carboxamide | 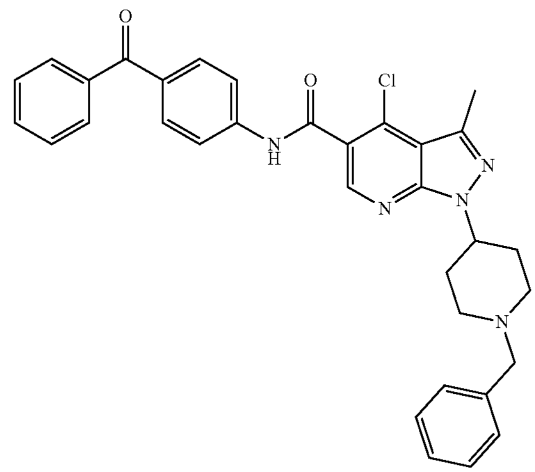 [SMILES: Cc1nn(C2CCN(Cc3ccccc3)CC2)c2ncc(C(=O)Nc3ccc(C(=O)c4ccccc4)cc3)c(Cl)c12] |
| 189 | tert-butyl 4-(4-chloro-5-((4-chlorophenyl)carbamoyl)-3-methyl-1H-pyrazolo[3,4-b]pyridin-1-yl)piperidine-1-carboxylate | 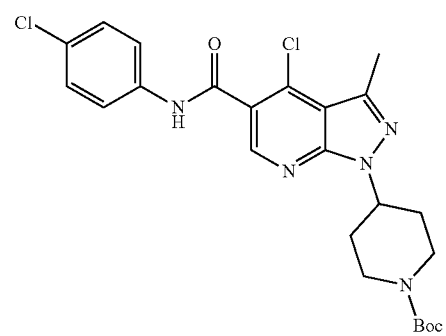 [SMILES: Cc1nn(C2CCN(C(=O)OC(C)(C)C)CC2)c2ncc(C(=O)Nc3ccc(Cl)cc3)c(Cl)c12] |
| 190 | 4-chloro-N-(4-chlorophenyl)-3-methyl-1-(piperidin-4-yl)-1H-pyrazolo[3,4-b]pyridine-5-carboxamide | 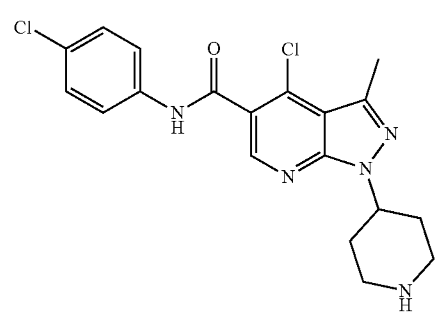 [SMILES: Cc1nn(C2CCNCC2)c2ncc(C(=O)Nc3ccc(Cl)cc3)c(Cl)c12] |
| 191 | 4-chloro-1-(1-(2-hydroxyethyl)piperidin-4-yl)-3-methyl-N-(4-(trifluoromethyl)phenyl)-1H-pyrazolo[3,4-b]pyridine-5-carboxamide | 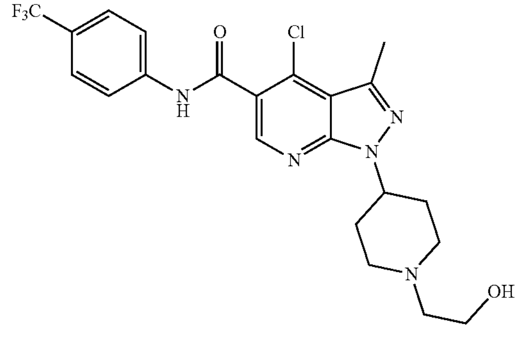 [SMILES: Cc1nn(C2CCN(CCO)CC2)c2ncc(C(=O)Nc3ccc(C(F)(F)F)cc3)c(Cl)c12] |

TABLE 1-continued

| Ex. | Names | Structures |
|---|---|---|
| 192 | 4-chloro-3-methyl-1-(1-(methylsulfonyl)piperidin-4-yl)-N-(4-(trifluoromethyl)phenyl)-1H-pyrazolo[3,4-b]pyridine-5-carboxamide | 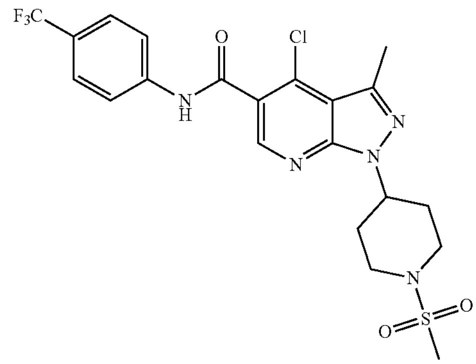 [SMILES: Cc1nn(C2CCN(S(C)(=O)=O)CC2)c2ncc(C(=O)Nc3ccc(C(F)(F)F)cc3)c(Cl)c12] |
| 193 | 1-(1-acetylpiperidin-4-yl)-4-chloro-3-methyl-N-(4-(trifluoromethyl)phenyl)-1H-pyrazolo[3,4-b]pyridine-5-carboxamide | 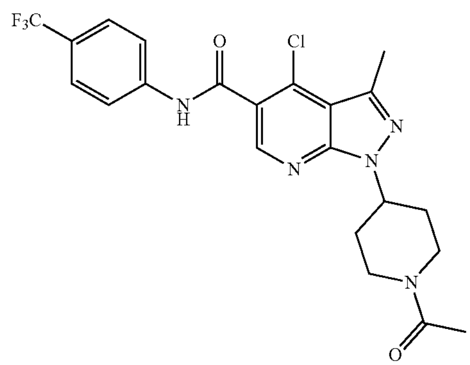 [SMILES: CC(=O)N1CCC(n2nc(C)c3c(Cl)c(C(=O)Nc4ccc(C(F)(F)F)cc4)cnc32)CC1] |
| 194 | N-(4-benzoylphenyl)-4-chloro-1-(1-(4-ethynylbenzyl)piperidin-4-yl)-3-methyl-1H-pyrazolo[3,4-b]pyridine-5-carboxamide | 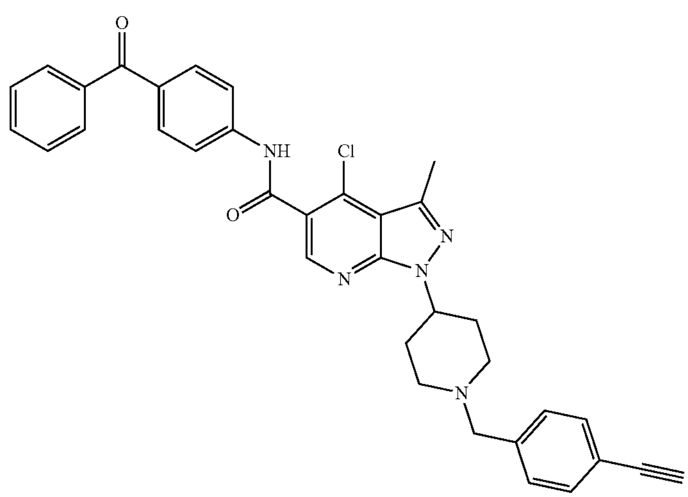 [SMILES: C#Cc1ccc(CN2CCC(n3nc(C)c4c(Cl)c(C(=O)Nc5ccc(C(=O)c6ccccc6)cc5)cnc43)CC2)cc1] |

TABLE 1-continued

| Ex. | Names | Structures |
|---|---|---|
| 195 | 1-(1-(4-(azidomethyl)benzyl)piperidin-4-yl)-N-(4-benzoylphenyl)-4-chloro-3-methyl-1H-pyrazolo[3,4-b]pyridine-5-carboxamide | 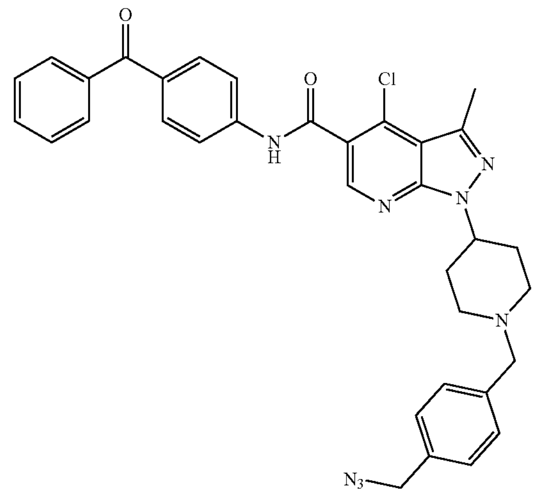 [SMILES: Cc1nn(C2CCN(Cc3ccc(CN=[N+]=[N-])cc3)CC2)c2ncc(C(=O)Nc3ccc(C(=O)c4ccccc4)cc3)c(Cl)c12] |
| 196 | 1-(1-(4-azidobenzyl)piperidin-4-yl)-4-chloro-N-(4-ethynylphenyl)-3-methyl-1H-pyrazolo[3,4-b]pyridine-5-carboxamide | 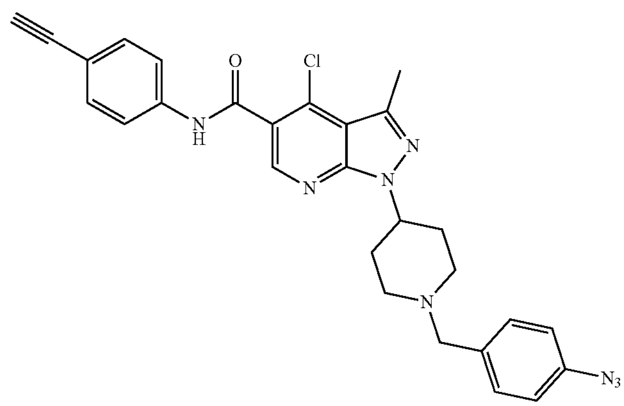 [SMILES: C#Cc1ccc(NC(=O)c2cnc3c(c(C)nn3C3CCN(Cc4ccc(N=[N+]=[N-])cc4)CC3)c2Cl)cc1] |
| 197 | 4-chloro-N-(4-chlorophenyl)-3-methyl-1-(tetrahydro-2H-thiopyran-4-yl)-1H-pyrazolo[3,4-b]pyridine-5-carboxamide | 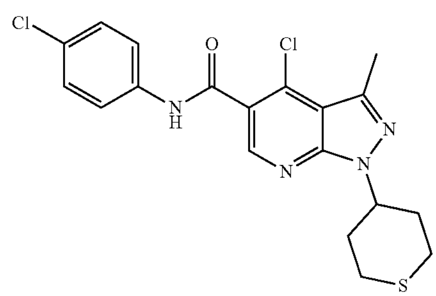 [SMILES: Cc1nn(C2CCSCC2)c2ncc(C(=O)Nc3ccc(Cl)cc3)c(Cl)c12] |
| 198 | 4-chloro-N-(4-isopropylphenyl)-3-methyl-1-(tetrahydro-2H-thiopyran-4-yl)-1H-pyrazolo[3,4-b]pyridine-5-carboxamide | 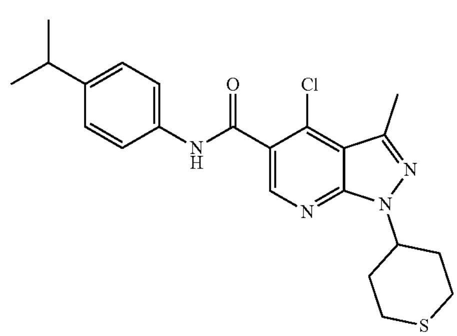 [SMILES: Cc1nn(C2CCSCC2)c2ncc(C(=O)Nc3ccc(C(C)C)cc3)c(Cl)c12] |

TABLE 1-continued

| Ex. | Names | Structures |
|---|---|---|
| 199 | 4-chloro-3-methyl-1-(tetrahydro-2H-thiopyran-4-yl)-N-(4-(trifluoromethyl)phenyl)-1H-pyrazolo[3,4-b]pyridine-5-carboxamide | 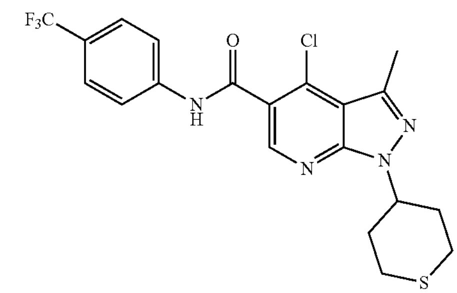 [SMILES: Cc1nn(C2CCSCC2)c2ncc(C(=O)Nc3ccc(C(F)(F)F)cc3)c(Cl)c12] |
| 200 | 4-chloro-1-(1,1-dioxidotetrahydro-2H-thiopyran-4-yl)-N-(4-isopropylphenyl)-3-methyl-1H-pyrazolo[3,4-b]pyridine-5-carboxamide | 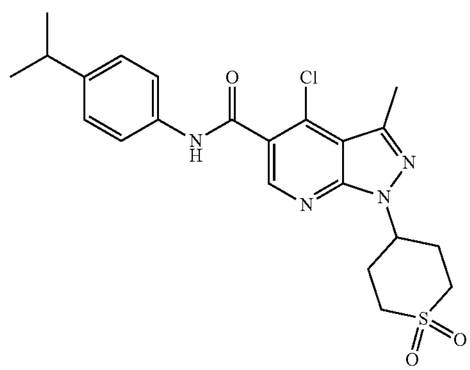 [SMILES: Cc1nn(C2CCS(=O)(=O)CC2)c2ncc(C(=O)Nc3ccc(C(C)C)cc3)c(Cl)c12] |
| 201 | 4-chloro-N-(4-chlorophenyl)-1-(1,1-dioxidotetrahydro-2H-thiopyran-4-yl)-3-methyl-1H-pyrazolo[3,4-b]pyridine-5-carboxamide | 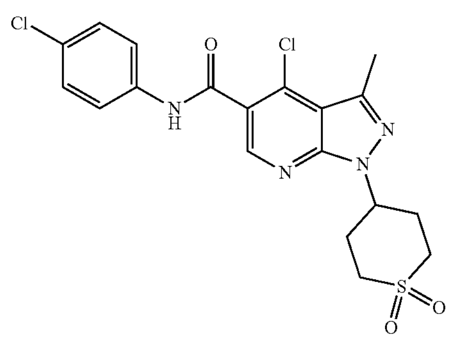 [SMILES: Cc1nn(C2CCS(=O)(=O)CC2)c2ncc(C(=O)Nc3ccc(Cl)cc3)c(Cl)c12] |
| 202 | 4-chloro-1-(1,1-dioxidotetrahydro-2H-thiopyran-4-yl)-3-methyl-N-(4-(trifluoromethyl)phenyl)-1H-pyrazolo[3,4-b]pyridine-5-carboxamide | 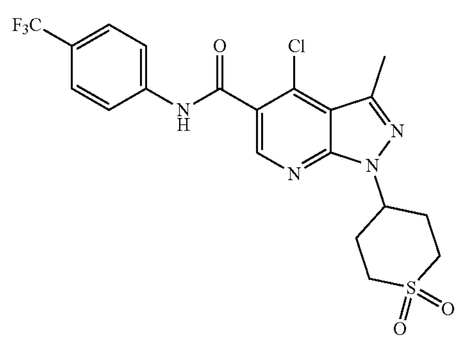 [SMILES: Cc1nn(C2CCS(=O)(=O)CC2)c2ncc(C(=O)Nc3ccc(C(F)(F)F)cc3)c(Cl)c12] |

TABLE 1-continued

| Ex. | Names | Structures |
|---|---|---|
| 203 | 4-chloro-N-(4-chlorophenyl)-1-(1-isopropylpiperidin-4-yl)-1H-pyrazolo[3,4-b]pyridine-5-carboxamide | 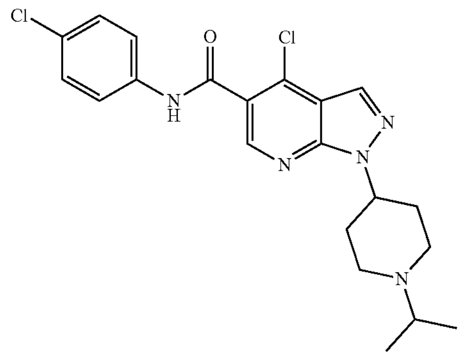 [SMILES: CC(C)N1CCC(n2ncc3c(Cl)c(C(=O)Nc4ccc(Cl)cc4)cnc32)CC1] |
| 204 | 4-Chloro-1-(1-isopropyl-piperidin-4-yl)-1H-pyrazolo[3,4-b]pyridine-5-carboxylic acid (4-trifluoromethyl-phenyl)-amide | 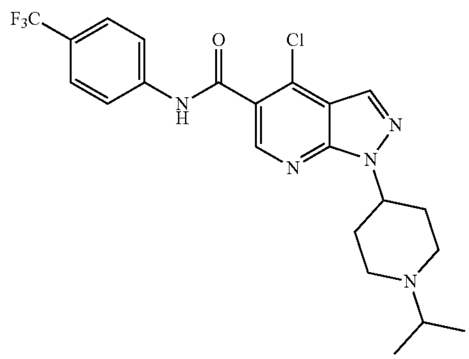 [SMILES: CC(C)N1CCC(n2ncc3c(Cl)c(C(=O)Nc4ccc(C(F)(F)F)cc4)cnc32)CC1] |
| 205 | 4-Chloro-1-(1-isopropyl-piperidin-4-yl)-1H-pyrazolo[3,4-b]pyridine-5-carboxylic acid (4-isopropyl-phenyl)-amide | 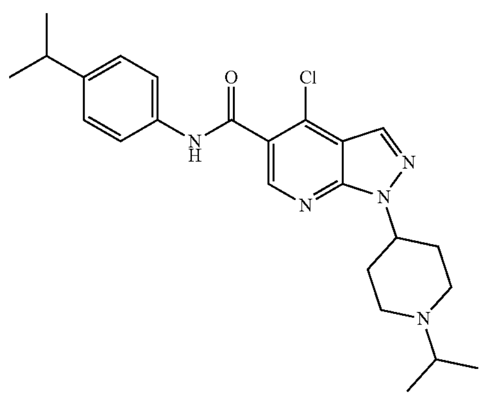 [SMILES: CC(C)c1ccc(NC(=O)c2cnc3c(cnn3C3CCN(C(C)C)CC3)c2Cl)cc1] |
| 206 | 4-Chloro-1-(1-ethyl-piperidin-4-yl)-1H-pyrazolo[3,4-b]pyridine-5-carboxylic acid (4-trifluoromethyl-phenyl)-amide | 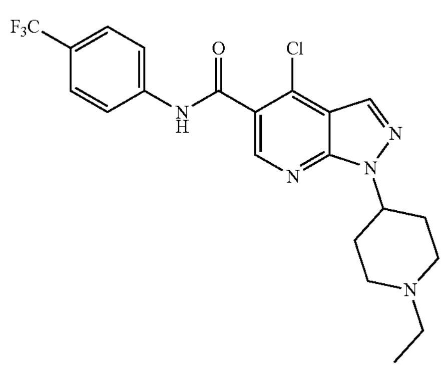 [SMILES: CCN1CCC(n2ncc3c(Cl)c(C(=O)Nc4ccc(C(F)(F)F)cc4)cnc32)CC1] |

TABLE 1-continued

| Ex. | Names | Structures |
|---|---|---|
| 207 | 4-chloro-1-(1-ethyl-piperidin-4-yl)-1H-pyrazolo[3,4-b]pyridine-5-carboxylic acid (4-isopropyl-phenyl)-amide | 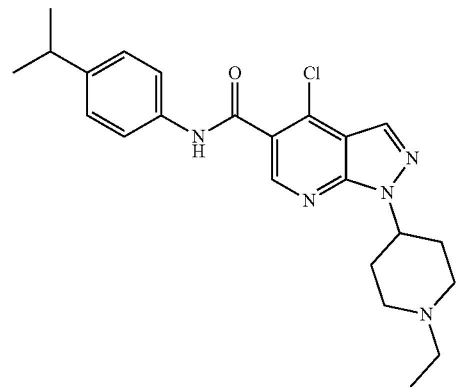 [SMILES: CCN1CCC(n2ncc3c(Cl)c(C(=O)Nc4ccc(C(C)C)cc4)cnc32)CC1] |
| 208 | 4-chloro-1-(1-ethyl-piperidin-4-yl)-1H-pyrazolo[3,4-b]pyridine-5-carboxylic acid (4-chloro-phenyl)-amide | 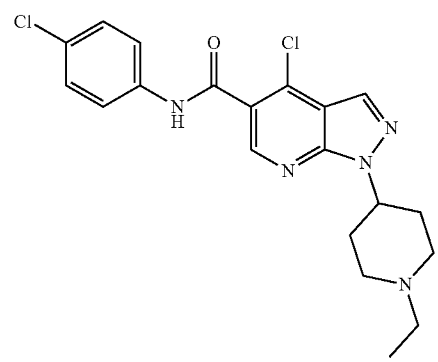 [SMILES: CCN1CCC(n2ncc3c(Cl)c(C(=O)Nc4ccc(Cl)cc4)cnc32)CC1] |
| 209 | 4-chloro-1-(1-methyl-piperidin-4-yl)-1H-pyrazolo[3,4-b]pyridine-5-carboxylic acid (4-chloro-phenyl)-amide | 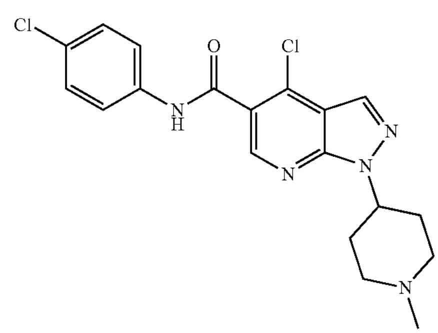 [SMILES: CN1CCC(n2ncc3c(Cl)c(C(=O)Nc4ccc(Cl)cc4)cnc32)CC1] |
| 210 | 4-chloro-1-(1-methyl-piperidin-4-yl)-1H-pyrazolo[3,4-b]pyridine-5-carboxylic acid (4-trifluoromethyl-phenyl)-amide | 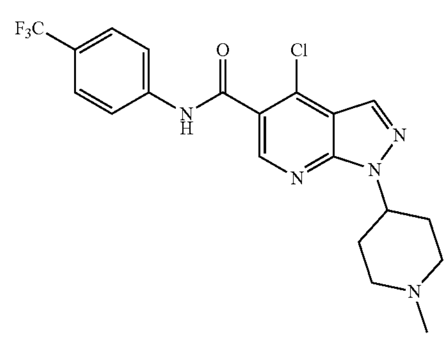 [SMILES: CN1CCC(n2ncc3c(Cl)c(C(=O)Nc4ccc(C(F)(F)F)cc4)cnc32)CC1] |

TABLE 1-continued

| Ex. | Names | Structures |
|---|---|---|
| 211 | 4-Chloro-1-(tetrahydro-pyran-4-yl)-1H-pyrazolo[3,4-b]pyridine-5-carboxylic acid (4-chloro-phenyl)-amide | 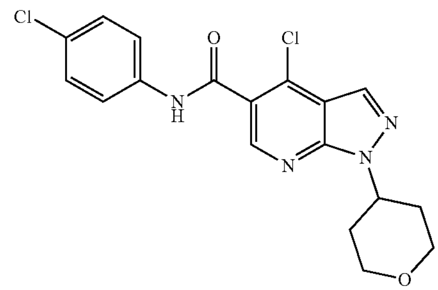 [SMILES: O=C(Nc1ccc(Cl)cc1)c1cnc2c(cnn2C2CCOCC2)c1Cl] |
| 212 | 4-Chloro-1-(tetrahydro-pyran-4-yl)-1H-pyrazolo[3,4-b]pyridine-5-carboxylic acid (4-trifluoromethyl-phenyl)-amide | 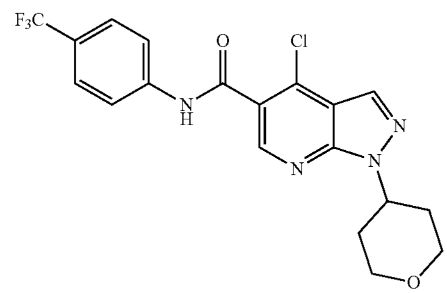 [SMILES: O=C(Nc1ccc(C(F)(F)F)cc1)c1cnc2c(cnn2C2CCOCC2)c1Cl] |
| 213 | 4-chloro-N-(4-isopropylphenyl)-1-(tetrahydro-2H-pyran-4-yl)-1H-pyrazolo[3,4-b]pyridine-5-carboxamide | 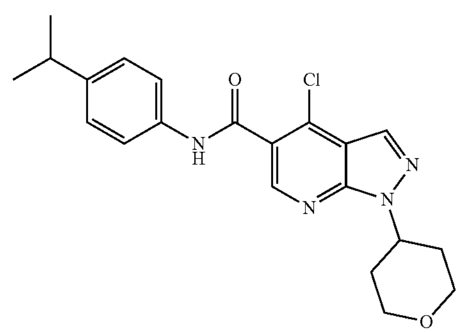 [SMILES: CC(C)c1ccc(NC(=O)c2cnc3c(cnn3C3CCOCC3)c2Cl)cc1] |
| 214 | 3,4-Dichloro-1-(tetrahydro-pyran-4-yl)-1H-pyrazolo[3,4-b]pyridine-5-carboxylic acid (4-trifluoromethyl-phenyl)-amide | 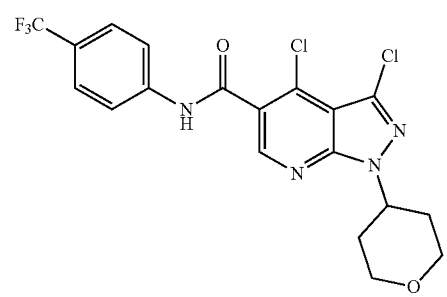 [SMILES: O=C(Nc1ccc(C(F)(F)F)cc1)c1cnc2c(c(Cl)nn2C2CCOCC2)c1Cl] |
| 215 | 3,4-Dichloro-1-(tetrahydro-pyran-4-yl)-1H-pyrazolo[3,4-b]pyridine-5-carboxylic acid (4-chloro-phenyl)-amide | 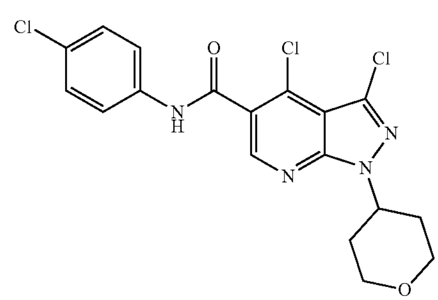 [SMILES: O=C(Nc1ccc(Cl)cc1)c1cnc2c(c(Cl)nn2C2CCOCC2)c1Cl] |

TABLE 1-continued

| Ex. | Names | Structures |
|---|---|---|
| 216 | 3,4-Dichloro-1-(tetrahydro-pyran-4-yl)-1H-pyrazolo[3,4-b]pyridine-5-carboxylic acid (4-isopropyl-phenyl)-amide | 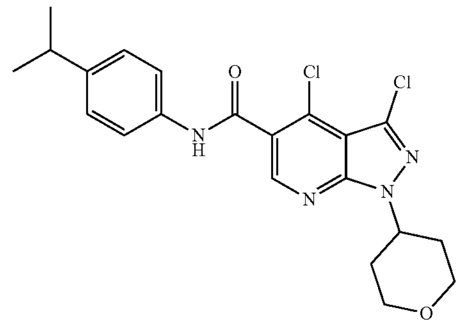 |
| 217 | 3-Chloro-4-methoxy-1-(tetrahydro-pyran-4-yl)-1H-pyrazolo[3,4-b]pyridine-5-carboxylic acid (4-trifluoromethyl-phenyl)-amide | 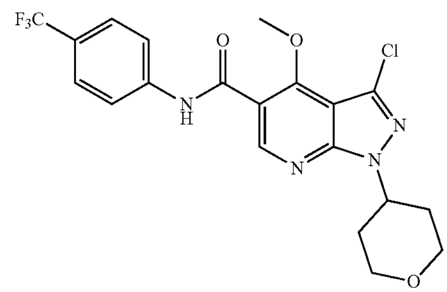 [SMILES: COc1c(C(=O)Nc2ccc(C(F)(F)F)cc2)cnc2c1c(Cl)nn2C1CCOCC1] |
| 218 | 3-Chloro-4-methoxy-1-(tetrahydro-pyran-4-yl)-1H-pyrazolo[3,4-b]pyridine-5-carboxylic acid (4-isopropyl-phenyl)-amide | 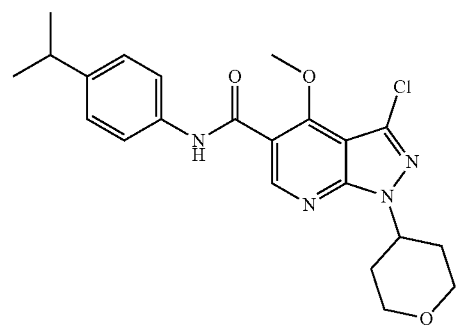 [SMILES: COc1c(C(=O)Nc2ccc(C(C)C)cc2)cnc2c1c(Cl)nn2C1CCOCC1] |
| 219 | 4-Chloro-3-fluoro-1-(tetrahydro-pyran-4-yl)-1H-pyrazolo[3,4-b]pyridine-5-carboxylic acid (4-trifluoromethyl-phenyl)-amide | 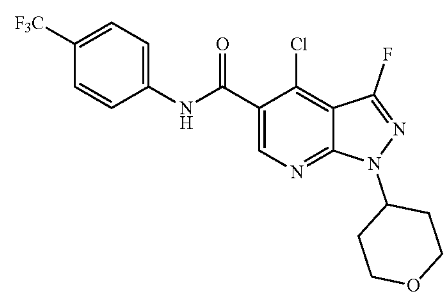 |
| 220 | 4-Chloro-3-fluoro-1-(tetrahydro-pyran-4-yl)-1H-pyrazolo[3,4-b]pyridine-5-carboxylic acid (4-chloro-phenyl)-amide | 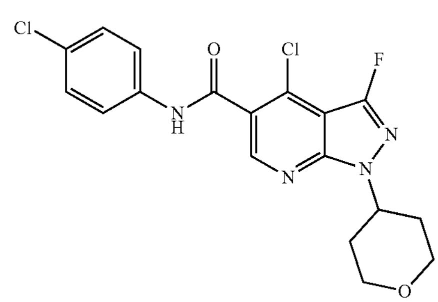 [SMILES: O=C(Nc1ccc(Cl)cc1)c1cnc2c(c(F)nn2C2CCOCC2)c1Cl] |

TABLE 1-continued

| Ex. | Names |
|---|---|
| 221 | 4-Chloro-3-fluoro-1-(tetrahydro-pyran-4-yl)-1H-pyrazolo[3,4-b]pyridine-5-carboxylic acid (4-isopropyl-phenyl)-amide |
| 222 | 4-chloro-N-(4-chlorophenyl)-1-(tetrahydro-2H-thiopyran-4-yl)-1H-pyrazolo[3,4-b]pyridine-5-carboxamide |
| 223 | 4-chloro-1-(tetrahydro-2H-thiopyran-4-yl)-N-(4-(trifluoromethyl)phenyl)-1H-pyrazolo[3,4-b]pyridine-5-carboxamide |
| 224 | 4-chloro-N-(4-isopropylphenyl)-1-(tetrahydro-2H-thiopyran-4-yl)-1H-pyrazolo[3,4-b]pyridine-5-carboxamide |
| 225 | N-(4-chlorophenyl)-4-methoxy-1-(tetrahydro-2H-thiopyran-4-yl)-1H-pyrazolo[3,4-b]pyridine-5-carboxamide |

TABLE 1-continued

| Ex. | Names | Structures |
|---|---|---|
| 226 | 4-methoxy-1-(tetrahydro-2H-thiopyran-4-yl)-N-(4-(trifluoromethyl)phenyl)-1H-pyrazolo[3,4-b]pyridine-5-carboxamide | 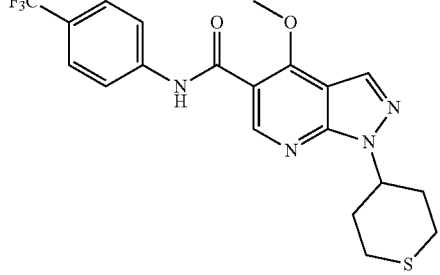 |
| 227 | N-(4-isopropylphenyl)-4-methoxy-1-(tetrahydro-2H-thiopyran-4-yl)-1H-pyrazolo[3,4-b]pyridine-5-carboxamide | 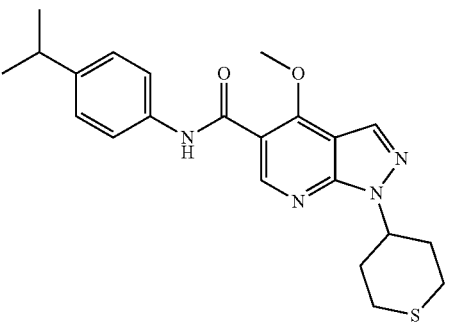 [SMILES: COc1c(C(=O)Nc2ccc(C(C)C)cc2)cnc2c1cnn2C1CCSCC1] |
| 228 | 4-chloro-N-(4-chlorophenyl)-1-(1,1-dioxidotetrahydro-2H-thiopyran-4-yl)-1H-pyrazolo[3,4-b]pyridine-5-carboxamide | 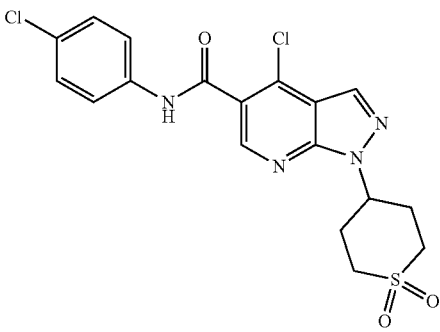 [SMILES: O=C(Nc1ccc(Cl)cc1)c1cnc2c(cnn2C2CCS(=O)(=O)CC2)c1Cl] |
| 229 | 4-chloro-1-(1,1-dioxidotetrahydro-2H-thiopyran-4-yl)-N-(4-isopropylphenyl)-1H-pyrazolo[3,4-b]pyridine-5-carboxamide | 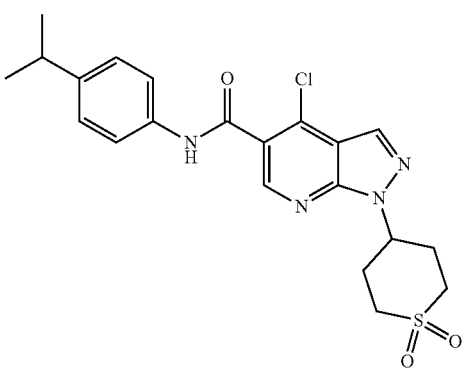 [SMILES: CC(C)c1ccc(NC(=O)c2cnc3c(cnn3C3CCS(=O)(=O)CC3)c2Cl)cc1] |

TABLE 1-continued

| Ex. | Names | Structures |
|---|---|---|
| 230 | 4-chloro-1-(1,1-dioxidotetrahydro-2H-thiopyran-4-yl)-N-(4-(trifluoromethyl)phenyl)-1H-pyrazolo[3,4-b]pyridine-5-carboxamide | 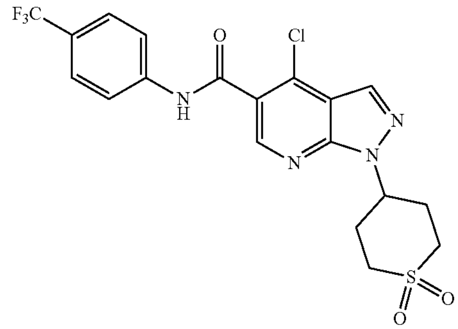 [SMILES: O=C(Nc1ccc(C(F)(F)F)cc1)c1cnc2c(cnn2C2CCS(=O)(=O)CC2)c1Cl] |
| 231 | 4-chloro-N-(4-chlorophenyl)-3-methyl-1-(pyridin-4-ylmethyl)-1H-pyrazolo[3,4-b]pyridine-5-carboxamide | 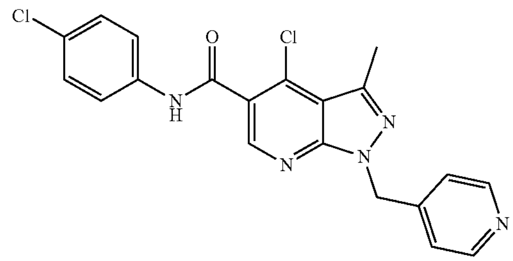 [SMILES: Cc1nn(Cc2ccncc2)c2ncc(C(=O)Nc3ccc(Cl)cc3)c(Cl)c12] |
| 232 | 4-chloro-3-methyl-1-(pyridin-4-ylmethyl)-N-(4-(trifluoromethyl)phenyl)-1H-pyrazolo[3,4-b]pyridine-5-carboxamide | 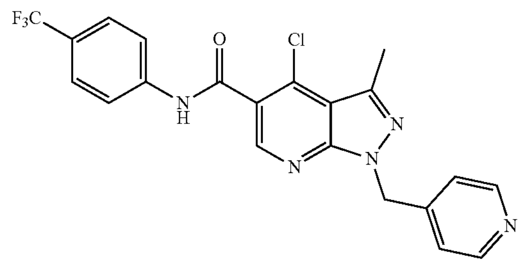 [SMILES: Cc1nn(Cc2ccncc2)c2ncc(C(=O)Nc3ccc(C(F)(F)F)cc3)c(Cl)c12] |
| 233 | 4-chloro-N-(4-isopropylphenyl)-3-methyl-1-(pyridin-4-ylmethyl)-1H-pyrazolo[3,4-b]pyridine-5-carboxamide | 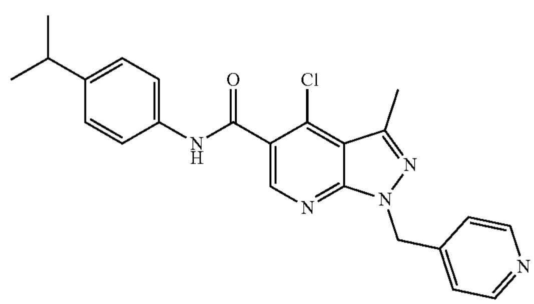 [SMILES: Cc1nn(Cc2ccncc2)c2ncc(C(=O)Nc3ccc(C(C)C)cc3)c(Cl)c12] |
| 234 | 4-Chloro-3-methyl-1-pyridin-2-ylmethyl-1H-pyrazolo[3,4-b]pyridine-5-carboxylic acid (4-chloro-phenyl)-amide | 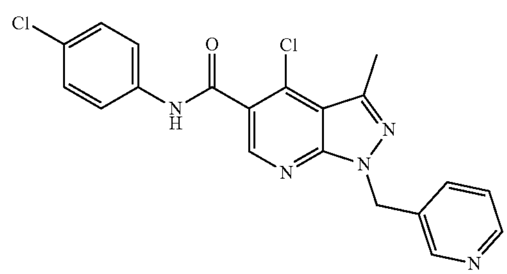 [SMILES: Cc1nn(Cc2cccnc2)c2ncc(C(=O)Nc3ccc(Cl)cc3)c(Cl)c12] |

TABLE 1-continued

| Ex. | Names | Structures |
|---|---|---|
| 235 | 4-Chloro-3-methyl-1-pyridin-3-ylmethyl-1H-pyrazolo[3,4-b]pyridine-5-carboxylic acid (4-trifluoromethyl-phenyl)-amide | 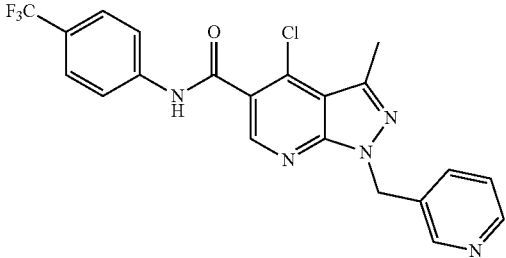 [SMILES: Cc1nn(Cc2cccnc2)c2ncc(C(=O)Nc3ccc(C(F)(F)F)cc3)c(Cl)c12] |
| 236 | 4-Chloro-3-methyl-1-pyridin-3-ylmethyl-1H-pyrazolo[3,4-b]pyridine-5-carboxylic acid (4-isopropyl-phenyl)-amide | 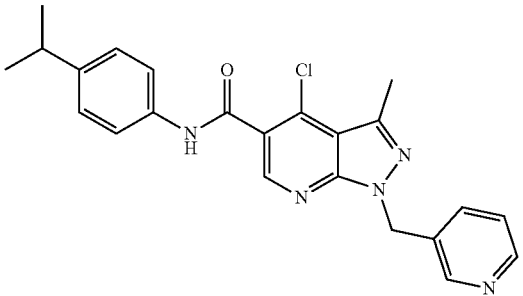 [SMILES: Cc1nn(Cc2cccnc2)c2ncc(C(=O)Nc3ccc(C(C)C)cc3)c(Cl)c12] |
| 237 | 4-Chloro-3-methyl-1-pyridin-2-ylmethyl-1H-pyrazolo[3,4-b]pyridine-5-carboxylic acid (4-chloro-phenyl)-amide | 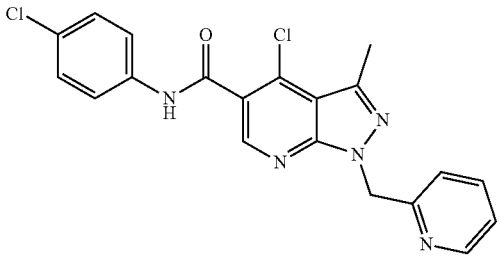 [SMILES: Cc1nn(Cc2ccccn2)c2ncc(C(=O)Nc3ccc(Cl)cc3)c(Cl)c12] |
| 238 | 4-Chloro-3-methyl-1-(pyridin-2-ylmethyl)-N-(4-(trifluoromethyl)phenyl)-1H-pyrazolo[3,4-b]pyridine-5-carboxamide | 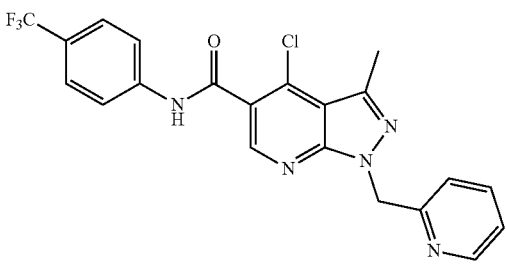 [SMILES: Cc1nn(Cc2ccccn2)c2ncc(C(=O)Nc3ccc(C(F)(F)F)cc3)c(Cl)c12] |
| 239 | 4-Chloro-N-(4-isopropylphenyl)-3-methyl-1-(pyridin-2-ylmethyl)-1H-pyrazolo[3,4-b]pyridine-5-carboxamide | 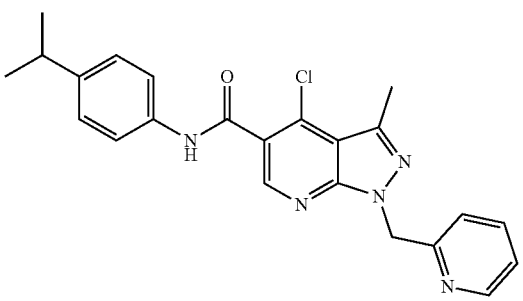 [SMILES: Cc1nn(Cc2ccccn2)c2ncc(C(=O)Nc3ccc(C(C)C)cc3)c(Cl)c12] |

TABLE 1-continued

| Ex. | Names | Structures |
|---|---|---|
| 240 | 1-benzyl-4-chloro-N-(4-chlorophenyl)-3-methyl-1H-pyrazolo[3,4-b]pyridine-5-carboxamide | 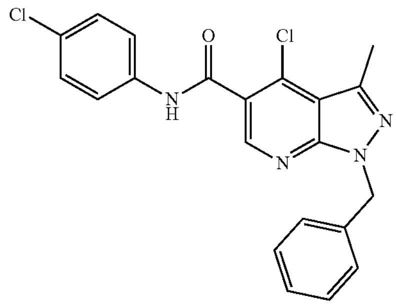 [SMILES: Cc1nn(Cc2ccccc2)c2ncc(C(=O)Nc3ccc(Cl)cc3)c(Cl)c12] |
| 241 | 1-benzyl-4-chloro-3-methyl-N-(4-(trifluoromethyl)phenyl)-1H-pyrazolo[3,4-b]pyridine-5-carboxamide | 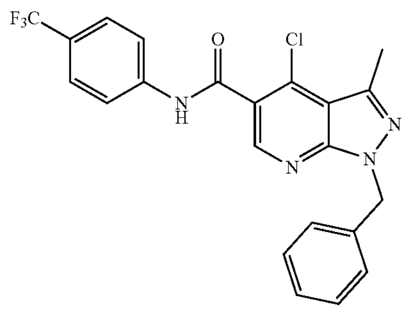 [SMILES: Cc1nn(Cc2ccccc2)c2ncc(C(=O)Nc3ccc(C(F)(F)F)cc3)c(Cl)c12] |
| 242 | 1-benzyl-4-chloro-N-(4-isopropylphenyl)-3-methyl-1H-pyrazolo[3,4-b]pyridine-5-carboxamide | 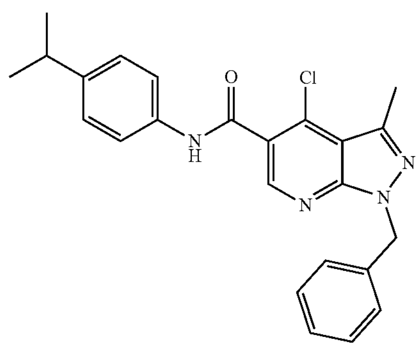 |
| 243 | 4-Chloro-3-methyl-1-(5-methyl-pyridin-3-ylmethyl)-1H-pyrazolo[3,4-b]pyridine-5-carboxylic acid (4-chloro-phenyl)-amide | 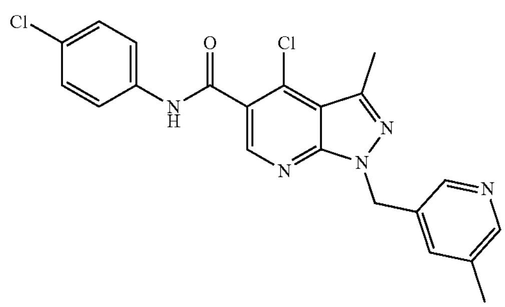 [SMILES: Cc1cncc(Cn2nc(C)c3c(Cl)c(C(=O)Nc4ccc(Cl)cc4)cnc32)c1] |
| 244 | 4-Chloro-3-methyl-1-(5-methyl-pyridin-3-ylmethyl)-1H-pyrazolo[3,4-b]pyridine-5-carboxylic acid (4-trifluoromethyl-phenyl)-amide | 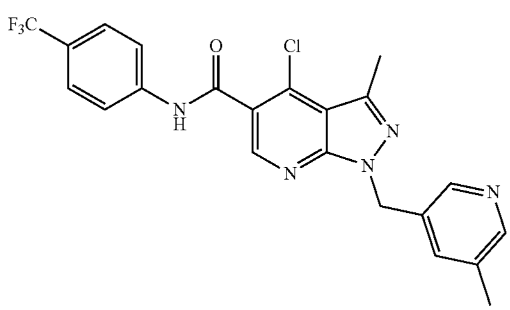 [SMILES: Cc1cncc(Cn2nc(C)c3c(Cl)c(C(=O)Nc4ccc(C(F)(F)F)cc4)cnc32)c1] |

TABLE 1-continued

| Ex. | Names | Structures |
|---|---|---|
| 245 | 4-Chloro-3-methyl-1-(6-methyl-pyridin-3-ylmethyl)-1H-pyrazolo[3,4-b]pyridine-5-carboxylic acid (4-chloro-phenyl)-amide | 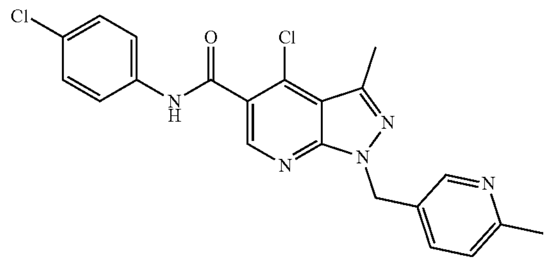 [SMILES: Cc1ccc(Cn2nc(C)c3c(Cl)c(C(=O)Nc4ccc(Cl)cc4)cnc32)cn1] |
| 246 | 4-Chloro-3-methyl-1-(6-methyl-pyridin-3-methyl)-1H-pyrazolo[3,4-b]pyridine-5-carboxylic acid (4-trifluoromethyl-phenyl)-amide | 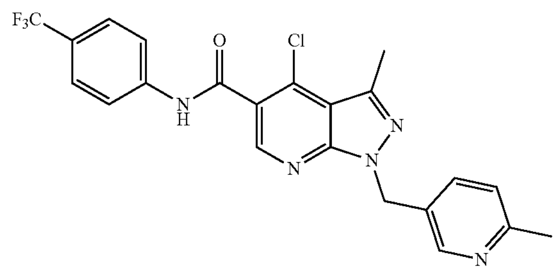 [SMILES: Cc1ccc(Cn2nc(C)c3c(Cl)c(C(=O)Nc4ccc(C(F)(F)F)cc4)cnc32)cn1] |
| 247 | 4-Chloro-1-(5-methoxy-pyridin-2-ylmethyl)-3-methyl-1H-pyrazolo[3,4-b]pyridine-5-carboxylic acid (4-chloro-phenyl)-amide | 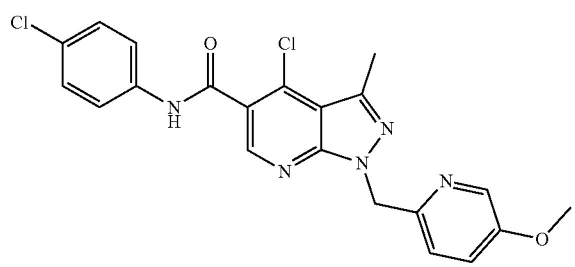 [SMILES: COc1ccc(Cn2nc(C)c3c(Cl)c(C(=O)Nc4ccc(Cl)cc4)cnc32)nc1] |
| 248 | 4-Chloro-1-(5-methoxy-pyridin-2-ylmethyl)-3-methyl-1H-pyrazolo[3,4-b]pyridine-5-carboxylic acid (4-trifluoromethyl-phenyl)-amide | 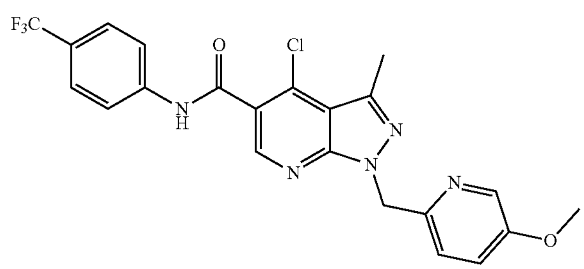 [SMILES: COc1ccc(Cn2nc(C)c3c(Cl)c(C(=O)Nc4ccc(C(F)(F)F)cc4)cnc32)nc1] |
| 249 | 4-Chloro-1-(5-fluoro-pyridin-2-ylmethyl)-3-methyl-1H-pyrazolo[3,4-b]pyridine-5-carboxylic acid (4-chloro-phenyl)-amide | 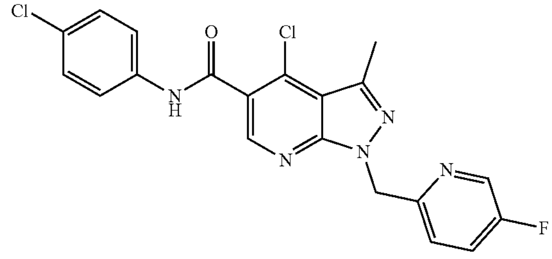 [SMILES: Cc1nn(Cc2ccc(F)cn2)c2ncc(C(=O)Nc3ccc(Cl)cc3)c(Cl)c12] |

TABLE 1-continued

| Ex. | Names | Structures |
|---|---|---|
| 250 | 4-Chloro-1-(4,6-dimethyl-pyridin-2-ylmethyl)-3-methyl-1H-pyrazolo[3,4-b]pyridine-5-carboxylic acid (4-chloro-phenyl)-amide | 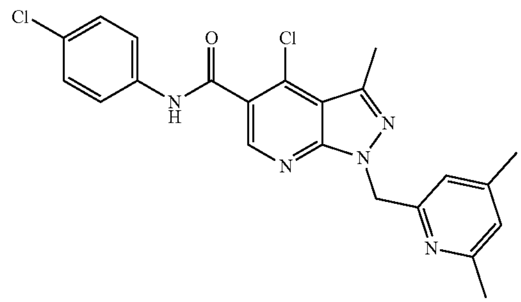 [SMILES: Cc1cc(C)nc(Cn2nc(C)c3c(Cl)c(C(=O)Nc4ccc(Cl)cc4)cnc32)c1] |
| 251 | 4-Chloro-1-(4,6-dimethyl-pyridin-2-ylmethyl)-3-methyl-1H-pyrazolo[3,4-b]pyridine-5-carboxylic acid (4-trifluoromethyl-phenyl)-amide | 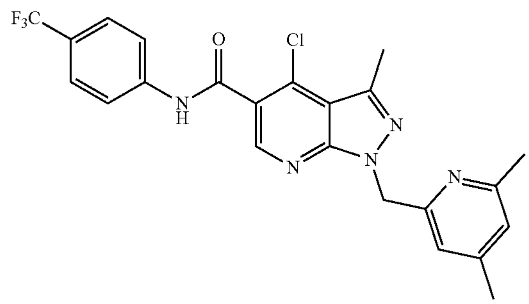 [SMILES: Cc1cc(C)nc(Cn2nc(C)c3c(Cl)c(C(=O)Nc4ccc(C(F)(F)F)cc4)cnc32)c1] |
| 252 | 4-Chloro-3-methyl-1-(6-methyl-pyridin-2-ylmethyl)-1H-pyrazolo[3,4-b]pyridine-5-carboxylic acid (4-chloro-phenyl)-amide | 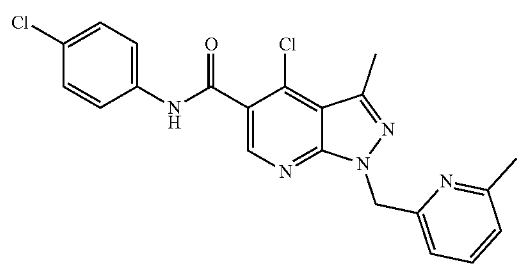 [SMILES: Cc1cccc(Cn2nc(C)c3c(Cl)c(C(=O)Nc4ccc(Cl)cc4)cnc32)n1] |
| 253 | 4-Chloro-3-methyl-1-(6-methyl-pyridin-2-ylmethyl)-1H-pyrazolo[3,4-b]pyridine-5-carboxylic acid (4-trifluoromethyl-phenyl)-amide | 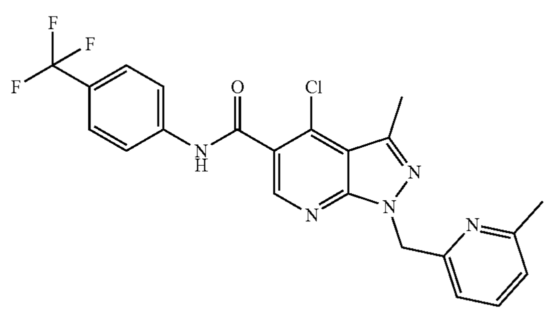 [SMILES: Cc1cccc(Cn2nc(C)c3c(Cl)c(C(=O)Nc4ccc(C(F)(F)F)cc4)cnc32)n1] |
| 254 | 4-Chloro-3-methyl-1-(6-trifluoromethyl-pyridin-3-ylmethyl)-1H-pyrazolo[3,4-b]pyridine-5-carboxylic acid (4-chloro-phenyl)-amide | 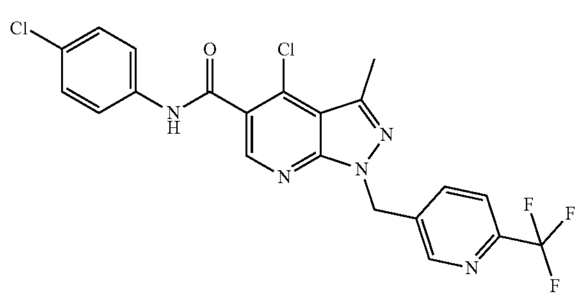 [SMILES: Cc1nn(Cc2ccc(C(F)(F)F)nc2)c2ncc(C(=O)Nc3ccc(Cl)cc3)c(Cl)c12] |

TABLE 1-continued

| Ex. | Names | Structures |
|---|---|---|
| 255 | 4-Chloro-3-methyl-1-(6-trifluoromethyl-pyridin-3-ylmethyl)-1H-pyrazolo[3,4-b]pyridine-5-carboxylic acid (4-trifluoromethyl-phenyl)-amide | 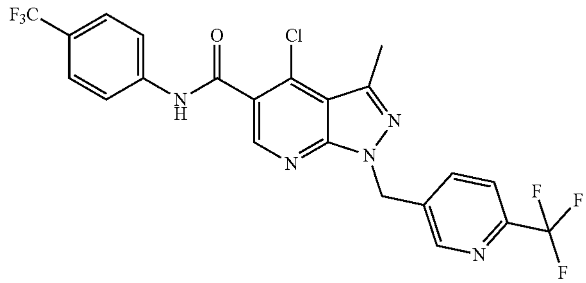 [SMILES: Cc1nn(Cc2ccc(C(F)(F)F)nc2)c2ncc(C(=O)Nc3ccc(C(F)(F)F)cc3)c(Cl)c12] |
| 256 | 4-Chloro-1-(5-methoxy-pyridin-3-ylmethyl)-3-methyl-1H-pyrazolo[3,4-b]pyridine-5-carboxylic acid (4-trifluoromethyl-phenyl)-amide | 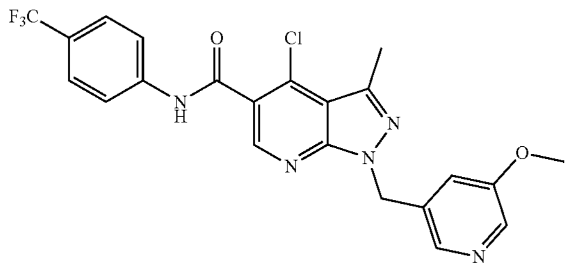 [SMILES: COc1cncc(Cn2nc(C)c3c(Cl)c(C(=O)Nc4ccc(C(F)(F)F)cc4)cnc32)c1] |
| 257 | 4-Chloro-1-(5-methoxy-pyridin-3-ylmethyl)-3-methyl-1H-pyrazolo[3,4-b]pyridine-5-carboxylic acid (4-chloro-phenyl)-amide | 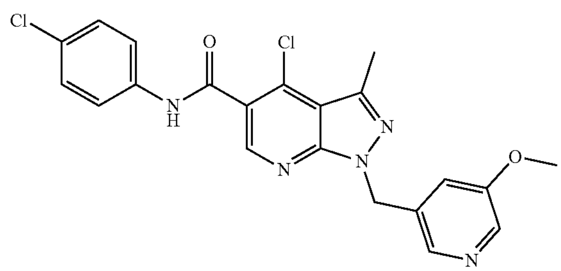 [SMILES: COc1cncc(Cn2nc(C)c3c(Cl)c(C(=O)Nc4ccc(Cl)cc4)cnc32)c1] |
| 258 | 4-Chloro-1-furan-2-ylmethyl-3-methyl-1H-pyrazolo[3,4-b]pyridine-5-carboxylic acid (4-chloro-phenyl)-amide | 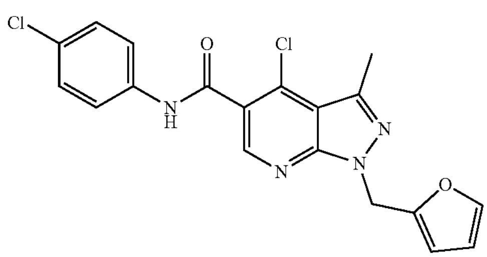 [SMILES: Cc1nn(Cc2ccco2)c2ncc(C(=O)Nc3ccc(Cl)cc3)c(Cl)c12] |
| 259 | 4-Chloro-1-furan-2-ylmethyl-3-methyl-1H-pyrazolo[3,4-b]pyridine-5-carboxylic acid (4-trifluoromethyl-phenyl)-amide | 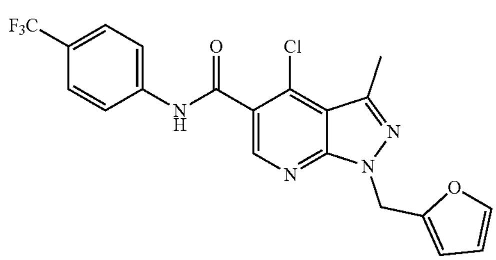 [SMILES: Cc1nn(Cc2ccco2)c2ncc(C(=O)Nc3ccc(C(F)(F)F)cc3)c(Cl)c12] |
| 260 | 4-Chloro-1-furan-3-ylmethyl-3-methyl-1H-pyrazolo[3,4-b]pyridine-5-carboxylic acid (4-chloro-phenyl)-amide | 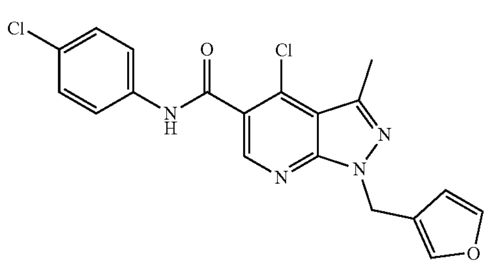 [SMILES: Cc1nn(Cc2ccoc2)c2ncc(C(=O)Nc3ccc(Cl)cc3)c(Cl)c12] |

| Ex. | Names | Structures |
|---|---|---|
| 261 | 4-Chloro-1-furan-3-ylmethyl-3-methyl-1H-pyrazolo[3,4-b]pyridine-5-carboxylic acid (4-trifluoromethyl-phenyl)-amide | 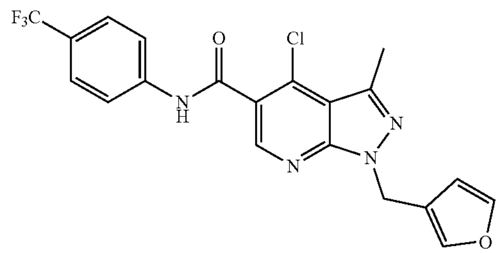 |
| 262 | 4-Chloro-3-methyl-1-thiophen-2-ylmethyl-1H-pyrazolo[3,4-b]pyridine-5-carboxylic acid (4-chloro-phenyl)-amide | 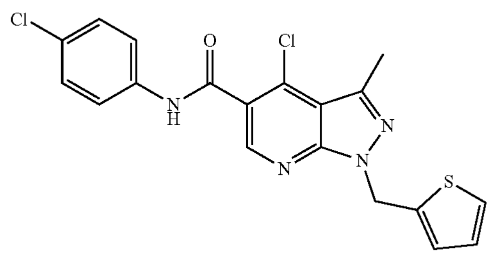 [SMILES: Cc1nn(Cc2cccs2)c2ncc(C(=O)Nc3ccc(Cl)cc3)c(Cl)c12] |
| 263 | 4-chloro-3-methyl-1-thiophen-2-ylmethyl-1H-pyrazolo[3,4-b]pyridine-5-carboxylic acid (4-trifluoromethyl-phenyl)-amide | 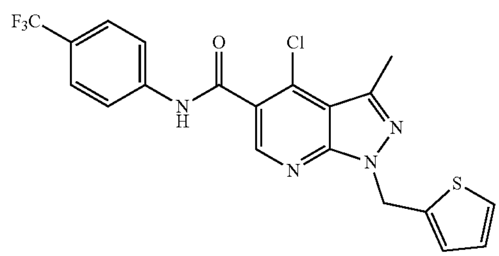 [SMILES: Cc1nn(Cc2cccs2)c2ncc(C(=O)Nc3ccc(C(F)(F)F)cc3)c(Cl)c12] |
| 264 | 4-Chloro-3-methyl-1-thiophen-3-ylmethyl-1H-pyrazolo[3,4-b]pyridine-5-carboxylic acid (4-chloro-phenyl)-amide | 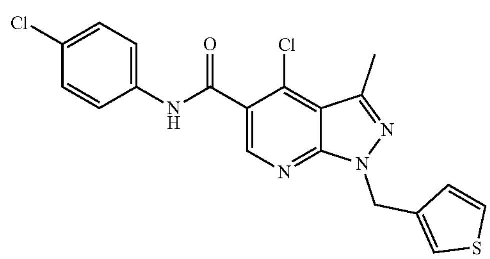 [SMILES: Cc1nn(Cc2ccsc2)c2ncc(C(=O)Nc3ccc(Cl)cc3)c(Cl)c12] |
| 265 | 4-Chloro-3-methyl-1-thiophen-3-ylmethyl-1H-pyrazolo[3,4-b]pyridine-5-carboxylic acid (4-trifluoromethyl-phenyl)-amide | 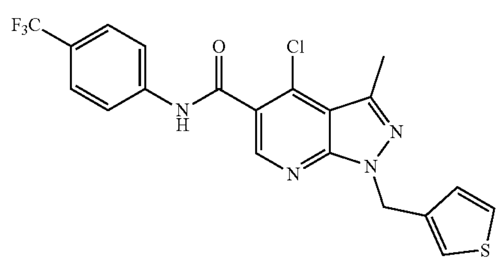 |
| 266 | 4-Chloro-3-methyl-1-thiazol-2-ylmethyl-1H-pyrazolo[3,4-b]pyridine-5-carboxylic acid (4-chloro-phenyl)-amide | 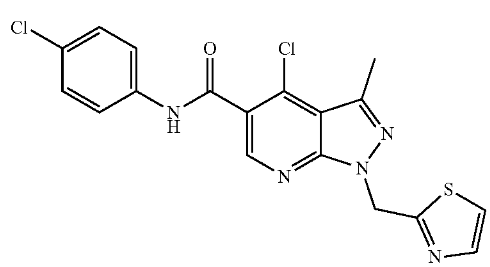 [SMILES: Cc1nn(Cc2nccs2)c2ncc(C(=O)Nc3ccc(Cl)cc3)c(Cl)c12] |

TABLE 1-continued

| Ex. | Names | Structures |
|---|---|---|
| 267 | 4-Chloro-3-methyl-1-thiazol-2-ylmethyl-1H-pyrazolo[3,4-b]pyridine-5-carboxylic acid (4-trifluoromethyl-phenyl)-amide | 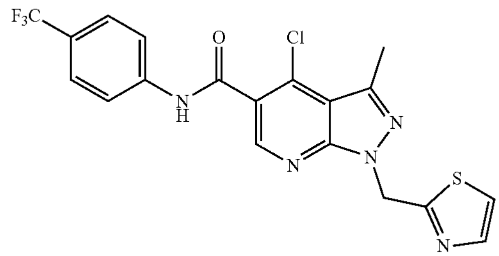 [SMILES: Cc1nn(Cc2nccs2)c2ncc(C(=O)Nc3ccc(C(F)(F)F)cc3)c(Cl)c12] |
| 268 | 4-Chloro-3-methyl-1-(5-methyl-thiazol-2-ylmethyl)-1H-pyrazolo[3,4-b]pyridine-5-carboxylic acid (4-chloro-phenyl)-amide | 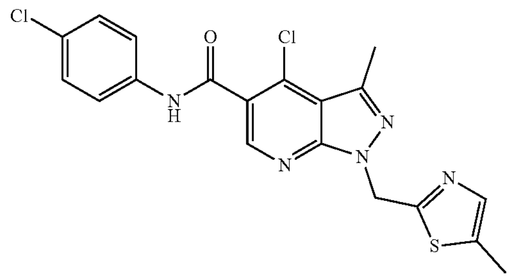 [SMILES: Cc1cnc(Cn2nc(C)c3c(Cl)c(C(=O)Nc4ccc(Cl)cc4)cnc32)s1] |
| 269 | 4-Chloro-3-methyl-1-(5-methyl-thiazol-2-ylmethyl)-1H-pyrazolo[3,4-b]pyridine-5-carboxylic acid (4-trifluoromethyl-phenyl)-amide | 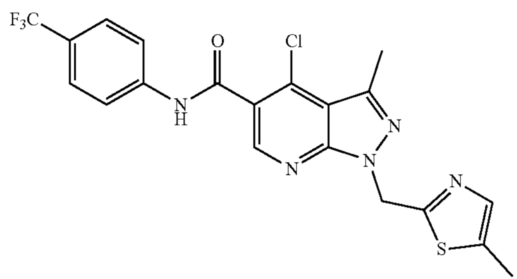 [SMILES: Cc1cnc(Cn2nc(C)c3c(Cl)c(C(=O)Nc4ccc(C(F)(F)F)cc4)cnc32)s1] |
| 270 | 4-chloro-N-(4-chlorophenyl)-3-methyl-1-((1-methyl-1H-imidazol-2-yl)methyl)-1H-pyrazolo[3,4-b]pyridine-5-carboxamide | 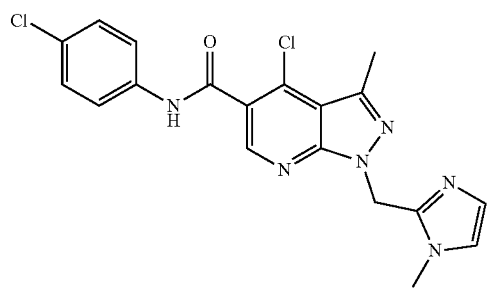 [SMILES: Cc1nn(Cc2nccn2C)c2ncc(C(=O)Nc3ccc(Cl)cc3)c(Cl)c12] |
| 271 | 4-chloro-3-methyl-1-((1-methyl-1H-imidazol-2-yl)methyl)-N-(4-(trifluoromethyl)phenyl)-1H-pyrazolo[3,4-b]pyridine-5-carboxamide | 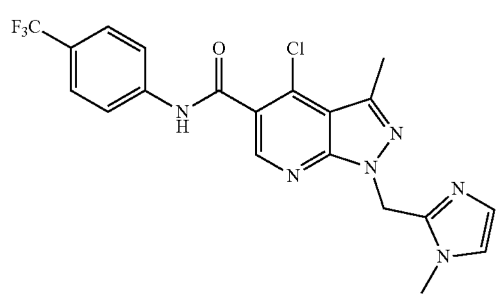 [SMILES: Cc1nn(Cc2nccn2C)c2ncc(C(=O)Nc3ccc(C(F)(F)F)cc3)c(Cl)c12] |

TABLE 1-continued

| Ex. | Names |
|---|---|
| 272 | 4-chloro-N-(4-chlorophenyl)-1-((1-ethyl-1H-imidazol-2-yl)methyl)-3-methyl-1H-pyrazolo[3,4-b]pyridine-5-carboxamide |
| 273 | 4-chloro-1-((1-ethyl-1H-imidazol-2-yl)methyl)-3-methyl-N-(4-(trifluoromethyl)phenyl)-1H-pyrazolo[3,4-b]pyridine-5-carboxamide |
| 274 | 4-chloro-N-(4-chlorophenyl)-1-((1-isopropyl-1H-imidazol-2-yl)methyl)-3-methyl-1H-pyrazolo[3,4-b]pyridine-5-carboxamide |
| 275 | 4-chloro-1-((1-isopropyl-1H-imidazol-2-yl)methyl)-3-methyl-N-(4-(trifluoromethyl)phenyl)-1H-pyrazolo[3,4-b]pyridine-5-carboxamide |

TABLE 1-continued

| Ex. | Names | Structures |
|---|---|---|
| 276 | 4-chloro-N-(4-chlorophenyl)-1-((1-(2-methoxyethyl)-1H-imidazol-2-yl)methyl)-3-methyl-1H-pyrazolo[3,4-b]pyridine-5-carboxamide | 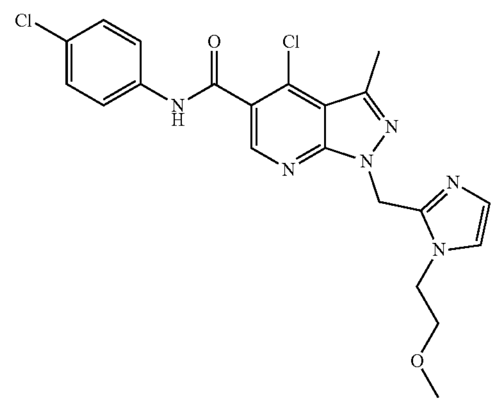 [SMILES: COCCn1ccnc1Cn1nc(C)c2c(Cl)c(C(=O)Nc3ccc(Cl)cc3)cnc21] |
| 277 | 4-chloro-1-((1-(2-methoxyethyl)-1H-imidazol-2-yl)methyl)-3-methyl-N-(4-(trifluoromethyl)phenyl)-1H-pyrazolo[3,4-b]pyridine-5-carboxamide | 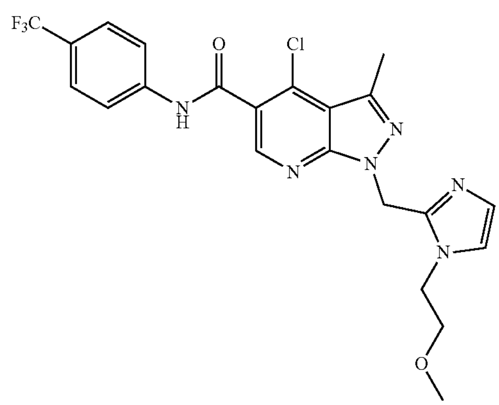 [SMILES: COCCn1ccnc1Cn1nc(C)c2c(Cl)c(C(=O)Nc3ccc(C(F)(F)F)cc3)cnc21] |
| 279 | 4-chloro-1-((1-(4-methoxybenzyl)-1H-imidazol-2-yl)methyl)-3-methyl-N-(4-(trifluoromethyl)phenyl)-1H-pyrazolo[3,4-b]pyridine-5-carboxamide | 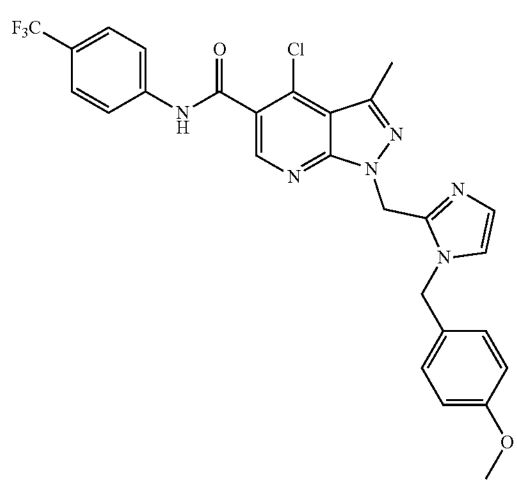 [SMILES: COc1ccc(Cn2ccnc2Cn2nc(C)c3c(Cl)c(C(=O)Nc4ccc(C(F)(F)F)cc4)cnc32)cc1] |
| 280 | 4-chloro-N-(4-chlorophenyl)-1-(pyridin-4-ylmethyl)-1H-pyrazolo[3,4-b]pyridine-5-carboxamide | 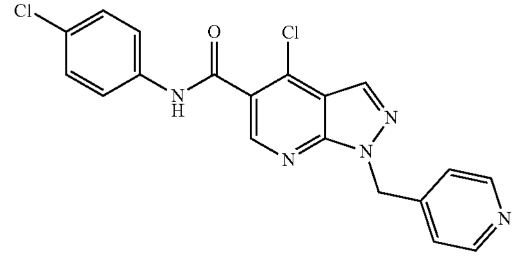 [SMILES: O=C(Nc1ccc(Cl)cc1)c1cnc2c(cnn2Cc2ccncc2)c1Cl] |

TABLE 1-continued

| Ex. | Names | Structures |
|---|---|---|
| 281 | 4-chloro-1-(pyridin-4-ylmethyl)-N-(4-(trifluoromethyl)phenyl)-1H-pyrazolo[3,4-b]pyridine-5-carboxamide | 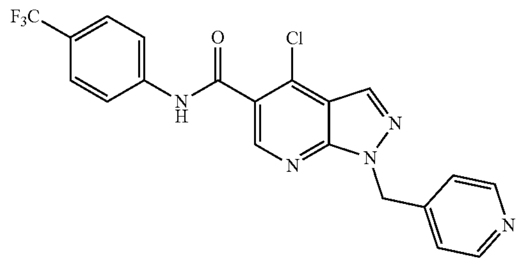 [SMILES: O=C(Nc1ccc(C(F)(F)F)cc1)c1cnc2c(cnn2Cc2ccncc2)c1Cl] |
| 282 | 4-chloro-N-(4-isopropylphenyl)-1-(pyridin-4-ylmethyl)-1H-pyrazolo[3,4-b]pyridine-5-carboxamide | 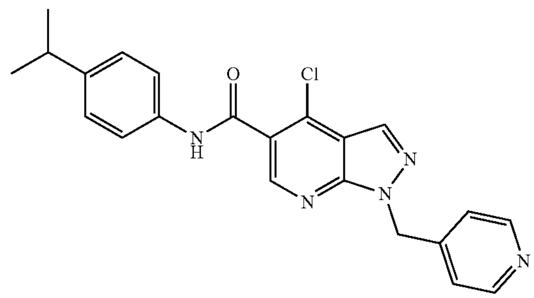 [SMILES: CC(C)c1ccc(NC(=O)c2cnc3c(cnn3Cc3ccncc3)c2Cl)cc1] |
| 283 | 4-chloro-N-(4-chlorophenyl)-1-(pyridin-3-ylmethyl)-1H-pyrazolo[3,4-b]pyridine-5-carboxamide | 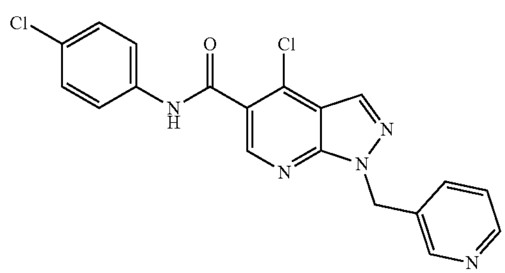 [SMILES: O=C(Nc1ccc(Cl)cc1)c1cnc2c(cnn2Cc2cccnc2)c1Cl] |
| 284 | 4-chloro-1-(pyridin-3-ylmethyl)-N-(4-(trifluoromethyl)phenyl)-1H-pyrazolo[3,4-b]pyridine-5-carboxamide | 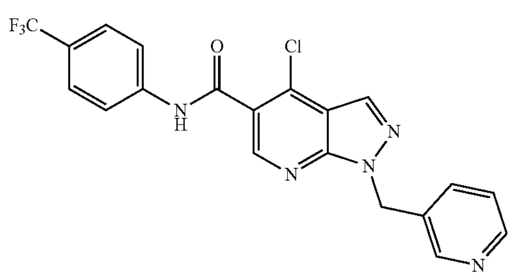 [SMILES: O=C(Nc1ccc(C(F)(F)F)cc1)c1cnc2c(cnn2Cc2cccnc2)c1Cl] |
| 285 | 4-chloro-N-(4-isopropylphenyl)-1-(pyridin-3-ylmethyl)-1H-pyrazolo[3,4-b]pyridine-5-carboxamide | 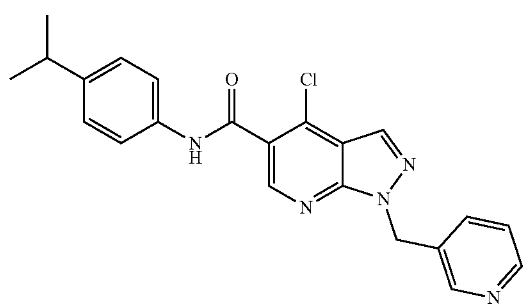 [SMILES: CC(C)c1ccc(NC(=O)c2cnc3c(cnn3Cc3cccnc3)c2Cl)cc1] |

TABLE 1-continued

| Ex. | Names | Structures |
|---|---|---|
| 286 | 4-chloro-N-(4-chlorophenyl)-1-(pyridin-2-ylmethyl)-1H-pyrazolo[3,4-b]pyridine-5-carboxamide | 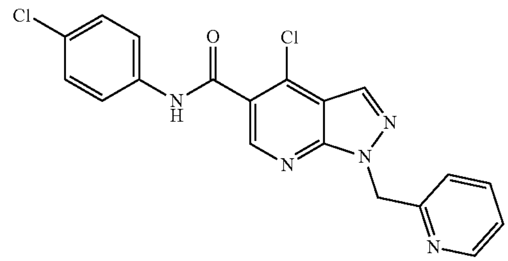 [SMILES: O=C(Nc1ccc(Cl)cc1)c1cnc2c(cnn2Cc2ccccn2)c1Cl] |
| 287 | 4-chloro-1-(pyridin-2-ylmethyl)-N-(4-(trifluoromethyl)phenyl)-1H-pyrazolo[3,4-b]pyridine-5-carboxamide | 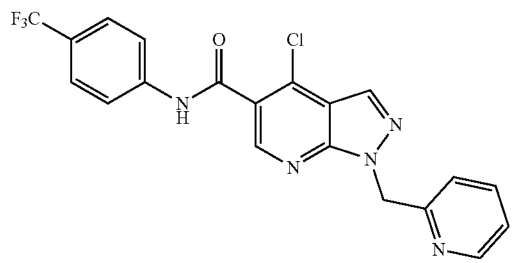 [SMILES: O=C(Nc1ccc(C(F)(F)F)cc1)c1cnc2c(cnn2Cc2ccccn2)c1Cl] |
| 288 | 4-chloro-N-(4-isopropylphenyl)-1-(pyridin-2-ylmethyl)-1H-pyrazolo[3,4-b]pyridine-5-carboxamide | 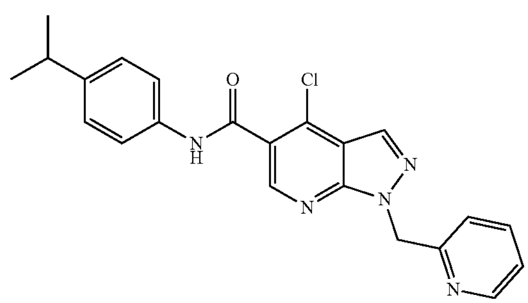 [SMILES: CC(C)c1ccc(NC(=O)c2cnc3c(cnn3Cc3ccccn3)c2Cl)cc1] |
| 289 | 3,4-Dichloro-1-pyridin-2-ylmethyl-1H-pyrazolo[3,4-b]pyridine-5-carboxylic acid (4-trifluoromethyl-phenyl)-amide | 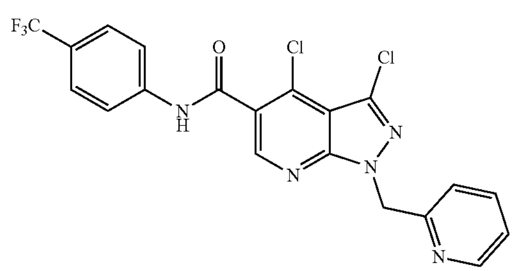 [SMILES: O=C(Nc1ccc(C(F)(F)F)cc1)c1cnc2c(c(Cl)nn2Cc2ccccn2)c1Cl] |
| 290 | 4-Chloro-1-(6-methyl-pyridin-2-ylmethyl)-1H-pyrazolo[3,4-b]pyridine-5-carboxylic acid (4-isopropyl-phenyl)-amide | 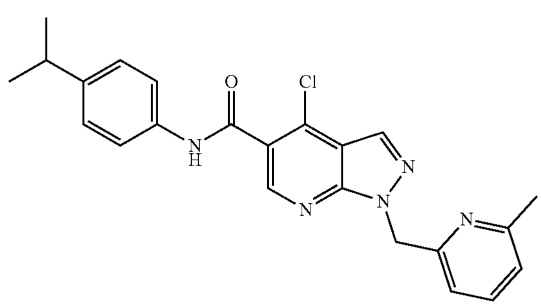 [SMILES: Cc1cccc(Cn2ncc3c(Cl)c(C(=O)Nc4ccc(C(C)C)cc4)cnc32)n1] |

TABLE 1-continued

| Ex. | Names |
|---|---|
| 291 | 4-Chloro-1-(6-methyl-pyridin-2-ylmethyl)-1H-pyrazolo[3,4-b]pyridine-5-carboxylic acid (4-trifluoromethyl-phenyl)-amide |
| 292 | 4-Chloro-1-(6-methyl-pyridin-2-ylmethyl)-1H-pyrazolo[3,4-b]pyridine-5-carboxylic acid (4-chloro-phenyl)-amide |
| 293 | 4-chloro-1-thiophen-2-ylmethyl-1H-pyrazolo[3,4-b]pyridine-5-carboxylic acid (4-trifluoromethyl-phenyl)-amide |
| 294 | 4-chloro-1-thiophen-2-ylmethyl-1H-pyrazolo[3,4-b]pyridine-5-carboxylic acid (4-chloro-phenyl)-amide |
| 295 | 4-Chloro-1-thiazol-2-ylmethyl-1H-pyrazolo[3,4-b]pyridine-5-carboxylic acid (4-chloro-phenyl)-amide |
| 296 | 4-Chloro-1-thiazol-2-ylmethyl-1H-pyrazolo[3,4-b]pyridine-5-carboxylic acid (4-trifluoromethyl-phenyl)-amide |

TABLE 1-continued

| Ex. | Names | Structures |
|---|---|---|
| 297 | 4-chloro-N-(4-chlorophenyl)-1-((1-methyl-1H-imidazol-5-yl)methyl)-1H-pyrazolo[3,4-b]pyridine-5-carboxamide | 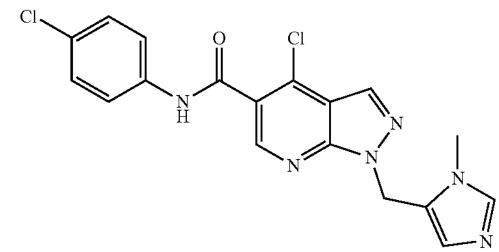 [SMILES: Cn1cncc1Cn1ncc2c(Cl)c(C(=O)Nc3ccc(Cl)cc3)cnc21] |
| 298 | 4-chloro-N-(4-methoxyphenyl)-1-((1-methyl-1H-imidazol-5-yl)methyl)-1H-pyrazolo[3,4-b]pyridine-5-carboxamide | 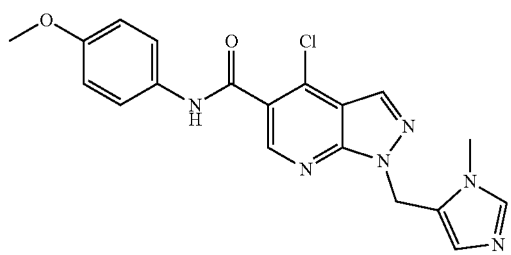 [SMILES: COc1ccc(NC(=O)c2cnc3c(cnn3Cc3cncn3C)c2Cl)cc1] |
| 299 | 4-chloro-N-(4-isopropylphenyl)-1-((1-methyl-1H-imidazol-5-yl)methyl)-1H-pyrazolo[3,4-b]pyridine-5-carboxamide | 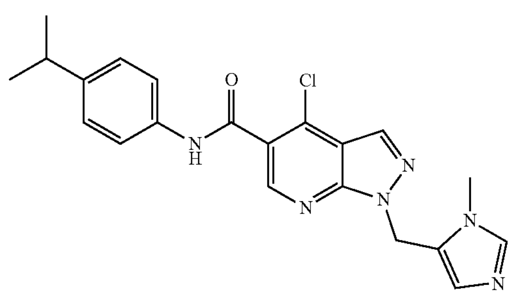 [SMILES: CC(C)c1ccc(NC(=O)c2cnc3c(cnn3Cc3cncn3C)c2Cl)cc1] |
| 300 | 4-chloro-1-((1-methyl-1H-imidazol-5-yl)methyl)-N-(4-(trifluoromethyl)phenyl)-1H-pyrazolo[3,4-b]pyridine-5-carboxamide | 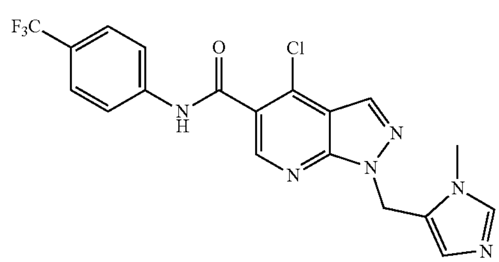 [SMILES: Cn1cncc1Cn1ncc2c(Cl)c(C(=O)Nc3ccc(C(F)(F)F)cc3)cnc21] |
| 301 | 4-chloro-N-(4-chlorophenyl)-1-((1-methyl-1H-imidazol-2-yl)methyl)-1H-pyrazolo[3,4-b]pyridine-5-carboxamide | 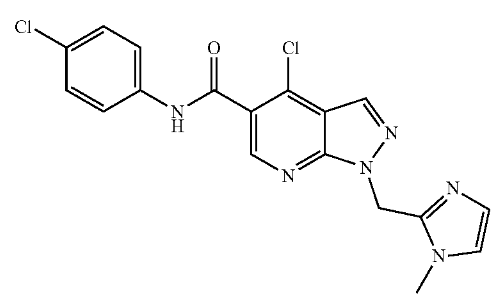 [SMILES: Cn1ccnc1Cn1ncc2c(Cl)c(C(=O)Nc3ccc(Cl)cc3)cnc21] |

TABLE 1-continued

| Ex. | Names | Structures |
| --- | --- | --- |
| 302 | 4-chloro-1-((1-methyl-1H-imidazol-2-yl)methyl)-N-(4-(trifluoromethyl)phenyl)-1H-pyrazolo[3,4-b]pyridine-5-carboxamide | 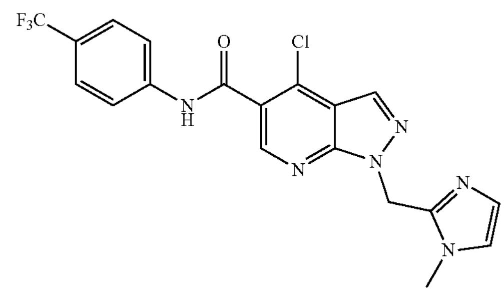 [SMILES: Cn1ccnc1Cn1ncc2c(Cl)c(C(=O)Nc3ccc(C(F)(F)F)cc3)cnc21] |
| 303 | 4-chloro-N-(4-isopropylphenyl)-1-((1-methyl-1H-imidazol-2-yl)methyl)-1H-pyrazolo[3,4-b]pyridine-5-carboxamide | 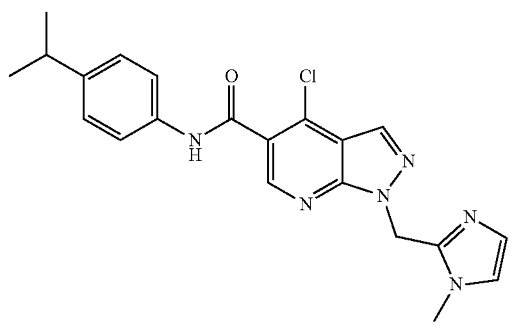 [SMILES: CC(C)c1ccc(NC(=O)c2cnc3c(cnn3Cc3nccn3C)c2Cl)cc1] |
| 304 | 1-((1-benzyl-1H-imidazol-2-yl)methyl)-4-chloro-N-(4-chlorophenyl)-1H-pyrazolo[3,4-b]pyridine-5-carboxamide | 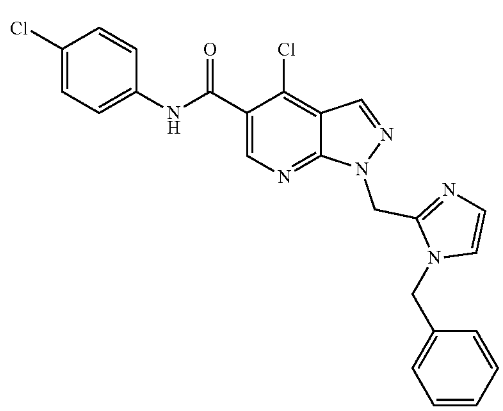 [SMILES: O=C(Nc1ccc(Cl)cc1)c1cnc2c(cnn2Cc2nccn2Cc2ccccc2)c1Cl] |
| 305 | 1-((1-benzyl-1H-imidazol-2-yl)methyl)-4-chloro-N-(4-(trifluoromethyl)phenyl)-1H-pyrazolo[3,4-b]pyridine-5-carboxamide | 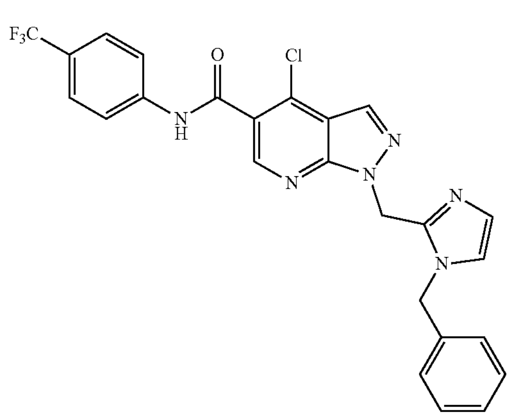 [SMILES: O=C(Nc1ccc(C(F)(F)F)cc1)c1cnc2c(cnn2Cc2nccn2Cc2ccccc2)c1Cl] |

TABLE 1-continued

| Ex. | Names | Structures |
|---|---|---|
| 306 | 7-chloro-N-(4-chlorophenyl)-3-methyl-3H-imidazo[4,5-b]pyridine-6-carboxamide | 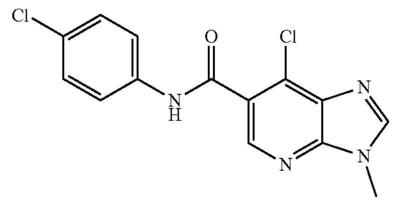 [SMILES: Cn1cnc2c(Cl)c(C(=O)Nc3ccc(Cl)cc3)cnc21] |
| 307 | 7-chloro-3-methyl-N-(4-(trifluoromethyl)phenyl)-3H-imidazo[4,5-b]pyridine-6-carboxamide | 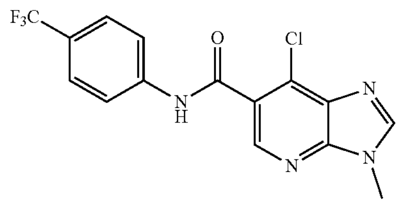 [SMILES: Cn1cnc2c(Cl)c(C(=O)Nc3ccc(C(F)(F)F)cc3)cnc21] |
| 308 | 7-chloro-N-(4-isopropylphenyl)-3-methyl-3H-imidazo[4,5-b]pyridine-6-carboxamide | 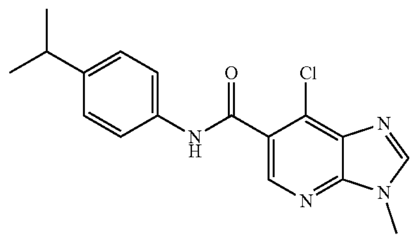 [SMILES: CC(C)c1ccc(NC(=O)c2cnc3c(ncn3C)c2Cl)cc1] |
| 309 | 7-chloro-N-(4-(2-methoxyethoxy)phenyl)-3-methyl-3H-imidazo[4,5-b]pyridine-6-carboxamide | 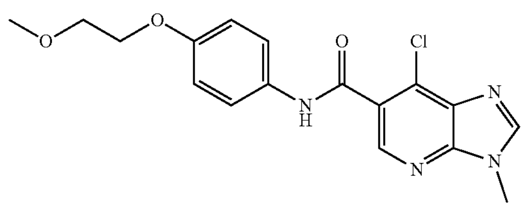 [SMILES: COCCOc1ccc(NC(=O)c2cnc3c(ncn3C)c2Cl)cc1] |
| 310 | 7-Chloro-2,3-dimethyl-3H-imidazo[4,5-b]pyridine-6-carboxylic acid (4-chloro-phenyl)-amide | 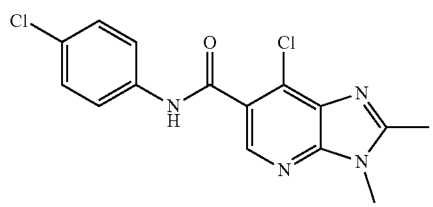 [SMILES: Cc1nc2c(Cl)c(C(=O)Nc3ccc(Cl)cc3)cnc2n1C] |
| 311 | 7-Chloro-2,3-dimethyl-3H-imidazo[4,5-b]pyridine-6-carboxylic acid (4-trifluoromethyl-phenyl)-amide | 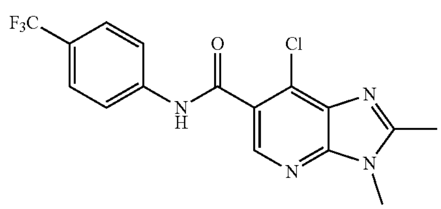 [SMILES: Cc1nc2c(Cl)c(C(=O)Nc3ccc(C(F)(F)F)cc3)cnc2n1C] |
| 312 | 7-Chloro-2,3-dimethyl-3H-imidazo[4,5-b]pyridine-6-carboxylic acid (4-isopropyl-phenyl)-amide | 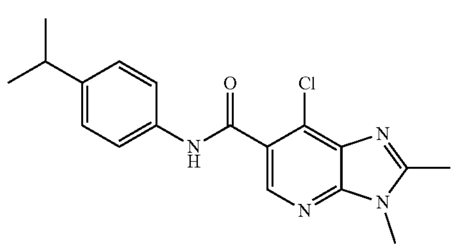 [SMILES: Cc1nc2c(Cl)c(C(=O)Nc3ccc(C(C)C)cc3)cnc2n1C] |

TABLE 1-continued

| Ex. | Names | Structures |
|---|---|---|
| 313 | 7-Chloro-3-(4-methyl-benzyl)-3H-imidazo[4,5-b]pyridine-6-carboxylic acid (4-trifluoromethyl-phenyl)-amide | 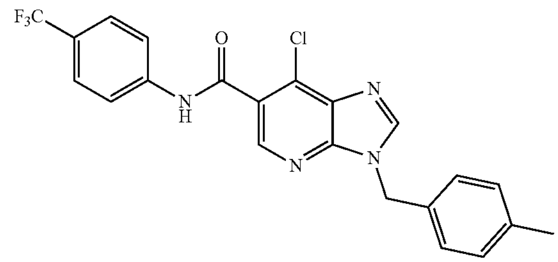 [SMILES: Cc1ccc(Cn2cnc3c(Cl)c(C(=O)Nc4ccc(C(F)(F)F)cc4)cnc32)cc1] |
| 314 | 7-Chloro-3-(4-methyl-benzyl)-3H-imidazo[4,5-b]pyridine-6-carboxylic acid (4-chloro-phenyl)-amide | 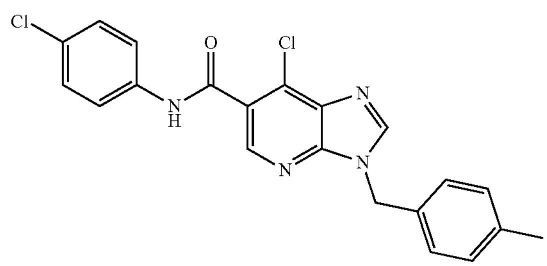 [SMILES: Cc1ccc(Cn2cnc3c(Cl)c(C(=O)Nc4ccc(Cl)cc4)cnc32)cc1] |
| 315 | 7-Chloro-3-(4-methyl-benzyl)-3H-imidazo[4,5-b]pyridine-6-carboxylic acid (4-isopropyl-phenyl)-amide | 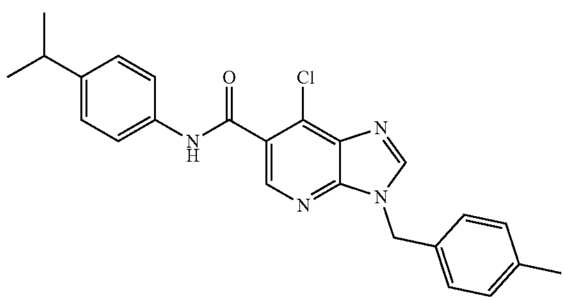 [SMILES: Cc1ccc(Cn2cnc3c(Cl)c(C(=O)Nc4ccc(C(C)C)cc4)cnc32)cc1] |
| 316 | 3-Benzyl-7-chloro-3H-imidazo[4,5-b]pyridine-6-carboxylic acid (4-chloro-phenyl)-amide | 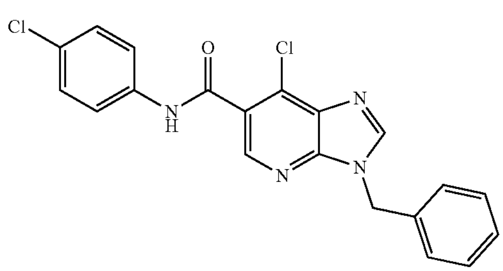 [SMILES: O=C(Nc1ccc(Cl)cc1)c1cnc2c(ncn2Cc2ccccc2)c1Cl] |
| 317 | 3-Benzyl-7-chloro-3H-imidazo[4,5-b]pyridine-6-carboxylic acid (4-isopropyl-phenyl)-amide | 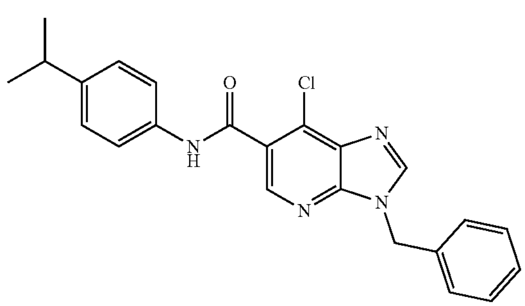 [SMILES: CC(C)c1ccc(NC(=O)c2cnc3c(ncn3Cc3ccccc3)c2Cl)cc1] |

TABLE 1-continued

| Ex. | Names | Structures |
|---|---|---|
| 318 | 3-Benzyl-7-chloro-3H-imidazo[4,5-b]pyridine-6-carboxylic acid (4-trifluoromethyl-phenyl)-amide | 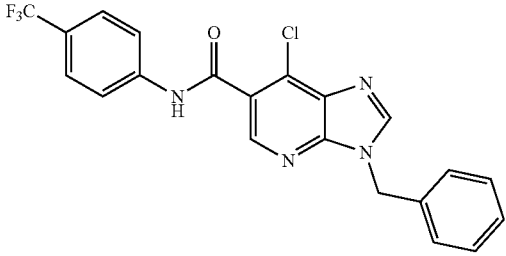 [SMILES: O=C(Nc1ccc(C(F)(F)F)cc1)c1cnc2c(ncn2Cc2ccccc2)c1Cl] |
| 319 | 3-Butyl-7-chloro-3H-imidazo[4,5-b]pyridine-6-carboxylic acid (4-chloro-phenyl)-amide | 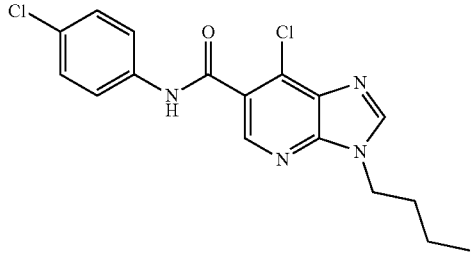 [SMILES: CCCCn1cnc2c(Cl)c(C(=O)Nc3ccc(Cl)cc3)cnc21] |
| 320 | 3-Butyl-7-chloro-3H-imidazo[4,5-b]pyridine-6-carboxylic acid (4-isopropyl-phenyl)-amide | 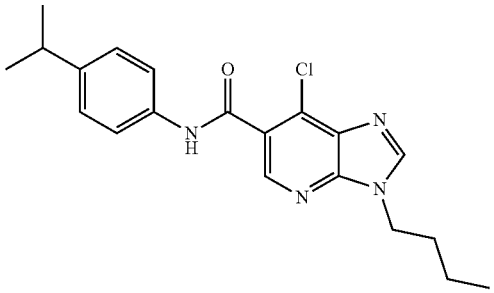 [SMILES: CCCCn1cnc2c(Cl)c(C(=O)Nc3ccc(C(C)C)cc3)cnc21] |
| 321 | 3-Butyl-7-chloro-3H-imidazo[4,5-b]pyridine-6-carboxylic acid (4-trifluoromethyl-phenyl)-amide | 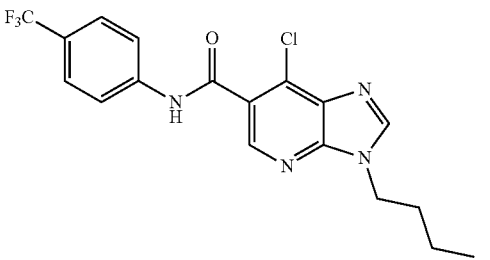 [SMILES: CCCCn1cnc2c(Cl)c(C(=O)Nc3ccc(C(F)(F)F)cc3)cnc21] |
| 322 | 7-Chloro-3-(4-methoxy-benzyl)-3H-imidazo[4,5-b]pyridine-6-carboxylic acid (4-chloro-phenyl)-amide | 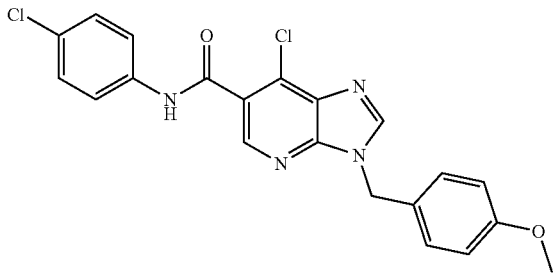 [SMILES: COc1ccc(Cn2cnc3c(Cl)c(C(=O)Nc4ccc(Cl)cc4)cnc32)cc1] |

TABLE 1-continued

| Ex. | Names | Structures |
|---|---|---|
| 323 | 7-Chloro-3-(4-methoxy-benzyl)-3H-imidazo[4,5-b]pyridine-6-carboxylic acid (4-trifluoromethyl-phenyl)-amide | 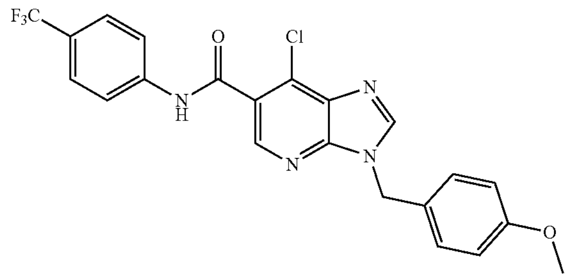 [SMILES: COc1ccc(Cn2cnc3c(Cl)c(C(=O)Nc4ccc(C(F)(F)F)cc4)cnc32)cc1] |
| 324 | 7-Chloro-3-(4-methoxy-benzyl)-3H-imidazo[4,5-b]pyridine-6-carboxylic acid (4-isopropyl-phenyl)-amide | 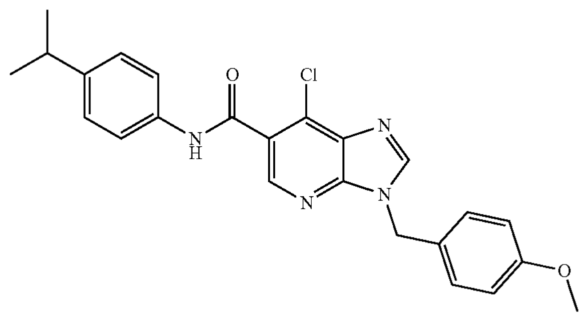 [SMILES: COc1ccc(Cn2cnc3c(Cl)c(C(=O)Nc4ccc(C(C)C)cc4)cnc32)cc1] |
| 325 | 7-Chloro-3-(2-methoxy-ethyl)-3H-imidazo[4,5-b]pyridine-6-carboxylic acid (4-chloro-phenyl)-amide | 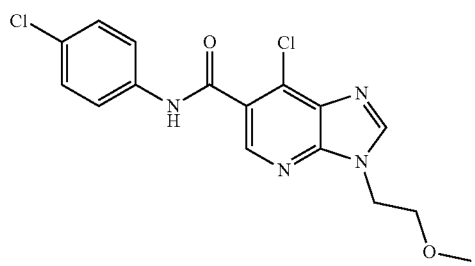 [SMILES: COCCn1cnc2c(Cl)c(C(=O)Nc3ccc(Cl)cc3)cnc21] |
| 326 | 7-Chloro-3-(2-methoxy-ethyl)-3H-imidazo[4,5-b]pyridine-6-carboxylic acid (4-trifluoromethyl-phenyl)-amide | 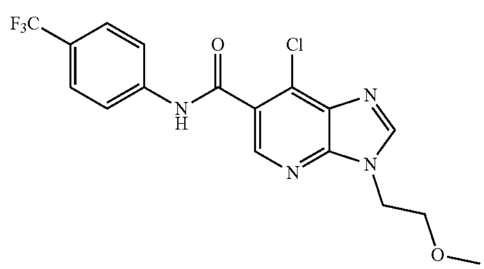 [SMILES: COCCn1cnc2c(Cl)c(C(=O)Nc3ccc(C(F)(F)F)cc3)cnc21] |
| 327 | 7-Chloro-3-(2-methoxy-ethyl)-3H-imidazo[4,5-b]pyridine-6-carboxylic acid (4-isopropyl-phenyl)-amide | 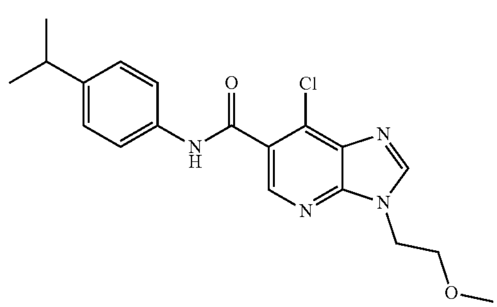 |

TABLE 1-continued

| Ex. | Names |
|---|---|
| 328 | 7-Chloro-3-(4-fluoro-benzyl)-3H-imidazo[4,5-b]pyridine-6-carboxylic acid (4-chloro-phenyl)-amide |
| 329 | 7-Chloro-3-(4-fluoro-benzyl)-3H-imidazo[4,5-b]pyridine-6-carboxylic acid (4-trifluoromethyl-phenyl)-amide |
| 330 | 7-Chloro-3-(4-fluoro-benzyl)-3H-imidazo[4,5-b]pyridine-6-carboxylic acid (4-isopropyl-phenyl)-amide |
| 331 | 7-chloro-3-(2-(piperidin-4-yl)ethyl)-N-(4-(trifluoromethyl)phenyl)-3H-imidazo[4,5-b]pyridine-6-carboxamide |

TABLE 1-continued

| Ex. | Names | Structures |
|---|---|---|
| 331a | 3-(2-(1-acetylpiperidin-4-yl)ethyl)-7-chloro-N-(4-(trifluoromethyl)phenyl)-3H-imidazo[4,5-b]pyridine-6-carboxamide | 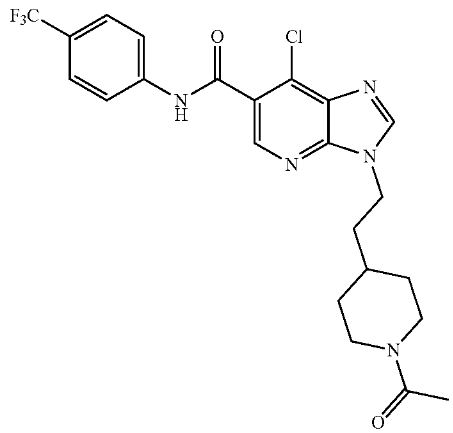 [SMILES: CC(=O)N1CCC(CCn2cnc3c(Cl)c(C(=O)Nc4ccc(C(F)(F)F)cc4)cnc32)CC1] |
| 332 | 7-chloro-1-(2-(piperidin-4-yl)ethyl)-N-(4-(trifluoromethyl)phenyl)-1H-imidazo[4,5-b]pyridine-6-carboxamide | 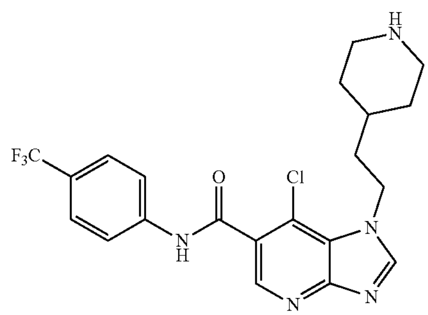 [SMILES: O=C(Nc1ccc(C(F)(F)F)cc1)c1cnc2ncn(CCC3CCNCC3)c2c1Cl] |
| 333 | 7-ethoxy-3-(2-(piperidin-4-yl)ethyl)-N-(4-(trifluoromethyl)phenyl)-3H-imidazo[4,5-b]pyridine-6-carboxamide | 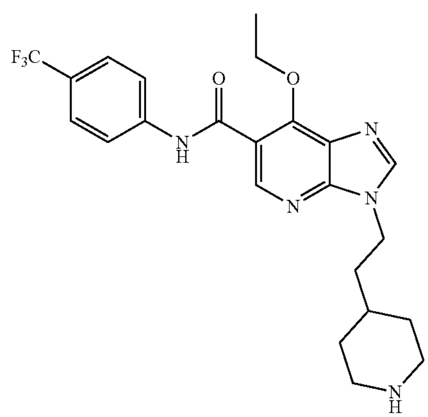 [SMILES: CCOc1c(C(=O)Nc2ccc(C(F)(F)F)cc2)cnc2c1ncn2CCC1CCNCC1] |
| 334 | 7-chloro-3-(2-(1-ethylpiperidin-4-yl)ethyl)-N-(4-(trifluoromethyl)phenyl)-3H-imidazo[4,5-b]pyridine-6-carboxamide | 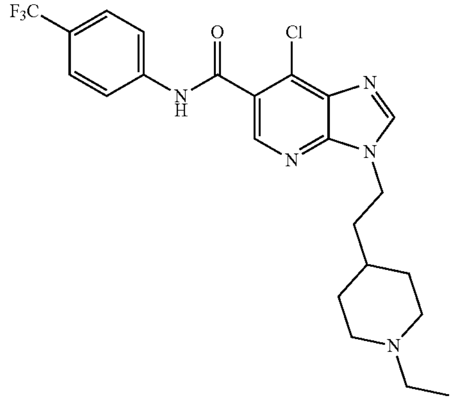 [SMILES: CCN1CCC(CCn2cnc3c(Cl)c(C(=O)Nc4ccc(C(F)(F)F)cc4)cnc32)CC1] |

TABLE 1-continued

| Ex. | Names | Structures |
|-----|-------|------------|
| 335 | 7-chloro-N-ethyl-3-(2-(1-ethylpiperidin-4-yl)ethyl)-N-(4-(trifluoromethyl)phenyl)-3H-imidazo[4,5-b]pyridine-6-carboxamide | 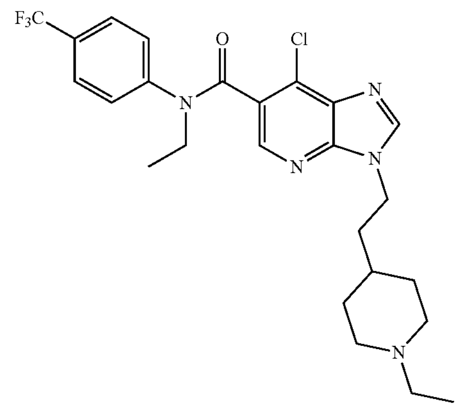 [SMILES: CCN1CCC(CCn2cnc3c(Cl)c(C(=O)N(CC)c4ccc(C(F)(F)F)cc4)cnc32)CC1] |
| 336 | 7-chloro-3-(2-(1-methylpiperidin-4-yl)ethyl)-N-(4-(trifluoromethyl)phenyl)-3H-imidazo[4,5-b]pyridine-6-carboxamide | 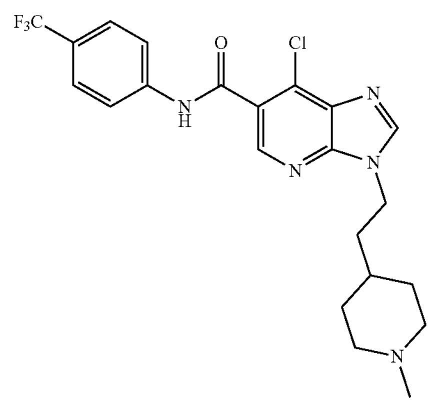 [SMILES: CN1CCC(CCn2cnc3c(Cl)c(C(=O)Nc4ccc(C(F)(F)F)cc4)cnc32)CC1] |
| 337 | 4-Chloro-1-cyclopropylmethyl-3-methyl-1H-pyrazolo[3,4-b]pyridine-5-carboxylic acid (4-chloro-phenyl)-amide | 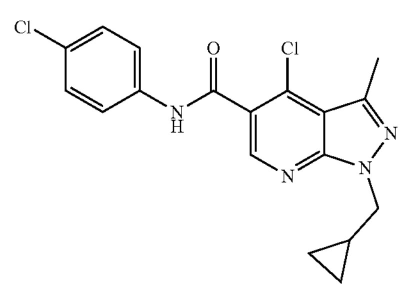 [SMILES: Cc1nn(CC2CC2)c2ncc(C(=O)Nc3ccc(Cl)cc3)c(Cl)c12] |
| 338 | 4-Chloro-1-cyclopropylmethyl-3-methyl-1H-pyrazolo[3,4-b]pyridine-5-carboxylic acid (4-trifluoromethyl-phenyl)-amide | 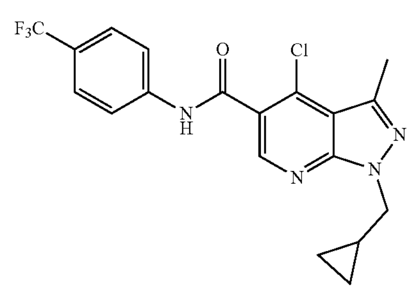 [SMILES: Cc1nn(CC2CC2)c2ncc(C(=O)Nc3ccc(C(F)(F)F)cc3)c(Cl)c12] |

TABLE 1-continued

| Ex. | Names | Structures |
|---|---|---|
| 339 | 4-Chloro-1-cyclopropylmethyl-3-methyl-1H-pyrazolo[3,4-b]pyridine-5-carboxylic acid (4-isopropyl-phenyl)-amide | 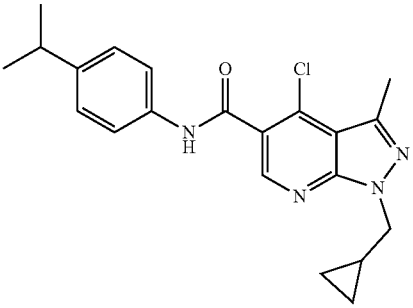 [SMILES: Cc1nn(CC2CC2)c2ncc(C(=O)Nc3ccc(C(C)C)cc3)c(Cl)c12] |
| 340 | 4-Chloro-1-cyclopropyl-3-methyl-1H-pyrazolo[3,4-b]pyridine-5-carboxylic acid (4-chloro-phenyl)-amide | 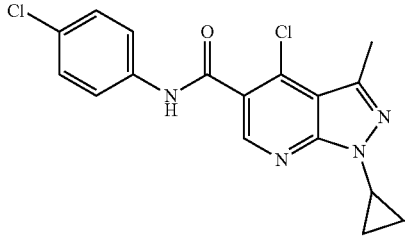 [SMILES: Cc1nn(C2CC2)c2ncc(C(=O)Nc3ccc(Cl)cc3)c(Cl)c12] |
| 341 | 4-Chloro-1-cyclopropyl-3-methyl-1H-pyrazolo[3,4-b]pyridine-5-carboxylic acid (4-trifluoromethyl-phenyl)-amide | 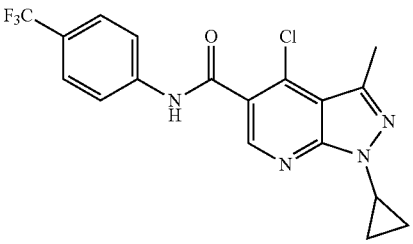 [SMILES: Cc1nn(C2CC2)c2ncc(C(=O)Nc3ccc(C(F)(F)F)cc3)c(Cl)c12] |
| 342 | 4-Chloro-1-cyclopropyl-3-methyl-1H-pyrazolo[3,4-b]pyridine-5-carboxylic acid (4-isopropyl-phenyl)-amide | 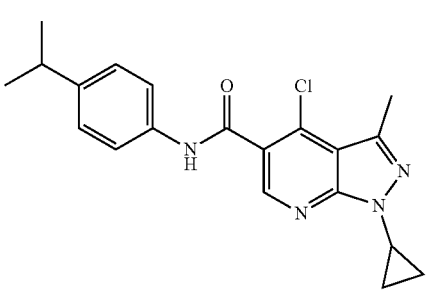 [SMILES: Cc1nn(C2CC2)c2ncc(C(=O)Nc3ccc(C(C)C)cc3)c(Cl)c12] |
| 343 | 4-Chloro-3-methyl-1-(2-morpholin-4-yl-ethyl)-1H-pyrazolo[3,4-b]pyridine-5-carboxylic acid (4-chloro-phenyl)-amide | 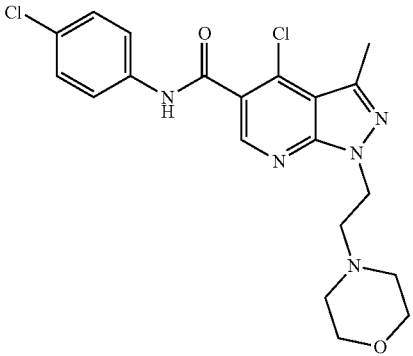 [SMILES: Cc1nn(CCN2CCOCC2)c2ncc(C(=O)Nc3ccc(Cl)cc3)c(Cl)c12] |

TABLE 1-continued

| Ex. | Names | Structures |
|---|---|---|
| 344 | 4-Chloro-3-methyl-1-(2-morpholin-4-yl-ethyl)-1H-pyrazolo[3,4-b]pyridine-5-carboxylic acid (4-trifluoromethyl-phenyl)-amide | 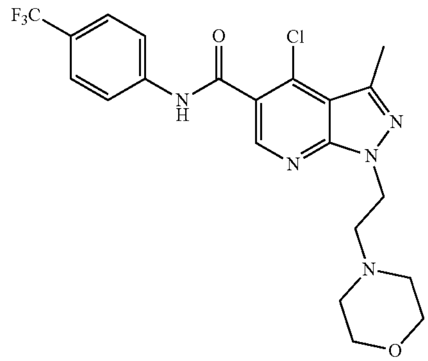 [SMILES: Cc1nn(CCN2CCOCC2)c2ncc(C(=O)Nc3ccc(C(F)(F)F)cc3)c(Cl)c12] |
| 345 | 4-Chloro-3-methyl-1-(2-morpholin-4-yl-ethyl)-1H-pyrazolo[3,4-b]pyridine-5-carboxylic acid (4-isopropyl-phenyl)-amide | 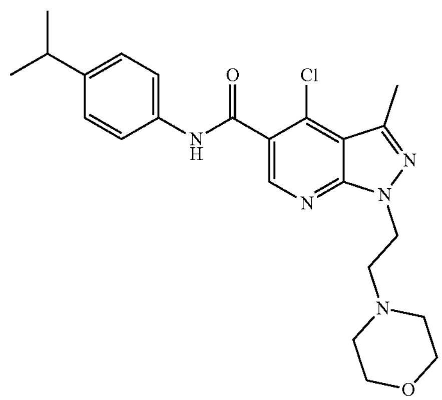 [SMILES: Cc1nn(CCN2CCOCC2)c2ncc(C(=O)Nc3ccc(C(C)C)cc3)c(Cl)c12] |
| 346 | 4-Chloro-3-methyl-1-(3-morpholin-4-yl-propyl)-1H-pyrazolo[3,4-b]pyridine-5-carboxylic acid (4-chloro-phenyl)-amide | 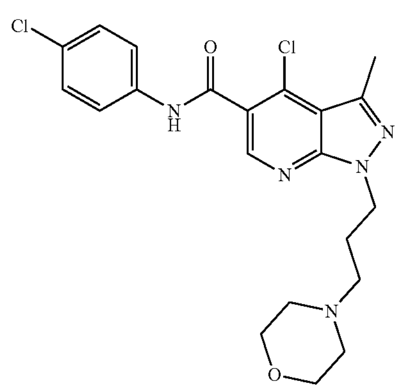 [SMILES: Cc1nn(CCCN2CCOCC2)c2ncc(C(=O)Nc3ccc(Cl)cc3)c(Cl)c12] |
| 347 | 4-Chloro-3-methyl-1-(3-morpholin-4-yl-propyl)-1H-pyrazolo[3,4-b]pyridine-5-carboxylic acid (4-trifluoromethyl-phenyl)-amide | 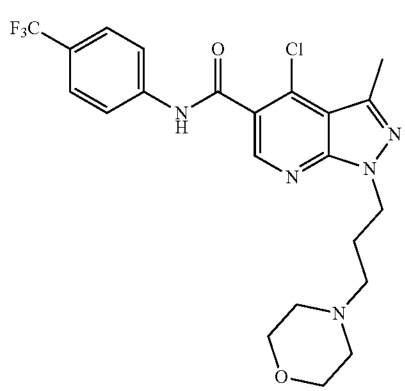 [SMILES: Cc1nn(CCCN2CCOCC2)c2ncc(C(=O)Nc3ccc(C(F)(F)F)cc3)c(Cl)c12] |

TABLE 1-continued

| Ex. | Names | Structures |
|---|---|---|
| 348 | 4-Chloro-3-methyl-1-(3-pyrrolidin-1-yl-propyl)-1H-pyrazolo[3,4-b]pyridine-5-carboxylic acid (4-chloro-phenyl)-amide | 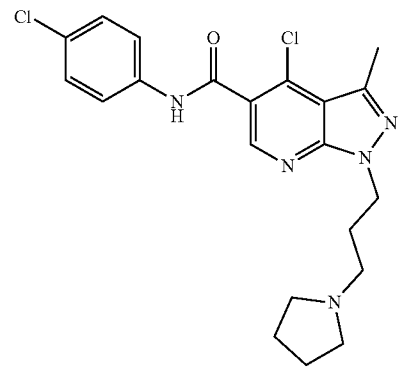 [SMILES: Cc1nn(CCCN2CCCC2)c2ncc(C(=O)Nc3ccc(Cl)cc3)c(Cl)c12] |
| 349 | 4-Chloro-3-methyl-1-(3-pyrrolidin-1-yl-propyl)-1H-pyrazolo[3,4-b]pyridine-5-carboxylic acid (4-trifluoromethyl-phenyl)-amide | 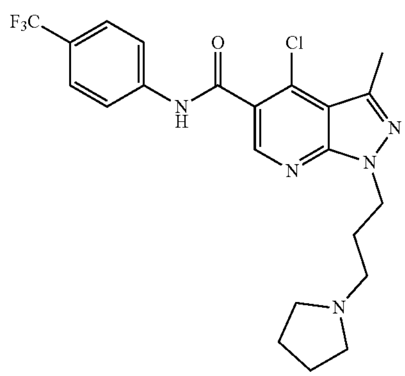 [SMILES: Cc1nn(CCCN2CCCC2)c2ncc(C(=O)Nc3ccc(C(F)(F)F)cc3)c(Cl)c12] |
| 350 | 4-Chloro-1-(3-dimethylamino-propyl)-3-methyl-1H-pyrazolo[3,4-b]pyridine-5-carboxylic acid (4-chloro-phenyl)-amide | 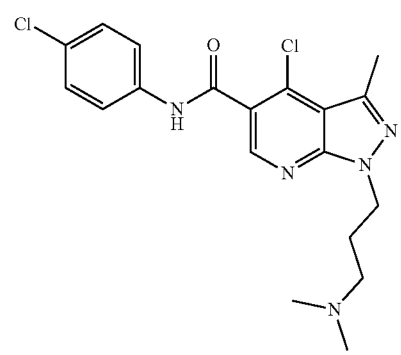 [SMILES: Cc1nn(CCCN(C)C)c2ncc(C(=O)Nc3ccc(Cl)cc3)c(Cl)c12] |
| 351 | 4-Chloro-1-(3-dimethylamino-propyl)-3-methyl-1H-pyrazolo[3,4-b]pyridine-5-carboxylic acid (4-trifluoromethyl-phenyl)-amide | 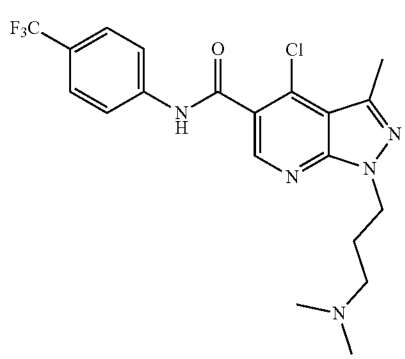 [SMILES: Cc1nn(CCCN(C)C)c2ncc(C(=O)Nc3ccc(C(F)(F)F)cc3)c(Cl)c12] |

TABLE 1-continued

| Ex. | Names | Structures |
|---|---|---|
| 352 | 4-Chloro-3-methyl-1-pyrimidin-4-ylmethyl-1H-pyrazolo[3,4-b]pyridine-5-carboxylic acid (4-chloro-phenyl)-amide | 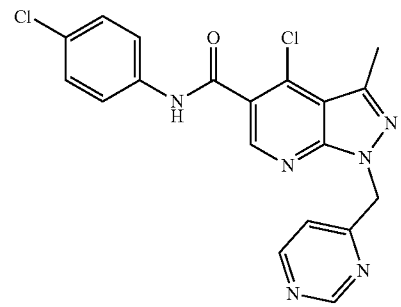 [SMILES: Cc1nn(Cc2ccncn2)c2ncc(C(=O)Nc3ccc(Cl)cc3)c(Cl)c12] |
| 353 | 4-Chloro-3-methyl-1-pyrimidin-4-ylmethyl-1H-pyrazolo[3,4-b]pyridine-5-carboxylic acid (4-trifluoromethyl-phenyl)-amide | 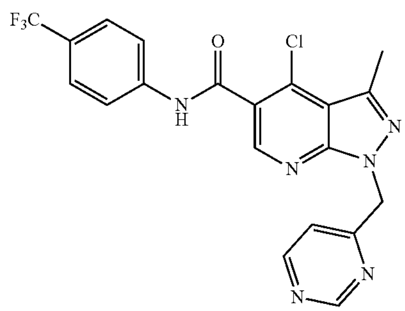 [SMILES: Cc1nn(Cc2ccncn2)c2ncc(C(=O)Nc3ccc(C(F)(F)F)cc3)c(Cl)c12] |
| 354 | 4-Chloro-3-methyl-1-pyrimidin-4-ylmethyl-1H-pyrazolo[3,4-b]pyridine-5-carboxylic acid (4-isopropyl-phenyl)-amide | 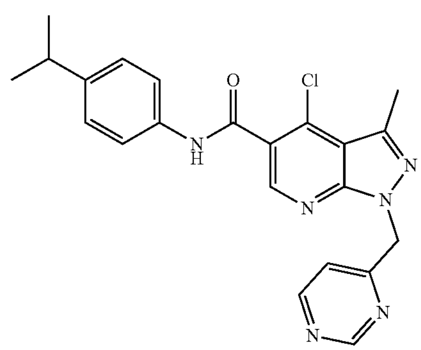 [SMILES: Cc1nn(Cc2ccncn2)c2ncc(C(=O)Nc3ccc(C(C)C)cc3)c(Cl)c12] |
| 355 | 4-chloro-1-((6-methoxypyridin-3-yl)methyl)-3-methyl-N-(4-(trifluoromethyl)phenyl)-1H-pyrazolo[3,4-b]pyridine-5-carboxamide | 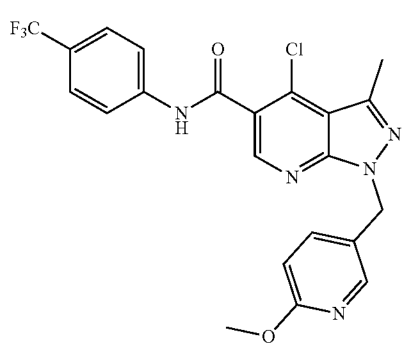 [SMILES: COc1ccc(Cn2nc(C)c3c(Cl)c(C(=O)Nc4ccc(C(F)(F)F)cc4)cnc32)cn1] |

TABLE 1-continued

| Ex. | Names | Structures |
|---|---|---|
| 356 | 4-Chloro-3-methyl-1-(6-methyl-pyridazin-3-ylmethyl)-1H-pyrazolo[3,4-b]pyridine-5-carboxylic acid (4-trifluoromethyl-phenyl)-amide | 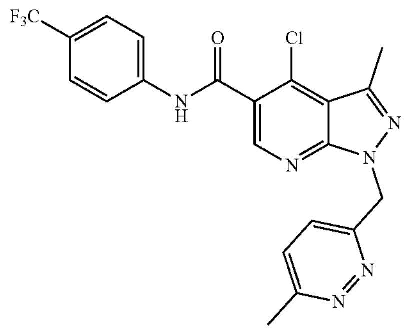 [SMILES: Cc1ccc(Cn2nc(C)c3c(Cl)c(C(=O)Nc4ccc(C(F)(F)F)cc4)cnc32)nn1] |
| 357 | 4-Chloro-3-methyl-1-pyrazin-2-ylmethyl-1H-pyrazolo[3,4-b]pyridine-5-carboxylic acid (4-chloro-phenyl)-amide | 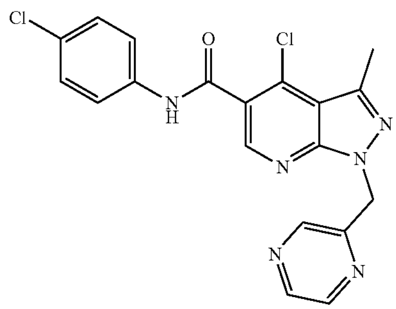 [SMILES: Cc1nn(Cc2cnccn2)c2ncc(C(=O)Nc3ccc(Cl)cc3)c(Cl)c12] |
| 358 | 4-Chloro-3-methyl-1-pyrazin-2-ylmethyl-1H-pyrazolo[3,4-b]pyridine-5-carboxylic acid (4-trifluoromethyl-phenyl)-amide | 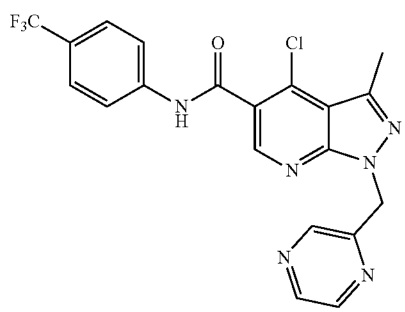 |
| 359 | 4-Chloro-3-methyl-1-(6-methyl-pyrimidin-4-ylmethyl)-1H-pyrazolo[3,4-b]pyridine-5-carboxylic acid (4-chloro-phenyl)-amide | 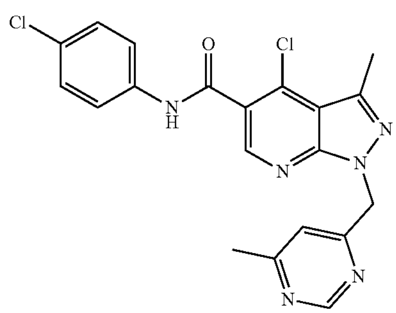 [SMILES: Cc1cc(Cn2nc(C)c3c(Cl)c(C(=O)Nc4ccc(Cl)cc4)cnc32)ncn1] |
| 360 | 4-Chloro-3-methyl-1-(6-methyl-pyrimidin-4-ylmethyl)-1H-pyrazolo[3,4-b]pyridine-5-carboxylic acid (4-trifluoromethyl-phenyl)-amide | 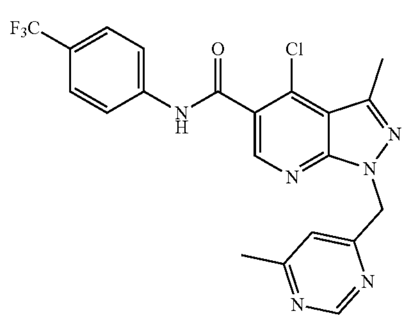 [SMILES: Cc1cc(Cn2nc(C)c3c(Cl)c(C(=O)Nc4ccc(C(F)(F)F)cc4)cnc32)ncn1] |

TABLE 1-continued

| Ex. | Names | Structures |
|---|---|---|
| 361 | 4-Chloro-3-methyl-1-(6-methyl-pyrimidin-4-ylmethyl)-1H-pyrazolo[3,4-b]pyridine-5-carboxylic acid (4-isopropyl-phenyl)-amide | 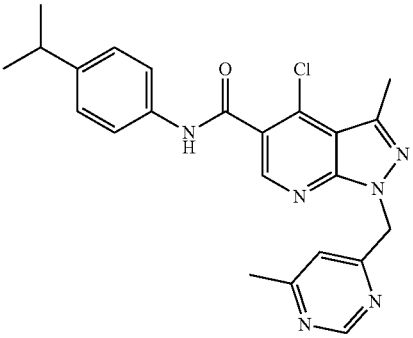 |
| 362 | 4-Chloro-3-methyl-1-(6-methyl-pyrimidin-4-ylmethyl)-1H-pyrazolo[3,4-b]pyridine-5-carboxylic acid (4-methoxy-phenyl)-amide | 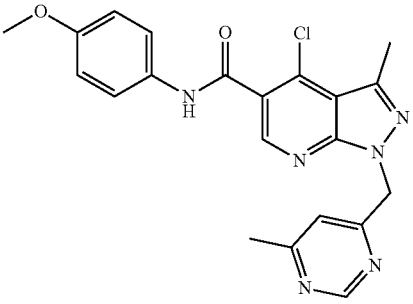 [SMILES: COc1ccc(NC(=O)c2cnc3c(c(C)nn3Cc3cc(C)ncn3)c2Cl)cc1] |
| 363 | 4-Chloro-1-(3,4-dimethoxy-pyridin-2-ylmethyl)-3-methyl-1H-pyrazolo[3,4-b]pyridine-5-carboxylic acid (4-chloro-phenyl)-amide | 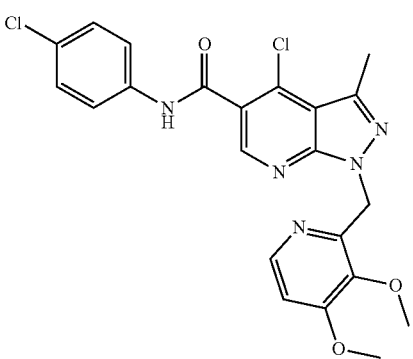 [SMILES: COc1ccnc(Cn2nc(C)c3c(Cl)c(C(=O)Nc4ccc(Cl)cc4)cnc32)c1OC] |
| 364 | 4-Chloro-1-(3,4-dimethoxy-pyridin-2-ylmethyl)-3-methyl-1H-pyrazolo[3,4-b]pyridine-5-carboxylic acid (4-trifluoromethyl-phenyl)-amide | 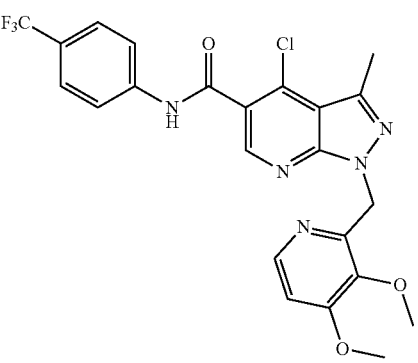 [SMILES: COc1ccnc(Cn2nc(C)c3c(Cl)c(C(=O)Nc4ccc(C(F)(F)F)cc4)cnc32)c1OC] |

TABLE 1-continued

| Ex. | Names | Structures |
|---|---|---|
| 365 | 4-Chloro-1-(6-methoxy-pyrimidin-4-ylmethyl)-3-methyl-1H-pyrazolo[3,4-b]pyridine-5-carboxylic acid (4-chloro-phenyl)-amide | 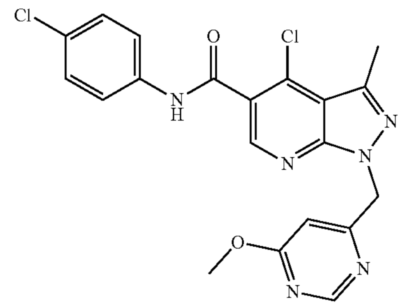 [SMILES: COc1cc(Cn2nc(C)c3c(Cl)c(C(=O)Nc4ccc(Cl)cc4)cnc32)ncn1] |
| 366 | 4-Chloro-1-(6-methoxy-pyrimidin-4-ylmethyl)-3-methyl-1H-pyrazolo[3,4-b]pyridine-5-carboxylic acid (4-trifluoromethyl-phenyl)-amide | 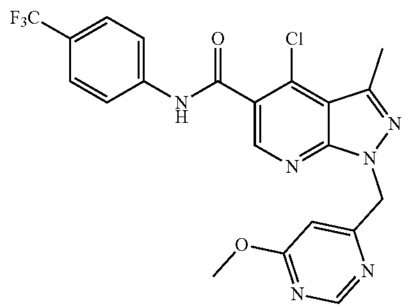 [SMILES: COc1cc(Cn2nc(C)c3c(Cl)c(C(=O)Nc4ccc(C(F)(F)F)cc4)cnc32)ncn1] |
| 367 | 4-Chloro-1-(6-methoxy-pyrimidin-4-ylmethyl)-3-methyl-1H-pyrazolo[3,4-b]pyridine-5-carboxylic acid (4-methoxy-phenyl)-amide | 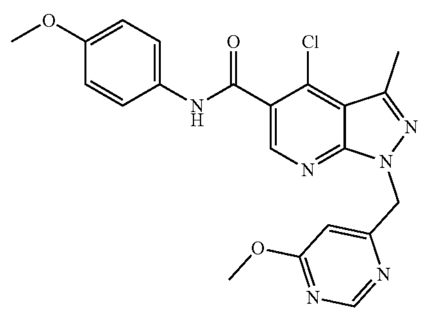 [SMILES: COc1ccc(NC(=O)c2cnc3c(c(C)nn3Cc3cc(OC)ncn3)c2Cl)cc1] |
| 368 | 4-Chloro-3-methyl-1-oxazol-5-ylmethyl-1H-pyrazolo[3,4-b]pyridine-5-carboxylic acid (4-trifluoromethyl-phenyl)-amide | 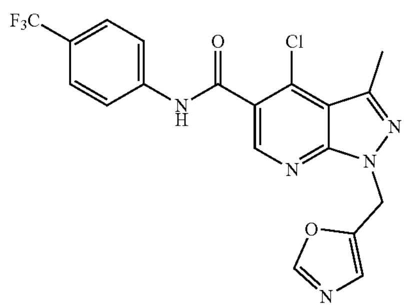 [SMILES: Cc1nn(Cc2cnco2)c2ncc(C(=O)Nc3ccc(C(F)(F)F)cc3)c(Cl)c12] |
| 369 | 4-Chloro-3-methyl-1-oxazol-5-ylmethyl-1H-pyrazolo[3,4-b]pyridine-5-carboxylic acid (4-chloro-phenyl)-amide | 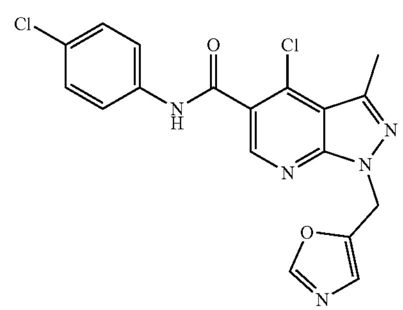 [SMILES: Cc1nn(Cc2cnco2)c2ncc(C(=O)Nc3ccc(Cl)cc3)c(Cl)c12] |

TABLE 1-continued

| Ex. | Names | Structures |
|---|---|---|
| 370 | 4-Chloro-3-methyl-1-oxazol-2-ylmethyl-1H-pyrazolo[3,4-b]pyridine-5-carboxylic acid (4-trifluoromethyl-phenyl)-amide | 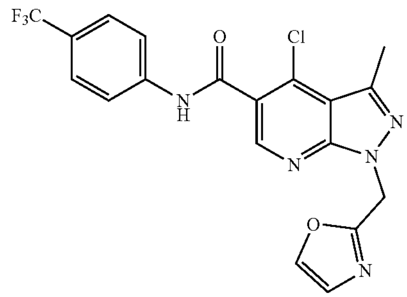 [SMILES: Cc1nn(Cc2ncco2)c2ncc(C(=O)Nc3ccc(C(F)(F)F)cc3)c(Cl)c12] |
| 371 | 4-Chloro-3-methyl-1-oxazol-2-ylmethyl-1H-pyrazolo[3,4-b]pyridine-5-carboxylic acid (4-chloro-phenyl)-amide | 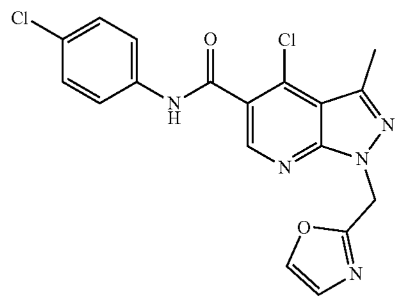 [SMILES: Cc1nn(Cc2ncco2)c2ncc(C(=O)Nc3ccc(Cl)cc3)c(Cl)c12] |
| 372 | 4-Chloro-1-(3,5-dimethyl-isoxazol-4-ylmethyl)-3-methyl-1H-pyrazolo[3,4-b]pyridine-5-carboxylic acid (4-chloro-phenyl)-amide | 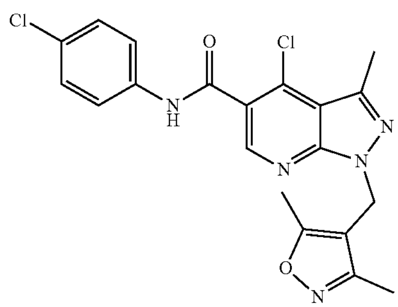 [SMILES: Cc1noc(C)c1Cn1nc(C)c2c(Cl)c(C(=O)Nc3ccc(Cl)cc3)cnc21] |
| 373 | 4-Chloro-1-(3,5-dimethyl-isoxazol-4-ylmethyl)-3-methyl-1H-pyrazolo[3,4-b]pyridine-5-carboxylic acid (4-trifluoromethyl-phenyl)-amide | 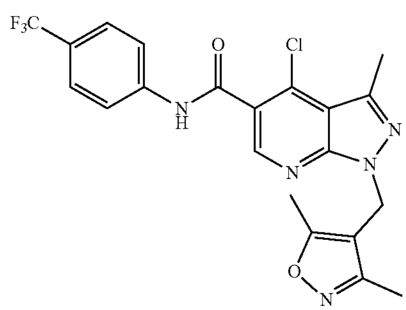 [SMILES: Cc1noc(C)c1Cn1nc(C)c2c(Cl)c(C(=O)Nc3ccc(C(F)(F)F)cc3)cnc21] |
| 374 | 4-Chloro-3-methyl-1-(3-p-tolyl-[1,2,4]oxadiazol-5-ylmethyl)-1H-pyrazolo[3,4-b]pyridine-5-carboxylic acid (4-chloro-phenyl)-amide | 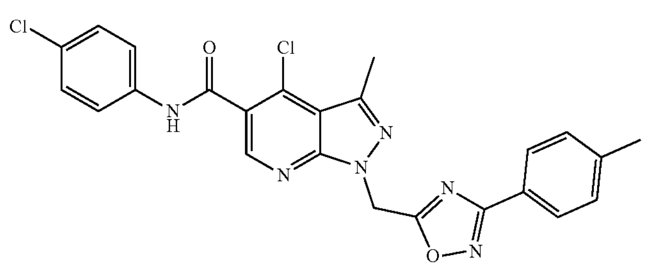 [SMILES: Cc1ccc(-c2noc(Cn3nc(C)c4c(Cl)c(C(=O)Nc5ccc(Cl)cc5)cnc43)n2)cc1] |

TABLE 1-continued

| Ex. | Names | Structures |
|---|---|---|
| 375 | 4-Chloro-3-methyl-1-(3-p-tolyl-[1,2,4]oxadiazol-5-ylmethyl)-1H-pyrazolo[3,4-b]pyridine-5-carboxylic acid (4-trifluoromethyl-phenyl)-amide | 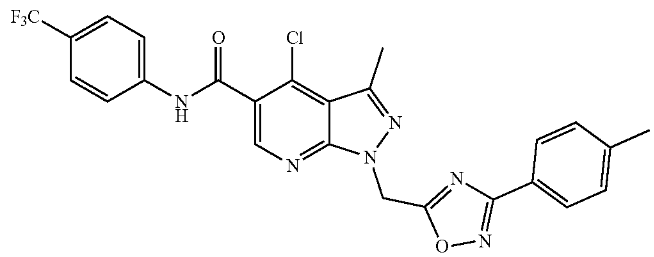 [SMILES: Cc1ccc(-c2noc(Cn3nc(C)c4c(Cl)c(C(=O)Nc5ccc(C(F)(F)F)cc5)cnc43)n2)cc1] |
| 376 | 4-Chloro-3-methyl-1-thiazol-4-ylmethyl-1H-pyrazolo[3,4-b]pyridine-5-carboxylic acid (4-chloro-phenyl)-amide | 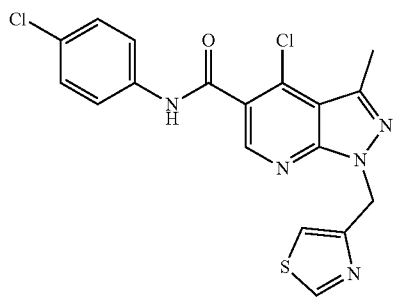 [SMILES: Cc1nn(Cc2cscn2)c2ncc(C(=O)Nc3ccc(Cl)cc3)c(Cl)c12] |
| 377 | 4-Chloro-3-methyl-1-thiazol-4-ylmethyl-1H-pyrazolo[3,4-b]pyridine-5-carboxylic acid (4-trifluoromethyl-phenyl)-amide | 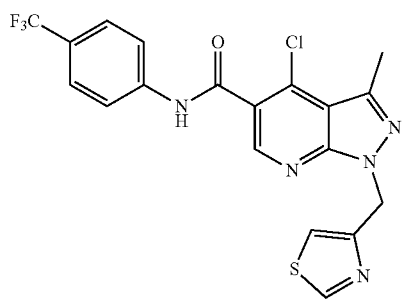 [SMILES: Cc1nn(Cc2cscn2)c2ncc(C(=O)Nc3ccc(C(F)(F)F)cc3)c(Cl)c12] |
| 378 | 4-Chloro-3-methyl-1-(1H-tetrazol-5-ylmethyl)-1H-pyrazolo[3,4-b]pyridine-5-carboxylic acid (4-trifluoromethyl-phenyl)-amide | 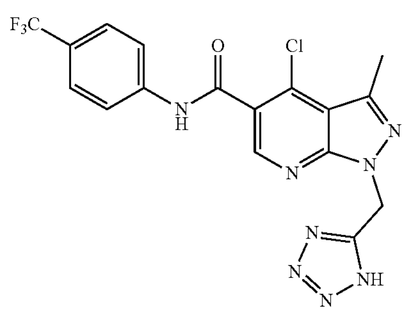 [SMILES: Cc1nn(Cc2nnn[nH]2)c2ncc(C(=O)Nc3ccc(C(F)(F)F)cc3)c(Cl)c12] |
| 379 | 4-Chloro-3-methyl-1-(1H-tetrazol-5-ylmethyl)-1H-pyrazolo[3,4-b]pyridine-5-carboxylic acid (4-chloro-phenyl)-amide | 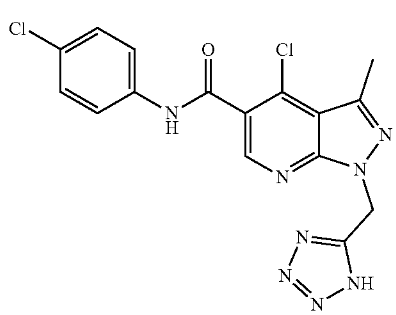 [SMILES: Cc1nn(Cc2nnn[nH]2)c2ncc(C(=O)Nc3ccc(Cl)cc3)c(Cl)c12] |

TABLE 1-continued

| Ex. | Names |
|---|---|
| 380 | 4-Chloro-3-methyl-1-(2-piperazin-1-yl-ethyl)-1H-pyrazolo[3,4-b]pyridine-5-carboxylic acid (4-trifluoromethyl-phenyl)-amide |
| 381 | 4-Chloro-3-methyl-1-(2-piperazin-1-yl-ethyl)-1H-pyrazolo[3,4-b]pyridine-5-carboxylic acid (4-chloro-phenyl)-amide |
| 382 | 4-Chloro-3-methyl-1-[2-(4-methyl-piperazin-1-yl)-ethyl]-1H-pyrazolo[3,4-b]pyridine-5-carboxylic acid (4-trifluoromethyl-phenyl)-amide |
| 383 | 4-Chloro-1-[2-(4-ethyl-piperazin-1-yl)-ethyl]-3-methyl-1H-pyrazolo[3,4-b]pyridine-5-carboxylic acid (4-trifluoromethyl-phenyl)-amide |

TABLE 1-continued

| Ex. | Names | Structures |
|---|---|---|
| 384 | 4-Chloro-1-[2-(4-isopropyl-piperazin-1-yl)-ethyl]-3-methyl-1H-pyrazolo[3,4-b]pyridine-5-carboxylic acid (4-trifluoromethyl-phenyl)-amide | 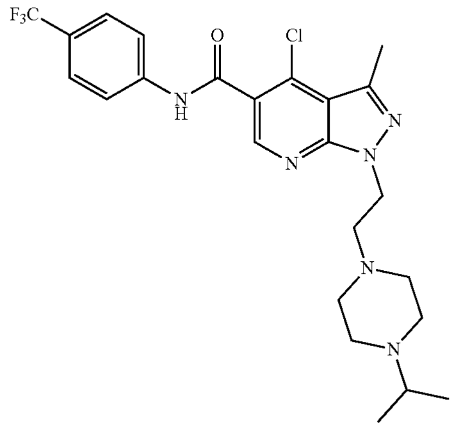 [SMILES: Cc1nn(CCN2CCN(C(C)C)CC2)c2ncc(C(=O)Nc3ccc(C(F)(F)F)cc3)c(Cl)c12] |
| 385 | 4-Chloro-3-methyl-1-[2-(4-methyl-piperazin-1-yl)-ethyl]-1H-pyrazolo[3,4-b]pyridine-5-carboxylic acid (4-chloro-phenyl)-amide | 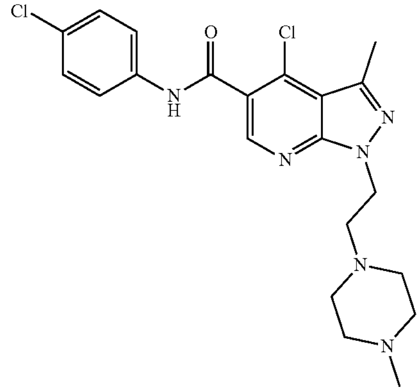 [SMILES: Cc1nn(CCN2CCN(C)CC2)c2ncc(C(=O)Nc3ccc(Cl)cc3)c(Cl)c12] |
| 386 | 4-Chloro-1-[2-(4-ethyl-piperazin-1-yl)-ethyl]-3-methyl-1H-pyrazolo[3,4-b]pyridine-5-carboxylic acid (4-chloro-phenyl)-amide | 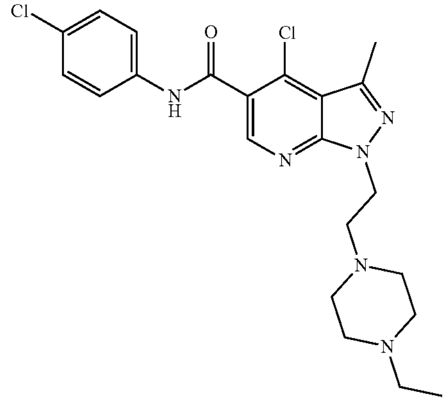 [SMILES: CCN1CCN(CCn2nc(C)c3c(Cl)c(C(=O)Nc4ccc(Cl)cc4)cnc32)CC1] |

TABLE 1-continued

| Ex. | Names | Structures |
|---|---|---|
| 387 | 4-Chloro-1-[2-(4-isopropyl-piperazin-1-yl)-ethyl]-3-methyl-1H-pyrazolo[3,4-b]pyridine-5-carboxylic acid (4-chloro-phenyl)-amide | 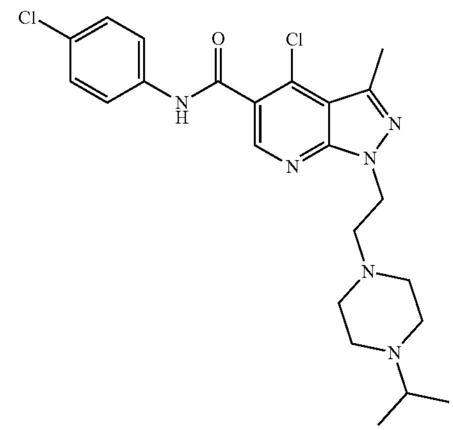 [SMILES: Cc1nn(CCN2CCN(C(C)C)CC2)c2ncc(C(=O)Nc3ccc(Cl)cc3)c(Cl)c12] |
| 388 | 4-Chloro-1-[2-(4-methanesulfonyl-piperazin-1-yl)-ethyl]-3-methyl-1H-pyrazolo[3,4-b]pyridine-5-carboxylic acid (4-trifluoromethyl-phenyl)-amide | 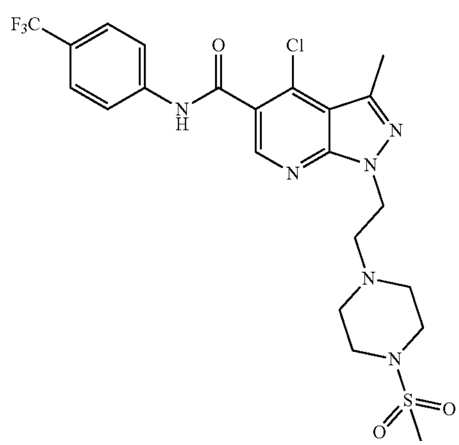 [SMILES: Cc1nn(CCN2CCN(S(C)(=O)=O)CC2)c2ncc(C(=O)Nc3ccc(C(F)(F)F)cc3)c(Cl)c12] |
| 389 | 4-Chloro-1-[2-(4-methanesulfonyl-piperazin-1-yl)-ethyl]-3-methyl-1H-pyrazolo[3,4-b]pyridine-5-carboxylic acid (4-chloro-phenyl)-amide | 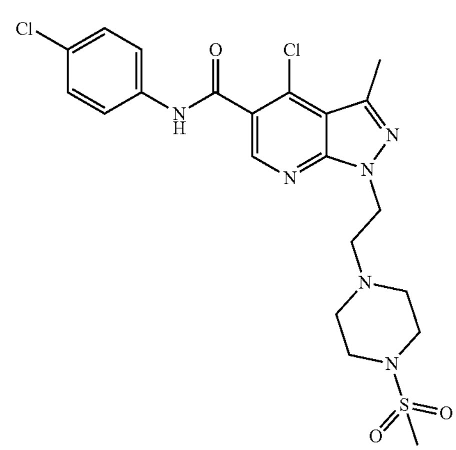 [SMILES: Cc1nn(CCN2CCN(S(C)(=O)=O)CC2)c2ncc(C(=O)Nc3ccc(Cl)cc3)c(Cl)c12] |

TABLE 1-continued

| Ex. | Names | Structures |
|---|---|---|
| 390 | 1-[2-(4-Acetyl-piperazin-1-yl)-ethyl]-4-chloro-3-methyl-1H-pyrazolo[3,4-b]pyridine-5-carboxylic acid (4-trifluoromethyl-phenyl)-amide | 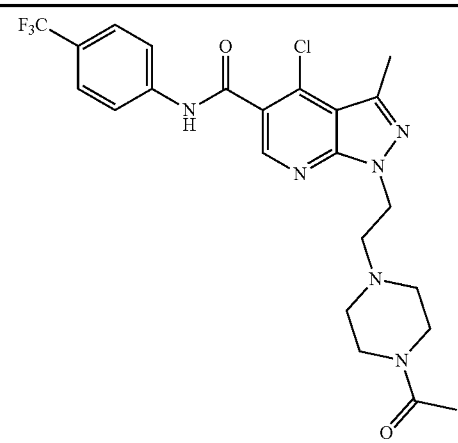 |
| 391 | 1-[2-(4-Acetyl-piperazin-1-yl)-ethyl]-4-chloro-3-methyl-1H-pyrazolo[3,4-b]pyridine-5-carboxylic acid (4-chloro-phenyl)-amide | 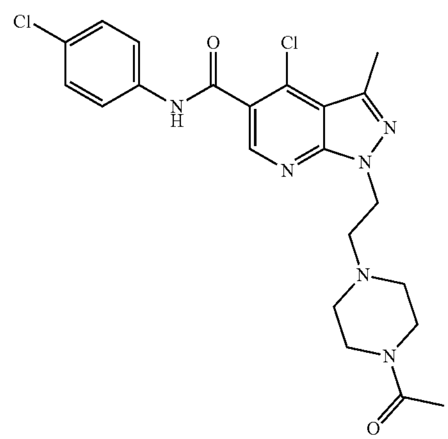 [SMILES: CC(=O)N1CCN(CCn2nc(C)c3c(Cl)c(C(=O)Nc4ccc(Cl)cc4)cnc32)CC1] |
| 392 | 4-Hydroxy-3-methyl-1-(2-piperazin-1-yl-ethyl)-1H-pyrazolo[3,4-b]pyridine-5-carboxylic acid (4-trifluoromethyl-phenyl)-amide | 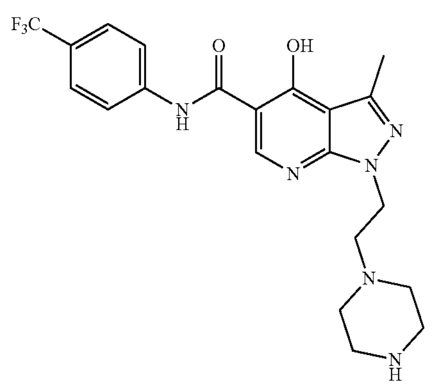 |
| 393 | 4-Methoxy-3-methyl-1-(2-piperazin-1-yl-ethyl)-1H-pyrazolo[3,4-b]pyridine-5-carboxylic acid (4-chloro-phenyl)-amide | 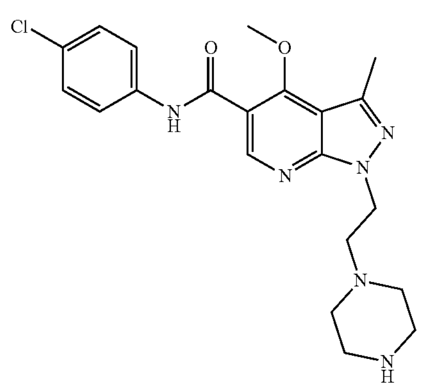 [SMILES: COc1c(C(=O)Nc2ccc(Cl)cc2)cnc2c1c(C)nn2CCN1CCNCC1] |

TABLE 1-continued

| Ex. | Names | Structures |
|---|---|---|
| 394 | 4-chloro-1-phenyl-N-(4-(trifluoromethyl)phenyl)-1H-pyrazolo[3,4-c]pyridine-5-carboxamide | 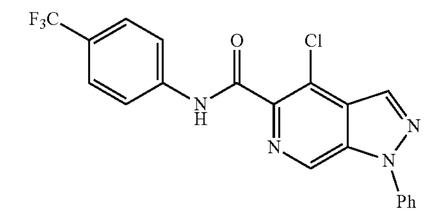 [SMILES: O=C(Nc1ccc(C(F)(F)F)cc1)c1ncc2c(cnn2-c2ccccc2)c1Cl] |
| 395 | 4-methoxy-1-phenyl-N-(4-(trifluoromethyl)phenyl)-1H-pyrazolo[3,4-c]pyridine-5-carboxamide | 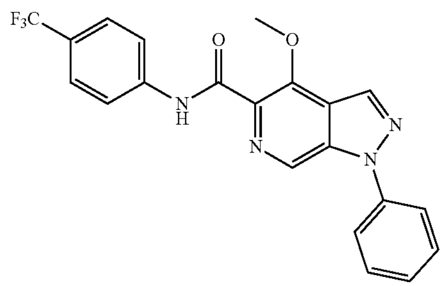 [SMILES: COc1c(C(=O)Nc2ccc(C(F)(F)F)cc2)ncc2c1cnn2-c1ccccc1] |
| 396 | 4-chloro-N-(4-chlorophenyl)-1-phenyl-1H-pyrazolo[3,4-c]pyridine-5-carboxamide | 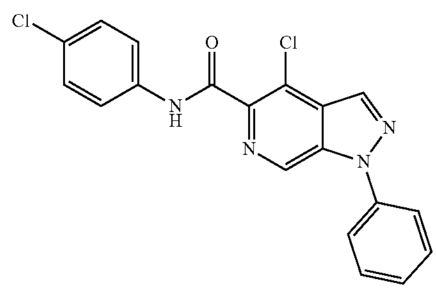 [SMILES: O=C(Nc1ccc(Cl)cc1)c1ncc2c(cnn2-c2ccccc2)c1Cl] |
| 397 | N-(4-chlorophenyl)-4-methoxy-1-phenyl-1H-pyrazolo[3,4-c]pyridine-5-carboxamide | 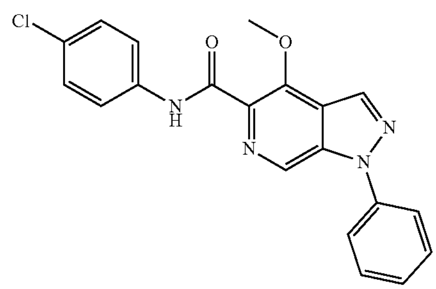 [SMILES: COc1c(C(=O)Nc2ccc(Cl)cc2)ncc2c1cnn2-c1ccccc1] |
| 398 | 1-Methyl-1H-pyrrolo[2,3-b]pyridine-5-carboxylic acid (4-chloro-phenyl)-amide | 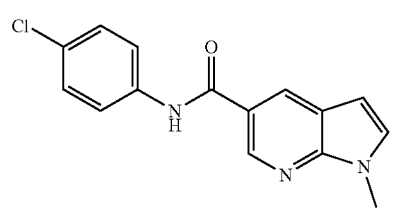 [SMILES: Cn1ccc2cc(C(=O)Nc3ccc(Cl)cc3)cnc21] |
| 399 | 1-Methyl-1H-pyrrolo[2,3-b]pyridine-5-carboxylic acid (4-trifluoromethyl-phenyl)-amide | 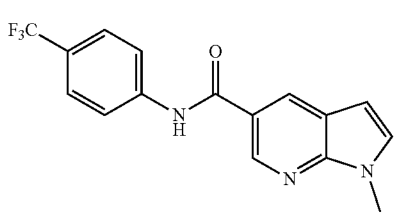 |

TABLE 1-continued

| Ex. | Names | Structures |
|---|---|---|
| 400 | 1-Methyl-1H-pyrrolo[2,3-b]pyridine-5-carboxylic acid (4-isopropyl-phenyl)-amide | 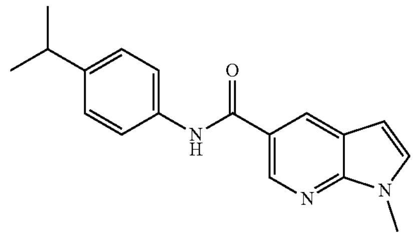 [SMILES: CC(C)c1ccc(NC(=O)c2cnc3c(ccn3C)c2)cc1] |
| 401 | 1,3-Dimethyl-1H-pyrrolo[2,3-b]pyridine-5-carboxylic acid (4-chloro-phenyl)-amide | 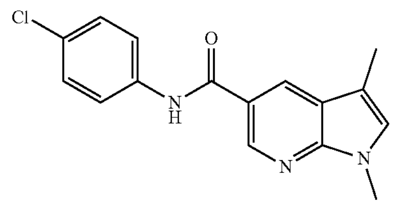 [SMILES: Cc1cn(C)c2ncc(C(=O)Nc3ccc(Cl)cc3)cc12] |
| 402 | 1,3-Dimethyl-1H-pyrrolo[2,3-b]pyridine-5-carboxylic acid (4-isopropyl-phenyl)-amide | 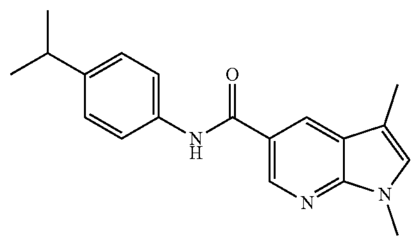 [SMILES: Cc1cn(C)c2ncc(C(=O)Nc3ccc(C(C)C)cc3)cc12] |
| 403 | 3-Hydroxymethyl-1-methyl-1H-pyrrolo[2,3-b]pyridine-5-carboxylic acid (4-chloro-phenyl)-amide | 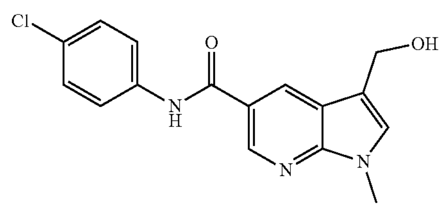 [SMILES: Cn1cc(CO)c2cc(C(=O)Nc3ccc(Cl)cc3)cnc21] |
| 404 | 3-Hydroxymethyl-1-methyl-1H-pyrrolo[2,3-b]pyridine-5-carboxylic acid (4-isopropyl-phenyl)-amide | 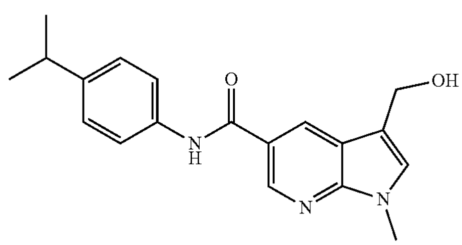 [SMILES: CC(C)c1ccc(NC(=O)c2cnc3c(c2)c(CO)cn3C)cc1] |
| 405 | 3-Hydroxymethyl-1-methyl-2,3-dihydro-1H-pyrrolo[2,3-b]pyridine-5-carboxylic acid (4-chloro-phenyl)-amide | 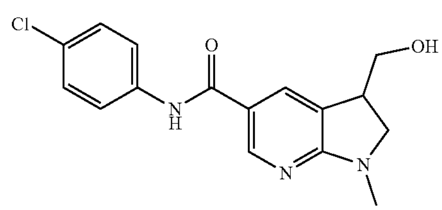 [SMILES: CN1CC(CO)c2cc(C(=O)Nc3ccc(Cl)cc3)cnc21] |
| 406 | 4-Chloro-1-methyl-1H-pyrrolo[2,3-b]pyridine-5-carboxylic acid (4-isopropyl-phenyl)-amide ( | 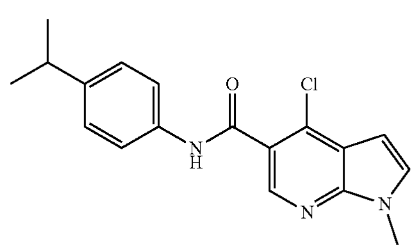 [SMILES: CC(C)c1ccc(NC(=O)c2cnc3c(ccn3C)c2Cl)cc1] |

TABLE 1-continued

| Ex. | Names | Structures |
|---|---|---|
| 407 | 4-Chloro-1-methyl-1H-pyrrolo[2,3-b]pyridine-5-carboxylic acid (4-chloro-phenyl)-amide | 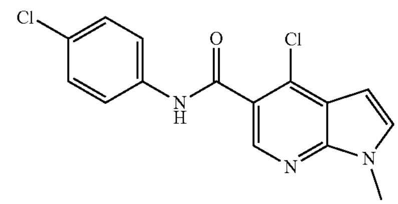 [SMILES: Cn1ccc2c(Cl)c(C(=O)Nc3ccc(Cl)cc3)cnc21] |
| 408 | 4-Chloro-1-methyl-1H-pyrrolo[2,3-b]pyridine-5-carboxylic acid (4-trifluoromethyl-phenyl)-amide | 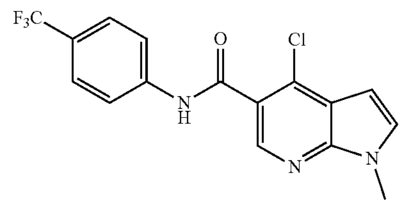 [SMILES: Cn1ccc2c(Cl)c(C(=O)Nc3ccc(C(F)(F)F)cc3)cnc21] |
| 409 | 4-Methoxy-1-methyl-1H-pyrrolo[2,3-b]pyridine-5-carboxylic acid (4-isopropyl-phenyl)-amide | 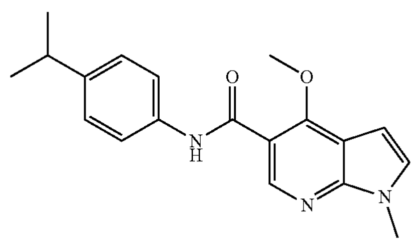 [SMILES: COc1c(C(=O)Nc2ccc(C(C)C)cc2)cnc2c1ccn2C] |
| 410 | 4-Methoxy-1-methyl-1H-pyrrolo[2,3-b]pyridine-5-carboxylic acid (4-chloro-phenyl)-amide | 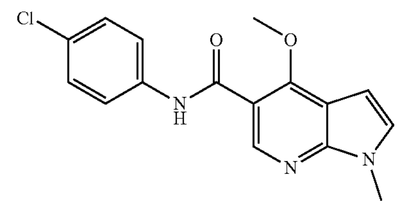 [SMILES: COc1c(C(=O)Nc2ccc(Cl)cc2)cnc2c1ccn2C] |
| 411 | 4-Chloro-1,3-dimethyl-1H-pyrrolo[2,3-b]pyridine-5-carboxylic acid (4-chloro-phenyl)-amide | 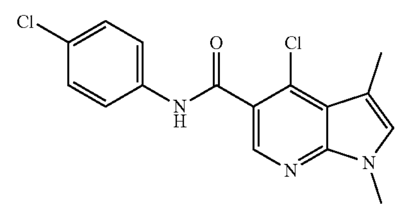 [SMILES: Cc1cn(C)c2ncc(C(=O)Nc3ccc(Cl)cc3)c(Cl)c12] |
| 412 | 4-Chloro-1,3-dimethyl-1H-pyrrolo[2,3-b]pyridine-5-carboxylic acid (4-isopropyl-phenyl)-amide | 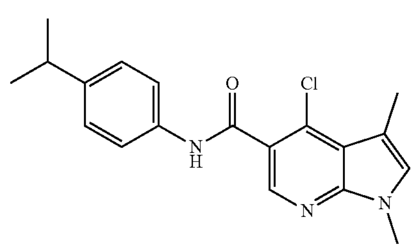 [SMILES: Cc1cn(C)c2ncc(C(=O)Nc3ccc(C(C)C)cc3)c(Cl)c12] |
| 413 | 4-Chloro-1,3-dimethyl-1H-pyrrolo[2,3-b]pyridine-5-carboxylic acid (4-trifluoromethyl-phenyl)-amide | 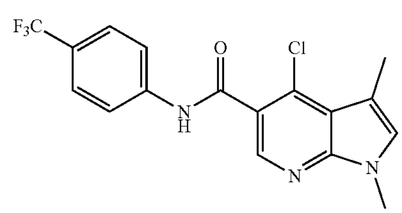 [SMILES: Cc1cn(C)c2ncc(C(=O)Nc3ccc(C(F)(F)F)cc3)c(Cl)c12] |

TABLE 1-continued

| Ex. | Names | Structures |
|-----|-------|------------|
| 414 | 4-Chloro-3-hydroxymethyl-1-methyl-1H-pyrrolo[2,3-b]pyridine-5-carboxylic acid (4-chloro-phenyl)-amide | 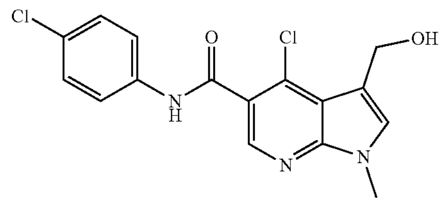 [SMILES: Cn1cc(CO)c2c(Cl)c(C(=O)Nc3ccc(Cl)cc3)cnc21] |
| 415 | 4-Chloro-3-hydroxymethyl-1-methyl-1H-pyrrolo[2,3-b]pyridine-5-carboxylic acid (4-isopropyl-phenyl)-amide | 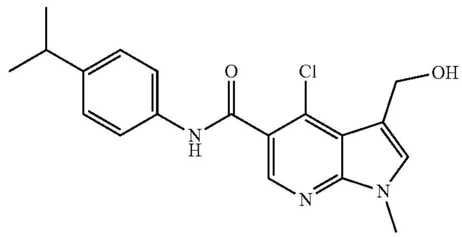 [SMILES: CC(C)c1ccc(NC(=O)c2cnc3c(c(CO)cn3C)c2Cl)cc1] |
| 416 | 4-Chloro-3-hydroxymethyl-1-methyl-1H-pyrrolo[2,3-b]pyridine-5-carboxylic acid (4-trifluoromethyl-phenyl)-amide | 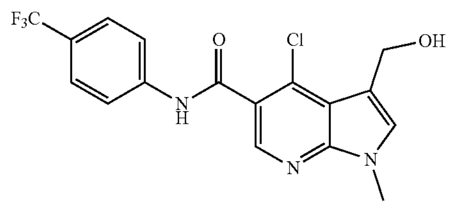 [SMILES: Cn1cc(CO)c2c(Cl)c(C(=O)Nc3ccc(C(F)(F)F)cc3)cnc21] |
| 417 | 4-chloro-1-((1-(4-methoxybenzyl)-1H-1,2,3-triazol-4-yl)methyl)-N-(4-methoxyphenyl)-3-methyl-1H-pyrazolo[3,4-b]pyridine-5-carboxamide | 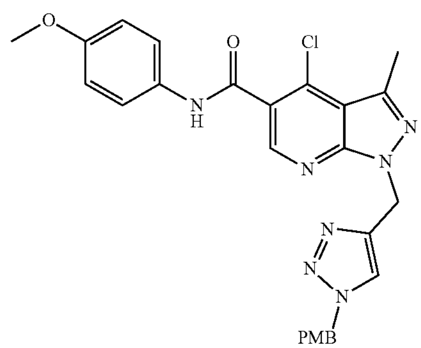 |
| 418 | 4-chloro-N-(4-chlorophenyl)-1-((1-(4-methoxybenzyl)-1H-1,2,3-triazol-4-yl)methyl)-3-methyl-1H-pyrazolo[3,4-b]pyridine-5-carboxamide | 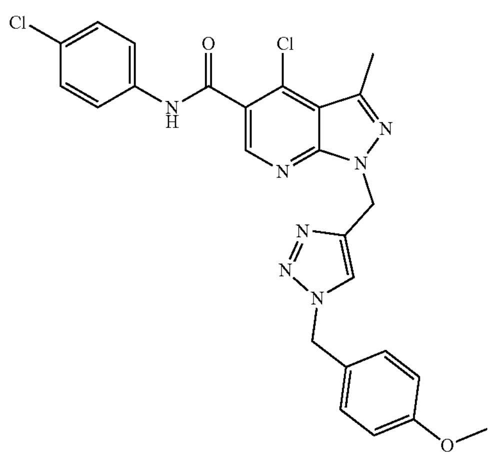 [SMILES: COc1ccc(Cn2cc(Cn3nc(C)c4c(Cl)c(C(=O)Nc5ccc(Cl)cc5)cnc43)nn2)cc1] |

TABLE 1-continued

| Ex. | Names | Structures |
|---|---|---|
| 419 | 4-Chloro-1-[1-(4-methoxy-benzyl)-1H-[1,2,3]triazol-4-ylmethyl]-3-methyl-1H-pyrazolo[3,4-b]pyridine-5-carboxylic acid (4-trifluoromethyl-phenyl)-amide | 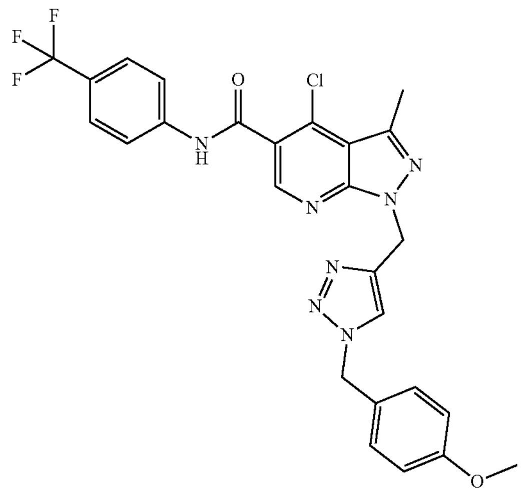 [SMILES: COc1ccc(Cn2cc(Cn3nc(C)c4c(Cl)c(C(=O)Nc5ccc(C(F)(F)F)cc5)cnc43)nn2)cc1] |
| 420 | 4-Chloro-3-methyl-1-(1H-[1,2,3]triazol-4-ylmethyl)-1H-pyrazolo[3,4-b]pyridine-5-carboxylic acid (4-methoxy-phenyl)-amide | 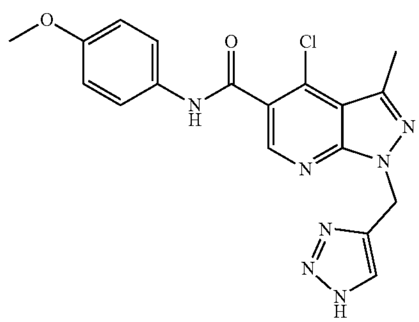 [SMILES: COc1ccc(NC(=O)c2cnc3c(c(C)nn3Cc3c[nH]nn3)c2Cl)cc1] |
| 421 | 4-Chloro-3-methyl-1-(1H-[1,2,3]triazol-4-ylmethyl)-1H-pyrazolo[3,4-b]pyridine-5-carboxylic acid (4-chloro-phenyl)-amide | 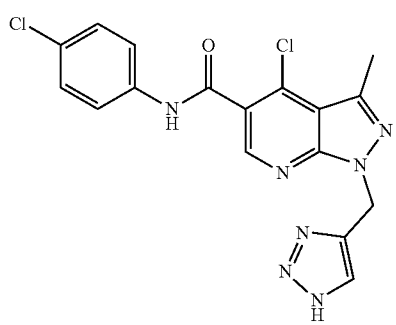 [SMILES: Cc1nn(Cc2c[nH]nn2)c2ncc(C(=O)Nc3ccc(Cl)cc3)c(Cl)c12] |
| 422 | 4-Chloro-3-methyl-1-(1H-[1,2,3]triazol-4-ylmethyl)-1H-pyrazolo[3,4-b]pyridine-5-carboxylic acid (4-trifluoromethyl-phenyl)-amide | 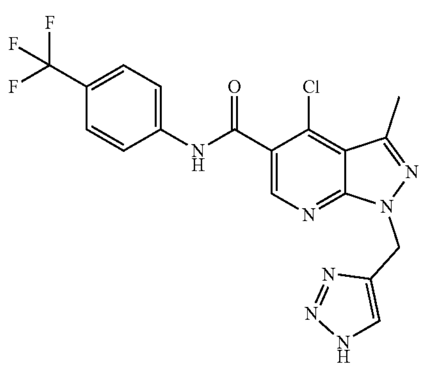 [SMILES: Cc1nn(Cc2c[nH]nn2)c2ncc(C(=O)Nc3ccc(C(F)(F)F)cc3)c(Cl)c12] |

TABLE 1-continued

| Ex. | Names | Structures |
|---|---|---|
| 423 | 4-chloro-1-((1-(4-methoxybenzyl)-5-methyl-1H-1,2,3-triazol-4-yl)methyl)-N-(4-methoxyphenyl)-3-methyl-1H-pyrazolo[3,4-b]pyridine-5-carboxamide | 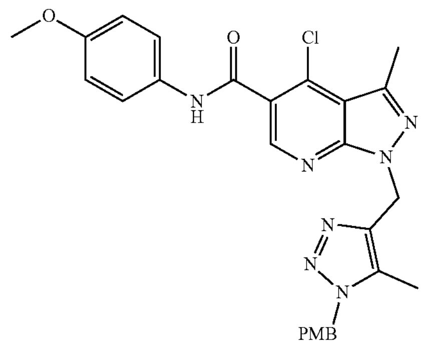 |
| 424 | 4-chloro-N-(4-chlorophenyl)-1-((1-(4-methoxybenzyl)-5-methyl-1H-1,2,3-triazol-4-yl)methyl)-3-methyl-1H-pyrazolo[3,4-b]pyridine-5-carboxamide | 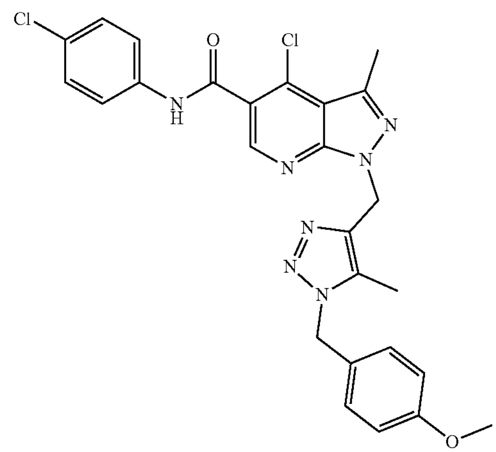 [SMILES: COc1ccc(Cn2nnc(Cn3nc(C)c4c(Cl)c(C(=O)Nc5ccc(Cl)cc5)cnc43)c2C)cc1] |
| 425 | 4-chloro-1-((1-(4-methoxybenzyl)-5-methyl-1H-1,2,3-triazol-4-yl)methyl)-3-methyl-N-(4-(trifluoromethyl)phenyl)-1H-pyrazolo[3,4-b]pyridine-5-carboxamide | 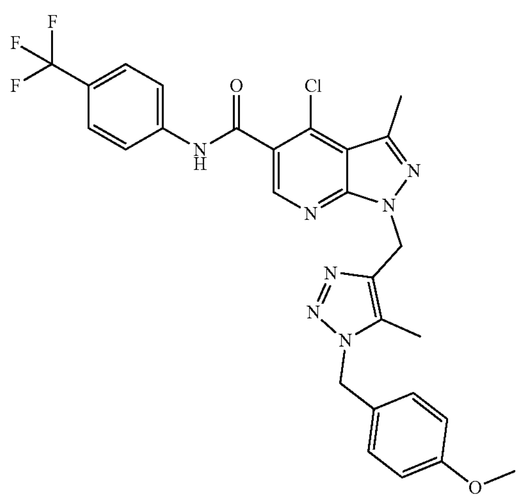 [SMILES: COc1ccc(Cn2nnc(Cn3nc(C)c4c(Cl)c(C(=O)Nc5ccc(C(F)(F)F)cc5)cnc43)c2C)cc1] |
| 426 | 4-chloro-N-(4-methoxyphenyl)-3-methyl-1-((5-methyl-1H-1,2,3-triazol-4-yl)methyl)-1H-pyrazolo[3,4-b]pyridine-5-carboxamide | 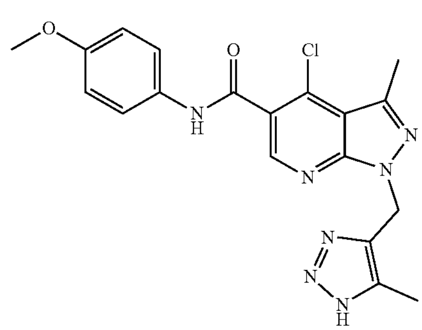 |

TABLE 1-continued

| Ex. | Names |
|---|---|
| 427 | 4-chloro-N-(4-chlorophenyl)-3-methyl-1-((5-methyl-1H-1,2,3-triazol-4-yl)methyl)-1H-pyrazolo[3,4-b]pyridine-5-carboxamide |
| 428 | 4-chloro-3-methyl-1-((5-methyl-1H-1,2,3-triazol-4-yl)methyl)-N-(4-(trifluoromethyl)phenyl)-1H-pyrazolo[3,4-b]pyridine-5-carboxamide |
| 429 | 4-Chloro-3-methyl-1-(5-methyl-4H-[1,2,4]triazol-3-ylmethyl)-1H-pyrazolo[3,4-b]pyridine-5-carboxylic acid (4-methoxy-phenyl)-amide |
| 430 | 4-Chloro-3-methyl-1-(5-methyl-4H-[1,2,4]triazol-3-ylmethyl)-1H-pyrazolo[3,4-b]pyridine-5-carboxylic acid (4-chloro-phenyl)-amide |

TABLE 1-continued

| Ex. | Names | Structures |
|---|---|---|
| 431 | 4-Chloro-3-methyl-1-(5-methyl-4H-[1,2,4]triazol-3-ylmethyl)-1H-pyrazolo[3,4-b]pyridine-5-carboxylic acid (4-trifluoromethyl-phenyl)-amide | 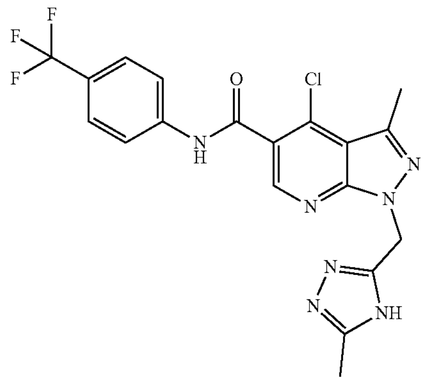 [SMILES: Cc1nnc(Cn2nc(C)c3c(Cl)c(C(=O)Nc4ccc(C(F)(F)F)cc4)cnc32)[nH]1] |
| 432 | 4-Chloro-3-methyl-1-(4H-[1,2,4]triazol-3-ylmethyl)-1H-pyrazolo[3,4-b]pyridine-5-carboxylic acid (4-methoxy-phenyl)-amide | 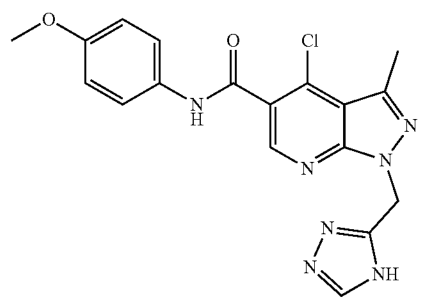 [SMILES: COc1ccc(NC(=O)c2cnc3c(c(C)nn3Cc3nnc[nH]3)c2Cl)cc1] |
| 433 | 4-Chloro-3-methyl-1-(4H-[1,2,4]triazol-3-ylmethyl)-1H-pyrazolo[3,4-b]pyridine-5-carboxylic acid (4-chloro-phenyl)-amide | 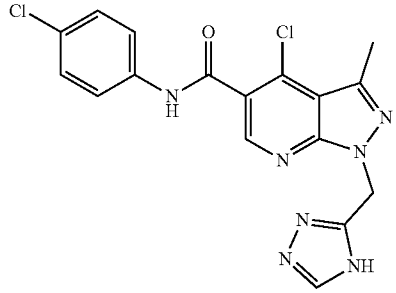 [SMILES: Cc1nn(Cc2nnc[nH]2)c2ncc(C(=O)Nc3ccc(Cl)cc3)c(Cl)c12] |
| 434 | 4-Chloro-3-methyl-1-(4H-[1,2,4]triazol-3-ylmethyl)-1H-pyrazolo[3,4-b]pyridine-5-carboxylic acid (4-trifluoromethyl-phenyl)-amide | 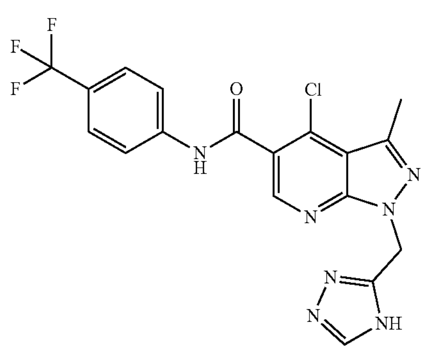 [SMILES: Cc1nn(Cc2nnc[nH]2)c2ncc(C(=O)Nc3ccc(C(F)(F)F)cc3)c(Cl)c12] |

TABLE 1-continued

| Ex. | Names |
|---|---|
| 435 | 4-chloro-1-((1,3-dimethyl-1H-pyrazol-5-yl)methyl)-3-methyl-N-(4-(trifluoromethyl)phenyl)-1H-pyrazolo[3,4-b]pyridine-5-carboxamide |
| 436 | 4-chloro-N-(4-chlorophenyl)-1-((1,3-dimethyl-1H-pyrazol-5-yl)methyl)-3-methyl-1H-pyrazolo[3,4-b]pyridine-5-carboxamide |
| 437 | 4-chloro-1-((1,5-dimethyl-1H-pyrazol-3-yl)methyl)-3-methyl-N-(4-(trifluoromethyl)phenyl)-1H-pyrazolo[3,4-b]pyridine-5-carboxamide |
| 438 | 4-chloro-N-(4-chlorophenyl)-1-((1,5-dimethyl-1H-pyrazol-3-yl)methyl)-3-methyl-1H-pyrazolo[3,4-b]pyridine-5-carboxamide |

TABLE 1-continued

| Ex. | Names | Structures |
|---|---|---|
| 439 | 4-Chloro-1-(5,6-dihydro-4H-pyrrolo[1,2-b]pyrazol-2-ylmethyl)-3-methyl-1H-pyrazolo[3,4-b]pyridine-5-carboxylic acid (4-trifluoromethyl-phenyl)-amide | 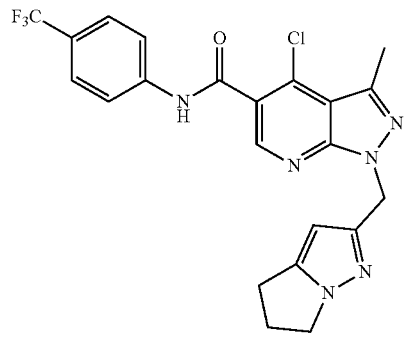 [SMILES: Cc1nn(Cc2cc3n(n2)CCC3)c2ncc(C(=O)Nc3ccc(C(F)(F)F)cc3)c(Cl)c12] |
| 440 | 4-Chloro-1-(5,6-dihydro-4H-pyrrolo[1,2-b]pyrazol-2-ylmethyl)-3-methyl-1H-pyrazolo[3,4-b]pyridine-5-carboxylic acid (4-chloro-phenyl)-amide | 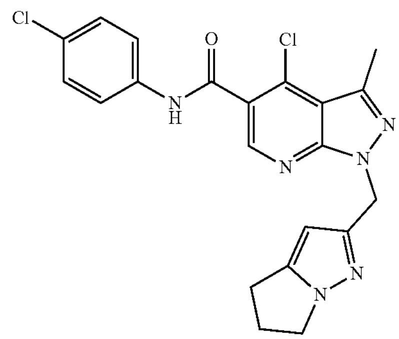 [SMILES: Cc1nn(Cc2cc3n(n2)CCC3)c2ncc(C(=O)Nc3ccc(Cl)cc3)c(Cl)c12] |
| 441 | 4-chloro-3-methyl-1-((1-methyl-1H-pyrazol-5-yl)methyl)-N-(4-(trifluoromethyl)phenyl)-1H-pyrazolo[3,4-b]pyridine-5-carboxamide | 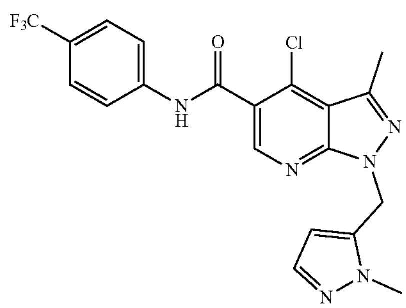 [SMILES: Cc1nn(Cc2ccnn2C)c2ncc(C(=O)Nc3ccc(C(F)(F)F)cc3)c(Cl)c12] |
| 442 | 4-chloro-N-(4-chlorophenyl)-3-methyl-1-((1-methyl-1H-pyrazol-5-yl)methyl)-1H-pyrazolo[3,4-b]pyridine-5-carboxamide | 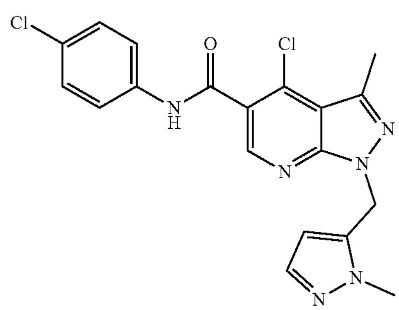 [SMILES: Cc1nn(Cc2ccnn2C)c2ncc(C(=O)Nc3ccc(Cl)cc3)c(Cl)c12] |
| 443 | 4-Chloro-3-methyl-1-(tetrahydro-pyran-4-ylmethyl)-1H-pyrazolo[3,4-b]pyridine-5-carboxylic acid (4-trifluoromethyl-phenyl)-amide | 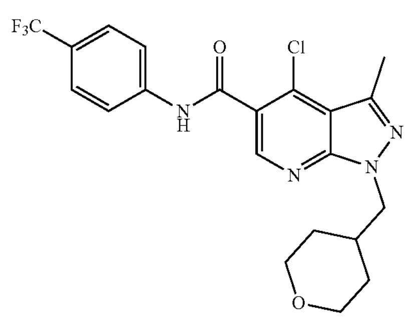 [SMILES: Cc1nn(CC2CCOCC2)c2ncc(C(=O)Nc3ccc(C(F)(F)F)cc3)c(Cl)c12] |

TABLE 1-continued

| Ex. | Names | Structures |
|---|---|---|
| 444 | 4-Chloro-3-methyl-1-(tetrahydro-pyran-4-ylmethyl)-1H-pyrazolo[3,4-b]pyridine-5-carboxylic acid (4-chloro-phenyl)-amide | 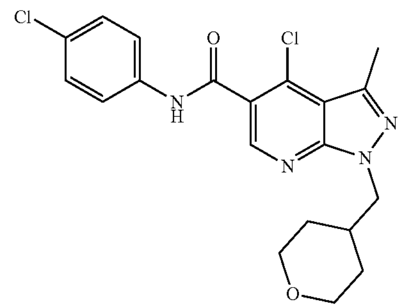 [SMILES: Cc1nn(CC2CCOCC2)c2ncc(C(=O)Nc3ccc(Cl)cc3)c(Cl)c12] |
| 445 | 4-Chloro-3-methyl-1-piperidin-4-ylmethyl-1H-pyrazolo[3,4-b]pyridine-5-carboxylic acid (4-chloro-phenyl)-amide | 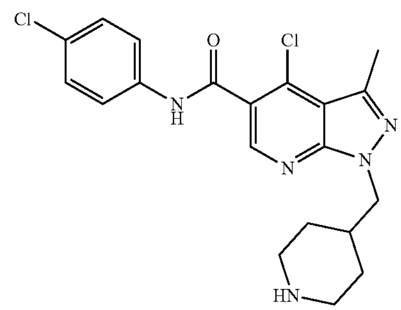 [SMILES: Cc1nn(CC2CCNCC2)c2ncc(C(=O)Nc3ccc(Cl)cc3)c(Cl)c12] |
| 446 | 4-Chloro-3-methyl-1-piperidin-4-ylmethyl-1H-pyrazolo[3,4-b]pyridine-5-carboxylic acid (4-trifluoromethyl-phenyl)-amide | 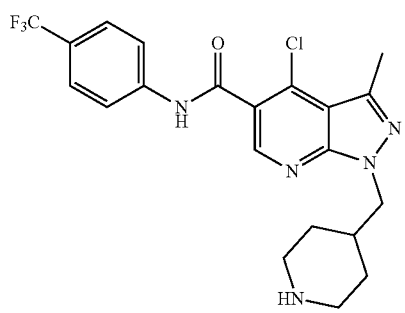 [SMILES: Cc1nn(CC2CCNCC2)c2ncc(C(=O)Nc3ccc(C(F)(F)F)cc3)c(Cl)c12] |
| 447 | 4-Chloro-3-methyl-1-(1-methyl-piperidin-4-ylmethyl)-1H-pyrazolo[3,4-b]pyridine-5-carboxylic acid (4-chloro-phenyl)-amide | 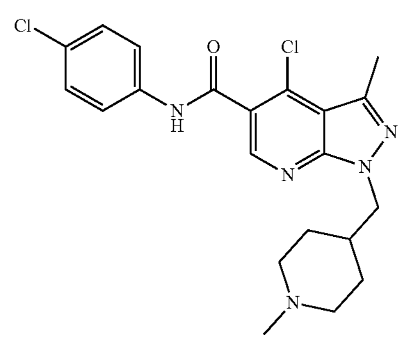 [SMILES: Cc1nn(CC2CCN(C)CC2)c2ncc(C(=O)Nc3ccc(Cl)cc3)c(Cl)c12] |
| 448 | 4-Chloro-3-methyl-1-(1-methyl-piperidin-4-ylmethyl)-1H-pyrazolo[3,4-b]pyridine-5-carboxylic acid (4-trifluoromethyl-phenyl)-amide | 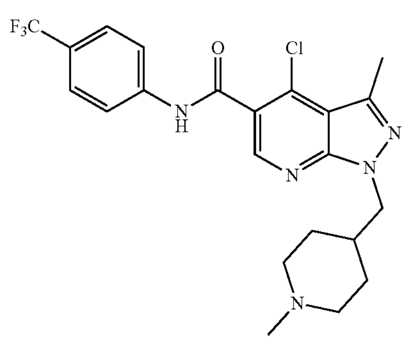 [SMILES: Cc1nn(CC2CCN(C)CC2)c2ncc(C(=O)Nc3ccc(C(F)(F)F)cc3)c(Cl)c12] |

TABLE 1-continued

| Ex. | Names | Structures |
|---|---|---|
| 449 | 4-Chloro-1-(1-methanesulfonyl-piperidin-4-ylmethyl)-3-methyl-1H-pyrazolo[3,4-b]pyridine-5-carboxylic acid (4-chloro-phenyl)-amide | 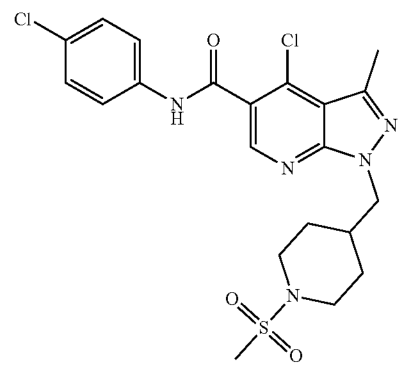 [SMILES: Cc1nn(CC2CCN(S(C)(=O)=O)CC2)c2ncc(C(=O)Nc3ccc(Cl)cc3)c(Cl)c12] |
| 450 | 4-Chloro-1-(1-methanesulfonyl-piperidin-4-ylmethyl)-3-methyl-1H-pyrazolo[3,4-b]pyridine-5-carboxylic acid (4-trifluoromethyl-phenyl)-amide | 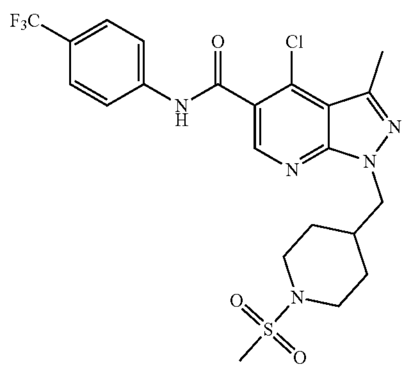 [SMILES: Cc1nn(CC2CCN(S(C)(=O)=O)CC2)c2ncc(C(=O)Nc3ccc(C(F)(F)F)cc3)c(Cl)c12] |
| 451 | 1-(1-Acetyl-piperidin-4-ylmethyl)-4-chloro-3-methyl-1H-pyrazolo[3,4-b]pyridine-5-carboxylic acid (4-chloro-phenyl)-amide | 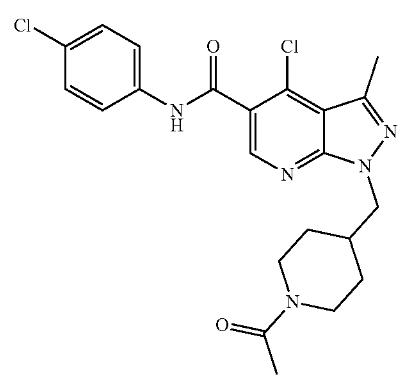 [SMILES: CC(=O)N1CCC(Cn2nc(C)c3c(Cl)c(C(=O)Nc4ccc(Cl)cc4)cnc32)CC1] |
| 452 | 1-(1-Acetyl-piperidin-4-ylmethyl)-4-chloro-3-methyl-1H-pyrazolo[3,4-b]pyridine-5-carboxylic acid (4-trifluoromethyl-phenyl)-amide | 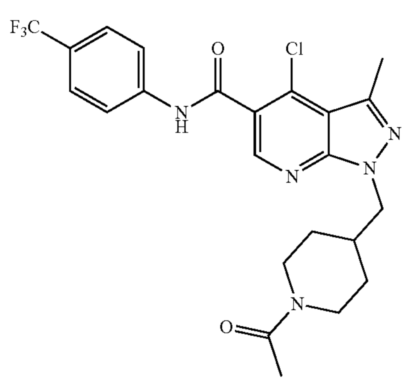 [SMILES: CC(=O)N1CCC(Cn2nc(C)c3c(Cl)c(C(=O)Nc4ccc(C(F)(F)F)cc4)cnc32)CC1] |

TABLE 1-continued

| Ex. | Names |
|---|---|
| 453 | 4-chloro-N-(4-chlorophenyl)-1-((1-(4-methoxybenzyl)-1H-imidazol-2-yl)methyl)-3-methyl-1H-pyrazolo[3,4-b]pyridine-5-carboxamide |
| 454 | 4-Chloro-1-(1H-imidazol-2-ylmethyl)-3-methyl-1H-pyrazolo[3,4-b]pyridine-5-carboxylic acid (4-chloro-phenyl)-amide |
| 455 | 4-Chloro-1-(1H-imidazol-2-ylmethyl)-3-methyl-1H-pyrazolo[3,4-b]pyridine-5-carboxylic acid (4-trifluoromethyl-phenyl)-amide |
| 456 | 4-Chloro-1-(1H-imidazol-4-ylmethyl)-3-methyl-1H-pyrazolo[3,4-b]pyridine-5-carboxylic acid (4-trifluoromethyl-phenyl)-amide |
| 457 | 4-chloro-N-(2-chlorobenzyl)-1-(4-fluorophenyl)-3-methyl-1H-pyrazolo[3,4-b]pyridine-5-carboxamide |

TABLE 1-continued

| Ex. | Names | Structures |
|---|---|---|
| 458 | 4-chloro-N-(4-methoxybenzyl)-3-methyl-1-phenyl-1H-pyrazolo[3,4-b]pyridine-5-carboxamide | 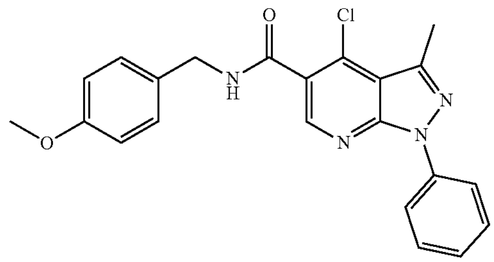 [SMILES: COc1ccc(CNC(=O)c2cnc3c(c(C)nn3-c3ccccc3)c2Cl)cc1] |
| 459 | 4-chloro-N-(furan-2-ylmethyl)-3-methyl-1-phenyl-1H-pyrazolo[3,4-b]pyridine-5-carboxamide | 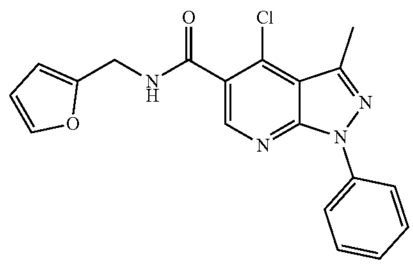 [SMILES: Cc1nn(-c2ccccc2)c2ncc(C(=O)NCc3ccco3)c(Cl)c12] |
| 460 | 4-chloro-3-methyl-N-phenethyl-1-phenyl-1H-pyrazolo[3,4-b]pyridine-5-carboxamide | 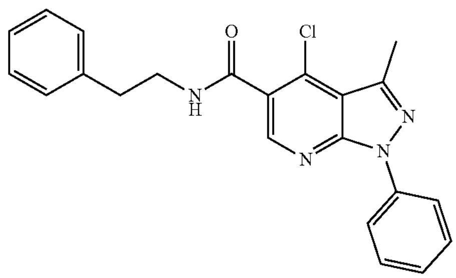 [SMILES: Cc1nn(-c2ccccc2)c2ncc(C(=O)NCCc3ccccc3)c(Cl)c12] |
| 461 | 4-chloro-N-(4-chlorobenzyl)-3-methyl-1-phenyl-1H-pyrazolo[3,4-b]pyridine-5-carboxamide | 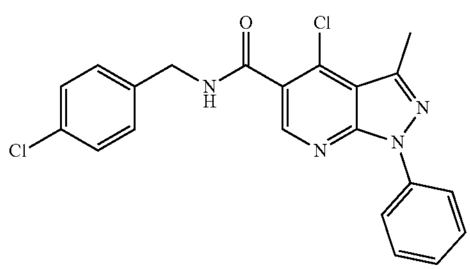 [SMILES: Cc1nn(-c2ccccc2)c2ncc(C(=O)NCc3ccc(Cl)cc3)c(Cl)c12] |
| 462 | 4-chloro-N-(3-chlorophenyl)-3-methyl-1-phenyl-1H-pyrazolo[3,4-b]pyridine-5-carboxamide | 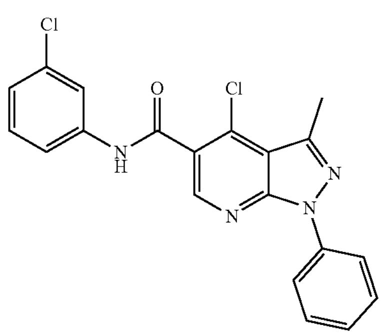 [SMILES: Cc1nn(-c2ccccc2)c2ncc(C(=O)Nc3cccc(Cl)c3)c(Cl)c12] |

TABLE 1-continued

| Ex. | Names | Structures |
|---|---|---|
| 463 | 4-chloro-3-methyl-N,1-diphenyl-1H-pyrazolo[3,4-b]pyridine-5-carboxamide | 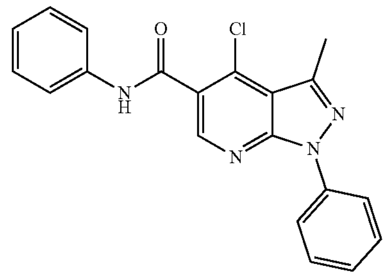 [SMILES: Cc1nn(-c2ccccc2)c2ncc(C(=O)Nc3ccccc3)c(Cl)c12] |
| 464 | 4-chloro-N-(2-methoxyphenyl)-3-methyl-1-phenyl-1H-pyrazolo[3,4-b]pyridine-5-carboxamide | 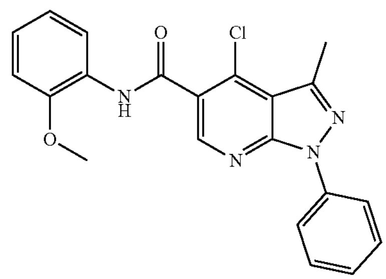 [SMILES: COc1ccccc1NC(=O)c1cnc2c(c(C)nn2-c2ccccc2)c1Cl] |
| 465 | 4-chloro-3-methyl-1-phenyl-N-(pyridin-3-yl)-1H-pyrazolo[3,4-b]pyridine-5-carboxamide | 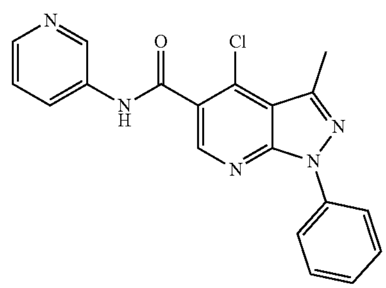 [SMILES: Cc1nn(-c2ccccc2)c2ncc(C(=O)Nc3cccnc3)c(Cl)c12] |
| 466 | 1-(1-benzylpiperidin-4-yl)-4-chloro-N-(4-chlorophenyl)-1H-pyrazolo[3,4-b]pyridine-5-carboxamide | 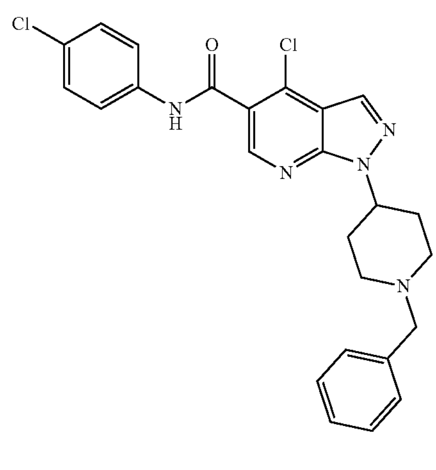 [SMILES: O=C(Nc1ccc(Cl)cc1)c1cnc2c(cnn2C2CCN(Cc3ccccc3)CC2)c1Cl] |

TABLE 1-continued

| Ex. | Names | Structures |
|---|---|---|
| 467 | 1-(1-benzylpiperidin-4-yl)-4-chloro-N-(4-(trifluoromethyl)phenyl)-1H-pyrazolo[3,4-b]pyridine-5-carboxamide | 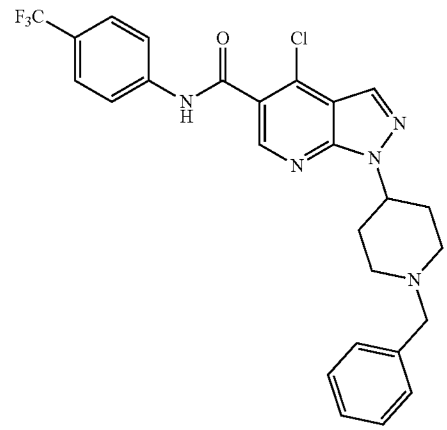 [SMILES: O=C(Nc1ccc(C(F)(F)F)cc1)c1cnc2c(cnn2C2CCN(Cc3ccccc3)CC2)c1Cl] |
| 468 | 1-(1-benzylpiperidin-4-yl)-4-chloro-N-(4-isopropylphenyl)-3-methyl-1H-pyrazolo[3,4-b]pyridine-5-carboxamide | 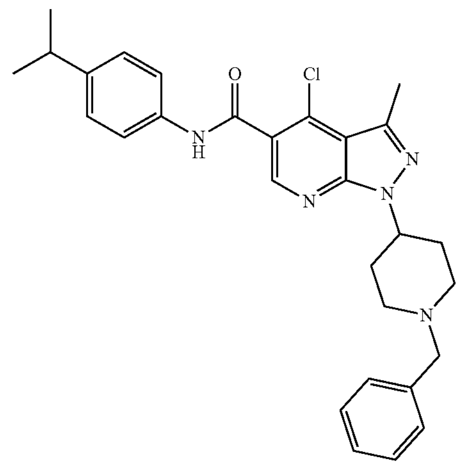 [SMILES: Cc1nn(C2CCN(Cc3ccccc3)CC2)c2ncc(C(=O)Nc3ccc(C(C)C)cc3)c(Cl)c12] |
| 469 | tert-butyl 4-(4-chloro-5-(4-chlorophenylcarbamoyl)-1H-pyrazolo[3,4-b]pyridin-1-yl)piperidine-1-carboxylate | 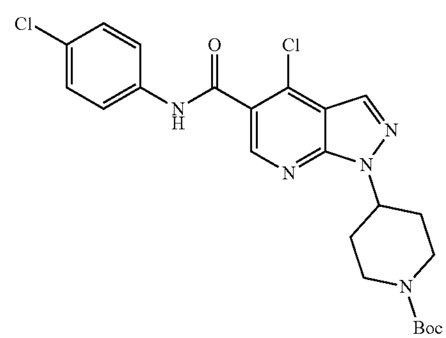 [SMILES: CC(C)(C)OC(=O)N1CCC(n2ncc3c(Cl)c(C(=O)Nc4ccc(Cl)cc4)cnc32)CC1] |
| 470 | tert-butyl 4-(4-chloro-5-(4-isopropylphenylcarbamoyl)-1H-pyrazolo[3,4-b]pyridin-1-yl)piperidine-1-carboxylate | 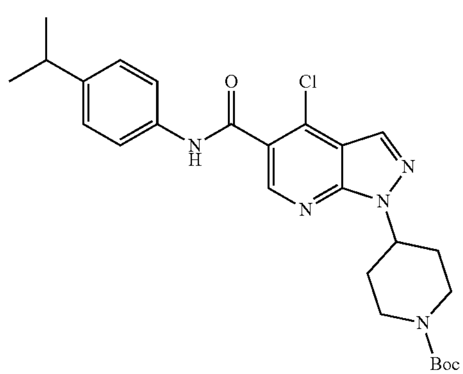 [SMILES: CC(C)c1ccc(NC(=O)c2cnc3c(cnn3C3CCN(C(=O)OC(C)(C)C)CC3)c2Cl)cc1] |

TABLE 1-continued

| Ex. | Names | Structures |
|---|---|---|
| 471 | 4-chloro-N-(4-isopropylphenyl)-1-(piperidin-4-yl)-1H-pyrazolo[3,4-b]pyridine-5-carboxamide | 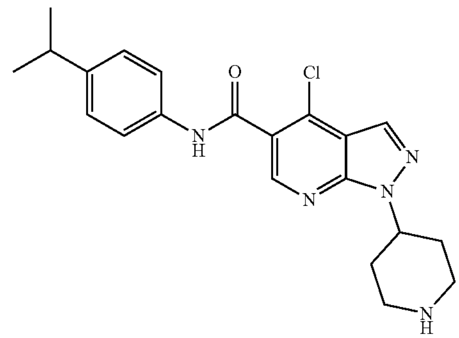 [SMILES: CC(C)c1ccc(NC(=O)c2cnc3c(cnn3C3CCNCC3)c2Cl)cc1] |
| 472 | 4-chloro-N-(4-chlorophenyl)-1-(piperidin-4-yl)-1H-pyrazolo[3,4-b]pyridine-5-carboxamide | 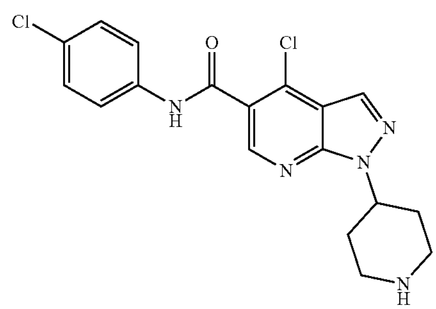 [SMILES: O=C(Nc1ccc(Cl)cc1)c1cnc2c(cnn2C2CCNCC2)c1Cl] |
| 473 | tert-butyl 4-(4-chloro-3-methyl-5-(4-(trifluoromethyl)phenylcarbamoyl)-1H-pyrazolo[3,4-b]pyridin-1-yl)piperidine-1-carboxylate | 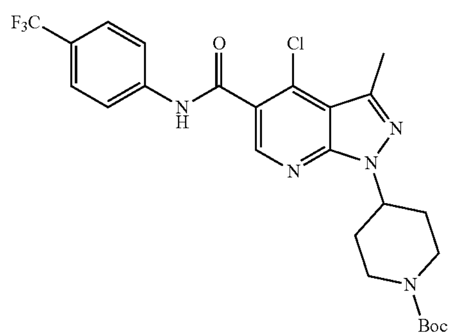 [SMILES: Cc1nn(C2CCN(C(=O)OC(C)(C)C)CC2)c2ncc(C(=O)Nc3ccc(C(F)(F)F)cc3)c(Cl)c12] |
| 474 | tert-butyl 4-(4-chloro-5-(4-isopropylphenylcarbamoyl)-3-methyl-1H-pyrazolo[3,4-b]pyridin-1-yl)piperidine-1-carboxylate | 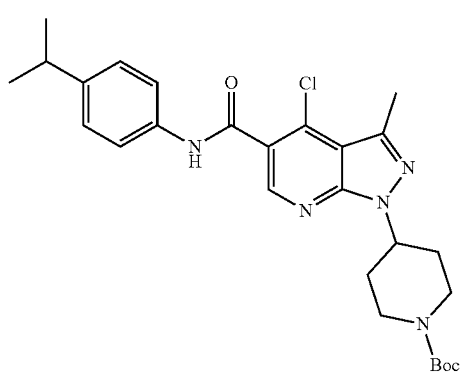 [SMILES: Cc1nn(C2CCN(C(=O)OC(C)(C)C)CC2)c2ncc(C(=O)Nc3ccc(C(C)C)cc3)c(Cl)c12] |

TABLE 1-continued

| Ex. | Names | Structures |
|---|---|---|
| 475 | methyl 4-(5-(4-chlorophenylcarbamoyl)-4-hydroxy-3-methyl-1H-pyrazolo[3,4-b]pyridin-1-yl)piperidine-1-carboxylate | 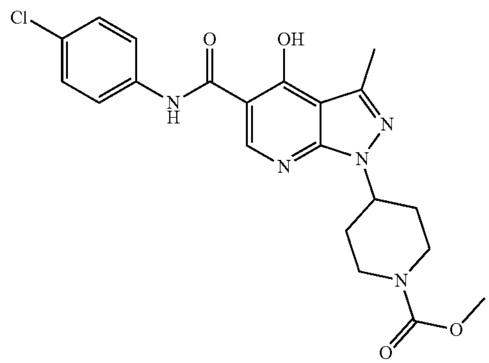 [SMILES: COC(=O)N1CCC(n2nc(C)c3c(O)c(C(=O)Nc4ccc(Cl)cc4)cnc32)CC1] |
| 476 | 4-chloro-3-methyl-1-(piperidin-4-yl)-N-(4-(trifluoromethyl)phenyl)-1H-pyrazolo[3,4-b]pyridine-5-carboxamide | 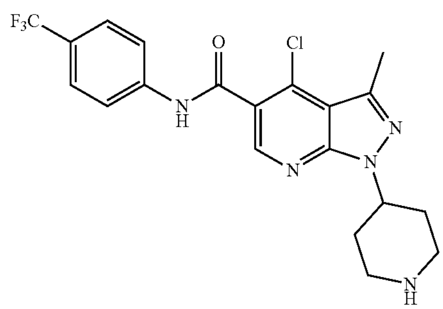 [SMILES: Cc1nn(C2CCNCC2)c2ncc(C(=O)Nc3ccc(C(F)(F)F)cc3)c(Cl)c12] |
| 477 | 4-chloro-N-(4-isopropylphenyl)-3-methyl-1-(piperidin-4-yl)-1H-pyrazolo[3,4-b]pyridine-5-carboxamide | 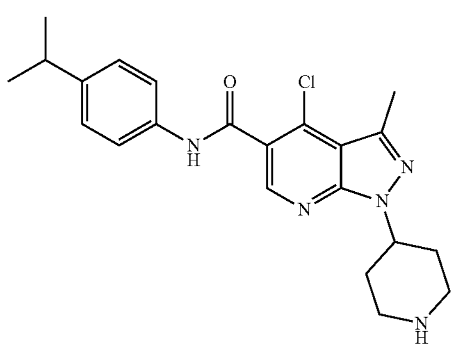 [SMILES: Cc1nn(C2CCNCC2)c2ncc(C(=O)Nc3ccc(C(C)C)cc3)c(Cl)c12] |
| 478 | 3-butyl-7-chloro-N-(4-isopropylphenyl)-3H-imidazo[4,5-b]pyridine-6-carboxamide | 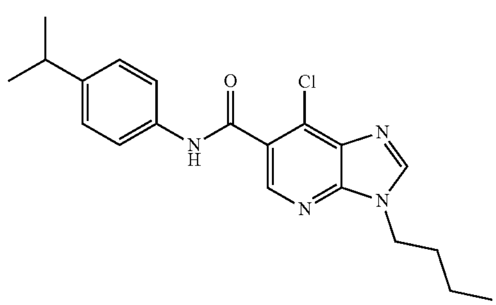 [SMILES: CCCCn1cnc2c(Cl)c(C(=O)Nc3ccc(C(C)C)cc3)cnc21] |

TABLE 1-continued

| Ex. | Names | Structures |
|---|---|---|
| 479 | 1-(1-benzylpiperidin-4-yl)-4-chloro-N-(4-ethynylphenyl)-3-methyl-1H-pyrazolo[3,4-b]pyridine-5-carboxamide | 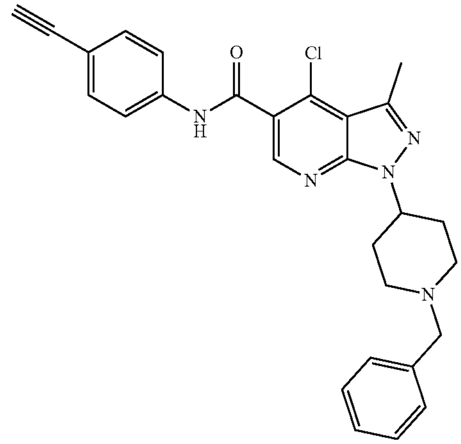 [SMILES: C#Cc1ccc(NC(=O)c2cnc3c(c(C)nn3C3CCN(Cc4ccccc4)CC3)c2Cl)cc1] |
| 480 | 3-methyl-1-(piperidin-4-yl)-N-(4-(trifluoromethyl)phenyl)-1H-pyrazolo[3,4-b]pyridine-5-carboxamide | 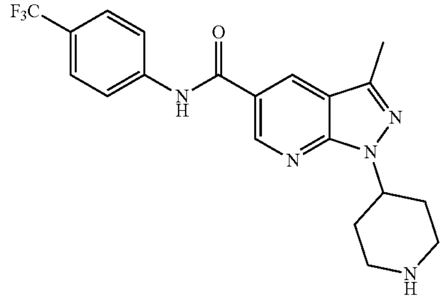 [SMILES: Cc1nn(C2CCNCC2)c2ncc(C(=O)Nc3ccc(C(F)(F)F)cc3)cc12] |

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, UT), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^{3}$H and $^{14}$C are incorporated, are useful in drug and/or substrate tissue distribution assays. Tritiated, i. e., $^{3}$H and carbon-14, i. e., $^{14}$C, isotopes are particularly preferred for their ease of preparation and detectability. Further, substitution with heavy isotopes such as deuterium, i.e., $^{2}$H, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases in a subject mediated by glucocorticoid receptor. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In any case, regardless of the disease, disorder or condition being treated, the overall benefit experienced by the patient may be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Disclosed herein are methods of modulating or inhibiting glucocorticoid receptor translocation. Contemplated methods, for example, comprise exposing said protein to a compound described herein. In some embodiments, the compound utilized by one or more of the foregoing methods is one of the generic, subgeneric, or specific compounds described herein, such as a compound of Formula (I), (II), or (III). The ability of compounds described herein to modulate or inhibit glucocorticoid receptor translocation is evaluated by procedures known in the art and/or described herein. Another aspect of this disclosure provides methods of treating a disease mediated by glucocorticoid receptor in a subject. For example, provided herein are compounds that are selective in inhibiting glucocorticoid receptor translocation over other nuclear receptors, e.g., 10, 100, 1000 or more fold inhibition of GR over mineralocorticoid receptor (MR), progesterone receptor (PR), estrogen receptor (ER), or androgen receptor (AR). In some embodiments the compounds disclosed herein are selective over mineralocorticoid receptor (MR) or progesterone receptor (PR), and more specifically over progesterone receptor (PR).

Also disclosed herein are methods of treating and/or preventing in a patient in need thereof a disorder mediated by glucocorticoid receptor, such as metabolic disease, neuropsychiatric disorders, cancer, and inflammation.

In some embodiments, the methods of treating and/or preventing in a patient in need thereof a disease involving dysfunction of the hypothalamic-pituitary-adrenal (HPA) axis. In some embodiments, the disease involving dysfunction of the hypothalamic-pituitary-adrenal (HPA) axis is selected from metabolic diseases (Cushing's syndrome, obesity, type 2 diabetes, AAPD induced weight gain), neuropsychiatric diseases (bipolar disorder, post-traumatic stress disorder, depression, sleep disorders, or other stress disorders), cardiovascular disease and osteoporosis.

In some embodiments, compounds disclosed herein, or a pharmaceutically acceptable salt, solvate, tautomer, or N-oxide thereof, are used for treating or preventing the following exemplary, non-limiting diseases or conditions.

Metabolic Disease

In some embodiments, compounds disclosed herein, or a pharmaceutically acceptable salt, solvate, tautomer, or N-oxide thereof, are used for the treatment of metabolic disease including obesity, diabetes, hypertension, and cardiovascular disease, are diseases driven by both mulitfactorial genetics (thrifty genotypes) as well as lifestyle habits. In some embodiments, the metabolic disease is Acid Lipase Disease, Barth Syndrome (BTHS), central Pontine Myelinolysis, Farber's Disease, Gangliosidoses, Hurler Syndrome, Hyperoxaluria, Lesch-Nyhan Syndrome, Lipid Storage Diseases, mitochondrial Myopathies, mucolipidoses, mucopolysaccharidoses, Pompe Disease, Type I Glycogen Storage Disease, or urea Cycle Disease. Cancer In some embodiments, compounds disclosed herein, or a pharmaceutically acceptable salt, solvate, tautomer, or N-oxide thereof, are used for treating or preventing leukemias and lymphomas. In some embodiments, compounds disclosed herein, or a pharmaceutically acceptable salt, solvate, tautomer, or N-oxide thereof, are used for the treatment of diverse neoplastic diseases such as brain cancer, bone cancer, basal cell carcinoma, adenocarcinoma, lip cancer, mouth cancer, esophogeal cancer, small bowel cancer, stomach cancer, colon cancer, rectal cancer, liver cancer, bladder cancer, pancreas cancer, ovary cancer, cervical cancer, lung cancer, breast cancer, head and neck cancer, skin cancer, prostate cancer, gall bladder cancer, thyroid cancer, adrenal cancer, and renal cell carcinoma.

In some embodiments, the cancer is prostate cancer. In some embodiments, the prostate cancer is a drug resistant prostate cancer. In some embodiments, the resistant prostate cancer is resistant to an antiandrogen treatment. In some embodiments, the antiandrogen treatment is abiraterone enzalutamide, AR-509, or RD162.

In some embodiments, the cancer is breast cancer. In some embodiments, the breast cancer is a drug resistant breast cancer. In some embodiments, the resistant breast cancer is resistant to an antiestrogen treatment. In some embodiments, the antiestrogen treatment is tamoxifen, raloxifine or toremifene. In some embodiments, the resistant breast cancer is resistant to an aromatase inhibitor. In some embodiments, the aromatase inhibitor is aminoglutethimide, testolactone, anastrozole, letrozole, exemestane, vorozole, formestane, fadrozole, 4-hydroxyandrostenedione, 1,4,6-androstatrien-3,17-dione (ATD), or 4-androstene-3,6,17-trione ("6-OXO").

In some embodiments, the cancer is ovarian cancer. In some embodiments, the ovarian cancer includes ovarian stromal tumors. In some embodiments, the ovarian cancer is a drug resistant ovarian cancer. In some embodiments, the resistant ovarian cancer is resistant to an antiestrogen treatment. In some embodiments, the antiestrogen treatment is tamoxifen, raloxifine or toremifene. In some embodiments, the resistant ovarian cancer is resistant to an aromatase inhibitor. In some embodiments, the aromatase inhibitor is aminoglutethimide, testolactone, anastrozole, letrozole, exemestane, vorozole, formestane, fadrozole, 4-hydroxyandrostenedione, 1,4,6-androstatrien-3,17-dione (ATD), or 4-androstene-3,6,17-trione ("6-OXO").

CNS Diseases

In some embodiments, compounds disclosed herein, or a pharmaceutically acceptable salt, solvate, tautomer, or N-oxide thereof, are used for the treatment of HPA axis dysregulation in psychiatric disease, schizophrenia, bipolar disorder, psychotic major depression, posttraumatic syndrome, and alcohol dependency.

In some embodiments, the glucocorticoid receptor mediated disease or disorder is selected from the group consisting of: tissue rejection, leukemias, lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, obesity, metabolic syndrome, inflammatory bowel disease, systemic lupus erythematosus, polyartitis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, inflammatory scalp alopecia, panniculitis, psoriasis, discoid lupus erythematosus, inflamed cysts, atopic dermatitis, pyoderma gangrenosum, pemphigus vulgaris, buflous pemphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitis, erythema nodosum, acne, hirsutism, toxic epidermal necrolysis, erythema multiform, cutaneous T-cell lymphoma, Human Immunodeficiency Virus (HIV), cell apoptosis, cancer, Kaposi's sarcoma, retinitis pigmentosa, Amyotrophic lateral sclerosis, cognitive performance, memory and learning enhancement, depression, addiction, mood disorders, chronic fatigue syndrome, schizophrenia, sleep disorders, and anxiety.

Combination Therapy

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

In some embodiments, a compound described herein, or a pharmaceutically acceptable salt thereof, is administered in combination with a glucocorticoid receptor agonist. In some embodiments, the glucocorticoid receptor agonist is dexamethasone.

Rheumatic Disorders

In some embodiments, compounds disclosed herein, or a pharmaceutically acceptable salt, solvate, tautomer, or N-oxide thereof, are used in combination with GR agonist for the treatment of psoriatic arthritis; rheumatoid arthritis including juvenile rheumatoid arthritis; ankylosing spondylitis; acute and subacute bursitis; acute nonspecific tenosynovitis; acute gouty arthritis; post-traumatic osteoarthritis; synovitis of osteoarthritis; and epicondylitis.

Dermatologic Diseases

In some embodiments, compounds disclosed herein, or a pharmaceutically acceptable salt, solvate, tautomer, or N-oxide thereof, are used in combination with GR agonist for treating or preventing pemphigus; bullous dermatitis herpetiformis; severe erythema multiforme (Stevens-Johnson syndrome); exfoliative dermatitis; mycosis fungo'ides; severe psoriasis; and severe seborrheic dermatitis.

Ophthalmic Diseases

In some embodiments, compounds disclosed herein, or a pharmaceutically acceptable salt, solvate, tautomer, or N-oxide thereof, are used in combination with GR agonist for treating or preventing severe acute and chronic allergic and inflammatory processes involving the eye and its adnexa such as: allergic conjunctivitis; keratitis; allergic corneal marginal ulcers; herpes zoster ophthalmicus; iritis and iridocyclitis; chorioretinitis; anterior segment inflammation; diffuse posterior uveitis and choroiditis; optic neuritis; and sympathetic ophthalmia.

Gastrointestinal Diseases

In some embodiments, compounds disclosed herein, or a pharmaceutically acceptable salt, solvate, tautomer, or N-oxide thereof, are used in combination with a GR agonist for treating or preventing ulcerative colitis and regional enteritis.

Multiple Sclerosis

In some embodiments, compounds disclosed herein, or a pharmaceutically acceptable salt, solvate, tautomer, or N-oxide thereof, are used in combination with a GR agonist for treating or preventing multiple sclerosis.

Inflammation

In some embodiments, compounds disclosed herein, or a pharmaceutically acceptable salt, solvate, tautomer, or N-oxide thereof, are used for treating or preventing inflammation either as single agents or in combination with GR agonists.

Cancer

In some embodiments, compounds described herein, or a pharmaceutically acceptable salt, solvate, tautomer, or N-oxide thereof, are administered in combination an additional cancer agent. In some embodiments, the additional cancer agent is chemotherapy, hormone blocking therapy, radiation therapy, monoclonal antibodies, or combinations thereof. Chemotherapy includes the use of anti-cancer agents. In one aspect, the compound described herein, or a pharmaceutically acceptable salt thereof, is administered or formulated in combination with one or more anti-cancer agents.

EXAMPLES

The following examples are provided for illustrative purposes only and not to limit the scope of the claims provided herein.

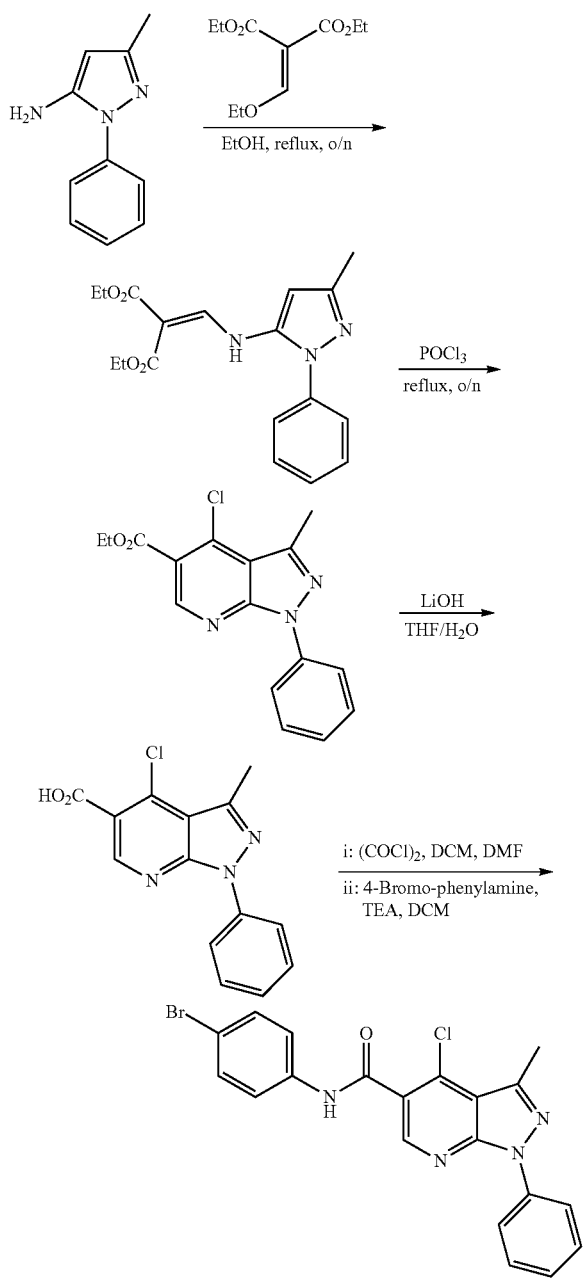

Example 1

4-Chloro-3-methyl-1-phenyl-1H-pyrazolo[3,4-b]pyridine-5-carboxylic acid (4-bromo-phenyl)-amide Step 1

To a solution of 5-methyl-2-phenyl-2H-pyrazol-3-ylamine (8.0 g, 0.046 mol) in ethanol was added 2-ethoxymethylene-malonic acid diethyl ester (10.98 g, 0.051 mol). The mixture was stirred at 85° C. overnight. The solvent was removed and the residue was poured into ice-cold NaOH solution (1N, 200 mL). The aqueous phase was extracted with EA (200 mL×2). The organic layers were washed with brine and evapourated to dryness. The residue was purified by silica gel column (EA/PE=1/10) to give 24(5-methyl-2-phenyl-2H-pyrazol-3-ylamino)-methylenel-malonic acid diethyl ester (13.3 g, yield: 84%).

$^1$HNMR (400 MHz, CDCl$_3$): δ=10.99 (d, J=12.8 Hz, 1H), 8.19 (d, J=12.8 Hz, 1H), 7.54-7.39 (m, 5H), 6.03 (s, 1H), 4.26-4.19 (m, 4H), 2.32 (s, 3H), 1.33-1.26 (m, 6H).

Step 2

A mixture of 2[(5-methyl-2-phenyl-2H-pyrazol-3-ylamino)-methylene]-malonic acid diethyl ester (16.0 g, 0.047 mol) and POCl$_3$(280 mL) was stirred at 120° C. overnight. The solvent was removed and the residue was poured into ice water (400 mL) slowly. The aqueous phase was extracted with DCM (300 mL×2). The organic layers were combined, washed with brine (200 mL) and dried over anhydrous Na$_2$SO$_4$ The solvent was removed and the residue was purified by silica gel column (EA/PE=1/40~1/10) to give 4-chloro-3-methyl-1-phenyl-1H-pyrazolo[3,4-b]pyridine-5-carboxylic acid ethyl ester (7.6 g, yield: 51%).

$^1$HNMR (300 MHz, CDCl$_3$): δ=9.04 (s, 1H), 8.20-8.17 (m, 2H), 7.57-7.52 (m, 2H), 7.38-7.32 (m, 1H), 4.48 (q, J=7.2 Hz, 2H), 2.88 (s, 3H), 1.46 (t, J=7.2 Hz, 3H).

Step 3

To a solution of 4-chloro-3-methyl-1-phenyl-1H-pyrazolo[3,4-b]pyridine-5-carboxylic acid ethyl ester (7.6 g, 0.024 mol) in THF (300 mL), a solution of LiOH.H$_2$O (3.0 g, 0.07 mmol) in water (20 mL) was added. The mixture was stirred at rt for 12 h. The solvent was removed and the residue was poured into ice water (20 mL). The aqueous was acidified with 6N HCl to pH=2. The resulting was filtered. The filter cake was washed with water (5 mL) and dried to give 4-chloro-3-methyl-1-phenyl-1H-pyrazolo[3,4-b]pyridine-5-carboxylic acid (6.2 g, yield: 89%).

$^1$HNMR (400 MHz, DMSO-d6): δ=13.7 (brs, 1H), 8.99 (s, 1H), 8.16 (d, J=8.0 Hz, 2H), 7.58 (t, J=8.0 Hz, 2H), 7.38 (t, J=7.4 Hz, 1H), 2.78 (s, 3H).

Step 4

To a suspension of 4-chloro-3-methyl-1-phenyl-1H-pyrazolo[3,4-b]pyridine-5-carboxylic acid (105 mg, 0.365 mmol) in DCM (10 mL), 1 drop of DMF was added. Oxalyl chloride (93 mg, 0.87 mmol) was added to the reaction mixture at 0° C. The reaction was stirred at room temperature for 1 h. The solvent was removed and the residue was dissolved in DCM (10 mL) followed by the addition of TEA (110 mg, 1.1 mmol) at 0° C. Then 4-bromo-phenylamine (126 mg, 0.73 mmol) was added. The mixture was stirred at room temperature for 1 h. The reaction was quenched with water (15 mL). The organic layer was separated, washed with brine (20 mL) and dried over anhydrous Na$_2$SO$_4$ The solvent was removed and the residue was triturated with CH$_3$CN (3 mL) to give 4-chloro-3-methyl-1-phenyl-1H-pyrazolo[3,4-b]pyridine-5-carboxylic acid (4-bromo-phenyl)-amide(40 mg, yield: 25%).

$^1$HNMR (300 MHz, DMSO-d6): δ=10.85 (s, 1H), 8.82 (s, 1H), 8.22-8.19 (m, 2H), 7.74-7.70 (m, 2H), 7.62-7.57 (m, 4H), 7.39 (t, J=7.8 Hz, 1H), 2.80 (s, 3H). MS: m/z 442.9 (M+H$^+$).

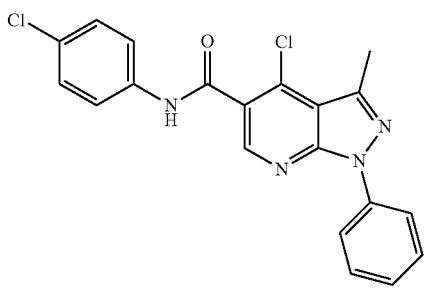 [SMILES: Cc1nn(-c2ccccc2)c2ncc(C(=O)Nc3ccc(Cl)cc3)c(Cl)c12]

Example 2

4-Chloro-3-methyl-1-phenyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.83 (s, 1H), 8.82 (s, 1H), 8.20 (d, J=8.0 Hz, 2H), 7.77 (d, J=8.8 Hz, 2H), 7.59 (t, J=8.0 Hz, 2H), 7.45 (d, J=8.8 Hz, 2H), 7.41-7.39 (m, 1H), 2.80 (s, 3H). MS: m/z 397.1 (M+H$^+$).

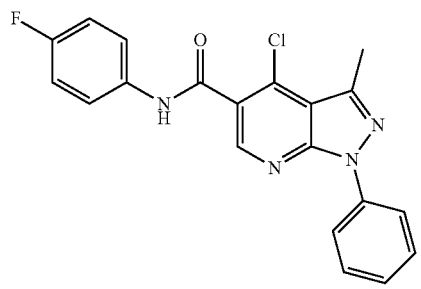 [SMILES: Cc1nn(-c2ccccc2)c2ncc(C(=O)Nc3ccc(F)cc3)c(Cl)c12]

Example 3

4-Chloro-3-methyl-1-phenyl-1H-pyrazolo[3,4-b]pyridine-5-carboxylic acid (4-fluoro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.76 (brs, 1H), 8.82 (s, 1H), 8.20 (d, J=7.5 Hz, 2H), 7.79-7.75 (m, 2H), 7.60 (t, J=7.5 Hz, 2H), 7.41-7.39 (m, 1H), 7.24 (t, J=8.7 Hz, 2H), 2.80 (s, 3H). MS: m/z 381.1 (M+H$^+$).

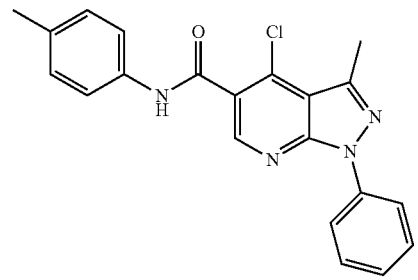 [SMILES: Cc1ccc(NC(=O)c2cnc3c(c(C)nn3-c3ccccc3)c2Cl)cc1]

Example 4

4-Chloro-3-methyl-1-phenyl-1H-pyrazolo[3,4-b]pyridine-5-carboxylic acid p-tolylamide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.60 (brs, 1H), 8.79 (s, 1H), 8.21 (d, J=7.6 Hz, 2H), 7.64-7.57 (m, 4H), 7.40-7.38 (m, 1H), 7.19 (d, J=8.0 Hz, 2H), 2.80 (s, 3H), 2.30 (s, 3H). MS: m/z 377.1 (M+H$^+$).

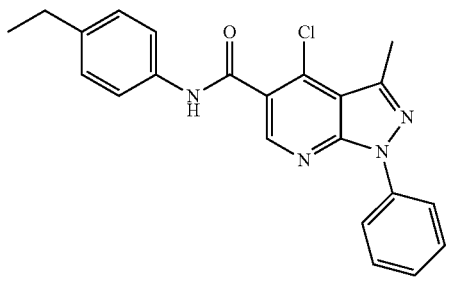 [SMILES: CCc1ccc(NC(=O)c2cnc3c(c(C)nn3-c3ccccc3)c2Cl)cc1]

Example 5

4-Chloro-3-methyl-1-phenyl-1H-pyrazolo[3,4-b]pyridine-5-carboxylic acid (4-ethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.87 (s, 1H), 8.19 (d, J=8.1 Hz, 2H), 7.94 (brs, 1H), 7.61-7.52 (m, 4H), 7.36 (t, J=7.2 Hz, 1H), 7.26 (overlap, 2H), 2.85 (s, 3H), 2.68 (q, J=7.5 Hz, 2H), 1.27 (t, J=7.5 Hz, 3H). MS: m/z 391.1 (M+H$^+$).

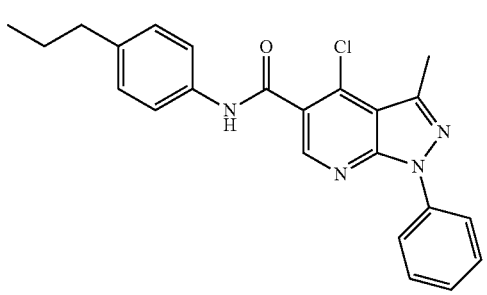 [SMILES: CCCc1ccc(NC(=O)c2cnc3c(c(C)nn3-c3ccccc3)c2Cl)cc1]

Example 6

4-Chloro-3-methyl-1-phenyl-1H-pyrazolo[3,4-b]pyridine-5-carboxylic acid (4-propyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.89 (s, 1H), 8.19 (d, J=7.8 Hz, 2H), 7.90 (brs, 1H), 7.60-7.52 (m, 4H), 7.38 (m, 1H), 7.26-7.22 (m, 2H), 2.87 (s, 3H), 2.62 (t, J=7.5 Hz, 2H), 1.71-1.63 (m, 2H), 0.97 (t, J=7.5 Hz, 3H). MS: m/z 405.1 (M+H$^+$).

357

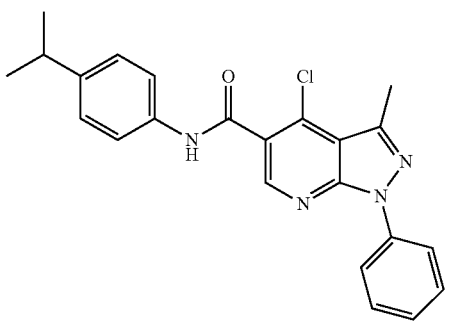 [SMILES: Cc1nn(-c2ccccc2)c2ncc(C(=O)Nc3ccc(C(C)C)cc3)c(Cl)c12]

Example 7

4-Chloro-3-methyl-1-phenyl-1H-pyrazolo[3,4-b] pyridine-5-carboxylic acid (4-isopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=8.87 (s, 1H), 8.18 (d, J=7.6 Hz, 2H), 7.89 (brs, 1H), 7.59 (d, J=8.0 Hz, 2H), 7.53 (t, J=7.8 Hz, 2H), 7.36-7.32 (m, 1H), 7.26 (overlap, 2H), 2.95-2.91 (m, 1H), 2.85 (s, 3H), 1.27 (d, J=7.2 Hz, 6H). MS: m/z 405.1 (M+H$^+$).

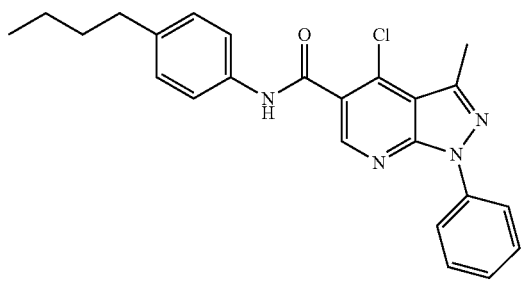 [SMILES: CCCCc1ccc(NC(=O)c2cnc3c(c(C)nn3-c3ccccc3)c2Cl)cc1]

Example 8

4-Chloro-3-methyl-1-phenyl-1H-pyrazolo[3,4-b] pyridine-5-carboxylic acid (4-butyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.62 (brs, 1H), 8.79 (s, 1H), 8.21-8.18 (m, 2H), 7.65-7.57 (m, 4H), 7.38 (t, J=7.2 Hz, 1H), 7.20 (d, J=8.1 Hz, 2H), 2.80 (s, 3H), 2.59-2.50 (m, 2H), 1.58-1.50 (m, 2H), 1.34-1.27 (m, 2H), 0.90 (t, J=7.4 Hz, 3H). MS: m/z 419.2 (M+H$^+$).

358

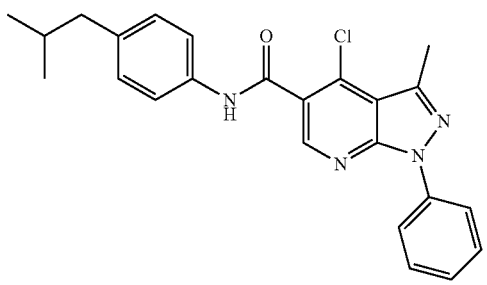 [SMILES: Cc1nn(-c2ccccc2)c2ncc(C(=O)Nc3ccc(CC(C)C)cc3)c(Cl)c12]

Example 9

4-Chloro-3-methyl-1-phenyl-1H-pyrazolo[3,4-b] pyridine-5-carboxylic acid (4-isobutyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=8.87 (s, 1H), 8.18 (d, J=7.8 Hz, 2H), 7.88 (brs, 1H), 7.58-7.51 (m, 4H), 7.34 (t, J=7.2 Hz, 1H), 7.18 (d, J=8.4 Hz, 2H), 2.85 (s, 3H), 2.48 (d, J=7.2 Hz, 2H), 1.85-1.82 (m, 1H), 0.92 (d, J=6.8 Hz, 6H). MS: m/z 419.1 (M+H$^+$).

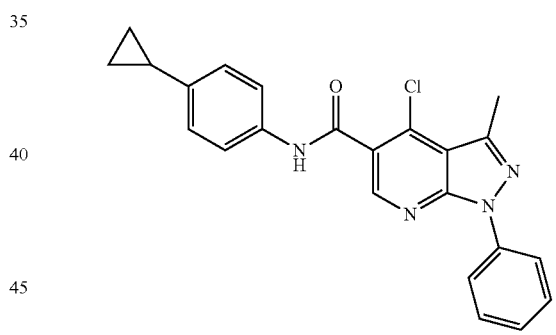

Example 10

4-Chloro-3-methyl-1-phenyl-1H-pyrazolo[3,4-b] pyridine-5-carboxylic acid (4-cyclopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=8.86 (s, 1H), 8.17 (d, J=8.0 Hz, 2H), 7.89 (brs, 1H), 7.56-7.51 (m, 4H), 7.34 (t, J=7.6 Hz, 1H), 7.11 (d, J=8.4 Hz, 2H), 2.84 (s, 3H), 2.00-1.91 (m, 1H), 0.99-0.95 (m, 2H), 0,71-0.70 (m, 2H). MS: m/z 403.1 (M+H$^+$).

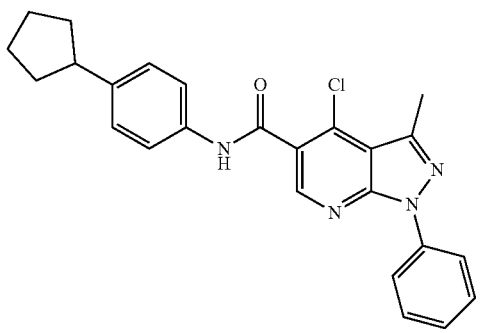 [SMILES: Cc1nn(-c2ccccc2)c2ncc(C(=O)Nc3ccc(C4CCCC4)cc3)c(Cl)c12]

Example 11

4-Chloro-3-methyl-1-phenyl-1H-pyrazolo[3,4-b]
pyridine-5-carboxylic acid (4-cyclopentyl-phenyl)-
amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=8.86 (brs, 1H), 8.17 (d, J=8.0 Hz, 2H), 7.89 (brs, 1H), 7.60-7.51 (m, 4H), 7.34 (t, J=7.4 Hz, 1H), 7.26 (overlap, 2H), 3.01-2.99 (m, 1H), 2.85 (m, 3H), 2.10-2.05 (m, 2H), 1.84-1.25 (6H, m). MS: m/z 431.1 (M+H$^+$).

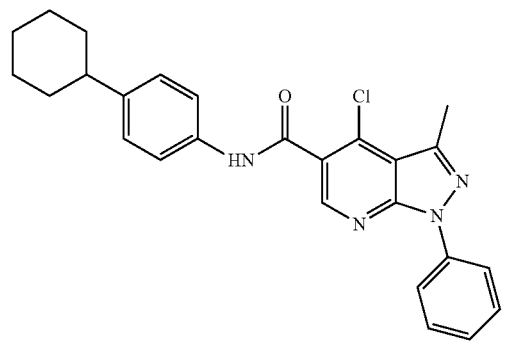 [SMILES: Cc1nn(-c2ccccc2)c2ncc(C(=O)Nc3ccc(C4CCCCC4)cc3)c(Cl)c12]

Example 12

4-Chloro-3-methyl-1-phenyl-1H-pyrazolo[3,4-b]
pyridine-5-carboxylic acid (4-cyclohexyl-phenyl)-
amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=8.85 (s, 1H), 8.17 (d, J=7.6 Hz, 2H), 7.89 (brs, 1H), 7.59-7.51 (m, 4H), 7.34 (t, J=7.6 Hz, 1H), 7.26 (overlap, 2H), 2.84 (s, 3H), 2.54-2.50 (m, 1H), 1.87-1.85 (m, 4H), 1.78-1.74 (m, 1H), 1.48-1.39 (m, 4H), 1.27-1.25 (m, 1H). MS: m/z 445.1 (M+H$^+$).

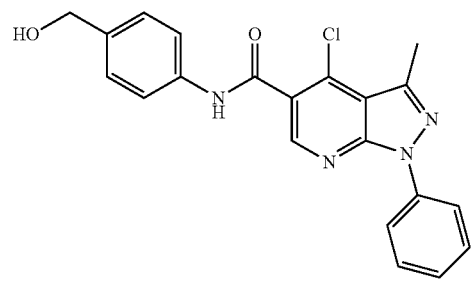 [SMILES: Cc1nn(-c2ccccc2)c2ncc(C(=O)Nc3ccc(CO)cc3)c(Cl)c12]

Example 13

4-Chloro-3-methyl-1-phenyl-1H-pyrazolo[3,4-b]
pyridine-5-carboxylic acid (4-hydroxymethyl-phe-
nyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.67 (brs, 1H), 8.81 (s, 1H), 8.21 (d, J=7.8 Hz, 2H), 7.69 (d, J=8.4 Hz, 2H), 7.60 (t, J=7.8 Hz, 2H), 7.41-7.31 (m, 3H), 5.15 (t, J=5.7 Hz, 1H), 4.48 (d, J=5.4 Hz, 2H), 2.80 (s, 3H). MS: m/z 393.0 (M+H$^+$).

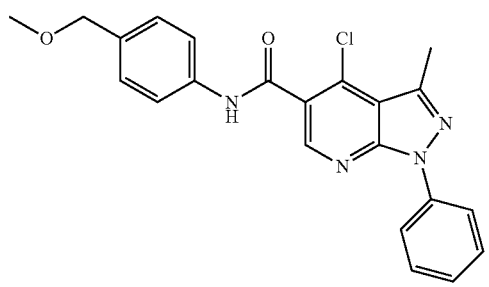 [SMILES: COCc1ccc(NC(=O)c2cnc3c(c(C)nn3-c3ccccc3)c2Cl)cc1]

Example 14

4-Chloro-3-methyl-1-phenyl-1H-pyrazolo[3,4-b]
pyridine-5-carboxylic acid (4-methoxymethyl-phe-
nyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.73 (brs, 1H), 8.81 (s, 1H), 8.21 (d, J=8.1 Hz, 2H), 7.73 (d, J=8.1 Hz, 2H), 7.61-7.57 (m, 2H), 7.35-7.32 (m, 3H), 4.39 (s, 2H), 3.28 (s, 3H), 2.80 (s, 3H). MS: m/z 407.1 (M+H$^+$).

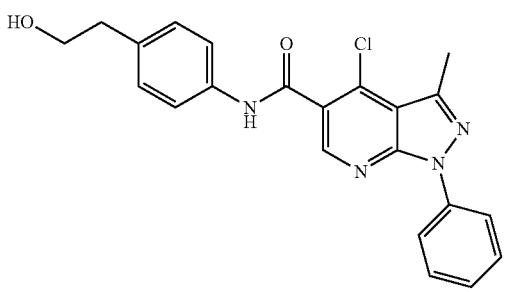 [SMILES: Cc1nn(-c2ccccc2)c2ncc(C(=O)Nc3ccc(CCO)cc3)c(Cl)c12]

Example 15

4-Chloro-3-methyl-1-phenyl-1H-pyrazolo[3,4-b]pyridine-5-carboxylic acid [4-(2-hydroxy-ethyl)-phenyl]-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, DMSO-d6): δ=10.62 (brs, 1H), 8.79 (s, 1H), 8.20 (d, J=8.0 Hz, 2H), 7.65-7.57 (m, 4H), 7.40-7.37 (m, 1H), 7.22 (d, J=8.0 Hz, 2H), 4.62 (s, 1H), 3.60-3.59 (m, 2H), 2.80 (s, 3H), 2.73-2.70 (m, 2H). MS: m/z 405.1 (M–H$^+$).

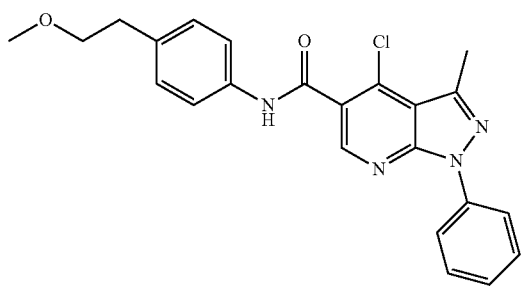 [SMILES: COCCc1ccc(NC(=O)c2cnc3c(c(C)nn3-c3ccccc3)c2Cl)cc1]

Example 16

4-Chloro-3-methyl-1-phenyl-1H-pyrazolo[3,4-b]pyridine-5-carboxylic acid [4-(2-methoxy-ethyl)-phenyl]-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, CDCl₃): δ=8.84 (s, 1H), 8.17 (d, J=8.0 Hz, 2H), 7.95 (brs, 1H), 7.59 (d, J=8.0 Hz, 2H), 7.53 (t, J=8.0 Hz, 2H), 7.33 (t, J=7.6 Hz, 1H), 7.26 (overlap, 2H), 3.61 (t, J=7.2 Hz, 2H), 3.36 (s, 3H), 2.89 (t, J=7.2 Hz, 2H), 2.83 (s, 3H). MS: m/z 421.1 (M+1).

Example 17

4-Chloro-3-methyl-1-phenyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, DMSO-d6): δ=11.07 (s, 1H), 8.85 (s, 1H), 8.21 (d, J=8.0 Hz, 2H), 7.96 (d, J=8.4 Hz, 2H), 7.77 (d, J=8.4 Hz, 2H), 7.59 (t, J=8.0 Hz, 2H), 7.41-7.39 (m, 1H), 2.81 (s, 3H). MS: m/z 431.1 (M+H$^+$).

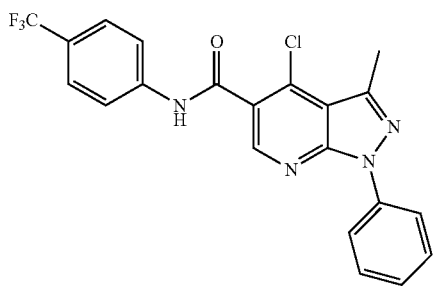 [SMILES: Cc1nn(-c2ccccc2)c2ncc(C(=O)Nc3ccc(C(F)(F)F)cc3)c(Cl)c12]

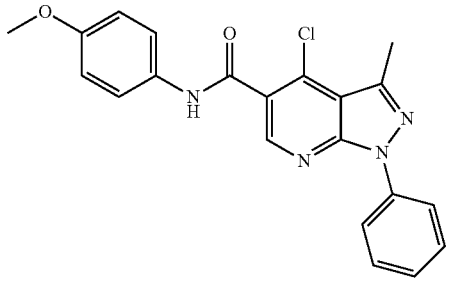 [SMILES: COc1ccc(NC(=O)c2cnc3c(c(C)nn3-c3ccccc3)c2Cl)cc1]

Example 18

4-Chloro-3-methyl-1-phenyl-1H-pyrazolo[3,4-b]pyridine-5-carboxylic acid (4-methoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, DMSO-d6): δ=10.60 (brs, 1H), 8.78 (s, 1H), 8.21 (d, J=8.4 Hz, 2H), 7.67 (d, J=8.8 Hz, 2H), 7.59 (t, J=8.0 Hz, 2H), 7.38 (t, J=7.4 Hz, 1H), 6.96 (d, J=9.2 Hz, 2H), 3.76 (s, 3H), 2.80 (s, 3H). MS: m/z 393.1 (M+H$^+$).

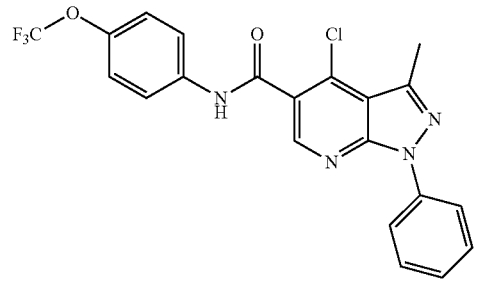 [SMILES: Cc1nn(-c2ccccc2)c2ncc(C(=O)Nc3ccc(OC(F)(F)F)cc3)c(Cl)c12]

Example 19

4-Chloro-3-methyl-1-phenyl-1H-pyrazolo[3,4-b]pyridine-5-carboxylic acid (4-trifluoromethoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, DMSO-d6): δ=10.90 (brs, 1H), 8.82 (s, 1H), 8.21 (d, J=8.0 Hz, 2H), 7.86 (d, J=8.8 Hz, 2H), 7.59 (t, J=8.0 Hz, 2H), 7.42-7.40 (m, 3H), 2.81 (s, 3H). MS: m/z 447.1 (M+H$^+$).

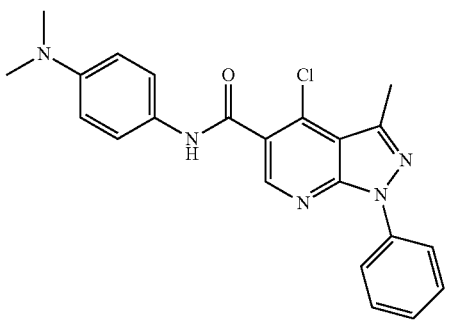 [SMILES: Cc1nn(-c2ccccc2)c2ncc(C(=O)Nc3ccc(N(C)C)cc3)c(Cl)c12]

Example 20

4-Chloro-3-methyl-1-phenyl-1H-pyrazolo[3,4-b]pyridine-5-carboxylic acid (4-dimethylamino-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.86 (s, 1H), 8.19 (d, J=7.5 Hz, 2H), 7.86 (brs, 1H), 7.57-7.50 (m, 4H), 7.35 (t, J=7.5 Hz, 1H), 6.78-6.75 (m, 2H), 2.97 (s, 6H), 2.84 (s, 3H). MS: m/z 406.1 (M+H$^+$).

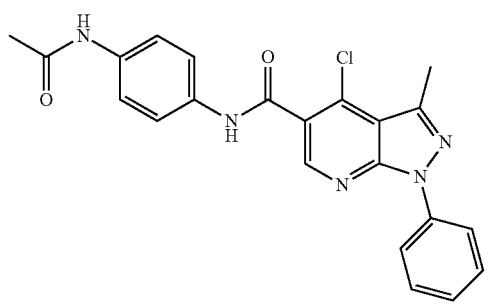 [SMILES: CC(=O)Nc1ccc(NC(=O)c2cnc3c(c(C)nn3-c3ccccc3)c2Cl)cc1]

Example 21

4-Chloro-3-methyl-1-phenyl-1H-pyrazolo[3,4-b]pyridine-5-carboxylic acid (4-acetylamino-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.63 (brs, 1H), 9.94 (brs, 1H), 8.80 (s, 1H), 8.21 (d, J=8.0 Hz, 2H), 7.67-7.57 (m, 6H), 7.40-7.39 (m, 1H), 2.80 (s, 3H), 2.04 (s, 3H). MS: m/z 420.1 (M+H$^+$).

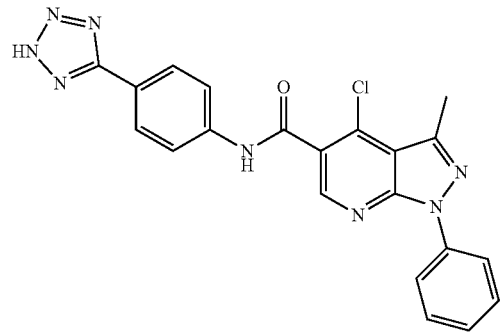 [SMILES: Cc1nn(-c2ccccc2)c2ncc(C(=O)Nc3ccc(-c4nn[nH]n4)cc3)c(Cl)c12]

Example 22

4-Chloro-3-methyl-1-phenyl-1H-pyrazolo[3,4-b]pyridine-5-carboxylic acid [4-(2H-tetrazol-5-yl)-phenyl]-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=11.04 (brs, 1H), 8.86 (s, 1H), 8.21 (d, J=7.6 Hz, 2H), 8.07 (d, J=7.8 Hz, 2H), 7.97 (d, J=7.8 Hz, 2H), 7.60 (d, J=8.0 Hz, 2H), 7.41-7.40 (m, 1H), 2.81 (s, 3H). MS: m/z 429.1 (M−H$^+$).

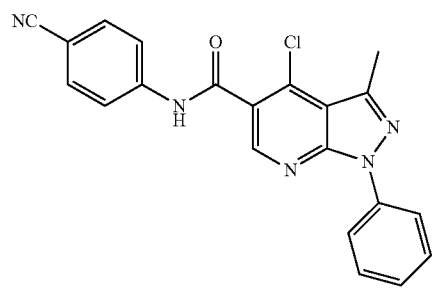 [SMILES: Cc1nn(-c2ccccc2)c2ncc(C(=O)Nc3ccc(C#N)cc3)c(Cl)c12]

Example 23

4-Chloro-3-methyl-1-phenyl-1H-pyrazolo[3,4-b]pyridine-5-carboxylic acid (4-cyano-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=11.14 (brs, 1H), 8.85 (s, 1H), 8.20 (d, J=8.4 Hz, 2H), 7.94-7.85 (m, 4H), 7.59 (t, J=8.0 Hz, 2H), 7.39 (t, J=8.0 Hz, 1H), 2.80 (s, 3H). MS: m/z 388.1 (M+H$^+$).

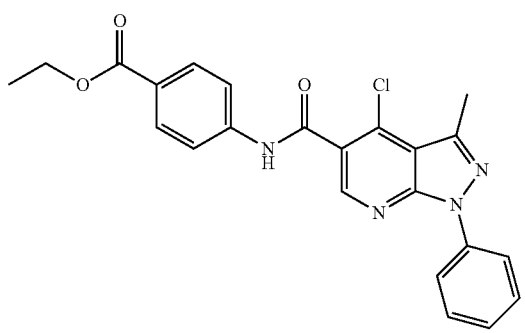 [SMILES: CCOC(=O)c1ccc(NC(=O)c2cnc3c(c(C)nn3-c3ccccc3)c2Cl)cc1]

Example 24

4-1-[(4-Chloro-3-methyl-1-phenyl-1H-pyrazolo[3,4-b]pyridine-5-carbonyl)-amino]-benzoic acid ethyl ester The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=8.85 (s, 1H), 8.22 (s, 1H), 8.17 (d, J=7.6 Hz, 2H), 8.08 (d, J=8.8 Hz, 2H), 7.76 (d, J=8.4 Hz, 2H), 7.53 (t, J=8.0 Hz, 2H), 7.35 (t, J=7.2 Hz, 1H), 4.39 (q, J=7.2 Hz, 2H), 2.84 (s, 3H), 1.41 (t, J=7.0 Hz, 3H). MS: m/z 435.0 (M+H$^+$).

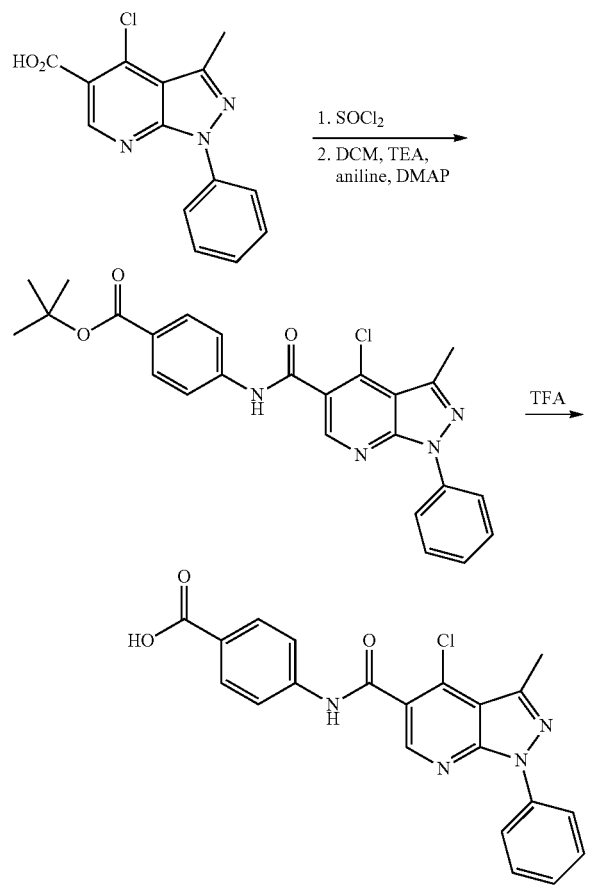

Example 25

4-[(4-Chloro-3-methyl-1-phenyl-1H-pyrazolo[3,4-b]pyridine-5-carbonyl)-amino]-benzoic acid Step 1
This step was similar to 4-chloro-3-methyl-1-phenyl-1H-pyrazolo[3,4-b]pyridine-5-carboxylic acid (4-bromo-phenyl)-amide (Example 1).

Step 2
To a solution of 4-[(4-chloro-3-methyl-1-phenyl-1H-pyrazolo[3,4-b]pyridine-5-carbonyl)-amino]-benzoic acid tert-butyl ester (112 mg, 0.24 mmol) in DCM (6 mL) was added TFA (2 mL), the mixture was stirred at rt for 2 h. The mixture was concentrated and the residue was washed with 6N HCl solution. The aqueous phase was extracted with EA (20 mL×2). The extracts were dried over Na$_2$SO$_4$, concentrated, and the residue was purified by prep-HPLC to give 4-[(4-chloro-3-methyl-1-phenyl-1H-pyrazolo[3,4-b]pyridine-5-carbonyl)-amino]-benzoic acid (5.2 mg, yield: 5%) as a white solid. $^1$HNMR (400 MHz, DMSO-d6): δ=12.80 (brs, 1H), 11.02 (brs, 1H), 8.84 (s, 1H), 8.21 (d, J=7.2 Hz, 2H), 7.98 (d, J=8.8 Hz, 2H), 7.86 (d, J=8.4 Hz, 2H), 7.60 (t, J=8.0 Hz, 2H), 7.41-7.39 (m, 1H), 2.81 (s, 3H). MS: m/z 405.1 (M−H$^+$).

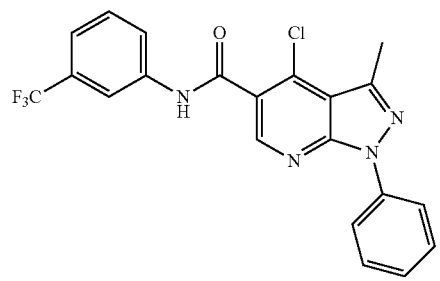 [SMILES: Cc1nn(-c2ccccc2)c2ncc(C(=O)Nc3cccc(C(F)(F)F)c3)c(Cl)c12]

Example 26

4-Chloro-3-methyl-1-phenyl-1H-pyrazolo[3,4-b]pyridine-5-carboxylic acid (3-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.85 (s, 1H), 8.19-8.17 (m, 3H), 8.00 (s, 1H), 7.89 (d, J=7.8 Hz, 1H), 7.58-7.45 (m, 4H), 7.39-7.37 (m, 1H), 2.84 (s, 3H). MS: m/z 431.1 (M+H$^+$).

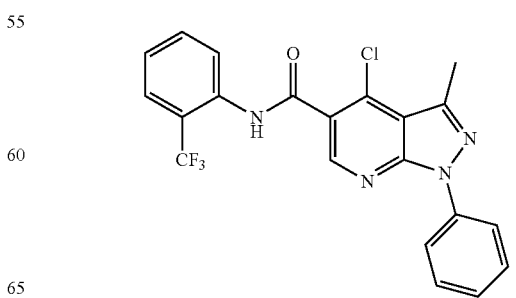

Example 27

4-Chloro-3-methyl-1-phenyl-1H-pyrazolo[3,4-b]pyridine-5-carboxylic acid (2-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, CDCl₃): δ=8.92 (s, 1H), 8.44-8.42 (m, 1H), 8.28 (d, J=7.2 Hz, 1H), 8.18-8.15 (m, 2H), 7.71-7.64 (m, 2H), 7.54 (t, J=8.0 Hz, 1H), 7.37-7.30 (m, 2H), 2.84 (s, 3H). MS: m/z 431.0 (M+H⁺).

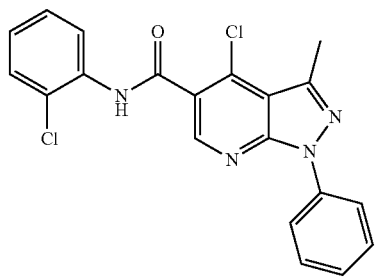 [SMILES: Cc1nn(-c2ccccc2)c2ncc(C(=O)Nc3ccccc3Cl)c(Cl)c12]

Example 28

4-Chloro-3-methyl-1-phenyl-1H-pyrazolo[3,4-b]pyridine-5-carboxylic acid (2-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, DMSO-d6): δ=10.41 (brs, 1H), 8.82 (s, 1H), 8.21 (d, J=8.0 Hz, 2H), 7.82 (d, J=7.8 Hz, 1H), 7.62-7.58 (m, 3H), 7.45-7.29 (m, 3H), 2.81 (s, 3H). MS: m/z 397.0 (M+H⁺).

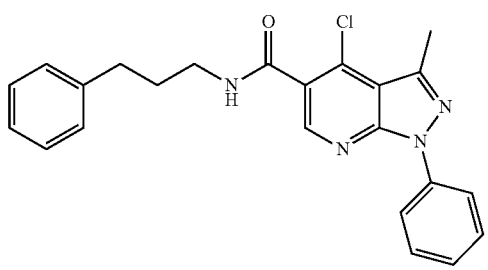 [SMILES: Cc1nn(-c2ccccc2)c2ncc(C(=O)NCCCc3ccccc3)c(Cl)c12]

Example 29

4-Chloro-3-methyl-1-phenyl-1H-pyrazolo[3,4-b]pyridine-5-carboxylic acid (3-phenyl-propyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, CDCl₃): δ=8.72 (s, 1H), 8.17-8.15 (m, 2H), 7.52 (t, J=8.0 Hz, 2H), 7.34-7.18 (m, 6H), 6.30 (brs, 1H), 3.55 (q, J=7.2 Hz, 2H), 2.80 (s, 3H), 2.77 (t, J=8.0 Hz, 2H), 2.05-1.98 (m, 2H). MS: m/z 405.1 (M+H⁺).

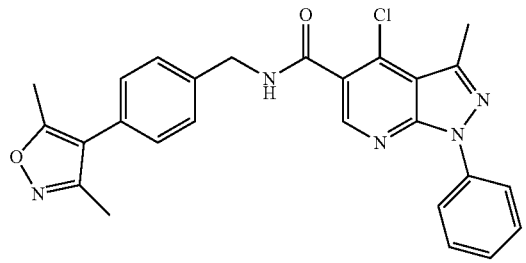 [SMILES: Cc1noc(C)c1-c1ccc(CNC(=O)c2cnc3c(c(C)nn3-c3ccccc3)c2Cl)cc1]

Example 30

4-Chloro-3-methyl-1-phenyl-1H-pyrazolo[3,4-b]pyridine-5-carboxylic acid 4-(3,5-dimethyl-isoxazol-4-yl)-benzylamide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.85 (s, 1H), 8.17 (d, J=7.8 Hz, 2H), 7.56-7.49 (m, 4H), 7.37-7.28 (m, 3H), 6.71 (m, 1H), 4.79-4.77 (d, J=5.7 Hz, 2H), 2.83 (s, 3H), 2.42 (s, 3H), 2.29 (s, 3H). MS: m/z 470.1 (M−H⁺).

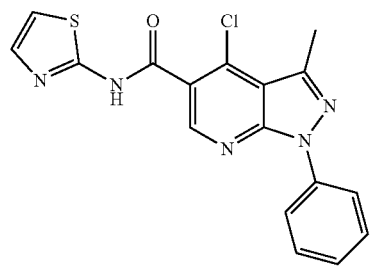 [SMILES: Cc1nn(-c2ccccc2)c2ncc(C(=O)Nc3nccs3)c(Cl)c12]

Example 31

4-Chloro-3-methyl-1-phenyl-1H-pyrazolo[3,4-b]pyridine-5-carboxylic acid thiazol-2-ylamide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, CDCl₃): δ=9.47 (s, 1H), 8.22-8.20 (dd, J=8.0 Hz, 1.2 Hz, 2H), 8.08 (d, J=4.8 Hz, 1H), 7.56-7.52 (m, 2H), 7.36-7.35 (m, 1H), 6.99 (d, J=5.2 Hz, 1H), 2.94 (s, 3H). MS: m/z 334.0 (M+H⁺).

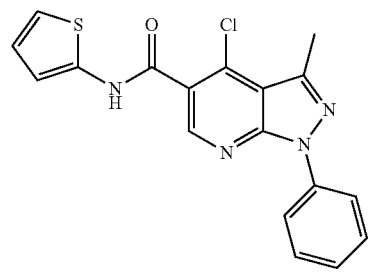 [SMILES: Cc1nn(-c2ccccc2)c2ncc(C(=O)Nc3cccs3)c(Cl)c12]

Example 32

4-Chloro-3-methyl-1-phenyl-1H-pyrazolo[3,4-b]pyridine-5-carboxylic acid thiophen-2-ylamide

The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=8.96 (s, 1H), 8.82-8.81 (m, 1H), 8.17 (d, J=7.6 Hz, 2H), 7.56-7.52 (m, 2H), 7.37-7.35 (m, 1H), 7.01 (d, J=6.0 Hz, 1H), 6.94 (dd, J=5.6 Hz, 3.6 Hz, 1H), 6.84 (dd, J=4.4 Hz, 1.2 Hz, 1H), 2.86 (s, 3H). MS: m/z 369.0 (M+H$^+$).

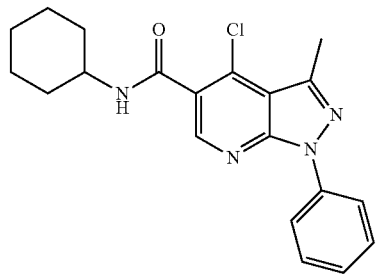 [SMILES: Cc1nn(-c2ccccc2)c2ncc(C(=O)NC3CCCCC3)c(Cl)c12]

Example 33

4-Chloro-3-methyl-1-phenyl-1H-pyrazolo[3,4-b]pyridine-5-carboxylic acid cyclohexylamide

The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=8.77 (s, 1H), 8.18-8.16 (m, 2H), 7.52 (t, J=8.2 Hz, 2H), 7.35-7.33 (m, 1H), 6.10-6.07 (m, 1H), 4.10-4.03 (m, 1H), 2.83 (s, 3H), 2.10-2.07 (m, 2H), 1.79-1.76 (m, 2H), 1.54-1.49 (m, 1H), 1.33-1.30 (m, 2H), 1.27-1.25 (m, 3H). MS: m/z 369.1 (M+H$^+$).

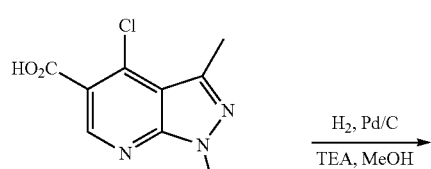

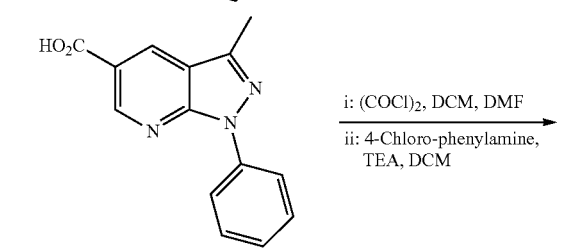

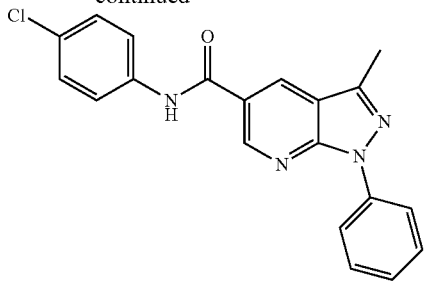

Example 34

3-Methyl-1-phenyl-1H-pyrazolo[3,4-b]pyridine-5-carboxylic acid (4-chloro-phenyl)-amide

Step 1

To a solution of 4-chloro-3-methyl-1-phenyl-1H-pyrazolo[3,4-b]pyridine-5-carboxylic acid (300 mg, 1.04 mmol) in MeOH (30 mL) was added TEA (0.29 mL, 2.08 mmol) and Pd/C (wet 10%, 30 mg) under N$_2$. The mixture was stirred at rt under hydrogen (50 psi) for 2 h. The reaction mixture was filtered and the filtrate was concentrated. The residue was triturated with 10% HCl solution to give 3-Methyl-1-phenyl-1H-pyrazolo[3,4-b]pyridine-5-carboxylic acid (188 mg, 71% yield) as a white solid. $^1$HNMR (400 MHz, DMSO-d6): δ=13.35 (s, 1H), 9.13 (d, J=2.0 Hz, 1H), 8.87 (d, J=2.0 Hz, 1H), 8.25-8.23 (d, J=8.4 Hz, 2H), 7.59-7.55 (m, 2H), 7.35 (t, J=7.2 Hz, 1H), 2.67 (s, 3H).

Step 2

The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=9.05 (d, J=2.0 Hz, 1H), 8.58 (d, J=2.0 Hz, 1H), 8.24 (d, J=8.4 Hz, 2H), 7.92 (brs, 1H), 7.63 (d, J=8.8 Hz, 2H), 7.53 (t, J=8.0 Hz, 2H), 7.38-7.31 (m, 3H), 2.69 (s, 3H). MS: m/z 361.1 (M−H$^+$).

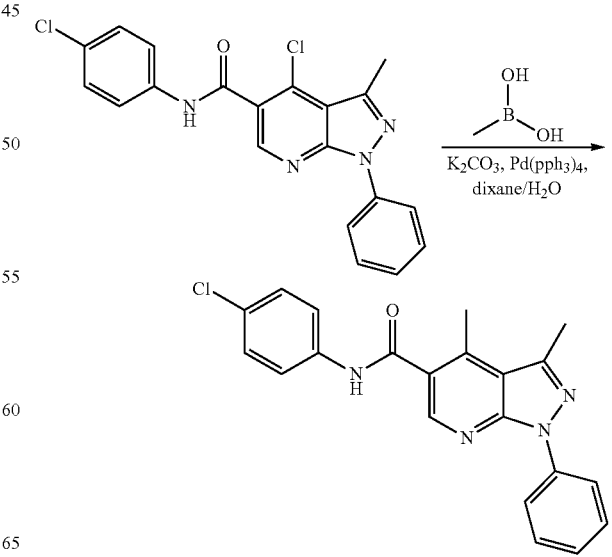

Example 35

3,4-Dimethyl-1-phenyl-1H-pyrazolo[3,4-b]pyridine-5-carboxylic acid (4-chloro-phenyl)-amide To a mixture of 4-chloro-3-methyl-1-phenyl-1H-pyrazolo[3,4-b]pyridine-5-carboxylic acid (4-chloro-phenyl)-amide (100 mg, 0.25 mmol), methyiboronic acid (30 mg, 0.5 mmol) and $K_2CO_3$ (104 mg, 0.75 mmol) in dioxane/water (10 mL/2 mL) was added Pd (pph$_3$)$_4$ (20%×100 mg), the vessel was evacuated and back-filled three times with $N_2$ before the reaction mixture was heated to 100° C. for 17 hrs. The reaction mixture was poured into water (50 mL) and extracted with EA (50 mL×2). The organic layers were combined, dried over $Na_2SO_4$ and concentrated. The residue was purified by prep-HPLC to give 3,4-dimethyl-1-phenyl-1H-pyrazolo[3,4-b]pyridine-5-carboxylic acid (4-chloro-phenyl)-amide (16.1 mg, yield: 17%) as a white solid. $^1$HNMR (400 MHz, CDCl$_3$): δ=8.65 (s, 1H), 8.19 (d, J=8.0 Hz, 2H), 7.63-7.60 (m, 3H), 7.52 (t, J=8.0 Hz, 2H), 7.38-7.32 (m, 3H), 2.89 (s, 3H), 2.81 (s, 3H). MS: m/z 375.1 (M–H$^+$).

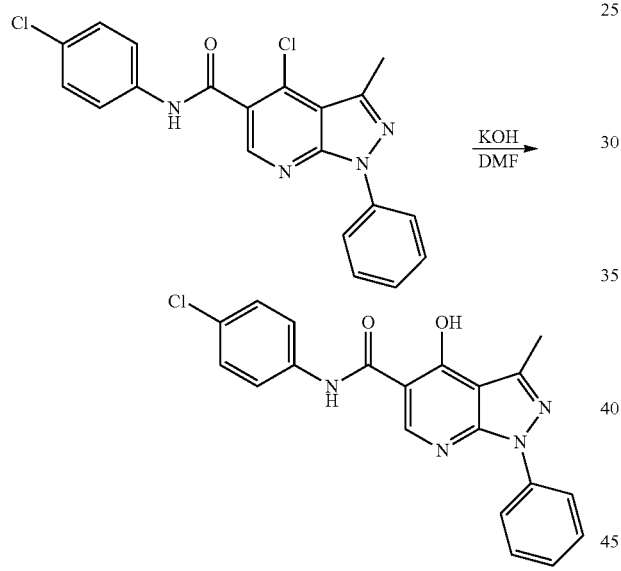

Example 36

4-Hydroxy-3-methyl-1-phenyl-1H-pyrazolo[3,4-b]pyridine-5-carboxylic acid (4-chloro-phenyl)-amide To a solution of 4-chloro-3-methyl-1-phenyl-1H-pyrazolo[3,4-b]pyridine-5-carboxylic acid (4-chloro-phenyl)-amide (100 mg, 0.25 mmol) in DMF (20 mL) was added KOH (35 mg, 0.63 mmol). The reaction mixture was stirred at 70° C. overnight. The reaction mixture was poured into water (50 mL) and extracted with DCM (50 mL×2). The organic layers were combined, dried over $Na_2SO_4$ and concentrated. The residue was purified by prep-TLC (PE/EA=2/1) to give 4-hydroxy-3-methyl-1-phenyl-1H-pyrazolo[3,4-b]pyridine-5-carboxylic acid (4-chloro-phenyl)-amide (12.1 mg, yield: 13%) as a yellow solid. $^1$HNMR (400 MHz, DMSO-d6): δ=13.16 (brs, 1H), 12.52 (brs, 1H), 8.48 (s, 1H), 7.77-7.75 (m, 4H), 7.62 (t, J=7.8 Hz, 2H), 7.52-7.50 (m, 1H), 7.40 (d, J=8.4 Hz, 2H), 2.62 (s, 3H). MS: m/z 377.1 (M–H$^+$).

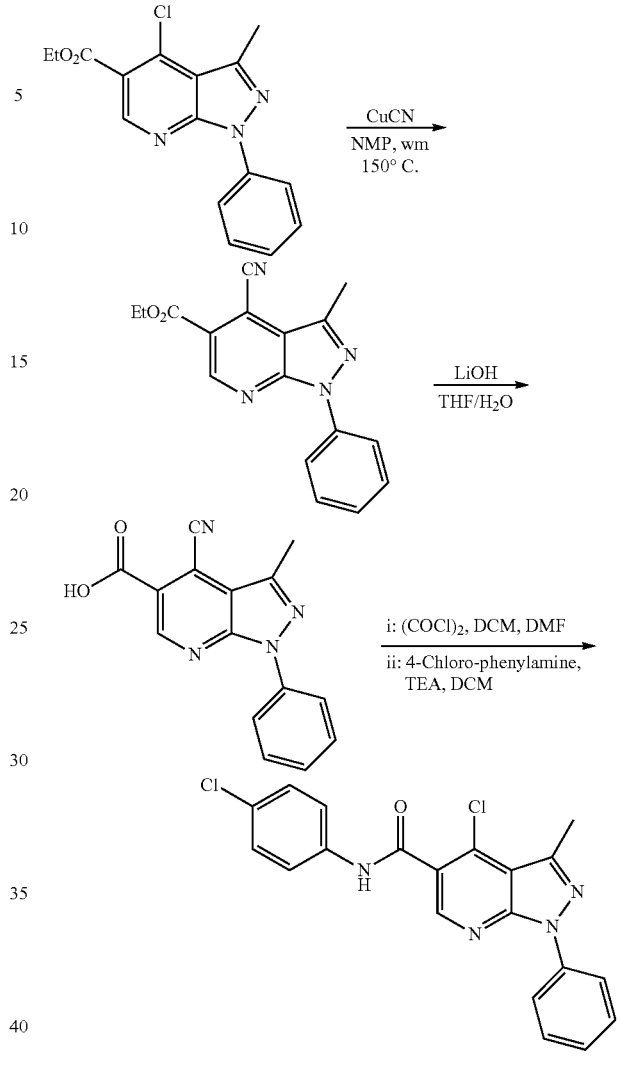

Example 37

4-Cyano-3-methyl-1-phenyl-1H-pyrazolo[3,4-b]pyridine-5-carboxylic acid (4-chloro-phenyl)-amide

Step 1

To a solution of 4-chloro-3-methyl-1-phenyl-1H-pyrazolo[3,4-b]pyridine-5-carboxylic acid ethyl ester (300 mg, 0.95 mmol) in NMP (10 mL) was added CuCN (170 mg, 1.9 mmol). The mixture was stirred at 150° C. under microwave for 5 hrs. The reaction mixture was poured into water (100 mL) and extracted with DCM (100 mL×2). The organic layers were combined, dried over $Na_2SO_4$ and concentrated. The residue was triturated with EA (5 mL) to give 4-cyano-3-methyl-1-phenyl-1H-pyrazolo[3,4-b]pyridine-5-carboxylic acid ethyl ester (135 mg, yield: 46%) as a yellow solid. $^1$HNMR (400 MHz, CDCl$_3$): δ=9.32 (s, 1H), 8.18 (d, J=8.0 Hz, 2H), 7.55 (t, J=8.0 Hz, 2H), 7.37 (d, J=8.0 Hz, 1H), 4.55 (q, J=7.2 Hz, 2H), 2.92 (s, 3H), 1.50 (t, J=7.0 Hz, 3H).

Step 2-3

These two steps were similar to 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl₃): δ=9.13 (s, 1H), 8.89 (brs, 1H), 8.24-8.22 (m, 2H), 7.60-7.55 (m, 4H), 7.38-7.30 (m, 3H), 3.02 (s, 3H). MS: m/z 388.0 (M+H⁺).

(4-chloro-phenyl)-amide (15.9 mg, yield: 16%) of as a white solid. ¹HNMR (300 MHz, DMSO-d6): δ=10.75 (s, 1H), 8.92 (d, J=9.3 Hz, 1H), 8.22 (d, J=7.5 Hz, 2H), 7.79-7.76 (m, 2H), 7.60 (t, J=7.9 Hz, 2H), 7.47-7.39 (m, 3H), 2.73 (s, 3H). MS: m/z 379.0 (M−H⁺).

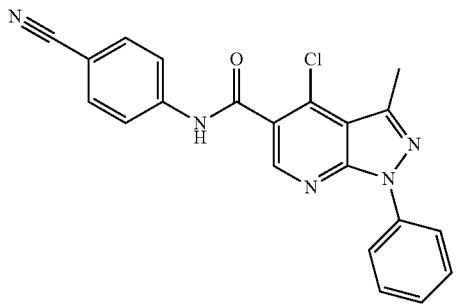 [SMILES: Cc1nn(-c2ccccc2)c2ncc(C(=O)Nc3ccc(C#N)cc3)c(Cl)c12]

Example 38

4-Cyano-3-methyl-1-phenyl-1H-pyrazolo[3,4-b]pyridine-5-carboxylic acid (4-cyano-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, DMSO-d6): δ=8.55 (s, 1H), 7.87-7.85 (m, 2H), 7.75 (d, J=8.8, 2H), 7.62-7.55 (m, 3H), 7.43-7.37 (m, 3H), 2.61 (s, 3H). MS: m/z 379.1(M+H⁺).

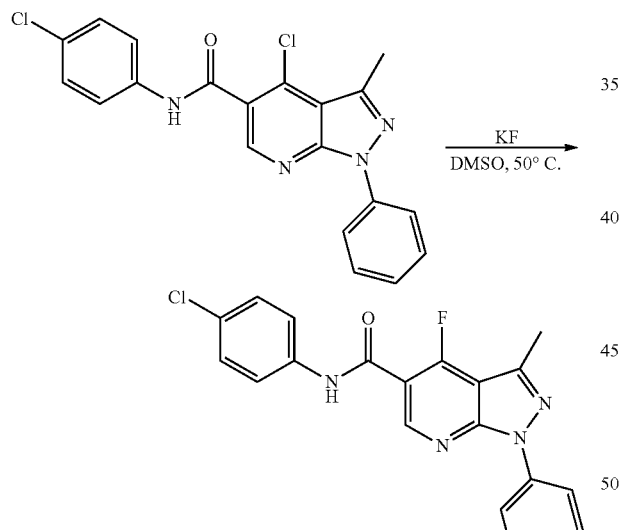

Example 39

4-Fluoro-3-methyl-1-phenyl-1H-pyrazolo[3,4-b]pyridine-5-carboxylic acid (4-chloro-phenyl)-amide A solution of 4-chloro-3-methyl-1-phenyl-1H-pyrazolo[3,4-b]pyridine-5-carboxylic acid (4-chloro-phenyl)-amide (100 mg, 0.25 mmol) and spray dried KF (29 mg, 0.5 mmol) in DMSO (5 mL) was stirred at 80° C. for 1 hr. The reaction mixture was poured into water and filtered. The filter cake was purified by prep-HPLC to give 4-fluoro-3-methyl-1-phenyl-1H-pyrazolo[3,4-b]pyridine-5-carboxylic acid

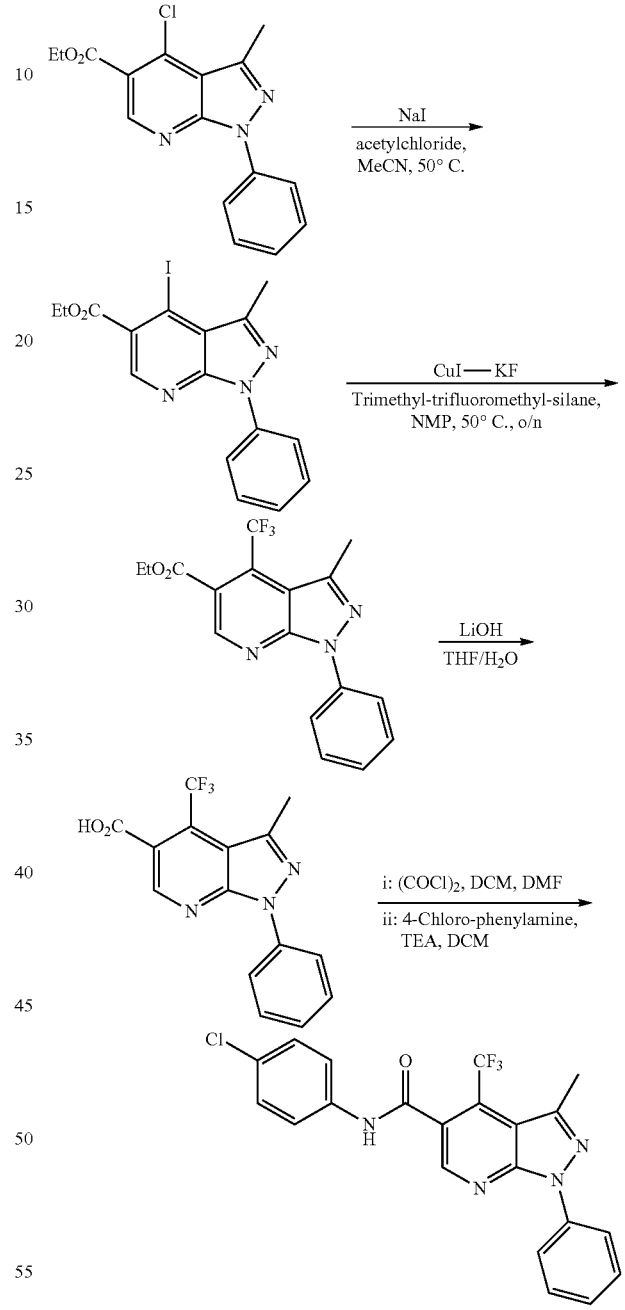

Example 40

3-Methyl-1-phenyl-4-trifluoromethyl-1H-pyrazolo[3,4-b]pyridine-5-carboxylic acid (4-chloro-phenyl)-amide Step 1

To a solution of 4-chloro-3-methyl-1-phenyl-1H-pyrazolo[3,4-b]pyridine-5-carboxylic acid ethyl ester 1 (2 g, 6.3 mmol) in ACN (100 mL) was added NaI (1.9 g, 12.7 mmol) and acetylchloride (10 mL). The reaction was stirred at 50° C. for 4 hrs. The reaction mixture was diluted with DCM (50 mL), washed with saturated aqueous NaHCO$_3$ solution (50 mL), saturated aqueous Na$_2$SO$_3$ solution (35 mL) and brine (35 mL), dried over Na$_2$SO$_4$, concentrated, purified by column (PE/EA=15/1) to give crude 4-iodo-3-methyl-1-phenyl-1H-pyrazolo[3,4-b]pyridine-5-carboxylic acid ethyl ester (2.5 g, yield: 96%) as a white solid. $^1$HNMR (300 MHz, CDCl$_3$): δ=8.81 (s, 1H), 8.20-8.15 (m, 2H), 7.57-7.51 (m, 2H), 7.38-7.33 (m, 1H), 4.52-4.45 (m, 2H), 2.90 (s, 3H), 1.49-1.44 (m, 3H).

Step 2

A mixture of CuI (1.1 g, 5.9 mmol) and KF (343 mg, 5.9 mmol) was heated at 210° C. under vacuum for 3 hrs before 4-iodo-3-methyl-1-phenyl-1H-pyrazolo[3,4-b]pyridine-5-carboxylic acid ethyl ester (1.5 g, 3.7 mmol) and trimethyl-trifluoromethyl-silane (1.1 mL, 7.4 mmol) in NMP (10 mL) was added. The mixture was then stirred at 50° C. overnight. The reaction mixture was poured into aqueous NH$_3$.H$_2$O (12%, 300 mL) and extracted with EA (200 mL×3). The combined organic layers were dried and evaporated. The residue was purified by column (PE/EA=200/1) to give 3-methyl-1-phenyl-4-trifluoromethyl-1H-pyrazolo[3,4-b]pyridine-5-carboxylic acid ethyl ester (959 mg, yield: 75%) as a yellow solid. $^1$HNMR (400 MHz, CDCl$_3$): δ=8.78 (s, 1H), 8.16-8.14 (m, 2H), 7.56-7.52 (m, 2H), 7.36 (t, J=7.2 Hz, 1H), 4.46 (q, J=7.2 Hz, 2H), 2.75-2.73 (m, 3H), 1.42 (t, J=7.2 Hz, 3H).

Step 3-4

These two steps were similar to 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.96 (s, 1H), 9.01 (s, 1H), 8.16 (d, J=7.6 Hz, 2H), 7.72 (d, J=8.8 Hz, 2H), 7.62-7.60 (m, 2H), 7.47-7.45 (m, 3H), 2.69 (s, 3H). MS: m/z 429.0 (M−H$^+$).

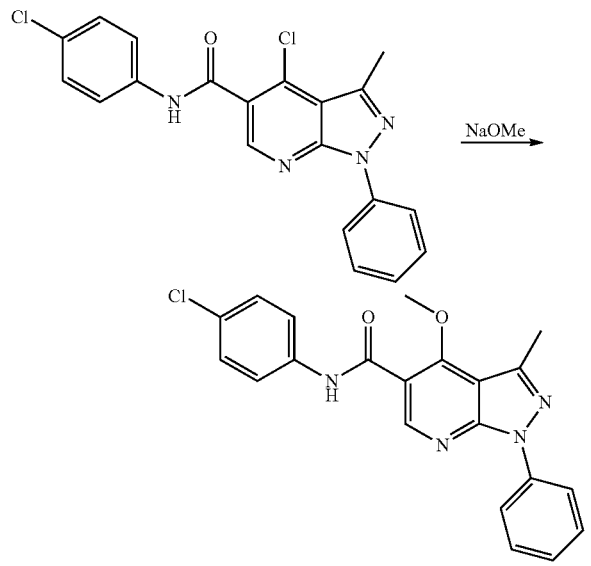

Example 41

4-Methoxy-3-methyl-1-phenyl-1H-pyrazolo[3,4-b]pyridine-5-carboxylic acid (4-chloro-phenyl)-amide To a freshly prepared solution of Na (6 mg, 0.26) in MeOH (20 mL) was added 4-chloro-N-(4-chlorophenyl)-3-methyl-1-phenyl-1H-pyrazolo[3,4-b]pyridine-5-carboxamide (50 mg, 0.13 mmol), and the mixture was stirred at reflux overnight. The reactant was evaporated to dryness in vacuum prior to the quench with water (5 mL). The aqueous phase was extracted with EA (10 mL×3) and the extracts were dried over Na2SO4. The solution was concentrated to dryness and the residue was purified by prep-TLC (PE/EA=1/1) to afford N-(4-chlorophenyl)-4-methoxy-3-methyl-1-phenyl-1H-pyrazolo[3,4-b]pyridine-5-carboxamide (26 mg, yield: 53%) as a white solid. $^1$HNMR (400 MHz, DMSO-d6): δ=10.81 (s, 1H), 8.64 (s, 1H), 8.23 (d, J=8.4 Hz, 2H), 7.79 (d, J=9.2 Hz, 2H), 7.56 (t, J=8.2 Hz, 2H), 7.44 (m, 2H), 7.33 (t, J=7.4 Hz, 1H), 3.31 (s, 3H), 2.68 (s, 3H). MS: m/z 393.1 (M+H$^+$).

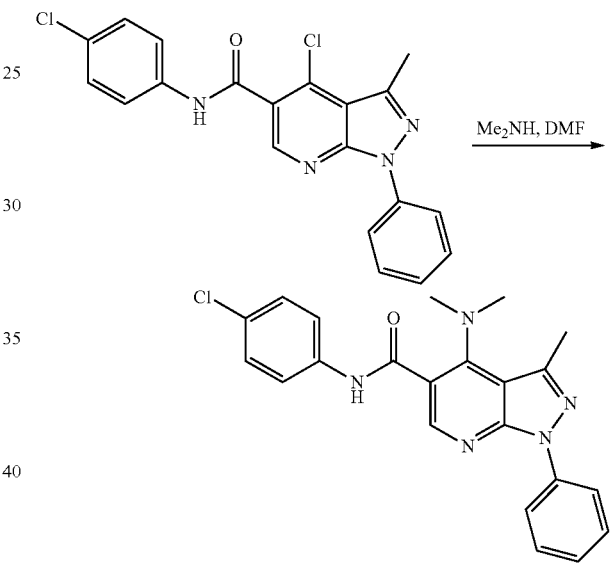

Example 42

N-(4-chlorophenyl)-4-(dimethylamino)-3-methyl-1-phenyl-1H-pyrazolo[3,4-b]pyridine-5-carboxamide To a solution of 4-chloro-N-(4-chlorophenyl)-3-methyl-1-phenyl-1H-pyrazolo[3,4-b]pyridine-5-carboxamide (30 mg, 0.075 mmol) in DMF (20 mL) was added dimethylamine.HCl (30 mg, 0.37 mmol) and TEA (0.5 mL). The mixture was irradiated under MW at 120° C. for 2 hrs. The reactant was evaporated to remove most of DMF and the residue was diluted with EA and water (each 5 mL). The organic layer was concentrated and purified by prep-TLC (PE/EA=1/1) to afford N-(4-chlorophenyl)-4-(dimethylamino)-3-methyl-1-phenyl-1H-pyrazolo[3,4-b]pyridine-5-carboxamide (21 mg, yield: 75%) as a white solid. $^1$HNMR (400 MHz, DMSO-d6): δ=10.77 (s, 1H), 8.39 (s, 1H), 8.21 (d, J=7.6 Hz, 2H), 7.78 (d, J=8.8 Hz, 2H), 7.54 (t, J=7.8 Hz, 2H), 7.42 (d, J=8.8 Hz, 2H), 7.31 (t, J=7.6 Hz, 1H), 3.04 (s, 6H), 2.70 (s, 3H). MS: m/z 406.1 (M+H$^+$).

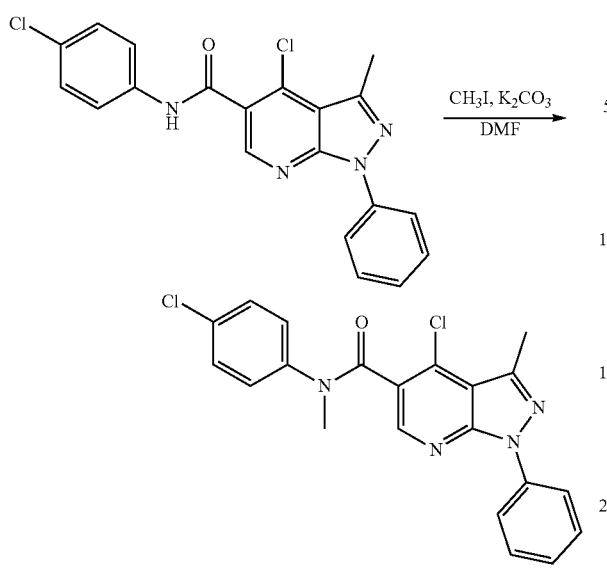

Example 43

4-Chloro-3-methyl-1-phenyl-1H-pyrazolo[3,4-b]pyridine-5-carboxylic acid (4-chloro-phenyl)-methyl-amide To a solution of 4-chloro-3-methyl-1-phenyl-1H-pyrazolo[3,4-b]pyridine-5-carboxylic acid (4-chloro-phenyl)-amide (50 mg, 0.13 mmol) in DMF (6 mL) was added iodomethane (0.02 mL, 0.33 mmol) and K$_2$CO$_3$ (54 mg, 0.39 mmol). Then the reaction mixture was stirred at room temperature overnight. Water was added and stirred for 30 min, then extracted with EA (20 mL×2). The organic layers were combined, dried over Na$_2$SO$_4$ and concentrated. The residue was purified by prep-TLC (PE/EA=3/1) to afford 4-chloro-3-methyl-1-phenyl-1H-pyrazolo[3,4-b]pyridine-5-carboxylic acid (4-chloro-phenyl)-methyl-amide (8.8 mg, yield: 16%) as a white solid.
$^1$HNMR (400 MHz, CDCl$_3$): δ=8.26 (s, 1H), 8.07 (d, J=7.6 Hz, 2H), 7.52-7.47 (m, 2H), 7.32-7.27 (m, 1H), 7.19-7.17 (m, 2H), 7.09-7.07 (m, 2H), 3.54 (s, 3H), 2.76 (s, 3H). MS: m/z 411.1 (M+H$^+$).

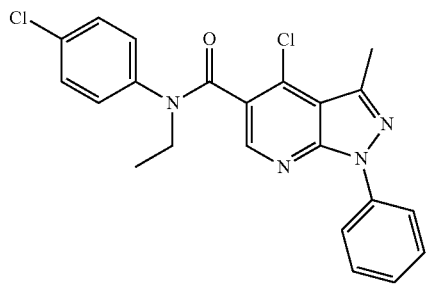 [SMILES: CCN(C(=O)c1cnc2c(c(C)nn2-c2ccccc2)c1Cl)c1ccc(Cl)cc1]

Example 44

4-Chloro-3-methyl-1-phenyl-1H-pyrazolo[3,4-b]pyridine-5-carboxylic acid (4-chloro-phenyl)-ethyl-amide The title compound was prepared using general procedure for 4-chloro-3-methyl-1-phenyl-1H-pyrazolo[3,4-b]pyridine-5-carboxylic acid (4-chloro-phenyl)-methyl-amide (Example 43). $^1$HNMR (400 MHz, CDCl$_3$): δ=8.24 (s, 1H), 8.06 (d, J=8.0 Hz, 2H), 7.48 (t, J=7.8 Hz, 2H), 7.31-7.30 (m, 1H), 7.18 (d, J=8.4 Hz, 2H), 7.08 (d, J=8.4 Hz, 2H), 4.02-4.00 (m, 2H), 2.76 (s, 3H), 1.29 (t, J=7.2 Hz, 3H). MS: m/z 425.1 (M+H$^+$).

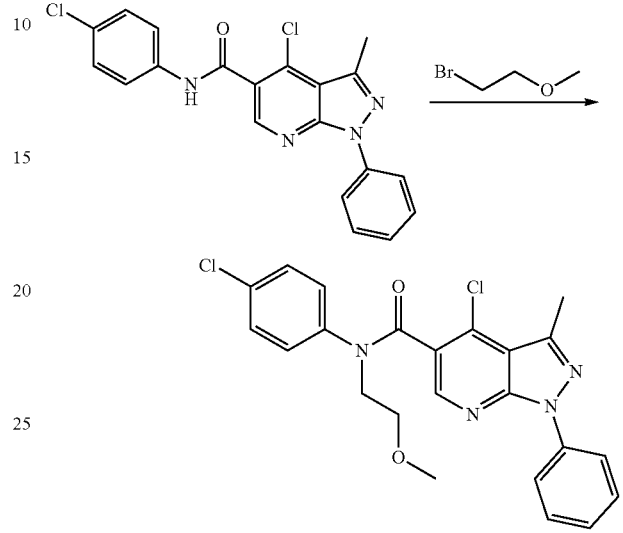

Example 45

4-Chloro-3-methyl-1-phenyl-1H-pyrazolo[3,4-b]pyridine-5-carboxylic acid (4-chloro-phenyl)-(2-methoxy-ethyl)-amide To a mixture of 4-chloro-3-methyl-1-phenyl-1H-pyrazolo[3,4-b]pyridine-5-carboxylic acid (4-chloro-phenyl)-amide (50 mg, 0.13 mmol) and Cs$_2$CO$_3$ (85 mg, 0.26 mmol) in DMF (10 mL) was added 1-bromo-2-methoxy-ethane (0.025 mL, 0.26 mmol). The reaction mixture was heated to 50° C. overnight. The reaction mixture was filtered and the filtrate was evaporated to afford a residue which was extracted into DCM and washed with water, brine and dried over Na$_2$SO$_4$. The solution was evaporated and the residue was purified by prep-HPLC to give 4-chloro-3-methyl-1-phenyl-1H-pyrazolo[3,4-b]pyridine -5-carboxylic acid (4-chloro-phenyl)-(2-methoxy-ethyl)-amide (10.2 mg, yield: 17%) as a white solid. $^1$HNMR (400 MHz, CDCl$_3$): δ=8.26 (s, 1H), 8.06 (d, J=7.6 Hz, 2H), 7.48 (t, J=8.2 Hz, 2H), 7.31-7.30 (m, 1H), 7.19-7.15 (m, 4H), 4.11 (t, J=5.6 Hz, 2H), 3.71 (t, J=5.6 Hz, 2H), 3.40 (s, 3H), 2.76 (s, 3H). MS: m/z 455.1 (M+H$^+$).

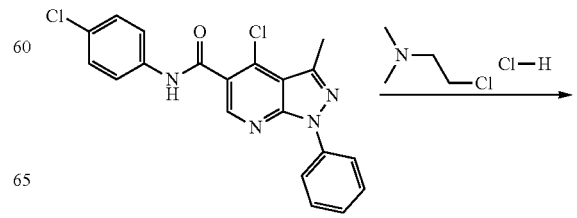

-continued

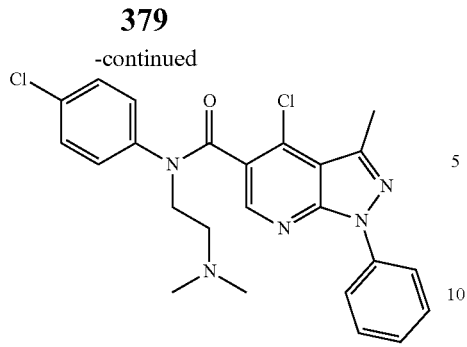

Example 46

4-Chloro-3-methyl-1-phenyl-1H-pyrazolo[3,4-b]pyridine-5-carboxylic acid (4-chloro-phenyl)-(2-dimethylamino-ethyl)-amide Sodium hydride (24 mg, 0.6 mmol, 60 percent) was added to a solution of 4-chloro-3-methyl -1-phenyl-1H-pyrazolo[3,4-b]pyridine-5-carboxylic acid (4-chloro-phenyl)-amide (100 mg, 0.25 mmol) in dry DMF (5 mL) under $N_2$. The mixture was stirred at rt for 30 mins, then (2-chloro-ethyl)-dimethyl-amine HCl salt (45 mg, 0.3 mmol) was added. The mixture was heated to 70° C. for 4 hrs. The mixture was cooled to rt, then diluted with 5% $NaHCO_3$ solution (30 mL) and extracted with EA (30 mL×3). The combined organic extracts were washed with brine (60 mL), dried over $Na_2SO_4$ and concentrated. The residue was purified by prep-HPLC to give 4-chloro-3-methyl-1-phenyl-1H-pyrazolo[3,4-b]pyridine-5-carboxylic acid (4-chloro-phenyl)-(2-dimethylamino-ethyl)-amide (19.5 mg, yield: 16%) as a white solid. $^1$HNMR (300 MHz, $CDCl_3$): δ=8.28 (s, 1H), 8.08 (d, J=7.5 Hz, 2H), 7.52-7.47 (m, 2H), 7.34-7.31 (m, 1H), 7.19-7.17 (m, 4H), 4.10-4.06 (m, 2H), 2.77 (s, 3H), 2.64-2.59 (m, 2H), 2.33 (s, 6H). MS: m/z 468.1 (M+H$^+$).

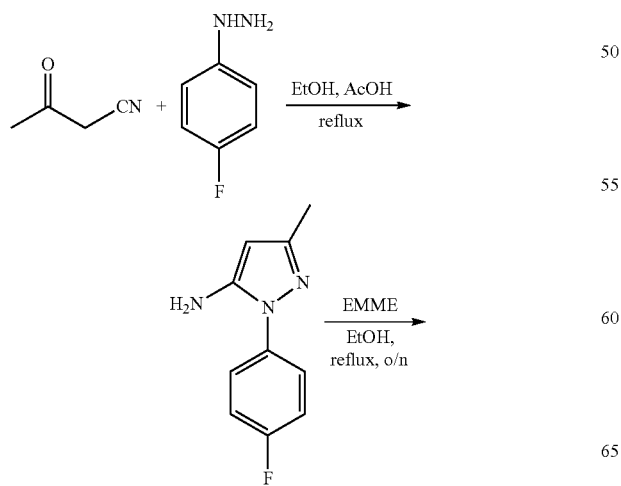

-continued

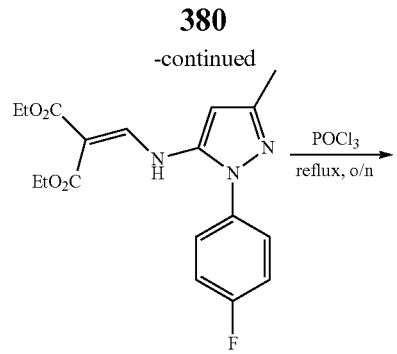

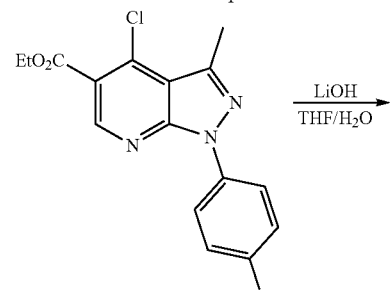

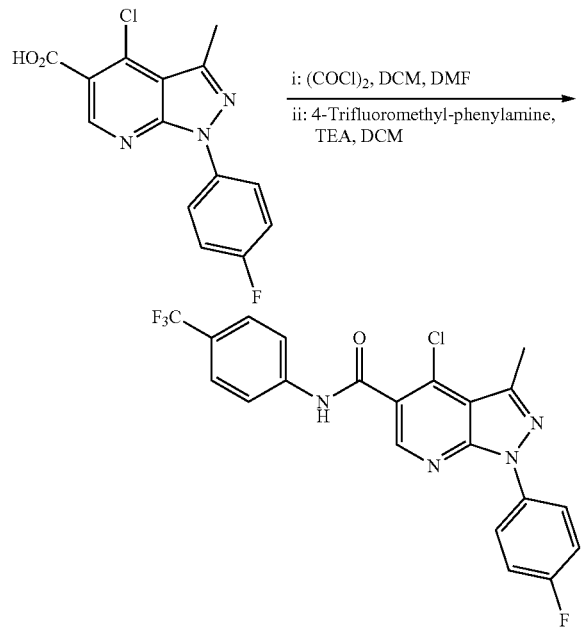

Example 47

4-Chloro-1-(4-fluoro-phenyl)-3-methyl-1H-pyrazolo[3,4-b]pyridine-5-carboxylic acid (4-trifluoromethyl-phenyl)-amide Step 1

A solution of (4-fluoro-phenyl)-hydrazine (HCl salt, 802 mg, 5.8 mmol) and 3-oxo-butyronitrile (500 mg, 5.8 mmol) in EtOH/AcOH (10 mL/0.2 mL) was stirred at refluxing overnight. The reaction solution was concentrated in vacuum to give crude 2-(4-fluoro-phenyl)-5-methyl-2H-pyrazol-3-ylamine (1.1 g, yield: quantitative) as a yellow solid which was used for the next step without any purification. $^1$H NMR (400 MHz, DMSO-d6): δ=7.6-7.64 (m, 2H), 7.45 (t, J=8.8 Hz, 1H), 5.66 (s, 1H), 2.24 (s, 3H).

Step 2-5

These four steps were similar to 4-chloro-3-methyl-1-phenyl-1H-pyrazolo[3,4-b]pyridine-5-carboxylic acid (4-bromo-phenyl)-amide (Example 1). ¹HNMR (400 MHz, DMSO-d6): δ=11.08 (s, 1H), 8.85 (s, 1H), 8.22 (dd, J=8.8, 4.8 Hz, 2H), 7.95 (d, J=8.0 Hz, 2H), 7.77 (d, J=8.4 Hz, 2H), 7.45 (t, J=8.8 Hz, 1H), 2.80 (s, 3H). MS: m/z 447.0 (M–H⁺).

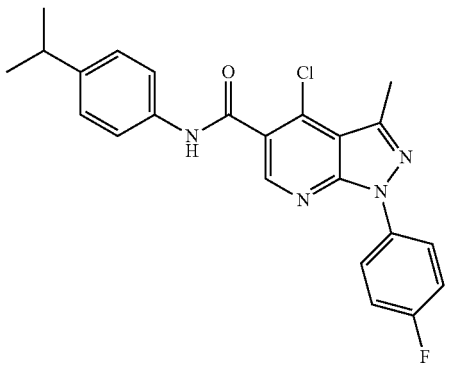

Example 48

4-Chloro-1-(4-fluoro-phenyl)-3-methyl-1H-pyrazolo[3,4-b]pyridine-5-carboxylic acid (4-isopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1).
¹HNMR (300 MHz, DMSO-d6): δ=10.62 (s, 1H), 8.79 (s, 1H), 8.24-8.19 (m, 2H), 7.65 (d, J=8.4 Hz, 2H), 7.47-7.42 (m, 2H), 7.25 (m, 2H), 2.90-2.85 (m, 1H), 2.78 (s, 3H), 1.23 (d, J=9.6 Hz, 6H). MS: m/z 423.1 (M+H⁺).

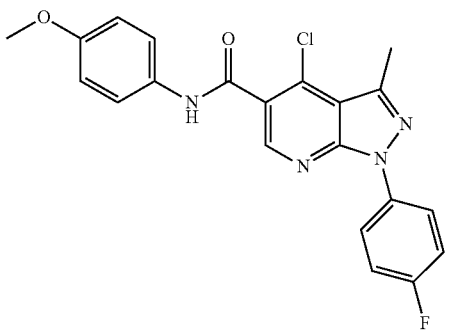 [SMILES: COc1ccc(NC(=O)c2cnc3c(c(C)nn3-c3ccc(F)cc3)c2Cl)cc1]

Example 49

4-Chloro-1-(4-fluoro-phenyl)-3-methyl-1H-pyrazolo[3,4-b]pyridine-5-carboxylic acid (4-methoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=10.57 (s, 1H), 8.79 ((s, 1H), 8.24-8.19 (m, 2H), 7.65 (d, J=9.0 Hz, 2H), 7.47-7.41 (d, J=9.0 Hz, 2H), 6.95 (m, 2H), 3.76 (s, 3H), 2.79 (s, 3H). MS: m/z 409.0 (M–H⁺).

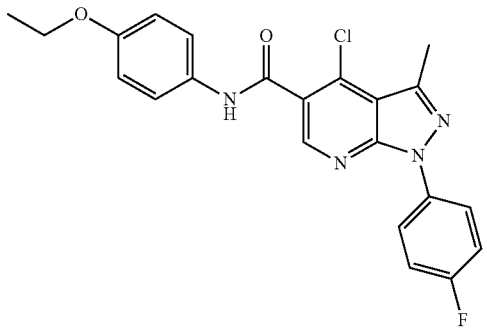 [SMILES: CCOc1ccc(NC(=O)c2cnc3c(c(C)nn3-c3ccc(F)cc3)c2Cl)cc1]

Example 50

4-Chloro-1-(4-fluoro-phenyl)-3-methyl-1H-pyrazolo[3,4-b]pyridine-5-carboxylic acid (4-ethoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=10.55 (s, 1H), 8.79 (s, 1H), 8.24-8.19 (m, 2H), 7.65 (d, J=9.0 Hz, 2H), 7.47-7.44 (m, 2H), 6.94 (m, 2H), 4.01 (q, J=7.2 Hz, 2H), 2.76 (s, 3H), 1.35-1.23 (t, J=7.2 Hz, 3H). MS: m/z 423.1 (M–H⁺).

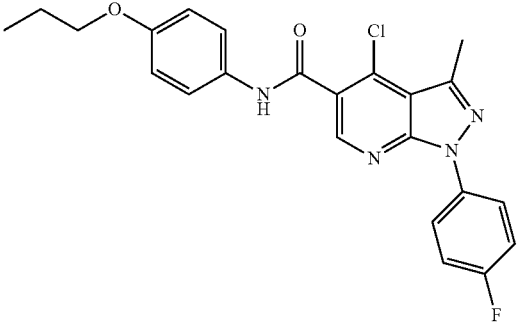 [SMILES: CCCOc1ccc(NC(=O)c2cnc3c(c(C)nn3-c3ccc(F)cc3)c2Cl)cc1]

Example 51

4-Chloro-1-(4-fluoro-phenyl)-3-methyl-1H-pyrazolo[3,4-b]pyridine-5-carboxylic acid (4-propoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=10.55 (s, 1H), 8.79 (s, 1H), 8.24-8.19 (m, 2H), 7.64 (d, J=8.7 Hz, 2H), 7.47-7.42 (m, 2H), 6.95 (d, J=8.7 Hz, 2H), 3.92 (t, J=6.6 Hz, 2H), 2.79 (s, 3H), 1.77-1.70 (m, 2H), 1.01-0.96 (t, J=7.5 Hz, 3H). MS: m/z 437.0 (M–H⁺).

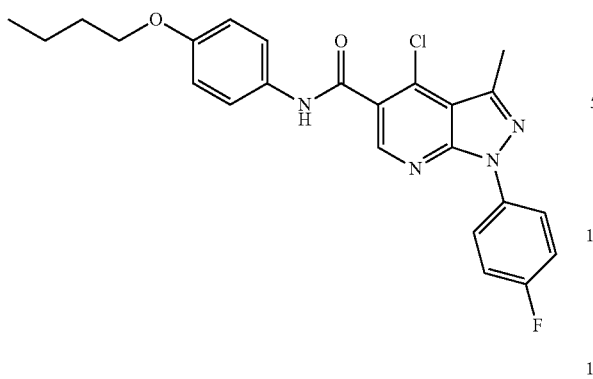

Example 52

4-Chloro-1-(4-fluoro-phenyl)-3-methyl-1H-pyrazolo[3,4-b]pyridine-5-carboxylic acid (4-butoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.55 (s, 1H), 8.79 (s, 1H), 8.24-8.19 (m, 2H), 7.64 (d, J=8.7 Hz, 2H), 7.47-7.42 (m, 2H), 6.95 (d, J=8.7 Hz, 2H), 3.96 (t, J=6.3 Hz, 2H), 2.79 (s, 3H), 1.72-1.67 (m, 2H), 1.48-1.40 (m, 2H), 0.94 (t, J=7.2 Hz, 3H). MS: m/z 451.1 (M−H$^+$).

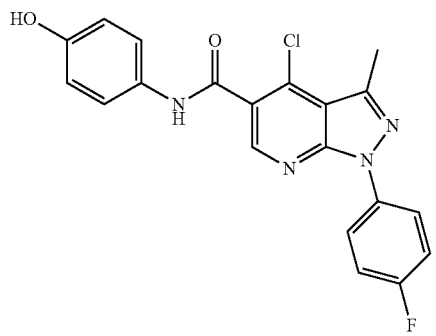 [SMILES: Cc1nn(-c2ccc(F)cc2)c2ncc(C(=O)Nc3ccc(O)cc3)c(Cl)c12]

Example 53

4-Chloro-1-(4-fluoro-phenyl)-3-methyl-1H-pyrazolo[3,4-b]pyridine-5-carboxylic acid (4-hydroxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.45 (s, 1H), 9.32 (s, 1H), 8.77 (s, 1H), 8.24-8.19 (m, 2H), 7.54-7.41 (m, 4H), 6.77 (, J=8.7 Hz, 2H), 2.79 (s, 3H). MS: m/z 395.0 (M−H$^+$).

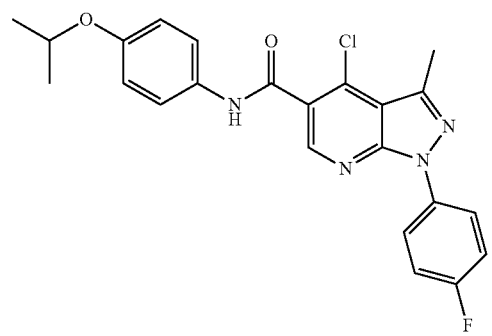 [SMILES: Cc1nn(-c2ccc(F)cc2)c2ncc(C(=O)Nc3ccc(OC(C)C)cc3)c(Cl)c12]

Example 54

4-Chloro-1-(4-fluoro-phenyl)-3-methyl-1H-pyrazolo[3,4-b]pyridine-5-carboxylic acid (4-isopropoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.56 (s, 1H), 8.79 (s, 1H), 8.24-8.19 (m, 2H), 7.64 (d, J=8.7 Hz, 2H), 7.48-7.42 (m, 2H), 6.94 (d, J=8.7 Hz, 2H), 4.60-4.56 (m, 1H), 2.79 (s, 3H), 1.25 (d, J=6.0 Hz, 6H). MS: m/z 436.9 (M−H$^+$).

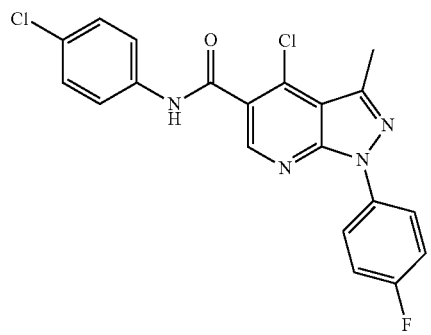

Example 55

4-Chloro-1-(4-fluoro-phenyl)-3-methyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.85 (s, 1H), 8.82 (s, 1H), 8.27-8.18 (m, 2H), 7.83-7.73 (m, 2H), 7.51-7.40 (4 m, 4H), 2.80 (s, 3H). MS: m/z: 415.1 (M+H$^+$).

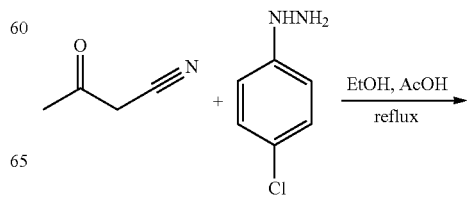

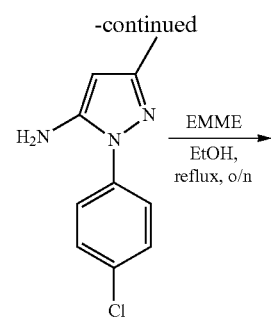
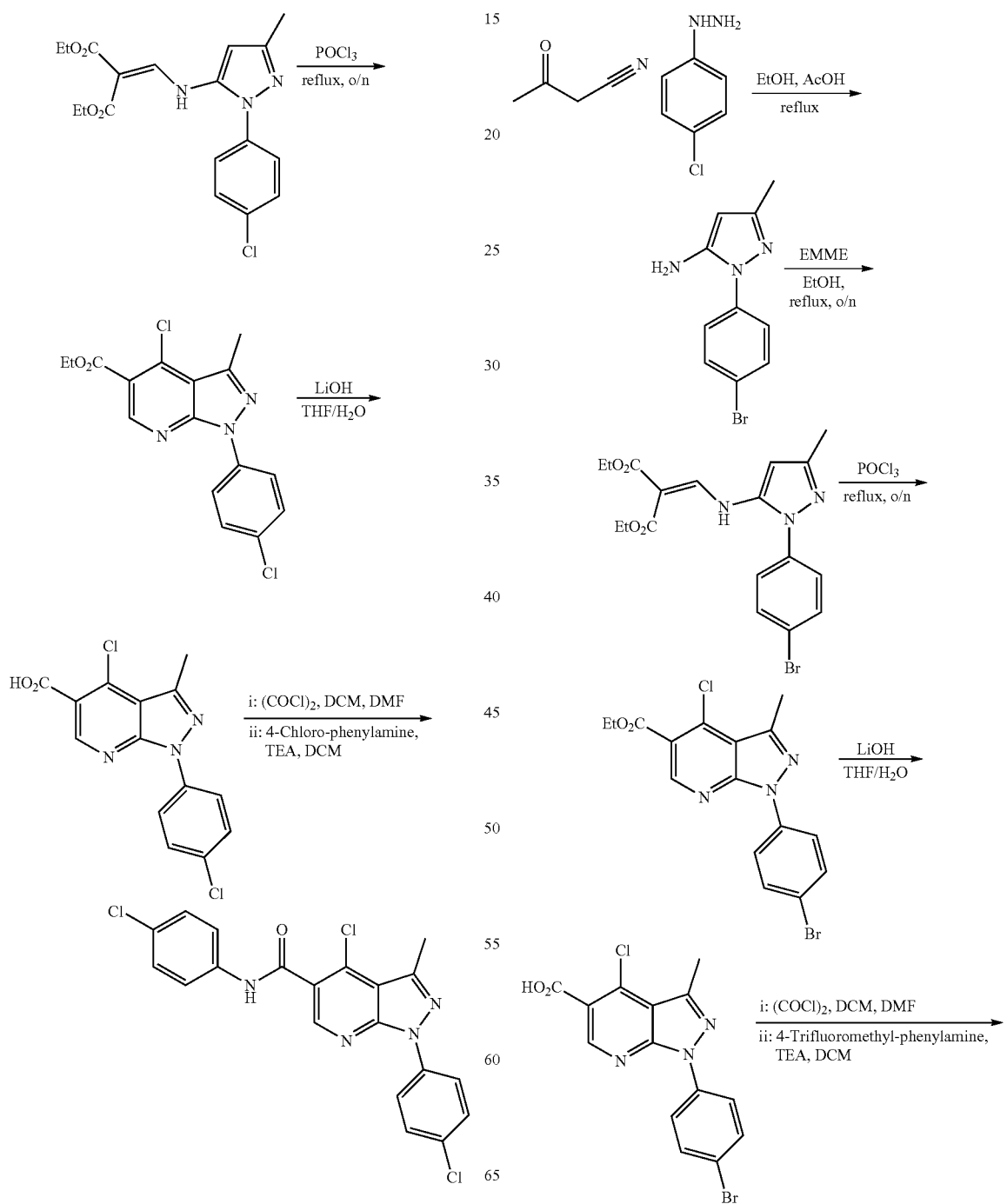
Example 56
4-Chloro-1-(4-chloro-phenyl)-3-methyl-1H-pyrazolo[3,4-b]pyridine-5-carboxylic acid (4-chloro-phenyl)-amide
The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.09 (s, 1H), 8.83 (s, 1H), 8.28 (d, J=9.2, 2H), 7.78 (d, J=9.2, 2H), 7.66 (d, J=8.4, 2H), 7.45 (d, J=8.4, 2H), 2.97 (s, 3H); MS: m/z 431.1.

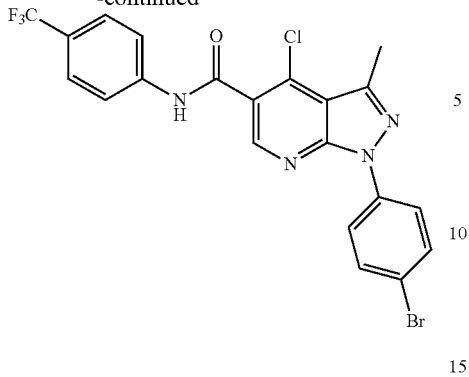

Example 57

1-(4-Bromo-phenyl)-4-chloro-3-methyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.89 (s, 1H), 8.19-8.14 (m, 3H), 7.85-7.82 (m, 2H), 7.71-7.63 (m, 4H), 2.86 (s, 3H). MS: m/z 509.0 (M+H$^+$).

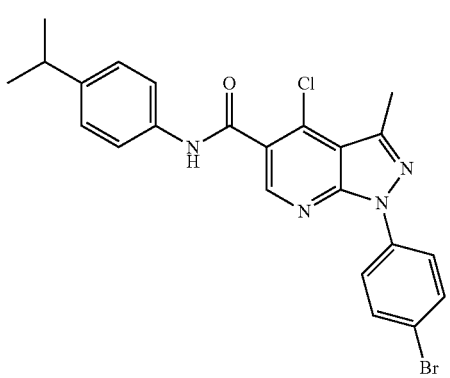

Example 58

1-(4-Bromo-phenyl)-4-chloro-3-methyl-1H-pyrazolo[3,4-b]pyridine-5-carboxylic acid (4-isopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.86 (brs, 1H), 8.18-8.14 (m, 2H), 7.94-7.92 (m, 1H), 7.66-7.56 (m, 4H), 7.32-7.25 (m, 2H), 2.99-2.90 (m, 1H), 2.84 (s, 3H), 1.29-1.22 (m, 6H). MS: m/z 483.1 (M+H$^+$).

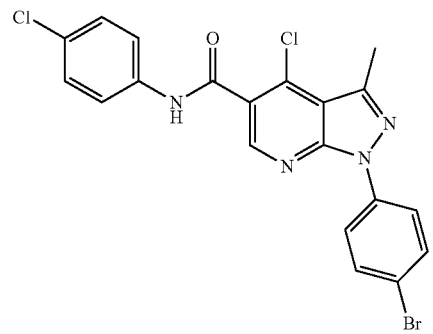

Example 59

1-(4-Bromo-phenyl)-4-chloro-3-methyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.89 (s, 1H), 8.85 (s, 1H), 8.23 (d, J=7.8 Hz, 2H), 7.80-7.76 (m, 4H), 7.46 (d, J=8.4 Hz, 2H), 2.79 (s, 3H). MS: m/z 475.0 (M+H$^+$).

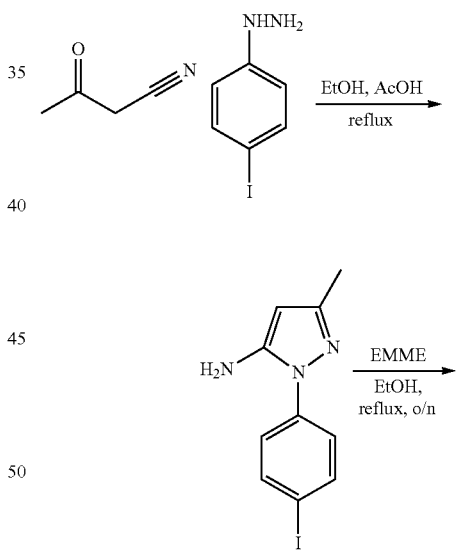

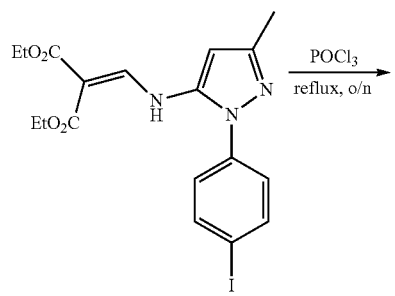

389
-continued

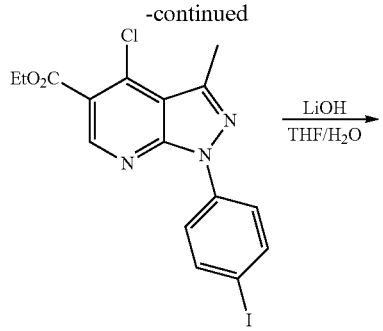

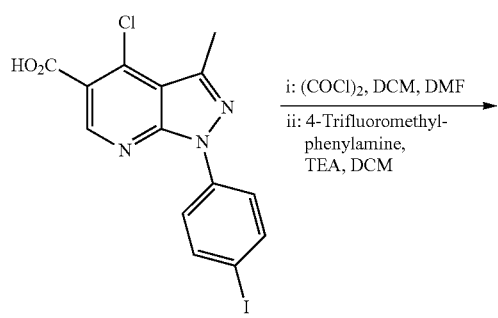

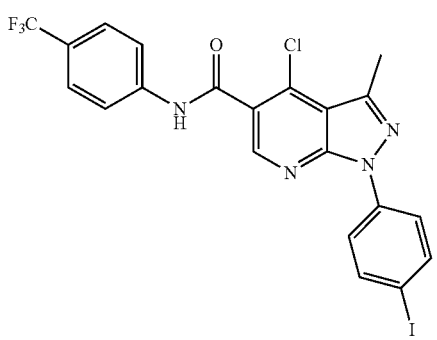

Example 60

4-Chloro-1-(4-iodo-phenyl)-3-methyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.85 (s, 1H), 8.26 (brs, 1H), 8.03 (d, J=8.7 Hz, 2H), 7.85-7.82 (m, 4H), 7.68 (d, J=8.7 Hz, 2H), 2.83 (s, 3H). MS: m/z 555.0 (M+H$^+$).

390

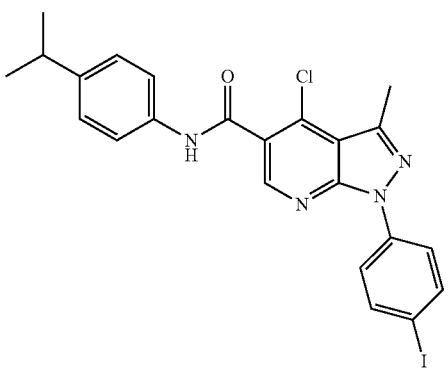 [SMILES: Cc1nn(-c2ccc(I)cc2)c2ncc(C(=O)Nc3ccc(C(C)C)cc3)c(Cl)c12]

Example 61

4-Chloro-1-(4-iodo-phenyl)-3-methyl-1H-pyrazolo[3,4-b]pyridine-5-carboxylic acid (4-isopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.83 (s, 1H), 8.05-8.01 (m, 3H), 7.83 (d, J=9.0 Hz, 2H), 7.60 (d, J=8.4 Hz, 2H), 7.29-7.26 (m, 2H), 2.97-2.91 (m, 1H), 2.82 (s, 3H), 1.28 (d, J=6.9 Hz, 6H). MS: m/z 531.0 (M+H$^+$).

Example 62

4-Chloro-1-(4-iodo-phenyl)-3-methyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.87 (s, 1H), 8.84 (s, 1H), 8.09 (d, J=8.4 Hz, 2H), 7.94 (d, J=8.4 Hz, 2H), 7.77 (d, J=9.0 Hz, 2H), 7.45 (d, J=8.7 Hz, 2H), 2.79 (s, 3H). MS: m/z 522.6 (M+H$^+$).

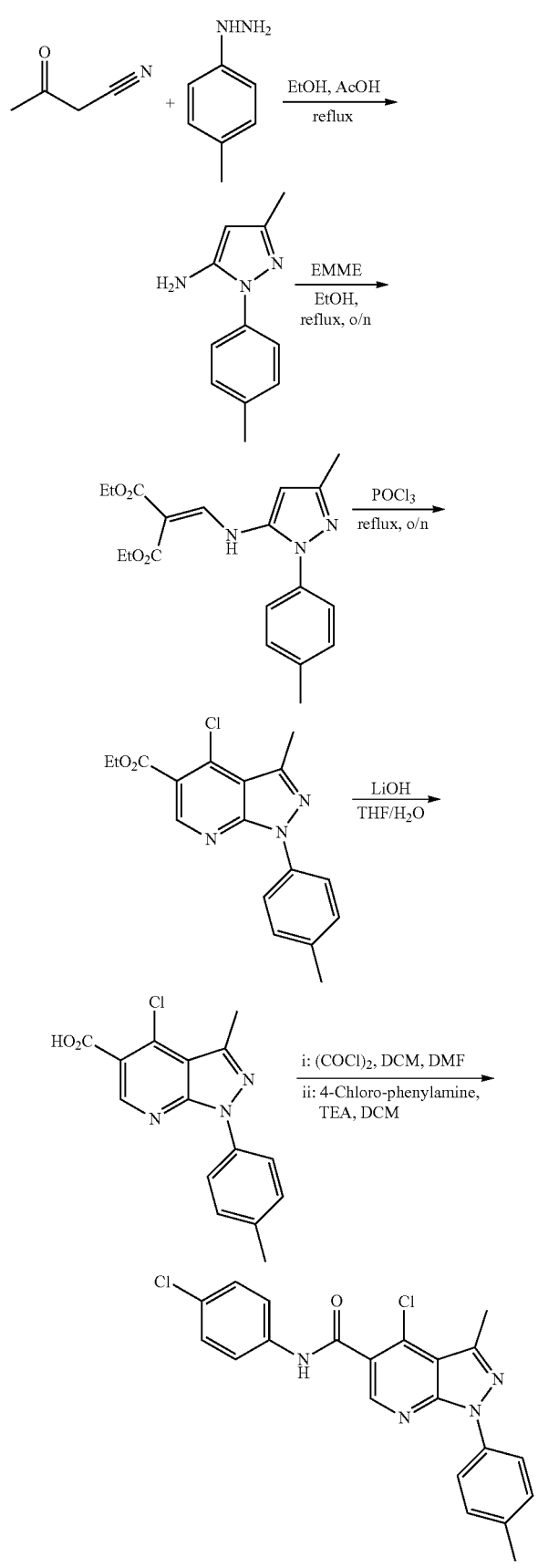

Example 63

4-Chloro-3-methyl-1-p-tolyl-1H-pyrazolo[3,4-b]pyridine-5-carboxylic acid (4-chloro-phenyl)-amide

The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.83 (s, 1H), 8.79 (s, 1H), 8.06 (d, J=8.4 Hz, 2H), 7.77 (d, J=8.8 Hz, 2H), 7.48-7.43 (m, 2H), 7.39 (d, J=8.4 Hz, 2H), 2.79 (s, 3H), 2.38 (s, 3H). MS: m/z 411.0 (M+H$^+$).

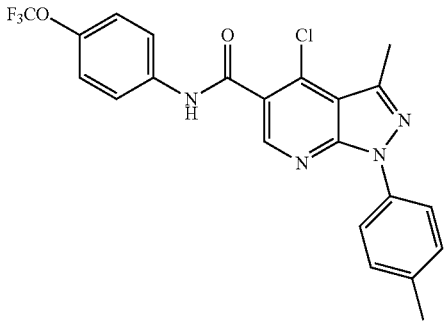 [SMILES: Cc1ccc(-n2nc(C)c3c(Cl)c(C(=O)Nc4ccc(OC(F)(F)F)cc4)cnc32)cc1]

Example 64

4-Chloro-3-methyl-1-p-tolyl-1H-pyrazolo[3,4-b]pyridine-5-carboxylic acid (4-trifluoromethoxy-phenyl)-amide

The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.86 (s, 1H), 8.04-8.00 (m, 3H), 7.74 (d, J=8.4 Hz, 2H), 7.34 (d, J=8.4 Hz, 2H), 7.28 (d, J=8.4 Hz, 2H), 2.86 (s, 1H), 2.44 (s, 3H). MS: m/z 459.0 (M−H$^+$)

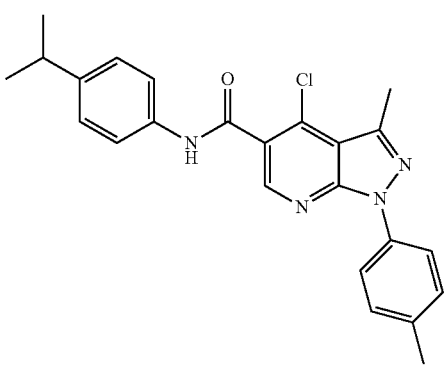 [SMILES: Cc1ccc(-n2nc(C)c3c(Cl)c(C(=O)Nc4ccc(C(C)C)cc4)cnc32)cc1]

Example 65

4-Chloro-3-methyl-1-p-tolyl-1H-pyrazolo[3,4-b]pyridine-5-carboxylic acid (4-isopropyl-phenyl)-amide

The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, DMSO-d6): δ=10.60 (s, 1H), 8.77 (s, 1H), 8.07 (d, J=8.4 Hz, 2H), 7.65 (d, J=8.4 Hz, 2H), 7.39 (d, J=8.4 Hz, 2H), 7.25 (d, J=8.4 Hz, 2H), 2.90-2.86 (m, 1H), 2.79 (s, 1H), 2.38 (s, 1H), 1.20 (d, J=6.4 Hz, 6H). MS: m/z 419.1 (M+H⁺).

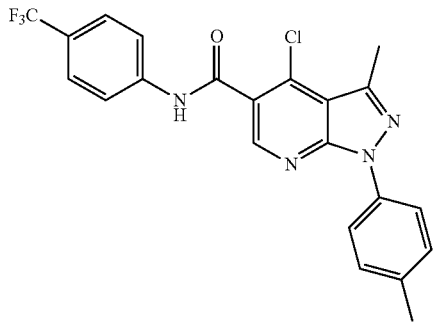 [SMILES: Cc1ccc(-n2nc(C)c3c(Cl)c(C(=O)Nc4ccc(C(F)(F)F)cc4)cnc32)cc1]

Example 66

4-Chloro-3-methyl-1-p-tolyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=11.07 (s, 1H), 8.84 (s, 1H), 8.07 (d, J=8.4 Hz, 2H), 7.95 (d, J=8.4 Hz, 2H), 7.77 (d, J=8.4 Hz, 2H), 7.40 (d, J=8.4 Hz, 2H), 2.80 (s, 3H), 2.39 (s, 3H). MS: m/z 443.0 (M−H⁺).

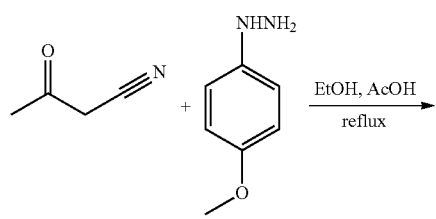

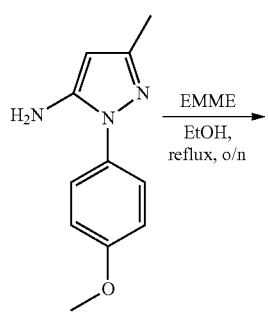

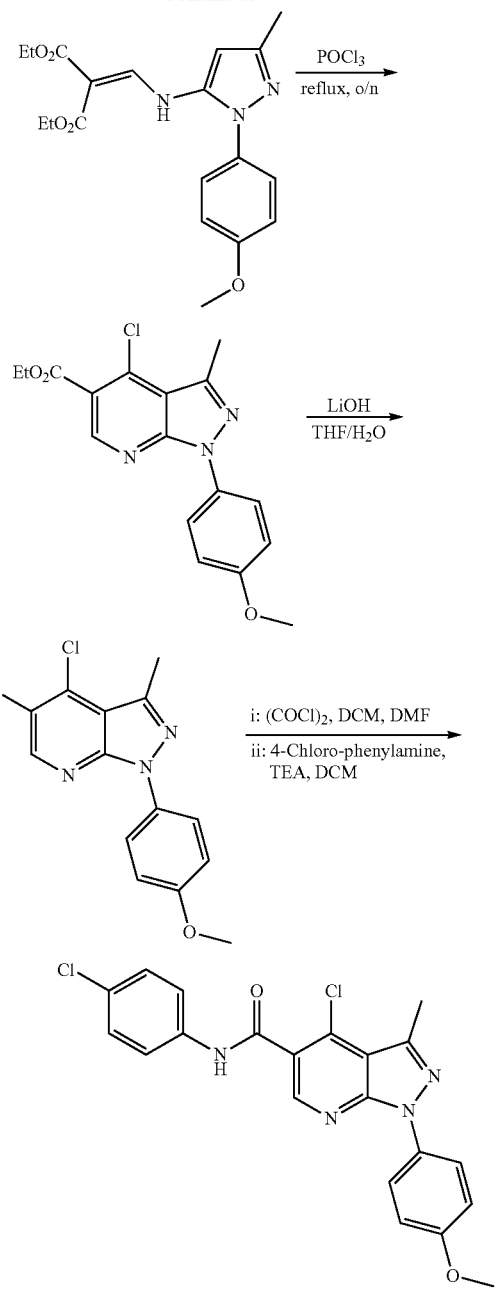

Example 67

4-Chloro-1-(4-methoxy-phenyl)-3-methyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹H NMR (400 MHz, DMSO) δ=10.83 (s, 1H), 8.79 (s, 1H), 8.01 (d, J=8.8 Hz, 2H), 7.77 (d, J=8.4 Hz, 2H), 7.43 (d, J=9.2 Hz, 2H), 7.14 (d, J=8.8 Hz, 2H), 3.83 (s, 3H), 2.78 (s, 3H). MS: m/z 427.0 (M+H⁺).

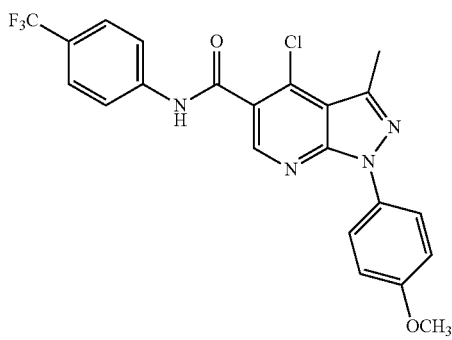 [SMILES: COc1ccc(-n2nc(C)c3c(Cl)c(C(=O)Nc4ccc(C(F)(F)F)cc4)cnc32)cc1]

Example 68

4-Chloro-1-(4-methoxy-phenyl)-3-methyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=11.07 (s, 1H), 8.81 (s, 1H), 8.03-7.95 (m, 4H), 7.78-7.76 (m, 2H), 7.15 (d, J=5.6 Hz, 2H), 3.84 (s, 3H), 2.79 (s, 3H). MS: m/z 459.0 (M−H$^+$).

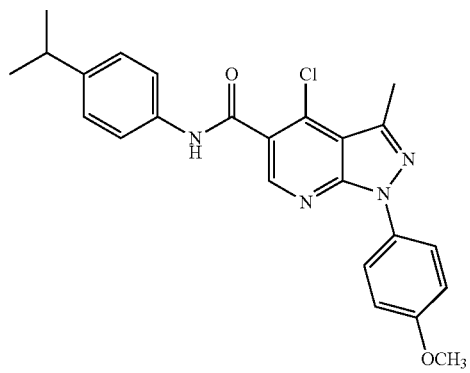 [SMILES: COc1ccc(-n2nc(C)c3c(Cl)c(C(=O)Nc4ccc(C(C)C)cc4)cnc32)cc1]

Example 69

4-Chloro-1-(4-methoxy-phenyl)-3-methyl-1H-pyrazolo[3,4-b]pyridine-5-carboxylic acid (4-isopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.60 (s, 1H), 8.75 (s, 1H), 8.02 (d, J=8.0 Hz, 2H), 7.65 (d, J=8.0 Hz, 2H), 7.25 (d, J=8.0 Hz, 2H), 7.14 (d, J=5.6 Hz, 2H), 3.83 (s, 3H), 2.90-2.87 (m, 1H), 2.79 (s, 3H), 1.22-1.20 (m, 6H). MS: m/z 435.1 (M+H$^+$).

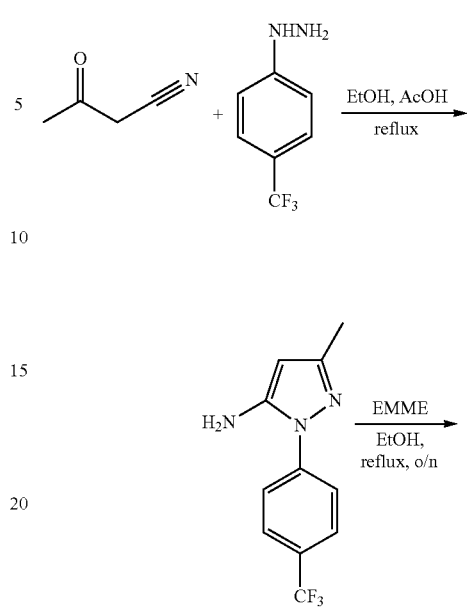

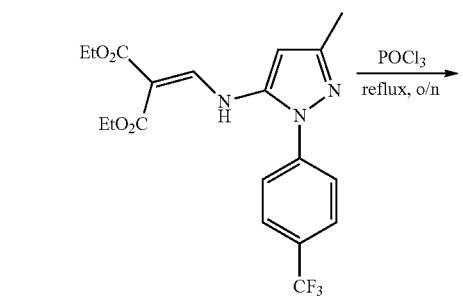

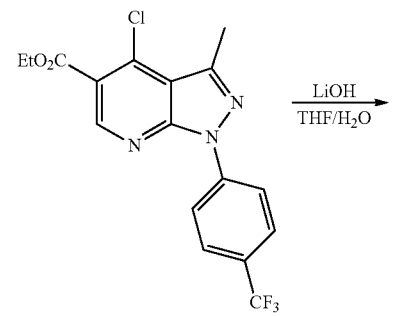

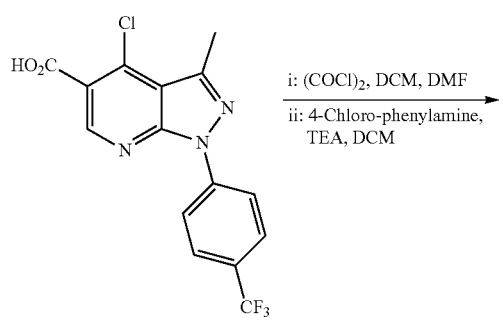

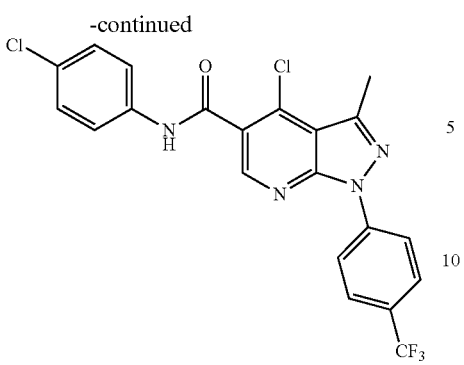

Example 70

4-Chloro-3-methyl-1-(4-trifluoromethyl-phenyl)-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.88 (s, 1H), 8.89 (s ,1 H), 8.55 (d, J=8.4 Hz, 2H), 7.97 (d, J=8.8 Hz, 2 H), 7.79-7.75 (m, 2 H), 7.48-7.43 (m, 2H), 2.82 (s, 3H). MS: m/z: no desired [M+H$^+$] is observed by LCMS (positive condition).

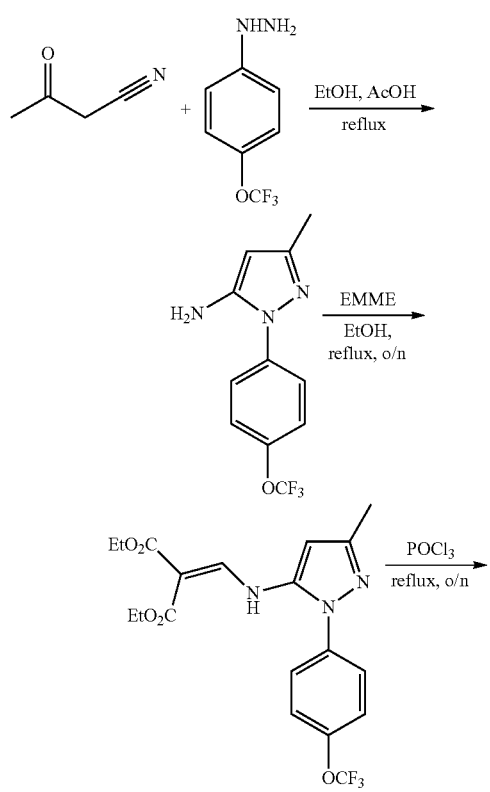

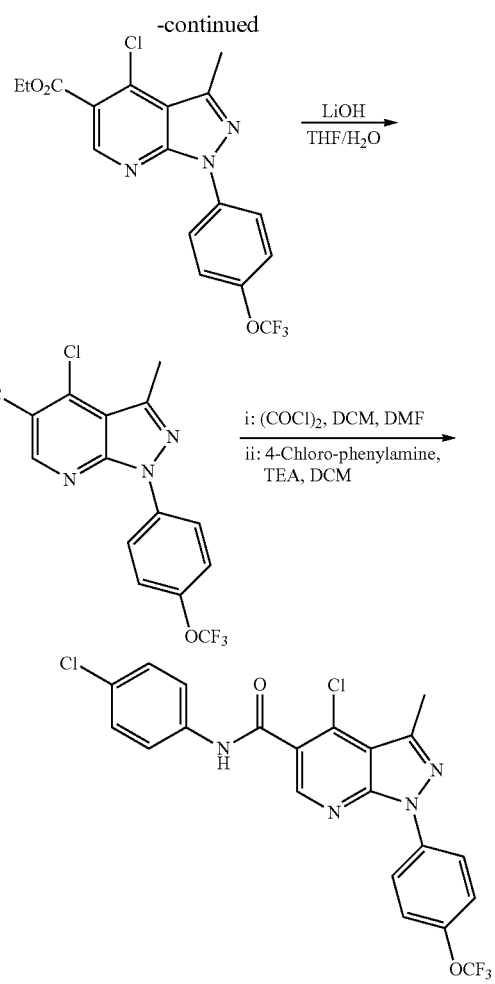

Example 71

4-Chloro-3-methyl-1-(4-trifluoromethoxy-phenyl)-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.87 (s, 1H), 8.85 (s, 1H), 8.36 (d, J=7.2 Hz, 2H), 7.77 (d, J=8.8 Hz, 2H), 7.61 (d, J=8.4 Hz, 2H), 7.45 (d, J=7.2 Hz, 2H), 2.81 (s, 3H). MS: m/z 480.9 (M+H$^+$).

-continued

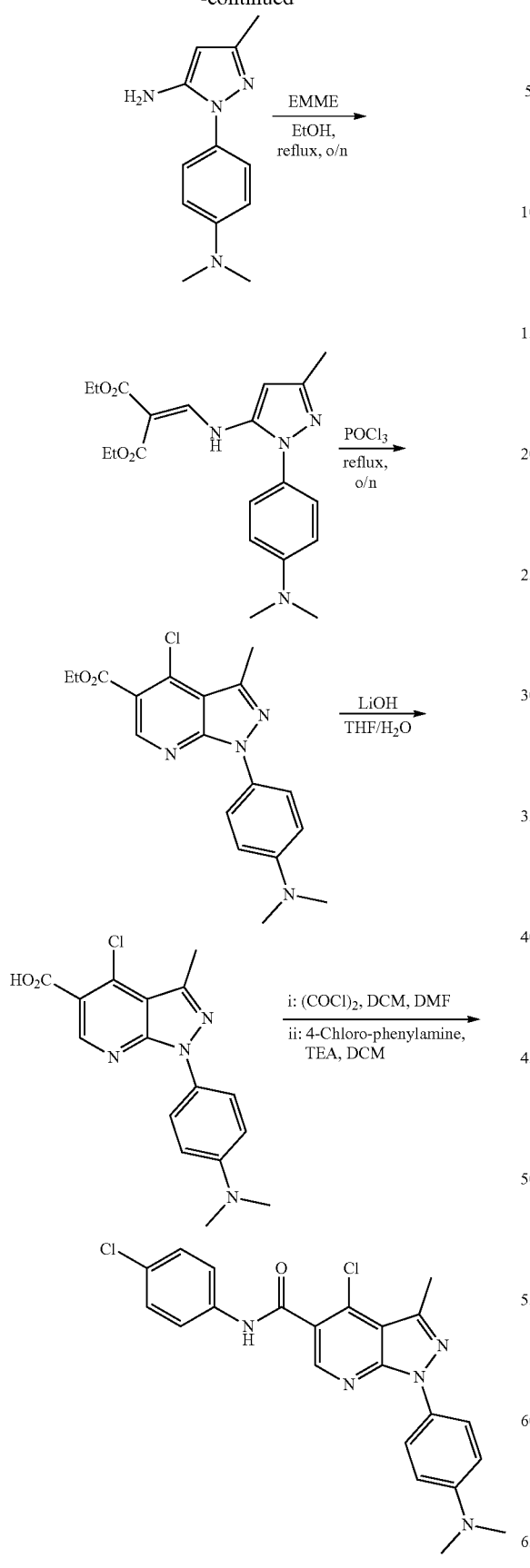

Example 72

4-Chloro-1-(4-dimethylamino-phenyl)-3-methyl-1H-pyrazolo[3,4-b]pyridine-5-carboxylic acid (4-chloro-phenyl)-amide Step 1:

To a solution of 2-(4-bromo-phenyl)-5-methyl-2H-pyrazol-3-ylamine (2.2 g, 8.7 mmol) in DMSO (40 mL) was added L-proline (599.6 mg, 5.2 mmol), $K_2CO_3$ (2.4 g, 17.4 mmol) and dimethyl-amine (13.1 mL, 26.2 mmol, 2 M), then the mixture was stirred at 100° C. at a sealed tube for 1 day. The mixture was extracted with EA (100 mL×2). The organic layer was dried over $Na_2SO_4$, filtered and concentrated to dryness in vacuum. The residue was purified by column (PE/EA=20/1-10/1-5/1) to give 2-(4-Dimethyl-amino-phenyl)-5-methyl-2H-pyrazol-3-ylamine (520 mg, yield: 27%) as a brown solid. $^1$HNMR (300 MHz, $CDCl_3$): δ=7.35 (d, J=8.7 Hz, 2H), 6.77 (d, J=9.0 Hz, 2H), 5.43 (s, 1H), 3.67 (brs, 2H), 2.99 (s, 6H), 2.24 (s, 3H).

Step 2-5:

These four steps were similar to 4-chloro-3-methyl-1-phenyl-1H-pyrazolo[3,4-b]pyridine-5-carboxylic acid (4-bromo-phenyl)-amide (Example 1). HNMR (300 MHz, $CDCl_3$): δ=8.82 (s, 1H), 7.99 (s, 1H), 7.81 (d, J=8.8 Hz, 2H), 7.64 (d, J=8.8 Hz, 2H), 7.37 (d, J=8.8 Hz, 2H), 6.84 (d, J=8.8 Hz, 2H), 3.01 (s, 6H), 2.84 (s, 3H). MS: m/z 440.1 (M+H$^+$).

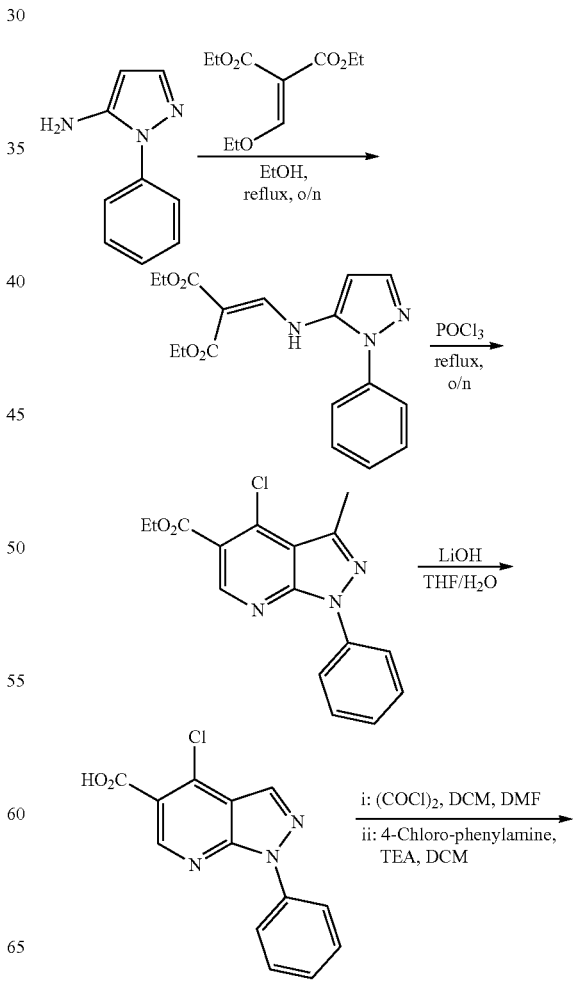

-continued

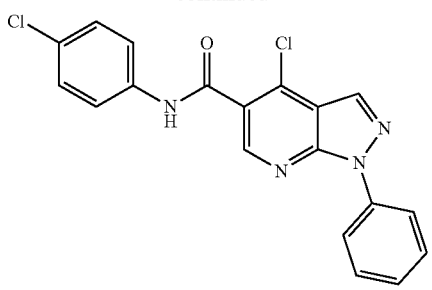

Example 73

4-Chloro-1-phenyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.88 (brs, 1H), 8.90 (s, 1H), 8.73 (s, 1H), 8.23 (d, J=7.6 Hz, 2H), 7.78 (d, J=8.8 Hz, 2H), 7.63 (t, J=7.6 Hz, 2H), 7.47-7.44 (m, 3H). MS: m/z 381.0 (M–H$^+$).

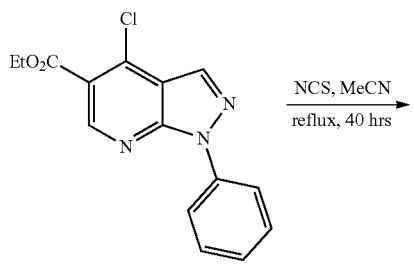

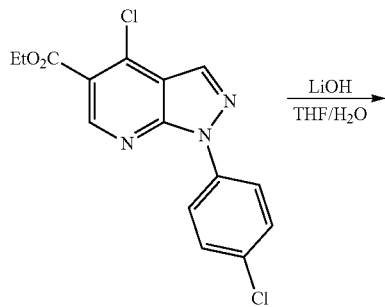

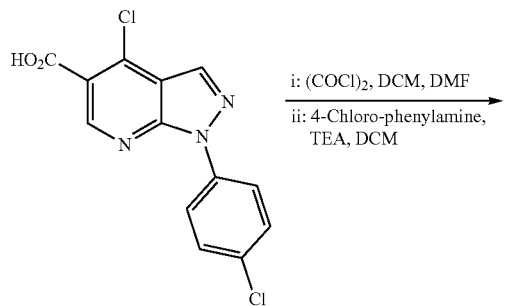

-continued

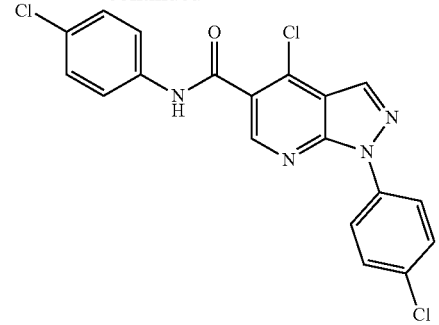

Example 74

4-Chloro-1-(4-chloro-phenyl)-1H-pyrazolo[3,4-b]pyridine-5-carboxylic acid (4-chloro-phenyl)-amide Step 1:
To a solution of 4-chloro-1-phenyl-1H-pyrazolo[3,4-b]pyridine-5-carboxylic acid ethyl ester (300 mg, 1.0 mmol) in MeCN (20 mL), was added NCS (267 mg, 2.0 mmol). The reaction was stirred at refluxing for 40 hrs. The reaction mixture was concentrated under reduced pressure. The residue was taken up with water (20 mL) and extracted with EA (20 mL×3). The organic layers were combined and washed with brine (50 mL), dried over Na$_2$SO$_4$ and concentrated. The residue was purified by silica gel column (PE/EA=20/1) to give 4-chloro-1-(4-chloro-phenyl)-1H-pyrazolo[3,4-b]pyridine-5-carboxylic acid ethyl ester (40 mg, yield: 12%) as a white solid.

$^1$HNMR (400 MHz, DMSO-d6): δ=9.10 (s, 1H), 8.78 (s, 1H), 8.27 (d, J=8.8 Hz, 2H), 7.71 (d, J=9.2 Hz, 2H), 4.42 (q, J=6.8 Hz, 2H), 1.39 (t, J=7.2 Hz, 3H).

Step 2-3:
These two steps were similar to 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=9.00 (s, 1H), 8.37 (s, 1H), 8.24 (d, J=8.8 Hz, 2H), 8.05 (brs, 1H), 7.64 (d, J=7.6 Hz, 2H), 7.52 (d, J=8.8 Hz, 2H), 7.38 (d, J=8.4 Hz, 2H). MS: m/z 319.0 (M+H$^+$).

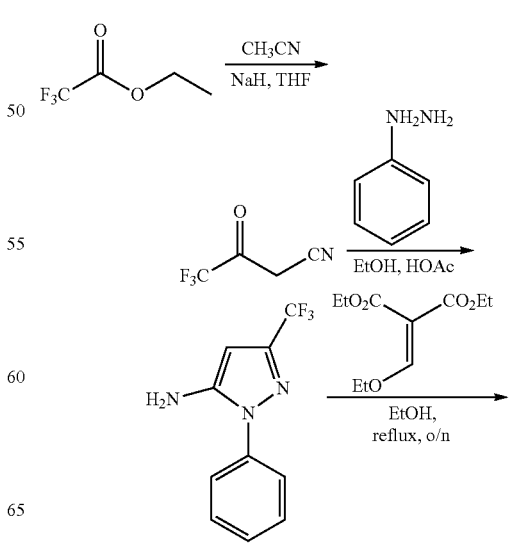

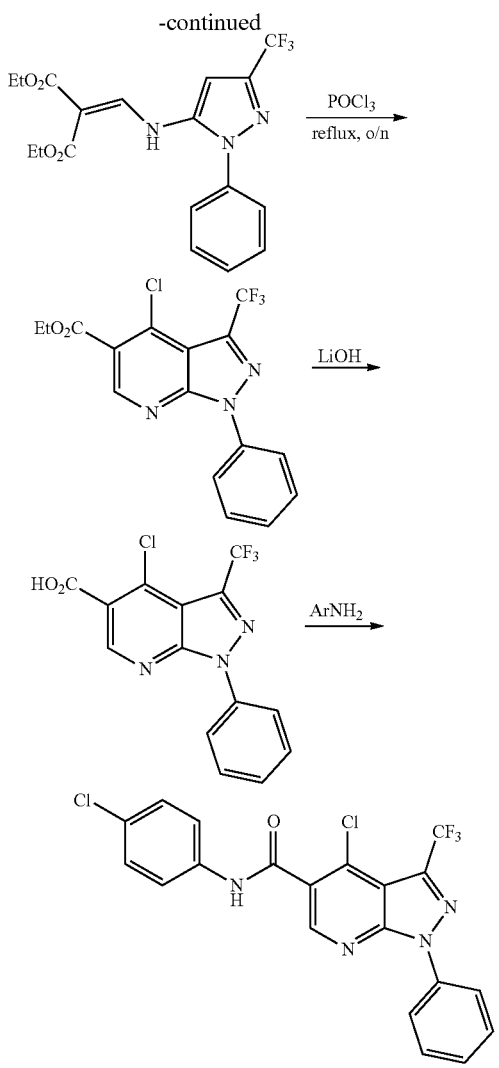

Example 75

4-Chloro-1-phenyl-3-trifluoromethyl-1H-pyrazolo[3,4-b]pyridine-5-carboxylic acid (4-chloro-phenyl)-amide Step 1:

To a suspension of NaH (1.8 g, 4.2 mmol) in THF (35 mL), was added trifluoro-acetic acid ethyl ester (4.26 g, 30 mmol) dropwise at room temperature. Then acetonitrile (1.72 g, 42 mmol) was added dropwise. The mixture was stirred at 75° C. for 12 hrs. The solvent was removed and the residue was dissolved in DCM (40 mL). The mixture was washed with aq.10% HCl solution (30 mL) and brine (50 mL). The organic layer was separated and dried over anhydrous $Na_2SO_4$ The solution was concentrated to dryness and used for next step without further purification.

Step 2:

To a solution of 3,3,3-trifluoro-2-oxo-propionitrile (2.8 g, 20.7 mmol) in ethanol (40 mL), phenyl-hydrazine (2.24 g, 20.7 mmol) and HOAc (1 mL) was added. The mixture was stirred at 85° C. for 12 hrs. The solvent was removed and the residue was dissolved in EA (50 mL), washed with $NaHCO_3$ solution (30 mL) and brine (50 mL). The organic layer was separated and dried over anhydrous $Na_2SO_4$ The solvent was removed and the residue was purified by silica gel column (EA/PE=1/10) to give 2-phenyl-5-trifluoromethyl-2H-pyrazol-3-ylamine (0.63 g, yield: 13.4%) as a yellow solid. $^1$HNMR (400 MHz, $CDCl_3$): δ=7.56-7.49 (m, 4H), 7.44-7.42 (m, 1H), 5.86 (s, 1H), 3.92 (brs, 1H).

Step 3-6:

These two steps were similar to 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.97 (brs, 1H), 9.02 (s, 1H)), 8.12 (d, J=7.8 Hz, 2H), 7.79-7.76 (m, 2H), 770-7.65 (m, 2H), 7.58-7.55 (m, 1H), 7.48-7.45 (m, 2H). MS: m/z 449.0 (M−H⁺).

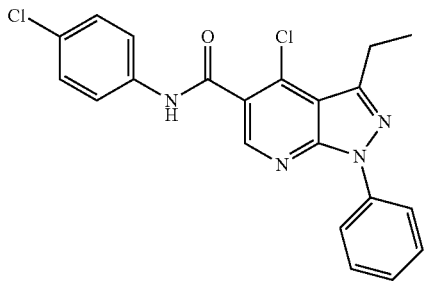 [SMILES: CCc1nn(-c2ccccc2)c2ncc(C(=O)Nc3ccc(Cl)cc3)c(Cl)c12]

Example 76

4-Chloro-3-ethyl-1-phenyl-1H-pyrazolo[3,4-b]pyridine-5-carboxylic acid (4-chloro-phenyl)-amide These two steps were similar to 4-chloro-3-methyl-1-phenyl-1H-pyrazolo[3,4-b]pyridine-5-carboxylic acid (4-bromo-phenyl)-amide (Example 1). $^1$HNMR (400 MHz, $CDCl_3$): δ=8.84 (brs, 1H), 8.19 (d, J=7.6 Hz, 2H), 7.97 (brs 1H), 7.64-7.62 (2(m, 2H), 755-7.51 (m, 2H), 7.38-7.33 (m, 3H), 3.24 (q, J=7.6 Hz, 2H), 1.48 (t, J=7.6 Hz, 3H). MS: m/z 409.0 (M−H⁺).

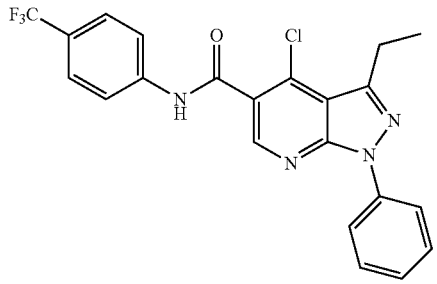 [SMILES: CCc1nn(-c2ccccc2)c2ncc(C(=O)Nc3ccc(C(F)(F)F)cc3)c(Cl)c12]

Example 77

4-Chloro-3-ethyl-1-phenyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, $CDCl_3$): δ=8.86 (1H, bs), 8.19 (d, J=7.6 Hz, 2H), 8.12 (brs 1H), 7.82-7.80 ((m, 2H), 7.68-7.66

((m, 2H), 7.56-7.52 (m, 2H), 7.37-7.35 ((m, 1H), 3.26 ((q, J=7.6 Hz, 2H), 1.56-1.51 ((t, J=7.6 Hz, 3H). MS: m/z 443 (M−1).

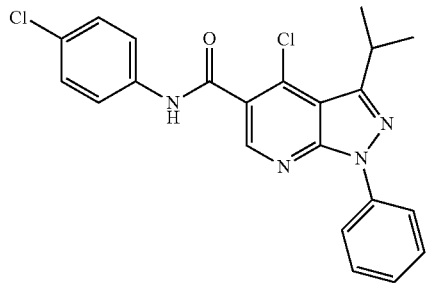 [SMILES: CC(C)c1nn(-c2ccccc2)c2ncc(C(=O)Nc3ccc(Cl)cc3)c(Cl)c12]

Example 78

4-Chloro-3-isopropyl-1-phenyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.86 (1H, bs), 8.22 (d, J=7.8 Hz, 2H), 7.91 (brs 1H), 7.66-7.63 (m, 2H), 758-7.53 ((m, 2H), 7.40-7.36 ((m, 3H), 3.87-3.72 ((m, 1H), 1.54 (d, J=6.9 Hz, 6H). MS: m/z 499.1 (M+H⁺).

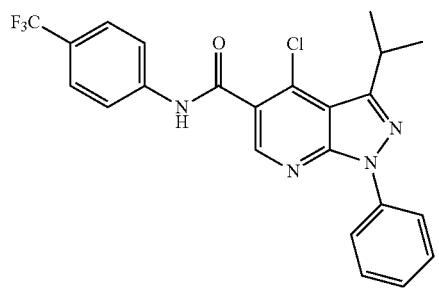 [SMILES: CC(C)c1nn(-c2ccccc2)c2ncc(C(=O)Nc3ccc(C(F)(F)F)cc3)c(Cl)c12]

Example 79

4-Chloro-3-isopropyl-1-phenyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, CDCl₃): δ=8.86 (1H, bs), 8.21 (d, J=7.6 Hz, 2H), 8.03 (brs, 1H), 7.81(d, J=7.6 Hz, 2H), 7.67 (d, J=7.6 Hz, 2H), 7.56-7.52 (m, 2H), 7.37-7.35 (m, 1H), 3.84 (m, 1H), 1.54 (d, J=6.9 Hz, 6H). MS: m/z 459.1 (M+H⁺).

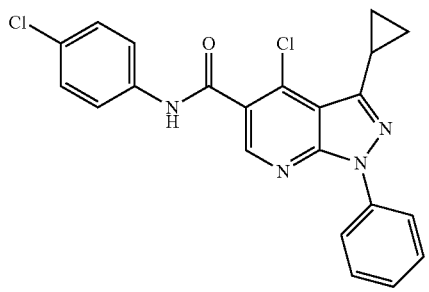 [SMILES: O=C(Nc1ccc(Cl)cc1)c1cnc2c(c(C3CC3)nn2-c2ccccc2)c1Cl]

Example 80

4-Chloro-3-cyclopropyl-1-phenyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, DMSO-d6): δ=10.85 (brs 1H), 8.82 (s 1H), 8.18 (d, J=7.6 Hz, 2H), 7.78 (d, J=7.6 Hz, 2H), 760-7.56 (m, 2H), 7.47-7.45 (m, 2H), 7.39-7.38 (m, 1H), 2.68-2.66 (m, 1H), 1.14-1.12 (m, 4H). MS: m/z 421.0 (M−H⁺).

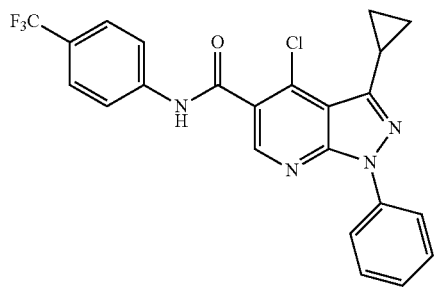 [SMILES: O=C(Nc1ccc(C(F)(F)F)cc1)c1cnc2c(c(C3CC3)nn2-c2ccccc2)c1Cl]

Example 81

4-Chloro-3-cyclopropyl-1-phenyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, CDCl₃): δ=8.86 (brs, 1H), 8.18-8.15 (m, 3H), 7.81 (d, J=7.6 Hz, 2H), 7.68-7.66 (m, 2H), 7.54-7.50 (m, 2H), 7.33-7.31 (m, 1H), 2.63-2.59 (m, 1H), 1.24-1.12 (m, 4H). MS: m/z 455.0 (M−H⁺).

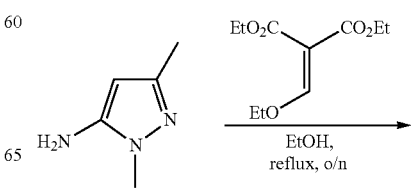

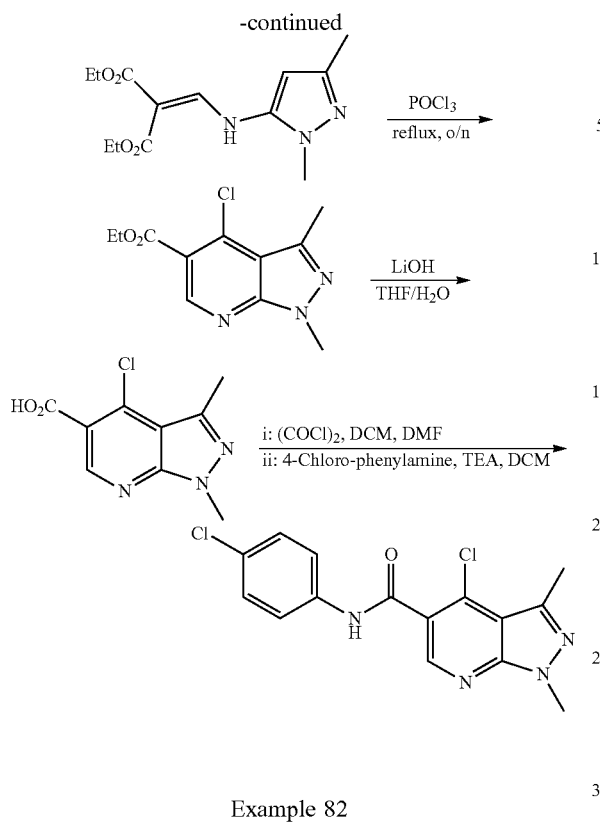

Example 82

4-Chloro-1,3-dimethyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.82 (s, 1H), 8.19 (brs, 1H), 7.82 (d, J=8.7 Hz, 2H), 7.68 (d, J=8.4 Hz, 2H), 4.11 (s, 3H), 2.76 (s, 3H). MS: m/z 335.0 (M+H⁺).

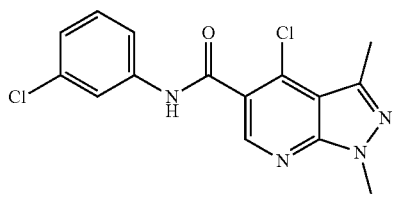 [SMILES: Cc1nn(C)c2ncc(C(=O)Nc3cccc(Cl)c3)c(Cl)c12]

Example 83

4-Chloro-1,3-dimethyl-1H-pyrazolo[3,4-b]pyridine-5-carboxylic acid (3-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.84 (s, 1H), 7.96 (s, 1H), 7.81 (s, 1H), 7.52 (d, J=9.0 Hz, 1H), 7.36-7.31 (m, 1H), 7.21 (d, J=3.0 Hz, 1H), 4.11 (s, 3H), 2.78 (s, 3H). MS: m/z 334.8 (M+H⁺).

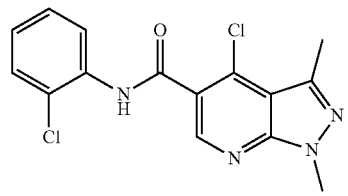

Example 84

4-Chloro-1,3-dimethyl-1H-pyrazolo[3,4-b]pyridine-5-carboxylic acid (2-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.91 (s, 1H), 8.63-8.60 (m, 2H), 7.45 (d, J=6.0 Hz, 1H), 7.40 (t, J=9.0 Hz, 1H), 7.14 (t, J=9.0 Hz, 1H), 4.09 (s, 3H), 4.12 (s, 3H), 2.74 (s, 3H). MS: m/z 334.8 (M+H⁺).

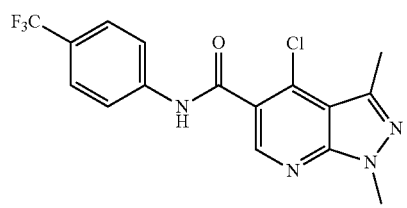

Example 85

4-Chloro-1,3-dimethyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=10.76 (s, 1H), 8.69 s, 1H), 7.76 (d, J=8.7 Hz, 2H), 7.44 (d, J=9.0, Hz, 2H), 4.02 (s, 3H), 2.68 (s, 3H). MS: m/z 369.1 (M+H⁺).

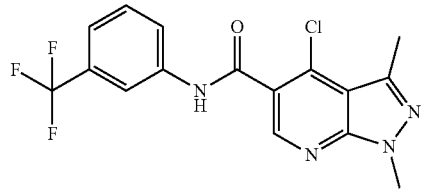 [SMILES: Cc1nn(C)c2ncc(C(=O)Nc3cccc(C(F)(F)F)c3)c(Cl)c12]

Example 86

4-Chloro-1,3-dimethyl-1H-pyrazolo[3,4-b]pyridine-5-carboxylic acid (3-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.84 (s, 1H), 8.14 (s, 1H), 7.99 (s, 1H), 7.90 (d, J=9.0 Hz, 1H), 7.58-7.46 (m, 2H), 4.11 (s, 3H), 2.78 (s, 3H). MS: m/z 368.8 (M+H$^+$).

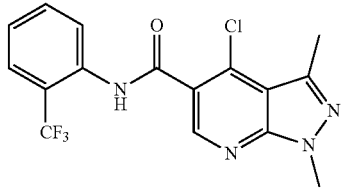

Example 87

4-Chloro-1,3-dimethyl-1H-pyrazolo[3,4-b]pyridine-5-carboxylic acid (2-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.87 (s, 1H), 8.46 (d, J=3.0 Hz, 1H), 7.56 (s, 1H), 8.43 (s, 1H), 7.72-7.66 (m, 2H), 7.36-7.66 (m, 2H), 7.36-7.27 (m, 1H), 4.12 (s, 3H), 2.79 (s, 3H). MS: m/z 369.1 (M+H$^+$).

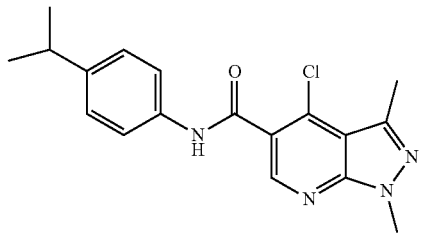 [SMILES: Cc1nn(C)c2ncc(C(=O)Nc3ccc(C(C)C)cc3)c(Cl)c12]

Example 88

4-Chloro-1,3-dimethyl-1H-pyrazolo[3,4-b]pyridine-5-carboxylic acid (4-isopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.53 (s, 1H), 8.66 (s, 1H), 7.63 (d, J=8.4 Hz, 2H), 7.23 (d, J=8.4 Hz, 2H), 4.02 (s, 3H), 2.89-2.86 (m, 1H), 2.88 (s, 3H), 1.20 (d, J=8.4 Hz, 2H). MS: m/z 343.0 (M+H$^+$).

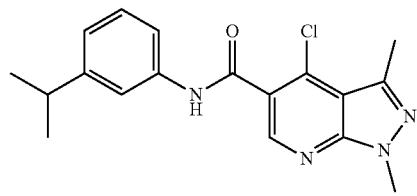 [SMILES: Cc1nn(C)c2ncc(C(=O)Nc3cccc(C(C)C)c3)c(Cl)c12]

Example 89

4-Chloro-1,3-dimethyl-1H-pyrazolo[3,4-b]pyridine-5-carboxylic acid (3-isopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.84 (s, 1H), 7.91 (s, 1H), 7.56 (s, 1H), 7.51-7.49 (m, 1H), 7.36 (t, J=7.8 Hz, 1H), 7.11 (d, J=7.5 Hz, 1H), 4.11 (s, 3H), 2.99-2.94 (m, 1H), 2.78 (s, 3H), 1.32 (d, J=6.6 Hz, 6H). MS: m/z 343.1 (M+H$^+$).

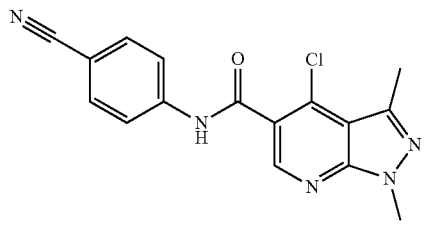 [SMILES: Cc1nn(C)c2ncc(C(=O)Nc3ccc(C#N)cc3)c(Cl)c12]

Example 90

4-Chloro-1,3-dimethyl-1H-pyrazolo[3,4-b]pyridine-5-carboxylic acid (5-cyano-pyridin-2-yl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.83 (s, 1H), 8.21 (s, 1H), 7.83 (d, J=8.7 Hz, 2H), 7.71 (d, J=8.7 Hz, 2H), 4.11 (s, 3H), 2.77 (s, 3H). MS: m/z 325.9 (M+H$^+$).

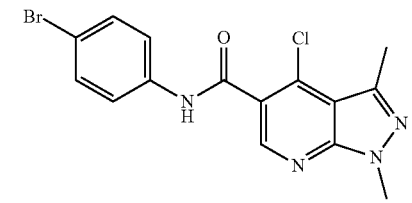 [SMILES: Cc1nn(C)c2ncc(C(=O)Nc3ccc(Br)cc3)c(Cl)c12]

Example 91

4-Chloro-1,3-dimethyl-1H-pyrazolo[3,4-b]pyridine-5-carboxylic acid (4-bromo-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.81 (s, 1H), 8.00 (s, 1H), 7.61-7.51 (m, 4H), 7.53-7.50 (m, 4H), 4.11 (s, 3H), 2.76 (s, 3H). MS: m/z 378.7 (M+H$^+$).

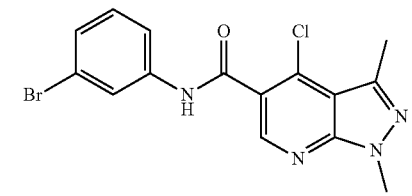 [SMILES: Cc1nn(C)c2ncc(C(=O)Nc3cccc(Br)c3)c(Cl)c12]

Example 92

4-Chloro-1,3-dimethyl-1H-pyrazolo[3,4-b]pyridine-5-carboxylic acid (3-bromo-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.76 (s, 1H), 8.15 (s, 1H), 7.96 (s, 1H), 7.60 (d, J=6.0 Hz, 1H), 7.36-7.28 (m, 2H), 4.09 (s, 3H), 2.74 (s, 3H). MS: m/z 380.8 (M+H⁺).

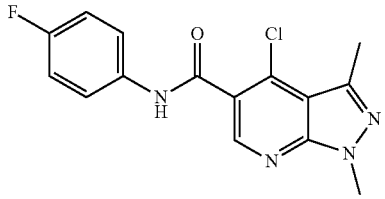 [SMILES: Cc1nn(C)c2ncc(C(=O)Nc3ccc(F)cc3)c(Cl)c12]

Example 93

4-Chloro-1,3-dimethyl-1H-pyrazolo[3,4-b]pyridine-5-carboxylic acid (4-fluoro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.84 (s, 1H), 7.95 (s, 1H), 7.68-7.63 (m, 2H), 7.13 (t, J=9.0 Hz, 2H), 4.11 (s, 3H), 2.78 (s, 3H). MS: m/z 318.9 (M+H⁺).

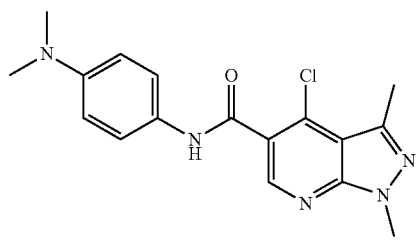 [SMILES: Cc1nn(C)c2ncc(C(=O)Nc3ccc(N(C)C)cc3)c(Cl)c12]

Example 94

4-Chloro-1,3-dimethyl-1H-pyrazolo[3,4-b]pyridine-5-carboxylic acid (4-dimethylamino-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.84 (s, 1H), 7.82 (s, 1H), 7.51 (d, J=9.0 Hz, 2H), 6.76 (d, J=9.0 Hz, 2H), 4.10 (s, 3H), 2.97 (d, J=9.6Hz, 2H). MS: m/z 343.9 (M+H⁺).

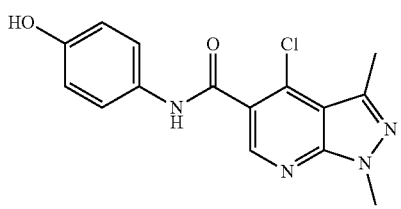 [SMILES: Cc1nn(C)c2ncc(C(=O)Nc3ccc(O)cc3)c(Cl)c12]

Example 95

4-Chloro-1,3-dimethyl-1H-pyrazolo[3,4-b]pyridine-5-carboxylic acid (4-hydroxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=10.37 (s, 1H), 9.31 (s, 1H), 8.64 (s, 1H), 7.51 (d, J=8.7 Hz, 2H), 7.75 (d, J=8.7 Hz, 2H), 4.01 (s, 3H), 2.68 (s, 3H). MS: m/z 316.8 (M+H⁺).

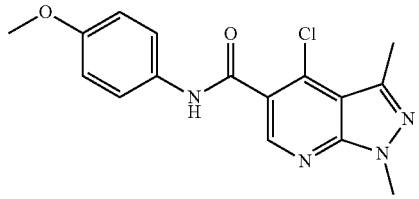 [SMILES: COc1ccc(NC(=O)c2cnc3c(c(C)nn3C)c2Cl)cc1]

Example 96

4-Chloro-1,3-dimethyl-1H-pyrazolo[3,4-b]pyridine-5-carboxylic acid (5-methoxy-pyridin-2-yl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.82 (s, 1H), 7.90 (s, 1H), 7.60 (d, J=9.0 Hz, 2H), 6.95 (d, J=9.0 Hz, 2H), 4.10 (s, 3H), 3.85 (s, 3H), 2.77 (s, 3H). MS: m/z 331.0 (M+H⁺).

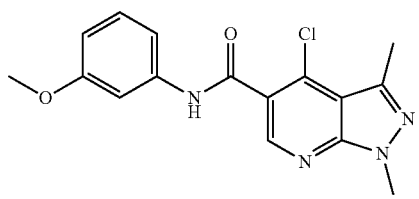 [SMILES: COc1cccc(NC(=O)c2cnc3c(c(C)nn3C)c2Cl)c1]

Example 97

4-Chloro-1,3-dimethyl-1H-pyrazolo[3,4-b]pyridine-5-carboxylic acid (3-methoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.71 (s, 1H), 8.25 (s, 1H), 7.48 (s, 1H), 7.32-7.27 (m, 1H), 7.18 (d, J=7.8 Hz, 1H), 6.75 (dd, J=8.1, 2.4 Hz, 1H), 4.07 (s, 3H), 3.86 (s, 3H), 2.70 (s, 3H). MS: m/z 331.1 (M+H⁺).

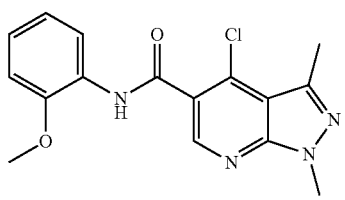 [SMILES: COc1ccccc1NC(=O)c1cnc2c(c(C)nn2C)c1Cl]

Example 98

4-Chloro-1,3-dimethyl-1H-pyrazolo[3,4-b]pyridine-5-carboxylic acid (2-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, CDCl₃): δ=8.86 (s, 1H), 8.67 (s, 1H), 8.58 (s, 1H), 7.17-7.03 (m, 2H), 6.95 (d, J=9.0 Hz, 1H), 4.11 (s, 3H), 3.92 (s, 3H), 2.78 (s, 3H). MS: m/z 331.1 (M+H⁺).

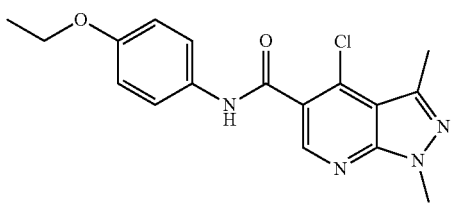 [SMILES: CCOc1ccc(NC(=O)c2cnc3c(c(C)nn3C)c2Cl)cc1]

Example 99

4-Chloro-1,3-dimethyl-1H-pyrazolo[3,4-b]pyridine-5-carboxylic acid (4-ethoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.81 (s, 1H), 7.91 (s, 1H), 7.59 (d, J=8.7 Hz, 2H), 6.95 (t, J=8.7 Hz, 2H), 4.10-4.03 (m, 5H), 2.76 (s, 3H), 1.44 (t, J=7.2 Hz, 3H). MS: m/z 345.0 (M+H⁺).

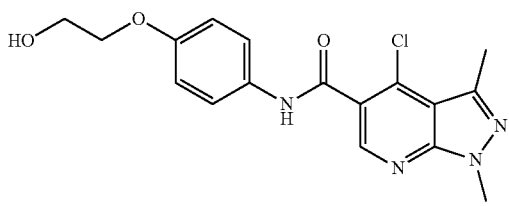 [SMILES: Cc1nn(C)c2ncc(C(=O)Nc3ccc(OCCO)cc3)c(Cl)c12]

Example 100

4-Chloro-1,3-dimethyl-1H-pyrazolo[3,4-b]pyridine-5-carboxylic acid [4-(2-hydroxy-ethoxy)-phenyl]-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.84 (s, 1H), 7.87 (s, 1H), 7.91 (m, 1H), 7.60 (d, J=9.0 Hz, 2H), 6.99-6.95 (m, 2H), 4.13-4.10 (m, 5H), 4.01-3.98 (m, 2H), 2.77 (s, 3H). MS: m/z 361.1 (M+H⁺).

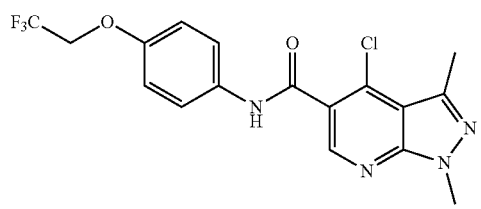 [SMILES: Cc1nn(C)c2ncc(C(=O)Nc3ccc(OCC(F)(F)F)cc3)c(Cl)c12]

Example 101

4-Chloro-1,3-dimethyl-1H-pyrazolo[3,4-b]pyridine-5-carboxylic acid [4-(2, 2, 2-trifluoro-ethoxy)-phenyl]-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=10.60 (s, 1H), 8.67 (s, 1H), 7.68 (d, J=9.0 Hz, 2H), 7.08 (d, J=9.0 Hz, 2H), 4.79-4.70 (m, 2H), 4.02 (s, 3H), 2.68 (s, 3H). MS: m/z 399.0 (M+H⁺).

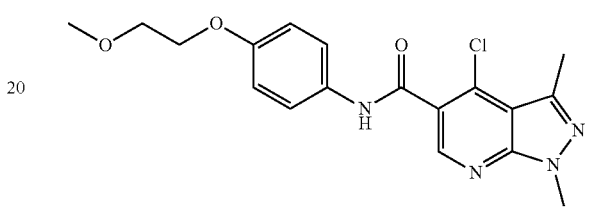

Example 102

4-chloro-N-(4-(2-methoxyethoxy)phenyl)-1,3-dimethyl-1H-pyrazolo[3,4-b]pyridine-5-carboxamide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=10.50 (s, 1H), 8.86 (s, 1H), 7.62 (d, J=9.0 Hz, 2H), 6.94 (d, J=9.0 Hz, 2H), 4.09-4.05 (m, 2H), 4.02 (s, 3H), 3.88-3.82 (m, 2H), 3.31 (s, 3H), 2.68 (s, 3H). MS: m/z 374.9 (M+H⁺).

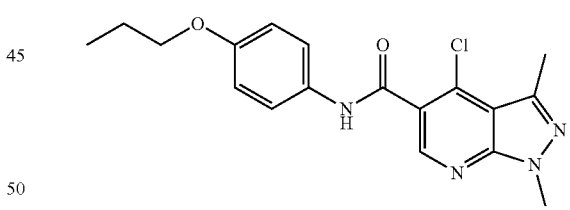

Example 103

4-Chloro-1,3-dimethyl-1H-pyrazolo[3,4-b]pyridine-5-carboxylic acid (4-propoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.79 (s, 1H), 7.96 (s, 1H), 7.58 (d, J=9.0 Hz, 2H), 6.93 (d, J=9.3 Hz, 2H), 4.07 (s, 3H), 3.95 (t, J=6.6 Hz, 2H), 2.75 (s, 3H), 1.87-1.80 (m, 2H), 1.06 (t, J=7.5 Hz, 3H). MS: m/z 359.0 (M+H⁺).

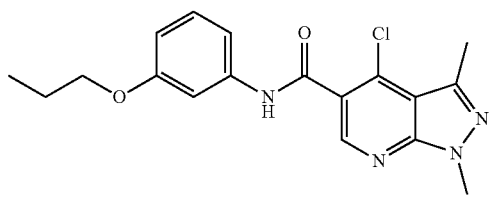 [SMILES: CCCOc1cccc(NC(=O)c2cnc3c(c(C)nn3C)c2Cl)c1]

Example 104

4-chloro-1,3-dimethyl-N-(3-propoxyphenyl)-1H-pyrazolo[3,4-b]pyridine-5-carboxamide The title compound was prepared using general procedure for 4-chloro-3-methyl-1-phenyl-1H-pyrazolo[3,4-b]pyridine-5-carboxylic acid (4-bromo-phenyl)-amide (Example 1).
$^1$HNMR (300 MHz, DMSO-d6): δ=10.60 (s, 1H), 8.67 (s, 1H), 7.73 (s, 1H), 7.27-7.20 (m, 2H), 6.73-6.67 (m, 1H), 4.02 (s, 3H), 3.92 (t, J=6.6 Hz, 2H), 2.68 (s, 3H), 1.78-1.69 (m, 2H), 0.98 (t, J=7.2 Hz, 3H). MS: m/z 357.1 (M−H$^+$).

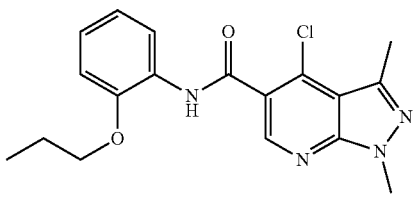 [SMILES: CCCOc1ccccc1NC(=O)c1cnc2c(c(C)nn2C)c1Cl]

Example 105

4-chloro-1,3-dimethyl-N-(2-propoxyphenyl)-1H-pyrazolo[3,4-b]pyridine-5-carboxamide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=9.74 (s, 1H), 8.67 (s, 1H), 7.92 (d, J=7.2 Hz, 1H), 7.17 (t, J=7.5 Hz, 1H), 7.07 (d, J=8.1 Hz, 1H), 6.97 (t, J=7.5 Hz, 1H), 4.02-3.96 (m, 2H), 3.33 (s, 3H), 2.68 (s, 3H), 1.80-1.69 (m, 2H), 0.99 (t, J=7.2 Hz, 3H). MS: m/z 357.1 (M−H$^+$).

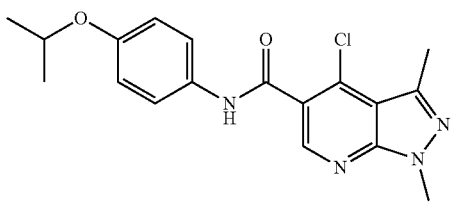

Example 106

4-Chloro-1,3-dimethyl-1H-pyrazolo[3,4-b]pyridine-5-carboxylic acid (5-isopropoxy-pyridin-2-yl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.82 (s, 1H), 7.86 (s, 1H), 7.57 (d, J=8.4 Hz, 2H), 6.93 (d, J=8.7 Hz, 2H), 4.58-4.54 (m, 1H), 4.10 (s, 3H), 2.77 (s, 3H), 1.36 (d, J=4.0 Hz, 6H). MS: m/z 358.9 (M+H$^+$).

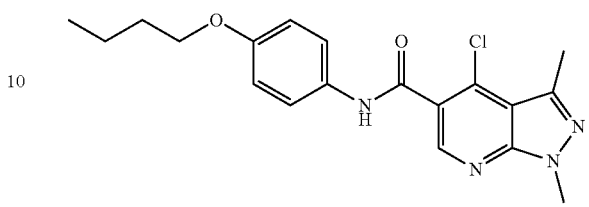

Example 107

4-Chloro-1,3-dimethyl-1H-pyrazolo[3,4-b]pyridine-5-carboxylic acid (4-butoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.80 (s, 1H), 7.93 (s, 1H), 7.59 (d, J=6.0 Hz, 2H), 6.93 (d, J=9.0 Hz, 2H), 4.09 (s, 3H), 3.99 (t, J=6.3 Hz, 2H), 2.75 (s, 3H), 1.82-1.77 (m, 2H), 1.58-1.51 (m, 2H), 0.98 (t, J=6.9 Hz, 3H). MS: m/z 373.1 (M+H$^+$).

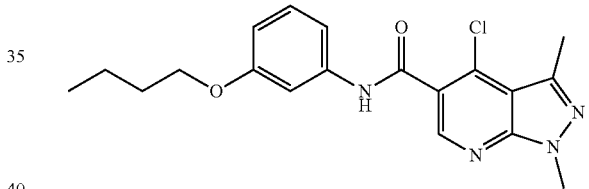

Example 108

4-Chloro-1,3-dimethyl-1H-pyrazolo[3,4-b]pyridine-5-carboxylic acid (3-butoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=8.82 (s, 1H), 7.90 (s, 1H), 7.44 (s, 1H), 7.29 (d, J=6.0 Hz, 1H), 7.10 (d, J=3.0 Hz, 1H), 6.75-6.74 (d, J=3.0 Hz, 1H), 4.10 (s, 3H), 4.02 (t, J=9.0 Hz, 2H), 2.76 (s, 3H), 1.80-1.77 (m, 2H), 1.54-1.48 (m, 2H), 0.97 (t, J=9.0 Hz, 3H). MS: m/z 373.1 (M+H$^+$).

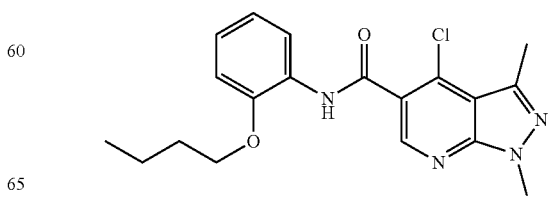

Example 109

4-Chloro-1,3-dimethyl-1H-pyrazolo[3,4-b]pyridine-5-carboxylic acid (2-butoxy-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.92 (s, 1H), 8.82 (s, 1H), 8.58 (d, J=6.0 Hz, 1H), 7.13 (t, J=6.0 Hz, 1H), 7.03 (t, J=6.0 Hz, 1H), 6.94 (d, J=6.0 Hz, 1H), 4.10-4.06 (m, 5H), 2.78 (s, 3H), 1.85-1.78 (m, 2H), 1.59-1.47 (m, 2H), 1.00-0.96 (t, J=6.0 Hz, 3H). MS: m/z 373.1 (M+H$^+$).

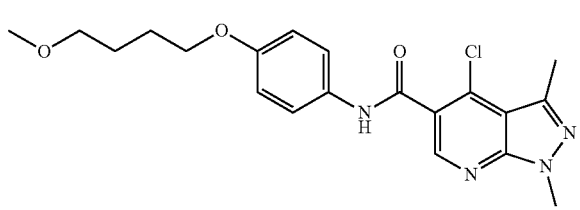 [SMILES: COCCCCOc1ccc(NC(=O)c2cnc3c(c(C)nn3C)c2Cl)cc1]

Example 110

4-Chloro-1,3-dimethyl-1H-pyrazolo[3,4-b]pyridine-5-carboxylic acid [4-(4-methoxy-butoxy)-phenyl]-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, DMSO-d6): δ=10.47 (s, 1H), 8.66 (s, 1H), 7.63 (d, J=8.8 Hz, 2H), 6.93 (d, J=9.2 Hz, 2H), 4.02 (s, 3H), 3.98-3.95 (m, 2H), 3.39-3.33 (m, 2H), 3.24 (s, 3H), 2.68 (s, 3H), 1.74-1.72 (m, 2H), 1.66-1.64 (m, 2H). MS: m/z 403.1 (M+H$^+$).

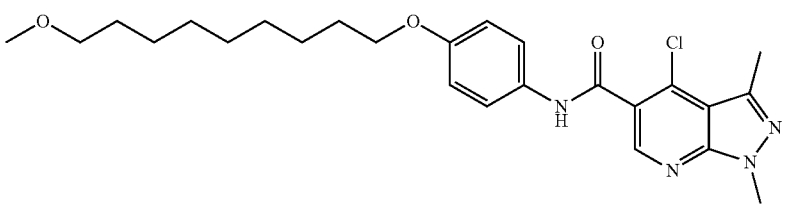 [SMILES: COCCCCCCCCCOc1ccc(NC(=O)c2cnc3c(c(C)nn3C)c2Cl)cc1]

Example 111

4-Chloro-1,3-dimethyl-1H-pyrazolo[3,4-b]pyridine-5-carboxylic acid [4-(9-methoxy-nonyloxy)-phenyl]-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$,): δ=8.80 (s, 1H), 7.89 (s, 1H), 7.56 (d, J=8.8 Hz, 2H), 6.92 (d, J=9.2 Hz, 2H), 4.08 (s, 3H), 3.98-3.93 (m, 2H), 3.39-3.35 (m, 2H), 3.34 (s, 3H), 2.75 (s, 3H), 1.80-1.77 (m, 2H), 1.59-1.55 (m, 2H), 1.48-1.44 (m, 2H), 1.41-1.33 (m, 8H). MS: m/z 473.2 (M+H$^+$).

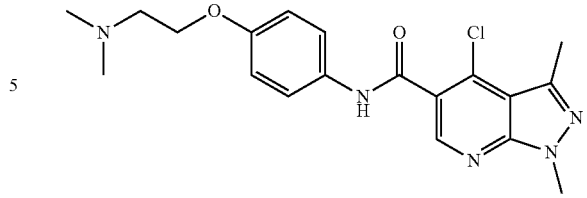

Example 112

4-Chloro-1,3-dimethyl-1H-pyrazolo[3,4-b]pyridine-5-carboxylic acid [4-(2-dimethylamino-ethoxy)-phenyl]-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.83 (s, 1H), 7.91 (s, 1H), 7.64 (m, 2H), 6.96 (d, J=9.0 Hz, 2H), 4.46-4.43 (m, 2H), 4.09 (s, 3H), 3.53-3.50 (m, 2H), 2.96 (s, 6H), 2.77 (s, 3H). MS: m/z 387.9 (M+H$^+$).

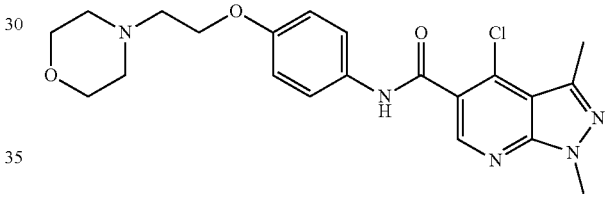

Example 113

4-Chloro-1,3-dimethyl-1H-pyrazolo[3,4-b]pyridine-5-carboxylic acid [4-(2-morpholin-4-yl-ethoxy)-phenyl]-amide The title compound was prepared using general procedure for 4-chloro-3-methyl-1-phenyl-1H-pyrazolo[3,4-b]pyridine-5-carboxylic acid (4-bromo-phenyl)-amide (Example 1).

$^1$HNMR (300 MHz, CDCl$_3$): δ=10.48 (s, 1H), 8.67 (s, 1H), 7.62 (d, J=7.2 Hz, 2H), 6.95 (d, J=7.2 Hz, 2H), 4.10-4.07 (m, 2H), 4.02 (s, 3H), 3.60-3.57 (m, 4H), 3.32 (s, 2H), 2.72-2.70 (m, 2H), 2.66 (s, 3H), 2.00-1.96 (m, 2H).MS: m/z 430.1 (M+H$^+$).

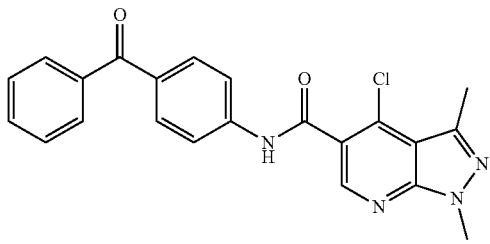 [SMILES: Cc1nn(C)c2ncc(C(=O)Nc3ccc(C(=O)c4ccccc4)cc3)c(Cl)c12]

Example 114

4-Chloro-1,3-dimethyl-1H-pyrazolo[3,4-b]pyridine-5-carboxylic acid (4-benzoyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (400 MHz, CDCl$_3$): δ=8.78 (s, 1H), 8.41 (s, 1H), 7.90-7.78 (m, 6H), 7.60-7.58 (m, 1H), 7.51-7.48 (m, 2H), 4.08 (s, 3H), 3.73 (s, 3H). MS: m/z 405.1 (M+H$^+$)

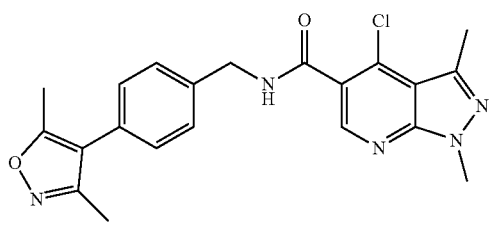 [SMILES: Cc1noc(C)c1-c1ccc(CNC(=O)c2cnc3c(c(C)nn3C)c2Cl)cc1]

Example 115

4-Chloro-1,3-dimethyl-1H-pyrazolo[3,4-b]pyridine-5-carboxylic acid 4-(3,5-dimethyl-isoxazol-4-yl)-benzylamide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.80 (s, 1H), 7.49 (d, J=8.1 Hz, 2H), 7.29-7.27 (m, 2H), 6.70 (brs, 1H), 4.77 (d, J=6.0 Hz, 2H), 4.08 (s, 3H), 2.74 (s, 3H), 2.42 (s, 3H), 2.28 (s, 3H). MS: m/z 410.1 (M+H$^+$).

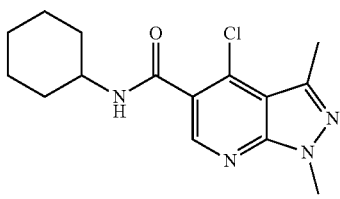 [SMILES: Cc1nn(C)c2ncc(C(=O)NC3CCCCC3)c(Cl)c12]

Example 116

4-Chloro-1,3-dimethyl-1H-pyrazolo[3,4-b]pyridine-5-carboxylic acid cyclohexylamide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.71 (s, 1H), 6.14-6.11 (m, 1H), 4.10 (s, 3H), 4.08-4.04 (m, 1H), 2.74 (s, 3H), 2.12-2.05 (m, 2H), 1.82-1.74 (m, 2H), 1.71-1.66 (m, 2H), 1.65-1.58 (m, 2H), 1.53-1.49 (m, 2H). MS: m/z 307.1 (M+H$^+$).

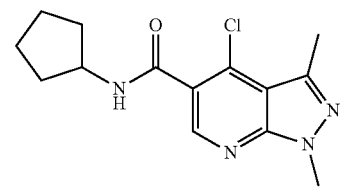 [SMILES: Cc1nn(C)c2ncc(C(=O)NC3CCCC3)c(Cl)c12]

Example 117

4-Chloro-1,3-dimethyl-1H-pyrazolo[3,4-b]pyridine-5-carboxylic acid cyclopentylamide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.70 (s, 1H), 6.34 (d, J=9.0 Hz, 1H), 4.51-4.40 (m, 2H), 4.11 (s, 3H), 2.77 (s, 3H), 2.17-2.08 (m, 2H), 1.80-1.65 (m, 5H). MS: m/z 292.9 (M+H$^+$).

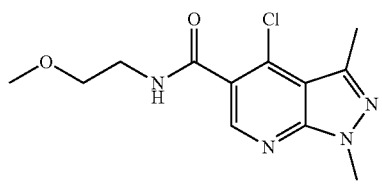 [SMILES: COCCNC(=O)c1cnc2c(c(C)nn2C)c1Cl]

Example 118

4-Chloro-1,3-dimethyl-1H-pyrazolo[3,4-b]pyridine-5-carboxylic acid (2-methoxy-ethyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.74 (s, 1H), 6.70-6.66 (m, 1H), 4.08 (s, 3H), 3.75-3.78 (m, 2H), 3.70-3.69 (m, 2H), 3.44 (s, 3H), 2.75 (s, 3H). MS: m/z 282.9 (M+H$^+$).

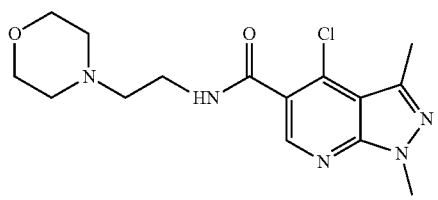 [SMILES: Cc1nn(C)c2ncc(C(=O)NCCN3CCOCC3)c(Cl)c12]

Example 119

4-Chloro-1,3-dimethyl-1H-pyrazolo[3,4-b]pyridine-5-carboxylic acid (2-morpholin-4-yl-ethyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, CDCl₃): δ=8.79 (s, 1H), 7.04 (s, 1H), 4.09 (s, 3H), 3.74-3.70 (m, 4H), 3.66-3.60 (m, 2H), 2.76 (s, 3H), 2.66 (t, J=6.0 Hz, 2H), 2.64-2.52 (m, 4H). MS: m/z 337.9 (M+H⁺).

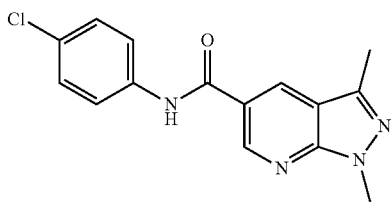 [SMILES: Cc1nn(C)c2ncc(C(=O)Nc3ccc(Cl)cc3)cc12]

Example 120

1,3-Dimethyl-1H-pyrazolo[3,4-b]pyridine-5-carboxylic acid (4-chloro-phenyl)-amide The title compound was prepared using general procedure for 3-methyl-1-phenyl-1H-pyrazolo[3,4-b]pyridine-5-carboxylic acid (4-chloro-phenyl)-amide (Example 34). ¹HNMR (300 MHz, CDCl₃): δ=9.02 (s, 1H), 8.55 (s, 1H), 7.93 (brs, 1H), 7.64 (d, J=9.0 Hz, 2H), 7.38 (d, J=8.7 Hz, 2H), 4.14 (s, 3H), 2.63 (s, 3H). MS: m/z 301.1 (M+H⁺).

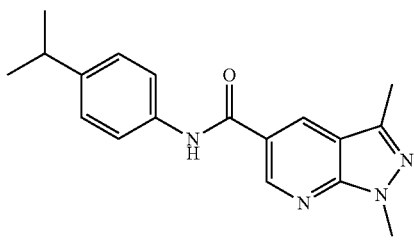 [SMILES: Cc1nn(C)c2ncc(C(=O)Nc3ccc(C(C)C)cc3)cc12]

Example 121

1,3-Dimethyl-1H-pyrazolo[3,4-b]pyridine-5-carboxylic acid (4-isopropyl-phenyl)-amide The title compound was prepared using general procedure for 3-methyl-1-phenyl-1H-pyrazolo[3,4-b]pyridine-5-carboxylic acid (4-chloro-phenyl)-amide (Example 34). ¹HNMR (300 MHz, CDCl₃): δ=9.01 (s, 1H), 8.53 (s, 1H), 7.96 (brs, 1H), 7.58 (d, J=8.4 Hz, 2H), 7.26 (d, J=9.6 Hz, 2H), 4.12 (s, 3H), 2.95-2.91 (m, 1H), 2.61 (s, 3H), 1.27 (d, J=6.9 Hz, 6H). MS: m/z 309.1 (M+H⁺).

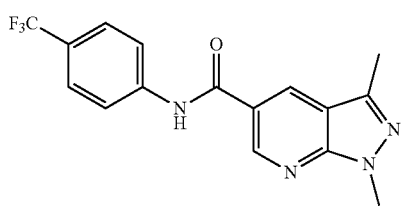

Example 122

1,3-Dimethyl-1H-pyrazolo[3,4-b]pyridine-5-carboxylic acid (4-trifluoromethyl-phenyl)-amide The title compound was prepared using general procedure for 3-methyl-1-phenyl-1H-pyrazolo[3,4-b]pyridine-5-carboxylic acid (4-chloro-phenyl)-amide (Example 34). ¹HNMR (300 MHz, CDCl₃): δ=9.05 (s, 1H), 8.58 (s, 1H), 7.99 (brs, 1H), 7.83 (d, J=8.4 Hz, 2H), 7.68 (d, J=9.0 Hz, 2H), 4.15 (s, 3H), 2.65 (s, 3H). MS: m/z 335.1 (M+H⁺).

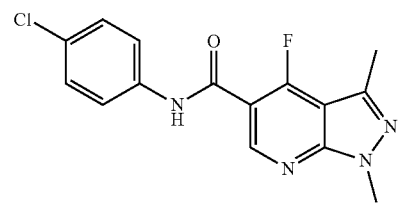 [SMILES: Cc1nn(C)c2ncc(C(=O)Nc3ccc(Cl)cc3)c(F)c12]

Example 123

4-Fluoro-1,3-dimethyl-1H-pyrazolo[3,4-b]pyridine-5-carboxylic acid (4-chloro-phenyl)-amide The title compound was prepared using general procedure for 4-fluoro-3-methyl-1-phenyl-1H-pyrazolo[3,4-b]pyridine-5-carboxylic acid (4-chloro-phenyl)-amide (Example 39). ¹HNMR (300 MHz, CDCl₃): δ=9.22 (d, J=10.2 Hz, 1H), 8.27-8.22 (m, 1H), 7.64 (d, J=8.7 Hz, 2H), 7.39-7.35 (m, 2H), 4.12 (s, 3H), 2.72 (s, 3H). MS: m/z 318.9 (M+H⁺).

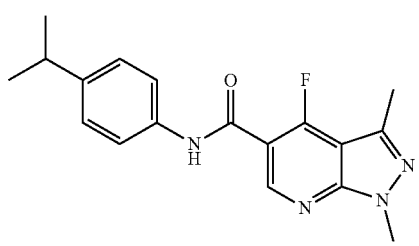 [SMILES: Cc1nn(C)c2ncc(C(=O)Nc3ccc(C(C)C)cc3)c(F)c12]

Example 124

4-Fluoro-1,3-dimethyl-1H-pyrazolo[3,4-b]pyridine-5-carboxylic acid (4-isopropyl-phenyl)-amide The title compound was prepared using general procedure for 4-fluoro-3-methyl-1-phenyl-1H-pyrazolo[3,4-b]pyridine-5-carboxylic acid (4-chloro-phenyl)-amide (Example 39). ¹HNMR (300 MHz, CDCl₃): δ=9.24 (d, J=10.2 Hz, 1H), 8.20 (d, J=12.6 Hz, 1H), 7.61-7.58 (m, 2H), 7.29-7.26 (m, 2H), 4.12 (s, 3H), 2.96-2.92 (m, 1H), 2.72 (s, 3H), 1.32-1.25 (m, 6H). MS: m/z 325.2 (M+H⁺).

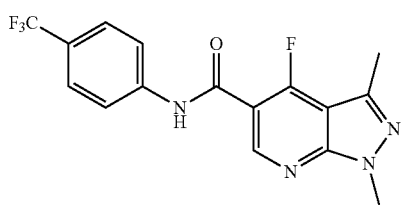 [SMILES: Cc1nn(C)c2ncc(C(=O)Nc3ccc(C(F)(F)F)cc3)c(F)c12]

Example 125

4-Fluoro-1,3-dimethyl-1H-pyrazolo[3,4-b]pyridine-5-carboxylic acid (4-trifluoromethyl-phenyl)-amide The title compound was prepared using general procedure for 4-fluoro-3-methyl-1-phenyl-1H-pyrazolo[3,4-b]pyridine-5-carboxylic acid (4-chloro-phenyl)-amide (Example 39). ¹HNMR (300 MHz, CDCl₃): δ=9.24 (d, J=10.5 Hz, 1H), 8.39 (d, J=12.6 Hz, 1H), 7.83 (d, J=8.1 Hz, 2H), 7.67 (d, J=8.7 Hz, 2H), 4.13 (s, 3H), 2.73 (s, 3H). MS: m/z 351.1 (M−H⁺).

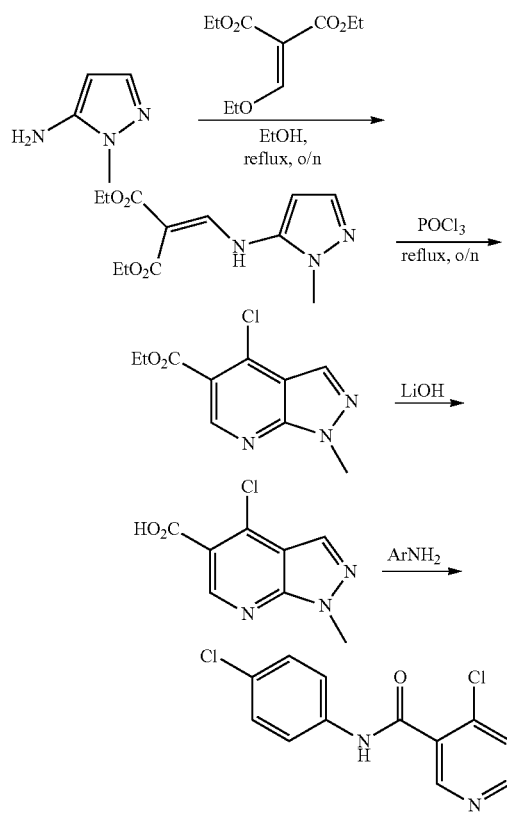

Example 126

4-Chloro-1-methyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=10.80 (s, 1H), 8.78 (s, 1H), 8.41(s, 1H), 7.77 (d, J=8.7 Hz, 2H), 7.45 (d, J=8.7 Hz, 2H), 4.13 (s, 3H). MS: m/z 319.0 (M−H⁺).

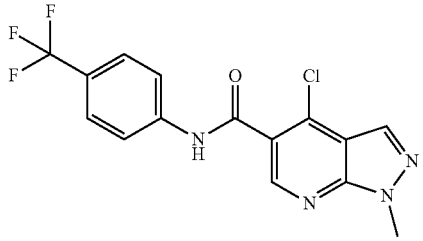 [SMILES: Cn1ncc2c(Cl)c(C(=O)Nc3ccc(C(F)(F)F)cc3)cnc21]

Example 127

4-Chloro-1-methyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=11.04 (s, 1H), 8.81 (s, 1H), 8.42 (s, 1H), 7.95 (d, J=8.7 Hz, 2H), 7.77 (d, J=8.7 Hz, 2H), 4.13 (s, 3H). MS: m/z 353.1 (M−H⁺).

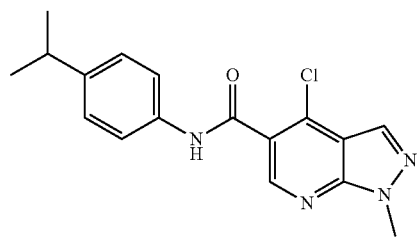 [SMILES: CC(C)c1ccc(NC(=O)c2cnc3c(cnn3C)c2Cl)cc1]

Example 128

4-Chloro-1-methyl-1H-pyrazolo[3,4-b]pyridine-5-carboxylic acid (4-isopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=10.58 (s, 1H), 8.75 (s, 1H), 8.40 (s, 1H), 7.64 (d, J=8.7 Hz, 2H), 7.24 (d, J=8.7 Hz, 2H), 4.13 (s, 3H), 2.90-2.84 (m, 1H), 1.20 (d, J=6.9 Hz, 6H). MS: m/z 327.1 (M−H⁺).

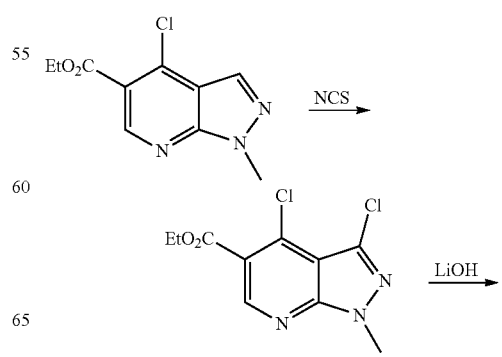

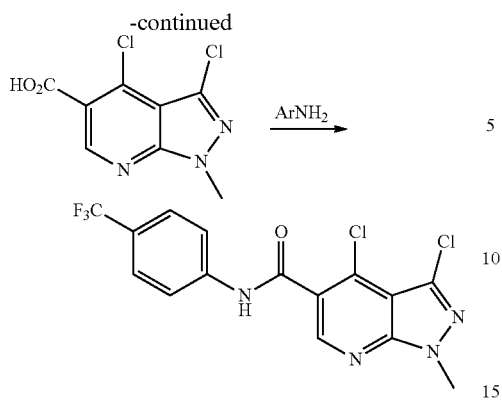

Example 129

3,4-Dichloro-1-methyl-1H-pyrazolo[3,4-b]pyridine-5-carboxylic acid (4-trifluoromethyl-phenyl)-amide Step 1:

To a solution of 4-Chloro-1-methyl-1H-pyrazolo[3,4-b]pyridine-5-carboxylic acid ethyl ester (1.2 g, 5 mmol) in DMF (30 mL), was added NCS (2.75 g, 20 mmol). The mixture was stirred at 100° C. for 14 hrs. The solvent was removed and the residue was purified by prep-HPLC to give 3,4-dichloro-1-methyl-1H-pyrazolo[3,4-b]pyridine-5-carboxylic acid ethyl ester (0.26 g, yield: 18%) as a white solid. $^1$HNMR (300 MHz, CDCl$_3$): δ=8.99 (s, 1H), 4.48 (q, J=7.2 Hz, 2H), 4.12 (s, 3H), 1.46 (t, J=7.2 Hz, 3H).

Step 2-3:

These two steps are similar to 4-chloro-3-methyl-1-phenyl-1H-pyrazolo[3,4-b]pyridine-5-carboxylic acid (4-isopropyl-phenyl)-amide (Example 7). $^1$HNMR (300 MHz, CDCl$_3$): δ=8.91 (s, 1H), 8.13 (brs, 1H), 7.83-7.80 (m, 2H), 7.70-7.67 (m, 2H), 4.13 (s, 3H). MS: m/z 387.0 (M−H$^+$).

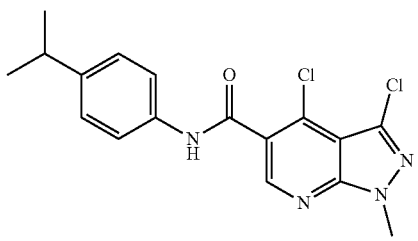 [SMILES: CC(C)c1ccc(NC(=O)c2cnc3c(c(Cl)nn3C)c2Cl)cc1]

Example 130

3,4-Dichloro-1-methyl-1H-pyrazolo[3,4-b]pyridine-5-carboxylic acid (4-isopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.61 (s, 1H), 8.79 (s, 1H), 7.63 (d, J=8.4 Hz, 2H), 7.25 (d, J=8.4 Hz, 2H), 4.13 (s, 3H), 2.90-2.85 (m, 1H), 1.205 (t, J=6.9 Hz, 6H). MS: m/z 361.1 (M−H$^+$).

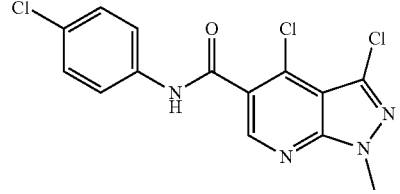 [SMILES: Cn1nc(Cl)c2c(Cl)c(C(=O)Nc3ccc(Cl)cc3)cnc21]

Example 131

3,4-Dichloro-1-methyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.85 (s, 1H), 8.83 (s, 1H), 7.75 (d, J=8.4 Hz, 2H), 7.45 (d, J=8.4 Hz, 2H), 4.09 (s, 3H). MS: m/z 353.0 (M−H$^+$).

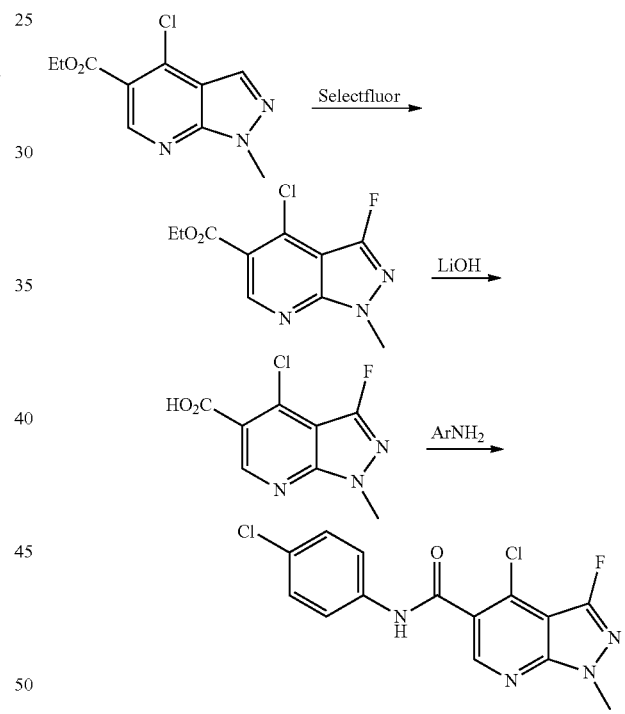

Example 132

4-Chloro-3-fluoro-1-methyl-1H-pyrazolo[3,4-b]pyridine-5-carboxylic acid (4-chloro-phenyl)-amide Step 1:

To a solution of 4-chloro-1-methyl-1H-pyrazolo[3,4-b]pyridine-5-carboxylic acid ethyl ester (0.12 g, 0.5 mmol) in CH$_3$CN (50 mL), HOAc (0.05 mL) and selectfluor (0.36 g, 1.0 mmol) was added. The mixture was stirred at 80° C. for 14 hrs. The solvent was removed and the residue was purified by prep-HPLC to give 4-chloro-3-fluoro-1-methyl-1H-pyrazolo[3,4-b]pyridine-5-carboxylic acid ethyl ester (0.15 g, yield: 13%). MS: m/z 258.1 (M−H$^+$).

Step 2 and 3:

These two steps are similar to 4-chloro-3-methyl-1-phenyl-1H-pyrazolo[3,4-b]pyridine-5-carboxylic acid (4-isopropyl-phenyl)-amide (Example 7). ¹HNMR (300 MHz, DMSO-d6): δ=10.85 (s, 1H), 8.84 (s, 1H), 7.75 (d, J=8.4 Hz, 2H), 7.45 (d, J=8.4 Hz, 2H), 4.01 (s, 3H). MS: m/z 336.9 (M−H⁺).

Example 133

4-Chloro-3-fluoro-1-methyl-1H-pyrazolo[3,4-b]pyridine-5-carboxylic acid (4-trifluoromethyl-phenyl)-amide The title compound was prepared using general procedure for 4-chloro-3-fluoro-1-methyl-1H-pyrazolo[3,4-b]pyridine-5-carboxylic acid (4-chloro-phenyl)-amide (Example 132). ¹HNMR (300 MHz, DMSO-d6): δ=11.07 (s, 1H), 8.87 (s, 1H), 7.94 (d, J=8.4 Hz, 2H), 7.77 (d, J=8.4 Hz, 2H), 4.01 (s, 3H). MS: m/z 370.9 (M−H⁺).

Example 134

4-Chloro-3-fluoro-1-methyl-1H-pyrazolo[3,4-b]pyridine-5-carboxylic acid (4-isopropyl-phenyl)-amide The title compound was prepared using general procedure for 4-chloro-3-fluoro-1-methyl-1H-pyrazolo[3,4-b]pyridine-5-carboxylic acid (4-chloro-phenyl)-amide (Example 132). ¹HNMR (300 MHz, DMSO-d6): δ=10.62 (s, 1H), 8.80 (s, 1H), 7.63 (d, J=8.4 Hz, 2H), 7.25 (d, J=8.4 Hz, 2H), 4.01 (s, 3H), 2.90-2.85 (m, 1H), 1.22 (t, J=6.9 Hz, 6H). MS: m/z 344.9 (M−H⁺).

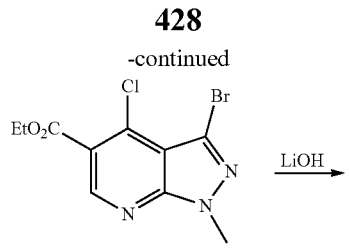

Example 135

3-Bromo-4-chloro-1-methyl-1H-pyrazolo[3,4-b]pyridine-5-carboxylic acid (4-chloro-phenyl)-amide This target compound was prepared similar to 3,4-dichloro-1-methyl-1H-pyrazolo[3,4-b]pyridine-5-carboxylic acid (4-trifluoromethyl-phenyl)-amide (Example 129). ¹HNMR (300 MHz, CDCl₃): δ=8.88 (s, 1H), 8.00 (brs, 1H), 7.64 (d, J=8.7 Hz, 2H), 7.39 (d, J=8.7 Hz, 2H), 4.16 (s, 3H). MS: m/z 399.0 (M+H⁺).

Example 136

3-Bromo-4-chloro-1-methyl-1H-pyrazolo[3,4-b]pyridine-5-carboxylic acid (4-trifluoromethyl-phenyl)-amide This target compound was prepared similar to 3,4-dichloro-1-methyl-1H-pyrazolo[3,4-b]pyridine-5-carboxylic acid (4-trifluoromethyl-phenyl)-amide (Example 129). ¹HNMR (300 MHz, CDCl₃): δ=8.88 (s, 1H), 8.22 (brs, 1H), 7.88-7.30 (m, 4H), 4.10 (s, 3H). MS: m/z 433.0 (M+H⁺).

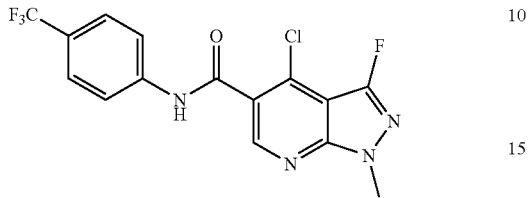

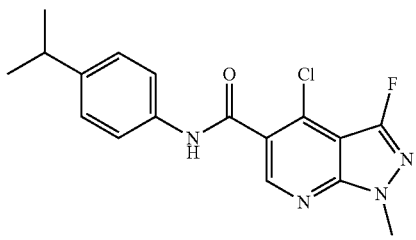

Example 137

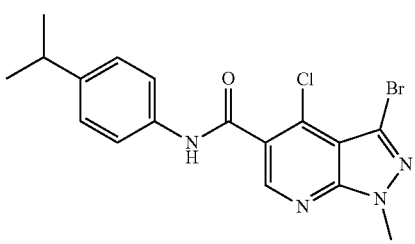 [SMILES: CC(C)c1ccc(NC(=O)c2cnc3c(c(Br)nn3C)c2Cl)cc1]

3-Bromo-4-chloro-1-methyl-1H-pyrazolo[3,4-b]pyridine-5-carboxylic acid (4-isopropyl-phenyl)-amide This target compound was prepared similar to 3,4-dichloro-1-methyl-1H-pyrazolo[3,4-b]pyridine-5-carboxylic acid (4-trifluoromethyl-phenyl)-amide (Example 129). $^1$HNMR (300 MHz, DMSO-d6): δ=10.61 (s, 1H), 8.78 (s, 1H), 7.64 (d, J=8.4 Hz, 2H), 7.25 (d, J=8.4 Hz, 2H), 4.10 (s, 3H), 2.90-2.85 (m, 1H), 1.21-1.17 (m, 6H). MS: m/z 405.1 (M+H$^+$).

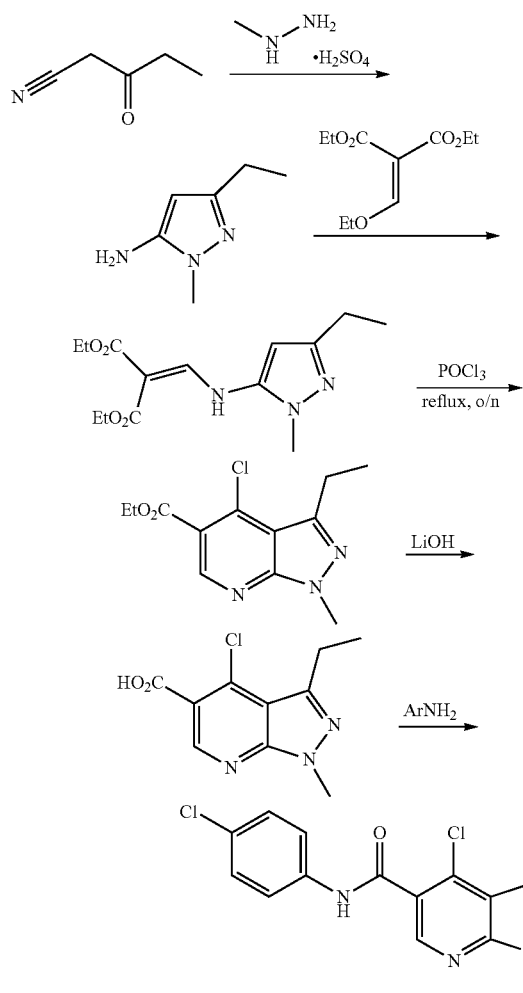

Example 138

4-Chloro-3-ethyl-1-methyl-1H-pyrazolo[3,4-b]pyridine-5-carboxylic acid (4-chloro-phenyl)-amide This target was prepared similar to 4-chloro-3-methyl-1-phenyl-1H-pyrazolo[3,4-b]pyridine-5-carboxylic acid (4-isopropyl-phenyl)-amide (Example 7). $^1$HNMR (300 MHz, DMSO-d6): δ=10.79 (s, 1H), 8.70 (s, 1H), 7.76 (d, J=8.7 Hz, 2H), 7.44 (d, J=8.7 Hz, 2H), 4.04 (s, 3H), 3.10 (q, J=7.5 Hz, 2H), 1.36-1.31 (t, J=7.5 Hz, 3H). MS: m/z 347.1 (M−H$^+$).

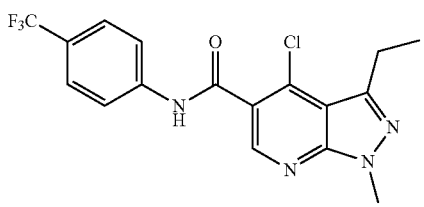 [SMILES: CCc1nn(C)c2ncc(C(=O)Nc3ccc(C(F)(F)F)cc3)c(Cl)c12]

Example 139

4-Chloro-3-ethyl-1-methyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=8.84 (s, 1H), 8.11 (brs, 1H), 7.82 (d, J=8.1 Hz, 2H), 7.80 (d, J=8.1 Hz, 2H), 4.13 (s, 3H), 3.22-3.15 (q, J=7.5 Hz, 2H), 1.47-1.27 (t, 3H). MS: m/z 381.1 (M−H$^+$).

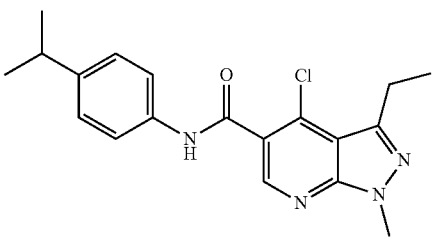 [SMILES: CCc1nn(C)c2ncc(C(=O)Nc3ccc(C(C)C)cc3)c(Cl)c12]

Example 140

4-Chloro-3-ethyl-1-methyl-1H-pyrazolo[3,4-b]pyridine-5-carboxylic acid (4-isopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, CDCl$_3$): δ=8.81 (s, 1H), 7.90 (brs, 1H), 7.61 (d, J=8.4 Hz, 2H), 7.28 (d, J=8.4 Hz, 2H), 4.12 (s, 3H), 3.21-3.11 (m, 2H), 2.97-2.92 (m, 1H), 1.42 (t, J=7.5 Hz, 3H), 1.27 (d, J=6.5 Hz, 6H). MS: m/z 357.1 (M+H$^+$).

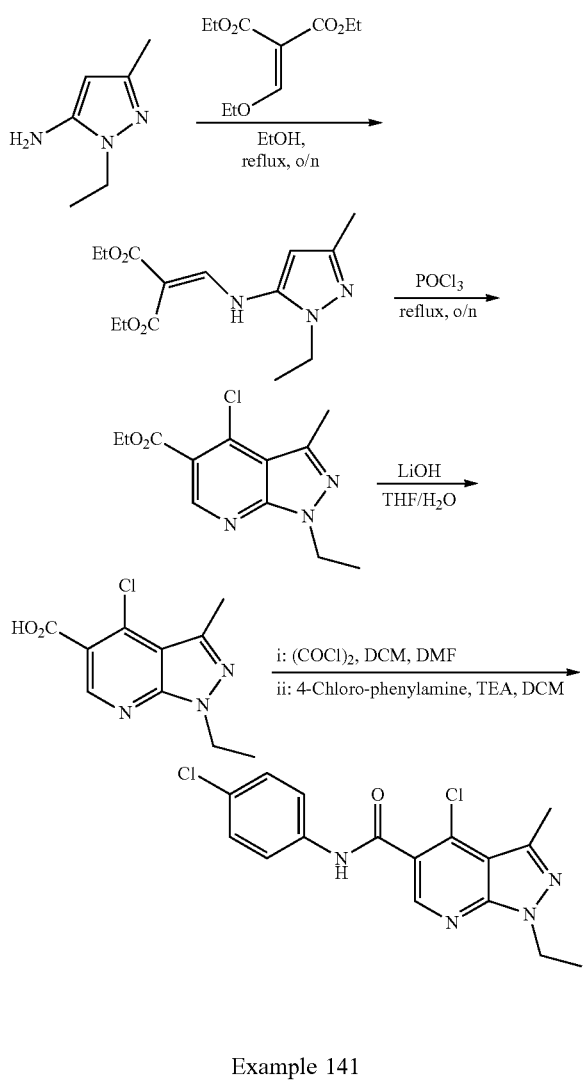

Example 141

4-Chloro-1-ethyl-3-methyl-1H-pyrazolo[3,4-b]pyridine-5-carboxylic acid (4-chloro-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=10.75 (s, 1H), 8.69 (s, 1H), 7.76 (d, J=9.0 Hz, 2H), 7.43 (d, J=8.7 Hz, 2H), 4.46 (q, J=7.2 Hz, 2H), 2.69 (s, 3H), 1.41 (t, J=7.2 Hz, 3H). MS: m/z 349.1 (M+H⁺).

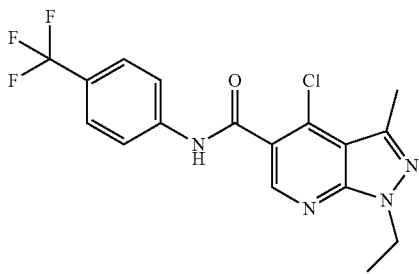 [SMILES: CCn1nc(C)c2c(Cl)c(C(=O)Nc3ccc(C(F)(F)F)cc3)cnc21]

Example 142

4-Chloro-1-ethyl-3-methyl-1H-pyrazolo[3,4-b]pyridine-5-carboxylic acid (4-trifluoromethyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (400 MHz, DMSO-d6): δ=10.98 (s, 1H), 8.72 (s, 1H), 7.94 (d, J=9.0 Hz, 2H), 7.76 (d, J=9.0 Hz, 2H), 4.49 (q, J=7.2 Hz, 2H), 2.70 (s, 3H), 1.41 (t, J=7.2 Hz, 3H). MS: 383.1 (M+H⁺).

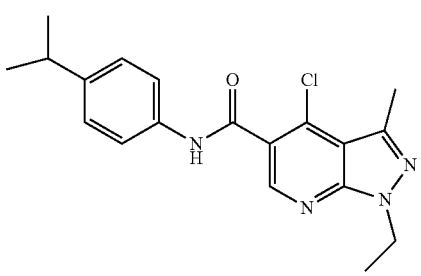 [SMILES: CCn1nc(C)c2c(Cl)c(C(=O)Nc3ccc(C(C)C)cc3)cnc21]

Example 143

4-Chloro-1-ethyl-3-methyl-1H-pyrazolo[3,4-b]pyridine-5-carboxylic acid (4-isopropyl-phenyl)-amide The title compound was prepared using general procedure for 4-chloro-3-methyl-1-phenyl-1H-pyrazolo[3,4-b]pyridine-5-carboxylic acid (4-bromo-phenyl)-amide (Example 1). ¹HNMR (300 MHz, DMSO-d6): δ=10.52 (s, 1H), 8.65 (s, 1H), 7.64 (d, J=8.4 Hz, 2H), 7.24 (d, J=8.4 Hz, 2H), 4.46 (q, J=7.2 Hz, 2H), 2.90-2.85 (m, 1H), 2.69 (s, 3H), 1.41 (t, q, J=7.2 Hz, 3H), 1.20 (d, q, J=6.9 Hz, 6H). MS: 355.2 (M−H⁺).

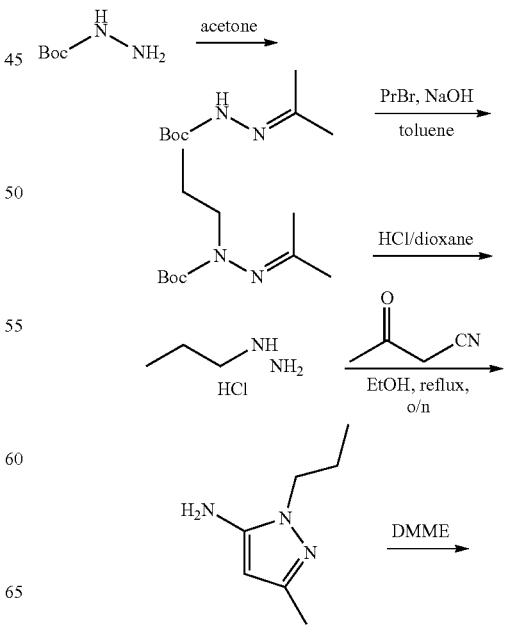

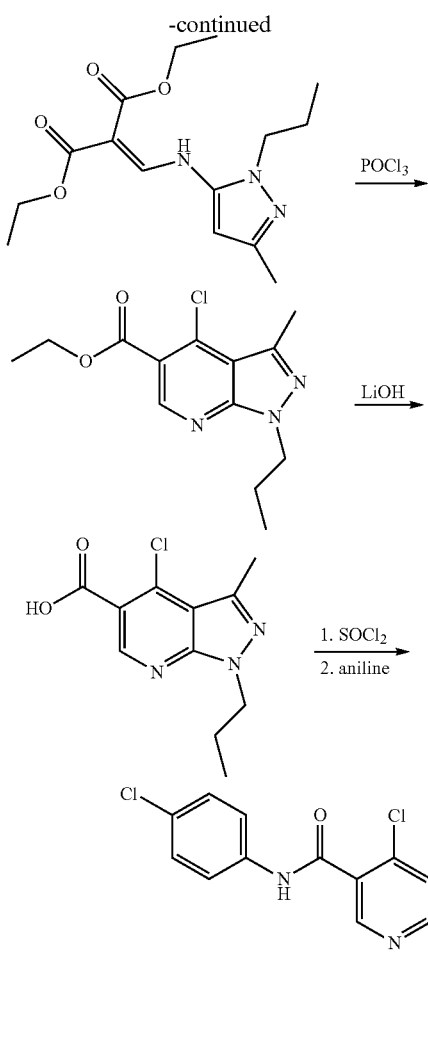

Example 144

4-chloro-N-(4-chlorophenyl)-3-methyl-1-propyl-1H-pyrazolo[3,4-b]pyridine-5-carboxamide Step 1:

A solution of tert-butyl hydrazinecarboxylate (5 g, 37.8 mmol) in acetone (50 mL) was refluxed overnight. Resultant was filtrated to afford tert-butyl 2-(propan-2-ylidene)hydrazine-1-carboxylate (6.3 g, yield: 97%) as a white solid, which was used directly without further purification. $^1$HNMR (300 MHz, DMSO-d6): δ=9.29 (s, 1H), 1.85 (s, 3H), 1.77 (s, 3H), 1.42 (s, 9H).

Step 2:

To a solution of tert-butyl 2-(propan-2-ylidene)hydrazine-1-carboxylate (6.3 g, 36.6 mmol) in toluene (100 mL) was added 1-bromopropane (5.7 g, 47.2 mmol) and NaOH (2.2 g 54.9 mmol), it was then refluxed overnight. Resultant was concentrated to dryness and the crude mixture was purified by flash column (EA in PE: 0 to 20%) directly to afford tert-butyl 2-(propan-2-ylidene)-1-propylhydrazine-1-carboxylate (6 g, yield: 77%) as white solid. $^1$HNMR (300 MHz, DMSO-d6): δ=3.35-3.32 (m, 2H), 1.96 (s, 3H), 1.77 (s, 3H), 1.37 (s, 11H), 0.82 (t, J=7.5 Hz, 3H);

Step 3:

To a solution of tert-butyl 2-(propan-2-ylidene)-1-propylhydrazine-1-carboxylate (6 g, 28 mmol) in dioxane (30 mL) was added HCl/dioxane (30 mL), it was then heated to 60° C. and stirred at this temperature overnight. Resultant was concentrated to complete dryness by repetitive addition of toluene under vacuum evaporation to afford propylhydrazine hydrochloride as white solid without further purification.

Step 4:

To a solution of propylhydrazine hydrochloride (crude, 28 mmol) in EtOH (50 mL) was added 3-oxobutanenitrile (2.3 g, 28 mmol), it was then refluxed overnight. Resultant was concentrated to remove EtOH. The residue was diluted with MeOH (10 mL) and adjusted pH to 8 with NH3H2O. The resulting solid was filtered and the filtrate was purified by flash column (C18-silica, MeCN in water: 5% to 95% 30 min) to afford 3-methyl-1-propyl-1H-pyrazol-5-amine (2.2 g crude, >80% purity, tracked by LC/MS) of as light brown oil. MS: m/z 140.1.

Step 5:

To a solution of 3-methyl-1-propyl-1H-pyrazol-5-amine (2.2 g, 15.8 mmol) in EtOH (50 mL) was added DMME (3.4 g, 15.8 mmol), it was then refluxed overnight. Resultant was concentrated under reduced pressure and the residue was purified by flash column (EA in PE: 0 to 30%) to afford diethyl 2-(((3-methyl-1-propyl-1H-pyrazol-5-yl)amino)methylene)malonate (1.8 g, yield: 47%) as light brown oil.

Step 6:

A solution of diethyl 2-(((3-methyl-1-propyl-1H-pyrazol-5-yl)amino)methylene)malonate (1.8 g, 5.8 mmol) in POCl3 (30 mL) was refluxed overnight. Resultant was evaporated to remove POCl3. The residue was diluted with EA (200 mL) and aqueous Na2CO3 (200 mL) and then stirred at rt for 1 h. The organic layer was concentrated under reduced pressure and purified by flash column (EA in PE: 0 to 30%) to afford 1.2 g (yield: 75%) of ethyl 4-chloro-3-methyl-1-propyl-1H-pyrazolo[3,4-b]pyridine-5-carboxylate as a white solid.

Step 7:

To a solution of ethyl 4-chloro-3-methyl-1-propyl-1H-pyrazolo[3,4-b]pyridine-5-carboxylate (200 mg, 0.71 mmol in THF/H20 (5/1, 20mL) was added LiOHH2O (149 mg, 3.55 mmol), it was then stirred at rt overnight. Resultant was evaporated to remove THF. The remaining mixture was diluted with water (30 mL) and adjusted pH to 2 with con. HCl. The precipitate was filtrated to afford 180 mg (yield: 98%) of 4-chloro-3-methyl-1-propyl-1H-pyrazolo[3,4-b]pyridine-5-carboxylic acid as a white solid.

Step 8:

To a solution of 4-chloro-3-methyl-1-propyl-1H-pyrazolo[3,4-b]pyridine-5-carboxylic acid (60 mg, 0.24 mmol) in anhydrous toluene (20 mL) was added SOCl$_2$ (1 mL), it was then refluxed for 2 hr. Resultant was concentrated to afford acyl chloride without further purification. The acyl chloride was dissolved in anhydrous DCM (1 mL), and dropped into a mixture of 4-chloro-phenylamine (30 mg, 0.24 mmol) and TEA (0.5 mL) in DCM (10 mL). The reaction was stirred at rt overnight. The resultant was concentrated to dryness and directly purified by flash column (EA in PE: 0 to 50%) to afford 20 mg (yield: 23%) of 4-chloro-N-(4-chlorophenyl)-3-methyl-1-propyl-1H-pyrazolo[3,4-b]pyridine-5-carboxamide as a white solid. $^1$HNMR (300 MHz, DMSO-d6): δ=10.77 (s, 1H), 8.68 (s, 1H), 7.75 (d, J=8.7, 2H), 7.44 (d, J=8.4, 2H), 4.39 (t, J=6.6, 2H), 2.69 (s, 3H), 1.90-1.83 (m, 2H), 0.81 (t, J=7.2, 3H); MS: m/z 363.1 (M+H$^+$).

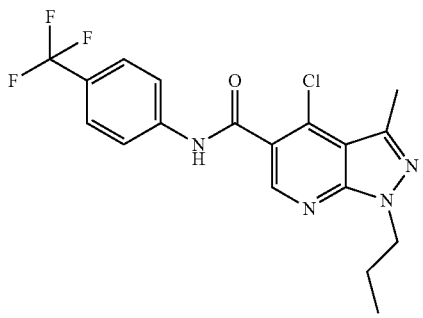 [SMILES: CCCn1nc(C)c2c(Cl)c(C(=O)Nc3ccc(C(F)(F)F)cc3)cnc21]

Example 145

4-chloro-3-methyl-1-propyl-N-(4-(trifluoromethyl)phenyl)-1H-pyrazolo[3,4-b]pyridine-5-carboxamide The title compound was prepared using general procedure for 4-chloro-N-(4-chlorophenyl)-3-methyl-1-propyl-1H-pyrazolo[3,4-b]pyridine-5-carboxamide (Example 144). $^1$HNMR (300 MHz, DMSO-d6): δ=10.99 (s, 1H), 8.71 (s, 1H), 7.94 (d, J=8.4 Hz, 2H), 7.75 (d, J=8.7 Hz, 2H), 4.39 (t, J=6.9 Hz, 2H), 2.69 (s, 3H), 1.88-1.85 (m, 2H), 0.81 (t, J=7.5 Hz, 3H); MS: m/z 397.1 (M+H$^+$).

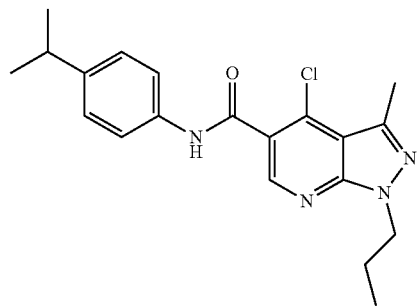 [SMILES: CCCn1nc(C)c2c(Cl)c(C(=O)Nc3ccc(C(C)C)cc3)cnc21]

Example 146

4-chloro-N-(4-isopropylphenyl)-3-methyl-1-propyl-1H-pyrazolo[3,4-b]pyridine-5-carboxamide The title compound was prepared using general procedure for 4-chloro-N-(4-chlorophenyl)-3-methyl-1-propyl-1H-pyrazolo[3,4-b]pyridine-5-carboxamide (Example 144). $^1$HNMR (300 MHz, DMSO-d6): δ=10.54 (s, 1H), 8.64 (s, 1H), 7.63 (d, J=8.4 Hz, 2H), 7.24 (d, J=8.7 Hz, 2H), 4.41-4.36 (q, J=6.6 Hz, 2H), 2.91-2.82 (m, 1H), 2.69 (s, 3H), 1.90-1.83 (m, 2H), 1.20 (d, J=6.8 Hz, 6H), 0.80 (t, J=7.5 Hz, 3H); MS: m/z 371.1 (M+H$^+$).

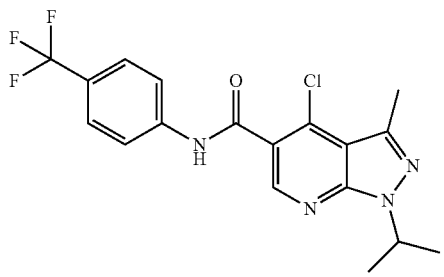 [SMILES: Cc1nn(C(C)C)c2ncc(C(=O)Nc3ccc(C(F)(F)F)cc3)c(Cl)c12]

Example 147

4-chloro-1-isopropyl-3-methyl-N-(4-(trifluoromethyl)phenyl)-1H-pyrazolo[3,4-b]pyridine-5-carboxamide The title compound was prepared using general procedure for 4-chloro-N-(4-chlorophenyl)-3-methyl-1-propyl-1H-pyrazolo[3,4-b]pyridine-5-carboxamide (Example 144). $^1$HNMR (300 MHz, DMSO-d6): δ=10.98 (s, 1H), 8.71 (s, 1H), 7.94 (d, J=8.4 Hz, 2H), 7.76 (d, J=8.7 Hz, 2H), 5.22-5.13 (m, 1H), 2.70 (s, 3H), 1.49 (d, J=6.6 Hz, 6H); MS: m/z 397.1 (M+H$^+$).

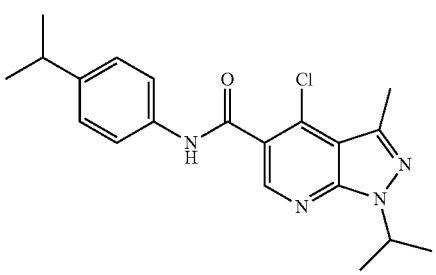 [SMILES: Cc1nn(C(C)C)c2ncc(C(=O)Nc3ccc(C(C)C)cc3)c(Cl)c12]

Example 148

4-chloro-1-isopropyl-N-(4-isopropylphenyl)-3-methyl-1H-pyrazolo[3,4-b]pyridine-5-carboxamide The title compound was prepared using general procedure for 4-chloro-N-(4-chlorophenyl)-3-methyl-1-propyl-1H-pyrazolo[3,4-b]pyridine-5-carboxamide (Example 144). $^1$HNMR (300 MHz, DMSO-d6): δ=10.52 (s, 1H), 8.64 (s, 1H), 7.63 (d, J=8.4, Hz 2H), 7.23 (d, J=8.7 Hz, 2H), 5.19-5.14 (m, 1H), 2.89-2.84 (m, 1H), 2.69 (s, 3H), 1.49 (d, J=6.9 Hz, 6H), 1.19 (d, J=6.9 Hz, 6H); MS: m/z 371.2 (M+H$^+$).

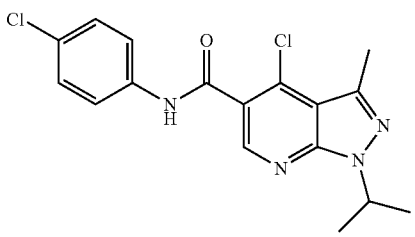 [SMILES: Cc1nn(C(C)C)c2ncc(C(=O)Nc3ccc(Cl)cc3)c(Cl)c12]

Example 149

4-chloro-N-(4-chlorophenyl)-1-isopropyl-3-methyl-1H-pyrazolo[3,4-b]pyridine-5-carboxamide The title compound was prepared using general procedure for 4-chloro-N-(4-chlorophenyl)-3-methyl-1-propyl-1H-pyrazolo[3,4-b]pyridine-5-carboxamide (Example 144). ¹HNMR (300 MHz, DMSO-d6): δ=10.75 (s, 1H), 8.67 (s, 1H), 7.75 (d, J=8.4 Hz, 2H), 7.44 (d, J=8.7 Hz, 2H), 5.10-5.14 (m, 1H), 2.69 (s, 3H), 1.49 (d, J=6.6 Hz, 6H); MS: m/z 363.1 (M+H⁺).

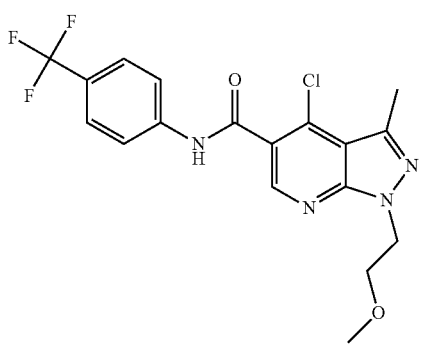 [SMILES: COCCn1nc(C)c2c(Cl)c(C(=O)Nc3ccc(C(F)(F)F)cc3)cnc21]

Example 150

4-chloro-1-(2-methoxyethyl)-3-methyl-N-(4-(trifluoromethyl)phenyl)-1H-pyrazolo[3,4-b]pyridine-5-carboxamide The title compound was prepared using general procedure for 4-chloro-N-(4-chlorophenyl)-3-methyl-1-propyl-1H-pyrazolo[3,4-b]pyridine-5-carboxamide (Example 144). ¹HNMR (300 MHz, DMSO-d6): δ=10.97 (s, 1H), 8.70 (s, 1H), 7.94 (d, J=8.4 Hz, 2H), 7.74 (d, J=8.7 Hz, 2H), 4.59 (t, J=5.1 Hz, 2H), 3.80 (t, J=5.4 Hz, 2H), 3.19 (s, 3H), 2.70 (s, 3H); HRMS (ESI+ve): MS: m/z 413.1 (M+H⁺).

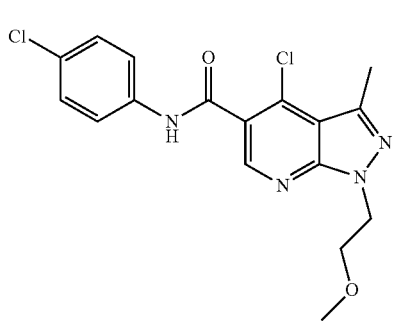 [SMILES: COCCn1nc(C)c2c(Cl)c(C(=O)Nc3ccc(Cl)cc3)cnc21]

Example 151

4-chloro-N-(4-chlorophenyl)-1-(2-methoxyethyl)-3-methyl-1H-pyrazolo[3,4-b]pyridine-5-carboxamide The title compound was prepared using general procedure for 4-chloro-N-(4-chlorophenyl)-3-methyl-1-propyl-1H-pyrazolo[3,4-b]pyridine-5-carboxamide (Example 144). ¹HNMR (300 MHz, DMSO-d6): δ=10.78 (s, 1H), 8.68 (s, 1H), 7.76 (d, J=8.4 Hz, 2H), 7.44 (d, J=8.7 Hz, 2H), 4.58 (t, J=5.1 Hz, 2H), 3.79 (t, J=5.1 Hz, 2H), 3.18 (s, 3H), 2.69 (s, 3H); MS: m/z 379.1 (M+H⁺).

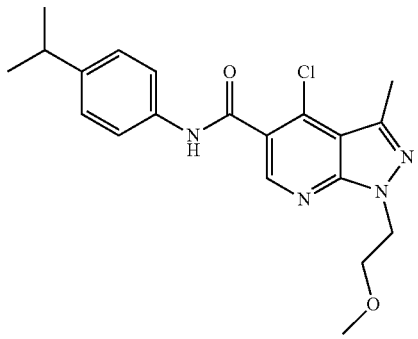 [SMILES: COCCn1nc(C)c2c(Cl)c(C(=O)Nc3ccc(C(C)C)cc3)cnc21]

Example 152

4-chloro-N-(4-isopropylphenyl)-1-(2-methoxyethyl)-3-methyl-1H-pyrazolo[3,4-b]pyridine-5-carboxamide The title compound was prepared using general procedure for 4-chloro-N-(4-chlorophenyl)-3-methyl-1-propyl-1H-pyrazolo[3,4-b]pyridine-5-carboxamide (Example 144). ¹HNMR (300 MHz, DMSO-d6): δ=10.50 (s, 1H), 8.63 (s, 1H), 7.61 (d, J=8.4, Hz 2H), 7.23 (d, J=8.4 Hz, 2H), 4.58 (t, J=5.1 Hz, 2H), 3.79 (t, J=5.1 Hz, 2H), 3.19 (s, 3H), 2.90-2.83 (m, 1H), 2.69 (s, 3H), 1.20 (d, J=6.9 Hz, 6H); MS: m/z 387.1 (M+H⁺).

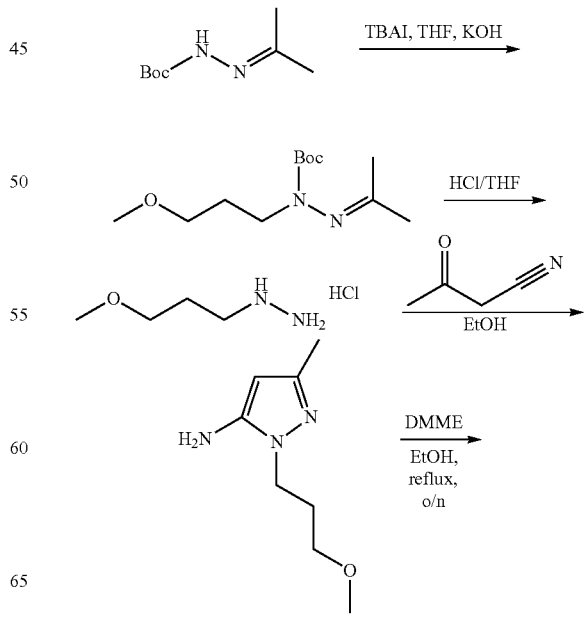

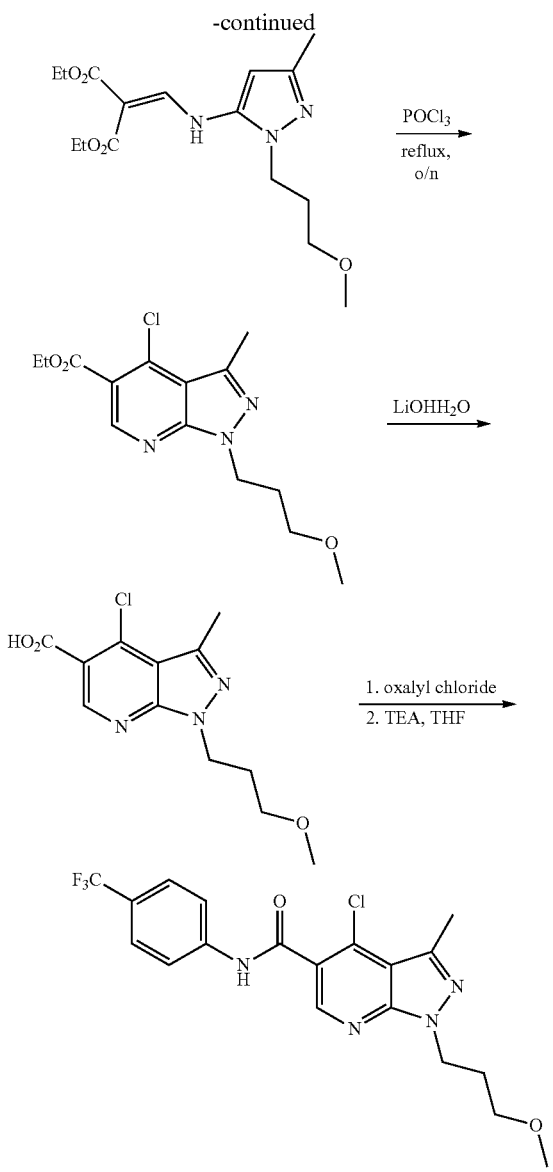

Example 153

4-Chloro-1-(3-methoxy-propyl)-3-methyl-1H-pyrazolo[3,4-b]pyridine-5-carboxylic acid (4-trifluoromethyl-phenyl)-amide Step 1:

The solution of hydrazinecarboxylic acid tert-butyl ester (10 g, 75.6 mmol) in acetone was stirred at 60° C. overnight. The solvent was removed in vacuum to give N'-isopropylidene-hydrazinecarboxylic acid tert-butyl ester (13 g, yield: 100%) as a white solid.

Step 2:

To a solution of N'-isopropylidene-hydrazinecarboxylic (7 g, 41 mmol) in THF (100 mL) was added TBAI (1.5 g, 4 mmol), KOH (2.98 g, 53 mmol), 1-bromo-3-methoxy-propane (6.885 g, 45 mmol). The mixture was then stirred at 60 oC overnight. The solvent was removed in vacuum. The resultant was added to water (50 mL) and the aqueous phase was extracted with EA (50 mL×3). The organic layer was washed with water (100 mL×3) and dried over Na2SO4. The solvent was removed in vacuum. The resulting solid was purified by column chramatoghraphy (PE:EA 10:1 to 7:1). The solvent was removed in vacuum to afford N'-isopropylidene-N-(3-methoxy-propyl)-hydrazinecarboxylic acid tert-butyl ester (7 g, yield: 70%) as a yellow oil.

Step 3:

The solution of N'-isopropylidene-N-(3-methoxy-propyl)-hydrazinecarboxylic acid tert-butyl ester (7 g, 28.7 mmol) in HCl/1,4-dioxane was stirred at rt overnight. The solvent was removed in vacuum to give (3-methoxy-propyl)-hydrazine acid tert-butyl ester (4.6 g, yield: 100%) as a white solid.

Step 4 and 5:

To a solution of (3-methoxy-propyl)-hydrazine acid tert-butyl ester (4.6 g, 28.7 mmol) in EtOH (100 Ml) was added 3-oxo-butyronitrile (2.382 g, 28.7 mmol). The mixture was then stirred at 80 oC for 1 h. To the mixture was added 2-ethoxymethylene-malonic acid diethyl ester (6.199 g, 28.7 mmol). The mixture was then stirred at 80 oC overnight. The solvent was removed in vacuum. The resultant was added to water (50 Ml) and the aqueous phase was extracted with EA (50 Ml×3). The organic layer was washed with water (100 Ml×3) and dried over Na2SO4. The solvent was removed in vacuum. The resulting solid was purified by column chramatoghraphy (PE:EA 8:1-3:1). The solvent was removed in vacuum to afford 2-{[2-(3-methoxy-propyl)-5-methyl-2H-pyrazol-3-ylamino]-methylene}-malonic acid diethyl ester (4.5 g, yield: 50%) as a yellow oil.

Step 6:

The solution of 2-{[2-(3-methoxy-propyl)-5-methyl-2H-pyrazol-3-ylamino]-methylene}-malonic acid diethyl ester (4.5 g, 13.27 mmol) in POCl3 was stirred at 110 oC overnight. The solvent was removed in vacuum. The resulting solid was added to aq NaHCO3 (100 mL) to pH=8 and the aqueous phase was extracted with EA (100 mL×3). The organic layer was washed with water (100 mL×3) and dried over Na2SO4. The solvent was removed in vacuum. The resulting solid was purified by column chromatoghraphy (PE:EA 8:1-3:1). The solvent was removed in vacuum to afford 4-chloro-1-(3-methoxy-propyl)-3-methyl-1H-pyrazolo[3,4-b]pyridine-5-carboxylic acid ethyl ester (0.72 g, yield: 17%) as a yellow oil.

Step 7:

To a solution of 4-chloro-1-(3-methoxy-propyl)-3-methyl-1H-pyrazolo[3,4-b]pyridine-5-carboxylic acid ethyl ester (720 mg, 2.4 mmol) in THF/H2O (1:1, 20 mL) was added LiOH (2 g, 47.6 mmol). The mixture was stirred at rt overnight. The mixture was quenched to 5<pH<7 and the aqueous phase was extracted with EA (100 mL×3). The organic layer was washed with water (100 mL×3) and dried over $Na_2SO_4$. The solvent was removed in vacuum to afford 4-chloro-1-(3-methoxy-propyl)-3-methyl-1H-pyrazolo[3,4-b]pyridine-5-carboxylic acid (0.6 g, yield: 88%) as a white solid.

Step 8:

To a suspension of 4-chloro-1-(3-methoxypropyl)-3-methyl-1H-pyrazolo[3,4-b]pyridine-5-carboxylic acid (81 mg, 0.28 mmol) in oxalyl chloride (5 mL), 0.1 mL of DMF was added. The reaction was stirred at room temperature for 3 hrs. The solvent was removed and the residue was dissolved in THF (2 mL) followed by the addition of 4-(trifluoromethyl)aniline (60 mg, 0.37 mmol) and TEA (85 mg, 0. 84 mmol) at 0° C. The mixture was stirred at room temperature for overnight. The solvent was removed and the residue was diluted with water (5 mL). The aqueous phase was extracted with EA (mL×2). The extracts were dried over anhydrous Na$_2$SO$_4$. The solvent was removed and the residue was concentrated to dryness. The residue was purified by prep-TLC (PE/EA=2/1) to give 4-chloro-1-(3-methoxy-propyl)-3-methyl-1H-pyrazolo[3,4-b]pyridine-5-carboxylic acid (4-trifluoromethyl-phenyl)-amide (90 mg, yield: 74%) as a white solid.

$^1$HNMR (400 MHz, DMSO-d6): δ=11.00 (s, 1H), 8.72 (s, 1H), 7.94 (d, J=8.4 Hz, 2H), 7.76 (d, J=8.8 Hz, 2H), 4.50-4.47 (m, 2H), 3.33-3.29 (m, 2H), 3.20 (s, 3H), 2.70 (s, 3H), 2.08-2.05(m, 2H). MS: m/z 425.1 (M–H$^+$)

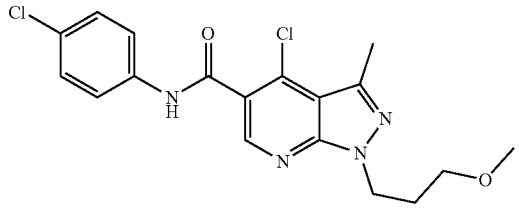 [SMILES: COCCCn1nc(C)c2c(Cl)c(C(=O)Nc3ccc(Cl)cc3)cnc21]

Example 154

4-chloro-1-(3-methoxy-propyl)-3-methyl-1H-pyrazolo[3,4-b]pyridine-5-carboxylic acid (4-chlorophenyl)-amide The title compound was prepared using general procedure for 4-chloro-1-(3-methoxy-propyl)-3-methyl-1H-pyrazolo[3,4-b]pyridine-5-carboxylic acid (4-trifluoromethyl-phenyl)-amide (Example 153).

$^1$HNMR (400 MHz, DMSO-d6): δ=10.78 (s, 1H), 8.69 (s, 1H), 7.76 (d, J=8.8 Hz, 2H), 7.44 (d, J=8.8 Hz, 2H), 4.50-4.46 (m, 2H), 3.33-3.29 (m, 2H), 3.20 (s, 3H), 2.69 (s, 3H), 2.05-2.08 (m, 2H). MS: m/z 391.1 (M–H$^+$)

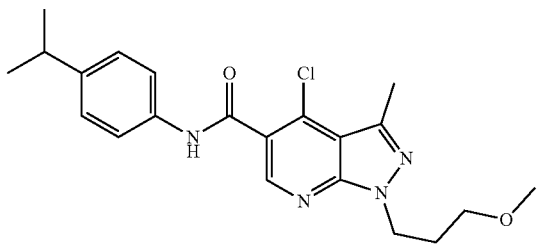 [SMILES: COCCCn1nc(C)c2c(Cl)c(C(=O)Nc3ccc(C(C)C)cc3)cnc21]

Example 155

4-chloro-1-(3-methoxy-propyl)-3-methyl-1H-pyrazolo[3,4-b]pyridine-5-carboxylic acid (4-isopropylphenyl)-amide The title compound was prepared using general procedure for 4-chloro-1-(3-methoxy-propyl)-3-methyl-1H-pyrazolo[3,4-b]pyridine-5-carboxylic acid (4-trifluoromethyl-phenyl)-amide (Example 153).

$^1$HNMR (400 MHz, DMSO-d6): δ=10.55 (s, 1H), 8.66 (s, 1H), 7.64 (d, J=8.4 Hz, 2H), 7.24 (d, J=8 Hz, 2H), 4.50-4.46 (m, 2H), 3.33-3.20 (m, 2H), 3.20 (s, 3H), 2.90-2.86 (m, 1H), 2.69 (s, 3H), 2.10-2.05 (m, 2H), 1.20 (d, J=7.2 Hz, 6H). MS: m/z 401.1 (M+H$^+$)

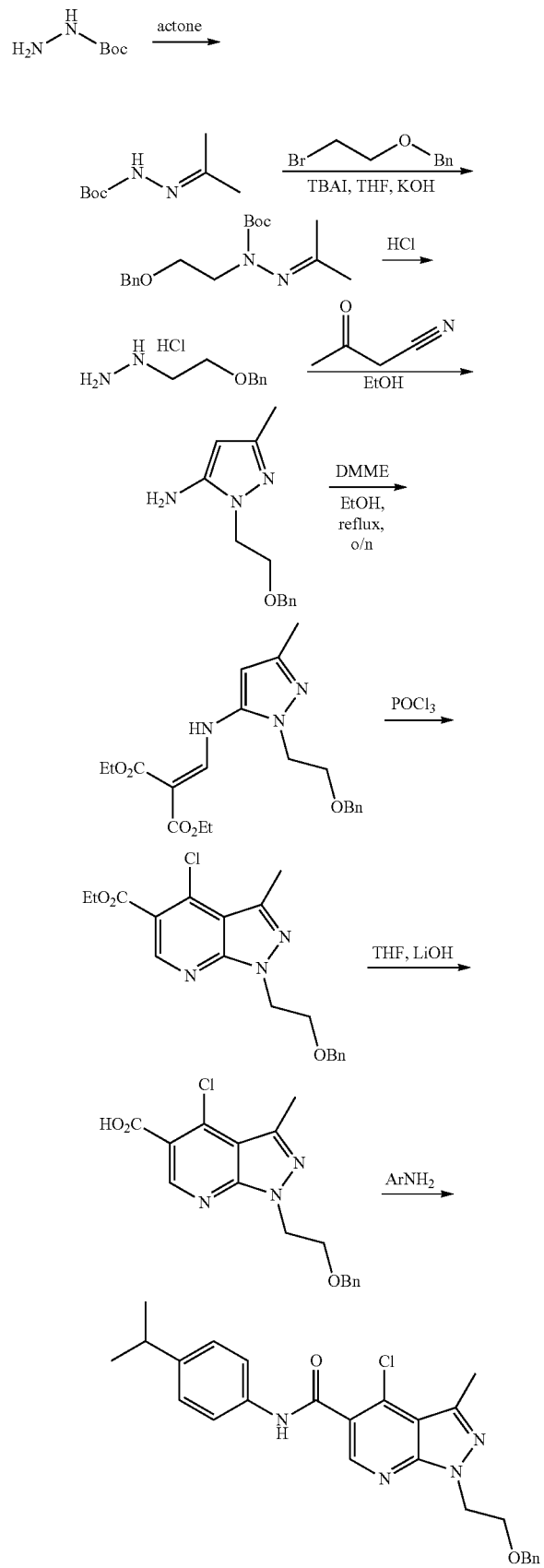

Example 156

1-(2-benzyloxy-ethyl)-4-chloro-3-methyl-1H-pyrazolo[3,4-b]pyridine-5-carboxylic acid (4-isopropyl-phenyl)-amide The title compound was prepared using general procedure for 4-chloro-1-(3-methoxy-propyl)-3-methyl-1H-pyrazolo[3,4-b]pyridine-5-carboxylic acid (4-trifluoromethyl-phenyl)-amide (Example 153).

$^1$HNMR (400 MHz, CDCl$_3$): δ=8.78 (s, 1H), 7.86 (s, 1H), 7.58 (d, J=8.0 Hz, 2H), 7.27-7.23 (m, 5H), 7.16-7.15 (m, 2H), 4.68-4.65 (m, 2H), 4.49 (s, 2H), 3.94-3.92 (m 2H), 2.94-2.94 (m, 1H), 2.75 (s, 3H), 1.26 (d, J=6.8 Hz, 6H). MS: m/z 463.2 (M+H$^+$)

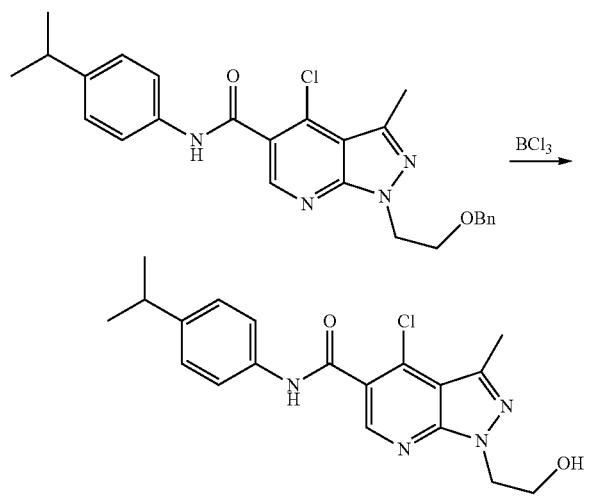

Example 157

4-chloro-1-(2-hydroxy-ethyl)-3-methyl-1H-pyrazolo[3,4-b]pyridine-5-carboxylic acid (4-isopropyl-phenyl)-amide To a solution of 1-(2-benzyloxy-ethyl)-4-chloro-3-methyl-1H-pyrazolo[3,4-b]pyridine-5-carboxylic acid (4-isopropyl-phenyl)-amide (40 mg, 0.086 mmol) in CH$_2$Cl$_2$ (10 mL) was added BCl$_3$/toluene (0.47 mL, 1.0 m/L) at −78° C. The mixture was then stirred at −78° C. for 2 hrs. To the mixture was added MeOH (5 mL). The solvent was removed in vacuum. The resulting solid was washed with EA/PE (1:1, 5 mL×2). The solid was removed in vacuum to afford 4-chloro-1-(2-hydroxy-ethyl)-3-methyl-1H-pyrazolo[3,4-b]pyridine-5-carboxylic acid (4-isopropyl-phenyl)-amide (9 mg, yield: 56%) as a white solid. $^1$HNMR (400 MHz, DMSO-d6): δ=10.56 (s, 1H), 8.64 (s, 1H), 7.65-7.64 (m, 2H), 7.24 (d, J=8.4 Hz, 2H), 4.87-4.84 (m, 1H), 4.49-4.45 (m, 2H), 3.86-3.80 (m, 2H), 2.90-2.87 (m, 1H), 2.70 (s, 3H), 1.20 (d, J=6.9 Hz, 6H). MS: m/z 373.1 (M+H$^+$)

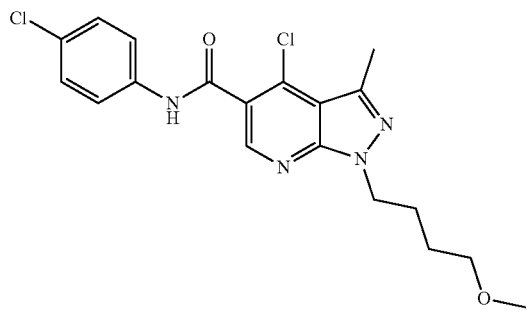 [SMILES: COCCCCn1nc(C)c2c(Cl)c(C(=O)Nc3ccc(Cl)cc3)cnc21]

Example 158

4-chloro-1-(4-methoxy-butyl)-3-methyl-1H-pyrazolo[3,4-b]pyridine-5-carboxylic acid (4-chloro-phenyl)-amide The title compound was prepared using general procedure for 4-chloro-1-(3-methoxy-propyl)-3-methyl-1H-pyrazolo[3,4-b]pyridine-5-carboxylic acid (4-trifluoromethyl-phenyl)-amide (Example 153).

$^1$HNMR (300 MHz, DMSO-d6): δ=10.78 (s, 1H), 8.69 (s, 1H), 7.76 (d, J=9 Hz, 2H), 7.44 (d, J=9 Hz, 2H), 4.46-4.42 (m, 2H), 3.33-3.28 (m, 2H), 3.19 (s, 3H), 2.69 (s, 3H), 1.90-1.85 (m, 2H), 1.45-1.40 (s, 2H). MS: m/z 407.1 (M+H$^+$)

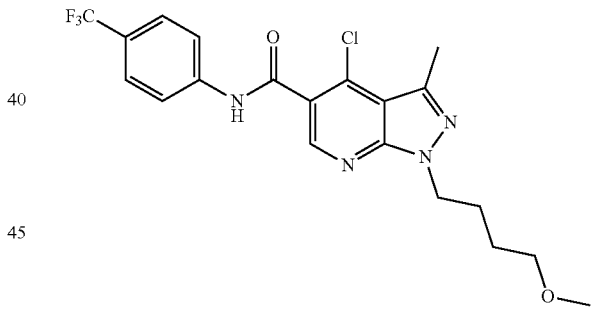

Example 159

4-Chloro-1-(4-methoxy-butyl)-3-methyl-1H-pyrazolo[3,4-b]pyridine-5-carboxylic acid (4-trifluoromethyl-phenyl)-amide The title compound was prepared using general procedure for 4-chloro-1-(3-methoxy-propyl)-3-methyl-1H-pyrazolo[3,4-b]pyridine-5-carboxylic acid (4-trifluoromethyl-phenyl)-amide (Example 153).

$^1$HNMR (300 MHz, DMSO-d6): δ=11.01 (s, 1H), 8.72 (s, 1H), 7.94 (d, J=8.4 Hz, 2H), 7.76 (d, J=8.7 Hz, 2H), 4.47-4.42 (m, 2H), 3.34-3.28 (m, 2H), 3.19 (s, 3H), 2.70 (s, 3H), 1.90-1.85 (m, 2H), 1.45-1.40 (m, 2H). MS: m/z 441.1 (M+H$^+$)

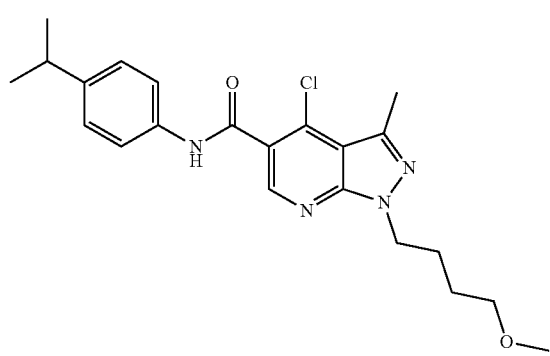 [SMILES: COCCCCn1nc(C)c2c(Cl)c(C(=O)Nc3ccc(C(C)C)cc3)cnc21]

Example 160

4-chloro-1-(4-methoxy-butyl)-3-methyl-1H-pyrazolo[3,4-b]pyridine-5-carboxylic acid (4-isopropyl-phenyl)-amide The title compound was prepared using general procedure for 4-chloro-1-(3-methoxy-propyl)-3-methyl-1H-pyrazolo[3,4-b]pyridine-5-carboxylic acid (4-trifluoromethyl-phenyl)-amide (Example 153).

$^1$HNMR (300 MHz, DMSO-d6): δ=10.55 (s, 1H), 8.65 (s, 1H), 7.64 (d, J=8.4 Hz, 2H), 7.24 (d, J=8.4 Hz, 2H), 4.46-4.44 (m, 2H), 3.34-3.28 (m, 2H), 3.19 (s, 3H), 2.89-2.85 (m, 1H), 2.69 (s, 3H), 1.90-1.85 (m, 2H), 1.45-1.40 (m, 2H), 1.20 (d, J=6.9 Hz, 6H),. MS: m/z 415.1 (M+H$^+$)

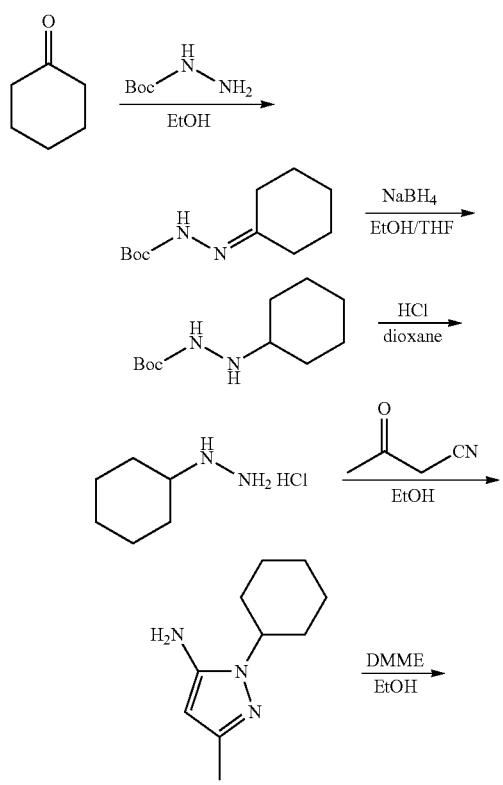

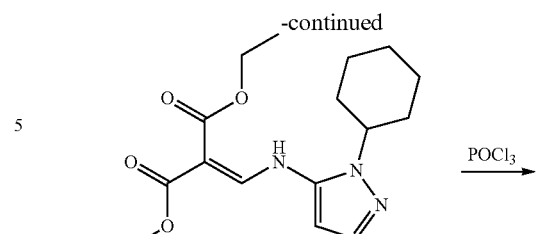

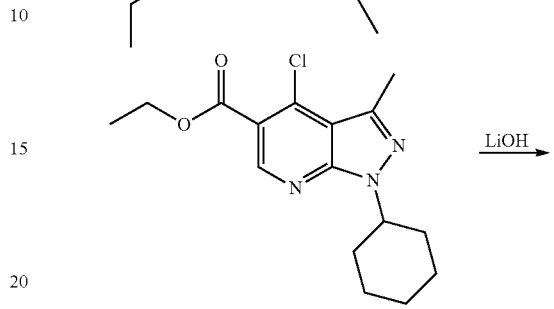

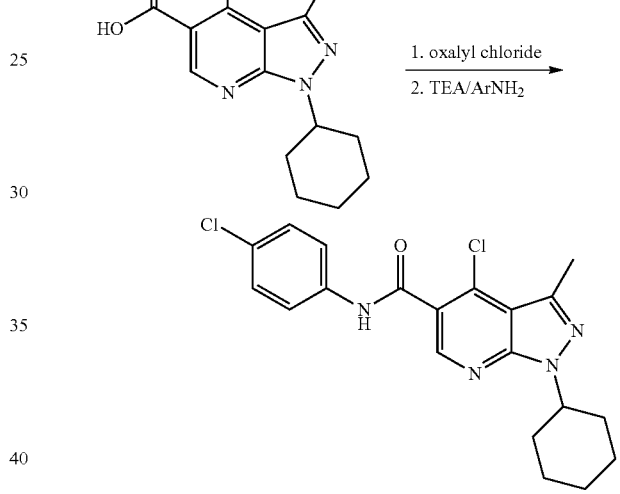

Example 161

4-chloro-N-(4-chlorophenyl)-1-cyclohexyl-3-methyl-1H-pyrazolo[3,4-b]pyridine-5-carboxamide Step 1:
To a solution of tert-butyl hydrazinecarboxylate (2 g, 15.1 mmol) in hexane (20 mL) was added cyclohexanone (1.48 g, 15.1 mmol), it was then refluxed overnight. Resultant was concentrated to remove hexane to afford crude product without further purification.

Step 2:
To a solution of tert-butyl 2-cyclohexylidenehydrazine-1-carboxylate (crude, 15.1 mmol) in THF/MeOH (1/1, 50 mL) was added NaBH4 (2.8 g, 75.5 mmol), it was then refluxed overnight. Resultant was evaporated to remove solvent, then residue was diluted with EA (100 mL) and quenched by water (100 mL), organic layer was concentrated to afford 1.9 g (yield: 58%) of tert-butyl 2-cyclohexylhydrazine-1-carboxylate as colorless oil.

$^1$HNMR (300 MHz, DMSO-d6): δ=8.15 (s, 1H), 4.11 (s, 1H), 2.65-2.58 (m, 1H), 1.70-1.66 (m, 5H), 1.41 (s, 9H), 1.19-0.93 (m, 5H);

Step 3:

To a solution of tert-butyl 2-cyclohexylhydrazine-1-carboxylate (1.9g, 8.87 mmol) in dioxane was added HCl/dioxane (20 mL), it was then refluxed overnight. The white precipitate was filtrated to afford 1.8 g (yield: >100%) of cyclohexylhydrazine hydrochloride as a white solid.

Step 4:

To a solution of cyclohexylhydrazine hydrochloride (1.8g, 12mmol) in EtOH was added 3-oxobutanenitrile (996 mg, 12 mmol), it was then refluxed overnight to afford desired product. The resultant was directly use to next step without further purification. $^1$HNMR (300 MHz, DMSO-d6): δ=5.03 (s, 1H), 4.94 (s, 2H), 3.79-3.84 (m, 1H), 1.95 (s, 3H), 1.87-1.61 (m, 7H), 1.38-1.09 (m, 3H);

Step 5:

To a solution of 1-cyclohexyl-3-methyl-1H-pyrazol-5-amine (crude, 12 mmol) in EtOH was added DMME (2.5 g, 12 mmol), it was then refluxed overnight. The resultant was concentrated under reduced pressure and purified directly by flash column (EA in PE: 0 to 50%) to afford 2.2 g (yield: 63%) of diethyl 2-(((1-cyclohexyl-3-methyl-1H-pyrazol-5-yl)amino)methylene)malonate as brown oil.

Step 6-8:

These 3 steps are similar to the general procedure for 4-chloro-3-methyl-1-phenyl-1H-pyrazolo[3,4-b]pyridine-5-carboxylic acid (4-bromo-phenyl)-amide (Example 1). $^1$HNMR (300 MHz, DMSO-d6): δ=10.77 (s, 1H), 8.66 (s, 1H), 7.74 (d, J=8.4 Hz, 2H), 7.43 (d, J=8.4 Hz, 2H), 4.80-4.73 (m, 1H), 2.69 (s, 3H), 1.92-1.89 (m, 6H), 1.71-1.67 (m, 1H), 1.51-1.45 (m, 2H), 1.24-1.20 (m, 1H); MS: m/z 402.1 (M+H$^+$).

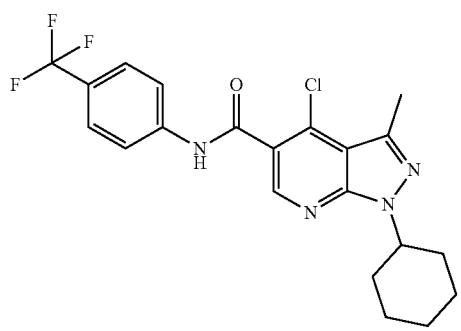 [SMILES: Cc1nn(C2CCCCC2)c2ncc(C(=O)Nc3ccc(C(F)(F)F)cc3)c(Cl)c12]

Example 162

4-chloro-1-cyclohexyl-3-methyl-N-(4-(trifluoromethyl)phenyl)-1H-pyrazolo[3,4-b]pyridine-5-carboxamide The title compound was prepared using general procedure for 4-chloro-N-(4-chlorophenyl)-1-cyclohexyl-3-methyl-1H-pyrazolo[3,4-b]pyridine-5-carboxamide (Example 161). $^1$HNMR (300 MHz, DMSO-d6): δ=10.99 (s, 1H), 8.69 (s, 1H), 7.94 (d, J=8.4 Hz, 2H), 7.76 (d, J=8.4 Hz, 2H), 4.80-4.74 (m, 1H), 2.69 (s, 3H), 1.97-1.81 (m, 6H), 1.71-1.68 (m, 1H), 1.52-1.45 (m, 2H), 1.24-1.22 (m, 1H); MS: m/z 436.1 (M+H$^+$).

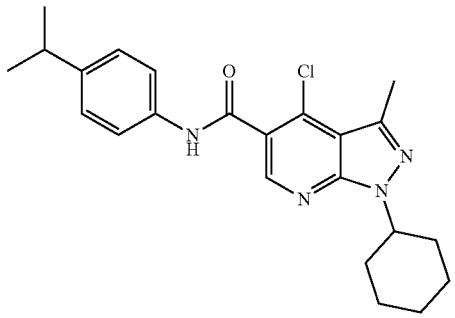 [SMILES: Cc1nn(C2CCCCC2)c2ncc(C(=O)Nc3ccc(C(C)C)cc3)c(Cl)c12]

Example 163

4-chloro-1-cyclohexyl-N-(4-isopropylphenyl)-3-methyl-1H-pyrazolo[3,4-b]pyridine-5-carboxamide The title compound was prepared using general procedure for 4-chloro-N-(4-chlorophenyl)-1-cyclohexyl-3-methyl-1H-pyrazolo[3,4-b]pyridine-5-carboxamide (Example 161). $^1$HNMR (300 MHz, DMSO-d6): δ=10.52 (s, 1H), 8.63 (s, 1H), 7.63 (d, J=8.4 Hz, 2H), 7.24 (d, J=8.4 Hz, 2H), 4.80-4.74 (m, 1H), 2.91-2.81 (m, 1H), 2.69 (s, 3H), 1.92-1.82 (m, 6H), 1.72-1.68 (m, 1H), 1.52-1.47 (m, 2H), 1.20-1.18 (m, 7H); MS: m/z 410.2 (M+H$^+$).

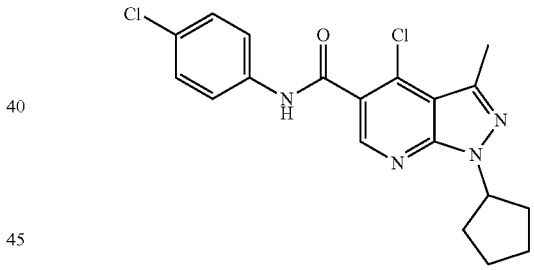

Example 164

4-Chloro-1-cyclopentyl-3-methyl-1H-pyrazolo[3,4-b]pyridine-5-carboxylic acid (4-chloro-phenyl)-amide The title compound was prepared using general procedure for 4-chloro-N-(4-chlorophenyl)-1-cyclohexyl-3-methyl-1H-pyrazolo[3,4-b]pyridine-5-carboxamide (Example 161). $^1$HNMR (300 MHz, DMSO-d6): δ=10.75 (s, 1H), 8.67 (s, 1H), 7.76 (d, J=8.8 Hz, 2H), 7.47 (dd, J=9.0 Hz, 1.8 Hz, 2H), 5.35-5.31 (m, 1H), 2.70 (s, 3H), 2.14-2.13 (m, 2H), 2.12-2.10 (m, 2H), 2.09-2.06 (m, 2H)2.05-1.99 (m, 2H). MS: m/z 388.8 (M+H$^+$).

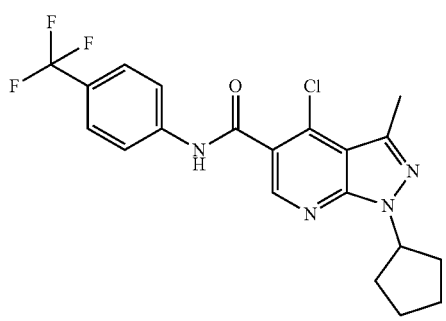 [SMILES: Cc1nn(C2CCCC2)c2ncc(C(=O)Nc3ccc(C(F)(F)F)cc3)c(Cl)c12]

Example 165

4-Chloro-1-cyclopentyl-3-methyl-1H-pyrazolo[3,4-b]pyridine-5-carboxylic acid (4-trifluoromethyl-phenyl)-amide The title compound was prepared using general procedure for 4-chloro-N-(4-chlorophenyl)-1-cyclohexyl-3-methyl-1H-pyrazolo[3,4-b]pyridine-5-carboxamide (Example 161). $^1$HNMR (300 MHz, DMSO-d6): δ=10.98 (s, 1H), 8.705 (s, 1H), 7.93 (d, J=9.0 Hz, 2H), 7.75 (d, J=9.0 Hz, 2H), 5.36-5.31 (m, 1H), 2.71-2.68 (s, 3H), 2.14-2.13 (m, 2H), 2.12-2.10 (m, 2H), 2.09-2.06 (m, 2H)2.05-1.99 (m, 2H). MS: m/z 422.9 (M+H$^+$).

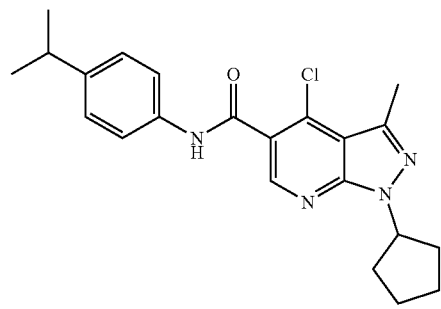 [SMILES: Cc1nn(C2CCCC2)c2ncc(C(=O)Nc3ccc(C(C)C)cc3)c(Cl)c12]

Example 166

4-Chloro-1-cyclopentyl-3-methyl-1H-pyrazolo[3,4-b]pyridine-5-carboxylic acid (4-isopropyl-phenyl)-amide The title compound was prepared using general procedure for 4-chloro-N-(4-chlorophenyl)-1-cyclohexyl-3-methyl-1H-pyrazolo[3,4-b]pyridine-5-carboxamide (Example 161). $^1$HNMR (300 MHz, DMSO-d6): δ=10.52 (brs, 1H), 8.64 (s, 1H), 7.73 (d, J=8.4 Hz, 2H), 7.47 (d, J=8.4 Hz, 2H), 5.35-5.31 (m, 1H), 2.80-2.77 (m, 1H), 2.69 (s, 3H), 2.18-1.65 (m, 8H), 1.20 (d, J=6.6 Hz, 6H). MS: m/z 396.9 (M+H$^+$).

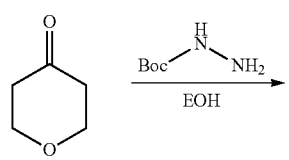

-continued

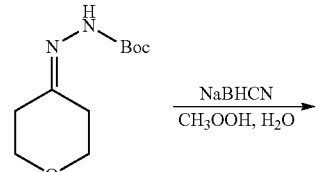

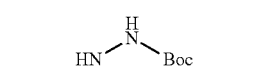

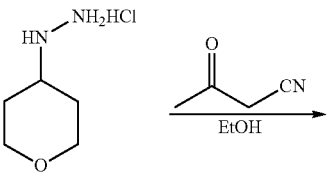

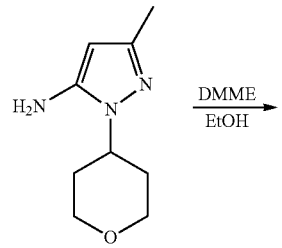

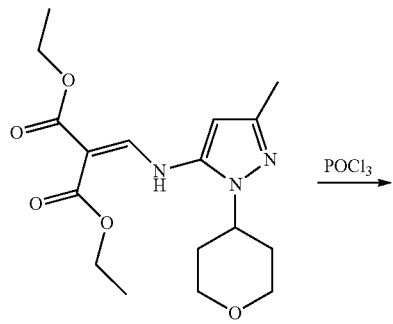

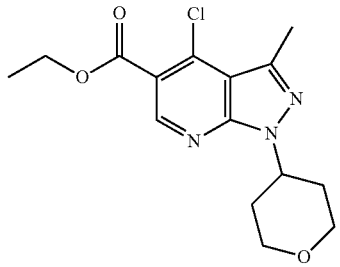

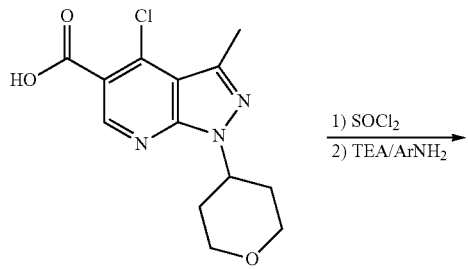

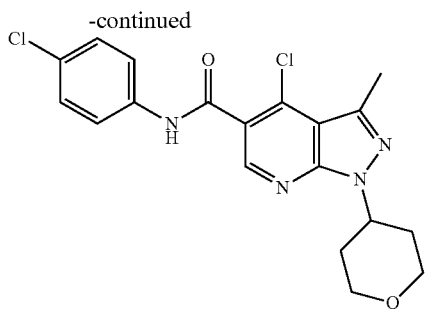

Example 167

4-Chloro-3-methyl-1-(tetrahydro-pyran-4-yl)-1H-pyrazolo[3,4-b]pyridine-5-carboxylic acid (4-chloro-phenyl)-amide Step 1:
A mixture of tetrahydro-pyran-4-one (4.0 g, 40 mmol), hydrazinecarboxylic acid tert-butyl ester (6.4 g, 4.8 mmol) in methanol (100 mL) was stirred at room temperature for overnight. The reaction mixture was evaporated in vacuum to get the desired product N'-(Tetrahydro-pyran-4-ylidene)-hydrazinecarboxylic acid tert-butyl ester (13.6 g, crude yield: >100%), which was used directdly next step without further purifition. MS: m/z 215.2 (M+H$^+$).

Step2:
A mixture of N'-(tetrahydro-pyran-4-ylidene)-hydrazinecarboxylic acid tert-butyl ester (13.6 g, 40 mmol), water (120 mL) and actic acid (40 mL) was stirred at room temperature for 1 hr. And NaBH$_3$CN(2.93 g, 48 mmol) was added dropwise at 0 oC. The mixture was stirred at room temperature for overnight. The aqueous mixture was neutralized with NaOH(3.0 N) to pH=7 and extracted with DCM (150 mL×2). The combined organic layers were washed with brine (30 mL×2), dried over anhydrous Na$_2$SO$_4$ and filtered. The filtrate was evaporated in vacuum to residue, which was purified by silica gel chromatography (from DCM to DCM/MeOH=20/1) to afford the desired product N'-(Tetrahydro-pyran-4-yl)-hydrazinecarboxylic acid tert-butyl ester (7.9 g, yield: 92.5%) as white solid. $^1$HNMR (300 MHz, CDCl3): δ=8.21 (brs, 1H), 3.81-3.77 (m, 2H), 3.36-3.22 (m,2H), 2.91-2.85 (m, 1H), 1.62(d, J=5.4 Hz, 2H), 1.38 (s, 9H), 1.22-1.14 (m, 2H).

Step3:
To a stirred solution of N'-(tetrahydro-pyran-4-yl)-hydrazinecarboxylic acid tert-butyl ester (7.9 g, 37 mmol) in DCM(30 mL) was added HCl/dioxane (4M, 30 mL) dropwise. The mixture was stirred at room temperature for 4 hrs. The suspended filtered to give the desired product (Tetrahydro-pyran-4-yl)-hydrazine (5.3 g, yield: 94.5%) as white solid. $^1$HNMR (300 MHz, DMSO-d6): δ=3.68 (d, J=5.4 Hz, 2H), 3.31-3.24 (m, 2H), 3.16-3.07 (m, 1H), 1.89(d, 2H), 1.48-1.39(m, 2H).

Step4:
A mixture of (tetrahydro-pyran-4-yl)-hydrazine (2.32 g, 20 mmol), 3-oxo-butyronitrile (1.66 g, 20 mmol) in ethanol (50 mL) was stirred at 90° C. for overnight. The reaction was cooled to room temperature and was concentrated. The residue was purified by flash HPLC(MeCN/H$_2$O=5/100 to 95/100) to afford the desired product 5-Methyl-2-(tetrahydro-pyran-4-yl)-2H-pyrazol-3-ylamine (2.6 g yield: 72%) as white solid. MS: m/z 182.3 (M+H$^+$).

Step5:
A mixture of 5-methyl-2-(tetrahydro-pyran-4-yl)-2H-pyrazol-3-ylamine (2.0 g, 11 mmol), 2-Methoxymethylene-malonic acid diethyl ester (1.67 g, 7.7 mmol) in ethanol (15 mL) was stirred at 150° C. in a microwave for 2 hrs and evaporated in vacuum. The residue was purified by silica gel chromatography (PE to PE/EA=4/1) to give the desired product 2-{[5-Methyl-2-(tetrahydro-pyran-4-yl)-2H-pyrazol-3-ylamino]-methylene}-malonic acid diethyl ester (600 mg, yield: 15%) as yellow oil. MS: m/z 352.3 (M+H$^+$).

Step6:
A mixture of 2-{[5-methyl-2-(tetrahydro-pyran-4-yl)-2H-pyrazol-3-ylamino]-methylene}-malonic acid diethyl ester (600 mg, 1.7 mmol) in POCl$_3$ (20 mL) was stirred at 120° C. for overnight and evaporated in vacuum to residue, and added into ice water (50 mL) dropwise. The aqueous mixture was neutralized with sat.NaHCO$_3$ to pH=7 and extracted with EA (30 mL×2). The combined organic layers were washed with brine (30 mL×2), dried over anhydrous Na$_2$SO$_4$ and filtered. The filtrate was evaporated in vacuum to residue, which was purified by silica gel chromatography (DCM to DCM/MeOH=50/1) to afford the desired product 4-chloro-3-methyl-1-(tetrahydro-pyran-4-yl)-1H-pyrazolo[3,4-b]pyridine-5-carboxylic acid ethyl ester (250 mg, yield: 50%) as yellow solid. $^1$HNMR (400 MHz, DMSO-d6): δ=8.88 (s, 1H), 5.06-4.98 (m, 1H), 4.36 (q, J=9.8 Hz, 2H), 4.04-3.98 (m, 2H), 3.60-3.52 (m, 2H), 2.70 (s, 2H), 2.21-2.08 (m, 2H), 1.36 (t, J=9.2 Hz, 3H),1.24-1.15 (m, 2H). MS: m/z 324.2 (M+H$^+$)

Step7:
A mixture of 4-chloro-3-methyl-1-(tetrahydro-pyran-4-yl)-1H-pyrazolo[3,4-b]pyridine-5-carboxylic acid ethyl ester (250 mg, 0.77 mmol) in THF (8 mL), and LiOH (162 mg, 3.86 mmol) in water was added doprwise. The reaction mixture was stirred at room tempertue for overnight. The aqueous mixture was acid with HCl to pH=2. The suspension was filtered and the cake was washed with water (10 mL×2), then evaporated in vacuum to dryness to give the desired product4-Chloro-3-methyl-1-(tetrahydro-pyran-4-yl)-1H-pyrazolo[3,4-b]pyridine-5-carboxylic acid (200 mg, yield: 72%) as white solid. MS: m/z 296.5 (M+H$^+$).

Step 8:
To a stirred solution of 4-chloro-3-methyl-1-(tetrahydro-pyran-4-yl)-1H-pyrazolo[3,4-b]pyridine-5-carboxylic acid (200 mg, 3.7 mmol) in dioxane (5 mL) was added SOCl$_2$ (4 M, 5 mL) dropwise. The mixture was stirred at 100° C. for 2 hrs and evaporated in vacuum to give the acyl chloride as a yellow solid.

To a stirred solution of 4-chloro-phenylamine(43 mg, 0.34 mmol), TEA (69 mg, 0.68 mmol) and DMAP (5 mg) in THF (5 mL), was added 4-chloro-3-methyl-1-(tetrahydro-pyran-4-yl)-1H-pyrazolo[3,4-b]pyridine-5-carbonyl chloride (100 mg, 0.28 mmol) in THF (1 mL) dropwise. The mixture was stirred at room temperature for 3 hrs. The reaction mixture was concentrated to dryness in vacuum. The residue was purified by prep-HPLC to afford the desired product 4-chloro-3-methyl-1-(tetrahydro-pyran-4-yl)-1H-pyrazolo[3,4-b]pyridine-5-carboxylic acid (4-chloro-phenyl)-amide (30 mg, yield: 26.4%) as yellow solid.

$^1$HNMR (400 MHz, CDCl$_3$): δ=8.84 (s, 1H), 7.97 (brs, 1H), 7.67 (d, J=8.4 Hz, 2H), 7.41 (d, J=8.8 Hz, 2H), 5.11-5.06(m, 1H), 4.22-4.18(m, 2H), 3.68(t, J=8.0 Hz, 2H), 2.82 (s, 3H), 2.50-2.40(m, 2H), 1.99-1.95(m, 2H). MS: m/z 405.1 (M+H$^+$).

453

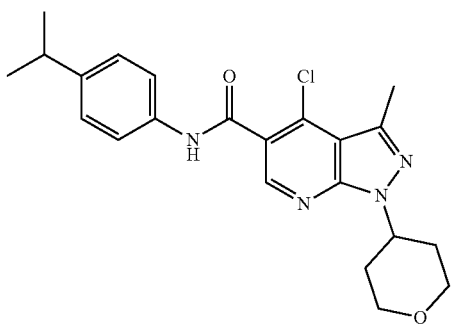 [SMILES: Cc1nn(C2CCOCC2)c2ncc(C(=O)Nc3ccc(C(C)C)cc3)c(Cl)c12]

Example 168

4-Chloro-3-methyl-1-(tetrahydro-pyran-4-yl)-1H-pyrazolo[3,4-b]pyridine-5-carboxylic acid (4-isopropyl-phenyl)-amide The title compound was prepared using general procedure for 4-Chloro-3-methyl-1-(tetrahydro-pyran-4-yl)-1H-pyrazolo[3,4-b]pyridine-5-carboxylic acid (4-chloro-phenyl)-amide (Example 167). $^1$HNMR (400 MHz, CDCl$_3$): δ=8.83 (s, 1H), 7.92 (s, 1H), 7.62 (d, J=8.4 Hz, 2H), 7.31 (d, J=8.0 Hz, 2H), 5.15-5.05(m, 1H), 4.22-4.18(m, 2H), 3.67(t, J=11.2 Hz, 2H), 2.99-2.95(m, 1H), 2.81 (s, 3H), 2.47-2.43(m, 2H), 1.99-1.95(m, 2H), 1.31-1.30 (d, J=7.6 Hz, 6H). MS: m/z 413.2 (M+H$^+$).

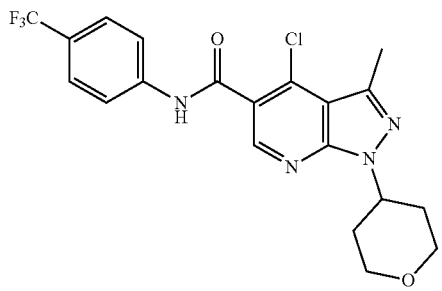 [SMILES: Cc1nn(C2CCOCC2)c2ncc(C(=O)Nc3ccc(C(F)(F)F)cc3)c(Cl)c12]

Example 169

4-Chloro-3-methyl-1-(tetrahydro-pyran-4-yl)-1H-pyrazolo[3,4-b]pyridine-5-carboxylic acid (4-trifluoromethyl-phenyl)-amide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167). $^1$HNMR (400 MHz, CDCl$_3$): δ=8.80 (s,1H), 8.29 (s, 1H), 7.83 (d, J=7.6 Hz, 2H), 7.68 (d, J=8.4 Hz, 2H), 5.09-5.03(m, 1H), 4.21-4.17(m, 2H), 3.65(t, J=7.6 Hz, 2H), 2.80 (s, 3H), 2.47-2.37(m, 2H), 1.98-1.95(m, 2H). MS: m/z 439.1 (M+H$^+$).

454

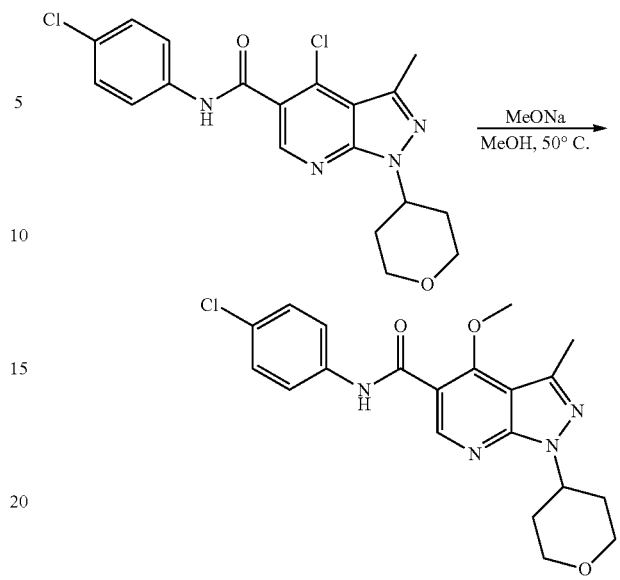

Example 170

4-Methoxy-3-methyl-1-(tetrahydro-pyran-4-yl)-1H-pyrazolo[3,4-b]pyridine-5-carboxylic acid (4-chloro-phenyl)-amide To a solution of 4-chloro-3-methyl-1-(tetrahydro-pyran-4-yl)-1H-pyrazolo[3,4-b]pyridine-5-carboxylic acid (4-chloro-phenyl)-amide (80 mg, 0.20 mmol) in methol (10 mL), Sodium methanolate (32 mg, 0.60 mmol) was added and the reaction mixture was stirred at 50° C. for 30 mins under nitrogen atmosphere, then the reaction mixture was quenched with aq. NH$_4$Cl (50 mL), and extracted with DCM (50 mL), the organic layer was washed with brine (50 mL) and dried over Na$_2$SO$_4$ and purified by Prep-TLC (PE:EA=1:1) to give 4-methoxy-3-methyl-1-(tetrahydro-pyran-4-yl)-1H-pyrazolo[3,4-b]pyridine-5-carboxylic acid (4-chloro-phenyl)-amide (29 mg, yield: 36%) as a white solid. $^1$HNMR (400 MHz, CDCl$_3$): δ=9.33 (brs, 1H), 9.17 (s, 1H), 7.66 (d, J=8.8 Hz, 2H), 7.36 (d, J=8.8 Hz, 2H), 5.10-5.04 (m, 1H), 4.17-4.14 (m, 5H), 3.64 (td, J=12.4, 1.2 Hz, 2H), 2.73 (s, 3H), 2.43-2.37 (m, 2H), 1.96-1.92 (m, 2H). MS: m/z 401.1 (M+H$^+$).

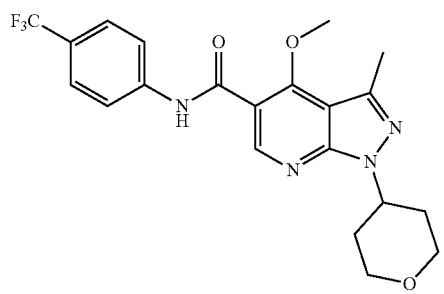 [SMILES: COc1c(C(=O)Nc2ccc(C(F)(F)F)cc2)cnc2c1c(C)nn2C1CCOCC1]

Example 171

N-(4-chlorophenyl)-4-methoxy-3-methyl-1-(tetrahydro-2H-pyran-4-yl)-1H-pyrazolo[3,4-b]pyridine-5-carboxamide The title compound was prepared using general procedure for 4-methoxy-3-methyl-1-(tetrahydro-pyran-4-yl)-1H-pyrazolo[3,4-b]pyridine-5-carboxylic acid (4-chloro-phenyl)-amide (Example 170).

$^1$HNMR (400 MHz, CDCl$_3$): δ=9.54 (brs, 1H), 9.19 (s, 1H), 7.83 (d, J=8.4 Hz, 2H), 7.63 (d, J=8.0 Hz, 2H), 5.14-5.00 (m, 1H), 4.17-4.14 (m, 5H), 3.65 (t, J=11.2 Hz, 2H), 2.74 (s, 3H), 2.47-2.33 (m, 2H), 1.97-1.90 (m, 2H). MS: m/z 434.9 (M+H$^+$).

Example 173

4-chloro-1-(1-ethyl-piperidin-4-yl)-3-methyl-1H-pyrazolo[3,4-b]pyridine-5-carboxylic acid (4-trifluoromethyl-phenyl)-amide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$HNMR (400 MHz, DMSO-d6): δ=10.98 (s, 1H), 8.71 (s, 1H), 7.94 (d, J=8.4 Hz, 2H), 7.76 (d, J=8.8 Hz, 2H), 4.79 (brs, 1H), 3.07 (brs, 2H), 2.70 (s, 3H), 2.47-2.45 (m, 2H), 2.23-2.20 (m, 4H), 1.93-1.91 (m, 2H), 1.07-1.04 (m, 3H). MS: m/z 466.1 (M+H$^+$)

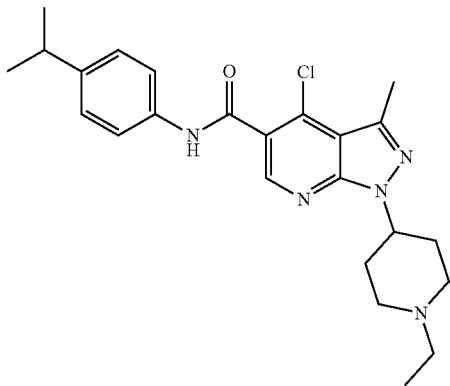 [SMILES: CCN1CCC(n2nc(C)c3c(Cl)c(C(=O)Nc4ccc(C(C)C)cc4)cnc32)CC1]

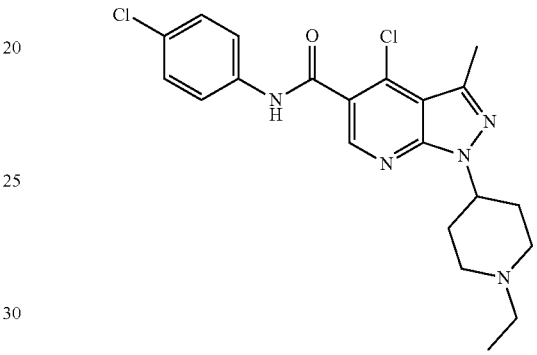

Example 172

4-chloro-1-(1-ethyl-piperidin-4-yl)-3-methyl-1H-pyrazolo[3,4-b]pyridine-5-carboxylic acid (4-isopropyl-phenyl)-amide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$HNMR (400 MHz, CDCl$_3$): δ=8.79 (s, 1H), 7.83 (s, 1H), 7.58-7.56 (d, J=8.0 Hz, 2H), 7.26 (d, J=8.0 Hz, 2H), 4.81-4.79 (m, 1H), 3.16-3.13 (m, 2H), 2.94-2.91 (m, 1H), 2.75 (s, 3H), 2.54-2.37 (m, 4H), 2.22-2.16 (m, 2H), 2.00-1.98 (m, 2H), 1.30-1.22 (m, 9H). MS: m/z 440.2 (M+H$^+$)

Example 174

4-chloro-1-(1-ethyl-piperidin-4-yl)-3-methyl-1H-pyrazolo[3,4-b]pyridine-5-carboxylic acid (4-chloro-phenyl)-amide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$HNMR (400 MHz, DMSO-d6): δ=10.83 (s, 1H), 10.36 (brs, 1H), 8.72 (s, 1H), 7.77 (d, J=8.8 Hz, 2H), 7.44 (d, J=8.4 Hz, 2H), 5.17-5.13 (m, 1H), 3.64-3.55 (m, 2H), 3.36-3.05 (m, 4H), 2.71 (s, 3H), 2.50-2.48 (m, 2H), 2.17-2.14 (m, 2H), 1.30-1.27 (m, 3H). MS: m/z 432.1 (M+H$^+$)

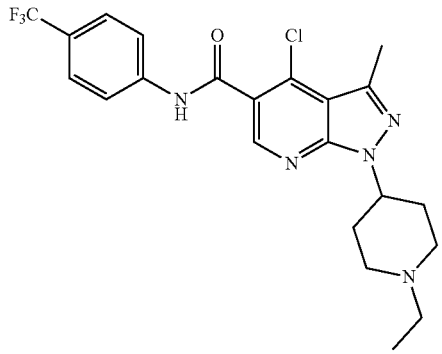 [SMILES: CCN1CCC(n2nc(C)c3c(Cl)c(C(=O)Nc4ccc(C(F)(F)F)cc4)cnc32)CC1]

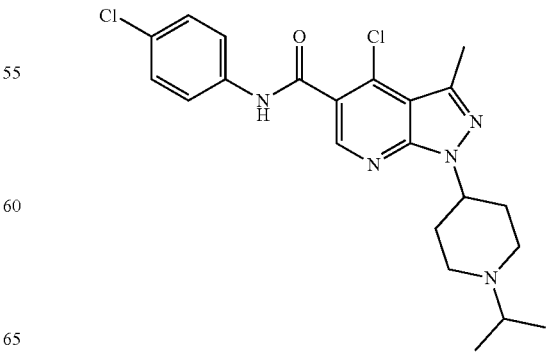

Example 175

4-Chloro-1-(1-isopropyl-piperidin-4-yl)-3-methyl-1H-pyrazolo[3,4-b]pyridine-5-carboxylic acid (4-chloro-phenyl)-amide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$H NMR (400 MHz, CDCl$_3$) δ=8.07 (s, 1H), 7.63 (d, J=8.4 Hz, 2H), 7.36 (d, J=8.8 Hz, 2H), 4.82-4.80 (brs, 1H), 3.16-3.10 (m, 2H), 2.96-2.94 (m, 1H), 2.64 (s, 3H), 2.55-2.33 (m, 5H), 2.08-1.99 (m, 2H), 1.20 (d, J=4.0 Hz, 6H). MS: m/z 446.1 (M+H$^+$)

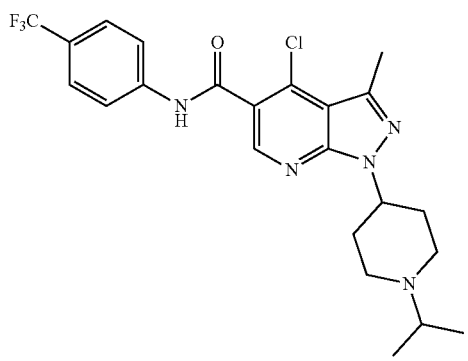

Example 176

4-Chloro-1-(1-isopropyl-piperidin-4-yl)-3-methyl-1H-pyrazolo[3,4-b]pyridine-5-carboxylic acid (4-trifluoromethyl-phenyl)-amide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$HNMR (400 MHz, DMSO-d$_6$) δ=10.98 (s, 1H), 8.70 (s, 1H), 7.93 (d, J=8.8 Hz, 2H), 7.76 (d, J=8.8 Hz, 2H), 4.76-4.70 (brs, 1H), 3.29-3.28 (m, 2H), 2.79-2.73 (m, 1H), 2.70 (s, 3H), 2.37-2.31 (m, 2H), 2.20-2.11 (m, 2H), 1.92-1.89 (m, 2H), 1.01 (d, J=7.2 Hz, 6H). MS: m/z 480.2 (M+H$^+$)

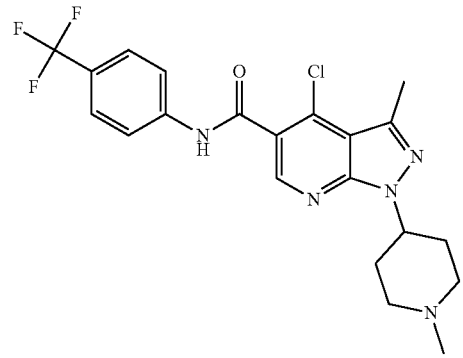 [SMILES: Cc1nn(C2CCN(C)CC2)c2ncc(C(=O)Nc3ccc(C(F)(F)F)cc3)c(Cl)c12]

Example 177

4-chloro-3-methyl-1-(1-methylpiperidin-4-yl)-N-(4-(trifluoromethyl)phenyl)-1H-pyrazolo[3,4-b]pyridine-5-carboxamide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$HNMR (400 MHz, CD3OD): δ=8.64 (s, 1H), 7.94 (d, J=8.4 Hz, 2H), 7.71 (d, J=8.4 Hz, 2H), 3.12-3.10 (m, 2H), 2.77 (s, 3H), 2.41-2.37 (m, 7H), 2.11-2.02 (m, 2H); MS: m/z 452.1 (M+H$^+$).

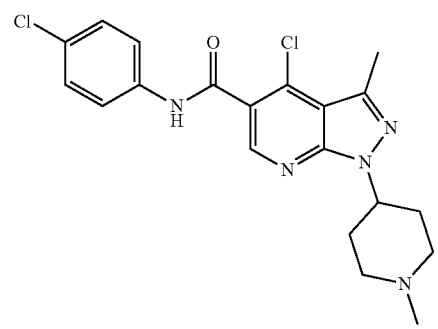

Example 178

4-chloro-N-(4-chlorophenyl)-3-methyl-1-(1-methyl-piperidin-4-yl)-1H-pyrazolo[3,4-b]pyridine-5-carboxamide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167). $^1$HNMR (400 MHz, DMSO-d6): δ=10.77 (s, 1H), 8.68 (s, 1H), 7.75 (d, J=8.4 Hz, 2H), 7.44 (d, J=8.4 Hz, 2H), 4.77-4.71 (m, 1H), 2.92 (d, J=10.8 Hz, 2H), 2.69 (s, 3H), 2.23-2.08 (m, 7H), 1.87 (d, J=11.6 Hz, 2H); MS: m/z 417.1 (M+H$^+$).

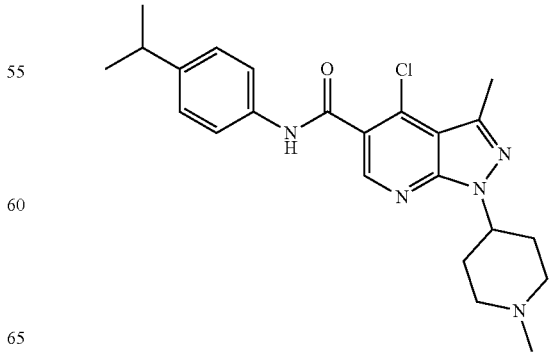

Example 179

4-chloro-N-(4-isopropylphenyl)-3-methyl-1-(1-methylpiperidin-4-yl)-1H-pyrazolo[3,4-b]pyridine-5-carboxamide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167). ¹HNMR (400 MHz, DMSO-d6): δ=10.54 (s, 1H), 8.64 (s, 1H), 7.63 (d, J=8.4 Hz, 2H), 7.23 (d, J=8.4 Hz, 2H), 4.76-4.71 (m, 1H), 2.92-2.83 (m, 3H), 2.69 (s, 3H), 2.23-1.86 (m, 7H), 1.85-1.20 (m, 2H), 1.19 (d, J=7.2 Hz, 6H); MS: m/z 426.2 (M+H⁺).

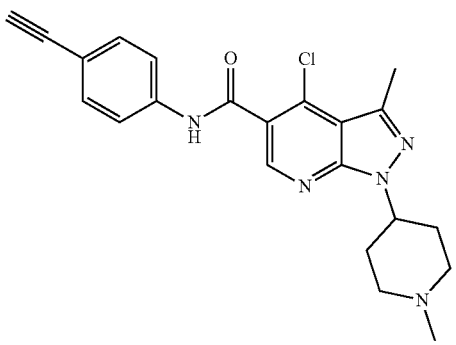 [SMILES: C#Cc1ccc(NC(=O)c2cnc3c(c(C)nn3C3CCN(C)CC3)c2Cl)cc1]

Example 180

4-Chloro-3-methyl-1-(1-methyl-piperidin-4-yl)-1H-pyrazolo[3,4-b]pyridine-5-carboxylic acid (4-ethynyl-phenyl)-amide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

¹HNMR (400 MHz, CDCl₃): δ=8.78 (s, 1H), 8.01 (s, 1H), 7.64 (d, J=8.4 Hz, 2H), 7.52 (d, J=8.8 Hz, 2H), 4.82-4.74 (m, 1H), 3.08 (s, 1H), 3.04 (d, J=12.0 Hz, 2H), 2.75 (s, 3H), 2.48-2.38 (m, 2H), 2.37 (s, 3H), 2.23 (t, J=12.8 Hz, 2H), 1.98 (d, J=11.2 Hz, 2H). MS: m/z 408.1 (M-H⁺).

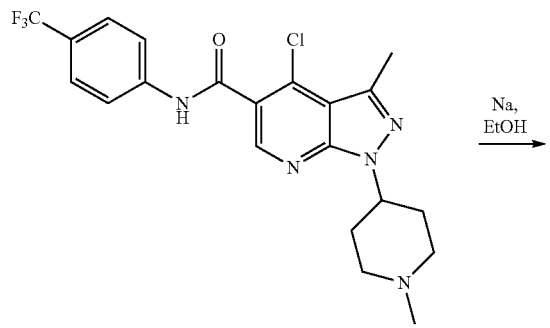

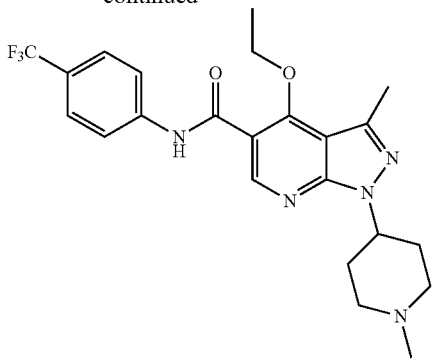

Example 181

4-ethoxy-3-methyl-1-(1-methylpiperidin-4-yl)-N-(4-(trifluoromethyl)phenyl)-1H-pyrazolo[3,4-b]pyridine-5-carboxamide To a solution of 4-chloro-3-methyl-1-(1-methylpiperidin-4-yl)-N-(4-(trifluoromethyl)phenyl)-1H-pyrazolo[3,4-b]pyridine-5-carboxamide (100 mg, 0.22 mmol) in EtOH (20 mL) was added Na (15 mg, 0.66 mmol) and the mixture was refluxed overnight. After cooling to room temperature, the reaction was quenched with MeOH and the mixture was concentrated to dryness in vacuum. The residue was purified by prep-HPLC to afford 4-ethoxy-3-methyl-1-(1-methylpiperidin-4-yl)-N-(4-(trifluoromethyl)phenyl)-1H-pyrazolo[3,4-b]pyridine-5-carboxamide (Example 181, 30 mg, yield: 30%) and the following 4-methoxy-3-methyl-1-(1-methylpiperidin-4-yl)-N-(4-(trifluoromethyl)phenyl)-1H-pyrazolo[3,4-b]pyridine-5-carboxamide (Example 182) (8 mg, yield: 8%) as a white solid for both of them. ¹HNMR (400 MHz, CD₃OD): δ=8.65 (s, 1H), 7.95 (d, J=8.4 Hz, 2H), 7.70 (d, J=8.4 Hz, 2H), 4.91-4.80 (m, 1H), 4.41 (q, J=7.2 Hz, 2H), 3.11-3.09 (m, 2H), 2.68 (s, 3H), 2.41-2.36 (m, 7H), 2.01-1.99 (m, 2H), 1.47 (t, J=6.8 Hz, 3H); MS: m/z 462.2 (M+H⁺).

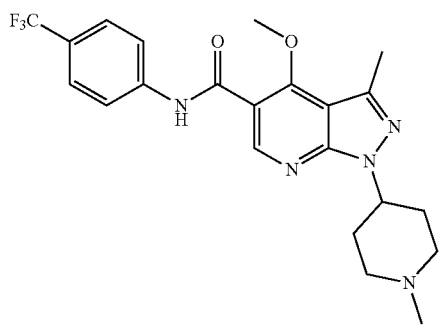 [SMILES: COc1c(C(=O)Nc2ccc(C(F)(F)F)cc2)cnc2c1c(C)nn2C1CCN(C)CC1]

Example 182

4-methoxy-3-methyl-1-(1-methylpiperidin-4-yl)-N-(4-(trifluoromethyl)phenyl)-1H-pyrazolo[3,4-b]pyridine-5-carboxamide ¹HNMR (400 MHz, CD₃OD): δ=8.62 (s, 1H), J=8.4 Hz, 2H), 7.71 (d, J=8.4 Hz, 2H), 4.91-4.78 (m, 1H), 4.18 (s, 3H), 3.10-3.08 (m, 2H), 2.67 (s, 3H), 2.41-2.34 (m, 7H), 2.00-1.98 (m, 2H); MS: m/z 448.2 (M+H$^+$).

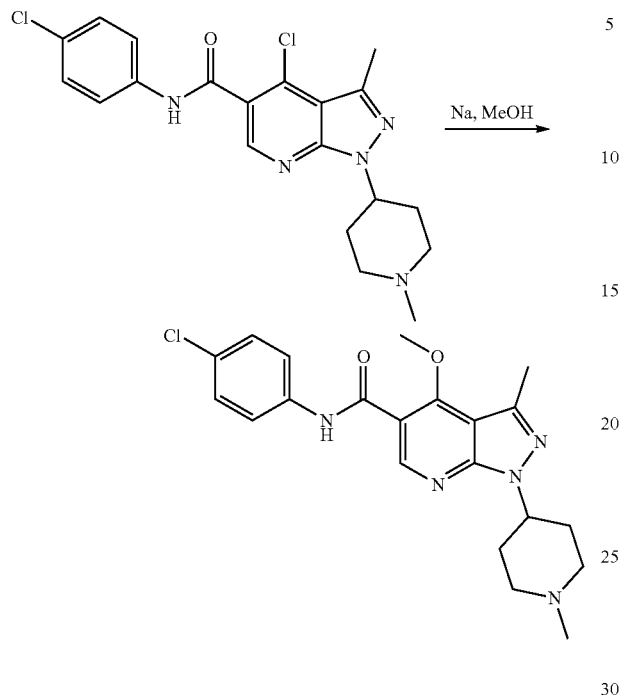

Example 183

N-(4-chlorophenyl)-4-methoxy-3-methyl-1-(1-methylpiperidin-4-yl)-1H-pyrazolo[3,4-b]pyridine-5-carboxamide N-(4-chlorophenyl)-4-methoxy-3-methyl-1-(1-methylpiperidin-4-yl)-1H-pyrazolo[3,4-b]pyridine-5-carboxamide (50 mg, 0.12 mmol) was added to the freshly-prepared NaOMe solution with Na (3.6 mg, 1.3 mmol) in MeOH (10 mL), and the mixture was stirred at room temperature overnight. The reactant was concentrated to dryness and the residue was purified by prep-HPLC to afford N-(4-chlorophenyl)-4-methoxy-3-methyl-1-(1-methylpiperidin-4-yl)-1H-pyrazolo[3,4-b]pyridine-5-carboxamide (30 mg, yield: 59%) as a white solid.

$^1$HNMR (400 MHz, DMSO-d6): δ=10.68 (s, 1H), 8.50 (s, 1H), 7.77 (d, J=8.8 Hz, 2H), 7.43 (d, J=8.8 Hz, 2H), 4.73-4.65 (m, 1H), 4.05 (s, 3H), 2.95 (brs, 2H), 2.58 (s, 3H), 2.27 (s, 3H), 2.20-2.16 (m, 4H), 1.85-1.84 (m, 2H); MS: m/z 414.2 (M+H$^+$).

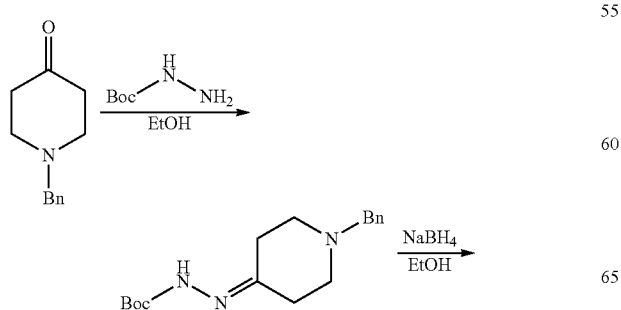

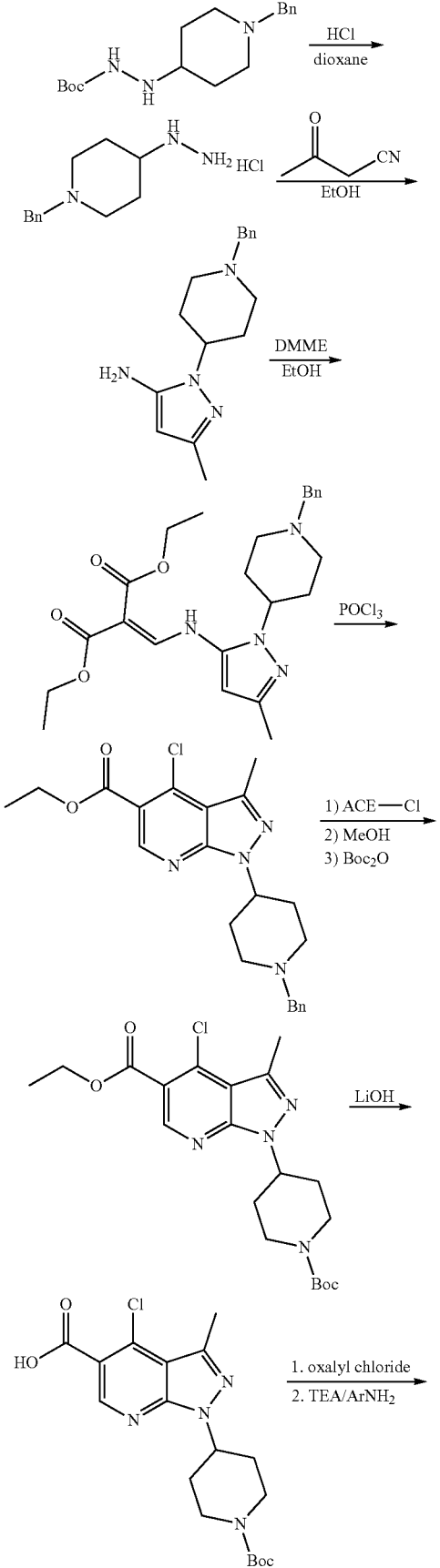

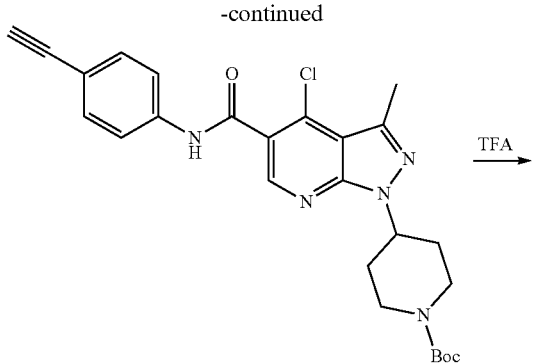

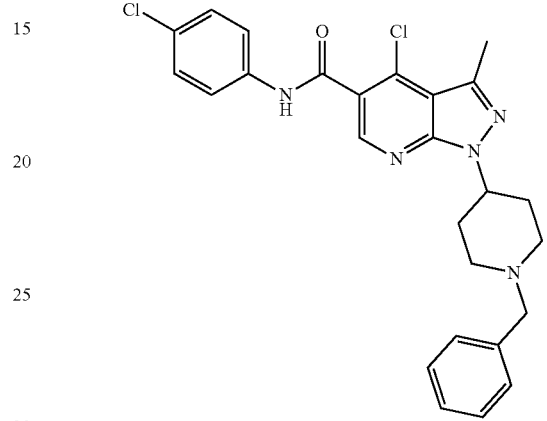

Example 184

4-chloro-N-(4-ethynylphenyl)-3-methyl-1-(piperidin-4-yl)-1H-pyrazolo[3,4-b]pyridine-5-carboxamide Step 1-6:

The procedures of 6 steps are similar to 4-chloro-3-methyl-1-(tetrahydro-pyran-4-yl)-1H-pyrazolo[3,4-b]pyridine-5-carboxylic acid (4-chloro-phenyl)-amide (Example 167).

Step 7:

To a solution of ethyl 1-(1-benzylpiperidin-4-yl)-4-chloro-3-methyl-1H-pyrazolo[3,4-b]pyridine-5-carboxylate (3 g, 7.3 mmol) in THF (50 mL) was added ACE-Cl (5.1 g, 36.4 mmol), it was then refluxed for 2 hrs. Then mixture was cooled to room temperature and aqueous $K_2CO_3$ (50 mL) was added. The mixture was stirred at room temperature for 30 mins. The aqueous phase was extracted with EA (100 mL) and the extracts were dried over $Na_2SO_4$. The solution was concentrated in vacuum to afford intermediate. It was then dissolved in THF/MeOH (1/1, 50 mL) and refluxed overnight. After that TEA (967 mg, 9.49 mmol) and $(Boc)_2O$ (1.6 g, 7.3 mmol) was added one by one. The mixture was stirred at room temperature for 2 hrs. The solution was concentrated to dryness and the residue was directly purified by flash column (EA in PE: 0 to 30%) to afford ethyl 1-(1-(tert-butoxycarbonyl)piperidin-4-yl)-4-chloro-3-methyl-1H-pyrazolo[3,4-b]pyridine-5-carboxylate (2.4 g, yield: 78%) as a white solid.

Step 8-9:

These two steps are similar to the last two steps of 4-chloro-N-(4-chlorophenyl)-3-methyl-1-propyl-1H-pyrazolo[3,4-b]pyridine-5-carboxamide (Example 144).

Step 10:

To solution of tert-butyl 4-(4-chloro-5-((4-ethynylphenyl)carbamoyl)-3-methyl-1H-pyrazolo[3,4-b]pyridin-1-yl)piperidine-1-carboxylate (30 mg, 0.06 mmol) in DCM (20 mL) was added TFA (2 mL), it was then stirred at rt for 1hour. Then resultant was concentrated under reduced pressure and the residue was diluted in MeOH (1 mL). It was purified by pre-HPLC to afford 4-chloro-N-(4-ethynylphenyl)-3-methyl-1-(piperidin-4-yl)-1H-pyrazolo[3,4-b]pyridine-5-carboxamide (9 mg, yield: 39%) as a white solid.

$^1$HNMR (400 MHz, CD$_3$OD): δ=8.65 (s, 1H), 7.73 (d, J=8.4 Hz, 2H 1H), 7.51 (d, J=8.8 Hz, 2H), 5.26-5.21 (m, 1H), 3.66-3.62 (m, 2H), 3.49 (s, 1H), 3.37-3.30 (m, 2H), 2.78 (s, 3H), 2.53-2.46 (m, 2H), 2.32-2.28 (m, 2H); MS: m/z 394.1 (M+H$^+$).

Example 185

1-(1-benzylpiperidin-4-yl)-4-chloro-N-(4-chlorophenyl)-3-methyl-1H-pyrazolo[3,4-b]pyridine-5-carboxamide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$HNMR (400 MHz, DMSO-d6): δ=10.76 (s, 1H), 8.67 (s, 1H), 7.75 (d, J=8.8 Hz, 2H), 7.43 (d, J=9.2 Hz, 2H), 7.35-7.25 (m, 5H), 4.79-4.77 (m, 1H), 3.55 (s, 2H), 2.97-2.95 (m, 2H), 2.69 (s, 3H), 2.22-2.16 (m, 4H), 1.89 (brs, 2H); $^1$HNMR 494.2 (M+H$^+$).

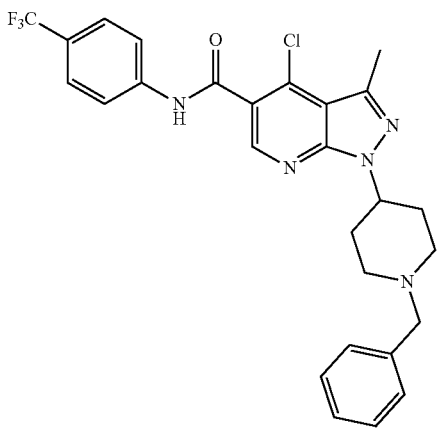 [SMILES: Cc1nn(C2CCN(Cc3ccccc3)CC2)c2ncc(C(=O)Nc3ccc(C(F)(F)F)cc3)c(Cl)c12]

Example 186

1-(1-benzylpiperidin-4-yl)-4-chloro-3-methyl-N-(4-(trifluoromethyl)phenyl)-1H-pyrazolo[3,4-b]pyridine-5-carboxamide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$HNMR (400 MHz, DMSO-d6): δ=10.99 (s, 1H), 8.71 (s, 1H), 7.93 (d, J=8.4 Hz, 2H), 7.76 (d, J=8.7 Hz, 2H), 7.35-7.26 (m, 5H), 4.80 (brs, 1H), 3.54 (s, 2H), 2.97-2.95 (m, 2H), 2.70 (s, 3H), 2.22-2.18 (m, 4H), 1.89-1.88 (brs, 2H); MS: m/z 528.2 (M+H$^+$).

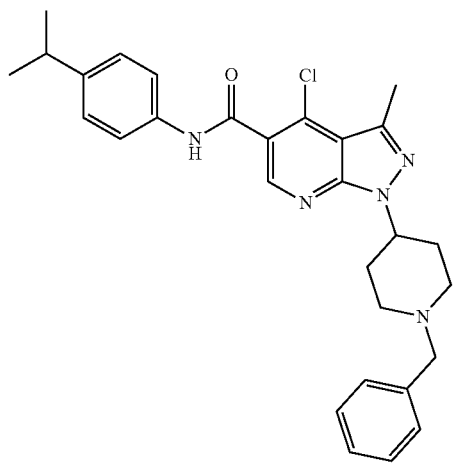 [SMILES: Cc1nn(C2CCN(Cc3ccccc3)CC2)c2ncc(C(=O)Nc3ccc(C(C)C)cc3)c(Cl)c12]

Example 187

1-(1-benzylpiperidin-4-yl)-4-chloro-N-(4-isopropyl-phenyl)-3-methyl-1H-pyrazolo[3,4-b]pyridine-5-carboxamide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$HNMR (400 MHz, DMSO-d6): δ=10.53 (s, 1H), 8.64 (s, 1H), 7.62 (d, J=8.8 Hz, 2H), 7.35-7.22 (m, 7H), 4.78 (brs, 1H), 3.54 (s, 2H), 2.90-2.83 (m, 3H), 2.69 (s, 3H), 2.22-2.16 (m, 4H), 1.88 (brs, 2H), 1.19 (d, J=6.8 Hz, 6H); MS: m/z 502.2 (M+H$^+$).

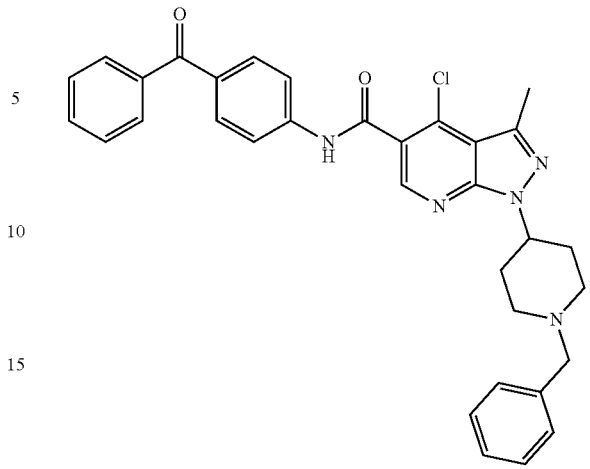

Example 188

N-(4-benzoylphenyl)-1-(1-benzylpiperidin-4-yl)-4-chloro-3-methyl-1H-pyrazolo[3,4-b]pyridine-5-carboxamide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$HNMR (400 MHz, DMSO-d6): δ=11.01 (s, 1H), 8.71 (s, 1H), 7.91 (d, J=8.4 Hz, 2H), 7.81, (d, J=8.4 Hz, 2H), 7.73 (d, J=7.2 Hz, 2H), 7.69-7.66 (m, 1H), 7.59-7.55 (m, 2H), 7.35-7.26 (m, 5H), 4.79 (brs, 1H), 3.55 (s, 2H), 2.97-2.95 (m, 2H), 2.70 (s, 3H), 2.21-2.19 (m, 4H), 1.89 (brs, 2H); MS: m/z 564.2 (M+H$^+$).

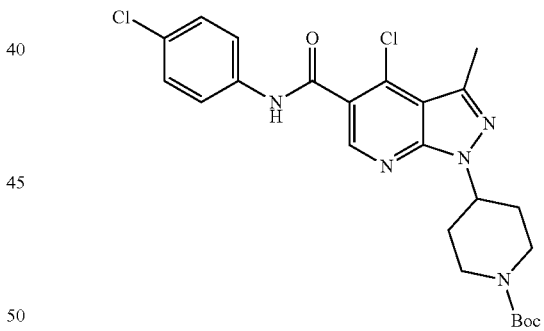

Example 189 tert-butyl 4-(4-chloro-5-((4-chlorophenyl)carbamoyl)-3-methyl-1H-pyrazolo[3,4-b]pyridin-1-yl)piperidine-1-carboxylate The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$HNMR (400 MHz, DMSO-d6): δ=10.75 (s, 1H), 8.68 (s, 1H), 7.75 (d, J=9.2 Hz, 2H), 7.44 (d, J=8.4 Hz, 2H), 5.05-4.98 (m, 1H), 4.10-4.08 (m, 2H), 3.09-2.98 (m, 2H), 2.69 (s, 3H), 2.01-1.90 (m, 4H), 1.43 (s, 9H); MS: m/z 504.1 (M+H$^+$).

467

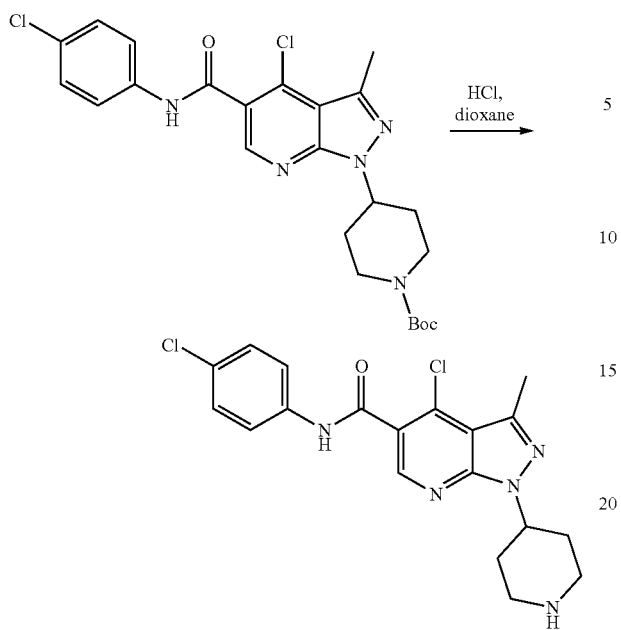

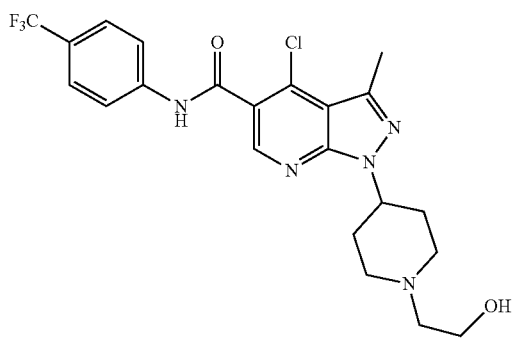

Example 190

4-chloro-N-(4-chlorophenyl)-3-methyl-1-(piperidin-4-yl)-1H-pyrazolo[3,4-b]pyridine-5-carboxamie To a solution of 4-(4-chloro-5-((4-chlorophenyl)carbamoyl)-3-methyl-1H-pyrazolo[3,4-b]pyridin-1-yl)piperidine-1-carboxylate (100 mg, 0.19 mmol) in dioxane (10 mL) was added HCl/dioxane (2 mL) and the mixture was stirred at room temperature overnight. The reactant was concentrated in vacuum and the residue was purified by prep-HPLC to afford 4-chloro-N-(4-chlorophenyl)-3-methyl-1-(piperidin-4-yl)-1H-pyrazolo[3,4-b]pyridine-5-carboxamide (31 mg, yield: 37%) as a white solid.

¹HNMR (300 MHz, DMSO-d6): δ=10.85 (s, 1H), 9.28 (s, 1H), 8.96 (s, 1H), 8.70 (s, 1H), 7.78 (d, J=7.6, 2H), 7.44 (d, J=9.0, 2H), 5.20-5.10 (m, 1H), 3.47-3.37 (m, 2H), 3.24-3.18 (m, 2H), 2.70 (s, 3H), 2.40-2.31 (m, 2H), 2.10-2.05 (m, 2H); MS: m/z 404.1 (M+H⁺).

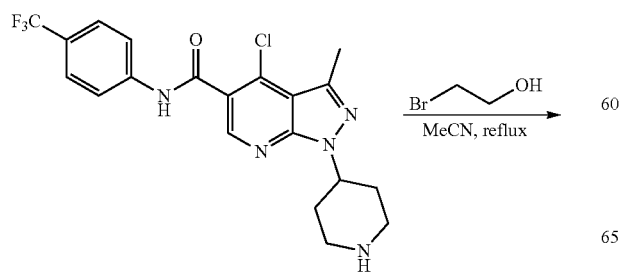

468

-continued

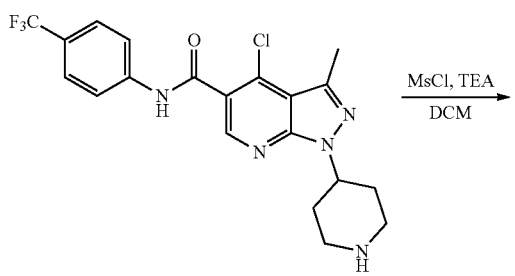

Example 191

4-chloro-1-(1-(2-hydroxyethyl)piperidin-4-yl)-3-methyl-N-(4-(trifluoromethyl)phenyl)-1H-pyrazolo[3,4-b]pyridine-5-carboxamide To a solution of 4-chloro-1-(1-(2-hydroxyethyl)piperidin-4-yl)-3-methyl-N-(4-(trifluoromethyl)phenyl)-1H-pyrazolo[3,4-b]pyridine-5-carboxamide (100 mg, 0.21 mmol) in MeCN (20 mL) was added 2-bromoethanol (0.2 mL) and TEA (0.5 mL). The mixture was stirred at reflux overnight. The reactant was concentrated to dryness and the residue was purified by prep-HPLC to give 4-chloro-1-(1-(2-hydroxyethyl)piperidin-4-yl)-3-methyl-N-(4-(trifluoromethyl)phenyl)-1H-pyrazolo[3,4-b]pyridine-5-carboxamide (48 mg, yield: 47%) as a white solid. ¹HNMR (400 MHz, DMSO-d6): δ=11.07 (s, 1H), 10.18 (brs, 1H), 8.74 (s, 1H), 7.95 (d, J=8.4 Hz, 2H), 7.76 (d, J=8.8 Hz, 2H), 5.17-5.09 (m, 1H), 3.82-3.80 (m, 2H), 3.71-3.68 (m, 2H), 3.40-3.19 (m, 5H), 2.71 (s, 3H), 2.60-2.55 (m, 2H), 2.16-2.13 (m, 2H); MS: m/z 482.1 (M+H⁺).

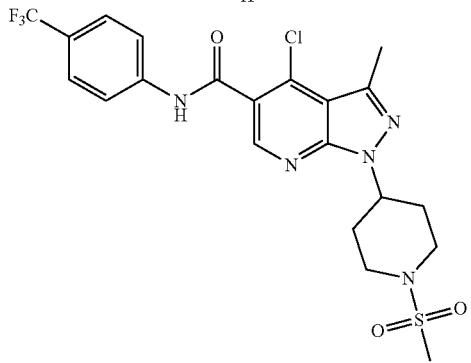

Example 192

4-chloro-3-methyl-1-(1-(methylsulfonyl)piperidin-4-yl)-N-(4-(trifluoromethyl)phenyl)-1H-pyrazolo[3,4-b]pyridine-5-carboxamide To a solution of 4-chloro-3-methyl-1-(piperidin-4-yl)-N-(4-(trifluoromethyl)phenyl)-1H-pyrazolo[3,4-b]pyridine-5-carboxamide (50 mg, 0.11 mmol) in DCM (10 mL) was added MsCl (14 mg, 0.12 mmol) and TEA (0.2 mL). The mixture was stirred at room temperature overnight. The reactant was concentrated to dryness in vacuum and the residue was purified by prep-HPLC to give 4-chloro-3-methyl-1-(1-(methylsulfonyl)piperidin-4-yl)-N-(4-(trifluoromethyl)phenyl)-1H-pyrazolo[3,4-b]pyridine-5-carboxamide (20 mg, yield: 30%) as a white solid. $^1$HNMR (400 MHz, DMSO-d6): δ=10.99 (s, 1H), 8.73 (s, 1H), 7.94 (d, J=8.4 Hz, 2H), 7.76 (d, J=8.8 Hz, 2H), 4.97-4.96 (m, 1H), 3.75-3.72 (m, 2H), 3.08-3.02 (m, 2H), 2.95 (s, 3H), 2.70 (s, 3H), 2.22-2.16 (m, 2H), 2.07-2.04 (m, 2H); MS: m/z 516.1 (M+H$^+$).

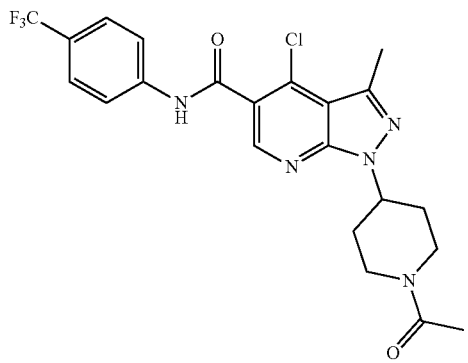 [SMILES: CC(=O)N1CCC(n2nc(C)c3c(Cl)c(C(=O)Nc4ccc(C(F)(F)F)cc4)cnc32)CC1]

Example 193

1-(1-acetylpiperidin-4-yl)-4-chloro-3-methyl-N-(4-(trifluoromethyl)phenyl)-1H-pyrazolo[3,4-b]pyridine-5-carboxamide The title compound was prepared using the similar procedure for 4-chloro-3-methyl-1-(tetrahydro-pyran-4-yl)-1H-pyrazolo[3,4-b]pyridine-5-carboxylic acid (4-chloro-phenyl)-amide (Example 167).

$^1$HNMR (400 MHz, CD$_3$OD): δ=8.66 (s, 1H), 7.94 (d, J=9.2 Hz, 2H), 7.71 (d, J=8.8 Hz, 2H), 5.19-5.14 (m, 1H), 4.72-4.68 (m, 1H), 4.16-4.12 (m, 1H), 3.45-3.38 (m, 1H), 2.97-2.92 (m, 1H), 2.77 (s, 3H), 2.20-2.11 (m, 5H), 2.06-2.03 (m, 2H); MS: m/z 480.1 (M+H$^+$).

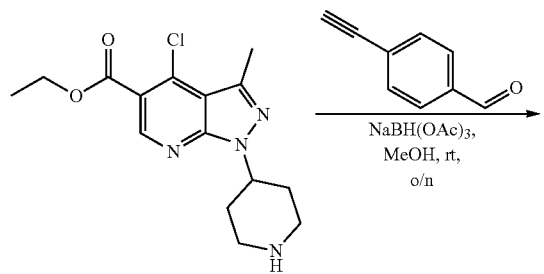

Example 194

N-(4-benzoylphenyl)-4-chloro-1-(1-(4-ethynylbenzyl)piperidin-4-yl)-3-methyl-1H-pyrazolo[3,4-b]pyridine-5-carboxamide Step 1:

To a solution of ethyl 4-chloro-3-methyl-1-(piperidin-4-yl)-1H-pyrazolo[3,4-b]pyridine-5-carboxylate (220 mg, 0.68 mmol) in MeOH(10 mL) was added 4-ethynylbenzaldehyde (98 mg, 0.75 mmol), and the mixture was stirred at room temperature before the addition of NaBH(OAc)$_3$ (636 mg, 3 mmol). Then the nixture was stirred at room temperature overnigt. The reactant was concentrated to dryness and the residue was partitioned between EA and water (each 10 mL). The organic layere was concentrated to drynss and the residue was purified by prep-HPLC to give crude ethyl 4-chloro-1-(1-(4-ethynylbenzyl)piperidin-4-yl)-3-methyl-1H-pyrazolo[3,4-b]pyridine-5-carboxylate as a white solid.

Step 2:

The above crude ester was dissolved in the mixture of THF (5 mL) and water (20 mL) and LiOH monohydrate (126 mg, 3 mmol) was added. After stirring overnight, the mixture was concentrated to dryness. The solvent was removed and the remaining aqueous solution was acidified with HCl to pH=2. The resulting solid was collected with filtration to give acid (110 mg, two-step yield: 40%).

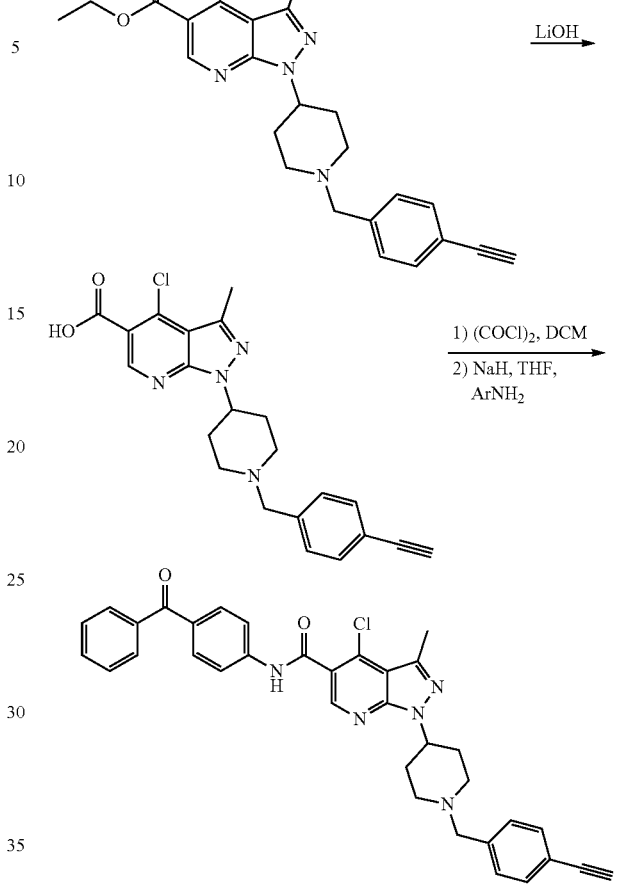

Step 3:

To a solution of the acid (110 mg, 0.26 mmol) in DCM (20 mL) was added oxalyl chloride (0.2 mL) and a drop of DMF. The mixture was stirred at room temperature for 2 hrs. The the mixture was concentrated to afford acyl chloride.

To a solution of (4-aminophenyl)(phenyl)methanone (53 mg, 0.27 mmol) in THF (5 mL) was added NaH (13 mg, 6.33 mmol), and the mixture was stirred at room temperature for 30 mins prior to the addition of the above acyl chloride. Then it was stirred overnight. The reaction was quenched with water (5 mL) and the mixture was extracted with EA (10 mL×3). The extracts were dried over $Na_2SO_4$ and the solution was concentrated to dryness. The residue was purified by prep-HPLC to afford N-(4-benzoylphenyl)-4-chloro-1-(1-(4-ethynylbenzyl)piperidin-4-yl)-3-methyl-1H-pyrazolo[3,4-b]pyridine-5-carboxamide (25 mg, yield: two-step yield: 16%) as a white solid.

$^1$HNMR (400 MHz, $CD_3OD$): δ=8.64 (s, 1H), 7.93-7.86 (m, 4H), 7.80 (d, J=7.6 Hz, 2H), 7.67-7.65 (m, 1H), 7.59-7.55 (m, 2H), 7.47 (d, J=8.0 Hz, 2H), 7.40 (d, J=8.4 Hz, 2H), 4.91-4.86 (m, 1H), 3.62 (s, 2H), 3.48 (s, 1H), 3.10-3.08 (m, 2H), 2.77 (s, 3H), 2.42-2.33 (m, 4H), 2.00-1.97 (m, 2H); MS: m/z 588.1 (M+H$^+$).

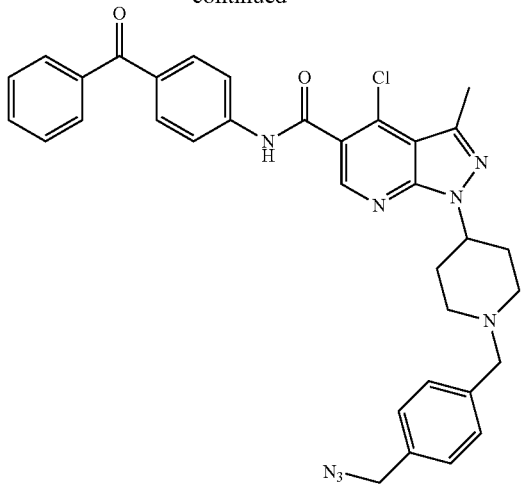

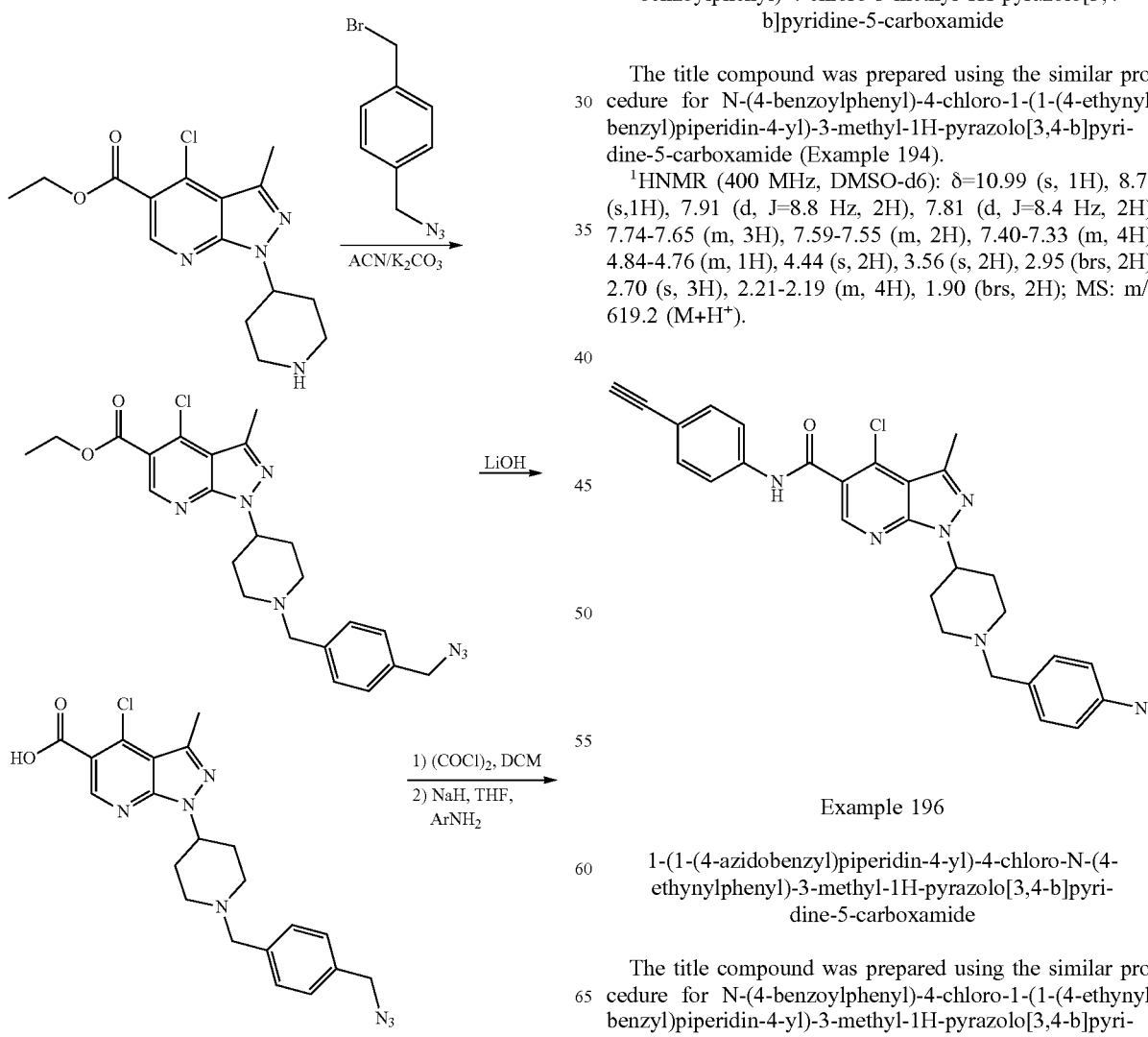

Example 195

1-(1-(4-(azidomethyl)benzyl)piperidin-4-yl)-N-(4-benzoylphenyl)-4-chloro-3-methyl-1H-pyrazolo[3,4-b]pyridine-5-carboxamide The title compound was prepared using the similar procedure for N-(4-benzoylphenyl)-4-chloro-1-(1-(4-ethynylbenzyl)piperidin-4-yl)-3-methyl-1H-pyrazolo[3,4-b]pyridine-5-carboxamide (Example 194).

$^1$HNMR (400 MHz, DMSO-d6): δ=10.99 (s, 1H), 8.71 (s,1H), 7.91 (d, J=8.8 Hz, 2H), 7.81 (d, J=8.4 Hz, 2H), 7.74-7.65 (m, 3H), 7.59-7.55 (m, 2H), 7.40-7.33 (m, 4H), 4.84-4.76 (m, 1H), 4.44 (s, 2H), 3.56 (s, 2H), 2.95 (brs, 2H), 2.70 (s, 3H), 2.21-2.19 (m, 4H), 1.90 (brs, 2H); MS: m/z 619.2 (M+H$^+$).

Example 196

1-(1-(4-azidobenzyl)piperidin-4-yl)-4-chloro-N-(4-ethynylphenyl)-3-methyl-1H-pyrazolo[3,4-b]pyridine-5-carboxamide The title compound was prepared using the similar procedure for N-(4-benzoylphenyl)-4-chloro-1-(1-(4-ethynylbenzyl)piperidin-4-yl)-3-methyl-1H-pyrazolo[3,4-b]pyridine-5-carboxamide (Example 194).

¹HNMR (400 MHz, CD₃OD): δ=8.61 (s, 1H), 7.73 (d, J=8.8 Hz, 2H), 7.50 (d, J=8.4 Hz, 2H), 7.44 (d, J=8.4 Hz, 2H), 7.08 (d, J=8.4 Hz, 2H), 4.90-4.86 (m, 1H), 3.62 (m, 2H), 3.48 (s, 1H), 3.10-3.08 (m, 2H), 2.76 (s, 3H), 2.41-2.28 (m, 4H), 1.99-1.96 (m, 2H); MS: m/z 525.2 (M+H⁺).

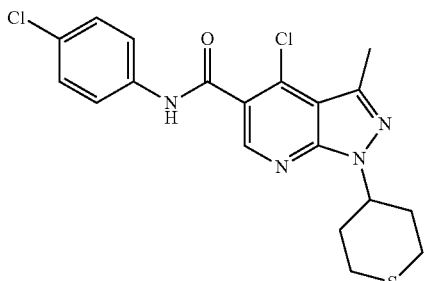

Example 197

4-chloro-N-(4-chlorophenyl)-3-methyl-1-(tetrahydro-2H-thiopyran-4-yl)-1H-pyrazolo[3,4-b]pyridine-5-carboxamide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

¹HNMR (400 MHz, DMSO-d6): δ=10.76 (s, 1H), 8.68 (s, 1H), 7.75 (d, J=8.8 Hz, 2H), 7.44 (d, J=8.8 Hz, 2H), 4.89-4.83 (m, 1H), 2.97-2.90 (m, 2H), 2.78-2.69 (m, 5H), 2.29-2.17 (m, 4H); MS: m/z 421.1 (M+H⁺).

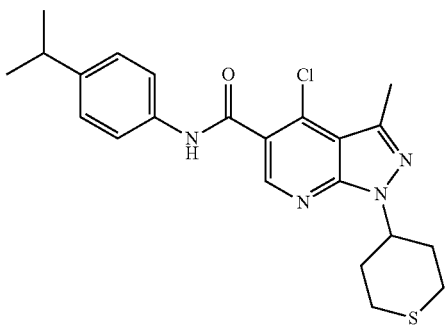 [SMILES: Cc1nn(C2CCSCC2)c2ncc(C(=O)Nc3ccc(C(C)C)cc3)c(Cl)c12]

Example 198

4-chloro-N-(4-isopropylphenyl)-3-methyl-1-(tetrahydro-2H-thiopyran-4-yl)-1H-pyrazolo[3,4-b]pyridine-5-carboxamide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

¹HNMR (400 MHz, DMSO-d6): δ=10.53 (s, 1H), 8.64 (s, 1H), 7.65 (d, J=8.8 Hz, 2H), 7.23 (d, J=8.4 Hz, 2H), 4.89-4.83 (m, 1H), 2.97-2.83 (m, 3H), 2.78-2.69 (m, 5H), 2.30-2.17 (m, 4H), 1.19 (d, J=7.6 Hz, 6H); MS: m/z 429.1 (M+H⁺).

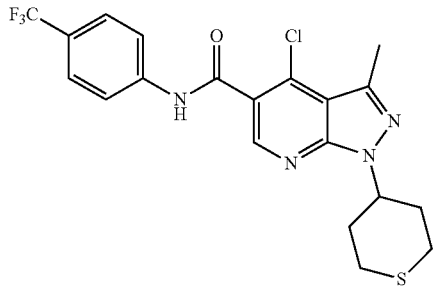

Example 199

4-chloro-3-methyl-1-(tetrahydro-2H-thiopyran-4-yl)-N-(4-(trifluoromethyl)phenyl)-1H-pyrazolo[3,4-b]pyridine-5-carboxamide The title compound was prepared using general procedure for 4-chloro-3-methyl-1-(tetrahydro-pyran-4-yl)-1H-pyrazolo[3,4-b]pyridine-5-carboxylic acid (4-chloro-phenyl)-amide (Example 167).

¹HNMR (400 MHz, DMSO-d6): δ=8.71 (s, 1H), 7.95-7.88 (m, 4H), 4.69-4.64 (m, 1H), 2.93-2.87 (m, 2H), 2.77-2.73 (m, 2H), 2.53 (s, 3H), 2.18-2.02 (m, 4H); MS: m/z 455.1 (M+H⁺).

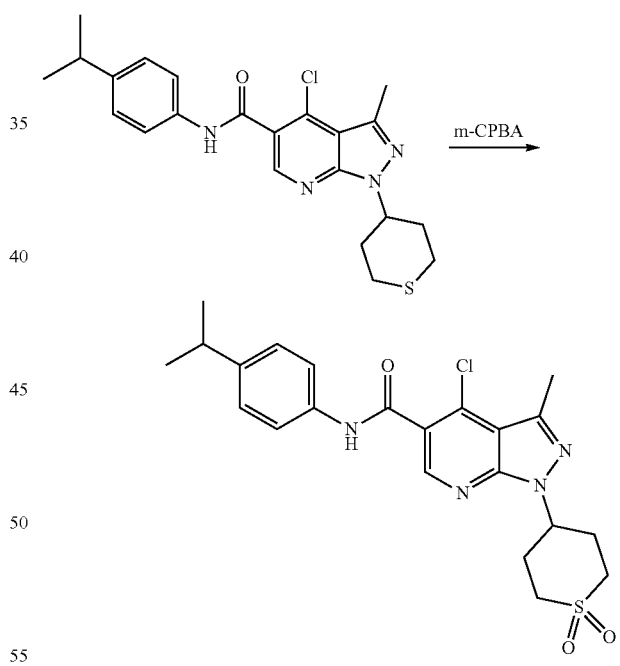

Example 200

4-chloro-1-(1,1-dioxidotetrahydro-2H-thiopyran-4-yl)-N-(4-isopropylphenyl)-3-methyl-1H-pyrazolo[3,4-b]pyridine-5-carboxamide To as solution of 4-chloro-3-methyl-1-(tetrahydro-thiopyran-4-yl)-1H-pyrazolo[3,4-b]pyridine-5-carboxylic acid (4-isopropyl-phenyl)-amide (50 mg, 0.12 mmol) in DCM (20 mL) was added m-CPBA (44 mg, 0.26 mmol), it was then stirred at rt overnight. Resultant was washed by water directly and organic layer was concentrated, purified by pre-HPLC to afford 18 mg (yield: 34%) of desired product as a white solid.

$^1$HNMR (400 MHz, DMSO-d6): δ=10.54 (s, 1H), 8.68 (s, 1H), 7.62 (d, J=8.4 Hz, 2H), 7.24 (d, J=8.4 Hz, 2H), 5.30-5.25 (m, 1H), 3.59-3.52 (m, 2H), 3.24-3.20 (m, 2H), 2.90-2.84 (m, 1H), 2.70 (s, 3H), 2.68-2.59 (m, 2H), 2.27-2.24 (m, 2H), 1.19 (d, J=7.8 Hz, 6H); MS: m/z 461.1 (M+H$^+$).

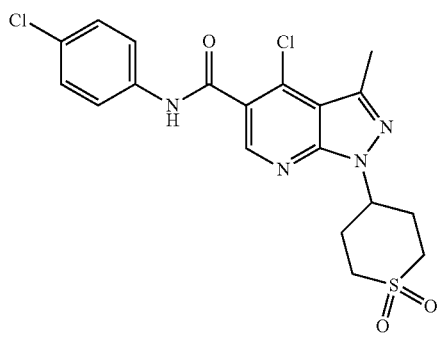 [SMILES: Cc1nn(C2CCS(=O)(=O)CC2)c2ncc(C(=O)Nc3ccc(Cl)cc3)c(Cl)c12]

Example 201

4-chloro-N-(4-chlorophenyl)-1-(1,1-dioxidotetrahydro-2H-thiopyran-4-yl)-3-methyl-1H-pyrazolo[3,4-b]pyridine-5-carboxamide The title compound was prepared using general procedure for 4-chloro-1-(1,1-dioxidotetrahydro-2H-thiopyran-4-yl)-N-(4-isopropylphenyl)-3-methyl-1H-pyrazolo[3,4-b]pyridine-5-carboxamide (Example 200).

$^1$HNMR (400 MHz, DMSO-d6): δ=10.76 (s, 1H), 8.72 (s, 1H), 7.75 (d, J=8.4 Hz, 2H), 7.44 (d, J=9.2 Hz, 2H), 5.30-5.25 (m, 1H), 3.59-3.52 (m, 2H), 3.24-3.20 (m, 2H), 2.70-2.59 (m, 5H), 2.27-2.24 (m, 2H); MS: m/z 453.1 (M+H$^+$).

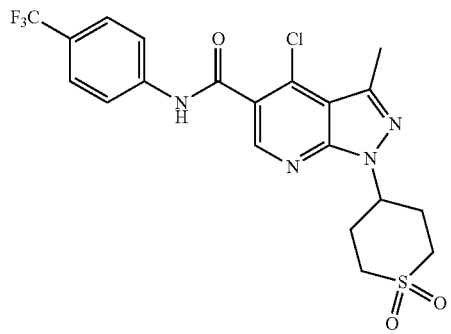 [SMILES: Cc1nn(C2CCS(=O)(=O)CC2)c2ncc(C(=O)Nc3ccc(C(F)(F)F)cc3)c(Cl)c12]

Example 202

4-chloro-1-(1,1-dioxidotetrahydro-2H-thiopyran-4-yl)-3-methyl-N-(4-(trifluoromethyl)phenyl)-1H-pyrazolo[3,4-b]pyridine-5-carboxamide The title compound was prepared using general procedure for 4-chloro-1-(1,1-dioxidotetrahydro-2H-thiopyran-4-yl)-N-(4-isopropylphenyl)-3-methyl-1H-pyrazolo[3,4-b]pyridine-5-carboxamide (Example 200).

$^1$HNMR (400 MHz, DMSO-d6): δ=11.01 (s, 1H), 8.75 (s, 1H), 7.94 (d, J=8.8 Hz, 2H), 7.76 (d, J=8.8 Hz, 2H), 5.31-5.25 (m, 1H), 3.60-3.52 (m, 2H), 3.32-3.20 (m, 2H), 2.71-2.58 (m, 5H), 2.27-2.24 (m, 2H); MS: m/z 487.1 (M+H$^+$).

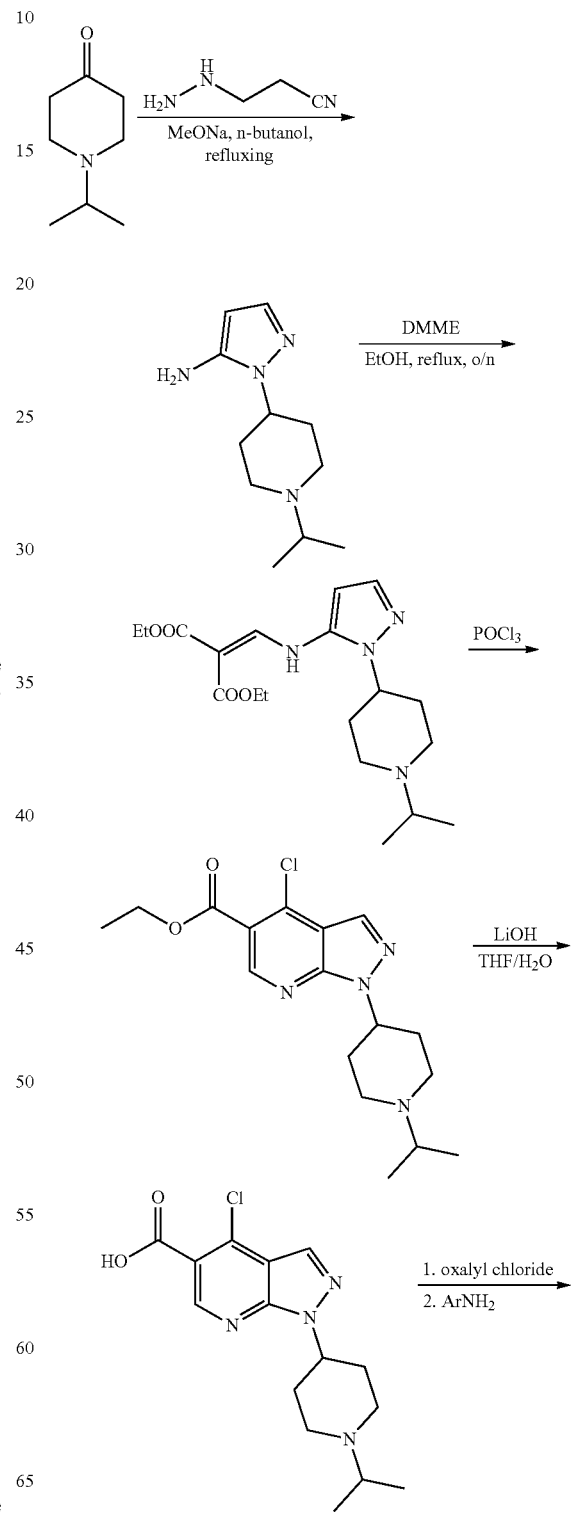

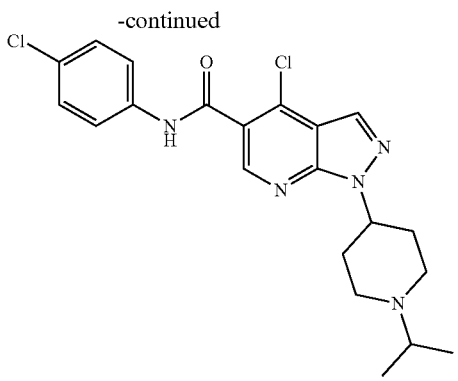

Example 203

4-chloro-N-(4-chlorophenyl)-1-(1-isopropylpiperidin-4-yl)-1H-pyrazolo[3,4-b]pyridine-5-carboxamide Step 1:

To the solution of 1-isopropyl-piperidin-4-one (13.98 g, 99.0 mmol) in n-butanol (100 mL) was added MeONa (8.63 g, 99.0 mmol). The mixture was stirred at 120° C. overnight. The solvent was removed in vacuum. Water (100 mL) was added. The mixture was extracted with ether (100 mL×3). The organic layer was treated with HCl (1N). The aqueous phrase was adjusted to pH=14 with aqueous NaOH. The mixture was extracted with DCM (100 mL×3) and the extracts were dried over Na₂SO₄. The solution was concentrated to give 2-(1-isopropyl-piperidin-4-yl)-2H-pyrazol-3-ylamine (18.76 g, yield: 91.04%) as a yellow solid.

Step 2:

To a solution of 2-(1-isopropyl-piperidin-4-yl)-2H-pyrazol-3-ylamine (18.76 g, 90.0 mmol) in EtOH (100 mL) was added 2-ethoxymethylene-malonic acid diethyl ester (19.44 g, 90.0 mmol). The mixture was then stirred at 80° C. overnight. The resultant was diluted with water (100 mL) and the aqueous phase was extracted with EA (100 mL×3). The organic layer was washed with water (100 mL×3) and dried over Na₂SO₄. The solvent was removed in vacuum. The resulting solid was purified by silica gel column chromatography (PE/EA=8/1-3/1). The solvent was removed in vacuum to afford 2-{[2-(1-isopropyl-piperidin-4-yl)-2H-pyrazol-3-ylamino]-methylene}1-malonic acid diethyl ester (16.34 g, yield: 46.60%) as a yellow oil.

Step 3:

The solution of 2-{[2-(1-isopropyl-piperidin-4-yl)-2H-pyrazol-3-ylamino]-methylene}-malonic acid diethyl ester (5.87 g, 15.54 mmol) in POCl₃ was stirred at 110° C. overnight. The solvent was removed in vacuum. The resulting solid was neutralized with NaHCO₃ (aq, 100 mL) to pH=8 and the aqueous phase was extracted with EA (100 mL×3). The organic layer was washed with water (100 mL×3) and dried over Na₂SO₄. The solvent was removed in vacuum. The resulting solid was purified by silica gel column chromatography (PE/EA=2/1) to afford 4-chloro-1-(1-isopropyl-piperidin-4-yl)-1H-pyrazolo[3,4-b]pyridine-5-carboxylic acid ethyl ester (3.87 g, yield: 71.3%) as a yellow solid.

¹HNMR (400 HMzs, CDCl₃): δ=9.02 (s, 1H), 8.20 (s, 1H), 4.87-4.84 (m, 1H), 4.46 (q, J=7.2 Hz, 2H), 3.12-3.05 (m 2H), 2.88-2.84 (m, 1H), 2.48-2.34 (m, 4H), 2.10-2.06 (m, 2H), 1.46 (t, J=7.2 Hz, 3H), 1.11 (d, J=6.6 Hz, 6H). MS: m/z 432.1 (M+H⁺)

Step 4:

To a solution of 4-chloro-1-(1-isopropyl-piperidin-4-yl)-1H-pyrazolo[3,4-b]pyridine-5-carboxylic acid ethyl ester (2.00 g, 5.72 mmol) in THF/H₂O (1/1, 100 mL) was added LiOH.H₂O (719 mg, 17.14 mmol). The mixture was stirred at room temperature overnight. The mixture was acidified with 1N HCl to pH=5-7. The aqueous phase was extracted with EA (100 mL×3). The organic layer was washed with water (100 mL×3) and dried over Na₂SO₄. The solvent was removed in vacuum to afford 4-chloro-1-(1-isopropyl-piperidin-4-yl)-1H-pyrazolo[3,4-b]pyridine-5-carboxylic acid (1.80 g, yield: 97.5%) as a yellow solid.

Step 5:

To a solution of 4-chloro-1-(1-isopropyl-piperidin-4-yl)-1H-pyrazolo[3,4-b]pyridine-5-carboxylic acid (300 mg, 0.93 mmol) in oxalyl chloride (3 mL) was added DMF (0.05 mL). The mixture was stirred at room temperature for 2 hrs. Then the mixture was concentrated to give 4-chloro-1-(1-isopropyl-piperidin-4-yl)-1H-pyrazolo[3,4-b]pyridine-5-carbonyl chloride. To a solution of 4-chloro-phenylamine (178 mg, 1.40 mmol), triethyl-amine (0.2 mL, 1.6 mmol) in THF (10 mL) was added a solution of 4-chloro-1-(1-isopropyl-piperidin-4-yl)-1H-pyrazolo[3,4-b]pyridine-5-carbonyl chloride in THF (5 mL) The mixture was stirred at room temperature. for 2 hrs. The resultant was washed with NaHCO₃ (25 mL) and the aqueous phase was extracted with EA (40 mL×3). The organic layer was washed with brine (50 mL) and dried over Na₂SO₄. The solvent was removed in vacuum. The residue was purified by silica gel column chromatography (DCM/MeOH=20/1). The solvent was removed in vacuum to afford 4-chloro-1-(1-isopropyl-piperidin-4-yl)-1H-pyrazolo[3,4-b]pyridine-5-carboxylic acid (4-chloro-phenyl)-amide (65 mg, yield: 16.2%) as a yellow solid.

¹H NMR (400 HMz, CDCl₃): δ=10.95 (s, 1H), 8.75 (s, 1H), 8.40 (s, 1H), 7.78 (d, J=12.8 Hz, 2H), 7.45 (d, J=6.0 Hz, 2H), 4.85-4.81 (brs, 1H), 2.97-2.80 (m, 3H), 2.43-2.15 (m 4H), 1.98-1.95 (m, 2H), 1.02 (d, J=3.6 Hz, 6H)). MS: m/z 432.1 (M+H⁺).

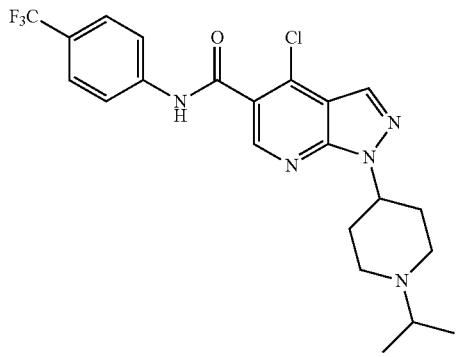 [SMILES: CC(C)N1CCC(n2ncc3c(Cl)c(C(=O)Nc4ccc(C(F)(F)F)cc4)cnc32)CC1]

Example 204

4-Chloro-1-(1-isopropyl-piperidin-4-yl)-1H-pyrazolo[3,4-b]pyridine-5-carboxylic acid (4-trifluoromethyl-phenyl)-amide The title compound was prepared using general procedure for 4-chloro-N-(4-chlorophenyl)-1-(1-isopropylpiperidin-4-yl)-1H-pyrazolo[3,4-b]pyridine-5-carboxamide (Example 203). ¹H NMR (400 MHz, DMSO-d₆) δ=11.22 (s, 1H), 8.79

(s, 1H), 8.43 (s, 1H), 7.98 (d, J=8.4 Hz, 2H), 7.76 (d, J=8.0 Hz, 2H), 4.88-4.87 (brs, 1H), 3.08-2.95 (m, 3H), 2.46-2.19 (m 4H), 2.03-1.98 (m, 2H), 1.22 (d, J=4.3 Hz, 6H). MS: m/z 466.1 (M+H⁺)

2H), 4.88 (brs, 1H),3.09 (brs, 2H), 2.47-2.44 (m, 2H), 2.22-2.24 (m, 4H), 1.99-1.97(m, 2H), 1.08-1.04 (m, 3H). MS: m/z 449.9 (M–H⁺)

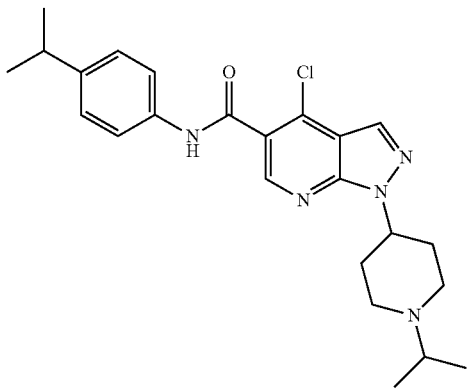 [SMILES: CC(C)c1ccc(NC(=O)c2cnc3c(cnn3C3CCN(C(C)C)CC3)c2Cl)cc1]

Example 205

4-Chloro-1-(1-isopropyl-piperidin-4-yl)-1H-pyrazolo[3,4-b]pyridine-5-carboxylic acid (4-isopropyl-phenyl)-amide The title compound was prepared using general procedure for 4-chloro-N-(4-chlorophenyl)-1-(1-isopropylpiperidin-4-yl)-1H-pyrazolo[3,4-b] pyridine-5-carboxamide (Example 203).

¹H NMR (400 MHz, DMSO-d₆) δ=10.68 (s, 1H), 8.73 (s, 1H), 8.41 (s, 1H), 7.65 (d, J=8.4 Hz, 2H), 7.24 (d, J=8.4 Hz, 2H), 4.90-4.87 (brs, 1H), 3.05-2.84 (m, 4H), 2.48-2.24 (m 4H), 2.02-2.00 (m, 2H), 1.20 (d, J=7.2 Hz, 6H), 1.07 (d, J=3.2 Hz, 6H). MS: m/z 440.2 (M+H⁺)

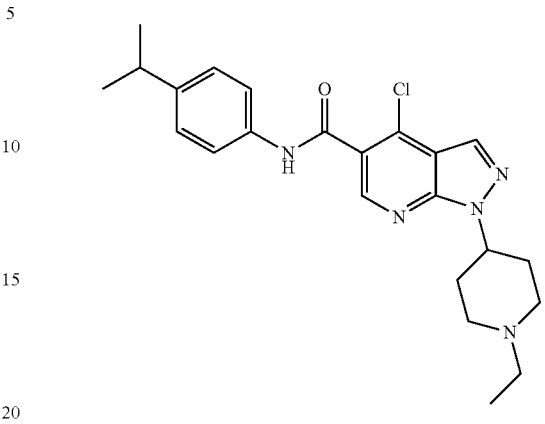

Example 207

4-chloro-1-(1-ethyl-piperidin-4-yl)-1H-pyrazolo[3,4-b]pyridine-5-carboxylic acid (4-isopropyl-phenyl)-amide The title compound was prepared using general procedure for 4-chloro-N-(4-chlorophenyl)-1-(1-isopropylpiperidin-4-yl)-1H-pyrazolo[3,4-b]pyridine-5-carboxamide (Example 203).

¹HNMR (400 MHz, DMSO-d6): δ=10.55 (s, 1H), 8.73 (s, 1H), 8.41 (s, 1H), 7.63 (d, J=8.4 Hz, 2H), 7.24 (d, J=8.4 Hz, 2H), 4.85 (brs, 1H), 3.05 (brs, 2H), 2.89-2.86 (m, 1H), 2.42-2.44 (m, 2H), 2.24-2.12 (m, 4H), 1.99-1.95 (m, 2H), 1.23-1.19 (m, 6H), 1.07-1.03 (m, 3H). MS: m/z 426.2 (M+H⁺)

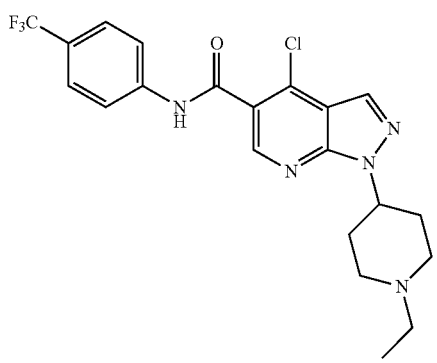 [SMILES: CCN1CCC(n2ncc3c(Cl)c(C(=O)Nc4ccc(C(F)(F)F)cc4)cnc32)CC1]

Example 206

4-Chloro-1-(1-ethyl-piperidin-4-yl)-1H-pyrazolo[3,4-b]pyridine-5-carboxylic acid (4-trifluoromethyl-phenyl)-amide The title compound was prepared using general procedure for 4-chloro-N-(4-chlorophenyl)-1-(1-isopropylpiperidin-4-yl)-1H-pyrazolo[3,4-b]pyridine-5-carboxamide (Example 203).

¹HNMR (400 MHz, DMSO-d6): δ=11.04 (s, 1H), 8.80 (s, 1H), 8.45 (s, 1H), 7.94 (d, J=8.4 Hz, 2H), 7.77 (d, J=8.4 Hz,

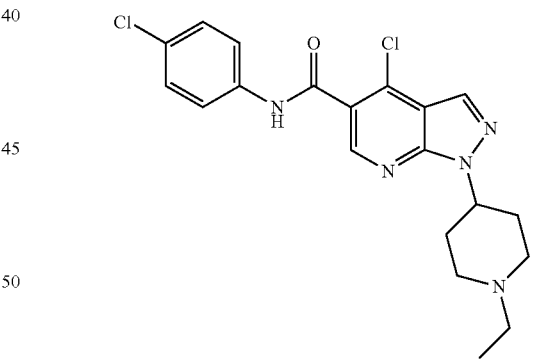

Example 208

4-chloro-1-(1-ethyl-piperidin-4-yl)-1H-pyrazolo[3,4-b]pyridine-5-carboxylic acid (4-chloro-phenyl)-amide The title compound was prepared using general procedure for 4-chloro-N-(4-chlorophenyl)-1-(1-isopropylpiperidin-4-yl)-1H-pyrazolo[3,4-b]pyridine-5-carboxamide (Example 203).

¹HNMR (400 MHz, CDCl₃): δ=8.91 (s, 1H), 8.18 (s, 1H), 8.08 (s, 1H), 7.63 (d, J=8.4 Hz, 2H), 7.37 (d, J=8.4 Hz, 2H), 4.92-4.94 (m, 1H), 3.19-3.17 (m, 2H), 2.56-2.55 (m, 2H), 2.50-2.40 (m, 2H), 2.32-2.25 (m, 2H), 2.11-2.04 (m, 2H), 1.25-1.17 (m, 3H). MS: m/z 418.1 (M+H$^+$)

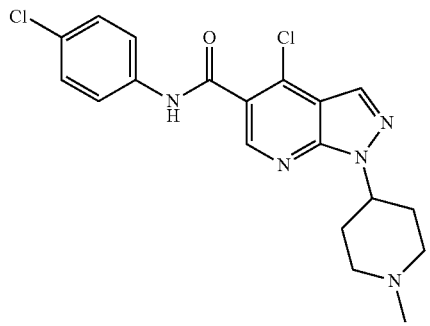 [SMILES: CN1CCC(n2ncc3c(Cl)c(C(=O)Nc4ccc(Cl)cc4)cnc32)CC1]

Example 209

4-chloro-1-(1-methyl-piperidin-4-yl)-1H-pyrazolo[3,4-b]pyridine-5-carboxylic acid (4-chloro-phenyl)-amide The title compound was prepared using general procedure for 4-chloro-N-(4-chlorophenyl)-1-(1-isopropylpiperidin-4-yl)-1H-pyrazolo[3,4-b]pyridine-5-carboxamide (Example 203).

$^1$HNMR (400 MHz, DMSO-d6): δ=10.78 (s, 1H), 8.76 (s, 1H), 8.42 (s, 1H), 7.76 (d, J=8.8 Hz, 2H), 7.46-7.43 (m, 2H), 4.86-4.80 (m, 1H), 2.93 (d, J=10.4 Hz, 2H), 2.28 (s, 3H), 2.27-2.12 (m, 4H), 1.95-1.91 (m, 2H). MS: m/z 404.1 (M+H$^+$)

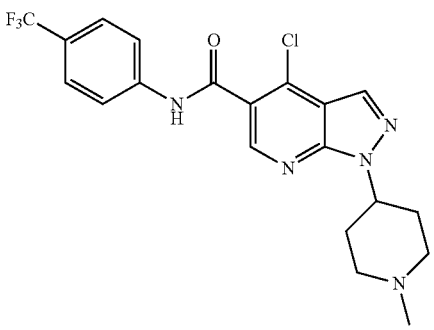 [SMILES: CN1CCC(n2ncc3c(Cl)c(C(=O)Nc4ccc(C(F)(F)F)cc4)cnc32)CC1]

Example 210

4-chloro-1-(1-methyl-piperidin-4-yl)-1H-pyrazolo[3,4-b]pyridine-5-carboxylic acid (4-trifluoromethyl-phenyl)-amide The title compound was prepared using general procedure for 4-chloro-N-(4-chlorophenyl)-1-(1-isopropylpiperidin-4-yl)-1H-pyrazolo[3,4-b]pyridine-5-carboxamide (Example 203). $^1$HNMR (300 MHz, DMSO-d6): δ=11.02 (s, 1H), 8.80 (s, 1H), 8.44 (s, 1H), 7.94 (d, J=8.4 Hz, 2H), 7.76 (d, J=8.7 Hz, 2H), 4.86-4.85 (m, 1H), 2.97 (d, J=6.0 Hz, 2H), 2.31 (s, 3H), 2.27-2.18 (m, 4H), 1.97-1.94 (m, 2H). MS: m/z 438.1 (M+H$^+$).

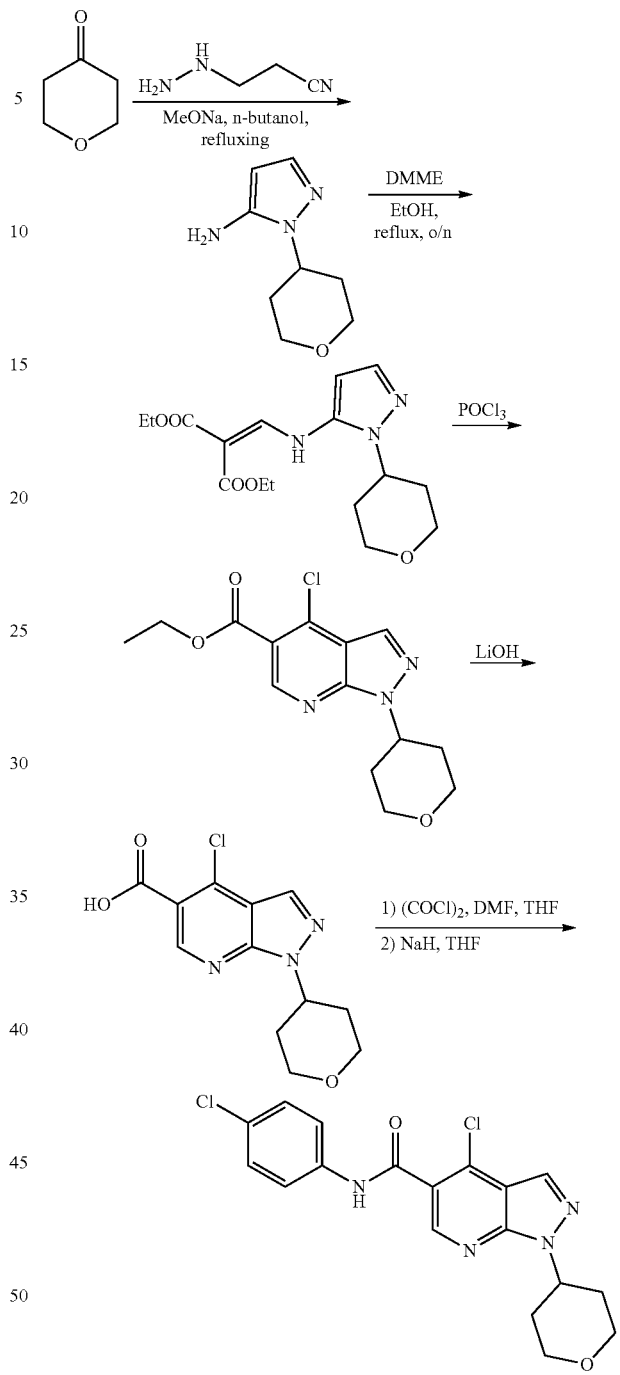

Example 211

4-Chloro-1-(tetrahydro-pyran-4-yl)-1H-pyrazolo[3,4-b]pyridine-5-carboxylic acid (4-chloro-phenyl)-amide Step 1:

To a solution of tetrahydro-pyran-4-one (4.00 g, 40 mmol) in EtOH (40 mL) was added 3-hydrazino-propionitrile (3.40 g, 40 mmol) dropwise at room temperature. The resulting mixture was stirred for 3 hrs at room temperature. Then the mixture was concentrated under reduced pressure and the residue was dissolved in n-butanol (80 mL), followed by the addition of MeONa (4.32 g, 80 mmol). The mixture was refluxed overnight. The mixture was concentrated under reduced pressure. The residue was treated with sat. NH₄Cl (80 mL). The aqueous phase was extracted with DCM (60 mL×2) and the extracts were dried over Na₂SO₄. The solution was concentrated and the residue was purified by Combi flash (CH₃CN/H₂O=30%) to give 5.34 g of crude 2-(tetrahydro-pyran-4-yl)-2H-pyrazol-3-ylamine as a yellow solid. MS: m/z 168.3 (M+H⁺).

Step 2:

To a mixture of 2-(tetrahydro-pyran-4-yl)-2H-pyrazol-3-ylamine (5.34 g, 32 mmol) in EtOH (150 mL) was added 2-ethoxymethylene-malonic acid diethyl ester (8.29 g, 38.4 mmol). The resulting mixture was stirred at 80° C. overnight. The mixture was concentrated under reduced pressure and the residue was purified by silica gel column chromatography (from 100% PE to PE/EA=25/1) to afford 2-{[2-(tetrahydro-pyran-4-yl)-2H-pyrazol-3-ylamino]-methylene}-malonic acid diethyl ester (430 mg, two-step yield: 3%) as a white solid. MS: m/z 338.1 (M+H⁺).

Step 3:

A suspension of 2-{[2-(tetrahydro-pyran-4-yl)-2H-pyrazol-3-ylamino]-methylene}-malonic acid diethyl ester (430 mg, 1.272 mmol) in POCl₃ (12 mL) was refluxed overnight. The excessive POCl₃ was removed under reduced pressure. The residue was partitioned between NaHCO₃ (sat. 30 mL) and EA (30 mL). The mixture was extracted with EA (30 mL×2). The extracts were washed with brine (50 mL×2), dried over Na₂SO₄ and concentrated to give 370 mg of crude 4-chloro-1-(tetrahydro-pyran-4-yl)-1H-pyrazolo[3,4-b]pyridine-5-carboxylic acid ethyl ester as a yellow solid. MS: m/z 309.9 (M+H⁺).

Step 4:

To a mixture of 4-chloro-1-(tetrahydro-pyran-4-yl)-1H-pyrazolo[3,4-b]pyridine-5-carboxylic acid ethyl ester (370 mg, 1.197 mmol) in THF (12 mL) and H₂O (3 mL) was added LiOH (aq. 2.4 mL, 4.790 mmol). The resulting mixture was stirred at room temperature overnight. The mixture was concentrated under reduced pressure and the residue was partitioned between water (30 mL) and EA (30 mL). The mixture was extracted with EA (20 mL×2). The aqeous phase was acidified with 2N HCl to pH=5 and extracted with DCM (30 mL×2). The organic layers were washd with water (40 mL×2), dried over Na₂SO₄ and concentrated to afford 200 mg of crude 4-chloro-1-(tetrahydro-pyran-4-yl)-1H-pyrazolo[3,4-b]pyridine-5-carboxylic acid as a white solid. MS: m/z 283.2 (M+H⁺).

Step 5:

To a solution of 4-chloro-1-(tetrahydro-2H-pyran-4-yl)-1H-pyrazolo[3,4-b]pyridine-5-carboxylic acid (70 mg, 0.25 mmol) in oxalyl chloride (5 mL) was added a drop of DMF and the mixture was stirred at room temperature for 1 hr The mixture was concentrated in vacuum to give the acyl chloride. In another flask, 4-chloroaniline (40 mg, 0.315 mmol) in THF (1 mL) was treated with NaH (60% in mineral oil, 20 mg, 0.5 mmol) at room temperature for 0.5 h. The above acyl chloride dissolved in THF (2 mL) was added thereto and the mixture was stirred at room temperature overnight. The starting material was consumed almost completely by TLC and LCMS. The reaction solution was poured into saturated aqueous NH₄Cl (15 mL) and the aqueous phase was extracted with EtOAc (10 mL×3). The organic layer was dried over Na₂SO₄. The solution was concentrated in vacuum and the residue was purified by prep-TLC (PE/EtOAc=1/1) to give 4-chloro-1-(tetrahydro-pyran-4-yl)-1H-pyrazolo[3,4-b]pyridine-5-carboxylic acid (4-chloro-phenyl)-amide (45 mg, yield: 46%) as white solid.

¹HNMR (400 HMz, CDCl₃): δ=8.93 (s, 1H), 8.20 (s, 1H), 8.06 (brs, 1H), 7.63 (d, J=8.8 Hz, 2H), 7.37 (d, J=8.8 Hz, 2H), 5.17-5.09 (m, 1H), 4.19-4.16 (m, 2H), 3.68-3.63 (m, 2H), 2.48-2.38 (m, 2H), 2.00-1.97 (m, 2H). MS: m/z 391.1 (M+H⁺).

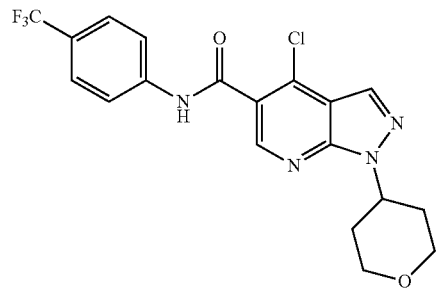 [SMILES: O=C(Nc1ccc(C(F)(F)F)cc1)c1cnc2c(cnn2C2CCOCC2)c1Cl]

Example 212

4-Chloro-1-(tetrahydro-pyran-4-yl)-1H-pyrazolo[3,4-b]pyridine-5-carboxylic acid (4-trifluoromethyl-phenyl)-amide The title compound was prepared using general procedure for 4-chloro-N-(4-chlorophenyl)-1-(1-isopropylpiperidin-4-yl)-1H-pyrazolo[3,4-b]pyridine-5-carboxamide (Example 203). ¹HNMR (300 HMz, CDCl₃): δ=8.94 (s, 1H), 8.23 (s, 1H), 8.22 (s, 1H), 7.82 (d, J=8.4 Hz, 2H), 7.68 (d, J=8.1 Hz, 2H), 5.01-5.23 (m, 1H), 4.22-4.16 (m, 2H), 3.71-3.63 (m, 2H), 2.47-2.42 (m, 2H), 2.06-1.98 (m, 2H). MS: m/z 425.1 (M+H⁺)

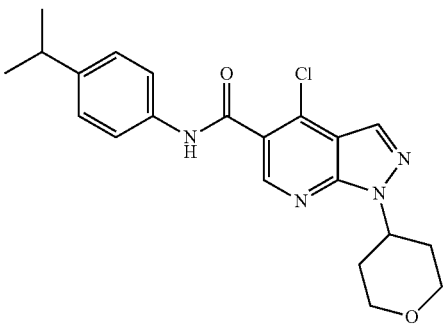 [SMILES: CC(C)c1ccc(NC(=O)c2cnc3c(cnn3C3CCOCC3)c2Cl)cc1]

Example 213

4-chloro-N-(4-isopropylphenyl)-1-(tetrahydro-2H-pyran-4-yl)-1H-pyrazolo[3,4-b]pyridine-5-carboxamide The title compound was prepared using general procedure for 4-chloro-N-(4-chlorophenyl)-1-(1-isopropylpiperidin-4-yl)-1H-pyrazolo[3,4-b]pyridine-5-carboxamide (Example 203).

¹HNMR (CDCl₃, 400 HMz): δ=8.92 (s, 1H), 8.19 (s, 1H), 7.96 (brs, 1H), 7.58 (d, J=8.0 Hz, 2H), 7.27 (d, J=7.2 Hz, 2H), 5.16-5.08 (m, 1H), 4.19-4.15 (m, 2H), 3.68-3.63 (m, 2H), 2.96-2.89 (m, 1H), 2.48-2.37 (m, 2H), 2.00-1.97 (m, 2H), 1.25 (d, J=14.8 Hz, 6H). MS: m/z 399.2(M+H⁺).

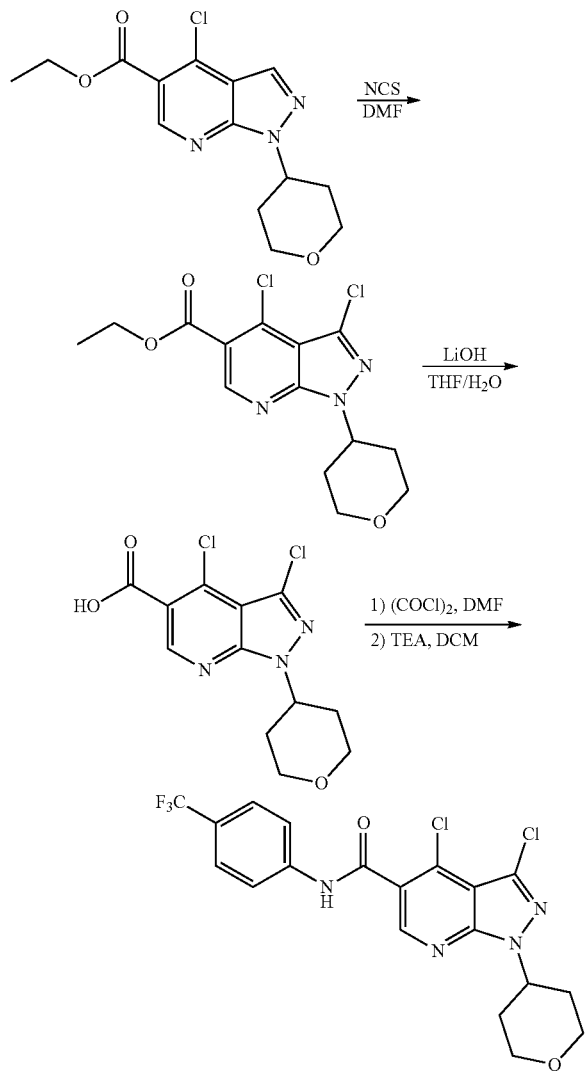

Example 214

3,4-Dichloro-1-(tetrahydro-pyran-4-yl)-1H-pyrazolo[3,4-b]pyridine-5-carboxylic acid (4-trifluoromethyl-phenyl)-amide Step 1:
To a solution of 4-chloro-1-(tetrahydro-pyran-4-yl)-1H-pyrazolo[3,4-b]pyridine-5-carboxylic acid ethyl ester (80 mg, 0.26 mmol) in DMF (1.5 mL), was added NCS (175 mg, 1.3 mmol). The mixture was then stirred at 90° C. under N₂ overnight. The resultant was poured into water (15 mL) and extracted with EA (20 mL). The organic layer was concentrated and purified by prep-HPLC to give 3,4-dichloro-1-(tetrahydro-pyran-4-yl)-1H-pyrazolo[3,4-b]pyridine-5-carboxylic acid ethyl ester (34 mg, yield: 38%) as a white solid. MS: m/z 343.8 (M+H⁺)

Step 2:
A mixture of 3,4-dichloro-1-(tetrahydro-pyran-4-yl)-1H-pyrazolo[3,4-b]pyridine-5-carboxylic acid ethyl ester (42 mg, 0.123 mmol) and LiOH.H₂O (21 mg, 0.5 mmol) in THF/H₂O (4/1, 1.4 mL) was stirred at room temperature overnight. The reaction solution was acidified with conc. HCl to pH=5 and the organic solvent was removed under reduced pressure. The remained aqueous solution was separated between water (15 mL) and EA (30 mL). The organic layer was dried over Na₂SO₄ and concentrated to give 3,4-dichloro-1-(tetrahydro-pyran-4-yl)-1H-pyrazolo[3,4-b]pyridine-5-carboxylic acid (34 mg, yield: 81%) as a white solid.

Step 3:
To a suspension of 3,4-dichloro-1-(tetrahydro-pyran-4-yl)-1H-pyrazolo[3,4-b]pyridine-5-carboxylic acid (17 mg, 0.054 mmol) in (COCl)₂(2 mL) was added a drop of DMF. The reaction was stirred at room temperature for 1.5 hrs and concentrated to give the acyl chloride. The acyl chloride was dissolved in dry DCM (3 mL). To the solution, was added 4-trifluoromethyl-phenylamine (11.3 mg, 0.07 mmol), followed by TEA (22 mg, 0.22 mmol). After stirring overnight at room temperature, the mixture was separated between sat.NaHCO₃ solution (15 mL) and DCM (5 mL). The organic layer was dried over Na₂SO₄, concentrated and purified by prep-TLC (DCM/EA=4/1) to give 3,4-dichloro-1-(tetrahydro-pyran-4-yl)-1H-pyrazolo[3,4-b]pyridine-5-carboxylic acid (4-trifluoromethyl-phenyl)-amide (12 mg, yield: 49%) as a white solid.
¹HNMR (400 MHz, CDCl₃): δ=8.88 (s, 1H), 8.09 (brs, 1H), 7.79 (d, J=8.4 Hz, 2H), 7.67 (d, J=8.4 Hz, 2H), 5.14-5.08 (m, 1H), 4.18-4.14 (m, 2H), 3.63 (t, J=11.4 Hz, 2H), 2.45-2.35 (m, 2H), 1.98-1.95 (m, 2H). MS: m/z 457.1 (M+H⁺).

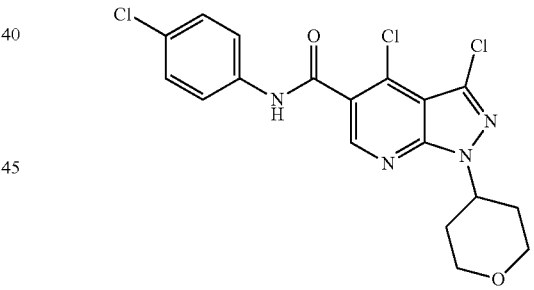

Example 215

3,4-Dichloro-1-(tetrahydro-pyran-4-yl)-1H-pyrazolo[3,4-b]pyridine-5-carboxylic acid (4-chloro-phenyl)-amide The title compound was prepared using general procedure for 3,4-dichloro-1-(tetrahydro-pyran-4-yl)-1H-pyrazolo[3,4-b]pyridine-5-carboxylic acid (4-trifluoromethyl-phenyl)-amide (Example 214).
¹HNMR (400 MHz, CDCl₃): δ=8.87 (s, 1H), 7.96 (brs, 1H), 7.62 (d, J=8.8 Hz, 2H), 7.37 (d, J=9.2 Hz, 2H), 5.13-5.07 (m, 1H), 4.18-4.14 (m, 2H), 3.66-3.59 (m, 2H), 2.44-2.35 (m, 2H), 1.98-1.94 (m, 2H). MS: m/z 423.1 (M+H⁺)

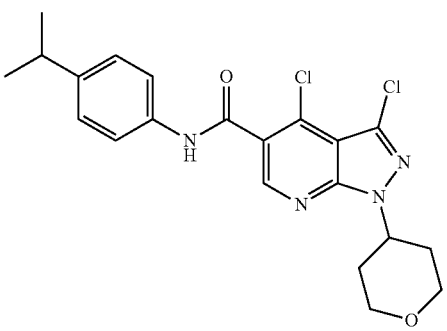 [SMILES: CC(C)c1ccc(NC(=O)c2cnc3c(c(Cl)nn3C3CCOCC3)c2Cl)cc1]

Example 216

3,4-Dichloro-1-(tetrahydro-pyran-4-yl)-1H-pyrazolo[3,4-b]pyridine-5-carboxylic acid (4-isopropyl-phenyl)-amide The title compound was prepared using general procedure for 3,4-dichloro-1-(tetrahydro-pyran-4-yl)-1H-pyrazolo[3,4-b]pyridine-5-carboxylic acid (4-trifluoromethyl-phenyl)-amide (Example 214).

$^1$HNMR (300 MHz, CDCl$_3$): δ=8.87 (s, 1H), 7.87 (brs, 1H), 7.57 (d, J=9.0 Hz, 2H), 7.26 (overlap, 2H), 5.14-5.06 (m, 1H), 4.18-4.13 (m, 2H), 3.66-3.58 (m, 2H), 2.95-2.90 (m, 1H), 2.46-2.32 (m, 2H), 1.98-1.93 (m, 2H), 1.27-1.22 (m, 6H). MS: m/z 431.1 (M+H$^+$)

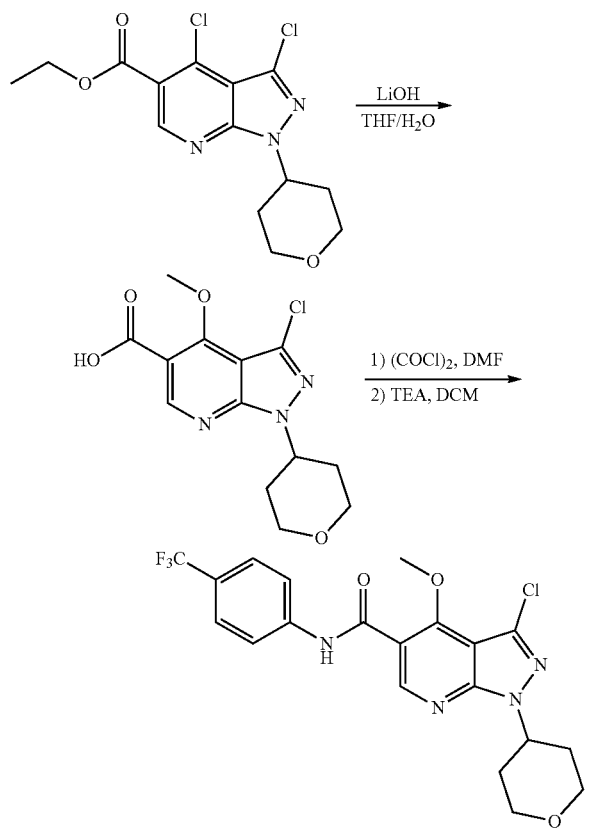

Example 217

3-Chloro-4-methoxy-1-(tetrahydro-pyran-4-yl)-1H-pyrazolo[3,4-b]pyridine-5-carboxylic acid (4-trifluoromethyl-phenyl)-amide Step 1:

A mixture of 3,4-dichloro-1-(tetrahydro-pyran-4-yl)-1H-pyrazolo[3,4-b]pyridine-5-carboxylic acid ethyl ester (130 mg, 0.37 mmol) and LiOH.H$_2$O (280 mg, 6.66 mmol) in MeOH/H$_2$O (4:1, 30 mL) was stirred at room temperature for 5 hrs. The reaction solution was acidified with conc. HCl to pH=5. The organic solvent was removed under reduced pressure. The remained aqueous solution was separated between water (20 mL) and EA (40 mL). The organic layer was dried over Na$_2$SO$_4$, concentrated to give 3-chloro-4-methoxy-1-(tetrahydro-pyran-4-yl)-1H-pyrazolo[3,4-b]pyridine-5-carboxylic acid (90 mg, yield: 75%) as a white solid.

Step 2:

This step was similar to 3,4-Dichloro-1-(tetrahydro-pyran-4-yl)-1H-pyrazolo[3,4-b]pyridine-5-carboxylic acid (4-trifluoromethyl-phenyl)-amide (Example 214).

$^1$HNMR (400 MHz, CDCl3): δ=9.64 (brs, 1H), 9.28 (s, 1H), 7.82 (d, J=8.8 Hz, 2H), 7.65 (d, J=8.4 Hz, 2H), 5.15-5.11 (m, 1H), 4.33 (s, 3H), 4.18-4.14 (m, 2H), 3.66-3.60 (m, 2H), 2.41-2.37 (m, 2H), 1.99-1.95 (m, 2H). MS: m/z 453.1 (M+H$^+$)

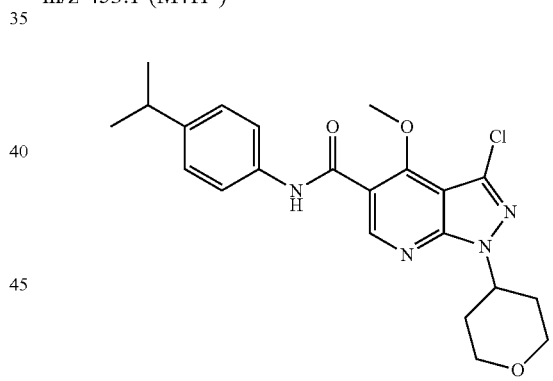

Example 218

3-Chloro-4-methoxy-1-(tetrahydro-pyran-4-yl)-1H-pyrazolo[3,4-b]pyridine-5-carboxylic acid (4-isopropyl-phenyl)-amide The title compound was prepared using general procedure for 3-chloro-4-methoxy-1-(tetrahydro-pyran-4-yl)-1H-pyrazolo[3,4-b]pyridine-5-carboxylic acid (4-trifluoromethyl-phenyl)-amide (Example 217).

$^1$HNMR (400 MHz, CDCl$_3$): δ=9.35 (brs, 1H), 9.27 (s, 1H), 7.60 (d, J=8.4 Hz, 2H), 7.26 (overlap, 2H), 5.16-5.10 (m, 1H), 4.28 (s, 3H), 4.17-4.14 (m, 2H), 3.65 (t, J=12.0 Hz, 2H), 2.94-2.90 (m, 1H), 2.44-2.34 (m, 2H), 1.99-1.95 (m, 2H), 1.27-1.25 (d, J=6.8 Hz, 6H). MS: m/z 429.2 (M+H$^+$)

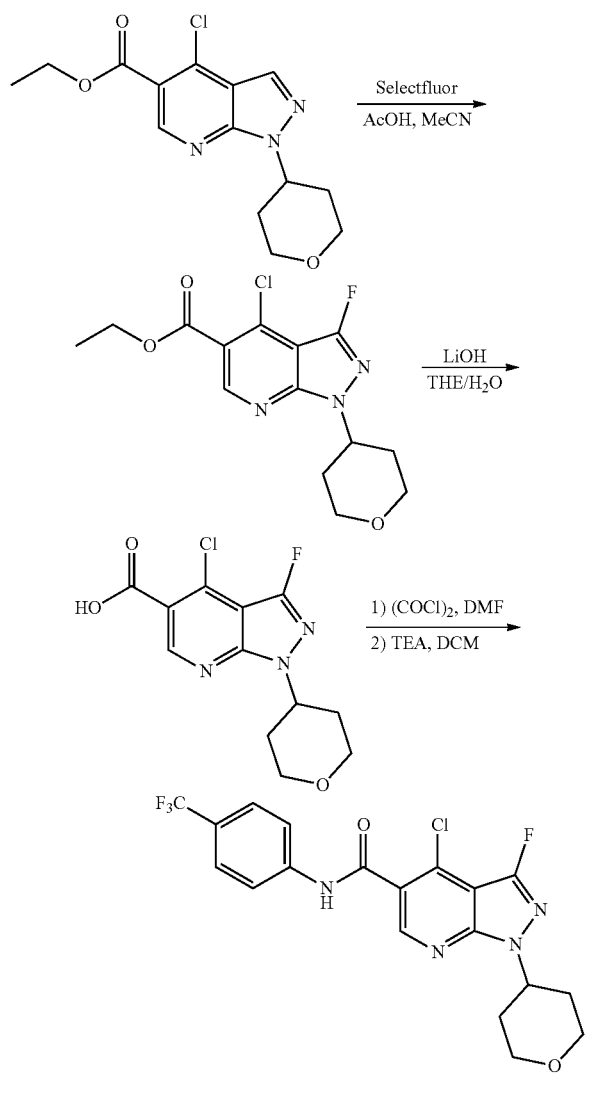

Example 219

4-Chloro-3-fluoro-1-(tetrahydro-pyran-4-yl)-1H-pyrazolo[3,4-b]pyridine-5-carboxylic acid (4-trifluoromethyl-phenyl)-amide Step 1:

To a solution of 4-chloro-1-(tetrahydro-pyran-4-yl)-1H-pyrazolo[3,4-b]pyridine-5-carboxylic acid ethyl ester (800 mg, 2.6 mmol) in MeCN/AcOH (40 mL/0.4 mL), was added selectfluor (2.75 g, 7.8 mmol). The mixture was then stirred at 80° C. for 3 days (additional 2.75 g of selectfluor and 1 mL of AcOH were added everyday). The resultant was poured into water (150 mL) and extracted with EA (100 mL). The organic layer was washed with water (50 mL) and brine (50 mL), dried over $Na_2SO_4$, concentrated and purified by prep-HPLC to give 4-chloro-3-fluoro-1-(tetrahydro-pyran-4-yl)-1H-pyrazolo[3,4-b]pyridine-5-carboxylic acid ethyl ester (130 mg, yield: 15%) as a white solid.

$^1$HNMR (400 MHz, CDCl$_3$): δ=8.99 (s, 1H), 5.07-5.01 (m, 1H), 4.46 (q, J=7.2 Hz, 2H), 4.16-4.11 (m, 2H), 3.64-3.58 (m, 2H), 2.38-2.25 (m, 2H), 1.94-1.90 (m, 2H), 1.44 (t, J=7.2 Hz, 2H). MS: m/z 327.9 (M+H$^+$).

Step 2-3:

These two steps were similar to 3,4-dichloro-1-(tetrahydro-pyran-4-yl)-1H-pyrazolo[3,4-b]pyridine-5-carboxylic acid (4-trifluoromethyl-phenyl)-amide (Example 214).

$^1$HNMR (400 MHz, CDCl$_3$): δ=8.91 (s, 1H), 8.19 (brs, 1H), 7.79 (d, J=8.4 Hz, 2H), 7.67 (d, J=8.4 Hz, 2H), 5.10-5.04 (m, 1H), 4.17-4.13 (m, 2H), 3.65-3.58 (m, 2H), 2.38-2.28 (m, 2H), 1.95-1.92 (m, 2H). MS: m/z 441.1 (M+H$^+$).

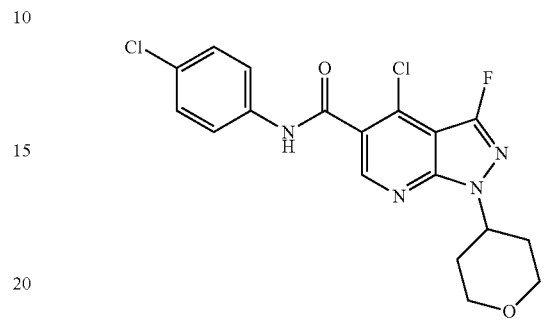

Example 220

4-Chloro-3-fluoro-1-(tetrahydro-pyran-4-yl)-1H-pyrazolo[3,4-b]pyridine-5-carboxylic acid (4-chloro-phenyl)-amide The title compound was prepared using general procedure for 4-chloro-3-fluoro-1-(tetrahydro-pyran-4-yl)-1H-pyrazolo[3,4-b]pyridine-5-carboxylic acid (4-trifluoromethyl-phenyl)-amide (Example 219).

$^1$HNMR (300 MHz, DMSO-d6): δ=10.82 (brs, 1H), 8.64 (s, 1H), 7.75 (d, J=9.0 Hz, 2H), 7.46-7.42 (m, 2H), 5.11-5.07 (m, 1H), 4.03-3.97 (m, 2H), 3.60-3.52 (m, 2H), 2.15-2.03 (m, 2H), 1.93-1.89 (m, 2H). MS: m/z 409.0 (M+H$^+$)

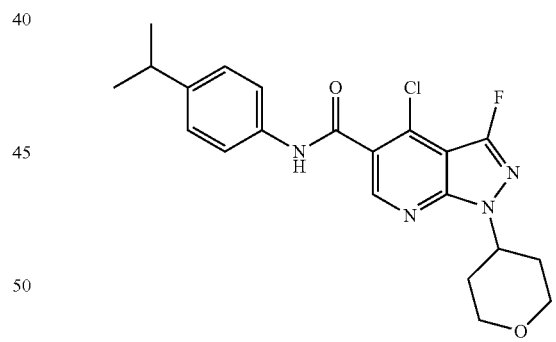

Example 221

4-Chloro-3-fluoro-1-(tetrahydro-pyran-4-yl)-1H-pyrazolo[3,4-b]pyridine-5-carboxylic acid (4-isopropyl-phenyl)-amide The title compound was prepared using general procedure for 4-chloro-3-fluoro-1-(tetrahydro-pyran-4-yl)-1H-pyrazolo[3,4-b]pyridine-5-carboxylic acid (4-trifluoromethyl-phenyl)-amide (Example 219).

$^1$HNMR (400 MHz, CDCl$_3$): δ=8.90 (s, 1H), 7.94 (brs, 1H), 7.57 (d, J=8.4 Hz, 2H), 7.26 (overlap, 2H), 5.09-5.03 (m, 1H), 4.16-4.13 (m, 2H), 3.64-3.58 (m, 2H), 2.94-2.91

(m, 1H), 2.38-2.28 (m, 2H), 1.95-1.91 (m, 2H), 1.27-1.25 (d, J=6.4 Hz, 6H). MS: m/z 417.1 (M+H⁺)

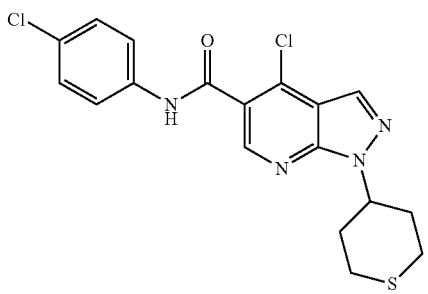 [SMILES: O=C(Nc1ccc(Cl)cc1)c1cnc2c(cnn2C2CCSCC2)c1Cl]

Example 222

4-chloro-N-(4-chlorophenyl)-1-(tetrahydro-2H-thiopyran-4-yl)-1H-pyrazolo[3,4-b]pyridine-5-carboxamide The title compound was prepared using general procedure for 4-chloro-N-(4-chlorophenyl)-1-(1-isopropylpiperidin-4-yl)-1H-pyrazolo[3,4-b]pyridine-5-carboxamide (Example 203).

¹HNMR (300 MHz, DMSO-d6): δ=10.82 (d, J=4.5, 1H), 8.77 (s, 1H), 8.44 (s, 1H), 7.75 (d, J=9.0, 2H), 7.44 (d, J=8.7, 2H), 4.97-4.92 (m, 1H), 3.01-2.99 (m, 2H), 2.81-2.76 (m, 2H), 2.30-2.22 (m, 4H); MS: m/z 407.1 (M+H⁺).

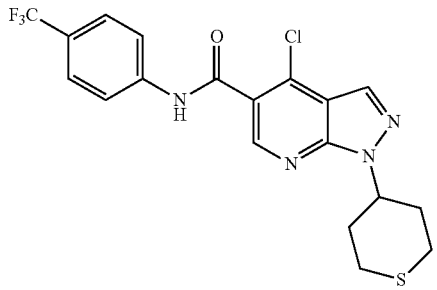

Example 223

4-chloro-1-(tetrahydro-2H-thiopyran-4-yl)-N-(4-(trifluoromethyl)phenyl)-1H-pyrazolo[3,4-b]pyridine-5-carboxamide The title compound was prepared using general procedure for 4-chloro-N-(4-chlorophenyl)-1-(1-isopropylpiperidin-4-yl)-1H-pyrazolo[3,4-b]pyridine-5-carboxamide (Example 203).

¹HNMR (300 MHz, DMSO-d6): δ=11.04 (s, 1H), 8.80 (s, 1H), 8.45 (s, 1H), 7.92 (d, J=9.0, 2H), 7.81 (d, J=8.7, 2H), 5.00-5.91 (m, 1H), 3.01-2.91 (m, 2H), 2.79-2.73 (m, 2H), 2.31-2.26 (m, 4H); MS: m/z 441.1 (M+H⁺).

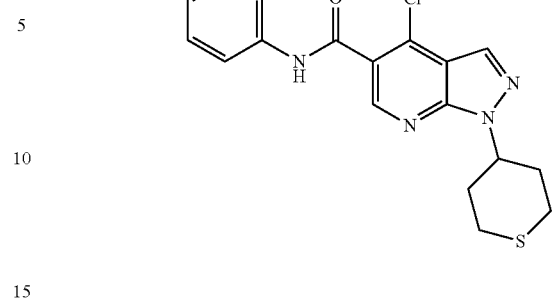

Example 224

4-chloro-N-(4-isopropylphenyl)-1-(tetrahydro-2H-thiopyran-4-yl)-1H-pyrazolo[3,4-b]pyridine-5-carboxamide The title compound was prepared using general procedure for 4-chloro-N-(4-chlorophenyl)-1-(1-isopropylpiperidin-4-yl)-1H-pyrazolo[3,4-b]pyridine-5-carboxamide (Example 203).

¹HNMR (300 MHz, DMSO-d6): δ=10.57 (s, 1H), 8.74 (s, 1H), 8.43 (s, 1H), 7.63 (d, J=8.4, 2H), 7.24 (d, J=7.6, 2H), 4.98-4.92 (m, 1H), 3.00-2.76 (m, 5H), 2.33-2.22 (m, 4H), 1.20 (d, J=7.2, 6H); MS: m/z 415.1 (M+H⁺).

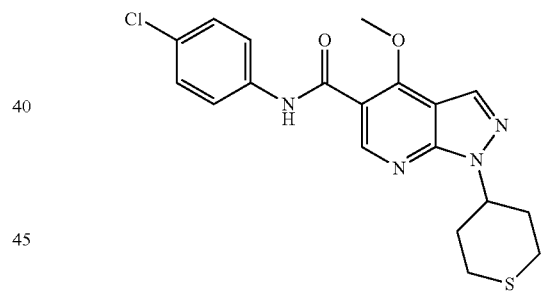

Example 225

N-(4-chlorophenyl)-4-methoxy-1-(tetrahydro-2H-thiopyran-4-yl)-1H-pyrazolo[3,4-b]pyridine-5-carboxamide This product was got as a byproduct along with 4-chloro-N-(4-chlorophenyl)-1-(tetrahydro-2H-thiopyran-4-yl)-1H-pyrazolo[3,4-b]pyridine-5-carboxamide (Example 222) because of the contact with MeOH during workup. ¹HNMR (300 MHz, DMSO-d6): δ=10.22 (s, 1H), 8.62 (s, 1H), 8.59 (s, 1H), 7.76 (d, J=9.3, 2H), 7.41 (d, J=9.0, 2H), 4.95-4.89 (m, 1H), 4.43 (s, 3H), 2.99-2.88 (m, 2H), 2.79-2.72 (m, 2H), 2.30-2.18 (m, 4H); MS: m/z 403.1 (M+H⁺).

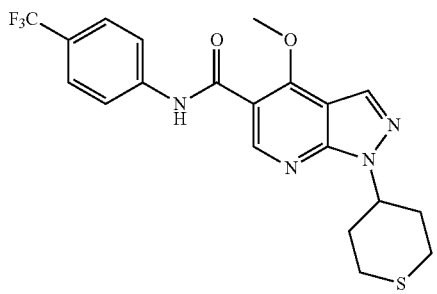 [SMILES: COc1c(C(=O)Nc2ccc(C(F)(F)F)cc2)cnc2c1cnn2C1CCSCC1]

Example 226

4-methoxy-1-(tetrahydro-2H-thiopyran-4-yl)-N-(4-(trifluoromethyl)phenyl)-1H-pyrazolo[3,4-b]pyridine-5-carboxamide This product was got as a byproduct along with 4-chloro-1-(tetrahydro-2H-thiopyran-4-yl)-N-(4-(trifluoromethyl)phenyl)-1H-pyrazolo[3,4-b]pyridine-5-carboxamide (Example 223) because of the contact with MeOH during workup. $^1$HNMR (300 MHz, DMSO-d6): δ=10.45 (s, 1H), 8.63 (s, 1H), 8.60 (s, 1H), 7.94 (d, J=8.1, 2H), 7.72 (d, J=9.3, 2H), 4.90 (brs, 1H), 4.43 (s, 3H), 3.00-2.90 (m, 2H), 2.79-2.72 (m, 2H), 2.28-2.18 (m, 4H); MS: m/z 437.1 (M+H$^+$).

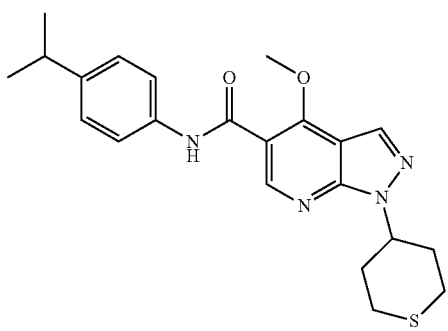 [SMILES: COc1c(C(=O)Nc2ccc(C(C)C)cc2)cnc2c1cnn2C1CCSCC1]

Example 227

N-(4-isopropylphenyl)-4-methoxy-1-(tetrahydro-2H-thiopyran-4-yl)-1H-pyrazolo[3,4-b]pyridine-5-carboxamide This product was got as a byproduct along with 4-chloro-N-(4-isopropylphenyl)-1-(tetrahydro-2H-thiopyran-4-yl)-1H-pyrazolo[3,4-b]pyridine-5-carboxamide (Example 224) because of the contact with MeOH during workup. $^1$HNMR (300 MHz, DMSO-d6): δ=10.00 (s, 1H), 8.61 (s, 1H), 8.60 (s, 1H), 7.63 (d, J=8.1, 2H), 7.21 (d, J=8.1, 2H), 4.96-4.86 (m, 1H), 4.43 (s, 3H), 2.95-2.74 (m, 4H), 2.26-2.19 (m, 4H), 1.19 (d, J=6.9, 6H); MS: m/z 411.1 (M+H$^+$).

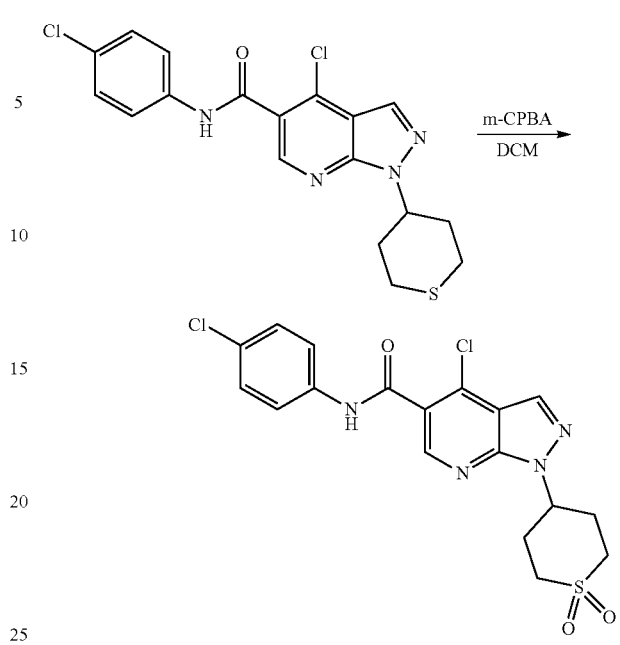

Example 228

4-chloro-N-(4-chlorophenyl)-1-(1,1-dioxidotetrahydro-2H-thiopyran-4-yl)-1H-pyrazolo[3,4-b]pyridine-5-carboxamide To a solution of 4-chloro-N-(4-chlorophenyl)-1-(tetrahydro-2H-thiopyran-4-yl)-1H-pyrazolo[3,4-b]pyridine-5-carboxamide (50 mg, 0.12 mmol) in DCM (20 mL) was added m-CPBA (47 mg, 0.27 mmol), and the mixture was stirred at room temperature overnight. The reactant was concentrated to dryness in vacuum and the residue was purified by prep-TLC (DCM/MeOH=10/1) to afford 4-chloro-N-(4-chlorophenyl)-1-(1,1-dioxidotetrahydro-2H-thiopyran-4-yl)-1H-pyrazolo[3,4-b]pyridine-5-carboxamide (18 mg, yield: 34%) as a white solid. $^1$HNMR (400 MHz, DMSO-d6): δ=10.84 (s, 1H), 8.80 (s, 1H), 8.48 (s, 1H), 7.76 (d, J=9.2, 2H), 7.45 (d, J=8.8, 2H), 5.37 (m, 1H), 3.60-3.54 (m, 2H), 3.33-3.23 (m, 2H), 2.70-2.61 (m, 2H), 2.32-2.30 (m, 2H); MS: m/z 439.1 (M+H$^+$).

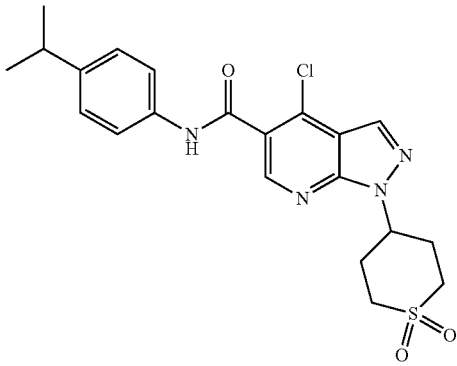 [SMILES: CC(C)c1ccc(NC(=O)c2cnc3c(cnn3C3CCS(=O)(=O)CC3)c2Cl)cc1]

Example 229

4-chloro-1-(1,1-dioxidotetrahydro-2H-thiopyran-4-yl)-N-(4-isopropylphenyl)-1H-pyrazolo[3,4-b]pyridine-5-carboxamide The title compound was prepared using general procedure for 4-chloro-N-(4-chlorophenyl)-1-(1,1-dioxidotetrahydro-2H-thiopyran-4-yl)-1H-pyrazolo[3,4-b]pyridine-5-carboxamide (Example 228).

$^1$HNMR (400 MHz, DMSO-d6): δ=10.58 (s, 1H), 8.77 (s, 1H), 8.47 (s, 1H), 7.63 (d, J=8.4, 2H), 7.24 (d, J=8.4, 2H), 5.40-5.34 (m, 1H), 3.61-3.54 (m, 2H), 3.33-3.23 (m, 2H), 2.91-2.84 (m, 1H), 2.70-2.61 (m, 2H), 2.33-2.30 (m, 2H), 1.20 (d, J=7.2, 6H); MS: m/z 447.1 (M+H$^+$).

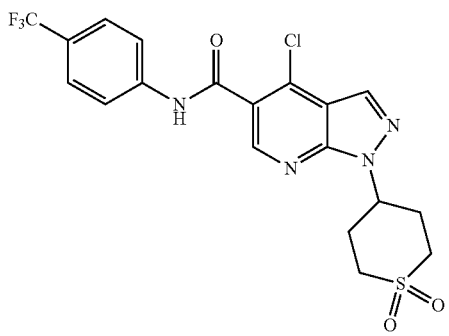 [SMILES: O=C(Nc1ccc(C(F)(F)F)cc1)c1cnc2c(cnn2C2CCS(=O)(=O)CC2)c1Cl]

Example 230

4-chloro-1-(1,1-dioxidotetrahydro-2H-thiopyran-4-yl)-N-(4-(trifluoromethyl)phenyl)-1H-pyrazolo[3,4-b]pyridine-5-carboxamide The title compound was prepared using general procedure for 4-chloro-N-(4-chlorophenyl)-1-(1,1-dioxidotetrahydro-2H-thiopyran-4-yl)-1H-pyrazolo[3,4-b]pyridine-5-carboxamide (Example 228).

$^1$HNMR (400 MHz, DMSO-d6): δ=11.07 (s, 1H), 8.84 (s, 1H), 8.50 (s, 1H), 7.95 (d, J=8.0, 2H), 7.77 (d, J=8.4, 2H), 5.41-5.38 (m, 1H), 3.61-3.55 (m, 2H), 3.27-3.24 (m, 2H), 2.71-2.62 (m, 2H), 2.34-2.31 (m, 2H); MS: m/z 473.1 (M+H$^+$).

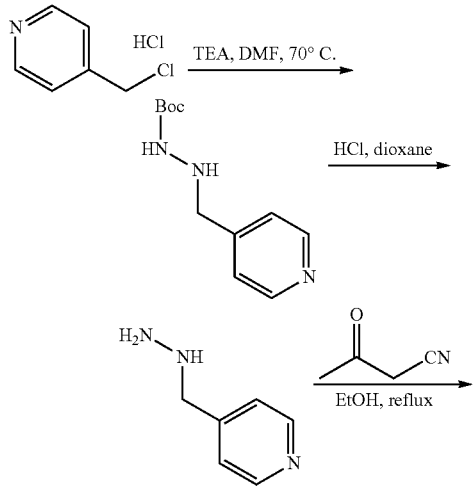

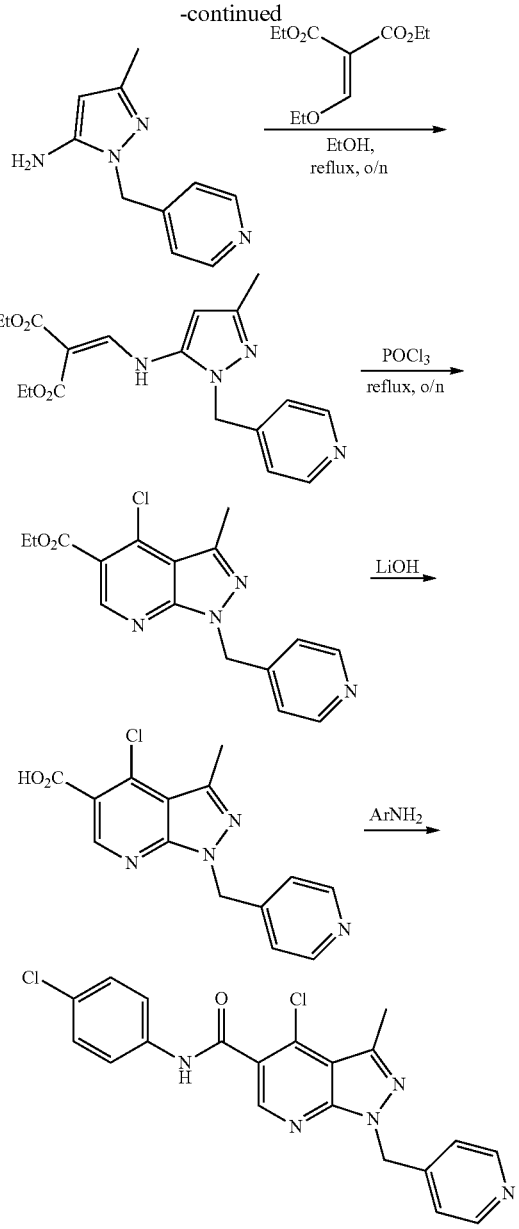

Example 231

4-chloro-N-(4-chlorophenyl)-3-methyl-1-(pyridin-4-ylmethyl)-1H-pyrazolo[3,4-b]pyridine-5-carboxamide To a solution of 4-(chloromethyl)pyridine HCl salt (10 g, 60.9 mmol) in DMF (80 mL) were added TEA (18 g, 182.7 mmol) and tert-butyl hydrazinecarboxylate (41 g, 310.9 mmol). The mixture was stirred at room temperature for 1 h and at 75° C. overnight. The mixture was poured into water and the aqueous phase was extracted with EtOAc (100 mL×2). The extracts were washed with brine (30 mL×5) and dried over Na$_2$SO$_4$. The solution was concentrated to dryness and the crude was purified by silica gel column (PE/EtOAc, 1/1-2/1) to give 4.5 g of crude tert-butyl 2-(pyridin-4-ylmethyl)hydrazinecarboxylate as white solid.

A solution of crude tert-butyl 2-(pyridin-4-ylmethyl)hydrazinecarboxylate (4.5 g crude) in HCl/dioxane (20 mL)

was stirred at room temperature overnight. The resulting solid was collected by filtration to give 6.5 g of crude 4-(hydrazinylmethyl)pyridine HCl salt as white solid. ¹HNMR (400 MHz, CD₃OD): δ=8.67 (d, J=6.0 Hz, 2H), 8.01 (d, J=6.0 Hz, 2H), 4.38 (s, 2H).

To a solution of crude 4-(hydrazinylmethyl)pyridine HCl salt (1.9 g) in EtOH (100 mL) was added 3-oxobutanenitrile (1 g, 11.9 mmol) and the mixture was stirred at gentle reflux overnight. The reaction solution was concentrated in vacuum to give 3 g of crude 3-methyl-1-(pyridin-4-ylmethyl)-1H-pyrazol-5-amine as brown oil.

To a solution of 3-methyl-1-(pyridin-4-ylmethyl)-1H-pyrazol-5-amine (1.8 g crude) in EtOH (50 mL) was added diethyl 2-(ethoxymethylene)malonate (2.4 g, 11.4 mmol) and the mixture was stirred at reflux overnight. The mixture was evaporated to dryness in vacuum and the crude product (2 g) was used for next step without further purification. MS: m/z 359.1 (M+H⁺).

diethyl 2-(((3-methyl-1-(pyridin-4-ylmethyl)-1H-pyrazol-5-yl)amino)methylene)malonate (2 g crude) was dissolved in POCl₃ (30 mL) and the mixture was stirred at 110° C. overnight. The excessive POCl₃ was removed in vacuum. The residue was diluted with DCM (50 mL). The mixture was washed with saturated aqeous NaHCO3, brine and dried over Na₂SO₄. The solution was concentrated to dryness and the residue was purified by silica gel column (PE/EtOAc, 5/1-1/1) to give ethyl 4-chloro-3-methyl-1-(pyridin-4-ylmethyl)-1H-pyrazolo[3,4-b]pyridine-5-carboxylate (130 mg, 5-step yield: 4%) as white solid. MS: m/z 331.1 (M+H⁺).

The hydrolysis and amidation is similar to 4-chloro-3-methyl-1-phenyl-1H-pyrazolo[3,4-b]pyridine-5-carboxylic acid (4-bromo-phenyl)-amide (Example 1).

¹H NMR (400 MHz, DMSO-d6): δ=10.81 (brs, 1H), 8.73 (s, 1H), 8.51 (dd, J=8.4, 1.6 Hz, 2H), 7.75 (dd, J=8.8, 2.0 Hz, 2H), 7.45 (dd, J=8.8, 2.0 Hz, 2H), 7.13 (d, J=6.0 Hz, 2H), 5.72 (s, 2H), 2.71 (s, 3H). MS: m/z 412.0 (M+H⁺).

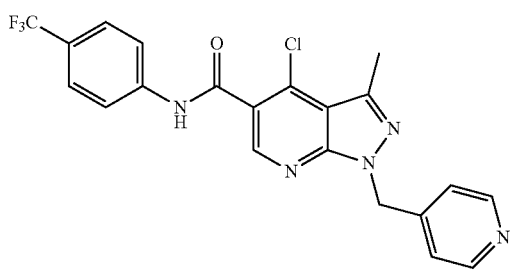 [SMILES: Cc1nn(Cc2ccncc2)c2ncc(C(=O)Nc3ccc(C(F)(F)F)cc3)c(Cl)c12]

Example 232

4-chloro-3-methyl-1-(pyridin-4-ylmethyl)-N-(4-(trifluoromethyl)phenyl)-1H-pyrazolo[3,4-b]pyridine-5-carboxamide The title compound was prepared using general procedure for 4-chloro-N-(4-chlorophenyl)-3-methyl-1-(pyridin-4-ylmethyl)-1H-pyrazolo[3,4-b]pyridine-5-carboxamide (Example 231).

¹H NMR (400 MHz, CDCl₃): δ=8.81 (brs, 1H), 8.49 (d, J=6.0 Hz, 2H), 8.43 (brs, 1H), 7.80 (d, J=8.8 Hz, 2H), 7.66 (d, J=8.4 Hz, 2H), 7.13 (d, J=5.6 Hz, 2H), 5.64 (s, 2H), 2.77 (s, 3H). MS: m/z 446.0 (M+H⁺).

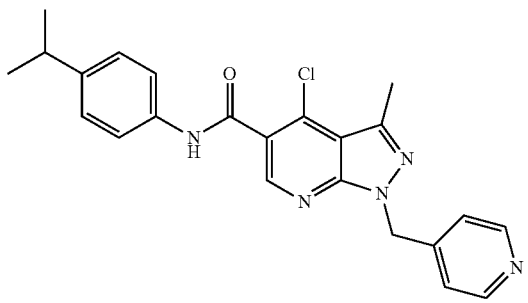 [SMILES: Cc1nn(Cc2ccncc2)c2ncc(C(=O)Nc3ccc(C(C)C)cc3)c(Cl)c12]

Example 233

4-chloro-N-(4-isopropylphenyl)-3-methyl-1-(pyridin-4-ylmethyl)-1H-pyrazolo[3,4-b]pyridine-5-carboxamide The title compound was prepared using general procedure for 4-chloro-N-(4-chlorophenyl)-3-methyl-1-(pyridin-4-ylmethyl)-1H-pyrazolo[3,4-b]pyridine-5-carboxamide (Example 231). ¹H NMR (400 MHz, CDCl3): δ=8.73 (s, 1H), 8.57 (brs, 1H), 8.43 (dd, J=4.4 Hz, 2H), 7.58 (d, J=8.4 Hz, 2H), 7.26 (overlap, 2H), 7.08 (d, J=6.0 Hz, 2H), 5.61 (s, 2H), 2.95-2.89 (m, 1H), 2.73 (s, 3H), 1.27-1.25 (m, 6H). MS: m/z 420.1 (M+H⁺).

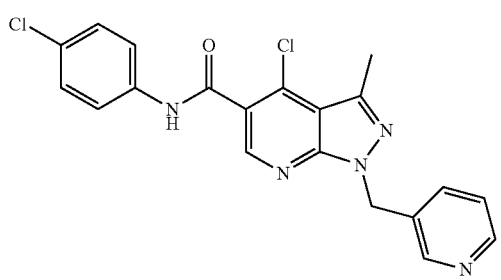 [SMILES: Cc1nn(Cc2cccnc2)c2ncc(C(=O)Nc3ccc(Cl)cc3)c(Cl)c12]

Example 234

4-Chloro-3-methyl-1-pyridin-2-ylmethyl-1H-pyrazolo[3,4-b]pyridine-5-carboxylic acid (4-chlorophenyl)-amide The title compound was prepared using general procedure for 4-chloro-N-(4-chlorophenyl)-3-methyl-1-(pyridin-4-ylmethyl)-1H-pyrazolo[3,4-b]pyridine-5-carboxamide (Example 231).

¹HNMR (400 MHz, CDCl₃): δ=8.78-8.74 (m, 3H), 8.30-8.28 (m, 2H), 7.80-7.76 (m, 1H), 7.63 (d, J=8.4 Hz, 2H), 7.36 (d, J=8.7 Hz, 2H), 5.83 (s, 2H), 2.75 (s, 3H). MS: m/z 412.0 (M+H⁺).

499

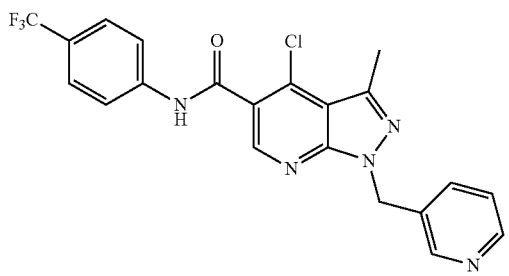 [SMILES: Cc1nn(Cc2cccnc2)c2ncc(C(=O)Nc3ccc(C(F)(F)F)cc3)c(Cl)c12]

Example 235

4-Chloro-3-methyl-1-pyridin-3-ylmethyl-1H-pyrazolo[3,4-b]pyridine-5-carboxylic acid (4-trifluoromethyl-phenyl)-amide The title compound was prepared using general procedure for 4-chloro-N-(4-chlorophenyl)-3-methyl-1-(pyridin-4-ylmethyl)-1H-pyrazolo[3,4-b]pyridine-5-carboxamide (Example 231).

$^1$HNMR (400 MHz, CDCl$_3$): δ=8.77-8.74 (m, 3H), 8.41 (brs, 1H), 8.32 (d, J=8.0 Hz, 1H), 7.82-7.78 (m, 3H), 7.65 (d, J=8.4 Hz, 2H), 5.80 (s, 2H), 2.75 (s, 3H). MS: m/z 446.1 (M+H$^+$).

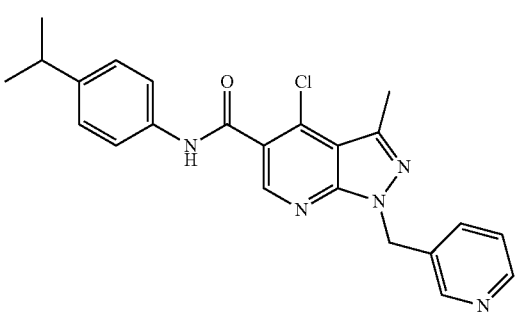 [SMILES: Cc1nn(Cc2cccnc2)c2ncc(C(=O)Nc3ccc(C(C)C)cc3)c(Cl)c12]

Example 236

4-Chloro-3-methyl-1-pyridin-3-ylmethyl-1H-pyrazolo[3,4-b]pyridine-5-carboxylic acid (4-isopropyl-phenyl)-amide The title compound was prepared using general procedure for 4-chloro-N-(4-chlorophenyl)-3-methyl-1-(pyridin-4-ylmethyl)-1H-pyrazolo[3,4-b]pyridine-5-carboxamide (Example 231). $^1$HNMR (400 MHz, CDCl$_3$): δ=8.84 (s, 1H), 8.67 (s, 1H), 8.54 (d, J=4.8 Hz, 1H), 7.85 (s, 1H), 7.67 (d, J=7.2 Hz, 2H), 7.31-7.23 (m, 3H), 5.66 (s, 2H), 3.00-2.94 (m, 1H), 2.77 (s, 3H), 1.27 (d, J=7.2 Hz, 6H). MS: m/z 420.1 (M+H$^+$).

500

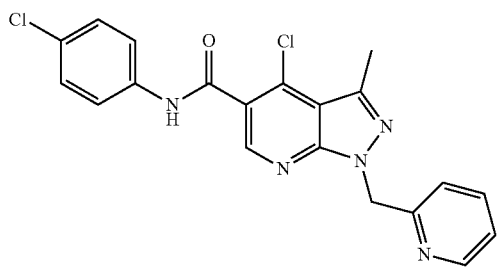 [SMILES: Cc1nn(Cc2ccccn2)c2ncc(C(=O)Nc3ccc(Cl)cc3)c(Cl)c12]

Example 237

4-Chloro-3-methyl-1-pyridin-2-ylmethyl-1H-pyrazolo[3,4-b]pyridine-5-carboxylic acid (4-chlorophenyl)-amide The title compound was prepared using general procedure for 4-chloro-N-(4-chlorophenyl)-3-methyl-1-(pyridin-4-ylmethyl)-1H-pyrazolo[3,4-b]pyridine-5-carboxamide (Example 231).

$^1$HNMR (400 MHz, CDCl$_3$): δ=8.83 (s, 1H), 8.57-8.56 (m,1H), 7.89 (s, 1H), 7.64-7.60 (m, 3H), 7.36 (d, J=8.8 Hz, 2H), 7.21-7.16 (m, 1H), 7.05(d, J=8.0 Hz, 1H), 5.80 (s, 2H), 2.78 (s, 3H). MS: m/z 412.0 (M+H$^+$).

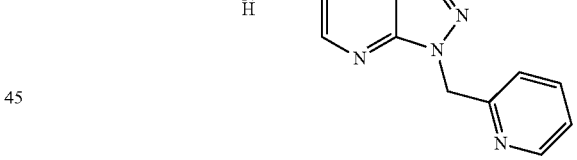

Example 238

4-Chloro-3-methyl-1-(pyridin-2-ylmethyl)-N-(4-(trifluoromethyl)phenyl)-1H-pyrazolo[3,4-b]pyridine-5-carboxamide The title compound was prepared using general procedure for 4-chloro-N-(4-chlorophenyl)-3-methyl-1-(pyridin-4-ylmethyl)-1H-pyrazolo[3,4-b]pyridine-5-carboxamide (Example 231).

$^1$H NMR (400 MHz, CDCl$_3$): δ=8.82 (s, 1H), 8.55 (d, J=4.4 Hz, 1H), 8.17 (s, 1H), 7.79 (d, J=8.8 Hz, 2H), 7.67-7.59 (m, 3H), 7.21-7.16 (m, 1H), 7.07 (d, J=8.4 Hz, 1H), 5.79 (s, 2H), 2.77 (s, 3H). MS: m/z 446.1 (M+H$^+$).

501

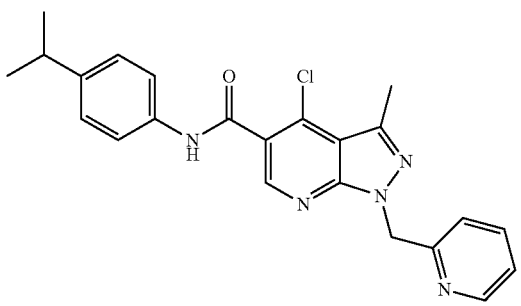 [SMILES: Cc1nn(Cc2ccccn2)c2ncc(C(=O)Nc3ccc(C(C)C)cc3)c(Cl)c12]

Example 239

4-Chloro-N-(4-isopropylphenyl)-3-methyl-1-(pyridin-2-ylmethyl)-1H-pyrazolo[3,4-b]pyridine-5-carboxamide The title compound was prepared using general procedure for 4-chloro-N-(4-chlorophenyl)-3-methyl-1-(pyridin-4-ylmethyl)-1H-pyrazolo[3,4-b]pyridine-5-carboxamide (Example 231). ¹H NMR (300 MHz, CDCl₃): δ=8.84 (s, 1H), 8.67 (s, 1H), 8.56-8.52 (m, 1H), 7.85 (s, 1H), 7.67 (d, J=7.2 Hz, 1H), 7.57 (d, J=8.4 Hz, 2H), 7.30-7.23 (m, 3H), 5.66 (s, 2H), 3.00-2.90 (m, 1H), 2.77 (s, 3H), 1.27 (d, J=7.2 Hz, 6H). MS: m/z 420.1 (M+H⁺).

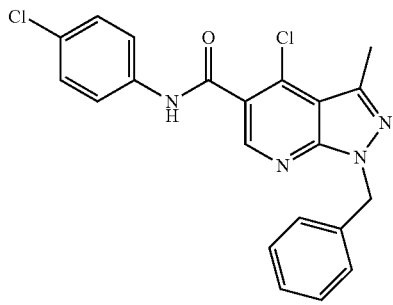 [SMILES: Cc1nn(Cc2ccccc2)c2ncc(C(=O)Nc3ccc(Cl)cc3)c(Cl)c12]

Example 240

1-benzyl-4-chloro-N-(4-chlorophenyl)-3-methyl-1H-pyrazolo[3,4-b]pyridine-5-carboxamide The title compound was prepared using general procedure for 4-chloro-N-(4-chlorophenyl)-3-methyl-1-(pyridin-4-ylmethyl)-1H-pyrazolo[3,4-b]pyridine-5-carboxamide (Example 231).

¹HNMR (300 MHz, DMSO-d6): δ=10.77 (s, 1H), 8.72 (s, 1H), 7.75 (d, J=8.7 Hz, 2H), 7.43 (d, J=8.7 Hz, 2H), 7.33-7.22 (m, 5H), 5.65 (s, 2H), 2.69 (s, 3H). MS: m/z 410.8 (M+H⁺).

502

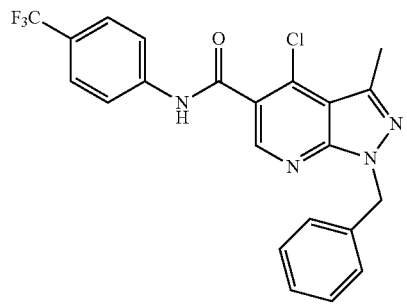 [SMILES: Cc1nn(Cc2ccccc2)c2ncc(C(=O)Nc3ccc(C(F)(F)F)cc3)c(Cl)c12]

Example 241

1-benzyl-4-chloro-3-methyl-N-(4-(trifluoromethyl)phenyl)-1H-pyrazolo[3,4-b]pyridine-5-carboxamide The title compound was prepared using general procedure for 4-chloro-N-(4-chlorophenyl)-3-methyl-1-(pyridin-4-ylmethyl)-1H-pyrazolo[3,4-b]pyridine-5-carboxamide (Example 231).
¹HNMR (300 MHz, DMSO-d6): δ=11.01 (s, 1H), 8.76 (s, 1H), 7.93 (d, J=8.4 Hz, 2H), 7.75 (d, J=8.7 Hz, 2H), 7.34-7.20 (m, 5H), 5.66 (s, 2H), 2.69 (s, 3H). MS: m/z 445.1 (M+H⁺).

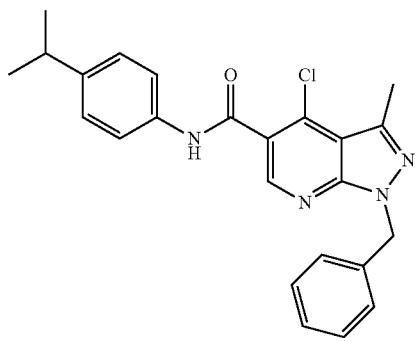 [SMILES: Cc1nn(Cc2ccccc2)c2ncc(C(=O)Nc3ccc(C(C)C)cc3)c(Cl)c12]

Example 242

1-benzyl-4-chloro-N-(4-isopropylphenyl)-3-methyl-1H-pyrazolo[3,4-b]pyridine-5-carboxamide The title compound was prepared using general procedure for 4-chloro-N-(4-chlorophenyl)-3-methyl-1-(pyridin-4-ylmethyl)-1H-pyrazolo[3,4-b]pyridine-5-carboxamide (Example 231).
¹HNMR (300 MHz, DMSO-d6): δ=10.54 (s, 1H), 8.69 (s, 1H), 7.62 (d, J=8.4 Hz, 2H), 7.35-7.20 (m, 7H), 5.65 (s, 2H), 2.75-2.70 (m, 1H), 2.69 (s, 3H), 1.19 (d, J=6.9 Hz, 3H). MS: m/z 417.2 (M-H⁺).

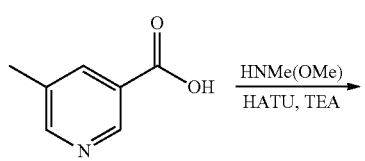

503

-continued

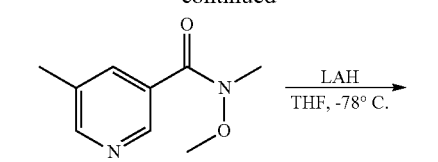

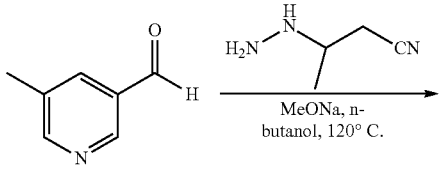

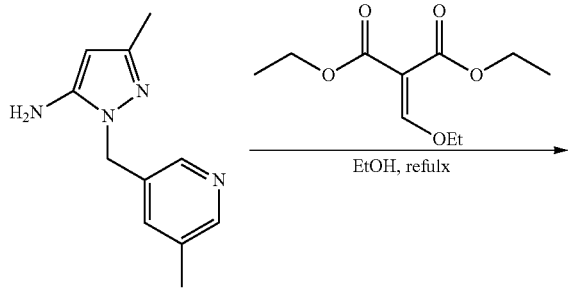

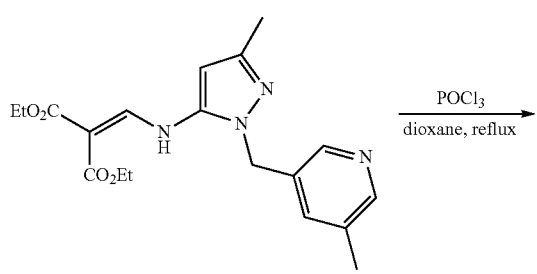

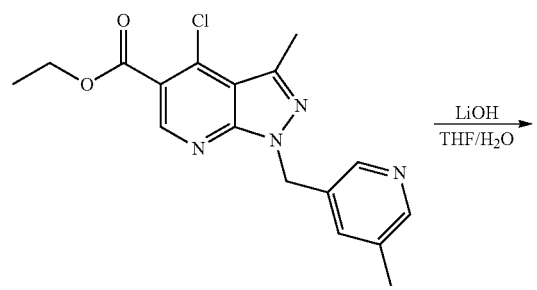

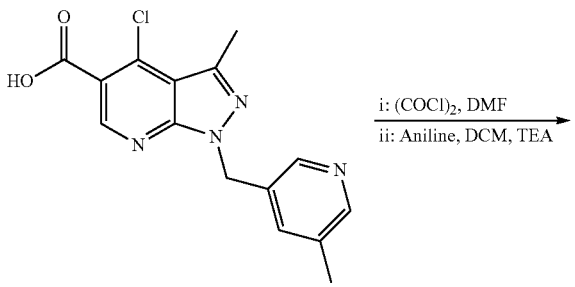

504

-continued

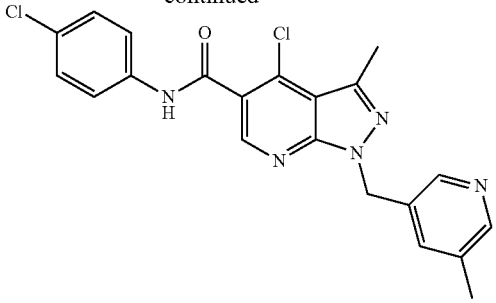

Example 243

4-Chloro-3-methyl-1-(5-methyl-pyridin-3-ylmethyl)-1H-pyrazolo[3,4-b]pyridine-5-carboxylic acid (4-chloro-phenyl)-amide Step 1:

A mixture of 5-methylnicotinic acid (5.0 g, 36.48 mmol), HATU (17.34 g, 45.6 mmol) and DIPEA 14.2 g, 109.44 mmol) in DMF (100 mL) was stirred for 30 min. Then to the reaction mixture was added O, N-Dimethyl-hydroxylamine hydrochloride (5.34 g, 54.72 mmol), and the resulting mixture was stirred at room temperature for 16 hrs. TLC showed the reaction was completed. Then the reaction mixture was poured into ice-water (200 mL), and the mixture was extracted with EtOAc (200 mL×2). The combined organic layers were washed with sat.NaHCO$_3$ (200 mL), 1N HCl (200 mL) and brine (200 mL), and then dried over Na$_2$SO$_4$. The solution was filtered and concentrated to give the desired N-methoxy-N,5-dimethylnicotinamide (6.0 g, 91% yield) as yellow oil.

Step 2:

To a solution of N-methoxy-N,5-dimethylnicotinamide (3.0 g, 16.65 mmol) in THF (50 mL) was added LAH (0.76 g, 19.98 mmol) at −78° C., and the resulting mixture was stirred at −78° C. for 30 mins. TLC showed the reaction was completed. The reaction was quenched with sat.NH$_4$Cl (100 mL), and the mixture was extracted with EtOAc (100 mL×2). The combined organic layers were washed with brine (200 mL), dried over Na$_2$SO$_4$, filtered and concentrated to give the desired 5-methylnicotinaldehyde (2.0 g, yield: 99%) as yellow oil.

$^1$HNMR (400 MHz, CDCl$_3$): δ=10.10 (s, 1H), 8.89 (s, 1H), 8.68 (s, 1H), 7.97 (s, 1H), 2.57 (s, 3H).

Step 3:

To a solution of compound But-3-enenitrile (1.05 g, 15.74 mmol) in THF (30 mL) was added N$_2$H$_4$.H$_2$O (0.826 g, 16.52 mmol) slowly at 0° C., and the resulting mixture was stirred room temperature for 16 hrs. Then to the reaction mixture was added 5-methylnicotinaldehyde (2.0 g, 16.52 mmol). After stirring for 2.5 hrs, the reaction mixture was concentrated to dryness in vacuum. To the residue in n-Butanol (30 mL) was added MeONa (0.85 g, 15.74 mmol), and the mixture was heated to 120° C. for 16 hrs. The reaction mixture was poured into 1N HCl (50 mL), and the mixture was extracted with EtOAc (100 mL×2). The aqueous layer was basified to pH=14 and extracted with EtOAc (100 mL×2). The extracts were dried over Na$_2$SO$_4$, filtered and concentrated to give 3-methyl-1-((5-methylpyridin-3-yl)methyl)-1H-pyrazol-5-amine (0.75 g, yield: 24%) as brown oil.

Step 4:

A mixture of 3-methyl-1-((5-methylpyridin-3-yl)methyl)-1H-pyrazol-5-amine (0.75 g, 3.71 mmol) and diethyl 2-(ethoxymethylene)malonate (0.80 g, 3.71 mmol) in EtOH (20 mL) was heated to reflux for overnight. LCMS showed the reaction was completed. The reaction mixture was concentrated to give the crude diethyl 2-(((3-methyl-1-((5-methylpyridin-3-yl)methyl)-1H-pyrazol-5-yl)amino)methylene)malonate (0.52 g, 38% yield) as brown oil.

Step 5:

A mixture diethyl 2-(((3-methyl-1-((5-methylpyridin-3-yl)methyl)-1H-pyrazol-5-yl)amino)methylene)malonate (0.52 g, 1.40 mmol) and POCl₃ (1.71 g, 11.18 mmol) in dioxane (10 mL) was heated to 100° C. for overnight. LCMS showed the reaction was completed. The reaction mixture was concentrated, and the residue was diluted with sat. NaHCO₃ (50 mL). The mixture was extracted with EtOAc (50 mL×2). The combined organic layers were washed brine (100 mL), dried over Na₂SO₄, filtered and concentrated to give the crude product, which was purified by column chromatography on silica gel (PE/EtOAc=3/1~DCM/EtOAc=3/1) to afford ethyl 4-chloro-3-methyl-1-((5-methylpyridin-3-yl)methyl)-1H-pyrazolo[3,4-b]pyridine-5-carboxylate (0.31 g, 63% yield) as a white solid.

Step 6:

A mixture of ethyl 4-chloro-3-methyl-1-((5-methylpyridin-3-yl)methyl)-1H-pyrazolo[3,4-b]pyridine-5-carboxylate (310 mg, 0.88 mmol) and LiOH.H₂O (150 mg, 3.50 mmol) in THF (12 mL) and water (3 mL) was stirred at room temperature for 4 hrs, TLC showed the reaction was completed. The reaction mixture was diluted with water (30 mL), and adjusted pH to 4. The precipitated solid was collected by filtration, and the filter cake was dried to give the crude acid (110 mg, 40% yield) as a white solid.

Step 7:

To a solution of the acid (50 mg, 0.158 mmol) in oxalyl dichloride (5 mL) was added a drop of DMF, and the reaction mixture was stirred at room temperature for 2 hrs. The reaction mixture was concentrated in vacuum. Then to a mixture of the crude residue in DCM (20 mL) was added 4-chloro-phenylamine (30 mg, 0.237 mmol), followed by TEA (50 mg, 0.475 mmol), and the resulting mixture was stirred room temperature for 2 hrs. The reaction mixture was diluted with sat.NaHCO₃ (50 mL), and the mixture was extracted with DCM (30 mL×3). The combined organic layers were washed with brine (100 mL), dried over Na₂SO₄, filtered and concentrated to give the crude product, which was purified by Prep-HPLC to afford the desired 4-chloro-3-methyl-1-(5-methyl-pyridin-3-ylmethyl)-1H-pyrazolo[3,4-b]pyridine-5-carboxylic acid (4-chloro-phenyl)-amide (Example 243) (35 mg, yield: 52%) as a white solid.

¹HNMR (400 HMz, CDCl₃): δ=8.81 (s, 1H), 8.12-8.05 (m, 2H), 8.01 (s, 1H), 7.62 (d, J=8.4 Hz, 2H), 7.46 (s, 1H), 7.36 (d, J=8.8 Hz, 2H), 5.60 (s, 2H), 2.75 (s, 3H), 2.29 (s, 3H). MS: m/z 426.1 (M+H⁺).

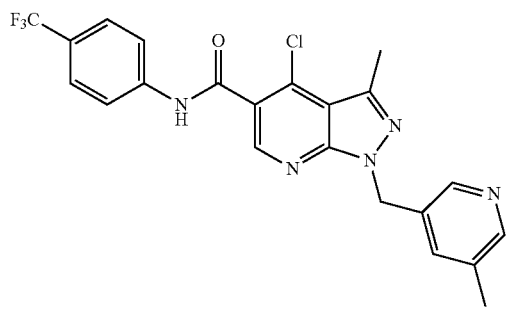 [SMILES: Cc1cncc(Cn2nc(C)c3c(Cl)c(C(=O)Nc4ccc(C(F)(F)F)cc4)cnc32)c1]

Example 244

4-Chloro-3-methyl-1-(5-methyl-pyridin-3-ylmethyl)-1H-pyrazolo[3,4-b]pyridine-5-carboxylic acid (4-trifluoromethyl-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

¹HNMR (400 HMz, CDCl₃): δ=8.83 (s, 1H), 8.10 (s, 1H), 8.16 (s, 1H), 7.80 (d, J=8.0 Hz, 2H), 7.66 (d, J=8.0 Hz, 2H), 7.48 (s, 1H), 5.62 (s, 2H), 2.76 (s, 3H), 2.30 (s, 3H). MS: m/z 460.1 (M+H⁺).

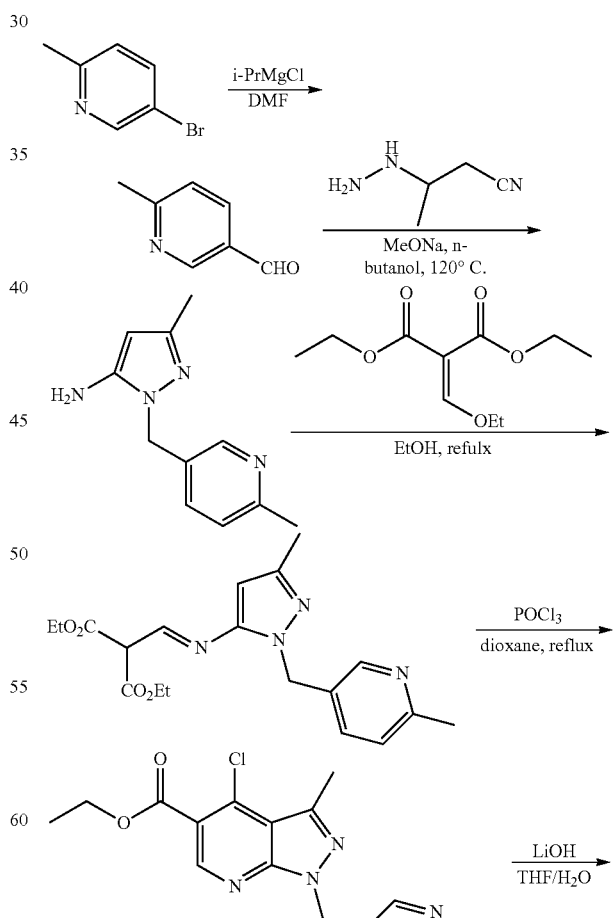

-continued

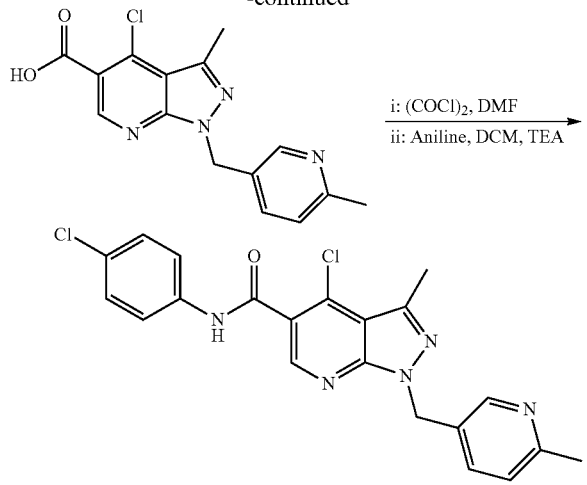

Example 245

4-Chloro-3-methyl-1-(6-methyl-pyridin-3-ylmethyl)-1H-pyrazolo[3,4-b]pyridine-5-carboxylic acid (4-chloro-phenyl)-amide Step 1:
To a solution of 5-bromo-2-methyl-pyridine (2.0 g, 11.6mmol) in anhydrous THF (20 mL) was added isopropylmagnesium chloride (2M in THF, 9.3 mL, 1.6 eq). dropwise over 30 mins at 0° C. under nitrogen atmosphere, then the reaction mixture was stirred at room temperature for 6 hrs. DMF (1.02 g, 1.2 eq) was added to the reation mixture at 0° C. for 30 min, amd the mixture was the stirred at room temperature for overnight. The reaction mixture was poured into water (50 mL), and the aqueous phase was extracted with EtOAc (50 mL×3). The extracts were washed with brine (50 mL), dried over Na$_2$SO$_4$ and concentrated in vacuum to give 4.5 g of crude 6-methyl-pyridine-3-carbaldehyde as yellow oil.

Step 2-6:
Other steps are similar to general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$H NMR (400 MHz, CDCl$_3$): δ=8.77 (s, 1H), 8.52 (d, J=2.4 Hz, 1H), 8.14 (brs, 1H), 7.61 (d, J=8.4 Hz, 2H), 7.56 (dd, J=7.8, 2.2 Hz, 1H), 7.35 (d, J=8.8 Hz, 2H), 7.07 (d, J=8.0 Hz, 1H), 5.58 (s, 2H), 2.73 (s, 3H), 2.50 (s, 3H). MS: m/z 426.0 (M+H$^+$).

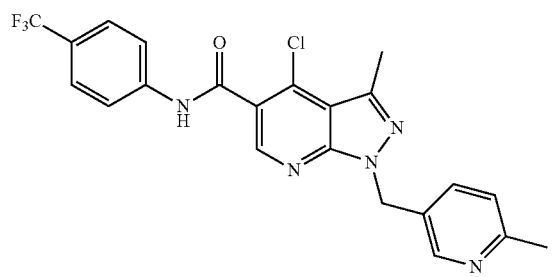 [SMILES: Cc1ccc(Cn2nc(C)c3c(Cl)c(C(=O)Nc4ccc(C(F)(F)F)cc4)cnc32)cn1]

Example 246

4-Chloro-3-methyl-1-(6-methyl-pyridin-3-ylmethyl)-1H-pyrazolo[3,4-b]pyridine-5-carboxylic acid (4-trifluoromethyl-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$H NMR (400 MHz, CDCl$_3$): δ=8.74 (s, 1H), 8.46 (d, J=2.0 Hz, 1H), 8.12 (brs, 1H), 7.72 (d, J=8.4 Hz, 2H), 7.59 (d, J=8.4 Hz, 2H), 7.50 (dd, J=8.0, 2.4 Hz, 1H), 7.02 (d, J=8.0 Hz, 1H), 5.53 (s, 2H), 2.67 (s, 3H), 2.44 (s, 3H). MS: m/z 460.1 (M+H$^+$).

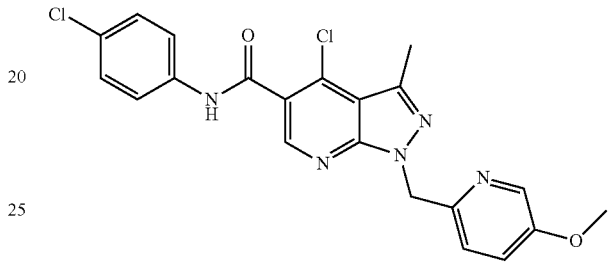

Example 247

4-Chloro-1-(5-methoxy-pyridin-2-ylmethyl)-3-methyl-1H-pyrazolo[3,4-b]pyridine-5-carboxylic acid (4-chloro-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$H NMR (400 MHz, CDCl$_3$): δ=8.75 (s, 1H), 8.17 (s, 1H), 7.90 (brs, 1H), 7.54 (d, J=8.4 Hz, 2H), 7.29 (d, J=8.8 Hz, 2H), 7.05 (s, 2H), 5.65 (s, 2H), 3.75 (s, 3H), 2.69 (s, 3H). MS: m/z 442.0 (M+H$^+$).

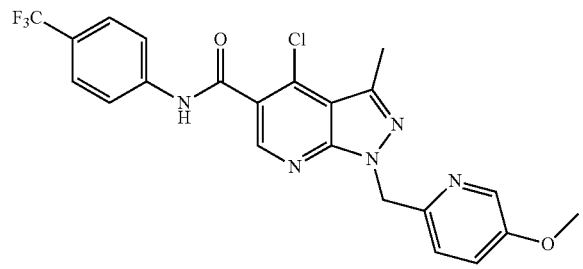 [SMILES: COc1ccc(Cn2nc(C)c3c(Cl)c(C(=O)Nc4ccc(C(F)(F)F)cc4)cnc32)nc1]

Example 248

4-Chloro-1-(5-methoxy-pyridin-2-ylmethyl)-3-methyl-1H-pyrazolo[3,4-b]pyridine-5-carboxylic acid (4-trifluoromethyl-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

¹H NMR (400 MHz, CDCl₃): δ=8.82 (s, 1H), 8.23 (m, 2H), 7.79 (d, J=8.4 Hz, 2H), 7.65 (d, J=8.4 Hz, 2H), 7.12 (d, J=2.0 Hz, 2H), 5.71 (s, 2H), 3.82 (s, 3H), 2.75 (s, 3H). MS: m/z 476.1 (M+H⁺).

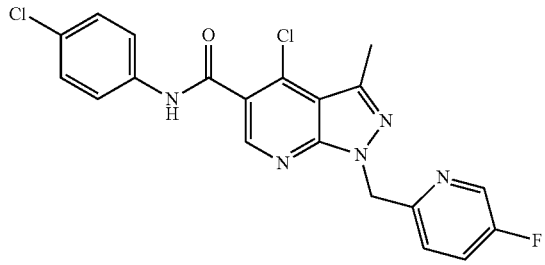 [SMILES: Cc1nn(Cc2ccc(F)cn2)c2ncc(C(=O)Nc3ccc(Cl)cc3)c(Cl)c12]

Example 249

4-Chloro-1-(5-fluoro-pyridin-2-ylmethyl)-3-methyl-1H-pyrazolo[3,4-b]pyridine-5-carboxylic acid (4-chloro-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

¹H NMR (400 MHz, CDCl₃): δ=8.76 (s, 1H), 8.34 (d, J=2.8 Hz, 1H), 7.84 (brs, 1H), 7.54 (d, J=8.4 Hz, 2H), 7.30 (d, J=8.8 Hz, 2H), 7.27-7.24 (m, 1H), 7.10-7.05 (m, 1H), 5.70 (s, 2H), 2.70 (s, 3H). MS: m/z 430.0 (M+H⁺).

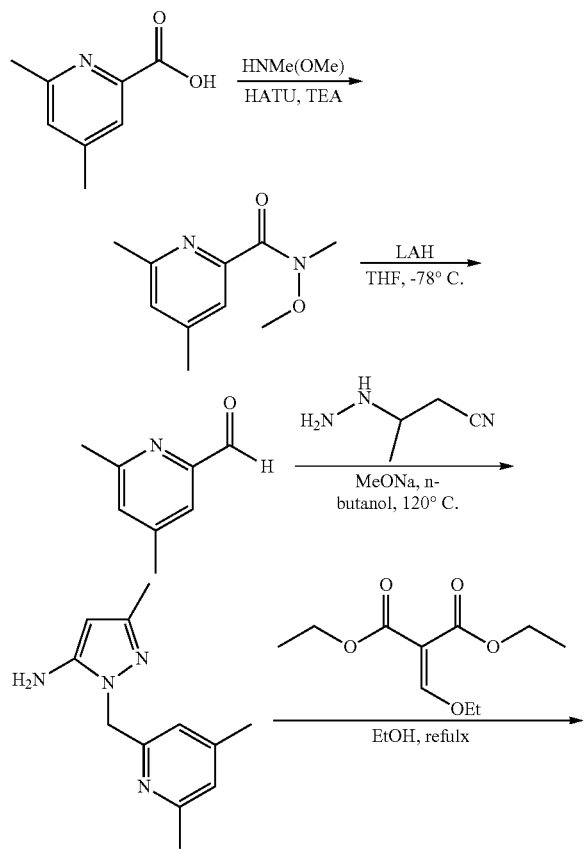

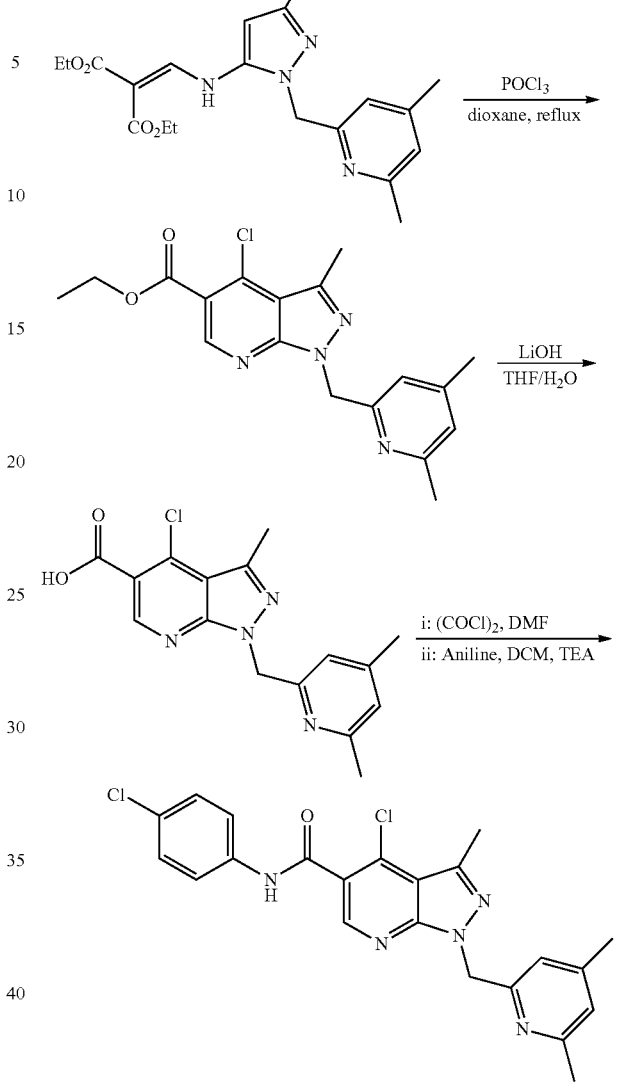

Example 250

4-Chloro-1-(4,6-dimethyl-pyridin-2-ylmethyl)-3-methyl-1H-pyrazolo[3,4-b]pyridine-5-carboxylic acid (4-chloro-phenyl)-amide Step 1:

A mixture of 4,6-dimethyl-pyridine-2-carboxylic acid (2.64 g, 17.46 mmol), HATU (8.3 g, 21.83 mmol) and DIPEA (6.77g, 52.38 mmol) in DMF (50 mL) was stirred at room temperature for 30 mins, then to the reaction mixture was added N,O-dimethylhydroxylamine hydrochloride (2.55 g, 26.20 mmol), and the reaction was stirred at room temperature overnight. The reaction mixture was dilluted with sat. sodium bicarbonate (100 mL), and the mixture was extracted with DCM (50 mL×2). The combined organic layers were washed with brine (50 mL), dried over Na₂SO₄, filtered and concentrated to give crude product, which was purified by silica gel column (PE/EtOAc=1/1) to give 4,6-dimethyl-pyridine-2-carboxylic acid methoxy-methyl-amide (2.73 g, yield: 81%). MS: m/z 195.0 (M+H⁺).

Step 2:

To a solution of 4,6-dimethyl-pyridine-2-carboxylic acid methoxy-methyl-amide (2.73 g, 14.06 mmol) in anhydrous THF (100 mL) was added LAH (0.64 g, 16.87 mmol) at −78° C. under nitrogen atmosphere, then the reaction mixture was stirred at −78° C. for 1 hr. The reaction mixture was quenched with sat. NH$_4$Cl (100 mL), and extracted with EtOAc (50mL×2), The combined organic layers were washed with brine (50 mL), dried over Na$_2$SO$_4$, filtered and concentrated in vacuum to give 4,6-dimethyl-pyridine-2-carbaldehyde (1.72g, yield: 91%) as brown oil.

$^1$HNMR (400 MHz, CDCl$_3$): δ=10.03 (s, 1H), 7.61 (s, 1H), 7.21 (s, 1H), 2.81 (s, 3H), 2.62 (s, 3H).

Step 3-7:

Other steps are similar to the general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$H NMR (400 MHz, CDCl$_3$): δ=8.81 (s, 1H), 8.01 (brs, 1H), 7.62 (d, J=8.8 Hz, 2H), 7.36 (d, J=8.4 Hz, 2H), 6.86 (s, 1H), 6.46 (s, 1H), 5.72 (s, 2H), 2.78 (s, 3H), 2.49 (s, 3H), 2.19 (s, 3H). MS: m/z 440.1 (M+H$^+$).

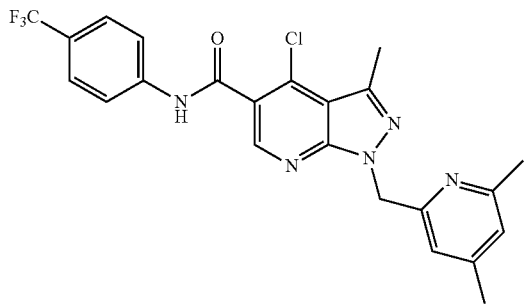 [SMILES: Cc1cc(C)nc(Cn2nc(C)c3c(Cl)c(C(=O)Nc4ccc(C(F)(F)F)cc4)cnc32)c1]

Example 251

4-Chloro-1-(4,6-dimethyl-pyridin-2-ylmethyl)-3-methyl-1H-pyrazolo[3,4-b]pyridine-5-carboxylic acid (4-trifluoromethyl-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 MHz, CDCl$_3$): δ=8.83 (s, 1H), 8.10 (brs, 1H), 7.80 (d, J=8.8 Hz, 2H), 7.66 (d, J=8.8 Hz, 2H), 6.87 (s, 1H), 6.48 (s, 1H), 5.73 (s, 2H), 2.79 (s, 3H), 2.49 (s, 3H), 2.20 (s, 3H). MS: m/z 474.1 (M+H$^+$).

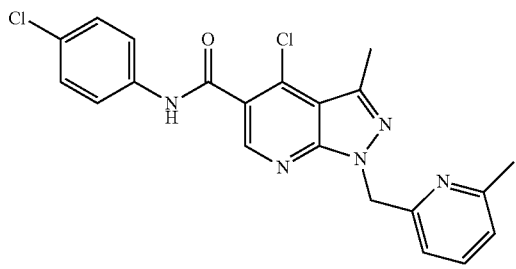 [SMILES: Cc1cccc(Cn2nc(C)c3c(Cl)c(C(=O)Nc4ccc(Cl)cc4)cnc32)n1]

Example 252

4-Chloro-3-methyl-1-(6-methyl-pyridin-2-ylmethyl)-1H-pyrazolo[3,4-b]pyridine-5-carboxylic acid (4-chloro-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243). $^1$H NMR (400 MHz, CDCl$_3$): δ=8.80 (s, 1H), 7.99 (brs, 1H), 7.62 (d, J=8.8 Hz, 2H), 7.45 (t, J=7.6 Hz, 1H), 7.36 (d, J=8.8 Hz, 2H), 7.03 (d, J=7.6 Hz, 1H), 6.65 (d, J=7.6 Hz, 1H), 5.76 (s, 2H), 2.77 (s, 3H), 2.54 (s, 3H). MS: m/z 426.1 (M+H$^+$).

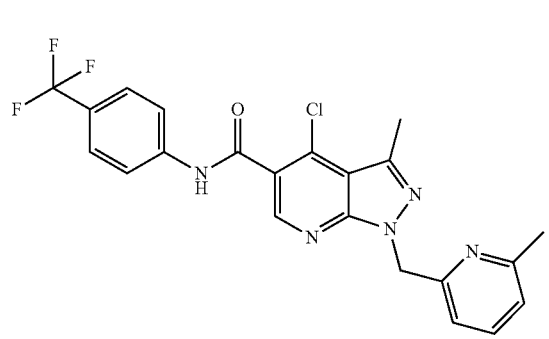 [SMILES: Cc1cccc(Cn2nc(C)c3c(Cl)c(C(=O)Nc4ccc(C(F)(F)F)cc4)cnc32)n1]

Example 253

4-Chloro-3-methyl-1-(6-methyl-pyridin-2-ylmethyl)-1H-pyrazolo[3,4-b]pyridine-5-carboxylic acid (4-trifluoromethyl-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$H NMR (400 MHz, DMSO-d6): δ=11.02 (brs, 1H), 8.73 (s, 1H), 7.94 (d, J=8.4 Hz, 2H), 7.76 (d, J=8.4 Hz, 2H), 7.60 (t, J=7.8 Hz, 1H), 7.16 (d, J=7.6 Hz, 1H), 6.73 (d, J=8.0 Hz, 1H), 5.70 (s, 2H), 2.71 (s, 3H), 2.43(s, 3H). MS: m/z 460.1 (M+H$^+$).

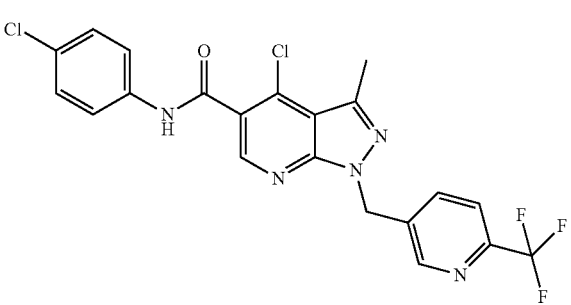 [SMILES: Cc1nn(Cc2ccc(C(F)(F)F)nc2)c2ncc(C(=O)Nc3ccc(Cl)cc3)c(Cl)c12]

Example 254

4-Chloro-3-methyl-1-(6-trifluoromethyl-pyridin-3-ylmethyl)-1H-pyrazolo[3,4-b]pyridine-5-carboxylic acid (4-chloro-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$H NMR (400 MHz, DMSO-d6): δ=10.78 (brs, 1H), 8.75 (s, 1H), 8.73 (s, 1H), 7.88 (d, J=1.6 Hz, 2H), 7.75 (d, J=8.8 Hz, 2H), 7.44 (d, J=8.8 Hz, 2H), 5.84 (s, 2H), 2.70 (s, 3H). MS: m/z 478.1 (M–H$^+$).


Example 255

4-Chloro-3-methyl-1-(6-trifluoromethyl-pyridin-3-ylmethyl)-1H-pyrazolo[3,4-b]pyridine-5-carboxylic acid (4-trifluoromethyl-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 MHz, CDCl$_3$): δ=8.84 (s, 1H), 8.77 (s, 1H), 8.03 (brs, 1H), 7.86 (dd, J=8.4, 1.6 Hz, 1H), 7.79 (d, J=8.8 Hz, 2H), 7.69-7.62 (m, 3H), 5.72 (s, 2H), 2.76 (s, 3H). MS: m/z 512.1 (M–H$^+$).

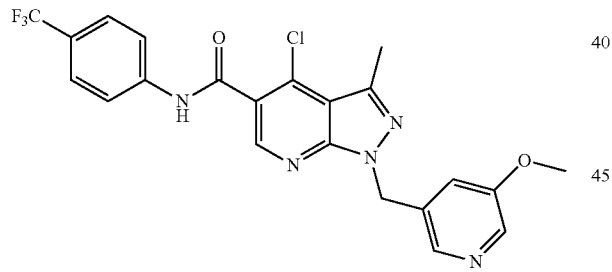

Example 256

4-Chloro-1-(5-methoxy-pyridin-3-ylmethyl)-3-methyl-1H-pyrazolo[3,4-b]pyridine-5-carboxylic acid (4-trifluoromethyl-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$H NMR (400 MHz, CDCl$_3$): δ=8.82 (s, 1H), 8.25-8.22 (m, 2H), 8.15 (s, 1H), 7.79 (d, J=9.2 Hz, 2H), 7.66 (d, J=8.0 Hz, 2H), 7.25 (s, 1H), 5.64 (s, 2H), 3.84 (s, 3H), 2.76 (s, 3H). MS: m/z 476.1 (M+H$^+$).

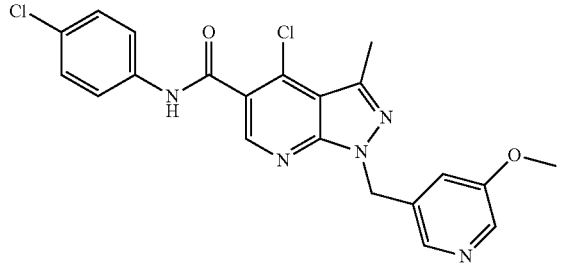 [SMILES: COc1cncc(Cn2nc(C)c3c(Cl)c(C(=O)Nc4ccc(Cl)cc4)cnc32)c1]

Example 257

4-Chloro-1-(5-methoxy-pyridin-3-ylmethyl)-3-methyl-1H-pyrazolo[3,4-b]pyridine-5-carboxylic acid (4-chloro-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$H NMR (400 MHz, CDCl$_3$): δ=8.80 (s, 1H), 8.23 (d, J=1.2 Hz, 1H), 8.21 (d, J=2.4 Hz, 1H), 8.04 (brs, 1H), 7.61 (d, J=8.8 Hz, 2H), 7.36 (d, J=8.8 Hz, 2H), 7.19 (t, J=2.2 Hz, 1H), 5.61 (s, 2H), 3.81 (s, 3H), 2.75 (s, 3H). MS: m/z 442.0 (M+H$^+$).

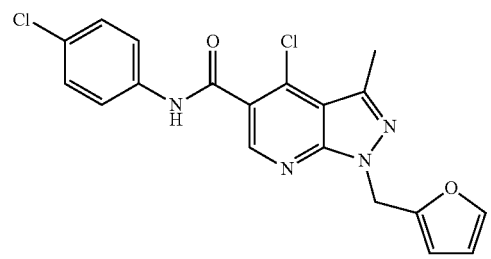 [SMILES: Cc1nn(Cc2ccco2)c2ncc(C(=O)Nc3ccc(Cl)cc3)c(Cl)c12]

Example 258

4-Chloro-1-furan-2-ylmethyl-3-methyl-1H-pyrazolo[3,4-b]pyridine-5-carboxylic acid (4-chloro-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$H NMR (400 MHz, CDCl$_3$): δ=8.85 (s, 1H), 7.87 (s, 1H), 7.62 (d, J=8.0 Hz, 2H), 7.38-7.34 (m, 3H), 6.40-6.39 (m, 1H), 6.32-6.31 (m, 1H), 5.63 (s, 2H), 2.76 (s, 3H),. MS: m/z 399.1 (M–H$^+$).

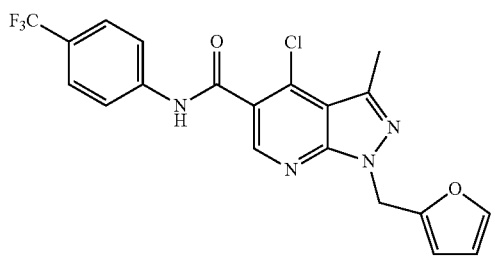 [SMILES: Cc1nn(Cc2ccco2)c2ncc(C(=O)Nc3ccc(C(F)(F)F)cc3)c(Cl)c12]

Example 259

4-Chloro-1-furan-2-ylmethyl-3-methyl-1H-pyrazolo[3,4-b]pyridine-5-carboxylic acid (4-trifluoromethyl-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$H NMR (300 MHz, CDCl$_3$): δ=8.88 (s, 1H), 8.08 (s, 1H), 7.81 (d, J=8.4 Hz, 2H), 7.68 (d, J=8.4 Hz, 2H), 7.36 (m, 1H), 6.43-6.42 (m, 1H), 6.34-6.33 (m, 1H), 5.65 (s, 2H), 2.78 (s, 3H). MS: m/z 435.0 (M+H$^+$).

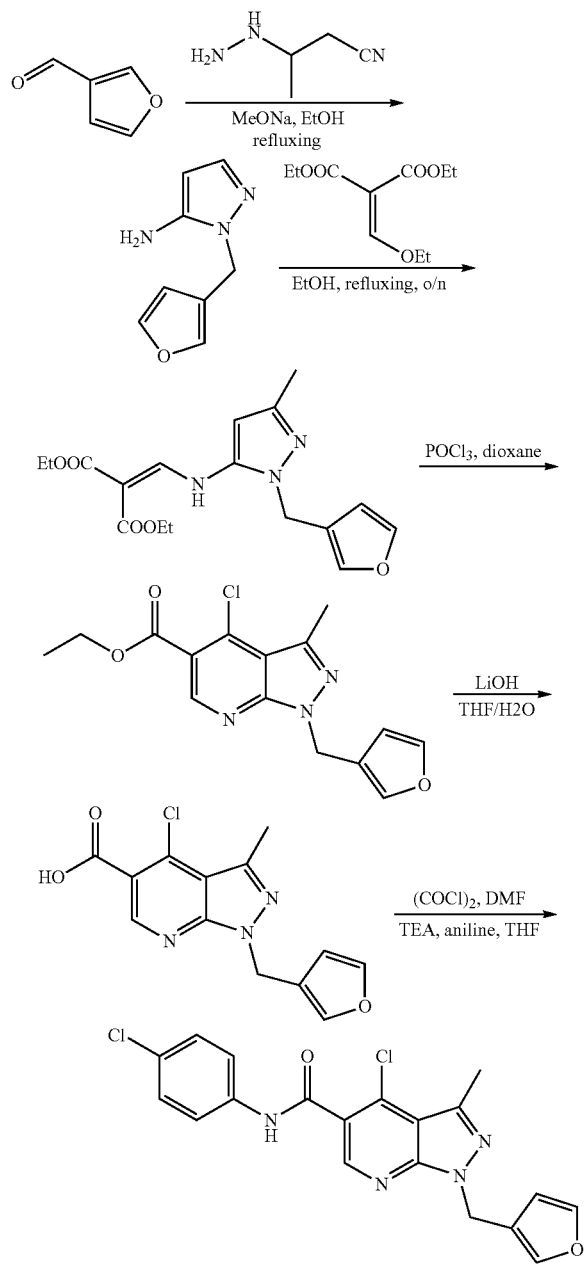

Example 260

4-Chloro-1-furan-3-ylmethyl-3-methyl-1H-pyrazolo[3,4-b]pyridine-5-carboxylic acid (4-chloro-phenyl)-amide Step 1

A solution of furan-3-carbaldehyde (4.0 g, 42.0 mmol) and 3-hydrazino-butyronitrile (4.1 g, 42.0 mmol) in EtOH (100 mL) was stirred at 80° C. for 3 hrs. After cooling to room temperature, the mixture was concentrated and co-evaporated with toluene. The residue was dissolved with EtOH (100 mL) and MeONa (4.5 g, 84.0 mmol) was added. After stirring at 80° C. overnight, the mixture was concentrated to dryness under reduced pressure. The residue was diluted with EtOAc (80 mL), washed with H$_2$O and concentrated to give a crude product of 2-furan-3-ylmethyl-2H-pyrazol-3-ylamine (5.6 g) as brown oil. MS: m/z 178.0 (M+H$^+$).

Step 2

A mixture of 2-furan-3-ylmethyl-2H-pyrazol-3-ylamine (5.6 g, crude, 31.6 mmol) and 2-ethoxymethylene-malonic acid diethyl ester (8.2 g, 38.0 mmol) in EtOH (100 mL) was stirred 90° C. overnight. The mixture was concentrated and the residue was purified by silica gel column (PE/EA=4/1-2/1 to give 2-[(2-furan-3-ylmethyl-5-methyl-2H-pyrazol-3-ylamino)-methylene]-malonic acid diethyl ester (3.2 g, yield: 29%) as a light yellow solid. MS: m/z 347.8 (M+H$^+$)

Step 3

The mixture of 24(2-furan-3-ylmethyl-5-methyl-2H-pyrazol-3-ylamino)-methylenel-malonic acid diethyl ester (3.2 g, 9.2 mmol) in POCl$_3$ (80 mL) was refluxed for 12 hrs. Then, the mixture was concentrated to dryness under reduced pressure. The residue was diluted with EtOAc (80 mL), washed with Na$_2$CO$_3$ (aq, 60 mL) and concentrated to dryness. The residue was purified by silica gel column (PE/EA=10/1-8/1) to give 4-chloro-1-furan-3-ylmethyl-3-methyl-1H-pyrazolo[3,4-b]pyridine-5-carboxylic acid ethyl ester (550 mg, yield: 20%) as a light yellow solid. MS: m/z 320.8 (M+H$^+$).

Step 4

The mixture of 4-chloro-1-furan-3-ylmethyl-3-methyl-1H-pyrazolo[3,4-b]pyridine-5-carboxylic acid ethyl ester (250.0 mg, 0.78 mmol) and LiOH.H$_2$O (132 mg, 3.13 mmol) in THF/H$_2$O (4:1,10 mL) was stirred at room temperature overnight. Then, to the reaction mixture was added HCl (1M) until pH=3. The resulting solid was filtered and the cake was co-evaporated with toluene to give 4-chloro-1-furan-3-ylmethyl-3-methyl-1H-pyrazolo[3,4-b]pyridine-5-carboxylic acid (135.0 mg, yield: 61%) as a white solid. MS: m/z 291.8 (M+H$^+$).

Step 5

A solution of 4-chloro-1-furan-3-ylmethyl-3-methyl-1H-pyrazolo[3,4-b]pyridine-5-carboxylic acid (40.0 mg, 0.14 mmol) in oxalyl chloride (5 mL) was stirred at room temperature for 2 hrs. The mixture was concentrated and co-evaporated with toluene to give the acyl chloride. To a solution of 4-chloro-phenylamine (17.5 mg, 0.14 mmol) and TEA (0.1 mL) in THF (10 mL) was added the solution of the above acyl chloride in THF (1 mL). After stirring for 5 hrs at room temperature, the mixture was concentrated and the residue was purified by prep-HPLC to give 4-chloro-1-furan-3-ylmethyl-3-methyl-1H-pyrazolo[3,4-b]pyridine-5-carboxylic acid (4-chloro-phenyl)-amide (10.0 mg, yield: 18%) as a white solid.

¹HNMR (300 MHz, CDCl₃): δ=8.81 (s, 1H), 8.02 (s, 1H), 7.62 (d, J=8.7 Hz, 2H), 7.51 (s, 1H), 7.38-7.34 (m, 3H), 6.42 (d, J=1.2 Hz, 1H), 5.49 (s, 2H), 2.76(s, 3H). MS: m/z 401.0 (M+H⁺).

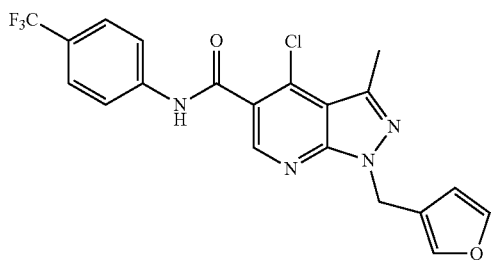 [SMILES: Cc1nn(Cc2ccoc2)c2ncc(C(=O)Nc3ccc(C(F)(F)F)cc3)c(Cl)c12]

Example 261

4-Chloro-1-furan-3-ylmethyl-3-methyl-1H-pyrazolo[3,4-b]pyridine-5-carboxylic acid (4-trifluoromethyl-phenyl)-amide The title compound was prepared using general procedure for 4-chloro-1-furan-3-ylmethyl-3-methyl-1H-pyrazolo[3,4-b]pyridine-5-carboxylic acid (4-chloro-phenyl)-amide (Example 260).

¹HNMR (300 HMz, CDCl₃): δ=8.83 (s, 1H), 8.17 (s, 1H), 7.92 (d, J=8.1 Hz, 2H), 7.67 (d, J=8.4 Hz, 2H), 7.52 (m, 1H), 7.35 (t, J=1.8 Hz, 1H), 6.43-6.42 (m, 1H), 5.50 (s, 2H), 2.77 (s, 3H). MS: m/z 433.1 (M–H⁺).

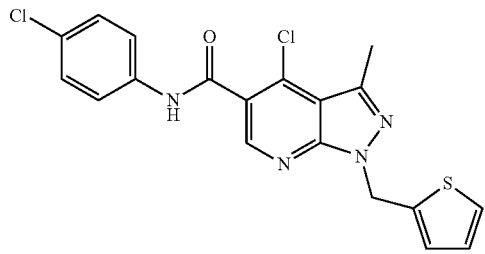

Example 262

4-Chloro-3-methyl-1-thiophen-2-ylmethyl-1H-pyrazolo[3,4-b]pyridine-5-carboxylic acid (4-chloro-phenyl)-amide The title compound was prepared using general procedure for 4-chloro-1-furan-3-ylmethyl-3-methyl-1H-pyrazolo[3,4-b]pyridine-5-carboxylic acid (4-chloro-phenyl)-amide (Example 260).

¹HNMR (400 MHz, DMSO-d6): δ=10.78 (s, 1H), 8.74 (s, 1H), 7.76 (d, J=8.8 Hz, 2H), 7.45-7.42 (m, 3H), 7.14-7.13 (m, 1H), 6.98-6.96 (m, 1H), 5.83 (s, 2H), 2.69 (s, 3H). MS: m/z 415.1 (M–H⁺).

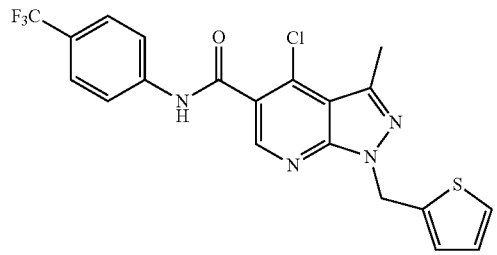 [SMILES: Cc1nn(Cc2cccs2)c2ncc(C(=O)Nc3ccc(C(F)(F)F)cc3)c(Cl)c12]

Example 263

4-chloro-3-methyl-1-thiophen-2-ylmethyl-1H-pyrazolo[3,4-b]pyridine-5-carboxylic acid (4-trifluoromethyl-phenyl)-amide The title compound was prepared using general procedure for 4-chloro-1-furan-3-ylmethyl-3-methyl-1H-pyrazolo[3,4-b]pyridine-5-carboxylic acid (4-chloro-phenyl)-amide (Example 260).

¹HNMR (400 MHz, DMSO-d6): δ=11.01 (s, 1H), 8.77 (s, 1H), 7.94 (d, J=8.4 Hz, 2H), 7.76 (d, J=8.4 Hz, 2H), 7.44-7.42 (m, 1H), 7.14-7.13 (m, 1H), 6.98-6.96 (m, 1H), 5.83 (s, 2H), 2.69 (s, 3H). MS: m/z 449.1 (M–H⁺)

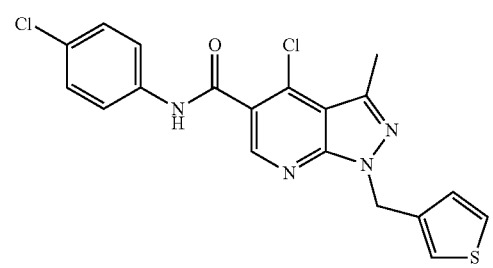 [SMILES: Cc1nn(Cc2ccsc2)c2ncc(C(=O)Nc3ccc(Cl)cc3)c(Cl)c12]

Example 264

4-Chloro-3-methyl-1-thiophen-3-ylmethyl-1H-pyrazolo[3,4-b]pyridine-5-carboxylic acid (4-chloro-phenyl)-amide The title compound was prepared using general procedure for 4-chloro-1-furan-3-ylmethyl-3-methyl-1H-pyrazolo[3,4-b]pyridine-5-carboxylic acid (4-chloro-phenyl)-amide (Example 260).

¹HNMR (400 HMz, CDCl₃): δ=8.82 (s, 1H), 7.93 (s, 1H), 7.61 (d, J=8.8 Hz, 2H), 7.36 (d, J=8.8 Hz, 2H), 7.24 (m, 1H), 7.08 (d, J=5.2Hz, 1H), 5.64 (s, 2H), 2.75(s, 3H). MS: m/z 417.0 (M+H⁺).

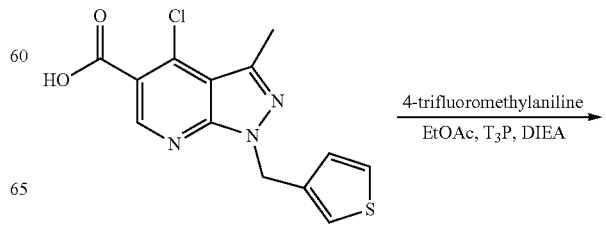

-continued

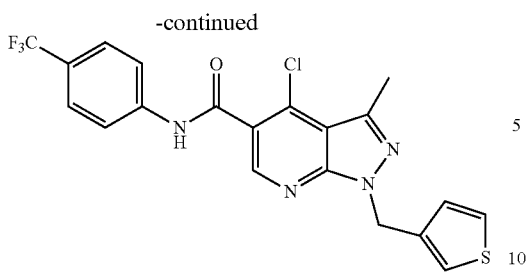

Example 265

4-Chloro-3-methyl-1-thiophen-3-ylmethyl-1H-pyrazolo[3,4-b]pyridine-5-carboxylic acid (4-trifluoromethyl-phenyl)-amide To a suspension of 4-chloro-3-methyl-1-thiophen-3-ylmethyl-1H-pyrazolo[3,4-b]pyridine-5-carboxylic acid (30 mg, 0.1 mmol) and DIEA (39 mg, 0.3 mmol) in EA (0.7 mL), was added $T_3P$ (50% solution in EA, 195 mg, 0.3 mmol). The mixture was stirred at room temperature for about 15 mins till a clear solution formed. To the solution was added 4-trifluoromethyl-phenylamine (19 mg, 0.12 mmol). The reaction was then stirred at room temperature overnight. The reaction solution was partioned between EA (10 mL) and saturated $NaHCO_3$ solution (15 mL). The organic layer was dried over anhydrous $Na_2SO_4$ and concentrated to dryness under reduced pressure. The residue was purified by prep-TLC (PE/EA=2.5/1) to give 4-chloro-3-methyl-1-thiophen-3-ylmethyl-1H-pyrazolo[3,4-b]pyridine-5-carboxylic acid (4-trifluoromethyl-phenyl)-amide (4.5 mg, yield: 10%) as a white solid.

$^1$HNMR (400 HMz, $CDCl_3$): δ=8.84 (s, 1H), 8.07 (brs, 1H), 7.79 (d, J=8.8 Hz, 2H), 7.66 (d, J=8.0 Hz, 2H), 7.26-7.24 (m, 2H), 7.09 (d, J=4.4Hz, 1H), 5.64 (s, 2H), 2.76 (s, 3H). MS: m/z 451.0 (M+H$^+$).

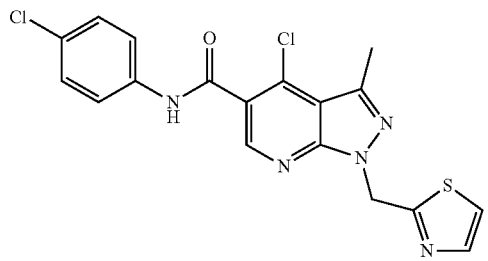 [SMILES: Cc1nn(Cc2nccs2)c2ncc(C(=O)Nc3ccc(Cl)cc3)c(Cl)c12]

Example 266

4-Chloro-3-methyl-1-thiazol-2-ylmethyl-1H-pyrazolo[3,4-b]pyridine-5-carboxylic acid (4-chloro-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 HMz, $CDCl_3$): δ=8.84 (s, 1H), 7.93 (brs, 1H), 7.76 (d, J=3.2 Hz, 1H), 7.61 (d, J=8.4 Hz, 2H), 7.36 (d, J=8.8 Hz, 2H), 7.28 (d, J=3.2 Hz, 1H), 5.98 (s, 2H), 2.73 (s, 3H). MS: m/z 418.0 (M+H$^+$).

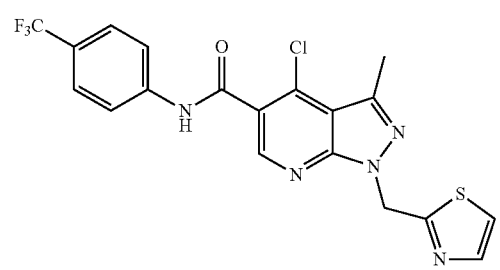 [SMILES: Cc1nn(Cc2nccs2)c2ncc(C(=O)Nc3ccc(C(F)(F)F)cc3)c(Cl)c12]

Example 267

4-Chloro-3-methyl-1-thiazol-2-ylmethyl-1H-pyrazolo[3,4-b]pyridine-5-carboxylic acid (4-trifluoromethyl-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 HMz, $CDCl_3$): δ=8.85 (s, 1H), 8.10 (brs, 1H), 7.80-7.76 (m, 3H), 7.66 (d, J=8.4 Hz, 2H), 7.30 (d, J=3.6 Hz, 1H), 6.00 (s, 2H), 2.79 (s, 3H). MS: m/z 452.0 (M+H$^+$).

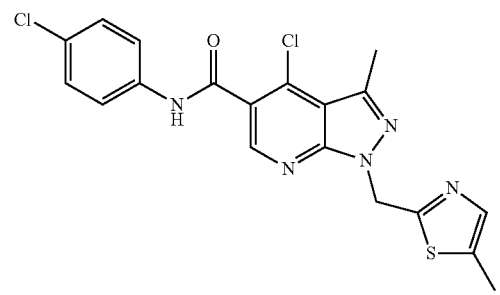 [SMILES: Cc1cnc(Cn2nc(C)c3c(Cl)c(C(=O)Nc4ccc(Cl)cc4)cnc32)s1]

Example 268

4-Chloro-3-methyl-1-(5-methyl-thiazol-2-ylmethyl)-1H-pyrazolo[3,4-b]pyridine-5-carboxylic acid (4-chloro-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 MHz, $CDCl_3$): δ=8.81 (s, 1H), 8.03 (s, 1H), 7.61 (d, J=8.4 Hz, 2H), 7.36-7.34 (m, 3H), 5.86 (s, 2H), 2.76 (s, 3H), 2.40 (s, 3H). MS: m/z 432.0 (M+H$^+$).

521

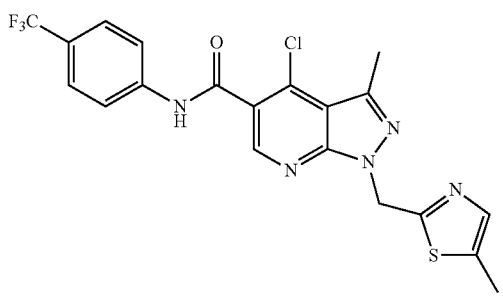 [SMILES: Cc1cnc(Cn2nc(C)c3c(Cl)c(C(=O)Nc4ccc(C(F)(F)F)cc4)cnc32)s1]

Example 269

4-Chloro-3-methyl-1-(5-methyl-thiazol-2-ylmethyl)-1H-pyrazolo[3,4-b]pyridine-5-carboxylic acid (4-trifluoromethyl-phenyl)-amide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 MHz, DMSO-d6): δ=11.03 (s, 1H), 8.77 (s, 1H), 7.94 (d, J=8.0 Hz, 2H), 7.76 (d, J=8.4 Hz, 2H), 7.40 (s, 1H), 5.90 (s, 2H), 2.70 (s, 3H), 2.37 (s, 3H). MS: m/z 466.0 (M+H$^+$).

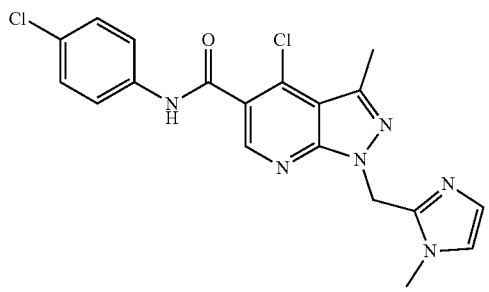 [SMILES: Cc1nn(Cc2nccn2C)c2ncc(C(=O)Nc3ccc(Cl)cc3)c(Cl)c12]

Example 270

4-chloro-N-(4-chlorophenyl)-3-methyl-1-((1-methyl-1H-imidazol-2-yl)methyl)-1H-pyrazolo[3,4-b]pyridine-5-carboxamide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (300 MHz, DMSO-d6): δ=10.79 (s, 1H), 8.72 (s, 1H), 7.76 (d, J=8.7 Hz, 2H), 7.44 (d, J=8.7 Hz, 2H), 7.10 (s, 1H), 6.75 (s, 1H), 5.69 (s, 2H), 3.70 (s, 3H), 2.66 (s, 3H). MS: m/z 415.1 (M+H$^+$).

522

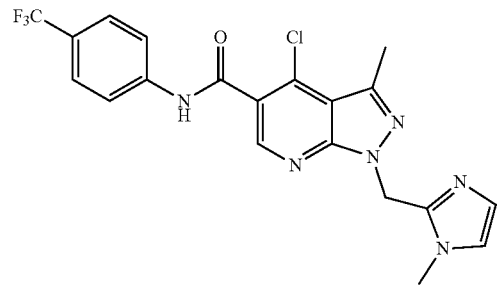 [SMILES: Cc1nn(Cc2nccn2C)c2ncc(C(=O)Nc3ccc(C(F)(F)F)cc3)c(Cl)c12]

Example 271

4-chloro-3-methyl-1-((1-methyl-1H-imidazol-2-yl)methyl)-N-(4-(trifluoromethyl)phenyl)-1H-pyrazolo[3,4-b]pyridine-5-carboxamide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 MHz, DMSO-d6): δ=11.02 (s, 1H), 8.76 (s, 1H), 7.94 (d, J=8.8 Hz, 2H), 7.76 (d, J=8.8 Hz, 2H), 7.11 (s, 1H), 6.76 (s, 1H), 5.71 (s, 2H), 3.76 (s, 3H), 2.72 (s, 3H). MS: m/z 449.1 (M+H$^+$).

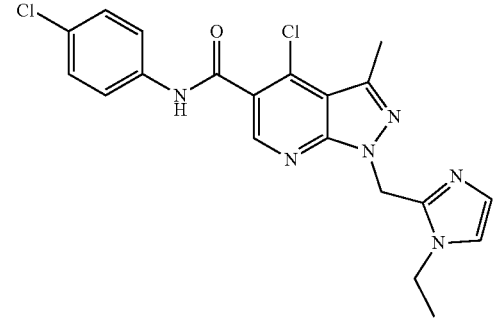 [SMILES: CCn1ccnc1Cn1nc(C)c2c(Cl)c(C(=O)Nc3ccc(Cl)cc3)cnc21]

Example 272

4-chloro-N-(4-chlorophenyl)-1-((1-ethyl-1H-imidazol-2-yl)methyl)-3-methyl-1H-pyrazolo[3,4-b]pyridine-5-carboxamide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 MHz, DMSO-d6): δ=10.79 (s, 1H), 8.72 (s, 1H), 7.76 (d, J=8.8 Hz, 2H), 7.44 (d, J=8.8 Hz, 2H), 7.17 (d, J=0.8 Hz, 1H), 6.78 (d, J=0.8 Hz, 1H), 5.71 (s, 2H), 4.19 (q, J=7.6 Hz, 2H), 2.66 (s, 3H), 1.21 (t, J=7.6 Hz, 3H). MS: m/z 429.1 (M+H$^+$).

523

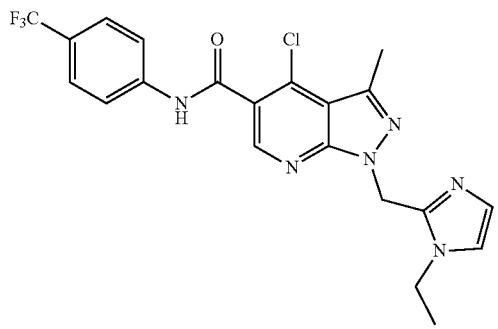 [SMILES: CCn1ccnc1Cn1nc(C)c2c(Cl)c(C(=O)Nc3ccc(C(F)(F)F)cc3)cnc21]

Example 273

4-chloro-1-((1-ethyl-1H-imidazol-2-yl)methyl)-3-methyl-N-(4-(trifluoromethyl)phenyl)-1H-pyrazolo[3,4-b]pyridine-5-carboxamide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 MHz, DMSO-d6): δ=11.02 (s, 1H), 8.76 (s, 1H), 7.94 (d, J=8.4 Hz, 2H), 7.76 (d, J=8.8 Hz, 2H), 7.18 (s, 1H), 6.78 (s, 1H), 5.72 (s, 2H), 4.10 (q, J=7.6 Hz, 2H), 2.67 (s, 3H), 1.21 (t, J=7.2 Hz, 3H). MS: m/z 463.1 (M+H$^+$).

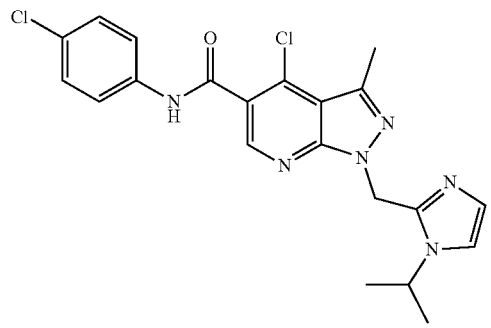 [SMILES: Cc1nn(Cc2nccn2C(C)C)c2ncc(C(=O)Nc3ccc(Cl)cc3)c(Cl)c12]

Example 274

4-chloro-N-(4-chlorophenyl)-1-((1-isopropyl-1H-imidazol-2-yl)methyl)-3-methyl-1H-pyrazolo[3,4-b]pyridine-5-carboxamide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 MHz, DMSO-d6): δ=10.79 (s, 1H), 8.73 (s, 1H), 7.76 (d, J=8.8 Hz, 2H), 7.44 (d, J=8.8 Hz, 2H), 7.29 (d, J=1.2 Hz, 1H), 6.80 (d, J=1.2 Hz, 1H), 5.73 (s, 2H), 4.77-4.74 (m, 1H), 2.66 (s, 3H), 1.29 (d, J=6.8 Hz, 6H). MS: m/z 443.0 (M+H$^+$).

524

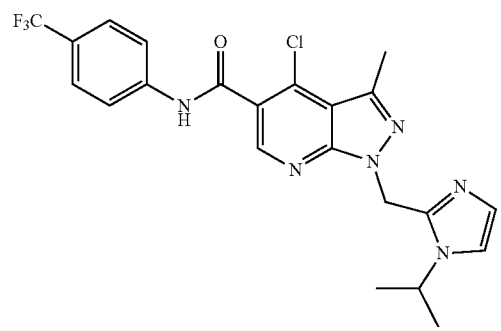 [SMILES: Cc1nn(Cc2nccn2C(C)C)c2ncc(C(=O)Nc3ccc(C(F)(F)F)cc3)c(Cl)c12]

Example 275

4-chloro-1-((1-isopropyl-1H-imidazol-2-yl)methyl)-3-methyl-N-(4-(trifluoromethyl)phenyl)-1H-pyrazolo[3,4-b]pyridine-5-carboxamide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 MHz, DMSO-d6): δ=11.01 (s, 1H), 8.75 (s, 1H), 7.94 (d, J=8.4 Hz, 2H), 7.76 (d, J=8.4 Hz, 2H), 7.29 (s, 1H), 6.80 (s, 1H), 5.73 (s, 2H), 4.77-4.74 (m, 1H), 2.67 (s, 3H), 1.29 (d, J=6.8 Hz, 6H). MS: m/z 477.1 (M+H$^+$).

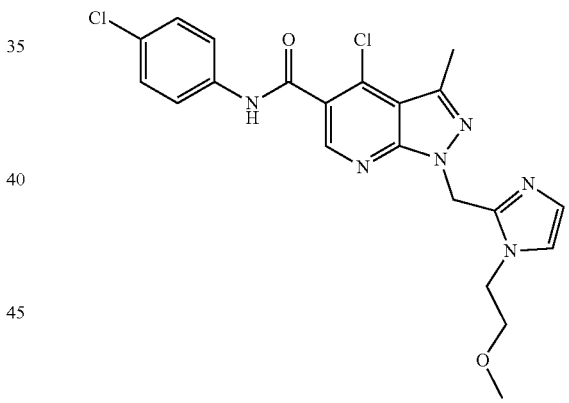

Example 276

4-chloro-N-(4-chlorophenyl)-1-((1-(2-methoxyethyl)-1H-imidazol-2-yl)methyl)-3-methyl-1H-pyrazolo[3,4-b]pyridine-5-carboxamide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 MHz, DMSO-d6): δ=10.79 (s, 1H), 8.72 (s, 1H), 7.76 (d, J=8.4 Hz, 2H), 7.44 (d, J=8.0 Hz, 2H), 7.14 (s, 1H), 6.75 (s, 1H), 5.72 (s, 2H), 4.23 (t, J=5.2 Hz, 2H), 3.54 (t, J=5.2 Hz, 2H), 3.23 (s, 3H), 2.67 (s, 3H). MS: m/z 459.1 (M+H$^+$).

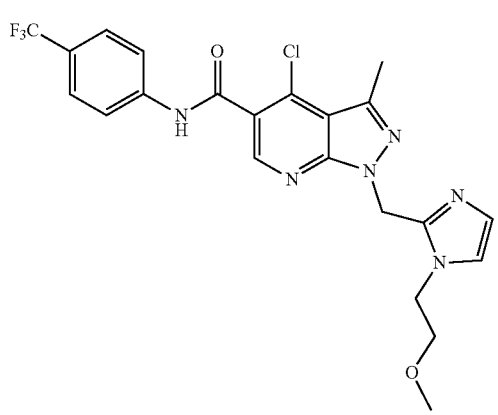 [SMILES: COCCn1ccnc1Cn1nc(C)c2c(Cl)c(C(=O)Nc3ccc(C(F)(F)F)cc3)cnc21]

Example 277

4-chloro-1-((1-(2-methoxyethyl)-1H-imidazol-2-yl)methyl)-3-methyl-N-(4-(trifluoromethyl)phenyl)-1H-pyrazolo[3,4-b]pyridine-5-carboxamide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (400 MHz, DMSO-d6): δ=11.04 (s, 1H), 8.75 (s, 1H), 7.95 (d, J=8.0 Hz, 2H), 7.76 (d, J=8.0 Hz, 2H), 7.16 (s, 1H), 6.79 (s, 1H), 5.74 (s, 2H), 4.29 (t, J=4.8 Hz, 2H), 3.55 (t, J=4.8 Hz, 2H), 3.23 (s, 3H), 2.67 (s, 3H). MS: m/z 493.1 (M+H$^+$).

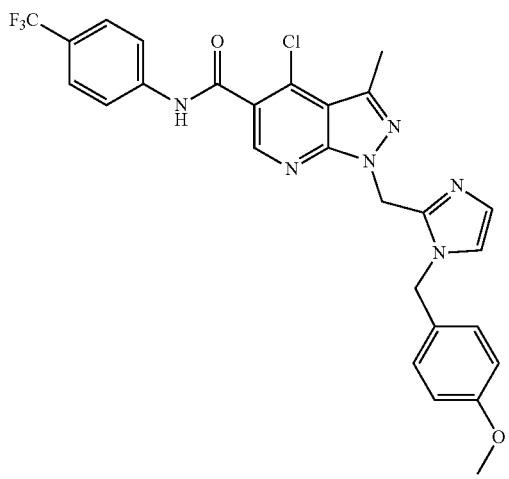 [SMILES: COc1ccc(Cn2ccnc2Cn2nc(C)c3c(Cl)c(C(=O)Nc4ccc(C(F)(F)F)cc4)cnc32)cc1]

Example 279

4-chloro-1-((1-(4-methoxybenzyl)-1H-imidazol-2-yl)methyl)-3-methyl-N-(4-(trifluoromethyl)phenyl)-1H-pyrazolo[3,4-b]pyridine-5-carboxamide The title compound was prepared using general procedure for 4-chloro-3-methyl-1-(5-methyl-pyridin-3-ylmethyl)-1H-pyrazolo[3,4-b]pyridine-5-carboxylic acid (4-chloro-phenyl)-amide (Example 243).

$^1$HNMR (300 MHz, CDCl$_3$): δ=8.64 (s, 1H), 8.52 (brs, 1H), 7.82 (d, J=8.7 Hz, 2H), 7.65 (d, J=8.4 Hz, 2H), 7.10 (d, J=0.9 Hz, 1H), 6.90 (d, J=1.2 Hz, 1H), 6.58 (d, J=8.7 Hz, 2H), 6.50 (d, J=8.7 Hz, 2H), 5.68 (s, 2H), 5.17 (s, 2H), 3.79 (s, 3H), 2.62 (s, 3H). MS: m/z 555.1 (M+H$^+$)

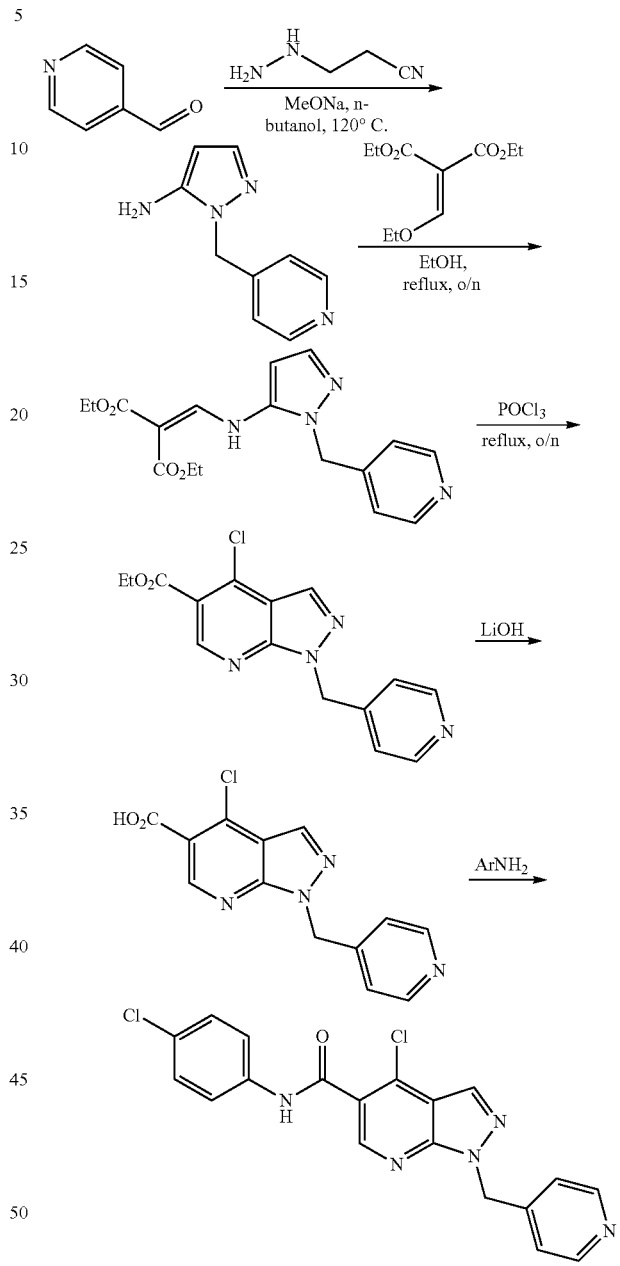

Example 280

4-chloro-N-(4-chlorophenyl)-1-(pyridin-4-ylmethyl)-1H-pyrazolo[3,4-b]pyridine-5-carboxamide Step 1:

To a solution of 3-hydrazinylpropanenitrile (3.1 g, 0.037 mol) in BuOH (20 mL) was added isonicotinaldehyde (4.0 g, 0.037 mol). After stirring overnight, NaOMe (2 g, 0.074 mmol) was added and the mixture was stirred at 120° C. for 3 hrs. The mixture was poured into ice water (100 mL) and extracted with EtOAc (100 mL×2). The extracts were washed with 1 N HCl (100 mL). The aqueous phase was neutralized with 5 N NaOH (100 mL) and extracted with DCM (100 mL×2). The solution was dried over Na$_2$SO$_4$ and concentrated in vacuum to give 4.5 g of crude 1-(pyridin-4-ylmethyl)-1H-pyrazol-5-amine as brown oil. MS: m/z 175.1 (M+H$^+$).

Step 2:

To a solution of 1-(pyridin-4-ylmethyl)-1H-pyrazol-5-amine (4.5 g crude) in EtOH (100 mL) was added diethyl 2-(ethoxymethylene)malonate (6.7 g, 31 mmol) and the mixture was stirred at 90° C. overnight.

The mixture was evaporated to dryness in vacuum and the crude product (3 g) was used for next step without further purification. MS: m/z 345.1 (M+H$^+$).

Step 3:

The above crude diethyl 2-((1-(pyridin-4-ylmethyl)-1H-pyrazol-5-yl)amino)methylene)malonate (3 g) was dissolved in POCl$_3$ (30 mL) and the mixture was stirred at reflux overnight. The excessive POCl$_3$ was removed in vacuum. The residue was diluted with DCM (50 mL). The mixture was washed with saturated aqeous NaHCO$_3$, brine and dried over Na$_2$SO$_4$. The solution was concentrated to dryness and the residue was purified by silica gel column (PE/EtOAc=10/1-1/1) to give ethyl 4-chloro-1-(pyridin-4-ylmethyl)-1H-pyrazolo[3,4-b]pyridine-5-carboxylate (2 g, 3-step yield: 17%) as white solid.

Step 4:

To a solution of ethyl 4-chloro-1-(pyridin-4-ylmethyl)-1H-pyrazolo[3,4-b]pyridine-5-carboxylate (450 mg, 1.36 mmol) in THF (20 mL) was added a solution of LiOH (172 mg, 4.09 mmol) in water (5 mL). The mixture was stirred at room temperature overnight. The solution was concentrated to remove most of THF. The reamining phase was acidied with HCl to pH=1-2. The resulting solid was collected by filtration and washed with water and dried in vauum to give 4-chloro-1-(pyridin-4-ylmethyl)-1H-pyrazolo[3,4-b]pyridine-5-carboxylic acid (180 mg, yield: 46%) as white solid.

Step 5:

The amidation is similar to 4-chloro-3-methyl-1-phenyl-1H-pyrazolo[3,4-b]pyridine-5-carboxylic acid (4-bromo-phenyl)-amide (Example 1).

$^1$HNMR (400 MHz, CDCl$_3$): δ=8.93 (s, 1H), 8.52 (d, J=6.0 Hz, 2H), 8.24 (s, 1H), 8.21 (brs, 1H), 7.62 (d, J=8.8 Hz, 2H), 7.37 (d, J=8.8 Hz, 2H), 7.15 (d, J=6.0 Hz, 2H), 5.73 (s, 2H). MS: m/z 398.1 (M+H$^+$).

Example 281

4-chloro-1-(pyridin-4-ylmethyl)-N-(4-(trifluoromethyl)phenyl)-1H-pyrazolo[3,4-b]pyridine-5-carboxamide

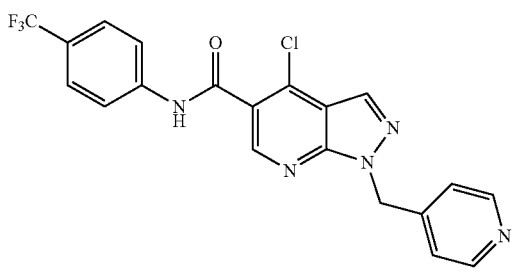 [SMILES: O=C(Nc1ccc(C(F)(F)F)cc1)c1cnc2c(cnn2Cc2ccncc2)c1Cl]

The title compound was prepared using general procedure for 4-chloro-N-(4-chlorophenyl)-1-(pyridin-4-ylmethyl)-1H-pyrazolo[3,4-b]pyridine-5-carboxamide (Example 280).

$^1$HNMR (400 MHz, CDCl$_3$): δ=8.94 (s, 1H), 8.53-8.44 (m, 3H), 8.25 (s, 1H), 7.80 (d, J=8.4 Hz, 2H), 7.65 (d, J=8.4 Hz, 2H), 7.15 (d, J=5.6 Hz, 2H), 5.73 (s, 2H). MS: m/z 432.1 (M+H$^+$).

Example 282

4-chloro-N-(4-isopropylphenyl)-1-(pyridin-4-ylmethyl)-1H-pyrazolo[3,4-b]pyridine-5-carboxamide

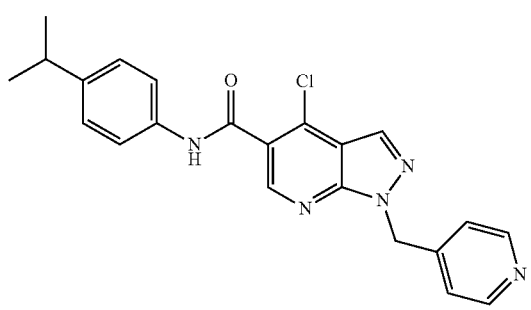 [SMILES: CC(C)c1ccc(NC(=O)c2cnc3c(cnn3Cc3ccncc3)c2Cl)cc1]

The title compound was prepared using general procedure for 4-chloro-N-(4-chlorophenyl)-1-(pyridin-4-ylmethyl)-1H-pyrazolo[3,4-b]pyridine-5-carboxamide (Example 280).

$^1$HNMR (400 MHz, CDCl$_3$): δ=8.93 (s, 1H), 8.54 (d, J=6.4 Hz, 2H), 8.24 (s, 1H), 8.02 (brs, 1H), 7.58 (d, J=8.0 Hz, 2H), 7.27 (d, J=8.0 Hz, 2H), 7.16 (d, J=5.6 Hz, 2H), 5.74 (s, 2H), 2.95-2.90 (m, 1H), 1.26 (d, J=6.8 Hz, 6H). MS: m/z 406.1 (M+H$^+$).

Example 283

4-chloro-N-(4-chlorophenyl)-1-(pyridin-3-ylmethyl)-1H-pyrazolo[3,4-b]pyridine-5-carboxamide

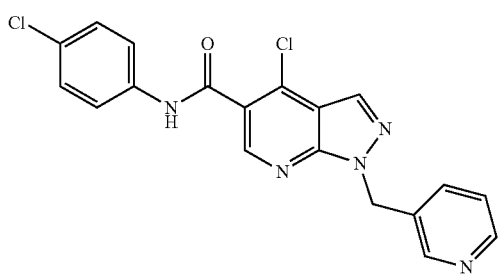 [SMILES: O=C(Nc1ccc(Cl)cc1)c1cnc2c(cnn2Cc2cccnc2)c1Cl]

The title compound was prepared using general procedure for 4-chloro-N-(4-chlorophenyl)-1-(pyridin-4-ylmethyl)-1H-pyrazolo[3,4-b]pyridine-5-carboxamide (Example 280)

$^1$HNMR (300 MHz, CDCl$_3$): δ=8.94 (s, 1H), 8.77 (s, H), 8.68 (d, J=4.2 Hz, 1H), 8.25 (s, 1H), 8.14-8.08 (m, 2H), 7.67-7.56 (m, 3H), 7.38 (d, J=8.1 Hz, 2H), 5.85 (s, 2H). MS: m/z 398.0 (M+H$^+$).

Example 284

4-chloro-1-(pyridin-3-ylmethyl)-N-(4-(trifluoromethyl)phenyl)-1H-pyrazolo[3,4-b]pyridine-5-carboxamide

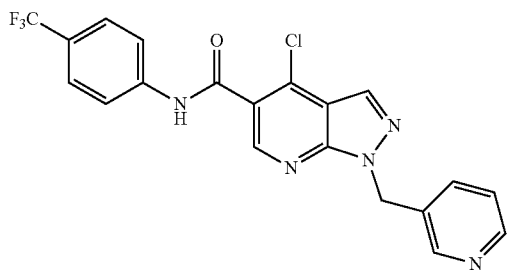 [SMILES: O=C(Nc1ccc(C(F)(F)F)cc1)c1cnc2c(cnn2Cc2cccnc2)c1Cl]

The title compound was prepared using general procedure for 4-chloro-N-(4-chlorophenyl)-1-(pyridin-4-ylmethyl)-1H-pyrazolo[3,4-b]pyridine-5-carboxamide (Example 280).
$^1$HNMR (300 MHz, CDCl$_3$): δ=8.89 (s, 1H), 8.64 (s, H), 8.57 (s, 1H), 8.50 (d, J=4.2 Hz, 1H), 8.19 (s, 1H), 7.80 (d, J=8.4 Hz, 2H), 7.72-7.62 (m, 3H), 7.26-7.20 (m, 1H), 5.71 (s, 2H). MS: m/z 432.1 (M+H$^+$).

Example 285

4-chloro-N-(4-isopropylphenyl)-1-(pyridin-3-ylmethyl)-1H-pyrazolo[3,4-b]pyridine-5-carboxamide

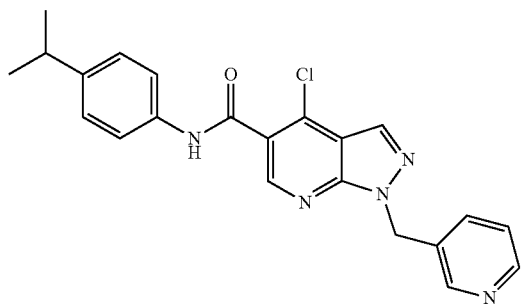 [SMILES: CC(C)c1ccc(NC(=O)c2cnc3c(cnn3Cc3cccnc3)c2Cl)cc1]

The title compound was prepared using general procedure for 4-chloro-N-(4-chlorophenyl)-1-(pyridin-4-ylmethyl)-1H-pyrazolo[3,4-b]pyridine-5-carboxamide (Example 280).
$^1$HNMR (300 MHz, CDCl$_3$): δ=8.96 (d, J=2.1 Hz, 1H), 8.70 (s, 1H), 8.57-8.56 (m, 1H), 8.55 (s, 1H), 8.22-7.93 (m, 1H), 7.73-7.69 (m, 1H), 7.60-7.58 (m, 1H), 7.28 (d, J=5.7 Hz, 2H), 5.76 (s, 2H), 2.95-2.92 (m, 1H), 1.32 (d, J=6.9 Hz, 6H) MS: m/z 406.1 (M+H$^+$).

Example 286

4-chloro-N-(4-chlorophenyl)-1-(pyridin-2-ylmethyl)-1H-pyrazolo[3,4-b]pyridine-5-carboxamide

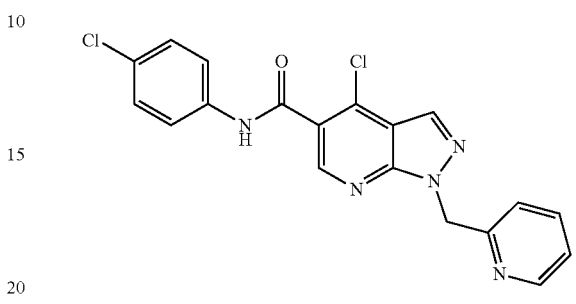

The title compound was prepared using general procedure for 4-chloro-N-(4-chlorophenyl)-1-(pyridin-4-ylmethyl)-1H-pyrazolo[3,4-b]pyridine-5-carboxamide (Example 280).
$^1$HNMR (400 MHz, CDCl$_3$): δ=8.94 (s, 1H), 8.56 (d, J=4.0 Hz, 1H), 8.25 (s, 1H), 8.08 (s, 1H), 7,67-7.60 (m, 3H), 7.36 (d, J=8.4 Hz, 2H), 7.22-7.17 (m, 1H), 7.09 (d, J=8.0 Hz, 1H), 5.88 (s, 2H). MS: m/z 398.1 (M+H$^+$).

Example 287

4-chloro-1-(pyridin-2-ylmethyl)-N-(4-(trifluoromethyl)phenyl)-1H-pyrazolo[3,4-b]pyridine-5-carboxamide

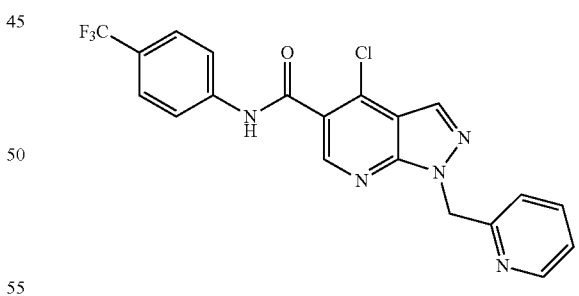

The title compound was prepared using general procedure for 4-chloro-N-(4-chlorophenyl)-1-(pyridin-4-ylmethyl)-1H-pyrazolo[3,4-b]pyridine-5-carboxamide (Example 280).
$^1$HNMR (400 MHz, CDCl$_3$): δ=8.95 (s, 1H), 8.58-8.55 (dd, J=5.2 Hz, 0.8 Hz, 1H), 8.25-8.24 (m, 2H), 7.80 (d, J=8.0 Hz, 2H), 7.67-7.62 (m, 3H), 7.23-7.19 (m, 1H), 7.12 (d, J=8.0 Hz, 1H), 5.88 (s, 2H). MS: m/z 432.1 (M+H$^+$).

Example 288

4-chloro-N-(4-isopropylphenyl)-1-(pyridin-2-ylmethyl)-1H-pyrazolo[3,4-b]pyridine-5-carboxamide

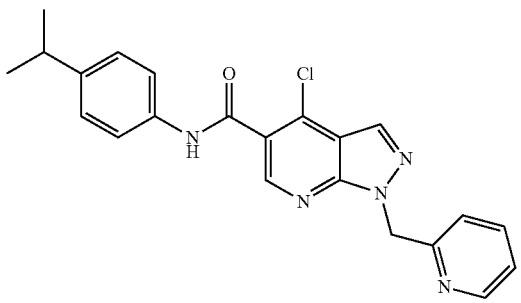 [SMILES: CC(C)c1ccc(NC(=O)c2cnc3c(cnn3Cc3ccccn3)c2Cl)cc1]

The title compound was prepared using general procedure for 4-chloro-N-(4-chlorophenyl)-1-(pyridin-4-ylmethyl)-1H-pyrazolo[3,4-b]pyridine-5-carboxamide (Example 280).

$^1$HNMR (400 MHz, CDCl$_3$): δ=8.92 (s, 1H), 8.58-8.55 (m, 1H), 8.23 (s, 1H), 8.04 (s, 1H), 7.65-7.55 (m, 3H), 7.27-7.23 (m, 2H), 7.22-7.17 (m, 1H), 7.07 (d, J=8.0 Hz, 1H), 5.87 (s, 2H). MS: m/z 406.1 (M+H$^+$).

Example 289

3,4-Dichloro-1-pyridin-2-ylmethyl-1H-pyrazolo[3,4-b]pyridine-5-carboxylic acid (4-trifluoromethyl-phenyl)-amide Step 1:

To a solution of 4-Chloro-1-pyridin-2-ylmethyl-1H-pyrazolo[3,4-b]pyridine-5-carboxylic acid ethyl ester (100 mg, 0.316 mmol) in DMF (5 mL), was added NCS (129 mg, 0.95 mmol). The mixture was then stirred at 80° C. under N$_2$ overnight. The reaction was worked up together with another batch (300 mg). The resultant was poured into water (15 mL) and extracted with EA (20 mL). The organic layer was concentrated and purified by prep-HPLC to give 3,4-dichloro-1-pyridin-2-ylmethyl-1H-pyrazolo[3,4-b]pyridine-5-carboxylic acid ethyl ester (16 mg, yield: 4%) as a yellow solid.

Step 2-3:

The hydrolysis and amidation is similar to 4-chloro-3-methyl-1-phenyl-1H-pyrazolo[3,4-b]pyridine-5-carboxylic acid (4-bromo-phenyl)-amide (Example 1).

$^1$HNMR (400 MHz, CDCl$_3$): δ=8.92 (s, 1H), 8.55 (d, J=4.8 Hz, 1H), 8.09 (brs, 1H), 7.79 (d, J=8.0 Hz, 2H), 7.68-7.64 (m, 3H), 7.24-7.17 (m, 2H), 5.82 (s, 2H). MS: m/z 466.0 (M+H$^+$).

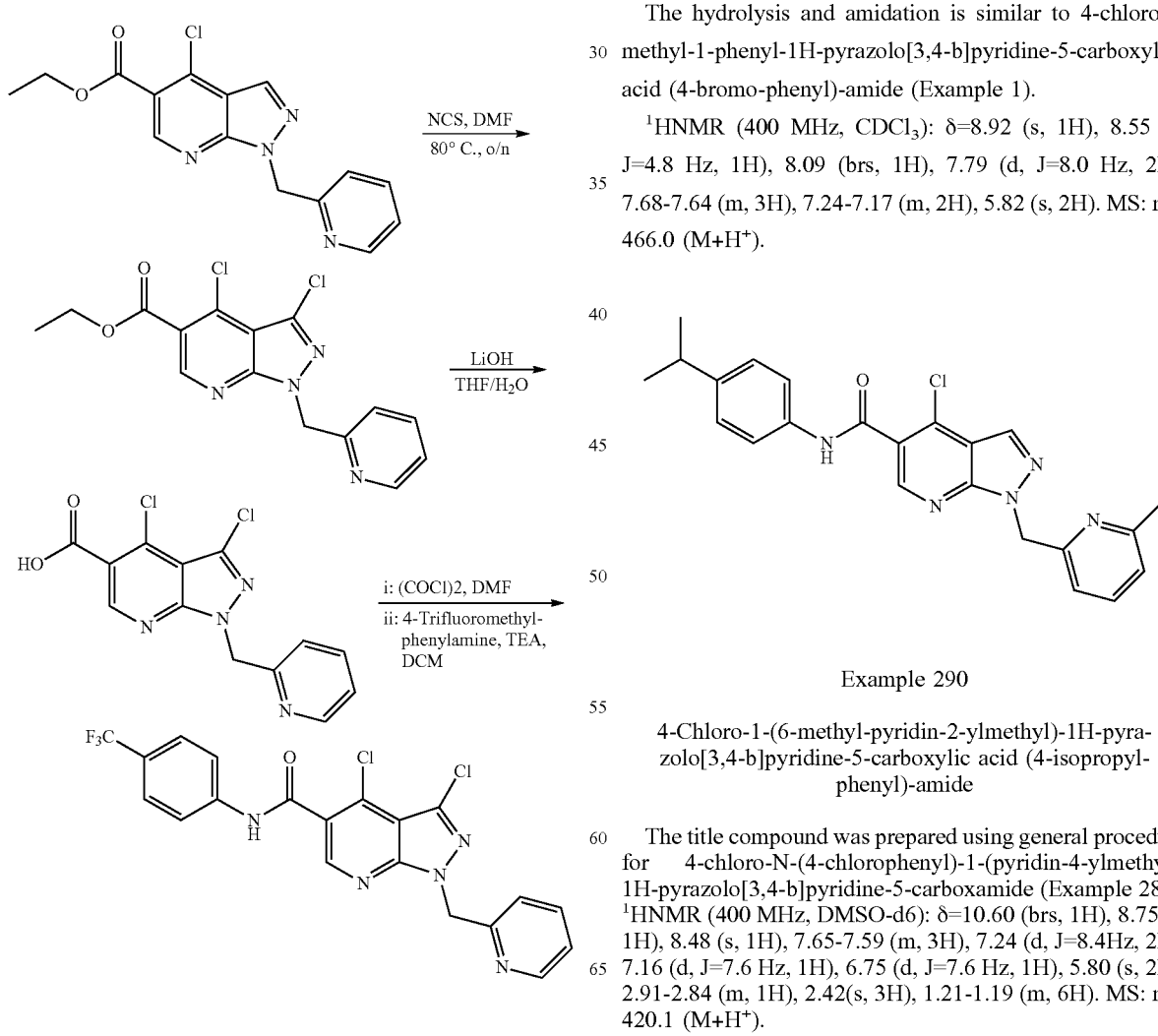

Example 290

4-Chloro-1-(6-methyl-pyridin-2-ylmethyl)-1H-pyrazolo[3,4-b]pyridine-5-carboxylic acid (4-isopropyl-phenyl)-amide The title compound was prepared using general procedure for 4-chloro-N-(4-chlorophenyl)-1-(pyridin-4-ylmethyl)-1H-pyrazolo[3,4-b]pyridine-5-carboxamide (Example 280).

$^1$HNMR (400 MHz, DMSO-d6): δ=10.60 (brs, 1H), 8.75 (s, 1H), 8.48 (s, 1H), 7.65-7.59 (m, 3H), 7.24 (d, J=8.4Hz, 2H), 7.16 (d, J=7.6 Hz, 1H), 6.75 (d, J=7.6 Hz, 1H), 5.80 (s, 2H), 2.91-2.84 (m, 1H), 2.42(s, 3H), 1.21-1.19 (m, 6H). MS: m/z 420.1 (M+H$^+$).

533

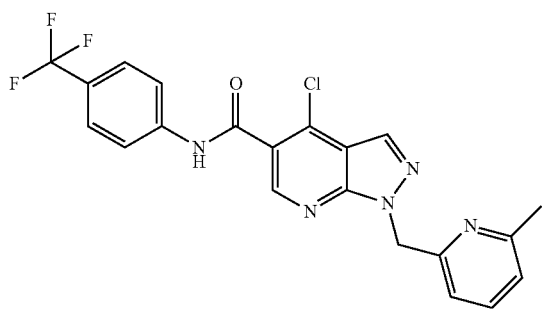 [SMILES: Cc1cccc(Cn2ncc3c(Cl)c(C(=O)Nc4ccc(C(F)(F)F)cc4)cnc32)n1]

Example 291

4-Chloro-1-(6-methyl-pyridin-2-ylmethyl)-1H-pyrazolo[3,4-b]pyridine-5-carboxylic acid (4-trifluoromethyl-phenyl)-amide The title compound was prepared using general procedure for 4-chloro-N-(4-chlorophenyl)-1-(pyridin-4-ylmethyl)-1H-pyrazolo[3,4-b]pyridine-5-carboxamide (Example 280). $^1$H NMR (400 MHz, DMSO-d6): δ=11.04 (brs, 1H), 8.81 (s, 1H), 8.50 (s, 1H), 7.93 (d, J=8.4 Hz, 2H), 7.75 (d, J=8.4 Hz, 2H), 7.60 (t, J=7.8 Hz, 1H), 7.15 (d, J=7.6 Hz, 1H), 6.75 (d, J=8.0 Hz, 1H), 5.79 (s, 2H), 2.42 (s, 3H). MS: m/z 446.0 (M+H$^+$).

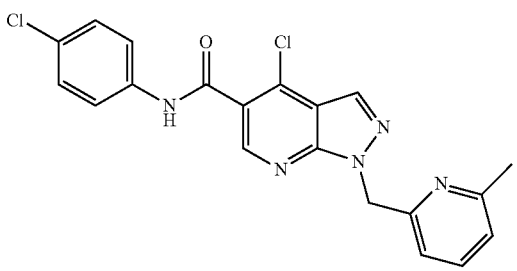 [SMILES: Cc1cccc(Cn2ncc3c(Cl)c(C(=O)Nc4ccc(Cl)cc4)cnc32)n1]

Example 292

4-Chloro-1-(6-methyl-pyridin-2-ylmethyl)-1H-pyrazolo[3,4-b]pyridine-5-carboxylic acid (4-chloro-phenyl)-amide The title compound was prepared using general procedure for 4-chloro-N-(4-chlorophenyl)-1-(pyridin-4-ylmethyl)-1H-pyrazolo[3,4-b]pyridine-5-carboxamide (Example 280). $^1$H NMR (400 MHz, DMSO-d6): δ=10.80 (brs, 1H), 8.78 (s, 1H), 8.49 (s, 1H), 7.76 (d, J=8.8 Hz, 2H), 7.61 (t, J=7.8 Hz, 1H), 7.44 (d, J=8.8 Hz, 2H), 7.16 (d, J=7.6 Hz, 1H), 6.75 (d, J=7.6 Hz, 1H), 5.79 (s, 2H), 2.41 (s, 3H). MS: m/z 412.0 (M+H$^+$).

534

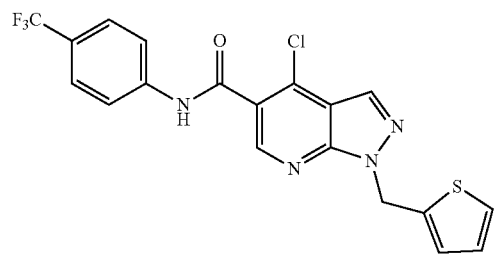

Example 293

4-chloro-1-thiophen-2-ylmethyl-1H-pyrazolo[3,4-b]pyridine-5-carboxylic acid (4-trifluoromethyl-phenyl)-amide The title compound was prepared using general procedure for 4-chloro-N-(4-chlorophenyl)-1-(pyridin-4-ylmethyl)-1H-pyrazolo[3,4-b]pyridine-5-carboxamide (Example 280). $^1$HNMR (400 MHz, CDCl$_3$): δ=8.98 (s, 1H), 8.22 (s, 1H), 8.13 (s, 1H), 7.80 (d, J=8.4 Hz, 2H), 7.67 (d, J=8.4 Hz, 2H), 7.24-7.23 (m, 1H), 7.17 (d, J=3.2 Hz, 1H), 6.96-6.94 (m, 1H), 5.90 (s, 2H). MS: m/z 437.0 (M+H$^+$)

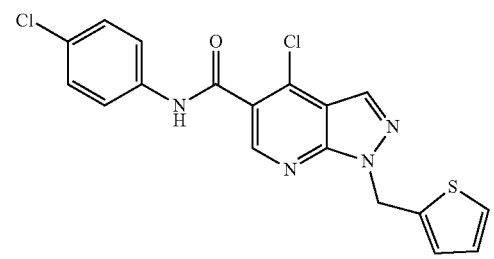 [SMILES: O=C(Nc1ccc(Cl)cc1)c1cnc2c(cnn2Cc2cccs2)c1Cl]

Example 294

4-chloro-1-thiophen-2-ylmethyl-1H-pyrazolo[3,4-b]pyridine-5-carboxylic acid (4-chloro-phenyl)-amide The title compound was prepared using general procedure for 4-chloro-N-(4-chlorophenyl)-1-(pyridin-4-ylmethyl)-1H-pyrazolo[3,4-b]pyridine-5-carboxamide (Example 280). $^1$HNMR (300 MHz, DMSO-d6): δ=10.80 (s, 1H), 8.82 (s, 1H), 8.46 (s, 1H), 7.75 (d, J=8.7 Hz, 2H), 7.46-7.43 (m, 3H), 7.16-7.15 (m, 1H), 6.99-6.96 (m, 1H), 5.93 (s, 2H). MS: m/z 403.0 (M+H$^+$)

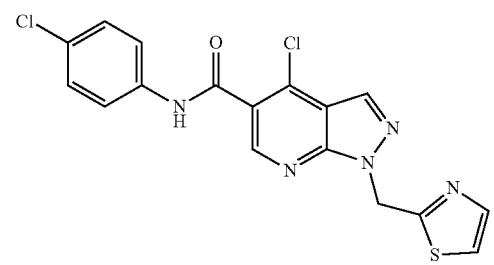 [SMILES: O=C(Nc1ccc(Cl)cc1)c1cnc2c(cnn2Cc2nccs2)c1Cl]

Example 295

4-Chloro-1-thiazol-2-ylmethyl-1H-pyrazolo[3,4-b]pyridine-5-carboxylic acid (4-chloro-phenyl)-amide The title compound was prepared using general procedure for 4-chloro-N-(4-chlorophenyl)-1-(pyridin-4-ylmethyl)-1H-pyrazolo[3,4-b]pyridine-5-carboxamide (Example 280).
$^1$H NMR (CDCl$_3$, 300 HMz): δ=8.98 (s, 1H), 8.28 (s, 1H), 8.02-8.01 (brs, 1H), 7.78 (d, J=3.30 Hz 1H), 7.63 (d, J=8.70 Hz, 2H), 7.40-7.31 (m, 3H), 6.09 (s, 2H). MS: m/z 404.0 (M+H$^+$)

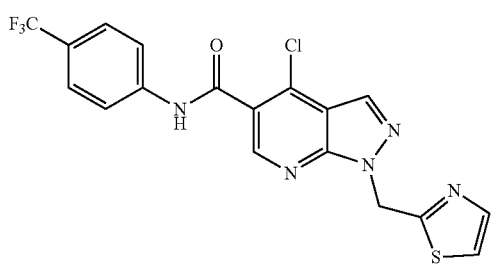 [SMILES: O=C(Nc1ccc(C(F)(F)F)cc1)c1cnc2c(cnn2Cc2nccs2)c1Cl]

Example 296

4-Chloro-1-thiazol-2-ylmethyl-1H-pyrazolo[3,4-b]pyridine-5-carboxylic acid (4-trifluoromethyl-phenyl)-amide The title compound was prepared using general procedure for 4-chloro-N-(4-chlorophenyl)-1-(pyridin-4-ylmethyl)-1H-pyrazolo[3,4-b]pyridine-5-carboxamide (Example 280).
$^1$H NMR (CDCl$_3$, 300 HMz): δ=8.99 (s, 1H), 8.29 (s, 1H), 8.17 (brs, 1H), 7.83-7.77 (m, 3H), 7.68 (d, J=8.40 Hz, 2H), 7.31 (s, 1H), 6.09 (s, 2H). MS: m/z 438.0 (M+H$^+$)

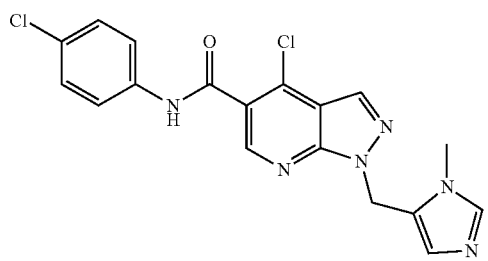 [SMILES: Cn1cncc1Cn1ncc2c(Cl)c(C(=O)Nc3ccc(Cl)cc3)cnc21]

Example 297

4-chloro-N-(4-chlorophenyl)-1-((1-methyl-1H-imidazol-5-yl)methyl)-1H-pyrazolo[3,4-b]pyridine-5-carboxamide The title compound was prepared using general procedure for 4-chloro-N-(4-chlorophenyl)-1-(pyridin-4-ylmethyl)-1H-pyrazolo[3,4-b]pyridine-5-carboxamide (Example 280).
$^1$HNMR (400 MHz, DMSO-d6): δ=10.79 (s, 1H), 8.82 (s, 1H), 8.43 (s, 1H), 7.76 (d, J=8.8 Hz, 2H), 7.58 (s, 1H), 7.45 (d, J=8.8 Hz, 2H), 6.93 (s, 1H), 5.76 (s, 2H), 3.64 (s, 3H). MS: m/z 401.0 (M+H$^+$)

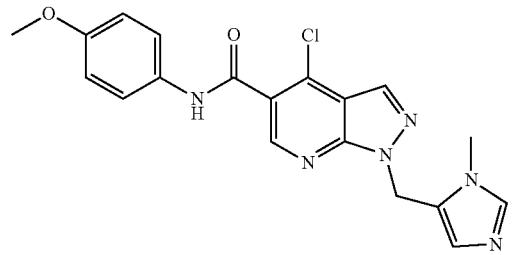 [SMILES: COc1ccc(NC(=O)c2cnc3c(cnn3Cc3cncn3C)c2Cl)cc1]

Example 298

4-chloro-N-(4-methoxyphenyl)-1-((1-methyl-1H-imidazol-5-yl)methyl)-1H-pyrazolo[3,4-b]pyridine-5-carboxamide The title compound was prepared using general procedure for 4-chloro-N-(4-chlorophenyl)-1-(pyridin-4-ylmethyl)-1H-pyrazolo[3,4-b]pyridine-5-carboxamide (Example 280).
$^1$HNMR (400 MHz, CDCl$_3$): δ=8.95 (s, 1H), 8.16 (s, 1H), 7.95 (s, 1H), 7.57 (d, J=9.2 Hz, 2H), 7.40 (s, 1H), 7.21 (s, 1H), 6.94 (d, J=9.6 Hz, 2H), 5.70 (s, 2H), 3.83 (s, 3H), 3.74 (s, 3H). MS: m/z 397.1 (M+H$^+$)

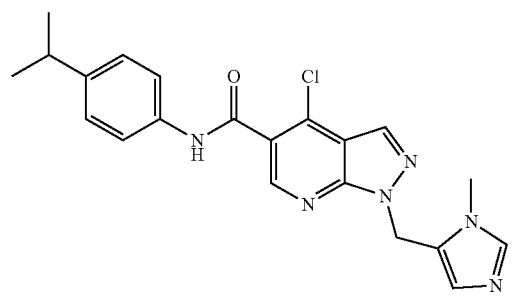 [SMILES: CC(C)c1ccc(NC(=O)c2cnc3c(cnn3Cc3cncn3C)c2Cl)cc1]

Example 299

4-chloro-N-(4-isopropylphenyl)-1-((1-methyl-1H-imidazol-5-yl)methyl)-1H-pyrazolo[3,4-b]pyridine-5-carboxamide The title compound was prepared using general procedure for 4-chloro-N-(4-chlorophenyl)-1-(pyridin-4-ylmethyl)-1H-pyrazolo[3,4-b]pyridine-5-carboxamide (Example 280).
$^1$HNMR (400 MHz, CDCl$_3$): δ=8.84 (s, 1H), 8.54 (brs, 1H), 8.10 (s, 1H), 7.58 (d, J=8.0 Hz, 2H), 7.43 (s, 1H), 7.26-7.20 (m, 2H), 7.16 (s, 1H), 5.64 (s, 2H), 3.71 (s, 3H), 2.95-2.88 (m, 1H), 1.26-1.21 (m, 6H). MS: m/z 409.1 (M+H$^+$)

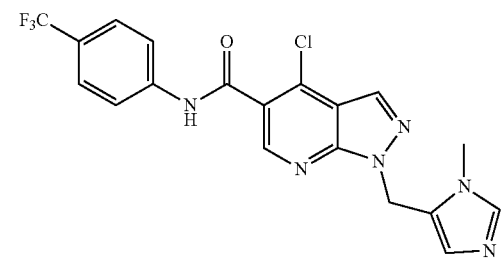 [SMILES: Cn1cncc1Cn1ncc2c(Cl)c(C(=O)Nc3ccc(C(F)(F)F)cc3)cnc21]

Example 300

4-chloro-1-((1-methyl-1H-imidazol-5-yl)methyl)-N-(4-(trifluoromethyl)phenyl)-1H-pyrazolo[3,4-b]pyridine-5-carboxamide The title compound was prepared using general procedure for 4-chloro-N-(4-chlorophenyl)-1-(pyridin-4-ylmethyl)-1H-pyrazolo[3,4-b]pyridine-5-carboxamide (Example 280).
¹HNMR (400 MHz, CDCl₃): δ=8.94 (s, 1H), 8.73 (brs, 1H), 8.15 (s, 1H), 7.81 (d, J=8.4 Hz, 2H), 7.64 (d, J=8.4 Hz, 2H), 7.41 (s, 1H), 7.16 (s, 1H), 5.67 (s, 2H), 3.74 (s, 3H). MS: m/z 435.1 (M+H⁺)

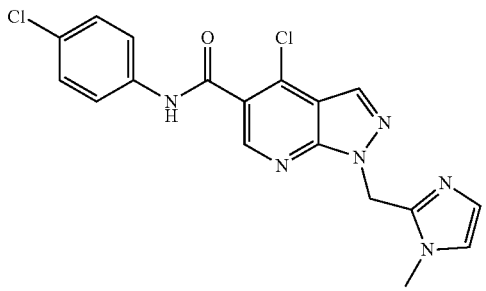 [SMILES: Cn1ccnc1Cn1ncc2c(Cl)c(C(=O)Nc3ccc(Cl)cc3)cnc21]

Example 301

4-chloro-N-(4-chlorophenyl)-1-((1-methyl-1H-imidazol-2-yl)methyl)-1H-pyrazolo[3,4-b]pyridine-5-carboxamide The title compound was prepared using general procedure for 4-chloro-N-(4-chlorophenyl)-1-(pyridin-4-ylmethyl)-1H-pyrazolo[3,4-b]pyridine-5-carboxamide (Example 280).
¹HNMR (400 MHz, CDCl₃): δ=8.92 (s, 1H), 8.40 (brs, 1H), 8.17 (s, 1H), 7.61 (d, J=8.8 Hz, 2H), 7.34 (d, J=8.8 Hz, 2H), 6.98 (s, 1H), 6.85 (s, 1H), 5.78 (s, 2H), 3.76 (s, 3H). MS: m/z 401.1 (M+H⁺)

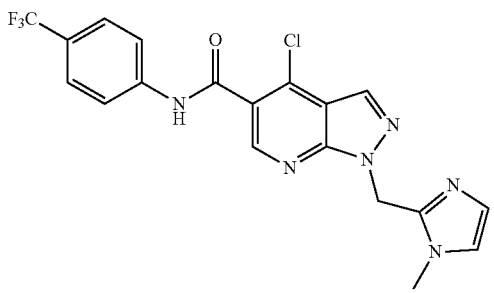 [SMILES: Cn1ccnc1Cn1ncc2c(Cl)c(C(=O)Nc3ccc(C(F)(F)F)cc3)cnc21]

Example 302

4-chloro-1-((1-methyl-1H-imidazol-2-yl)methyl)-N-(4-(trifluoromethyl)phenyl)-1H-pyrazolo[3,4-b]pyridine-5-carboxamide The title compound was prepared using general procedure for 4-chloro-N-(4-chlorophenyl)-1-(pyridin-4-ylmethyl)-1H-pyrazolo[3,4-b]pyridine-5-carboxamide (Example 280).
¹HNMR (400 MHz, CDCl₃): δ=8.92 (s, 1H), 8.74 (brs, 1H), 8.16 (s, 1H), 7.78 (d, J=8.4 Hz, 2H), 7.63 (d, J=8.4 Hz, 2H), 6.98 (s, 1H), 6.86 (s, 1H), 5.78 (s, 2H), 3.78 (s, 3H). MS: m/z 435.1 (M+H⁺)

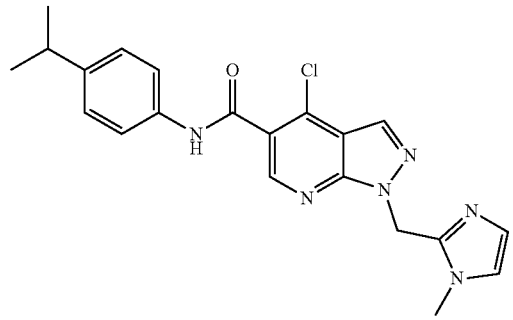 [SMILES: CC(C)c1ccc(NC(=O)c2cnc3c(cnn3Cc3nccn3C)c2Cl)cc1]

Example 303

4-chloro-N-(4-isopropylphenyl)-1-((1-methyl-1H-imidazol-2-yl)methyl)-1H-pyrazolo[3,4-b]pyridine-5-carboxamide The title compound was prepared using general procedure for 4-chloro-N-(4-chlorophenyl)-1-(pyridin-4-ylmethyl)-1H-pyrazolo[3,4-b]pyridine-5-carboxamide (Example 280).
¹HNMR (400 MHz, CDCl₃): δ=8.84 (s, 1H), 8.45 (brs, 1H), 8.07 (s, 1H), 7.56 (d, J=8.4 Hz, 2H), 7.23 (d, J=8.4 Hz, 2H), 7.04 (s, 1H), 6.85 (d, J=1.2 Hz, 1H), 5.82 (s, 2H), 3.72 (s, 3H), 2.95-2.88 (m, 1H), 1.26-1.24 (m, 6H). MS: m/z 409.1 (M+H⁺)

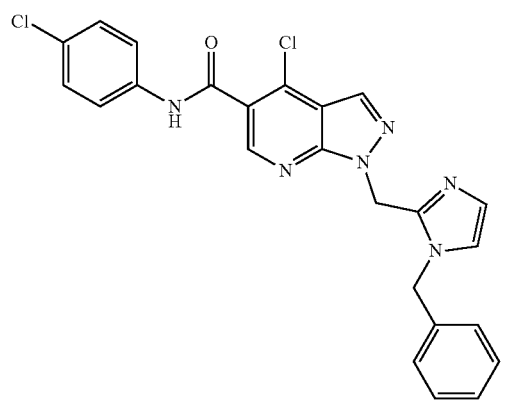 [SMILES: O=C(Nc1ccc(Cl)cc1)c1cnc2c(cnn2Cc2nccn2Cc2ccccc2)c1Cl]

Example 304

1-((1-benzyl-1H-imidazol-2-yl)methyl)-4-chloro-N-(4-chlorophenyl)-1H-pyrazolo[3,4-b]pyridine-5-carboxamide The title compound was prepared using general procedure for 4-chloro-N-(4-chlorophenyl)-1-(pyridin-4-ylmethyl)-1H-pyrazolo[3,4-b]pyridine-5-carboxamide (Example 280).
¹HNMR (400 MHz, DMSO-d6): δ=10.78 (s, 1H), 8.77 (s, 1H), 8.29 (s, 1H), 7.77 (d, J=8.8 Hz, 2H), 7.45 (d, J=8.8 Hz, 2H), 7.24-7.20 (m, 4H), 6.95-6.93 (m, 2H), 6.85 (s, 1H), 5.79 (s, 2H), 5.34 (s, 2H). MS: m/z 477.1 (M+H⁺).

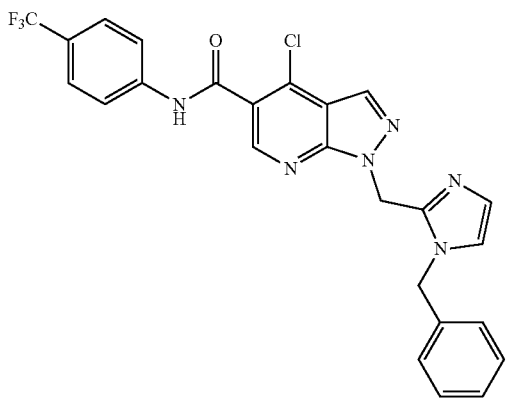 [SMILES: O=C(Nc1ccc(C(F)(F)F)cc1)c1cnc2c(cnn2Cc2nccn2Cc2ccccc2)c1Cl]

Example 305

1-((1-benzyl-1H-imidazol-2-yl)methyl)-4-chloro-N-(4-(trifluoromethyl)phenyl)-1H-pyrazolo[3,4-b]pyridine-5-carboxamide The title compound was prepared using general procedure for 4-chloro-N-(4-chlorophenyl)-1-(pyridin-4-ylmethyl)-1H-pyrazolo[3,4-b]pyridine-5-carboxamide (Example 280).

$^1$HNMR (400 MHz, DMSO-d6): δ=11.01 (s, 1H), 8.80 (s, 1H), 8.30 (s, 1H), 7.95 (d, J=8.8 Hz, 2H), 7.77 (d, J=8.4 Hz, 2H), 7.24-7.20 (m, 4H), 6.95-6.93 (m, 2H), 6.85 (s, 1H), 5.80 (s, 2H), 5.34 (s, 2H). MS: m/z 511.1 (M+H$^+$).

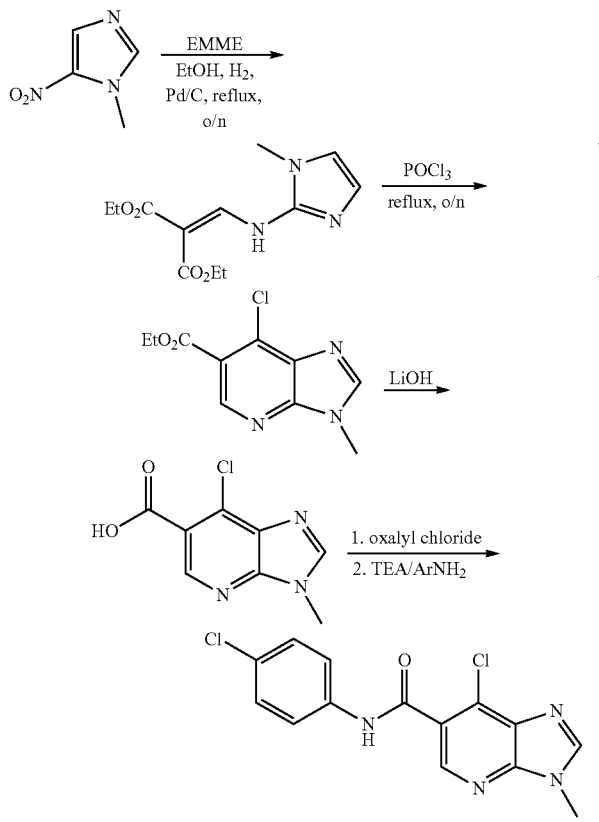

Example 306

7-chloro-N-(4-chlorophenyl)-3-methyl-3H-imidazo[4,5-b]pyridine-6-carboxamide

Step 1

To a solution of 1-methyl-5-nitro-1H-imidazole (10 g, 0.078 mol) in EtOH (400 mL) was added wet 10% Pd/C (2 g), and the mixture was stirred at room temperature for 1 hr. Then diethyl 2-(ethoxymethylene)malonate (20 g, 0.094 mol) was added. The mixture was stirred under H2 for overnight. Pd/C was removed after filtration and the solvent was evaporated in vacuum. The residue was purified by flash column (DCM/MeOH=10/1) to give diethyl 2-(((1-methyl-1H-imidazol-5-yl)amino)methylene)malonate (6 g, yield: 28.7%) as brown oil. MS: m/z 268.1 (M+H$^+$).

Step 2

A solution of diethyl 2-(((1-methyl-1H-imidazol-5-yl)amino)methylene)malonate (6g, 22.6 mmol) in POCl$_3$ (100 mL) was stirred at reflux for overnight. After cooling to room temperature, POCl$_3$ was removed in vacuum. The residue was diluted with DCM (50 mL) and the mixture was washed with NaHCO$_3$, water and brine, and then dried over Na$_2$SO$_4$. The solution was concentrated and the residue was purified by silica gel column (PE/EA=10/1) to give 7-chloro-3-methyl-3H-imidazo[4,5-b]pyridine-6-carboxylic acid ethyl ester (2 g, yield: 42%) as brown solid. $^1$HNMR (300 MHz, CDCl$_3$): δ=8.95 (s, 1H), 8.14 (s, 1H), 4.47 (q, J=7.2 Hz, 2H), 3.96 (s, 3H), 1.45 (t, J=7.2 Hz, 3H).

Step 3

To a solution of 7-chloro-3-methyl-3H-imidazo[4,5-b]pyridine-6-carboxylic acid ethyl ester (2 g, 8.33 mmol) in THF (120 mL) was added aq. LiOH (1.8 g, 25 mmol) in water (20 mL). The mixture was then stirred at room temperature for overnight. THF was removed in vacuum. The mixture was acidified with concentrated HCl till the pH=2. The resulting solid was filtered and dried in vacuum to give 7-chloro-3-methyl-3H-imidazo[4,5-b]pyridine-6-carboxylic acid (1.6 g, yield: 94%) as white solid. $^1$HNMR (300 MHz, DMSO-d$_6$): δ=13.51 (s, 1H), 8.83 (s, 1H), 8.61 (s, 1H), 3.87 (s, 3H).

Step 4

To a solution of 7-chloro-3-methyl-3H-imidazo[4,5-b]pyridine-6-carboxylic acid (100 mg, 0.47 mmol) in DCM (10 mL) was added oxalyl chloride (0.2 mL, 0.94 mmol) at 0° C. The mixture was stirred at room temperature for 1 hr. Then 4-chloroaniline (121 mg, 0.95 mmol) and TEA (96 mg, 0.97 mmol) was added at 0° C. The mixture was continued stirring at room temperature for 1 hr. The reaction mixture was diluted with DCM (20 mL) and washed with NaHCO$_3$ (20 mL) and brine (20 mL), then dried over anhydrous Na$_2$SO$_4$. The solvent was removed and the residue was purified by prep-HPLC to give 7-chloro-N-(4-chlorophenyl)-3-methyl-3H-imidazo[4,5-b]pyridine-6-carboxamide (5 mg, yield: 3.3%) as white solid.

$^1$HNMR (300 MHz, CD$_3$OD): δ=8.60 (s, 1H), 8.54 (s, 1H), 7.75 (d, J=9.0 Hz, 2H), 7.40 (d, J=9.0 Hz, 2H) 3.99 (s, 3H). MS: m/z 320.8 (M+H$^+$).

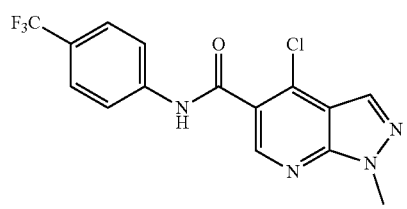

Example 307

7-chloro-3-methyl-N-(4-(trifluoromethyl)phenyl)-3H-imidazo[4,5-b]pyridine-6-carboxamide The title compound was prepared using general procedure for 7-chloro-N-(4-chlorophenyl)-3-methyl-3H-imidazo[4,5-b]pyridine-6-carboxamide (Example 306).

$^1$HNMR (300 MHz, DMSO-d6): δ=11.00 (s, 1H), 8.66 (s, 1H), 8.62 (s, 1H), 7.94 (d, J=8.7 Hz, 2H), 7.76 (d, J=8.7 Hz, 2H), 3.91 (s, 3H). MS: m/z 355.0 (M+H$^+$).

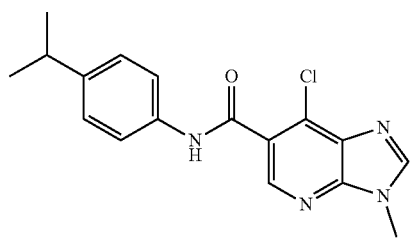 [SMILES: CC(C)c1ccc(NC(=O)c2cnc3c(ncn3C)c2Cl)cc1]

Example 308

7-chloro-N-(4-isopropylphenyl)-3-methyl-3H-imidazo[4,5-b]pyridine-6-carboxamide

The title compound was prepared using general procedure for 7-chloro-N-(4-chlorophenyl)-3-methyl-3H-imidazo[4,5-b]pyridine-6-carboxamide (Example 306).

$^1$HNMR (300 MHz, DMSO-d6): δ=10.53 (s, 1H), 8.64 (s, 1H), 8.55 (s, 1H), 7.63 (d, J=8.1 Hz, 2H), 7.24 (d, J=8.7 Hz, 2H), 3.90 (s, 3H), 2.89-2.85 (1H, m), 1.19 (d, J=6.9 Hz, 6H). MS: m/z 329.1 (M+H$^+$).

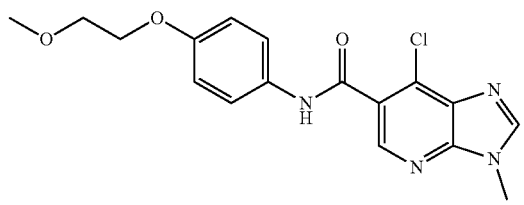 [SMILES: COCCOc1ccc(NC(=O)c2cnc3c(ncn3C)c2Cl)cc1]

Example 309

7-chloro-N-(4-(2-methoxyethoxy)phenyl)-3-methyl-3H-imidazo[4,5-b]pyridine-6-carboxamide The title compound was prepared using general procedure for 7-chloro-N-(4-chlorophenyl)-3-methyl-3H-imidazo[4,5-b]pyridine-6-carboxamide (Example 306).

$^1$HNMR (300 MHz, DMSO-d6): δ=10.49 (s, 1H), 8.63 (s, 1H), 8.56 (s, 1H), 7.63 (d, J=8.7 Hz, 2H), 6.94 (d, J=8.7 Hz, 2H), 4.09-4.03 (2H, m), 3.90 (s, 3H), 3.67-3.63 (2H, m), 3.35 (s, 3H). MS: m/z 361.1 (M+H$^+$).

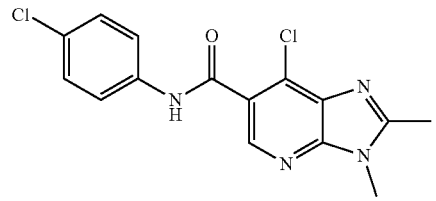 [SMILES: Cc1nc2c(Cl)c(C(=O)Nc3ccc(Cl)cc3)cnc2n1C]

Example 310

7-Chloro-2,3-dimethyl-3H-imidazo[4,5-b]pyridine-6-carboxylic acid (4-chloro-phenyl)-amide The title compound was prepared using general procedure for 7-chloro-N-(4-chlorophenyl)-3-methyl-3H-imidazo[4,5-b]pyridine-6-carboxamide (Example 306). $^1$HNMR (400 MHz, DMSO-d6): δ=10.74 (s, 1H), 8.49 (s, 1H), 7.77 (d, J=9.2 Hz, 2H), 7.44 (d, J=8.4 Hz, 2H), 3.80 (s, 3H), 2.64 (s, 3H). MS: m/z 335.0 (M+H$^+$).

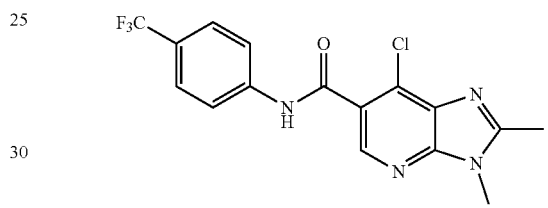

Example 311

7-Chloro-2,3-dimethyl-3H-imidazo[4,5-b]pyridine-6-carboxylic acid (4-trifluoromethyl-phenyl)-amide The title compound was prepared using general procedure for 7-chloro-N-(4-chlorophenyl)-3-methyl-3H-imidazo[4,5-b]pyridine-6-carboxamide (Example 306). $^1$HNMR (400 MHz, DMSO-d6): δ=11.03 (s, 1H), 8.51 (s, 1H), 7.96 (d, J=8.4 Hz, 2H), 7.74 (d, J=8.4 Hz, 2H), 3.80 (s, 3H), 2.64 (s, 3H). MS: m/z 369.0 (M+H$^+$).

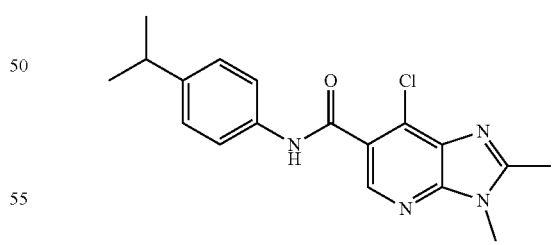

Example 312

7-Chloro-2,3-dimethyl-3H-imidazo[4,5-b]pyridine-6-carboxylic acid (4-isopropyl-phenyl)-amide The title compound was prepared using general procedure for 7-chloro-N-(4-chlorophenyl)-3-methyl-3H-imidazo[4,5-b]pyridine-6-carboxamide (Example 306).

¹HNMR (400 MHz, DMSO-d6): δ=10.51 (s, 1H), 8.45 (s, 1H), 7.64 (d, J=8.8 Hz, 2H), 7.24 (d, J=8.8 Hz, 2H), 3.80 (s, 3H), 2.89-2.85 (m, 1H), 2.64 (s, 3H), 1.20 (d, J=6.8 Hz, 6H). MS: m/z 343.1 (M+H⁺).

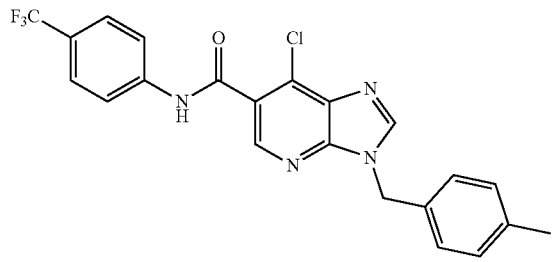 [SMILES: Cc1ccc(Cn2cnc3c(Cl)c(C(=O)Nc4ccc(C(F)(F)F)cc4)cnc32)cc1]

Example 313

7-Chloro-3-(4-methyl-benzyl)-3H-imidazo[4,5-b]pyridine-6-carboxylic acid (4-trifluoromethyl-phenyl)-amide The title compound was prepared using general procedure for 7-chloro-N-(4-chlorophenyl)-3-methyl-3H-imidazo[4,5-b]pyridine-6-carboxamide (Example 306).

¹HNMR (400 MHz, CDCl₃): δ=8.85 (s, 1H), 8.40 (s, 1H), 8.14 (s, 1H), 7.84 (d, J=8.8 Hz, 2H), 7.67 (d, J=8.4 Hz, 2H), 7.22 (d, J=8.0 Hz, 2H), 7.18 (d, J=8.0 Hz, 2H), 5.45 (s, 2H), 2.35 (s, 3H). MS: m/z 445.1 (M+H⁺).

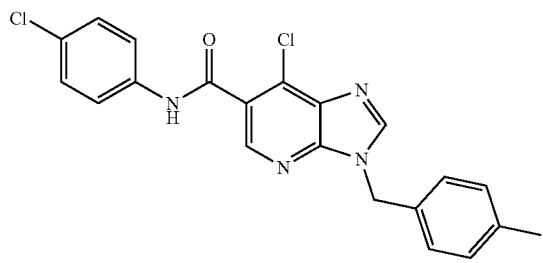 [SMILES: Cc1ccc(Cn2cnc3c(Cl)c(C(=O)Nc4ccc(Cl)cc4)cnc32)cc1]

Example 314

7-Chloro-3-(4-methyl-benzyl)-3H-imidazo[4,5-b]pyridine-6-carboxylic acid (4-chloro-phenyl)-amide The title compound was prepared using general procedure for 7-chloro-N-(4-chlorophenyl)-3-methyl-3H-imidazo[4,5-b]pyridine-6-carboxamide (Example 306).

¹HNMR (400 MHz, DMSO-d6): δ=10.75 (s, 1H), 8.84 (s, 1H), 8.58 (s, 1H), 7.75 (d, J=8.4 Hz, 2H), 7.44 (d, J=8.0 Hz, 2H), 7.24 (d, J=7.2 Hz, 2H), 7.15 (d, J=6.8 Hz, 2H), 5.52 (s, 2H), 2.25 (s, 3H). MS: m/z 411.1 (M+H⁺).

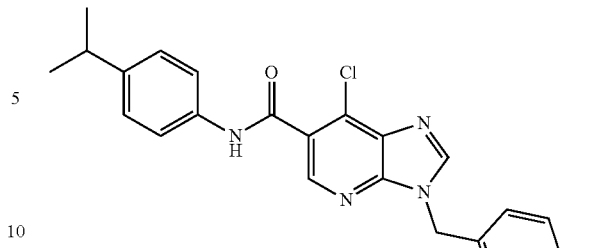

Example 315

7-Chloro-3-(4-methyl-benzyl)-3H-imidazo[4,5-b]pyridine-6-carboxylic acid (4-isopropyl-phenyl)-amide The title compound was prepared using general procedure for 7-chloro-N-(4-chlorophenyl)-3-methyl-3H-imidazo[4,5-b]pyridine-6-carboxamide (Example 306). ¹HNMR (400 MHz, CDCl₃): δ=8.76 (s, 1H), 8.30 (s, 1H), 8.09 (s, 1H), 7.62 (d, J=8.0 Hz, 2H), 7.26 (d, J=8.0 Hz, 2H), 7.21 (d, J=8.0 Hz, 2H), 7.16 (d, J=7.6 Hz, 2H), 5.42 (s, 2H), 2.94-2.91 (m, 1H), 2.34 (s, 3H), 1.26 (d, J=6.8 Hz, 6H). MS: m/z 419.1 (M+H⁺).

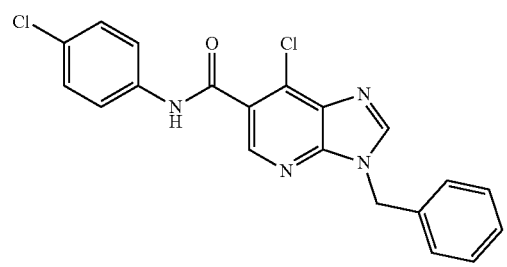 [SMILES: O=C(Nc1ccc(Cl)cc1)c1cnc2c(ncn2Cc2ccccc2)c1Cl]

Example 316

3-Benzyl-7-chloro-3H-imidazo[4,5-b]pyridine-6-carboxylic acid (4-chloro-phenyl)-amide The title compound was prepared using general procedure for 7-chloro-N-(4-chlorophenyl)-3-methyl-3H-imidazo[4,5-b]pyridine-6-carboxamide (Example 306).

¹HNMR (400 MHz, DMSO-d6): δ=10.75 (s, 1H), 8.86 (s, 1H), 8.59 (s, 1H), 7.76 (d, J=8.8 Hz, 2H), 7.43 (d, J=8.8 Hz, 2H), 7.37-7.28 (m, 5H), 5.58 (s, 2H). MS: m/z 397.0 (M+H⁺).

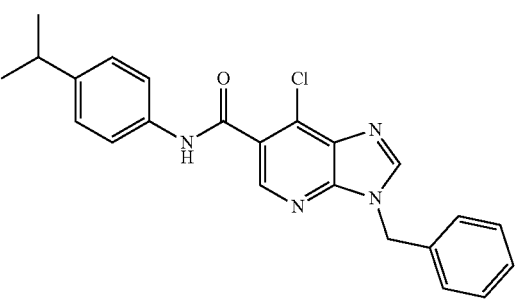 [SMILES: CC(C)c1ccc(NC(=O)c2cnc3c(ncn3Cc3ccccc3)c2Cl)cc1]

Example 317

3-Benzyl-7-chloro-3H-imidazo[4,5-b]pyridine-6-carboxylic acid (4-isopropyl-phenyl)-amide The title compound was prepared using general procedure for 7-chloro-N-(4-chlorophenyl)-3-methyl-3H-imidazo[4,5-b]pyridine-6-carboxamide (Example 306). ¹HNMR (400 MHz, DMSO-d6): δ=10.52 (s, 1H), 8.85 (s, 1H), 8.55 (s, 1H), 7.63 (d, J=8.4 Hz, 2H), 7.37-7.27 (m, 5H), 7.23 (d, J=8.4 Hz, 2H), 5.58 (s, 2H), 2.90-2.83 (m, 1H), 1.20 (d, J=6.8 Hz, 6H). MS: m/z 405.1 (M+H⁺).

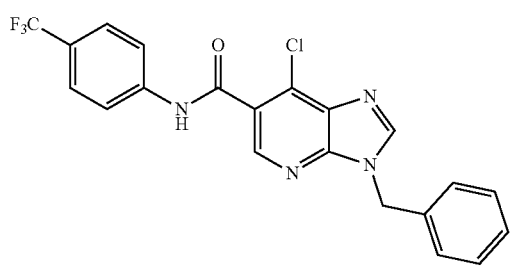 [SMILES: O=C(Nc1ccc(C(F)(F)F)cc1)c1cnc2c(ncn2Cc2ccccc2)c1Cl]

Example 318

3-Benzyl-7-chloro-3H-imidazo[4,5-b]pyridine-6-carboxylic acid (4-trifluoromethyl-phenyl)-amide The title compound was prepared using general procedure for 7-chloro-N-(4-chlorophenyl)-3-methyl-3H-imidazo[4,5-b]pyridine-6-carboxamide (Example 306). ¹HNMR (400 MHz, DMSO-d6): δ=10.98 (s, 1H), 8.88 (s, 1H), 8.62 (s, 1H), 7.94 (d, J=8.4 Hz, 2H), 7.75 (d, J=8.8 Hz, 2H), 7.35-7.28 (m, 5H), 5.59 (s, 2H). MS: m/z 431.0 (M+H⁺).

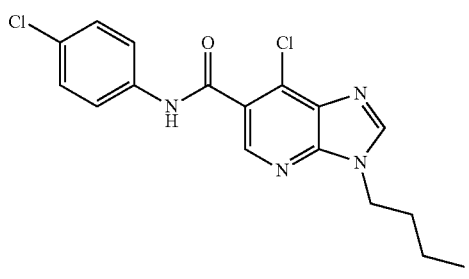 [SMILES: CCCCn1cnc2c(Cl)c(C(=O)Nc3ccc(Cl)cc3)cnc21]

Example 319

3-Butyl-7-chloro-3H-imidazo[4,5-b]pyridine-6-carboxylic acid (4-chloro-phenyl)-amide The title compound was prepared using general procedure for 7-chloro-N-(4-chlorophenyl)-3-methyl-3H-imidazo[4,5-b]pyridine-6-carboxamide (Example 306). ¹HNMR (400 MHz, DMSO-d6): δ=10.76 (s, 1H), 8.59 (s, 1H), 7.77 (d, J=8.8 Hz, 2H), 7.44 (d, J=8.8 Hz, 2H), 4.34 (t, J=6.8 Hz, 2H), 1.88-1.84 (m, 2H), 1.28-1.22 (m, 2H), 0.90 (t, J=7.2 Hz, 3H). MS: m/z 363.0 (M+H⁺).

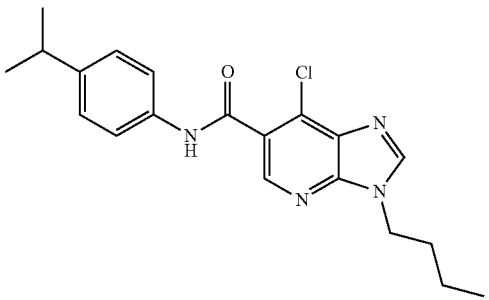

Example 320

3-Butyl-7-chloro-3H-imidazo[4,5-b]pyridine-6-carboxylic acid (4-isopropyl-phenyl)-amide The title compound was prepared using general procedure for 7-chloro-N-(4-chlorophenyl)-3-methyl-3H-imidazo[4,5-b]pyridine-6-carboxamide (Example 306).
¹HNMR (400 MHz, DMSO-d6): δ=10.53 (s, 1H), 8.70 (s, 1H), 8.55 (s, 1H), 7.64 (d, J=8.8 Hz, 2H), 7.24 (d, J=8.4 Hz, 2H), 4.34 (t, J=6.8 Hz, 2H), 2.90-2.86 (m, 1H), 1.88-1.84 (m, 2H), 1.28-1.22 (m, 2H), 1.20 (d, J=6.8 Hz, 6H), 0.90 (t, J=7.2 Hz, 3H). MS: m/z 371.1 (M+H⁺).

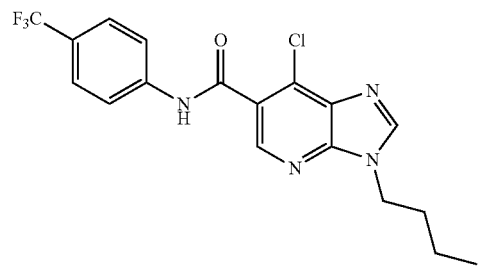

Example 321

3-Butyl-7-chloro-3H-imidazo[4,5-b]pyridine-6-carboxylic acid (4-trifluoromethyl-phenyl)-amide The title compound was prepared using general procedure for 7-chloro-N-(4-chlorophenyl)-3-methyl-3H-imidazo[4,5-b]pyridine-6-carboxamide (Example 306). ¹HNMR (400 MHz, DMSO-d6): δ=10.99 (s, 1H), 8.73 (s, 1H), 8.62 (s, 1H), 7.95 (d, J=8.4 Hz, 2H), 7.76 (d, J=8.8 Hz, 2H), 4.35 (t, J=6.8 Hz, 2H), 1.88-1.84 (m, 2H), 1.28-1.23 (m, 2H), 0.90 (t, J=7.2 Hz, 3H). MS: m/z 397.1 (M+H⁺).

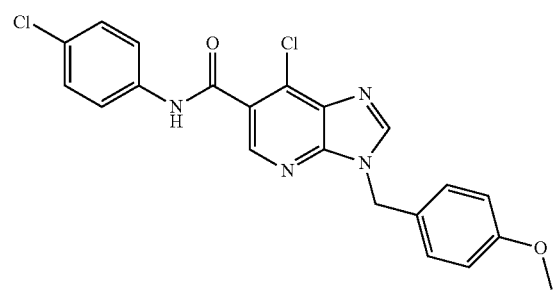 [SMILES: COc1ccc(Cn2cnc3c(Cl)c(C(=O)Nc4ccc(Cl)cc4)cnc32)cc1]

Example 322

7-Chloro-3-(4-methoxy-benzyl)-3H-imidazo[4,5-b]pyridine-6-carboxylic acid (4-chloro-phenyl)-amide The title compound was prepared using general procedure for 7-chloro-N-(4-chlorophenyl)-3-methyl-3H-imidazo[4,5-b]pyridine-6-carboxamide (Example 306).

¹HNMR (400 MHz, DMSO-d6): δ=10.74 (s, 1H), 8.83 (s, 1H), 8.59 (s, 1H), 7.76 (d, J=8.8 Hz, 2H), 7.43 (d, J=9.2 Hz, 2H), 7.33 (d, J=8.4 Hz, 2H), 6.91 (d, J=8.8 Hz, 2H), 5.49 (s, 2H), 3.71 (s, 3H). MS: m/z 427.0 (M+H⁺).

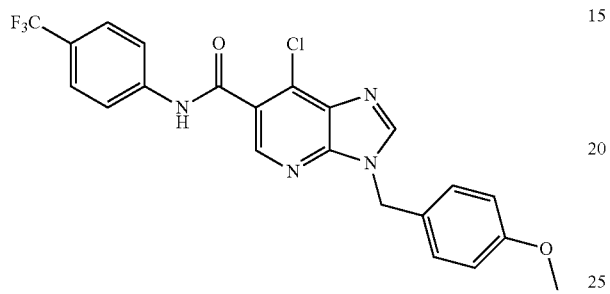

Example 323

7-Chloro-3-(4-methoxy-benzyl)-3H-imidazo[4,5-b]pyridine-6-carboxylic acid (4-trifluoromethyl-phenyl)-amide The title compound was prepared using general procedure for 7-chloro-N-(4-chlorophenyl)-3-methyl-3H-imidazo[4,5-b]pyridine-6-carboxamide (Example 306).

¹HNMR (400 MHz, DMSO-d6): δ=10.97 (s, 1H), 8.84 (s, 1H), 8.62 (s, 1H), 7.94 (d, J=8.8 Hz, 2H), 7.75 (d, J=8.4 Hz, 2H), 7.34 (d, J=8.4 Hz, 2H), 6.90 (d, J=8.8 Hz, 2H), 5.50 (s, 2H), 3.71 (s, 3H). MS: m/z 461.1 (M+H⁺).

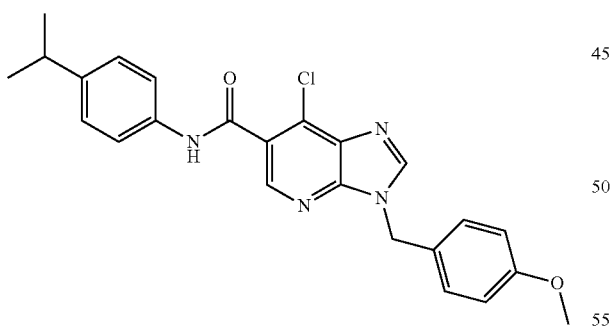

Example 324

7-Chloro-3-(4-methoxy-benzyl)-3H-imidazo[4,5-b]pyridine-6-carboxylic acid (4-isopropyl-phenyl)-amide The title compound was prepared using general procedure for 7-chloro-N-(4-chlorophenyl)-3-methyl-3H-imidazo[4,5-b]pyridine-6-carboxamide (Example 306). ¹HNMR (400 MHz, DMSO-d6): δ=10.51 (s, 1H), 8.81 (s, 1H), 8.55 (s, 1H), 7.63 (d, J=8.4 Hz, 2H), 7.33 (d, J=8.4 Hz, 2H), 7.23 (d, J=8.8 Hz, 2H), 6.90 (d, J=8.4 Hz, 2H), 5.49 (s, 2H), 3.71 (s, 3H), 2.89-2.85 (m, 1H), 1.20 (d, J=6.8 Hz, 6H). MS: m/z 435.1 (M+H⁺).

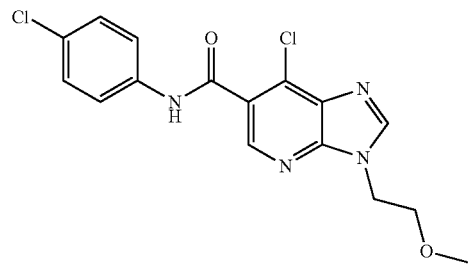 [SMILES: COCCn1cnc2c(Cl)c(C(=O)Nc3ccc(Cl)cc3)cnc21]

Example 325

7-Chloro-3-(2-methoxy-ethyl)-3H-imidazo[4,5-b]pyridine-6-carboxylic acid (4-chloro-phenyl)-amide The title compound was prepared using general procedure for 7-chloro-N-(4-chlorophenyl)-3-methyl-3H-imidazo[4,5-b]pyridine-6-carboxamide (Example 306).

¹HNMR (300 MHz, DMSO-d6): δ=10.77 (s, 1H), 8.64 (s, 1H), 8.59 (s, 1H), 7.77 (d, J=9.0 Hz, 2H), 7.44 (d, J=9.0 Hz, 2H), 4.51 (t, J=6.8 Hz, 2H), 3.76 (t, J=6.8 Hz, 2H), 3.23 (s, 3H). MS: m/z 365.0 (M+H⁺).

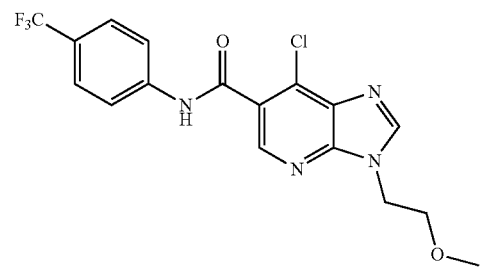 [SMILES: COCCn1cnc2c(Cl)c(C(=O)Nc3ccc(C(F)(F)F)cc3)cnc21]

Example 326

7-Chloro-3-(2-methoxy-ethyl)-3H-imidazo[4,5-b]pyridine-6-carboxylic acid (4-trifluoromethyl-phenyl)-amide The title compound was prepared using general procedure for 7-chloro-N-(4-chlorophenyl)-3-methyl-3H-imidazo[4,5-b]pyridine-6-carboxamide (Example 306).

¹HNMR (300 MHz, DMSO-d6): δ=11.00 (s, 1H), 8.66 (s, 1H), 8.62 (s, 1H), 7.95 (d, J=6.0 Hz, 2H), 7.76 (d, J=6.3 Hz, 2H), 4.52 (t, J=3.9 Hz, 2H), 3.77 (t, J=3.9 Hz, 2H), 3.24 (s, 3H). MS: m/z 399.1 (M+H⁺).

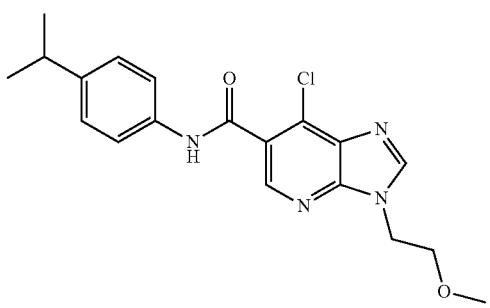 [SMILES: COCCn1cnc2c(Cl)c(C(=O)Nc3ccc(C(C)C)cc3)cnc21]

Example 327

7-Chloro-3-(2-methoxy-ethyl)-3H-imidazo[4,5-b]pyridine-6-carboxylic acid (4-isopropyl-phenyl)-amide The title compound was prepared using general procedure for 7-chloro-N-(4-chlorophenyl)-3-methyl-3H-imidazo[4,5-b]pyridine-6-carboxamide r (Example 306). $^1$HNMR (300 MHz, DMSO-d6): δ=10.54 (s, 1H), 8.63 (s, 1H), 8.55 (s, 1H), 7.64 (d, J=8.4 Hz, 2H), 7.24 (d, J=8.7 Hz, 2H), 4.51 (t, J=5.4 Hz, 2H), 3.76 (t, J=5.4 Hz, 2H), 3.23 (s, 3H), 2.90-2.85 (m, 1H), 1.20 (d, J=6.9 Hz, 6H). MS: m/z 373.1 (M+H$^+$).

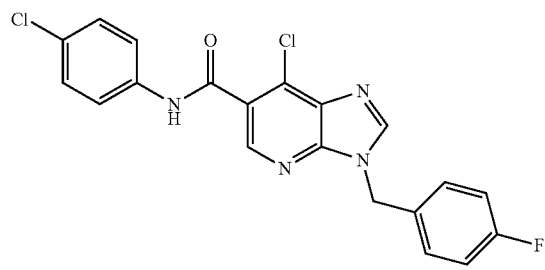 [SMILES: O=C(Nc1ccc(Cl)cc1)c1cnc2c(ncn2Cc2ccc(F)cc2)c1Cl]

Example 328

7-Chloro-3-(4-fluoro-benzyl)-3H-imidazo[4,5-b]pyridine-6-carboxylic acid (4-chloro-phenyl)-amide The title compound was prepared using general procedure for 7-chloro-N-(4-chlorophenyl)-3-methyl-3H-imidazo[4,5-b]pyridine-6-carboxamide (Example 306).
$^1$HNMR (400 MHz, DMSO-d6): δ=10.75 (s, 1H), 8.86 (s, 1H), 8.59 (s, 1H), 7.76 (d, J=8.8 Hz, 2H), 7.45-7.41 (m, 4H), 7.19 (t, J=9.2 Hz, 2H), 5.57 (s, 2H). MS: m/z 415.0 (M+H$^+$).

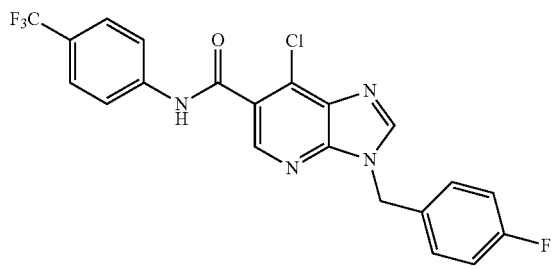 [SMILES: O=C(Nc1ccc(C(F)(F)F)cc1)c1cnc2c(ncn2Cc2ccc(F)cc2)c1Cl]

Example 329

7-Chloro-3-(4-fluoro-benzyl)-3H-imidazo[4,5-b]pyridine-6-carboxylic acid (4-trifluoromethyl-phenyl)-amide The title compound was prepared using general procedure for 7-chloro-N-(4-chlorophenyl)-3-methyl-3H-imidazo[4,5-b]pyridine-6-carboxamide (Example 306).
$^1$HNMR (400 MHz, DMSO-d6): δ=10.98 (s, 1H), 8.87 (s, 1H), 8.62 (s, 1H), 7.94 (d, J=8.4 Hz, 2H), 7.75 (d, J=8.4 Hz, 2H), 7.43 (dd, J=8.8 Hz, 5.6 Hz, 2H), 7.19 (t, J=8.8 Hz, 2H), 5.57 (s, 2H). MS: m/z 449.1 (M+H$^+$).

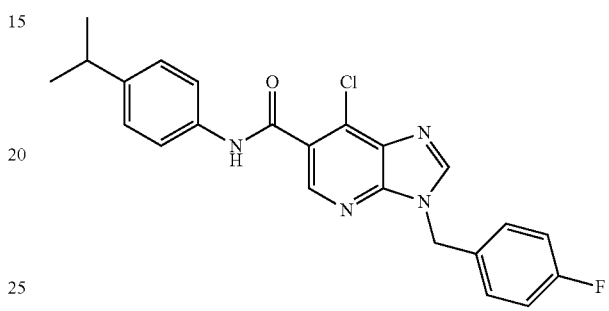

Example 330

7-Chloro-3-(4-fluoro-benzyl)-3H-imidazo[4,5-b]pyridine-6-carboxylic acid (4-isopropyl-phenyl)-amide The title compound was prepared using general procedure for 7-chloro-N-(4-chlorophenyl)-3-methyl-3H-imidazo[4,5-b]pyridine-6-carboxamide (Example 306). $^1$HNMR (400 MHz, DMSO-d6): δ=10.52 (s, 1H), 8.84 (s, 1H), 8.55 (s, 1H), 7.63 (d, J=8.4 Hz, 2H), 7.43 (dd, J=8.4 Hz, 5.6 Hz, 2H), 7.24-7.16 (4H), 5.56 (s, 2H), 2.89-2.85 (m, 1H), 1.20 (d, J=6.8 Hz, 6H). MS: m/z 423.1 (M+H$^+$).

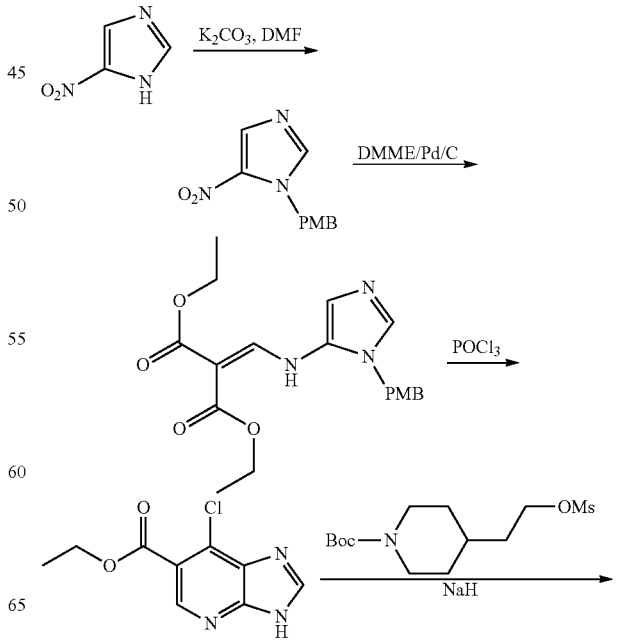

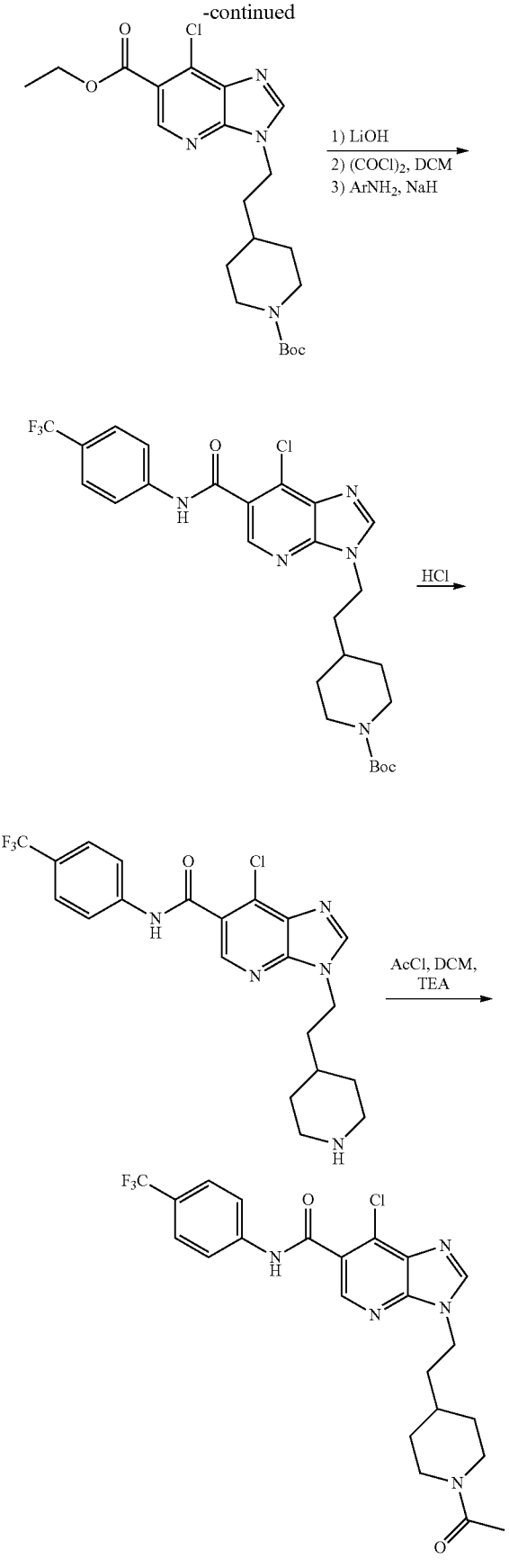

Example 331

7-chloro-3-(2-(piperidin-4-yl)ethyl)-N-(4-(trifluoromethyl)phenyl)-3H-imidazo[4,5-b]pyridine-6-carboxamide Step 1:

To a solution of 5-nitro-1H-imidazole (50 g, 442 mmol) in DMF (1 L) was added 1-chloromethyl-4-methoxy-benzene (75.8 g, 486 mmol) and $K_2CO_3$ (91 g, 663 mmol). The mixture was then heated to 60° C. and stirred overnight. Resultant was evaporated to remove DMF, then diluted with water (2 L) and EA (2 L) and stirred for 1 hr. Organic layer was concentrated under reduced pressure and the residue was purified by silica gel column (EA in PE: 0 to 30%) to afford 31 g (mixed with other isomer) of desired product which had 60% purity tracked by LCMS, MS: m/z 234.1 (M+H$^+$).

Step 2:

To a solution of 1-(4-methoxy-benzyl)-5-nitro-1H-imidazole (31 g, 133 mmol) in MeOH (1 L) was added Pd/C (10% wt; 10 g), it was then stirred under atmosphere of $H_2$ for 30 mins before diethyl 2-(ethoxymethylene)malonate (DMME in short, 28.7 g, 133 mmol) was injected. Then mixture was stirred under $H_2$ atmosphere at room temperature overnight. Resultant was filtrated to remove Pd/C and the filtrate was concentrated under reduced pressure. The residue was purified by flash column (EA in PE: 0 to 50%) to afford diethyl 2-(((1-(4-methoxybenzyl)-1H-imidazol-5-yl)amino)methylene)malonate (10 g, yield: 34%) as a brown honey-like solid. MS: m/z 374.1 (M+H$^+$).

Step 3:

A solution of 2-{[3-(4-methoxy-benzyl)-3H-imidazol-4-ylamino]-methylene}-malonic acid diethyl ester (10 g, 26.8 mmol) in $POCl_3$ (100 mL) was refluxed overnight. Resultant was evaporated to remove $POCl_3$. The residue was diluted with EA (300 mL) and water (300 mL), adjusted pH to 8 with solid $K_2CO_3$ while stirring. Then organic layer was concentrated under reduced pressure and the residue was purified by flash column (EA in PE: 0 to 100%) to afford diethyl 2-(((1-(4-methoxybenzyl)-1H-imidazol-5-yl)amino)methylene)malonate (5.4 g, yield: 90%) as a brown solid.

$^1$HNMR (400 MHz, DMSO-d6): δ=13.76 (s, 1H), 8.81 (s, 1H), 8.66 (s, 1H), 4.38 (q, J=7.2 Hz, 2H), 1.36 (t, J=7.2 Hz, 3H); MS: m/z 226.1 (M+H$^+$).

Step 4:

To a solution of diethyl 2-(((1-(4-methoxybenzyl)-1H-imidazol-5-yl)amino)methylene)malonate (2 g, 4.58 mmol) in DMF (30 mL) was added NaH (60%, 219 mg, 5.49 mmol) at 0° C. The mixture was stirred at room temperature for 30 mins before the addition of 4-(2-methanesulfonyloxy-ethyl)-piperidine-1-carboxylic acid tert-butyl ester (1.68 g, 5.49 mmol). The mixture was heated to 60° C. and stirred at this temperature overnight. Resultant was quenched with water (100 mL) and the aqueous phase was extracted with EA (150 mL). The extracts were concentrated under reduced pressure and purified by flash column (EA in PE: 0 to 50%) to afford ethyl 3-(2-(1-(tert-butoxycarbonyl)piperidin-4-yl)ethyl)-7-chloro-3H-imidazo[4,5-b]pyridine-6-carboxylate (1.2 g, yield: 31%) as a light brown solid, which was confirmed by NOE.

$^1$HNMR (400 MHz, DMSO-d6): δ=8.82 (s, 1H), 8.73 (s, 1H), 4.40-4.34 (m, 4H), 3.90-3.87 (m, 2H), 2.63-2.52 (m, 2H), 1.82-1.81 (m, 2H), 1.71-1.68 (m, 2H), 1.38-1.34 (m, 13H), 1.04-1.00 (m, 2H); MS: m/z 437.1 (M+H$^+$).

Step 5:

To a solution of ethyl 3-(2-(1-(tert-butoxycarbonyl)piperidin-4-yl)ethyl)-7-chloro-3H-imidazo[4,5-b]pyridine-6-carboxylate (1.2 g, 2.75 mmol) in THF/H₂O (5/1, 50 mL) was added LiOH.H₂O (577 mg, 13.7 mmol), it was then stirred at room temperature overnight. Resultant was evaporated to remove THF. The residue was diluted with water (20 mL) and adjusted pH to 2 with con. HCl. The aqueous phase was extracted with EA (100 mL). The organic layer was dried by Na₂SO₄ and concentrated to afford intermediate acid as a white solid. It was then dissolved in DCM (50 mL) followed by the addition of oxalyl chloride (419 mg, 3.3 mmol) and DMF (one drop). The mixture was stirred at room temperature over 1 hr. Then it was concentrated in vacuum to get acyl chloride. The above acyl chloride was dropped into a mixture of 4-trifluoromethyl-phenylamine (442 mg, 2.75 mmol) and NaH (60%, 143 mg, 3.57 mmol) in THF at 0° C. Then it was stirred at room temperature overnight. Resultant was quenched with water (50 mL) and the aqueous phase was extracted with EA (100 mL×2). The organic layer concentrated under reduced pressure and the residue was purified by flash column (EA in PE: 0 to 50%) to afford tert-butyl 4-(2-(7-chloro-6-((4-(trifluoromethyl)phenyl)carbamoyl)-3H-imidazo[4,5-b]pyridin-3-yl)ethyl)piperidine-1-carboxylate (480 mg, yield: 32%) as white solid.

Step 6:

To a solution of tert-butyl 4-(2-(7-chloro-6-((4-(trifluoromethyl)phenyl)carbamoyl)-3H-imidazo[4,5-b]pyridin-3-yl)ethyl)piperidine-1-carboxylate (480 mg, 0.87 mmol) in dioxane (50 mL) was added HCl (dissolved in EA, 4 M, 10 mL), it was then stirred at room temperature overnight. The white precipitate was collected by filtration to afford 7-chloro-3-(2-(piperidin-4-yl)ethyl)-N-(4-(trifluoromethyl)phenyl)-3H-imidazo[4,5-b]pyridine-6-carboxamide (350 mg, yield: 91%) as a white solid.

¹HNMR (400 MHz, DMSO-d6): δ=11.01 (s, 1H), 8.75 (s, 1H), 8.62 (s, 1H), 8.50 (brs, 1H), 8.21 (brs, 1H), 7.95 (d, J=8.4 Hz, 2H), 7.76 (d, J=8.4 Hz, 2H), 4.40-4.37 (m, 1H), 3.27-3.23 (m, 2H), 2.85-2.76 (m, 2H), 1.90-1.82 (m, 4H), 1.44-1.26 (m, 3H); MS: m/z 452.1 (M+H⁺).

Example 331a 3-(2-(1-acetylpiperidin-4-yl)ethyl)-7-chloro-N-(4-(trifluoromethyl)phenyl)-3H-imidazo[4,5-b]pyridine-6-carboxamide To a solution of 7-chloro-3-(2-(piperidin-4-yl)ethyl)-N-(4-(trifluoromethyl)phenyl)-3H-imidazo[4,5-b]pyridine-6-carboxamide (example 331, 100 mg, 0.22 mmol) in DCM (20 mL) was added acetyl chloride (21 mg, 0.26 mmol) and TEA (34 mg, 0.33 mmol). It was then stirred at room temperature overnight. Resultant was concentrated under reduced pressure and the residue was purified by pre-HPLC to afford 3-(2-(1-acetylpiperidin-4-yl)ethyl)-7-chloro-N-(4-(trifluoromethyl)phenyl)-3H-imidazo[4,5-b]pyridine-6-carboxamide (30 mg, yield: 28%) as a white solid.

¹HNMR (400 MHz, CD₃OD): 8.71 (d, J=8.0 Hz, 2H), 8.01 (d, J=8.0 Hz, 2H), 7.78 (d, J=8.4 Hz, 2H), 4.58-4.55 (m, 3H), 4.01-3.97 (m, 1H), 3.17-3.10 (m, 1H), 2.68-2.62 (m, 1H), 2.17 (s, 3H), 2.06-1.91 (m, 4H), 1.65-1.59 (m, 1H), 1.38-1.25 (m, 2H); MS: m/z 494.1 (M+H⁺).

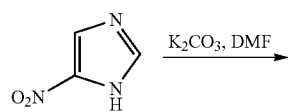

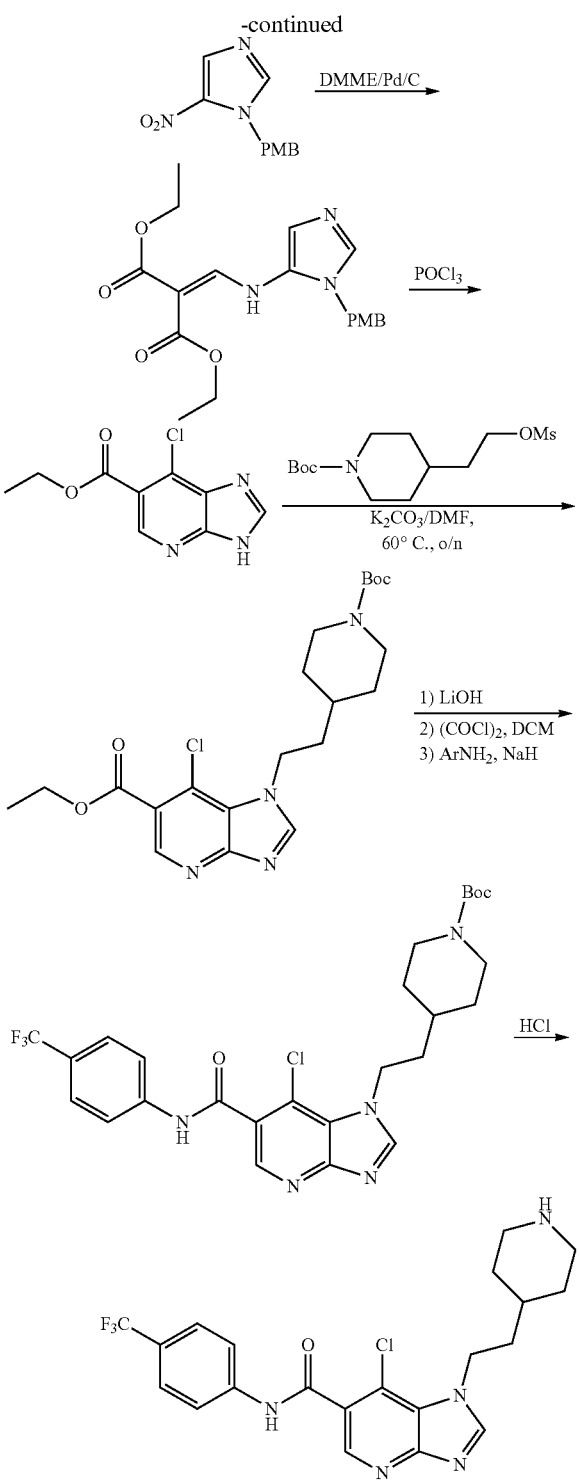

Example 332

7-chloro-1-(2-(piperidin-4-yl)ethyl)-N-(4-(trifluoromethyl)phenyl)-1H-imidazo[4,5-b]pyridine-6-carboxamide This route is the same as 3-(2-(1-acetylpiperidin-4-yl)ethyl)-7-chloro-N-(4-(trifluoromethyl)phenyl)-3H-imidazo[4,5-b]pyridine-6-carboxamide (Example 331) except the different condition of Step 4 (K₂CO₃, DMF, 60° C., overnight). It should be noted that its structure was confirmed by the NOE of its derivative of tert-butyl 4-(2-(7-ethoxy-6-((4-(trifluoromethyl)phenyl)carbamoyl)-1H-imidazo[4,5-b]pyridin-1-yl)ethyl)piperidine-1-carboxylate.

Analytical data of tert-butyl 4-(2-(7-ethoxy-6-((4-(trifluoromethyl)phenyl)carbamoyl)-1H-imidazo[4,5-b]pyridin-1-yl)ethyl)piperidine-1-carboxylate: ¹HNMR (300 MHz, CDCl): δ=9.01 (s, 1H), 8.68 (s, 1H), 8.16 (s, 1H), 7.87 (d, J=7.8 Hz, 2H), 7.64 (d, J=7.8 Hz, 2H), 4.36-4.31 (m, 2H), 4.10-4.05 (m, 2H), 3.08-3.05 (m, 2H), 2.60-2.58 (m, 2H), 1.91-1.86 (m, 2H), 1.73-1.69 (m, 2H), 1.48-1.34 (m, 13H), 1.18-1.10 (m, 2H). 7-chloro-1-(2-(piperidin-4-yl)ethyl)-N-(4-(trifluoromethyl)phenyl)-1H-imidazo[4,5-b]pyridine-6-carboxamide:

¹HNMR (400 MHz, CD₃OD): δ=8.66 (d, J=8.4 Hz, 2H), 7.96 (d, J=8.4 Hz, 2H), 7.72 (d, J=8.8 Hz, 2H), 4.72-4.69 (m, 2H), 3.44-3.41 (m, 2H), 3.06-2.99 (m, 2H), 2.09-1.97 (m, 4H), 1.79-1.75 (m, 1H), 1.57-1.50 (m, 2H); MS: m/z 452.1 (M+H⁺).

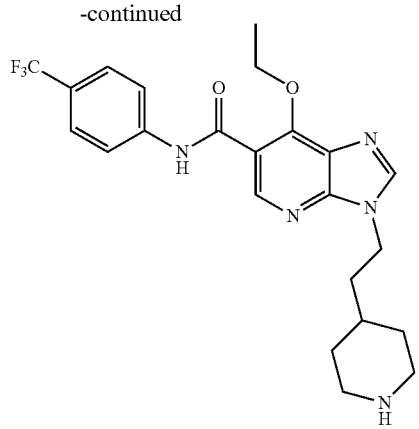

Example 333

7-ethoxy-3-(2-(piperidin-4-yl)ethyl)-N-(4-(trifluoromethyl)phenyl)-3H-imidazo[4,5-b]pyridine-6-carboxamide The title compound was prepared using general procedure for 4-ethoxy-3-methyl-1-(1-methylpiperidin-4-yl)-N-(4-(trifluoromethyl)phenyl)-1H-pyrazolo[3,4-b]pyridine-5-carboxamide (Example 181).

¹HNMR (400 MHz, CD₃OD): 8.78 (s, 1H), 8.37 (s, 1H), 7.92 (d, J=8.4 Hz, 2H), 7.69 (d, J=8.4 Hz, 2H), 5.25 (q, J=7.2 Hz, 2H), 4.44-4.40 (m, 2H), 3.40-3.39 (m, 2H), 2.99-2.93 (m, 2H), 2.10-2.07 (m, 2H), 1.98-1.93 (m, 2H), 1.62-1.58 (m, 4H), 1.51-1.47 (m, 2H); MS: m/z 462.2 (M+H⁺).

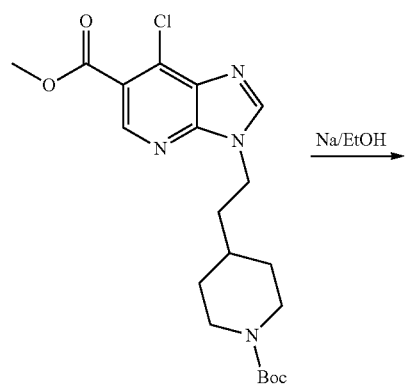

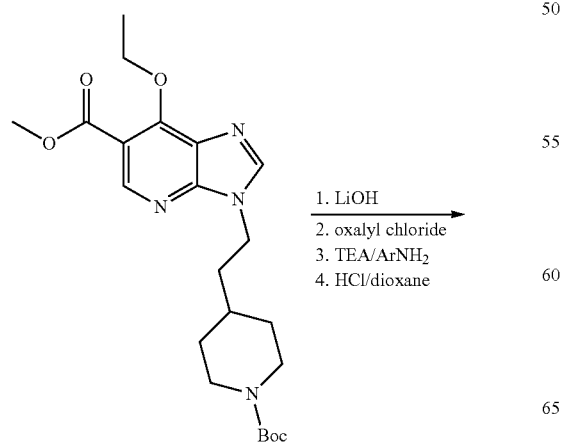

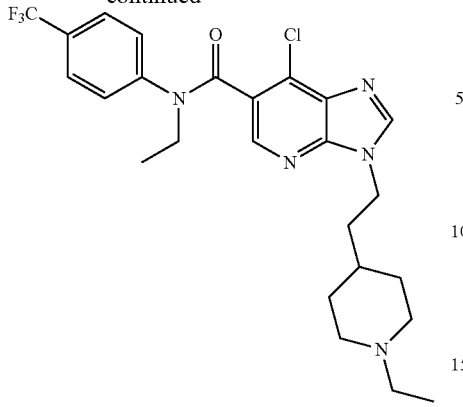

Example 334 and 335

7-chloro-3-(2-(1-ethylpiperidin-4-yl)ethyl)-N-(4-(trifluoromethyl)phenyl)-3H-imidazo[4,5-b]pyridine-6-carboxamide and 7-chloro-N-ethyl-3-(2-(1-ethylpiperidin-4-yl)ethyl)-N-(4-(trifluoromethyl)phenyl)-3H-imidazo[4,5-b]pyridine-6-carboxamide To a solution of 7-chloro-3-(2-(piperidin-4-yl)ethyl)-N-(4-(trifluoromethyl)phenyl)-3H-imidazo[4,5-b]pyridine-6-carboxamide (100 mg, 0.22 mmol) in DMF (10 mL) was added TEA (29 mg, 0.29 mmol) and iodoethane (37 mg, 0.24 mmol), it was stirred at room temperature overnight. Resultant was quenched with water (10 mL) and the aqueous phase was extracted with EA (30 mL). The organic layer was concentrated and purified by pre-HPLC to afford 7-chloro-3-(2-(1-ethylpiperidin-4-yl)ethyl)-N-(4-(trifluoromethyl)phenyl)-3H-imidazo[4,5-b]pyridine-6-carboxamide (Example 334) (12 mg, yield: 11%) and 7-chloro-N-ethyl-3-(2-(1-ethylpiperidin-4-yl)ethyl)-N-(4-(trifluoromethyl)phenyl)-3H-imidazo[4,5-b]pyridine-6-carboxamide (Example 335) (4.5 mg, yield: 4%) as white solid for both of them. 7-chloro-3-(2-(1-ethylpiperidin-4-yl)ethyl)-N-(4-(trifluoromethyl)phenyl)-3H-imidazo[4,5-b]pyridine-6-carboxamide (Example 334): $^1$HNMR (400 MHz, CD$_3$OD): 8.64 (d, J=9.2 Hz, 2H), 7.95 (d, J=8.4 Hz, 2H), 7.72 (d, J=8.8 Hz, 2H), 4.54-4.50 (m, 2H), 3.61-3.58 (m, 2H), 3.19-3.13 (m, 2H), 2.92-2.86 (m, 2H), 2.18-2.15 (m, 2H), 2.03-1.98 (m, 2H), 1.58-1.52 (m, 3H), 1.37-1.33 (m, 4H); MS: m/z 480.2(M+H$^+$). 7-chloro-N-ethyl-3-(2-(1-ethylpiperidin-4-yl)ethyl)-N-(4-(trifluoromethyl)phenyl)-3H-imidazo[4,5-b]pyridine-6-carboxamide (Example 335): $^1$HNMR (400 MHz, CD$_3$OD): 8.56 (brs, 2H), 8.35 (brs, 2H), 7.56-7.50 (m, 4H), 4.38 (brs, 2H), 4.10 (brs, 2H), 3.58-3.55 (m, 2H), 3.17-3.12 (m, 2H), 2.88-2.82 (m, 2H), 2.09-2.06 (m, 2H), 1.91 (brs, 2H), 1.52-1.48 (m, 3H), 1.36-1.32 (m, 6H); MS: m/z 508.2.

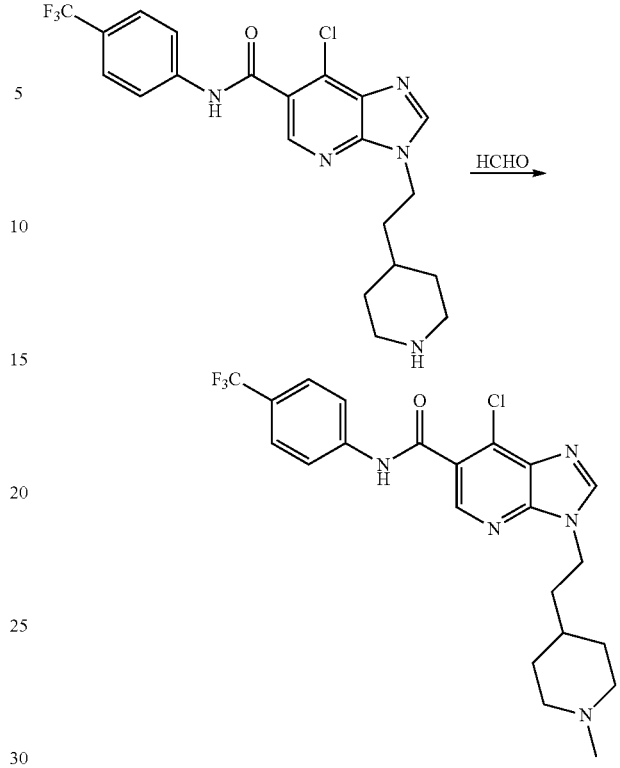

Example 336

7-chloro-3-(2-(1-methylpiperidin-4-yl)ethyl)-N-(4-(trifluoromethyl)phenyl)-3H-imidazo[4,5-b]pyridine-6-carboxamide To a solution of 7-chloro-3-(2-(piperidin-4-yl)ethyl)-N-(4-(trifluoromethyl)phenyl)-3H-imidazo[4,5-b]pyridine-6-carboxamide (100 mg, 0.22 mmol) in MeOH (10 mL) was added formaldehyde (35% in water, 53 mg, 0.66 mmol) and the mixture was stirred for 1 hr before NaBH$_3$CN (66 mg, 1.1 mmol) was added. Then it was stirred at room temperature overnight. Resultant was concentrated and the residue was diluted with water (20 mL). The aqueous phase was extracted with EA (20 mL). The organic layer was concentrated in vacuum and the residue was purified by prep-HPLC to afford 7-chloro-3-(2-(1-methylpiperidin-4-yl)ethyl)-N-(4-(trifluoromethyl)phenyl)-3H-imidazo[4,5-b]pyridine-6-carboxamide as a white solid. It should be mentioned that the mass value showed by LCMS 504.9 is not the same as calculated mass value (MS: m/z 466.1 (M+H$^+$)).

$^1$HNMR (400 MHz, CD$_3$OD): 8.49 (s, 1H), 8.40 (s, 1H), 7.95 (d, J=8.4 Hz, 2H), 7.72 (d, J=8.8 Hz, 2H), 4.51-4.48 (m, 2H), 3.20-3.17 (m, 2H), 2.72-2.70 (m, 5H), 2.05-1.99 (m, 2H), 1.89-1.83 (m, 4H), 1.48-1.52 (m, 1H); MS: m/z 480.2 (M+H$^+$).

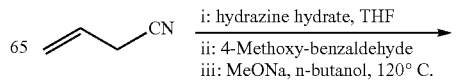

i: hydrazine hydrate, THF
ii: 4-Methoxy-benzaldehyde
iii: MeONa, n-butanol, 120° C.

-continued

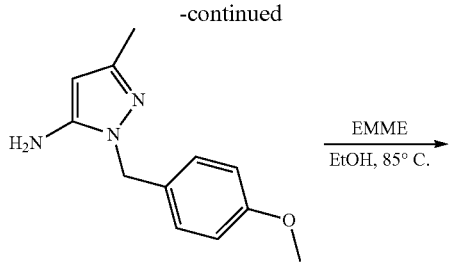

EMME
EtOH, 85° C.

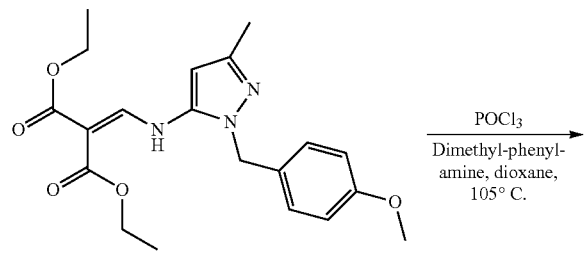

POCl₃
Dimethyl-phenyl-
amine, dioxane,
105° C.

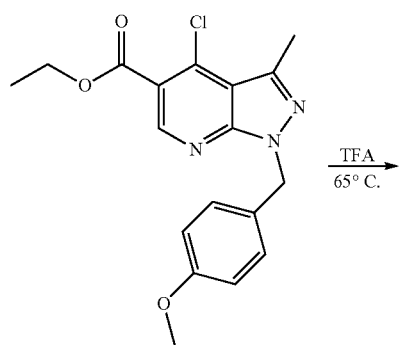

TFA
65° C.

K₂CO₃, DMF
65° C.

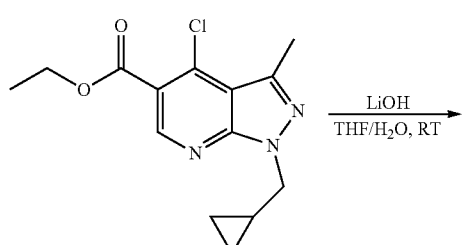

LiOH
THF/H₂O, RT

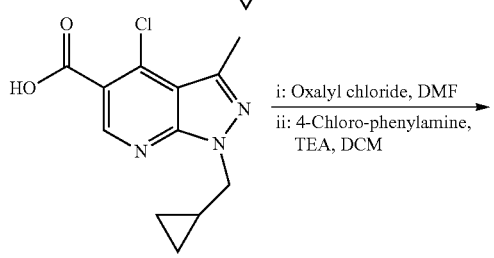

i: Oxalyl chloride, DMF
ii: 4-Chloro-phenylamine,
TEA, DCM

-continued

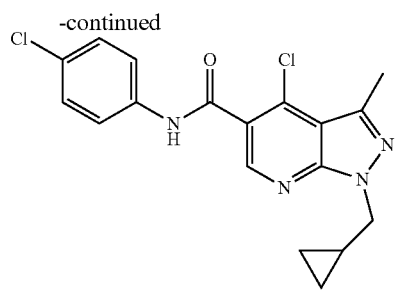

Example 337

4-Chloro-1-cyclopropylmethyl-3-methyl-1H-pyra-zolo[3,4-b]pyridine-5-carboxylic acid (4-chloro-phenyl)-amide Step 1

To a solution of allyl cyanide (50 g, 746 mmol) in THF (200 mL) was added hydrazine monohydrate (39.2 g, 38 mL, 784 mmol) slowly at 0° C. under N₂. The reaction mixture was stirred at room temperature overnight. Then 4-methoxy-benzaldehyde (106.5 g, 784 mmol) was added slowly and the mixture was stirred at room temperature for 8 hrs. After that, the solution was concentrated to dryness under reduced pressure and the crude was co-evaporated to remove remaining moisture in the presence of EtOH. n-BuOH (700 mL) and NaOMe (40.3 g, 746 mmol) were added to the residue. The mixture was stirred at 120° C. overnight. The reaction solution was poured into water (1 L) and the aq. phase was extracted with ether (1 L×2). The extracts were treated with 1 N HCl (1 L'2). The aqueous phase was adjusted with aq. NaOH to pH=14 followed by the extracting with DCM (1 L×2). The organic layer was washed with brine (1 L) and dried over Na₂SO₄. The solution was concentrated in vacuum to give 1-(4-methoxybenzyl)-3-methyl-1H-pyrazol-5-amine (98 g, yield: 60%) as a yellow solid. ¹HNMR (400 MHz, CDCl₃): δ=7.11 (d, J=8.4 Hz, 2H), 6.85 (d, J=8.8 Hz, 2H), 5.36 (s, 1H), 5.07 (s, 2H), 3.77 (s, 3H), 3.34 (brs, 2H), 2.18 (s, 3H).

Step 2

A solution of 2-(4-methoxy-benzyl)-5-methyl-2H-pyra-zol-3-ylamine (98 g, 0.45 mol) and 2-ethoxymethylene-malonic acid diethyl ester (98 g, 0.45 mol) in EtOH (800 mL) was stirred at 85° C. overnight. The starting material was consumed almost completely by TLC. The mixture was concentrated to give the crude 2-{[2-(4-methoxy-benzyl)-5-methyl-2H-pyrazol-3-ylamino]-methylene}-malonic acid diethyl ester (187 g, quantitative yield) as a yellow crystal. MS: m/z 388.1 (M+H⁺).

Step 3

A solution of 2-{[2-(4-methoxy-benzyl)-5-methyl-2H-pyrazol-3-ylamino]-methylene}-malonic acid diethyl ester (187 g, 0.48 mmol), dimethyl-phenyl-amine (174 g, 1.44 mol) and POCl₃ (589 g, 3.84 mol) in dioxane (1.5 L) stirred at 105° C. overnight. Then the reaction mixture was concentrated in vacuum. The residue was poured into sat-.NaHCO₃ solution (3 L) carefully and the aqueous phase was extracted with EA (1 L×2). The organic layers were combined, dried over Na₂SO₄ and concentrated. The residue was purified by silica gel column (PE/EA=16/1) to give 4-chloro-1-(4-methoxy-benzyl)-3-methyl-1H-pyrazolo[3,4-b]pyridine-5-carboxylic acid ethyl ester (73 g, yield: 45%) as a white solid. ¹HNMR (400 MHz, CDCl₃): δ=8.97 (s, 1H), 7.29 (d, J=8.4 Hz, 2H), 6.82 (d, J=8.4 Hz, 2H), 5.45 (s, 2H), 4.44 (q, J=7.2 Hz, 2H), 3.76 (s, 3H), 2.74 (s, 3H), 1.43 (t, J=7.2 Hz, 3H). MS: m/z 359.9 (M+H$^+$).

Step 4

A solution of 4-chloro-1-(4-methoxy-benzyl)-3-methyl-1H-pyrazolo[3,4-b]pyridine-5-carboxylic acid ethyl ester (15 g, 41.78 mmol) in TFA (150 mL) was stirred at 65° C. for 110 mins. The starting material was consumed almost completely by TLC. Then the reaction mixture was concentrated, the residue was treated with sat.NaHCO$_3$ solution (500 mL). The aqueous was extracted with EA (500 mL). The organic layer was washed with water (500 mL) and brine (500 mL), dried over Na$_2$SO$_4$, concentrated to give crude 4-chloro-3-methyl-1H-pyrazolo[3,4-b]pyridine-5-carboxylic acid ethyl ester (crude 15 g, yield: quantitative) as a yellow solid.

MS: m/z 239.9 (M+H$^+$).

Step 5

A mixture of 4-chloro-3-methyl-1H-pyrazolo[3,4-b]pyridine-5-carboxylic acid ethyl ester (240 mg, 1 mmol), bromomethyl-cyclopropane (176 mg, 1.3 mmol) and K$_2$CO$_3$ (345 mg, 2.5 mmol) in DMF (5 mL) was stirred at 65° C. for 1 hr. The starting material was consumed almost completely by TLC. The mixture was poured into water (25 mL) and extracted with EA (20 mL). The organic layer was washed with water (15 mL) and brine (15 mL), dried over Na$_2$SO$_4$ and concentrated. The residue was purified by silica gel column (PE/EA=8/1) to give 4-chloro-1-cyclopropylmethyl-3-methyl-1H-pyrazolo[3,4-b]pyridine-5-carboxylic acid ethyl ester (100 mg, yield: 34%) as a white semi-solid.

MS: m/z 293.9 (M+H$^+$)

Step 6

A mixture of 4-chloro-1-cyclopropylmethyl-3-methyl-1H-pyrazolo[3,4-b]pyridine-5-carboxylic acid ethyl ester (100 mg, 0.34 mmol) and LiOH.H$_2$O (57 mg, 1.37 mmol) in THF/H$_2$O (4:1, 5 mL) was stirred at room temperature overnight. The reaction solution was acidified with conc. HCl to pH=5 and partitioned between EA (20 mL) and water (10 mL). The organic layer was washed with brine (10 mL), dried over Na$_2$SO$_4$ and concentrated to give 4-chloro-1-cyclopropylmethyl-3-methyl-1H-pyrazolo[3,4-b]pyridine-5-carboxylic acid (90 mg, quantitative yield) as a white solid.

Step 7

To a suspension of 4-chloro-1-cyclopropylmethyl-3-methyl-1H-pyrazolo[3,4-b]pyridine-5-carboxylic acid (30 mg, 0.112 mmol) in oxalyl chloride (5 mL) was added a drop of DMF. The reaction mixture was stirred at room temperature for 1 hr and concentrated to give the acyl chloride. The acyl chloride was dissolved in dry DCM (5 mL). To the solution, was added 4-chloro-phenylamine (18 mg, 0.14 mmol), followed by TEA (0.1 mL). After stirring overnight at room temperature, the mixture was partitioned between sat.NaHCO$_3$ solution (15 mL) and DCM (15 mL). The organic layer was dried over Na$_2$SO$_4$, concentrated and purified by prep-TLC (DCM/EA=6/1) to give 4-chloro-1-cyclopropylmethyl-3-methyl-1H-pyrazolo[3,4-b]pyridine-5-carboxylic acid (4-chloro-phenyl)-amide (18 mg, yield: 43%) as a white solid. $^1$HNMR (400 MHz, CDCl$_3$): δ=8.78 (s, 1H), 7.93 (brs, 1H), 7.62 (d, J=8.4 Hz, 2H), 7.36 (d, J=8.8 Hz, 2H), 4.32 (d, J=6.8 Hz, 2H), 2.77 (s, 3H), 1.41-1.37 (m, 1H), 0.57-0.52 (m, 2H), 0.47-0.43 (m, 2H). MS: m/z 375.0 (M+H$^+$)

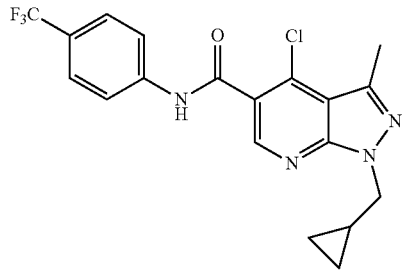 [SMILES: Cc1nn(CC2CC2)c2ncc(C(=O)Nc3ccc(C(F)(F)F)cc3)c(Cl)c12]

Example 338

4-Chloro-1-cyclopropylmethyl-3-methyl-1H-pyrazolo[3,4-b]pyridine-5-carboxylic acid (4-trifluoromethyl-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337). $^1$HNMR (400 MHz, CDCl$_3$): δ=8.80 (s, 1H), 8.08 (brs, 1H), 7.79 (d, J=8.0 Hz, 2H), 7.66 (d, J=8.4 Hz, 2H), 4.33 (d, J=7.2 Hz, 2H), 2.78 (s, 3H), 1.41-1.37 (m, 1H), 0.57-0.53 (m, 2H), 0.47-0.43 (m, 2H). MS: m/z 409.1 (M+H$^+$)

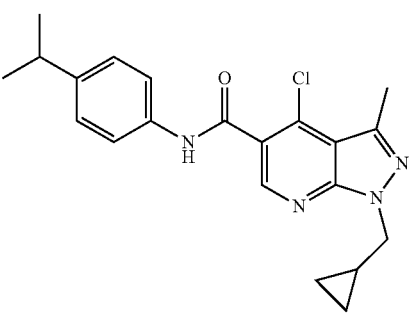 [SMILES: Cc1nn(CC2CC2)c2ncc(C(=O)Nc3ccc(C(C)C)cc3)c(Cl)c12]

Example 339

4-Chloro-1-cyclopropylmethyl-3-methyl-1H-pyrazolo[3,4-b]pyridine-5-carboxylic acid (4-isopropyl-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337).

$^1$HNMR (400 MHz, CDCl$_3$): δ=8.79 (s, 1H), 7.83 (brs, 1H), 7.57 (d, J=8.4 Hz, 2H), 7.26 (overlap, 2H), 4.32 (d, J=7.2 Hz, 2H), 2.94-2.90 (m, 1H), 2.78 (s, 3H), 1.41-1.37 (m, 1H), 1.27-1.25 (m, 6H), 0.57-0.52 (m, 2H), 0.47-0.44 (m, 2H). MS: m/z 383.1 (M+H$^+$)

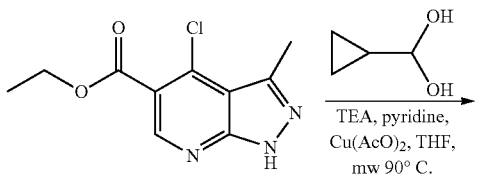

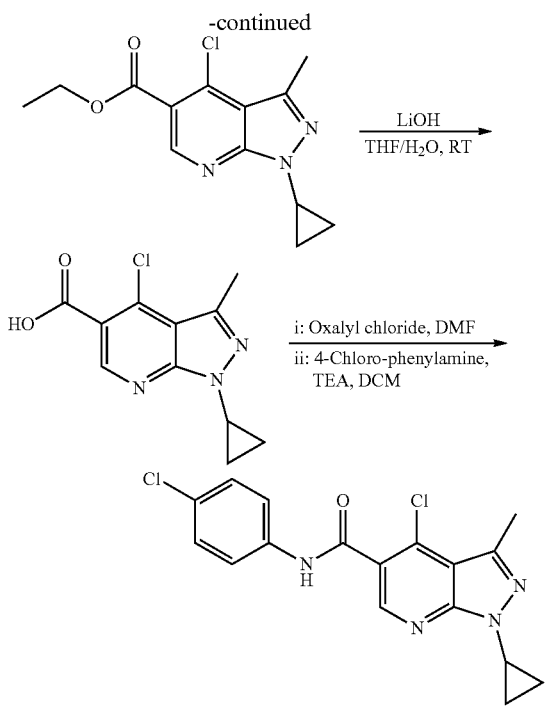

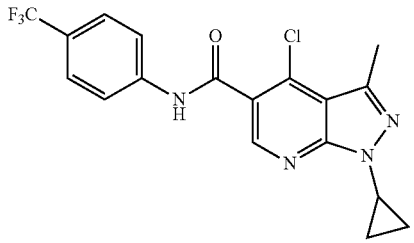 [SMILES: Cc1nn(C2CC2)c2ncc(C(=O)Nc3ccc(C(F)(F)F)cc3)c(Cl)c12]

Example 341

4-Chloro-1-cyclopropyl-3-methyl-1H-pyrazolo[3,4-b]pyridine-5-carboxylic acid (4-trifluoromethyl-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337).

$^1$HNMR (400 MHz, CDCl$_3$): δ=8.85 (s, 1H), 8.07 (brs, 1H), 7.79 (d, J=8.4 Hz, 2H), 7.66 (d, J=8.8 Hz, 2H), 3.84-3.79 (m, 1H), 2.73 (s, 3H), 1.33-1.29 (m, 2H), 1.21-1.16 (m, 2H). MS: m/z 395.1 (M+H$^+$).

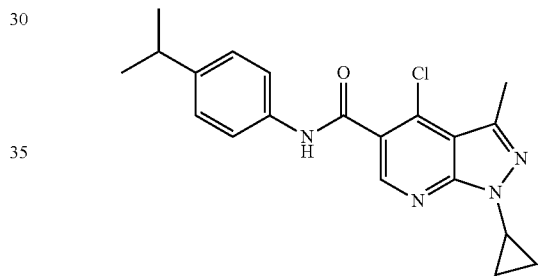

Example 342

4-Chloro-1-cyclopropyl-3-methyl-1H-pyrazolo[3,4-b]pyridine-5-carboxylic acid (4-isopropyl-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337).

$^1$HNMR (400 MHz, CDCl$_3$): δ=8.83 (s, 1H), 7.84 (brs, 1H), 7.57 (d, J=8.4 Hz, 2H), 7.26 (overlap, 2H), 3.82-3.785 (m, 1H), 2.95-2.89 (m, 1H), 2.73 (s, 3H), 1.32-1.15 (m, 10H). MS: m/z 369.1 (M+H$^+$)

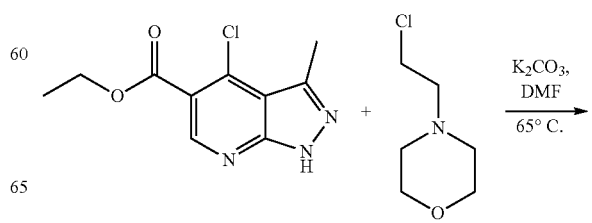

Example 340

4-Chloro-1-cyclopropyl-3-methyl-1H-pyrazolo[3,4-b]pyridine-5-carboxylic acid (4-chloro-phenyl)-amide Step 1

A mixture of 4-chloro-3-methyl-1H-pyrazolo[3,4-b]pyridine-5-carboxylic acid ethyl ester (300 mg, 1.26 mmol), cyclopropyl boronic acid (324 mg, 3.76 mmol), TEA (730 mg, 7.2 mmol), pyridine (1 g, 12.6 mmol) and Cu(AcO)$_2$ (114 mg, 0.63 mmol) in THF (8 mL) was stirred at 90° C. under microwave for 0.5 h.

The reaction was worked up together with another batch (120 mg). The reaction mixture was filtered. The filtrate was partitioned between 1N HCl (40 mL) and EA (40 mL). The organic layer was washed with water (30 mL) and brine (30 mL), dried over Na$_2$SO$_4$ and concentrated to dryness in vacuum. The residue was purified by silica gel column (PE/EA=8/1) to give 4-chloro-1-cyclopropyl-3-methyl-1H-pyrazolo[3,4-b]pyridine-5-carboxylic acid ethyl ester (110 mg, yield: 22%) as a white solid. $^1$HNMR (400 MHz, CDCl$_3$): δ=8.97 (s, 1H), 4.44 (q, J=7.2 Hz, 2H), 3.80-3.76 (m, 1H), 2.73 (s, 3H), 1.43 (t, J=7.2 Hz, 3H), 1.30-1.27 (m, 2H), 1.20-1.16 (m, 2H).

Step 2 and 3

These two steps are similar to general procedure for 4-chloro-1-cyclopropylmethyl-3-methyl-1H-pyrazolo[3,4-b]pyridine-5-carboxylic acid (4-chloro-phenyl)-amide (Example 337).

$^1$HNMR (400 MHz, DMSO-d6): δ=10.74 (brs, 1H), 8.69 (s, 1H), 7.75 (d, J=8.8 Hz, 2H), 7.44 (d, J=8.8 Hz, 2H), 3.92-3.86 (m, 1H), 2.65 (s, 3H), 1.19-1.09 (m, 4H). MS: m/z 361.0 (M+H$^+$).

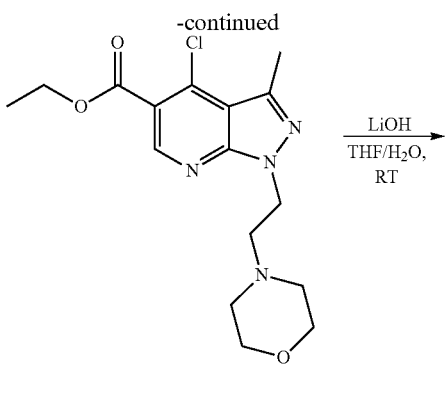

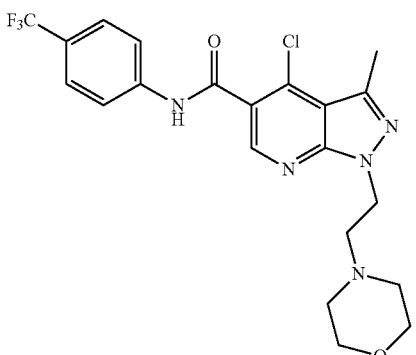

Example 344

4-Chloro-3-methyl-1-(2-morpholin-4-yl-ethyl)-1H-pyrazolo[3,4-b]pyridine-5-carboxylic acid (4-trifluoromethyl-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337). $^1$HNMR (400 MHz, CDCl$_3$): δ=8.81 (s, 1H), 8.08 (brs, 1H), 7.80 (d, J=8.4 Hz, 2H), 7.67 (d, J=8.4 Hz, 2H), 4.59 (t, J=6.6 Hz, 2H), 3.61 (t, J=4.4 Hz, 4H), 2.89 (t, J=6.4 Hz, 2H), 2.77 (s, 3H), 2.54-2.52 (m, 4H). MS: m/z 468.1 (M+H$^+$).

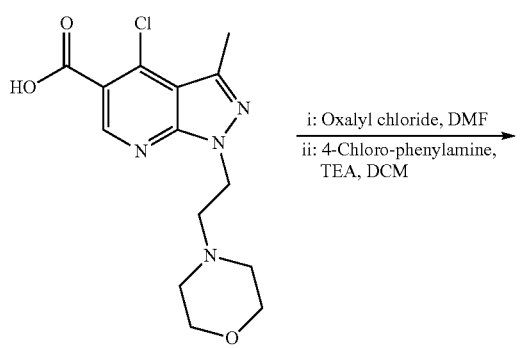

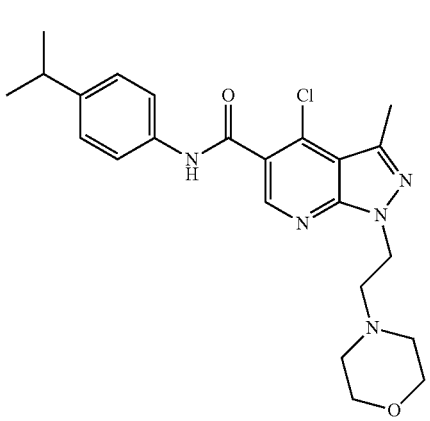 [SMILES: Cc1nn(CCN2CCOCC2)c2ncc(C(=O)Nc3ccc(C(C)C)cc3)c(Cl)c12]

Example 343

4-Chloro-3-methyl-1-(2-morpholin-4-yl-ethyl)-1H-pyrazolo[3,4-b]pyridine-5-carboxylic acid (4-chloro-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337). $^1$HNMR (400 MHz, CDCl$_3$): δ=8.78 (s, 1H), 7.98 (brs, 1H), 7.62 (d, J=8.4 Hz, 2H), 7.36 (d, J=8.4 Hz, 2H), 4.58 (t, J=6.8 Hz, 2H), 3.61 (t, J=4.4 Hz, 4H), 2.88 (t, J=6.8 Hz, 2H), 2.76 (s, 3H), 2.53 (t, J=4.4 Hz, 4H). MS: m/z 434.1 (M+H$^+$).

Example 345

4-Chloro-3-methyl-1-(2-m orpholin-4-yl-ethyl)-1H-pyrazolo[3,4-b]pyridine-5-carboxylic acid (4-isopropyl-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337). $^1$HNMR (400 MHz, CDCl$_3$): δ=8.79 (s, 1H), 7.84 (brs, 1H), 7.57 (d, J=8.0 Hz, 2H), 7.26 (overlap, 2H), 4.58 (t, J=6.6 Hz, 2H), 3.61 (t, J=4.4 Hz, 4H), 2.94-2.86 (m, 3H), 2.76 (s, 3H), 2.53 (t, J=4.2 Hz, 4H), 1.27-1.22 (m, 6H). MS: m/z 442.2 (M+H$^+$).

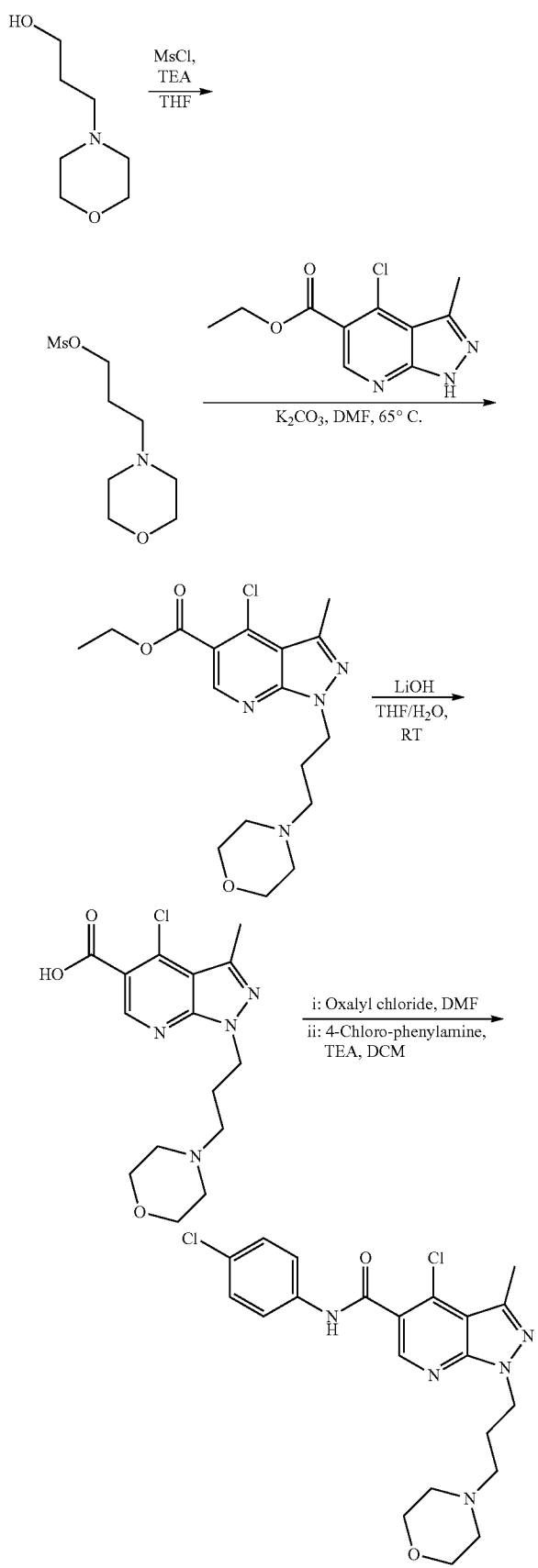

Example 346

4-Chloro-3-methyl-1-(3-morpholin-4-yl-propyl)-1H-pyrazolo[3,4-b]pyridine-5-carboxylic acid (4-chloro-phenyl)-amide Step 1 and 2

To a solution of 3-morpholin-4-yl-propan-1-ol (412 mg, 2.82 mmol) and TEA (854 mg, 8.46 mmol) in THF (10 mL) was added MsCl (356 mg, 3.1 mmol) at 0° C. under $N_2$. After stirring at room temperature for 1 hr, the reaction mixture was filtered. The filtrate was concentrated to give methanesulfonic acid 3-morpholin-4-yl-propyl ester. The freshly prepared methanesulfonic acid 3-morpholin-4-yl-propyl ester was mixed with 4-chloro-3-methyl-1H-pyrazolo[3,4-b]pyridine-5-carboxylic acid ethyl ester (404 mg, 1.69 mmol) and $K_2CO_3$ (1.17 g, 8.46 mmol) in DMF (15 mL). The mixture was stirred at 65° C. for 1 hr. The starting material was consumed almost completely by TLC. The mixture was poured into water (60 mL) and extracted with EA (50 mL). The organic layer was washed with water (50 mL) and brine (50 mL), dried over $Na_2SO_4$ and concentrated. The residue was purified by silica gel column (DCM/MeOH/TEA=20/1/0.2) to give 4-chloro-3-methyl-1-(3-morpholin-4-yl-propyl)-1H-pyrazolo[3,4-b]pyridine-5-carboxylic acid ethyl ester (90 mg, yield: 15%) as a yellow oil.

Step 3-4

These two steps are similar to general procedure for 4-chloro-1-cyclopropylmethyl-3-methyl-1H-pyrazolo[3,4-b]pyridine-5-carboxylic acid (4-chloro-phenyl)-amide (Example 337). $^1$HNMR (400 MHz, $CDCl_3$): δ=8.79 (s, 1H), 7.97 (brs, 1H), 7.62 (d, J=8.0 Hz, 2H), 7.37 (d, J=8.8 Hz, 2H), 4.52 (t, J=7.2 Hz, 2H), 3.66 (t, J=4.4 Hz, 4H), 2.76 (s, 3H), 2.40-2.37 (m, 6H), 2.15-2.09 (m, 2H). MS: m/z 448.1 (M+H$^+$)

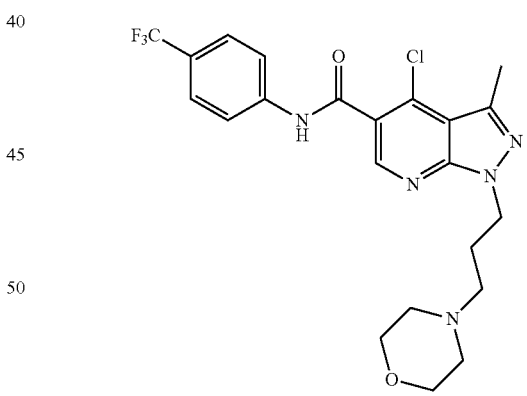

Example 347

4-Chloro-3-methyl-1-(3-morpholin-4-yl-propyl)-1H-pyrazolo[3,4-b]pyridine-5-carboxylic acid (4-trifluoromethyl-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337). $^1$HNMR (400 MHz, $CDCl_3$): δ=8.80 (s, 1H), 8.18 (brs, 1H), 7.81 (d, J=8.4 Hz, 2H), 7.66 (d, J=8.4

Hz, 2H), 4.53 (t, J=6.8 Hz, 2H), 3.68 (t, J=4.6 Hz, 4H), 2.76 (s, 3H), 2.44-2.41 (m, 6H), 2.15-2.12 (m, 2H). MS: m/z 482.1 (M+H$^+$).

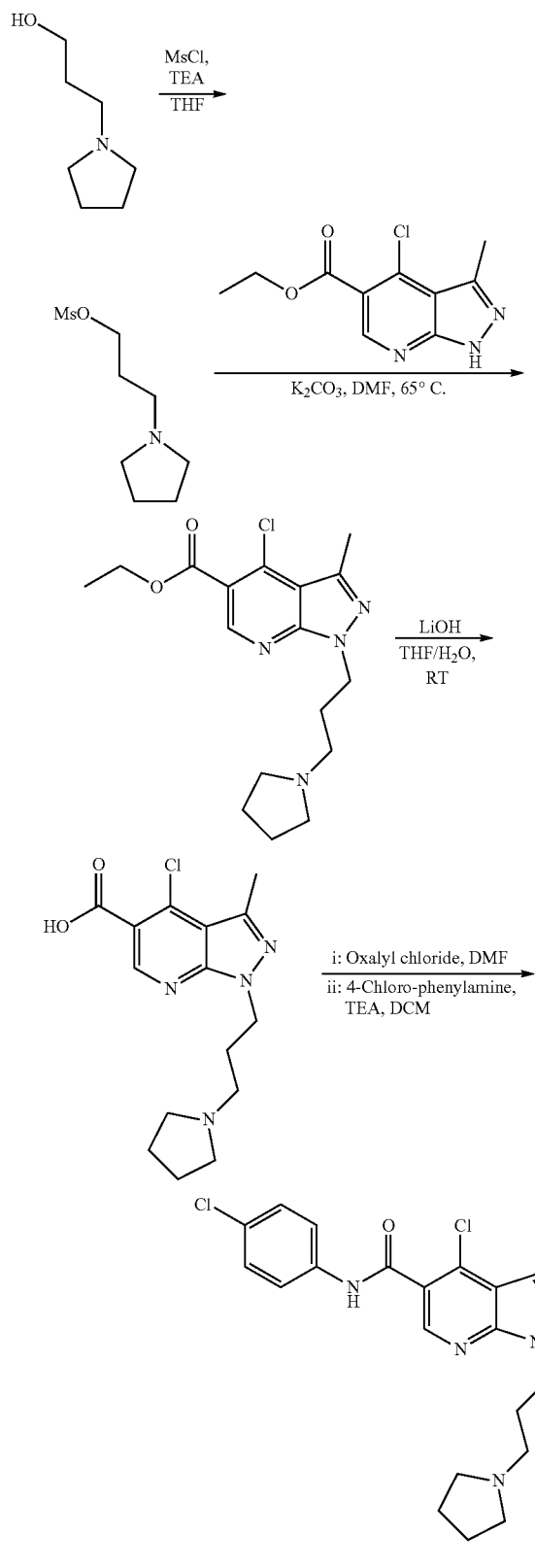

Example 348

4-Chloro-3-methyl-1-(3-pyrrolidin-1-yl-propyl)-1H-pyrazolo[3,4-b]pyridine-5-carboxylic acid (4-chloro-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337). $^1$HNMR (300 MHz, CDCl$_3$): δ=8.78 (s, 1H), 8.12 (brs, 1H), 7.64 (d, J=8.7 Hz, 2H), 7.37 (d, J=9.0 Hz, 2H), 4.53 (t, J=6.9 Hz, 2H), 2.76 (s, 3H), 2.56-2.51 (m, 6H), 2.23-2.13 (m, 2H), 1.82-1.77 (m, 4H). MS: m/z 432.1 (M+H$^+$).

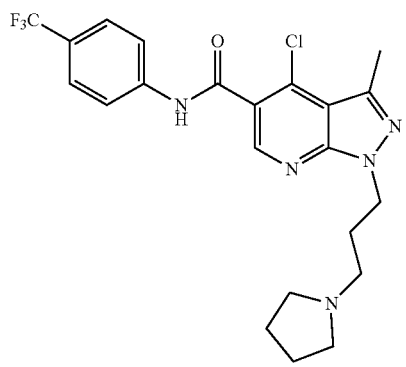 [SMILES: Cc1nn(CCCN2CCCC2)c2ncc(C(=O)Nc3ccc(C(F)(F)F)cc3)c(Cl)c12]

Example 349

4-Chloro-3-methyl-1-(3-pyrrolidin-1-yl-propyl)-1H-pyrazolo[3,4-b]pyridine-5-carboxylic acid (4-trifluoromethyl-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337). $^1$HNMR (300 MHz, CDCl$_3$): δ=8.80 (s, 1H), 8.27 (brs, 1H), 7.83 (d, J=8.1 Hz, 2H), 7.68 (d, J=8.4 Hz, 2H), 4.55 (t, J=6.9 Hz, 2H), 2.77 (s, 3H), 2.67-2.60 (m, 6H), 2.27-2.22 (m, 2H), 1.88-1.83 (m, 4H). MS: m/z 466.1 (M+H$^+$).

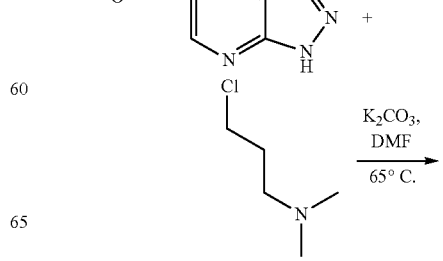

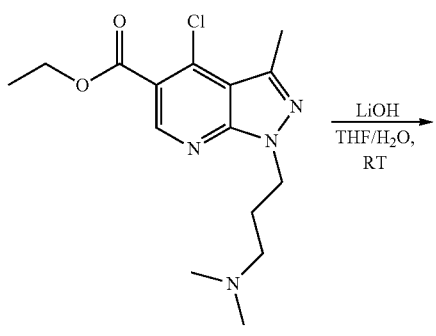

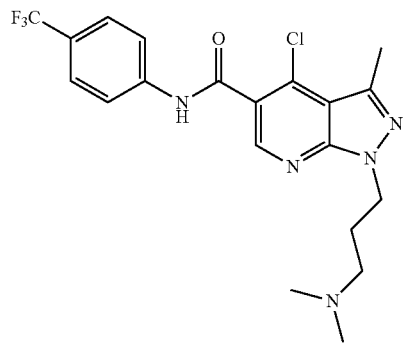 [SMILES: Cc1nn(CCCN(C)C)c2ncc(C(=O)Nc3ccc(C(F)(F)F)cc3)c(Cl)c12]

Example 351

4-Chloro-1-(3-dimethylamino-propyl)-3-methyl-1H-pyrazolo[3,4-b]pyridine-5-carboxylic acid (4-trifluoromethyl-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337). $^1$HNMR (400 MHz, CDCl$_3$): δ=8.80 (s, 1H), 8.16 (brs, 1H), 7.80 (d, J=8.4 Hz, 2H), 7.66 (d, J=8.8 Hz, 2H), 4.52 (t, J=7.2 Hz, 2H), 2.76 (s, 3H), 2.34 (t, J=7.2 Hz, 2H), 2.25 (s, 6H), 2.15-2.10 (m, 2H). MS: m/z 440.1 (M+H$^+$).

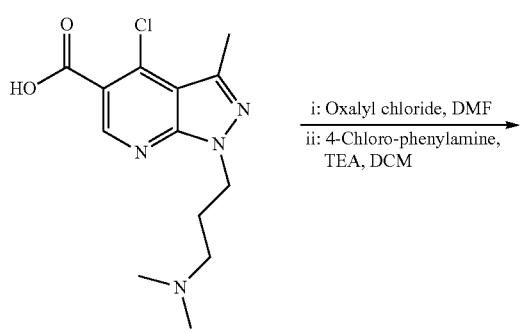

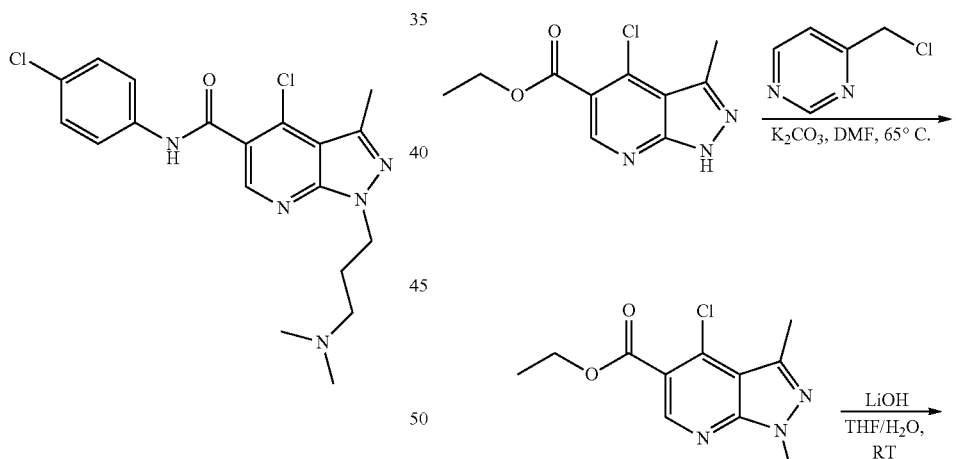

Example 350

4-Chloro-1-(3-dimethylamino-propyl)-3-methyl-1H-pyrazolo[3,4-b]pyridine-5-carboxylic acid (4-chloro-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337). $^1$HNMR (400 MHz, CDCl$_3$): δ=8.79 (s, 1H), 7.98 (brs, 1H), 7.62 (d, J=8.8 Hz, 2H), 7.37 (d, J=8.4 Hz, 2H), 4.51 (t, J=6.8 Hz, 2H), 2.76 (s, 3H), 2.32 (t, J=7.2 Hz, 2H), 2.23 (s, 6H), 2.13-2.08 (m, 2H). MS: m/z 406.1 (M+H$^+$).

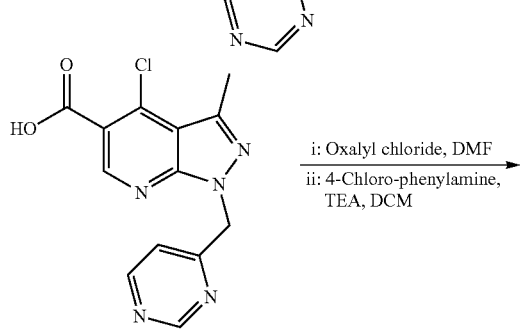

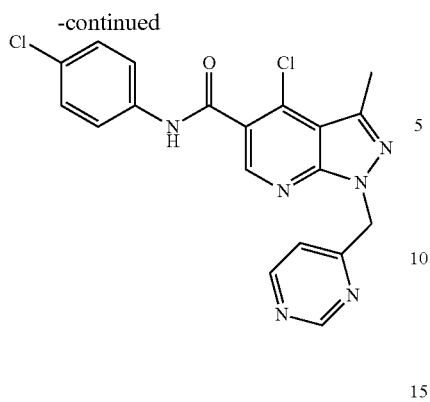

Example 352

4-Chloro-3-methyl-1-pyrimidin-4-ylmethyl-1H-pyrazolo[3,4-b]pyridine-5-carboxylic acid (4-chloro-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337). ¹HNMR (400 MHz, CDCl₃): δ=9.16 (s, 1H), 8.80 (s, 1H), 8.65 (d, J=4.8 Hz, 1H), 7.99 (brs, 1H), 7.62 (d, J=8.8 Hz, 2H), 7.37 (d, J=7.6 Hz, 2H), 6.99 (d, J=4.8 Hz, 1H), 5.77 (s, 2H), 2.79 (s, 3H). MS: m/z 413.1 (M+H⁺).

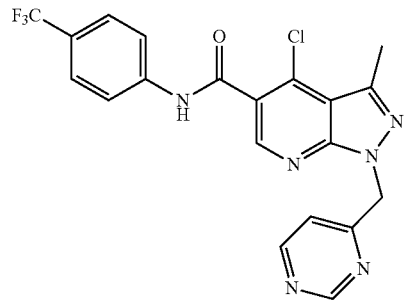 [SMILES: Cc1nn(Cc2ccncn2)c2ncc(C(=O)Nc3ccc(C(F)(F)F)cc3)c(Cl)c12]

Example 353

4-Chloro-3-methyl-1-pyrimidin-4-ylmethyl-1H-pyrazolo[3,4-b]pyridine-5-carboxylic acid (4-trifluoromethyl-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337).

¹HNMR (400 MHz, CDCl₃): δ=9.17 (s, 1H), 8.83 (s, 1H), 8.66 (d, J=3.6 Hz, 1H), 8.06 (brs, 1H), 7.79 (d, J=8.0 Hz, 2H), 7.67 (d, J=8.0 Hz, 2H), 7.01 (d, J=4.4 Hz, 1H), 5.77 (s, 2H), 2.80 (s, 3H). MS: m/z 447.0 (M+H⁺).

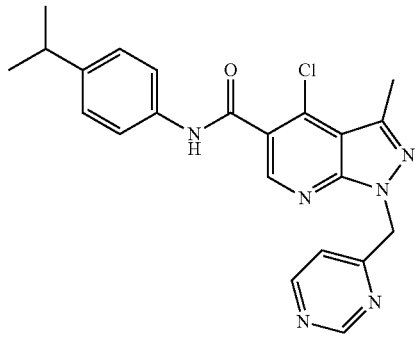 [SMILES: Cc1nn(Cc2ccncn2)c2ncc(C(=O)Nc3ccc(C(C)C)cc3)c(Cl)c12]

Example 354

4-Chloro-3-methyl-1-pyrimidin-4-ylmethyl-1H-pyrazolo[3,4-b]pyridine-5-carboxylic acid (4-isopropyl-phenyl)-amide The title compound was prepared using general procedure for 4-chloro-1-cyclopropylmethyl-3-methyl-1H-pyrazolo[3,4-b]pyridine-5-carboxylic acid (4-chloro-phenyl)-amide (Example 337).

¹HNMR (400 MHz, CDCl₃): δ=9.16 (s, 1H), 8.81 (s, 1H), 8.65 (d, J=5.2 Hz, 1H), 7.86 (brs, 1H), 7.57 (d, J=8.0 Hz, 2H), 7.26 (overlap, 2H), 6.97 (d, J=5.2 Hz, 1H), 5.77 (s, 2H), 2.95-2.91 (m, 1H), 2.79 (s, 3H), 1.27-1.21 (m, 6H). MS: m/z 421.1 (M+H⁺).

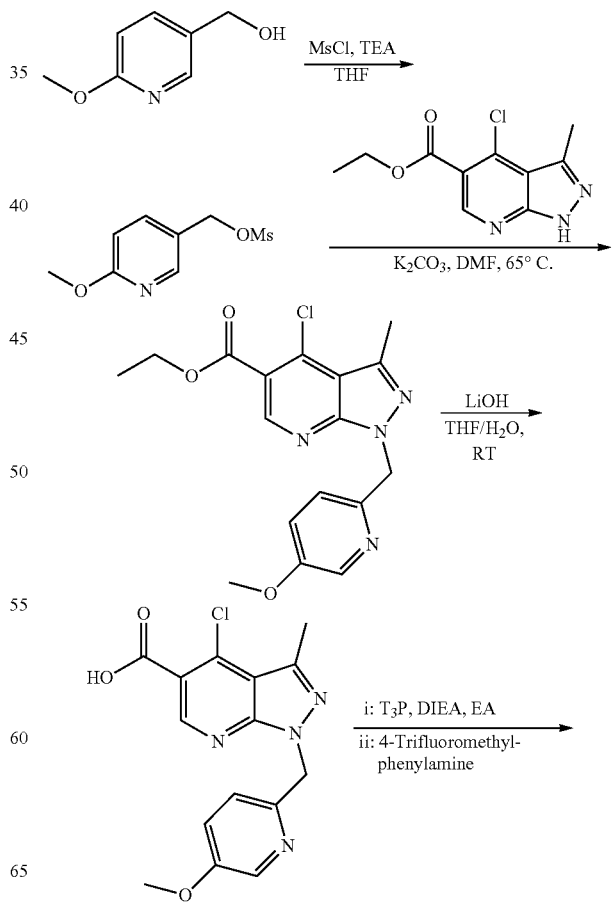

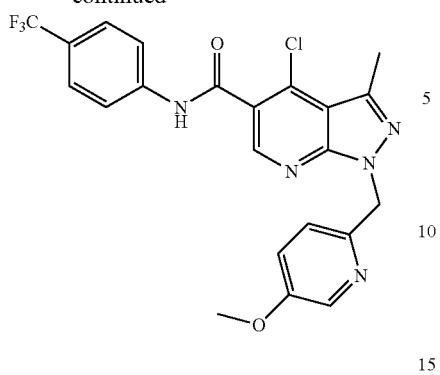

Example 355

4-chloro-1-((6-methoxypyridin-3-yl)methyl)-3-methyl-N-(4-(trifluoromethyl)phenyl)-1H-pyrazolo[3,4-b]pyridine-5-carboxamide Step 1-3

These three steps are similar to Step 5-6 of 4-chloro-1-cyclopropylmethyl-3-methyl-1H-pyrazolo[3,4-b]pyridine-5-carboxylic acid (4-chloro-phenyl)-amide (Example 337).

Step 4

To a suspension of 4-chloro-1-(6-methoxy-pyridin-3-ylmethyl)-3-methyl-1H-pyrazolo[3,4-b]pyridine-5-carboxylic acid (38 mg, 0.114 mmol) and DIEA (44 mg, 0.342 mmol) in EA (0.5 mL) was added T$_3$P (50% in EA, 218 mg, 0.342 mmol). The mixture was stirred at RT for 15 mins. To the mixture was added 4-trifluoromethyl-phenylamine (22 mg, 0.137 mmol). The reaction was then stirred at RT overnight. The reaction solution was partitioned between sat.NaHCO$_3$ solution (15 mL) and EA (15 mL). The organic layer was dried over Na$_2$SO$_4$ and concentrated. The residue was purified by prep-TLC (DCM/EA=10/1) to give 4-chloro-1-(6-methoxy-pyridin-3-ylmethyl)-3-methyl-1H-pyrazolo[3,4-b]pyridine-5-carboxylic acid (4-trifluoromethyl-phenyl)-amide (7 mg, yield 13%) as a white solid. $^1$HNMR (400 MHz, CDCl$_3$): δ=8.83 (s, 1H), 8.25 (s, 1H), 8.07 (brs, 1H), 7.79 (d, J=8.0 Hz, 2H), 7.67-7.62 (m, 3H), 6.68 (d, J=8.4 Hz, 1H), 5.56 (s, 2H), 3.90 (s, 3H), 2.74 (s, 3H). MS: m/z 476.1 (M+H$^+$).

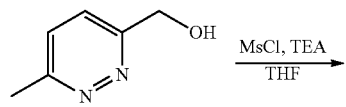

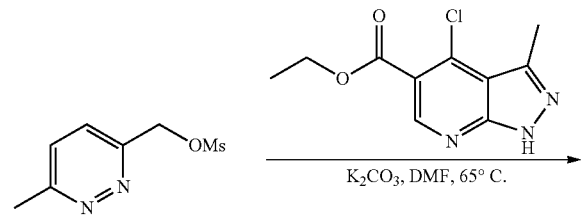

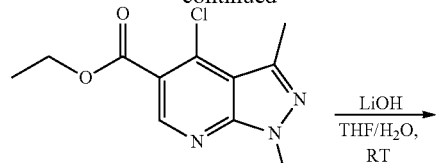

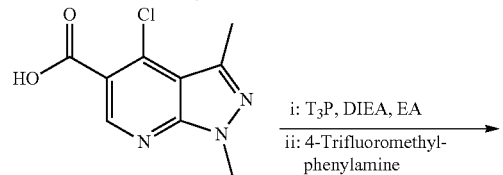

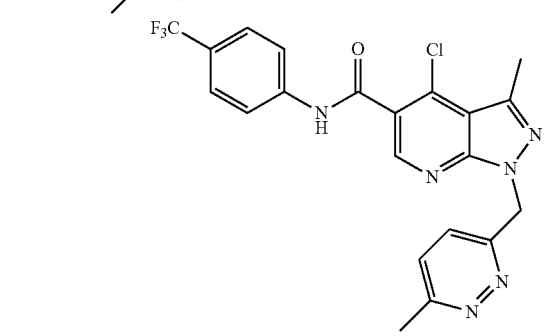

Example 356

4-Chloro-3-methyl-1-(6-methyl-pyridazin-3-ylmethyl)-1H-pyrazolo[3,4-b]pyridine-5-carboxylic acid (4-trifluoromethyl-phenyl)-amide The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.78 (s, 1H), 8.42 (brs, 1H), 7.81 (d, J=8.8 Hz, 2H), 7.65 (d, J=8.8 Hz, 2H), 7.28-7.20 (m, 2H), 5.95 (s, 2H), 2.74 (s, 3H), 2.67 (s, 3H). MS: m/z 461.1 (M+H$^+$).

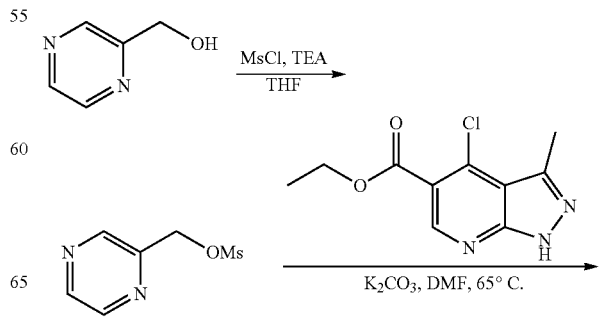

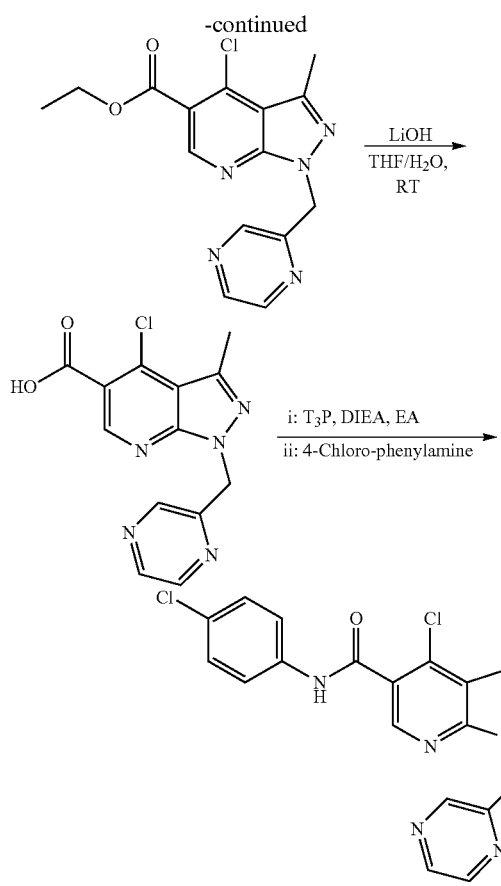

Example 357

4-Chloro-3-methyl-1-pyrazin-2-ylmethyl-1H-pyrazolo[3,4-b]pyridine-5-carboxylic acid (4-chlorophenyl)-amide The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.83 (s, 1H), 8.52-8.49 (m, 3H), 7.90 (brs, 1H), 7.62 (d, J=8.4 Hz, 2H), 7.37 (d, J=8.4 Hz, 2H), 5.83 (s, 2H), 2.77 (s, 3H). MS: m/z 413.0 (M+H$^+$).

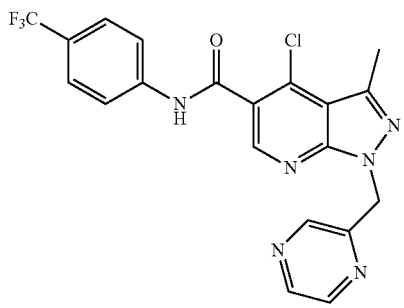 [SMILES: Cc1nn(Cc2cnccn2)c2ncc(C(=O)Nc3ccc(C(F)(F)F)cc3)c(Cl)c12]

Example 358

4-Chloro-3-methyl-1-pyrazin-2-ylmethyl-1H-pyrazolo[3,4-b]pyridine-5-carboxylic acid (4-trifluoromethyl-phenyl)-amide The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.84 (s, 1H), 8.52-8.50 (m, 3H), 8.08 (brs, 1H), 7.79 (d, J=8.4 Hz, 2H), 7.66 (d, J=8.0 Hz, 2H), 5.83 (s, 2H), 2.78 (s, 3H). MS: m/z 447.0 (M+H$^+$).

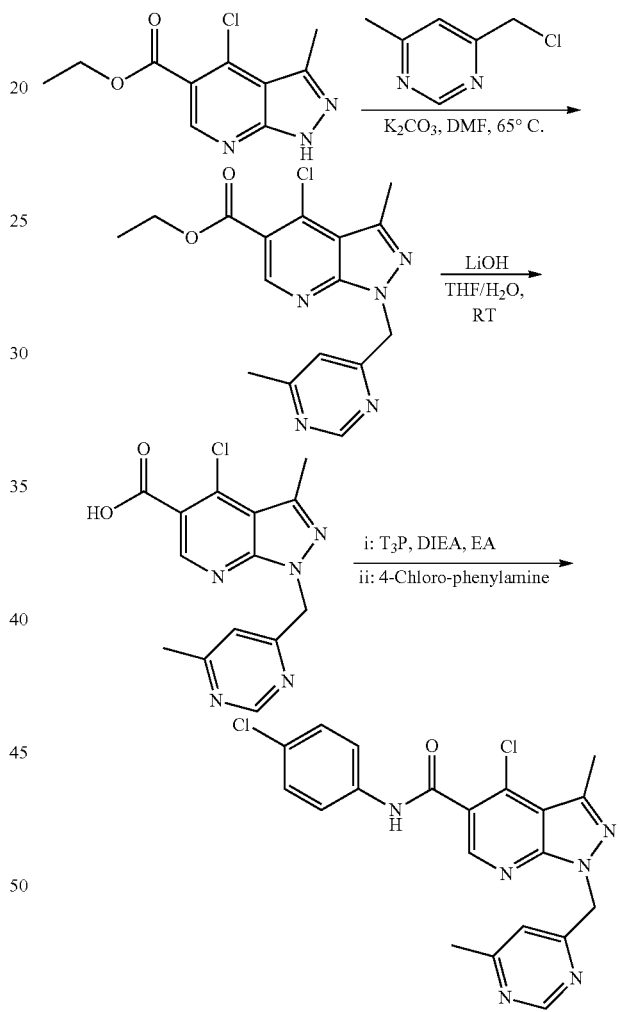

Example 359

4-Chloro-3-methyl-1-(6-methyl-pyrimidin-4-ylmethyl)-1H-pyrazolo[3,4-b]pyridine-5-carboxylic acid (4-chloro-phenyl)-amide The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (300 MHz, DMSO-d6): δ=10.81 (brs, 1H), 8.90 (d, J=1.2 Hz, 1H), 8.69 (s, 1H), 7.76 (d, J=9.0 Hz, 2H), 7.44 (d, J=9.0 Hz, 2H), 7.14 (s, 1H), 5.73 (s, 2H), 2.71 (s, 3H), 2.42 (s, 3H). MS: m/z 427.1 (M+H$^+$).

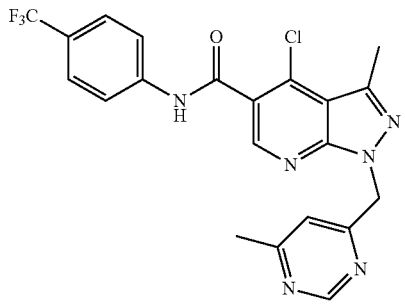 [SMILES: Cc1cc(Cn2nc(C)c3c(Cl)c(C(=O)Nc4ccc(C(F)(F)F)cc4)cnc32)ncn1]

Example 360

4-Chloro-3-methyl-1-(6-methyl-pyrimidin-4-ylmethyl)-1H-pyrazolo[3,4-b]pyridine-5-carboxylic acid (4-trifluoromethyl-phenyl)-amide The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=9.02 (s, 1H), 8.83 (s, 1H), 8.05 (brs, 1H), 7.79 (d, J=8.0 Hz, 2H), 7.67 (d, J=8.4 Hz, 2H), 6.84 (s, 1H), 5.72 (s, 2H), 2.80 (s, 3H), 2.47 (s, 3H). MS: m/z 461.1 (M+H$^+$).

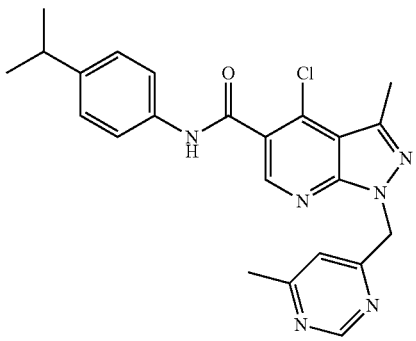 [SMILES: Cc1cc(Cn2nc(C)c3c(Cl)c(C(=O)Nc4ccc(C(C)C)cc4)cnc32)ncn1]

Example 361

4-Chloro-3-methyl-1-(6-methyl-pyrimidin-4-ylmethyl)-1H-pyrazolo[3,4-b]pyridine-5-carboxylic acid (4-isopropyl-phenyl)-amide The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (300 MHz, CDCl$_3$): δ=9.02 (s, 1H), 8.82 (s, 1H), 7.81 (brs, 1H), 7.57 (d, J=8.4 Hz, 2H), 7.26 (overlap, 2H), 6.79 (s, 1H), 5.72 (s, 2H), 2.95-2.91 (m, 1H), 2.80 (s, 3H), 2.46 (s, 3H), 1.28-1.25 (m, 6H). MS: m/z 435.2 (M+H$^+$).

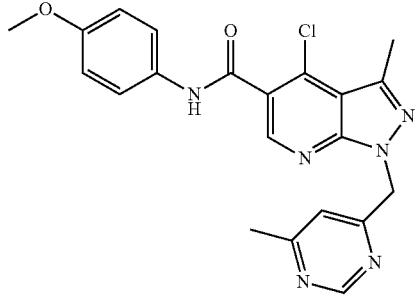 [SMILES: COc1ccc(NC(=O)c2cnc3c(c(C)nn3Cc3cc(C)ncn3)c2Cl)cc1]

Example 362

4-Chloro-3-methyl-1-(6-methyl-pyrimidin-4-ylmethyl)-1H-pyrazolo[3,4-b]pyridine-5-carboxylic acid (4-methoxy-phenyl)-amide The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (300 MHz, CDCl$_3$): δ=9.02 (s, 1H), 8.81 (s, 1H), 7.86 (brs, 1H), 7.58-7.55 (m, 2H), 6.95-6.91 (m, 2H), 6.79 (s, 1H), 5.71 (s, 2H), 3.82 (s, 3H), 2.79 (s, 3H), 2.45 (s, 3H). MS: m/z 423.1 (M+H$^+$).

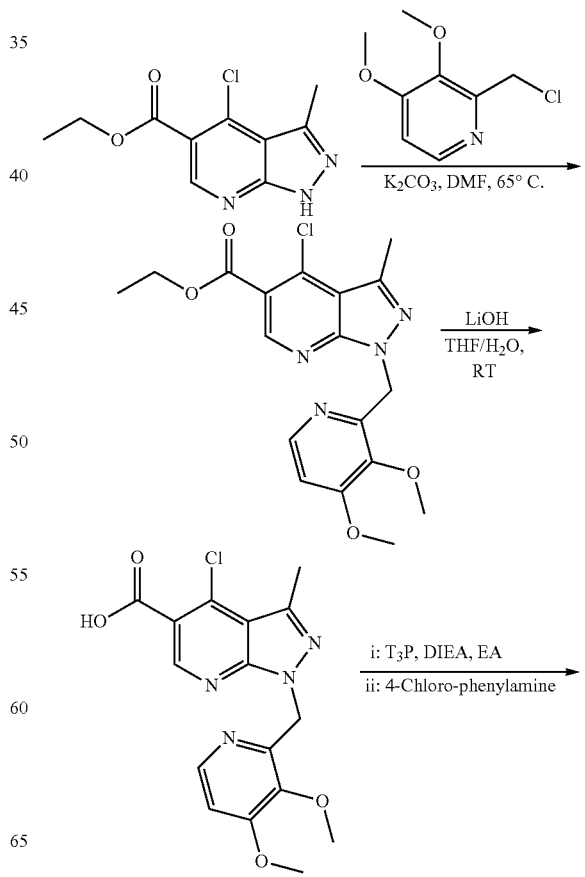

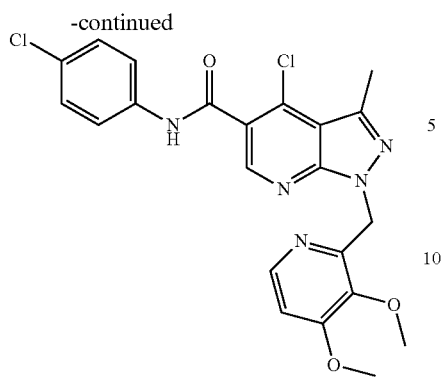

Example 363

4-Chloro-1-(3,4-dimethoxy-pyridin-2-ylmethyl)-3-methyl-1H-pyrazolo[3,4-b]pyridine-5-carboxylic acid (4-chloro-phenyl)-amide The title compound was prepared using general procedure for 4-chloro-1-(((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.81 (s, 1H), 8.11(d, J=5.2 Hz, 1H), 8.05 (brs, 1H), 7.62 (d, J=8.4 Hz, 2H), 7.35 (d, J=8.4 Hz, 2H), 6.76 (d, J=5.2 Hz, 1H), 5.81 (s, 2H), 3.90 (s, 3H), 3.89 (s, 3H), 2.74 (s, 3H). MS: m/z 472.0 (M+H$^+$).

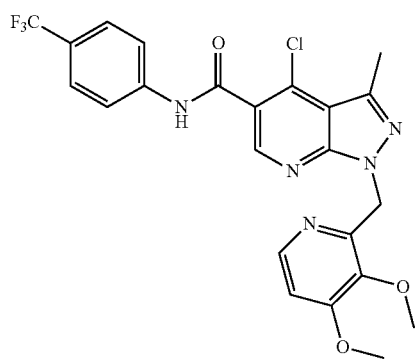 [SMILES: COc1ccnc(Cn2nc(C)c3c(Cl)c(C(=O)Nc4ccc(C(F)(F)F)cc4)cnc32)c1OC]

Example 364

4-Chloro-1-(3,4-dimethoxy-pyridin-2-ylmethyl)-3-methyl-1H-pyrazolo[3,4-b]pyridine-5-carboxylic acid (4-trifluoromethyl-phenyl)-amide The title compound was prepared using general procedure for 4-chloro-1-(((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.83 (s, 1H), 8.21 (brs, 1H), 8.11(d, J=5.2 Hz, 1H), 7.79 (d, J=8.8 Hz, 2H), 7.65 (d, J=8.8 Hz, 2H), 6.77 (d, J=5.6 Hz, 1H), 5.81 (s, 2H), 3.91 (s, 3H), 3.89 (s, 3H), 2.74 (s, 3H). MS: m/z 506.1 (M+H$^+$).

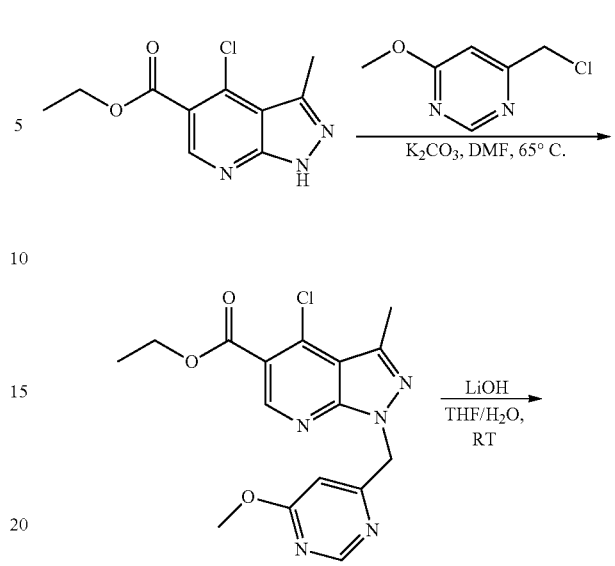

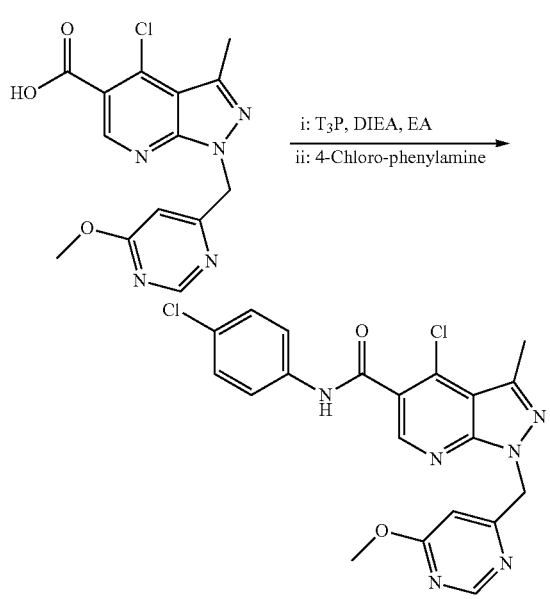

Example 365

4-Chloro-1-(6-methoxy-pyrimidin-4-ylmethyl)-3-methyl-1H-pyrazolo[3,4-b]pyridine-5-carboxylic acid (4-chloro-phenyl)-amide The title compound was prepared using general procedure for 4-chloro-1-(((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, DMSO-d6): δ=10.80 (brs, 1H), 8.69 (s, 1H), 8.67 (s, 1H), 7.76 (d, J=8.4 Hz, 2H), 7.44 (d, J=8.4 Hz, 2H), 6.60 (s, 1H), 5.70 (s, 2H), 3.90 (s, 3H), 2.70 (s, 3H). MS: m/z 443.0 (M+H$^+$).

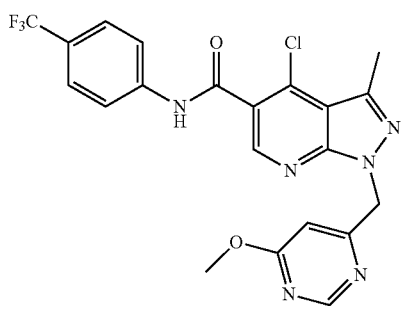 [SMILES: COc1cc(Cn2nc(C)c3c(Cl)c(C(=O)Nc4ccc(C(F)(F)F)cc4)cnc32)ncn1]

Example 366

4-Chloro-1-(6-methoxy-pyrimidin-4-ylmethyl)-3-methyl-1H-pyrazolo[3,4-b]pyridine-5-carboxylic acid (4-trifluoromethyl-phenyl)-amide The title compound was prepared using general procedure for 4-chloro-1-(((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, DMSO-d6): δ=11.03 (brs, 1H), 8.72 (s, 1H), 8.67 (s, 1H), 7.94 (d, J=8.4 Hz, 2H), 7.75 (d, J=8.4 Hz, 2H), 6.61 (s, 1H), 5.70 (s, 2H), 3.90 (s, 3H), 2.70 (s, 3H). MS: m/z 477.1 (M+H$^+$).

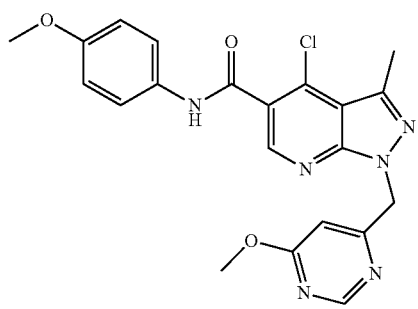 [SMILES: COc1ccc(NC(=O)c2cnc3c(c(C)nn3Cc3cc(OC)ncn3)c2Cl)cc1]

Example 367

4-Chloro-1-(6-methoxy-pyrimidin-4-ylmethyl)-3-methyl-1H-pyrazolo[3,4-b]pyridine-5-carboxylic acid (4-methoxy-phenyl)-amide The title compound was prepared using general procedure for 4-chloro-1-(((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (300 MHz, DMSO-d6): δ=10.51 (brs, 1H), 8.68-8.66 (m, 2H), 7.65 (d, J=8.7 Hz, 2H), 6.95 (d, J=9.0 Hz, 2H), 6.59 (s, 1H), 5.70 (s, 2H), 3.90 (s, 3H), 3.75 (s, 3H), 2.70 (s, 3H). MS: m/z 439.1 (M+H$^+$).

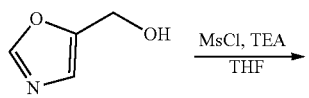

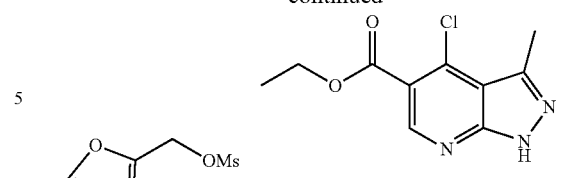

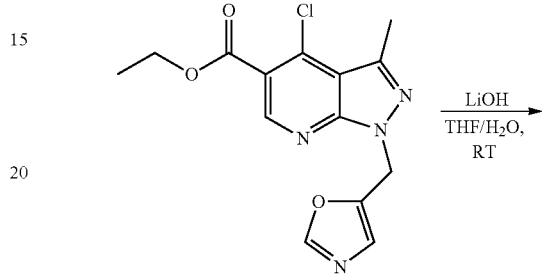

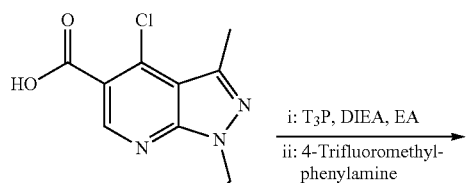

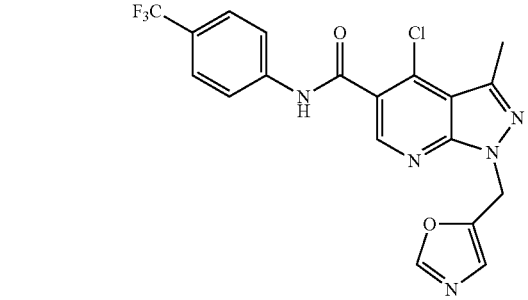

Example 368

4-Chloro-3-methyl-1-oxazol-5-ylmethyl-1H-pyrazolo[3,4-b]pyridine-5-carboxylic acid (4-trifluoromethyl-phenyl)-amide The title compound was prepared using general procedure for 4-chloro-1-(((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (300 MHz, CDCl$_3$): δ=8.86 (s, 1H), 8.07 (brs, 1H), 7.80-7.78 (m, 3H), 7.67 (d, J=8.7 Hz, 2H), 7.15 (s, 1H), 5.70 (s, 2H), 2.77 (s, 3H). MS: m/z 434.1 (M−H$^+$).

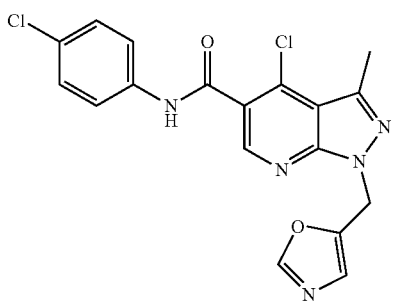 [SMILES: Cc1nn(Cc2cnco2)c2ncc(C(=O)Nc3ccc(Cl)cc3)c(Cl)c12]

Example 369

4-Chloro-3-methyl-1-oxazol-5-ylmethyl-1H-pyrazolo[3,4-b]pyridine-5-carboxylic acid (4-chlorophenyl)-amide The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.85 (s, 1H), 7.88 (brs, 1H), 7.80 (s, 1H), 7.62 (d, J=8.4 Hz, 2H), 7.37 (d, J=9.2 Hz, 2H), 7.15 (s, 1H), 5.70 (s, 2H), 2.76 (s, 3H). MS: m/z 400.1 (M−H$^+$).

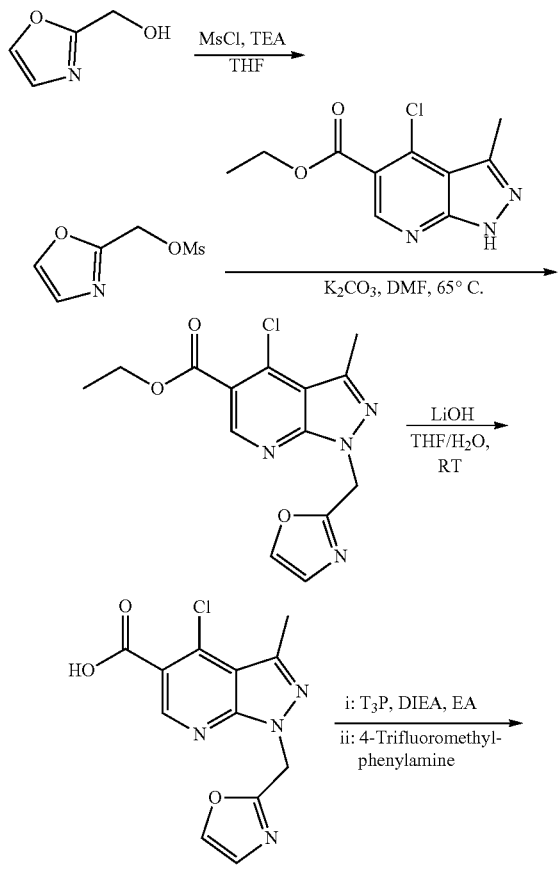

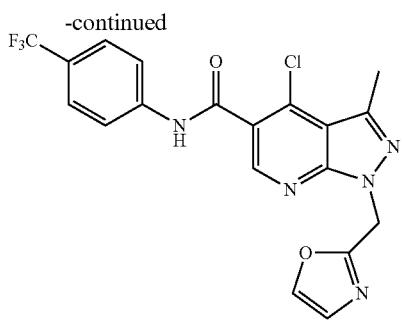

Example 370

4-Chloro-3-methyl-1-oxazol-2-ylmethyl-1H-pyrazolo[3,4-b]pyridine-5-carboxylic acid (4-trifluoromethyl-phenyl)-amide The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.85 (s, 1H), 8.08 (brs, 1H), 7.80 (d, J=8.0 Hz, 2H), 7.66 (d, J=8.8 Hz, 2H), 7.61 (s, 1H), 7.08 (s, 1H), 5.79 (s, 2H), 2.77 (s, 3H). MS: m/z 436.0 (M+H$^+$).

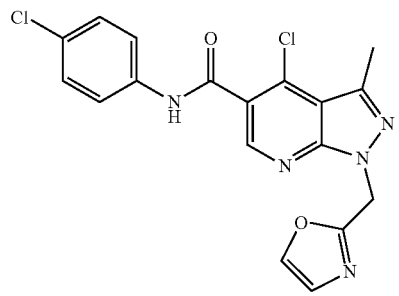 [SMILES: Cc1nn(Cc2ncco2)c2ncc(C(=O)Nc3ccc(Cl)cc3)c(Cl)c12]

Example 371

4-Chloro-3-methyl-1-oxazol-2-ylmethyl-1H-pyrazolo[3,4-b]pyridine-5-carboxylic acid (4-chlorophenyl)-amide The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.81 (s, 1H), 8.00 (brs, 1H), 7.61 (m, 3H), 7.36 (d, J=8.4 Hz, 2H), 7.08 (s, 1H), 5.77 (s, 2H), 2.76 (s, 3H). MS: m/z 402.0 (M+H$^+$).

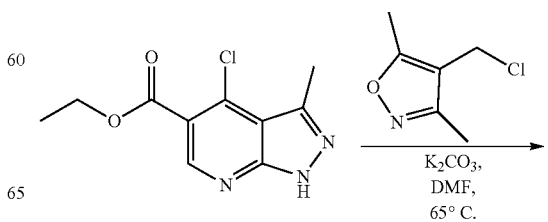

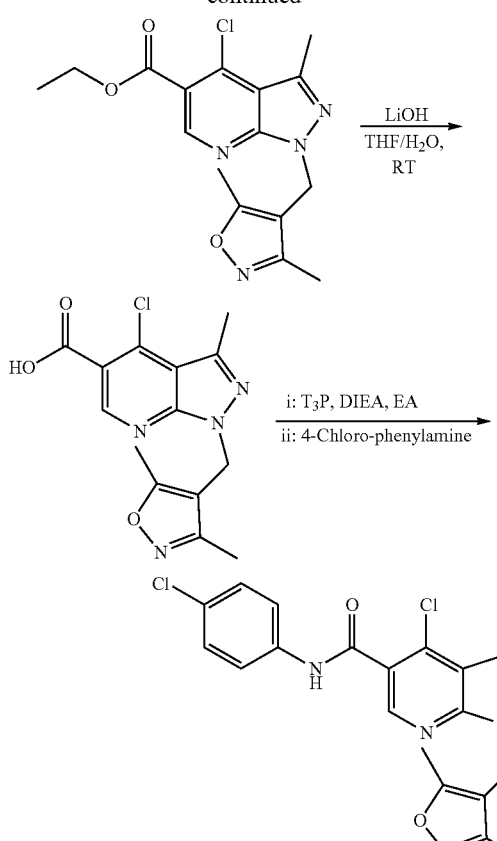

Example 372

4-Chloro-1-(3,5-dimethyl-isoxazol-4-ylmethyl)-3-methyl-1H-pyrazolo[3,4-b]pyridine-5-carboxylic acid (4-chloro-phenyl)-amide The title compound was prepared using general procedure for 4-chloro-1-(((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.82 (s, 1H), 7.91 (brs, 1H), 7.61 (d, J=8.0 Hz, 2H), 7.37 (d, J=8.8 Hz, 2H), 5.35 (s, 2H), 2.73 (s, 3H), 2.52 (s, 3H), 2.33 (s, 3H). MS: m/z 430.0 (M+H$^+$).

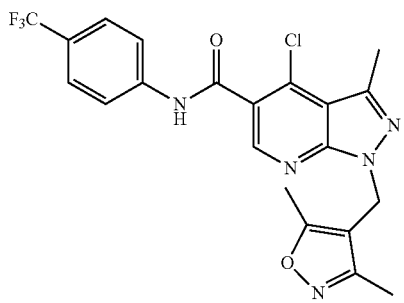 [SMILES: Cc1noc(C)c1Cn1nc(C)c2c(Cl)c(C(=O)Nc3ccc(C(F)(F)F)cc3)cnc21]

Example 373

4-Chloro-1-(3,5-dimethyl-isoxazol-4-ylmethyl)-3-methyl-1H-pyrazolo[3,4-b]pyridine-5-carboxylic acid (4-trifluoromethyl-phenyl)-amide The title compound was prepared using general procedure for 4-chloro-1-(((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.83 (s, 1H), 8.06 (brs, 1H), 7.79 (d, J=8.0 Hz, 2H), 7.66 (d, J=8.4 Hz, 2H), 5.35 (s, 2H), 2.73 (s, 3H), 2.52 (s, 3H), 2.33 (s, 3H). MS: m/z 462.1 (M−H$^+$).

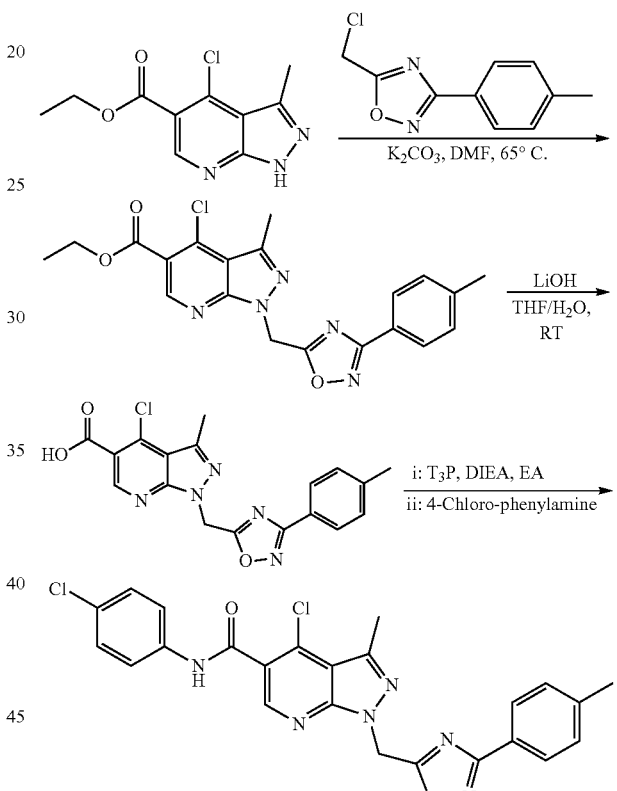

Example 374

4-Chloro-3-methyl-1-(3-p-tolyl-[1,2,4]oxadiazol-5-ylmethyl)-1H-pyrazolo[3,4-b]pyridine-5-carboxylic acid (4-chloro-phenyl)-amide The title compound was prepared using general procedure for 4-chloro-1-(((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (300 MHz, CDCl$_3$): δ=8.85 (s, 1H), 7.93-7.90 (m, 3H), 7.64 (d, J=8.1 Hz, 2H), 7.39 (d, J=9.0 Hz, 2H), 7.26 (overlap, 2H), 5.96 (s, 2H), 2.80 (s, 3H), 2.41 (s, 3H). MS: m/z 491.1 (M−H$^+$).

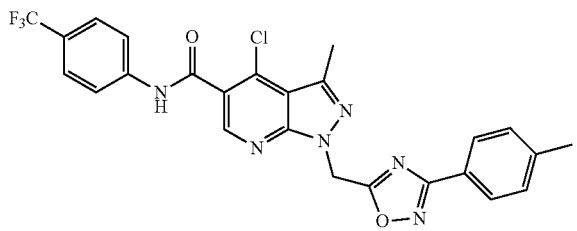 [SMILES: Cc1ccc(-c2noc(Cn3nc(C)c4c(Cl)c(C(=O)Nc5ccc(C(F)(F)F)cc5)cnc43)n2)cc1]

Example 375

4-Chloro-3-methyl-1-(3-p-tolyl-[1,2,4]oxadiazol-5-ylmethyl)-1H-pyrazolo[3,4-b]pyridine-5-carboxylic acid (4-trifluoromethyl-phenyl)-amide

The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.85 (s, 1H), 8.06 (brs, 1H), 7.91 (d, J=8.0 Hz, 2H), 7.80 (d, J=9.2 Hz, 2H), 7.67 (d, J=8.4 Hz, 2H), 7.26 (overlap, 2H), 5.95 (s, 2H), 2.79 (s, 3H), 2.40 (s, 3H). MS: m/z 527.1 (M+H$^+$).

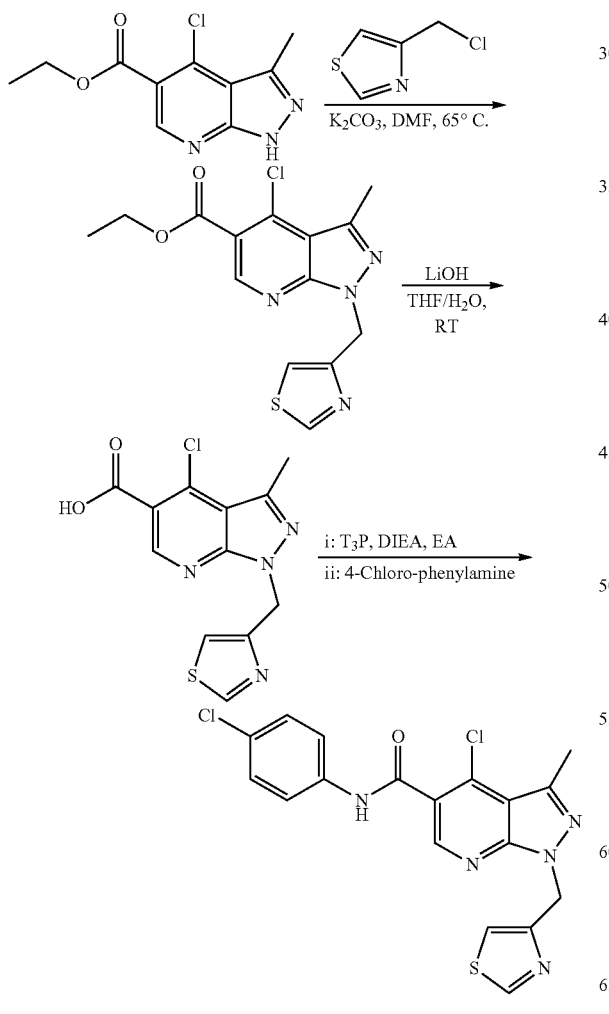

Example 376

4-Chloro-3-methyl-1-thiazol-4-ylmethyl-1H-pyrazolo[3,4-b]pyridine-5-carboxylic acid (4-chloro-phenyl)-amide

The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.84 (s, 1H), 8.76 (d, J=1.6 Hz, 1H), 7.92 (brs, 1H), 7.62 (d, J=8.4 Hz, 2H), 7.36 (d, J=8.4 Hz, 2H), 7.22 (d, J=1.6 Hz, 1H), 5.84 (s, 2H), 2.77 (s, 3H). MS: m/z 418.0 (M+H$^+$).

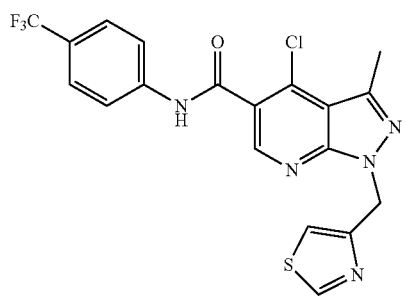 [SMILES: Cc1nn(Cc2cscn2)c2ncc(C(=O)Nc3ccc(C(F)(F)F)cc3)c(Cl)c12]

Example 377

4-Chloro-3-methyl-1-thiazol-4-ylmethyl-1H-pyrazolo[3,4-b]pyridine-5-carboxylic acid (4-trifluoromethyl-phenyl)-amide

The title compound was prepared using general procedure for 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

$^1$HNMR (400 MHz, CDCl$_3$): δ=8.87 (s, 1H), 8.80 (s, 1H), 8.08 (brs, 1H), 7.79 (d, J=8.0 Hz, 2H), 7.66 (d, J=8.0 Hz, 2H), 7.26 (overlap, 1H), 5.86 (s, 2H), 2.78 (s, 3H). MS: m/z 452.0 (M+H$^+$).

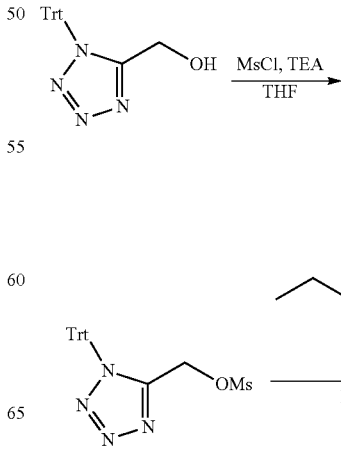

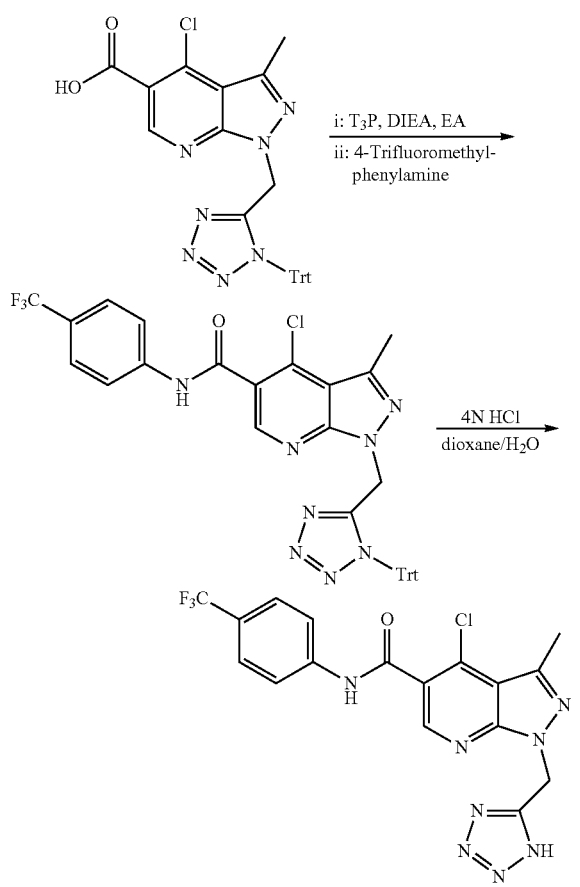

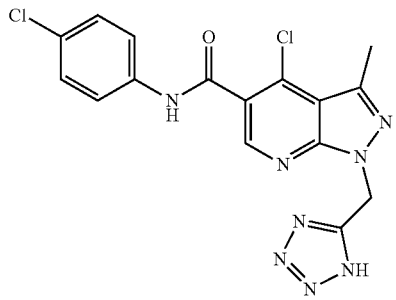

Example 379

4-Chloro-3-methyl-1-(1H-tetrazol-5-ylmethyl)-1H-pyrazolo[3,4-b]pyridine-5-carboxylic acid (4-chloro-phenyl)-amide The title compound was prepared using general procedure for 4-chloro-3-methyl-1-(1H-tetrazol-5-ylmethyl)-1H-pyrazolo[3,4-b]pyridine-5-carboxylic acid (4-trifluoromethyl-phenyl)-amide (Example 378).

$^1$HNMR (400 MHz, DMSO-d6): δ=10.82 (brs, 1H), 8.70 (s, 1H), 7.76 (d, J=8.4 Hz, 2H), 7.44 (d, J=8.4 Hz, 2H), 7.15 (brs, 1H), 5.82 (s, 2H), 2.66 (s, 3H). MS: m/z 403.0 (M+H$^+$).

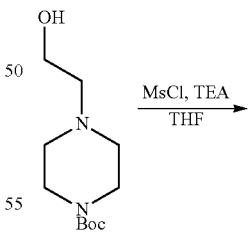

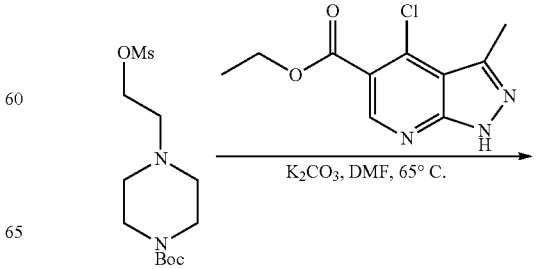

Example 378

4-Chloro-3-methyl-1-(1H-tetrazol-5-ylmethyl)-1H-pyrazolo[3,4-b]pyridine-5-carboxylic acid (4-trifluoromethyl-phenyl)-amide Step 1-4

These first four steps are similar to 4-chloro-1-((6-methoxypyridin-3-yl)methyl)-3-methyl-N-(4-(trifluoromethyl)phenyl)-1H-pyrazolo[3,4-b]pyridine-5-carboxamide (Example 355).

Step 5

To a solution of 4-chloro-3-methyl-1-(1-trityl-1H-tetrazol-5-ylmethyl)-1H-pyrazolo[3,4-b]pyridine-5-carboxylic acid (4-trifluoromethyl-phenyl)-amide (35 mg, 0.052 mmol) in dioxane/H$_2$O (4 mL/0.8 mL) was added 4N HCl (0.4 mL).

The mixture was stirred at room temperature for 4 hrs. NaHCO$_3$ (500 mg) was added to the mixture and the mixture was stirred for 10 mins. The mixture was dried over Na$_2$SO$_4$ and filtered. The filter cake was washed with DCM/MeOH (10/1, 15 mL). The filtrate was concentrated to dryness under reduced pressure. The residue was purified by prep-HPLC to give 4-chloro-3-methyl-1-(1H-tetrazol-5-ylmethyl)-1H-pyrazolo[3,4-b]pyridine-5-carboxylic acid (4-trifluoromethyl-phenyl)-amide (6.5 mg, yield: 29%) as a white solid.

$^1$HNMR (300 MHz, DMSO-d6): δ=11.04 (brs, 1H), 8.73 (s, 1H), 7.94 (d, J=8.1 Hz, 2H), 7.76 (d, J=9.0 Hz, 2H), 7.13 (brs, 1H), 5.79 (s, 2H), 2.67 (s, 3H). MS: m/z 435.1 (M−H$^+$).

593

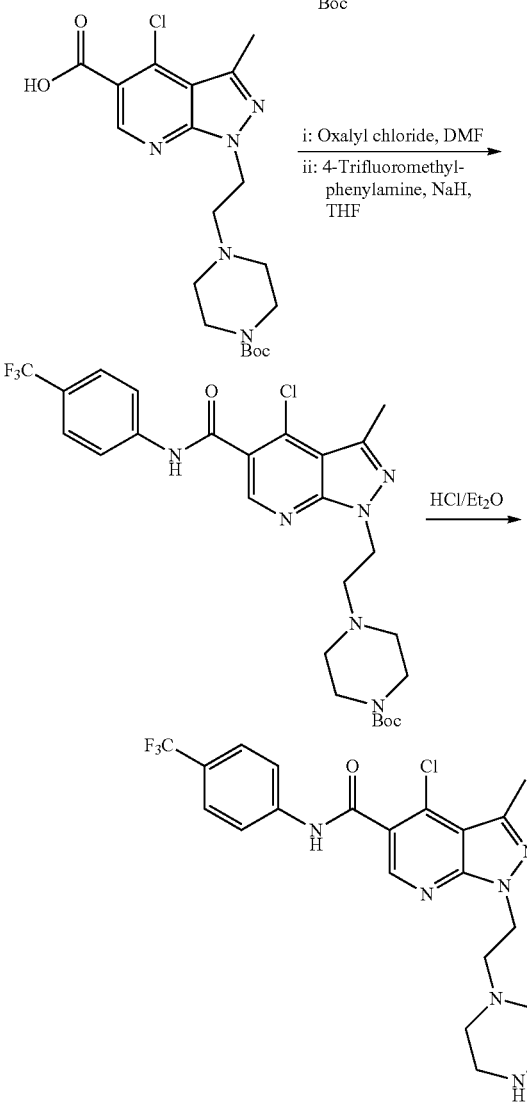

Example 380

4-Chloro-3-methyl-1-(2-piperazin-1-yl-ethyl)-1H-pyrazolo[3,4-b]pyridine-5-carboxylic acid (4-trifluoromethyl-phenyl)-amide Step 1-4

These first four steps are similar to 4-chloro-1-cyclopropylmethyl-3-methyl-1H-pyrazolo[3,4-b]pyridine-5-carboxylic acid (4-chloro-phenyl)-amide (Example 337).

594

Step 5

To a solution of 4-{2-[4-chloro-3-methyl-5-(4-trifluoromethyl-phenylcarbamoyl)-pyrazolo[3,4-b]pyridin-1-yl]-ethyl}-piperazine-1-carboxylic acid tert-butyl ester (250 mg, 0.44 mmol) in Et$_2$O (1 mL), was added HCl/Et$_2$O (2 M, 20 mL). The mixture was stirred at room temperature overnight. After concentration under reduced pressure below 35° C., the residue was triturated with MeOH to give HCl salt of 4-chloro-3-methyl-1-(2-piperazin-1-yl-ethyl)-1H-pyrazolo[3,4-b]pyridine-5-carboxylic acid (4-trifluoromethyl-phenyl)-amide (190 mg, yield: 80%) as a white solid. $^1$HNMR (400 MHz, D$_2$O): δ=8.72 (s, 1H), 7.76-7.75 (m, 4H), 4.92-4.85 (m, 2H), 3.73 (t, J=6.0 Hz, 2H), 3.61-3.55 (m, 8H), 2.75 (s, 3H). MS: m/z 467.1 (M+H$^+$).

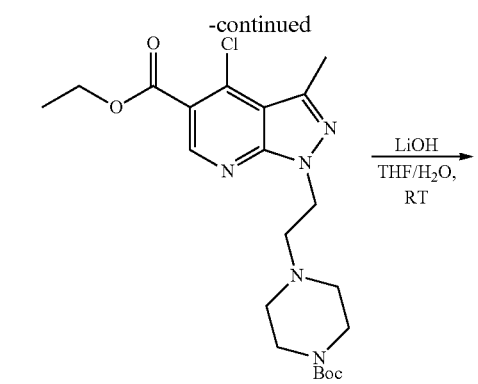

Example 381

4-Chloro-3-methyl-1-(2-piperazin-1-yl-ethyl)-1H-pyrazolo[3,4-b]pyridine-5-carboxylic acid (4-chloro-phenyl)-amide The title compound was prepared using general procedure for 4-chloro-3-methyl-1-(2-piperazin-1-yl-ethyl)-1H-pyrazolo[3,4-b]pyridine-5-carboxylic acid (4-trifluoromethyl-phenyl)-amide $^1$HNMR (400 MHz, D$_2$O): δ=8.71 (s, 1H), 7.55 (d, J=8.8 Hz, 2H), 7.43 (d, J=8.8 Hz, 2H), 4.90-4.84 (m, 2H), 3.75 (t, J=6.0 Hz, 2H), 3.62-3.56 (m, 8H), 2.77 (s, 3H). MS: m/z 433.1 (M+H$^+$).

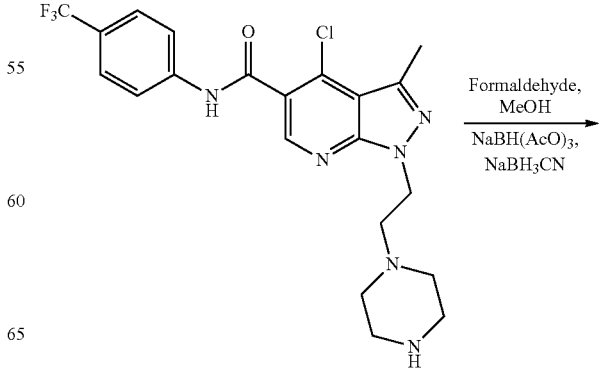

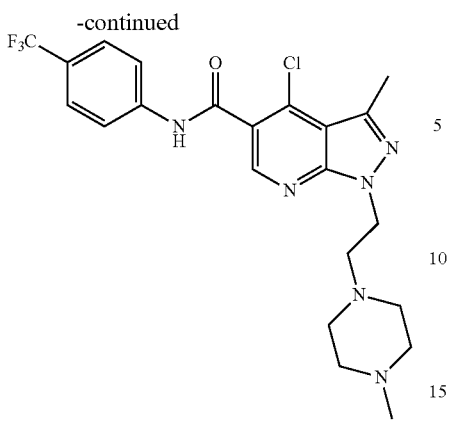

Example 382

4-Chloro-3-methyl-1-[2-(4-methyl-piperazin-1-yl)-ethyl]-1H-pyrazolo[3,4-b]pyridine-5-carboxylic acid (4-trifluoromethyl-phenyl)-amide To a solution of 4-chloro-3-methyl-1-(2-piperazin-1-yl-ethyl)-1H-pyrazolo[3,4-b]pyridine-5-carboxylic acid (4-trifluoromethyl-phenyl)-amide (HCl salt, 30 mg, 0.055 mmol) in MeOH (5 mL), was added formalin (0.5 mL). The mixture was stirred at room temperature for 10 mins. After addition of NaBH(AcO)$_3$ (47 mg, 0.22 mmol) and NaBH$_3$CN (20 mg, 0.22 mmol), the reaction was stirred at room temperature overnight. The reaction mixture was separated between saturated NaHCO$_3$ solution (30 mL) and EA (25 mL). The organic layer was dried over Na$_2$SO$_4$ and concentrated. The residue was purified by prep-HPLC to give HCl salt of 4-chloro-3-methyl-1-[2-(4-methyl-piperazin-1-yl)-ethyl]-1H-pyrazolo[3,4-b]pyridine-5-carboxylic acid (4-trifluoromethyl-phenyl)-amide (12 mg, yield: 39%) as a white solid. $^1$HNMR (400 MHz, D$_2$O): δ=8.71 (s, 1H), 7.75-7.69 (m, 4H), 4.89-4.82 (m, 2H), 3.68-3.50 (m, 10H), 3.01 (s, 3H), 2.72 (s, 3H). MS: m/z 481.1 (M+H$^+$).

ethyl]-1H-pyrazolo[3,4-b]pyridine-5-carboxylic acid (4-trifluoromethyl-phenyl)-amide (Example 382). $^1$HNMR (400 MHz, D$_2$O): δ=8.73 (s, 1H), 7.79 (s, 4H), 5.06-4.93 (m, 2H), 3.59-3.28 (m, 12H), 2.77 (s, 3H), 1.36 (t, J=7.2 Hz, 3H). MS: m/z 495.1 (M+H$^+$).

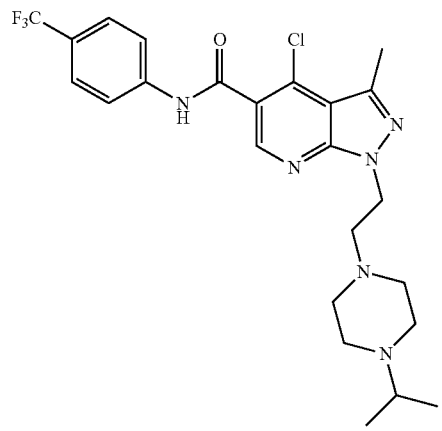

Example 384

4-Chloro-1-[2-(4-isopropyl-piperazin-1-yl)-ethyl]-3-methyl-1H-pyrazolo[3,4-b]pyridine-5-carboxylic acid (4-trifluoromethyl-phenyl)-amide The title compound was prepared using general procedure for 4-chloro-3-methyl-1-[2-(4-methyl-piperazin-1-yl)-ethyl]-1H-pyrazolo[3,4-b]pyridine-5-carboxylic acid (4-trifluoromethyl-phenyl)-amide (Example 382). $^1$HNMR (400 MHz, D$_2$O): δ=8.72 (s, 1H), 7.77 (s, 4H), 4.90(overlap, 2H), 3.67-3.38 (m, 11H), 2.76 (s, 3H), 1.37 (d, J=6.8 Hz, 6H). MS: m/z 509.2 (M+H$^+$).

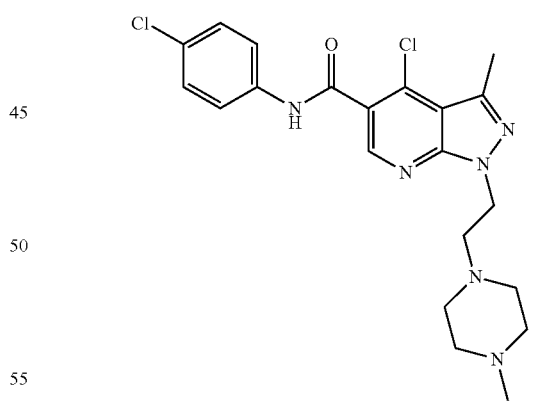

Example 385

4-Chloro-3-methyl-1-[2-(4-methyl-piperazin-1-yl)-ethyl]-1H-pyrazolo[3,4-b]pyridine-5-carboxylic acid (4-chloro-phenyl)-amide The title compound was prepared using general procedure for 4-chloro-3-methyl-1-[2-(4-methyl-piperazin-1-yl)-ethyl]-1H-pyrazolo[3,4-b]pyridine-5-carboxylic acid (4-tri-

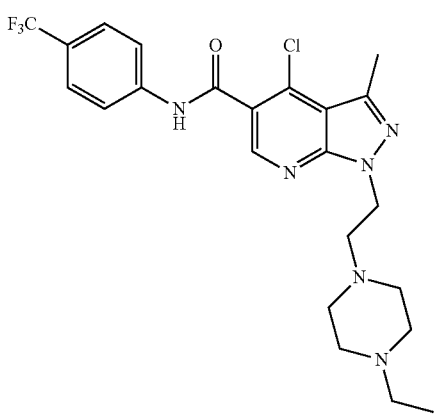 [SMILES: CCN1CCN(CCn2nc(C)c3c(Cl)c(C(=O)Nc4ccc(C(F)(F)F)cc4)cnc32)CC1]

Example 383

4-Chloro-1-[2-(4-ethyl-piperazin-1-yl)-ethyl]-3-methyl-1H-pyrazolo[3,4-b]pyridine-5-carboxylic acid (4-trifluoromethyl-phenyl)-amide The title compound was prepared using general procedure for 4-chloro-3-methyl-1-[2-(4-methyl-piperazin-1-yl)- fluoromethyl-phenyl)-amide (Example 382). ¹HNMR (400 MHz, CDCl₃): δ=8.77 (s, 1H), 8.13 (brs, 1H), 7.64 (d, J=8.4 Hz, 2H), 7.36 (d, J=8.8 Hz, 2H), 4.58 (t,J=6.6 Hz, 2H), 2.92 (t, J=6.8 Hz, 2H), 2.75 (s, 3H), 2.58 (m, 4H), 2.42 (m, 4H), 2.28 (s, 3H). MS: m/z 447.1 (M+H⁺).

ethyl]-1H-pyrazolo[3,4-b]pyridine-5-carboxylic acid (4-tri-fluoromethyl-phenyl)-amide (Example 382). ¹HNMR (400 MHz, D₂O): δ=8.61 (s, 1H), 7.44 (d, J=8.8 Hz, 2H), 7.19 (d, J=8.8 Hz, 2H), 4.79 (overlap, 2H), 3.73-3.50 (m, 11H), 2.62 (s, 3H), 1.38 (d, J=6.4 Hz, 6H). MS: m/z 475.1 (M+H⁺).

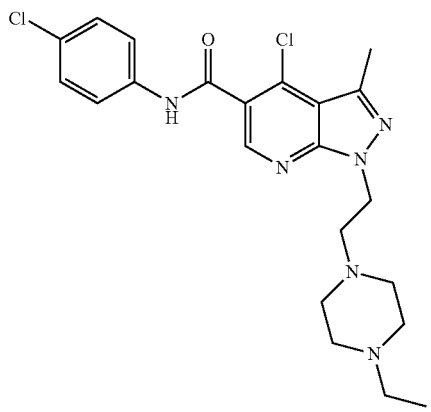 [SMILES: CCN1CCN(CCn2nc(C)c3c(Cl)c(C(=O)Nc4ccc(Cl)cc4)cnc32)CC1]

Example 386

4-Chloro-1-[2-(4-ethyl-piperazin-1-yl)-ethyl]-3-methyl-1H-pyrazolo 13,4-b]pyridine-5-carboxylic acid (4-chloro-phenyl)-amide The title compound was prepared using general procedure for 4-chloro-3-methyl-1-[2-(4-methyl-piperazin-1-yl)-ethyl]-1H-pyrazolo[3,4-b]pyridine-5-carboxylic acid (4-tri-fluoromethyl-phenyl)-amide (Example 382). ¹HNMR (400 MHz, CDCl₃): δ=8.78 (s, 1H), 8.03 (brs, 1H), 7.62 (d, J=8.0 Hz, 2H), 7.36 (d, J=8.0 Hz, 2H), 4.58 (t, J=6.8 Hz, 2H), 2.90 (t, J=6.8 Hz, 2H), 2.75 (s, 3H), 2.61-2.55 (m, 4H), 2.41-2.36 (m, 6H), 1.06 (t, J=6.8 Hz, 3H). MS: m/z 461.1 (M+H⁺).

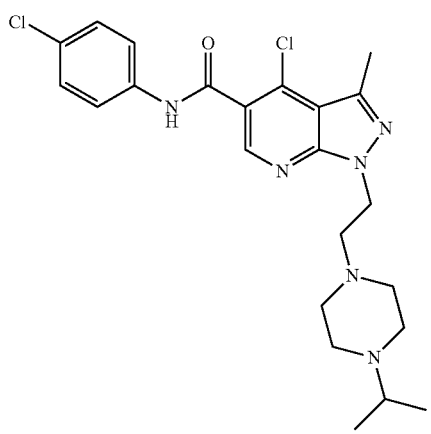 [SMILES: Cc1nn(CCN2CCN(C(C)C)CC2)c2ncc(C(=O)Nc3ccc(Cl)cc3)c(Cl)c12]

Example 387

4-Chloro-1-[2-(4-isopropyl-piperazin-1-yl)-ethyl]-3-methyl-1H-pyrazolo[3,4-b]pyridine-5-carboxylic acid (4-chloro-phenyl)-amide The title compound was prepared using general procedure for 4-chloro-3-methyl-1-[2-(4-methyl-piperazin-1-yl)-

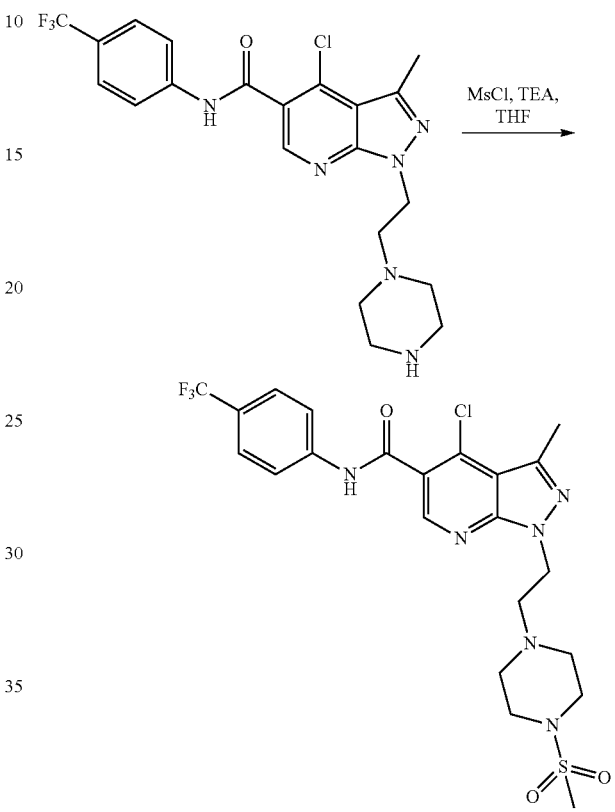

Example 388

4-Chloro-1-[2-(4-methanesulfonyl-piperazin-1-yl)-ethyl]-3-methyl-1H-pyrazolo[3,4-b]pyridine-5-carboxylic acid (4-trifluoromethyl-phenyl)-amide To a suspension of 4-chloro-3-methyl-1-(2-piperazin-1-yl-ethyl)-1H-pyrazolo[3,4-b]pyridine-5-carboxylic acid (4-trifluoromethyl-phenyl)-amide (HCl salt, 70 mg, 0.13 mmol) in THF (5 mL), was added TEA (66 mg, 0.65 mmol). After addition of MsCl (18 mg, 0.16 mmol), the reaction was stirred at room temperature for 30 mins. The reaction mixture was separated between saturated NaHCO₃ solution (50 mL) and EA (40 mL). The organic layer was dried over Na₂SO₄ and concentrated. The residue was triturated with EA/DCM=1/1 to give 4-chloro-1-[2-(4-methanesulfonyl-piperazin-1-yl)-ethyl]-3-methyl-1H-pyrazolo[3,4-b]pyridine-5-carboxylic acid (4-trifluoromethyl-phenyl)-amide (34 mg, yield: 48%) as a white solid. ¹HNMR (400 MHz, DMSO-d6): δ=11.02 (brs, 1H), 8.72 (s, 1H), 7.95 (d, J=8.8 Hz, 2H), 7.76 (d, J=8.8 Hz, 2H), 4.56 (t, J=6.4 Hz, 2H), 3.02-3.01 (m, 4H), 2.87 (t, J=6.4 Hz, 2H), 2.83 (s, 3H), 2.70 (s, 3H), 2.55 (m, 4H). MS: m/z 545.1 (M+H⁺).

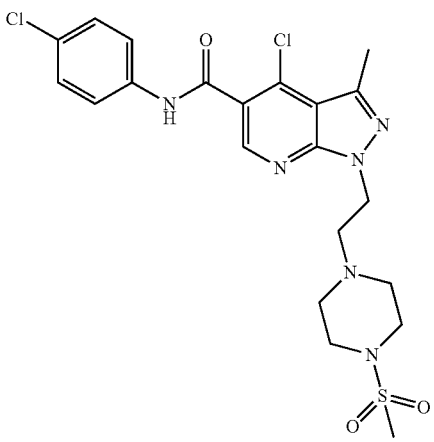 [SMILES: Cc1nn(CCN2CCN(S(C)(=O)=O)CC2)c2ncc(C(=O)Nc3ccc(Cl)cc3)c(Cl)c12]

Example 389

4-Chloro-1-((2-(4-methanesulfonyl-piperazin-1-yl)-ethyl]-3-methyl-1H-pyrazolo[3,4-b]pyridine-5-carboxylic acid (4-chloro-phenyl)-amide

The title compound was prepared using general procedure for 4-chloro-1-[2-(4-methanesulfonyl-piperazin-1-yl)-ethyl]-3-methyl-1H-pyrazolo[3,4-b]pyridine-5-carboxylic acid (4-trifluoromethyl-phenyl)-amide (Example 388). ¹HNMR (400 MHz, DMSO-d6): δ=10.77 (brs, 1H), 8.69 (s, 1H), 7.76 (d, J=8.4 Hz, 2H), 7.44 (d, J=8.8 Hz, 2H), 4.55 (t, J=6.8 Hz, 2H), 3.00-2.99 (m, 4H), 2.87 (t, J=6.4 Hz, 2H), 2.83 (s, 3H), 2.69 (s, 3H), 2.56-2.55 (m, 4H). MS: m/z 511.1 (M+H⁺).

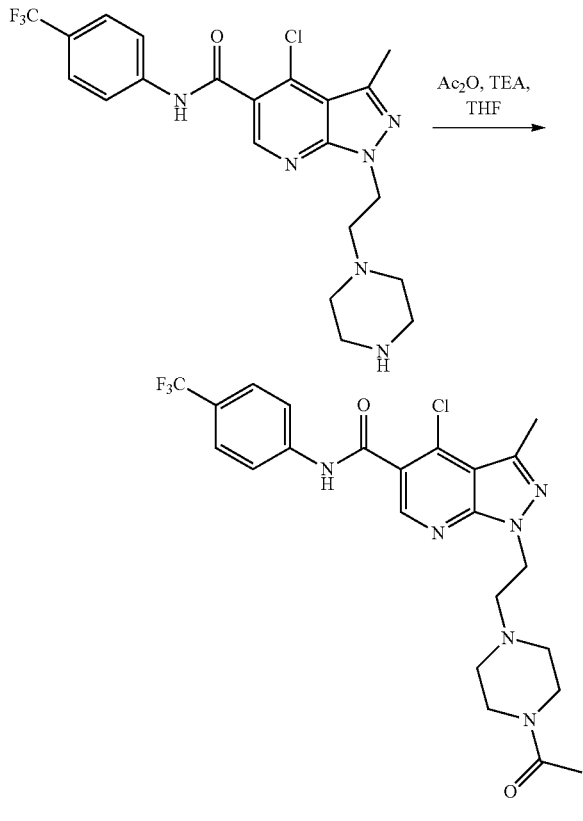

Example 390

1-((2-(4-Acetyl-piperazin-1-yl)-ethyl]-4-chloro-3-methyl-1H-pyrazolo[3,4-b]pyridine-5-carboxylic acid (4-trifluoromethyl-phenyl)-amide

To a suspension of 4-chloro-3-methyl-1-(2-piperazin-1-yl-ethyl)-1H-pyrazolo[3,4-b]pyridine-5-carboxylic acid (4-trifluoromethyl-phenyl)-amide (HCl salt, 70 mg, 0.13 mmol) in THF (5 mL), was added TEA (66 mg, 0.65 mmol). After addition of Ac₂O (16 mg, 0.16 mmol), the reaction was stirred at room temperature for 30 mins. The reaction mixture was separated between saturated NaHCO₃ solution (50 mL) and EA (40 mL). The organic layer was dried over Na₂SO₄ and concentrated. The residue was purified by prep-TLC (DCM/MeOH/NH₄OH=10/1/0.1) to give 1-[2-(4-acetyl-piperazin-1-yl)-ethyl]-4-chloro-3-methyl-1H-pyrazolo[3,4-b]pyridine-5-carboxylic acid (4-trifluoromethyl-phenyl)-amide (27 mg, yield: 41%) as a white solid.

¹HNMR (400 MHz, CDCl₃): δ=8.78 (s, 1H), 8.35 (brs, 1H), 7.82 (d, J=8.4 Hz, 2H), 7.66 (d, J=8.0 Hz, 2H), 4.61 (t, 2H), 3.49-3.46 (m, 2H), 3.38 (m, 2H), 2.99-2.98 (m, 2H), 2.77 (s, 3H), 2.60-2.57 (m, 2H), 2.45 (m, 2H), 2.05 (s, 3H). MS: m/z 509.1 (M+H⁺).

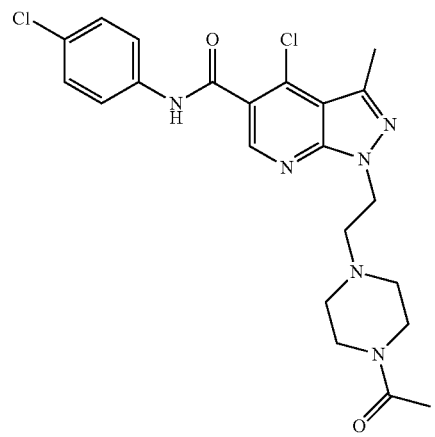 [SMILES: CC(=O)N1CCN(CCn2nc(C)c3c(Cl)c(C(=O)Nc4ccc(Cl)cc4)cnc32)CC1]

Example 391

1-[2-(4-Acetyl-piperazin-1-yl)-ethyl]-4-chloro-3-methyl-1H-pyrazolo[3,4-b]pyridine-5-carboxylic acid (4-chloro-phenyl)-amide

The title compound was prepared using general procedure for 1-[2-(4-acetyl-piperazin-1-yl)-ethyl]-4-chloro-3-methyl-1H-pyrazolo[3,4-b]pyridine-5-carboxylic acid (4-trifluoromethyl-phenyl)-amide (Example 390).

¹HNMR (400 MHz, CDCl₃): δ=8.75 (s, 1H), 8.27 (brs, 1H), 7.64 (d, J=8.8 Hz, 2H), 7.36 (d, J=8.8 Hz, 2H), 4.58 (t, J=6.4 Hz, 2H), 3.45 (t, J=4.8 Hz, 2H), 3.34 (t, J=4.8 Hz, 2H), 2.92 (t, J=6.4 Hz, 2H), 2.76 (s, 3H), 2.54 (t, J=4.6 Hz, 2H), 2.42 (t, J=4.8 Hz, 2H), 2.04 (s, 3H). MS: m/z 475.1 (M+H⁺).

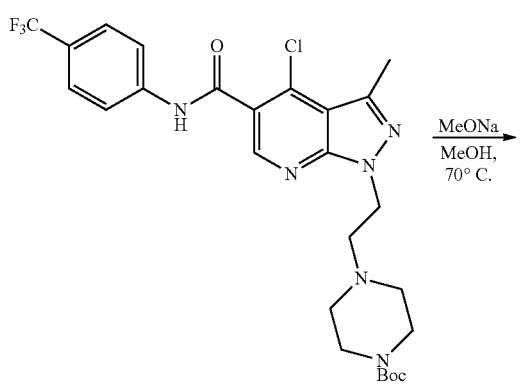

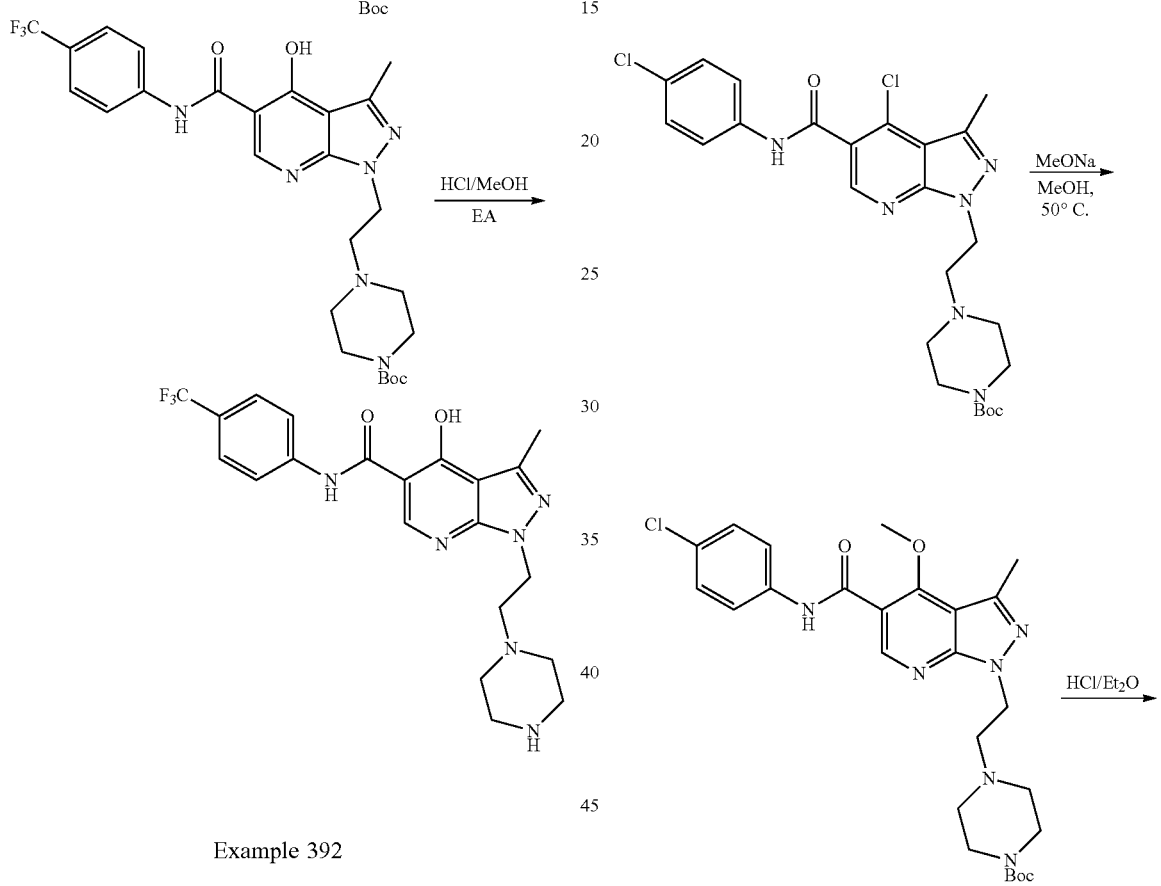

Example 392

4-Hydroxy-3-methyl-1-(2-piperazin-1-yl-ethyl)-1H-pyrazolo[3,4-b]pyridine-5-carboxylic acid (4-trifluoromethyl-phenyl)-amide Step 1

A mixture of MeONa (17 mg, 0.32 mmol) and 4-{2-[4-chloro-3-methyl-5-(4-trifluoromethyl-phenylcarbamoyl)-pyrazolo[3,4-b]pyridin-1-yl]-ethyl}-piperazine-1-carboxylic acid tert-butyl ester (180 mg, 0.32 mmol) in MeOH (5 mL) was stirred at 70° C. overnight. The reaction mixture was separated between saturated NH$_4$Cl solution (25 mL) and EA (25 mL). The organic layer was dried over Na$_2$SO$_4$ and concentrated. The residue was purified by prep-TLC (EA/TEA=200/1) to give 4-{2-[4-hydroxy-3-methyl-5-(4-trifluoromethyl-phenylcarbamoyl)-pyrazolo[3,4-b]pyridin-1-yl]-ethyl}-piperazine-1-carboxylic acid tert-butyl ester (50 mg, yield: 28%) as a white solid. MS: m/z 549.3 (M+H$^+$).

Step 2

To a solution of 4-{2-[4-hydroxy-3-methyl-5-(4-trifluoromethyl-phenylcarbamoyl)-pyrazolo[3,4-b]pyridin-1-yl]-ethyl}-piperazine-1-carboxylic acid tert-butyl ester (50 mg, 0.09 mmol) in EA (2 mL), was added HCl/MeOH (2.5 M, 5 mL). The mixture was stirred at room temperature for 2 hrs. The solid formed was collected by filtration to give HCl salt of 4-hydroxy-3-methyl-1-(2-piperazin-1-yl-ethyl)-1H-pyrazolo[3,4-b]pyridine-5-carboxylic acid (4-trifluoromethyl-phenyl)-amide (13 mg, yield: 28%) as a white solid.

$^1$HNMR (400 MHz, CD$_3$OD): δ=8.72 (s, 1H), 7.92 (d, J=8.0 Hz, 2H), 7.69 (d, J=8.8 Hz, 2H), 4.71 (t, J=6.0 Hz, 2H), 3.71 (t, J=5.6 Hz, 2H), 3.63-3.53 (m, 8H), 2.65 (s, 3H). MS: m/z 448.9 (M+H$^+$).

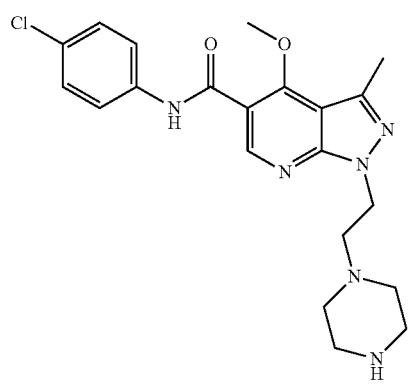

Example 393

4-Methoxy-3-methyl-1-(2-piperazin-1-yl-ethyl)-1H-pyrazolo[3,4-b]pyridine-5-carboxylic acid (4-chloro-phenyl)-amide

Step 1

A mixture of MeONa (49 mg, 0.9 mmol) and 4-{2-[4-chloro-5-(4-chloro-phenylcarbamoyl)-3-methyl-pyrazolo[3,4-b]pyridin-1-yl]-ethyl}-piperazine-1-carboxylic acid tert-butyl ester (160 mg, 0.3 mmol) in MeOH (5 mL) was stirred at 50° C. for 1 hr. The reaction mixture was separated between saturated NH$_4$Cl solution (20 mL) and EA (20 mL). The organic layer was dried over Na$_2$SO$_4$ and concentrated. The residue was purified by prep-TLC (EA/TEA=1000/1) to give 4-{2-[5-(4-chloro-phenylcarbamoyl)-4-methoxy-3-methyl-pyrazolo[3,4-b]pyridin-1-yl]-ethyl}-piperazine-1-carboxylic acid tert-butyl ester (120 mg, yield: 75%) as a white solid.

MS: m/z 529.2 (M+H$^+$).

Step 2

To a solution of 4-{2-[5-(4-chloro-phenylcarbamoyl)-4-methoxy-3-methyl-pyrazolo[3,4-b]pyridin-1-yl]-ethyl}-piperazine-1-carboxylic acid tert-butyl ester (50 mg, 0.1 mmol) in Et$_2$O (2.5 mL), was added HCl/Et$_2$O (2M, 5 mL). The mixture was stirred at room temperature overnight. After addition of saturated NaHCO$_3$ solution (35 mL), the mixture was extracted with EA (20 mL×2). The organic layers were combined, dried over Na$_2$SO$_4$ and concentrated. The residue was purified by prep-HPLC to give 4-methoxy-3-methyl-1-(2-piperazin-1-yl-ethyl)-1H-pyrazolo[3,4-b]pyridine-5-carboxylic acid (4-chloro-phenyl)-amide (8 mg, yield: 19%) as a white solid.

$^1$HNMR (300 MHz, DMSO-d6): δ=10.70 (brs, 1H), 8.51 (s, 1H), 7.77 (d, J=9.0 Hz, 2H), 7.43 (d, J=8.4 Hz, 2H), 4.48 (t, J=5.7 Hz, 2H), 4.06 (s, 3H), 2.75-2.65 (m, 6H), 2.58 (s, 3H), 2.46-2.40 (m, 4H). MS: m/z 429.2 (M+H$^+$).

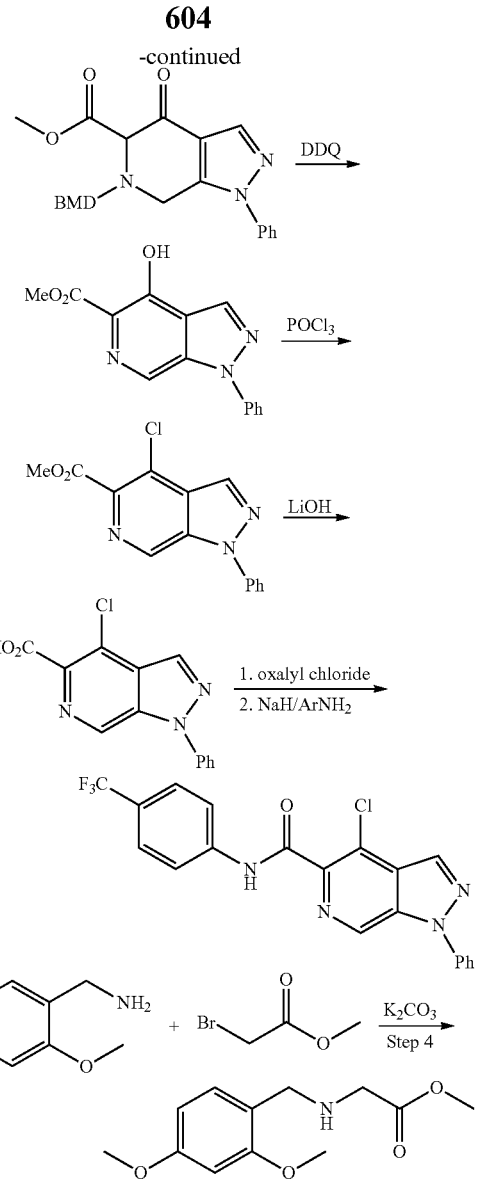

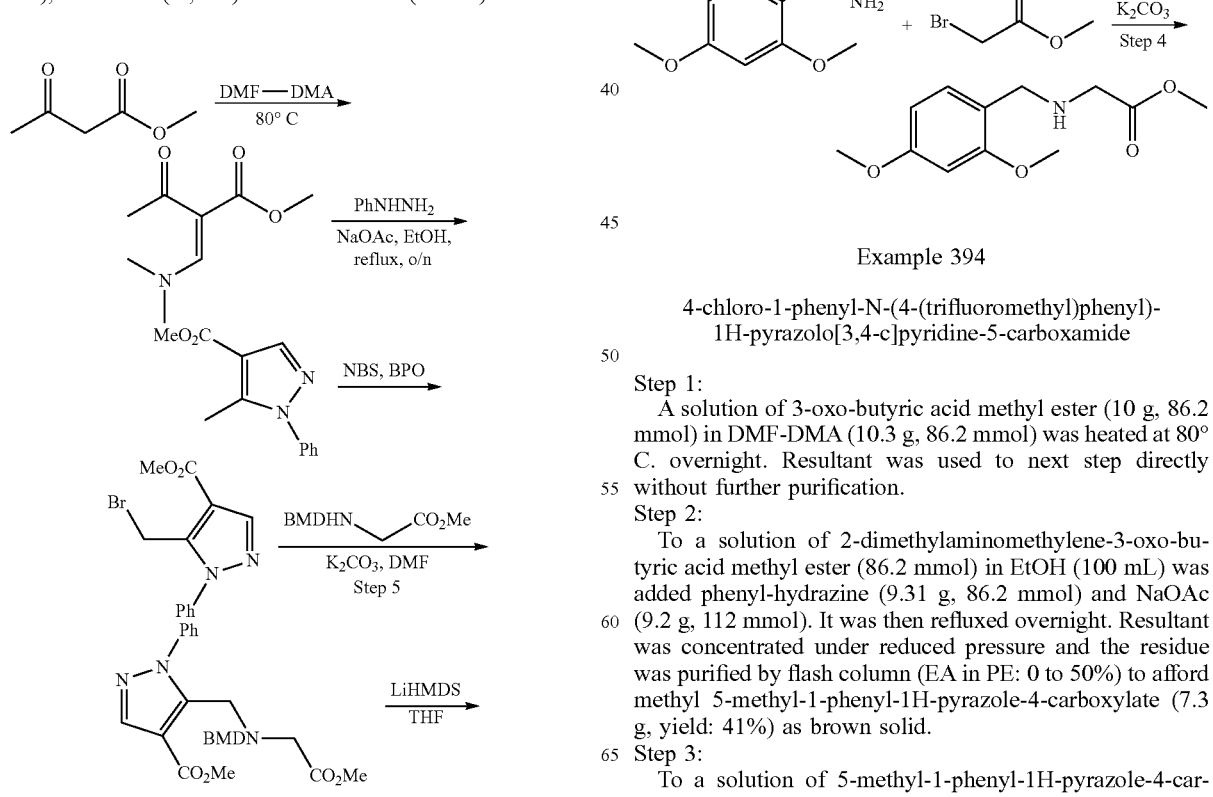

Example 394

4-chloro-1-phenyl-N-(4-(trifluoromethyl)phenyl)-1H-pyrazolo[3,4-c]pyridine-5-carboxamide

Step 1:

A solution of 3-oxo-butyric acid methyl ester (10 g, 86.2 mmol) in DMF-DMA (10.3 g, 86.2 mmol) was heated at 80° C. overnight. Resultant was used to next step directly without further purification.

Step 2:

To a solution of 2-dimethylaminomethylene-3-oxo-butyric acid methyl ester (86.2 mmol) in EtOH (100 mL) was added phenyl-hydrazine (9.31 g, 86.2 mmol) and NaOAc (9.2 g, 112 mmol). It was then refluxed overnight. Resultant was concentrated under reduced pressure and the residue was purified by flash column (EA in PE: 0 to 50%) to afford methyl 5-methyl-1-phenyl-1H-pyrazole-4-carboxylate (7.3 g, yield: 41%) as brown solid.

Step 3:

To a solution of 5-methyl-1-phenyl-1H-pyrazole-4-carboxylic acid methyl ester (7.3 g, 33.8 mmol) in CCl$_4$ (200 mL) was added BPO (4.09 g, 16.8 mmol). It was then refluxed overnight. Resultant was washed with water (200 mL) and the organic layer was concentrated under reduced pressure. The residue was purified by flash column (EA in PE: 0 to 30%) to afford methyl 5-(bromomethyl)-1-phenyl-1H-pyrazole-4-carboxylate (4.6 g, yield: 46%) as light brown oil.

Step 4:

To a solution of 2,4-dimethoxy-benzylamine (10 g, 59.8 mmol) in DMF (30 mL) was added bromo-acetic acid methyl ester (9.1 g, 59.8 mmol) and K$_2$CO$_3$ (9.8 g, 71.7 mmol). It was then stirred at room temperature overnight. Resultant was quenched with water (200 mL) and the mixture was extracted with EA (200 mL). The organic layer was concentrated under reduced pressure and the residue was purified by flash column (EA in PE: 0 to 30%) to afford methyl 2-((2,4-dimethoxybenzyl)amino)acetate (12 g, yield: 84%) as light brown oil.

Step 5:

To a solution of methyl 2-((2,4-dimethoxybenzyl)amino) acetate (2 g, 8.36 mmol) in DMF (20 mL) was added methyl 5-(bromomethyl)-1-phenyl-1H-pyrazole-4-carboxylate (2.46 g, 8.36 mmol) and K$_2$CO$_3$ (1.48 g, 10.86 mmol), and the mixture was heated to 60° C. and stirred overnight. The reaction was quenched with water (100 mL) and the aqueous phase was extracted with EA (100 mL). The organic layer was concentrated under reduced pressure and the residue was purified by flash column (EA in PE: 0 to 50%) to afford 5-{[(2,4-dimethoxy-benzyl)-methoxycarbonylmethyl-amino]-methyl}-1-phenyl-1H-pyrazole-4-carboxylic acid methyl ester (1.9 g, yield: 50%) as a light brown solid.

$^1$HNMR (300 MHz, CDCl$_3$): δ=8.07 (s, 1H), 7.82 (d, J=7.8 Hz, 2H), 7.44-7.42 (m, 3H), 6.98 (d, J=8.7 Hz, 2H), 6.39-6.37 (m, 2H), 4.33 (q, J=6.9 Hz, 2H), 4.16 (s, 2H), 3.79 (s, 5H), 3.66 (s, 3H), 3.59 (s, 3H), 3.24 (s, 2H), 1.38 (t, J=6.9 Hz, 3H);

Step 6:

To a solution of 5-{[(2,4-dimethoxy-benzyl)-methoxycarbonylmethyl-amino]-methyl}-1-phenyl-1H-pyrazole-4-carboxylic acid methyl ester (1 g, 2.37 mmol) in anhydrous THF (30 mL) was added LiHMDS (2 M, 1.18 mL) at −78° C., and the mixture was stirred at the same temperature for 1 hr. The reation was quenched with water (100 mL) and the aqueous phase was extracted with EA (100 mL). The organic layer was concentrated under reduced pressure and the residue was purified by flash column (EA in PE: 0 to 50%) to afford 6-(2,4-dimethoxy-benzyl)-4-hydroxy-1-phenyl-6,7-dihydro-1H-pyrazolo[3,4-c]pyridine-5-carboxylic acid methyl ester (450 mg, yield: 48%) as a white solid.

Step 7:

To a solution of 6-(2,4-dimethoxy-benzyl)-4-hydroxy-1-phenyl-6,7-dihydro-1H-pyrazolo[3,4-c]pyridine-5-carboxylic acid methyl ester (450 mg, 1.07 mmol) in CHCl$_3$ (100 mL) was added DDQ (2.43 g, 10.7 mmol), it was then refluxed overnight. Resultant was concentrated under reduced pressure and the residue was purified directly by column flash (EA in PE: 0 to 50%) to afford 4-hydroxy-1-phenyl-1H-pyrazolo[3,4-c]pyridine-5-carboxylic acid methyl ester (210 mg, yield: 73%) as a white solid. $^1$HNMR (300 MHz, DMSO-d6): δ=11.58 (s, 1H), 8.80 (s, 1H), 7.72 (s, 1H), 7.86 (d, J=7.8 Hz, 2H), 7.65 (t, J=7.5 Hz, 2H), 7.53-7.48 (m, 1H), 3.94 (s, 3H).

Step 8:

A solution of 4-hydroxy-1-phenyl-1H-pyrazolo[3,4-c]pyridine-5-carboxylic acid methyl ester (210 mg, 0.78 mmol) in POCl$_3$ (20 mL) was refluxed overnight. Resultant was evaporated to remove POCl$_3$, then diluted with EA (50 mL) and water (50 mL), adjusted pH to 8 with K$_2$CO$_3$. The organic layer was concentrated under reduced pressure and the residue was purified by flash column (EA in PE: 0 to 50%) to afford 4-chloro-1-phenyl-1H-pyrazolo[3,4-c]pyridine-5-carboxylic acid methyl ester (200 mg, yield: 89%) as a white solid.

$^1$HNMR (400 MHz, DMSO-d6): δ=9.27 (s, 1H), 8.79 (s, 1H), 7.90 (d, J=8.0 Hz, 2H), 7.67 (t, J=7.6 Hz, 2H), 7.54-7.52 (m, 1H), 3.94 (s, 3H).

Step 9:

To a solution of 4-chloro-1-phenyl-1H-pyrazolo[3,4-c]pyridine-5-carboxylic acid methyl ester (200 mg, 0.70 mmol) in THF/H$_2$O (5/1, 30 mL) was added LiOH.H$_2$O (161 mg, 3.5 mmol), it was then stirred at room temperature overnight. Resultant was evaporated to remove THF and then diluted with water (20 mL), adjusted pH to 2 with con. HCl. The resulting white solid was collected and dried in vacuum to afford 190 mg of intermediate acid. Subsequently, it was dissolved in DCM (20 mL), oxalyl chloride (116 mg, 0.91 mmol) and DMF (one drop) was added. Then it was stirred at room temperature for 1 hr before concentrated. The residue was added to a mixture of 4-trifluoromethyl-phenylamine (112 mg, 0.7 mmol) and NaH (40%, 36.4 mg, 0.91 mmol) in THF. Then it stirred at room temperature overnight. Resultant was quenched with water (50 mL). The aqueous phase was extracted with EA (50 mL). The organic layer was concentrated under reduced pressure and the residue was purified by prep-HPLC to afford 4-chloro-1-phenyl-N-(4-(trifluoromethyl)phenyl)-1H-pyrazolo[3,4-c]pyridine-5-carboxamide (20 mg, yield: 6.9%) as a white solid.

$^1$HNMR (400 MHz, CD$_3$OD): δ=9.02 (s, 1H), 8.61 (s, 1H), 7.97 (d, J=8.4 Hz, 2H), 7.85 (d, J=8.0 Hz, 2H), 7.68-7.64 (m, 4H), 7.55-7.53 (m, 1H); MS: m/z 417.1 (M+H$^+$).

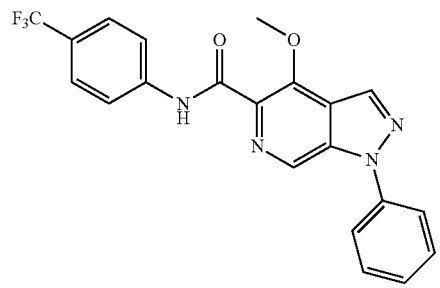

Example 395

4-methoxy-1-phenyl-N-(4-(trifluoromethyl)phenyl)-1H-pyrazolo[3,4-c]pyridine-5-carboxamide This target was got as a byproduct during the preparation of target 4-chloro-1-phenyl-N-(4-(trifluoromethyl)phenyl)-1H-pyrazolo[3,4-c]pyridine-5-carboxamide (Example 394).

$^1$HNMR (400 MHz, CDCl$_3$): δ=10.24 (s, 1H), 8.80 (s, 1H), 8.58 (s, 1H), 7.91 (d, J=8.0 Hz, 2H), 7.75 (d, J=7.6 Hz, 2H), 7.65-7.61 (m, 4H), 7.52-7.49 (m, 1H), 4.48 (s, 3H); MS: m/z 413.1 (M+H$^+$).

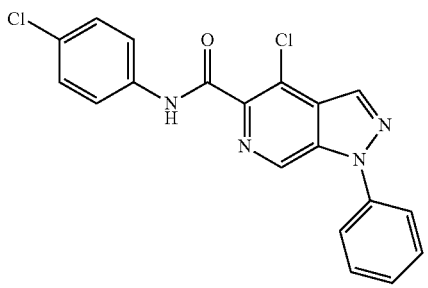 [SMILES: O=C(Nc1ccc(Cl)cc1)c1ncc2c(cnn2-c2ccccc2)c1Cl]

Example 396

4-chloro-N-(4-chlorophenyl)-1-phenyl-1H-pyrazolo[3,4-c]pyridine-5-carboxamide

The title compound was prepared using general procedure for 4-chloro-1-phenyl-N-(4-(trifluoromethyl)phenyl)-1H-pyrazolo[3,4-c]pyridine-5-carboxamide (Example 394).

$^1$HNMR (400 MHz, CDCl$_3$): δ=10.14 (s, 1H), 9.05 (s, 1H), 8.53 (s, 1H), 7.77-7.74 (m, 4H), 7.65-7.62 (m, 2H), 7.53-7.49 (m, 1H), 7.35 (d, J=8.4 Hz, 2H); MS: m/z 383.1 (M+H$^+$).

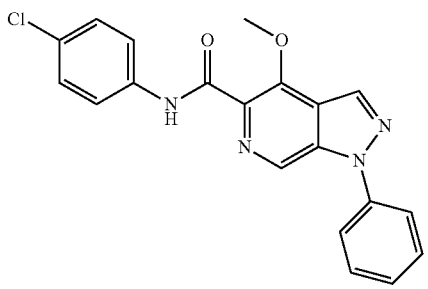 [SMILES: COc1c(C(=O)Nc2ccc(Cl)cc2)ncc2c1cnn2-c1ccccc1]

Example 397

N-(4-chlorophenyl)-4-methoxy-1-phenyl-1H-pyrazolo[3,4-c]pyridine-5-carboxamide

This target was obtained as a byproduct during the preparation of target 4-chloro-N-(4-chlorophenyl)-1-phenyl-1H-pyrazolo[3,4-c]pyridine-5-carboxamide $^1$HNMR (400 MHz, CDCl$_3$): δ=10.05 (s, 1H), 8.79 (s, 1H), 8.56 (s, 1H), 7.75 (d, J=7.2 Hz, 4H), 7.64-7.60 (m, 2H), 7.51-7.49 (m, 1H), 7.33 (d, J=8.8 Hz, 2H), 4.45 (s, 3H); MS: m/z 379.1 (M+H$^+$).

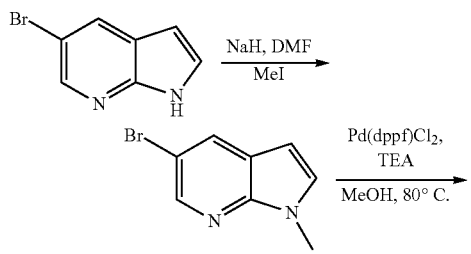

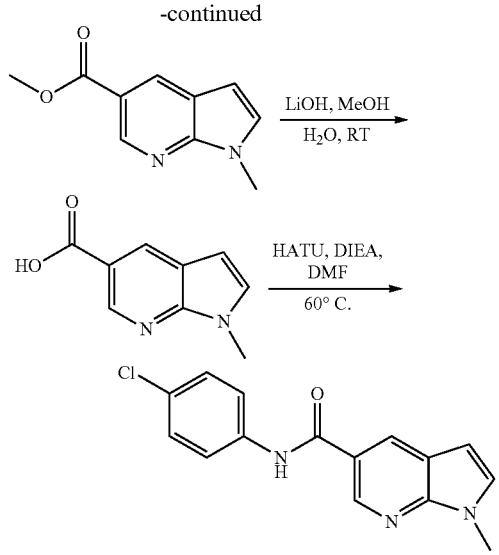

Example 398

1-Methyl-1H-pyrrolo[2,3-b]pyridine-5-carboxylic acid (4-chloro-phenyl)-amide

Step 1:

To a solution of 5-bromo-1H-pyrrolo[2,3-b]pyridine (1.5 g, 7.6 mmol) in DMF (10 mL) was added NaH (365 mg, 9.1 mmol) at 0° C. The mixture was stirred at rt for 1.5 hrs. MeI (1.4 g, 9.8 mmol) was added and stirred at rt overnight. The reaction was quenched with sat. NH$_4$Cl solution (10 mL) and separated between water (20 mL) and EA (20 mL). The organic layer was washed with water (10 mL) and brine (10 mL), dried over anhydrous Na$_2$SO$_4$. The solvent was removed to give 5-bromo-1-methyl-1H-pyrrolo[2,3-b]pyridine (1.7 g, yield: quantitative) as pale yellow crystal. $^1$HNMR (300 MHz, CDCl$_3$): δ=8.34 (d, J=2.1 Hz, 1H), 8.01 (d, J=2.4 Hz, 1H), 7.18 (d, J=3.6 Hz, 1H), 6.39 (d, J=3.3 Hz, 1H), 3.86 (s, 3H).

Step 2:

To a solution of 5-bromo-1-methyl-1H-pyrrolo[2,3-b]pyridine (800 mg, 3.8 mmol) in MeOH (15 mL) were added Pd(dppf)Cl$_2$ (272 mg, 0.38 mmol) and TEA (1.15 g, 11.4 mmol). The mixture was stirred at 80° C. under CO (1 atm) overnight. The solvent was removed and the residue was purified by silica gel column (100-200 mush, PE/EA=10/1) to give 1-methyl-1H-pyrrolo[2,3-b]pyridine-5-carboxylic acid methyl ester (665 mg, yield: 91%) as a yellow solid. $^1$HNMR (300 MHz, CDCl$_3$): δ=9.00 (s, 1H), 8.57 (d, J=1.2 Hz, 1H), 7.25 (d, J=3.6 Hz, 1H), 6.55 (d, J=3.3 Hz, 1H), 3.96 (s, 3H), 3.92 (s, 3H). MS: m/z 191.0 (M+H$^+$).

Step 3:

To a solution 1-methyl-1H-pyrrolo[2,3-b]pyridine-5-carboxylic acid methyl ester (380 mg, 2.0 mmol) in MeOH/H$_2$O=4:1 (10 mL) was added LiOH.H$_2$O (336 mg, 8 mmol). The mixture was stirred at RT for 4 hrs. The solution was adjusted to pH=8 with conc. HCl. Organic solvent was removed under reduced pressure. The water solution was adjusted to pH=5 with conc. HCl. The precipitates was collected by filtration and dried to give 1-methyl-1H-pyrrolo[2,3-b]pyridine-5-carboxylic acid (300 mg, yield: 85%) as a white solid.

Step 4:

To a mixture of 1-methyl-1H-pyrrolo[2,3-b]pyridine-5-carboxylic acid (70 mg, 0.4 mmol) and HATU (228 mg, 0.6 mmol) in DMF (5 mL), was added DIEA (206 mg, 1.6 mmol). The mixture was stirred at room temperature for 15 min. 4-chloro-phenylamine was then added to the mixture. The reaction was stirred at 60° C. overnight. Water (5 mL) was added to the reaction, stirred for 5 min. The solid formed was collected by filtration. The filter cake was washed with water (5 mL), EA (3.5 mL) and PE (5 mL), dried to give 1-methyl-1H-pyrrolo[2,3-b]pyridine-5-carboxylic acid (4-chloro-phenyl)-amide (57 mg, yield: 50%) as a pale white solid.

¹HNMR (300 MHz, DMSO-d6): δ=10.43 (brs, 1H), 8.85 (d, J=1.8 Hz, 1H), 8.57 (d, J=2.1 Hz, 1H), 7.84 (d, J=9.0 Hz, 2H), 7.65 (d, J=3.6 Hz, 1H), 7.42 (d, J=8.7 Hz, 2H), 6.64 (d, J=3.3 Hz, 1H), 3.88 (s, 3H). MS: m/z 286.0(M+H⁺).

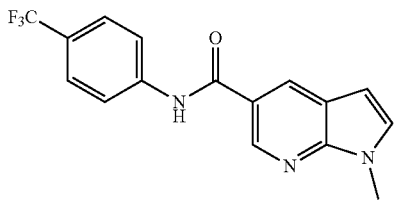 [SMILES: Cn1ccc2cc(C(=O)Nc3ccc(C(F)(F)F)cc3)cnc21]

Hz, 2H), 7.30 (d, J=3.6 Hz, 1H), 6.58 (d, J=3.6 Hz, 1H), 3.94 (s, 3H). MS: m/z 320.1 (M+H⁺).

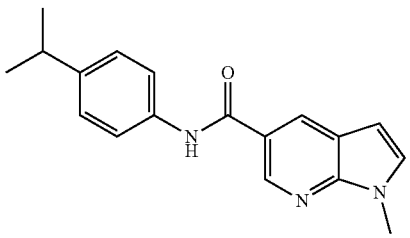 [SMILES: CC(C)c1ccc(NC(=O)c2cnc3c(ccn3C)c2)cc1]

Example 400

1-Methyl-1H-pyrrolo[2,3-b]pyridine-5-carboxylic acid (4-isopropyl-phenyl)-amide

The title compound was prepared using general procedure for 1-methyl-1H-pyrrolo[2,3-b]pyridine-5-carboxylic acid (4-chloro-phenyl)-amide (Example 398).

¹HNMR (300 MHz, CDCl₃): δ=8.85 (d, J=2.1 Hz, 1H), 8.42 (d, J=2.1 Hz, 1H), 7.84 (brs, 1H), 7.57 (d, J=8.7 Hz, 2H), 7.28-7.23 (m, 3H), 6.56 (d, J=3.6 Hz, 1H), 3.93 (s, 3H), 2.93-2.86 (m, 1H), 1.26 (d, J=7.2 Hz, 6H). MS: m/z 294.1 (M+H⁺).

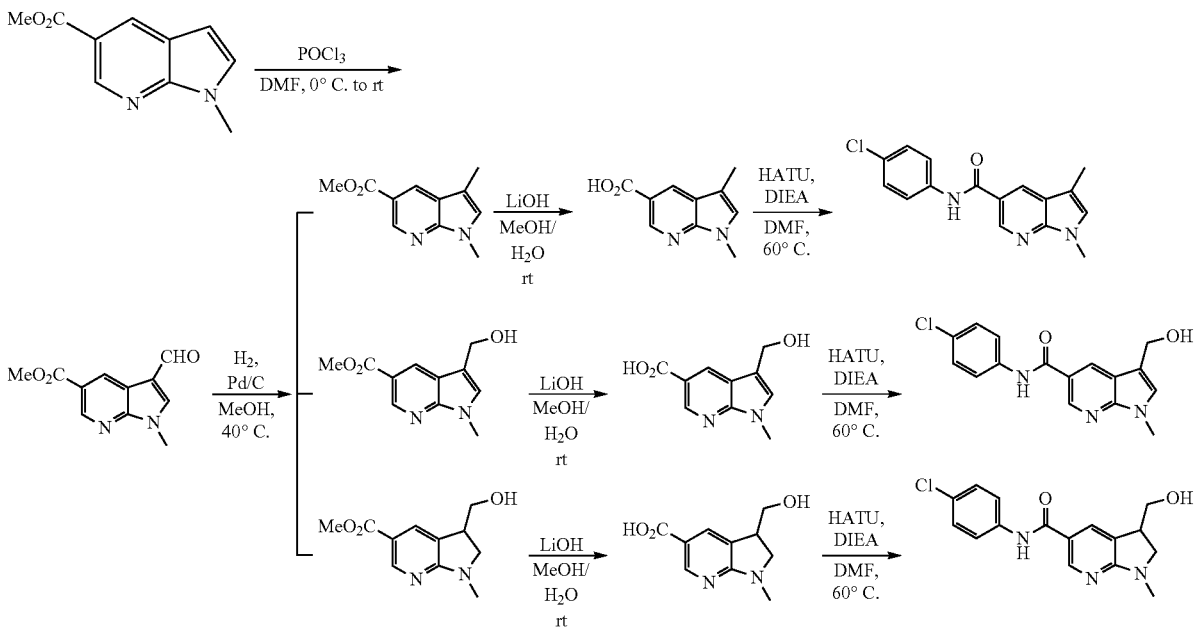

Example 399

1-Methyl-1H-pyrrolo[2,3-b]pyridine-5-carboxylic acid (4-trifluoromethyl-phenyl)-amide The title compound was prepared using general procedure for 1-methyl-1H-pyrrolo[2,3-b]pyridine-5-carboxylic acid (4-chloro-phenyl)-amide (Example 398). ¹HNMR (300 MHz, CDCl₃): δ=8.86 (d, J=2.1 Hz, 1H), 8.44 (d, J=2.1 Hz, 1H), 8.02 (brs, 1H), 7.81 (d, J=8.7 Hz, 2H), 7.64 (d, J=8.7

Example 401

1,3-Dimethyl-1H-pyrrolo[2,3-b]pyridine-5-carboxylic acid (4-chloro-phenyl)-amide Step 1:

POCl₃ (1.86 mL, 20.0 mmol) was added to DMF (15 mL) at 0° C., the solution was stirred for 10 min. To the above solution was added a solution of 1-methyl-1H-pyrrolo[2,3-b]pyridine-5-carboxylic acid methyl ester (380 mg, 2.0 mmol) in DMF (2.4 mL) at 0° C. The resulting was stirred at 0° C. for 30 mins, then at rt overnight. The solvents were removed under reduced pressure. The residue was treated with saturated NaHCO₃ solution (70 mL) and extracted with EA (70 mL). The organic layer was washed with water (70 mL) and brine (70 mL), and dried over anhydrous Na₂SO₄. The solution was concentrated to give 3-formyl-1-methyl-1H-pyrrolo[2,3-b]pyridine-5-carboxylic acid methyl ester (340 mg, yield: 78%) as a white solid. MS: m/z 219.0 (M+H⁺).

Step 2:

To a solution of 3-formyl-1-methyl-1H-pyrrolo[2,3-b]pyridine-5-carboxylic acid methyl ester (340 mg, 1.56 mmol) in MeOH, Pd/C (wet 10%, 120 mg) was added. The reaction was stirred at 40° C. under H₂ (1 atm) for 3 days. The reaction was then filtered. The filtrate was concentrated and purified by silica gel column (100-200 mush, 20%~100% EA in PE) to give fraction A and B.

A: 1,3-dimethyl-1H-pyrrolo[2,3-b]pyridine-5-carboxylic acid methyl ester (80 mg, yield: 25%) as a yellow crystal. ¹HNMR (300 MHz, CDCl₃): δ=8.98 (d, J=2.1 Hz, 1H), 8.52 (d, J=2.1 Hz, 1H), 7.00 (s, 1H), 3.96 (s, 3H), 3.86 (s, 3H), 2.33 (s, 3H). MS: m/z 205.0 (M+H⁺).

B: The mixture of 3-hydroxymethyl-1-methyl-1H-pyrrolo[2,3-b]pyridine-5-carboxylic acid methyl ester and 3-hydroxymethyl-1-methyl-2,3-dihydro-1H-pyrrolo[2,3-b]pyridine-5-carboxylic acid methyl ester (130 mg, yield: 38%) as a colorless gel. ¹HNMR (300 MHz, CDCl₃): δ=8.99 (d, J=2.1 Hz, 1H), 8.66 (d, J=2.1 Hz, 1H), 7.24 (s, 1H), 4.87 (s, 2H), 3.95 (s, 3H), 3.88 (s, 3H). MS: m/z 221.0 (M+H⁺).

¹HNMR (300 MHz, CDCl₃): δ=8.56 (d, J=1.8 Hz, 1H), 7.70 (t, J=1.5 Hz, 1H), 3.83 (s, 3H), 3.78 (d, J=6.0 Hz, 2H), 3.71 (t, J=9.6 Hz, 1H), 3.53-3.44 (m, 2H), 3.01 (s, 3H).

Step 3-4:

These two steps were similar to 1-methyl-1H-pyrrolo[2,3-b]pyridine-5-carboxylic acid (4-chloro-phenyl)-amide (Example 398). ¹HNMR (300 MHz, CDCl₃): δ=8.80 (d, J=2.1 Hz, 1H), 8.36 (d, J=2.1 Hz, 1H), 8.02 (brs, 1H), 7.63 (d, J=8.7 Hz, 2H), 7.33 (d, J=8.7 Hz, 2H), 7.02 (s, 1H), 3.85 (s, 3H), 2.32 (s, 3H). MS: m/z 300.1 (M+H⁺).

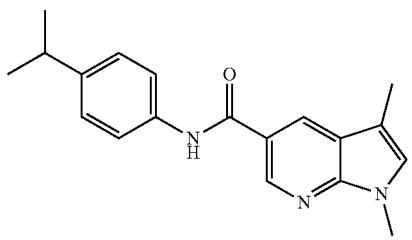 [SMILES: Cc1cn(C)c2ncc(C(=O)Nc3ccc(C(C)C)cc3)cc12]

Example 402

1,3-Dimethyl-1H-pyrrolo[2,3-b]pyridine-5-carboxylic acid (4-isopropyl-phenyl)-amide The title compound was prepared using general procedure for 1-methyl-1H-pyrrolo[2,3-b]pyridine-5-carboxylic acid (4-chloro-phenyl)-amide (Example 398).

¹HNMR (300 MHz, DMSO-d6): δ=10.23 (brs, 1H), 8.84 (d, J=1.8 Hz, 1H), 8.56 (d, J=2.1 Hz, 1H), 7.72-7.69 (m, 2H), 7.39 (s, 1H), 7.24-7.21 (m, 2H), 3.80 (s, 3H), 2.91-2.82 (m, 1H), 2.32 (s, 3H), 1.21-1.15 (m, 6H). MS: m/z 308.2 (M+H⁺).

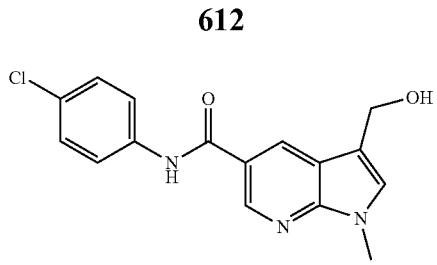

Example 403

3-Hydroxymethyl-1-methyl-1H-pyrrolo[2,3-b]pyridine-5-carboxylic acid (4-chloro-phenyl)-amide The title compound was prepared using general procedure for 1-methyl-1H-pyrrolo[2,3-b]pyridine-5-carboxylic acid (4-chloro-phenyl)-amide (Example 398). ¹HNMR (300 MHz, DMSO-d6): δ=10.46 (brs, 1H), 8.86 (d, J=1.8 Hz, 1H), 8.64 (d, J=1.8 Hz, 1H), 7.86 (d, J=8.7 Hz, 2H), 7.54 (s, 1H), 7.42 (d, J=8.7 Hz, 2H), 5.05 (t, J=5.3 Hz, 1H), 4.68 (d, J=5.1 Hz, 2H), 3.83 (s, 3H). MS: m/z 316.1 (M+H⁺).

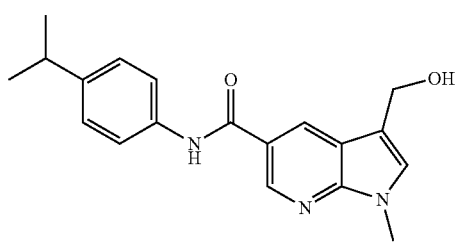 [SMILES: CC(C)c1ccc(NC(=O)c2cnc3c(c2)c(CO)cn3C)cc1]

Example 404

3-Hydroxymethyl-1-methyl-1H-pyrrolo[2,3-b]pyridine-5-carboxylic acid (4-isopropyl-phenyl)-amide The title compound was prepared using general procedure for 1-methyl-1H-pyrrolo[2,3-b]pyridine-5-carboxylic acid (4-chloro-phenyl)-amide (Example 398).

¹HNMR (400 MHz, DMSO-d6): δ=10.25 (brs, 1H), 8.86 (d, J=2.0 Hz, 1H), 8.64 (d, J=2.0 Hz, 1H), 7.69 (d, J=8.4 Hz, 2H), 7.53 (s, 1H), 7.23 (d, J=8.4 Hz, 2H), 5.02 (t, J=5.4 Hz, 1H), 4.68 (d, J=5.2 Hz, 2H), 3.83 (s, 3H), 2.88-2.85 (m, 1H), 1.22-1.19 (m, 6H). MS: m/z 324.1 (M+H⁺).

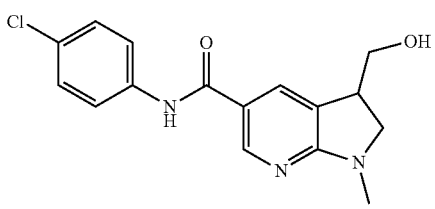 [SMILES: CN1CC(CO)c2cc(C(=O)Nc3ccc(Cl)cc3)cnc21]

Example 405

3-Hydroxymethyl-1-methyl-2,3-dihydro-1H-pyrrolo[2,3-b]pyridine-5-carboxylic acid (4-chloro-phenyl)-amide The title compound was prepared using general procedure for 1-methyl-1H-pyrrolo[2,3-b]pyridine-5-carboxylic acid (4-chloro-phenyl)-amide (Example 398).

¹HNMR (400 MHz, DMSO-d6): δ=10.01 (brs, 1H), 8.47 (d, J=1.2 Hz, 1H), 7.77-7.75 (m, 3H), 7.37 (d, J=8.8 Hz, 2H), 4.99 (t, J=5.2 Hz, 1H), 3.68-3.51 (m, 3H), 3.41-3.32 (m, 2H), 2.93 (s, 3H). MS: m/z 318.0 (M+H⁺).

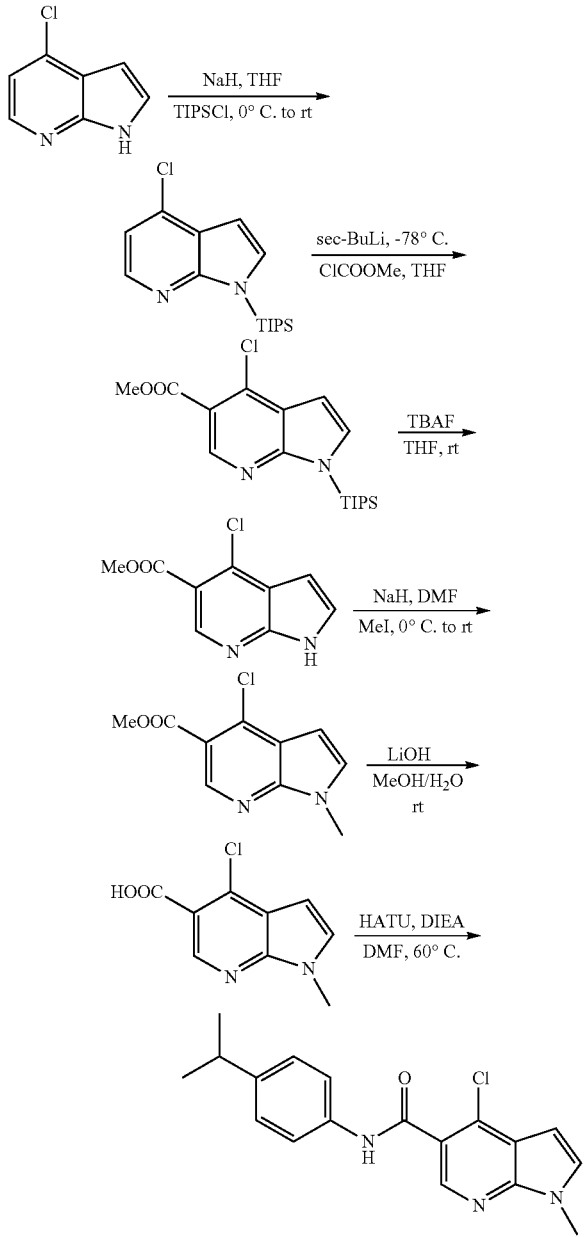

Example 406

4-Chloro-1-methyl-1H-pyrrolo[2,3-b]pyridine-5-carboxylic acid (4-isopropyl-phenyl)-amide Step 1:

To a solution of 4-chloro-1H-pyrrolo[2,3-b]pyridine (2.0 g, 13.3 mmol) in THF (15 mL) was added NaH (60%, 630 mg, 15.76 mmol) at 0° C. in portions. After stirring at room temperature for 1 hr, chloro-triisopropyl-silane (3.3 g, 17.1 mmol) was added and stirred at rt overnight. The reaction was poured into water (50 mL) and extracted with EA (30 mL). The organic layer was dried over anhydrous Na₂SO₄ and concentrated. The residue was purified by silica gel column (PE/EA=50/1) to give 4-chloro-1-triisopropylsilanyl-1H-pyrrolo[2,3-b]pyridine (1.5 g, yield: 37%) as a yellow oil.

¹HNMR (400 MHz, CDCl₃): δ=8.13 (d, J=5.2 Hz, 1H), 7.32 (d, J=3.6 Hz, 1H), 7.05 (d, J=4.8 Hz, 1H), 6.65 (d, J=3.2 Hz, 1H), 1.88-1.81 (m, 3H), 1.12-1.09 (m, 18H).

Step 2:

To a solution of 4-chloro-1-triisopropylsilanyl-1H-pyrrolo[2,3-b]pyridine (1.0 g, 3.24 mmol) in THF (30 mL) was added sec-BuLi (1.3 M, 5.4 mL, 7.13 mmol) drop wise at −78° C. under N₂. After stirred at this temperature for 0.5 hr, methyl chloroformate (0.76 mL, 9.96 mmol) was added slowly and stirred at −78° C. for an additional 0.5 hr. The reaction was warmed to rt gradually. The reaction was worked up with another batch (500 mg). Water (20 mL) was added to the reaction solution and extracted with EA (20 mL). The organic layer was washed with water (20 mL) and brine (20 mL), dried over anhydrous Na₂SO₄. The solvent was removed to give 4-chloro-1-triisopropylsilanyl-1H-pyrrolo[2,3-b]pyridine-5-carboxylic acid methyl ester (2.4 g, yield: quantitative) as a yellow oil. MS: m/z 210.9 (M+H⁺).

Step 3:

To a solution of 4-chloro-1-triisopropylsilanyl-1H-pyrrolo[2,3-b]pyridine-5-carboxylic acid methyl ester (2.03 g, 5.54 mmol) in THF, TBAF in THF (1 M, 5.54 mL) was added. The mixture was stirred at rt overnight. The reaction solution was combined with another batch (366 mg), concentrated, purified by silica gel column (100-200 mush, PE~PE/EA=2:1) to give 4-chloro-1H-pyrrolo[2,3-b]pyridine-5-carboxylic acid methyl ester (650 mg, yield: 47%) as a white solid.

Step 4:

To a solution of 4-chloro-1H-pyrrolo[2,3-b]pyridine-5-carboxylic acid methyl ester (0.65 g, 3.1 mmol) in DMF (6.0 mL) was added NaH (60%, 149 mg, 3.72 mmol) at 0° C. The mixture was stirred at rt for 1 h. MeI (572 mg, 4.03 mmol) was added to the reaction and stirred at rt overnight. The reaction was quenched with sat. NH₄Cl solution (10 mL) and separated between water (20 mL) and EA (30 mL). The organic layer was washed with water (10 mL) and brine (10 mL), dried over anhydrous Na₂SO₄. The solvent was removed to give 4-chloro-1-methyl-1H-pyrrolo[2,3-b]pyridine-5-carboxylic acid methyl ester (0.75 g, yield: quantitative) as yellow crystal.

¹HNMR (400 MHz, CDCl₃): δ=8.86 (s, 1H), 7.26 (overlap, 1H), 6.68 (d, J=3.6 Hz, 1H), 3.97 (s, 3H), 3.91 (s, 3H).

Step 5-6:

These two steps were similar to 1-methyl-1H-pyrrolo[2,3-b]pyridine-5-carboxylic acid (4-chloro-phenyl)-amide (Example 398). ¹HNMR (300 MHz, CDCl₃): δ=8.74 (s, 1H), 8.02 (brs, 1H), 7.61 (d, J=8.7 Hz, 2H), 7.30-7.24 (overlap, 3H), 6.64 (d, J=3.6 Hz, 1H), 3.93 (s, 3H), 2.94-2.89 (m, 1H), 1.27 (s, 3H), 1.25 (s, 3H). MS: m/z 328.1 (M+H⁺).

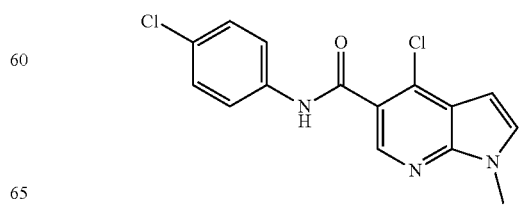

Example 407

4-Chloro-1-methyl-1H-pyrrolo[2,3-b]pyridine-5-carboxylic acid (4-chloro-phenyl)-amide The title compound was prepared using general procedure for 1-methyl-1H-pyrrolo[2,3-b]pyridine-5-carboxylic acid (4-chloro-phenyl)-amide (Example 398). ¹HNMR (300 MHz, DMSO-d6): δ=10.69 (brs, 1H), 8.46 (s, 1H), 7.79-7.76 (m, 3H), 7.43 (d, J=8.7 Hz, 2H), 6.64 (d, J=3.6 Hz, 1H), 3.88 (s, 3H). MS: m/z 320.1 (M+H⁺).

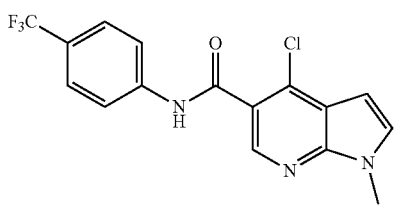

Example 408

4-Chloro-1-methyl-1H-pyrrolo[2,3-b]pyridine-5-carboxylic acid (4-trifluoromethyl-phenyl)-amide The title compound was prepared using general procedure for 1-methyl-1H-pyrrolo[2,3-b]pyridine-5-carboxylic acid (4-chloro-phenyl)-amide (Example 398). ¹HNMR (300 MHz, CDCl₃): δ=8.76 (s, 1H), 8.44 (d, J=2.1 Hz, 1H), 8.28 (brs, 1H), 7.81 (d, J=8.4 Hz, 2H), 7.64 (d, J=9.0 Hz, 2H), 7.31 (d, J=3.3 Hz, 1H), 6.66 (d, J=3.3 Hz, 1H), 3.94 (s, 3H). MS: m/z 354.0 (M+H⁺).

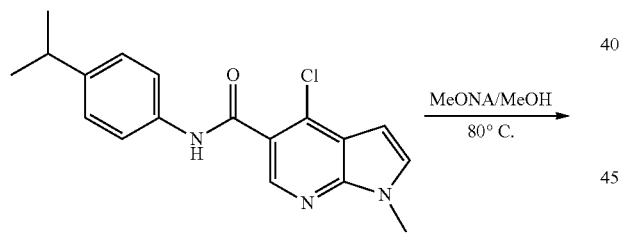

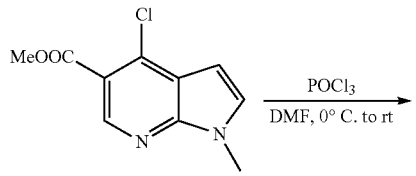

Example 409

4-Methoxy-1-methyl-1H-pyrrolo[2,3-b]pyridine-5-carboxylic acid (4-isopropyl-phenyl)-amide To a solution of 4-chloro-1-methyl-1H-pyrrolo[2,3-b]pyridine-5-carboxylic acid (4-isopropyl-phenyl)-amide (20 mg, 0.06 mmol) in MeOH (1 mL) was added MeONa (16 mg, 0.3 mmol). The reaction was stirred at 80° C. overnight. Sat. NH₄Cl solution (5 mL) and water (5 mL) were added to the reaction solution and the mixture was extracted with EA (15 mL). The organic layer was washed with water (10 mL) and brine (10 mL), dried over anhydrous Na₂SO₄ and concentrated. The residue was purified by prep-TLC to give 4-methoxy-1-methyl-1H-pyrrolo[2,3-b]pyridine-5-carboxylic acid (4-isopropyl-phenyl)-amide (14 mg, yield: 70%) as a white solid. ¹HNMR (300 MHz, DMSO-d6): δ=9.95 (brs, 1H), 8.43 (s, 1H), 7.64 (d, J=8.4 Hz, 2H), 7.50 (d, J=3.9 Hz, 1H), 7.20 (d, J=8.4 Hz, 2H), 6.90 (d, J=3.6 Hz, 1H), 4.35 (s, 3H), 3.81 (s, 3H), 2.88-2.83 (m, 1H), 1.23 (s, 3H), 1.20 (s, 3H). MS: m/z 324.2 (M+H⁺).

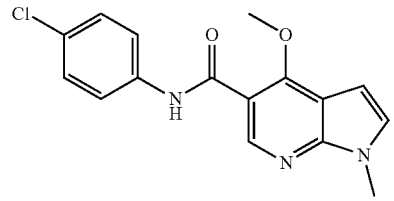 [SMILES: COc1c(C(=O)Nc2ccc(Cl)cc2)cnc2c1ccn2C]

Example 410

4-Methoxy-1-methyl-1H-pyrrolo[2,3-b]pyridine-5-carboxylic acid (4-chloro-phenyl)-amide The title compound was prepared using general procedure for 4-methoxy-1-methyl-1H-pyrrolo[2,3-b]pyridine-5-carboxylic acid (4-isopropyl-phenyl)-amide (Example 409).

¹HNMR (300 MHz, DMSO-d6): δ=10.17 (brs, 1H), 8.41 (s, 1H), 7.78 (d, J=8.7 Hz, 2H), 7.51 (d, J=3.3 Hz, 1H), 7.39 (d, J=8.7 Hz, 2H), 6.92 (d, J=3.9 Hz, 1H), 4.35 (s, 3H), 3.81 (s, 3H). MS: m/z 316.0 (M+H⁺).

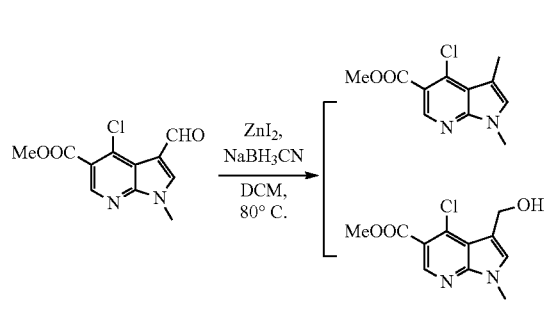
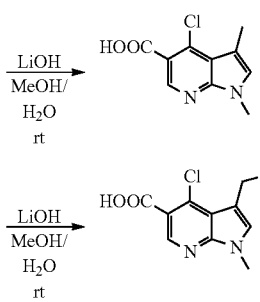
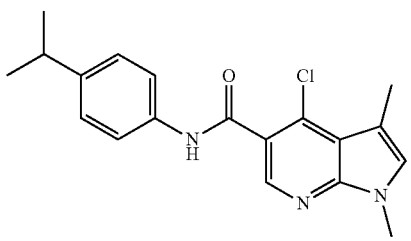 [SMILES: Cc1cn(C)c2ncc(C(=O)Nc3ccc(C(C)C)cc3)c(Cl)c12]

Example 411

4-Chloro-1,3-dimethyl-1H-pyrrolo[2,3-b]pyridine-5-carboxylic acid (4-chloro-phenyl)-amide Step 1:

POCl$_3$ (1.0 mL, 11.1 mmol) was added to DMF (8 mL) at 0° C., and the solution was stirred for 10 mins. To the solution, a solution of 4-chloro-1-methyl-1H-pyrrolo[2,3-b]pyridine-5-carboxylic acid methyl ester (250 mg, 1.11 mmol) in DMF (1.5 mL) was added at 0° C. The resulting was stirred at 0° C. for 30 mins, then at room temperature overnight. The solvents were removed under reduced pressure. The residue was treated with sat. NaHCO$_3$ solution (20 mL) and ice (20 g) and the aqeous phase was extracted with EA (70 mL×2). The organic layers were combined, washed with water (70 mL) and brine (70 mL), dried over anhydrous Na$_2$SO$_4$, concentrated to give 4-chloro-3-formyl-1-methyl-1H-pyrrolo[2,3-b]pyridine-5-carboxylic acid methyl ester (180 mg, yield: 64%) as a white solid. MS: m/z 252.9 (M+H$^+$).

Step 2:

To a solution of 4-chloro-3-formyl-1-methyl-1H-pyrrolo[2,3-b]pyridine-5-carboxylic acid methyl ester (130 mg, 0.51 mmol) in DCM (20 mL) was added NaBH$_3$CN (241 mg, 3.83 mmol) and ZnI$_2$ (244 mg, 0.77 mmol). After stiring at 80° C. for 1.5 hrs, the reaction was combined with another batch (55 mg). The reaction solution was poured into water (50 mL) and extracted with DCM (50 mL×2). The organic layers were combined and washed with water (20 mL) and brine (20 mL), dried over anhydrous Na$_2$SO$_4$, concentrated and purified by prep-TLC (DCM/MeOH=20/1) to give 2 compounds (C and D). C: 4-chloro-1,3-dimethyl-1H-pyrrolo[2,3-b]pyridine-5-carboxylic acid methyl ester(15 mg, yield: 8%) as a yellow semi-solid. MS: m/z 238.9 (M+H$^+$). D: 4-Chloro-3-hydroxymethyl-1-methyl-1H-pyrrolo[2,3-b]pyridine-5-carboxylic acid methyl ester (100 mg, yield: 55%) as a white solid. MS: m/z 254.9 (M+H$^+$).

Step 3-4:

These two steps were similar to 1-methyl-1H-pyrrolo[2,3-b]pyridine-5-carboxylic acid (4-chloro-phenyl)-amide (Example 398). $^1$HNMR (400 MHz, DMSO-d6): δ=10.68 (brs, 1H), 8.37 (s, 1H), 7.77 (d, J=8.8 Hz, 2H), 7.49 (s, 1H), 7.42 (d, J=8.4 Hz, 2H), 3.81 (s, 3H), 2.46 (s, 3H). MS: m/z 334.0 (M+H$^+$).

Example 412

4-Chloro-1,3-dimethyl-1H-pyrrolo[2,3-b]pyridine-5-carboxylic acid (4-isopropyl-phenyl)-amide The title compound was prepared using general procedure for 1-methyl-1H-pyrrolo[2,3-b]pyridine-5-carboxylic acid (4-chloro-phenyl)-amide (Example 398).

$^1$HNMR (400 MHz, DMSO-d6): δ=10.42 (brs, 1H), 8.33 (s, 1H), 7.64 (d, J=8.4 Hz, 2H), 7.48 (s, 1H), 7.22 (d, J=8.4 Hz, 2H), 3.79 (s, 3H), 2.88-2.84 (m, 1H), 2.47 (s, 3H), 1.20 (s, 3H), 1.19 (s, 3H). MS: m/z 342.1 (M+H$^+$).

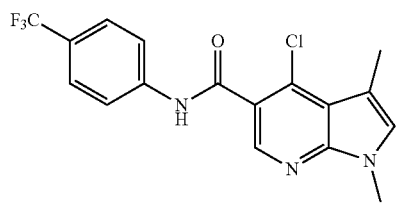

Example 413

4-Chloro-1,3-dimethyl-1H-pyrrolo[2,3-b]pyridine-5-carboxylic acid (4-trifluoromethyl-phenyl)-amide The title compound was prepared using general procedure for 1-methyl-1H-pyrrolo[2,3-b]pyridine-5-carboxylic acid (4-chloro-phenyl)-amide (Example 398). $^1$HNMR (400 MHz, CD$_3$OD): δ=8.36 (s, 1H), 7.91 (d, J=8.0 Hz, 2H), 7.68 (d, J=8.8 Hz, 2H), 7.28 (s, 1H), 3.84 (s, 3H), 2.53 (s, 3H). MS: m/z 368.1 (M+H$^+$).

Example 414

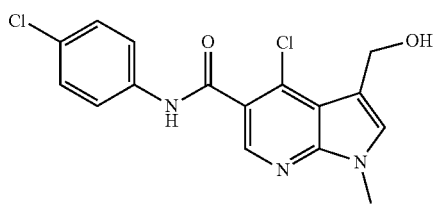 [SMILES: Cn1cc(CO)c2c(Cl)c(C(=O)Nc3ccc(Cl)cc3)cnc21]

4-Chloro-3-hydroxymethyl-1-methyl-1H-pyrrolo[2,3-b]pyridine-5-carboxylic acid (4-chloro-phenyl)-amide The title compound was prepared using general procedure for 1-methyl-1H-pyrrolo[2,3-b]pyridine-5-carboxylic acid (4-chloro-phenyl)-amide (Example 398).

$^1$HNMR (400 MHz, DMSO-d6): δ=10.68 (brs, 1H), 8.40 (s, 1H), 7.77 (d, J=8.8 Hz, 2H), 7.63 (s, 1H), 7.42 (d, J=8.8 Hz, 2H), 5.05 (t, J=4.8 Hz, 1H), 4.81 (d, J=4.8 Hz, 2H), 3.84 (s, 3H). MS: m/z 350.0 (M+H$^+$).

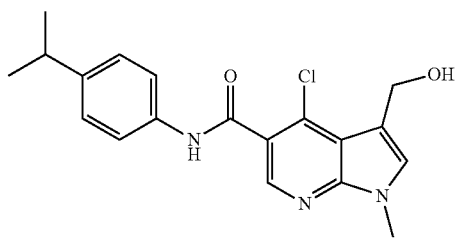 [SMILES: CC(C)c1ccc(NC(=O)c2cnc3c(c(CO)cn3C)c2Cl)cc1]

Example 415

4-Chloro-3-hydroxymethyl-1-methyl-1H-pyrrolo[2,3-b]pyridine-5-carboxylic acid (4-isopropyl-phenyl)-amide The title compound was prepared using general procedure for 1-methyl-1H-pyrrolo[2,3-b]pyridine-5-carboxylic acid (4-chloro-phenyl)-amide (Example 398). $^1$HNMR (400 MHz, DMSO-d6): δ=10.45 (brs, 1H), 8.37 (s, 1H), 7.65-7.62 (m, 3H), 7.48 (s, 1H), 7.22 (d, J=8.4 Hz, 2H), 5.04 (t, J=4.8 Hz, 1H), 4.82 (d, J=4.8 Hz, 2H), 3.83 (s, 3H), 2.88-2.83 (m, 1H), 1.20 (s, 3H), 1.19 (s, 3H). MS: m/z 358.1 (M+H$^+$).

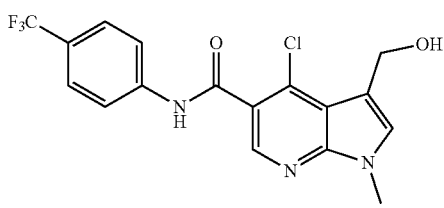 [SMILES: Cn1cc(CO)c2c(Cl)c(C(=O)Nc3ccc(C(F)(F)F)cc3)cnc21]

Example 416

4-Chloro-3-hydroxymethyl-1-methyl-1H-pyrrolo[2,3-b]pyridine-5-carboxylic acid (4-trifluoromethyl-phenyl)-amide The title compound was prepared using general procedure for 1-methyl-1H-pyrrolo[2,3-b]pyridine-5-carboxylic acid (4-chloro-phenyl)-amide (Example 398). $^1$HNMR (400 MHz, CD$_3$OD): δ=8.42 (s, 1H), 7.92 (d, J=8.8 Hz, 2H), 7.68 (d, J=8.8 Hz, 2H), 7.55 (s, 1H), 4.96 (s, 2H), 3.89 (s, 3H). MS: m/z 384.1 (M+H$^+$).

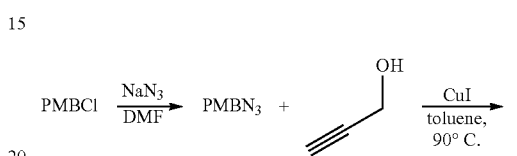

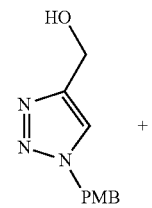

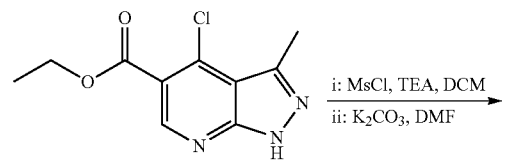

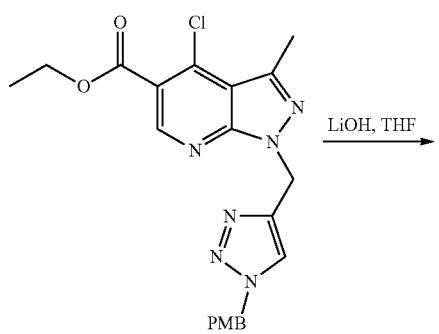

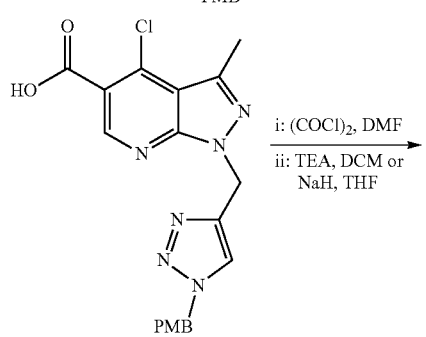

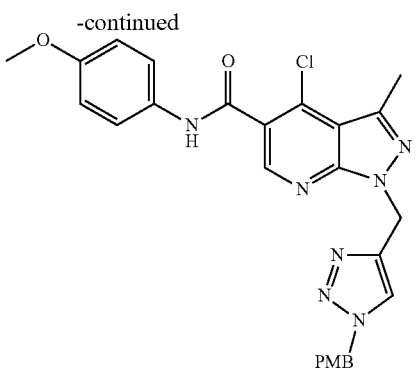

Example 417

4-chloro-1-((1-(4-methoxybenzyl)-1H-1,2,3-triazol-4-yl)methyl)-N-(4-methoxyphenyl)-3-methyl-1H-pyrazolo[3,4-b]pyridine-5-carboxamide Step 1

A mixture of 4-methoxylbenzyl chloride (9.6 g, 61.3 mmol) and NaN$_3$ (4.8 g, 73.8 mmol) in DMF (50 mL) was stirred at 70° C. overnight. The starting material was consumed almost completely by TLC. The mixture was poured into water (200 mL) and extracted with EA (200 mL). The organic layer was washed with brine (50 mL×4), dried over Na$_2$SO$_4$ and concentrated to give 4-methoxylbenzyl azide (10 g, yield: 100%) as a yellow oil.

$^1$HNMR (400 MHz, CDCl$_3$): δ=7.17 (d, J=8.8 Hz, 2H), 6.84 (d, J=8.8 Hz, 2H), 4.19 (s, 2H), 3.74 (s, 3H).

Step 2

A mixture of 4-methoxylbenzyl azide (4.0 g, 24.5 mmol), prop-2-yn-1-ol (1.5 g, 26.8 mmol) and CuI (230 mg, 1.2 mmol) in toluene (50 mL) was stirred at 90° C. overnight. The mixture was concentrated and purified by silica gel column (PE/EA=3/1 to EA=100%) to give [1-(4-methoxy-benzyl)-1H-[1,2,3]triazol-4-yl]-methanol (1.9 g, yield: 35%) as a yellow solid. MS: m/z 220.1 (M+H$^+$).

Step 3

To a solution of [1-(4-methoxy-benzyl)-1H-[1,2,3]triazol-4-yl]-methanol (1.85 g, 8.4 mmol) and TEA (2.4 mL, 16.8 mmol) in DCM (20 mL) was added MsCl (1.2 g, 10.4 mmol) at 0° C. under N$_2$. After stirring at room temperature for 1 hr, the reaction mixture was poured into water (50 mL) and extracted with DCM (50 mL). The organic layer was dried over Na$_2$SO$_4$ and concentrated to give methanesulfonic acid 1-(4-methoxy-benzyl)-1H-[1,2,3]triazol-4-ylmethyl ester. The freshly prepared methanesulfonic acid 1-(4-methoxy-benzyl)-1H-[1,2,3]triazol-4-ylmethyl ester was mixed with 4-chloro-3-methyl-1H-pyrazolo[3,4-b]pyridine-5-carboxylic acid ethyl ester (2.0 g, 8.4 mmol) and K$_2$CO$_3$ (2.3 g, 16.8 mmol) in DMF (30 mL). The mixture was stirred at room temperature overnight. The starting material was consumed almost completely by TLC. The mixture was poured into water (100 mL) and extracted with EA (50 mL×2). The organic layer was washed with brine (30 mL×3), dried over Na$_2$SO$_4$ and concentrated to dryness in vacuum. The residue was purified by silica gel column (PE/EA=3/1 to 1/3) to give 4-chloro-1-[1-(4-methoxy-benzyl)-1H-[1,2,3]triazol-4-ylmethyl]-3-methyl-1H-pyrazolo[3,4-b]pyridine-5-carboxylic acid ethyl ester (1.1 g, yield: 30%) as a pale yellow solid.

$^1$HNMR (300 MHz, DMSO-d6): δ=8.91 (s, 1H), 8.08 (s, 1H), 7.27 (d, J=8.7 Hz, 2H), 6.90 (d, J=8.4 Hz, 2H), 5.65 (s, 2H), 5.44 (s, 2H), 4.37 (q, J=7.5 Hz, 2H), 3.72 (s, 3H), 2.65 (s, 3H), 1.35 (t, J=7.2 Hz, 3H). MS: m/z 440.8 (M+H$^+$).

Step 4

To a solution of 4-chloro-1-[1-(4-methoxy-benzyl)-1H-[1,2,3]triazol-4-ylmethyl]-3-methyl-1H-pyrazolo[3,4-b]pyridine-5-carboxylic acid ethyl ester (1.05 g, 2.4 mmol) in THF (30 mL) was added aq.LiOH (1 M, 15 mL, 15 mmol). The mixture was stirred at room temperature overnight. The reaction solution was acidified with conc. HCl to pH=2 and partitioned between DCM (50 mL) and water (50 mL). The organic layer was dried over Na$_2$SO$_4$ and concentrated to give 4-chloro-1-[1-(4-methoxy-benzyl)-1H-[1,2,3]triazol-4-ylmethyl]-3-methyl-1H-pyrazolo[3,4-b]pyridine-5-carboxylic acid (880 mg, yield: 90%) as a white solid.

Step 5

To a suspension of 4-chloro-1-[1-(4-methoxy-benzyl)-1H-[1,2,3]triazol-4-ylmethyl]-3-methyl-1H-pyrazolo[3,4-b]pyridine-5-carboxylic acid (200 mg, 0.5 mmol) in DCM (5 mL) was added oxalyl chloride (190 mg, 1.5 mmol), then a drop of DMF. The reaction mixture was stirred at room temperature for 1 hr and concentrated to give the acyl chloride. The acyl chloride was dissolved in dry DCM (5 mL). To the solution, was added TEA (250 mg, 2.5 mmol), followed by 4-methoxy-phenylamine (60 mg, 0.5 mmol). After stirring at room temperature for 1 hr, the mixture was partitioned between water (30 mL) and DCM (30 mL). The organic layer was dried over Na$_2$SO$_4$, concentrated and purified by silica gel column (PE/EA=2/1 to 1/3) to give 4-chloro-1-[1-(4-methoxy-benzyl)-1H-[1,2,3]triazol-4-ylmethyl]-3-methyl-1H-pyrazolo[3,4-b]pyridine-5-carboxylic acid (4-methoxy-phenyl)-amide (170 mg, yield: 68%) as a yellow solid. $^1$HNMR (300 MHz, DMSO-d6): δ=10.50 (s, 1H), 8.68 (s, 1H), 8.08 (s, 1H), 7.64 (d, J=9.0 Hz, 2H), 7.28 (d, J=8.4 Hz, 2H), 6.96-6.89 (m, 4H), 5.68 (s, 2H), 5.46 (s, 2H), 3.75 (s, 3H), 3.72 (s, 3H), 2.66 (s, 3H). MS: m/z 518.2 (M+H$^+$).

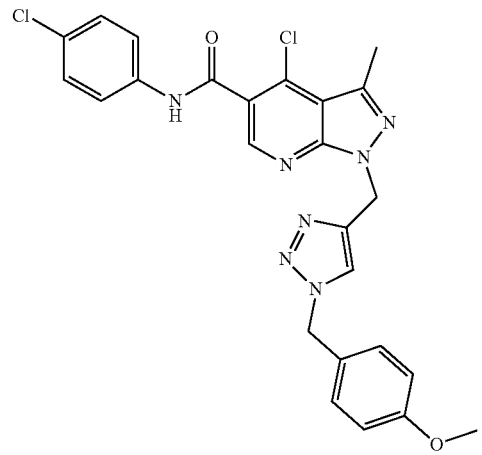 [SMILES: COc1ccc(Cn2cc(Cn3nc(C)c4c(Cl)c(C(=O)Nc5ccc(Cl)cc5)cnc43)nn2)cc1]

Example 418

4-chloro-N-(4-chlorophenyl)-1-((1-(4-methoxybenzyl)-1H-1,2,3-triazol-4-yl)methyl)-3-methyl-1H-pyrazolo[3,4-b]pyridine-5-carboxamide The title compound was prepared using general procedure for 4-chloro-1-((1-(4-methoxybenzyl)-1H-1,2,3-triazol-4-yl)methyl)-N-(4-methoxyphenyl)-3-methyl-1H-pyrazolo[3, 4-b]pyridine-5-carboxamide (Example 417). ¹HNMR (400 MHz, CDCl₃): δ=8.70 (s, 1H), 8.46 (s, 1H), 7.59 (d, J=8.4 Hz, 2H), 7.42 (s, 1H), 7.31 (d, J=8.4 Hz, 2H), 7.18 (d, J=8.4 Hz, 2H), 6.86 (d, J=8.8 Hz, 2H), 5.66 (s, 2H), 5.37 (s, 2H), 3.79 (s, 3H), 2.67 (s, 3H). MS: m/z 521.8 (M+H⁺).

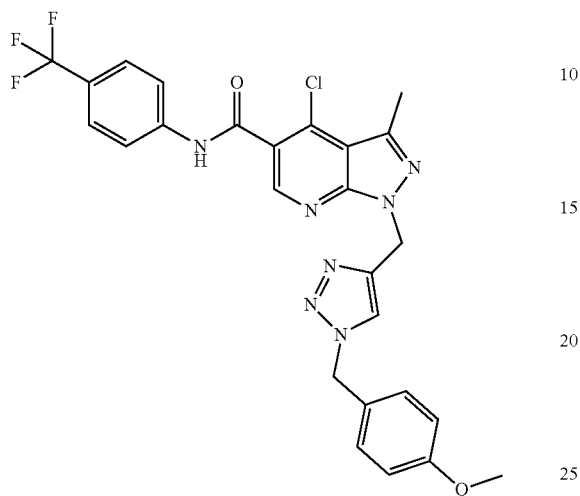

Example 419

4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide To a suspension of 4-chloro-1-[1-(4-methoxy-benzyl)-1H-[1,2,3]triazol-4-ylmethyl]-3-methyl-1H-pyrazolo[3,4-b]pyridine-5-carboxylic acid (200 mg, 0.5 mmol) in DCM (5 mL) was added oxalyl chloride (190 mg, 1.5 mmol), then a drop of DMF. The reaction mixture was stirred at room temperature for 1 hr and concentrated to give the acyl chloride. In another flask, a solution of 4-trifluoromethyl-phenylamine (100 mg, 0.6 mmol) in THF (5 mL) was treated with NaH (60%, 30 mg, 0.8 mmol) at room temperature for 1 hr. The resulting was added dropwise to a suspension of the acyl chloride above in THF (5 mL). After stirring at 40° C. overnight, the mixture was partitioned between water (50 mL) and DCM (50 mL). The organic layer was dried over Na₂SO₄, concentrated and purified by silica gel column (PE/EA=2/1 to 1/2) to give 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (65 mg, yield: 24%) as a yellow solid. ¹HNMR (400 MHz, DMSO-d6): δ=11.01 (s, 1H), 8.75 (s, 1H), 8.08 (s, 1H), 7.93 (d, J=8.8 Hz, 2H), 7.76 (d, J=8.8 Hz, 2H), 7.28 (d, J=8.8 Hz, 2H), 6.91 (d, J=8.8 Hz, 2H), 5.69 (s, 2H), 5.46 (s, 2H), 3.73 (s, 3H), 2.67 (s, 3H). MS: m/z 556.1 (M+H⁺).

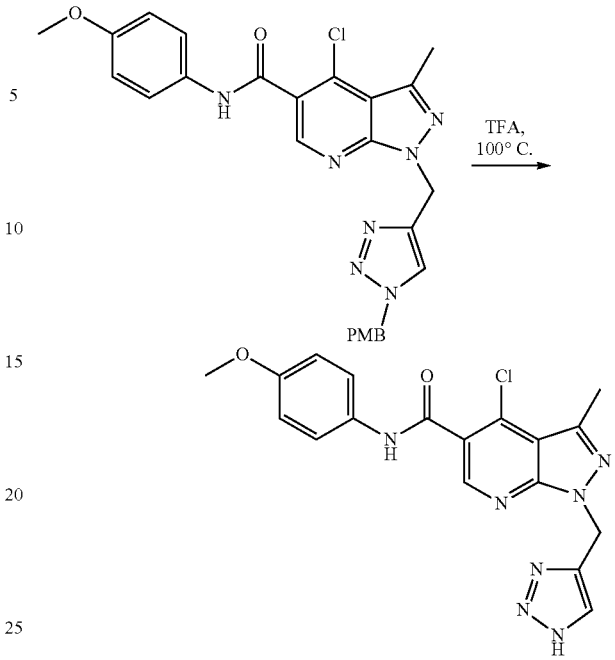

Example 420

4-Chloro-3-methyl-1-(1H-[1,2,3]triazol-4-ylmethyl)-1H-pyrazolo[3,4-b]pyridine-5-carboxylic acid (4-methoxy-phenyl)-amide A solution of 4-chloro-1-[1-(4-methoxy-benzyl)-1H-[1,2,3]triazol-4-ylmethyl]-3-methyl-1H-pyrazolo[3,4-b]pyridine-5-carboxylic acid (4-methoxy-phenyl)-amide (160 mg, 0.3 mmol) in TFA (6 mL) was refluxed at 100° C. for 4 hrs. Then the reaction mixture was concentrated to dryness. The residue was diluted with DCM/MeOH (10:1, 30 mL). The mixture was washed with sat.NaHCO₃ (30 mL), dried over Na₂SO₄ and concentrated to dryness in vacuum. The residue was purified by prep-HPLC (NH₄HCO₃) to give 4-chloro-3-methyl-1-(1H-[1,2,3]triazol-4-ylmethyl)-1H-pyrazolo[3,4-b]pyridine-5-carboxylic acid (4-methoxy-phenyl)-amide (10 mg, yield: 8%) as a yellow solid. ¹HNMR (300 MHz, DMSO-d6): δ=15.01 (brs, 1H), 10.51 (s, 1H), 8.69 (s, 1H), 7.77 (s, 1H), 7.64 (d, J=8.7 Hz, 2H), 6.95 (d, J=8.4 Hz, 2H), 5.73 (s, 2H), 3.75 (s, 3H), 2.67 (s, 3H). MS: m/z 397.8 (M+H⁺).

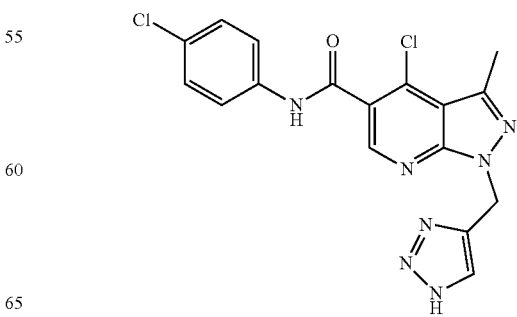

Example 421

4-Chloro-3-methyl-1-(1H-[1,2,3]triazol-4-ylmethyl)-1H-pyrazolo[3,4-b]pyridine-5-carboxylic acid (4-chloro-phenyl)-amide The title compound was prepared using general procedure for 4-chloro-3-methyl-1-(1H-[1,2,3]triazol-4-ylmethyl)-1H-pyrazolo[3,4-b]pyridine-5-carboxylic acid (4-methoxy-phenyl)-amide (Example 420).

$^1$HNMR (400 MHz, DMSO-d6): δ=14.93 (brs, 1H), 10.82 (s, 1H), 8.73 (s, 1H), 7.76 (d, J=8.8 Hz, 3H), 7.45 (d, J=8.8 Hz, 2H), 5.74 (s, 2H), 2.67 (s, 3H). MS: m/z 401.8 (M+H$^+$).

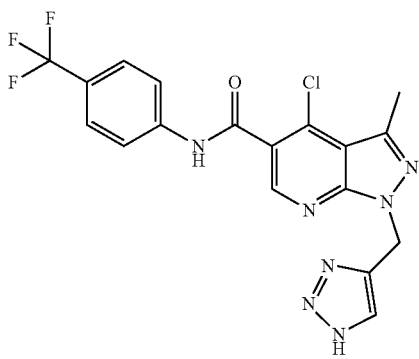 [SMILES: Cc1nn(Cc2c[nH]nn2)c2ncc(C(=O)Nc3ccc(C(F)(F)F)cc3)c(Cl)c12]

Example 422

4-Chloro-3-methyl-1-(1H-[1,2,3]triazol-4-ylmethyl)-1H-pyrazolo[3,4-b]pyridine-5-carboxylic acid (4-trifluoromethyl-phenyl)-amide The title compound was prepared using general procedure for 4-chloro-3-methyl-1-(1H-[1,2,3]triazol-4-ylmethyl)-1H-pyrazolo[3,4-b]pyridine-5-carboxylic acid (4-methoxy-phenyl)-amide (Example 420).

$^1$HNMR (400 MHz, DMSO-d6): δ=14.88 (brs, 1H), 11.03 (s, 1H), 8.76 (s, 1H), 7.94 (d, J=8.4 Hz, 2H), 7.76 (d, J=8.4 Hz, 3H), 5.74 (s, 2H), 2.68 (s, 3H). MS: m/z 435.8 (M+H$^+$).

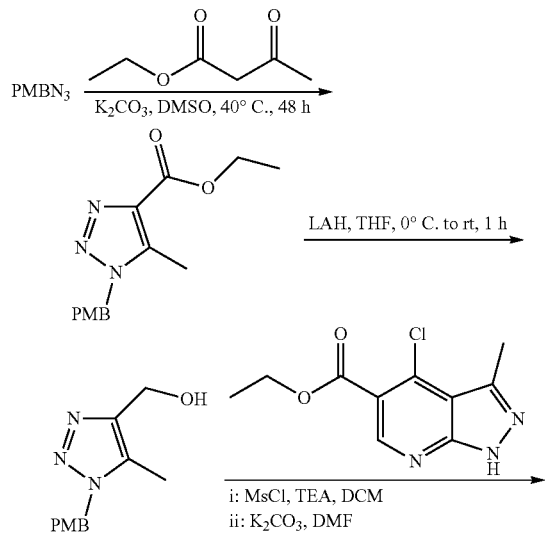

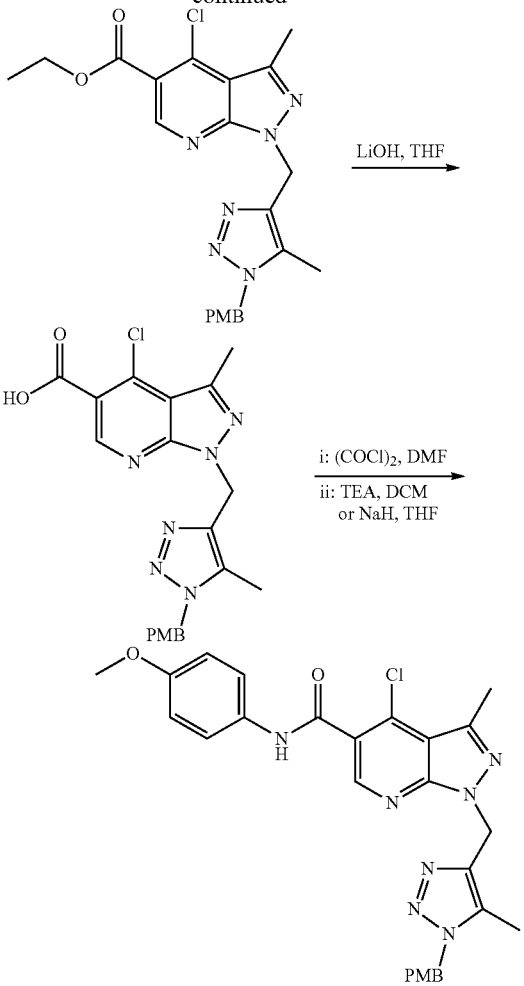

Example 423

4-chloro-1-((1-(4-methoxybenzyl)-5-methyl-1H-1,2,3-triazol-4-yl)methyl)-N-(4-methoxyphenyl)-3-methyl-1H-pyrazolo[3,4-b]pyridine-5-carboxamide Step 1

A mixture of 4-methoxylbenzyl azide (2.5 g, 15.3 mmol), 3-oxo-butyric acid ethyl ester (3.0 g, 23.0 mmol) and K$_2$CO$_3$ (8.5 g, 61.3 mmol) in DMSO (25 mL) was stirred at 40° C. for 48 hrs. The starting material was consumed almost completely by TLC. The mixture was poured into water (100 mL) and extracted with EA (100 mL). The organic layer was washed with brine (50 mL×3), dried over Na$_2$SO$_4$ and concentrated to dryness in vacuum. The residue was purified by silica gel column (PE/EA=2/1) to give 1-(4-methoxybenzyl)-5-methyl-1H-[1,2,3]triazole-4-carboxylic acid ethyl ester (3.3 g, yield: 79%) as a white solid.

$^1$HNMR (400 MHz, CDCl$_3$): δ=7.13 (d, J=8.4 Hz, 2H), 6.86 (d, J=8.8 Hz, 2H), 5.47 (s, 2H), 4.41 (q, J=7.2 Hz, 2H), 3.79 (s, 3H), 2.46 (s, 3H), 1.41 (t, J=7.2 Hz, 3H). MS: m/z 276.1 (M+H$^+$).

Step 2

To a solution of 1-(4-methoxy-benzyl)-5-methyl-1H-[1,2,3]triazole-4-carboxylic acid ethyl ester (2.5 g, 9.1 mmol) in THF (30 mL) was added LAH (420 mg, 11.1 mmol) at 0° C.

After stirring at room temperature for 1 hr, H$_2$O (0.4 mL), 15% NaOH (0.4 mL) and H$_2$O (1.2 mL) was then added dropwise at 0° C. The mixture was stirred at room temperature for another 30 mins, MgSO$_4$ was added and the mixture was filtered. The filtrate was concentrated to give [1-(4-methoxy-benzyl)-5-methyl-1H-[1,2,3]triazol-4-yl]-methanol (1.8 g, yield: 86%) as a white solid. MS: m/z 234.1 (M+H$^+$).

Step 3-5

These three steps are similar to general procedure for 4-chloro-1-((1-(4-methoxybenzyl)-1H-1,2,3-triazol-4-yl)methyl)-N-(4-methoxyphenyl)-3-methyl-1H-pyrazolo[3,4-b]pyridine-5-carboxamide (Example 417).

$^1$HNMR (300 MHz, DMSO-d6): δ=10.50 (s, 1H), 8.68 (s, 1H), 7.64 (d, J=8.7 Hz, 2H), 7.16 (d, J=8.1 Hz, 2H), 6.96-6.88 (m, 4H), 5.63 (s, 2H), 5.44 (s, 2H), 3.75 and 3.72 (s, 6H), 2.64 (s, 3H), 2.28 (s, 3H). MS: m/z 531.8 (M+H$^+$).

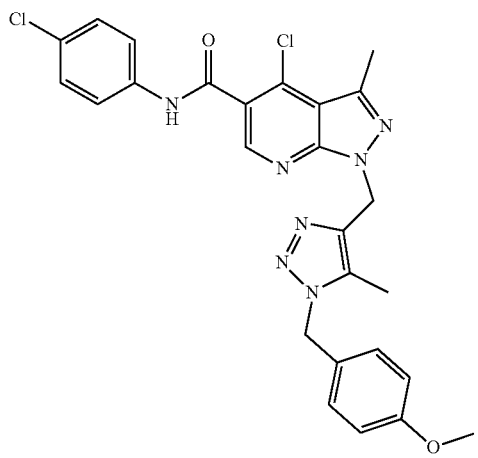 [SMILES: COc1ccc(Cn2nnc(Cn3nc(C)c4c(Cl)c(C(=O)Nc5ccc(Cl)cc5)cnc43)c2C)cc1]

Example 424

4-chloro-N-(4-chlorophenyl)-1-((1-(4-methoxybenzyl)-5-methyl-1H-1,2,3-triazol-4-yl)methyl)-3-methyl-1H-pyrazolo[3,4-b]pyridine-5-carboxamide The title compound was prepared using general procedure for 4-chloro-1-((1-(4-methoxybenzyl)-1H-1,2,3-triazol-4-yl)methyl)-N-(4-methoxyphenyl)-3-methyl-1H-pyrazolo[3,4-b]pyridine-5-carboxamide (Example 417). $^1$HNMR (400 MHz, DMSO-d6): δ=10.78 (s, 1H), 8.72 (s, 1H), 7.76 (d, J=8.4 Hz, 2H), 7.44 (d, J=8.8 Hz, 2H), 7.16 (d, J=8.4 Hz, 2H), 6.91 (d, J=8.4 Hz, 2H), 5.63 (s, 2H), 5.45 (s, 2H), 3.72 (s, 3H), 2.65 (s, 3H), 2.28 (s, 3H). MS: m/z 535.8 (M+H$^+$).

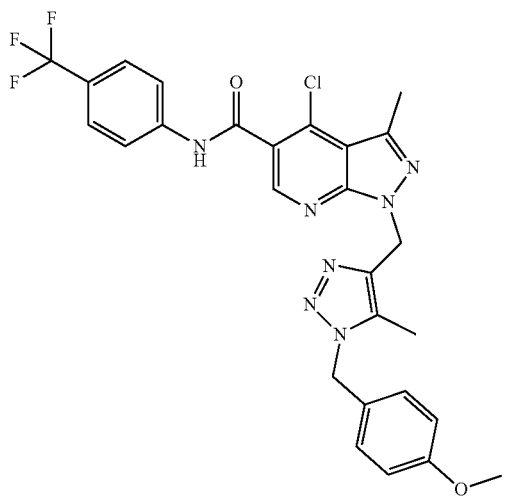 [SMILES: COc1ccc(Cn2nnc(Cn3nc(C)c4c(Cl)c(C(=O)Nc5ccc(C(F)(F)F)cc5)cnc43)c2C)cc1]

Example 425

4-chloro-1-((1-(4-methoxybenzyl)-5-methyl-1H-1,2,3-triazol-4-yl)methyl)-3-methyl-N-(4-(trifluoromethyl)phenyl)-1H-pyrazolo[3,4-b]pyridine-5-carboxamide The title compound was prepared using general procedure for 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (Example 419). $^1$HNMR (300 MHz, DMSO-d6): δ=11.01 (s, 1H), 8.75 (s, 1H), 7.94 (d, J=8.7 Hz, 2H), 7.76 (d, J=8.7 Hz, 2H), 7.17 (d, J=8.7 Hz, 2H), 6.91 (d, J=8.7 Hz, 2H), 5.64 (s, 2H), 5.45 (s, 2H), 3.72 (s, 3H), 2.65 (s, 3H), 2.29 (s, 3H). MS: m/z 569.9 (M+H$^+$).

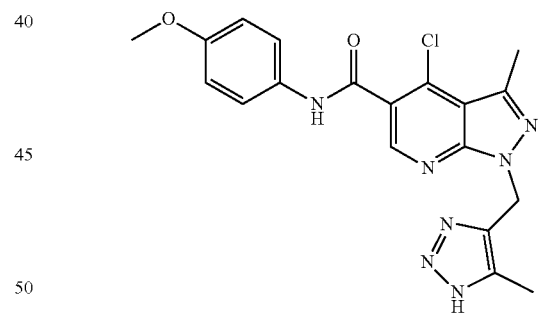

Example 426

4-chloro-N-(4-methoxyphenyl)-3-methyl-1-((5-methyl-1H-1,2,3-triazol-4-yl)methyl)-1H-pyrazolo[3,4-b]pyridine-5-carboxamide The title compound was prepared using general procedure for 4-chloro-3-methyl-1-(1H-[1,2,3]triazol-4-ylmethyl)-1H-pyrazolo[3,4-b]pyridine-5-carboxylic acid (4-methoxy-phenyl)-amide (Example 420).

$^1$HNMR (400 MHz, DMSO-d6): δ=14.48 (s, 1H), 10.51 (s, 1H), 8.70 (s, 1H), 7.64 (d, J=8.4 Hz, 2H), 6.95 (d, J=8.8 Hz, 2H), 5.66 (s, 2H), 3.75 (s, 3H), 2.66 (s, 3H), 2.18 (s, 3H). MS: m/z 411.9 (M+H$^+$).

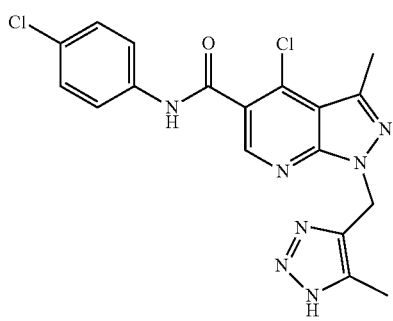 [SMILES: Cc1[nH]nnc1Cn1nc(C)c2c(Cl)c(C(=O)Nc3ccc(Cl)cc3)cnc21]

Example 427

4-chloro-N-(4-chlorophenyl)-3-methyl-1-((5-methyl-1H-1,2,3-triazol-4-yl)methyl)-1H-pyrazolo[3,4-b]pyridine-5-carboxamide

The title compound was prepared using general procedure for 4-chloro-3-methyl-1-(1H-[1,2,3]triazol-4-ylmethyl)-1H-pyrazolo[3,4-b]pyridine-5-carboxylic acid (4-methoxy-phenyl)-amide (Example 420).

¹HNMR (400 MHz, DMSO-d6): δ=14.63 (brs, 1H), 10.80 (s, 1H), 8.73 (s, 1H), 7.76 (d, J=8.4 Hz, 2H), 7.45 (d, J=8.4 Hz, 2H), 5.67 (s, 2H), 2.66 (s, 3H), 2.21 (s, 3H). MS: m/z 415.8 (M+H⁺).

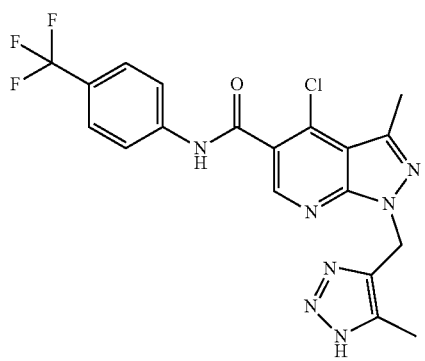 [SMILES: Cc1[nH]nnc1Cn1nc(C)c2c(Cl)c(C(=O)Nc3ccc(C(F)(F)F)cc3)cnc21]

Example 428

4-chloro-3-methyl-1-((5-methyl-1H-1,2,3-triazol-4-yl)methyl)-N-(4-(trifluoromethyl)phenyl)-1H-pyrazolo[3,4-b]pyridine-5-carboxamide

The title compound was prepared using general procedure for 4-chloro-3-methyl-1-(1H-[1,2,3]triazol-4-ylmethyl)-1H-pyrazolo[3,4-b]pyridine-5-carboxylic acid (4-methoxy-phenyl)-amide (Example 420).

¹HNMR (400 MHz, DMSO-d6): δ=14.91 and 14.49 (s, 1H), 11.03 (s, 1H), 8.77 (s, 1H), 7.94 (d, J=8.0 Hz, 2H), 7.77 (d, J=8.4 Hz, 2H), 5.68 and 5.66 (s, 2H), 2.67 (s, 3H), 2.30 and 2.18 (s, 3H). MS: m/z 449.8 (M+H⁺).

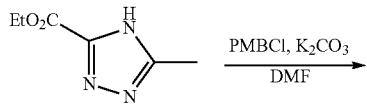

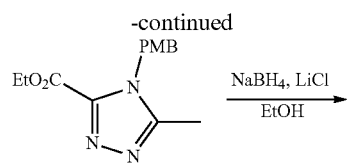

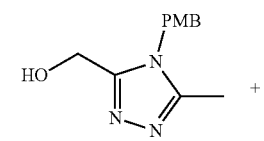

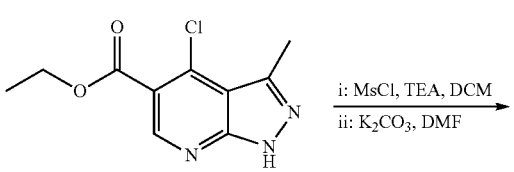

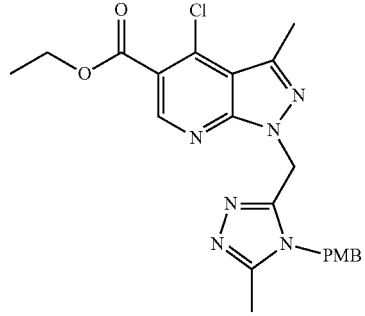

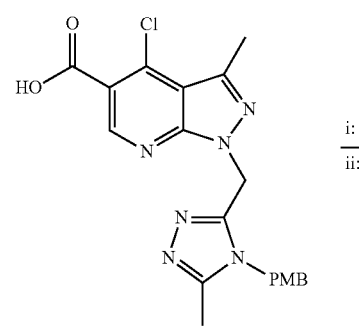

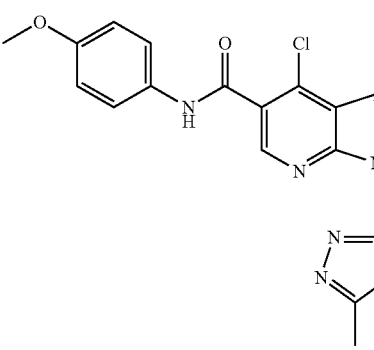

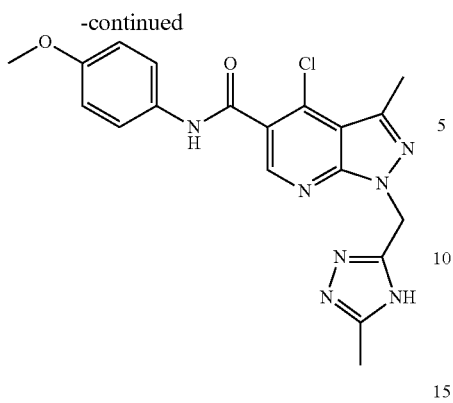

Example 429

4-Chloro-3-methyl-1-(5-methyl-4H-[1,2,3]triazol-3-ylmethyl)-1H-pyrazolo[3,4-b]pyridine-5-carboxylic acid (4-methoxy-phenyl)-amide Step 1

A mixture of 5-methyl-4H-[1,2,3]triazole-3-carboxylic acid ethyl ester (970 mg, 6.3 mmol), 4-methoxylbenzyl chloride (1.2 g, 7.5 mmol) and $K_2CO_3$ (1.3 g, 9.4 mmol) in DMF (15 mL) was stirred at 60° C. for 2 hrs. The starting material was consumed almost completely by TLC. The mixture was poured into water (60 mL) and extracted with EA (60 mL). The organic layer was washed with brine (30 mL×3), dried over $Na_2SO_4$ and concentrated to dryness in vacuum. The residue was purified by silica gel column (PE/EA=2/1 to 1/2) to give 4-(4-methoxy-benzyl)-5-methyl-4H-[1,2,3]triazole-3-carboxylic acid ethyl ester (1.3 g, yield: 76%) as a colorless oil. MS: m/z 276.1 (M+H$^+$).

Step 2

A mixture of 4-(4-methoxy-benzyl)-5-methyl-4H-[1,2,3]triazole-3-carboxylic acid ethyl ester (1.3 g, 4.7 mmol), LiCl (400 mg, 9.4 mmol) and $NaBH_4$ (360 mg, 9.4 mmol) in EtOH (20 mL) was stirred at 50° C. for 4 hrs. The starting material was consumed almost completely by TLC. The mixture was poured into water (100 mL) and extracted with DCM (100 mL). The organic layer was washed with brine (50 mL), dried over $Na_2SO_4$ and concentrated to give [4-(4-methoxy-benzyl)-5-methyl-4H-[1,2,3]triazol-3-yl]-methanol (1.0 g, yield: 91%) as a pale yellow solid. MS: m/z 233.9 (M+H$^+$).

Step 3-5

These three steps are similar to general procedure for 4-chloro-1-((1-(4-methoxybenzyl)-1H-1,2,3-triazol-4-yl)methyl)-N-(4-methoxyphenyl)-3-methyl-1H-pyrazolo[3,4-b]pyridine-5-carboxamide (Example 417).

Step 6

This step is similar to the general procedure for 4-chloro-3-methyl-1-(1H-[1,2,3]triazol-4-ylmethyl)-1H-pyrazolo[3,4-b]pyridine-5-carboxylic acid (4-methoxy-phenyl)-amide (Example 420). $^1$HNMR (400 MHz, DMSO-d6): δ=13.51 (brs, 1H), 10.54 (s, 1H), 8.67 (s, 1H), 7.65 (d, J=8.8 Hz, 2H), 6.95 (d, J=9.2 Hz, 2H), 5.60 (s, 2H), 3.75 (s, 3H), 2.67 (s, 3H), 2.25 (s, 3H). MS: m/z 411.9 (M+H$^+$).

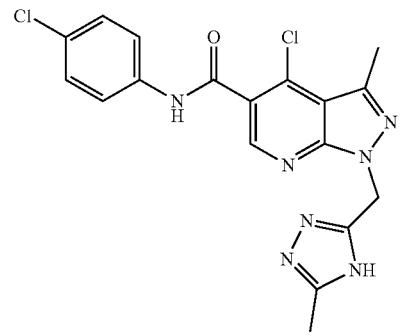 [SMILES: Cc1nnc(Cn2nc(C)c3c(Cl)c(C(=O)Nc4ccc(Cl)cc4)cnc32)[nH]1]

Example 430

4-Chloro-3-methyl-1-(5-methyl-4H-[1,2,3]triazol-3-ylmethyl)-1H-pyrazolo[3,4-b]pyridine-5-carboxylic acid (4-chloro-phenyl)-amide The title compound was prepared using general procedure for 4-chloro-3-methyl-1-(1H-[1,2,3]triazol-4-ylmethyl)-1H-pyrazolo[3,4-b]pyridine-5-carboxylic acid (4-methoxy-phenyl)-amide (Example 420).

$^1$HNMR (300 MHz, DMSO-d6): δ=13.48 (s, 1H), 10.83 (s, 1H), 8.70 (s, 1H), 7.77 (d, J=9.0 Hz, 2H), 7.45 (d, J=9.0 Hz, 2H), 5.59 (s, 2H), 2.66 (s, 3H), 2.25 (s, 3H). MS: m/z 415.9 (M+H$^+$)

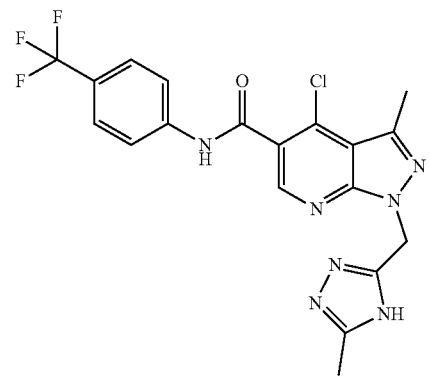 [SMILES: Cc1nnc(Cn2nc(C)c3c(Cl)c(C(=O)Nc4ccc(C(F)(F)F)cc4)cnc32)[nH]1]

Example 431

4-Chloro-3-methyl-1-(5-methyl-4H-[1,2,3]triazol-3-ylmethyl)-1H-pyrazolo[3,4-b]pyridine-5-carboxylic acid (4-trifluoromethyl-phenyl)-amide The title compound was prepared using general procedure for 4-chloro-3-methyl-1-(1H-[1,2,3]triazol-4-ylmethyl)-1H-pyrazolo[3,4-b]pyridine-5-carboxylic acid (4-methoxy-phenyl)-amide (Example 420).

$^1$HNMR (400 MHz, DMSO-d6): δ=13.47 (s, 1H), 11.05 (s, 1H), 8.74 (s, 1H), 7.95 (d, J=8.8 Hz, 2H), 7.77 (d, J=8.8 Hz, 2H), 5.60 (s, 2H), 2.67 (s, 3H), 2.26 (s, 3H). MS: m/z 449.9 (M+H$^+$).

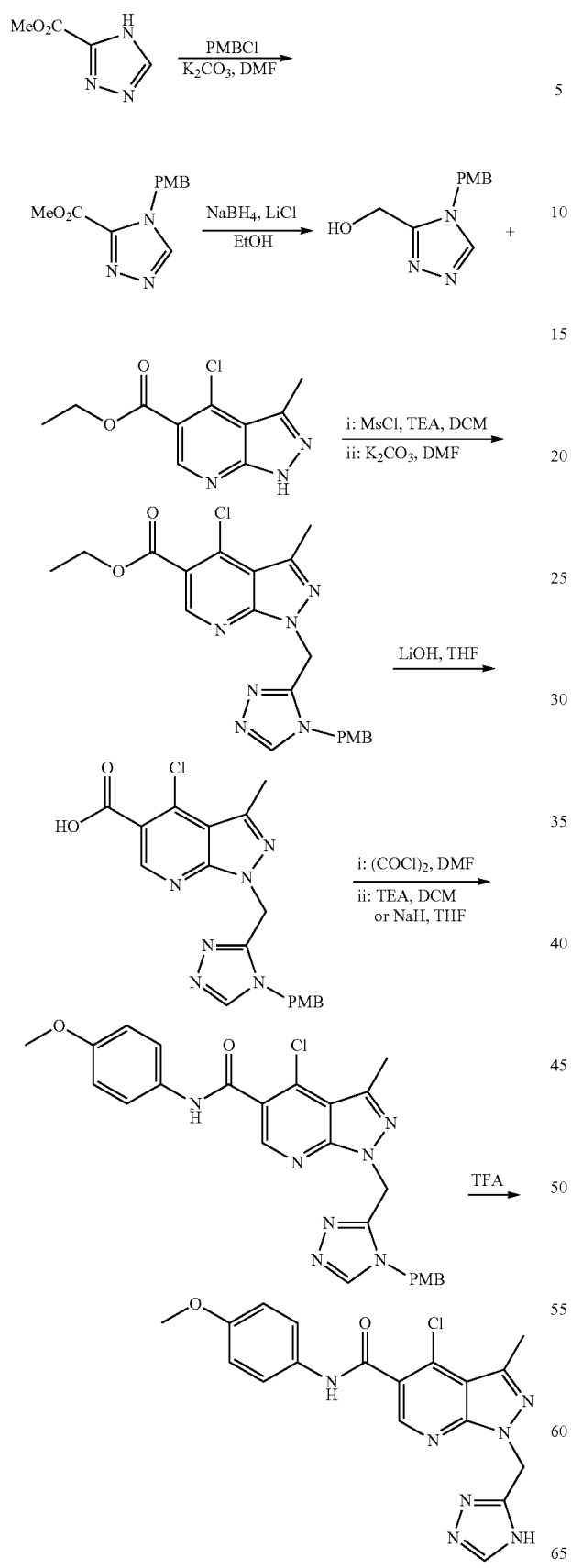

Example 432

4-Chloro-3-methyl-1-(4H-[1,2,4]triazol-3-ylmethyl)-1H-pyrazolo[3,4-b]pyridine-5-carboxylic acid (4-methoxy-phenyl)-amide The title compound was prepared using general procedure for 4-chloro-3-methyl-1-(5-methyl-4H-[1,2,4]triazol-3-ylmethyl)-1H-pyrazolo[3,4-b]pyridine-5-carboxylic acid (4-methoxy-phenyl)-amide (Example 429). $^1$HNMR (400 MHz, DMSO-d6): δ=13.92 (s, 1H), 10.53 (s, 1H), 8.67 (s, 1H), 8.45 (s, 1H), 7.65 (d, J=8.0 Hz, 2H), 6.95 (d, J=8.4 Hz, 2H), 5.68 (s, 2H), 3.75 (s, 3H), 2.67 (s, 3H). MS: m/z 397.9 (M+H$^+$).

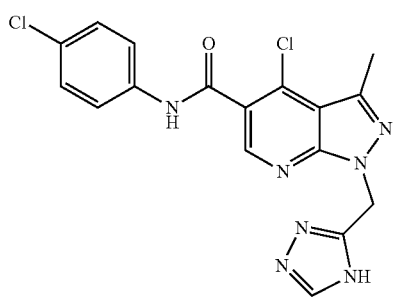 [SMILES: Cc1nn(Cc2nnc[nH]2)c2ncc(C(=O)Nc3ccc(Cl)cc3)c(Cl)c12]

Example 433

4-Chloro-3-methyl-1-(4H-[1,2,4]triazol-3-ylmethyl)-1H-pyrazolo[3,4-b]pyridine-5-carboxylic acid (4-chloro-phenyl)-amide The title compound was prepared using general procedure for 4-chloro-3-methyl-1-(5-methyl-4H-[1,2,4]triazol-3-ylmethyl)-1H-pyrazolo[3,4-b]pyridine-5-carboxylic acid (4-methoxy-phenyl)-amide (Example 429). $^1$HNMR (400 MHz, DMSO-d6): δ=13.92 (s, 1H), 10.82 (s, 1H), 8.71 (s, 1H), 8.45 (s, 1H), 7.76 (d, J=8.8 Hz, 2H), 7.45 (d, J=8.4 Hz, 2H), 5.68 (s, 2H), 2.67 (s, 3H). MS: m/z 401.9 (M+H$^+$).

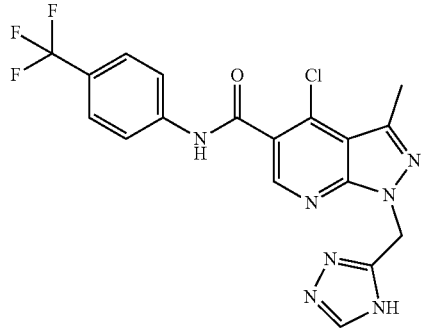 [SMILES: Cc1nn(Cc2nnc[nH]2)c2ncc(C(=O)Nc3ccc(C(F)(F)F)cc3)c(Cl)c12]

Example 434

4-Chloro-3-methyl-1-(4H-[1,2,4]triazol-3-ylmethyl)-1H-pyrazolo[3,4-b]pyridine-5-carboxylic acid (4-trifluoromethyl-phenyl)-amide The title compound was prepared using general procedure for 4-chloro-3-methyl-1-(5-methyl-4H-[1,2,4]triazol-3-ylmethyl)-1H-pyrazolo[3,4-b]pyridine-5-carboxylic acid (4-methoxy-phenyl)-amide (Example 429). ¹HNMR (400 MHz, DMSO-d6): δ=13.96 (brs, 1H), 11.05 (s, 1H), 8.74 (s, 1H), 8.45 (s, 1H), 7.95 (d, J=8.0 Hz, 2H), 7.77 (d, J=8.8 Hz, 2H), 5.71 (s, 2H), 2.68 (s, 3H). MS: m/z 435.9 (M+H⁺).

7.79 (d, J=8.4 Hz, 2H), 7.66 (d, J=8.4 Hz, 2H), 6.07 (s, 1H), 5.58 (s, 2H), 3.89 (s, 3H), 2.74 (s, 3H), 2.18 (s, 3H). MS: m/z 462.9 (M+H⁺).

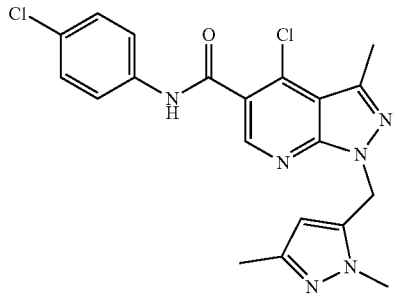 [SMILES: Cc1cc(Cn2nc(C)c3c(Cl)c(C(=O)Nc4ccc(Cl)cc4)cnc32)n(C)n1]

Example 436

4-chloro-N-(4-chlorophenyl)-1-((1,3-dimethyl-1H-pyrazol-5-yl)methyl)-3-methyl-1H-pyrazolo[3,4-b]pyridine-5-carboxamide The title compound was prepared using general procedure for 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (Example 419). ¹HNMR (400 MHz, CDCl₃): δ=8.80 (s, 1H), 8.03 (brs, 1H), 7.61 (d, J=8.4 Hz, 2H), 7.36 (d, J=8.8 Hz, 2H), 6.07 (s, 1H), 5.57 (s, 2H), 3.89 (s, 3H), 2.73 (s, 3H), 2.18 (s, 3H). MS: m/z 428.9 (M+H⁺).

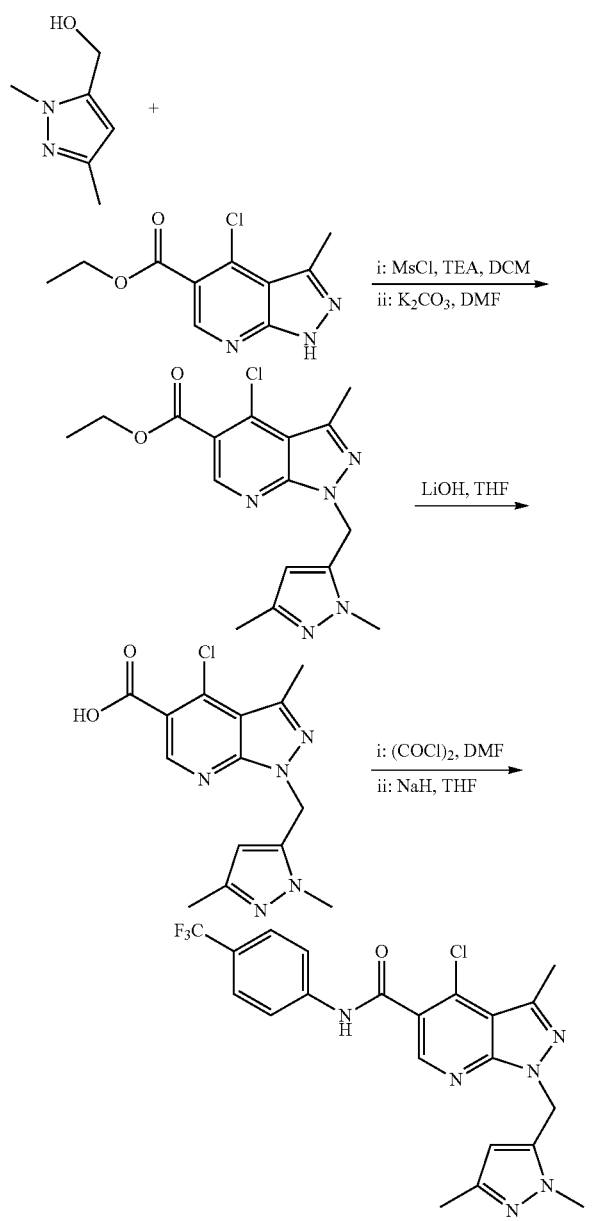

Example 435

4-chloro-1-((1,3-dimethyl-1H-pyrazol-5-yl)methyl)-3-methyl-N-(4-(trifluoromethyl)phenyl)-1H-pyrazolo13,4-b]pyridine-5-carboxamide The title compound was prepared using general procedure for 4-chloro-1-[1-(4-methoxy-benzyl)-1H-[1,2,3]triazol-4-ylmethyl]-3-methyl-1H-pyrazolo[3,4-b]pyridine-5-carboxylic acid (4-trifluoromethyl-phenyl)-amide (Example 419). ¹HNMR (400 MHz, CDCl₃): δ=8.81 (s, 1H), 8.21 (brs, 1H),

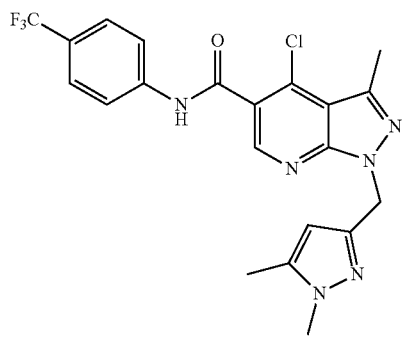 [SMILES: Cc1nn(Cc2cc(C)n(C)n2)c2ncc(C(=O)Nc3ccc(C(F)(F)F)cc3)c(Cl)c12]

Example 437

4-chloro-1-((1,5-dimethyl-1H-pyrazol-3-yl)methyl)-3-methyl-N-(4-(trifluoromethyl)phenyl)-1H-pyrazolo[3,4-b]pyridine-5-carboxamide The title compound was prepared using general procedure for 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (Example 419). ¹HNMR (400 MHz, CDCl₃): δ=8.84 (s, 1H), 8.14 (brs, 1H), 7.79 (d, J=8.4 Hz, 2H), 7.65 (d, J=8.4 Hz, 2H), 5.89 (s, 1H), 5.59 (s, 2H), 3.71 (s, 3H), 2.75 (s, 3H), 2.18 (s, 3H). MS: m/z 462.9 (M+H⁺).

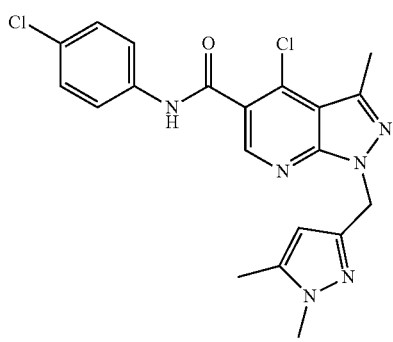 [SMILES: Cc1nn(Cc2cc(C)n(C)n2)c2ncc(C(=O)Nc3ccc(Cl)cc3)c(Cl)c12]

Example 438

4-chloro-N-(4-chlorophenyl)-1-((1,5-dimethyl-1H-pyrazol-3-yl)methyl)-3-methyl-1H-pyrazolo[3,4-b]pyridine-5-carboxamide The title compound was prepared using general procedure for 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (Example 419). $^1$HNMR (400 MHz, CDCl$_3$): δ=8.82 (s, 1H), 8.01 (brs, 1H), 7.62 (d, J=8.4 Hz, 2H), 7.36 (d, J=8.4 Hz, 2H), 5.88 (s, 1H), 5.58 (s, 2H), 3.71 (s, 3H), 2.74 (s, 3H), 2.17 (s, 3H). MS: m/z 428.8 (M+H$^+$).

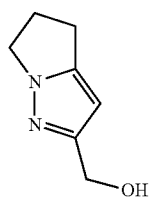

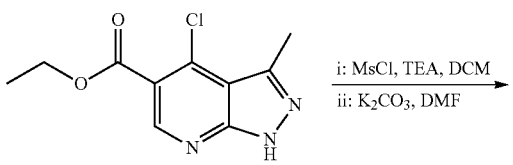

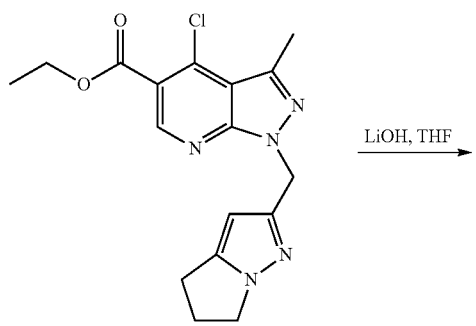

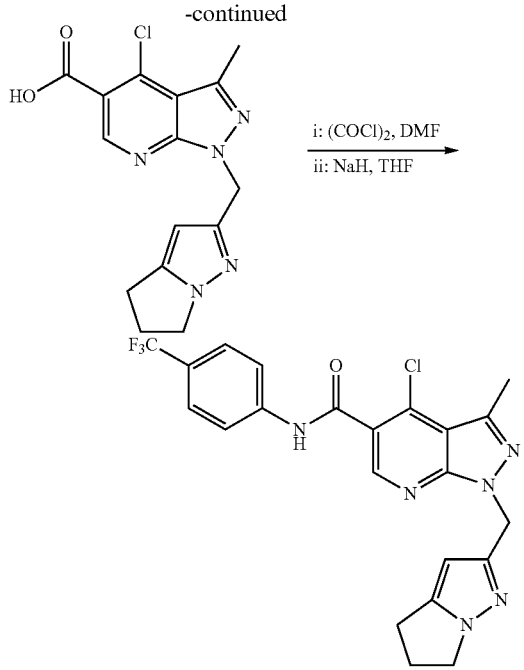

Example 439

4-Chloro-1-(5,6-dihydro-4H-pyrrolo[1,2-b]pyrazol-2-ylmethyl)-3-methyl-1H-pyrazolo[3,4-b]pyridine-5-carboxylic acid (4-trifluoromethyl-phenyl)-amide The title compound was prepared using general procedure for 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (Example 419). $^1$HNMR (400 MHz, CDCl$_3$): δ=8.78 (s, 1H), 8.04 (brs, 1H), 7.72 (d, J=7.6 Hz, 2H), 7.59 (d, J=8.4 Hz, 2H), 5.82 (s, 1H), 5.56 (s, 2H), 4.00 (t, J=7.2 Hz, 2H), 2.75-2.69 (m, 5H), 2.45 (t, J=7.2 Hz, 2H). MS: m/z 474.9 (M+H$^+$).

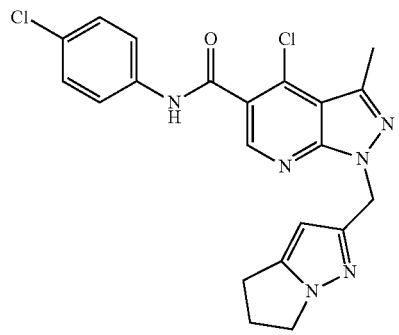 [SMILES: Cc1nn(Cc2cc3n(n2)CCC3)c2ncc(C(=O)Nc3ccc(Cl)cc3)c(Cl)c12]

Example 440

4-Chloro-1-(5,6-dihydro-4H-pyrrolo[1,2-b]pyrazol-2-ylmethyl)-3-methyl-1H-pyrazolo[3,4-b]pyridine-5-carboxylic acid (4-chloro-phenyl)-amide The title compound was prepared using general procedure for 4-chloro-1-((1-(4-methoxybenzyl)-1H-1,2,3-triazol-4- yl)methyl)-3-methyl-N-(4-(trifluoromethyl)phenyl)-1H-pyrazolo[3,4-b]pyridine-5-carboxamide (Example 419). ¹HNMR (400 MHz, DMSO-d6): δ=10.79 (brs, 1H), 8.71 (s, 1H), 7.76 (d, J=8.8 Hz, 2H), 7.44 (d, J=8.8 Hz, 2H), 5.79 (s, 1H), 5.52 (s, 2H), 3.96 (t, J=7.2 Hz, 2H), 2.73 (t, J=7.2 Hz, 2H), 2.67 (s, 3H), 2.45 (t, J=7.2 Hz, 2H). MS: m/z 440.9 (M+H⁺).

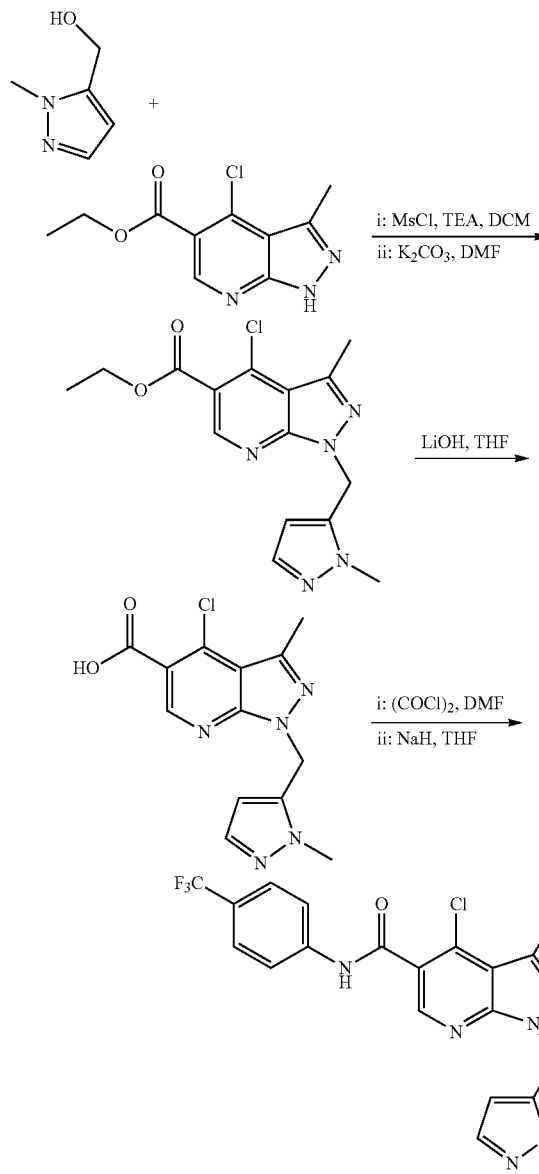

Example 441

4-chloro-3-methyl-1-((1-methyl-1H-pyrazol-5-yl)methyl)-N-(4-(trifluoromethyl)phenyl)-1H-pyrazolo[3,4-b]pyridine-5-carboxamide The title compound was prepared using general procedure for 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (Example 419). ¹HNMR (400 MHz, CDCl₃): δ=8.76 (s, 1H), 8.05 (brs, 1H), 7.72 (d, J=8.4 Hz, 2H), 7.59 (d, J=8.4 Hz, 2H), 7.31 (s, 1H), 6.25 (s, 1H), 5.58 (s, 2H), 3.92 (s, 3H), 2.67 (s, 3H). MS: m/z 448.9 (M+H⁺).

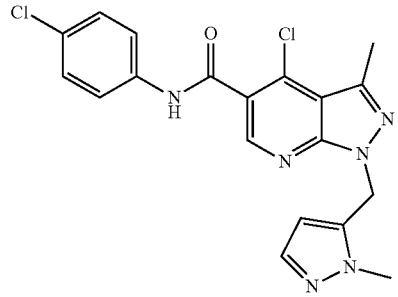 [SMILES: Cc1nn(Cc2ccnn2C)c2ncc(C(=O)Nc3ccc(Cl)cc3)c(Cl)c12]

Example 442

4-chloro-N-(4-chlorophenyl)-3-methyl-1-((1-methyl-1H-pyrazol-5-yl)methyl)-1H-pyrazolo[3,4-b]pyridine-5-carboxamide The title compound was prepared using general procedure for 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (Example 419). ¹HNMR (400 MHz, DMSO-d6): δ=10.79 (brs, 1H), 8.75 (s, 1H), 7.76 (d, J=8.8 Hz, 2H), 7.44 (d, J=8.8 Hz, 2H), 7.30 (d, J=1.2 Hz, 1H), 7.11 (d, J=1.6 Hz, 1H), 5.74 (s, 2H), 3.88 (s, 3H), 2.68 (s, 3H). MS: m/z 414.9 (M+H⁺).

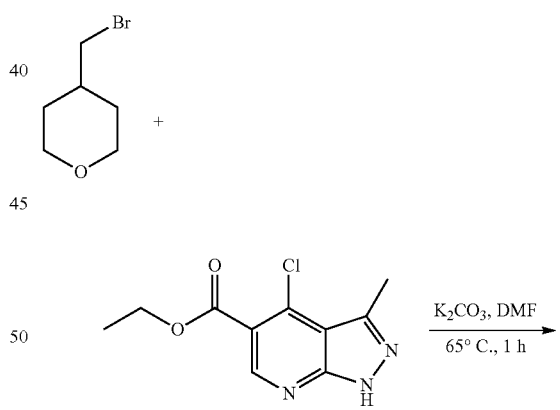

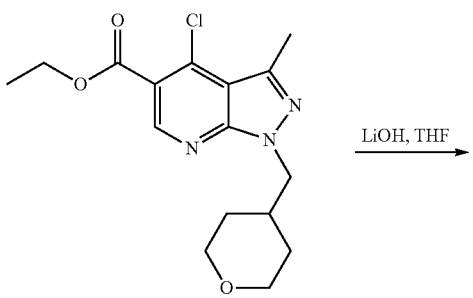

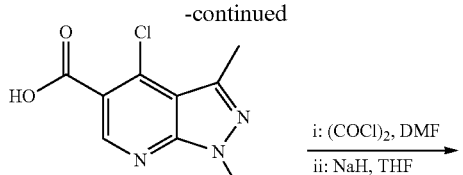

i: (COCl)₂, DMF
ii: NaH, THF

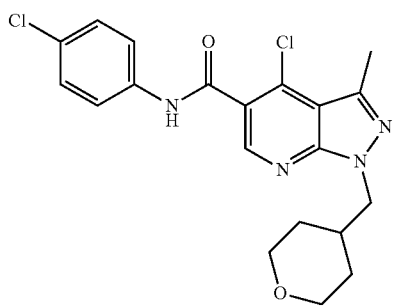 [SMILES: Cc1nn(CC2CCOCC2)c2ncc(C(=O)Nc3ccc(Cl)cc3)c(Cl)c12]

Example 443

4-Chloro-3-methyl-1-(tetrahydro-pyran-4-ylmethyl)-1H-pyrazolo[3,4-b]pyridine-5-carboxylic acid (4-trifluoromethyl-phenyl)-amide The title compound was prepared using general procedure for 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (Example 419). ¹HNMR (400 MHz, CDCl₃): δ=8.81 (s, 1H), 8.07 (brs, 1H), 7.80 (d, J=8.0 Hz, 2H), 7.67 (d, J=8.4 Hz, 2H), 4.36 (d, J=7.2 Hz, 2H), 3.97-3.94 (m, 2H), 3.38-3.32 (m, 2H), 2.78 (s, 3H), 2.31-2.27 (m, 1H), 1.48-1.42 (m, 4H). MS: m/z 450.9 (M−H⁺).

Example 444

4-Chloro-3-methyl-1-(tetrahydro-pyran-4-ylmethyl)-1H-pyrazolo[3,4-b]pyridine-5-carboxylic acid (4-chloro-phenyl)-amide The title compound was prepared using general procedure for 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (Example 419). ¹HNMR (400 MHz, CDCl₃): δ=8.79 (s, 1H), 7.96 (brs, 1H), 7.62 (d, J=8.4 Hz, 2H), 7.37 (d, J=8.4 Hz, 2H), 4.35 (d, J=7.2 Hz, 2H), 4.13-4.11 (m, 2H), 3.37-3.31 (m, 2H), 2.76 (s, 3H), 2.30-2.24 (m, 1H), 1.46-1.41 (m, 4H). MS: m/z 416.9 (M−H⁺).

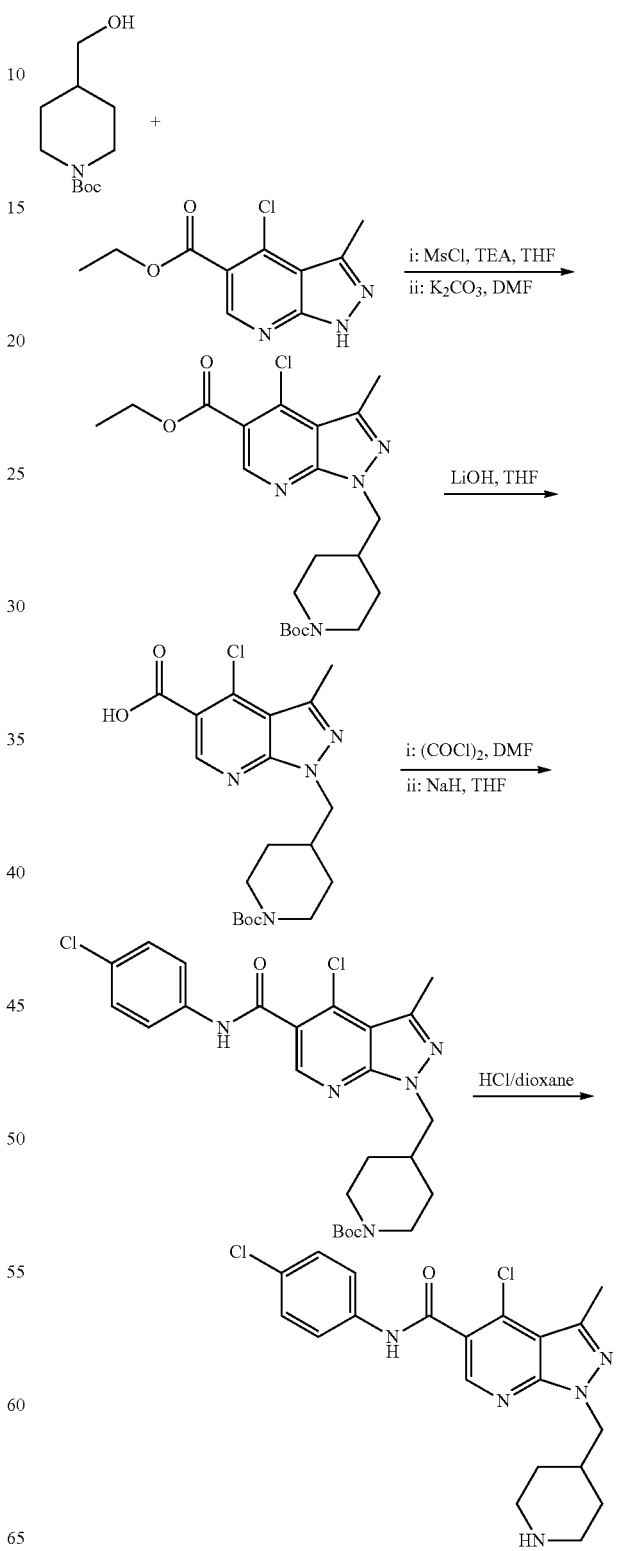

Example 445

4-Chloro-3-methyl-1-piperidin-4-ylmethyl-1H-pyrazolo[3,4-b]pyridine-5-carboxylic acid (4-chlorophenyl)-amide Step 1-3

These three steps are similar to general procedure for 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (Example 419).

Step 4

A solution of 4-[4-chloro-5-(4-chloro-phenylcarbamoyl)-3-methyl-pyrazolo[3,4-b]pyridin-1-ylmethyl]-piperidine-1-carboxylic acid tert-butyl ester (70 mg, 0.135 mmol) in HCl/dioxane (2 M, 10 mL) was stirred at room temperature overnight. The reaction was concentrated and the residue was triturated with ether to give HCl salt of 4-chloro-3-methyl-1-piperidin-4-ylmethyl-1H-pyrazolo[3,4-b]pyridine-5-carboxylic acid (4-chloro-phenyl)-amide (65 mg, yield: quantitative) as a light yellow solid. $^1$HNMR (400 MHz, CD$_3$OD): δ=8.62 (s, 1H), 7.71 (d, J=8.8 Hz, 2H), 7.38 (d, J=8.4 Hz, 2H), 4.43 (d, J=6.8 Hz, 2H), 3.40-3.37 (m, 2H), 2.99-2.93 (m, 2H), 2.75 (s, 3H), 2.39-2.36 (m, 1H), 1.85-1.81 (m, 2H), 1.59-1.52 (m, 2H). MS: m/z 417.8 (M+H$^+$).

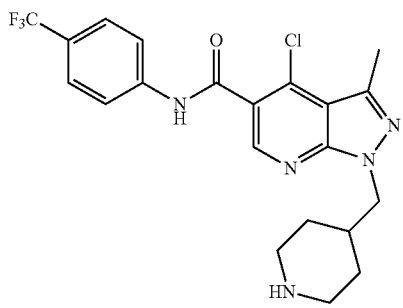 [SMILES: Cc1nn(CC2CCNCC2)c2ncc(C(=O)Nc3ccc(C(F)(F)F)cc3)c(Cl)c12]

Example 446

4-Chloro-3-methyl-1-piperidin-4-ylmethyl-1H-pyrazolo[3,4-b]pyridine-5-carboxylic acid (4-trifluoromethyl-phenyl)-amide The title compound was prepared using general procedure for 4-chloro-3-methyl-1-piperidin-4-ylmethyl-1H-pyrazolo[3,4-b]pyridine-5-carboxylic acid (4-chloro-phenyl)-amide (Example 445).

$^1$HNMR (400 MHz, CD$_3$OD): δ=8.64 (s, 1H), 7.91 (d, J=8.4 Hz, 2H), 7.69 (d, J=8.8 Hz, 2H), 4.44 (d, J=7.2 Hz, 2H), 3.40-3.37 (m, 2H), 2.99-2.94 (m, 2H), 2.75 (s, 3H), 2.39-2.36 (m, 1H), 1.85-1.82 (m, 2H), 1.60-1.53 (m, 2H). MS: m/z 451.8 (M+H$^+$).

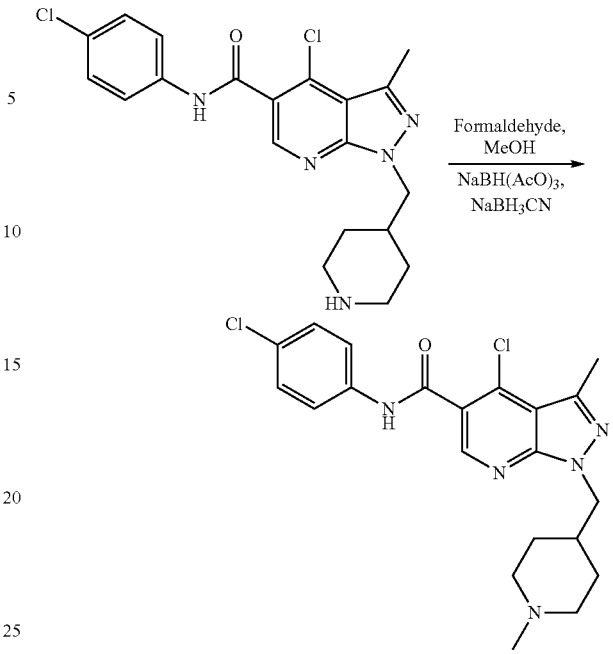

Example 447

4-Chloro-3-methyl-1-(1-methyl-piperidin-4-ylmethyl)-1H-pyrazolo[3,4-b]pyridine-5-carboxylic acid (4-chloro-phenyl)-amide To a solution of 4-chloro-3-methyl-1-piperidin-4-ylmethyl-1H-pyrazolo[3,4-b]pyridine-5-carboxylic acid (4-chloro-phenyl)-amide (HCl salt, 20 mg, 0.044 mmol) in MeOH (2 mL), was added formalin (0.5 mL). The mixture was stirred at room temperature for 10 mins. After the addition of NaBH(AcO)$_3$ (19 mg, 0.088 mmol) and NaBH$_3$CN (6.5 mg, 0.088 mmol), the reaction was stirred at room temperature overnight. The reaction mixture was partitioned between saturated NaHCO$_3$ solution (20 mL) and EA (20 mL). The organic layer was dried over Na$_2$SO$_4$ and concentrated to dryness in vacuum. The residue was purified by prep-TLC (DCM/MeOH/NH$_4$OH=15/1/0.1) to give 4-chloro-3-methyl-1-(1-methyl-piperidin-4-ylmethyl)-1H-pyrazolo[3,4-b]pyridine-5-carboxylic acid (4-chloro-phenyl)-amide (5 mg, yield: 26%) as a white solid. $^1$HNMR (400 MHz, CDCl$_3$): δ=8.65 (s, 1H), 8.24 (brs, 1H), 7.57 (d, J=8.0 Hz, 2H), 7.28 (d, J=8.8 Hz, 2H), 4.29 (d, J=6.8 Hz, 2H), 2.93-2.90 (m, 2H), 2.66 (s, 3H), 2.31 (s, 3H), 2.08-2.02 (m, 3H), 1.54-1.47 (m, 4H). MS: m/z 431.8 (M+H$^+$).

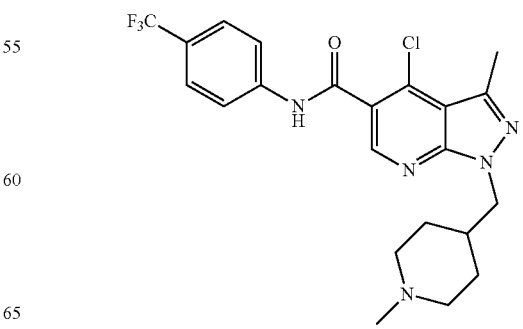

Example 448

4-Chloro-3-methyl-1-(1-methyl-piperidin-4-ylmethyl)-1H-pyrazolo[3,4-b]pyridine-5-carboxylic acid (4-trifluoromethyl-phenyl)-amide The title compound was prepared using general procedure for 4-chloro-3-methyl-1-(1-methyl-piperidin-4-ylmethyl)-1H-pyrazolo[3,4-b]pyridine-5-carboxylic acid (4-chlorophenyl)-amide (Example 447).

$^1$HNMR (400 MHz, CDCl$_3$): δ=8.68 (s, 1H), 8.28 (brs, 1H), 7.75 (d, J=7.6 Hz, 2H), 7.58 (d, J=8.4 Hz, 2H), 4.30 (d, J=7.2 Hz, 2H), 2.91-2.88 (m, 2H), 2.68 (s, 3H), 2.29 (s, 3H), 2.05-1.97 (m, 3H), 1.56-1.47 (m, 4H). MS: m/z 465.8 (M+H$^+$).

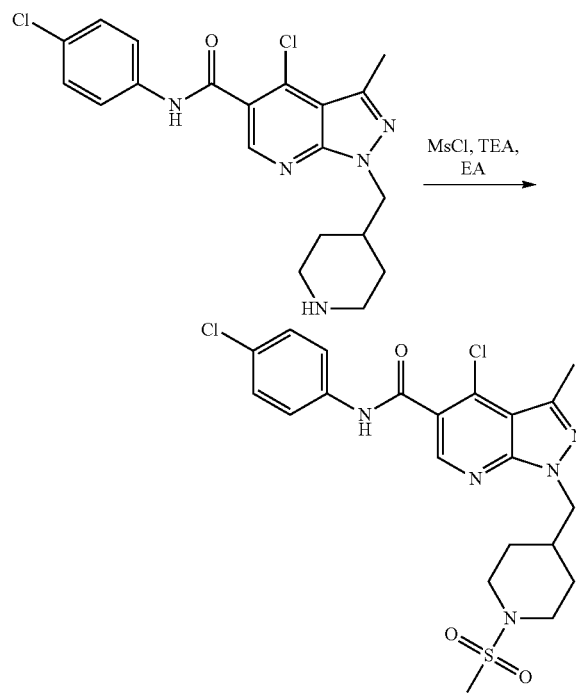

Example 449

4-Chloro-1-(1-methanesulfonyl-piperidin-4-ylmethyl)-3-methyl-1H-pyrazolo[3,4-b]pyridine-5-carboxylic acid (4-chloro-phenyl)-amide To a suspension of 4-chloro-3-methyl-1-piperidin-4-ylmethyl-1H-pyrazolo[3,4-b]pyridine-5-carboxylic acid (4-chloro-phenyl)-amide (HCl salt, 20 mg, 0.044 mmol) in EA (5 mL), was added TEA (0.2 mL). After addition of MsCl (0.05 mL), the reaction was stirred at room temperature for 1 hr. The reaction mixture was separated between sat. NaHCO$_3$ solution (20 mL) and EA (15 mL). The organic layer was dried over Na$_2$SO$_4$ and concentrated to dryness in vacuum. The residue was purified by prep-TLC (EA) to give 4-chloro-1-(1-methanesulfonyl-piperidin-4-ylmethyl)-3-methyl-1H-pyrazolo[3,4-b]pyridine-5-carboxylic acid (4-chloro-phenyl)-amide (5 mg, yield: 23%) as a white solid.

$^1$HNMR (400 MHz, CDCl$_3$): δ=8.71 (s, 1H), 7.90 (brs, 1H), 7.55 (d, J=8.4 Hz, 2H), 7.30 (d, J=8.0 Hz, 2H), 4.32 (d, J=6.8 Hz, 2H), 3.73-3.70 (m, 2H), 2.69 (s, 6H), 2.59-2.53 (m, 3H), 2.13-2.09 (m, 1H), 1.61-1.53 (m, 2H), 1.43-1.37 (m, 2H). MS: m/z 495.9 (M+H$^+$).

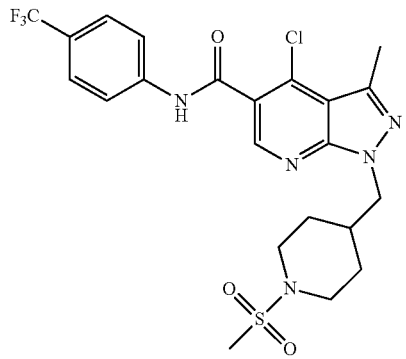 [SMILES: Cc1nn(CC2CCN(S(C)(=O)=O)CC2)c2ncc(C(=O)Nc3ccc(C(F)(F)F)cc3)c(Cl)c12]

Example 450

4-Chloro-1-(1-methanesulfonyl-piperidin-4-ylmethyl)-3-methyl-1H-pyrazolo[3,4-b]pyridine-5-carboxylic acid (4-trifluoromethyl-phenyl)-amide The title compound was prepared using general procedure for 4-chloro-1-(1-methanesulfonyl-piperidin-4-ylmethyl)-3-methyl-1H-pyrazolo[3,4-b]pyridine-5-carboxylic acid (4-chloro-phenyl)-amide (Example 449).

$^1$HNMR (400 MHz, DMSO-d6): δ=11.04 (brs, 1H), 8.73 (s, 1H), 7.95 (d, J=8.8 Hz, 2H), 7.76 (d, J=8.8 Hz, 2H), 4.38 (d, J=6.4 Hz, 2H), 3.54-3.52 (m, 2H), 2.83 (s, 3H), 2.70-2.63 (m, 5H), 2.12-2.10 (m, 1H), 1.59-1.56 (m, 2H), 1.34-1.30 (m, 2H). MS: m/z 529.8 (M+H$^+$).

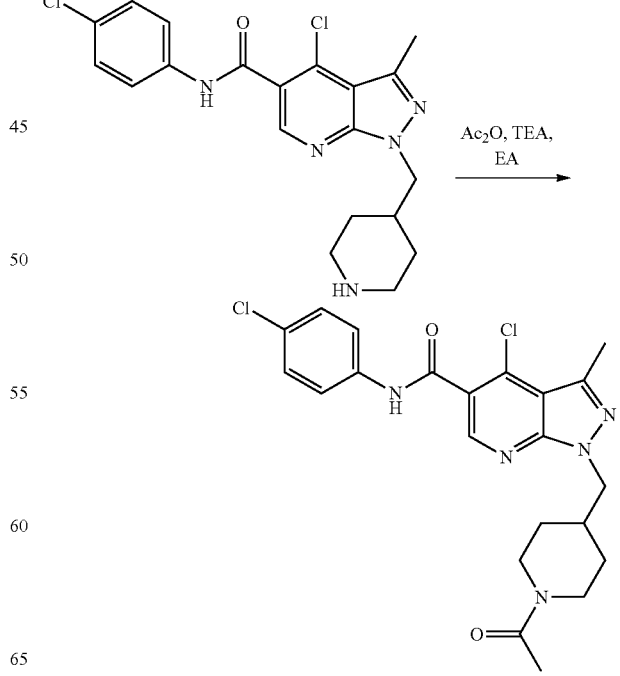

Example 451

1-(1-Acetyl-piperidin-4-ylmethyl)-4-chloro-3-methyl-1H-pyrazolo[3,4-b]pyridine-5-carboxylic acid (4-chloro-phenyl)-amide To a suspension of 4-chloro-3-methyl-1-piperidin-4-ylmethyl-1H-pyrazolo[3,4-b]pyridine-5-carboxylic acid (4-chloro-phenyl)-amide (HCl salt, 20 mg, 0.044 mmol) in EA (5 mL), was added TEA (0.2 mL). After addition of $Ac_2O$ (0.05 mL), the reaction was stirred at room temperature for 1 hr. The reaction mixture was separated between sat. $NaHCO_3$ solution (20 mL) and EA (15 mL). The organic layer was washed with water (15 mL) and brine (15 ml), dried over $Na_2SO_4$, filtered and concentrated to dryness in vacuum. The residue was triturate with MeOH to give 1-(1-acetyl-piperidin-4-ylmethyl)-4-chloro-3-methyl-1H-pyrazolo[3,4-b]pyridine-5-carboxylic acid (4-chloro-phenyl)-amide (10 mg, yield: 50%) as a white solid.

$^1$HNMR (400 MHz, $CDCl_3$): δ=8.71 (s, 1H), 7.95 (brs, 1H), 7.56 (d, J=8.4 Hz, 2H), 7.30 (d, J=8.8 Hz, 2H), 4.53-4.49 (m, 1H), 4.29 (d, J=7.2 Hz, 2H), 3.73-3.70 (m, 1H), 2.95-2.89 (m, 1H), 2.71 (s, 3H), 2.46-2.40 (m, 1H), 2.23-2.18 (m, 1H), 1.99 (s, 3H), 1.54-1.51 (m, 2H), 1.22-1.14 (m, 2H). MS: m/z 459.9 (M+H$^+$).

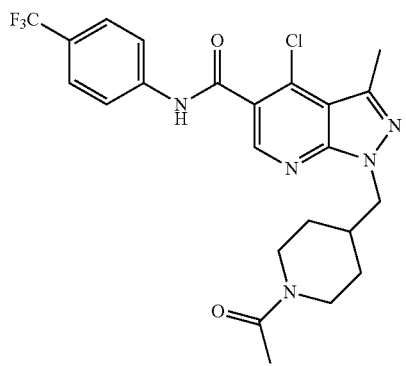 [SMILES: CC(=O)N1CCC(Cn2nc(C)c3c(Cl)c(C(=O)Nc4ccc(C(F)(F)F)cc4)cnc32)CC1]

Example 452

1-(1-Acetyl-piperidin-4-ylmethyl)-4-chloro-3-methyl-1H-pyrazolo[3,4-b]pyridine-5-carboxylic acid (4-trifluoromethyl-phenyl)-amide The title compound was prepared using general procedure for 1-(1-acetyl-piperidin-4-ylmethyl)-4-chloro-3-methyl-1H-pyrazolo[3,4-b]pyridine-5-carboxylic acid (4-chlorophenyl)-amide (Example 451).

$^1$HNMR (300 MHz, $CDCl_3$): δ=8.67 (s, 1H), 8.53 (brs, 1H), 7.76 (d, J=8.1 Hz, 2H), 7.58 (d, J=8.7 Hz, 2H), 4.45-4.39 (m, 1H), 4.27 (d, J=6.9 Hz, 2H), 3.72-3.67 (m, 1H), 2.93-2.85 (m, 1H), 2.68 (s, 3H), 2.40-2.32 (m, 1H), 2.20-2.14 (m, 1H), 1.96 (s, 3H), 1.56-1.45 (m, 2H), 1.24-1.10 (m, 2H). MS: m/z 493.8 (M+H$^+$).

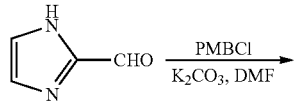

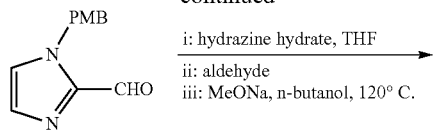

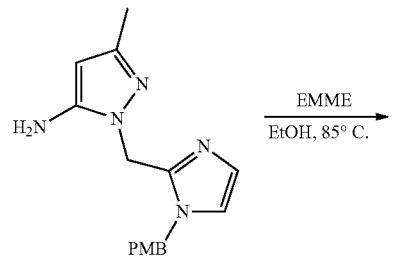

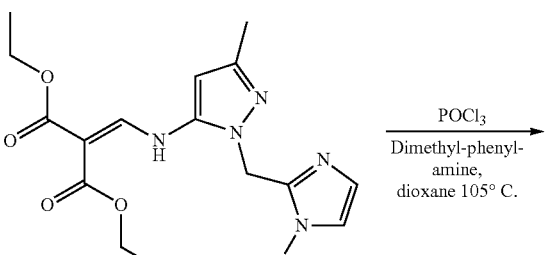

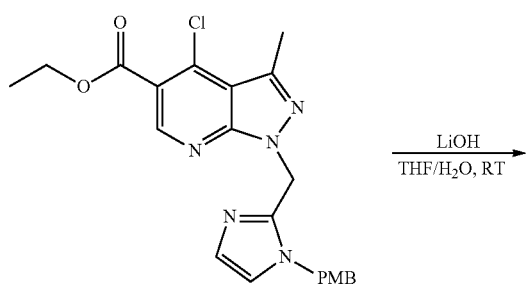

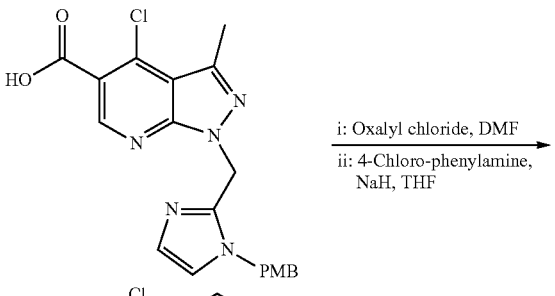

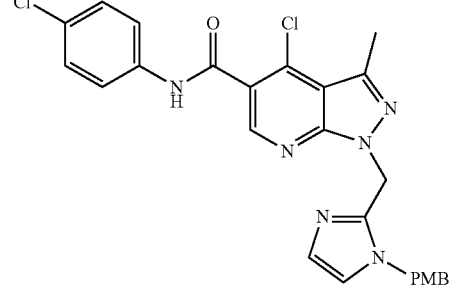

Example 453

4-chloro-N-(4-chlorophenyl)-1-((1-(4-methoxybenzyl)-1H-imidazol-2-yl)methyl)-3-methyl-1H-pyrazolo[3,4-b]pyridine-5-carboxamide Step 1

A mixture of 1H-imidazole-2-carbaldehyde (4 g, 41.6 mmol), 4-methoxylbenzyl chloride (6.5 g, 41.6 mmol) and K$_2$CO$_3$ (11.5 g, 83.2 mmol) in DMF (50 mL) was stirred at room temperature overnight. The reactant was poured into water (400 mL) and the aqueous phase was extracted with EA (300 mL). The organic layer was washed with water (300 mL) and brine (300 mL), dried over Na$_2$SO$_4$ and concentrated to give 1-(4-methoxy-benzyl)-1H-imidazole-2-carbaldehyde (9.1 g, yield: quantitative) as a white solid.

$^1$HNMR (300 MHz, CDCl$_3$): δ=9.84 (s, 1H), 7.26 (overlap, 1H), 7.17 (d, J=8.7 Hz, 2H), 7.11 (s, 1H), 6.86 (d, J=8.7 Hz, 2H), 5.53 (s, 2H), 3.78 (s, 3H).

Step 2

To a solution of allyl cyanide (2.68 g, 40 mmol) in THF (20 mL) was added hydrazine monohydrate (2.1 g, 42 mmol) slowly at 0° C. under N$_2$. The reaction was stirred at room temperature overnight. Then 1-(4-methoxy-benzyl)-1H-imidazole-2-carbaldehyde (9.1 g, 40 mmol) was added slowly and the mixture was stirred at room temperature for 3 hrs. After that, the solution was concentrated to dryness under reduced pressure and the crude was co-evaporated to remove remaining moisture in the presence of EtOH. n-BuOH (20 mL) and NaOMe (2.27 g, 42 mmol) were added to the residue and the mixture was stirred at 120° C. overnight. The reaction solution was poured into water (200 mL) and the aq. phase was extracted with ether (200 mL×2). The extracts were treated with 1 N HCl (200 mL×2). The aqueous phase was adjusted with aq. NaOH to pH=14 followed by the extracting with DCM (200 mL×2). The DCM layer was washed with brine (200 mL) and dried over Na$_2$SO$_4$. The solution was concentrated in vacuum to give 241-(4-methoxy-benzyl)-1H-imidazol-2-ylmethyl]-5-methyl-2H-pyrazol-3-ylamine (7.3 g, yield: 59%) as a yellow solid.

Step 3

A solution of 2-[1-(4-methoxy-benzyl)-1H-imidazol-2-ylmethyl]-5-methyl-2H-pyrazol-3-ylamine (7.3 g, 24.6 mol) and 2-ethoxymethylene-malonic acid diethyl ester (5.34 g, 24.6 mol) in EtOH (100 mL) was stirred at 85° C. overnight. The mixture was concentrated and purified by silica gel column (100-200 mush, DCM/EA=1/1) to give 2-({2-[1-(4-methoxy-benzyl)-1H-imidazol-2-ylmethyl]-5-methyl-2H-pyrazol-3-ylamino}-methylene)-malonic acid diethyl ester (6.9 g, yield: 60%) as a yellow gel.

MS: m/z 468.2 (M+H$^+$).

Step 4

A solution of 2-({2-[1-(4-methoxy-benzyl)-1H-imidazol-2-ylmethyl]-5-methyl-2H-pyrazol-3-ylamino}-methylene)-malonic acid diethyl ester (6.9 g, 14.7 mmol), dimethyl-phenyl-amine (5.34 g, 44.1 mmol) and POCl$_3$ (18 g, 118 mmol) in dioxane (50 mL) stirred at 105° C. overnight. Then the reaction mixture was concentrated in vacuum. The residue was poured into sat.NaHCO$_3$ solution (500 mL) carefully and the aqueous phase was extracted with EA (100 L×2). The organic layers were combined, dried over Na$_2$SO$_4$ and concentrated to dryness in vacuum. The residue was purified by silica gel column (DCM/EA=1/1) to give 4-chloro-1-[1-(4-methoxy-benzyl)-1H-imidazol-2-ylmethyl]-3-methyl-1H-pyrazolo[3,4-b]pyridine-5-carboxylic acid ethyl ester (3.5 g, yield: 55%) as a yellow gel.

$^1$HNMR (400 MHz, CDCl3): δ=8.91 (s, 1H), 7.08 (s, 1H), 6.88 (s, 1H), 6.64-6.59 (m, 4H), 5.68 (s, 2H), 5.18 (s, 2H), 4.44 (q, J=7.2 Hz, 2H), 3.73 (s, 3H), 2.62 (s, 3H), 1.44 (t, J=7.2 Hz, 2H). MS: m/z 440.1 (M+H$^+$).

Step 5 and 6

These two steps are similar to general procedure for 4-chloro-1-((1-(4-methoxybenzyl)-1H-1,2,3-triazol-4-yl)methyl)-3-methyl-N-(4-(trifluoromethyl)phenyl)-1H-pyrazolo[3,4-b]pyridine-5-carboxamide (Example 419).

$^1$HNMR (300 MHz, CDCl$_3$): δ=8.64 (s, 1H), 8.09 (brs, 1H), 7.64 (d, J=8.7 Hz, 2H), 7.36 (d, J=8.7 Hz, 2H), 7.10 (s, 1H), 6.90 (d, J=1.2 Hz, 1H), 6.57 (d, J=8.4 Hz, 2H), 6.48 (d, J=9.0 Hz, 2H), 5.70 (s, 2H), 5.17 (s, 2H), 3.79 (s, 3H), 2.63 (s, 3H). MS: m/z 520.8 (M+H$^+$).

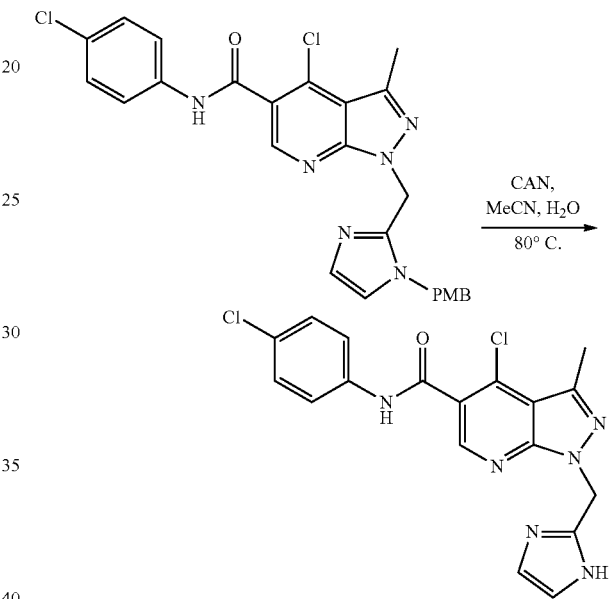

Example 454

4-Chloro-1-(1H-imidazol-2-ylmethyl)-3-methyl-1H-pyrazolo[3,4-b]pyridine-5-carboxylic acid (4-chloro-phenyl)-amide A solution of 4-chloro-1-8 1-(4-methoxy-benzyl)-1H-imidazol-2-ylmethyl]-3-methyl-1H-pyrazolo[3,4-b]pyridine-5-carboxylic acid (4-chloro-phenyl)-amide (180 mg, 0.35 mmol) and CAN (570 mg, 1.04 mmol) in MeCN/H$_2$O (22 mL/7 mL) was stirred at 80° C. for 48 hrs. The reaction solution was poured into water (80 mL) and extracted with EA (50 mL). The organic layer was dried over Na$_2$SO$_4$ and concentrated to dryness in vacuum. The residue was purified by prep-HPLC (NH$_4$OH) to give 4-chloro-1-(1H-imidazol-2-ylmethyl)-3-methyl-1H-pyrazolo[3,4-b]pyridine-5-carboxylic acid (4-chloro-phenyl)-amide (6 mg, yield: 4%) as a pale white solid.

$^1$HNMR (400 MHz, DMSO-d6): δ=12.14 (brs, 1H), 10.81 (s, 1H), 8.72 (s, 1H), 7.76 (d, J=8.4 Hz, 2H), 7.44 (d, J=8.8 Hz, 2H), 6.92 (s, 2H), 5.63 (s, 2H), 2.67 (s, 3H). MS: m/z 400.8 (M+H$^+$).

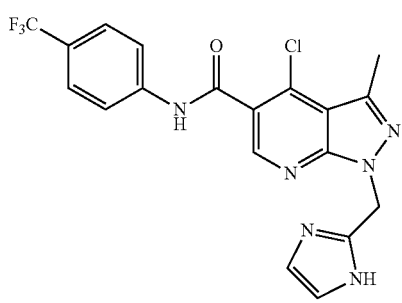 [SMILES: Cc1nn(Cc2ncc[nH]2)c2ncc(C(=O)Nc3ccc(C(F)(F)F)cc3)c(Cl)c12]

Example 455

4-Chloro-1-(1H-imidazol-2-ylmethyl)-3-methyl-1H-pyrazolo[3,4-b]pyridine-5-carboxylic acid (4-trifluoromethyl-phenyl)-amide The title compound was prepared using general procedure for 4-chloro-1-(1H-imidazol-2-ylmethyl)-3-methyl-1H-pyrazolo[3,4-b]pyridine-5-carboxylic acid (4-chloro-phenyl)-amide (Example 454).

$^1$HNMR (400 MHz, DMSO-d6): δ=12.11 (brs, 1H), 11.05 (s, 1H), 8.75 (s, 1H), 7.94 (d, J=8.8 Hz, 2H), 7.76 (d, J=8.8 Hz, 2H), 7.05 (s, 1H), 6.79 (s, 1H), 5.64 (s, 2H), 2.68 (s, 3H). MS: m/z 434.8 (M+H$^+$).

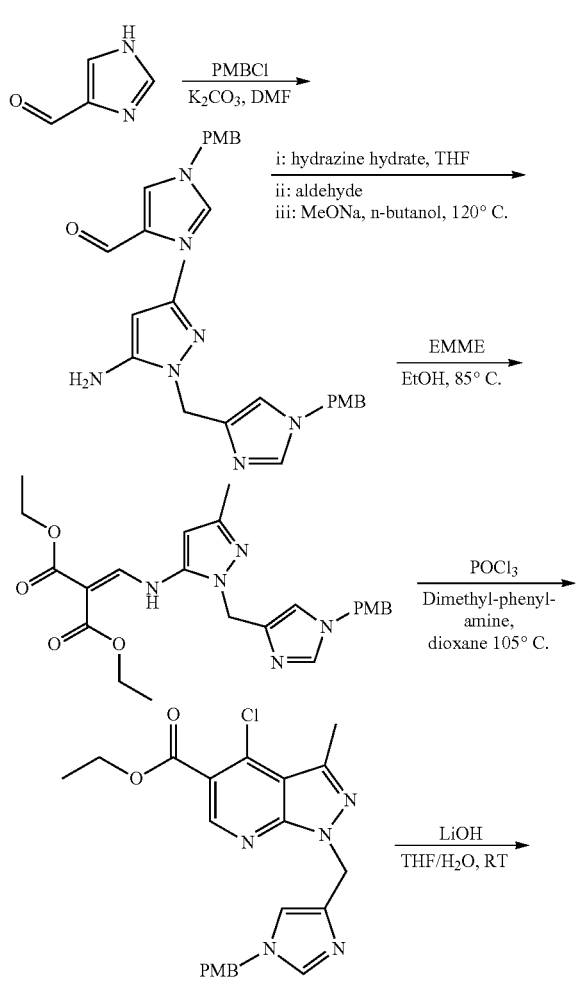

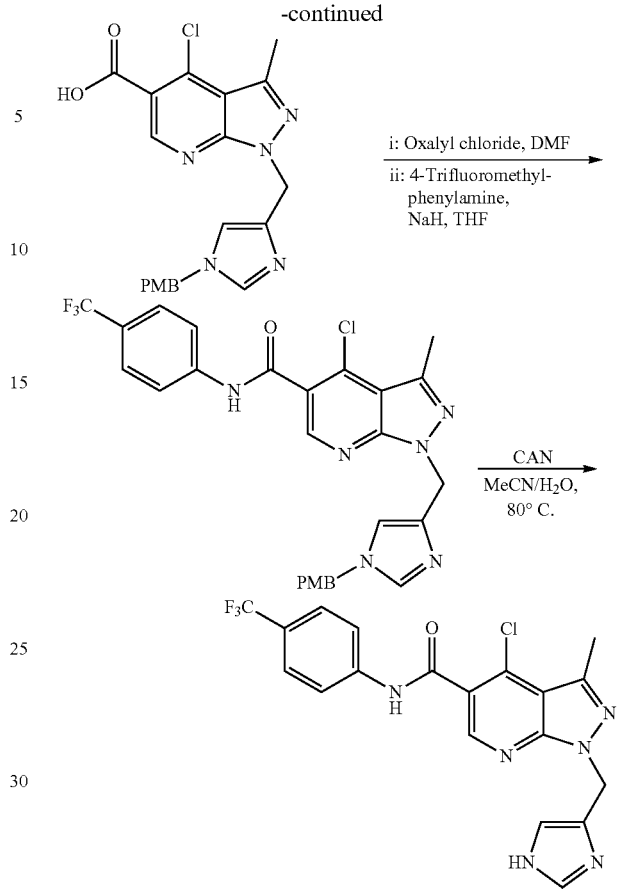

Example 456

4-Chloro-1-(1H-imidazol-4-ylmethyl)-3-methyl-1H-pyrazolo[3,4-b]pyridine-5-carboxylic acid (4-trifluoromethyl-phenyl)-amide Step 1~Step 6

These six steps are similar to general procedure for 4-chloro-1-[1-(4-methoxy-benzyl)-1H-imidazol-2-ylmethyl]-3-methyl-1H-pyrazolo[3,4-b]pyridine-5-carboxylic acid (4-chloro-phenyl)-amide (Example 453).

Step 7

The title compound was prepared using general procedure for 4-chloro-1-(1H-imidazol-2-ylmethyl)-3-methyl-1H-pyrazolo[3,4-b]pyridine-5-carboxylic acid (4-chloro-phenyl)-amide (Example 454).

$^1$HNMR (300 MHz, DMSO-d6): δ=12.14 (brs, 1H), 11.04 (s, 1H), 8.75 (s, 1H), 7.94 (d, J=8.4 Hz, 2H), 7.76 (d, J=9.0 Hz, 2H), 6.92-6.91 (m, 2H), 5.63 (s, 2H), 2.67 (s, 3H). MS: m/z 434.9 (M+H$^+$).

II. Biological Evaluation

The assay was performed using H4 neuroglioma cells and using indirect immunofluorescence detection of the endogenous GR receptor.

Cell Culture

Cell Culture Medium: DMEM, without phenol-red (HyClone SH30585.02)+5% heat-inactivated charcoal/dextran treated FBS (HyClone SH30068.03)+100 ug/ml penicillin/100 i.u./ml streptomycin (Cellgro 30-002-CI) +2mM L-glutamine (Cellgro 25-005-CI) +1mM sodium pyruvate (Sigma S8636 or Lonza 13-115E). Cells grow for 2-3 weeks in media containing charcoal stripped serum Seeding Seeded 1536 well assay plates with 5 μl/well of prepared cells (1000 cells/well). Incubated plates overnight at 37° C., 5% $CO_2$ Screening Procedure:
1. Test compounds and DMSO added to assay plates at a final concentration of 10 μM
2. Plates spun down 1500-2000 rpm, 1 min.
3. Returned to incubator for 25 min.
4. Cortisone added to assay plates at a final concentration of 10 μM
5. Plates spun down 1500-2000 rpm, 1 min.
6. Returned to incubator for 60 min.
7. 2 μl/well 14% ice-cold PFA added to assay plates.
8. Plates spun down 1500-2000 rpm, 1 min.
9. Plates allowed to fix at room temperature for 30 minutes.
10. Plates washed 2× with 10 μl PBS.

Labeling and Staining

Materials: Permeabilization buffer stock: 0.6% Triton X-100 in PBS. Primary Ab: Santa Cruz H-300. cat # sc-8992. Secondary Ab: Alexafluor 488. Molecular Probes cat # A-11034. HCS Cell Mask Deep Red: Molecular Probes cat # H32721. DAPI: Molecular Probes cat # D1306.

Procedure:
1. 2 μl/well permeabilization buffer added to plates.
2. Spun down, 1500-2000 rpm, 1 minute.
3. Plates allowed to permeabilize at RT for 5-10 minutes.
4. Plates aspirated to 2 μl per well.
5. 2 μl/well prepared primary antibody added to plates.
6. Spun down, 1500-2000 rpm, 1 minute.
7. Incubated at RT for 1 hour.
8. Plates washed 2× with 10 μl PBS.
9. 2 μl/well prepared secondary antibody added to plates.
10. Spun down, 1500-2000 rpm, 1 minute.
11. Incubated at RT for 1 hour.
12. Plates washed 2× with 10 μl PBS.
13. 2 μl/well prepared HCS Cell Mask added to plates.
14. Spun down, 1500-2000 rpm, 1 minute.
15. Incubated at RT for 30 min.
16. Plates washed 3× with 10μl PBS.
17. 4 μl DAPI solution added to plates.
18. Spun down, 1500-2000 rpm, 1 minute.
19. Plates sealed and store at 4° C.

Final conditions:

Fixative: 4% PFA. Permeabilization buffer: 0.3% Triton X-100 in PBS. Primary antibody: 1:200 in 5% BSA block. Secondary antibody: 1:800 in 5% BSA block. HCS Cell Mask: 1:6000 in PBS. DAPI: 100 ng/ml.

Imaging: The nuclear GR translocation assay plates were imaged on a PerkinElmer Opera with the following acquisition parameters: Lens: 20× air, Binning: 2×2, Images/well: 5, Exp2Cam1: 488nm, Exp2Cam3: 640 nm, Exp3Cam4: UV.

Compounds demonstrated activity in the assay described herein as indicated in the following Table 2.

TABLE 2

| Ex. | $IC_{50}$ (μM) |
|---|---|
| 1 | B |
| 2 | B |
| 3 | B |
| 4 | B |
| 5 | B |
| 6 | B |
| 7 | A |
| 8 | B |
| 9 | B |
| 10 | B |
| 11 | B |
| 12 | C |
| 13 | C |
| 14 | A |
| 15 | B |
| 16 | B |
| 17 | B |
| 18 | B |
| 19 | B |
| 20 | B |
| 21 | D |
| 22 | D |
| 23 | B |
| 24 | B |
| 25 | D |
| 26 | B |
| 27 | C |
| 28 | B |
| 29 | C |
| 30 | C |
| 31 | D |
| 32 | C |
| 33 | C |
| 34 | C |
| 35 | D |
| 36 | D |
| 37 | D |
| 38 | D |
| 39 | C |
| 40 | D |
| 41 | D |
| 42 | D |
| 43 | D |
| 44 | D |
| 45 | D |
| 46 | D |
| 47 | C |
| 48 | B |
| 49 | B |
| 50 | C |
| 51 | B |
| 52 | D |
| 53 | B |
| 54 | B |
| 55 | B |
| 56 | C |
| 57 | B |
| 58 | C |
| 59 | B |
| 60 | B |
| 61 | C |
| 62 | C |
| 63 | B |
| 64 | B |
| 65 | B |
| 66 | B |
| 67 | B |
| 68 | B |
| 69 | B |
| 70 | C |
| 71 | C |
| 72 | A |
| 73 | B |
| 74 | C |
| 75 | B |
| 76 | C |
| 77 | B |
| 78 | D |
| 79 | D |
| 80 | C |
| 81 | B |

TABLE 2-continued

| Ex. | IC$_{50}$ (μM) |
|---|---|
| 82 | A |
| 83 | A |
| 84 | B |
| 85 | A |
| 86 | A |
| 87 | B |
| 88 | A |
| 89 | A |
| 90 | B |
| 91 | A |
| 92 | A |
| 93 | B |
| 94 | B |
| 95 | C |
| 96 | B |
| 97 | B |
| 98 | B |
| 99 | B |
| 100 | D |
| 101 | B |
| 102 | C |
| 103 | B |
| 104 | B |
| 105 | B |
| 106 | C |
| 107 | B |
| 108 | B |
| 109 | B |
| 110 | B |
| 111 | B |
| 112 | D |
| 113 | C |
| 114 | B |
| 115 | B |
| 116 | C |
| 117 | C |
| 118 | C |
| 119 | D |
| 120 | D |
| 121 | D |
| 122 | D |
| 123 | B |
| 124 | A |
| 125 | B |
| 126 | A |
| 127 | A |
| 128 | A |
| 129 | B |
| 130 | A |
| 131 | B |
| 132 | B |
| 133 | A |
| 134 | A |
| 135 | B |
| 136 | B |
| 137 | A |
| 138 | B |
| 139 | A |
| 140 | B |
| 141 | A |
| 142 | A |
| 143 | A |
| 144 | B |
| 145 | A |
| 146 | A |
| 147 | A |
| 148 | B |
| 149 | A |
| 150 | A |
| 151 | B |
| 152 | A |
| 153 | A |
| 154 | B |
| 155 | A |
| 156 | B |
| 157 | A |
| 158 | B |
| 159 | A |
| 160 | A |
| 161 | B |
| 162 | B |
| 163 | B |
| 164 | B |
| 165 | B |
| 166 | B |
| 167 | A |
| 168 | A |
| 169 | A |
| 170 | D |
| 171 | D |
| 172 | A |
| 173 | A |
| 174 | B |
| 175 | C |
| 176 | B |
| 177 | A |
| 178 | A |
| 179 | A |
| 180 | B |
| 181 | D |
| 182 | D |
| 183 | D |
| 184 | B |
| 185 | B |
| 186 | A |
| 187 | B |
| 188 | B |
| 189 | B |
| 190 | B |
| 191 | B |
| 192 | B |
| 193 | A |
| 194 | C |
| 195 | C |
| 196 | C |
| 197 | B |
| 198 | A |
| 199 | A |
| 200 | A |
| 201 | A |
| 202 | A |
| 203 | B |
| 204 | B |
| 205 | A |
| 206 | A |
| 207 | A |
| 208 | B |
| 209 | A |
| 210 | A |
| 211 | A |
| 212 | A |
| 213 | A |
| 214 | B |
| 215 | B |
| 216 | B |
| 217 | C |
| 218 | C |
| 219 | B |
| 220 | A |
| 221 | A |
| 222 | B |
| 223 | A |
| 224 | A |
| 225 | D |
| 226 | D |
| 227 | D |
| 228 | B |
| 229 | A |
| 230 | A |
| 231 | A |
| 232 | A |
| 233 | A |
| 234 | B |
| 235 | B |
| 236 | B |
| 237 | B |

TABLE 2-continued

| Ex. | IC$_{50}$ (μM) |
|---|---|
| 238 | B |
| 239 | B |
| 240 | B |
| 241 | B |
| 242 | B |
| 243 | B |
| 244 | B |
| 245 | B |
| 246 | A |
| 247 | A |
| 248 | A |
| 249 | B |
| 250 | B |
| 251 | B |
| 252 | B |
| 253 | B |
| 254 | C |
| 255 | B |
| 256 | B |
| 257 | B |
| 258 | B |
| 259 | B |
| 260 | B |
| 261 | B |
| 262 | B |
| 263 | B |
| 264 | B |
| 265 | B |
| 266 | B |
| 267 | B |
| 268 | A |
| 269 | A |
| 270 | B |
| 271 | B |
| 272 | A |
| 273 | A |
| 274 | B |
| 275 | A |
| 276 | B |
| 277 | B |
| 279 | B |
| 280 | B |
| 281 | A |
| 282 | A |
| 283 | B |
| 284 | A |
| 285 | A |
| 286 | B |
| 287 | A |
| 288 | A |
| 289 | B |
| 290 | B |
| 291 | B |
| 292 | B |
| 293 | B |
| 294 | B |
| 295 | B |
| 296 | B |
| 297 | B |
| 299 | A |
| 300 | B |
| 301 | B |
| 302 | A |
| 303 | A |
| 304 | B |
| 305 | B |
| 306 | D |
| 307 | C |
| 308 | C |
| 309 | D |
| 310 | D |
| 311 | C |
| 312 | D |
| 313 | C |
| 314 | C |
| 315 | D |
| 316 | D |
| 317 | D |

TABLE 2-continued

| Ex. | IC$_{50}$ (μM) |
|---|---|
| 318 | C |
| 319 | D |
| 320 | C |
| 321 | C |
| 322 | C |
| 323 | C |
| 324 | C |
| 325 | D |
| 326 | C |
| 327 | C |
| 328 | D |
| 329 | C |
| 330 | D |
| 331 | C |
| 331a | C |
| 332 | D |
| 333 | D |
| 334 | C |
| 335 | D |
| 336 | C |
| 337 | B |
| 338 | B |
| 339 | B |
| 340 | B |
| 341 | A |
| 342 | A |
| 343 | B |
| 344 | A |
| 345 | A |
| 346 | B |
| 347 | B |
| 348 | B |
| 349 | B |
| 350 | B |
| 351 | B |
| 352 | B |
| 353 | A |
| 354 | B |
| 355 | B |
| 356 | B |
| 357 | B |
| 358 | B |
| 359 | B |
| 360 | B |
| 361 | A |
| 362 | A |
| 363 | B |
| 364 | A |
| 365 | B |
| 366 | A |
| 367 | B |
| 368 | B |
| 369 | B |
| 370 | A |
| 371 | A |
| 372 | B |
| 373 | B |
| 374 | B |
| 375 | B |
| 376 | B |
| 377 | A |
| 378 | D |
| 379 | D |
| 380 | A |
| 382 | B |
| 383 | B |
| 384 | B |
| 385 | B |
| 386 | B |
| 387 | B |
| 388 | A |
| 389 | B |
| 390 | A |
| 391 | A |
| 392 | D |
| 393 | D |
| 394 | D |
| 395 | D |

TABLE 2-continued

| Ex. | IC$_{50}$ (μM) |
|---|---|
| 396 | D |
| 397 | D |
| 398 | D |
| 399 | D |
| 400 | D |
| 401 | D |
| 402 | D |
| 403 | D |
| 404 | D |
| 405 | D |
| 406 | D |
| 407 | D |
| 408 | D |
| 409 | D |
| 410 | D |
| 411 | D |
| 412 | D |
| 413 | D |
| 414 | D |
| 415 | D |
| 416 | D |
| 417 | A |
| 418 | B |
| 419 | A |
| 420 | C |
| 421 | B |
| 422 | A |
| 423 | B |
| 424 | B |
| 425 | B |
| 426 | B |
| 427 | B |
| 428 | A |
| 429 | B |
| 430 | A |
| 431 | A |
| 432 | B |
| 433 | A |
| 434 | A |
| 435 | A |
| 436 | A |
| 437 | A |
| 438 | A |
| 439 | A |
| 440 | A |
| 441 | A |
| 442 | A |
| 443 | A |
| 444 | B |
| 445 | B |
| 446 | B |
| 447 | B |
| 448 | B |
| 449 | B |
| 450 | A |
| 451 | B |
| 452 | A |
| 453 | B |
| 454 | A |
| 455 | A |
| 457 | C |
| 458 | C |
| 459 | B |
| 460 | C |
| 461 | B |
| 462 | B |
| 463 | B |
| 464 | B |
| 465 | C |
| 466 | B |
| 467 | B |
| 468 | A |
| 469 | B |
| 470 | B |
| 471 | A |
| 472 | A |
| 473 | B |
| 474 | B |
| 475 | D |
| 476 | A |
| 477 | A |
| 478 | C |
| 479 | B |
| 480 | D |

A < 50 nM
50 nM ≤ B < 500 nM
500 nM ≤ C < 5 μM
5 μM ≤ D

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A compound of Formula (II), or a pharmaceutically acceptable salt, solvate, tautomer, or N-oxide thereof:

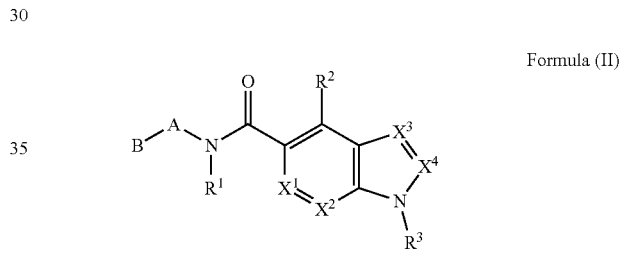

Formula (II)

wherein:
  $X^1$ is $CR^4$;
  $X^2$ is N;
  $X^3$ and $X^4$ are independently selected from the group consisting of N and $CR^4$;
  A is selected from the group consisting of bond and —$CH_2CH_2$—;
  B is selected from the group consisting of heterocycloalkyl, phenyl, and 5- or 6-membered heteroaryl;
    wherein the heterocycloalkyl, phenyl, and heteroaryl are optionally substituted with one or more groups independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —(C=O)$OR^c$, —CN, —(C=O)$R^d$, alkynyl, and —O($C_1$-$C_4$ alkylene)$NR^aR^b$;
  $R^1$ is selected from the group consisting of hydrogen, alkyl, and cycloalkyl;
    wherein the alkyl and cycloalkyl are optionally substituted with one or more groups independently selected from the group consisting of halogen, alkoxy, and —$NR^aR^b$;
  $R^2$ is selected from the group consisting of halogen, hydroxyl, alkoxy, alkyl, and cycloalkyl;
    wherein the alkyl and cycloalkyl are optionally substituted with one or more halogen;

R³ is alkyl substituted with one or more groups independently selected from the group consisting of halogen, hydroxyl, haloalkyl, alkoxy, haloalkoxy, hydroxyalkyl, —NR$^a$R$^b$, —Oaralkyl, —C(=O)Otbutyl, —S(=O)$_{0-2}$R$^e$, acetyl, aryl, heteroaryl, aralkyl, cycloalkyl, and heterocycloalkyl;
  wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}$R$^e$, acetyl, azidyl, —CH$_2$azidyl, aryl, and aralkyl;
    wherein the aryl and aralkyl are optionally substituted with one or more groups independently selected from the group consisting of alkyl and alkoxy; or
R³ is selected from the group consisting of cycloalkyl, heterocycloalkyl, and 5-membered heteroaryl;
  wherein the cycloalkyl, heterocycloalkyl, and heteroaryl are optionally substituted with one or more groups independently selected from the group consisting of halogen, hydroxyl, alkyl, haloalkyl, alkoxy, haloalkoxy, hydroxyalkyl, —NR$^a$R$^b$, -Oaralkyl, —C(=O)Otbutyl, —S(=O)$_{0-2}$R$^e$, acetyl, aryl, heteroaryl, aralkyl, cycloalkyl, and heterocycloalkyl;
    wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}$R$^e$, acetyl, azidyl, —CH$_2$azidyl, aryl, and aralkyl;
      wherein the aryl and aralkyl are optionally substituted with one or more groups independently selected from the group consisting of alkyl and alkoxy;
each R⁴ is independently selected from the group consisting of hydrogen, halogen, alkyl, and cycloalkyl;
  wherein the alkyl and cycloalkyl are optionally substituted with one or more groups independently selected from the group consisting of halogen and hydroxy;
each R$^a$ and R$^b$ are independently selected from the group consisting of hydrogen and alkyl;
  or R$^a$ and R$^b$ taken together with the nitrogen to which they are attached form a heterocycloalkyl optionally substituted with alkyl;
R$^c$ is selected from the group consisting of hydrogen and alkyl;
R$^d$ is selected from the group consisting of aryl or heteroaryl; wherein the aryl and heteroaryl are optionally substituted with one or more groups independently selected from halogen, alkyl, and alkoxy; and
R$^e$ is selected from the group consisting of alkyl and —NR$^a$R$^b$.

2. The compound of claim 1, or a pharmaceutically acceptable salt, solvate, tautomer, or N-oxide thereof, wherein:
  (A) X¹ is CH;
    X³ is CR⁴; and
    X² and X⁴ are N; or
  (B) X¹ and X⁴ are CH; and
    X² and X³ are N; or
  (C) X¹ and X⁴ are CH;
    X² is N; and
    X³ is CR⁴.

3. The compound of claim 1, or a pharmaceutically acceptable salt, solvate, tautomer, or N-oxide thereof, wherein the compound of Formula (II) is of Formula (IIa):

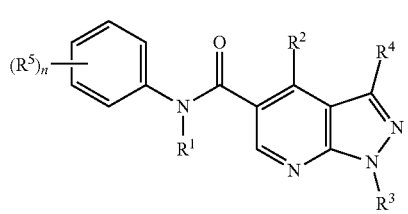

Formula (IIa)

wherein:
  R¹ is selected from the group consisting of hydrogen, alkyl, and cycloalkyl;
    wherein the alkyl and cycloalkyl are optionally substituted with one or more groups independently selected from the group consisting of halogen, alkoxy, and —NR$^a$R$^b$;
  R² is selected from the group consisting of halogen, hydroxyl, alkoxy, alkyl, and cycloalkyl;
    wherein the alkyl and cycloalkyl are optionally substituted with one or more halogen;
  R³ is alkyl substituted with one or more groups independently selected from the group consisting of halogen, hydroxyl, haloalkyl, alkoxy, haloalkoxy, hydroxyalkyl, —NR$^a$R$^b$,-Oaralkyl, —C(=O)Otbutyl, —S(=O)$_{0-2}$R$^e$, acetyl, aryl, heteroaryl, aralkyl, cycloalkyl, and heterocycloalkyl;
    wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}$R$^e$, acetyl, azidyl, —CH$_2$azidyl, aryl, and aralkyl;
      wherein the aryl and aralkyl are optionally substituted with one or more groups independently selected from the group consisting of alkyl and alkoxy; or
  R³ is selected from the group consisting of cycloalkyl, heterocycloalkyl, and 5-membered heteroaryl;
    wherein the cycloalkyl, heterocycloalkyl, and heteroaryl are optionally substituted with one or more groups independently selected from the group consisting of halogen, hydroxyl, alkyl, haloalkyl, alkoxy, haloalkoxy, hydroxyalkyl, —NR$^a$R$^b$-Oaralkyl, —C(=O)Otbutyl, —S(=O)$_{0-2}$R$^e$, acetyl, aryl, heteroaryl, aralkyl, cycloalkyl, and heterocycloalkyl;
      wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}$R$^e$, acetyl, azidyl, —CH$_2$azidyl, aryl, and aralkyl;
        wherein the aryl and aralkyl are optionally substituted with one or more groups independently selected from the group consisting of alkyl and alkoxy;
  R⁴ is selected from the group consisting of hydrogen, halogen, alkyl, and cycloalkyl;

wherein the alkyl and cycloalkyl are optionally substituted with one or more groups independently selected from the group consisting of halogen and hydroxy;

each $R^5$ is independently selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —(C=O)$OR^c$, —CN, —(C=O)$R^d$, alkynyl, and —O($C_1$-$C_4$ alkylene)$NR^aR^b$;

each $R^a$ and $R^b$ are independently selected from the group consisting of hydrogen and alkyl;

or $R^a$ and $R^b$ taken together with the nitrogen to which they are attached form a heterocycloalkyl optionally substituted with alkyl;

$R^c$ is selected from the group consisting of hydrogen and alkyl;

$R^d$ is selected from the group consisting of aryl or heteroaryl; wherein the aryl and heteroaryl are optionally substituted with one or more groups independently selected from halogen, alkyl, and alkoxy;

$R^e$ is selected from the group consisting of alkyl and —$NR^aR^b$; and n is 1, 2, 3, 4, or 5.

4. The compound of claim 3, or a pharmaceutically acceptable salt, solvate, tautomer, or N-oxide thereof, wherein:

$R^3$ is alkyl substituted with one or more groups independently selected from the group consisting of halogen, hydroxyl, haloalkyl, alkoxy, haloalkoxy, hydroxyalkyl, —$NR^aR^b$, -Oaralkyl, acetyl, aryl, heteroaryl, cycloalkyl, and heterocycloalkyl;

wherein the aryl, heteroaryl, cycloalkyl, and heterocycloalkyl are optionally substituted with one or more groups independently selected from the group consisting of halogen, alkyl, haloalkyl, alkoxy, haloalkoxy, heteroalkyl, —S(=O)$_{0-2}R^e$, acetyl, and aralkyl;

wherein the aralkyl is optionally substituted with one or more groups independently selected from the group consisting of alkyl and alkoxy.

5. The compound of claim 3, or a pharmaceutically acceptable salt, solvate, tautomer, or N-oxide thereof, wherein:

$R^3$ is heterocycloalkyl optionally substituted with one or more groups independently selected from the group consisting of alkyl, haloalkyl, alkoxy, haloalkoxy, hydroxyalkyl, —C(=O)Otbutyl, —S(=O)$_{0-2}R^e$, acetyl, aryl, and aralkyl;

wherein the aralkyl is optionally substituted with one or more groups independently selected from the group consisting of alkylnyl, alkoxy, azidyl, and —$CH_2$azidyl.

6. The compound of claim 3, or a pharmaceutically acceptable salt, solvate, tautomer, or N-oxide thereof, wherein:

n is 1.

7. The compound of claim 3, or a pharmaceutically acceptable salt, solvate, tautomer, or N-oxide thereof, wherein the compound of Formula (IIa) is of Formula (IIa-2):

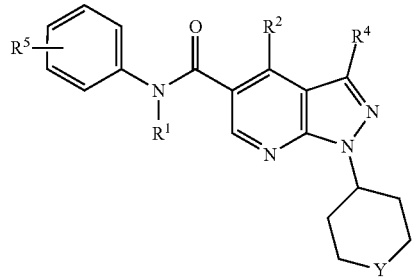

Formula (IIa-2)

wherein:

Y is is selected from the group consisting of —O—, —S—, —S(=O)—, —S(=O)$_2$—, and —$CH_2$—;

$R^1$ is selected from the group consisting of hydrogen, alkyl, and cycloalkyl;

wherein the alkyl and cycloalkyl are optionally substituted with one or more groups independently selected from the group consisting of halogen, alkoxy, and —$NR^aR^b$;

$R^2$ is selected from the group consisting of halogen, hydroxyl, alkoxy, alkyl, and cycloalkyl;

wherein the alkyl and cycloalkyl are optionally substituted with one or more halogen;

$R^4$ is selected from the group consisting of hydrogen, halogen, alkyl, and cycloalkyl;

wherein the alkyl and cycloalkyl are optionally substituted with one or more groups independently selected from the group consisting of halogen and hydroxyl;

$R^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —(C=O)$OR^c$, —CN, —(C=O)$R^d$, alkynyl, and —O($C_1$-$C_4$ alkylene)$NR^aR^b$;

$R^7$ is selected from the group consisting of hydrogen, alkyl, haloalkyl, hydroxyalkyl, —C(=O)Otbutyl, —S(=O)$_{0-2}R^e$, acetyl, aryl, heteroaryl, aralkyl, cycloalkyl, and heterocycloalkyl;

wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —S(=O)$_{0-2}R^e$, acetyl, azidyl, —$CH_2$azidyl, aryl, and aralkyl;

wherein the aryl and aralkyl are optionally substituted with one or more groups independently selected from the group consisting of alkyl and alkoxy;

each $R^a$ and $R^b$ are independently selected from the group consisting of hydrogen and alkyl;

or $R^a$ and $R^b$ taken together with the nitrogen to which they are attached form a heterocycloalkyl optionally substituted with alkyl;

$R^c$ is selected from the group consisting of hydrogen and alkyl;

$R^d$ is selected from the group consisting of aryl or heteroaryl; wherein the aryl and heteroaryl are optionally substituted with one or more groups independently selected from halogen, alkyl, and alkoxy; and $R^e$ is selected from the group consisting of alkyl and —$NR^aR^b$.

8. The compound of claim 7, or a pharmaceutically acceptable salt, solvate, tautomer, or N-oxide thereof, wherein the compound of Formula (IIa-2) is of Formula (IIa-2a):

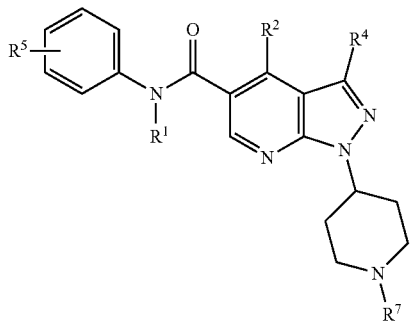

Formula (IIa-2a)

wherein:
- $R^1$ is selected from the group consisting of hydrogen, alkyl, and cycloalkyl;
  - wherein the alkyl and cycloalkyl are optionally substituted with one or more groups independently selected from the group consisting of halogen, alkoxy, and —$NR^aR^b$;
- $R^2$ is selected from the group consisting of halogen, hydroxyl, alkoxy, alkyl, and cycloalkyl;
  - wherein the alkyl and cycloalkyl are optionally substituted with one or more halogen;
- $R^4$ is selected from the group consisting of hydrogen, halogen, alkyl, and cycloalkyl;
  - wherein the alkyl and cycloalkyl are optionally substituted with one or more groups independently selected from the group consisting of halogen and hydroxyl;
- $R^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$ tetrazoyl, —(C=O)$OR^c$, —CN, —(C=O)$R^d$, alkynyl, and —$O(C_1\text{-}C_4$ alkylene)$NR^aR^b$;
- $R^7$ is selected from the group consisting of hydrogen, alkyl, haloalkyl, hydroxyalkyl, —C(=O)Otbutyl, —$S(=O)_{0\text{-}2}R^e$, acetyl, aryl, heteroaryl, aralkyl, cycloalkyl, and heterocycloalkyl;
  - wherein the aryl, heteroaryl, aralkyl, cycloalkyl, heterocycloalkyl are optionally substituted with one or more groups independently selected from the group consisting of halogen, alkyl, alkylnyl, haloalkyl, alkoxy, haloalkoxy, heteroalkyl, —$S(=O)_{0\text{-}2}R^e$, acetyl, azidyl, —$CH_2$azidyl, aryl, and aralkyl;
    - wherein the aryl and aralkyl are optionally substituted with one or more groups independently selected from the group consisting of alkyl and alkoxy;
- each $R^a$ and $R^b$ are independently selected from the group consisting of hydrogen and alkyl;
  - or $R^a$ and $R^b$ taken together with the nitrogen to which they are attached form a heterocycloalkyl optionally substituted with alkyl;
- $R^c$ is selected from the group consisting of hydrogen and alkyl;
- $R^d$ is selected from the group consisting of aryl or heteroaryl; wherein the aryl and heteroaryl are optionally substituted with one or more groups independently selected from halogen, alkyl, and alkoxy; and
- $R^e$ is selected from the group consisting of alkyl and —$NR^aR^b$.

9. The compound of claim 8, or a pharmaceutically acceptable salt, solvate, tautomer, or N-oxide thereof, wherein:
- $R^7$ is selected from the group consisting of hydrogen, alkyl, hydroxyalkyl, —C(=O)Otbutyl, —$S(=O)_{0\text{-}2}R^e$, acetyl, and aralkyl;
  - wherein the aralkyl is optionally substituted with one or more groups independently selected from the group consisting of alkylnyl, azidyl, and —$CH_2$azidyl.

10. The compound of claim 3, or a pharmaceutically acceptable salt, solvate, tautomer, or N-oxide thereof, wherein the compound of Formula (IIa) is of Formula (IIa-3):

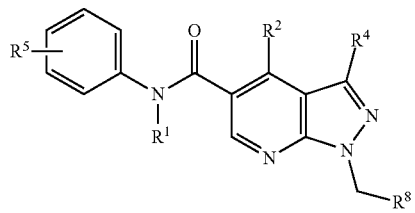

Formula (IIa-3)

wherein:
- $R^1$ is selected from the group consisting of hydrogen, alkyl, and cycloalkyl;
  - wherein the alkyl and cycloalkyl are optionally substituted with one or more groups independently selected from the group consisting of halogen, alkoxy, and —$NR^aR^b$;
- $R^2$ is selected from the group consisting of halogen, hydroxyl, alkoxy, alkyl, and cycloalkyl;
  - wherein the alkyl and cycloalkyl are optionally substituted with one or more halogen;
- $R^4$ is selected from the group consisting of hydrogen, halogen, alkyl, and cycloalkyl;
  - wherein the alkyl and cycloalkyl are optionally substituted with one or more groups independently selected from the group consisting of halogen and hydroxyl;
- $R^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, —$NR^aR^b$, tetrazoyl, —(C=O)$OR^c$, —CN, —(C=O)$R^d$, alkynyl, and —$O(C_1\text{-}C_4$ alkylene)$NR^aR^b$;
- $R^8$ is selected from the group consisting of aryl, heteroaryl, and heterocycloalkyl;
  - wherein the aryl, heteroaryl, and heterocycloalkyl are optionally substituted with one or more groups independently selected from the group consisting of halogen, alkyl, haloalkyl, alkoxy, haloalkoxy, heteroalkyl, —$S(=O)_{0\text{-}2}R^e$, acetyl, and aralkyl;
    - wherein the aralkyl is optionally substituted with one or more groups independently selected from the group consisting of alkyl and alkoxy;
- each $R^a$ and $R^b$ are independently selected from the group consisting of hydrogen and alkyl;

or $R^a$ and $R^b$ taken together with the nitrogen to which they are attached form a heterocycloalkyl optionally substituted with alkyl;

$R^c$ is selected from the group consisting of hydrogen and alkyl;

$R^d$ is selected from the group consisting of aryl or heteroaryl; wherein the aryl and heteroaryl are optionally substituted with one or more groups independently selected from halogen, alkyl, and alkoxy; and $R^e$ is selected from the group consisting of alkyl and $-NR^aR^b$.

11. The compound of claim 10, or a pharmaceutically acceptable salt, solvate, tautomer, or N-oxide thereof, wherein:

$R^8$ is heteroaryl optionally substituted with one or more groups independently selected from the group consisting of halogen, alkyl, haloalkyl, alkoxy, haloalkoxy, heteroalkyl, and aralkyl;

wherein the aralkyl is optionally substituted with one or more groups independently selected from the group consisting of alkyl and alkoxy.

12. The compound of claim 11, or a pharmaceutically acceptable salt, solvate, tautomer, or N-oxide thereof, wherein:

the heteroaryl is selected from the group consisting of pyridinyl, pyrimidinyl, pyrazinyl, furanyl, thiophenyl, pyrrolyl, thiazolyl, imidazolyl, triazolyl, tetrazolyl, pyrazolyl, and 4,5,6,7-tetrahydropyrazolo[1,5-a]pyridinyl.

13. The compound of claim 3, or a pharmaceutically acceptable salt, solvate, tautomer, or N-oxide thereof, wherein:

$R^5$ is selected from the group consisting of halogen, alkyl, haloalkyl, alkoxy, haloalkoxy, hydroxyalkyl, alkoxyalkyl, heteroalkyl, heterohaloalkoxy, cycloalkyl, heterocycloalkyl, $-NR^aR^b$, $-CN$, and alkynyl.

14. The compound of claim 1, or a pharmaceutically acceptable salt, solvate, tautomer, or N-oxide thereof, wherein:

$R^1$ is selected from the group consisting of hydrogen, methyl, ethyl, $-CH_2CH_2OCH_3$, and $-CH_2CH_2N(CH_3)_2$;

$R^2$ is selected from the group consisting of chloro, fluoro, hydroxyl, $-CF_3$, methoxy, ethoxy, and methyl; and $R^4$ is selected from the group consisting of hydrogen, methyl, ethyl, isopropyl, cyclopropyl, fluoro, chloro, and bromo.

15. The compound of claim 1, or a pharmaceutically acceptable salt, solvate, tautomer, or N-oxide thereof, wherein the compound of Formula (II) is selected from:

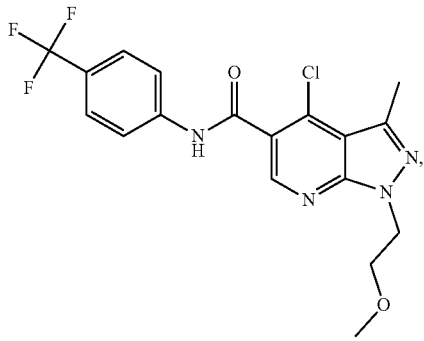

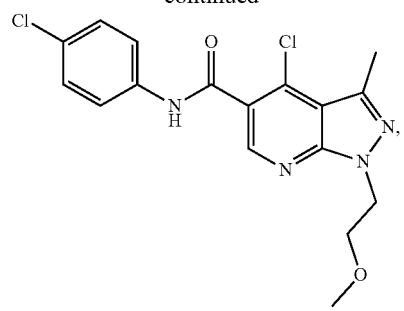

-continued

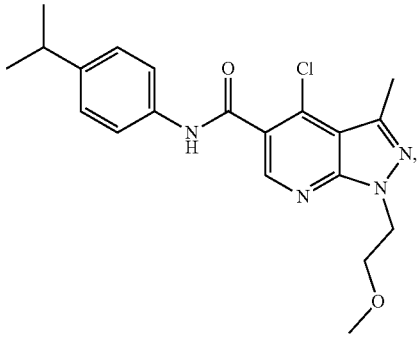

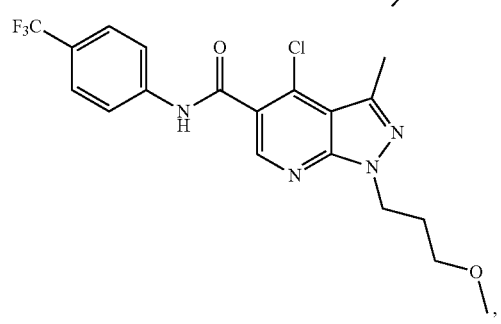

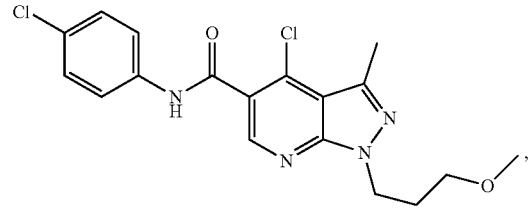

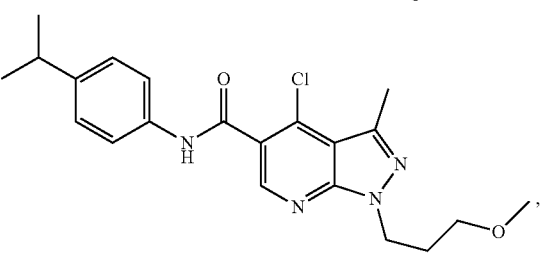

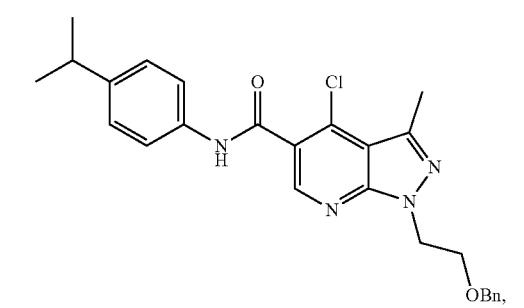

669
-continued
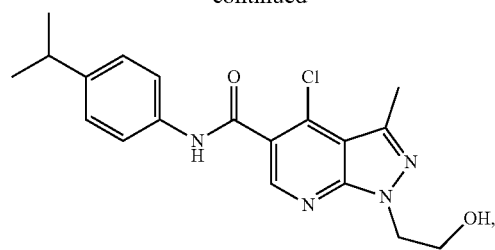
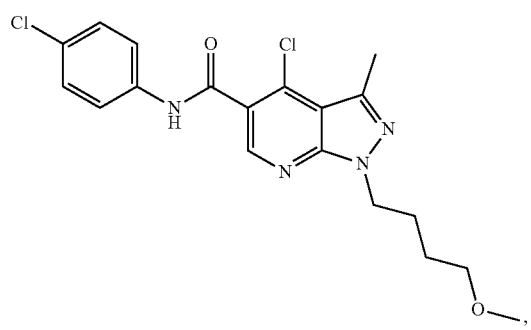
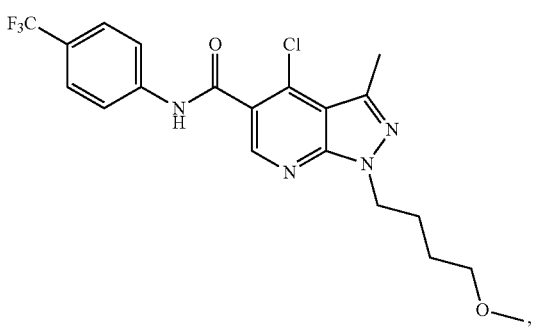
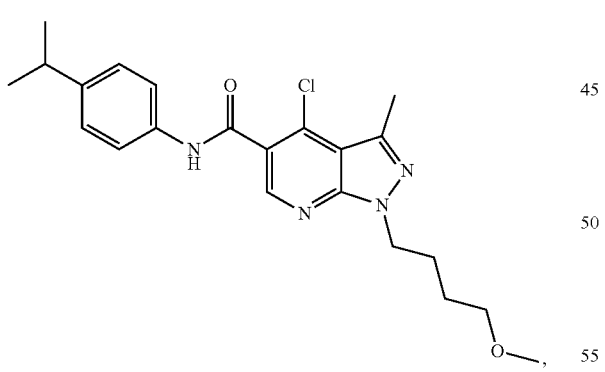
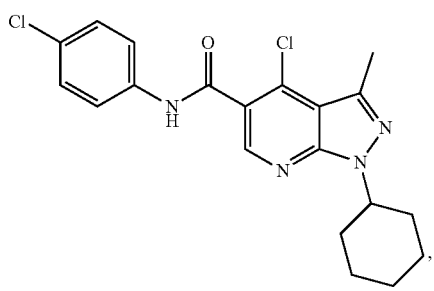
670
-continued
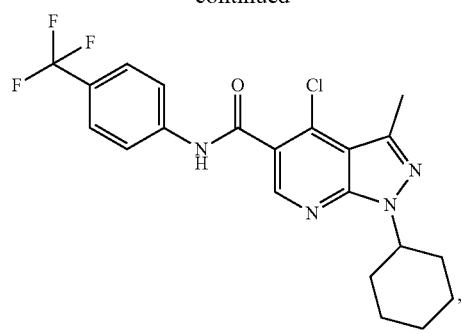
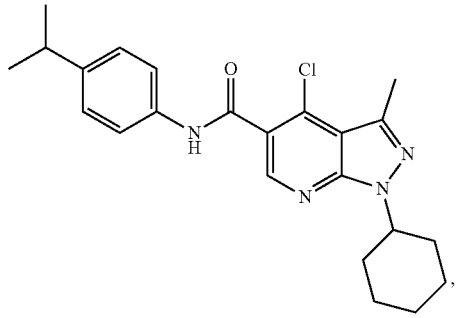
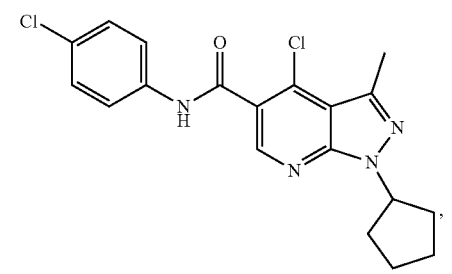
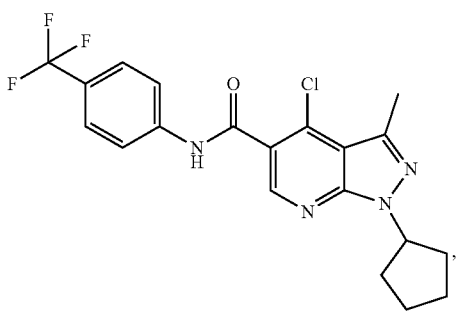
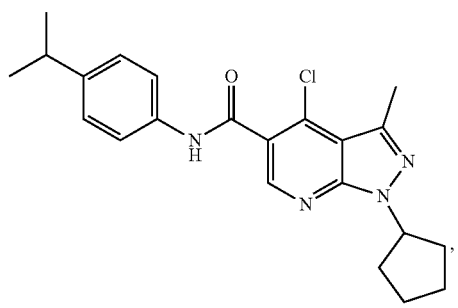

671
-continued
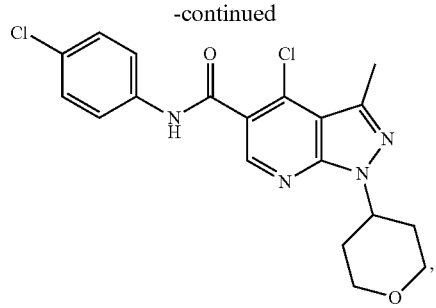
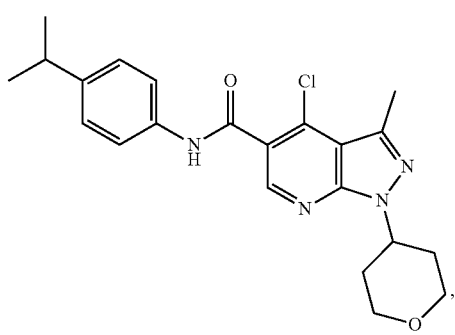
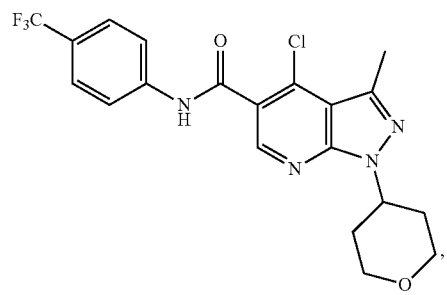
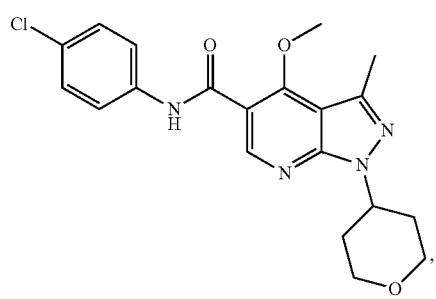
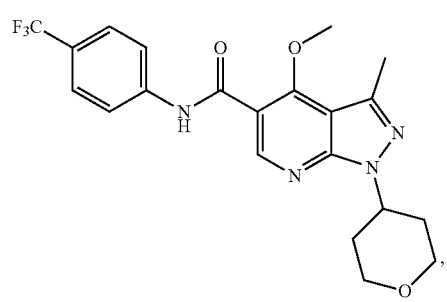
672
-continued
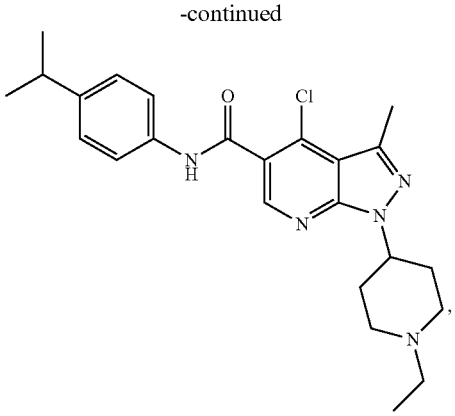
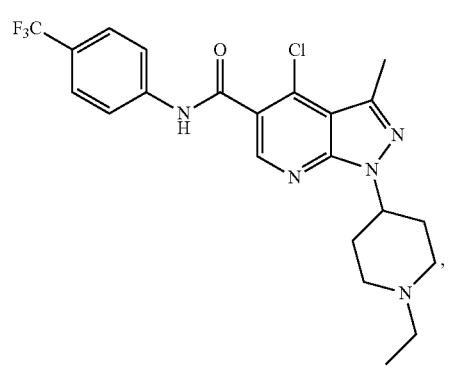
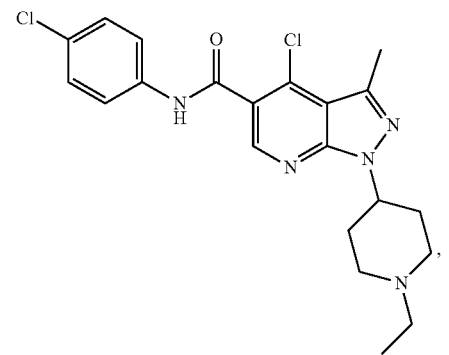
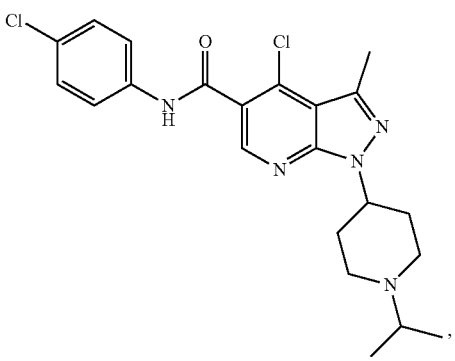

673
-continued
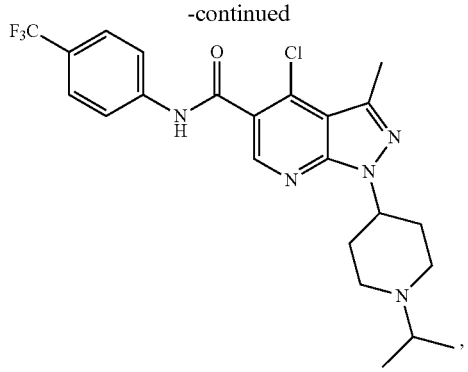
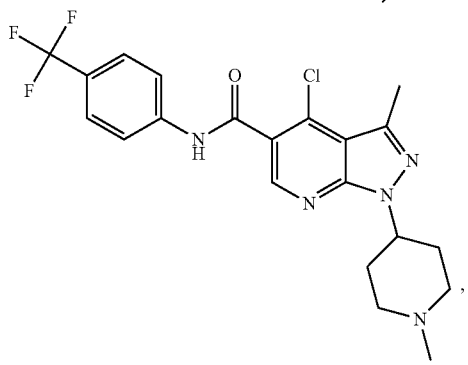
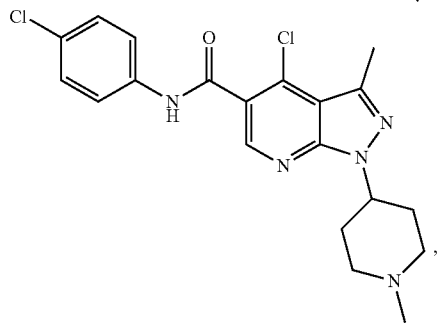
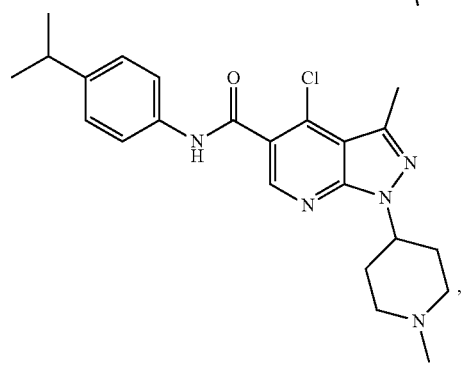
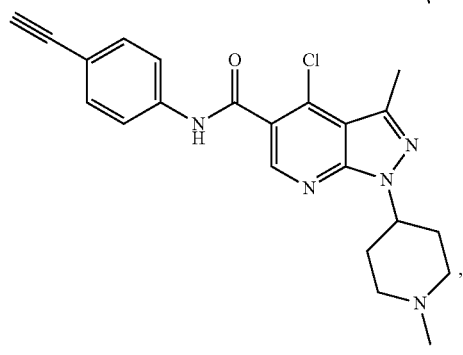
674
-continued
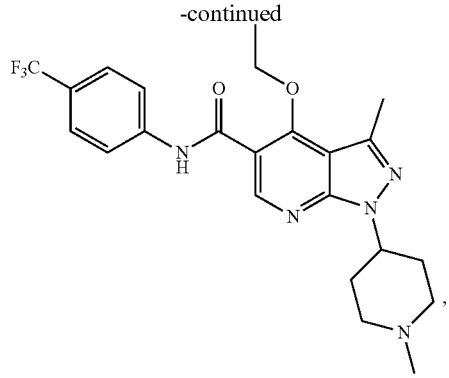
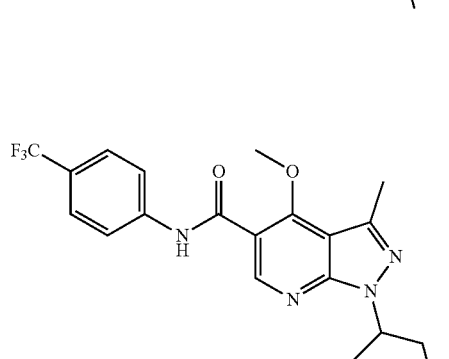
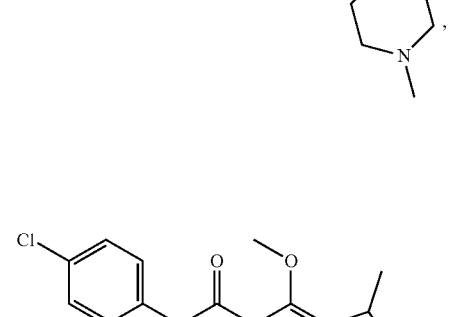
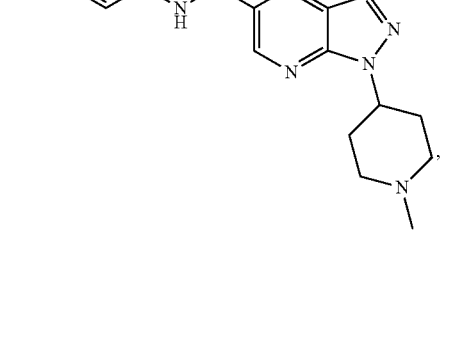
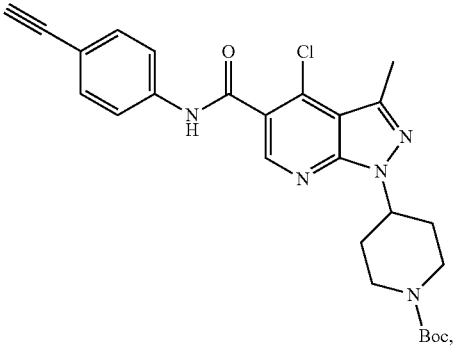

675
-continued
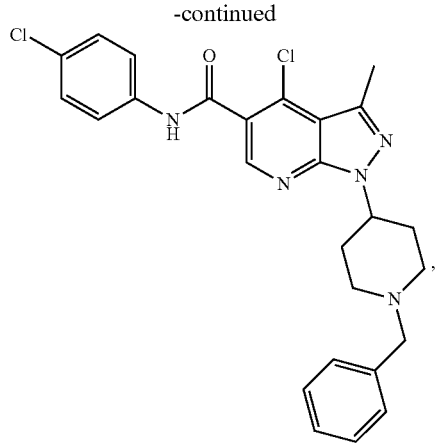
676
-continued
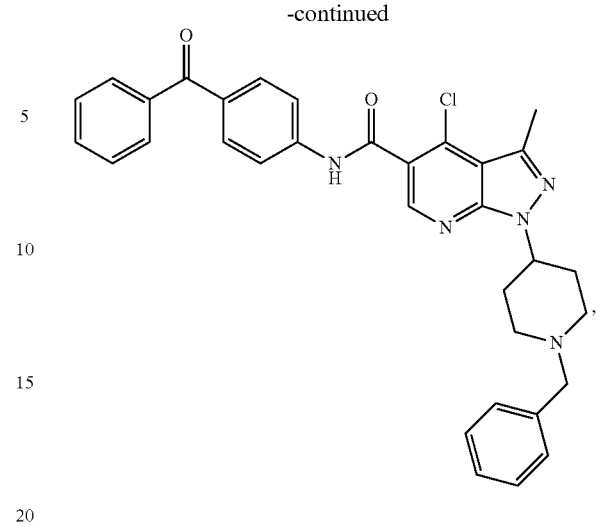
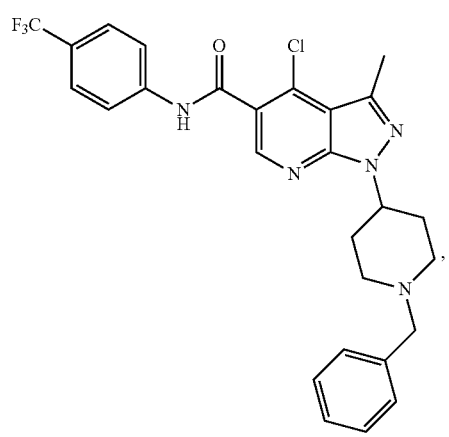
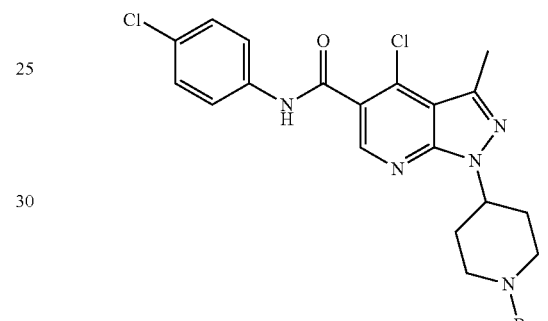
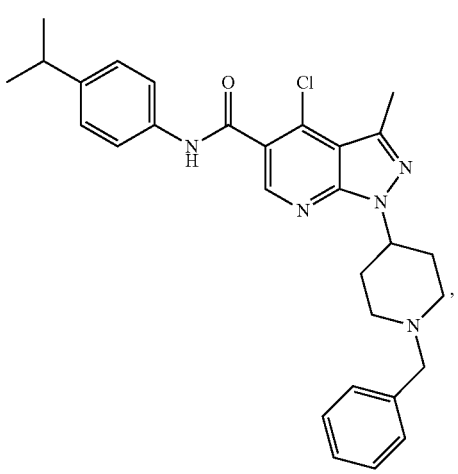

677
-continued
678
-continued
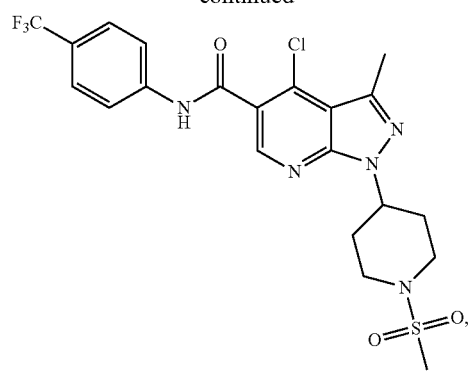
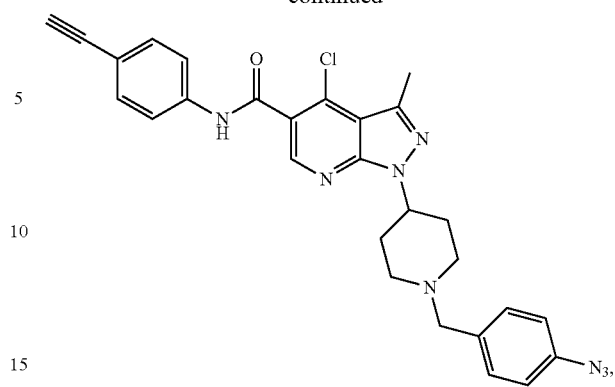
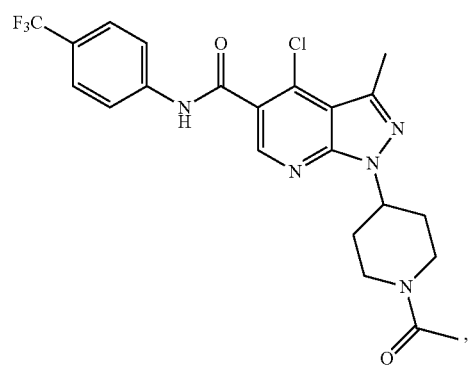
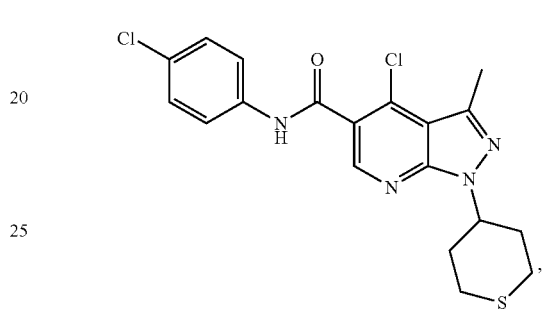
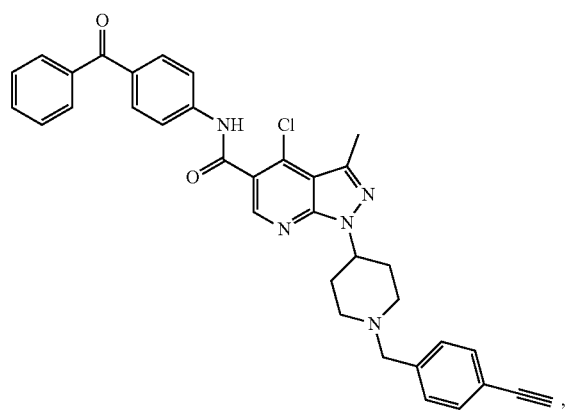
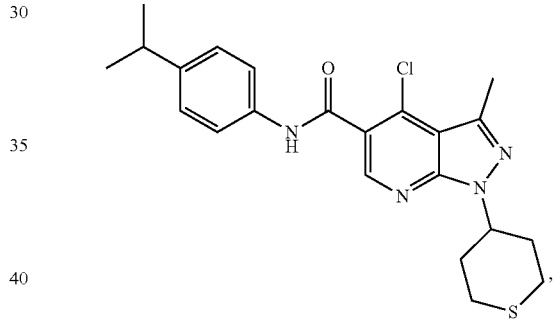
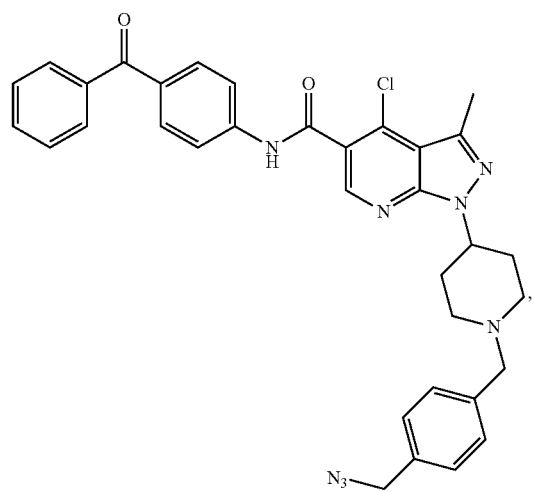
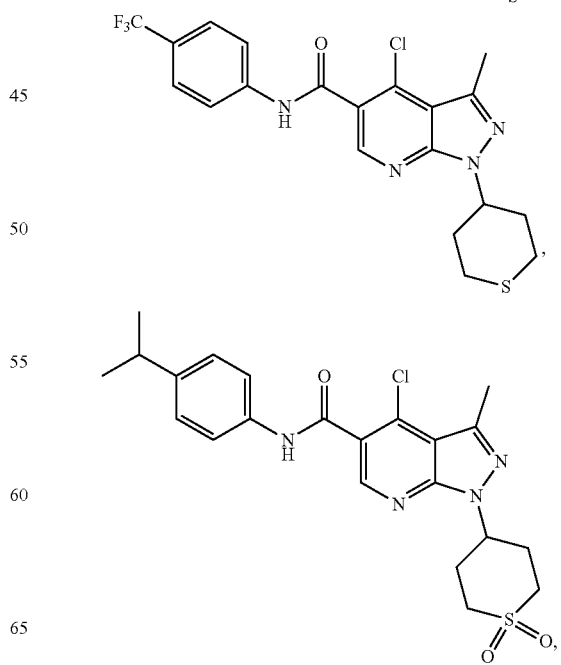

679
-continued
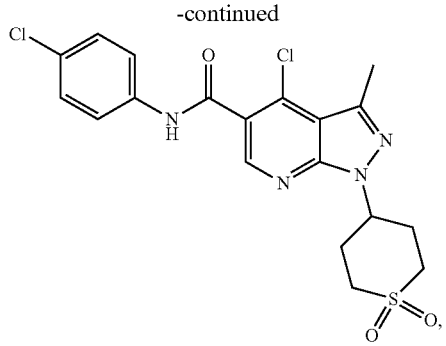
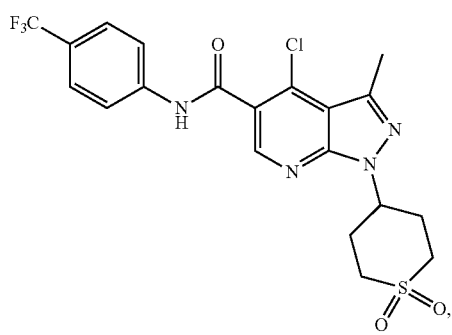
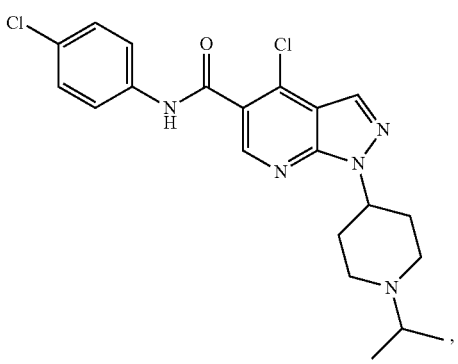
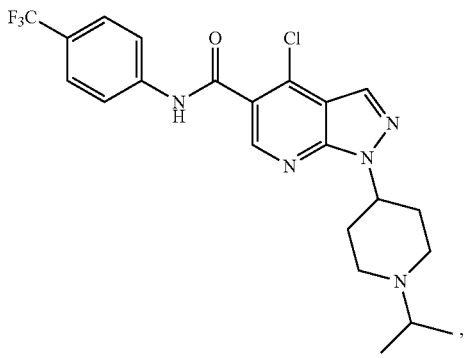
680
-continued
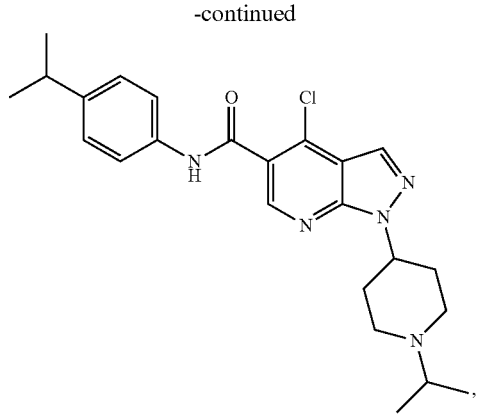
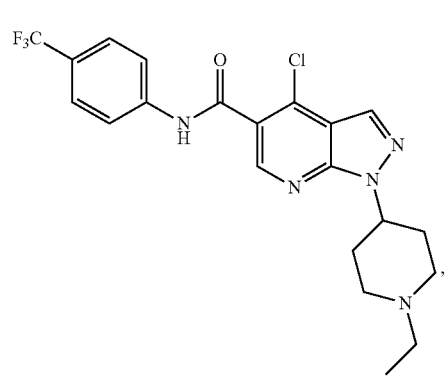
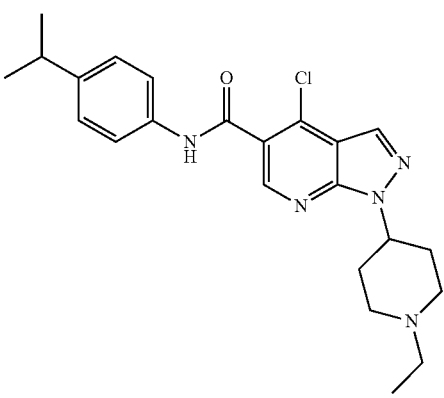
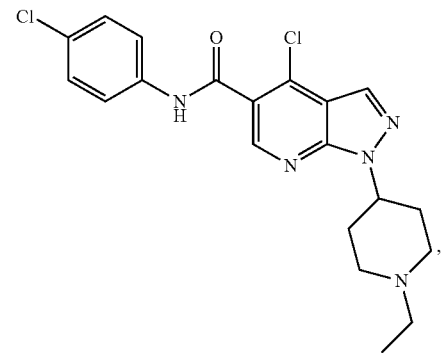

681
-continued
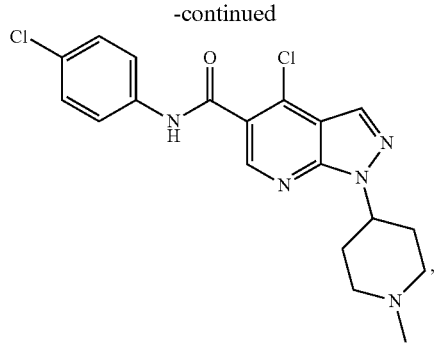
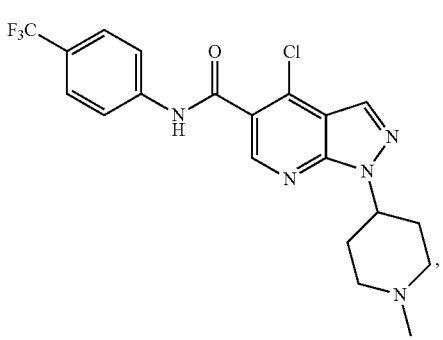
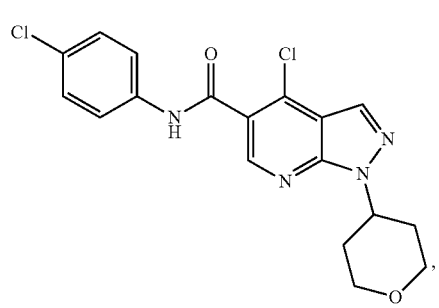
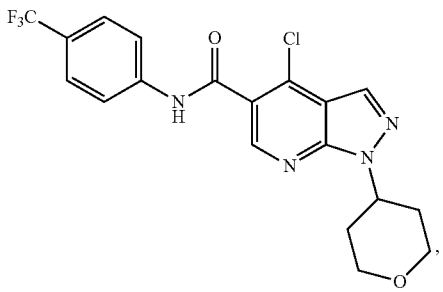
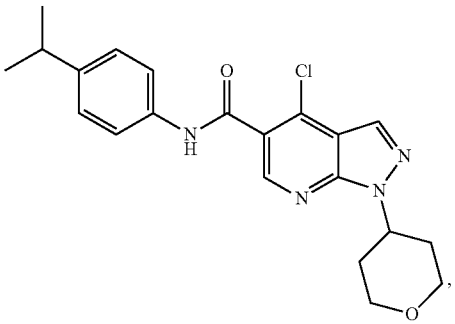
682
-continued
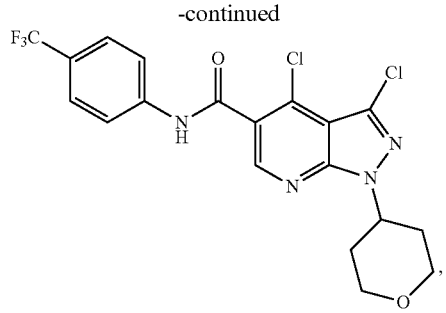
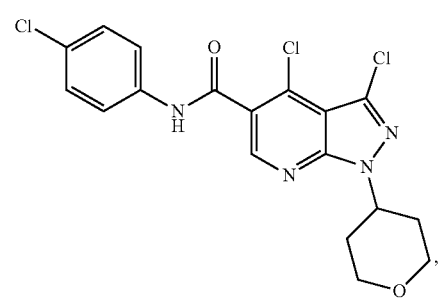
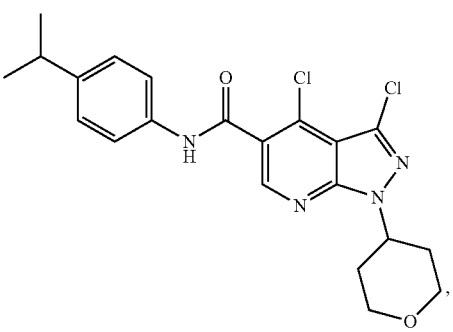
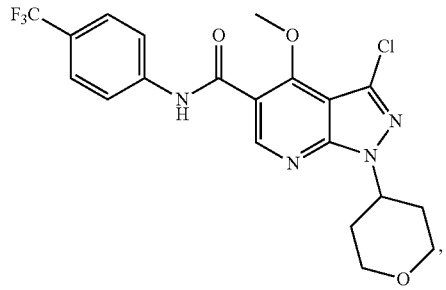
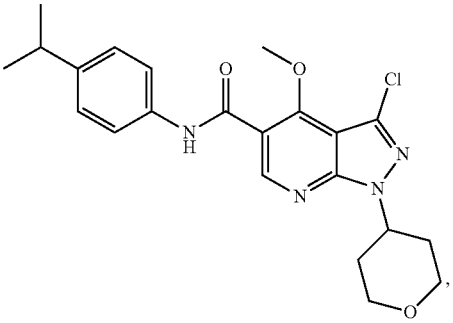

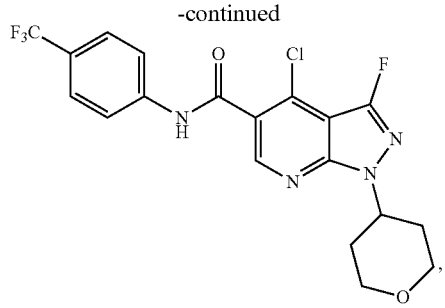
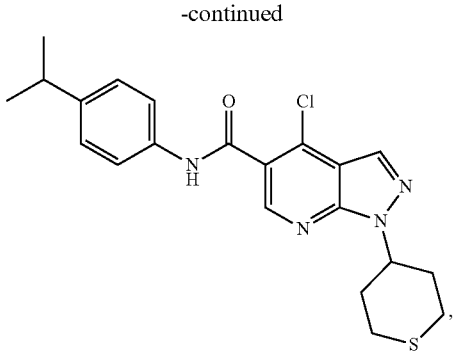
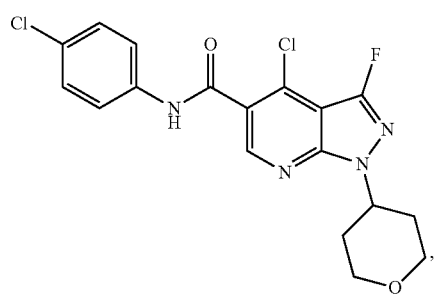
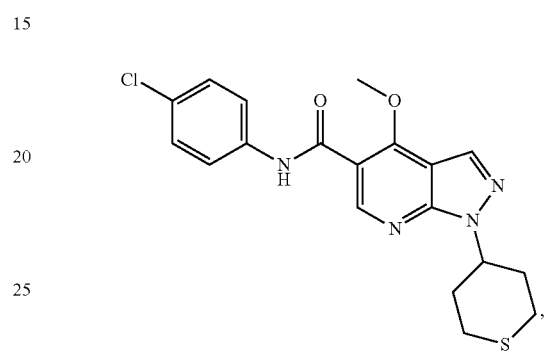
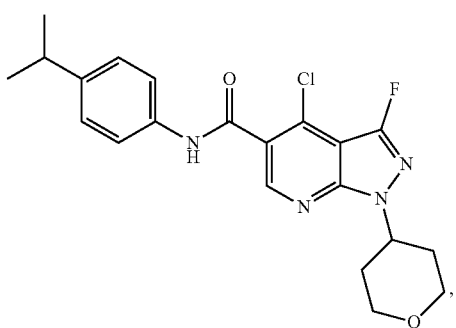
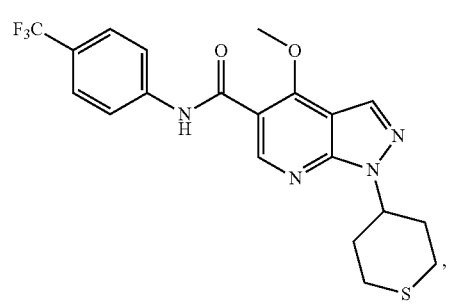
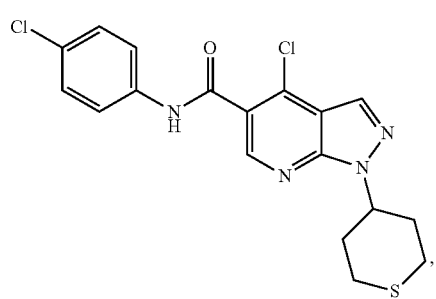
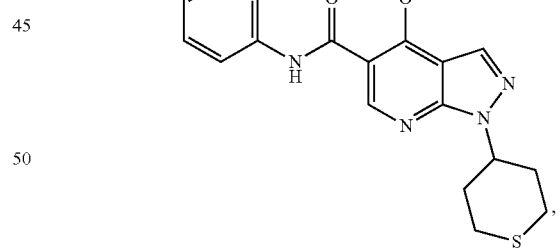
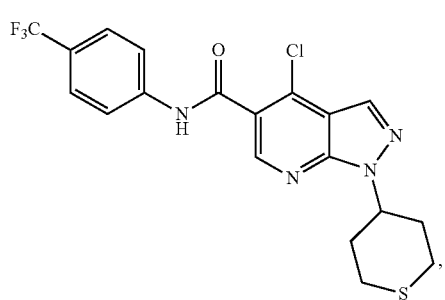
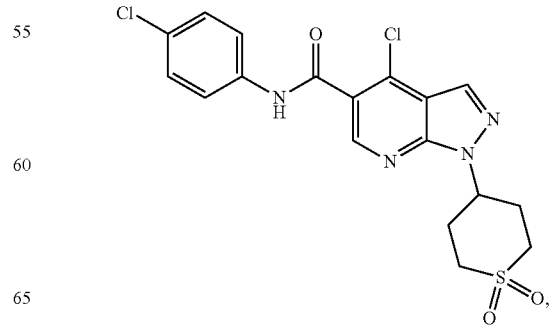

685
-continued
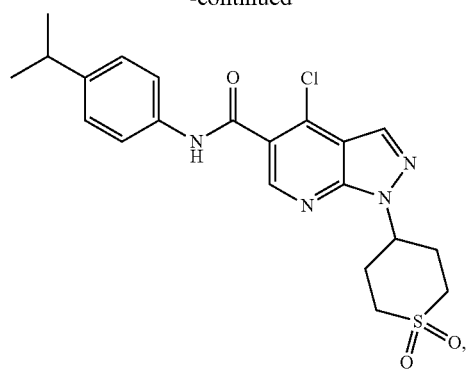
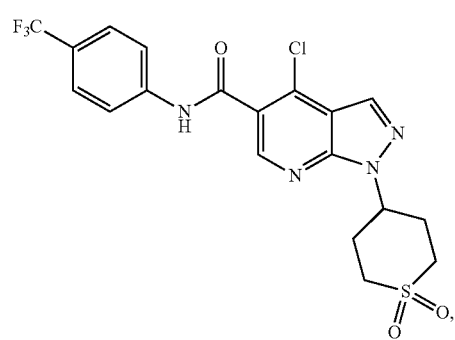
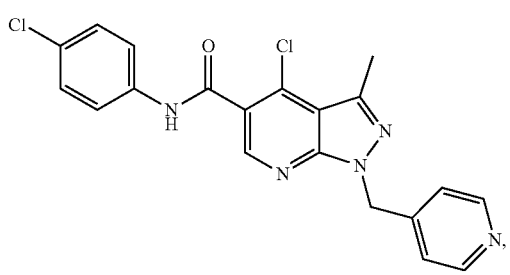
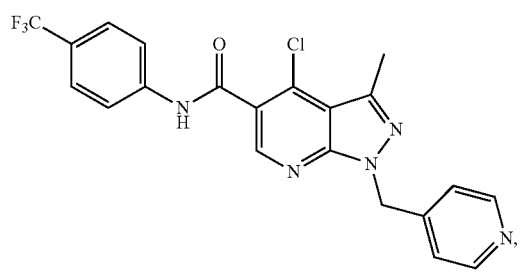
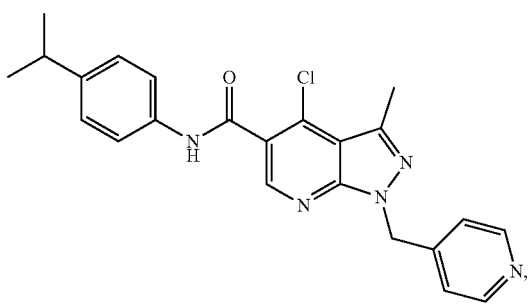
686
-continued
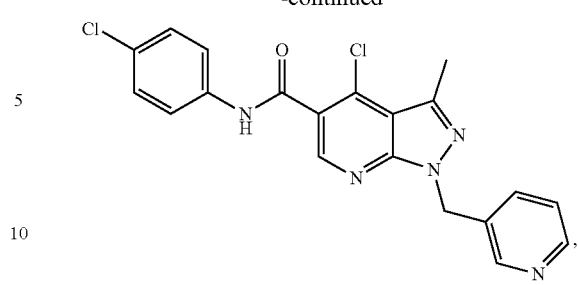
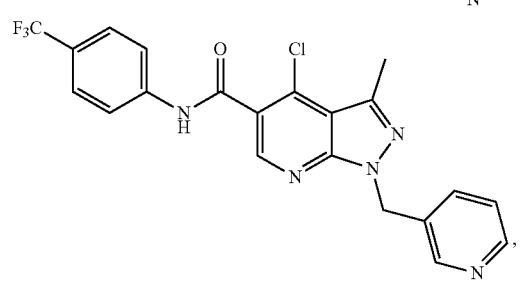
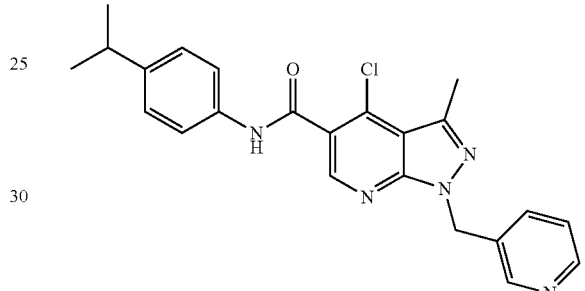
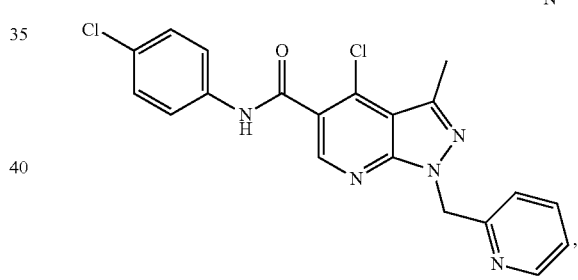
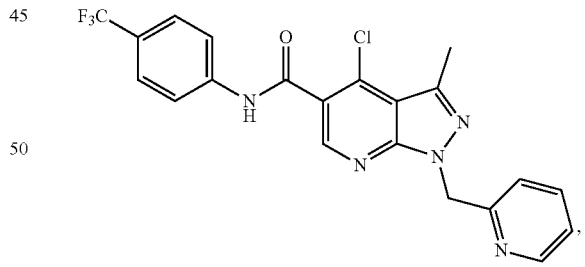
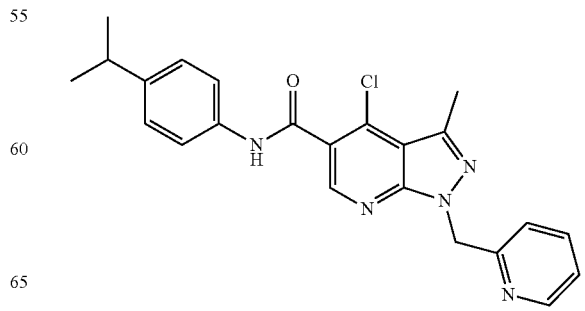

687
-continued
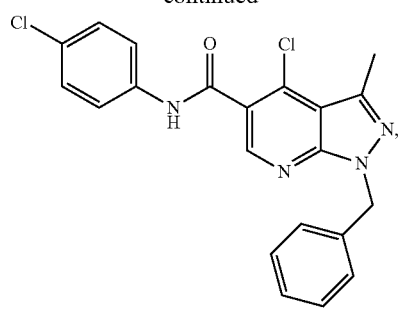
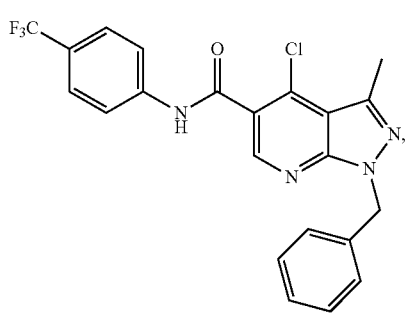
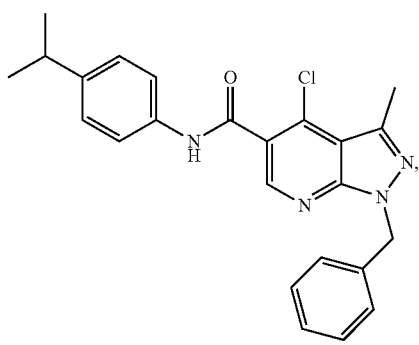
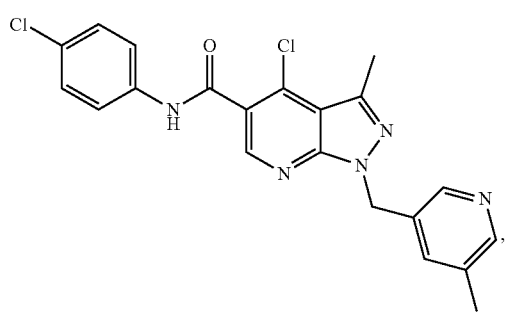
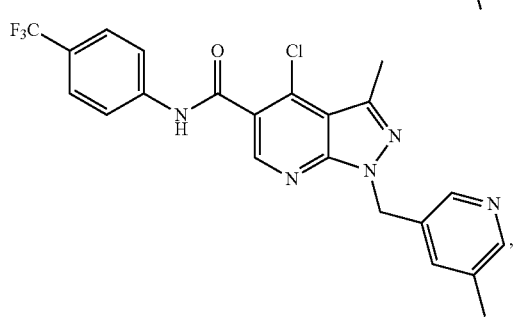
688
-continued
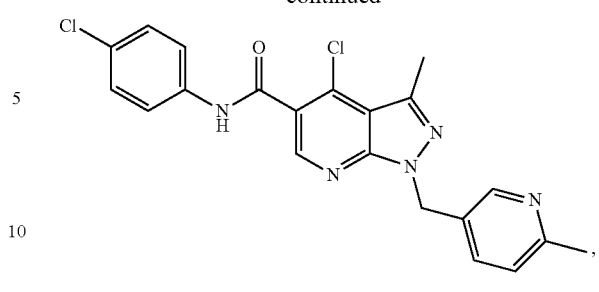
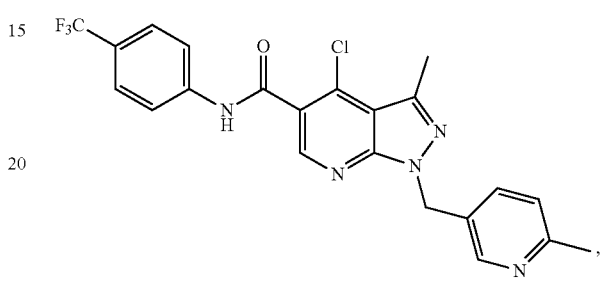
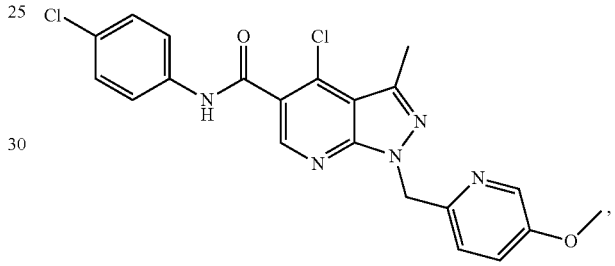
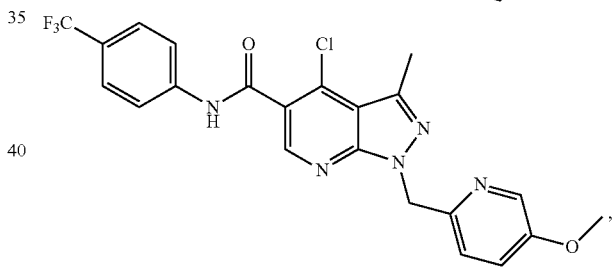
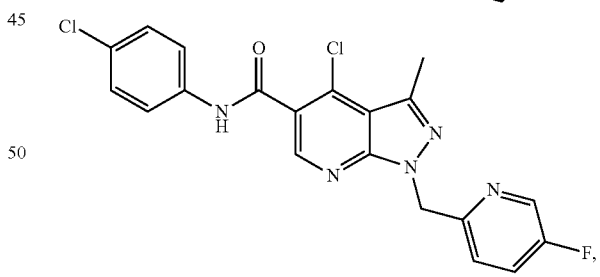
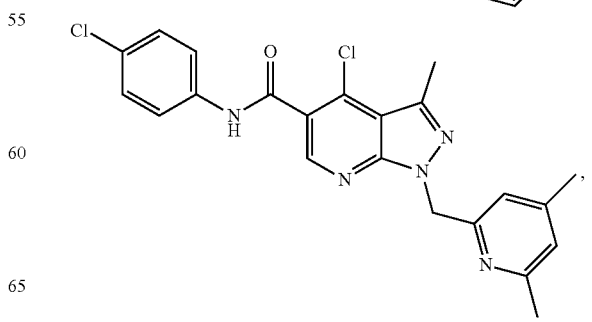

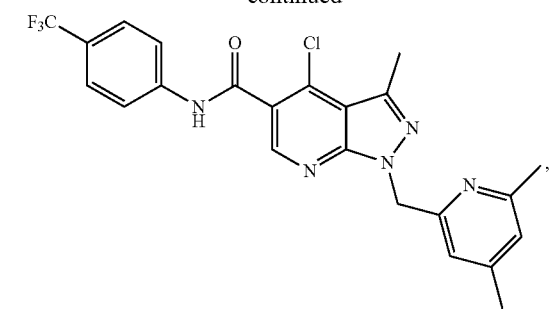
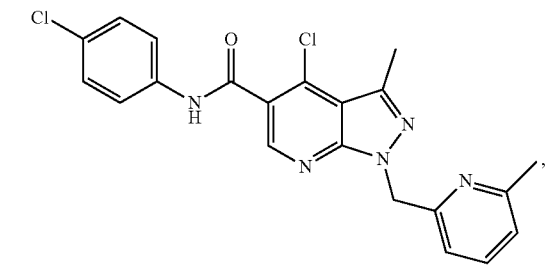
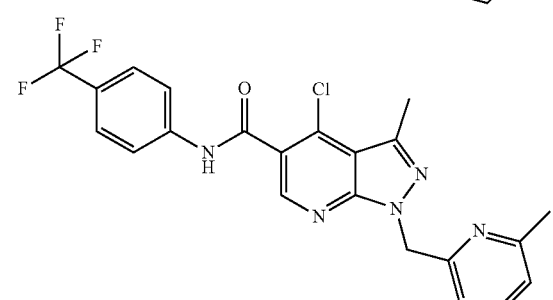
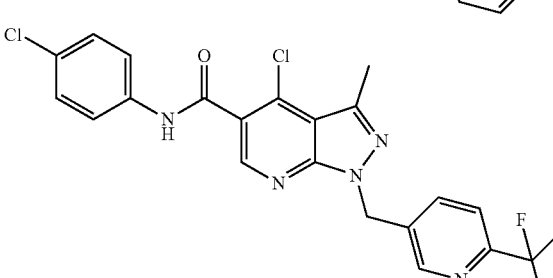
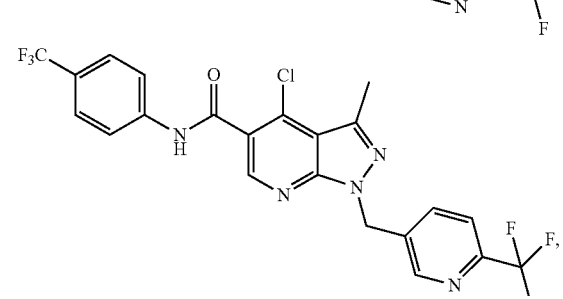
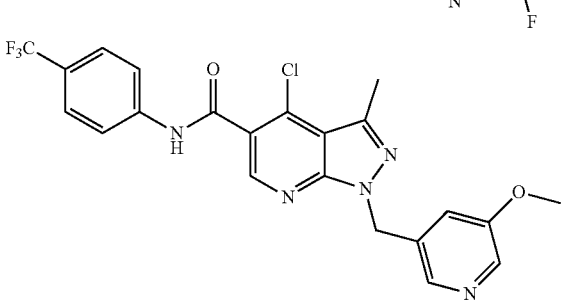
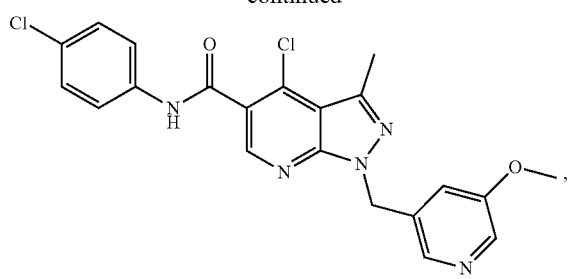
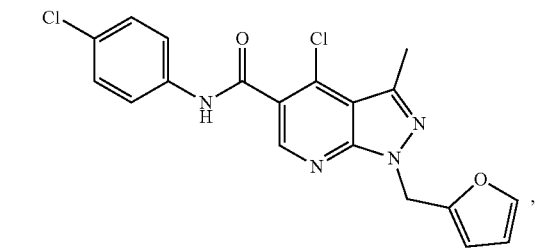
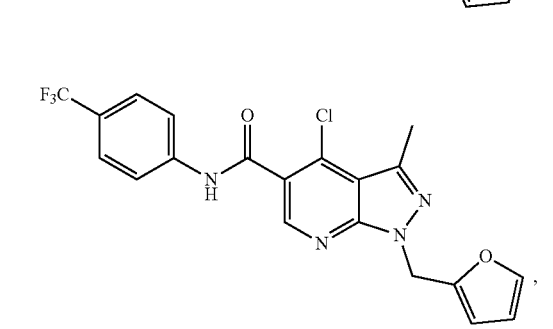
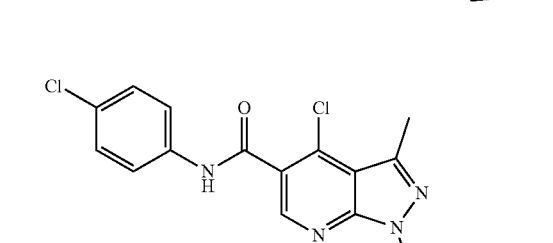
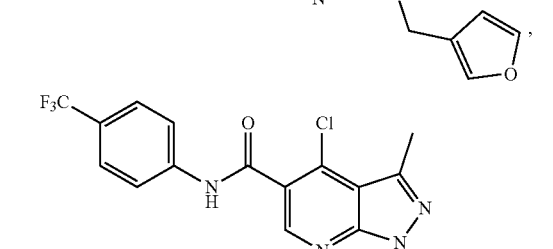
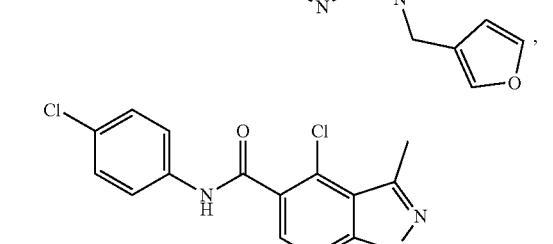
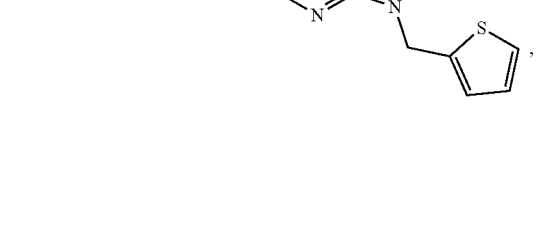

691
-continued
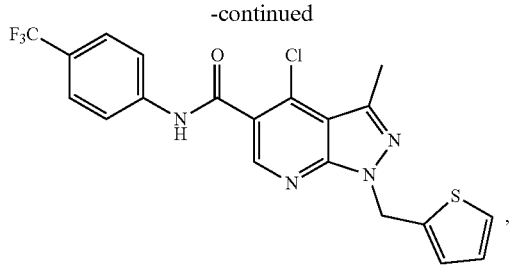
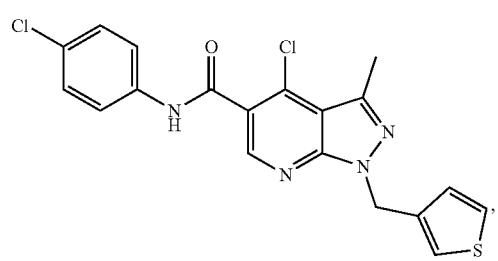
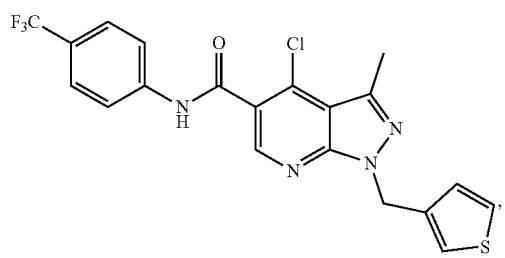
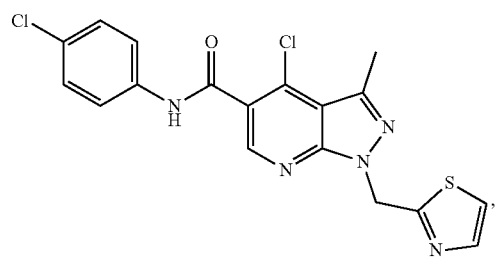
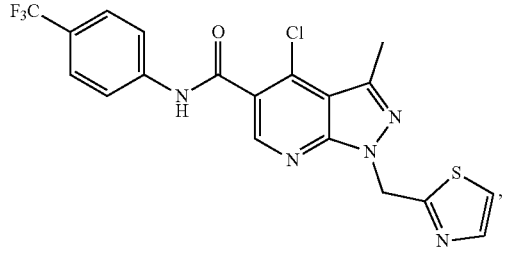
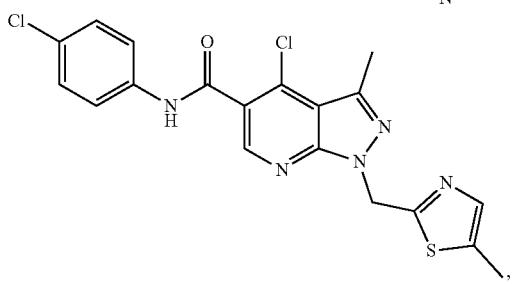
692
-continued
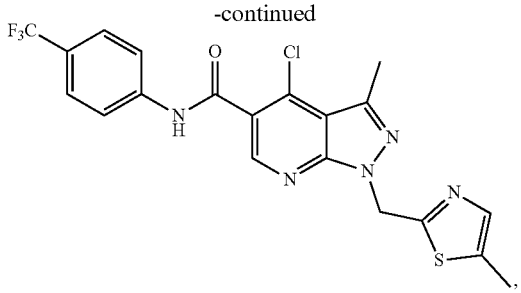
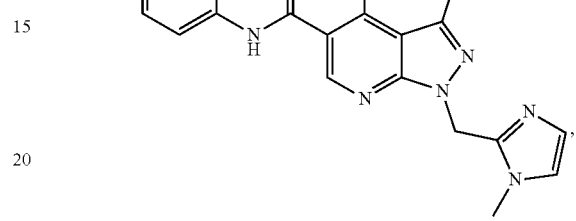
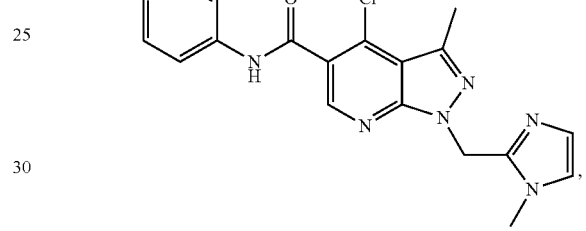
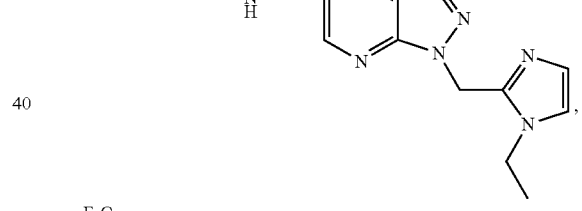
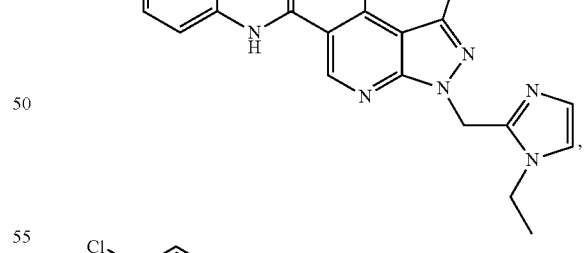

693
-continued
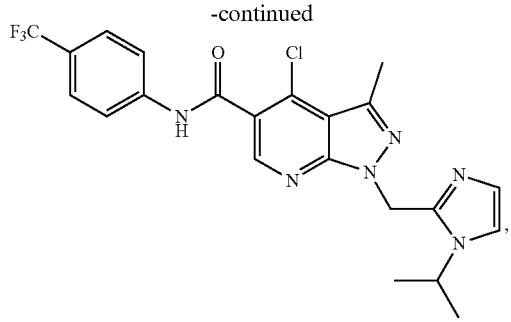
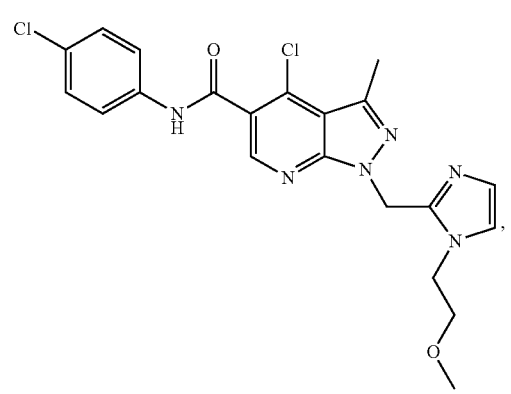
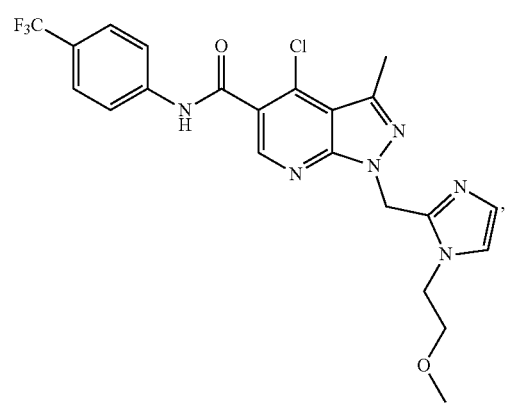
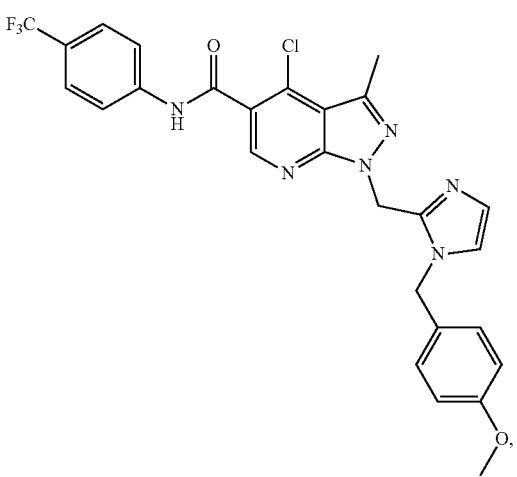
694
-continued
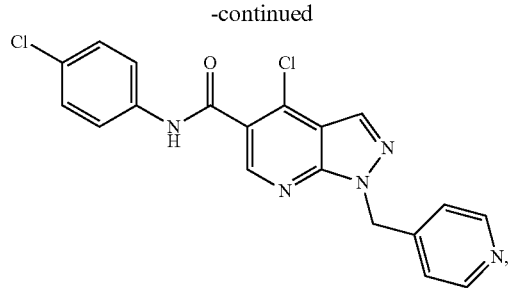
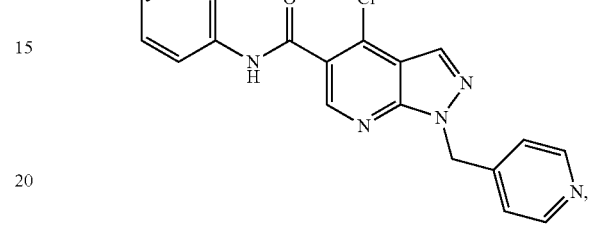
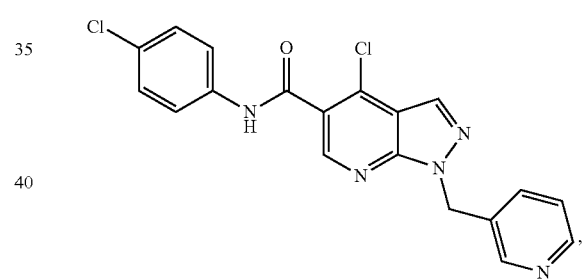
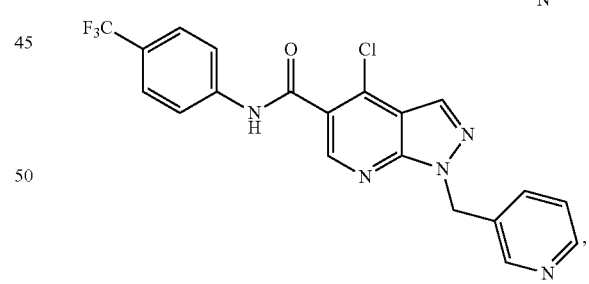
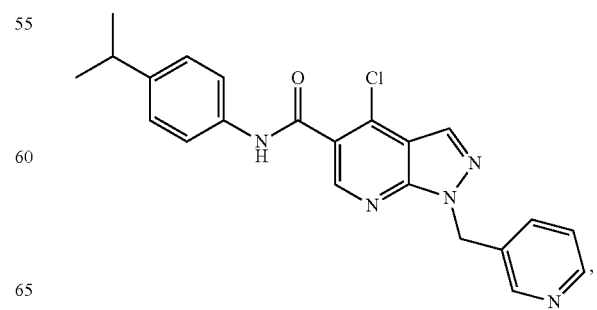

695
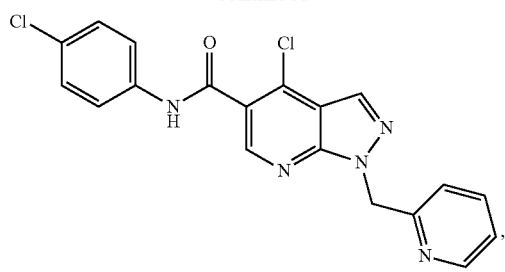
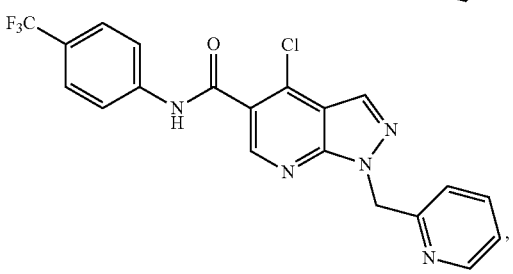
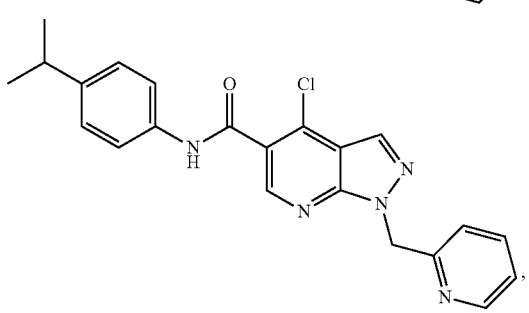
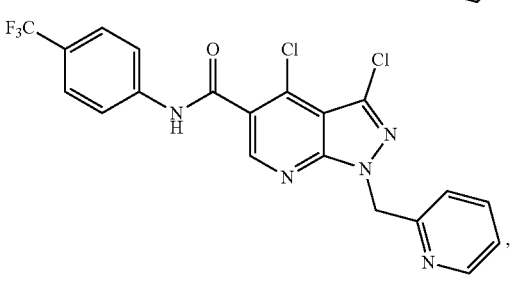
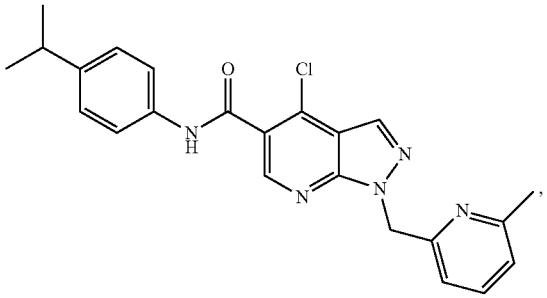
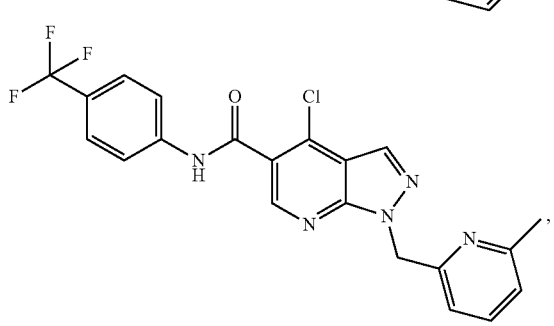
696
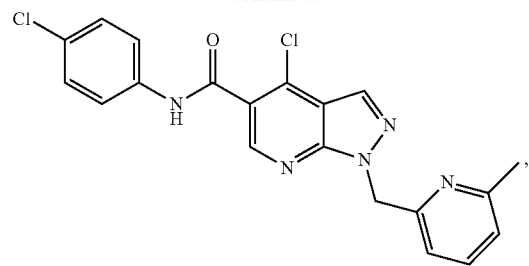
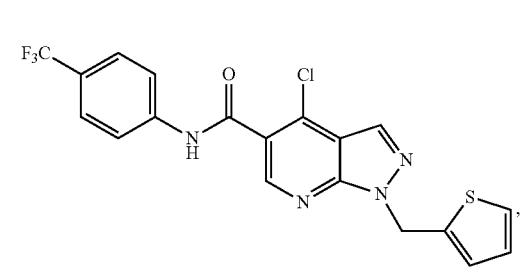
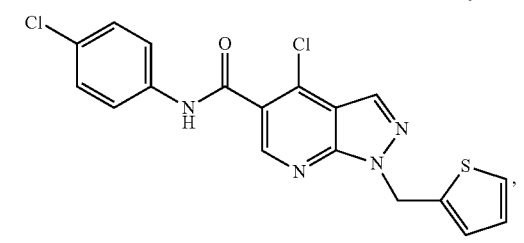
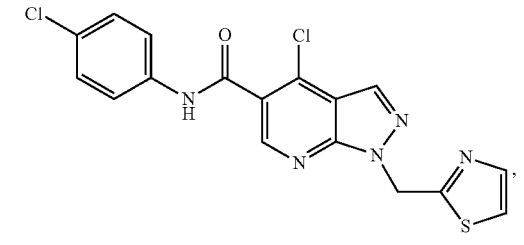
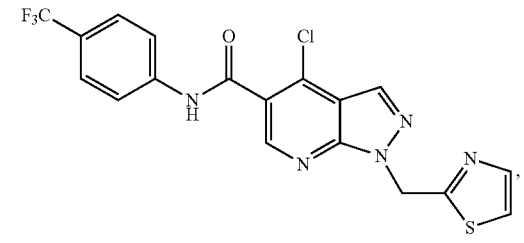
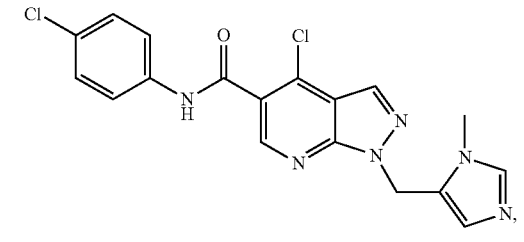
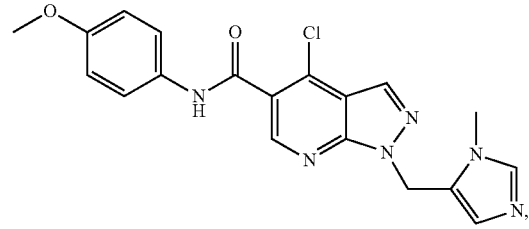

697
-continued
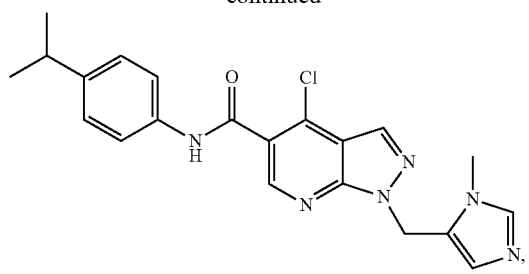
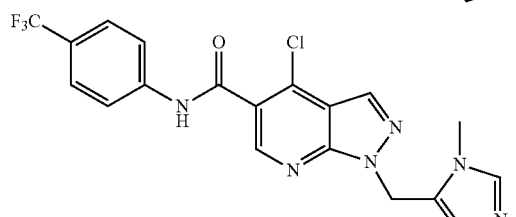
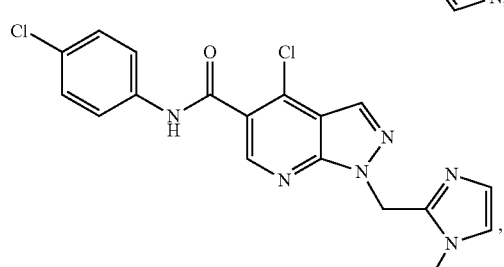
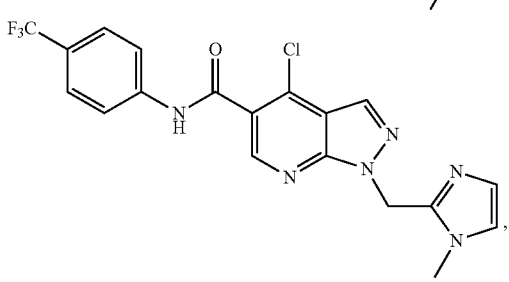
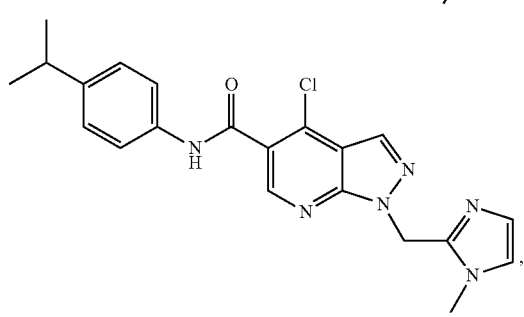
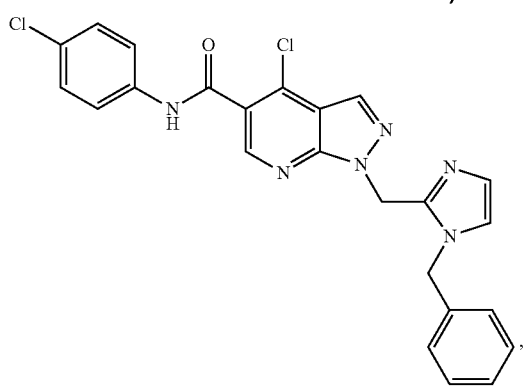
698
-continued
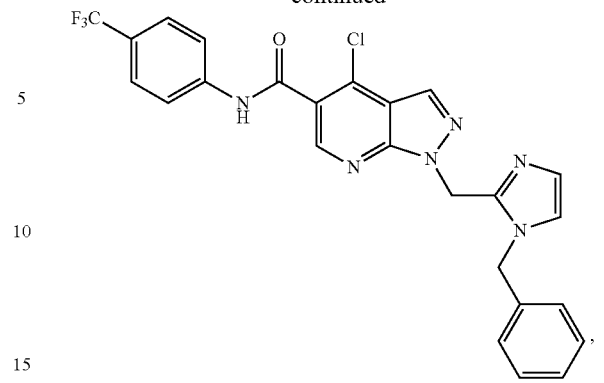
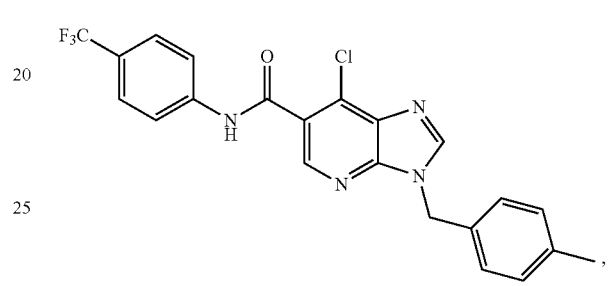
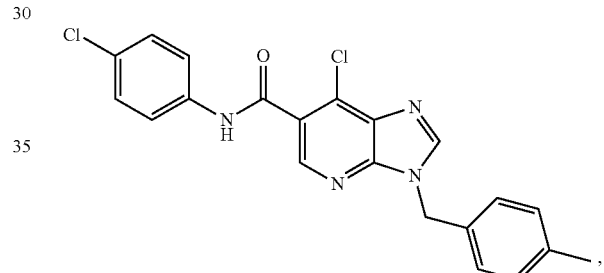
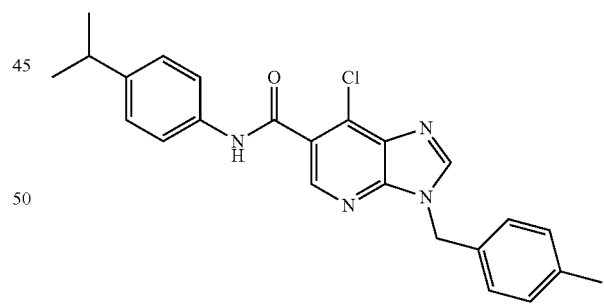
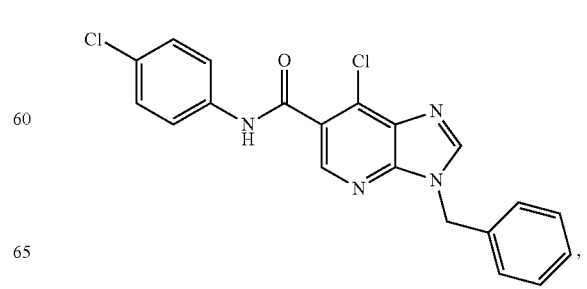

699
-continued
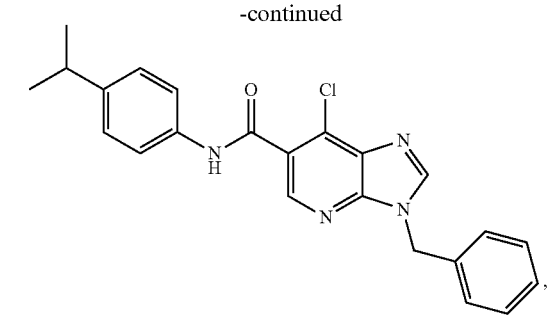
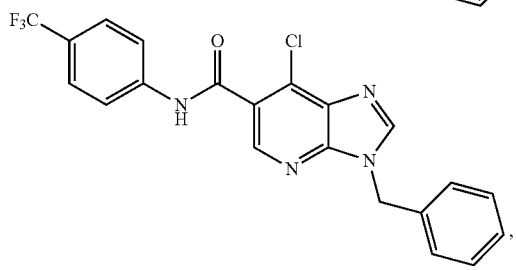
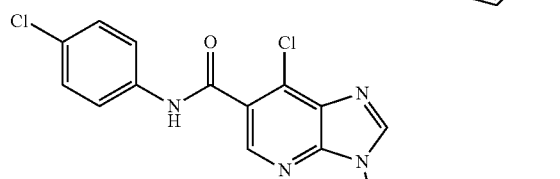
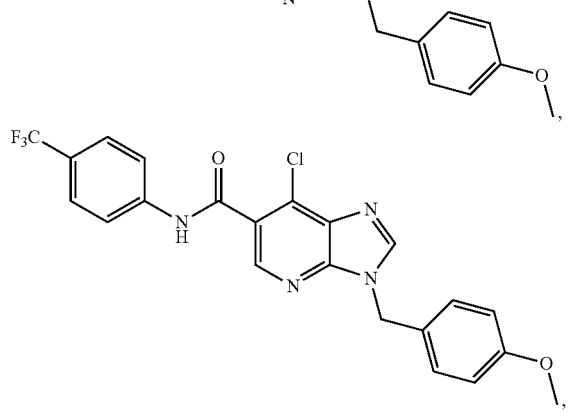
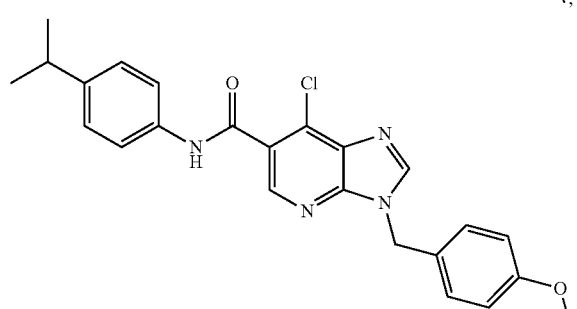
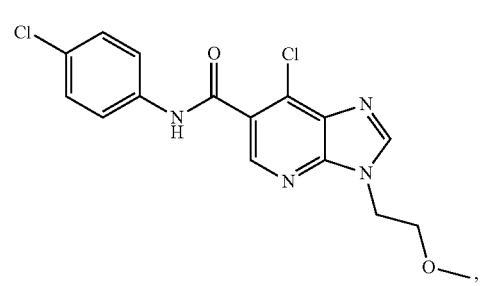
700
-continued
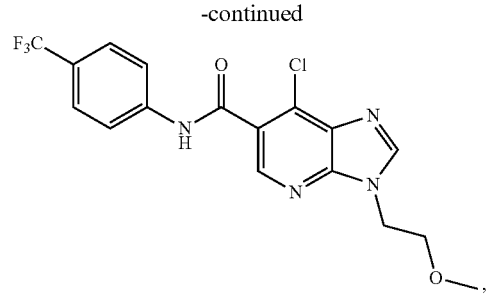
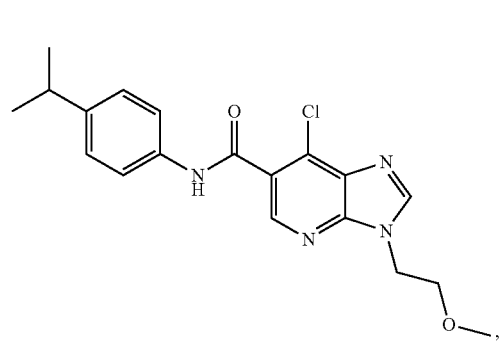
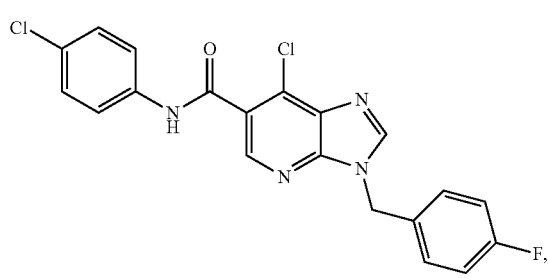
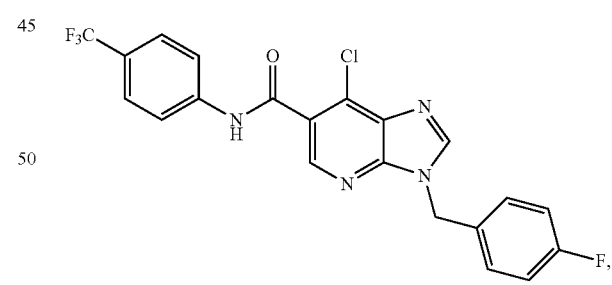
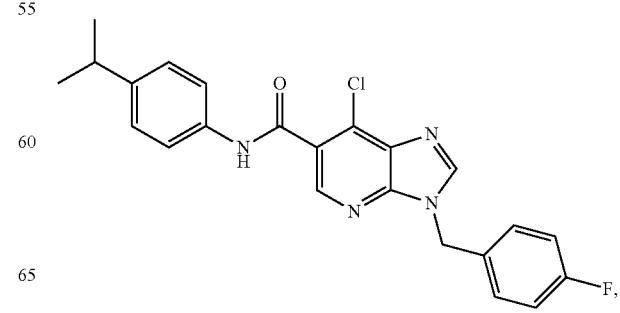

701
-continued
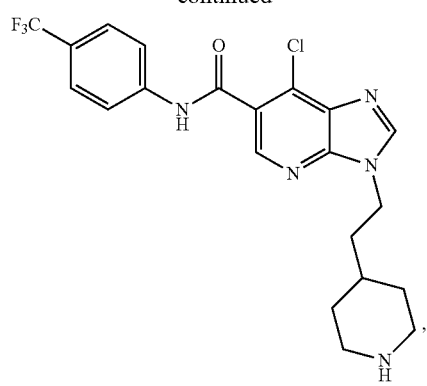
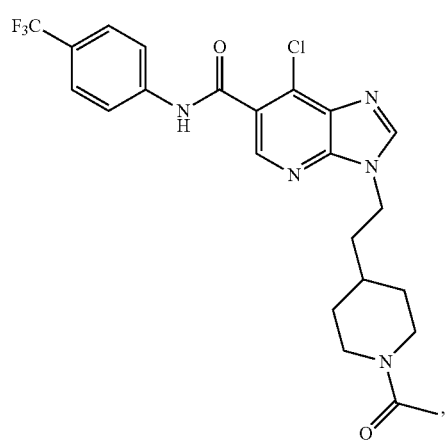
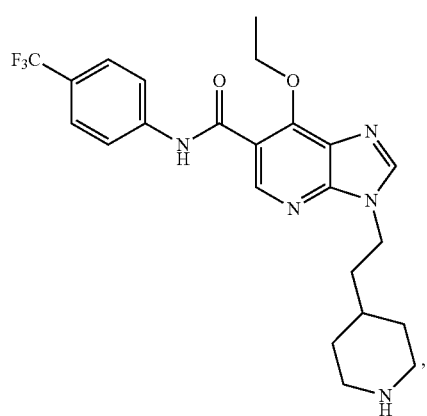
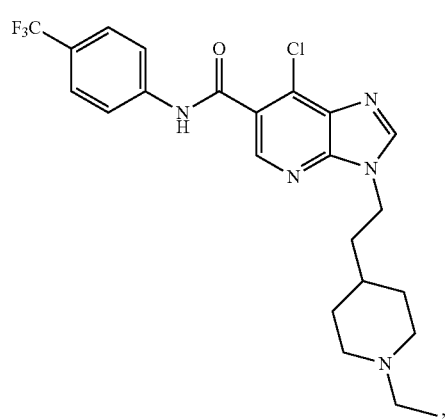
702
-continued
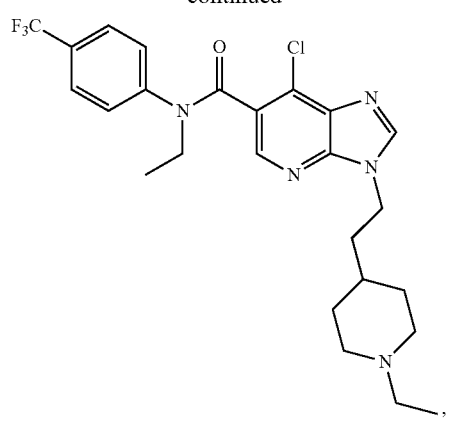
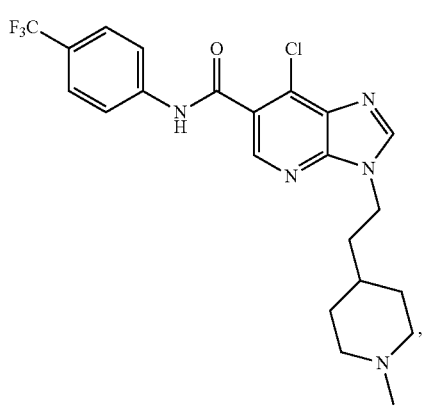
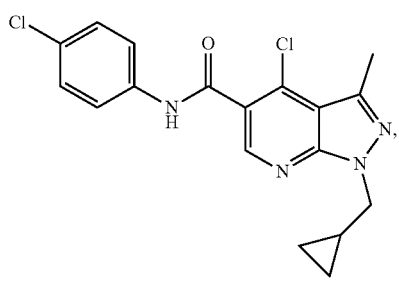
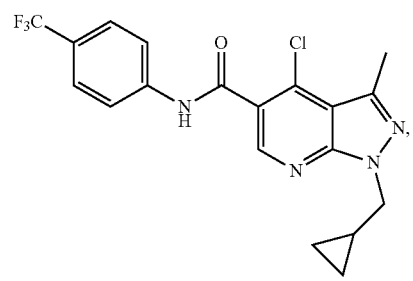
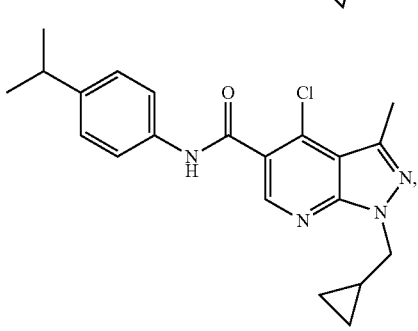

703
-continued
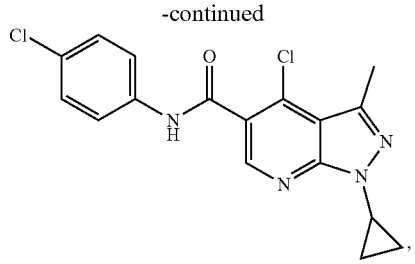
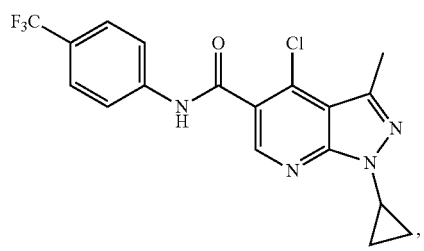
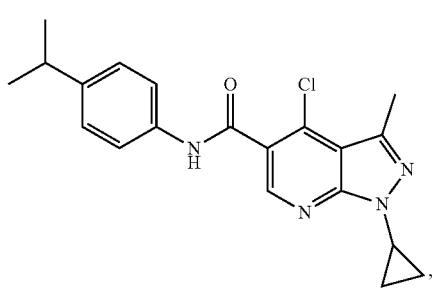
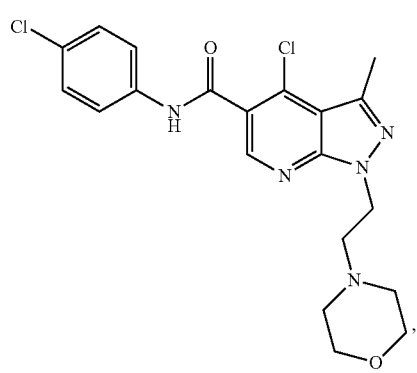
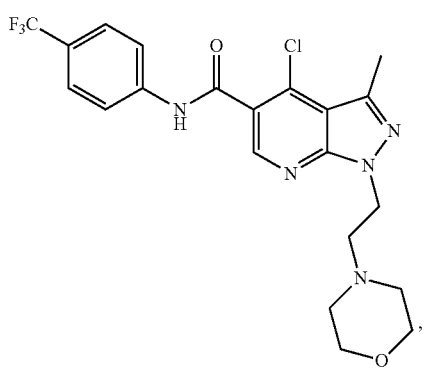
704
-continued
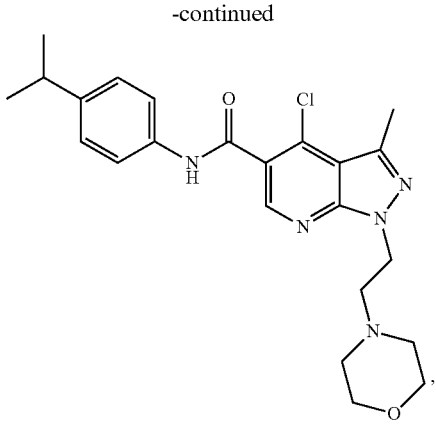
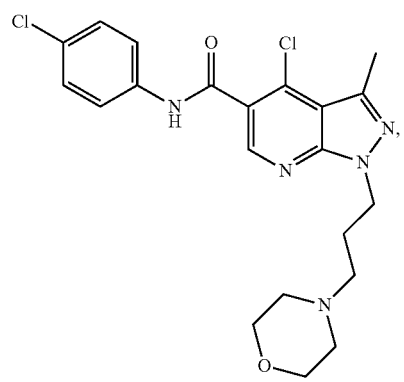
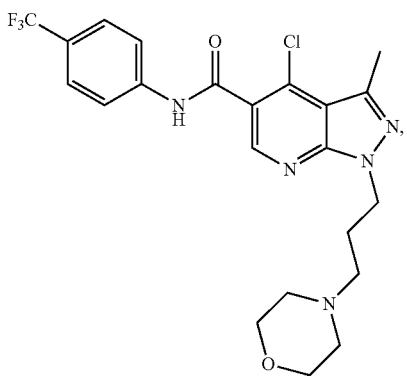
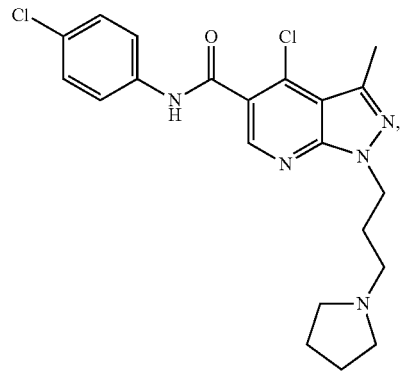

705
-continued
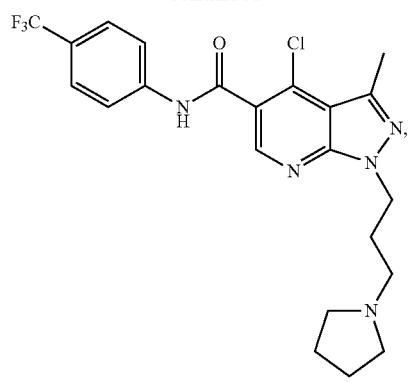
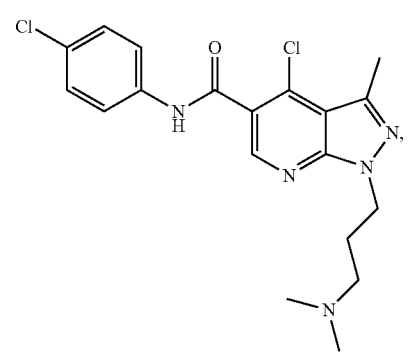
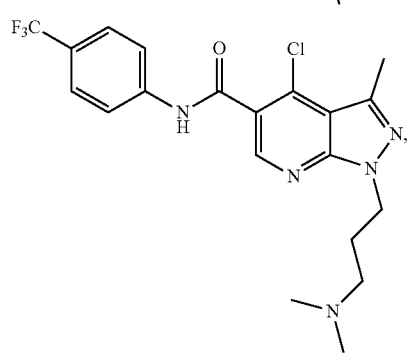
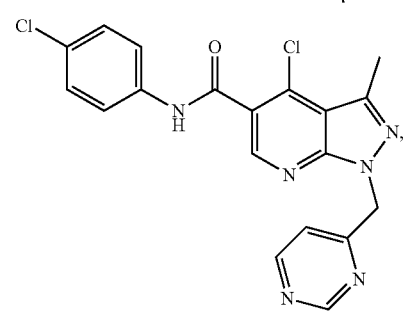
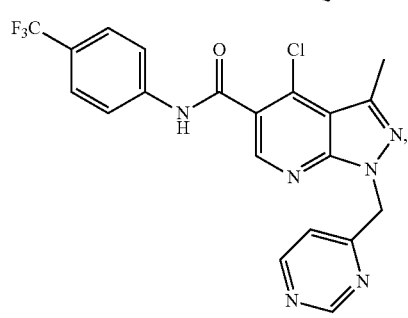
706
-continued
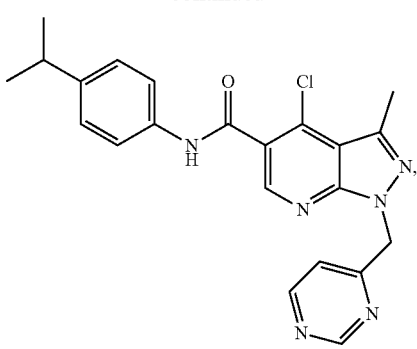
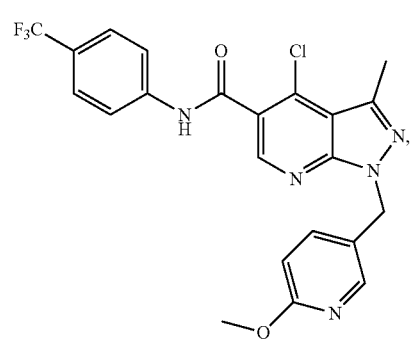
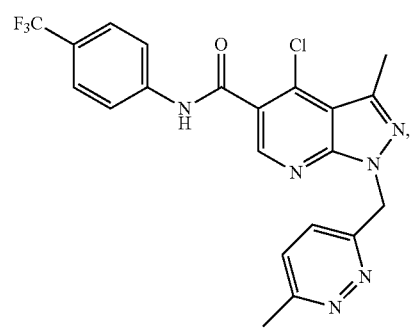
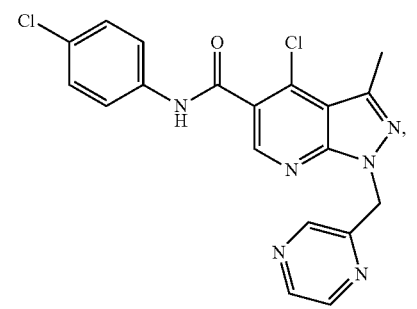
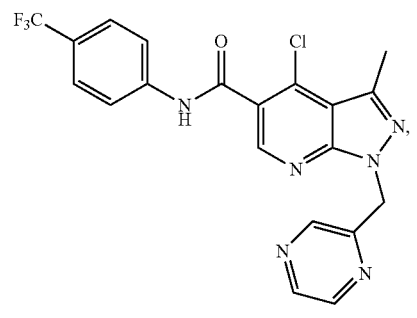

707
-continued
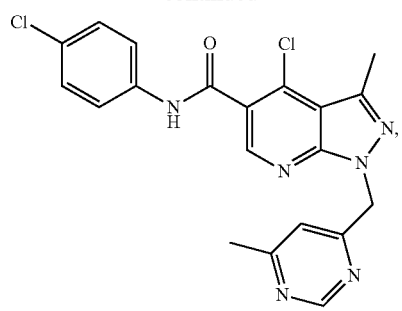
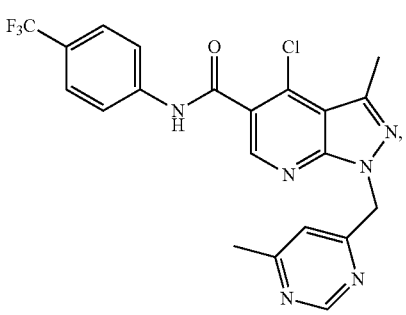
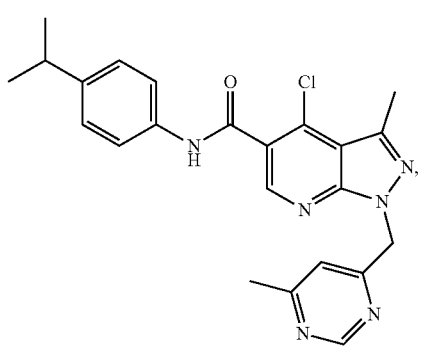
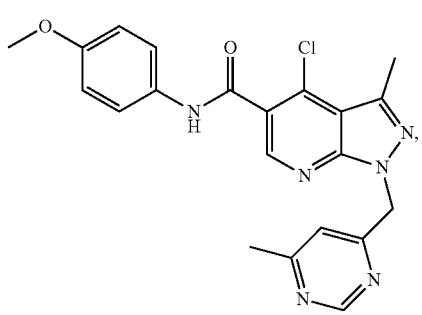
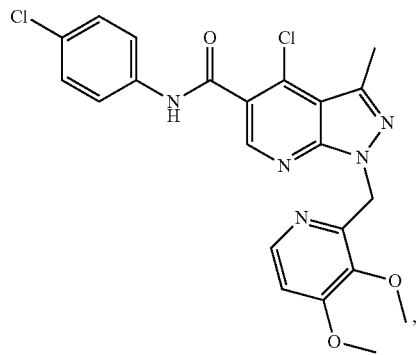
708
-continued
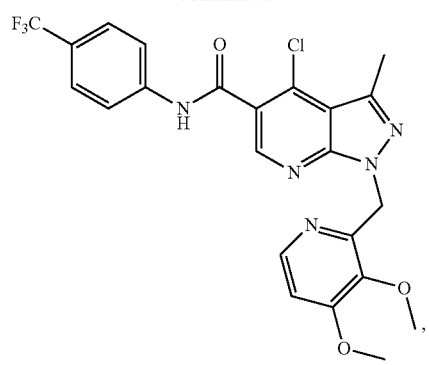
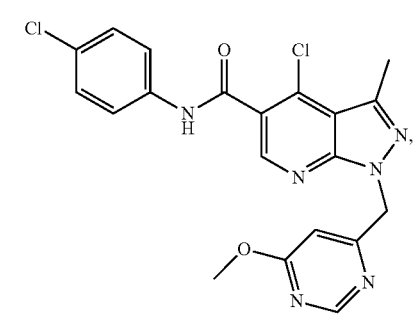
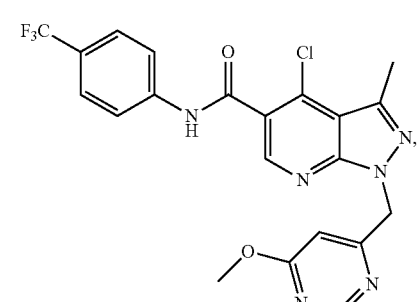
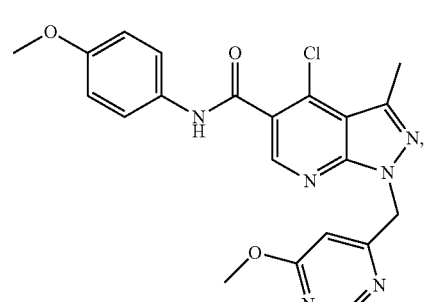
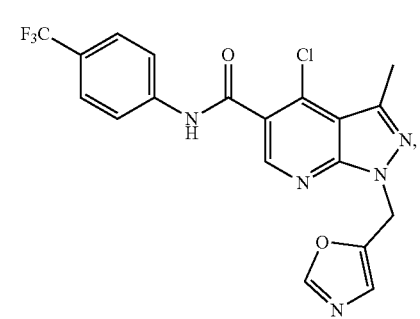

709
-continued
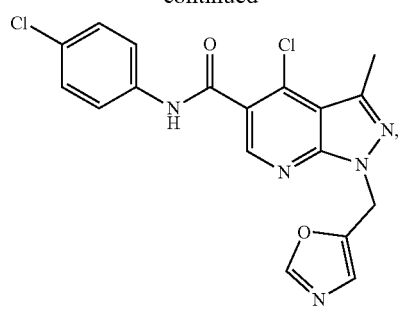
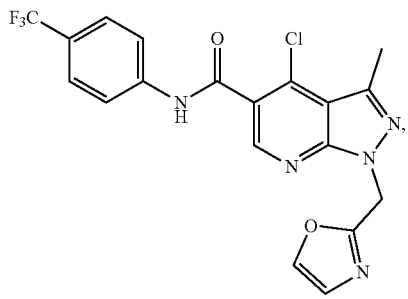
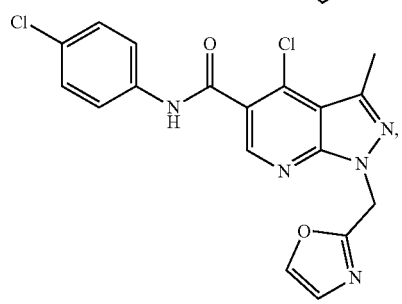
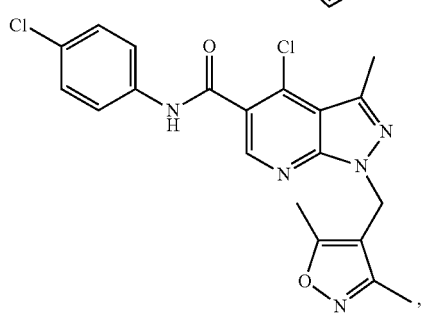
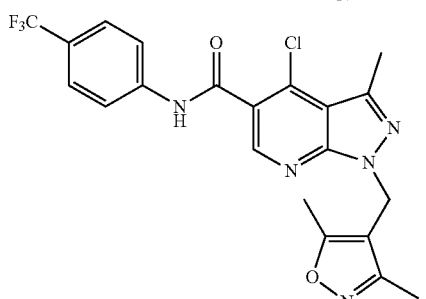
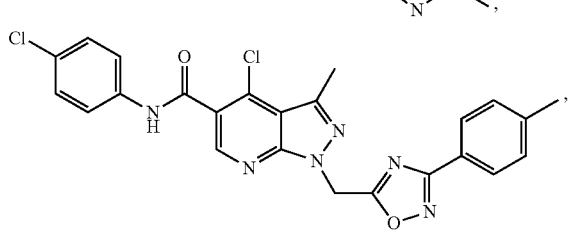
710
-continued
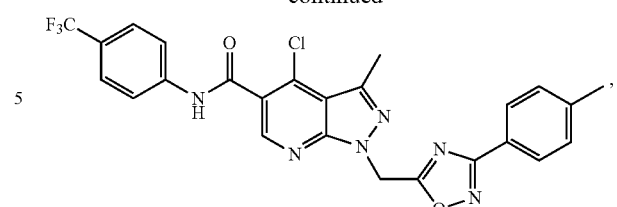
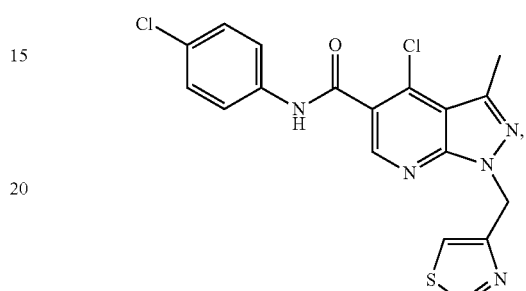
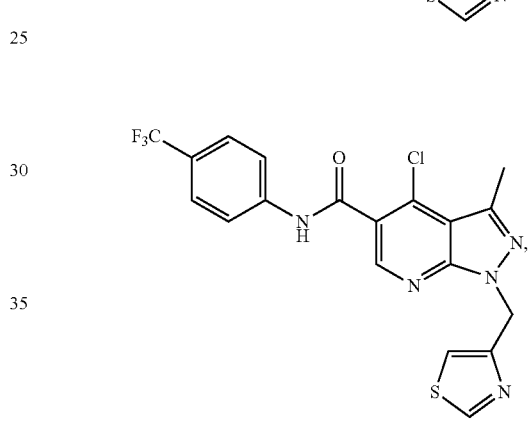
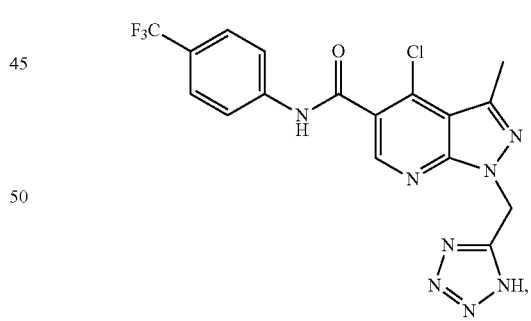
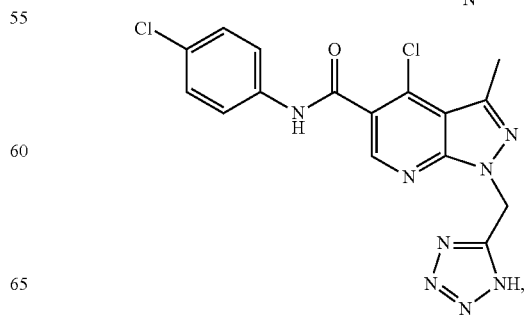

711
-continued
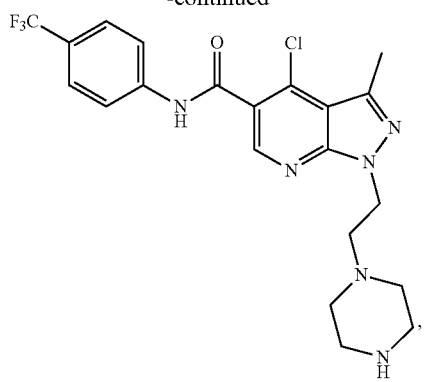
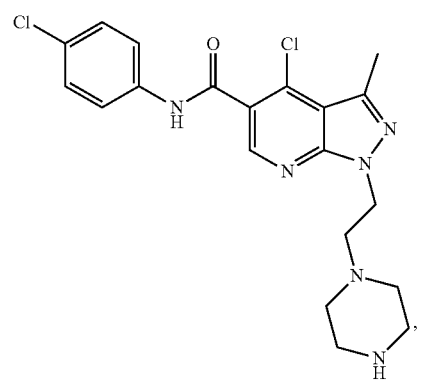
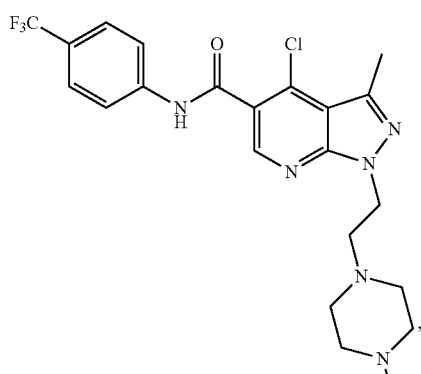
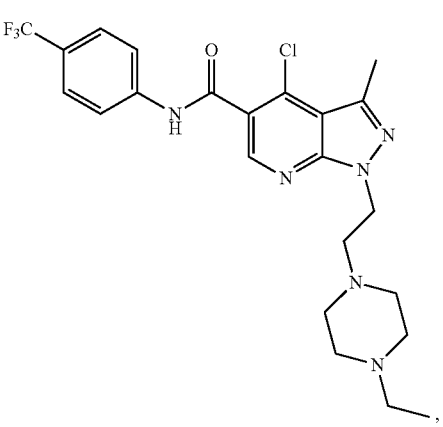
712
-continued
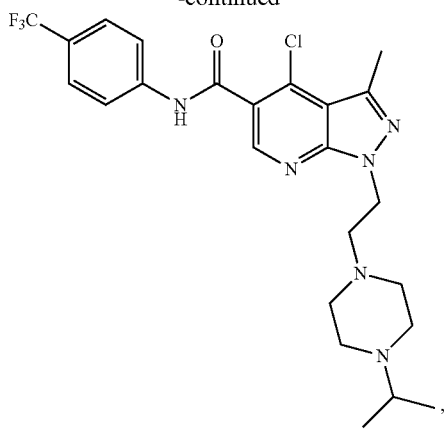
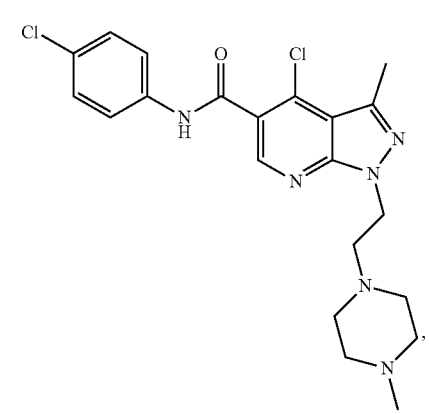
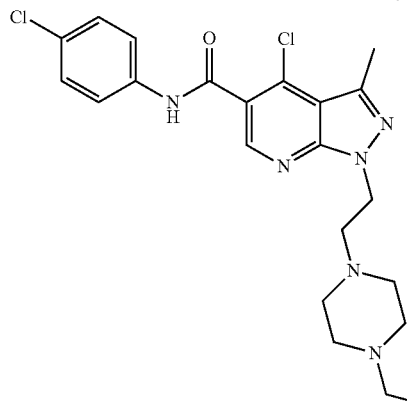
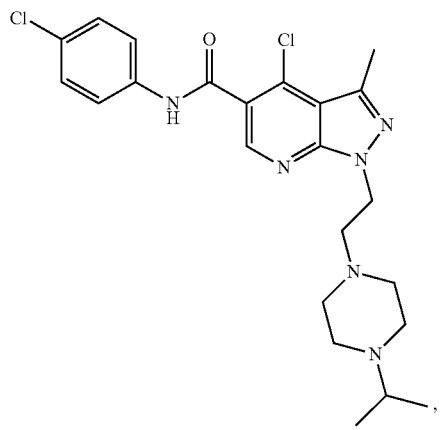

713
-continued
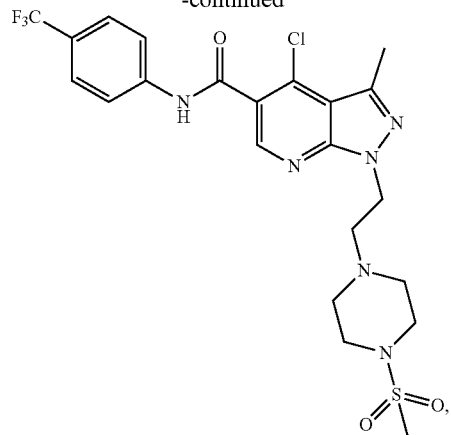
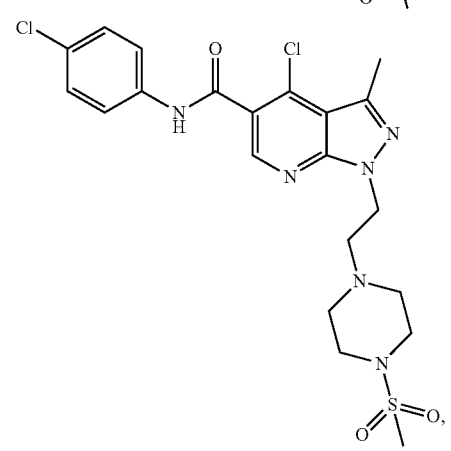
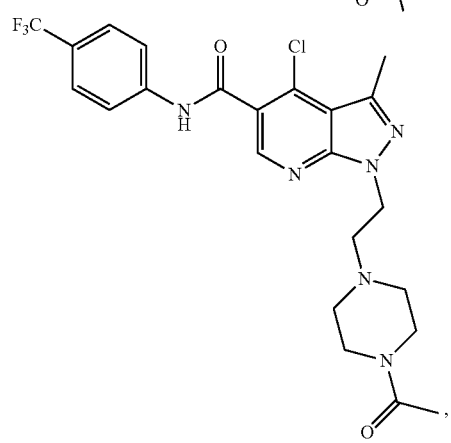
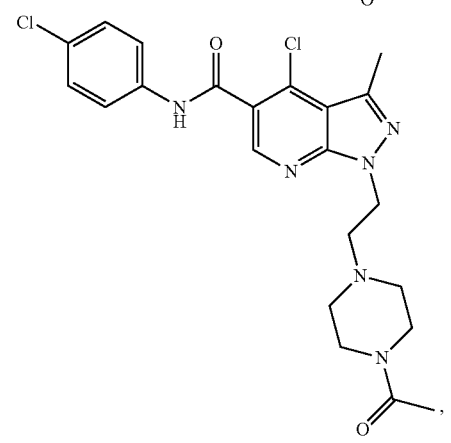
714
-continued
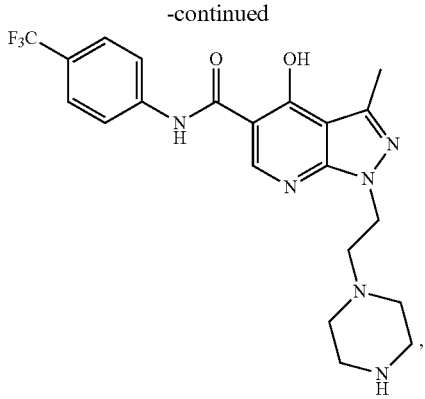
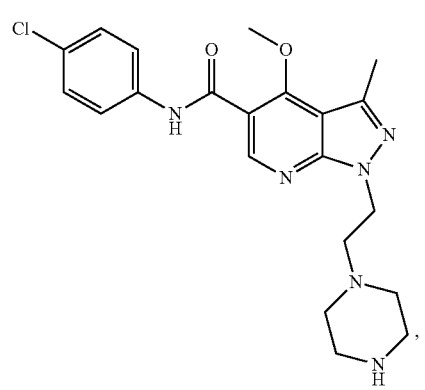
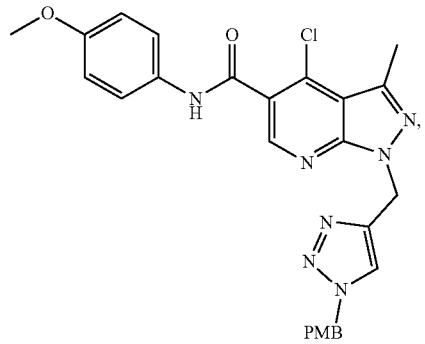
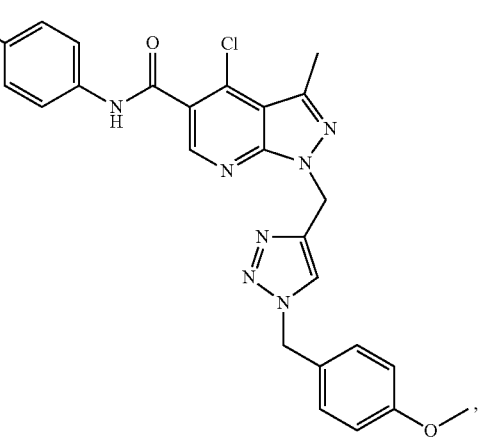

715
-continued
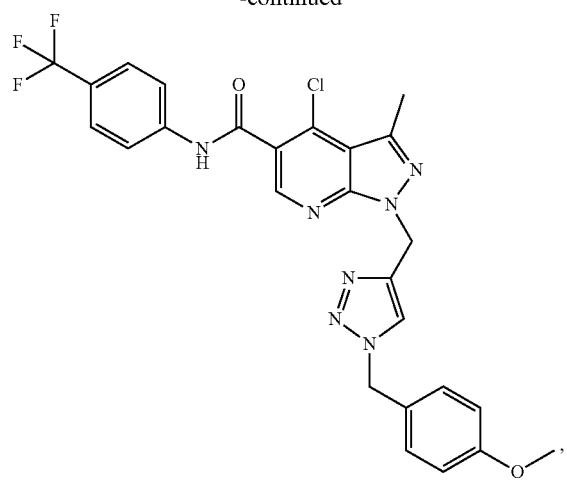
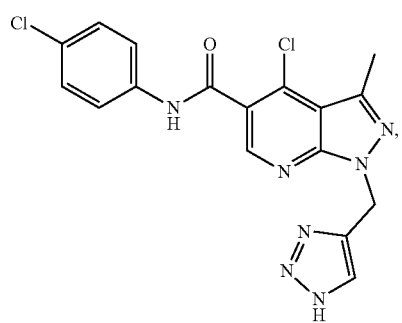
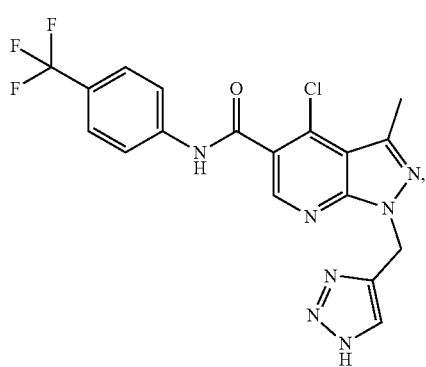
716
-continued
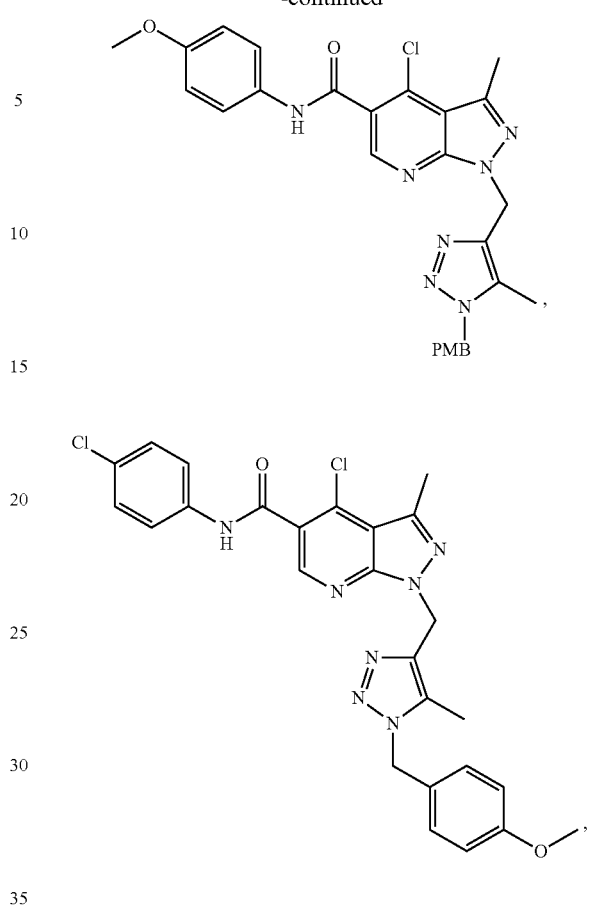
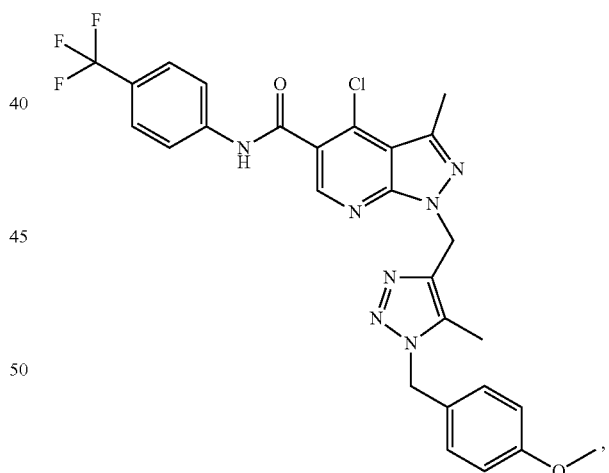
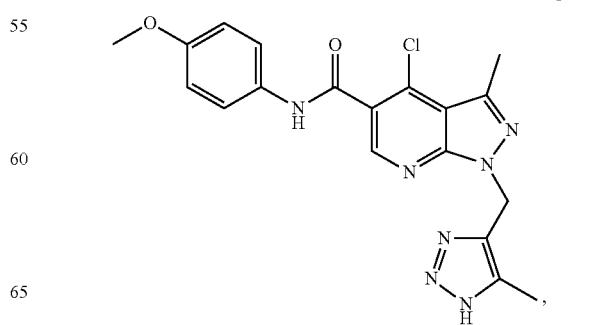

717
-continued
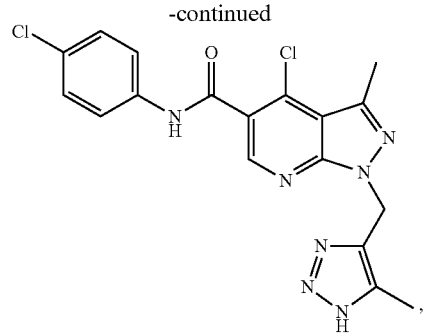
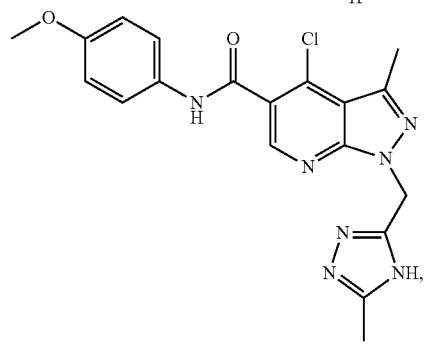
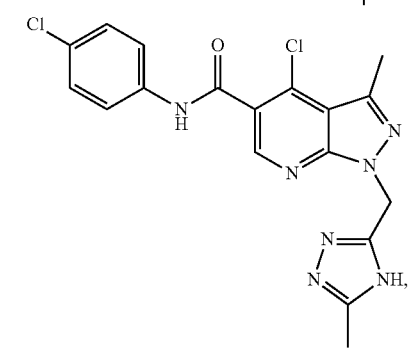
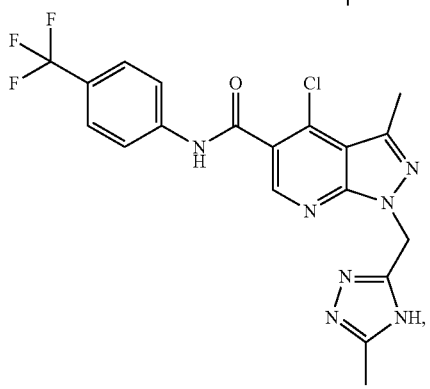
718
-continued
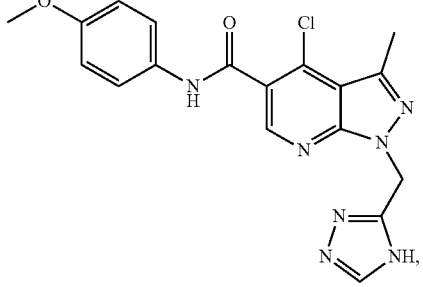
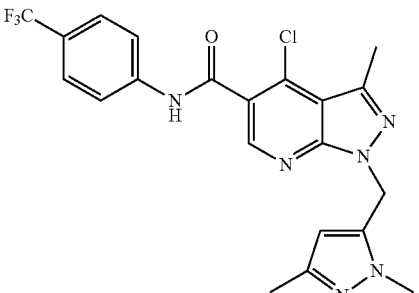
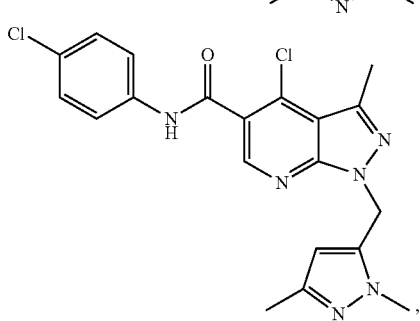

719
-continued
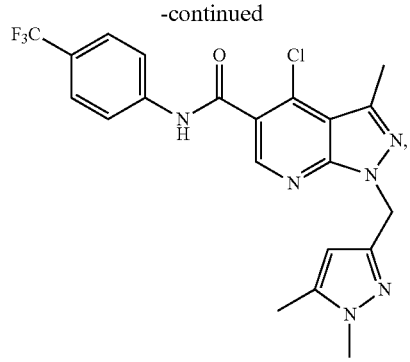
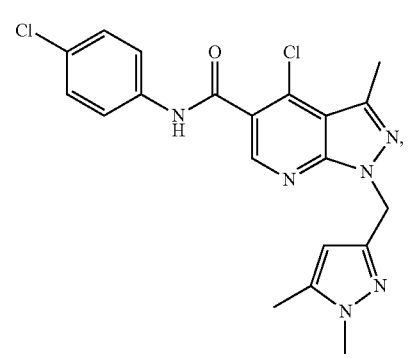
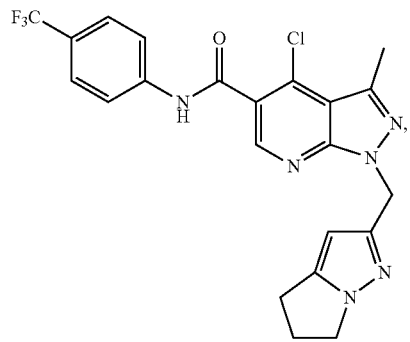
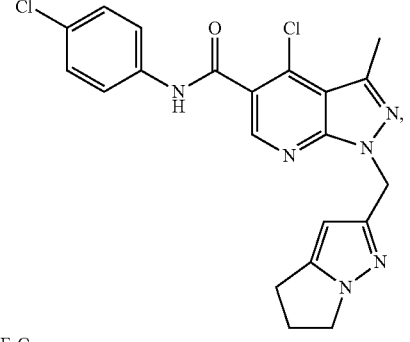
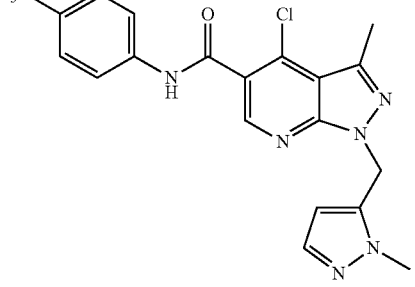
720
-continued
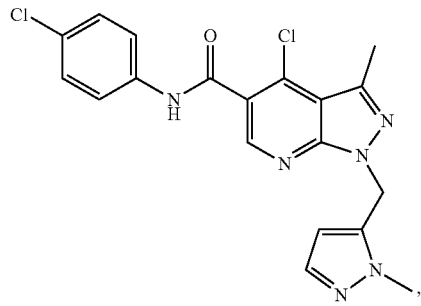
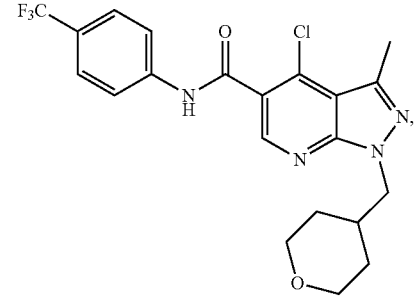
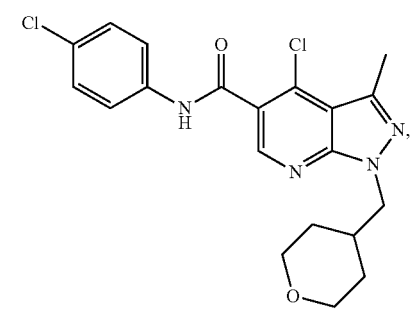
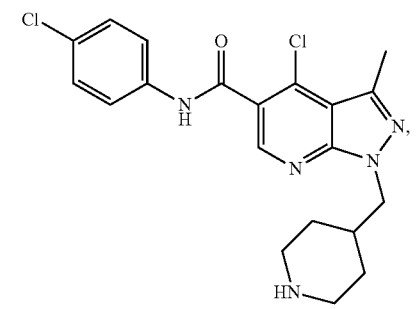
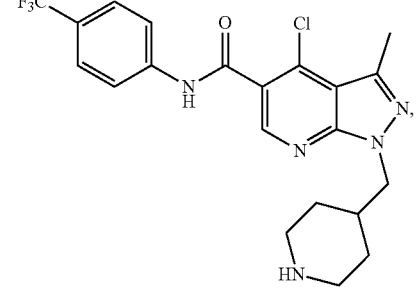

721
-continued
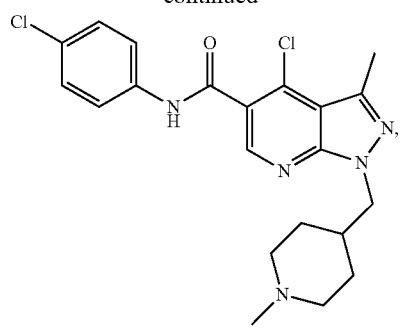
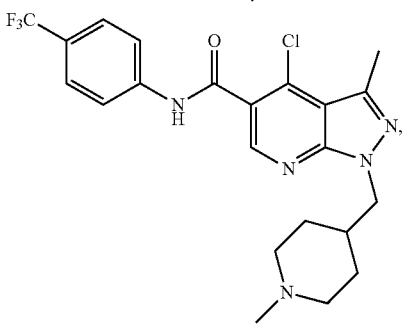
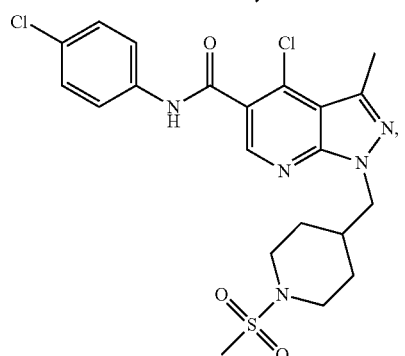
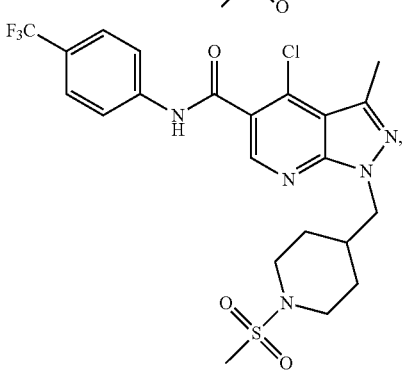
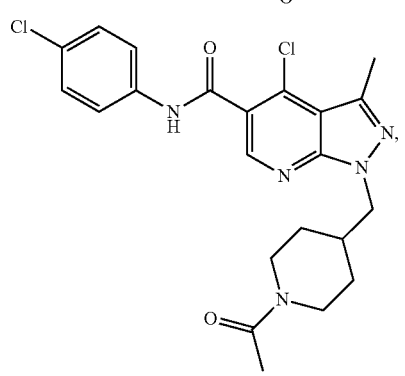
722
-continued
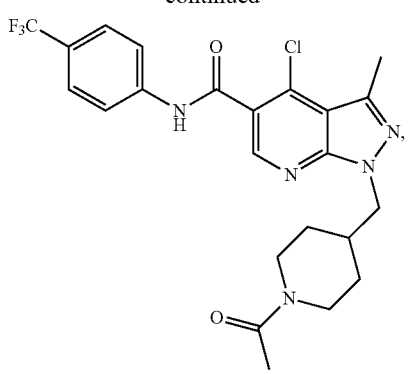
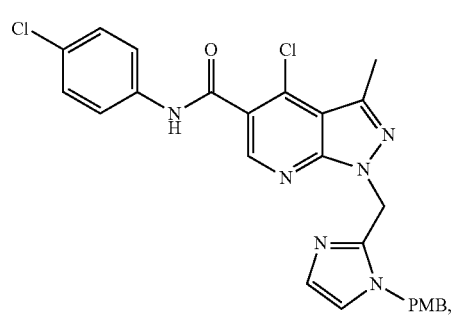
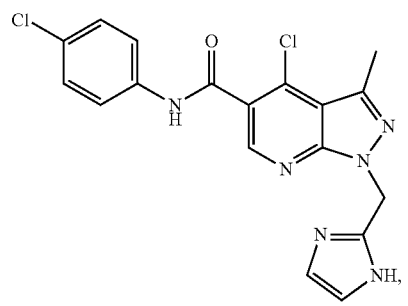
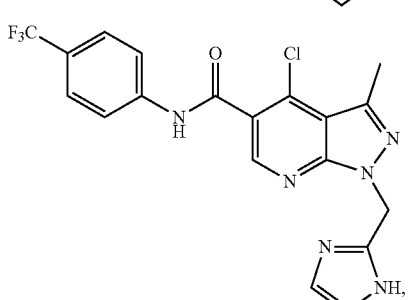
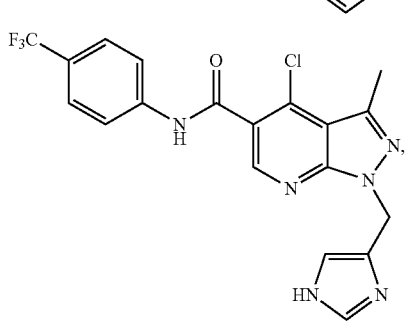

723
-continued
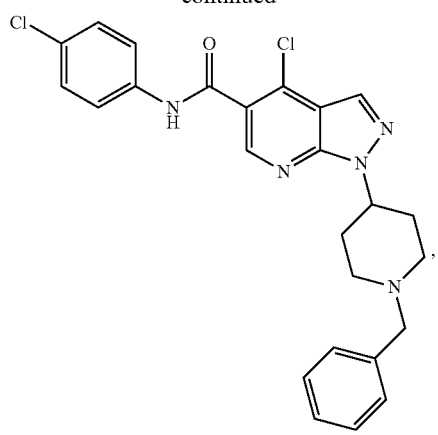
724
-continued
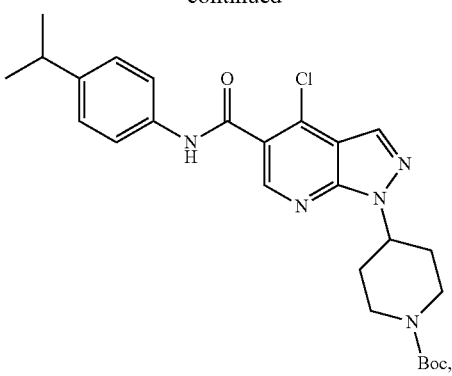
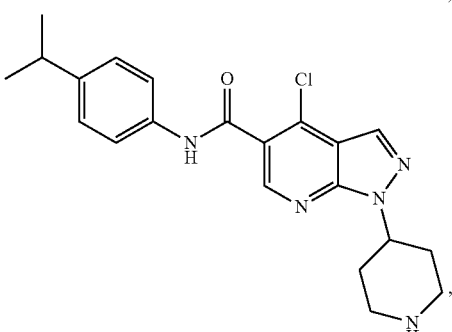
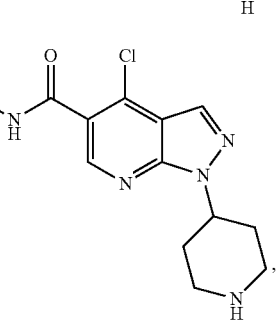
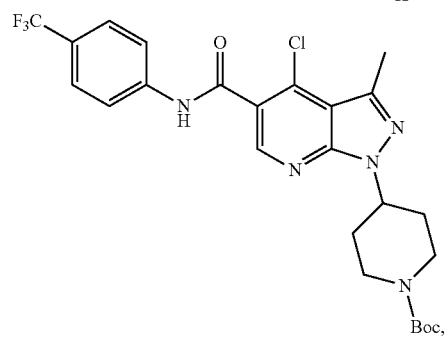
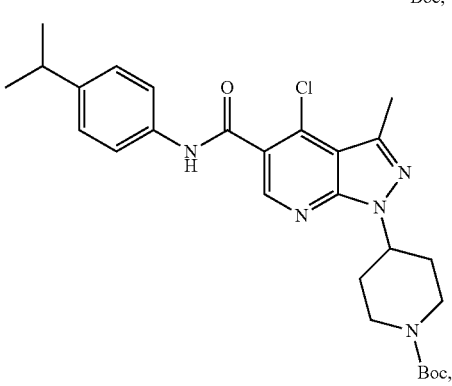

725
-continued
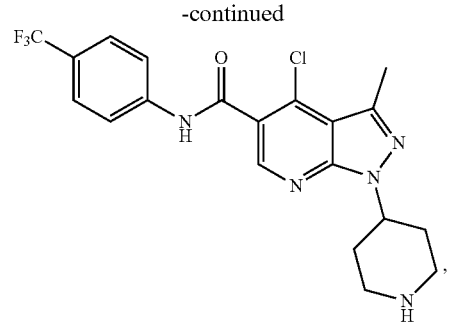
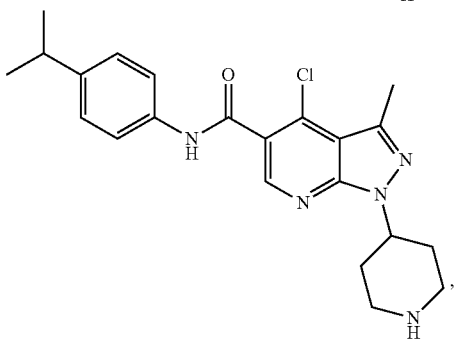
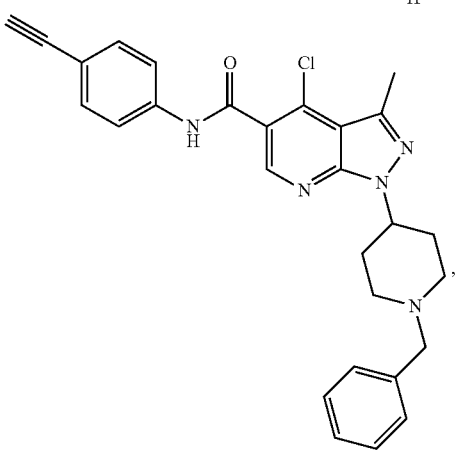
726
-continued
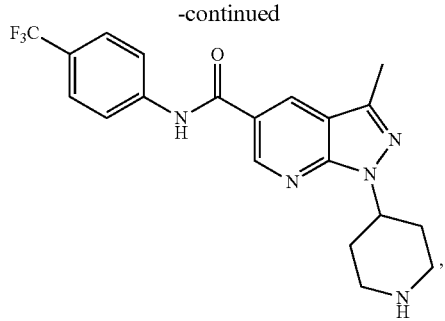
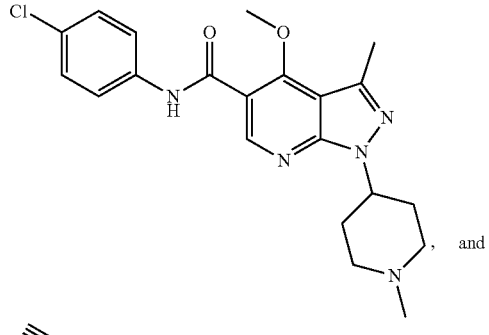
and
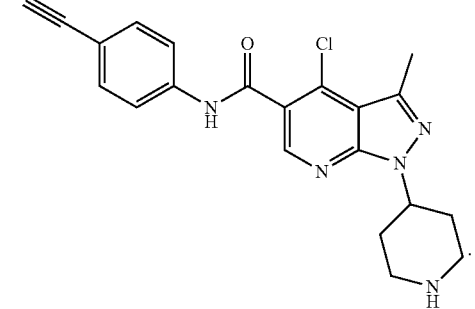
16. A pharmaceutical composition comprising a compound of claim 1, or a pharmaceutically acceptable salt, solvate, tautomer, or N-oxide thereof, and a pharmaceutically acceptable excipient.
* * * * *

UNITED STATES PATENT AND TRADEMARK OFFICE
CERTIFICATE OF CORRECTION

PATENT NO. : 10,272,074 B2
APPLICATION NO. : 15/546165
DATED : April 30, 2019
INVENTOR(S) : Anthony B. Pinkerton et al.

Page 1 of 2

It is certified that error appears in the above-identified patent and that said Letters Patent is hereby corrected as shown below:

In the Claims

Claim 1, Column 661, Lines 7-8, delete "wherein the aryl, heteroaryl, aralkyl, cycloalkyl, heterocycloalkyl" and insert --wherein the aryl, heteroaryl, aralkyl, cycloalkyl, and heterocycloalkyl--.

Claim 1, Column 661, Line 10, delete "alkylnyl" and insert --alkynyl--.

Claim 1, Column 661, Lines 27-28, delete "wherein the aryl, heteroaryl, aralkyl, cycloalkyl, heterocycloalkyl" and insert --wherein the aryl, heteroaryl, aralkyl, cycloalkyl, and heterocycloalkyl--.

Claim 1, Column 661, Line 30, delete "alkylnyl" and insert --alkynyl--.

Claim 1, Column 661, Lines 51-52, delete "$R^d$ is selected from the group consisting of aryl or heteroaryl;" and insert --$R^d$ is selected from the group consisting of aryl and heteroaryl--.

Claim 3, Column 662, Lines 34-35, delete "wherein the aryl, heteroaryl, aralkyl, cycloalkyl, heterocycloalkyl" and insert --wherein the aryl, heteroaryl, aralkyl, cycloalkyl, and heterocycloalkyl--.

Claim 3, Column 662, Line 37, delete "alkylnyl" and insert --alkynyl--.

Claim 3, Column 662, Lines 55-56, delete "wherein the aryl, heteroaryl, aralkyl, cycloalkyl, heterocycloalkyl" and insert --wherein the aryl, heteroaryl, aralkyl, cycloalkyl, and heterocycloalkyl--.

Claim 3, Column 662, Line 58, delete "alkylnyl" and insert --alkynyl--.

Claim 5, Column 663, Line 57, delete "alkylnyl" and insert --alkynyl--.

Claim 7, Column 664, Lines 17-18, delete "Y is is selected from the group consisting of -O-, -S-, -S(=O)-, -S(=O)$_2$-, and -CH$_2$-," and insert --Y is selected from the group consisting of -O-, -S-, -S(=O)-, -S(=O)$_2$-, -NR$^7$-, and -CH$_2$-,--.

Signed and Sealed this
Sixth Day of August, 2019

Andrei Iancu
*Director of the United States Patent and Trademark Office*

CERTIFICATE OF CORRECTION (continued)
U.S. Pat. No. 10,272,074 B2

Claim 7, Column 664, Lines 45-46, delete "wherein the aryl, heteroaryl, aralkyl, cycloalkyl, heterocycloalkyl" and insert --wherein the aryl, heteroaryl, aralkyl, cycloalkyl, and heterocycloalkyl--.

Claim 7, Column 664, Line 48, delete "alkylnyl" and insert --alkynyl--.

Claim 7, Column 664, Lines 62-63, delete "$R^d$ is selected from the group consisting of aryl or heteroaryl;" and insert --$R^d$ is selected from the group consisting of aryl and heteroaryl--.

Claim 8, Column 665, Lines 49-50, delete "wherein the aryl, heteroaryl, aralkyl, cycloalkyl, heterocycloalkyl" and insert --wherein the aryl, heteroaryl, aralkyl, cycloalkyl, and heterocycloalkyl--.

Claim 8, Column 665, Line 52, delete "alkylnyl" and insert --alkynyl--.

Claim 8, Column 665, Lines 66-67, delete "$R^d$ is selected from the group consisting of aryl or heteroaryl;" and insert --$R^d$ is selected from the group consisting of aryl and heteroaryl--.

Claim 9, Column 666, Line 14, delete "alkylnyl" and insert --alkynyl--.

Claim 10, Column 667, Lines 4-5, delete "$R^d$ is selected from the group consisting of aryl or heteroaryl;" and insert --$R^d$ is selected from the group consisting of aryl and heteroaryl--.